US012466842B2

(12) United States Patent
Bartberger et al.

(10) Patent No.: US 12,466,842 B2
(45) Date of Patent: *Nov. 11, 2025

(54) SUBSTITUTED PYRIDO [4,3-D]PYRIMIDINES AS KRAS MODULATORS

(71) Applicant: Alterome Therapeutics, Inc., San Diego, CA (US)

(72) Inventors: Michael David Bartberger, Sherman Oaks, CA (US); Yi Fan, San Diego, CA (US); Eric Anthony Murphy, San Marcos, CA (US); Xuefeng Zhu, San Diego, CA (US)

(73) Assignee: ALTEROME THERAPEUTICS, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 19/213,875

(22) Filed: May 20, 2025

(65) Prior Publication Data

US 2025/0282799 A1 Sep. 11, 2025

Related U.S. Application Data

(63) Continuation of application No. 19/015,403, filed on Jan. 9, 2025, which is a continuation of application No. PCT/US2024/047282, filed on Sep. 18, 2024.

(60) Provisional application No. 63/671,340, filed on Jul. 15, 2024, provisional application No. 63/636,328, filed on Apr. 19, 2024, provisional application No. 63/611,382, filed on Dec. 18, 2023, provisional application No. 63/584,247, filed on Sep. 21, 2023, provisional application No. 63/583,975, filed on Sep. 20, 2023.

(51) Int. Cl.

| | |
|---|---|
| ***A61K 31/519*** | (2006.01) |
| ***A61K 31/538*** | (2006.01) |
| ***A61K 31/553*** | (2006.01) |
| ***C07B 59/00*** | (2006.01) |
| ***C07D 487/04*** | (2006.01) |
| ***C07D 519/00*** | (2006.01) |

(52) U.S. Cl.

CPC .......... *C07D 519/00* (2013.01); *A61K 31/519* (2013.01); *A61K 31/538* (2013.01); *A61K 31/553* (2013.01); *C07B 59/002* (2013.01); *C07D 487/04* (2013.01)

(58) Field of Classification Search

CPC ............................ A61K 31/519; C07D 487/04

USPC ........................................ 514/264.1; 544/279

See application file for complete search history.

(56) References Cited

U.S. PATENT DOCUMENTS

| | | | |
|---|---|---|---|
| 5,846,514 A | 12/1998 | Foster et al. | |
| 6,334,997 B1 | 1/2002 | Foster et al. | |

FOREIGN PATENT DOCUMENTS

| | | |
|---|---|---|
| WO | WO-2022132200 A1 | 6/2022 |
| WO | WO-2022237649 A1 | 11/2022 |
| WO | WO-2022256459 A1 | 12/2022 |
| WO | WO-2023018809 A1 | 2/2023 |
| WO | WO-2023020519 A1 | 2/2023 |
| WO | WO-2023020523 A1 | 2/2023 |
| WO | WO-2023061294 A1 | 4/2023 |
| WO | WO-2024008068 A1 | 1/2024 |
| WO | WO-2024083246 A1 | 4/2024 |
| WO | WO-2024118966 A1 | 6/2024 |
| WO | WO-2024119277 A1 | 6/2024 |
| WO | WO-2024178313 A1 | 8/2024 |
| WO | WO-2024179546 A1 | 9/2024 |
| WO | WO-2025064542 A1 | 3/2025 |

OTHER PUBLICATIONS

Bachovchin, Daniel A. et al. Identification of selective inhibitors of uncharacterized enzymes by high-throughput screening with fluorescent activity-based probes. Nature Biotechnology 27(4):387-394 (2009).
Berge, Stephen M. et al. Pharmaceutical Salts. Journal of Pharmaceutical Sciences 66(1):1-19 (1977).
Chemical Abstracts Service. CAS Registry: 2385193-87-1. 1,4-Oxazepine-4(5H)-carboxylic acid, tetrahydro-5-methoxy-, 1,1-dimethylethyl ester]-. STN Entry Date Nov. 29, 2019.
Chemical Abstracts Service. CAS Registry: 2904566-02-3. 5-Oxa-2-azabicyclo[5.1.0]octane, 2-(2,7-dichloro- 8-fluoropyrido[4,3-d]pyrimidin-4-yl)-. STN Entry Date Mar. 6, 2023.
Chemical Abstracts Service. CAS Registry: 2904566-03-4. 5-Oxa-2-azabicyclo[5.1.0]octane, 2-[7-chloro-8- fluoro-2-[[(2R,7aS)-2-fluorotetrahydro-1H-pyrrolizin-7a(5H)-yl]methoxy]pyrido[4,3-d]pyrimidin-4-yl]-. STN Entry Date Mar. 6, 2023.
(Continued)

*Primary Examiner* — Douglas M Willis

(74) *Attorney, Agent, or Firm* — WILSON SONSINI GOODRICH & ROSATI

(57) ABSTRACT

Provided herein are inhibitors of KRAS, pharmaceutical compositions comprising the inhibitory compounds, and methods for using the KRAS inhibitory compounds for the treatment of diseases or disorders.

(I)

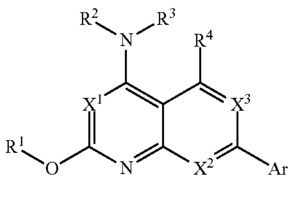

30 Claims, 26 Drawing Sheets

(56) References Cited

OTHER PUBLICATIONS

Chemical Abstracts Service. CAS Registry: 2904566-84-1. 5-Oxa-2-azabicyclo[5.1.0]octane, 2-[7-chloro-8- fluoro-2-[[(2R,7aS)-2-fluorotetrahydro-1H-pyrrolizin-7a(5H)-yl]methoxy]pyrido[4,3-d]pyrimidin-4-yl]-, (1S,7R)-. STN Entry Date Mar. 6, 2023.
Chemical Abstracts Service. CAS Registry: 2904566-85-2. 5-Oxa-2-azabicyclo[5.1.0]octane, 2-[7-chloro-8- fluoro-2-[[(2R,7aS)-2-fluorotetrahydro-1H-pyrrolizin-7a(5H)-yl]methoxy]pyrido[4,3-d]pyrimidin-4-yl]-, (1R,7S)-. STN Entry Date Mar. 6, 2023.
Co-pending U.S. Appl. No. 19/015,403, inventors Bartberger; Michael David et al., filed on Jan. 9, 2025.
Dean, Dennis C. Recent Advances in the Synthesis and Applications of Radiolabeled Compounds for Drug Discovery and Development. Current Pharmaceutical Design 6:1-2 (2000).
Dillon, Myles BC et al. Novel inhibitors for PRMT1 discovered by high-throughput screening using activity-based fluorescence polarization. ACS Chemical Biology 7(7):1198-1204 (2012).
Evans, Anthony E. Synthesis of Radiolabeled Compounds. Journal of Radioanalytical and Nuclear Chemistry 64(1-2):9-32 (1981).
Hackam, Daniel G. et al. Redelmeier. Translation of Research Evidence from Animals to Humans. JAMA 296(14):1727-1732 (2006).
Hofmann, Marco H. et al. Expanding the Reach of Precision Oncology by Drugging All KRAS Mutants. Cancer Discovery 12(4):924-937 (2022).
Huang, Lamei et al. KRAS mutation: from undruggable to druggable in cancer. Signal transduction and targeted therapy 6(1):386, 1-20 (2021).
Jordan. Tamoxifen: A most unlikely pioneering medicine. Nature Reviews: Drug Discovery 2:205-213 (2003).
Kabalka, George W. et al. The Synthesis of Radiolabeled Compounds via Organometallic Intermediates. Tetrahedron 45(21):6601-6621 (1989).
Kawamata, Yu et al. Chemoselective electrosynthesis using rapid alternating polarity. Journal of the American Chemical Society 143(40):16580-16588 (2021).
Kubyshkin, Vladimir et al. Synthesis and studies on gem-fluorinated 2-azabicyclo [n. 1.0] alkanes. Journal of Fluorine Chemistry 175:73-83 (2015).
Lanman, Brian A. et al. Discovery of a Covalent Inhibitor of KRASG12C (AMG 510) for the Treatment of Solid Tumors. Journal of Medicinal Chemistry 63:52-65 (2020).
Larock, Richard C. et al. Comprehensive Organic Transformations: A Guide to Functional Group Preparations: Second Edition, Wiley-VCH 1-18 (1999).
Lone, Anna Mari et al. A substrate-free activity-based protein profiling screen for the discovery of selective PREPL inhibitors. Journal of the American Chemical Society 133(30):11665-11674 (2011).
Ostrem, Jonathan M. et al. K-Ras(G12C) inhibitors allosterically control GTP affinity and effector interactions. Nature 503:548-551 (2013).
PCT/US2024/047282 International Search Report and Written Opinion dated Dec. 4, 2024.
Prior, Ian A. et al. The frequency of Ras mutations in cancer. Cancer Research 80(14):2969-2974 (2020).
Ryan, Meagan B. et al. Therapeutic strategies to target RAS-mutant cancers. Nature Reviews Clinical Oncology 15(11):709-720 (2018).
U.S. Appl. No. 19/015,403 Office Action dated Mar. 27, 2025.
Vasta, James D. et al. KRAS is vulnerable to reversible switch-II pocket engagement in cells. Nature Chemical Biology 18(6):596-604 (2022).
Vippagunta, Sudha R. et al. Crystalline Solids. Advanced Drug Delivery Reviews 48(1):3-26 (2001).

SUBSTITUTED PYRIDO [4,3-D]PYRIMIDINES AS KRAS MODULATORS

CROSS-REFERENCE TO RELATED APPLICATIONS

This application is a continuation of U.S. application Ser. No. 19/015,403, filed Jan. 9, 2025, which is a continuation of PCT/US2024/047282, filed Sep. 18, 2024, which claims the benefit of U.S. Patent Application No. 63/583,975, filed on Sep. 20, 2023; U.S. Patent Application No. 63/584,247, filed on Sep. 21, 2023; U.S. Patent Application No. 63/611,382, filed on Dec. 18, 2023; U.S. Patent Application No. 63/636,328, filed on Apr. 19, 2024; and U.S. Patent Application No. 63/671,340, filed on Jul. 15, 2024, all of which are hereby incorporated by reference in their entirety.

BACKGROUND

KRAS (Kirsten rat sarcoma viral oncogene homologue) is an oncoprotein that is a part of the RAS/MAPK pathway, and relays signals from outside of the cell to the cell's nucleus. KRAS protein is a GTPase and involved in cellular signaling such as regulation of cell proliferation. KRAS can activate cellular signaling pathways including, but not limited to, the mitogen-activated protein kinase (MAPK) pathway. KRAS was previously considered un-targetable, but recent studies have shown that targeting codon 12 can lead to therapeutic effects. There remains an unmet need to identify and develop novel compounds for KRAS inhibition.

BRIEF SUMMARY OF THE INVENTION

Provided herein are inhibitors of KRAS, pharmaceutical compositions comprising said inhibitory compounds, and methods for using said inhibitory compounds for the treatment of cancer and neoplastic disease.

One embodiment provides a compound having the structure of Formula (I), or a pharmaceutically acceptable salt or solvate, thereof:

(I)

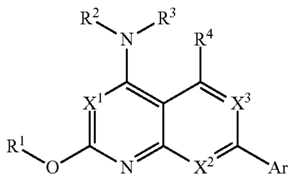

wherein:

$X^1$ is N or C—CN;

$X^2$ is N, C—H, C—F, C—$CH_3$, C—Cl, C-(optionally substituted C1-C6 alkyl), C-(optionally substituted C2-C6 alkenyl), or C-(optionally substituted C3-C6 carbocyclyl);

$X^3$ is N, C—H, C—F, C—Cl, C—CN, or C—$CF_3$;

Ar is an optionally substituted mono or bicyclic aryl, or optionally substituted mono or bicyclic heteroaryl ring system;

$R^1$ is L-G; wherein L is optionally substituted C1-C4 alkylene,

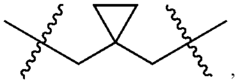

,

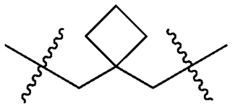

or

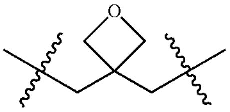

;

and G is an optionally substituted 5- to 10-membered heterocyclyl;

—$N(R^2)R^3$ form an optionally substituted heterocyclyl substituent selected from the group consisting of:

(a) optionally substituted azabicyclo[3.1.0]hexane;
(b) optionally substituted azabicyclo[4.1.0]heptane;
(c) optionally substituted oxazabicyclo[4.1.0]heptane;
(d) optionally substituted azabicyclo[5.1.0]octane;
(e) optionally substituted oxazabicyclo[5.1.0]octane;
(f) optionally substituted azabicyclo[6.1.0]nonane;
(g) optionally substituted oxazabicyclo[6.1.0]nonane;
(h) optionally substituted azabicyclo[5.1.0]oct-5-en-2-yl;
(i) optionally substituted azabicyclo[5.1.0]oct-4-en-2-yl;
(j) optionally substituted azabicyclo[6.1.0]non-6-en-2-yl;
(k) optionally substituted azabicyclo[6.1.0]non-5-en-2-yl;
(l) optionally substituted azabicyclo[6.1.0]non-4-en-2-yl;
(m) optionally substituted 3-oxa-2,6-diazabicyclo[5.1.0]oct-1-en-6-yl;
(n) optionally substituted 2-oxa-3,6-diazabicyclo[5.1.0]oct-3-en-6-yl;
(o) optionally substituted 4-oxa-2,5-diazabicyclo[5.1.0]oct-5-en-2-yl;
(p) optionally substituted 3-oxa-2,7-diazabicyclo[6.1.0]non-1-en-7-yl;
(q) optionally substituted 2-oxa-3,7-diazabicyclo[6.1.0]non-3-en-7-yl;
(r) optionally substituted 5-oxa-2,6-diazabicyclo[6.1.0]non-6-en-2-yl;
(s) optionally substituted 6-oxa-2,5-diazabicyclo[6.1.0]non-4-en-2-yl; and
(t) optionally substituted 4-oxa-2,5-diazabicyclo[6.1.0]non-5-en-2-yl; and $R^4$ is selected from H, —OH, —CN, halogen, optionally substituted C1-C4 alkoxy, optionally substituted C1-C6 alkyl, optionally substituted C1-C6 cycloalkyl, or $C_1$-C6 cycloalkylalkyl.

One embodiment provides a compound having the structure of Formula (Ia), or a pharmaceutically acceptable salt or solvate, thereof:

(Ia)

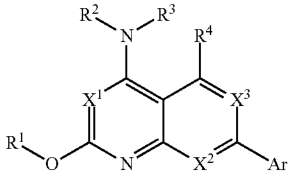

wherein:

$X^1$ is N or C—CN;

$X^2$ is N, C—H, C—F, C—$CH_3$, or C—Cl;

$X^3$ is N, C—H, C—F, C—Cl, C—CN, or C—$CF_3$;

Ar is an optionally substituted mono or bicyclic aryl, or optionally substituted mono or bicyclic heteroaryl ring system;

$R^1$ is L-G; wherein L is optionally substituted C1-C4 alkylene,

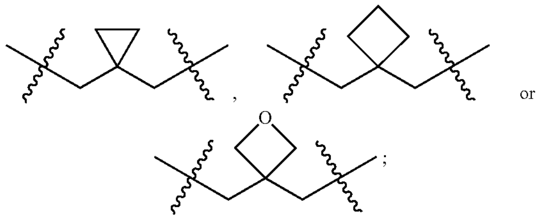

and G is an optionally substituted 5- to 10-membered heterocyclyl;

—N($R^2$)$R^3$ form an optionally substituted heterocyclyl substituent selected from the group consisting of:

(a) optionally substituted azabicyclo[3.1.0]hexane;
(b) optionally substituted azabicyclo[4.1.0]heptane;
(c) optionally substituted oxazabicyclo[4.1.0]heptane;
(d) optionally substituted azabicyclo[5.1.0]octane;
(e) optionally substituted oxazabicyclo[5.1.0]octane;
(f) optionally substituted azabicyclo[6.1.0]nonane;
(g) optionally substituted oxazabicyclo[6.1.0]nonane;
(h) optionally substituted azabicyclo[5.1.0]oct-5-en-2-yl;
(i) optionally substituted azabicyclo[5.1.0]oct-4-en-2-yl;
(j) optionally substituted azabicyclo[6.1.0]non-6-en-2-yl;
(k) optionally substituted azabicyclo[6.1.0]non-5-en-2-yl;
(l) optionally substituted azabicyclo[6.1.0]non-4-en-2-yl;
(m) optionally substituted 3-oxa-2,6-diazabicyclo[5.1.0]oct-1-en-6-yl;
(n) optionally substituted 2-oxa-3,6-diazabicyclo[5.1.0]oct-3-en-6-yl;
(o) optionally substituted 4-oxa-2,5-diazabicyclo[5.1.0]oct-5-en-2-yl;
(q) optionally substituted 2-oxa-3,7-diazabicyclo[6.1.0]non-3-en-7-yl;
(r) optionally substituted 5-oxa-2,6-diazabicyclo[6.1.0]non-6-en-2-yl;
(s) optionally substituted 6-oxa-2,5-diazabicyclo[6.1.0]non-4-en-2-yl; and
(t) optionally substituted 4-oxa-2,5-diazabicyclo[6.1.0]non-5-en-2-yl; and $R^4$ is selected from H, optionally substituted C1-C4 alkoxy, optionally substituted C1-C6 alkyl, optionally substituted $C_1$-C6 cycloalkyl, C1-C6 cycloalkylalkyl, cyano, or halogen.

One embodiment provides a compound having the structure of Formula (Ib), or a pharmaceutically acceptable salt or solvate, thereof:

(Ib)

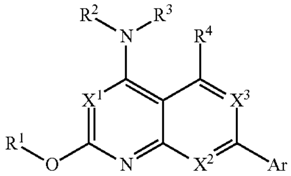

wherein:

$X^1$ is N or C—CN;

$X^2$ is N, C—H, C—F, C—$CH_3$, or C—Cl;

$X^3$ is N, C—H, C—F, C—Cl or C—$CF_3$;

Ar is an optionally substituted mono or bicyclic aryl, or optionally substituted mono or bicyclic heteroaryl ring system;

R' is L-G, wherein L is optionally substituted C1-C4 alkylene,

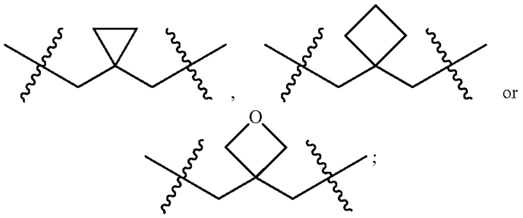

and G is an optionally substituted 5- to 10-membered heterocyclyl;

—N($R^2$)$R^3$ form an optionally substituted heterocyclyl substituent selected from the group consisting of:

(a) optionally substituted azabicyclo[3.1.0]hexane;
(b) optionally substituted azabicyclo[4.1.0]heptane;
(c) optionally substituted oxazabicyclo[4.1.0]heptane;
(d) optionally substituted azabicyclo[5.1.0]octane;
(c) optionally substituted oxazabicyclo[5.1.0]octane;
(f) optionally substituted azabicyclo[6.1.0]nonane;
(g) optionally substituted oxazabicyclo[6.1.0]nonane;
(h) optionally substituted azabicyclo[5.1.0]oct-5-en-2-yl;
(i) optionally substituted azabicyclo[5.1.0]oct-4-en-2-yl;
(j) optionally substituted azabicyclo[6.1.0]non-6-en-2-yl;
(k) optionally substituted azabicyclo[6.1.0]non-S-en-2-yl;
(l) optionally substituted azabicyclo[6.1.0]non-4-en-2-yl;
(m) optionally substituted 3-oxa-2,6-diazabicyclo[5.1.0]oct-1-en-6-yl;
(n) optionally substituted 2-oxa-3,6-diazabicyclo[5.1.0]oct-3-en-6-yl;
(o) optionally substituted 4-oxa-2,5-diazabicyclo[5.1.0]oct-5-en-2-yl;
(p) optionally substituted 3-oxa-2,7-diazabicyclo[6.1.0]non-1-en-7-yl;
(q) optionally substituted 2-oxa-3,7-diazabicyclo[6.1.0]non-3-en-7-yl;
(r) optionally substituted 5-oxa-2,6-diazabicyclo[6.1.0]non-6-en-2-yl;
(s) optionally substituted 6-oxa-2,5-diazabicyclo[6.1.0]non-4-en-2-yl; and (t) optionally substituted 4-oxa-2,5-diazabicyclo[6.1.0]non-5-en-2-yl; and $R^1$ is selected from H, optionally substituted C1-C4 alkoxy, optionally substituted C1-C6 alkyl, optionally substituted C1-C6 cycloalkyl, C1-C6 cycloalkylalkyl, cyano, or halogen.

One embodiment provides a compound having the structure of Formula (Ic), or a pharmaceutically acceptable salt or solvate, thereof:

(Ic)

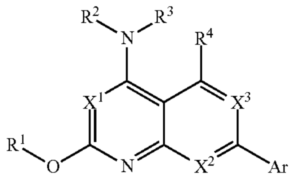

wherein:

$X^1$ is N or C—CN;

$X^2$ is N, C—H, C—F, or C—Cl;

$X^3$ is N, C—H, C—F, C—Cl or C—$CF_3$;

Ar is an optionally substituted mono or bicyclic aryl, or optionally substituted mono or bicyclic heteroaryl ring system;

$R^1$ is L-G; wherein L is optionally substituted C1-C4 alkylene,

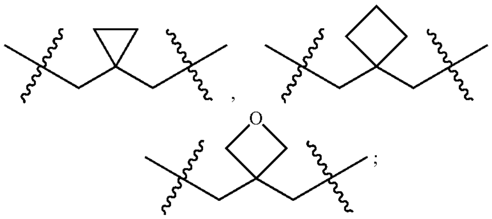

, or ;

and G is an optionally substituted 5- to 10-membered heterocyclyl;

—$N(R^2)R^3$ form an optionally substituted heterocyclyl substituent selected from the group consisting of:

(a) optionally substituted azabicyclo[3.1.0]hexane;

(b) optionally substituted azabicyclo[4.1.0]heptane;

(c) optionally substituted oxazabicyclo[4.1.0]heptane;

(d) optionally substituted azabicyclo[5.1.0]octane;

(e) optionally substituted oxazabicyclo[5.1.0]octane;

(f) optionally substituted azabicyclo[6.1.0]nonane;

(g) optionally substituted oxazabicyclo[6.1.0]nonane;

(h) optionally substituted azabicyclo[5.1.0]oct-5-en-2-yl;

(i) optionally substituted azabicyclo[5.1.0]oct-4-en-2-yl;

(j) optionally substituted azabicyclo[6.1.0]non-6-en-2-yl;

(k) optionally substituted azabicyclo[6.1.0]non-5-en-2-yl;

(l) optionally substituted azabicyclo[6.1.0]non-4-en-2-yl;

(m) optionally substituted 3-oxa-2,6-diazabicyclo[5.1.0]oct-1-en-6-yl;

(n) optionally substituted 2-oxa-3,6-diazabicyclo[5.1.0]oct-3-en-6-yl;

(o) optionally substituted 4-oxa-2,5-diazabicyclo[5.1.0]oct-5-en-2-yl;

(p) optionally substituted 3-oxa-2,7-diazabicyclo[6.1.0]non-1-en-7-yl;

(q) optionally substituted 2-oxa-3,7-diazabicyclo[6.1.0]non-3-en-7-yl;

(r) optionally substituted 5-oxa-2,6-diazabicyclo[6.1.0]non-6-en-2-yl;

(s) optionally substituted 6-oxa-2,5-diazabicyclo[6.1.0]non-4-en-2-yl; and (t) optionally substituted 4-oxa-2,5-diazabicyclo[6.1.0]non-5-en-2-yl; and $R^4$ is selected from H or optionally substituted C1-C4 alkoxy.

One embodiment provides a compound having the structure of Formula (Id), or a pharmaceutically acceptable salt or solvate thereof:

(Id)

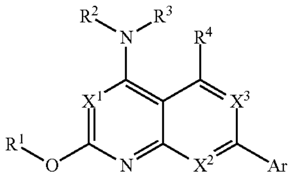

wherein:

$X^1$ is N or C—CN;

$X^2$ is N, C—H, C—F, or C—Cl;

$X^3$ is N, C—H, C—F, or C—Cl;

Ar is an optionally substituted mono or bicyclic aryl, or optionally substituted mono or bicyclic heteroaryl ring system;

$R^1$ is L-G; wherein L is optionally substituted C1-C4 alkylene,

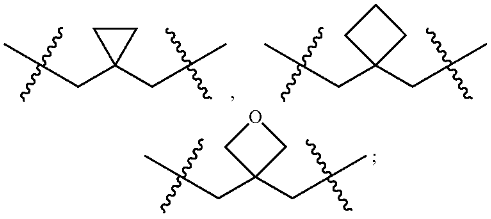

, or ;

and G is an optionally substituted 5- to 10-membered heterocyclyl;

—$N(R^2)R^3$ form an optionally substituted heterocyclyl selected from:

(a) optionally substituted azabicyclo[4.1.0]heptane;

(b) optionally substituted oxazabicyclo[4.1.0]heptane;

(c) optionally substituted azabicyclo[5.1.0]octane;

(d) optionally substituted oxazabicyclo[5.1.0]octane;

(c) optionally substituted azabicyclo[6.1.0]nonane;

(f) optionally substituted oxazabicyclo[6.1.0]nonane; or (g) optionally substituted azabicyclo[5.1.0]oct-5-en-2-yl; and $R^4$ is selected from H or optionally substituted $C_1$-C4 alkoxy.

One embodiment provides a pharmaceutical composition comprising a compound of Formula (I), or pharmaceutically acceptable salt or solvate thereof, and at least one pharmaceutically acceptable excipient. One embodiment provides a pharmaceutical composition comprising a compound of Formula (Ia), or pharmaceutically acceptable salt or solvate thereof, and at least one pharmaceutically acceptable excipient. One embodiment provides a pharmaceutical composition comprising a compound of Formula (Ib), or pharmaceutically acceptable salt or solvate thereof, and at least one pharmaceutically acceptable excipient. One embodiment provides a pharmaceutical composition comprising a compound of Formula (Ic), or pharmaceutically acceptable salt or solvate thereof, and at least one pharmaceutically acceptable excipient. One embodiment provides a pharmaceutical composition comprising a compound of Formula (Id), or pharmaceutically acceptable salt or solvate thereof, and at least one pharmaceutically acceptable excipient.

One embodiment provides a method of treating cancer in a patient in need thereof comprising administering to the patient a compound of Formula (I), or pharmaceutically acceptable salt or solvate thereof. One embodiment provides a method of treating cancer in a patient in need thereof comprising administering to the patient a compound of Formula (Ia), or pharmaceutically acceptable salt or solvate thereof. One embodiment provides a method of treating cancer in a patient in need thereof comprising administering to the patient a compound of Formula (Ib), or pharmaceutically acceptable salt or solvate thereof. One embodiment provides a method of treating cancer in a patient in need thereof comprising administering to the patient a compound of Formula (Ic), or pharmaceutically acceptable salt or solvate thereof. One embodiment provides a method of treating cancer in a patient in need thereof comprising administering to the patient a compound of Formula (Id), or pharmaceutically acceptable salt or solvate thereof.

One embodiment provides a method of inhibiting KRAS protein activity comprising contacting the KRAS protein with a compound of Formula (I), wherein the KRAS protein is contacted in an in vitro setting. One embodiment provides a method of inhibiting KRAS protein activity comprising contacting the KRAS protein with a compound of Formula (Ia), wherein the KRAS protein is contacted in an in vitro setting. One embodiment provides a method of inhibiting KRAS protein activity comprising contacting the KRAS protein with a compound of Formula (Ib), wherein the KRAS protein is contacted in an in vitro setting. One embodiment provides a method of inhibiting KRAS protein activity comprising contacting the KRAS protein with a compound of Formula (Ic), wherein the KRAS protein is contacted in an in vitro setting. One embodiment provides a method of inhibiting KRAS protein activity comprising contacting the KRAS protein with a compound of Formula (Id), wherein the KRAS protein is contacted in an in vitro setting.

One embodiment provides a method of inhibiting KRAS protein activity comprising contacting the KRAS protein with a compound of Formula (I), wherein the KRAS protein is contacted in an in vivo setting. One embodiment provides a method of inhibiting KRAS protein activity comprising contacting the KRAS protein with a compound of Formula (Ia), wherein the KRAS protein is contacted in an in vivo setting. One embodiment provides a method of inhibiting KRAS protein activity comprising contacting the KRAS protein with a compound of Formula (Ib), wherein the KRAS protein is contacted in an in vivo setting. One embodiment provides a method of inhibiting KRAS protein activity comprising contacting the KRAS protein with a compound of Formula (Ic), wherein the KRAS protein is contacted in an in vivo setting. One embodiment provides a method of inhibiting KRAS protein activity comprising contacting the KRAS protein with a compound of Formula (Id), wherein the KRAS protein is contacted in an in vivo setting.

INCORPORATION BY REFERENCE

All publications, patents, and patent applications mentioned in this specification are herein incorporated by reference for the specific purposes identified herein.

BRIEF DESCRIPTION OF THE DRAWINGS

The features of the invention are set forth with particularity in the appended claims. A better understanding of the features of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
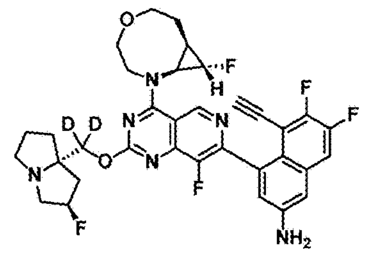
FIG. 1 provides additional structures of compounds of Formula (I)
Figure 1:
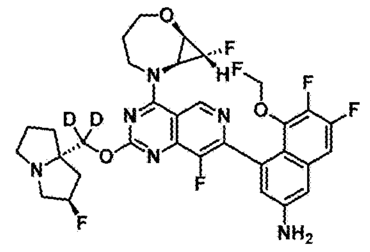
Figure 1:
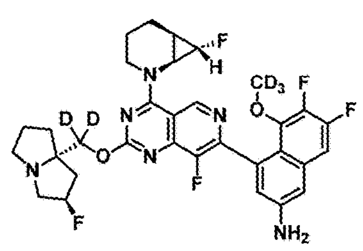
Figure 1:
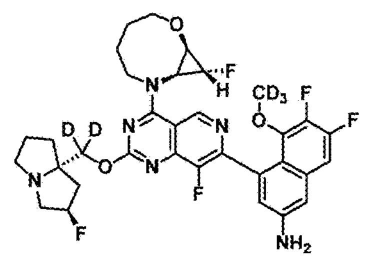
Figure 1:
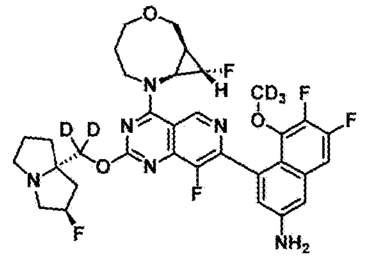
Figure 1:
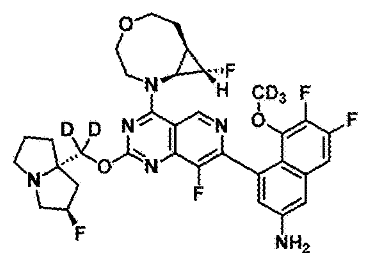
Figure 1:
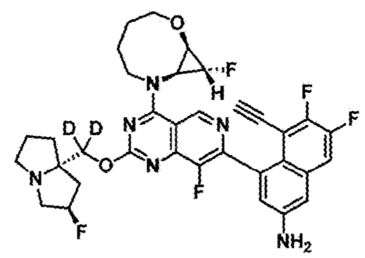
Figure 1:
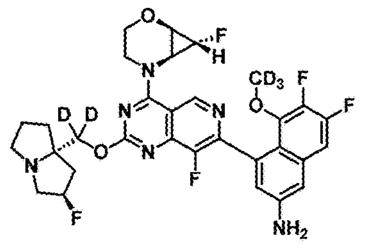
Figure 1:
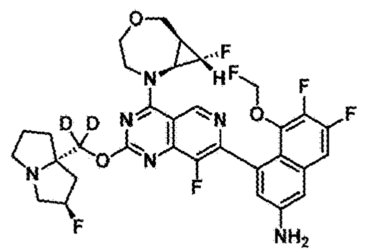

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.

"Cyano" refers to the —CN radical.

"Nitro" refers to the —$NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_8$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5C_8$alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR_3$, —$C(O)N(R^a)_2$, —$N(R^a)C(O)OR^a$, —OC(O)—$N(R^a)_2$, —$N(R^3)C(O)R^a$, —$N(R^a)S(O)_tR^a$ (where t is 1 or 2), —$S(O)OR^a$ (where tis 1 or 2), —$S(O)_tR^a$ (where t is 1 or 2) and —$S(O)N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, oxo or trifluoromethyl), heteroaryl (optionally substituted with halogen, hydroxy, methoxy, oxo or trifluoromethyl), or heteroarylalkyl (optionally substituted with halogen, hydroxy, methoxy, or trifluoromethyl). In certain embodiments, an optionally substituted alkyl is a haloalkyl. In other embodiments, an optionally substituted alkyl is a fluoroalkyl. In other embodiments, an optionally substituted alkyl is a —$CF_3$ group.

"Alkoxy" refers to a radical bonded through an oxygen atom of the formula-O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^3)_2$, —$N(R^a)C(O)OR^a$, —OC(O)—$N(R^a)_2$, —$N(R^a)C(O)R^a$, —$N(R^a)S(O)R^a$ (where t is 1 or 2), —$S(O)_tOR^a$ (where tis 1 or 2), —$S(O)R^a$ (where t is 1 or 2) and —$S(O)IN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)$N(R^a)_2$, —$N(R^a)$C(O)O$R^a$, —OC(O)—$N(R^a)_2$, —$N(R^a)$C(O)$R^a$, —$N(R^a)S(O)_tR^a$ (where t is 1 or 2), —S(O)O$R^a$ (where t is 1 or 2), —S(O)$R^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_8$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)$N(R^a)_2$, —$N(R^a)$C(O)O$R^a$, —OC(O)—$N(R^a)_2$, —$N(R^a)$C(O)$R^a$, —$N(R^a)S(O)_tR^a$ (where t is 1 or 2), —S(O)O$R^a$ (where t is 1 or 2), —S(O)$R^a$ (where t is 1 or 2) and —S(O)$N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_5$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5C_8$alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)$N(R^a)_2$, —$N(R^a)$C(O)O$R^a$, —OC(O)—$N(R^a)_2$, —$N(R^a)$C(O)$R^a$, —$N(R^a)S(O)_tR^a$ (where t is 1 or 2), —S(O)O$R^a$ (where t is 1 or 2), —$S(O)_tR^a$ (where t is 1 or 2) and —S(O)$N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5C_8$alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^3)$C(O)$OR^a$, —OC(O)—$N(R^a)_2$, —$N(R^a)$C(O)$R^a$, —$N(R^a)S(O)_tR^a$ (where t is 1 or 2), —S(O)$OR^a$ (where t is 1 or 2), —S(O): $R^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from optionally substituted alkyl, optionally substituted alkenyl, optionally substituted alkynyl, halo, cyano, nitro, —$R^b$—$OR^a$, —$R^b$—OC(O)—$R^a$, —$R^b$—OC(O)—$OR^a$, —$R^b$—OC(O)—$N(R^a)_2$, —$R^b$—$N(R)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$R^a$ (where t is 1 or 2), —$R^b$—S(O)$R^a$ (where t is 1 or 2), —$R^b$—S(O)$OR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each RD is independently a direct bond or a straight or branched alkylene or alkenylene chain, and Re is a straight or branched alkylene or alkenylene chain, and where each of the $R^a$, $R^b$, or Re substituents is unsubstituted unless otherwise indicated.

"Aralkyl" refers to a radical of the formula-Re-aryl where Re is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula-Rd-aryl where Re is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula-Re-aryl, where Re is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^o$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from optionally substituted alkyl, optionally substituted alkenyl, optionally substituted alkynyl, halo, oxo, thioxo, cyano, nitro, —$R^b$—$OR^a$, —$R^b$—OC(O)—$R^a$, —$R^b$—OC(O)—$OR^a$, —$R^b$—OC(O)—$N(R^a)_2$, —$R^b$—N $(R^a)_2$, —$R^b$—C(O)$R^a$, —$R^b$—C(O)O$R^a$, —$R^b$—C(O)N$(R^a)_2$, —$R^b$—O—$R^c$—C(O)N$(R^a)_2$, —$R^b$—N($R^3$)C(O)O$R^a$, —$R^b$—N($R^a$)C(O)$R^a$, —$R^b$—N($R^a$)S$(O)_t$$R^a$ (where t is 1 or 2), —$R^b$—S$(O)_t$$R^a$ (where t is 1 or 2), —$R^b$—S$(O)_t$O$R^a$ (where t is 1 or 2) and —$R^b$—S(O)N$(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each RD is independently a direct bond or a straight or branched alkylene or alkenylene chain, and Re is a straight or branched alkylene or alkenylene chain, and where each of the $R^a$, $R^b$, or Re substituents is unsubstituted unless otherwise indicated.

"Carbocyclylalkyl" refers to a radical of the formula-Re-carbocyclyl where Re is an alkylene chain as defined above. The alkylene chain and the carbocyclyl radical is optionally substituted as defined above.

"Carbocyclylalkynyl" refers to a radical of the formula-R°-carbocyclyl where Re is an alkynylene chain as defined above. The alkynylene chain and the carbocyclyl radical is optionally substituted as defined above.

"Carbocyclylalkoxy" refers to a radical bonded through an oxygen atom of the formula —O—$R^e$-carbocyclyl where Re is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic, or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, tritbianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from optionally substituted alkyl, optionally substituted alkenyl, optionally substituted alkynyl, halo, fluoroalkyl, oxo, thioxo, cyano, nitro, —$R^b$—O$R^a$, —$R^b$—OC(O)—$R^a$, —$R^b$—OC(O)—O$R^a$, —$R^b$—OC(O)—N$(R^a)_2$, —$R^b$—N$(R^a)_2$, —$R^b$—C(O)$R^a$, —$R^b$—C(O)O$R^a$, —$R^b$—C(O)N$(R^a)_2$, —$R^b$—O—$R^c$—C(O)N$(R^a)_2$, —$R^b$—N($R^a$)C(O)O$R^a$, —$R^b$—N($R^a$)C(O)$R^a$, —$R^b$—N($R^a$)S$(O)_t$$R^a$ (where t is 1 or 2), —$R^b$—S(O): $R^a$ (where t is 1 or 2), —$R^b$—S(O)O$R^a$ (where t is 1 or 2) and —$R^b$—S$(O)_t$N$(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula-Re-heterocyclyl where Re is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where Re is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen, and sulfur. As used herein, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta [d]pyrimidinyl, 6,7-dihydro-5H-cyclopenta [4,5]thieno[2,3-d]pyrimidinyl, 5,6-dihydrobenzo [h]quinazolinyl, 5,6-dihydrobenzo[h]cinnolinyl, 6,7-dihydro-5H-benzo[6,7]cyclohepta [1,2-c]pyridazinyl, dibenzofuranyl, dibenzothiophenyl, furanyl, furanonyl, furo [3,2-c]pyridinyl, 5,6,7,8,9,10-hexahydrocycloocta [d]pyrimidinyl, 5,6,7,8,9,10-hexahydrocycloocta [d]pyridazinyl, 5,6,7,8,9,10-hexahydrocycloocta [d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a, 7,8,9,10,10a-octahydrobenzo[h]quinazolinyl, 1-phenyl-1//-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d] pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno [2,3-d]pyrimidinyl, 6,7,8,9-tetrahydro-5H-cyclohepta [4,5] thieno[2,3-d]pyrimidinyl, 5,6,7,8-tetrahydropyrido[4,5-c] pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from optionally substituted alkyl, optionally substituted cycloalkylalkyl, optionally substituted heterocyclylalkyl, optionally substituted alkenyl, optionally substituted alkynyl, halo, optionally substituted fluoroalkyl, optionally substituted haloalkenyl, optionally substituted haloalkynyl, oxo, thioxo, cyano, nitro, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—N($R^a$)C(O)$OR^a$, —$R^b$—N($R^a$)C(O)$R^a$, —$R^b$—N($R^a$)$S(O)_tR^a$ (where t is 1 or 2), —$R^b$—S(O)$R^a$ (where t is 1 or 2), —$R^b$—S(O)$OR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R' is independently a direct bond or a straight or branched alkylene or alkenylene chain, and Re is a straight or branched alkylene or alkenylene chain, and where each of the $R^a$, $R^b$, or Re substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula-Re-heteroaryl, where Re is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^e$-heteroaryl, where Re is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

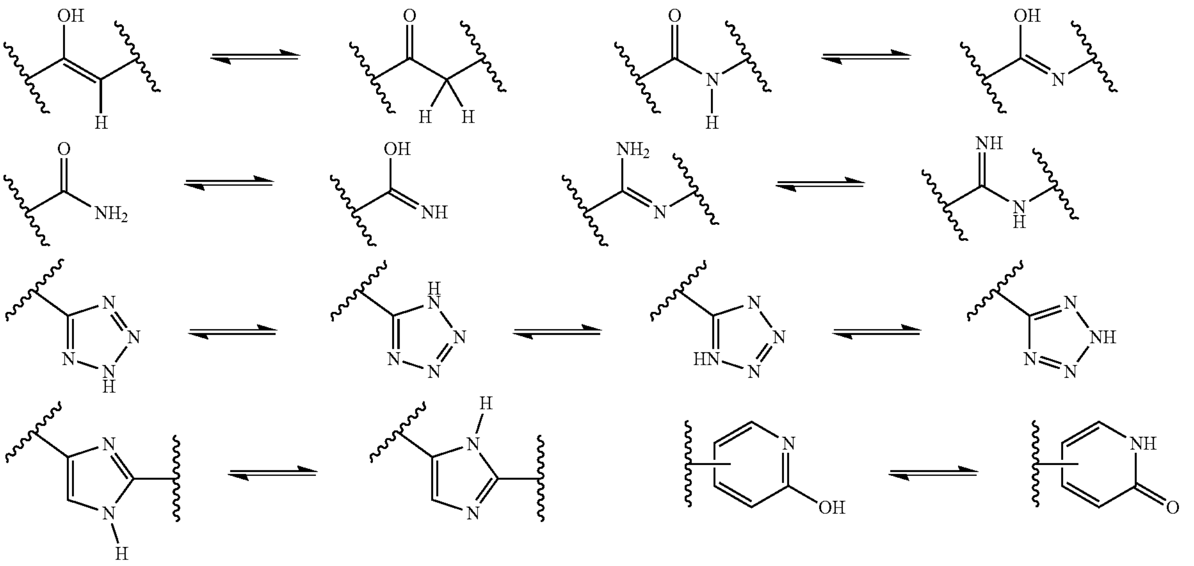

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in, for example, U.S. Pat. Nos. 5,846,514 and 6,334,997. As described in U.S. Pat. Nos. 5,846,514 and 6,334,997, deuteration can, in some instances, improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}H$), tritium ($^{3}H$), iodine-125 ($^{125}I$) or carbon-14 ($^{14}C$.). Isotopic substitution with $^{2}H$, $^{1}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{33}S$, $^{36}S$, $^{35}Cl$, $^{37}Cl$, $^{79}Br$, $^{81}Br$, $^{125}I$ are all contemplated. In some embodiments, isotopic substitution with $^{18}F$ is contemplated. All isotopic variations of the compounds of the present invention, whether radioactive or not, are encompassed within the scope of the present invention.

In certain embodiments, the compounds disclosed herein have some or all of the H atoms replaced with $^{2}H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6 (10)] 2000, 110 pp; George W.; Varma, Rajender S. The Synthesis of Radiolabeled Compounds via Organometallic Intermediates, Tetrahedron, 1989, 45 (21), 6601-21; and Evans, E. Anthony. Synthesis of radiolabeled compounds, J. Radioanal. Chem., 1981, 64 (1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

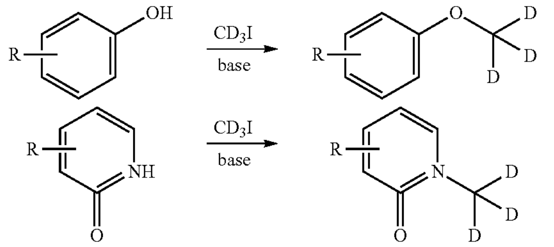

Deuterium-transfer reagents, such as lithium aluminum deuteride ($LiAlD_4$), are employed to transfer deuterium under reducing conditions to the reaction substrate. The use of $LiAlD_4$ is illustrated, by way of example only, in the reaction schemes below.

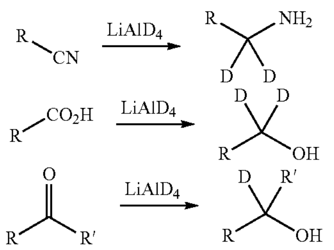

Deuterium gas and palladium catalyst are employed to reduce unsaturated carbon-carbon linkages and to perform a reductive substitution of aryl carbon-halogen bonds as illustrated, by way of example only, in the reaction schemes below.

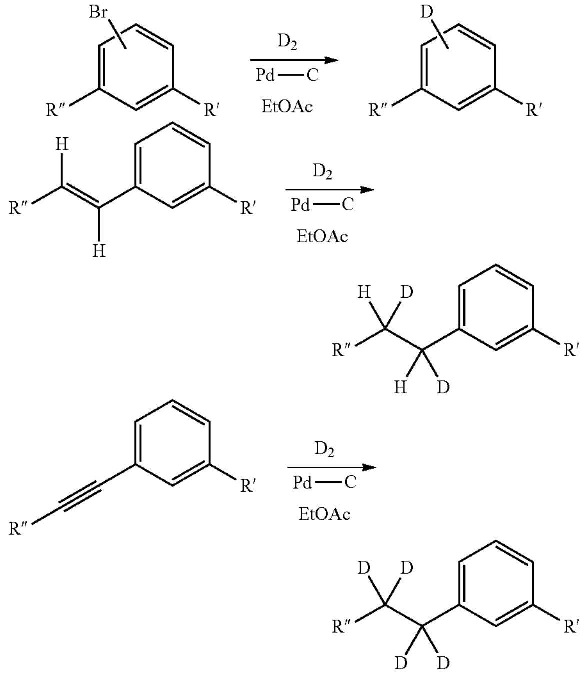

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^{1}H$ hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the KRAS inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S.M. et al., "Pharmaceutical Salts," Journal of Pharmaceutical Science, 66: 1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein exist in either unsolvated or solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

KRAS Protein and Function

RAS mutation is frequent in cancer, with approximately 19% of patients with cancer harboring RAS mutations (I.A. Prior et al., Cancer Res 2020; 80: 2969-74). Ras proteins are important for activating signaling networks for controlling cell differentiation, proliferation, and survival, encoded by three genes HRAS, KRAS, and NRAS. The three genes share significant sequence homology and largely overlapping functions. Activation of RAS is facilitated by guanine nucleotide exchange factors (GEF), and activation causes conformational changes.

The KRAS gene encodes two highly related protein isoforms, KRAS-4A and KRAS-4B, which comprise of 189 and 188 amino acids. KRAS generally refers to KRAS-4B, because of the high level of mRNA encoding KRAS-4B in cells. KRAS has two major domains, the catalytic G domain and a hypervariable region (HVR).

KRAS G domain is the basis of biological function of GTPase proteins. The G domain comprises 6 beta-strands of the protein core, surrounded by five alpha-helices, and comprises residues 1-166. The G domain also consists of other regions: switch I, switch II, and the P loop. KRAS-GTP binding alters the conformation of the switches I and II in the G domain. When activated, KRAS binds to its downstream molecules as monomers or dimers to mediate series of signaling cascades. KRAS also has a flexible C-terminal, the hypervariable region (HVR), which is important for localizing KRAS to the membrane.

The RAS family comprises three isoforms, but about 85% of RAS-related cancers are caused by mutations in the KRAS isoform. The mutations in KRAS isoform occurs most frequently in solid tumors such as colorectal carcinoma, lung adenocarcinoma, and pancreatic ductal carcinoma. Further, nearly 80% of KRAS mutant tumors are located within codon 12, with the most common mutations being p.G12D, p.G12V, and p.G12C.

KRAS protein functions as a molecular switch in growth factor signaling pathways by regulating proliferation by alternating between a GDP-bound inactive form and a GTP-bound active form. The GTP-bound active form is capable of engaging downstream effector proteins to trigger a pro-proliferative response. This regulation cycle is impaired by mutations in codon 12 which disrupts association of GTPase activating proteins, which impairs the inactivation of KRAS, which leads to accumulation of the pro-proliferative form. Many growth factors such as but not limited to epidermal growth factor (EGF), platelet-derived growth factor (PDGF), and fibroblast growth factors (FGF) can activate KRAS proteins through intermediary molecules after activating receptor tyrosine kinases. Upstream regulation can promote binding of GTP and KRAS, converting KRAS from an inactive to an active state. Molecules upstream of KRAS mainly mediate the activation or inactivation of KRAS by regulating guanine nucleotide exchange factors (GEFs) and GTPase-activating proteins (GAPs) (L. Huang et al., Signal Transduction and Targeted Therapy, 2021, 6, 386). Another molecule in KRAS activation is Src homology phosphatase 2 (SHP2) which plays a role in KRAS activation. SHP2 is a common signaling regulatory that mediates receptor tyrosine kinases signals to KRAS-ERK signaling, and dephosphorylation substrates of SHP2 have been shown to promote KRAS activation.

The RAF-MEK-ERK pathway is a downstream target of KRAS signaling. Another pathway KRAS is involved in is the PI3K-AKT-mTOR pathway (L. Huang et al., Signal Transduction and Targeted Therapy, 2021, 6, 386).

KRAS was previously considered to be an undruggable protein, but recently there have been advances in targeting codon 12, and specifically in G12C inhibitors. Many efforts have been focused on indirectly targeting KRAS, so there remains an unmet need of targeting KRAS, which the compounds provided herein fulfill. With the discovery of a new allosteric site of KRAS, G12C, several covalently binding inhibitors of KRAS have emerged and are under clinical investigation. However, KRAS inhibition is a complex issue with a lack of understanding of the underlying principles, and there still remains an unmet need for new inhibitors which target other KRAS mutations such as, but not limited to G12D and G12V.

KRAS mutations are frequently found in colorectal cancer, pancreatic cancer, and non-small cell lung cancer (M.H. Hofmann et al., Cancer Discov 2022; 12: 924-37). The KRAS allelic distribution varies between the tumor types, with G12C mutations in 13.6% of lung adenocarcinomas, whereas the G12D and G12V mutations are most common in colorectal and pancreatic cancer. The G12D, G12V, and G12C mutations are the three most frequent allele mutations. KRAS mutations, especially at codon 12, is strongly associated with cellular KRAS dependency, indicating that KRAS acts as an oncogenic driver.

Prior Art Small Molecules Inhibitors

There have been advances for KRAS G12C inhibitors, such as sotorasib (AMG510) and adagrasib (MRTX849). Sotorasib is the first to be approved by the US Food and Drug Administration (FDA). Both inhibitors rely on the interaction with the nucleophilic cysteine 12 in the GDP state and occupy the switch II pocket.

NMR studies have shown that MRTX849 can engage mutant KRAS proteins lacking the nucleophilic mutant cysteine 12, but that the engagement is selected for inactive GDP-loaded state of KRAS protein. AMG510 exhibits weak binding and relies on irreversible reaction of the mutant cysteine 12 for KRAS (G12C) inhibitory activity (J.D. Vasta et al., Nature Chemical Biology, 2022, 18, 596-604).

AMG510 and additional KRAS inhibitors are described in Discovery of a Covalent Inhibitor of KRASG12C(AMG 510) for the Treatment of Solid Tumors (B.A Lanman et al., J. Med. Chem. 2020, 63, 52-65).

Novel Compounds Inhibiting KRAS

In one aspect, provided herein are KRAS inhibitory compounds.

One embodiment provides a compound having the structure of Formula (I), or a pharmaceutically acceptable salt or solvate, thereof:

(I)

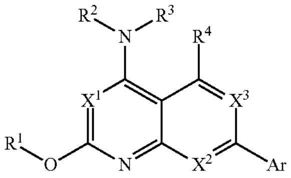

wherein:

$X^1$ is N or C—CN;

$X^2$ is N, C—H, C—F, C—$CH_3$, C—Cl, C-(optionally substituted C1-C6 alkyl), C-(optionally substituted C2-C6 alkenyl), or C-(optionally substituted C3-C6 carbocyclyl);

$X^3$ is N, C—H, C—F, C—Cl, C—CN, or C—$CF_3$;

Ar is an optionally substituted mono or bicyclic aryl, or optionally substituted mono or bicyclic heteroaryl ring system;

$R^1$ is L-G; wherein L is optionally substituted C1-C4 alkylene,

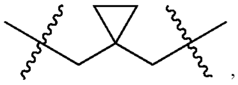
,
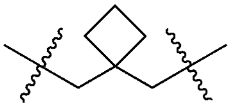
or
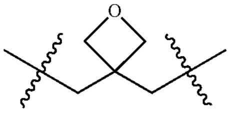
;

and G is an optionally substituted 5- to 10-membered heterocyclyl;

—$N(R^2)R^3$ form an optionally substituted heterocyclyl substituent selected from the group consisting of:

(a) optionally substituted azabicyclo[3.1.0]hexane;
(b) optionally substituted azabicyclo[4.1.0]heptane;
(c) optionally substituted oxazabicyclo[4.1.0]heptane,
(d) optionally substituted azabicyclo[5.1.0]octane;
(e) optionally substituted oxazabicyclo[5.1.0]octane;
(f) optionally substituted azabicyclo[6.1.0]nonane;
(g) optionally substituted oxazabicyclo[6.1.0]nonane;
(h) optionally substituted azabicyclo[5.1.0]oct-5-en-2-yl;
(i) optionally substituted azabicyclo[5.1.0]oct-4-en-2-yl;
(j) optionally substituted azabicyclo[6.1.0]non-6-en-2-yl;
(k) optionally substituted azabicyclo[6.1.0]non-5-en-2-yl;
(l) optionally substituted azabicyclo[6.1.0]non-4-en-2-yl;
(m) optionally substituted 3-oxa-2,6-diazabicyclo[5.1.0]oct-1-en-6-yl;
(n) optionally substituted 2-oxa-3,6-diazabicyclo[5.1.0]oct-3-en-6-yl;
(o) optionally substituted 4-oxa-2,5-diazabicyclo[5.1.0]oct-5-en-2-yl;
(q) optionally substituted 2-oxa-3,7-diazabicyclo[6.1.0]non-3-en-7-yl;
(r) optionally substituted 5-oxa-2,6-diazabicyclo[6.1.0]non-6-en-2-yl;
(s) optionally substituted 6-oxa-2,5-diazabicyclo[6.1.0]non-4-en-2-yl; and
(t) optionally substituted 4-oxa-2,5-diazabicyclo[6.1.0]non-5-en-2-yl; and $R^4$ is selected from H, —OH, —CN, halogen, optionally substituted C1-C4 alkoxy, optionally substituted C1-C6 alkyl, optionally substituted C1-C6 cycloalkyl, or C1-C6 cycloalkylalkyl.

One embodiment provides a compound having the structure of Formula (Ia), or a pharmaceutically acceptable salt or solvate, thereof:

(Ia)

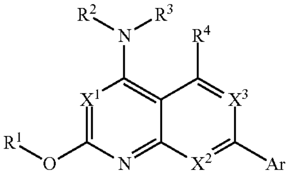

wherein:

$X^1$ is N or C—CN;

$X^2$ is N, C—H, C—F, C—$CH_3$, or C—Cl;

$X^3$ is N, C—H, C—F, C—Cl, C—CN, or C—$CF_3$;

Ar is an optionally substituted mono or bicyclic aryl, or optionally substituted mono or bicyclic heteroaryl ring system;

$R^1$ is L-G; wherein L is optionally substituted $C_1$-$C_4$ alkylene,

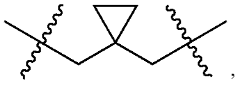
,
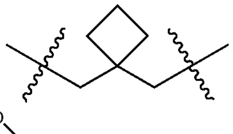
or
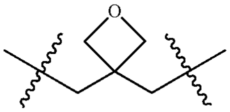
;

and G is an optionally substituted 5- to 10-membered heterocyclyl;

—$N(R^2)R^3$ form an optionally substituted heterocyclyl substituent selected from the group consisting of:

(a) optionally substituted azabicyclo[3.1.0]hexane;
(b) optionally substituted azabicyclo[4.1.0]heptane;
(c) optionally substituted oxazabicyclo[4.1.0]heptane;
(d) optionally substituted azabicyclo[5.1.0]octane;
(e) optionally substituted oxazabicyclo[5.1.0]octane;
(f) optionally substituted azabicyclo[6.1.0]nonane;
(g) optionally substituted oxazabicyclo[6.1.0]nonane;

(h) optionally substituted azabicyclo[5.1.0]oct-5-en-2-yl;

(i) optionally substituted azabicyclo[5.1.0]oct-4-en-2-yl;

(j) optionally substituted azabicyclo[6.1.0]non-6-en-2-yl;

(k) optionally substituted azabicyclo[6.1.0]non-5-en-2-yl;

(l) optionally substituted azabicyclo[6.1.0]non-4-en-2-yl;

(m) optionally substituted 3-oxa-2,6-diazabicyclo [5.1.0]oct-1-en-6-yl;

(n) optionally substituted 2-oxa-3,6-diazabicyclo [5.1.0]oct-3-en-6-yl;

(o) optionally substituted 4-oxa-2,5-diazabicyclo [5.1.0]oct-5-en-2-yl;

(p) optionally substituted 3-oxa-2,7-diazabicyclo [6.1.0]non-1-en-7-yl;

(q) optionally substituted 2-oxa-3,7-diazabicyclo [6.1.0]non-3-en-7-yl;

(r) optionally substituted 5-oxa-2,6-diazabicyclo[6.1.0] non-6-en-2-yl;

(s) optionally substituted 6-oxa-2,5-diazabicyclo[6.1.0] non-4-en-2-yl; and (t) optionally substituted 4-oxa-2,5-diazabicyclo[6.1.0] non-5-en-2-yl; and $R^4$ is selected from H, optionally substituted $C_1$-$C_4$ alkoxy, optionally substituted $C_1$-$C_6$ alkyl, optionally substituted $C_1$-$C_6$ cycloalkyl, $C_1$-$C_6$ cycloalkylalkyl, cyano, or halogen.

One embodiment provides a compound having the structure of Formula (Ib), or a pharmaceutically acceptable salt or solvate, thereof:

(Ib)

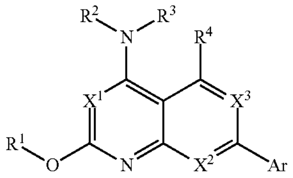

wherein:

$X^1$ is N or C—CN;

$X^2$ is N, C—H, C—F, C—$CH_3$, or C—Cl;

$X^3$ is N, C—H, C—F, C—Cl or C—$CF_3$;

Ar is an optionally substituted mono or bicyclic aryl, or optionally substituted mono or bicyclic heteroaryl ring system;

$R^1$ is L-G; wherein L is optionally substituted $C_1$-$C_4$ alkylene,

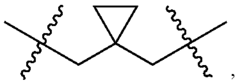
,
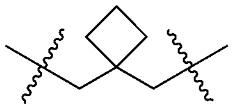
or
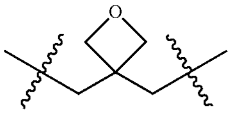
;

and G is an optionally substituted 5- to 10-membered heterocyclyl;

—$N(R^2)R^3$ form an optionally substituted heterocyclyl substituent selected from the group consisting of:

(a) optionally substituted azabicyclo[3.1.0]hexane;

(b) optionally substituted azabicyclo[4.1.0]heptane;

(c) optionally substituted oxazabicyclo[4.1.0]heptane;

(d) optionally substituted azabicyclo [5.1.0]octane;

(e) optionally substituted oxazabicyclo[5.1.0]octane;

(f) optionally substituted azabicyclo[6.1.0]nonane;

(g) optionally substituted oxazabicyclo[6.1.0]nonane;

(h) optionally substituted azabicyclo[5.1.0]oct-5-en-2-yl;

(i) optionally substituted azabicyclo[5.1.0]oct-4-en-2-yl;

(i) optionally substituted azabicyclo[6.1.0]non-6-en-2-yl;

(k) optionally substituted azabicyclo[6.1.0]non-5-en-2-yl;

(l) optionally substituted azabicyclo[6.1.0]non-4-en-2-yl;

(m) optionally substituted 3-oxa-2,6-diazabicyclo [5.1.0]oct-1-en-6-yl;

(n) optionally substituted 2-oxa-3,6-diazabicyclo [5.1.0]oct-3-en-6-yl;

(o) optionally substituted 4-oxa-2,5-diazabicyclo [5.1.0]oct-5-en-2-yl;

(p) optionally substituted 3-oxa-2,7-diazabicyclo [6.1.0]non-1-en-7-yl;

(q) optionally substituted 2-oxa-3,7-diazabicyclo [6.1.0]non-3-en-7-yl;

(r) optionally substituted 5-oxa-2,6-diazabicyclo[6.1.0] non-6-en-2-yl;

(s) optionally substituted 6-oxa-2,5-diazabicyclo[6.1.0] non-4-en-2-yl; and (t) optionally substituted 4-oxa-2,5-diazabicyclo[6.1.0] non-5-en-2-yl; and $R^4$ is selected from H, optionally substituted C1-C4 alkoxy, optionally substituted C1-C6 alkyl, optionally substituted C1-C6 cycloalkyl, C1-C6 cycloalkylalkyl, cyano, or halogen.

One embodiment provides a compound having the structure of Formula (Ic), or a pharmaceutically acceptable salt or solvate, thereof:

(Ic)

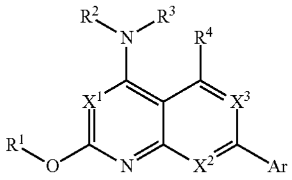

wherein:

$X^1$ is N or C—CN;

$X^2$ is N, C—H, C—F, or C—Cl;

$X^3$ is N, C—H, C—F, C—Cl or C—$CF_3$;

Ar is an optionally substituted mono or bicyclic aryl, or optionally substituted mono or bicyclic heteroaryl ring system;

$R^1$ is L-G; wherein L is optionally substituted C1-C4 alkylene,

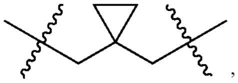
,
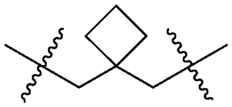
or

-continued

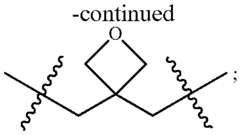

;

and G is an optionally substituted 5- to 10-membered heterocyclyl;

—$N(R^2)R^3$ form an optionally substituted heterocyclyl substituent selected from the group consisting of:

(a) optionally substituted azabicyclo[3.1.0]hexane;

(b) optionally substituted azabicyclo[4.1.0]heptane;

(c) optionally substituted oxazabicyclo[4.1.0]heptane;

(d) optionally substituted azabicyclo[5.1.0]octane;

(e) optionally substituted oxazabicyclo[5.1.0]octane;

(f) optionally substituted azabicyclo[6.1.0]nonane;

(g) optionally substituted oxazabicyclo[6.1.0]nonane;

(h) optionally substituted azabicyclo[5.1.0]oct-5-en-2-yl;

(i) optionally substituted azabicyclo[5.1.0]oct-4-en-2-yl;

(j) optionally substituted azabicyclo[6.1.0]non-6-en-2-yl;

(k) optionally substituted azabicyclo[6.1.0]non-5-en-2-yl;

(l) optionally substituted azabicyclo[6.1.0]non-4-en-2-yl;

(m) optionally substituted 3-oxa-2,6-diazabicyclo[5.1.0]oct-1-en-6-yl;

(n) optionally substituted 2-oxa-3,6-diazabicyclo[5.1.0]oct-3-en-6-yl;

(o) optionally substituted 4-oxa-2,5-diazabicyclo[5.1.0]oct-5-en-2-yl;

(p) optionally substituted 3-oxa-2,7-diazabicyclo[6.1.0]non-1-en-7-yl;

(q) optionally substituted 2-oxa-3,7-diazabicyclo[6.1.0]non-3-en-7-yl;

(r) optionally substituted 5-oxa-2,6-diazabicyclo[6.1.0]non-6-en-2-yl;

(s) optionally substituted 6-oxa-2,5-diazabicyclo[6.1.0]non-4-en-2-yl; and (t) optionally substituted 4-oxa-2,5-diazabicyclo[6.1.0]non-5-en-2-yl; and $R^4$ is selected from H or optionally substituted C1-C4 alkoxy.

One embodiment provides a compound having the structure of Formula (Id), or a pharmaceutically acceptable salt or solvate thereof:

(Id)

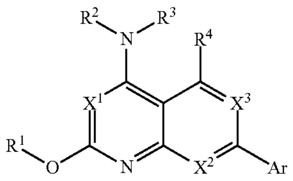

wherein:

$X^1$ is N or C—CN;

$X^2$ is N, C—H, C—F, or C—Cl;

$X^3$ is N, C—H, C—F, or C—Cl;

Ar is an optionally substituted mono or bicyclic aryl, or optionally substituted mono or bicyclic heteroaryl ring system;

$R^1$ is L-G; wherein L is optionally substituted C1-C4 alkylene,

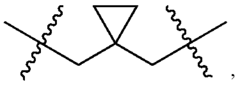

,

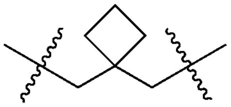

or

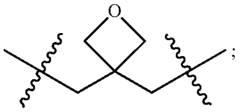

;

and G is an optionally substituted 5- to 10-membered heterocyclyl;

—$N(R^2)R^3$ form an optionally substituted heterocyclyl selected from:

(a) optionally substituted azabicyclo[4.1.0]heptane;

(b) optionally substituted oxazabicyclo[4.1.0]heptane;

(c) optionally substituted azabicyclo[5.1.0]octane;

(d) optionally substituted oxazabicyclo[5.1.0]octane;

(e) optionally substituted azabicyclo[6.1.0]nonane;

(f) optionally substituted oxazabicyclo[6.1.0]nonane; or (g) optionally substituted azabicyclo[5.1.0]oct-5-en-2-yl; and $R^4$ is selected from H or optionally substituted C1-C4 alkoxy.

Another embodiment provides the compound of Formula (I), (Ia), (Ib), (Ic), or (Id), or a pharmaceutically acceptable salt or solvate thereof, wherein $X^1$ is N.

Another embodiment provides the compound of Formula (I), (Ia), (Ib), (Ic), or (Id), or a pharmaceutically acceptable salt or solvate thereof, wherein $X^1$ is C—CN.

Another embodiment provides the compound of Formula (I), (Ia), (Ib), (Ic), or (Id), or a pharmaceutically acceptable salt or solvate thereof, wherein $X^2$ is N.

Another embodiment provides the compound of Formula (I), (Ia), (Ib), (Ic), or (Id), or a pharmaceutically acceptable salt or solvate thereof, wherein $X^2$ is C—$CH_3$.

Another embodiment provides the compound of Formula (I), (Ia), (Ib), (Ic), or (Id), or a pharmaceutically acceptable salt or solvate thereof, wherein $X^2$ is C-(optionally substituted C1-C6 alkyl).

Another embodiment provides the compound of Formula (I), (Ia), (Ib), (Ic), or (Id), or a pharmaceutically acceptable salt or solvate thereof, wherein $X^2$ is C-(optionally substituted C2-C6 alkenyl).

Another embodiment provides the compound of Formula (I), (Ia), (Ib), (Ic), or (Id), or a pharmaceutically acceptable salt or solvate thereof, wherein $X^2$ is C-(optionally substituted C3-C6 carbocyclyl).

Another embodiment provides the compound of Formula (I), (Ia), (Ib), (Ic), or (Id), or a pharmaceutically acceptable salt or solvate thereof, $X^2$ is C—H, C—F, or C—Cl.

Another embodiment provides the compound of Formula (I), (Ia), (Ib), (Ic), or (Id), or a pharmaceutically acceptable salt or solvate thereof, $X^3$ is N.

Another embodiment provides the compound of Formula (I), (Ia), (Ib), (Ic), or (Id), or a pharmaceutically acceptable salt or solvate thereof, $X^3$ is C—F.

Another embodiment provides the compound of Formula (I), (Ia), (Ib), (Ic), or (Id), or a pharmaceutically acceptable salt or solvate thereof, $X^3$ is C—$CF_3$.

Another embodiment provides the compound of Formula (I), (Ia), (Ib), (Ic), or (Id), or a pharmaceutically acceptable salt or solvate thereof, wherein Ar is a monocyclic optionally substituted aryl.

Another embodiment provides the compound of Formula (I), (Ia), (Ib), (Ic), or (Id), or a pharmaceutically acceptable salt or solvate thereof, wherein the monocyclic optionally substituted aryl is an optionally substituted phenyl.

Another embodiment provides the compound of Formula (I), (Ia), (Ib), (Ic), or (Id), or a pharmaceutically acceptable salt or solvate thereof, wherein the optionally substituted phenyl is substituted with an —OH group at the meta-position.

Another embodiment provides the compound of Formula (I), (Ia), (Ib), (Ic), or (Id), or a pharmaceutically acceptable salt or solvate thereof, wherein the optionally substituted phenyl is

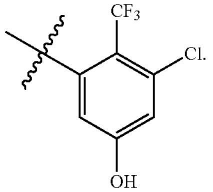 [SMILES: *c1cc(O)cc(Cl)c1C(F)(F)F]

Another embodiment provides the compound of Formula (I), (Ia), (Ib), (Ic), or (Id), or a pharmaceutically acceptable salt or solvate thereof, wherein the optionally substituted phenyl is selected from:

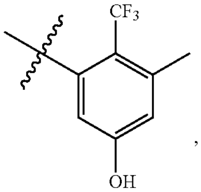
,
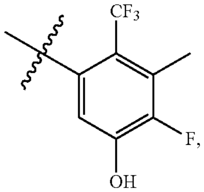
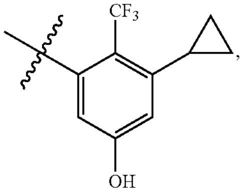
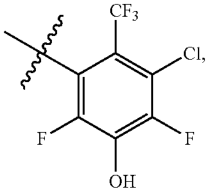
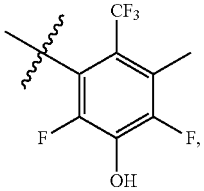
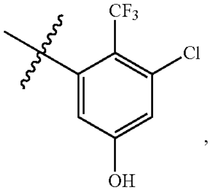
,
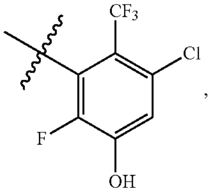
, and
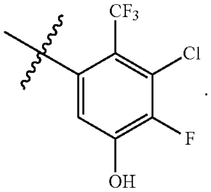
.

Another embodiment provides the compound of Formula (I), (Ia), (Ib), (Ic), or (Id), or a pharmaceutically acceptable salt or solvate thereof, wherein the optionally substituted phenyl is substituted with an —$NH_2$ group at the meta-position.

Another embodiment provides the compound of Formula (I), (Ia), (Ib), (Ic), or (Id), or a pharmaceutically acceptable salt or solvate thereof, wherein the optionally substituted phenyl is selected from:

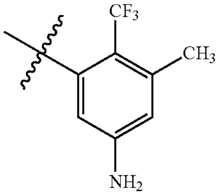
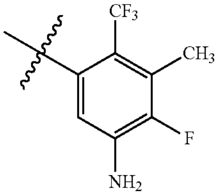
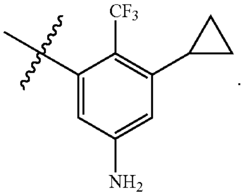
.

Another embodiment provides the compound of Formula (I), (Ia), (Ib), (Ic), or (Id), or a pharmaceutically acceptable salt or solvate thereof, wherein the optionally substituted phenyl is selected from:

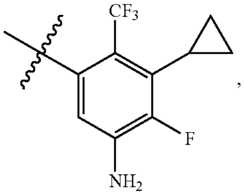
,
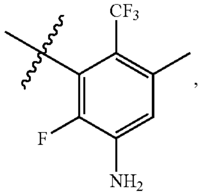
,
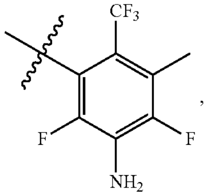
,
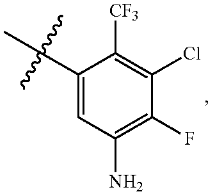
,
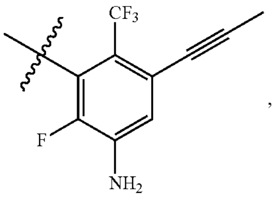
,
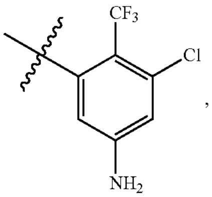
,
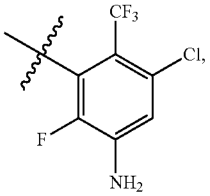
and
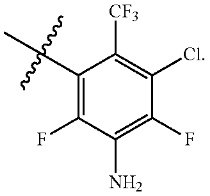

Another embodiment provides the compound of Formula (I), (Ia), (Ib), (Ic), or (Id), or a pharmaceutically acceptable salt or solvate thereof, wherein the optionally substituted phenyl is a 2,3,5-trisubstituted phenyl.

Another embodiment provides the compound of Formula (I), (Ia), (Ib), (Ic), or (Id), or a pharmaceutically acceptable salt or solvate thereof, wherein the 2,3,5-trisubstituted phenyl is substituted with a 3-hydroxy group.

Another embodiment provides the compound of Formula (I), (Ia), (Ib), (Ic), or (Id), or a pharmaceutically acceptable salt or solvate thereof, wherein Ar is a bicyclic optionally substituted aryl.

Another embodiment provides the compound of Formula (I), (Ia), (Ib), (Ic), or (Id), or a pharmaceutically acceptable salt or solvate thereof, wherein the bicyclic optionally substituted aryl is an optionally substituted naphthyl.

Another embodiment provides the compound of Formula (I), (Ia), (Ib), (Ic), or (Id), or a pharmaceutically acceptable salt or solvate thereof, wherein the optionally substituted naphthyl is an optionally substituted 1-naphthyl.

Another embodiment provides the compound of Formula (I), (Ia), (Ib), (Ic), or (Id), or a pharmaceutically acceptable salt or solvate thereof, wherein the optionally substituted 1-naphthyl is further substituted at the 8-position.

Another embodiment provides the compound of Formula (I), (Ia), (Ib), (Ic), or (Id), or a pharmaceutically acceptable salt or solvate thereof, wherein Ar is selected from:

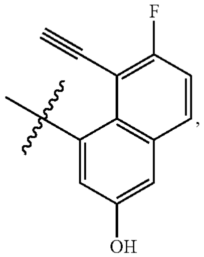
,
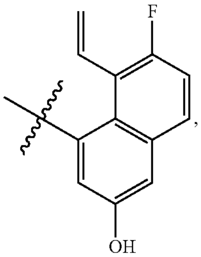
,
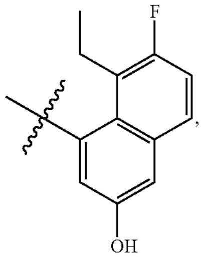
,
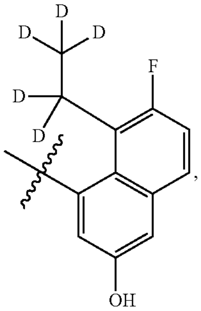
,
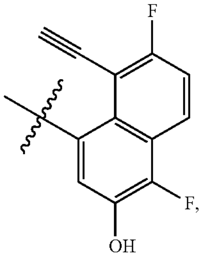
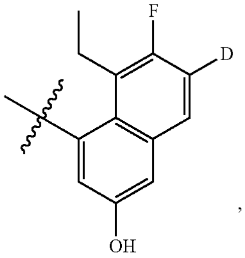
,
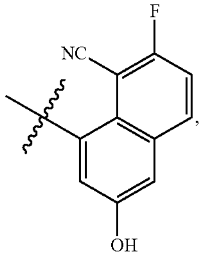
,
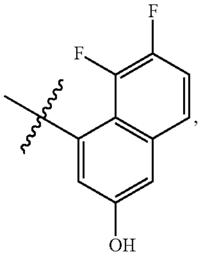
, -continued

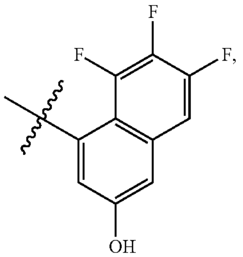
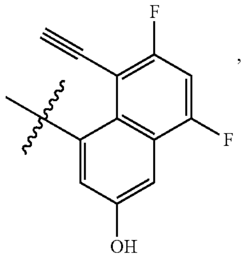
,
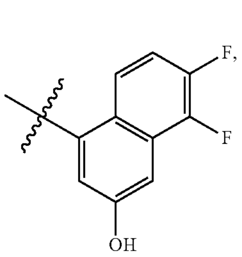
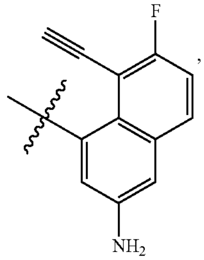
,
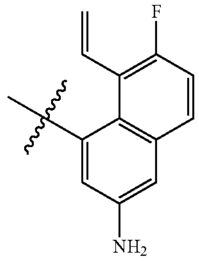
and
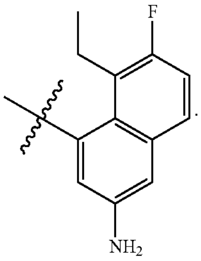
.

Another embodiment provides the compound of Formula (I), (Ia), (Ib), (Ic), or (Id), or a pharmaceutically acceptable salt or solvate thereof, wherein Ar is selected from:

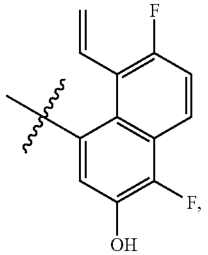
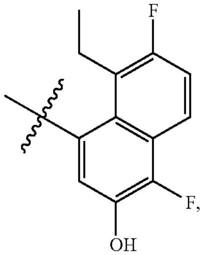
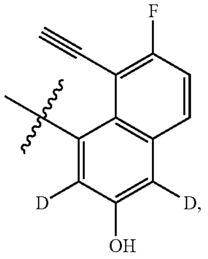
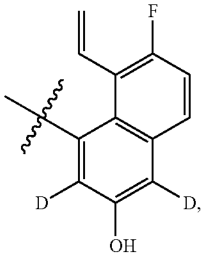

-continued
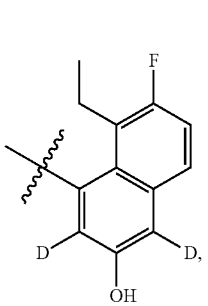
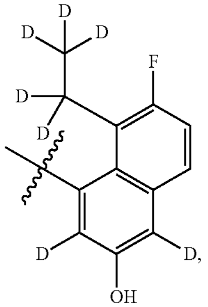
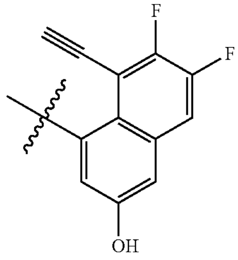
,
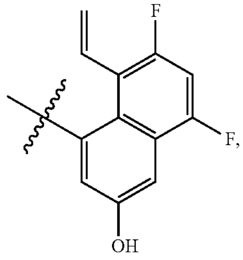
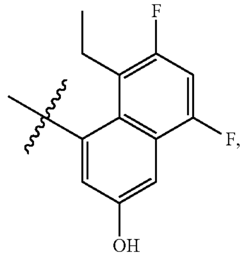
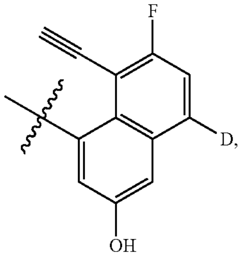
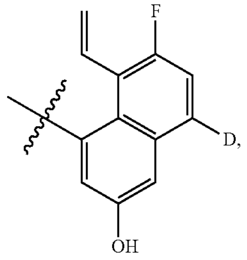
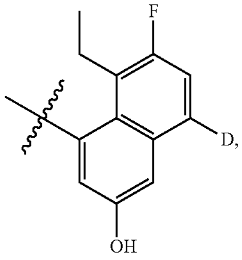
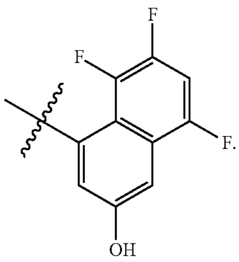
Another embodiment provides the compound of Formula (I), (Ia), (Ib), (Ic), or (Id), or a pharmaceutically acceptable salt or solvate thereof, wherein Ar is selected from:
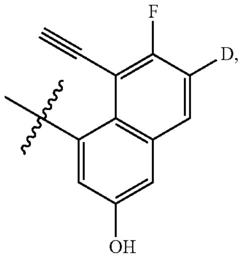
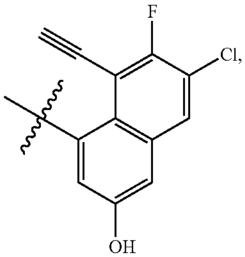
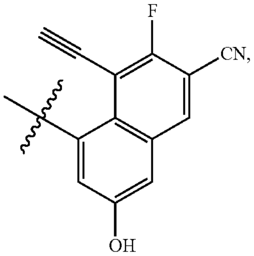
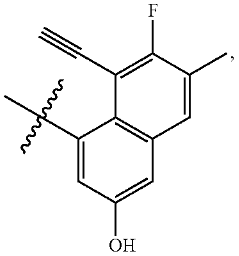
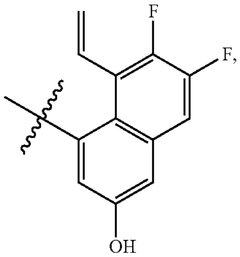
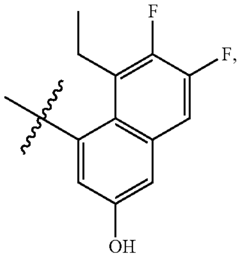
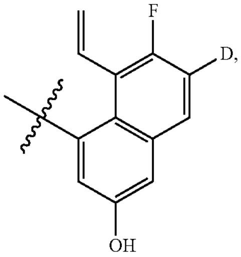
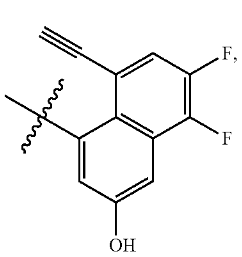
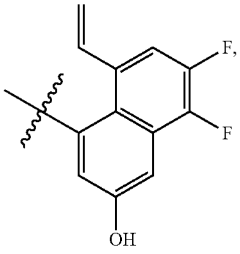
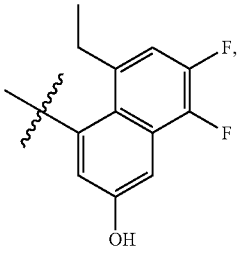
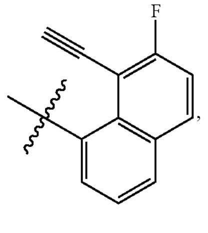
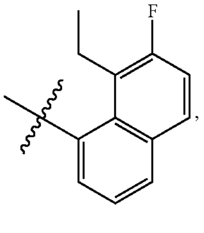

-continued

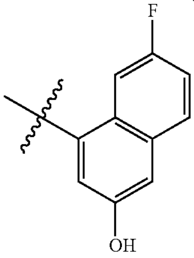
,
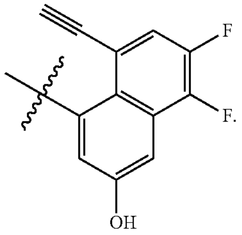

Another embodiment provides the compound of Formula (I), (Ia), (Ib), (Ic), or (Id), or a pharmaceutically acceptable salt or solvate thereof, wherein Ar is selected from:

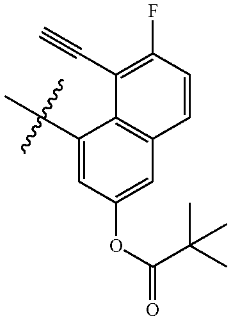
,
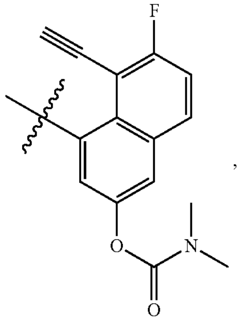
,
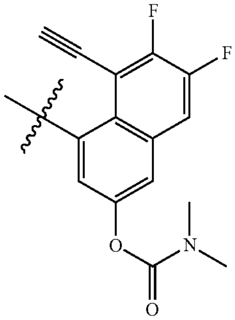
,
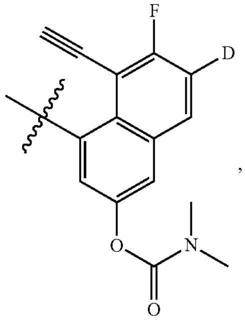
,
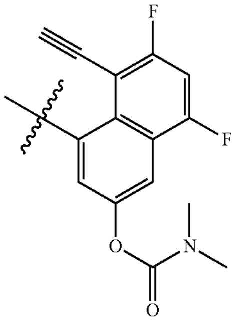
,
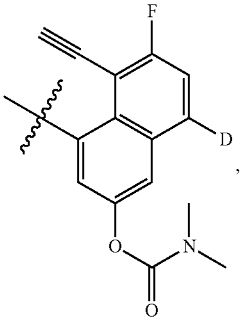
, and
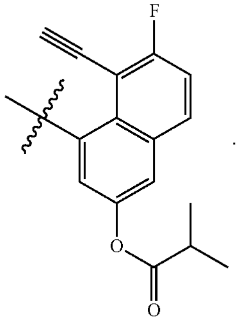
.

Another embodiment provides the compound of Formula (I), (Ia), (Ib), (Ic), or (Id), or a pharmaceutically acceptable salt or solvate thereof, wherein Ar is selected from:

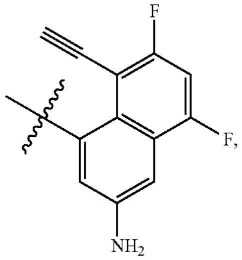
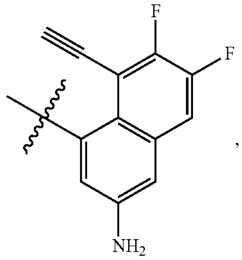
,
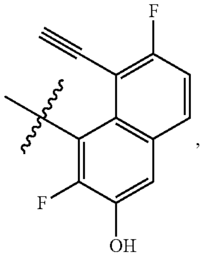
,
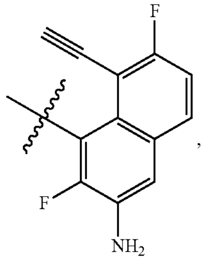
,
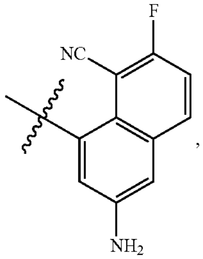
,
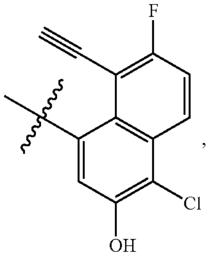
,
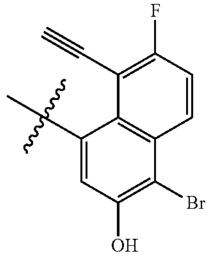
and
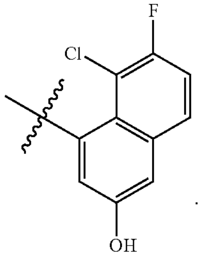
.

Another embodiment provides the compound of Formula (I), (Ia), (Ib), (Ic), or (Id), or a pharmaceutically acceptable salt or solvate thereof, wherein Ar is selected from:

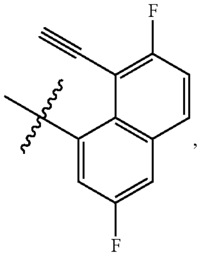
,
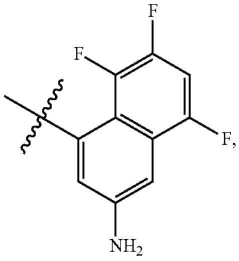

-continued
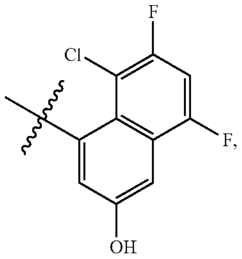
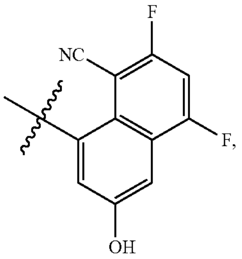
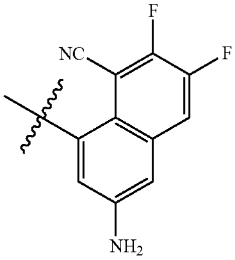
,
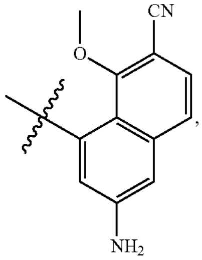
,
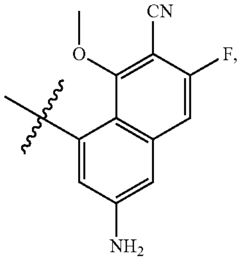
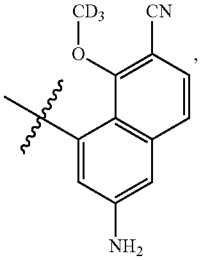
,
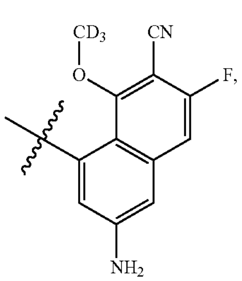
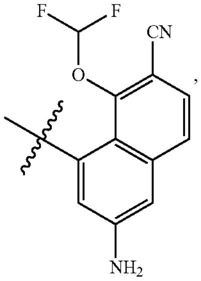
,
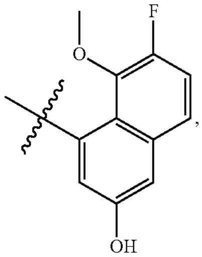
,
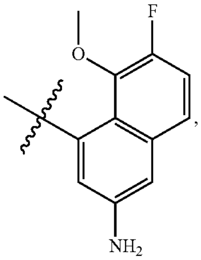
,
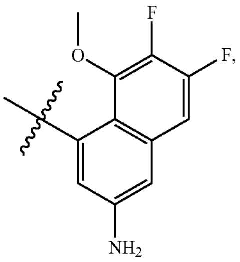
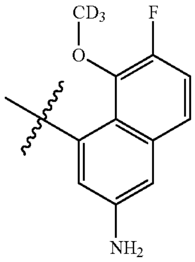
and
-continued
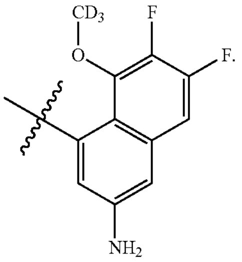
Another embodiment provides the compound of Formula (I), (Ia), (Ib), (Ic), or (Id), or a pharmaceutically acceptable salt or solvate thereof, wherein Ar is selected from:
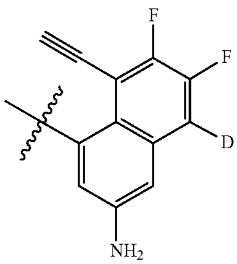
,
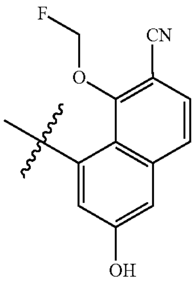
,
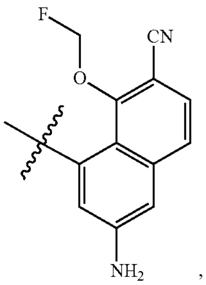
,
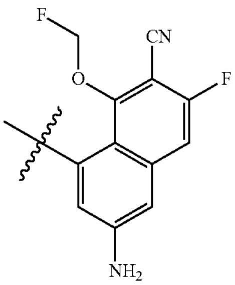
,
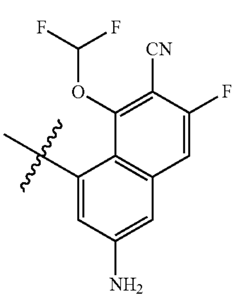
,
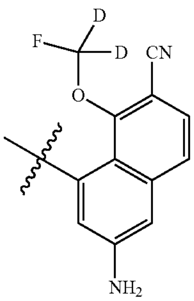
,
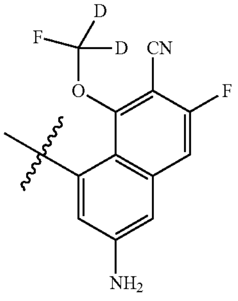
and -continued

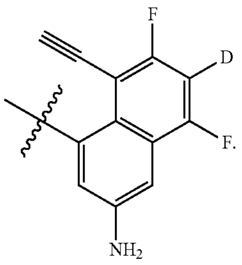

Another embodiment provides the compound of Formula (I), (Ia), (Ib), (Ic), or (Id), or a pharmaceutically acceptable salt or solvate thereof, wherein Ar is selected from:

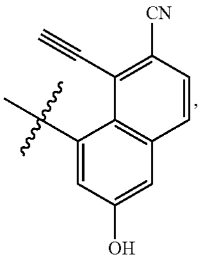
,
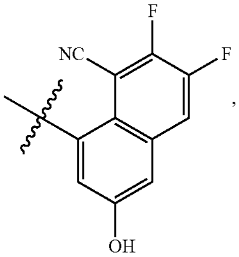
,
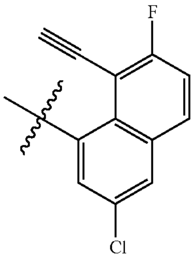
,
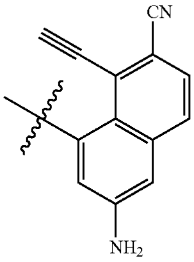
and
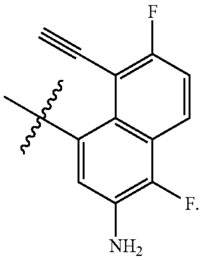

Another embodiment provides the compound of Formula (I), (Ia), (Ib), (Ic), or (Id), or a pharmaceutically acceptable salt or solvate thereof, wherein Ar is selected from:

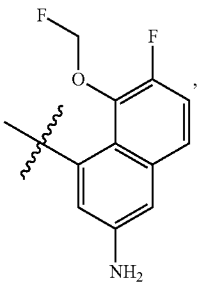
,
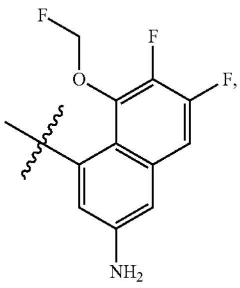

-continued

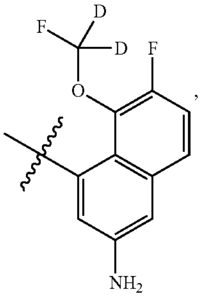
,
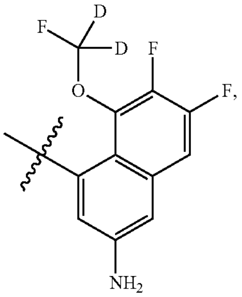
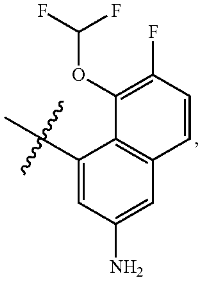
,
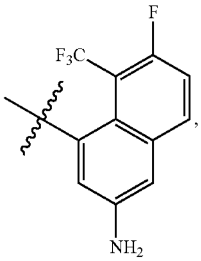
,
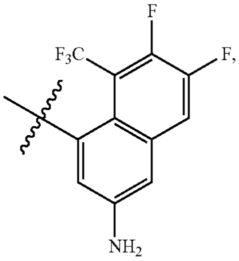
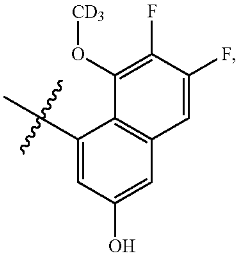
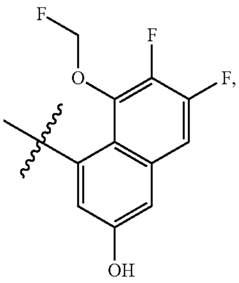
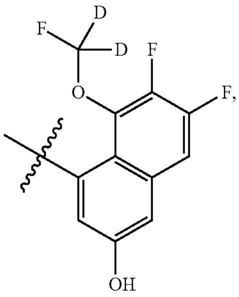
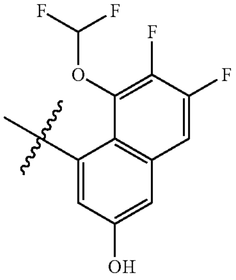
and
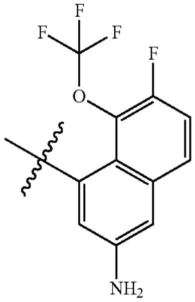
.

Another embodiment provides the compound of Formula (I), (Ia), (Ib), (Ic), or (Id), or a pharmaceutically acceptable salt or solvate thereof, wherein Ar is selected from:

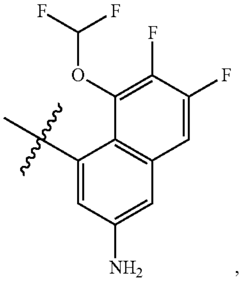 , 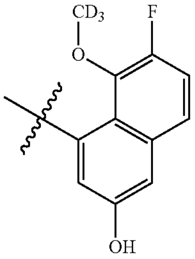 ,

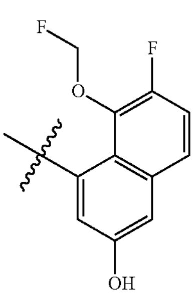 , 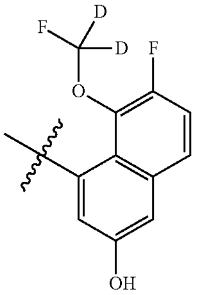 ,

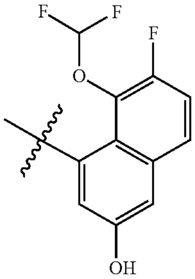 , 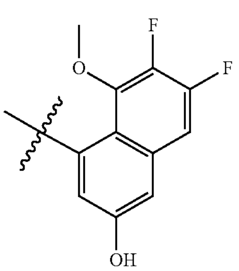 ,

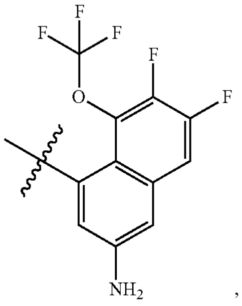 , 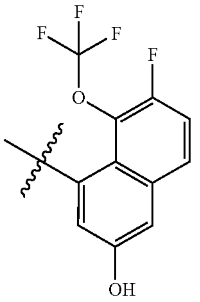 and

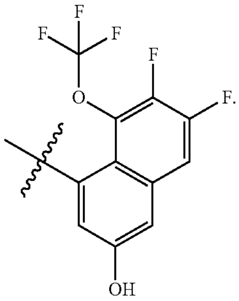

Another embodiment provides the compound of Formula (I), (Ia), (Ib), (Ic), or (Id), or a pharmaceutically acceptable salt or solvate thereof, wherein Ar is selected from:

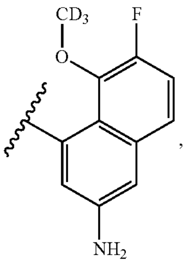 , 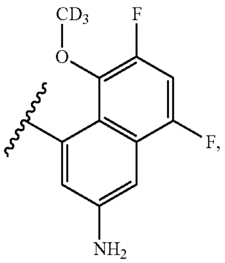

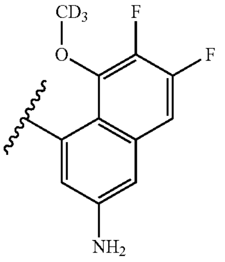 and 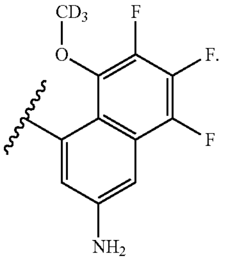

Another embodiment provides the compound of Formula (I), (Ia), (Ib), (Ic), or (Id), or a pharmaceutically acceptable salt or solvate thereof, wherein Ar is selected from:

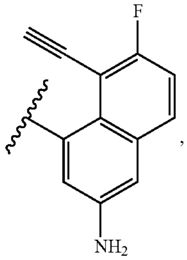 , 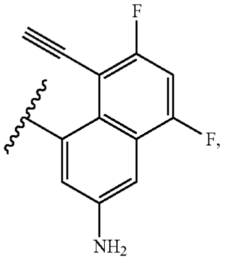

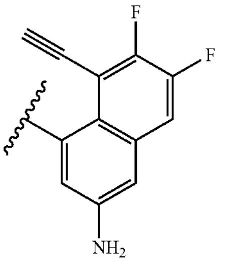 and 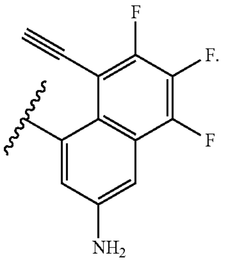

Another embodiment provides the compound of Formula (I), (Ia), (Ib), (Ic), or (Id), or a pharmaceutically acceptable salt or solvate thereof, wherein Ar is selected from:

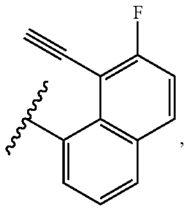 , 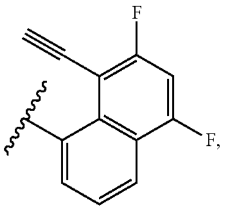

-continued
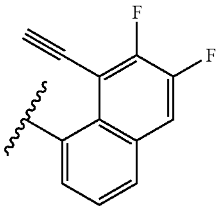
and
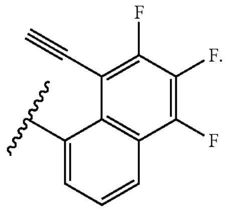
-continued
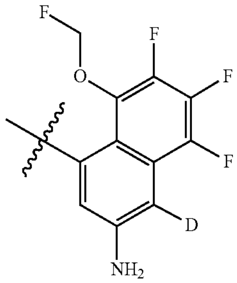
and
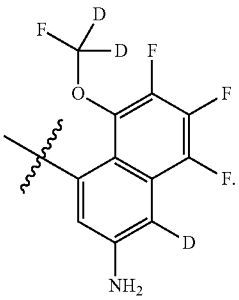
Another embodiment provides the compound of Formula (I), (Ia), (Ib), (Ic), or (Id), or a pharmaceutically acceptable salt or solvate thereof, wherein Ar is selected from:
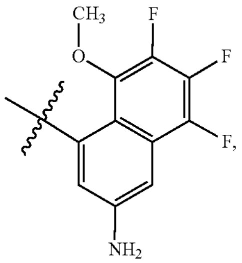
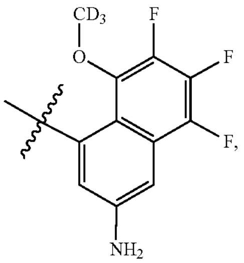
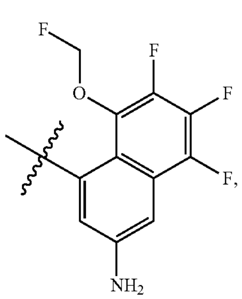
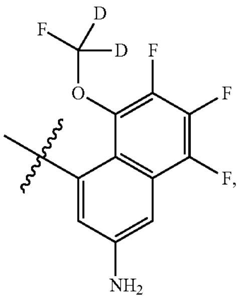
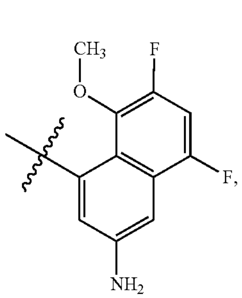
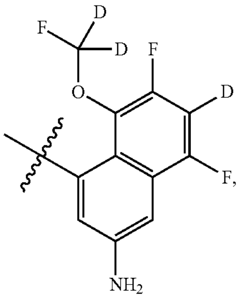
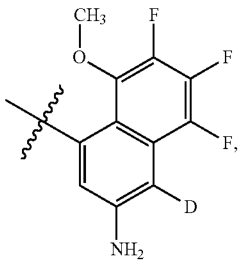
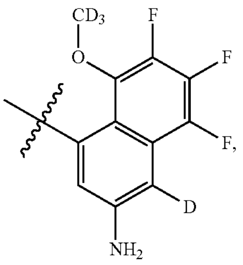
Another embodiment provides the compound of Formula (I), (Ia), (Ib), (Ic), or (Id), or a pharmaceutically acceptable salt or solvate thereof, wherein Ar is selected from:
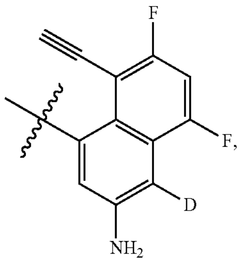
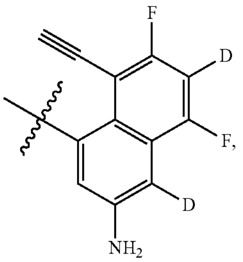
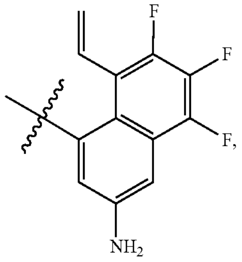
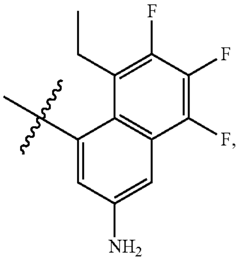
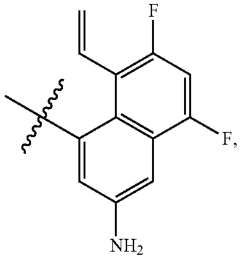
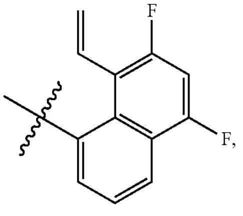
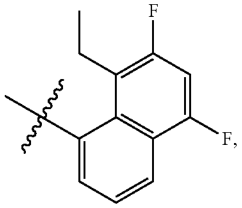
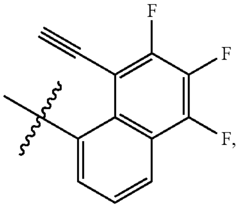
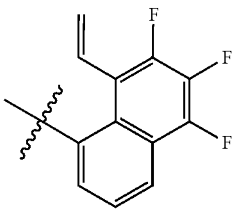
and
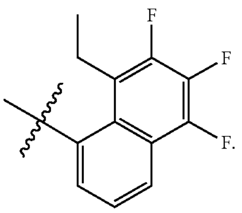

Another embodiment provides the compound of Formula (I), (Ia), (Ib), (Ic), or (Id), or a pharmaceutically acceptable salt or solvate thereof, wherein Ar is selected from:

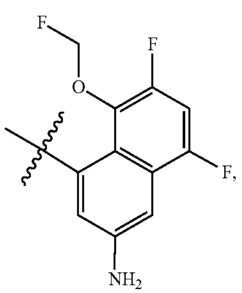
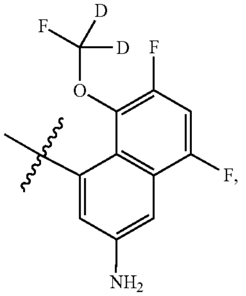
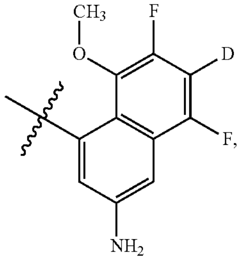
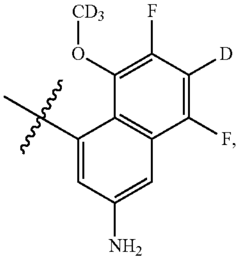
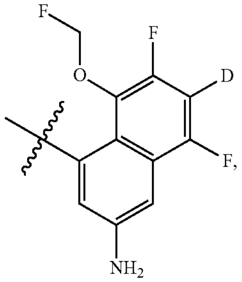
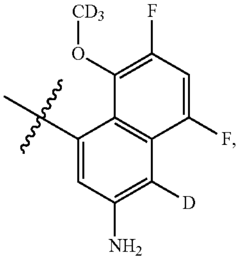
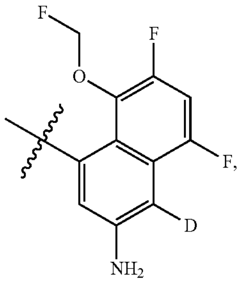
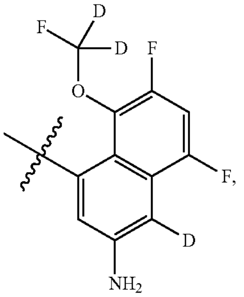
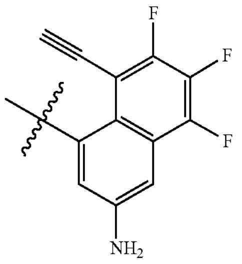

and

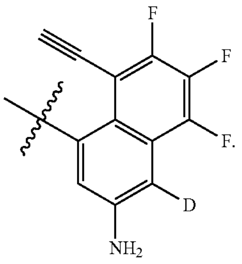

Another embodiment provides the compound of Formula (I), (Ia), (Ib), (Ic), or (Id), or a pharmaceutically acceptable salt or solvate thereof, wherein Ar is selected from:

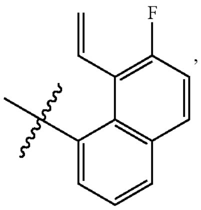
,
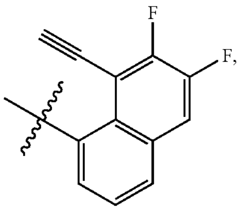
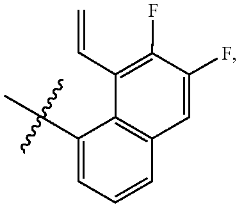
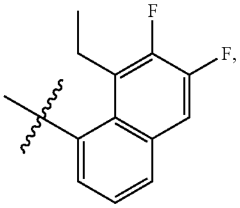
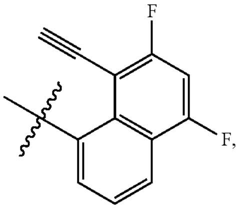
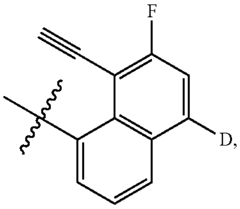
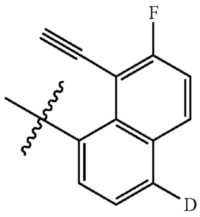
,
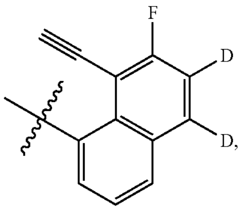
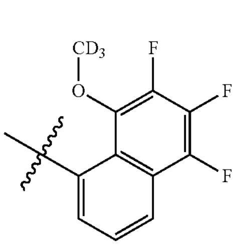

and

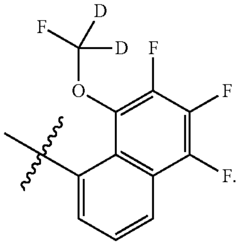

Another embodiment provides the compound of Formula (I), (Ia), (Ib), (Ic), or (Id), or a pharmaceutically acceptable salt or solvate thereof, wherein Ar is selected from:

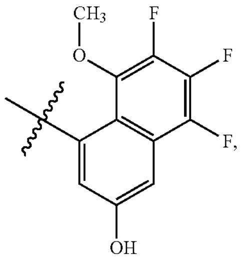
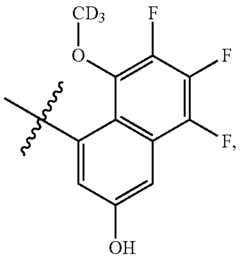

-continued

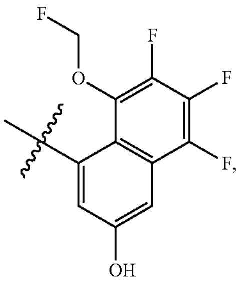

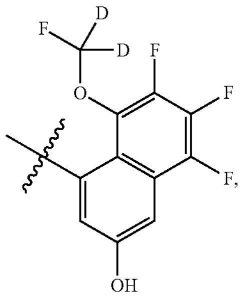

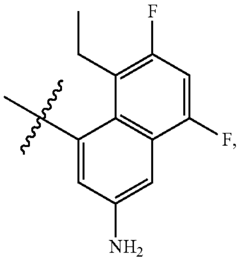

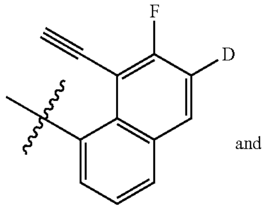

and

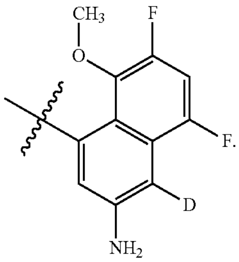

Another embodiment provides the compound of Formula (I), (Ia), (Ib), (Ic), or (Id), or a pharmaceutically acceptable salt or solvate thereof, wherein Ar is selected from:

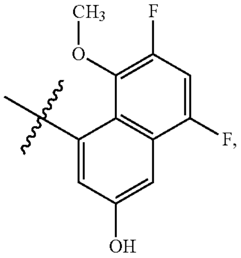

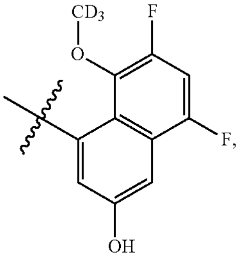

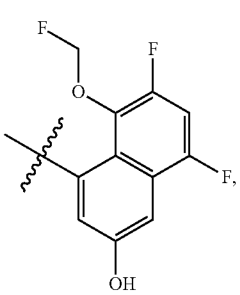

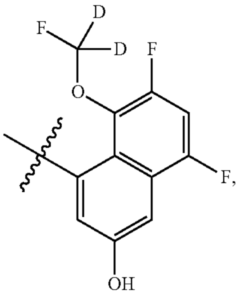

-continued

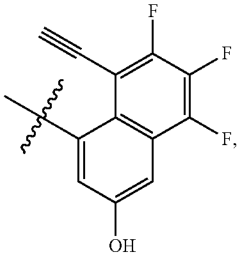

and

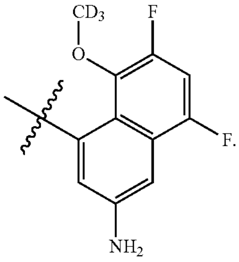

Another embodiment provides the compound of Formula (I), (Ia), (Ib), (Ic), or (Id), or a pharmaceutically acceptable salt or solvate thereof, wherein Ar is selected from:

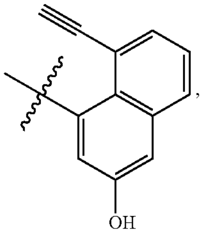

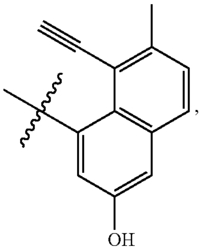

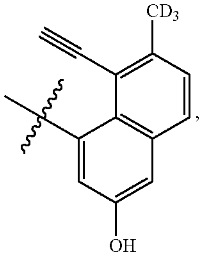

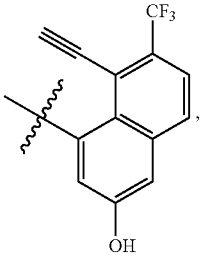

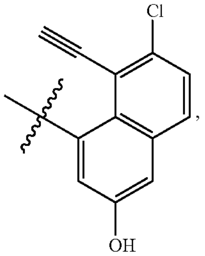

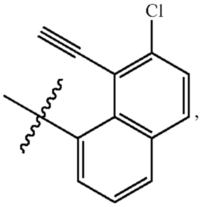

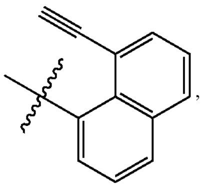

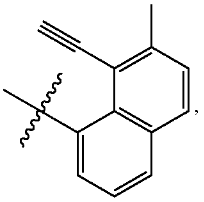

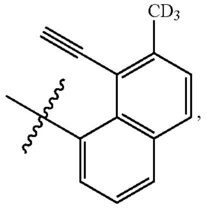

and

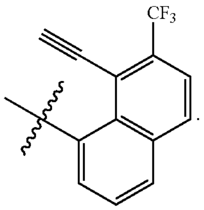

Another embodiment provides the compound of Formula (I), (Ia), (Ib), (Ic), or (Id), or a pharmaceutically acceptable salt or solvate thereof, wherein Ar is selected from:

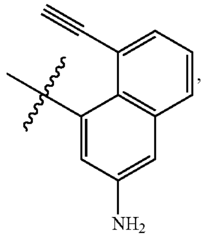,
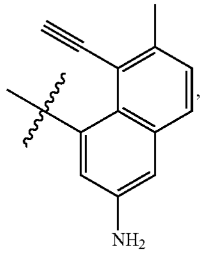,
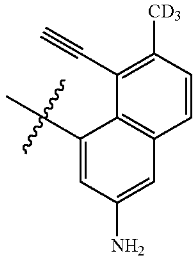,
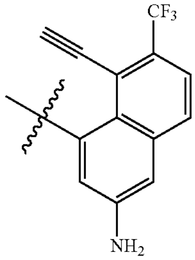, and
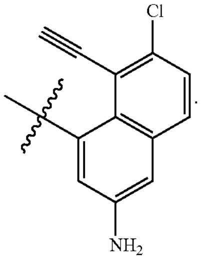.

Another embodiment provides the compound of Formula (I), (Ia), (Ib), (Ic), or (Id), or a pharmaceutically acceptable salt or solvate thereof, wherein Ar is selected from:

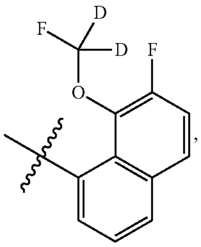,
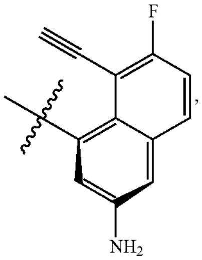, and
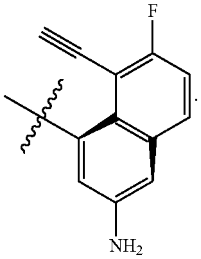.

Another embodiment provides the compound of Formula (I), (Ia), (Ib), (Ic), or (Id), or a pharmaceutically acceptable salt or solvate thereof, wherein Ar is selected from:

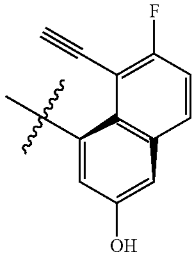
and
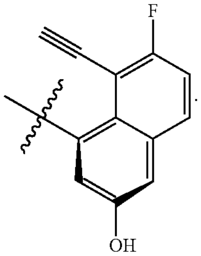.

Another embodiment provides the compound of Formula (I), (Ia), (Ib), (Ic), or (Id), or a pharmaceutically acceptable salt or solvate thereof, wherein Ar is selected from:

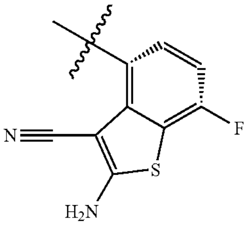
and
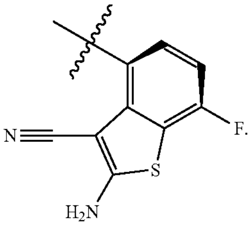.

Another embodiment provides the compound of Formula (I), (Ia), (Ib), (Ic), or (Id), or a pharmaceutically acceptable salt or solvate thereof, wherein the bicyclic optionally substituted aryl is described by Formula (a):

(a)

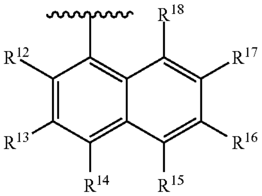

wherein:

$R^{12}$ is hydrogen, deuterium, or F;

$R^{13}$ is hydrogen, deuterium, —OH, —$NH_2$, Cl, —CN, —OCONHMe, —$NHCO_2Me$;

$R^{14}$ is hydrogen, deuterium, F, $C_1$, or Br;

$R^{15}$ is hydrogen, deuterium, F, $C_1$, or Br;

$R^{16}$ is hydrogen, deuterium, F, Cl, Br, —CN, or —$CH_3$;

$R^{17}$ is hydrogen, deuterium, F, $C_1$, or —CN; and $R^{18}$ is hydrogen, deuterium, —$CH_3$, —$CH_2CH_3$, —$CD_2CD_3$, —CH=$CH_2$, —C≡CH, —$OCHF_2$, —$OCF_3$, —$CH_2F$, —$CHF_2$, —$CF_3$, —CN, Cl, F, —$OCH_3$, —$OCD_3$, —$OCH_2F$, or —$OCD_2F$.

Another embodiment provides the compound of Formula (I), (Ia), (Ib), (Ic), or (Id), or a pharmaceutically acceptable salt or solvate thereof, wherein Ar is a monocyclic optionally substituted heteroaryl.

Another embodiment provides the compound of Formula (I), (Ia), (Ib), (Ic), or (Id), or a pharmaceutically acceptable salt or solvate thereof, wherein the monocyclic optionally substituted heteroaryl is an optionally substituted 2-pyridinyl.

Another embodiment provides the compound of Formula (I), (Ia), (Ib), (Ic), or (Id), or a pharmaceutically acceptable salt or solvate thereof, wherein the optionally substituted 2-pyridinyl is

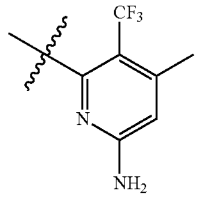 [SMILES: *c1nc(N)cc(C)c1C(F)(F)F]

Another embodiment provides the compound of Formula (I), (Ia), (Ib), (Ic), or (Id), or a pharmaceutically acceptable salt or solvate thereof, wherein the optionally substituted 2-pyridinyl is

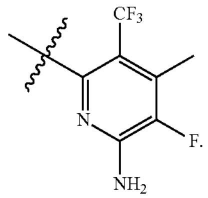 [SMILES: *c1nc(N)c(F)c(C)c1C(F)(F)F]

Another embodiment provides the compound of Formula (I), (Ia), (Ib), (Ic), or (Id), or a pharmaceutically acceptable salt or solvate thereof, wherein the monocyclic optionally substituted heteroaryl is an optionally substituted 4-pyridinyl. In some embodiments, the optionally substituted 4-pyridinyl is:

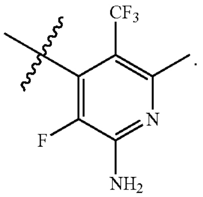 [SMILES: *c1c(F)c(N)nc(C)c1C(F)(F)F]

In some embodiments, the optionally substituted 4-pyridinyl is:

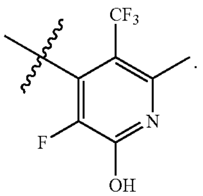 [SMILES: *c1c(F)c(O)nc(C)c1C(F)(F)F]

Another embodiment provides the compound of Formula (I), (Ia), (Ib), (Ic), or (Id), or a pharmaceutically acceptable salt or solvate thereof, wherein Ar is a bicyclic optionally substituted heteroaryl.

In some embodiments, the bicyclic optionally substituted heteroaryl is selected from:

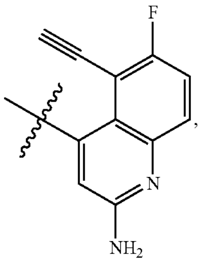,
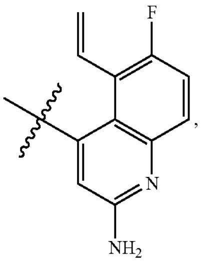,
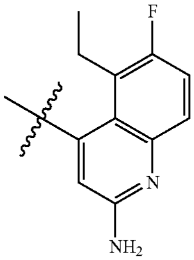,
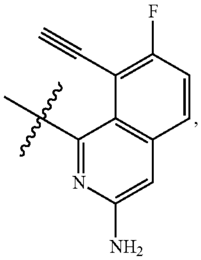,
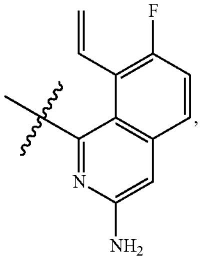,
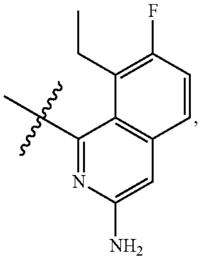,
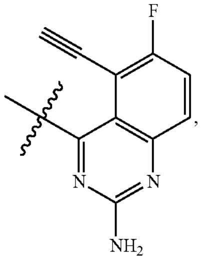,
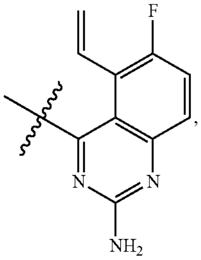,
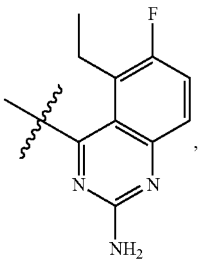,
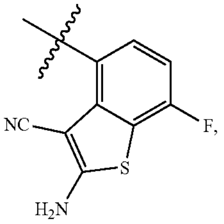

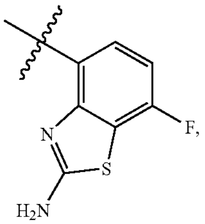

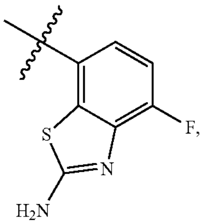

-continued
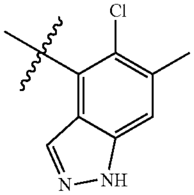
and
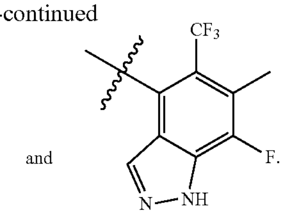
In some embodiments, the bicyclic optionally substituted heteroaryl is selected from:
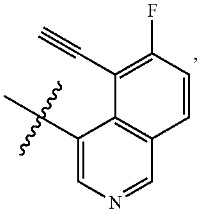
,
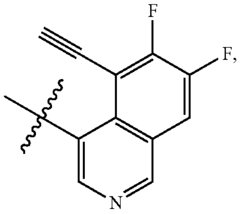
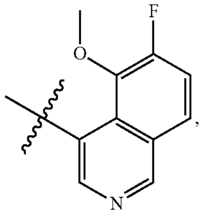
,
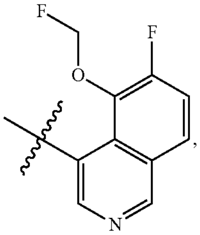
,
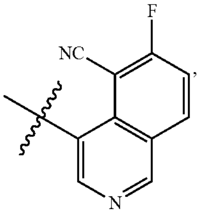
,
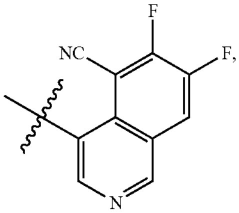
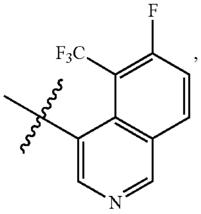
,
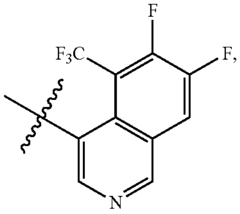
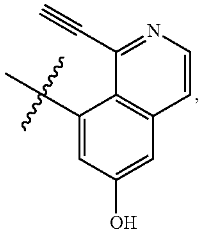
,
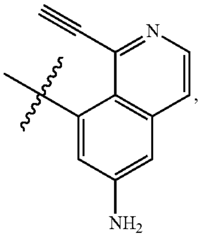
,
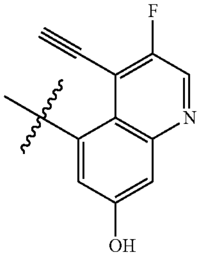
and
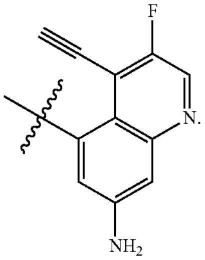
In some embodiments, the bicyclic optionally substituted heteroaryl is selected from:
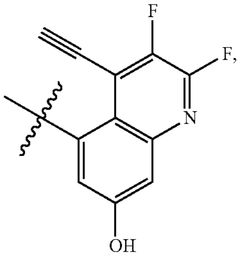
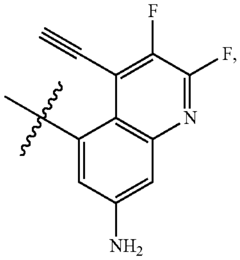
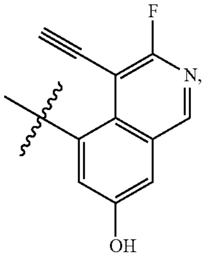
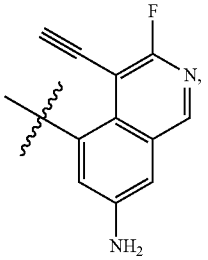
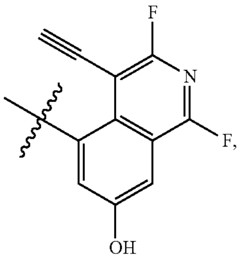
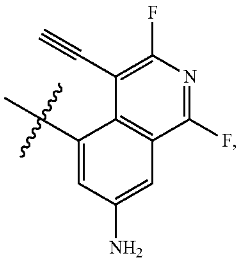
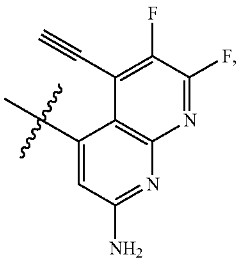
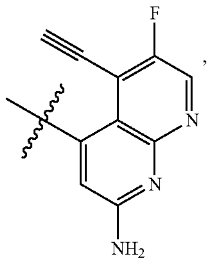
,
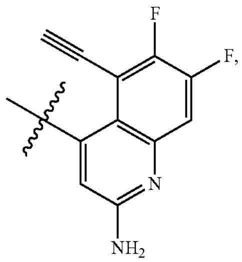
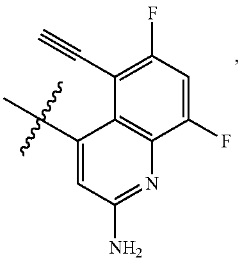
,
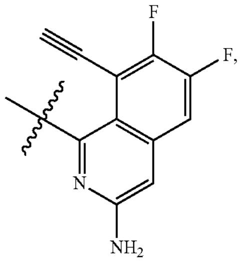
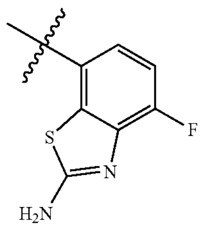
, -continued

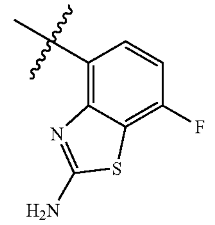

and

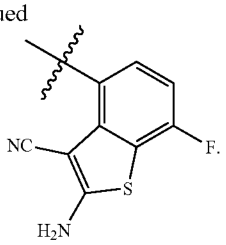

In some embodiments, the bicyclic optionally substituted heteroaryl is selected from:

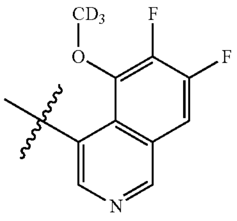

or

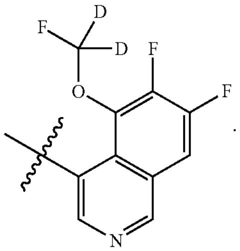

In some embodiments, the bicyclic optionally substituted heteroaryl is:

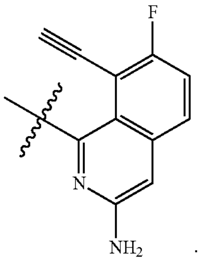 [SMILES: *c1nc(N)cc2ccc(F)c(C#C)c12]

In some embodiments, the bicyclic optionally substituted heteroaryl is described by Formula (b1):

(b1)

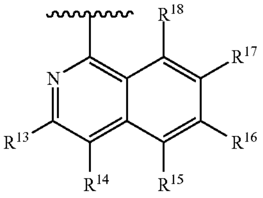

wherein:

$R^{13}$ is hydrogen, deuterium, —OH, —$NH_2$, Cl, —CN, —OCONHMe, —$NHCO_2Me$;

$R^{14}$ is hydrogen, deuterium, F, $C_1$, or Br;

$R^{15}$ is hydrogen, deuterium, F, $C_1$, or Br;

$R^{16}$ is hydrogen, deuterium, F, Cl, Br, —CN, or —$CH_3$;

$R^{17}$ is hydrogen, deuterium, F, $C_1$, or —CN; and $R^{18}$ is hydrogen, deuterium, —$CH_3$, —$CH_2CH_3$, —$CD_2CD_3$, —CH═$CH_2$, —C≡CH, —$OCHF_2$, —$OCF_3$, —$CH_2F$, —$CHF_2$, —$CF_3$, —CN, Cl, F, —$OCH_3$, —$OCD_3$, —$OCH_2F$, or —$OCD_2F$.

In some embodiments, the bicyclic optionally substituted heteroaryl is described by Formula (b2):

(b2)

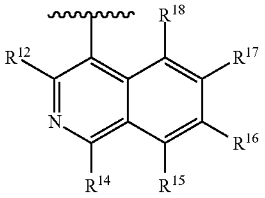

wherein:

$R^{12}$ is hydrogen, deuterium, or F;

$R^{14}$ is hydrogen, deuterium, F, $C_1$, or Br;

$R^{15}$ is hydrogen, deuterium, F, $C_1$, or Br;

$R^{16}$ is hydrogen, deuterium, F, Cl, Br, —CN, or —$CH_3$;

$R^{17}$ is hydrogen, deuterium, F, $C_1$, or —CN; and $R^{18}$ is hydrogen, deuterium, —$CH_3$, —$CH_2CH_3$, —$CD_2CD_3$, —CH═$CH_2$, —C≡CH, —$OCHF_2$, —$OCF_3$, —$CH_2F$, —$CHF_2$, —$CF_3$, —CN, Cl, F, —$OCH_3$, —$OCD_3$, —$OCH_2F$, or —$OCD_2F$.

In some embodiments, the bicyclic optionally substituted heteroaryl is described by Formula (b3):

(b3)

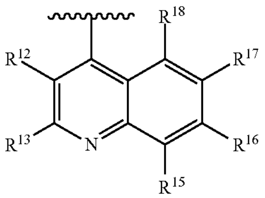

wherein:

$R^{12}$ is hydrogen, deuterium, or F;

$R^{13}$ is hydrogen, deuterium, —OH, —$NH_2$, Cl, —CN, —OCONHMe, —$NHCO_2Me$;

$R^{15}$ is hydrogen, deuterium, F, $C_1$, or Br;

$R^{16}$ is hydrogen, deuterium, F, Cl, Br, —CN, or —$CH_3$;

$R^{17}$ is hydrogen, deuterium, F, $C_1$, or —CN; and $R^{18}$ is hydrogen, deuterium, —$CH_3$, —$CH_2CH_3$, —$CD_2CD_3$, —CH═$CH_2$, —C≡CH, —$OCHF_2$, —$OCF_3$, —$CH_2F$, —$CHF_2$, —$CF_3$, —CN, Cl, F, —$OCH_3$, —$OCD_3$, —$OCH_2F$, or —$OCD_2F$.

In some embodiments, the bicyclic optionally substituted heteroaryl is described by Formula (b4):

(b4)

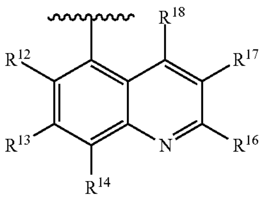

wherein:

$R^{12}$ is hydrogen, deuterium, or F;

$R^{13}$ is hydrogen, deuterium, —OH, —$NH_2$, Cl, —CN, —OCONHMe, —$NHCO_2Me$;

$R^{14}$ is hydrogen, deuterium, F, $C_1$, or Br;

$R^{16}$ is hydrogen, deuterium, F, Cl, Br, —CN, or —$CH_3$;

$R^{17}$ is hydrogen, deuterium, F, $C_1$, or —CN; and $R^{18}$ is hydrogen, deuterium, —$CH_3$, —$CH_2CH_3$, —$CD_2CD_3$, —CH═$CH_2$, —C≡CH, —$OCHF_2$, —$OCF_3$, —$CH_2F$, —$CHF_2$, —$CF_3$, —CN, Cl, F, —$OCH_3$, —$OCD_3$, —$OCH_2F$, or —$OCD_2F$.

In some embodiments, the bicyclic optionally substituted heteroaryl is described by Formula (b5):

(b5)

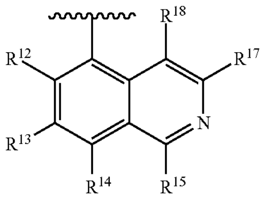

wherein:

$R^{12}$ is hydrogen, deuterium, or F;

$R^{13}$ is hydrogen, deuterium, —OH, —$NH_2$, Cl, —CN, —OCONHMe, —$NHCO_2Me$;

$R^{14}$ is hydrogen, deuterium, F, $C_1$, or Br;

$R^{15}$ is hydrogen, deuterium, F, $C_1$, or Br;

$R^{17}$ is hydrogen, deuterium, F, $C_1$, or —CN; and $R^{18}$ is hydrogen, deuterium, —$CH_3$, —$CH_2CH_3$, —$CD_2CD_3$, —CH═$CH_2$, —C≡CH, —$OCHF_2$, —$OCF_3$, —$CH_2F$, —$CHF_2$, —$CF_3$, —CN, Cl, F, —$OCH_3$, —$OCD_3$, —$OCH_2F$, or —$OCD_2F$.

In some embodiments, the bicyclic optionally substituted heteroaryl is described by Formula (b6):

(b6)

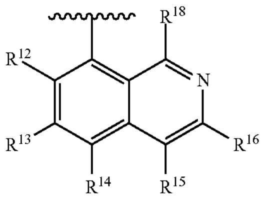

wherein:

$R^{12}$ is hydrogen, deuterium, or F;

$R^{13}$ is hydrogen, deuterium, —OH, —$NH_2$, Cl, —CN, —OCONHMe, —$NHCO_2Me$;

$R^{14}$ is hydrogen, deuterium, F, $C_1$, or Br;

$R^{15}$ is hydrogen, deuterium, F, $C_1$, or Br;

$R^{16}$ is hydrogen, deuterium, F, Cl, Br, —CN, or —$CH_3$; and $R^{18}$ is hydrogen, deuterium, —$CH_3$, —$CH_2CH_3$, —$CD_2CD_3$, —CH═$CH_2$, —C≡CH, —$OCHF_2$, —$OCF_3$, —$CH_2F$, —$CHF_2$, —$CF_3$, —CN, Cl, F, —$OCH_3$, —$OCD_3$, —$OCH_2F$, or —$OCD_2F$.

In some embodiments, the bicyclic optionally substituted heteroaryl is is described by Formula (b8):

(b8)

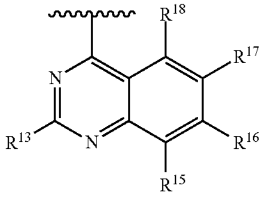

wherein:

$R^{13}$ is hydrogen, deuterium, —OH, —$NH_2$, Cl, —CN, —OCONHMe, —$NHCO_2Me$;

$R^{15}$ is hydrogen, deuterium, F, $C_1$, or Br;

$R^{16}$ is hydrogen, deuterium, F, Cl, Br, —CN, or —$CH_3$;

$R^{17}$ is hydrogen, deuterium, F, $C_1$, or —CN; and $R^{18}$ is hydrogen, deuterium, —$CH_3$, —$CH_2CH_3$, —$CD_2CD_3$, —CH═$CH_2$, —C≡CH, —$OCHF_2$, —$OCF_3$, —$CH_2F$, —$CHF_2$, —$CF_3$, —CN, Cl, F, —$OCH_3$, —$OCD_3$, —$OCH_2F$, or —$OCD_2F$.

Another embodiment provides the compound of Formula (I), (Ia), (Ib), (Ic), or (Id), or a pharmaceutically acceptable salt or solvate thereof, wherein L is optionally substituted C1-C4 alkylene.

Another embodiment provides the compound of Formula (I), (Ia), (Ib), (Ic), or (Id), or a pharmaceutically acceptable salt or solvate thereof, wherein L is

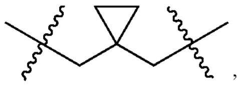
,
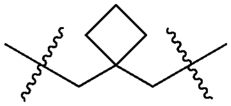
or
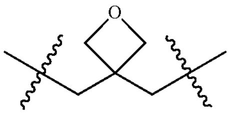
.

Another embodiment provides the compound of Formula (I), (Ia), (Ib), (Ic), or (Id), or a pharmaceutically acceptable salt or solvate thereof, wherein L is

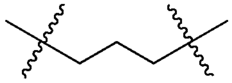
,
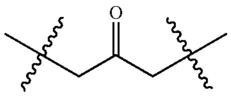
or
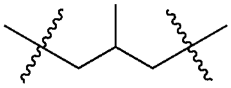
.

Another embodiment provides the compound of Formula (I), (Ia), (Ib), (Ic), or (Id), or a pharmaceutically acceptable salt or solvate thereof, wherein L is optionally substituted $C_1$ alkylene.

Another embodiment provides the compound of Formula (I), (Ia), (Ib), (Ic), or (Id), or a pharmaceutically acceptable salt or solvate thereof, wherein G is an optionally substituted 5- to 10-membered heterocyclyl.

Another embodiment provides the compound of Formula (I), (Ia), (Ib), (Ic), or (Id), or a pharmaceutically acceptable salt or solvate thereof, wherein G is selected from:

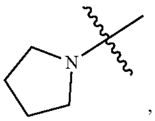
,
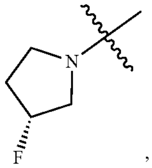
,
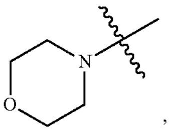
,

-continued

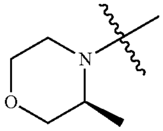, 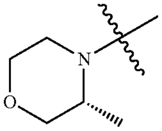, 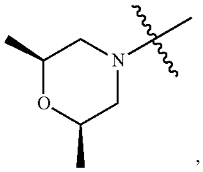,

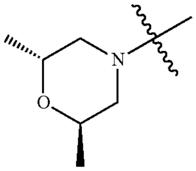 and 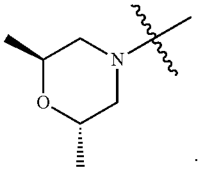.

Another embodiment provides the compound of Formula (I), (Ia), (Ib), (Ic), or (Id), or a pharmaceutically acceptable salt or solvate thereof, wherein G is selected from:

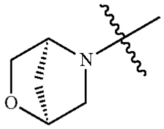, 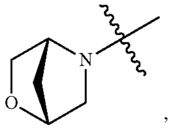, 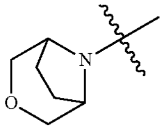,

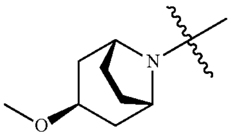 and 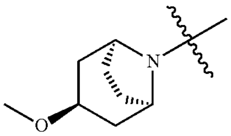.

Another embodiment provides the compound of Formula (I), (Ia), (Ib), (Ic), or (Id), or a pharmaceutically acceptable salt or solvate thereof, wherein G is selected from:

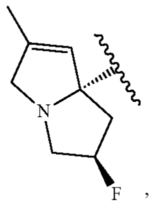, 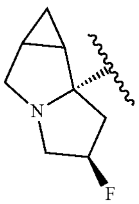, 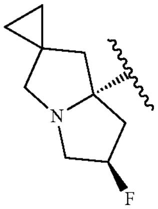 or

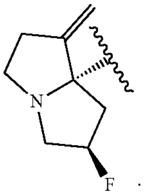.

Another embodiment provides the compound of Formula (I), (Ia), (Ib), (Ic), or (Id), or a pharmaceutically acceptable salt or solvate thereof, wherein G is described by Formula (c):

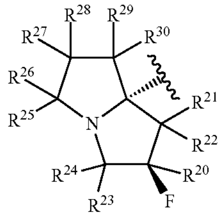

(c)

wherein, each $R^{20}$-$R^{30}$ is independently selected from hydrogen or deuterium.

Another embodiment provides the compound of Formula (I), (Ia), (Ib), (Ic), or (Id), or a pharmaceutically acceptable salt or solvate thereof, wherein G is described by Formula (d):

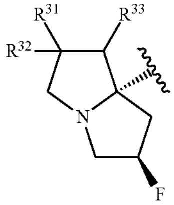

(d)

wherein, $R^{31}$ is selected from hydrogen, F, Cl, —CN, —OH, or optionally substituted C1-C4 alkyl;

$R^{32}$ is hydrogen, deuterium or optionally substituted C1-C4 alkyl; and $R^{33}$ is hydrogen, deuterium, F, or optionally substituted C1-C4 alkyl.

Another embodiment provides the compound of Formula (I), (Ia), (Ib), (Ic), or (Id), or a pharmaceutically acceptable salt or solvate thereof, wherein G is selected from:

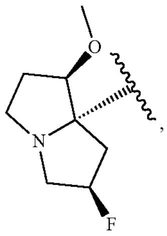, 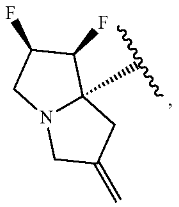, 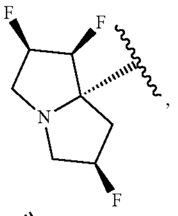,

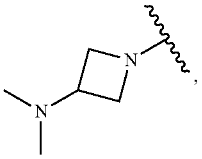 [SMILES: *N1CC(N(C)C)C1], 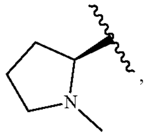, 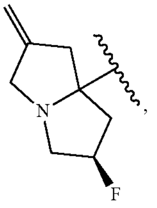,

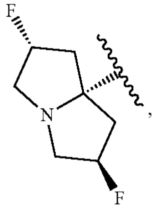, 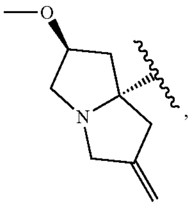, 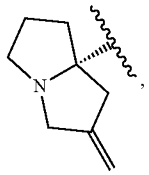,

-continued

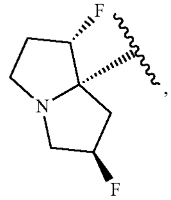,
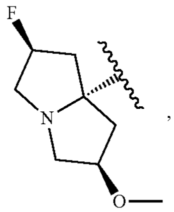,
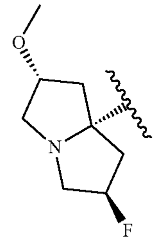 or
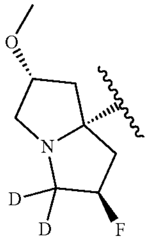.

Another embodiment provides the compound of Formula (I), (Ia), (Ib), (Ic), or (Id), or a pharmaceutically acceptable salt or solvate thereof, wherein G is selected from:

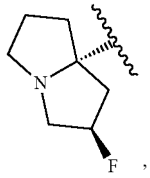,
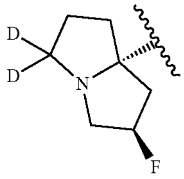,
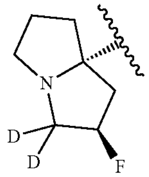,
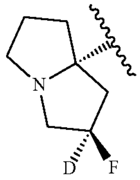,
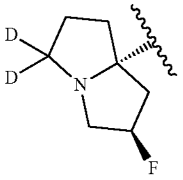,
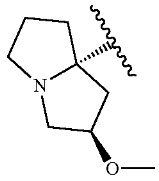,
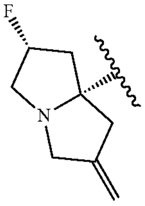,
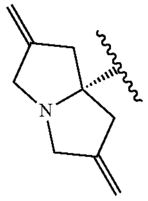,
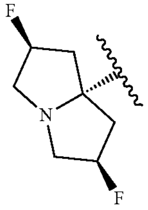,
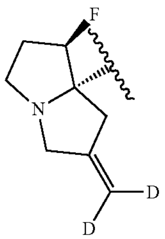 or
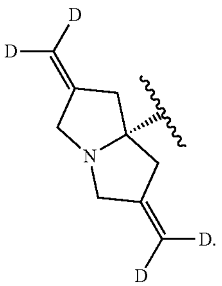

Another embodiment provides the compound of Formula (I), (Ia), (Ib), (Ic), or (Id), or a pharmaceutically acceptable salt or solvate thereof, wherein G is selected from:

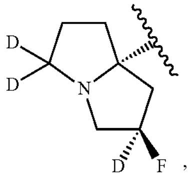,
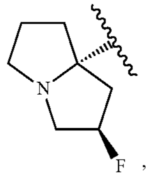,
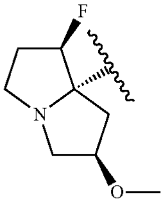,
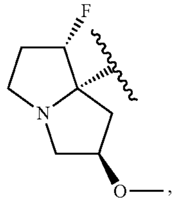,
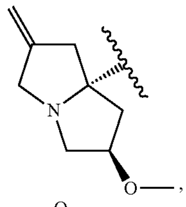,
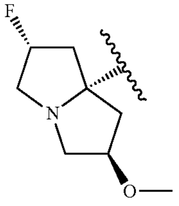 or
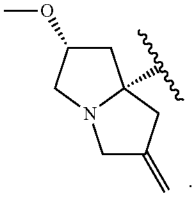.

Another embodiment provides the compound of Formula (I), (Ia), (Ib), (Ic), or (Id), or a pharmaceutically acceptable salt or solvate thereof, wherein G is selected from:

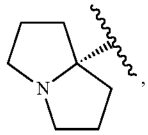,
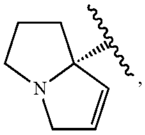,
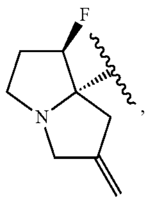,
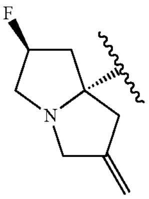 or
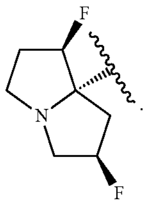.

Another embodiment provides the compound of Formula (I), (Ia), (Ib), (Ic), or (Id), or a pharmaceutically acceptable salt or solvate thereof, wherein R' is selected from:

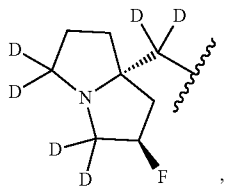,
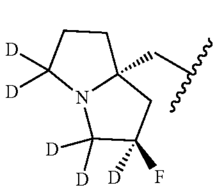,
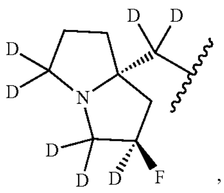,
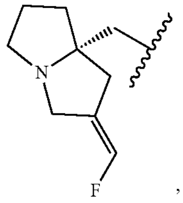,

-continued
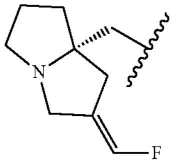 ,
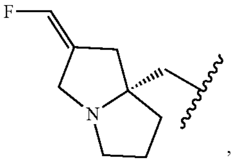 ,
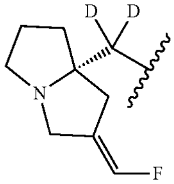 ,
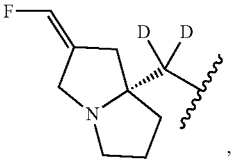 ,
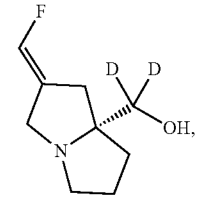
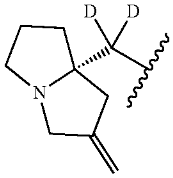 ,
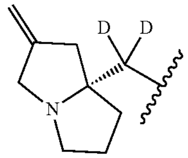
and
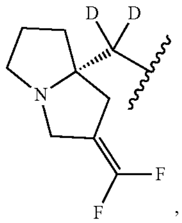 ,
Another embodiment provides the compound of Formula (I), (Ia), (Ib), (Ic), or (Id), or a pharmaceutically acceptable salt or solvate thereof, wherein $R^1$ is selected from:
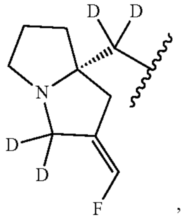 ,
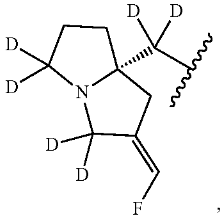 ,
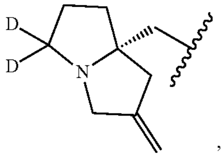 ,
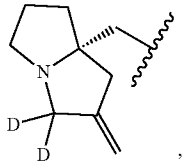 ,
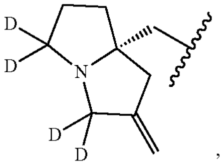 ,
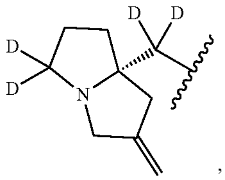 ,
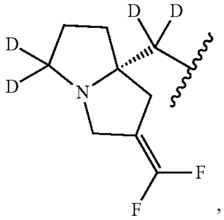 ,
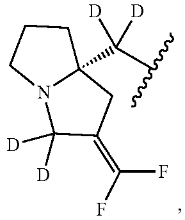 ,
-continued
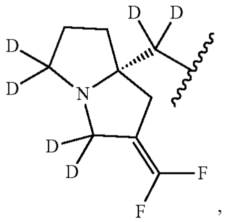 ,
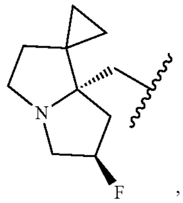 ,
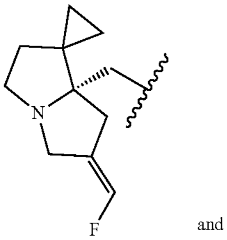
and
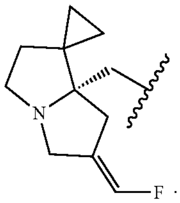 .
Another embodiment provides the compound of Formula (I), (Ia), (Ib), (Ic), or (Id), or a pharmaceutically acceptable salt or solvate thereof, wherein $R^1$ is selected from:
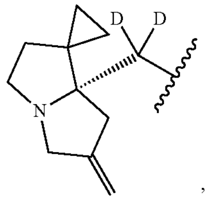 ,
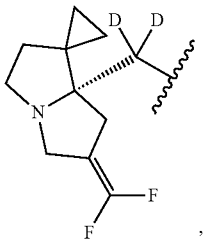 ,
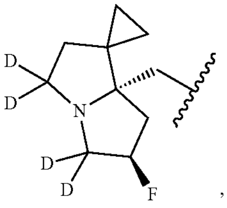 ,
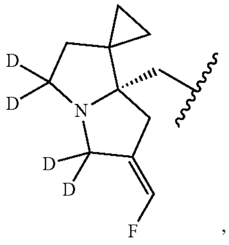 ,
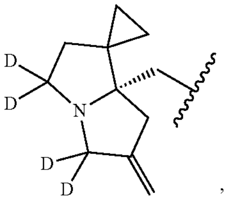 ,
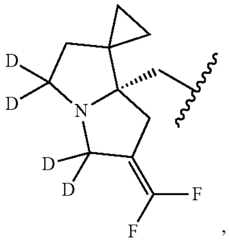 ,
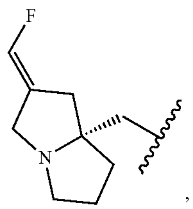 ,
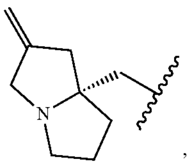 , -continued

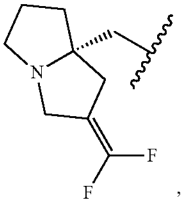

,

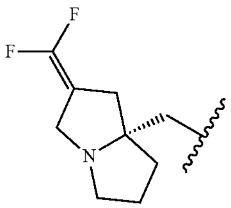

and

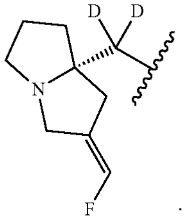

.

Another embodiment provides the compound of Formula (I), (Ia), (Ib), (Ic), or (Id), or a

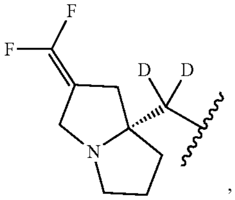

,

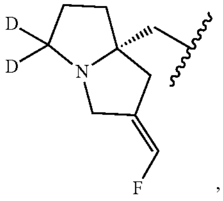

,

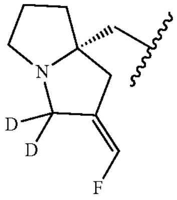

,

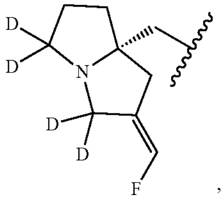

,

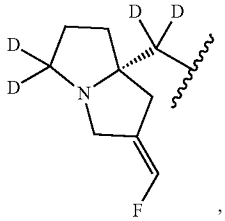

,

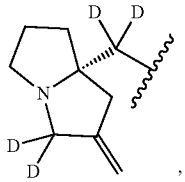

,

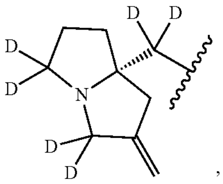

,

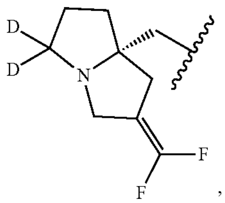

,

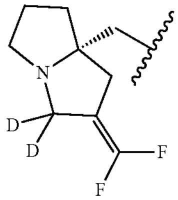

and

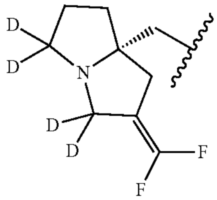

.

Another embodiment provides the compound of Formula (I), (Ia), (Ib), (Ic), or (Id), or a pharmaceutically acceptable salt or solvate thereof, wherein $R^1$ is selected from:

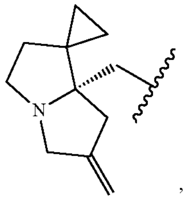

,

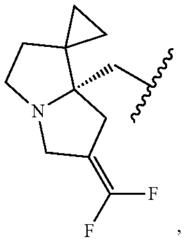

,

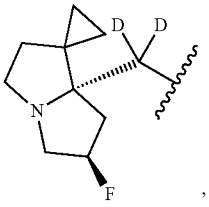

,

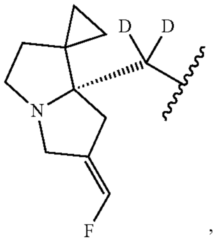

,

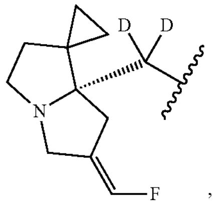

,

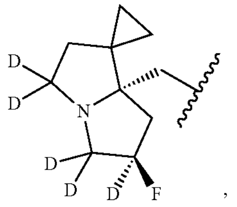

,

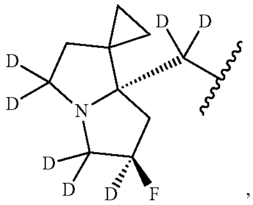

,

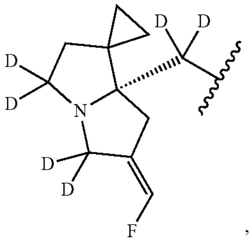

,

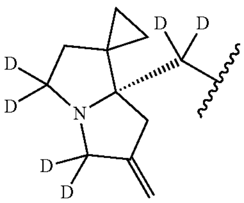

and

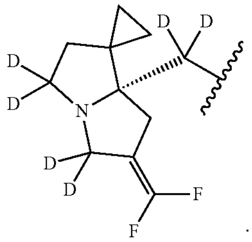

.

Another embodiment provides the compound of Formula (I), (Ia), (Ib), (Ic), or (Id), or a pharmaceutically acceptable salt or solvate thereof, wherein $R^1$ is selected from:

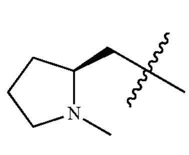

or

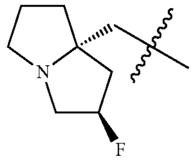

.

Another embodiment provides the compound of Formula (I), (Ia), (Ib), (Ic), or (Id), or a pharmaceutically acceptable salt or solvate thereof, wherein $R^1$ is selected from:

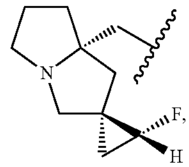
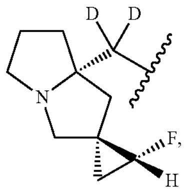
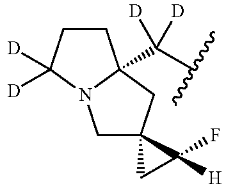
or
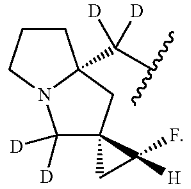

Another embodiment provides the compound of Formula (I), (Ia), (Ib), (Ic), or (Id), or a

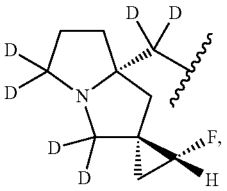
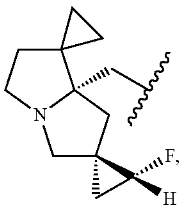
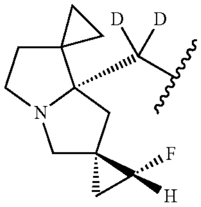
or
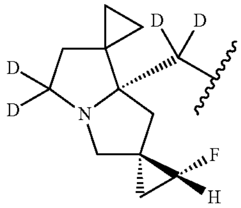

Another embodiment provides the compound of Formula (I), (Ia), (Ib), (Ic), or (Id), or a pharmaceutically acceptable salt or solvate thereof, wherein $R^1$ is selected from:

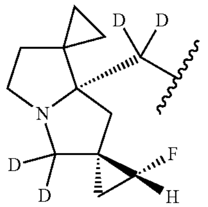
or
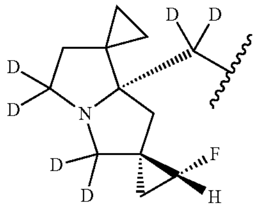

Another embodiment provides the compound of Formula (I), (Ia), (Ib), (Ic), or (Id), or a pharmaceutically acceptable salt or solvate thereof, wherein $R^1$ is selected from:

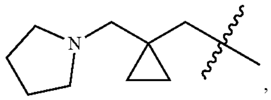
,
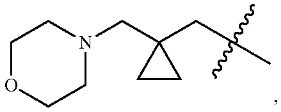
,
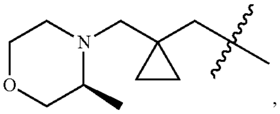
,
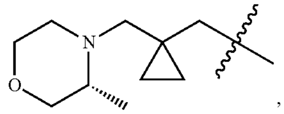
,

-continued

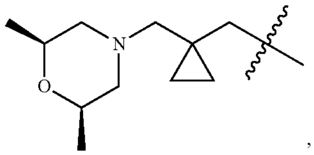
,
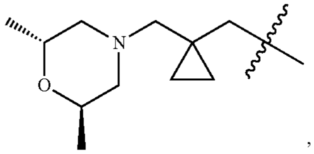
,
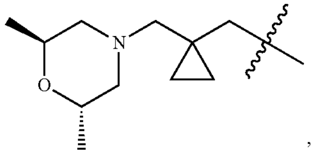
,
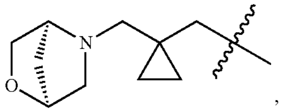
,
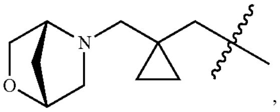
,
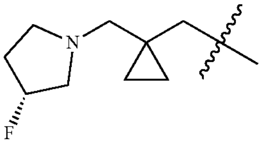
and
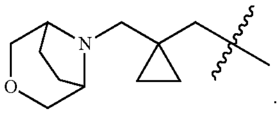
.

Another embodiment provides the compound of Formula (I), (Ia), (Ib), (Ic), or (Id), or a pharmaceutically acceptable salt or solvate thereof, wherein $R^1$ is selected from:

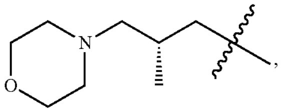
,
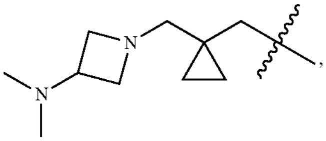
,
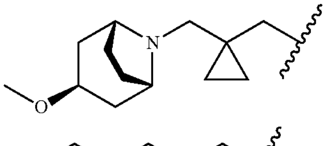
,
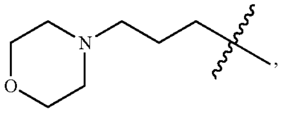
,
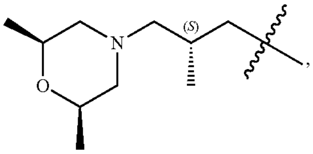
,

-continued

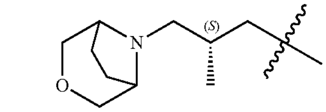,

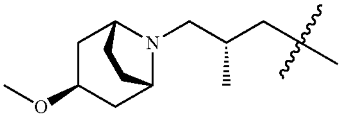 and

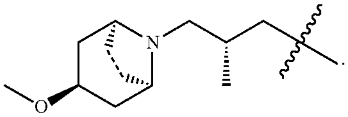.

Another embodiment provides the compound of Formula (I), (Ia), (Ib), (Ic), or (Id), or a

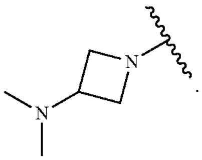.

Another embodiment provides the compound of Formula (I), (Ia), (Ib), (Ic), or (Id), or a pharmaceutically acceptable salt or solvate thereof, wherein $R^1$ is selected from:

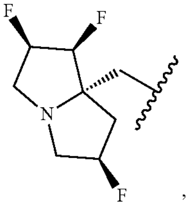, 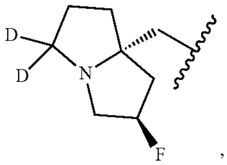,

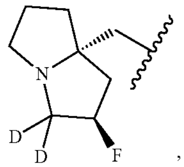, 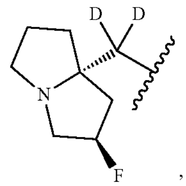, 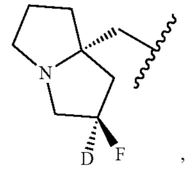,

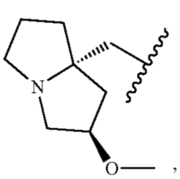, 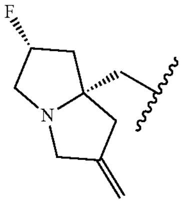,

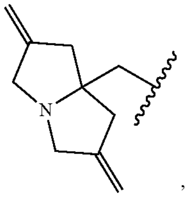, 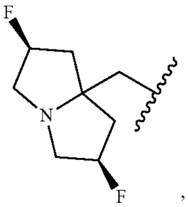, and

-continued

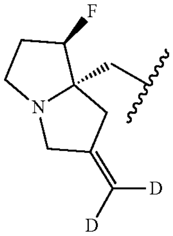.

Another embodiment provides the compound of Formula (I), (Ia), (Ib), (Ic), or (Id), or a pharmaceutically acceptable salt or solvate thereof, wherein $R^1$ is selected from:

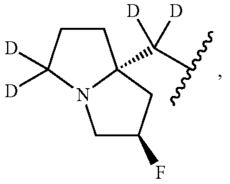, 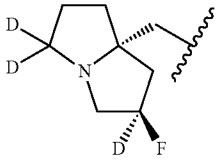,

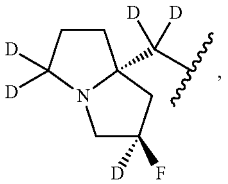, 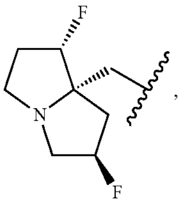,

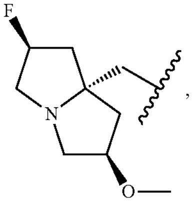, 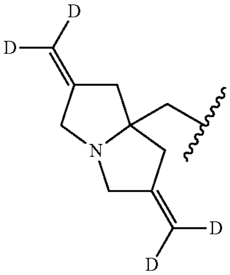,

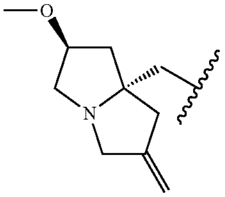 and 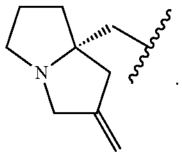.

Another embodiment provides the compound of Formula (I), (Ia), (Ib), (Ic), or (Id), or a

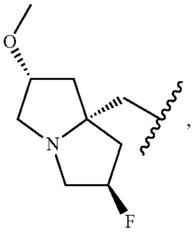, 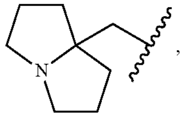, 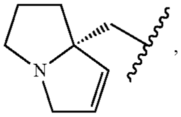,

-continued

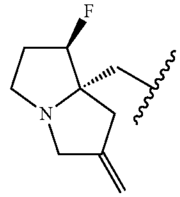,
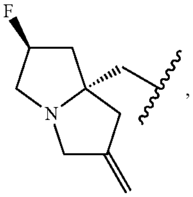,
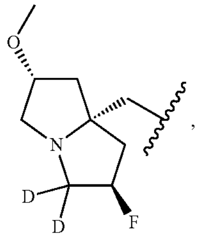,
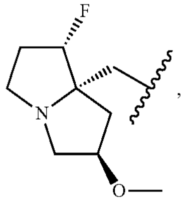,
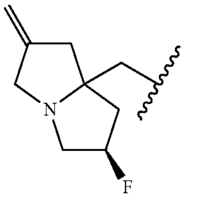
and
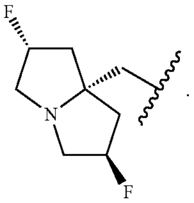.

Another embodiment provides the compound of Formula (I), (Ia), (Ib), (Ic), or (Id), or a pharmaceutically acceptable salt or solvate thereof, wherein R[1] is selected from:

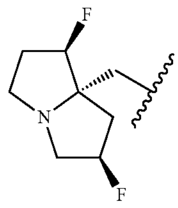,
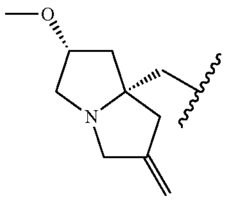,
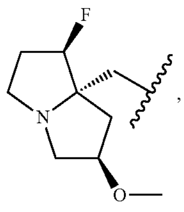,
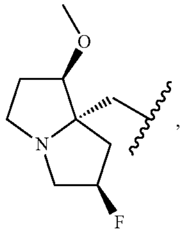,
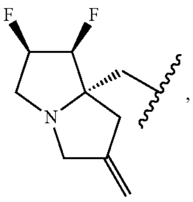,
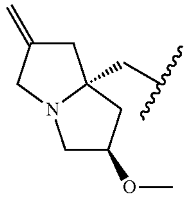
and
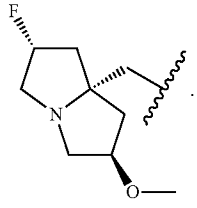.

Another embodiment provides the compound of Formula (I), (Ia), (Ib), (Ic), or (Id), or a pharmaceutically acceptable salt or solvate thereof, wherein R[1] is selected from:

cis

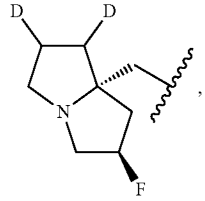,
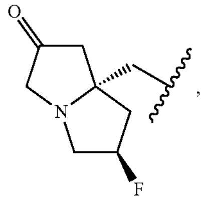,
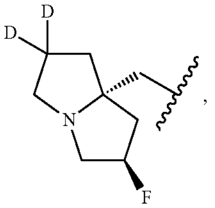,
cis

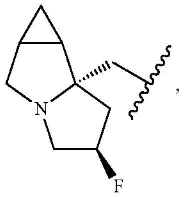,
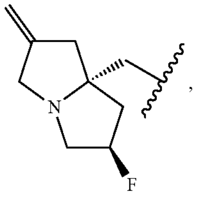,
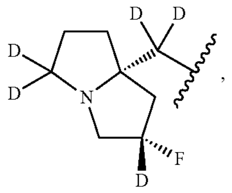,
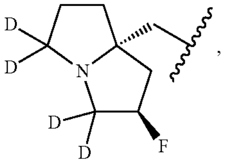,
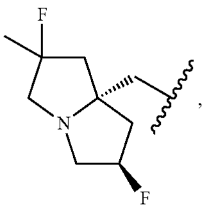,
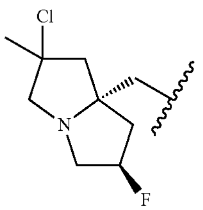
and
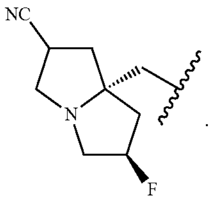.

Another embodiment provides the compound of Formula (I), (Ia), (Ib), (Ic), or (Id), or a

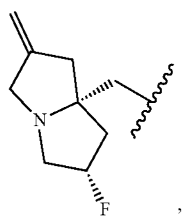,
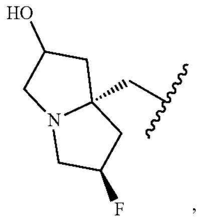,
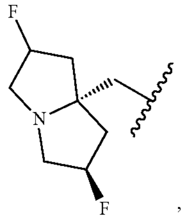,
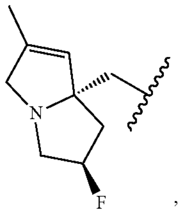,

-continued

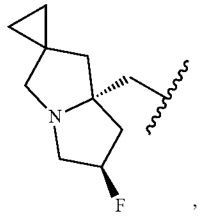 , 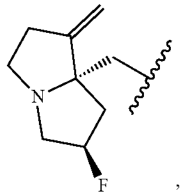 ,

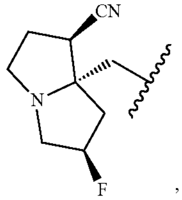 , 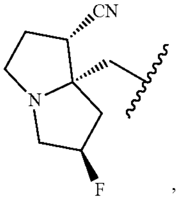 ,

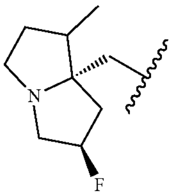 and 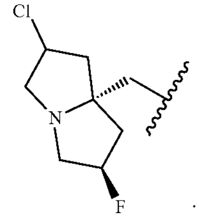 .

Another embodiment provides the compound of Formula (I), (Ia), (Ib), (Ic), or (Id), or a pharmaceutically acceptable salt or solvate thereof, wherein $R^1$ is selected from:

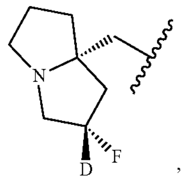 , 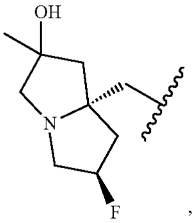 ,

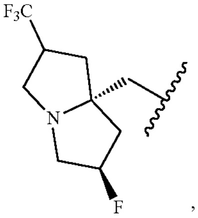 , 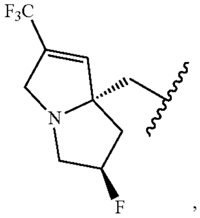 ,

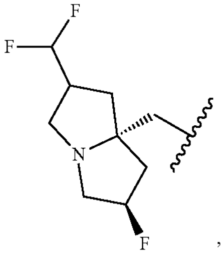 , 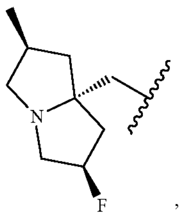 ,

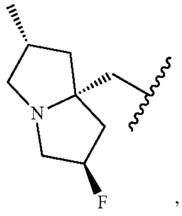 , 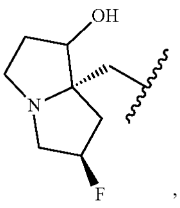 ,

-continued

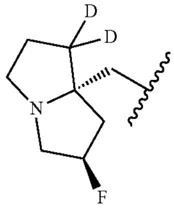 and 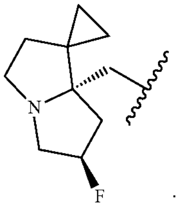 .

Another embodiment provides the compound of Formula (I), (Ia), (Ib), (Ic), or (Id), or a pharmaceutically acceptable salt or solvate thereof, wherein $R^1$ is selected from:

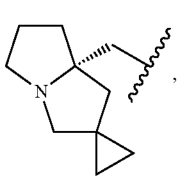 , 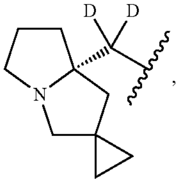 ,

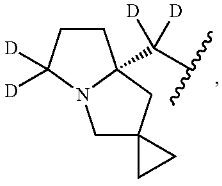 , 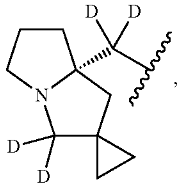 ,

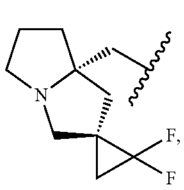 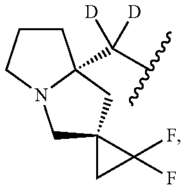

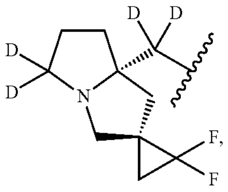 and 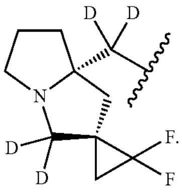

Another embodiment provides the compound of Formula (I), (Ia), (Ib), (Ic), or (Id), or a

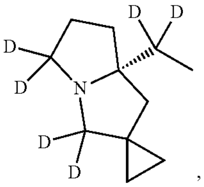 , 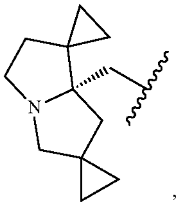 ,

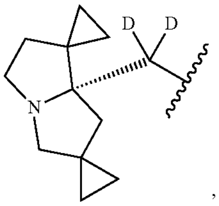 , 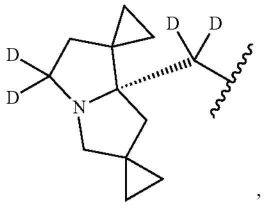 ,

-continued

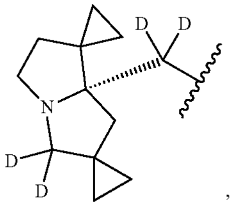 ,
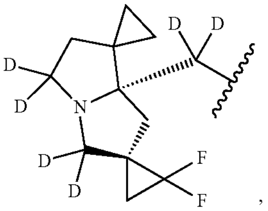 ,
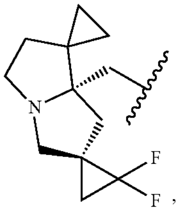 ,
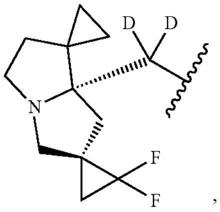 ,
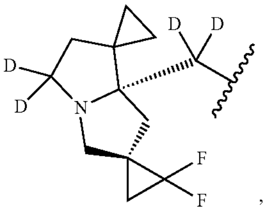 , and
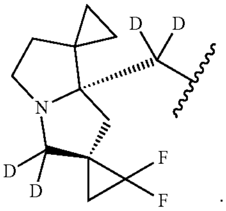 .

Another embodiment provides the compound of Formula (I), (Ia), (Ib), (Ic), or (Id), or a pharmaceutically acceptable salt or solvate thereof, wherein $R^1$ is selected from:

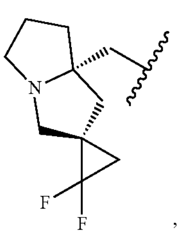 ,
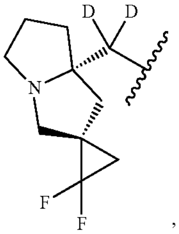 ,
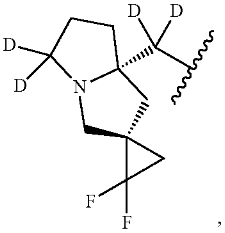 ,
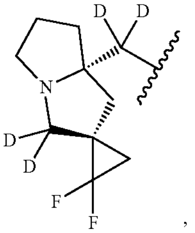 ,
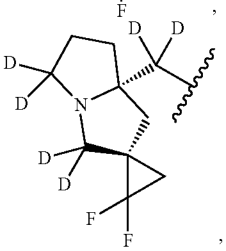 ,
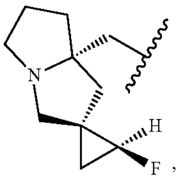 , -continued

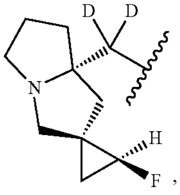 ,
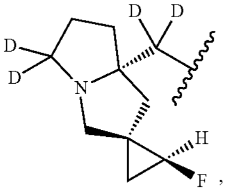 ,
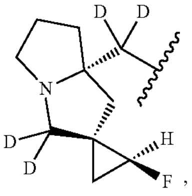 , and
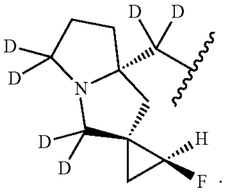 .

Another embodiment provides the compound of Formula (I), (Ia), (Ib), (Ic), or (Id), or a

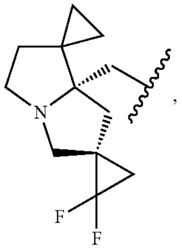 ,
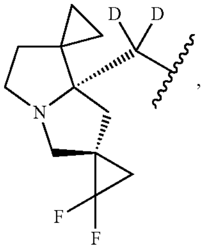 ,
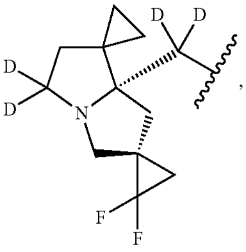 ,
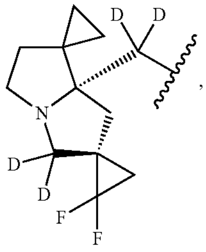 ,
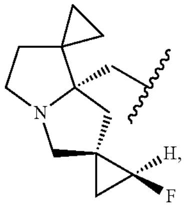
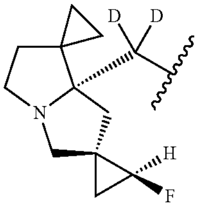 ,
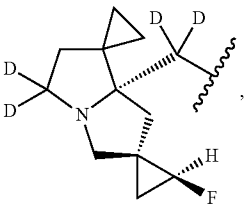 , and
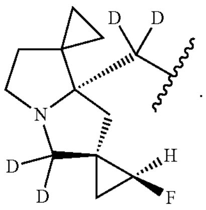 .

Another embodiment provides the compound of Formula (I), (Ia), (Ib), (Ic), or (Id), or a pharmaceutically acceptable salt or solvate thereof, wherein $R^1$ is selected from:

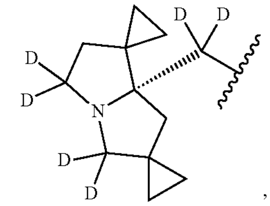
,
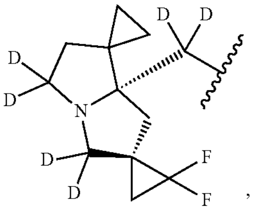
,
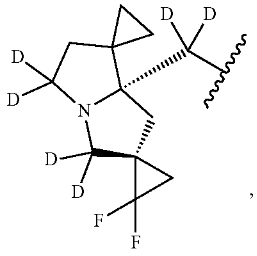
, and
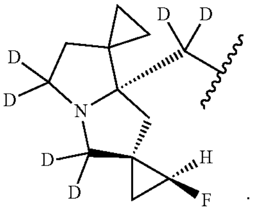
.

Another embodiment provides the compound of Formula (I), (Ia), (Ib), (Ic), or (Id), or a pharmaceutically acceptable salt or solvate thereof, wherein $R^1$ is selected from:

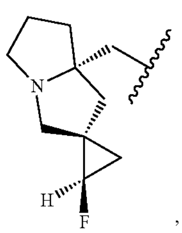
,
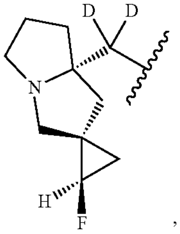
,
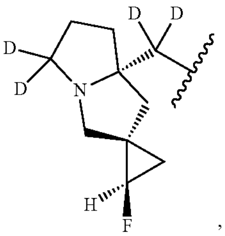
,
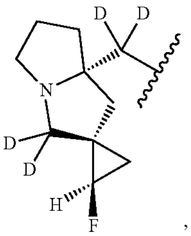
,
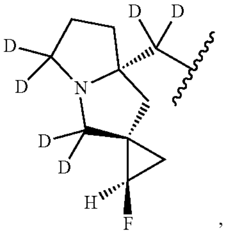
,
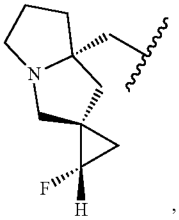
,
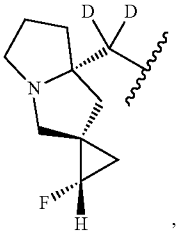
,
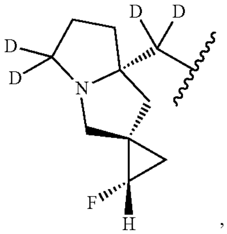
, -continued

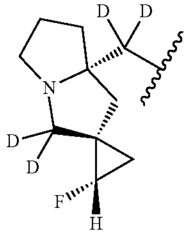
, and
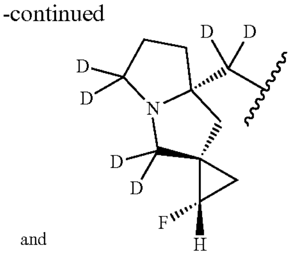
.

Another embodiment provides the compound of Formula (I), (Ia), (Ib), (Ic), or (Id), or a

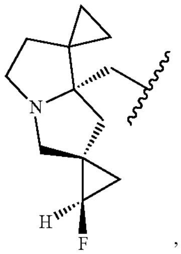
,
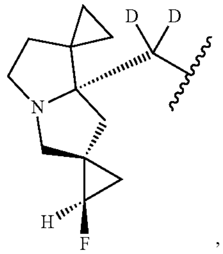
,
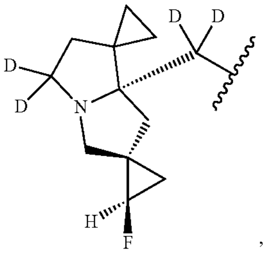
,
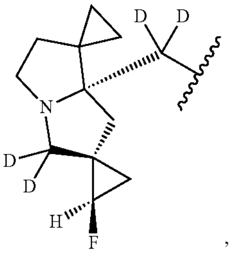
,
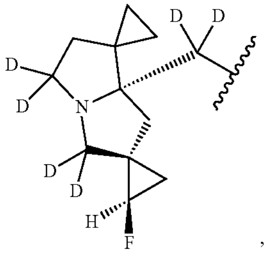
,
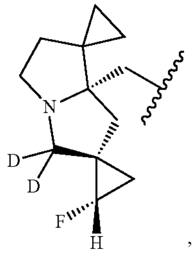
,
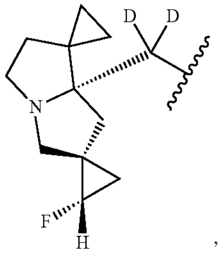
,
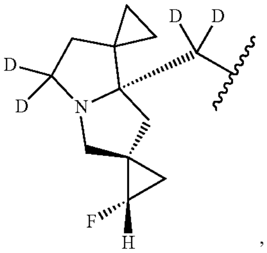
,
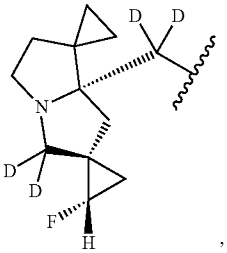
, and
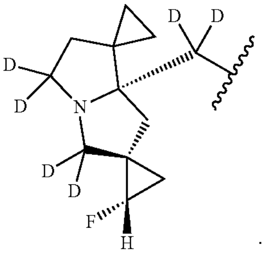
.

Another embodiment provides the compound of Formula (I), (Ia), (Ib), (Ic), or (Id), or a pharmaceutically acceptable salt or solvate thereof, wherein $R^1$ is selected from:

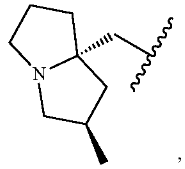 , 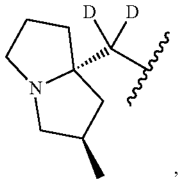 , 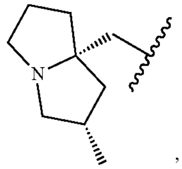 ,
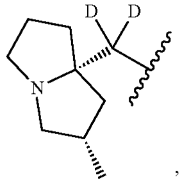 , 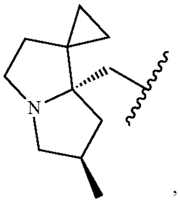 ,
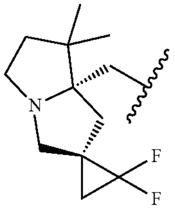 , 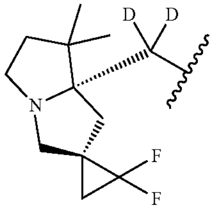 ,
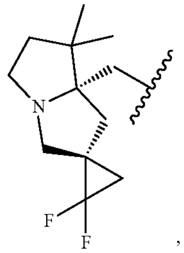 , 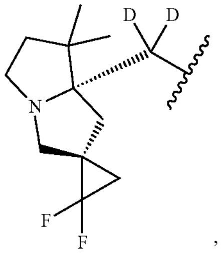 , and
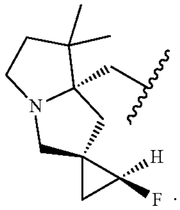 .
Another embodiment provides the compound of Formula (I), (Ia), (Ib), (Ic), or (Id), or a pharmaceutically acceptable salt or solvate thereof, wherein $R^1$ is selected from:
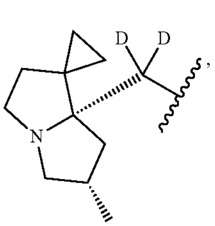 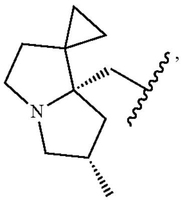
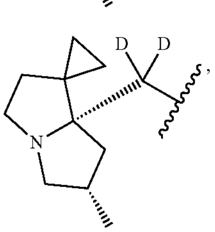 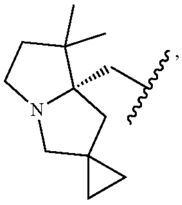
-continued
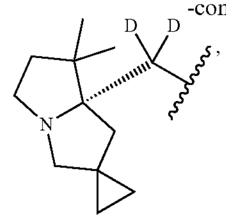 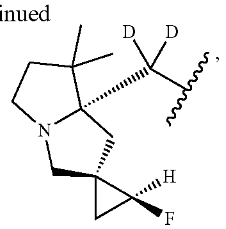
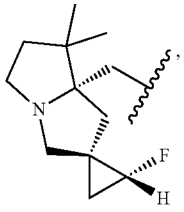 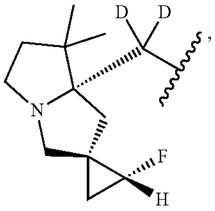
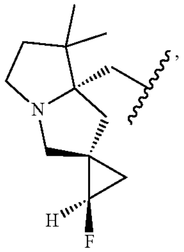 and 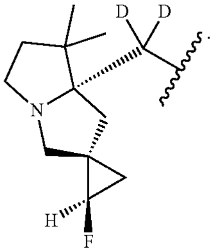
Another embodiment provides the compound of Formula (I), (Ia), (Ib), (Ic), or (Id), or a
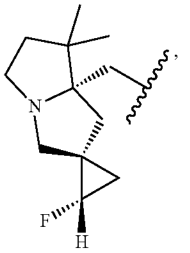 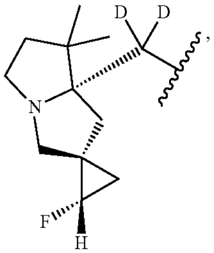
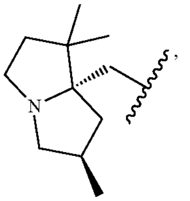 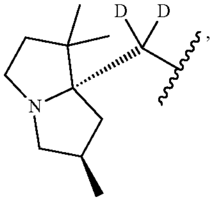
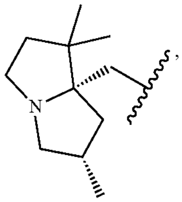 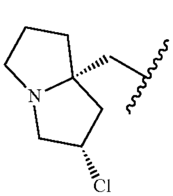
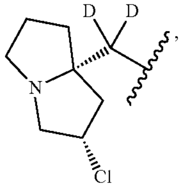 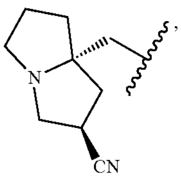

-continued

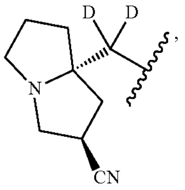

and

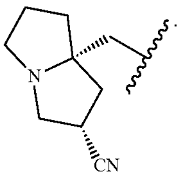

Another embodiment provides the compound of Formula (I), (Ia), (Ib), (Ic), or (Id), or a pharmaceutically acceptable salt or solvate thereof, wherein $R^1$ is selected from:

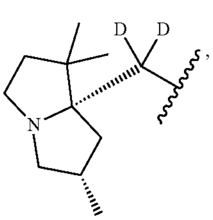
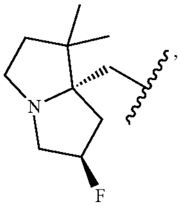
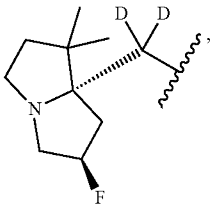
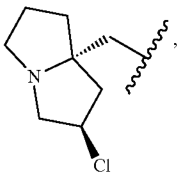
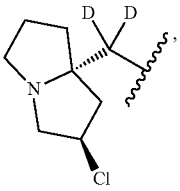
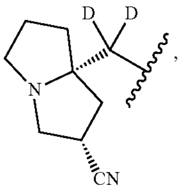
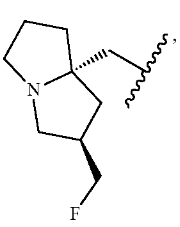
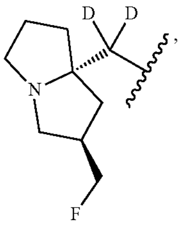
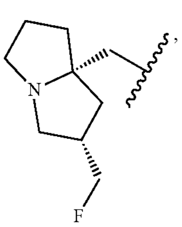

and

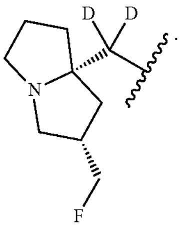

Another embodiment provides the compound of Formula (I), (Ia), (Ib), (Ic), or (Id), or a pharmaceutically acceptable salt or solvate thereof, wherein $R^1$ is selected from:

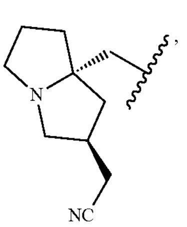
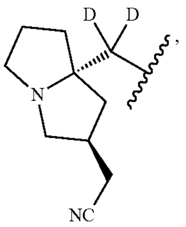
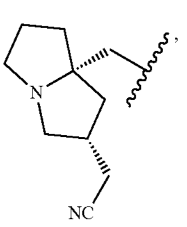
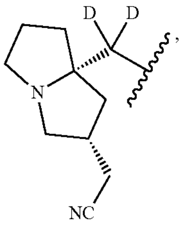
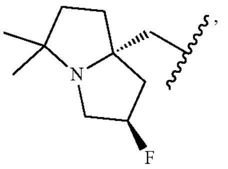
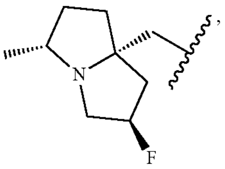
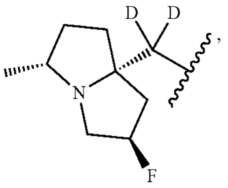
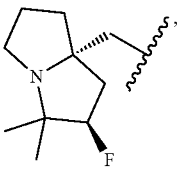
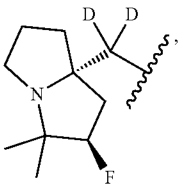

and

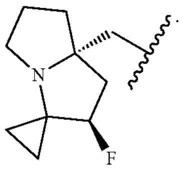

Another embodiment provides the compound of Formula (I), (Ia), (Ib), (Ic), or (Id), or a

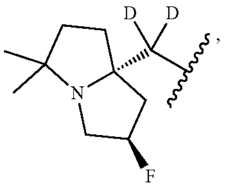
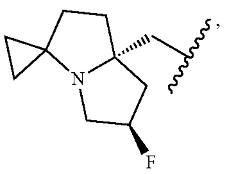
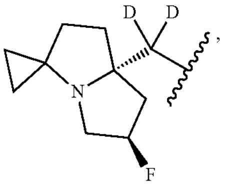
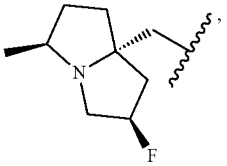
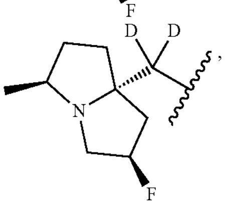
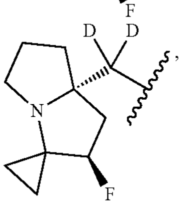

-continued

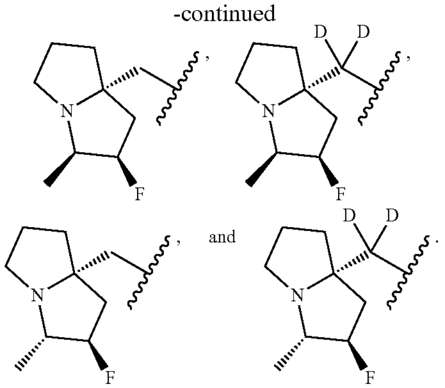

, , and .

Another embodiment provides the compound of Formula (I), (Ia), (Ib), (Ic), or (Id), or a pharmaceutically acceptable salt or solvate thereof, wherein $R^1$ is selected from:

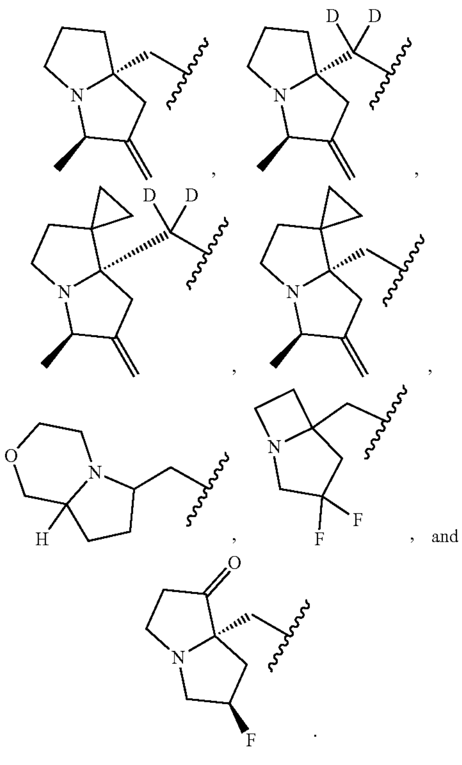

, , , , , and .

Another embodiment provides the compound of Formula (I), (Ia), (Ib), (Ic), or (Id), or a pharmaceutically acceptable salt or solvate thereof, wherein —$N(R^2)R^3$ form an optionally substituted heterocyclyl selected from:

(a) optionally substituted 2-azabicyclo[4.1.0]heptan-2-yl;

(b) optionally substituted 2-oxa-5-azabicyclo[4.1.0]heptan-5-yl;

(c) optionally substituted 2-azabicyclo[5.1.0]octan-2-yl;

(d) optionally substituted 2-oxa-6-azabicyclo[5.1.0]octan-6-yl (e) optionally substituted 5-oxa-2-azabicyclo[5.1.0]octan-2-yl;

(f) optionally substituted 2-azabicyclo[6.1.0]nonan-2-yl;

(g) optionally substituted 2-oxa-7-azabicyclo[6.1.0]nonan-7-yl;

(h) optionally substituted 6-oxa-2-azabicyclo[6.1.0]nonan-2-yl;

(i) optionally substituted 5-oxa-2-azabicyclo[6.1.0]nonan-2-yl (i) optionally substituted 2-azabicyclo[5.1.0]oct-5-en-2-yl;

(k) optionally substituted 2-azabicyclo[5.1.0]oct-4-en-2-yl;

(l) optionally substituted 2-azabicyclo[3.1.0]hexan-2-yl;

(m) optionally substituted 2-azabicyclo[6.1.0]non-4-en-2-yl;

(n) optionally substituted 2-azabicyclo[6.1.0]non-5-en-2-yl; or (o) optionally substituted 2-azabicyclo[6.1.0]non-6-en-2-yl.

In some embodiments, —$N(R^2)R^3$ form an optionally substituted 2-azabicyclo[4.1.0]heptan-2-yl. In some embodiments, —$N(R^2)R^3$ form an optionally substituted 2-oxa-5-azabicyclo[4.1.0]heptan-5-yl. In some embodiments, —$N(R^2)R^3$ form an optionally substituted 2-azabicyclo[5.1.0]octan-2-yl. In some embodiments, the optionally substituted 2-azabicyclo[5.1.0]octan-2-yl is substituted with an oxo group. In some embodiments, —$N(R^2)R^3$ form an optionally substituted 2-oxa-6-azabicyclo[5.1.0]octan-6-yl. In some embodiments, —N $(R^2)R^3$ form an optionally substituted 5-oxa-2-azabicyclo[5.1.0]octan-2-yl. In some embodiments, —$N(R^2)R^3$ form an optionally substituted 2-azabicyclo[6.1.0]nonan-2-yl. In some embodiments, —$N(R^2)R^3$ form an optionally substituted 2-oxa-7-azabicyclo[6.1.0]nonan-7-yl. In some embodiments, —$N(R^2)R^3$ form an optionally substituted 6-oxa-2-azabicyclo[6.1.0]nonan-2-yl. In some embodiments, —$N(R^2)R^3$ form an optionally substituted 5-oxa-2-azabicyclo[6.1.0]nonan-2-yl. In some embodiments, —$N(R^2)R^3$ form an optionally substituted 2-azabicyclo[5.1.0]oct-5-en-2-yl. In some embodiments, —$N(R^2)R^3$ form an optionally substituted 2-azabicyclo[5.1.0]oct-4-en-2-yl. In some embodiments, —$N(R^2)$ $R^3$ form an optionally substituted 2-azabicyclo[3.1.0]hexan-2-yl. In some embodiments, —$N(R^2)R^3$ form an optionally substituted 2-azabicyclo[6.1.0]non-4-en-2-yl. In some embodiments, —$N(R^2)R^3$ form an optionally substituted 2-azabicyclo[6.1.0]non-5-en-2-yl. In some embodiments, N $(R^2)R^3$ form an optionally substituted 2-azabicyclo[6.1.0]non-6-en-2-yl. In some embodiments, the optionally substituted heterocyclyl is optionally substituted with a group selected from the group consisting of halogen, cyano, and hydroxyl. In some embodiments, the group is chloro. In some embodiments, the group is fluoro.

Another embodiment provides the compound of Formula (I), (Ia), (Ib), (Ic), or (Id), or a pharmaceutically acceptable salt or solvate thereof, wherein the optionally substituted azabicyclo[5.1.0]octane heterocyclyl has a structure selected from:

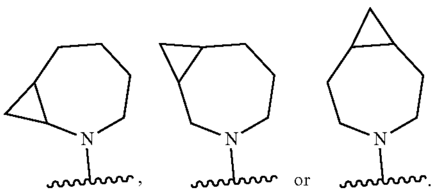

, or .

Another embodiment provides the compound of Formula (I), (Ia), (Ib), (Ic), or (Id), or a pharmaceutically acceptable salt or solvate thereof, wherein the optionally substituted azabicyclo[5.1.0]octane heterocyclyl has a structure selected from:

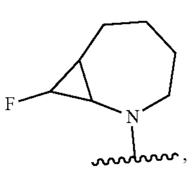, 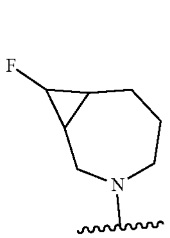 or 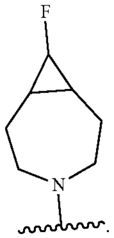.

Another embodiment provides the compound of Formula (I), (Ia), (Ib), (Ic), or (Id), or a pharmaceutically acceptable salt or solvate thereof, wherein the optionally substituted azabicyclo[5.1.0]octane heterocyclyl has a structure selected from:

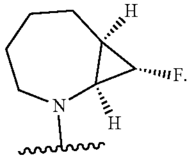 [SMILES: *N1CCCC[C@H]2[C@H](F)[C@H]21]

Another embodiment provides the compound of Formula (I), (Ia), (Ib), (Ic), or (Id), or a pharmaceutically acceptable salt or solvate thereof, wherein the optionally substituted azabicyclo[5.1.0]octane heterocyclyl has a structure selected from:

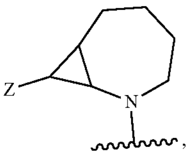, 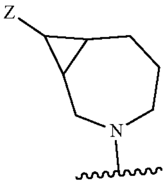 or 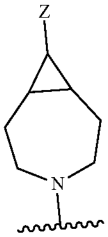

wherein Z is selected from the group consisting of halogen, cyano, and hydroxyl. In some embodiments, the halogen is fluor or chloro.

Another embodiment provides the compound of Formula (I), (Ia), (Ib), (Ic), or (Id), or a pharmaceutically acceptable salt or solvate thereof, wherein the optionally substituted azabicyclo[5.1.0]octane heterocyclyl has a structure selected from:

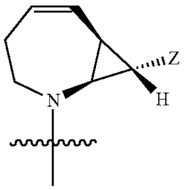 or 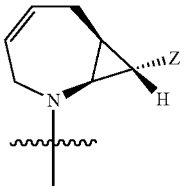

wherein Z is selected from the group consisting of halogen, cyano, and hydroxyl. In some embodiments, the halogen is fluoro or chloro.

Another embodiment provides the compound of Formula (I), (Ia), (Ib), (Ic), or (Id), or a pharmaceutically acceptable salt or solvate thereof, wherein the optionally substituted oxazabicyclo[4.1.0]heptane heterocyclyl has a structure selected from:

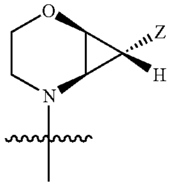

wherein Z is selected from the group consisting of halogen, cyano, and hydroxyl. In some embodiments, the halogen is fluoro or chloro.

Another embodiment provides the compound of Formula (I), (Ia), (Ib), (Ic), or (Id), or a pharmaceutically acceptable salt or solvate thereof, wherein the optionally substituted azabicyclo[4.1.0]heptane heterocyclyl has a structure selected from:

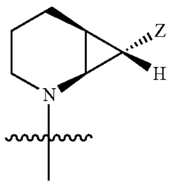

wherein Z is selected from the group consisting of halogen, cyano, and hydroxyl. In some embodiments, the halogen is fluoro or chloro.

Another embodiment provides the compound of Formula (I), (Ia), (Ib), (Ic), or (Id), or a pharmaceutically acceptable salt or solvate thereof, wherein the optionally substituted azabicyclo[3.1.0]hexane heterocyclyl has a structure selected from:

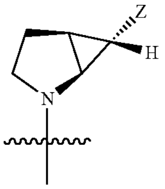

wherein Z is selected from the group consisting of halogen, cyano, and hydroxyl. In some embodiments, the halogen is fluoro or chloro.

Another embodiment provides the compound of Formula (I), (Ia), (Ib), (Ic), or (Id), or a pharmaceutically acceptable salt or solvate thereof, wherein the optionally substituted azabicyclo[5.1.0]octane heterocyclyl has a structure selected from:

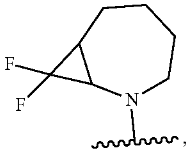, 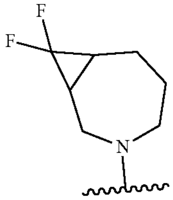 or 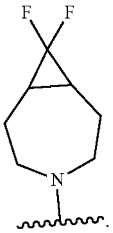.

Another embodiment provides the compound of Formula (I), (Ia), (Ib), (Ic), or (Id), or a pharmaceutically acceptable salt or solvate thereof, wherein the optionally substituted oxazabicyclo[5.1.0]octane heterocyclyl has a structure selected from:

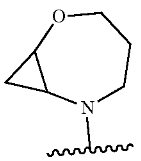 or 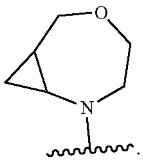.

Another embodiment provides the compound of Formula (I), (Ia), (Ib), (Ic), or (Id), or a pharmaceutically acceptable salt or solvate thereof, wherein the optionally substituted oxazabicyclo[5.1.0]octane heterocyclyl is:

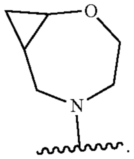 [SMILES: *N1CCOC2CC2C1].

Another embodiment provides the compound of Formula (I), (Ia), (Ib), (Ic), or (Id), or a pharmaceutically acceptable salt or solvate thereof, wherein the optionally substituted oxazabicyclo[5.1.0]octane heterocyclyl has a structure selected from:

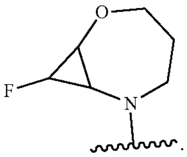 [SMILES: *N1CCCOC2C(F)C21].

Another embodiment provides the compound of Formula (I), (Ia), (Ib), (Ic), or (Id), or a pharmaceutically acceptable salt or solvate thereof, wherein the optionally substituted oxazabicyclo[5.1.0]octane heterocyclyl has a structure selected from:

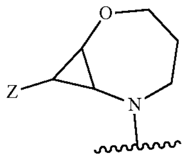

wherein Z is selected from the group consisting of halogen, cyano, and hydroxyl. In some embodiments, the halogen is fluoro or chloro.

Another embodiment provides the compound of Formula (I), (Ia), (Ib), (Ic), or (Id), or a pharmaceutically acceptable salt or solvate thereof, wherein the optionally substituted oxazabicyclo[5.1.0]octane heterocyclyl has a structure selected from:

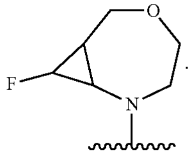.

Another embodiment provides the compound of Formula (I), (Ia), (Ib), (Ic), or (Id), or a pharmaceutically acceptable salt or solvate thereof, wherein the optionally substituted oxazabicyclo[5.1.0]octane heterocyclyl has a structure selected from:

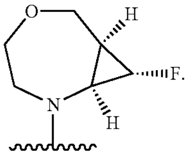 [SMILES: *N1CCOC[C@H]2[C@H](F)[C@H]21].

Another embodiment provides the compound of Formula (I), (Ia), (Ib), (Ic), or (Id), or a pharmaceutically acceptable salt or solvate thereof, wherein the optionally substituted oxazabicyclo[5.1.0]octane heterocyclyl has a structure selected from:

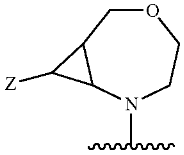

wherein Z is selected from the group consisting of halogen, cyano, and hydroxyl. In some embodiments, the halogen is fluoro or chloro.

Another embodiment provides the compound of Formula (I), (Ia), (Ib), (Ic), or (Id), or a pharmaceutically acceptable salt or solvate thereof, wherein the optionally substituted oxazabicyclo[5.1.0]octane heterocyclyl has a structure selected from:

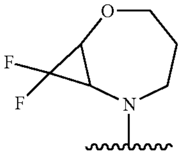 or 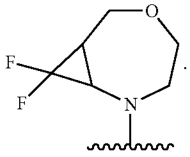.

Another embodiment provides the compound of Formula (I), (Ia), (Ib), (Ic), or (Id), or a pharmaceutically acceptable salt or solvate thereof, wherein the optionally substituted oxazabicyclo[6.1.0]nonane heterocyclyl has a structure selected from:

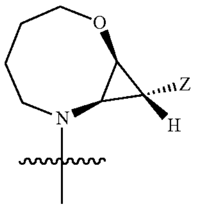
or
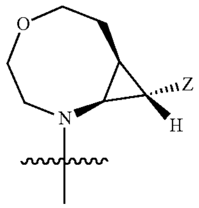

wherein Z is selected from the group consisting of halogen, cyano, and hydroxyl. In some embodiments, the halogen is fluoro or chloro.

Another embodiment provides the compound of Formula (I), (Ia), (Ib), (Ic), or (Id), or a pharmaceutically acceptable salt or solvate thereof, wherein the optionally substituted azabicyclo[6.1.0]nonane heterocyclyl has a structure selected from:

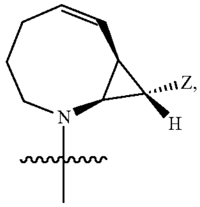
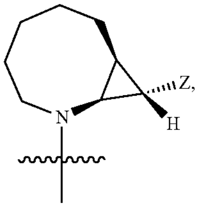
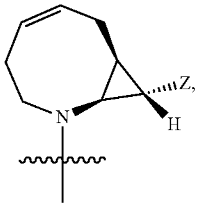
or
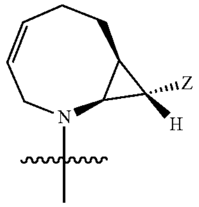

wherein Z is selected from the group consisting of halogen, cyano, and hydroxyl. In some embodiments, the halogen is fluoro or chloro.

Another embodiment provides the compound of Formula (I), (Ia), (Ib), (Ic), or (Id), or a pharmaceutically acceptable salt or solvate thereof, wherein —N($R^2$)$R^3$ form an optionally substituted azabicyclo[4.1.0]heptane heterocyclyl.

Another embodiment provides the compound of Formula (I), (Ia), (Ib), (Ic), or (Id), or a pharmaceutically acceptable salt or solvate thereof, wherein —N($R^2$)$R^3$ form an optionally substituted oxazabicyclo[4.1.0]heptane heterocyclyl.

Another embodiment provides the compound of Formula (I), (Ia), (Ib), (Ic), or (Id), or a pharmaceutically acceptable salt or solvate thereof, wherein —N($R^2$)$R^3$ form an optionally substituted azabicyclo[6.1.0]nonane heterocyclyl.

Another embodiment provides the compound of Formula (I), (Ia), (Ib), (Ic), or (Id), or a pharmaceutically acceptable salt or solvate thereof, wherein —N($R^2$)$R^3$ form an optionally substituted oxazabicyclo[6.1.0]nonane heterocyclyl.

Another embodiment provides the compound of Formula (I), (Ia), (Ib), (Ic), or (Id), or a pharmaceutically acceptable salt or solvate thereof, wherein —N($R^2$)$R^3$ form a group selected from:

optionally substituted 3-oxa-2,6-diazabicyclo[5.1.0]oct-1-en-6-yl;

optionally substituted 2-oxa-3,6-diazabicyclo[5.1.0]oct-3-en-6-yl;

optionally substituted 4-oxa-2,5-diazabicyclo[5.1.0]oct-5-en-2-yl;

optionally substituted 3-oxa-2,7-diazabicyclo[6.1.0]non-1-en-7-yl;

optionally substituted 2-oxa-3,7-diazabicyclo[6.1.0]non-3-en-7-yl;

optionally substituted 5-oxa-2,6-diazabicyclo[6.1.0]non-6-en-2-yl;

optionally substituted 6-oxa-2,5-diazabicyclo[6.1.0]non-4-en-2-yl; and optionally substituted 4-oxa-2,5-diazabicyclo[6.1.0]non-5-en-2-yl.

In some embodiments, the group is optionally substituted with a halogen.

In some embodiments, N ($R^2$)$R^3$ form a group selected from:

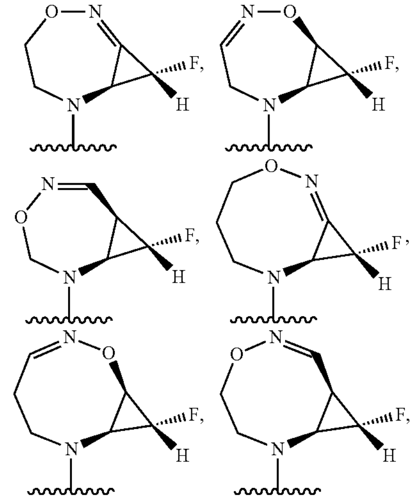
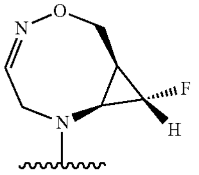
and
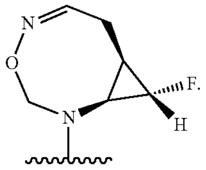

In some embodiments, —N($R^2$)$R^3$ form a group selected from:

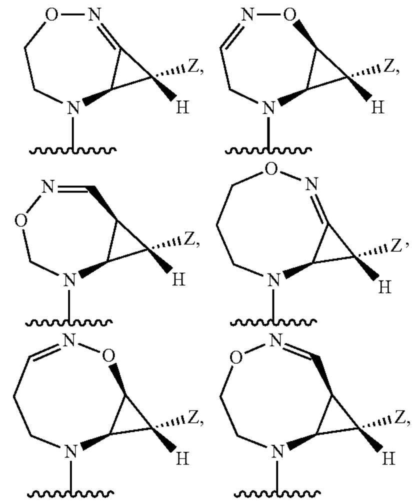

-continued

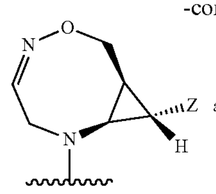 and 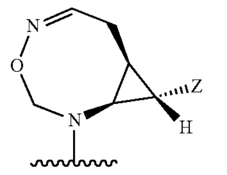

wherein Z is selected from the group consisting of halogen, cyano, and hydroxyl.

Another embodiment provides the compound of Formula (I), (Ia), (Ib), (Ic), or (Id), or a pharmaceutically acceptable salt or solvate thereof, wherein $R^4$ is H. In some embodiments, $R^4$ is optionally substituted $C_1$-$C_4$ alkoxy. In some embodiments, $R^4$ is-$OCH_3$. In some embodiments, $R^4$ is optionally substituted $C_1$-$C_6$ alkyl. In some embodiments, $R^4$ is selected from optionally substituted $C_1$-$C_6$ cycloalkyl or $C_1$-$C_6$ cycloalkylalkyl. In some embodiments, $R^4$ is cyano. In some embodiments, $R^4$ is halogen. In some embodiments, $R^4$ is selected from H, optionally substituted $C_1$-$C_6$ alkyl, optionally substituted $C_1$-$C_6$ cycloalkyl, $C_1$-$C_6$ cycloalkylalkyl, cyano, or halogen.

Another embodiment provides the compound of Formula (I), (Ia), (Ib), (Ic), or (Id), or a pharmaceutically acceptable salt or solvate thereof, wherein $R^4$ is H, and Rè is:

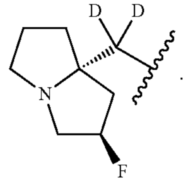 [SMILES: *C([2H])([2H])[C@@]12CCCN1C[C@H](F)C2].

In some embodiments, $X^1$ and $X^3$ are N, and $X^2$ is C—F.

In some embodiments, Ar is selected from:

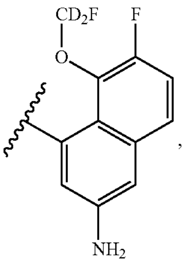, 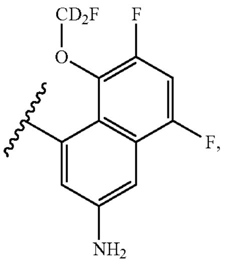,

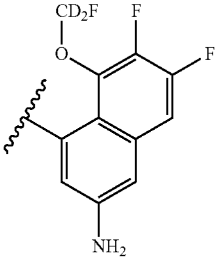 and 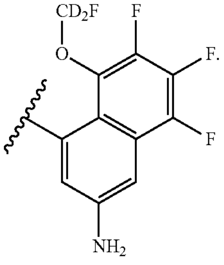.

In some embodiments, Ar is selected from:

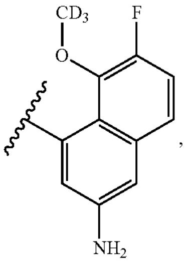, 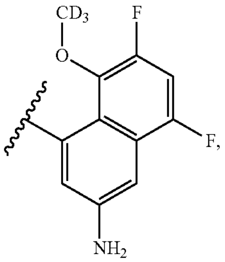,

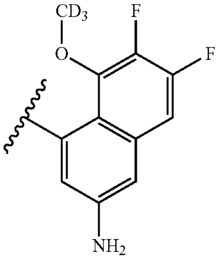 and 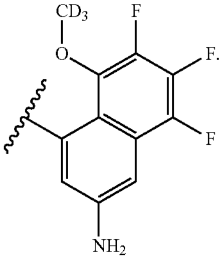.

In some embodiments, Ar is selected from:

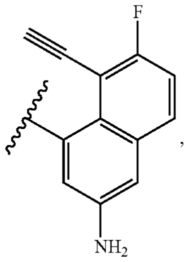, 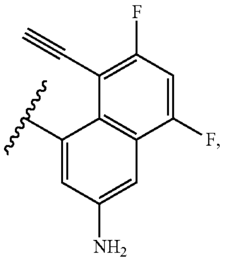,

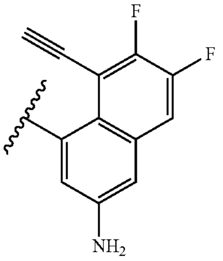 and 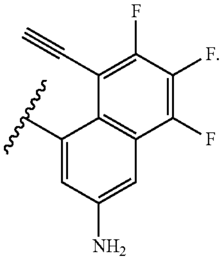.

In some embodiments, Ar is selected from:

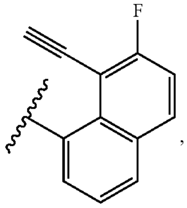, 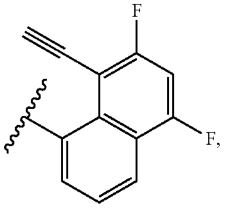,

-continued

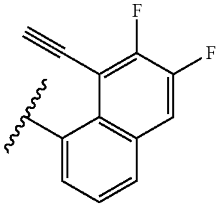 and 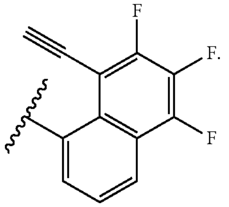

In some embodiments, Ar is selected from:

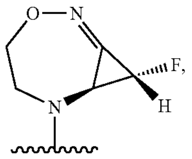 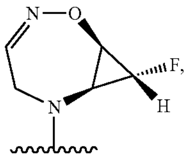

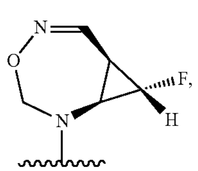 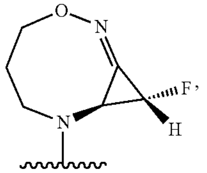

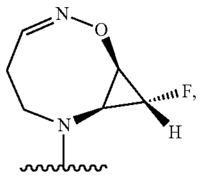 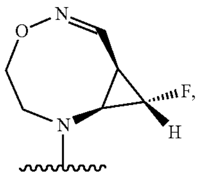

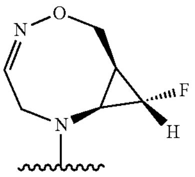 and 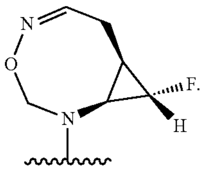

In some embodiments, Ar is selected from:

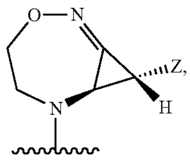 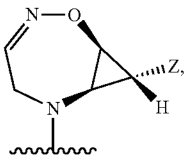

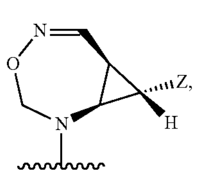 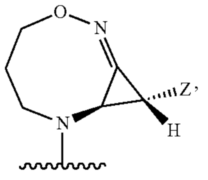

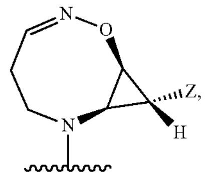 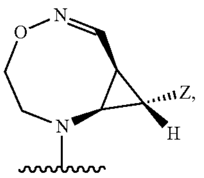

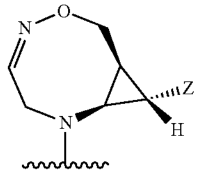 and 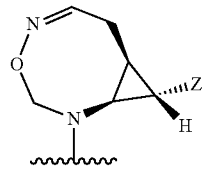

wherein Z is selected from the group consisting of halogen, cyano, and hydroxyl. In some embodiments, the halogen is fluoro or chloro.

One embodiment provides a KRAS inhibitory compound, or a pharmaceutically acceptable salt or solvate thereof, having a structure presented in Table 1.

TABLE 1

| Example No. | Structure | Name |
|---|---|---|
| 1 | 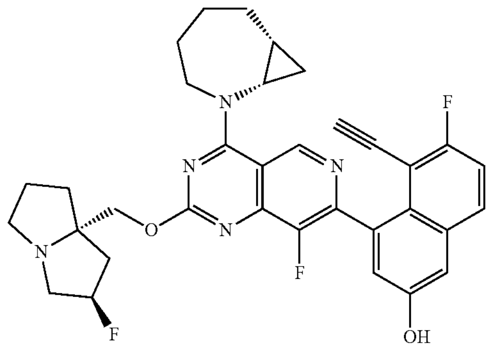 [SMILES: C#Cc1c(F)ccc2cc(O)cc(-c3ncc4c(N5CCCC[C@@H]6C[C@@H]65)nc(OC[C@@]56CCCN5C[C@H](F)C6)nc4c3F)c12] | 4-(4-((1S,7R)-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-ol |

TABLE 1-continued

| Example No. | Structure | Name |
|---|---|---|
| 2 | 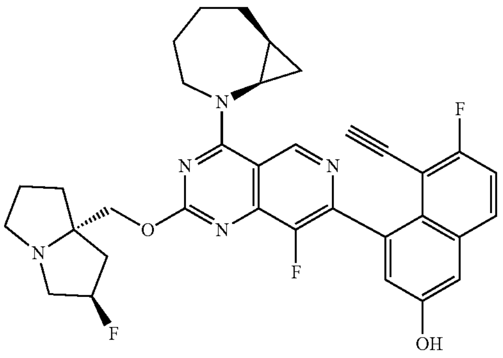 [SMILES: C#Cc1c(F)ccc2cc(O)cc(-c3ncc4c(N5CCCC[C@H]6C[C@H]65)nc(OC[C@@]56CCCN5C[C@H](F)C6)nc4c3F)c12] | 4-(4-((1R,7S)-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-ol |
| 3 | 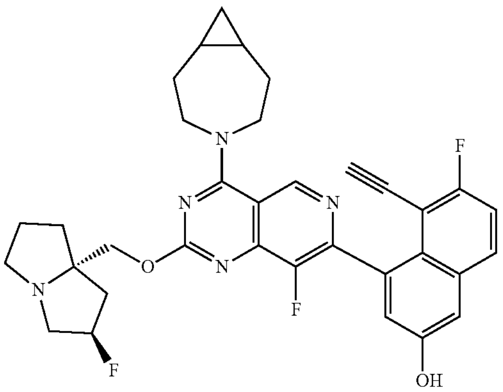 [SMILES: C#Cc1c(F)ccc2cc(O)cc(-c3ncc4c(N5CCC6CC6CC5)nc(OC[C@@]56CCCN5C[C@H](F)C6)nc4c3F)c12] | 4-(4-(4-azabicyclo[5.1.0]octan-4-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-ol |
| 4 | 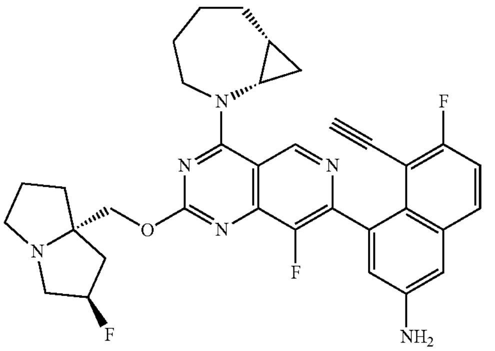 [SMILES: C#Cc1c(F)ccc2cc(N)cc(-c3ncc4c(N5CCCC[C@@H]6C[C@@H]65)nc(OC[C@@]56CCCN5C[C@H](F)C6)nc4c3F)c12] | 4-(4-((1S,7R)-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-amine |
| 5 | 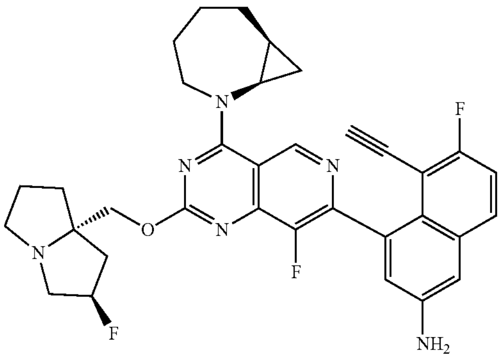 [SMILES: C#Cc1c(F)ccc2cc(N)cc(-c3ncc4c(N5CCCC[C@H]6C[C@H]65)nc(OC[C@@]56CCCN5C[C@H](F)C6)nc4c3F)c12] | 4-(4-((1R,7S)-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-amine |

TABLE 1-continued

| Example No. | Structure | Name |
|---|---|---|
| 6 | 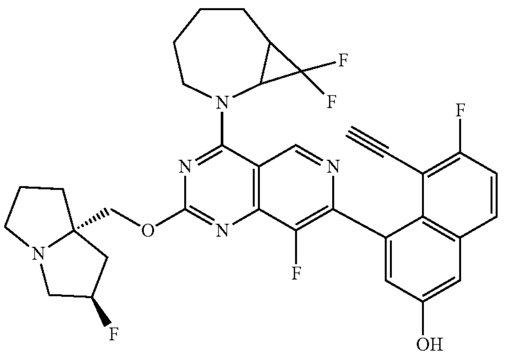 [SMILES: C#Cc1c(F)ccc2cc(O)cc(-c3ncc4c(N5CCCCC6C5C6(F)F)nc(OC[C@@]56CCCN5C[C@H](F)C6)nc4c3F)c12] | 4-(4-(8,8-difluoro-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-ol |
| 7 | 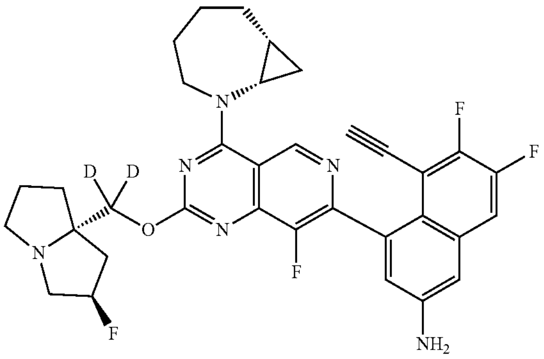 [SMILES: [2H]C([2H])(Oc1nc(N2CCCC[C@@H]3C[C@@H]32)c2cnc(-c3cc(N)cc4cc(F)c(F)c(C#C)c34)c(F)c2n1)[C@@]12CCCN1C[C@H](F)C2] | 4-(4-((1S,7R)-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6.7-difluoronaphthalen-2-amme |
| 8 | 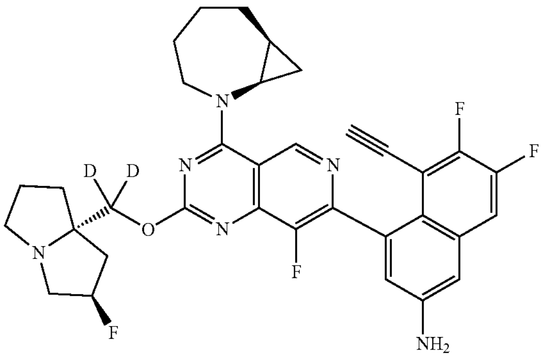 [SMILES: [2H]C([2H])(Oc1nc(N2CCCC[C@H]3C[C@H]32)c2cnc(-c3cc(N)cc4cc(F)c(F)c(C#C)c34)c(F)c2n1)[C@@]12CCCN1C[C@H](F)C2] | 4-(4-((1R,7S)-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 9 | 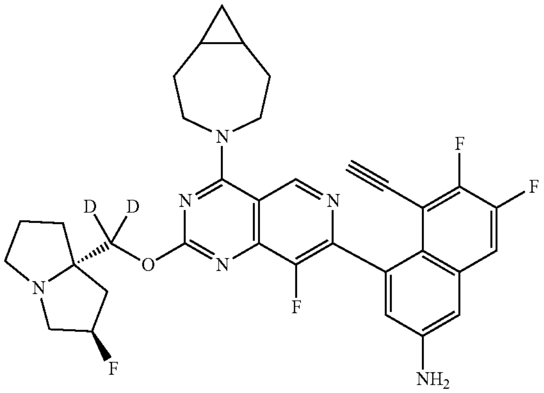 [SMILES: [2H]C([2H])(Oc1nc(N2CCC3CC3CC2)c2cnc(-c3cc(N)cc4cc(F)c(F)c(C#C)c34)c(F)c2n1)[C@@]12CCCN1C[C@H](F)C2] | 4-(4-(4-azabicyclo[5.1.0]octan-4-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |

TABLE 1-continued

| Example No. | Structure | Name |
| --- | --- | --- |
| 10 | 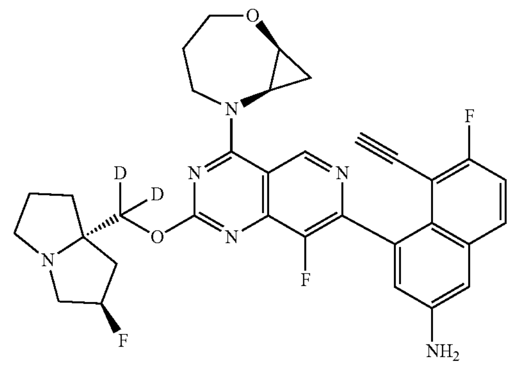 [SMILES: [2H]C([2H])(Oc1nc(N2CCCO[C@H]3C[C@H]32)c2cnc(-c3cc(N)cc4ccc(F)c(C#C)c34)c(F)c2n1)[C@@]12CCCN1C[C@H](F)C2] | 4-(4-((1S,7R)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-ol |
| 11 | 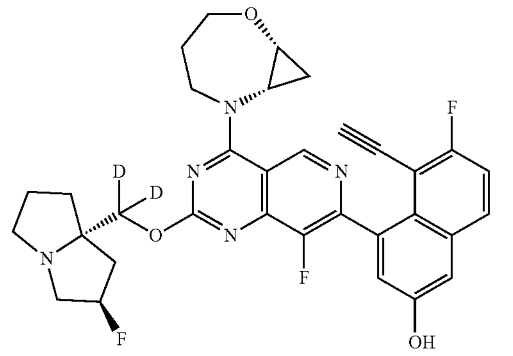 [SMILES: [2H]C([2H])(Oc1nc(N2CCCO[C@@H]3C[C@@H]32)c2cnc(-c3cc(O)cc4ccc(F)c(C#C)c34)c(F)c2n1)[C@@]12CCCN1C[C@H](F)C2] | 4-(4-((1R,7S)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-ol |
| 12 | 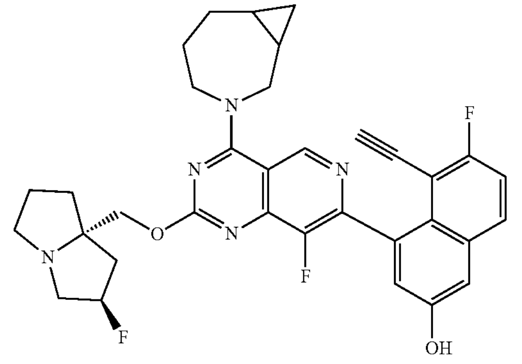 [SMILES: C#Cc1c(F)ccc2cc(O)cc(-c3ncc4c(N5CCCC6CC6C5)nc(OC[C@@]56CCCN5C[C@H](F)C6)nc4c3F)c12] | 4-(4-(3-azabicyclo[5.1.0]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-ol |
| 13 | 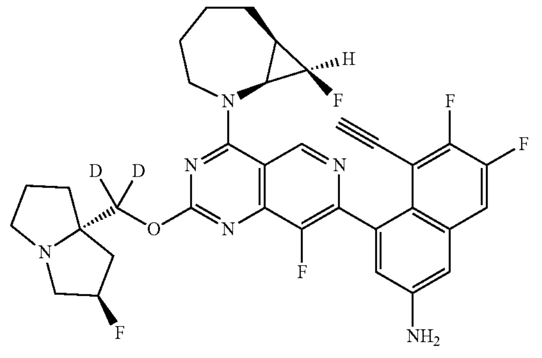 [SMILES: [2H]C([2H])(Oc1nc(N2CCCC[C@H]3[C@@H](F)[C@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1S,7R,8R)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
|---|---|---|
| 14 | 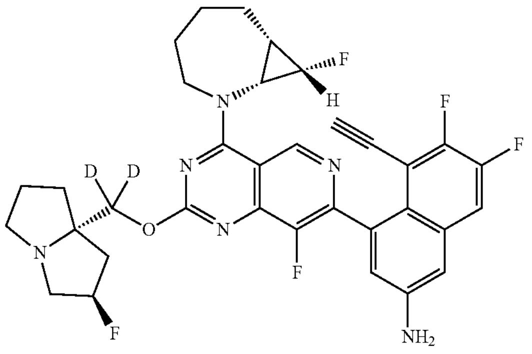 [SMILES: [2H]C([2H])(Oc1nc(N2CCCC[C@@H]3[C@@H](F)[C@@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1R,7S,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 15 | 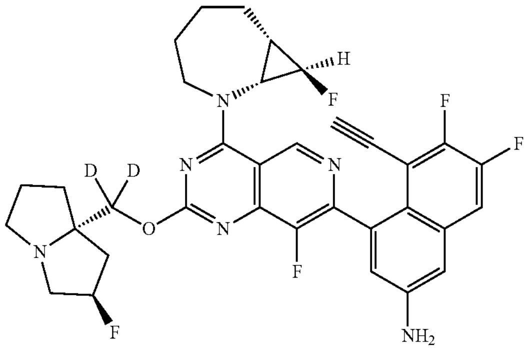 | 5-ethynyl-6,7-difluoro-4-(8-fluoro-4-((1R,7S,8R)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 16 | 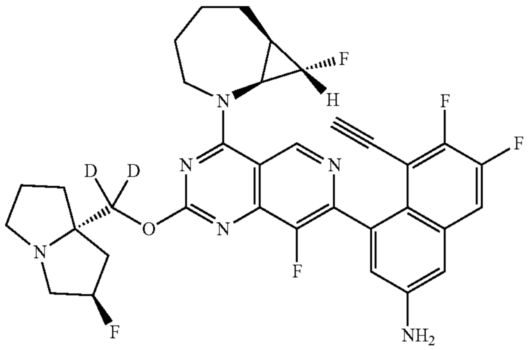 [SMILES: [2H]C([2H])(Oc1nc(N2CCCC[C@H]3[C@H](F)[C@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)ynaphthalen-2-amine |
| 17 | 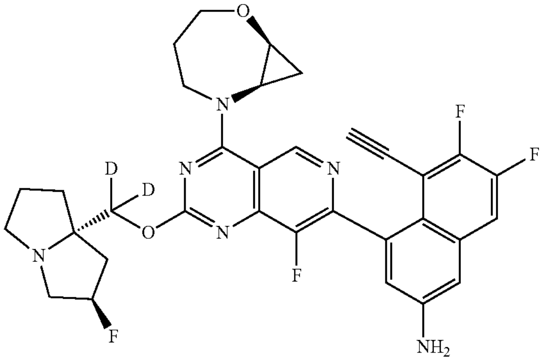 [SMILES: [2H]C([2H])(Oc1nc(N2CCCO[C@H]3C[C@H]32)c2cnc(-c3cc(N)cc4cc(F)c(F)c(C#C)c34)c(F)c2n1)[C@@]12CCCN1C[C@H](F)C2] | 4-(4-((1S,7R)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |

TABLE 1-continued

| Example No. | Structure | Name |
|---|---|---|
| 18 | 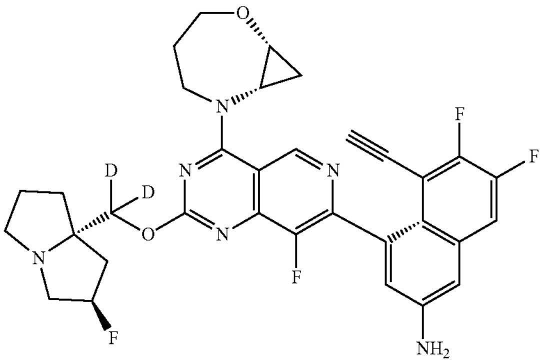 | 4-(4-((1R,7S)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 19 | 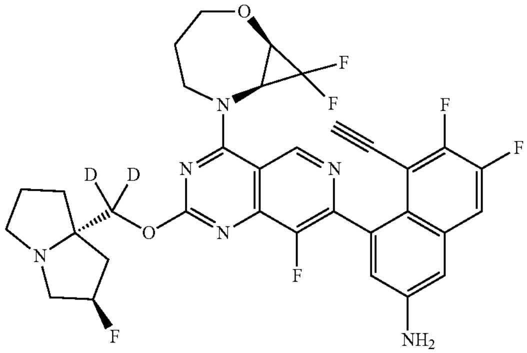 [SMILES: [2H]C([2H])(Oc1nc(N2CCCO[C@@H]3[C@H]2C3(F)F)c2cnc(-c3cc(N)cc4cc(F)c(F)c(C#C)c34)c(F)c2n1)[C@@]12CCCN1C[C@H](F)C2] | 4-(4-((1S,7S)-8,8-difluoro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 20 | 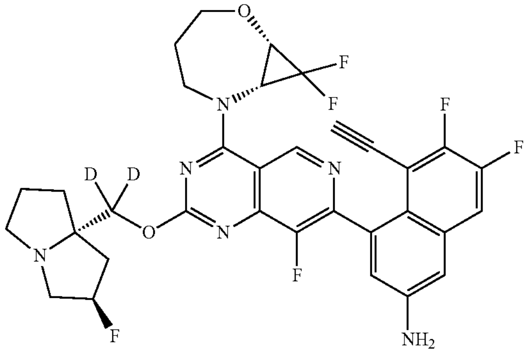 [SMILES: [2H]C([2H])(Oc1nc(N2CCCO[C@H]3[C@@H]2C3(F)F)c2cnc(-c3cc(N)cc4cc(F)c(F)c(C#C)c34)c(F)c2n1)[C@@]12CCCN1C[C@H](F)C2] | 4-(4-((1R,7R)-8,8-difluoro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 21 | 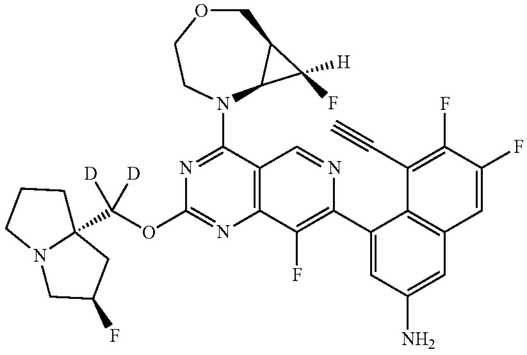 [SMILES: [2H]C([2H])(Oc1nc(N2CCOC[C@H]3[C@@H](F)[C@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1R,7S,8S)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
| --- | --- | --- |
| 22 | 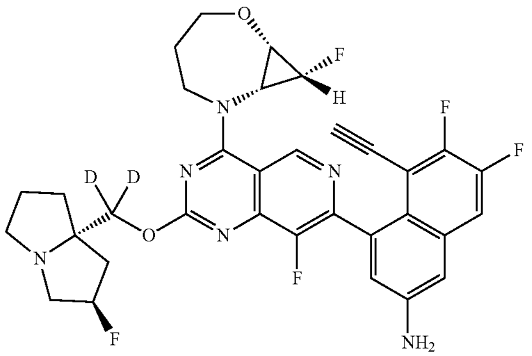 [SMILES: [2H]C([2H])(Oc1nc(N2CCCO[C@@H]3[C@H](F)[C@@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1S,7R,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 23 | 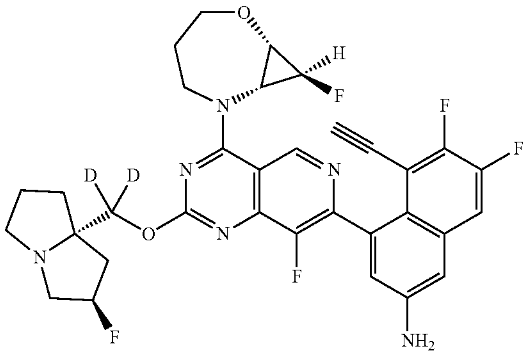 [SMILES: [2H]C([2H])(Oc1nc(N2CCCO[C@@H]3[C@@H](F)[C@@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1S,7R,8S)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 24 | 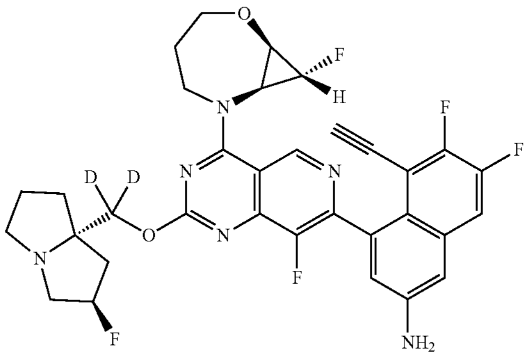 [SMILES: [2H]C([2H])(Oc1nc(N2CCCO[C@H]3[C@H](F)[C@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 25 | 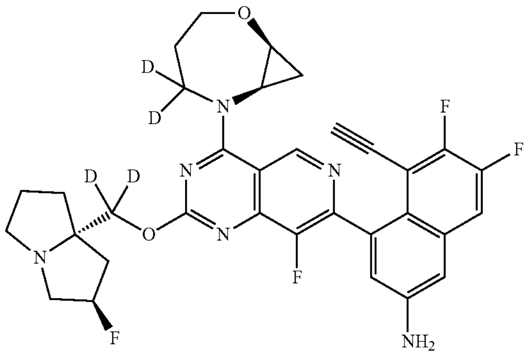 [SMILES: [2H]C1([2H])CCO[C@H]2C[C@H]2N1c1nc(OC([2H])([2H])[C@@]23CCCN2C[C@H](F)C3)nc2c(F)c(-c3cc(N)cc4cc(F)c(F)c(C#C)c34)ncc12] | 4-(4-((1S,7R)-2-oxa-6-azabicyclo[5.1.0]octan-6-yl-5,5-d2)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |

TABLE 1-continued

| Example No. | Structure | Name |
|---|---|---|
| 26 | 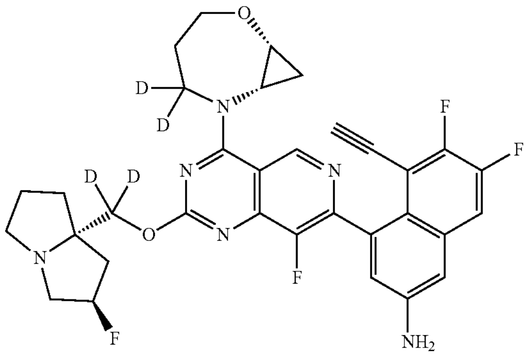 [SMILES: [2H]C1([2H])CCO[C@@H]2C[C@@H]2N1c1nc(OC([2H])([2H])[C@@]23CCCN2C[C@H](F)C3)nc2c(F)c(-c3cc(N)cc4cc(F)c(F)c(C#C)c34)ncc12] | 4-(4-((1R,7S)-2-oxa-6-azabicyclo[5.1.0]octan-6-yl-5,5-d2)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 27 | 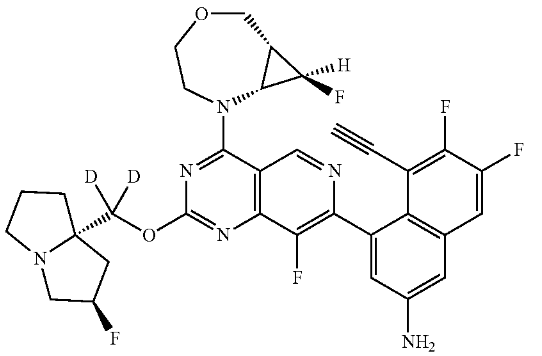 [SMILES: [2H]C([2H])(Oc1nc(N2CCOC[C@@H]3[C@@H](F)[C@@H]32)c2cnc(-c3cc(N)cc4cc(F)c(F)c(C#C)c34)c(F)c2n1)[C@@]12CCCN1C[C@H](F)C2] | 5-ethynyl-6.7-difluoro-4-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 28 | 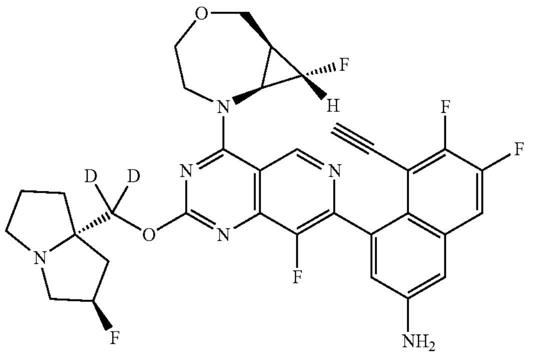 | 5-ethynyl-6,7-difluoro-4~(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 29 | 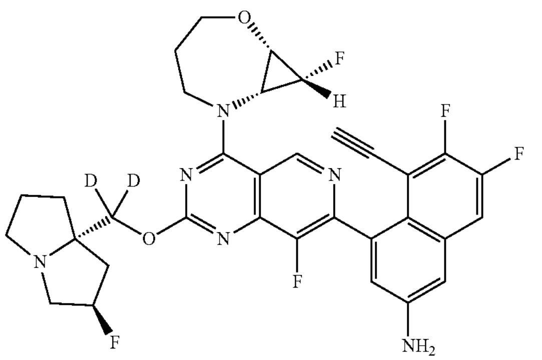 [SMILES: [2H]C([2H])(Oc1nc(N2CCCO[C@@H]3[C@H](F)[C@@H]32)c2cnc(-c3cc(N)cc4cc(F)c(F)c(C#C)c34)c(F)c2n1)[C@@]12CCCN1C[C@H](F)C2] | 5-Ethynyl-6,7-difluoro-4-(8-fluoro-4-((1R,7R,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
|---|---|---|
| 30 | 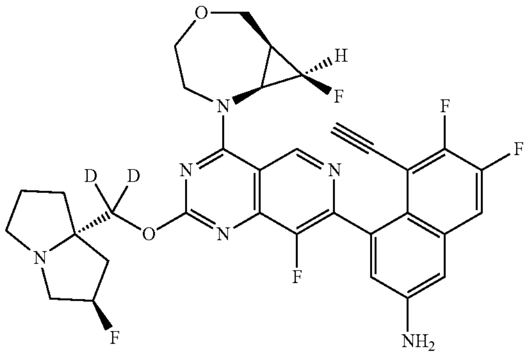 [SMILES: [2H]C([2H])(Oc1nc(N2CCOC[C@H]3[C@@H](F)[C@H]32)c2cnc(-c3cc(N)cc4cc(F)c(F)c(C#C)c34)c(F)c2n1)[C@@]12CCCN1C[C@H](F)C2] | 5-Ethynyl-6,7-difluoro-4-(8-fluoro-4-((1S,7S,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 31 | 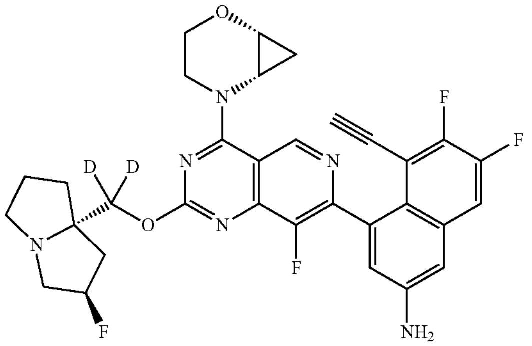 [SMILES: [2H]C([2H])(Oc1nc(N2CCO[C@@H]3C[C@@H]32)c2cnc(-c3cc(N)cc4cc(F)c(F)c(C#C)c34)c(F)c2n1)[C@@]12CCCN1C[C@H](F)C2] | 4-(4-((1R,6S)-2-oxa-5-azabicyclo[4.1.0]heptan-5-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 32 | 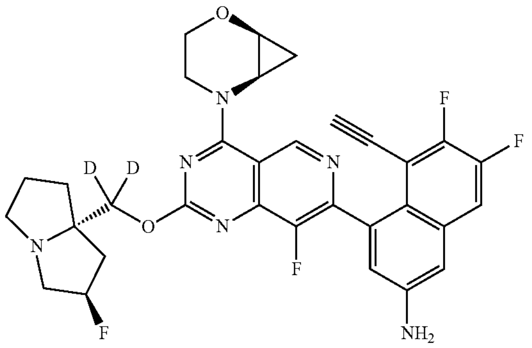 [SMILES: [2H]C([2H])(Oc1nc(N2CCO[C@H]3C[C@H]32)c2cnc(-c3cc(N)cc4cc(F)c(F)c(C#C)c34)c(F)c2n1)[C@@]12CCCN1C[C@H](F)C2] | 4-(4-((1S,6R)-2-oxa-5-azabicyclo[4.1.0]heptan-5-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 33 | 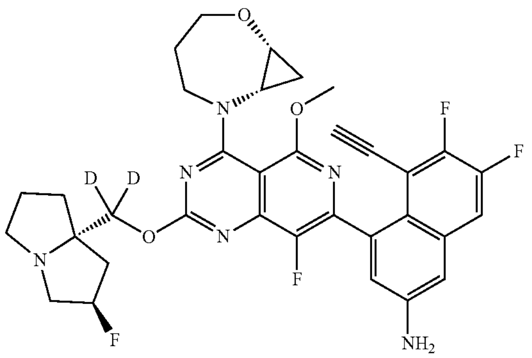 [SMILES: [2H]C([2H])(Oc1nc(N2CCCO[C@@H]3C[C@@H]32)c2c(OC)nc(-c3cc(N)cc4cc(F)c(F)c(C#C)c34)c(F)c2n1)[C@@]12CCCN1C[C@H](F)C2] | 4-(4-((1R,7S)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)-5-methoxypyrido[4,3-d]pyrimidin-7-yl)-5-ethynyl-6,7-difluoronaphthalen-2-amine |

TABLE 1-continued

| Example No. | Structure | Name |
|---|---|---|
| 34 | 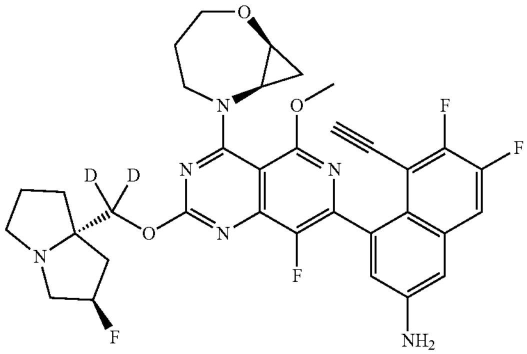 [SMILES: [2H]C([2H])(Oc1nc(N2CCCO[C@H]3C[C@H]32)c2c(OC)nc(-c3cc(N)cc4cc(F)c(F)c(C#C)c34)c(F)c2n1)[C@@]12CCCN1C[C@H](F)C2] | 4-(4-((1S,7R)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)-5-methoxypyrido[4,3-d]pyrimidin-7-yl)-5-ethynyl-6,7-difluoronaphthalen-2-amine |
| 35 | 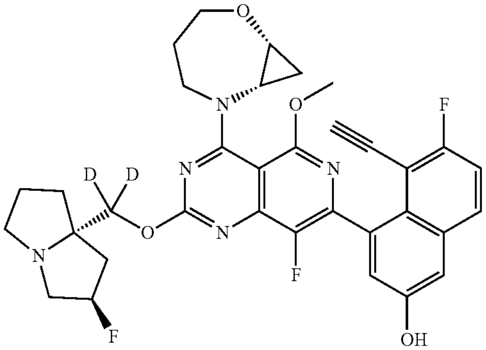 [SMILES: [2H]C([2H])(Oc1nc(N2CCCO[C@@H]3C[C@@H]32)c2c(OC)nc(-c3cc(O)cc4ccc(F)c(C#C)c34)c(F)c2n1)[C@@]12CCCN1C[C@H](F)C2] | 4-(4-((1R,7S)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)-5-methoxypyrido[4,3-d]pyrimidin-7-yl)-5-ethynyl-6-fluoronaphthalen-2-ol |
| 36 | 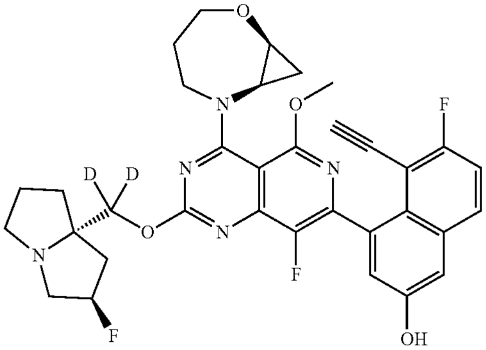 [SMILES: [2H]C([2H])(Oc1nc(N2CCCO[C@H]3C[C@H]32)c2c(OC)nc(-c3cc(O)cc4ccc(F)c(C#C)c34)c(F)c2n1)[C@@]12CCCN1C[C@H](F)C2] | 4-(4-((1S,7R)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)-5-methoxypyrido[4,3-d]pyrimidin-7-yl)-5-ethynyl-6-fluoronaphthalen-2-ol |
| 37 | 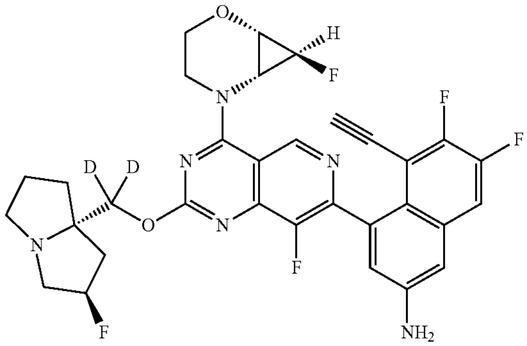 [SMILES: [2H]C([2H])(Oc1nc(N2CCO[C@@H]3[C@@H](F)[C@@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1S,6R,7S)-7-fluoro-2-oxa-5-azabicyclo[4.1.0]heptan-5-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine |

TABLE 1-continued

| Example No. | Structure | Name |
|---|---|---|
| 38 | 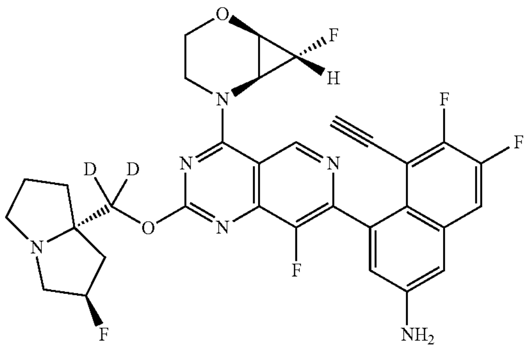 [SMILES: [2H]C([2H])(Oc1nc(N2CCO[C@H]3[C@H](F)[C@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1R,6S,7R)-7-fluoro-2-oxa-5-azabicyclo[4.1.0]heptan-5-yl)-2-(((2R,7aS)-2-fluorotetrahydro-1H-pyrrolizin-7a(5H)-methoxy-d2)pyrido[4,3-d]pyrimidin-7-yl)naphthalen-2-amine |
| 39 | 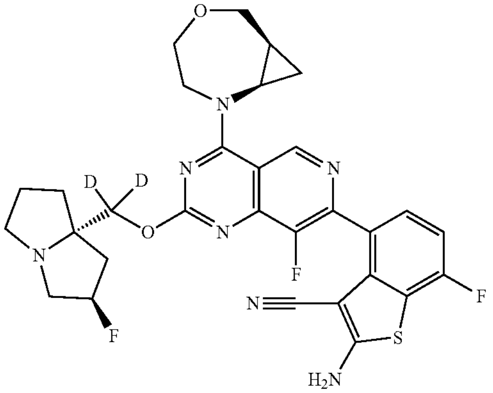 [SMILES: [2H]C([2H])(Oc1nc(N2CCOC[C@H]3C[C@H]32)c2cnc(-c3ccc(F)c4sc(N)c(C#N)c34)c(F)c2n1)[C@@]12CCCN1C[C@H](F)C2] | 4-(4-((1S,7R)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-2-amino-7-fluorobenzo[b]thiophene-3-carbonitrile |
| 40 | 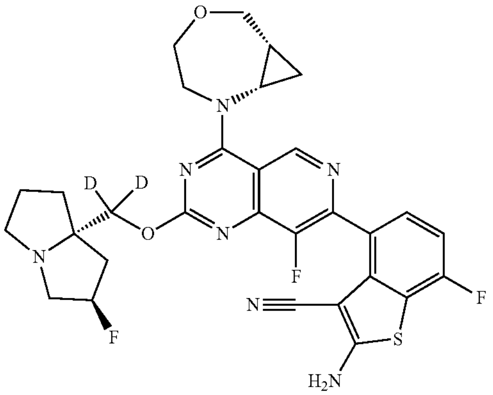 [SMILES: [2H]C([2H])(Oc1nc(N2CCOC[C@@H]3C[C@@H]32)c2cnc(-c3ccc(F)c4sc(N)c(C#N)c34)c(F)c2n1)[C@@]12CCCN1C[C@H](F)C2] | 4-(4-((1R,7S)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-2-amino-7-fluorobenzo[b]thiophene-3-carbonitrile |
| 41 | 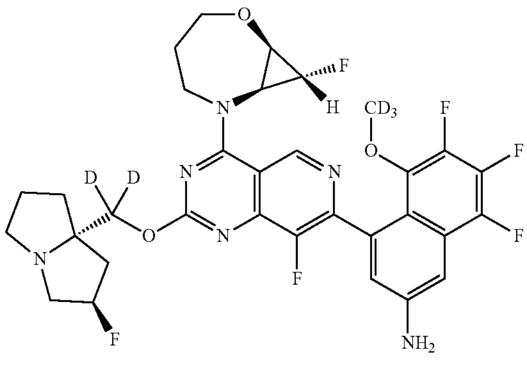 [SMILES: [2H]C([2H])([2H])Oc1c(F)c(F)c(F)c2cc(N)cc(-c3ncc4c(N5CCCO[C@H]6[C@H](F)[C@H]65)nc(OC([2H])([2H])[C@@]56CCCN5C[C@H](F)C6)nc4c3F)c12] | 6,7,8-trifluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |

TABLE 1-continued

| Example No. | Structure | Name |
|---|---|---|
| 42 | 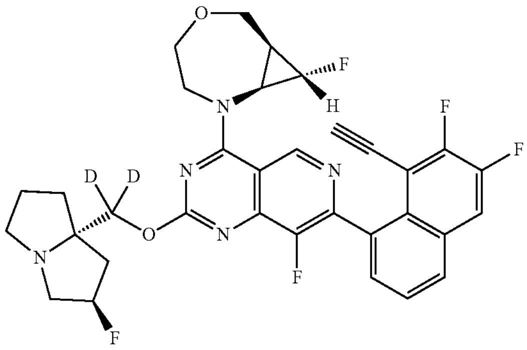 [SMILES: [2H]C([2H])(Oc1nc(N2CCOC[C@H]3[C@H](F)[C@H]32)c2cnc(-c3cccc4cc(F)c(F)c(C#C)c34)c(F)c2n1)[C@@]12CCCN1C[C@H](F)C2] | (1S,7S,8S)-2-(7-(8-ethynyl-6,7-difluoronaphthalen-1-yl)-8-fluoro-2-(((2R,7a.S)-2-fluorotetrahydro-1H-pyrrolizin-7a(5H)-yl)methoxy-$d_2$)pyrido[4,3-d]pyrimidin-4-yl)-8-fluoro-5-oxa-2-azabicyclo[5.1.0]octane |
| 43 | 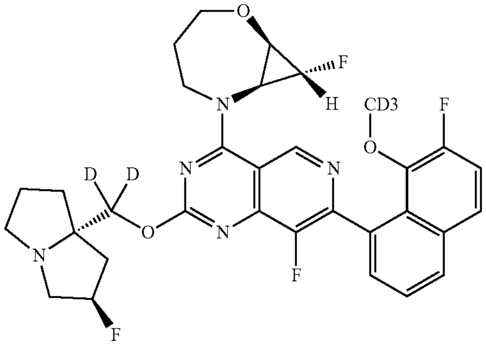 [SMILES: [2H]C([2H])([2H])Oc1c(F)ccc2cccc(-c3ncc4c(N5CCCO[C@H]6[C@H](F)[C@H]65)nc(OC([2H])([2H])[C@@]56CCCN5C[C@H](F)C6)nc4c3F)c12] | (1S,7S,8S)-8-fluoro-2-(8-fluoro-7-(7-fluoro-8-(methoxy-d3)naphthalen-1-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane |
| 44 | 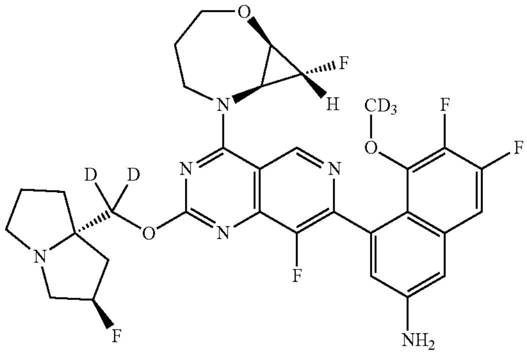 [SMILES: [2H]C([2H])([2H])Oc1c(F)c(F)cc2cc(N)cc(-c3ncc4c(N5CCCO[C@H]6[C@H](F)[C@H]65)nc(OC([2H])([2H])[C@@]56CCCN5C[C@H](F)C6)nc4c3F)c12] | 6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |
| 45 | 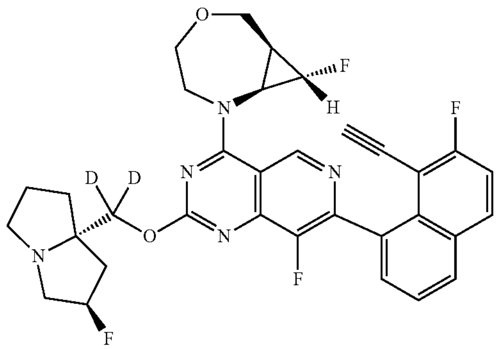 [SMILES: [2H]C([2H])(Oc1nc(N2CCOC[C@H]3[C@H](F)[C@H]32)c2cnc(-c3cccc4ccc(F)c(C#C)c34)c(F)c2n1)[C@@]12CCCN1C[C@H](F)C2] | (1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane |

TABLE 1-continued

| Example No. | Structure | Name |
|---|---|---|
| 46 | 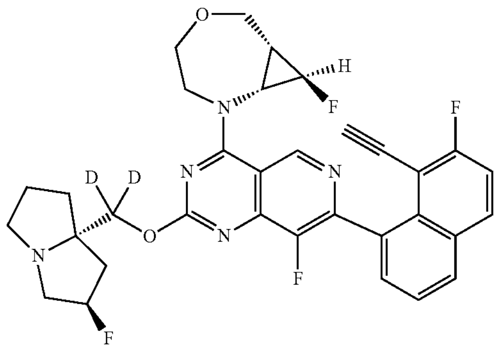 [SMILES: [2H]C([2H])(Oc1nc(N2CCOC[C@@H]3[C@@H](F)[C@@H]32)c2cnc(-c3cccc4ccc(F)c(C#C)c34)c(F)c2n1)[C@@]12CCCN1C[C@H](F)C2] | (1R,7R,8R)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane |
| 47 | 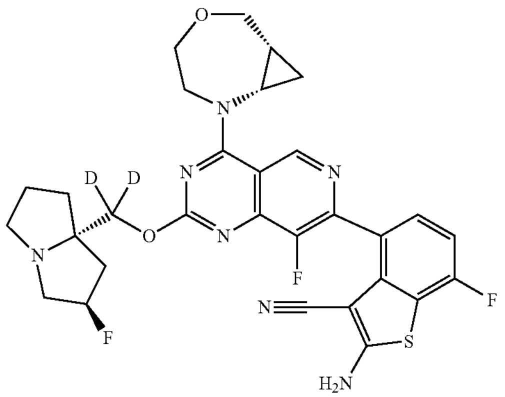 [SMILES: [2H]C([2H])(Oc1nc(N2CCOC[C@@H]3C[C@@H]32)c2cnc(-c3ccc(F)c4sc(N)c(C#N)c34)c(F)c2n1)[C@@]12CCCN1C[C@H](F)C2] | 4-(4-((1S,7R)-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-2-amino-7-fluorobenzo[b]thiophene-3-carbonitrile |
| 48 | 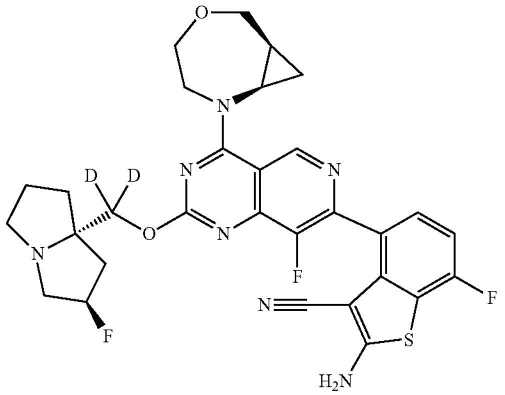 [SMILES: [2H]C([2H])(Oc1nc(N2CCOC[C@H]3C[C@H]32)c2cnc(-c3ccc(F)c4sc(N)c(C#N)c34)c(F)c2n1)[C@@]12CCCN1C[C@H](F)C2] | 4-(4-((1R,7S)-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-2-amino-7-fluorobenzo[b]thiophene-3-carbonitrile |
| 49 | 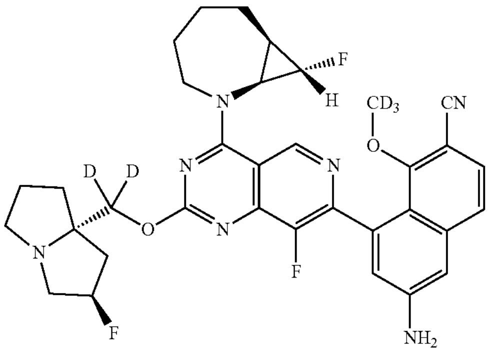 [SMILES: [2H]C([2H])([2H])Oc1c(C#N)ccc2cc(N)cc(-c3ncc4c(N5CCCC[C@H]6[C@H](F)[C@H]65)nc(OC([2H])([2H])[C@@]56CCCN5C[C@H](F)C6)nc4c3F)c12] | 6-amino-8-(8-fluoro-4-((1S,7R,8S)-8-fluoro-2-azabicyclo[5.1.0]octan-2-~2-(((2R,7aS)-2-fluorotetrahydro-1H-pyrrolizin-7a(5H)-yl)methoxy-d2)pyrido[4,3-d]pyrimidin-7-yl)-1-(methoxy-d3)-2-naphthonitrile |

TABLE 1-continued

| Example No. | Structure | Name |
| --- | --- | --- |
| 50 | 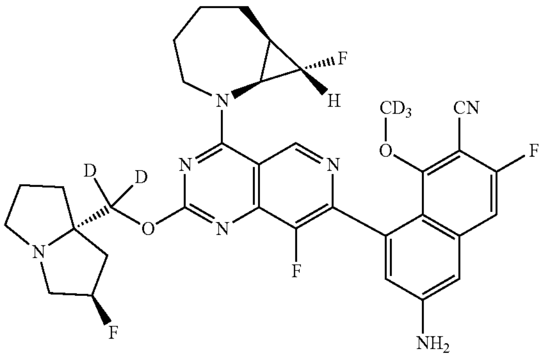 [SMILES: [2H]C([2H])([2H])Oc1c(C#N)c(F)cc2cc(N)cc(-c3ncc4c(N5CCCC[C@H]6[C@H](F)[C@H]65)nc(OC([2H])([2H])[C@@]56CCCN5C[C@H](F)C6)nc4c3F)c12] | 6-amino-3-fluoro-8-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-1-(methoxy-d3)-2-naphthonitrile |
| 51 | 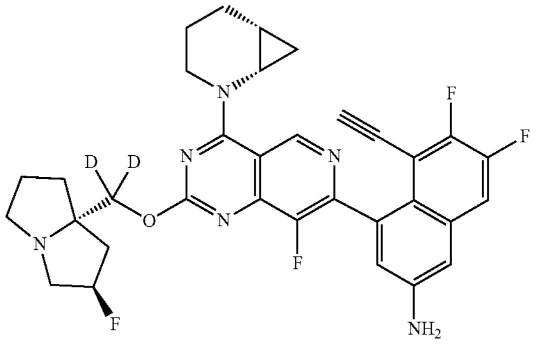 [SMILES: [2H]C([2H])(Oc1nc(N2CCC[C@@H]3C[C@@H]32)c2cnc(-c3cc(N)cc4cc(F)c(F)c(C#C)c34)c(F)c2n1)[C@@]12CCCN1C[C@H](F)C2] | 4-(4-((1S,6R)-2-azabicyclo[4.1.0]heptan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 52 | 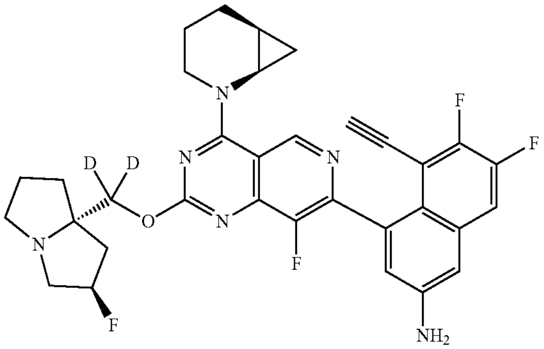 [SMILES: [2H]C([2H])(Oc1nc(N2CCC[C@H]3C[C@H]32)c2cnc(-c3cc(N)cc4cc(F)c(F)c(C#C)c34)c(F)c2n1)[C@@]12CCCN1C[C@H](F)C2] | 4-(4-((1R,6S)-2-azabicyclo[4.1.0]heptan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 53 | 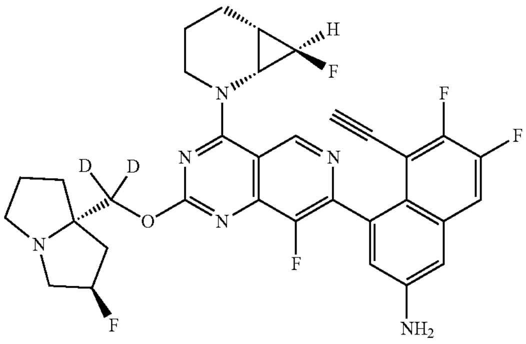 [SMILES: [2H]C([2H])(Oc1nc(N2CCC[C@@H]3[C@@H](F)[C@@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1R,6S,7R)-7-fluoro-2-azabicyclo[4.1.0]heptan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
|---|---|---|
| 54 | 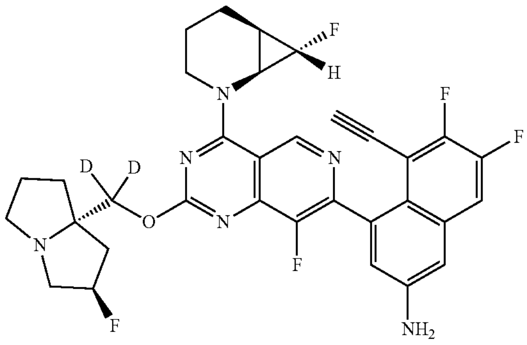 [SMILES: [2H]C([2H])(Oc1nc(N2CCC[C@H]3[C@H](F)[C@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1S,6R,7S)-7-fluoro-2-azabicyclo[4.1.0]heptan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 55 | 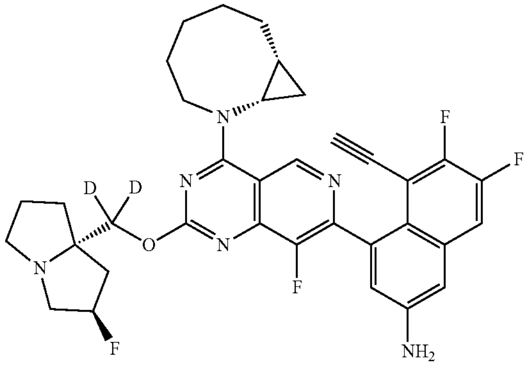 [SMILES: [2H]C([2H])(Oc1nc(N2CCCCC[C@@H]3C[C@@H]32)c2cnc(-c3cc(N)cc4cc(F)c(F)c(C#C)c34)c(F)c2n1)[C@@]12CCCN1C[C@H](F)C2] | 4-(4-((1S,8R)-2-azabicyclo[6.1.0]nonan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 56 | 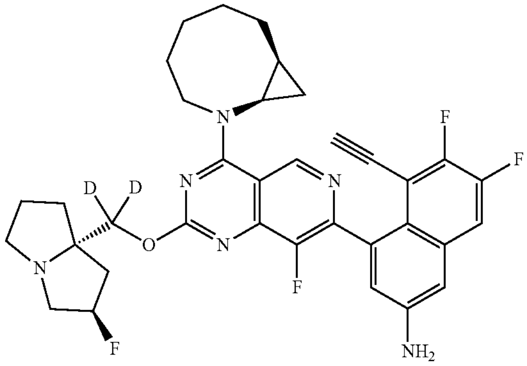 [SMILES: [2H]C([2H])(Oc1nc(N2CCCCC[C@H]3C[C@H]32)c2cnc(-c3cc(N)cc4cc(F)c(F)c(C#C)c34)c(F)c2n1)[C@@]12CCCN1C[C@H](F)C2] | 4-(4-((1R,8S)-2-azabicyclo[6.1.0]nonan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 57 | 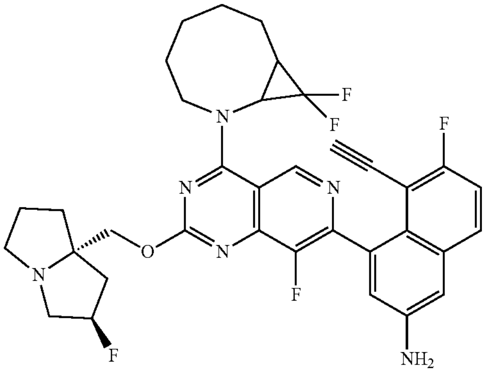 [SMILES: C#Cc1c(F)ccc2cc(N)cc(-c3ncc4c(N5CCCCCC6C5C6(F)F)nc(OC[C@@]56CCCN5C[C@H](F)C6)nc4c3F)c12] | 4-(4-(8,8-difluoro-2-azabicyclo [5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-amine |

TABLE 1-continued

| Example No. | Structure | Name |
|---|---|---|
| 58 | 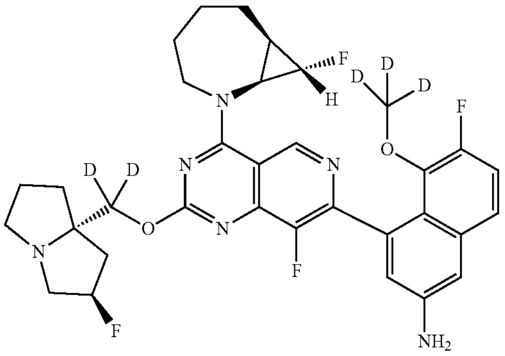 [SMILES: [2H]C([2H])([2H])Oc1c(F)ccc2cc(N)cc(-c3ncc4c(N5CCCC[C@H]6[C@H](F)[C@H]65)nc(OC([2H])([2H])[C@@]56CCCN5C[C@H](F)C6)nc4c3F)c12] | 6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |
| 59 | 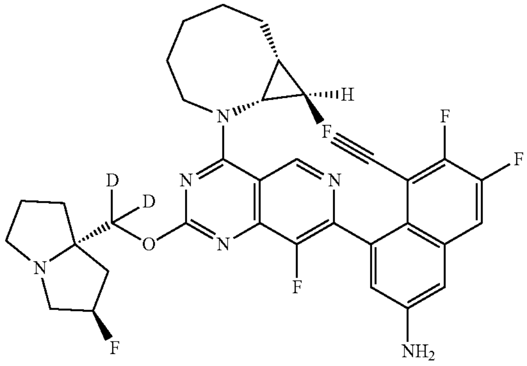 [SMILES: [2H]C([2H])(Oc1nc(N2CCCCC[C@@H]3[C@@H](F)[C@@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1R,8S,9R)-9-fluoro-2-azabicyclo[6.1.0]nonan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 60 | 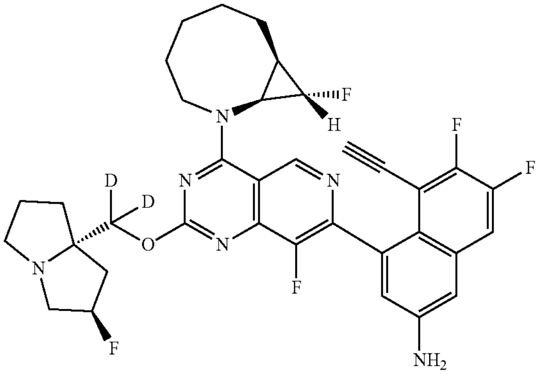 [SMILES: [2H]C([2H])(Oc1nc(N2CCCCC[C@H]3[C@H](F)[C@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1S,8R,9S)-9-fluoro-2-azabicyclo[6.1.0]nonan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 61 | 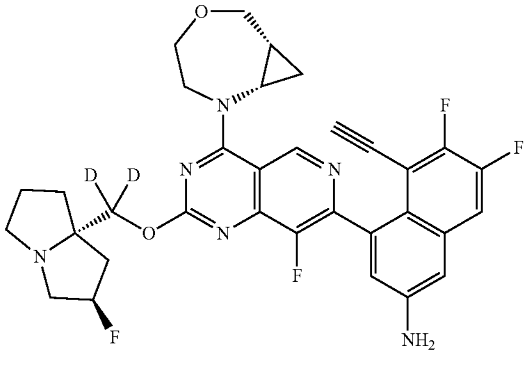 [SMILES: [2H]C([2H])(Oc1nc(N2CCOC[C@@H]3C[C@@H]32)c2cnc(-c3cc(N)cc4cc(F)c(F)c(C#C)c34)c(F)c2n1)[C@@]12CCCN1C[C@H](F)C2] | 4-(4-((1S,7R)-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-y)-5-ethynyl-6,7-difluoronaphthalen-2-amine |

TABLE 1-continued

| Example No. | Structure | Name |
|---|---|---|
| 62 | 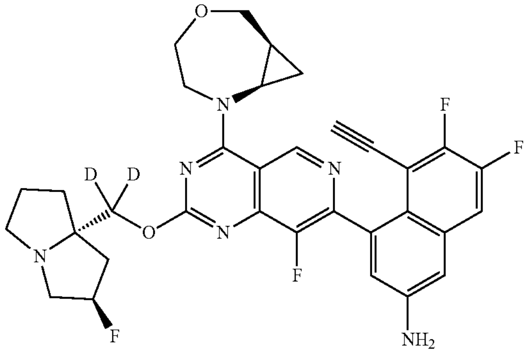 [SMILES: [2H]C([2H])(Oc1nc(N2CCOC[C@H]3C[C@H]32)c2cnc(-c3cc(N)cc4cc(F)c(F)c(C#C)c34)c(F)c2n1)[C@@]12CCCN1C[C@H](F)C2] | 4-(4-((1R,7S)-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine |
| 63 | 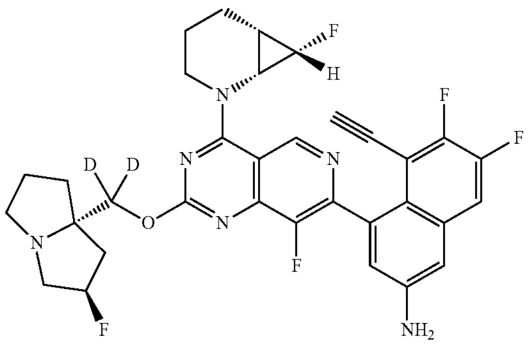 [SMILES: [2H]C([2H])(Oc1nc(N2CCC[C@@H]3[C@H](F)[C@@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1R,6S,7S)-7-fluoro-2-azabicyclo[4.1.0]heptan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 64 | 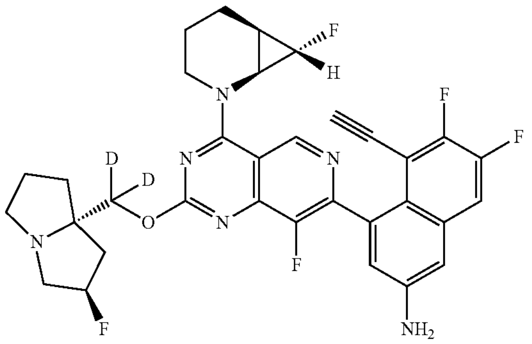 [SMILES: [2H]C([2H])(Oc1nc(N2CCC[C@H]3[C@H](F)[C@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1S,6R,7R)-7-fluoro-2-azabicyclo[4.1.0]heptan-2-yl)-2-(((2R,7aS)-2-fluorotetrahydro-1H-pyrrolizin-7a(5H)-yl)yl)methoxy-d2)pyrido[4,3-d]pyrimidin-7-yl)naphthalen-2-amine |
| 65 | 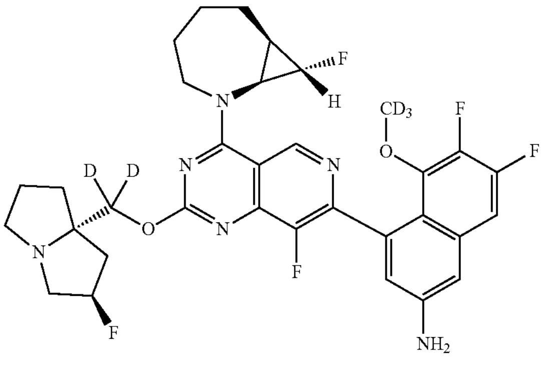 [SMILES: [2H]C([2H])([2H])Oc1c(F)c(F)cc2cc(N)cc(-c3ncc4c(N5CCCC[C@H]6[C@H](F)[C@H]65)nc(OC([2H])([2H])[C@@]56CCCN5C[C@H](F)C6)nc4c3F)c12] | 6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |

TABLE 1-continued

| Example No. | Structure | Name |
|---|---|---|
| 66 | 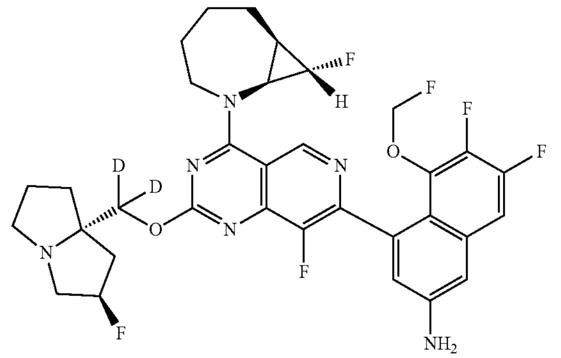 [SMILES: [2H]C([2H])(Oc1nc(N2CCCC[C@H]3[C@H](F)[C@H]32)c2cnc(-c3cc(N)cc4cc(F)c(F)c(OCF)c34)c(F)c2n1)[C@@]12CCCN1C[C@H](F)C2] | 6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy)naphthalen-2-amine |
| 67 | 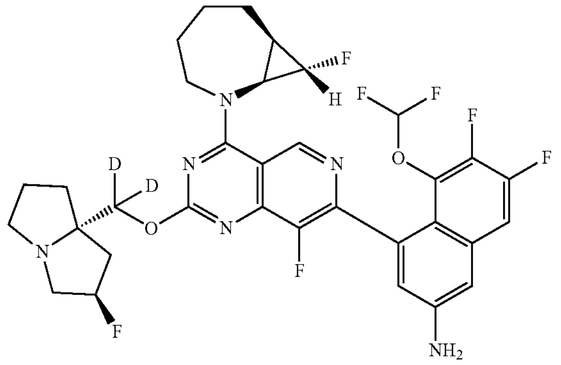 [SMILES: [2H]C([2H])(Oc1nc(N2CCCC[C@H]3[C@H](F)[C@H]32)c2cnc(-c3cc(N)cc4cc(F)c(F)c(OC(F)F)c34)c(F)c2n1)[C@@]12CCCN1C[C@H](F)C2] | 5-(difluoromethoxy)-6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 68 | 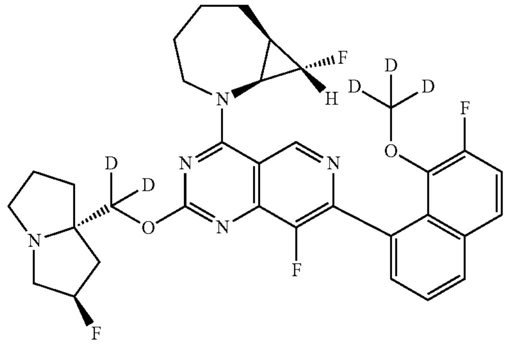 [SMILES: [2H]C([2H])([2H])Oc1c(F)ccc2cccc(-c3ncc4c(N5CCCC[C@H]6[C@H](F)[C@H]65)nc(OC([2H])([2H])[C@@]56CCCN5C[C@H](F)C6)nc4c3F)c12] | 8-fluoro-7-(7-fluoro~8-(methoxy-d3)naphthalen-1-yl)-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine |
| 69 | 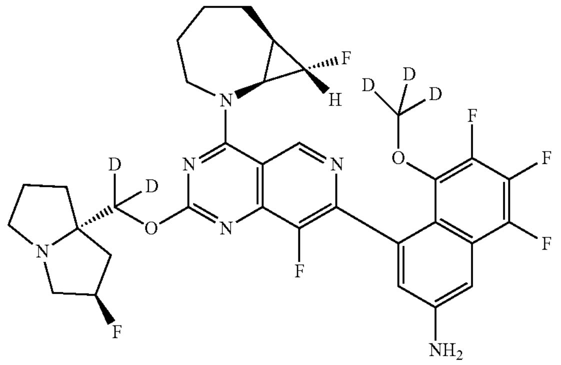 [SMILES: [2H]C([2H])([2H])Oc1c(F)c(F)c(F)c2cc(N)cc(-c3ncc4c(N5CCCC[C@H]6[C@H](F)[C@H]65)nc(OC([2H])([2H])[C@@]56CCCN5C[C@H](F)C6)nc4c3F)c12] | 6,7,8-trifluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |

TABLE 1-continued

| Example No. | Structure | Name |
|---|---|---|
| 70 | 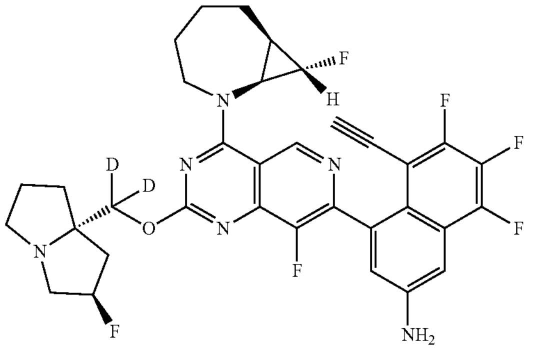 [SMILES: [2H]C([2H])(Oc1nc(N2CCCC[C@H]3[C@H](F)[C@H]32)c2cnc(-c3cc(N)cc4c(F)c(F)c(F)c(C#C)c34)c(F)c2n1)[C@@]12CCCN1C[C@H](F)C2] | 5-ethynyl-6,7,8-trifluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 71 | 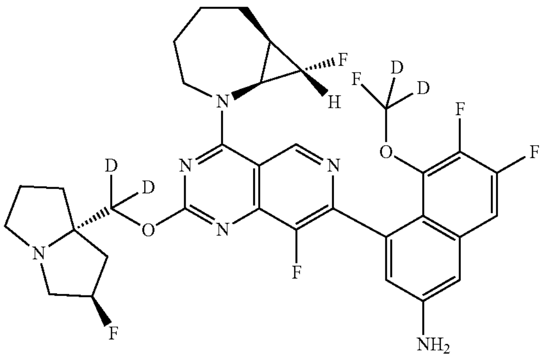 [SMILES: [2H]C([2H])(F)Oc1c(F)c(F)cc2cc(N)cc(-c3ncc4c(N5CCCC[C@H]6[C@H](F)[C@H]65)nc(OC([2H])([2H])[C@@]56CCCN5C[C@H](F)C6)nc4c3F)c12] | 6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine |
| 72 | 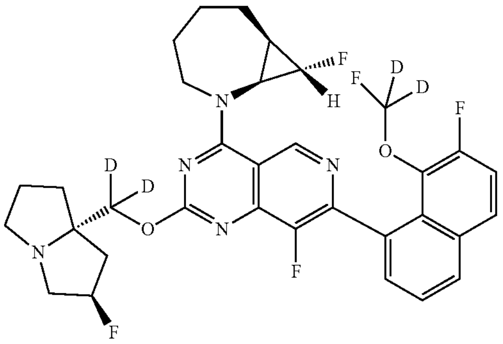 [SMILES: [2H]C([2H])(F)Oc1c(F)ccc2cccc(-c3ncc4c(N5CCCC[C@H]6[C@H](F)[C@H]65)nc(OC([2H])([2H])[C@@]56CCCN5C[C@H](F)C6)nc4c3F)c12] | 8-fluoro-7-(7-fluoro-8-(fluoromethoxy-d2)naphthalen-1-yl)-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine |
| 73 | 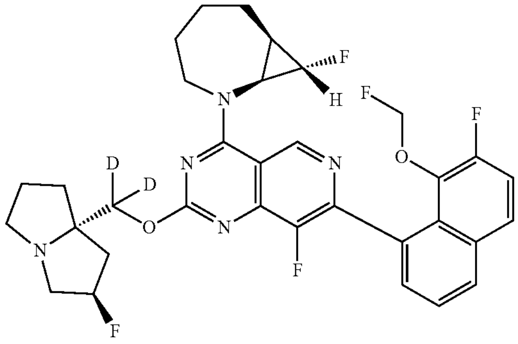 [SMILES: [2H]C([2H])(Oc1nc(N2CCCC[C@H]3[C@H](F)[C@H]32)c2cnc(-c3cccc4ccc(F)c(OCF)c34)c(F)c2n1)[C@@]12CCCN1C[C@H](F)C2] | 8-fluoro-7-(7-fluoro-8-(fluoromethoxy)naphthalen-1-yl)-4-((1S,7R,8S)-8-fluoro-2-azabicyclo[5.1.0]octan-2-yl)-2-(((2R,7aS)-2-fluorotetrahydro-1H-pyrrolizin-7a(5H)-methoxy-d2)pyrido[4,3-d]pyrimidine |

TABLE 1-continued

| Example No. | Structure | Name |
|---|---|---|
| 74 | 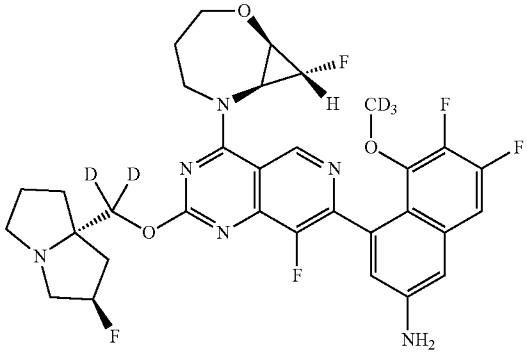 [SMILES: [2H]C([2H])([2H])Oc1c(F)c(F)cc2cc(N)cc(-c3ncc4c(N5CCCO[C@H]6[C@H](F)[C@H]65)nc(OC([2H])([2H])[C@@]56CCCN5C[C@H](F)C6)nc4c3F)c12] | 6,7-difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |
| 75 | 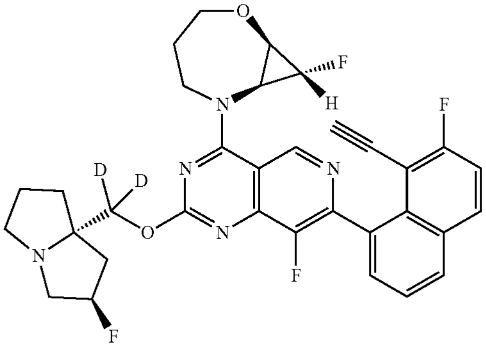 [SMILES: [2H]C([2H])(Oc1nc(N2CCCO[C@H]3[C@H](F)[C@H]32)c2cnc(-c3cccc4ccc(F)c(C#C)c34)c(F)c2n1)[C@@]12CCCN1C[C@H](F)C2] | (1R,7S,8R)-6-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-oxa-6-azabicyclo[5.1.0]octane |
| 76 | 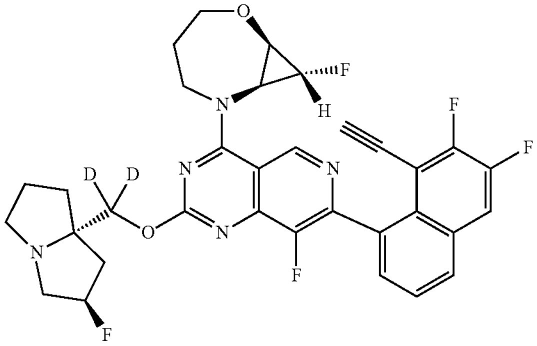 [SMILES: [2H]C([2H])(Oc1nc(N2CCCO[C@H]3[C@H](F)[C@H]32)c2cnc(-c3cccc4cc(F)c(F)c(C#C)c34)c(F)c2n1)[C@@]12CCCN1C[C@H](F)C2] | (1R,7S,8R)-6-(7-(8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-oxa-6-azabicyclo[5.1.0]octane |
| 77 | 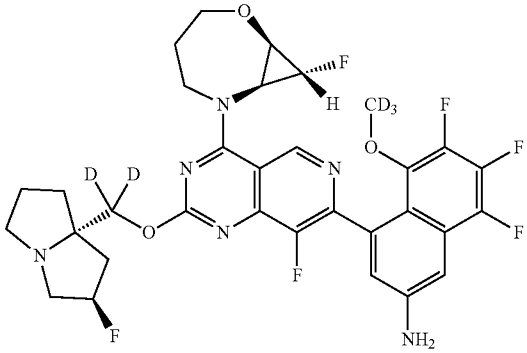 [SMILES: [2H]C([2H])([2H])Oc1c(F)c(F)c(F)c2cc(N)cc(-c3ncc4c(N5CCCO[C@H]6[C@H](F)[C@H]65)nc(OC([2H])([2H])[C@@]56CCCN5C[C@H](F)C6)nc4c3F)c12] | 6,7,8-trifluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |

TABLE 1-continued

| Example No. | Structure | Name |
| --- | --- | --- |
| 78 | 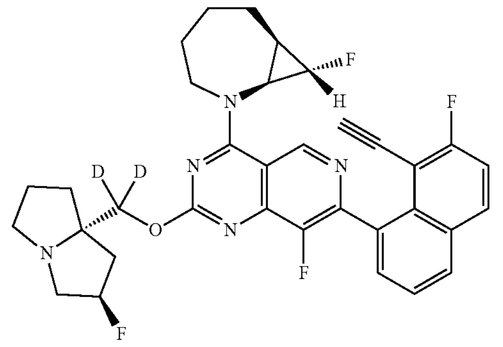 [SMILES: [2H]C([2H])(Oc1nc(N2CCCC[C@H]3[C@H](F)[C@H]32)c2cnc(-c3cccc4ccc(F)c(C#C)c34)c(F)c2n1)[C@@]12CCCN1C[C@H](F)C2] | 7-(8-ethynyl-7-fluoronaphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine |
| 79 | 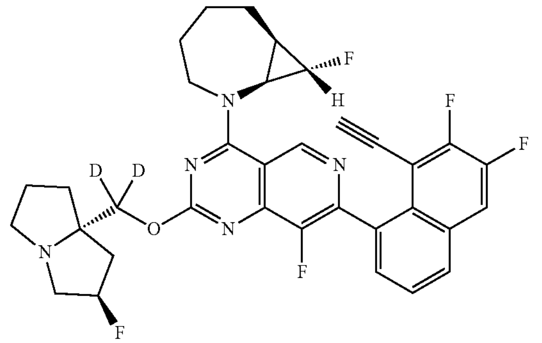 [SMILES: [2H]C([2H])(Oc1nc(N2CCCC[C@H]3[C@H](F)[C@H]32)c2cnc(-c3cccc4cc(F)c(F)c(C#C)c34)c(F)c2n1)[C@@]12CCCN1C[C@H](F)C2] | 7-(8-ethynyl-6,7-difluoronaphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine |
| 80 | 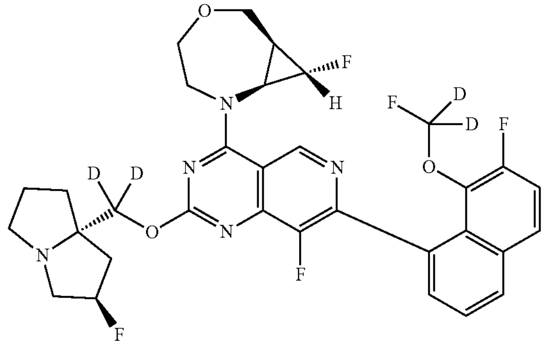 [SMILES: [2H]C([2H])(F)Oc1c(F)ccc2cccc(-c3ncc4c(N5CCOC[C@H]6[C@H](F)[C@H]65)nc(OC([2H])([2H])[C@@]56CCCN5C[C@H](F)C6)nc4c3F)c12] | (1S,7S,8S)-8-fluoro-2-(8-fluoro-7-(7-fluoro-8-(fluoromethoxy-d2)naphthalen-1-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane |
| 81 | 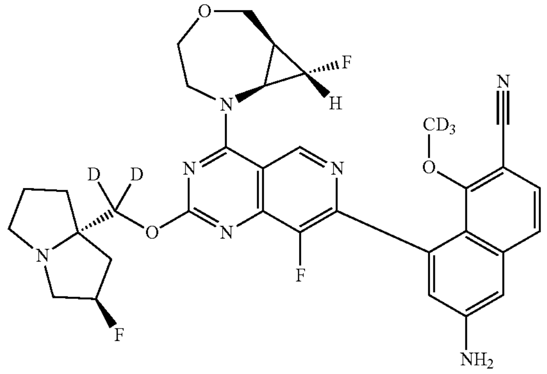 [SMILES: [2H]C([2H])([2H])Oc1c(C#N)ccc2cc(N)cc(-c3ncc4c(N5CCOC[C@H]6[C@H](F)[C@H]65)nc(OC([2H])([2H])[C@@]56CCCN5C[C@H](F)C6)nc4c3F)c12] | 6-amino-8-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-1-(methoxy-d3)-2-naphthonitrile |

TABLE 1-continued

| Example No. | Structure | Name |
| --- | --- | --- |
| 82 | 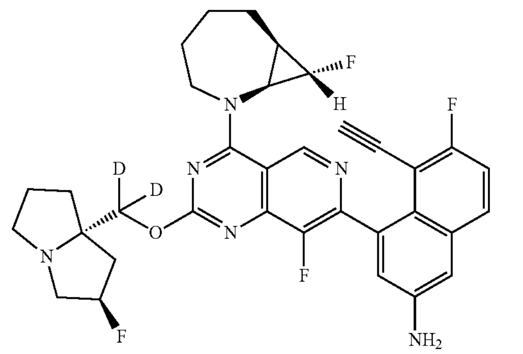 | 5-ethynyl-6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 83 | 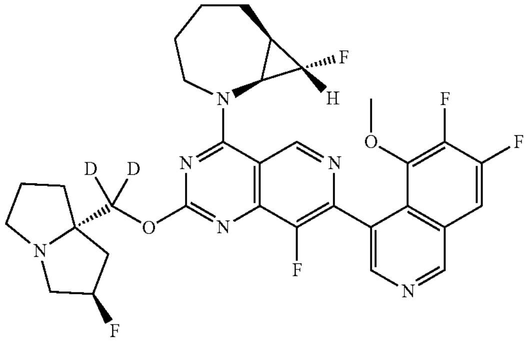 [SMILES: [2H]C([2H])(Oc1nc(N2CCCC[C@H]3[C@H](F)[C@H]32)c2cnc(-c3cncc4cc(F)c(F)c(OC)c34)c(F)c2n1)[C@@]12CCCN1C[C@H](F)C2] | 7-(6,7-difluoro-5-methoxyisoquinolin-4-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine |
| 84 | 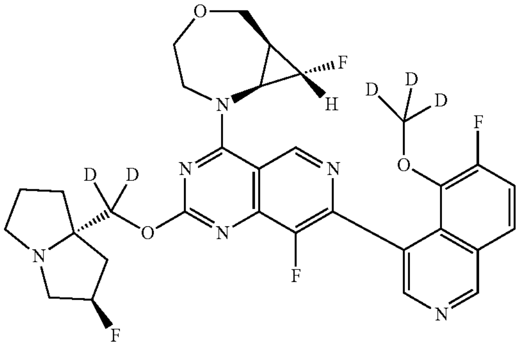 [SMILES: [2H]C([2H])([2H])Oc1c(F)ccc2cncc(-c3ncc4c(N5CCOC[C@H]6[C@H](F)[C@H]65)nc(OC([2H])([2H])[C@@]56CCCN5C[C@H](F)C6)nc4c3F)c12] | (1S,7S,8S)-8-fluoro-2-(8-fluoro-7-(6-fluoro-5-(methoxy-d3)isoquinolin-4-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane |
| 85 | 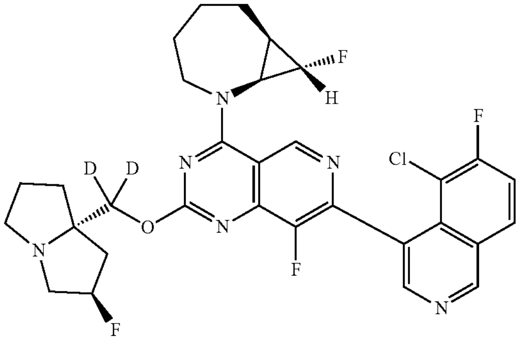 [SMILES: [2H]C([2H])(Oc1nc(N2CCCC[C@H]3[C@H](F)[C@H]32)c2cnc(-c3cncc4ccc(F)c(Cl)c34)c(F)c2n1)[C@@]12CCCN1C[C@H](F)C2] | 7-(5-chloro-6-fluoroisoquinolin-4-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine |

TABLE 1-continued

| Example No. | Structure | Name |
|---|---|---|
| 86 | 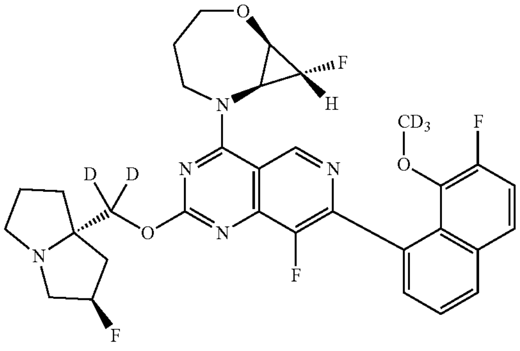 [SMILES: [2H]C([2H])([2H])Oc1c(F)ccc2cccc(-c3ncc4c(N5CCCO[C@H]6[C@H](F)[C@H]65)nc(OC([2H])([2H])[C@@]56CCCN5C[C@H](F)C6)nc4c3F)c12] | (1R,7S,8R)-8-fluoro-6-(8-fluoro-7-(7-fluoro-8-(methoxy-d3)naphthalen-1-yl)-2-(((2R,7aS)-2-fluorotetrahydro-1H-pyrrolizin-7a(5H)-yl)methoxy-d2)pyrido[4,3-d]pyrimidin-4-yl)-2-oxa-6-azabicyclo[5.1.0]octane |
| 87 | 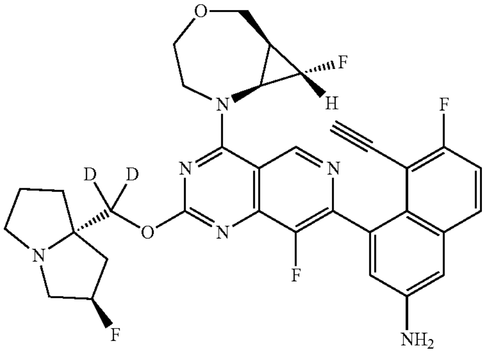 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 88 | 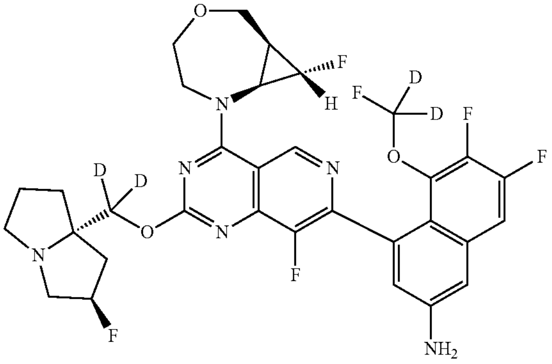 [SMILES: [2H]C([2H])(F)Oc1c(F)c(F)cc2cc(N)cc(-c3ncc4c(N5CCOC[C@H]6[C@H](F)[C@H]65)nc(OC([2H])([2H])[C@@]56CCCN5C[C@H](F)C6)nc4c3F)c12] | 6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine |
| 89 | 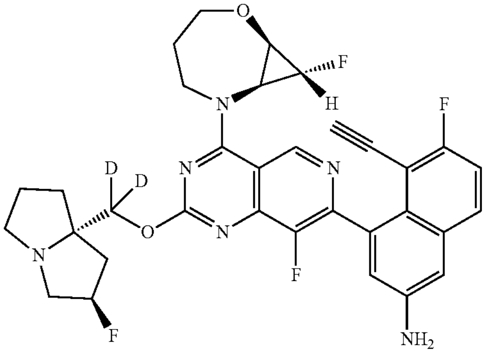 [SMILES: [2H]C([2H])(Oc1nc(N2CCCO[C@H]3[C@H](F)[C@H]32)c2cnc(-c3cc(N)cc4ccc(F)c(C#C)c34)c(F)c2n1)[C@@]12CCCN1C[C@H](F)C2] | 5-ethynyl-6-fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
|---|---|---|
| 90 | 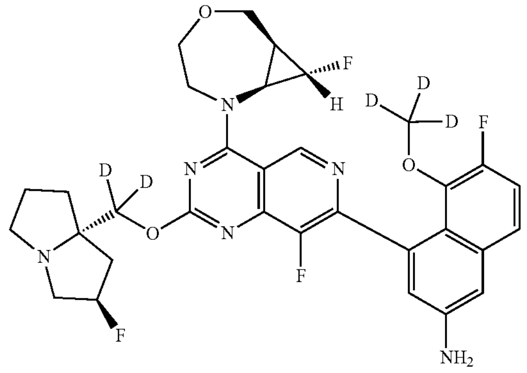 [SMILES: [2H]C([2H])([2H])Oc1c(F)ccc2cc(N)cc(-c3ncc4c(N5CCOC[C@H]6[C@H](F)[C@H]65)nc(OC([2H])([2H])[C@@]56CCCN5C[C@H](F)C6)nc4c3F)c12] | 6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |
| 91 | 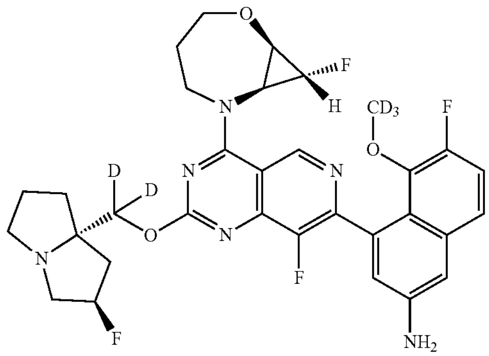 [SMILES: [2H]C([2H])([2H])Oc1c(F)ccc2cc(N)cc(-c3ncc4c(N5CCCO[C@H]6[C@H](F)[C@H]65)nc(OC([2H])([2H])[C@@]56CCCN5C[C@H](F)C6)nc4c3F)c12] | 6-fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |
| 92 | 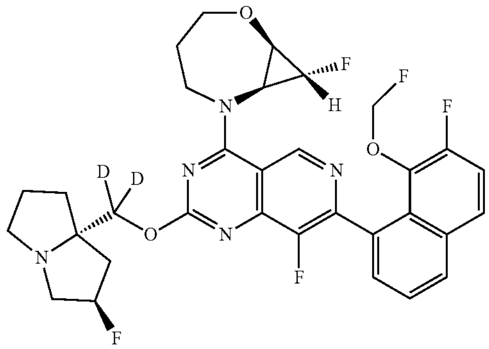 [SMILES: [2H]C([2H])(Oc1nc(N2CCCO[C@H]3[C@H](F)[C@H]32)c2cnc(-c3cccc4ccc(F)c(OCF)c34)c(F)c2n1)[C@@]12CCCN1C[C@H](F)C2] | (1R,7S,8R)-8-fluoro-6-(8-fluoro-7-(7-fluoro-8-(fluoromethoxy)naphthalen-1-yl)-2-(((2R,7aS)-2-fluorotetrahydro-1H-pyrrolizin-7a(5H)-yl)methoxy-d2)pyrido[4,3-d]pyrimidin-4-yl)-2-oxa-6-azabicyclo[5.1.0]octane |
| 93 | 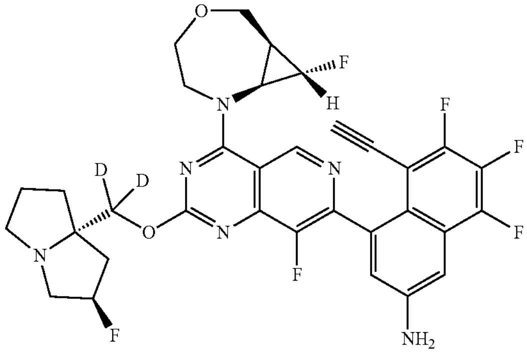 [SMILES: [2H]C([2H])(Oc1nc(N2CCOC[C@H]3[C@H](F)[C@H]32)c2cnc(-c3cc(N)cc4c(F)c(F)c(F)c(C#C)c34)c(F)c2n1)[C@@]12CCCN1C[C@H](F)C2] | 5-ethynyl-6,7,8-trifluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
|---|---|---|
| 94 | 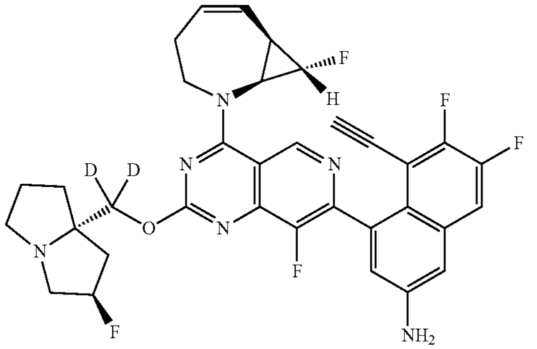 [SMILES: [2H]C([2H])(Oc1nc(N2CCC=C[C@H]3[C@H](F)[C@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 95 | 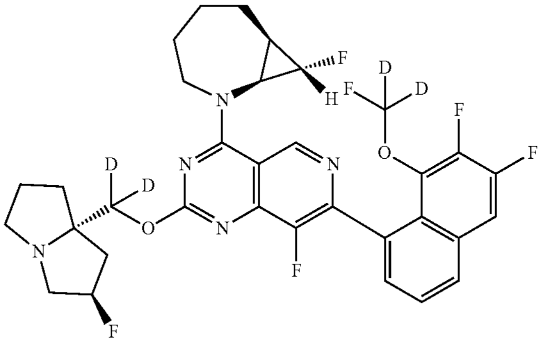 [SMILES: [2H]C([2H])(F)Oc1c(F)c(F)cc2cccc(-c3ncc4c(N5CCCC[C@H]6[C@H](F)[C@H]65)nc(OC([2H])([2H])[C@@]56CCCN5C[C@H](F)C6)nc4c3F)c12] | 7-(6,7-difluoro-8-(fluoromethoxy-d2)naphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine |
| 96 | 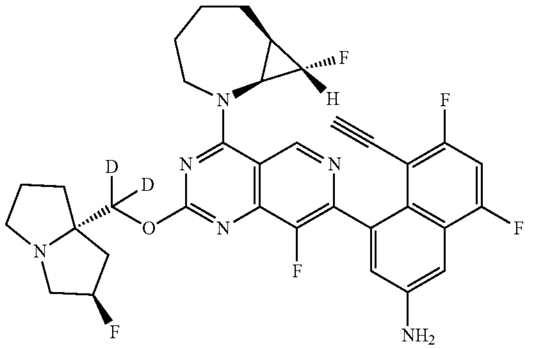 [SMILES: [2H]C([2H])(Oc1nc(N2CCCC[C@H]3[C@H](F)[C@H]32)c2cnc(-c3cc(N)cc4c(F)cc(F)c(C#C)c34)c(F)c2n1)[C@@]12CCCN1C[C@H](F)C2] | 5-ethynyl-6,8-difluoro-4~(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 97 | 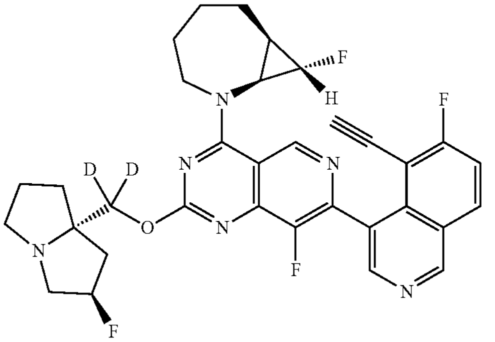 [SMILES: [2H]C([2H])(Oc1nc(N2CCCC[C@H]3[C@H](F)[C@H]32)c2cnc(-c3cncc4ccc(F)c(C#C)c34)c(F)c2n1)[C@@]12CCCN1C[C@H](F)C2] | 7-(5-ethynyl-6-fluoroisoquinolin-4-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine |

TABLE 1-continued

| Example No. | Structure | Name |
|---|---|---|
| 98 | 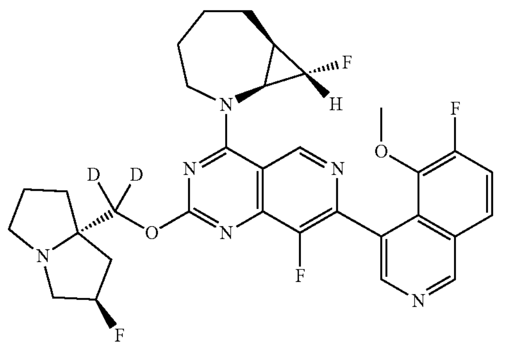 [SMILES: [2H]C([2H])(Oc1nc(N2CCCC[C@H]3[C@H](F)[C@H]32)c2cnc(-c3cncc4ccc(F)c(OC)c34)c(F)c2n1)[C@@]12CCCN1C[C@H](F)C2] | 8-fluoro-7-(6-fluoro-5-methoxyisoquinolin-4-yl)-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine |
| 99 | 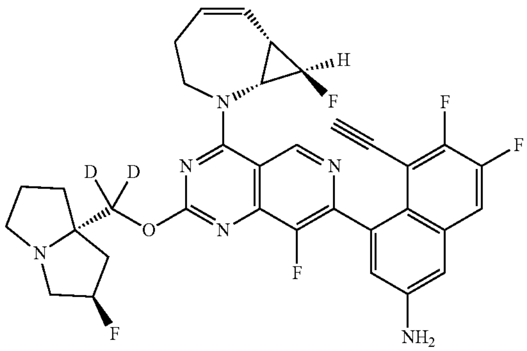 | 5-ethynyl-6,7-difluoro-4-(8-fluoro-4-((1R,7S,8R)-8-fluoro-2-azabicyclo[5.1.0]oct-5-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 100 | 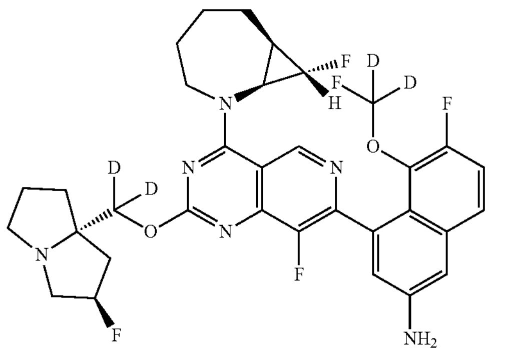 [SMILES: [2H]C([2H])(F)Oc1c(F)ccc2cc(N)cc(-c3ncc4c(N5CCCC[C@H]6[C@H](F)[C@H]65)nc(OC([2H])([2H])[C@@]56CCCN5C[C@H](F)C6)nc4c3F)c12] | 6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine |
| 101 | 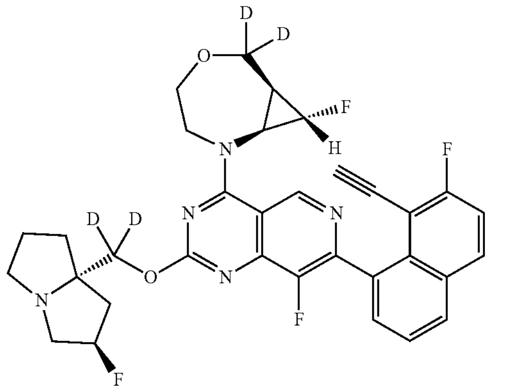 [SMILES: [2H]C1([2H])OCCN(c2nc(OC([2H])([2H])[C@@]34CCCN3C[C@H](F)C4)nc3c(F)c(-c4cccc5ccc(F)c(C#C)c45)ncc23)[C@@H]2[C@@H](F)[C@@H]21] | (1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane-6,6-d2 |

TABLE 1-continued

| Example No. | Structure | Name |
|---|---|---|
| 102 | 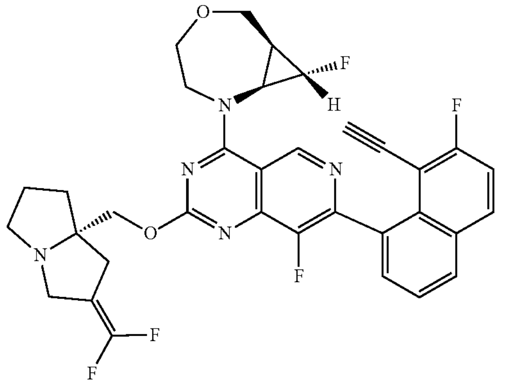 [SMILES: C#Cc1c(F)ccc2cccc(-c3ncc4c(N5CCOC[C@H]6[C@H](F)[C@H]65)nc(OC[C@@]56CCCN5CC(=C(F)F)C6)nc4c3F)c12] | (1S,7S,8S)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane |
| 103 | 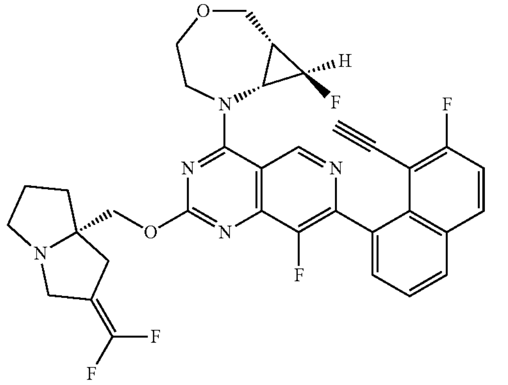 [SMILES: C#Cc1c(F)ccc2cccc(-c3ncc4c(N5CCOC[C@@H]6[C@@H](F)[C@@H]65)nc(OC[C@@]56CCCN5CC(=C(F)F)C6)nc4c3F)c12] | (1R,7R,8R)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane |
| 104 | 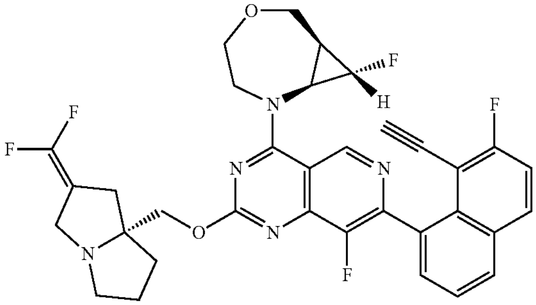 [SMILES: C#Cc1c(F)ccc2cccc(-c3ncc4c(N5CCOC[C@H]6[C@H](F)[C@H]65)nc(OC[C@]56CCCN5CC(=C(F)F)C6)nc4c3F)c12] | (1S,7S,8S)-2-(2-(((R)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane |
| 105 | 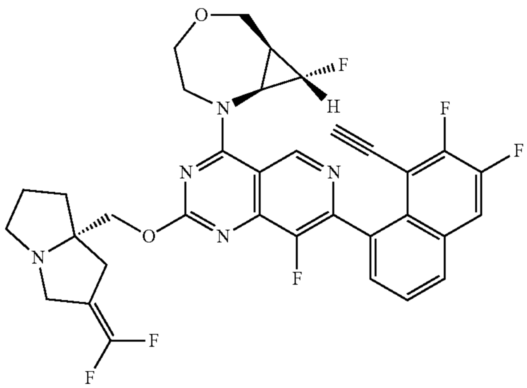 [SMILES: C#Cc1c(F)c(F)cc2cccc(-c3ncc4c(N5CCOC[C@H]6[C@H](F)[C@H]65)nc(OC[C@@]56CCCN5CC(=C(F)F)C6)nc4c3F)c12] | (1S,7S,8S)-2-(2-(((S)-2-(difluoromethylene)tetrahydro-1H-pyrrolizin-7a(5H)-methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane |

TABLE 1-continued

| Example No. | Structure | Name |
|---|---|---|
| 106 | 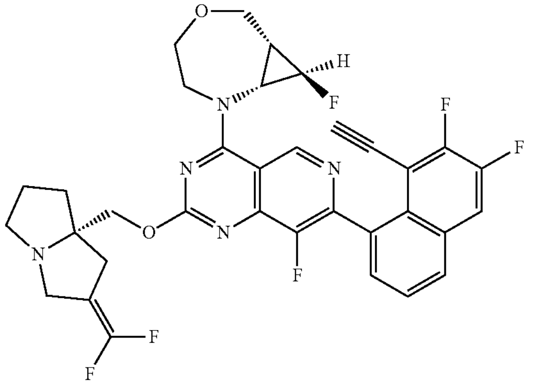 [SMILES: C#Cc1c(F)c(F)cc2cccc(-c3ncc4c(N5CCOC[C@@H]6[C@@H](F)[C@@H]65)nc(OC[C@@]56CCCN5CC(=C(F)F)C6)nc4c3F)c12] | (1R,7R,8R)-2-(2-(((S)-2-(difluoromethylene)tetrahydro-1H-pyrrolizin-7a(5H)-methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane |
| 107 | 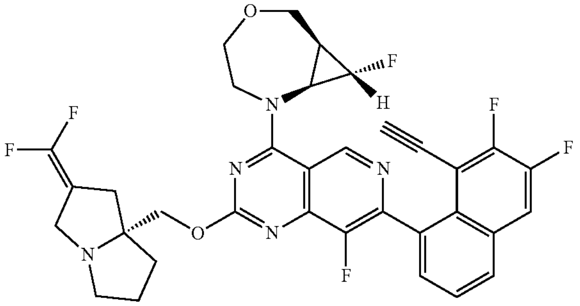 [SMILES: C#Cc1c(F)c(F)cc2cccc(-c3ncc4c(N5CCOC[C@H]6[C@H](F)[C@H]65)nc(OC[C@]56CCCN5CC(=C(F)F)C6)nc4c3F)c12] | (1S,7S,8S)-2-(2-(((R)-2-(difluoromethylene)tetrahydro-1H-pyrrolizin-7a(5H)-methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane |
| 108 | 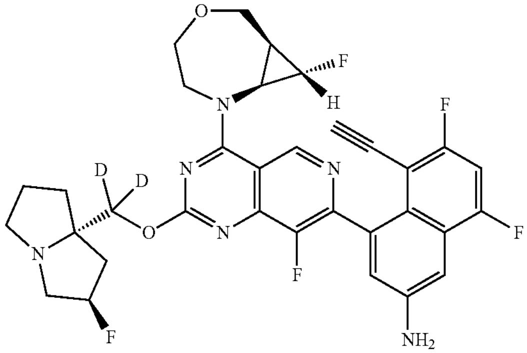 [SMILES: [2H]C([2H])(Oc1nc(N2CCOC[C@H]3[C@H](F)[C@H]32)c2cnc(-c3cc(N)cc4c(F)cc(F)c(C#C)c34)c(F)c2n1)[C@@]12CCCN1C[C@H](F)C2] | 5-ethynyl-6,8-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 109 | 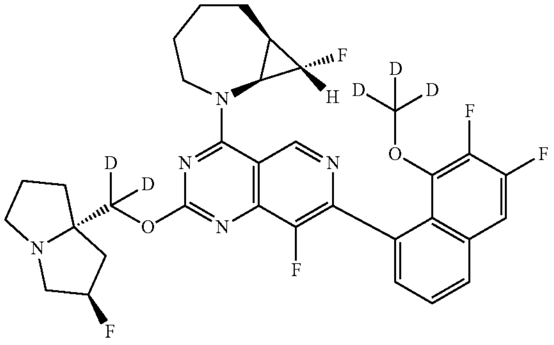 [SMILES: [2H]C([2H])([2H])Oc1c(F)c(F)cc2cccc(-c3ncc4c(N5CCCC[C@H]6[C@H](F)[C@H]65)nc(OC([2H])([2H])[C@@]56CCCN5C[C@H](F)C6)nc4c3F)c12] | 7-(6,7-difluoro-8-(methoxy-d3)naphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-methoxy-d2)pyrido[4,3-d]pyrimidine |

TABLE 1-continued

| Example No. | Structure | Name |
|---|---|---|
| 110 | 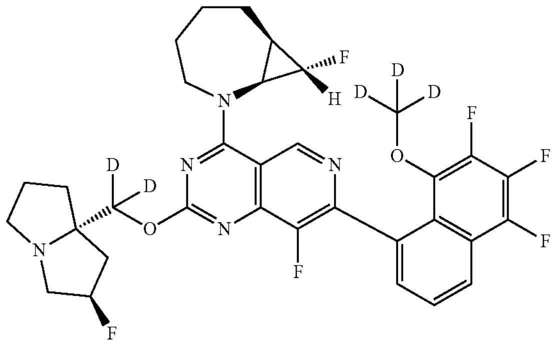 [SMILES: [2H]C([2H])([2H])Oc1c(F)c(F)c(F)c2cccc(-c3ncc4c(N5CCCC[C@H]6[C@H](F)[C@H]65)nc(OC([2H])([2H])[C@@]56CCCN5C[C@H](F)C6)nc4c3F)c12] | 8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)-7-(5,6,7-trifluoro-8-(methoxy-d3)naphthalen-1-pyrido[4,3-d]pyrimidine |
| 111 | 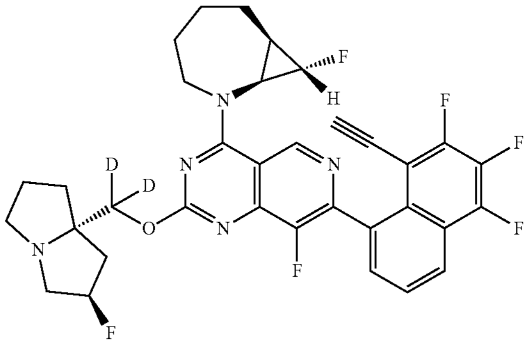 [SMILES: [2H]C([2H])(Oc1nc(N2CCCC[C@H]3[C@H](F)[C@H]32)c2cnc(-c3cccc4c(F)c(F)c(F)c(C#C)c34)c(F)c2n1)[C@@]12CCCN1C[C@H](F)C2] | 7-(8-ethynyl-5,6,7-trifluoronaphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine |
| 112 | 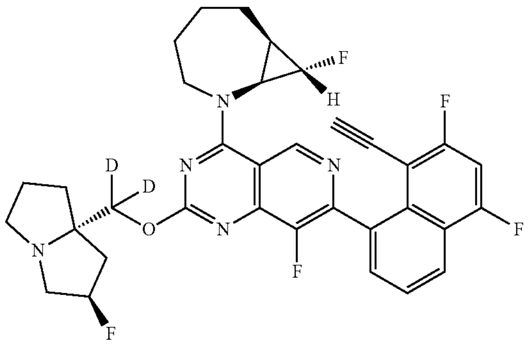 [SMILES: [2H]C([2H])(Oc1nc(N2CCCC[C@H]3[C@H](F)[C@H]32)c2cnc(-c3cccc4c(F)cc(F)c(C#C)c34)c(F)c2n1)[C@@]12CCCN1C[C@H](F)C2] | 7-(8-ethynyl-5,7-difluoronaphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine |
| 113 | 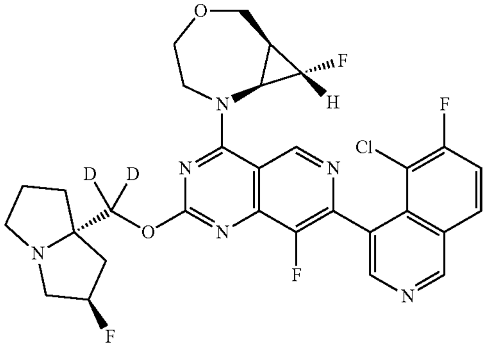 [SMILES: [2H]C([2H])(Oc1nc(N2CCOC[C@H]3[C@H](F)[C@H]32)c2cnc(-c3cncc4ccc(F)c(Cl)c34)c(F)c2n1)[C@@]12CCCN1C[C@H](F)C2] | (1S,7S,8S)-2-(7-(5-chloro-6-fluoroisoquinolin-4-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane |

TABLE 1-continued

| Example No. | Structure | Name |
| --- | --- | --- |
| 114 | 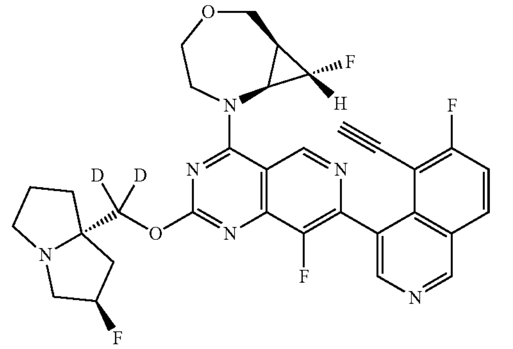 [SMILES: [2H]C([2H])(Oc1nc(N2CCOC[C@H]3[C@H](F)[C@H]32)c2cnc(-c3cncc4ccc(F)c(C#C)c34)c(F)c2n1)[C@@]12CCCN1C[C@H](F)C2] | (1S,7S,8S)-2-(7-(5-ethynyl-6-fluoroisoquinolin-4-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane |
| 115 | 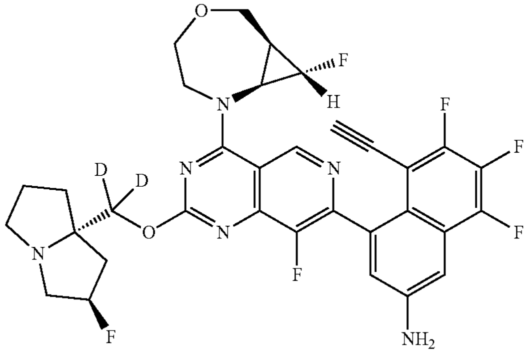 [SMILES: [2H]C([2H])(Oc1nc(N2CCOC[C@H]3[C@H](F)[C@H]32)c2cnc(-c3cc(N)cc4c(F)c(F)c(F)c(C#C)c34)c(F)c2n1)[C@@]12CCCN1C[C@H](F)C2] | 5-ethynyl-6,7,8-trifluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 116 | 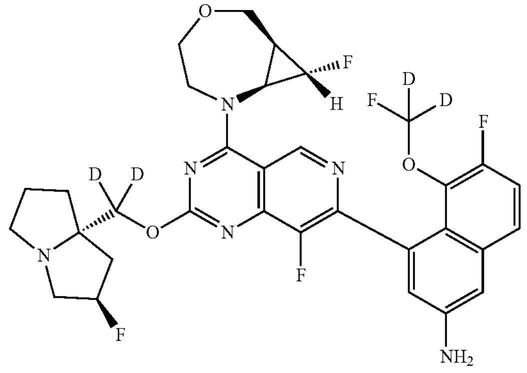 [SMILES: [2H]C([2H])(F)Oc1c(F)ccc2cc(N)cc(-c3ncc4c(N5CCOC[C@H]6[C@H](F)[C@H]65)nc(OC([2H])([2H])[C@@]56CCCN5C[C@H](F)C6)nc4c3F)c12] | 6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine |
| 117 | 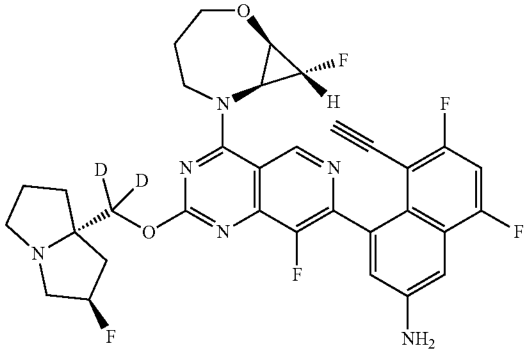 [SMILES: [2H]C([2H])(Oc1nc(N2CCCO[C@H]3[C@H](F)[C@H]32)c2cnc(-c3cc(N)cc4c(F)cc(F)c(C#C)c34)c(F)c2n1)[C@@]12CCCN1C[C@H](F)C2] | 5-ethynyl-6,8-difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
| --- | --- | --- |
| 118 | 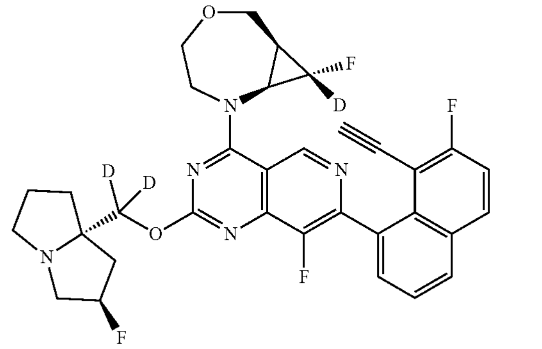 [SMILES: [2H]C([2H])(Oc1nc(N2CCOC[C@@H]3[C@H]2[C@@]3([2H])F)c2cnc(-c3cccc4ccc(F)c(C#C)c34)c(F)c2n1)[C@@]12CCCN1C[C@H](F)C2] | (1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane-8-d |
| 119 | 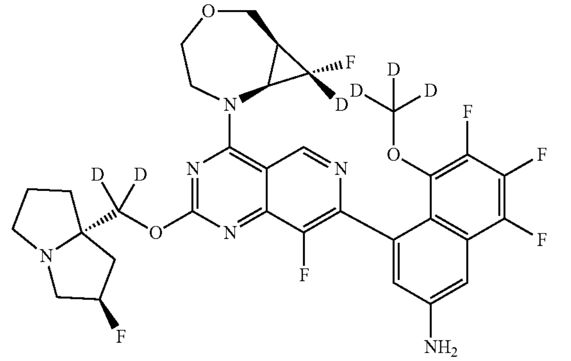 [SMILES: [2H]C([2H])([2H])Oc1c(F)c(F)c(F)c2cc(N)cc(-c3ncc4c(N5CCOC[C@@H]6[C@H]5[C@@]6([2H])F)nc(OC([2H])([2H])[C@@]56CCCN5C[C@H](F)C6)nc4c3F)c12] | 6,7,8-trifluoro-4-(8-fluoro-4-((1S,7S,8S)-8-fluoro-5-oxa-2-azabicyclo [5.1.0]octan-2-yl-8-d)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |
| 120 | 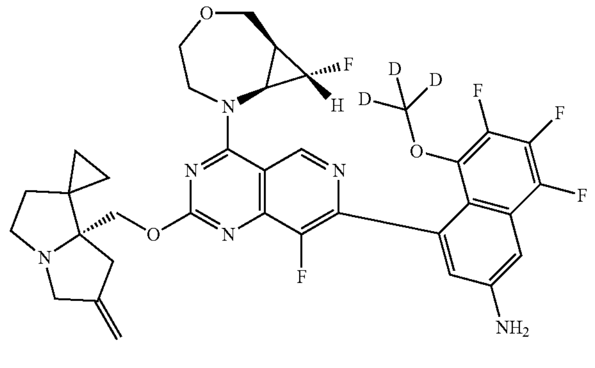 [SMILES: [2H]C([2H])([2H])Oc1c(F)c(F)c(F)c2cc(N)cc(-c3ncc4c(N5CCOC[C@H]6[C@H](F)[C@H]65)nc(OC[C@]56CC(=C)CN5CCC65CC5)nc4c3F)c12] | 6,7,8-trifluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)-5-(methoxy-d3)naphthalen-2-amine |
| 121 | 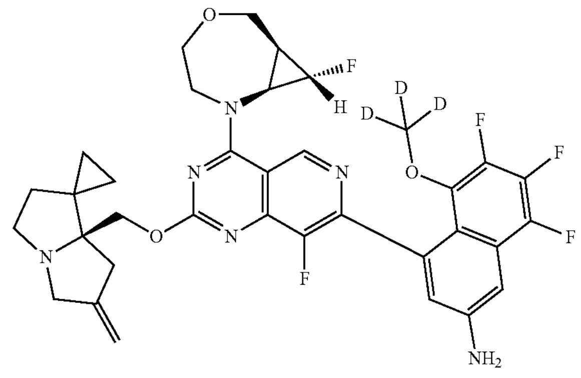 [SMILES: [2H]C([2H])([2H])Oc1c(F)c(F)c(F)c2cc(N)cc(-c3ncc4c(N5CCOC[C@H]6[C@H](F)[C@H]65)nc(OC[C@@]56CC(=C)CN5CCC65CC5)nc4c3F)c12] | 6,7,8-trifluoro-4-(8-fluoro-4-((1S,7S,8S)-8-fluoro-5-oxa-2-azabicyclo[5.1.0]octan-2-yl)-2-(((S)-6'-methylenetetrahydrospiro[cyclopropane-1,1'-pyrrolizin]-7a'(5'H)-yl)methoxy)pyrido[4,3-d]pyrimidin-7-yl)-5-(methoxy-d3)naphthalen-2-amine |

TABLE 1-continued

| Example No. | Structure | Name |
|---|---|---|
| 122 | 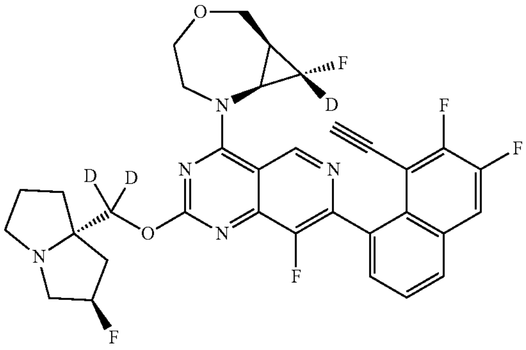 [SMILES: [2H]C([2H])(Oc1nc(N2CCOC[C@@H]3[C@H]2[C@@]3([2H])F)c2cnc(-c3cccc4cc(F)c(F)c(C#C)c34)c(F)c2n1)[C@@]12CCCN1C[C@H](F)C2] | (1S,7S,8S)-2-(7-(8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane-8-d |
| 123 | 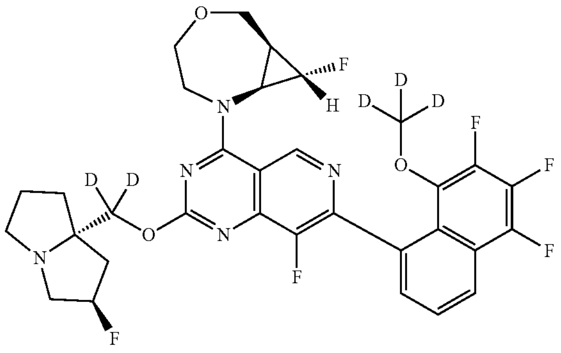 [SMILES: [2H]C([2H])([2H])Oc1c(F)c(F)c(F)c2cccc(-c3ncc4c(N5CCOC[C@H]6[C@H](F)[C@H]65)nc(OC([2H])([2H])[C@@]56CCCN5C[C@H](F)C6)nc4c3F)c12] | (1S,7S,8S)-8-fluoro-2-(8-fluoro-2-(((2R,7aS)-2-fluorotetrahydro-1H-pyrrolizin-7a(5H)-yl)methoxy-d2)-7-(5,6,7-trifluoro-8-(methoxy-d3)naphthalen-1-yl)pyrido[4,3-d]pyrimidin-4-yl)-5-oxa-2-azabicyclo[5.1.0]octane |
| 124 | 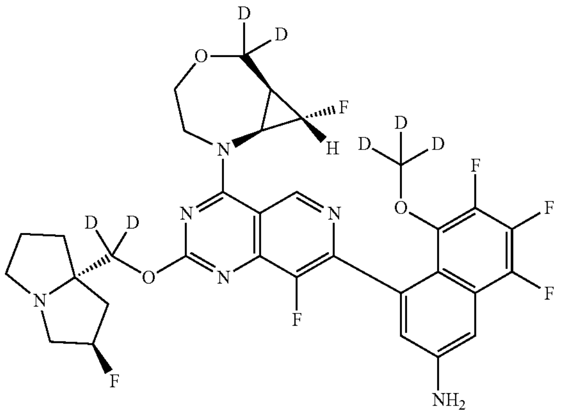 [SMILES: [2H]C([2H])([2H])Oc1c(F)c(F)c(F)c2cc(N)cc(-c3ncc4c(N5CCOC([2H])([2H])[C@H]6[C@H](F)[C@H]65)nc(OC([2H])([2H])[C@@]56CCCN5C[C@H](F)C6)nc4c3F)c12] | 6,7,8-trifluoro-4-(8-fluoro-4-((1S,7S,8S)-8-fluoro-5-oxa-2-azabicyclo[5.1.0]octan-2-yl-6,6-d2)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |
| 125 | 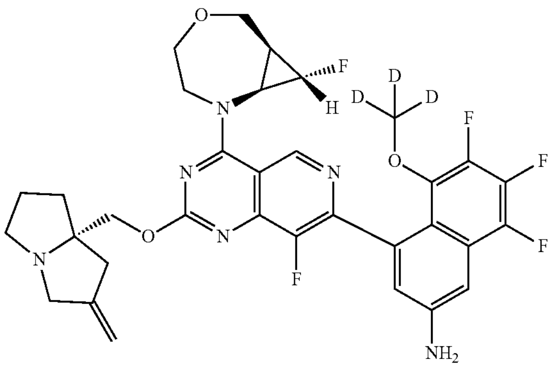 [SMILES: [2H]C([2H])([2H])Oc1c(F)c(F)c(F)c2cc(N)cc(-c3ncc4c(N5CCOC[C@H]6[C@H](F)[C@H]65)nc(OC[C@@]56CCCN5CC(=C)C6)nc4c3F)c12] | 6,7,8-trifluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-methoxy)pyrido[4,3-d]pyrimidin-7-yl)-5-(methoxy-d3)naphthalen-2-amine |

TABLE 1-continued

| Example No. | Structure | Name |
|---|---|---|
| 126 | 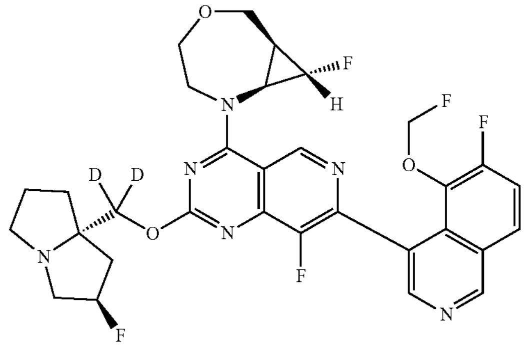 [SMILES: [2H]C([2H])(Oc1nc(N2CCOC[C@H]3[C@H](F)[C@H]32)c2cnc(-c3cncc4ccc(F)c(OCF)c34)c(F)c2n1)[C@@]12CCCN1C[C@H](F)C2] | (1S,7S,8S)-8-fluoro-2-(8-fluoro-7-(6-fluoro-5-(fluoromethoxy)isoquinolin-4-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane |
| 127 | 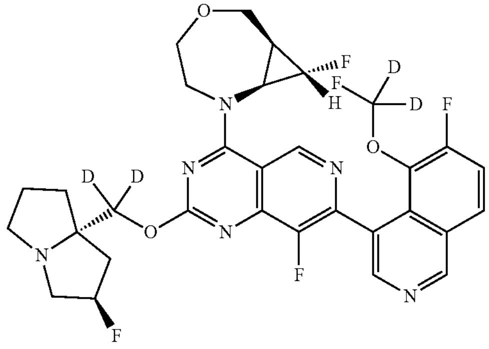 [SMILES: [2H]C([2H])(F)Oc1c(F)ccc2cncc(-c3ncc4c(N5CCOC[C@H]6[C@H](F)[C@H]65)nc(OC([2H])([2H])[C@@]56CCCN5C[C@H](F)C6)nc4c3F)c12] | (1S,7S,8S)-8-fluoro-2-(8-fluoro-7-(6-fluoro-5-(fluoromethoxy-d2)isoquinolin-4-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane |
| 128 | 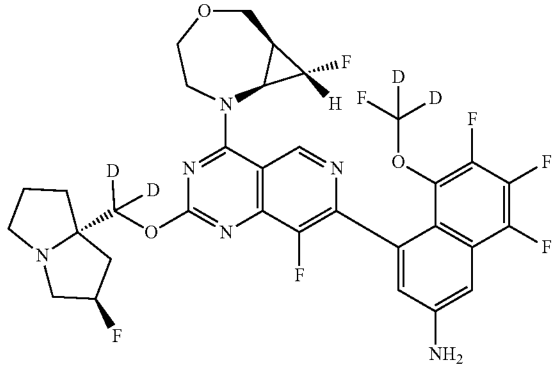 [SMILES: [2H]C([2H])(F)Oc1c(F)c(F)c(F)c2cc(N)cc(-c3ncc4c(N5CCOC[C@H]6[C@H](F)[C@H]65)nc(OC([2H])([2H])[C@@]56CCCN5C[C@H](F)C6)nc4c3F)c12] | 6,7,8-trifluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine |
| 129 | 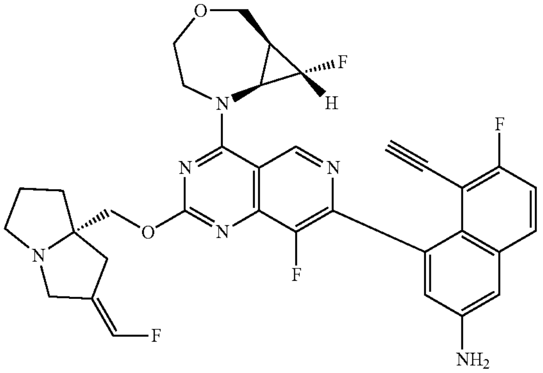 [SMILES: C#Cc1c(F)ccc2cc(N)cc(-c3ncc4c(N5CCOC[C@H]6[C@H](F)[C@H]65)nc(OC[C@@]56CCCN5C/C(=C/F)C6)nc4c3F)c12] | (1S,7S,8S)-2-(7-(8-ethynyl-7-fluoronaphthalen-1-yl)-8-fluoro-2-(((S,E)-2-(fluoromethylene)tetrahydro-1H-pyrrolizin-7a(5H)-methoxy)pyrido[4,3-d]pyrimidin-4-yl)-8-fluoro-5-oxa-2-azabicyclo[5.1.0]octane |

TABLE 1-continued

| Example No. | Structure | Name |
| --- | --- | --- |
| 130 | 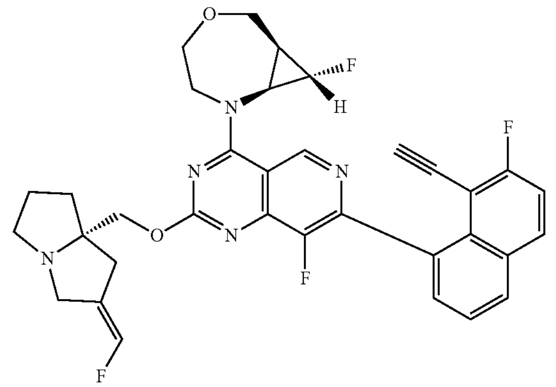 [SMILES: C#Cc1c(F)ccc2cccc(-c3ncc4c(N5CCOC[C@H]6[C@H](F)[C@H]65)nc(OC[C@@]56CCCN5C/C(=C\F)C6)nc4c3F)c12] | (1S,7S,8S)-2-(7-(8-ethynyl-7-fluoronaphthalen-1-yl)-8-fluoro-2-(((S,Z)-2-(fluoromethylene)tetrahydro-1H-pyrrolizin-7a(5H)-methoxy)pyrido[4,3-d]pyrimidin-4-yl)-8-fluoro-5-oxa-2-azabicyclo[5.1.0]octane |
| 131 | 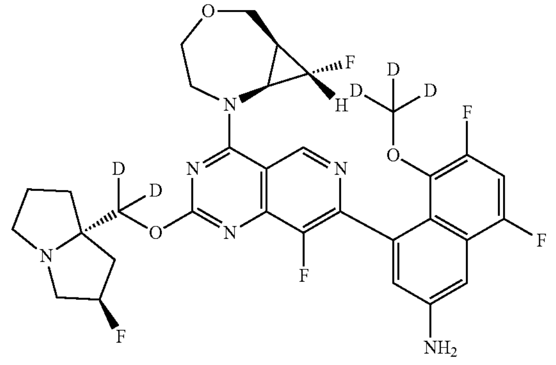 [SMILES: [2H]C([2H])([2H])Oc1c(F)cc(F)c2cc(N)cc(-c3ncc4c(N5CCOC[C@H]6[C@H](F)[C@H]65)nc(OC([2H])([2H])[C@@]56CCCN5C[C@H](F)C6)nc4c3F)c12] | 6,8-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |
| 132 | 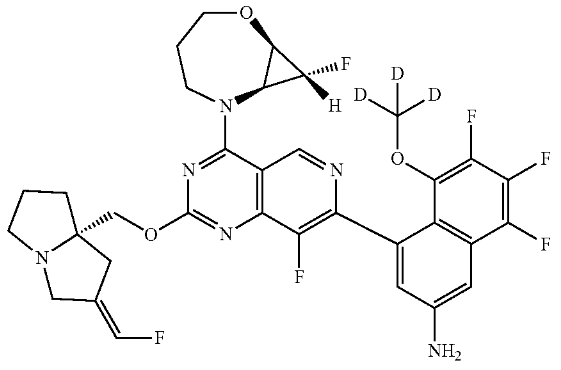 [SMILES: [2H]C([2H])([2H])Oc1c(F)c(F)c(F)c2cc(N)cc(-c3ncc4c(N5CCCO[C@H]6[C@H](F)[C@H]65)nc(OC[C@@]56CCCN5C/C(=C/F)C6)nc4c3F)c12] | 6,7,8-trifluoro-4-(8-fluoro-4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)-5-(methoxy-d3)naphthalen-2-amine |
| 133 | 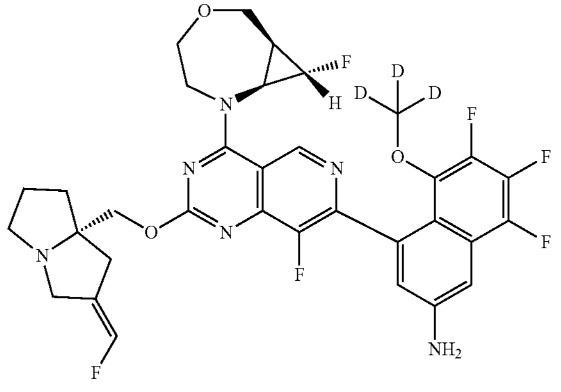 [SMILES: [2H]C([2H])([2H])Oc1c(F)c(F)c(F)c2cc(N)cc(-c3ncc4c(N5CCOC[C@H]6[C@H](F)[C@H]65)nc(OC[C@@]56CCCN5C/C(=C\F)C6)nc4c3F)c12] | 6,7,8-trifluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(methoxy-d3)naphthalen-2-amine |

TABLE 1-continued

| Example No. | Structure | Name |
|---|---|---|
| 134 | 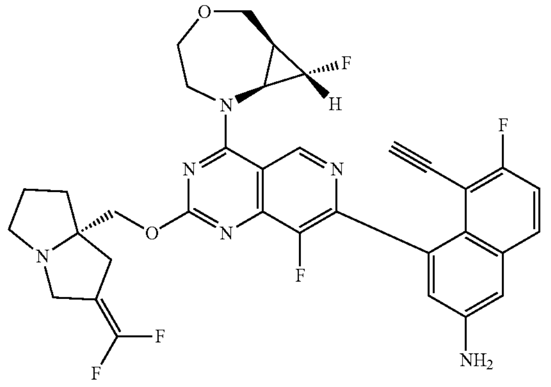 [SMILES: C#Cc1c(F)ccc2cc(N)cc(-c3ncc4c(N5CCOC[C@H]6[C@H](F)[C@H]65)nc(OC[C@@]56CCCN5CC(=C(F)F)C6)nc4c3F)c12] | 4-(2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 135 | 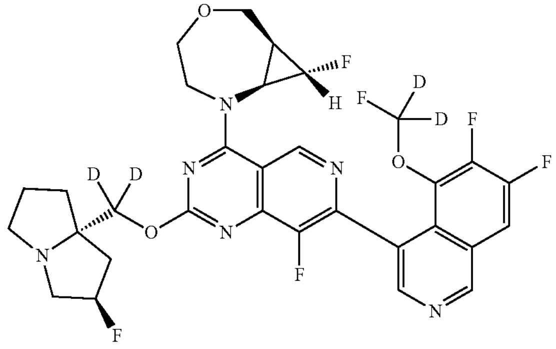 [SMILES: [2H]C([2H])(F)Oc1c(F)c(F)cc2cncc(-c3ncc4c(N5CCOC[C@H]6[C@H](F)[C@H]65)nc(OC([2H])([2H])[C@@]56CCCN5C[C@H](F)C6)nc4c3F)c12] | (1S,7S,8S)-2-(7-(6,7-difluoro-5-(fluoromethoxy-d2)isoquinolin-4-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane |
| 136 | 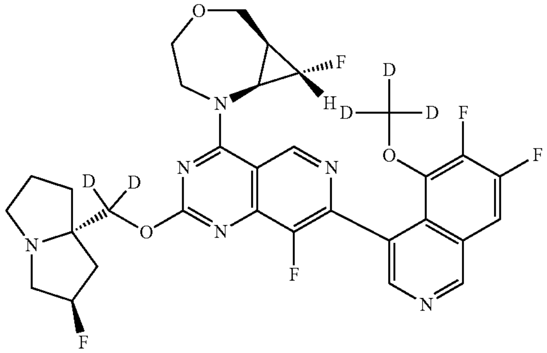 [SMILES: [2H]C([2H])([2H])Oc1c(F)c(F)cc2cncc(-c3ncc4c(N5CCOC[C@H]6[C@H](F)[C@H]65)nc(OC([2H])([2H])[C@@]56CCCN5C[C@H](F)C6)nc4c3F)c12] | (1S,7S,8S)-2-(7-(6,7-difluoro-5-(methoxy-d3)isoquinolin-4-yl)-8-fluoro-2-(((2R,7aS)-2-fluorotetrahydro-1H-pyrrolizin-7a(5H)-methoxy-d2)pyrido[4,3-d]pyrimidin-4-yl)-8-fluoro-5-oxa-2-azabicyclo[5.1.0]octane |
| 137 | 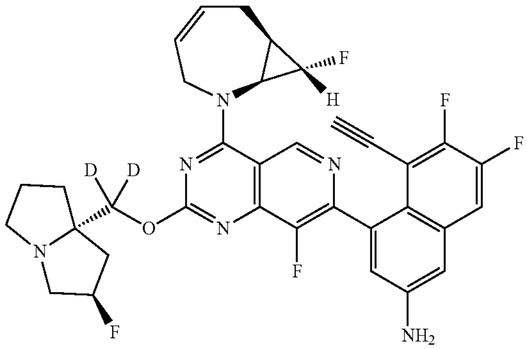 [SMILES: [2H]C([2H])(Oc1nc(N2CC=CC[C@H]3[C@H](F)[C@H]32)c2cnc(-c3cc(N)cc4cc(F)c(F)c(C#C)c34)c(F)c2n1)[C@@]12CCCN1C[C@H](F)C2] | 5-ethynyl-6,7-difluoro-4-(8-fluoro-4-((1S,7R,8S)-8-fluoro-2-azabicyclo[5.1.0]oct-4-en-2-yl)-2-(((2R,7aS)-2-fluorotetrahydro~1H-pyrrolizin-7a(5H)-yl)methoxy-d2)pyrido[4,3-d]pyrimidin-7-yl)naphthalen-2-amine |

TABLE 1-continued

| Example No. | Structure | Name |
|---|---|---|
| 138 | 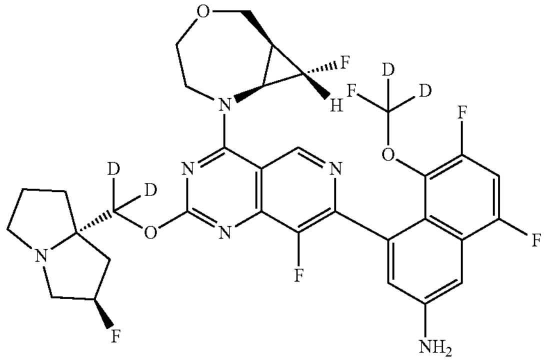 [SMILES: [2H]C([2H])(F)Oc1c(F)cc(F)c2cc(N)cc(-c3ncc4c(N5CCOC[C@H]6[C@H](F)[C@H]65)nc(OC([2H])([2H])[C@@]56CCCN5C[C@H](F)C6)nc4c3F)c12] | 5-ethynyl-6,7-difluoro-4-(8-fluoro-4-((1R,7S,8R)-8-fluoro-2-azabicyclo[5.1.0]oct-4-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 139 | 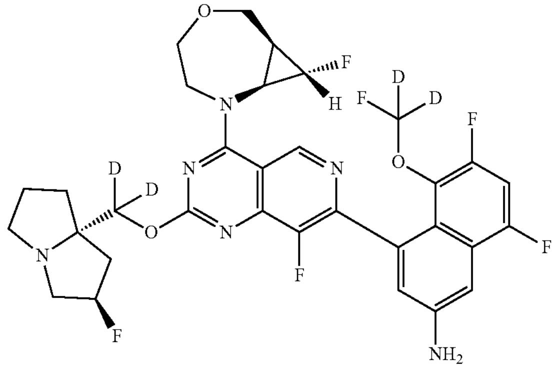 [SMILES: [2H]C([2H])(F)Oc1c(F)cc(F)c2cc(N)cc(-c3ncc4c(N5CCOC[C@H]6[C@H](F)[C@H]65)nc(OC([2H])([2H])[C@@]56CCCN5C[C@H](F)C6)nc4c3F)c12] | 6,8-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine |
| 140 | 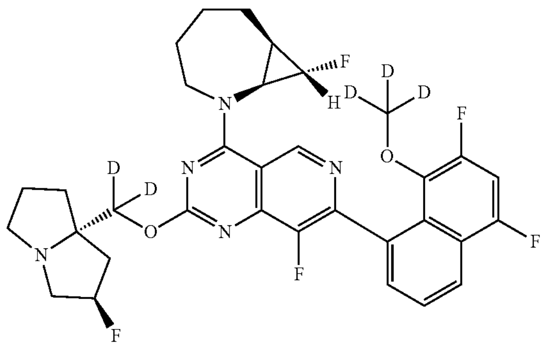 [SMILES: [2H]C([2H])([2H])Oc1c(F)cc(F)c2cccc(-c3ncc4c(N5CCCC[C@H]6[C@H](F)[C@H]65)nc(OC([2H])([2H])[C@@]56CCCN5C[C@H](F)C6)nc4c3F)c12] | 7-(5,7-difluoro-8-(methoxy-d3)naphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-methoxy-d2)pyrido[4,3-d]pyrimidine |
| 141 | 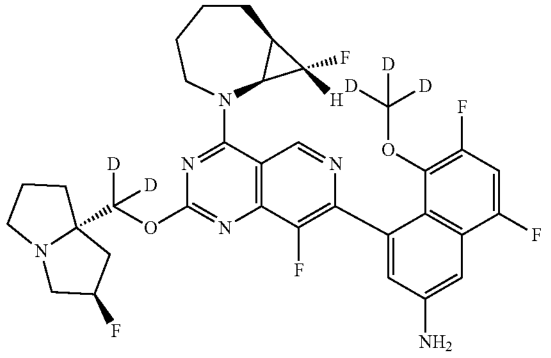 [SMILES: [2H]C([2H])([2H])Oc1c(F)cc(F)c2cc(N)cc(-c3ncc4c(N5CCCC[C@H]6[C@H](F)[C@H]65)nc(OC([2H])([2H])[C@@]56CCCN5C[C@H](F)C6)nc4c3F)c12] | 6,8-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |

TABLE 1-continued

| Example No. | Structure | Name |
|---|---|---|
| 142 | 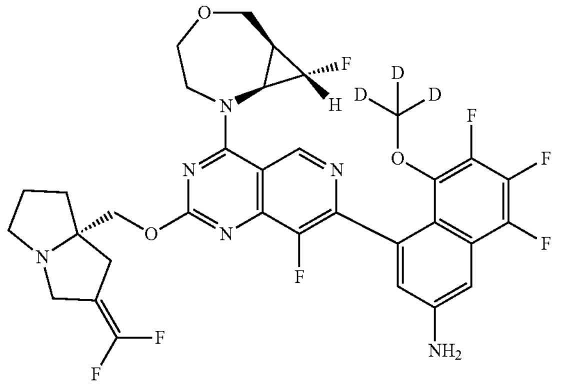 [SMILES: [2H]C([2H])([2H])Oc1c(F)c(F)c(F)c2cc(N)cc(-c3ncc4c(N5CCOC[C@H]6[C@H](F)[C@H]65)nc(OC[C@@]56CCCN5CC(=C(F)F)C6)nc4c3F)c12] | 4-(2-(((S)-2-(difluoromethylene)tetrahydro-1H-pyrrolizin-7a(5H)-methoxy)-8-fluoro-4-((1S,7S,8S)-8-fluoro-5-oxa-2-azabicyclo[5.1.0]octan-2-yl)pyrido[4,3-d]pyrimidin-7-yl)-6,7,8-trifluoro-5-(methoxy-d3)naphthalen-2-amine |
| 143 | 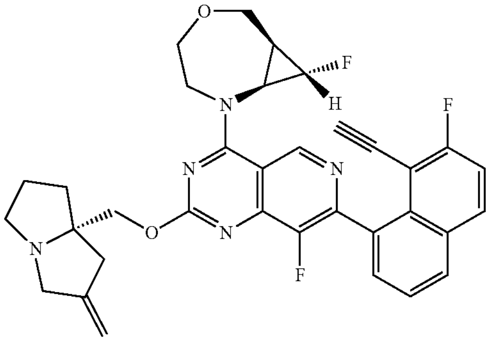 [SMILES: C#Cc1c(F)ccc2cccc(-c3ncc4c(N5CCOC[C@H]6[C@H](F)[C@H]65)nc(OC[C@@]56CCCN5CC(=C)C6)nc4c3F)c12] | (1S,7S,8S)-2-(7-(8-ethynyl-7-fluoronaphthalen-1-yl)-8-fluoro-2-(((S)-2-methylenetetrahydro-1H-pyrrolizin-7a(5H)-yl)methoxy)pyrido[4,3-d]pyrimidin-4-yl)-8-fluoro-5-oxa-2-azabicyclo[5.1.0]octane |
| 144 | 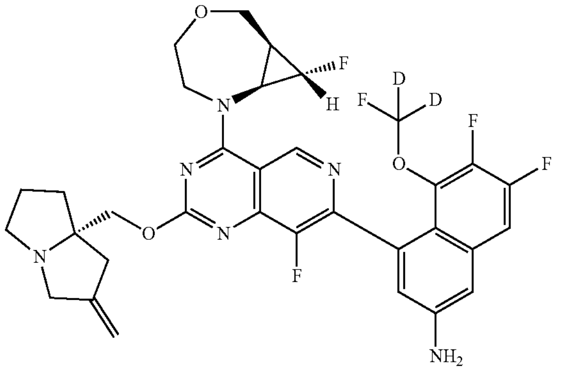 [SMILES: [2H]C([2H])(F)Oc1c(F)c(F)cc2cc(N)cc(-c3ncc4c(N5CCOC[C@H]6[C@H](F)[C@H]65)nc(OC[C@@]56CCCN5CC(=C)C6)nc4c3F)c12] | 6,7-difluoro-4-(8-fluoro-4-((1S,7,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(fluoromethoxy-d2)naphthalen-2-amine |
| 145 | 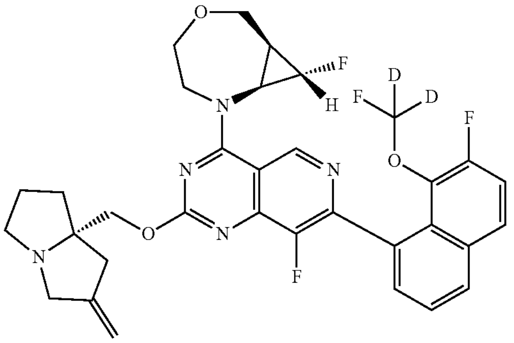 [SMILES: [2H]C([2H])(F)Oc1c(F)ccc2cccc(-c3ncc4c(N5CCOC[C@H]6[C@H](F)[C@H]65)nc(OC[C@@]56CCCN5CC(=C)C6)nc4c3F)c12] | (1S,7S,8S)-8-fluoro-2-(8-fluoro-7-(7-fluoro-8-(fluoromethoxy-d2)naphthalen-1-yl)-2-(((S)-2-methylenetetrahydro-1H-pyrrolizin-7a(5H)-methoxy)pyrido[4,3-d]pyrimidin-4-yl)-5-oxa-2-azabicyclo[5.1.0]octane |

TABLE 1-continued

| Example No. | Structure | Name |
|---|---|---|
| 146 | 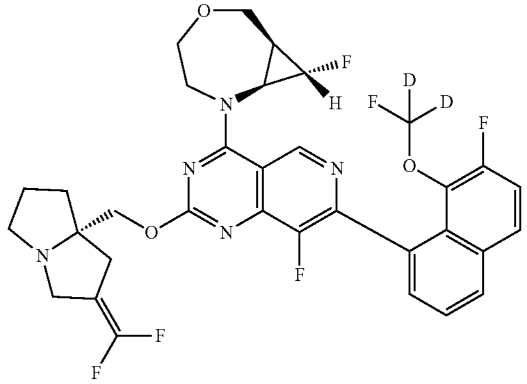 [SMILES: [2H]C([2H])(F)Oc1c(F)ccc2cccc(-c3ncc4c(N5CCOC[C@H]6[C@H](F)[C@H]65)nc(OC[C@@]56CCCN5CC(=C(F)F)C6)nc4c3F)c12] | (1S,7S,8S)-2-(2-(((S)-2-(difluoromethylene)tetrahydro-1H~pyrrolizin-7a(5H)-methoxy)-8-fluoro-7-(7-fluoro-8-(fluoromethoxy-d2)naphthalen-1-pyrido[4,3-d]pyrimidin-4-yl)-8-fluoro-5-oxa-2-azabicyclo[5.1.0]octane |
| 147 | 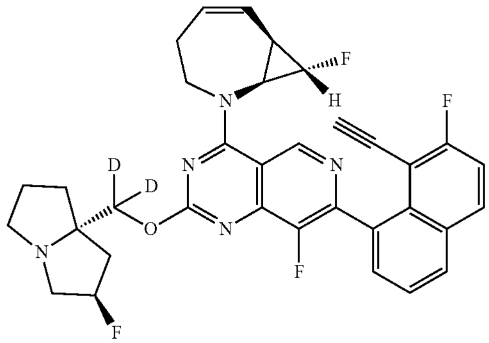 [SMILES: [2H]C([2H])(Oc1nc(N2CCC=C[C@H]3[C@H](F)[C@H]32)c2cnc(-c3cccc4ccc(F)c(C#C)c34)c(F)c2n1)[C@@]12CCCN1C[C@H](F)C2] | 7-(8-ethynyl-7-fluoronaphthalen-1-yl)-8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a(5H)-yl)methoxy-d2)pyrido[4,3-d]pyrimidine |
| 148 | 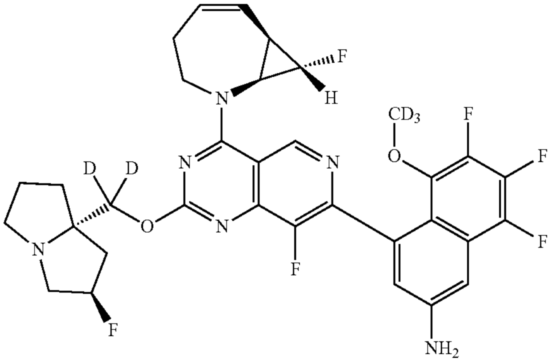 [SMILES: [2H]C([2H])([2H])Oc1c(F)c(F)c(F)c2cc(N)cc(-c3ncc4c(N5CCC=C[C@H]6[C@H](F)[C@H]65)nc(OC([2H])([2H])[C@@]56CCCN5C[C@H](F)C6)nc4c3F)c12] | 6,7,8-trifluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |
| 149 | 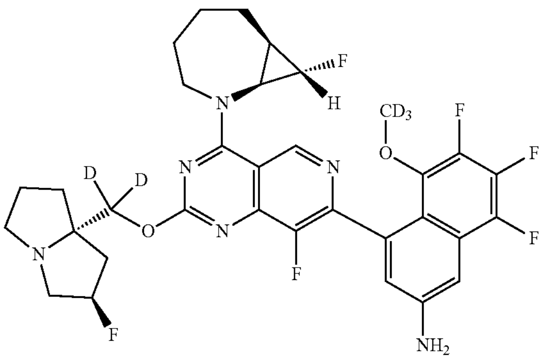 [SMILES: [2H]C([2H])([2H])Oc1c(F)c(F)c(F)c2cc(N)cc(-c3ncc4c(N5CCCC[C@H]6[C@H](F)[C@H]65)nc(OC([2H])([2H])[C@@]56CCCN5C[C@H](F)C6)nc4c3F)c12] | 6,8-difluoro-4-(8-fluoro-4-((1S,7R,8S)-8-fluoro-2-azabicyclo [5.1.0]oct-5-en-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine |

TABLE 1-continued

| Example No. | Structure | Name |
|---|---|---|
| 150 | 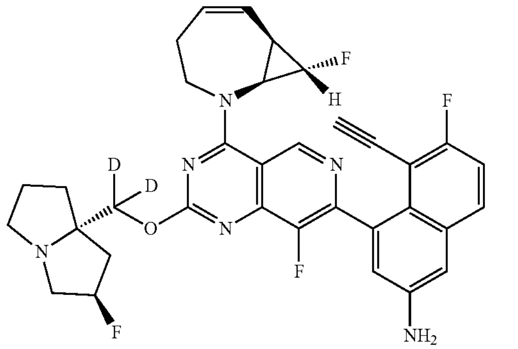 [SMILES: [2H]C([2H])(Oc1nc(N2CCC=C[C@H]3[C@H](F)[C@H]32)c2cnc(-c3cc(N)cc4ccc(F)c(C#C)c34)c(F)c2n1)[C@@]12CCCN1C[C@H](F)C2] | 5-ethynyl-6-fluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 151 | 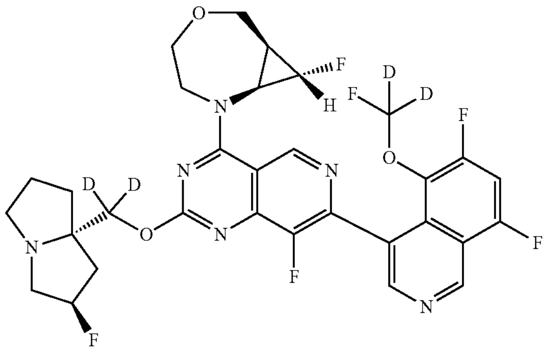 [SMILES: [2H]C([2H])(F)Oc1c(F)cc(F)c2cncc(-c3ncc4c(N5CCOC[C@H]6[C@H](F)[C@H]65)nc(OC([2H])([2H])[C@@]56CCCN5C[C@H](F)C6)nc4c3F)c12] | (1S,7S,8S)-2-(7-(5,7-difluoro-8-(fluoromethoxy-d2)naphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane |
| 152 | 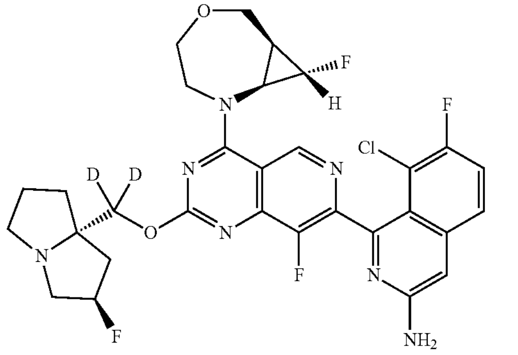 | 8-chloro-7-fluoro-1-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)isoquinolin-3-amine |
| 153 | 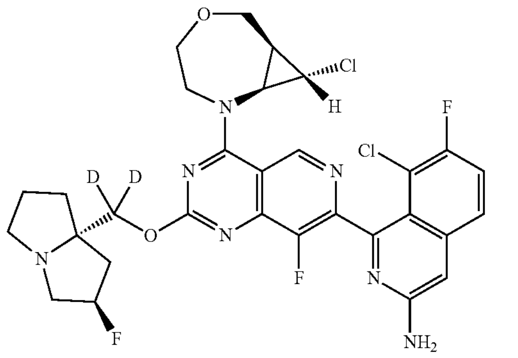 [SMILES: [2H]C([2H])(Oc1nc(N2CCOC[C@H]3[C@H](Cl)[C@H]32)c2cnc(-c3nc(N)cc4ccc(F)c(Cl)c34)c(F)c2n1)[C@@]12CCCN1C[C@H](F)C2] | 8-chloro-7-fluoro-1-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)isoquinolin-3-amine |

TABLE 1-continued

| Example No. | Structure | Name |
|---|---|---|
| 154 | 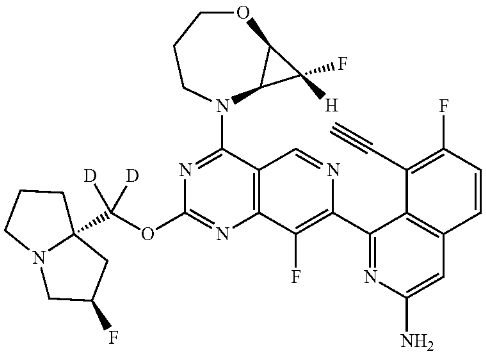 [SMILES: [2H]C([2H])(Oc1nc(N2CCCO[C@H]3[C@H](F)[C@H]32)c2cnc(-c3nc(N)cc4ccc(F)c(C#C)c34)c(F)c2n1)[C@@]12CCCN1C[C@H](F)C2] | 8-ethynyl-7-fluoro-1-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)isoquinolin-3-amine |
| 155 | 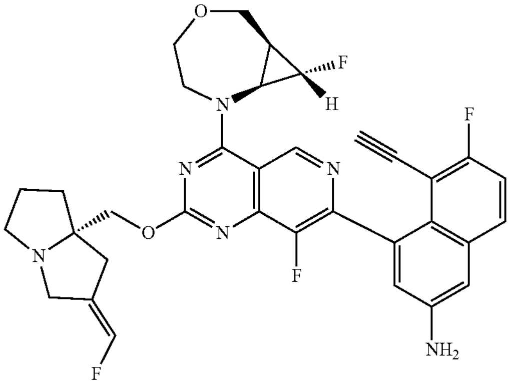 [SMILES: C#Cc1c(F)ccc2cc(N)cc(-c3ncc4c(N5CCOC[C@H]6[C@H](F)[C@H]65)nc(OC[C@@]56CCCN5C/C(=C\F)C6)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)naphthalen-2-amine |
| 156 | 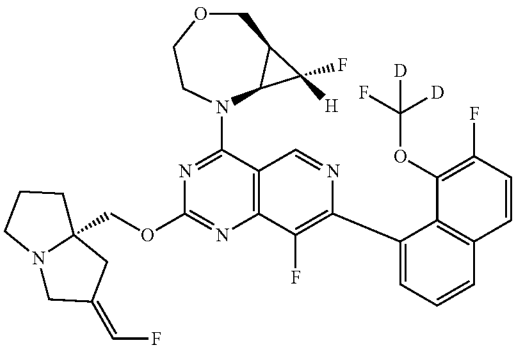 [SMILES: [2H]C([2H])(F)Oc1c(F)ccc2cccc(-c3ncc4c(N5CCOC[C@H]6[C@H](F)[C@H]65)nc(OC[C@@]56CCCN5C/C(=C/F)C6)nc4c3F)c12] | (1S,7S,8S)-8-fluoro-2-(8-fluoro-7-(7-fluoro-8-(fluoromethoxy-d2)naphthalen-1-yl)-2-(((S,E)-2-(fluoromethylene)tetrahydro-1H-pyrrolizin-7a(5H)-yl)methoxy)pyrido[4,3-d]pyrimidin-4-yl)-5-oxa-2-azabicyclo[5.1.0]octane |
| 157 | 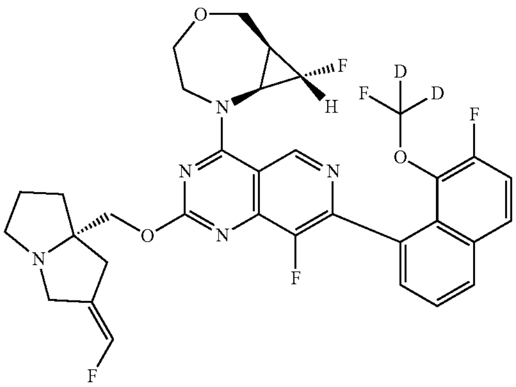 [SMILES: [2H]C([2H])(F)Oc1c(F)ccc2cccc(-c3ncc4c(N5CCOC[C@H]6[C@H](F)[C@H]65)nc(OC[C@@]56CCCN5C/C(=C\F)C6)nc4c3F)c12] | (1S,7S,8S)-8-fluoro-2-(8-fluoro-7-(7-fluoro-8-(fluoro methoxy-d2)naphthalen-1-yl)-2-(((S,Z)-2-(fluoromethylene)tetrahydro-1H-pyrrolizin-7a(5H)-yl)methoxy)pyrido[4,3-d]pyrimidin-4-yl)-5-oxa-2-azabicyclo[5.1.0]octane |

TABLE 1-continued

| Example No. | Structure | Name |
| --- | --- | --- |
| 158 | 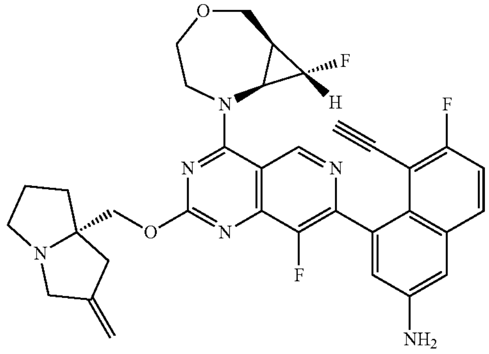 [SMILES: C#Cc1c(F)ccc2cc(N)cc(-c3ncc4c(N5CCOC[C@H]6[C@H](F)[C@H]65)nc(OC[C@@]56CCCN5CC(=C)C6)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)naphthalen-2-amine |
| 159 | 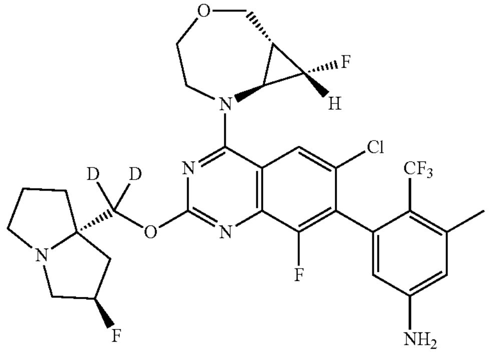 [SMILES: [2H]C([2H])(Oc1nc(N2CCOC[C@@H]3[C@H](F)[C@H]32)c2cc(Cl)c(-c3cc(N)cc(C)c3C(F)(F)F)c(F)c2n1)[C@@]12CCCN1C[C@H](F)C2] | 6-(6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-4-methyl-5-(trifluoromethpyridin-2-amine |
| 160 | 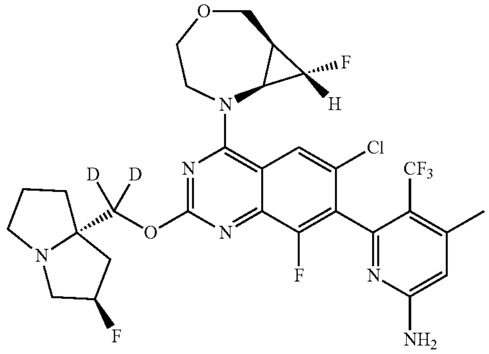 [SMILES: [2H]C([2H])(Oc1nc(N2CCOC[C@H]3[C@H](F)[C@H]32)c2cc(Cl)c(-c3nc(N)cc(C)c3C(F)(F)F)c(F)c2n1)[C@@]12CCCN1C[C@H](F)C2] | 6-(6-chloro-8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-4-methyl-5-(trifluoromethpyridin-2-amine |
| 161 | 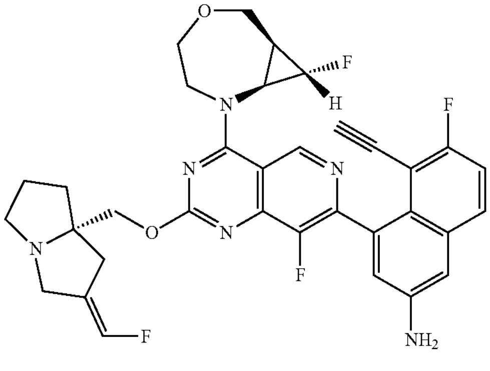 [SMILES: C#Cc1c(F)ccc2cc(N)cc(-c3ncc4c(N5CCOC[C@H]6[C@H](F)[C@H]65)nc(OC[C@@]56CCCN5C/C(=C/F)C6)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-methoxy)pyrido[4,3-d]pyrimidin-7-yl)naphthalen-2-amine |

TABLE 1-continued

| Example No. | Structure | Name |
|---|---|---|
| 162 | 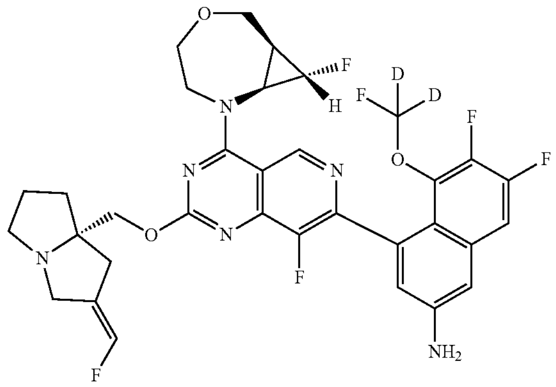 [SMILES: [2H]C([2H])(F)Oc1c(F)c(F)cc2cc(N)cc(-c3ncc4c(N5CCOC[C@H]6[C@H](F)[C@H]65)nc(OC[C@@]56CCCN5C/C(=C\F)C6)nc4c3F)c12] | 6,7-difluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-methoxy)pyrido[4,3-d]pyrimidin-7-yl)-5-(fluoromethoxy-d2)naphthalen-2-amine |
| 163 | 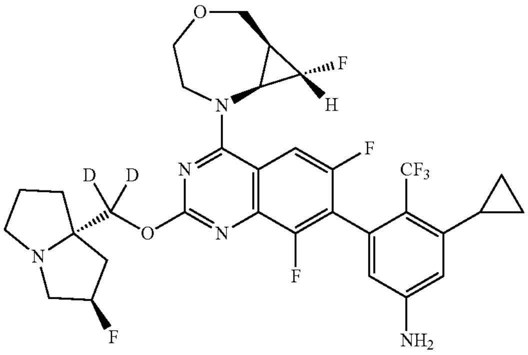 [SMILES: [2H]C([2H])(Oc1nc(N2CCOC[C@H]3[C@H](F)[C@H]32)c2cc(F)c(-c3cc(N)cc(C4CC4)c3C(F)(F)F)c(F)c2n1)[C@@]12CCCN1C[C@H](F)C2] | 3-cyclopropyl-5-(6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-4-(trifluoromethyl)aniline |
| 164 | 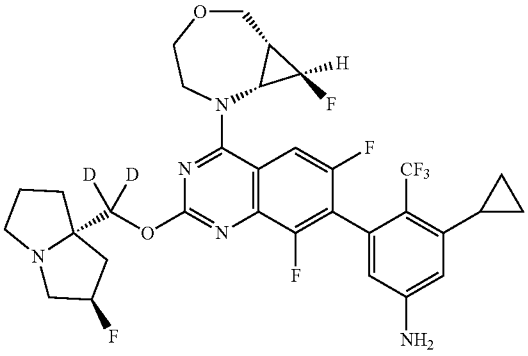 [SMILES: [2H]C([2H])(Oc1nc(N2CCOC[C@@H]3[C@@H](F)[C@@H]32)c2cc(F)c(-c3cc(N)cc(C4CC4)c3C(F)(F)F)c(F)c2n1)[C@@]12CCCN1C[C@H](F)C2] | 3-cyclopropyl-5-(6,8-difluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-4-(trifluoromethyl)aniline |
| 165 | 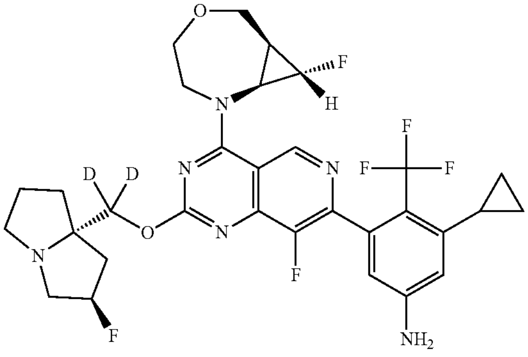 [SMILES: [2H]C([2H])(Oc1nc(N2CCOC[C@H]3[C@H](F)[C@H]32)c2cnc(-c3cc(N)cc(C4CC4)c3C(F)(F)F)c(F)c2n1)[C@@]12CCCN1C[C@H](F)C2] | 3-cyclopropyl-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-(trifluoromethyl)aniline |

TABLE 1-continued

| Example No. | Structure | Name |
| --- | --- | --- |
| 166 | 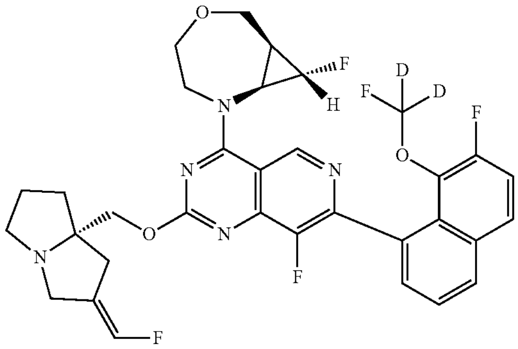 [SMILES: [2H]C([2H])(F)Oc1c(F)ccc2cccc(-c3ncc4c(N5CCOC[C@H]6[C@H](F)[C@H]65)nc(OC[C@@]56CCCN5C/C(=C/F)C6)nc4c3F)c12] | (1S,7S,8S)-2-(7-(8-ethynyl-7-fluoronaphthalen-1-yl)-8-fluoro-2-(((R)-6'-methylenetetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane |
| 167 | 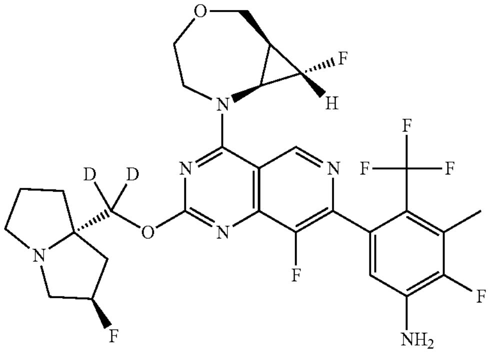 [SMILES: [2H]C([2H])(Oc1nc(N2CCOC[C@H]3[C@H](F)[C@H]32)c2cnc(-c3cc(N)c(F)c(C)c3C(F)(F)F)c(F)c2n1)[C@@]12CCCN1C[C@H](F)C2] | 2-fluoro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-3-methyl-4-(trifluoromethyl)aniline |
| 168 | 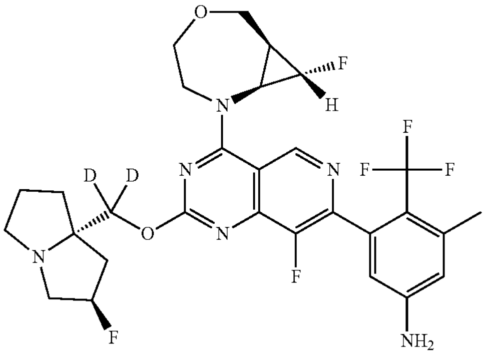 [SMILES: [2H]C([2H])(Oc1nc(N2CCOC[C@H]3[C@H](F)[C@H]32)c2cnc(-c3cc(N)cc(C)c3C(F)(F)F)c(F)c2n1)[C@@]12CCCN1C[C@H](F)C2] | 3-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-methyl-4-(trifluoromethyl)aniline |
| 169 | 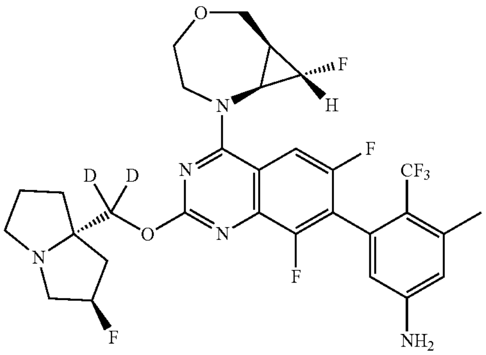 [SMILES: [2H]C([2H])(Oc1nc(N2CCOC[C@H]3[C@H](F)[C@H]32)c2cc(F)c(-c3cc(N)cc(C)c3C(F)(F)F)c(F)c2n1)[C@@]12CCCN1C[C@H](F)C2] | 3-(6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-methyl-4-(trifluoromethyl)aniline |

TABLE 1-continued

| Example No. | Structure | Name |
|---|---|---|
| 170 | 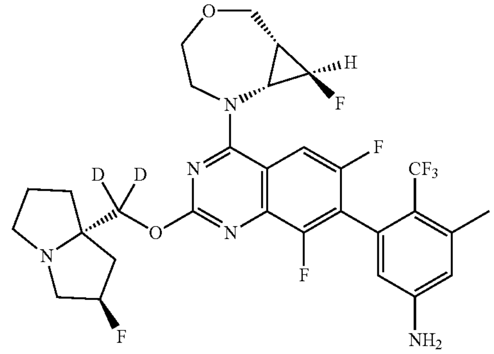 [SMILES: [2H]C([2H])(Oc1nc(N2CCOC[C@@H]3[C@@H](F)[C@@H]32)c2cc(F)c(-c3cc(N)cc(C)c3C(F)(F)F)c(F)c2n1)[C@@]12CCCN1C[C@H](F)C2] | 3-(6,8-difluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-methyl-4-(trifluoromethyl)aniline |
| 171 | 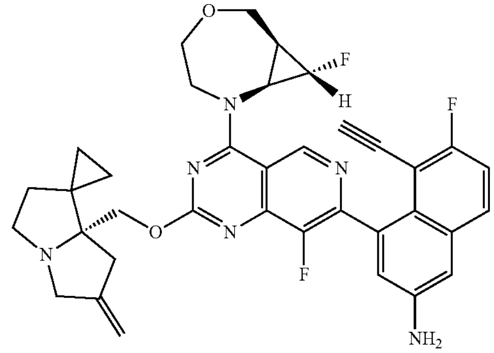 [SMILES: C#Cc1c(F)ccc2cc(N)cc(-c3ncc4c(N5CCOC[C@H]6[C@H](F)[C@H]65)nc(OC[C@]56CC(=C)CN5CCC65CC5)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)naphthalen-2-amine |
| 172 | 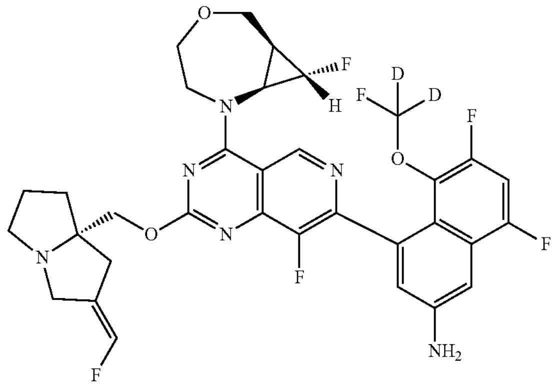 [SMILES: [2H]C([2H])(F)Oc1c(F)cc(F)c2cc(N)cc(-c3ncc4c(N5CCOC[C@H]6[C@H](F)[C@H]65)nc(OC[C@@]56CCCN5C/C(=C\F)C6)nc4c3F)c12] | 6,8-difluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(methoxy-d3)naphthalen-2-amine |
| 173 | 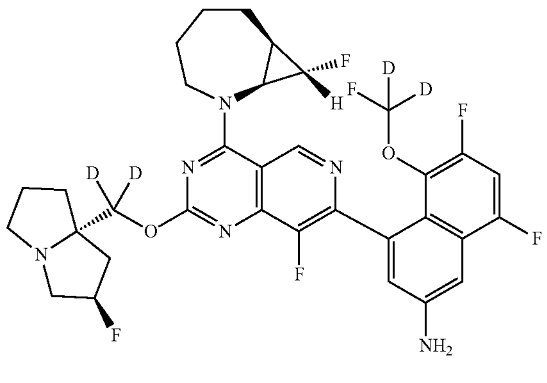 [SMILES: [2H]C([2H])(F)Oc1c(F)cc(F)c2cc(N)cc(-c3ncc4c(N5CCCC[C@H]6[C@H](F)[C@H]65)nc(OC([2H])([2H])[C@@]56CCCN5C[C@H](F)C6)nc4c3F)c12] | 6,8-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine |

TABLE 1-continued

| Example No. | Structure | Name |
|---|---|---|
| 174 | 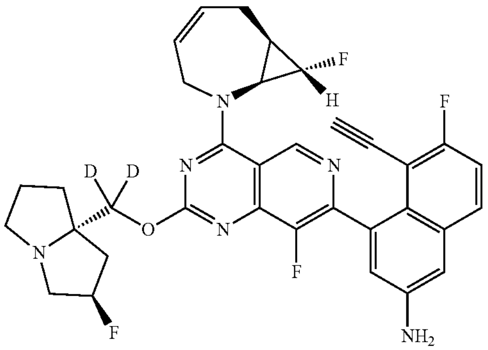 [SMILES: [2H]C([2H])(Oc1nc(N2CC=CC[C@H]3[C@H](F)[C@H]32)c2cnc(-c3cc(N)cc4ccc(F)c(C#C)c34)c(F)c2n1)[C@@]12CCCN1C[C@H](F)C2] | 5-ethynyl-6-fluoro-4-(8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 175 | 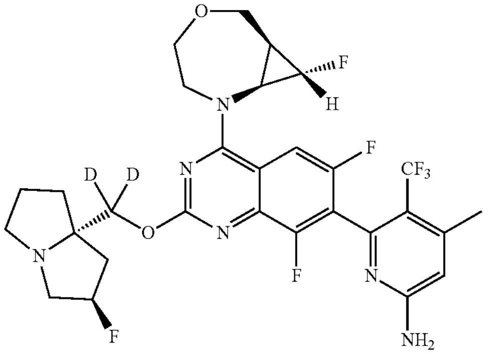 | 6-(6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-4-methyl-5-(trifluoromethpyridin-2-amine |
| 176 | 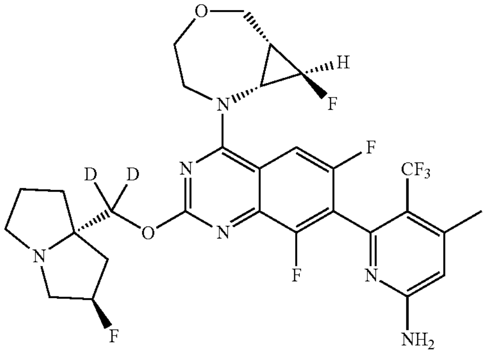 [SMILES: [2H]C([2H])(Oc1nc(N2CCOC[C@@H]3[C@@H](F)[C@@H]32)c2cc(F)c(-c3nc(N)cc(C)c3C(F)(F)F)c(F)c2n1)[C@@]12CCCN1C[C@H](F)C2] | 6-(6,8-difluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-4-methyl-5-(trifluoromethpyridin-2-amine |
| 177 | 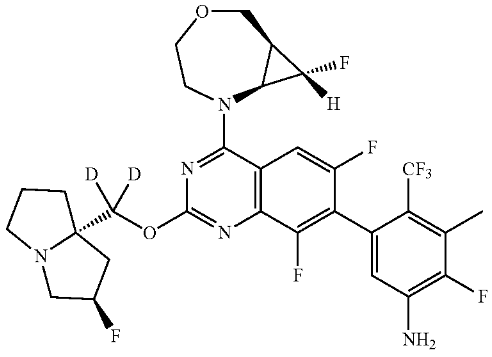 [SMILES: [2H]C([2H])(Oc1nc(N2CCOC[C@H]3[C@H](F)[C@H]32)c2cc(F)c(-c3cc(N)c(F)c(C)c3C(F)(F)F)c(F)c2n1)[C@@]12CCCN1C[C@H](F)C2] | 5-(6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-2-fluoro-3-methyl-4-(trifluoromethyl)aniline |

TABLE 1-continued

| Example No. | Structure | Name |
|---|---|---|
| 178 | 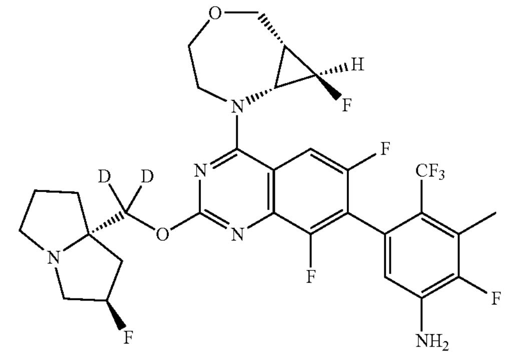 [SMILES: [2H]C([2H])(Oc1nc(N2CCOC[C@@H]3[C@@H](F)[C@@H]32)c2cc(F)c(-c3cc(N)c(F)c(C)c3C(F)(F)F)c(F)c2n1)[C@@]12CCCN1C[C@H](F)C2] | 5-(6,8-difluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-2-fluoro-3-methyl-4-(trifluoromethyl)aniline |
| 179 | 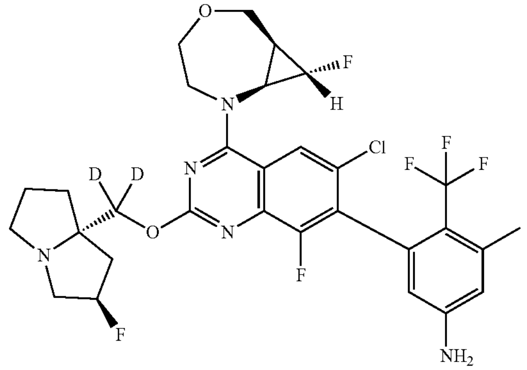 [SMILES: [2H]C([2H])(Oc1nc(N2CCOC[C@H]3[C@H](F)[C@H]32)c2cc(Cl)c(-c3cc(N)cc(C)c3C(F)(F)F)c(F)c2n1)[C@@]12CCCN1C[C@H](F)C2] | 3-(6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-methyl-4-(trifluoromethyl)aniline |
| 180 | 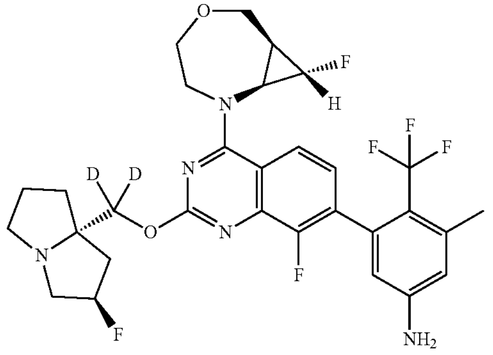 [SMILES: [2H]C([2H])(Oc1nc(N2CCOC[C@H]3[C@H](F)[C@H]32)c2ccc(-c3cc(N)cc(C)c3C(F)(F)F)c(F)c2n1)[C@@]12CCCN1C[C@H](F)C2] | 3-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-methyl-4-(trifluoromethyl)aniline |
| 181 | 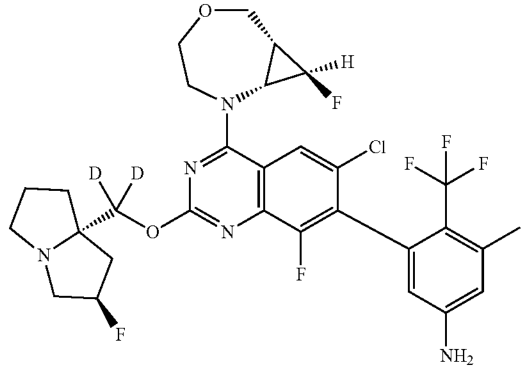 [SMILES: [2H]C([2H])(Oc1nc(N2CCOC[C@@H]3[C@@H](F)[C@@H]32)c2cc(Cl)c(-c3cc(N)cc(C)c3C(F)(F)F)c(F)c2n1)[C@@]12CCCN1C[C@H](F)C2] | 3-(6-chloro-8-fluoro-4-(IR,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-methyl-4-(trifluoromethyl)aniline |

TABLE 1-continued

| Example No. | Structure | Name |
|---|---|---|
| 182 | 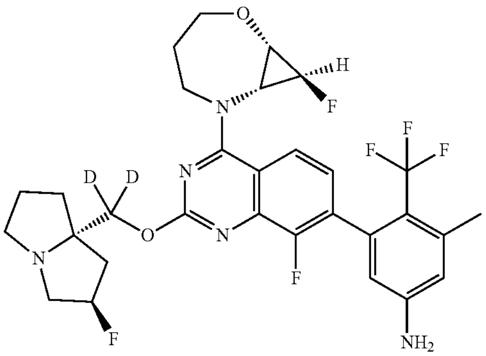 [SMILES: [2H]C([2H])(Oc1nc(N2CCCO[C@@H]3[C@@H](F)[C@@H]32)c2ccc(-c3cc(N)cc(C)c3C(F)(F)F)c(F)c2n1)[C@@]12CCCN1C[C@H](F)C2] | 3-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-methyl-4-(trifluoromethyl)aniline |
| 183 | 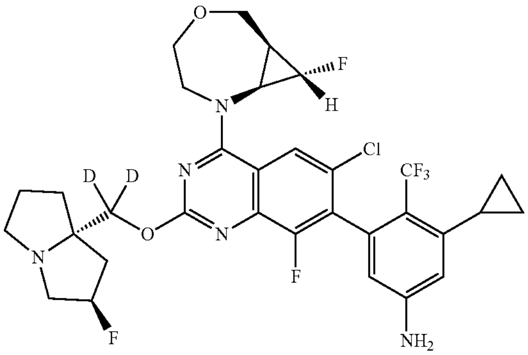 [SMILES: [2H]C([2H])(Oc1nc(N2CCOC[C@H]3[C@H](F)[C@H]32)c2cc(Cl)c(-c3cc(N)cc(C4CC4)c3C(F)(F)F)c(F)c2n1)[C@@]12CCCN1C[C@H](F)C2] | 3-(6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-cyclopropyl-4-(trifluoromethyl)aniline |
| 184 | 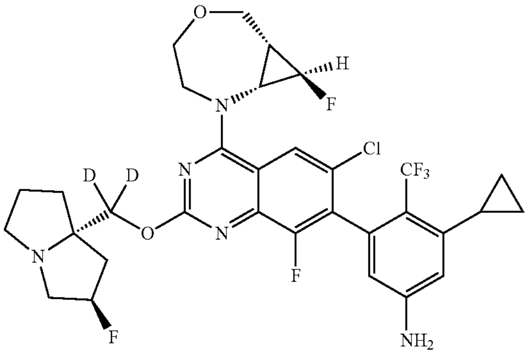 [SMILES: [2H]C([2H])(Oc1nc(N2CCOC[C@@H]3[C@@H](F)[C@@H]32)c2cc(Cl)c(-c3cc(N)cc(C4CC4)c3C(F)(F)F)c(F)c2n1)[C@@]12CCCN1C[C@H](F)C2] | 3-(6-chloro-8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-cyclopropyl-4-(trifluoromethyl)aniline |
| 185 | 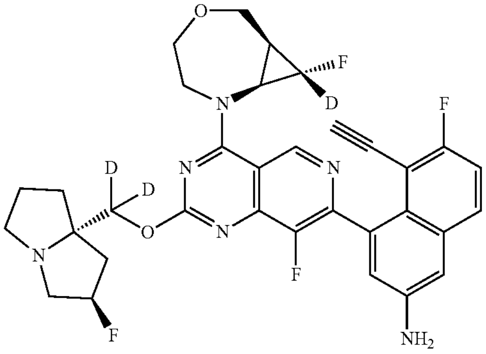 [SMILES: [2H]C([2H])(Oc1nc(N2CCOC[C@@H]3[C@H]2[C@@]3([2H])F)c2cnc(-c3cc(N)cc4ccc(F)c(C#C)c34)c(F)c2n1)[C@@]12CCCN1C[C@H](F)C2] | 5-ethynyl-6-fluoro-4-(8-fluoro-4-((1S,7S,8S)-8-fluoro-5-oxa-2-azabicyclo[5.1.0]octan-2-yl-8-d)-2-(((2R,7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
|---|---|---|
| 186 | 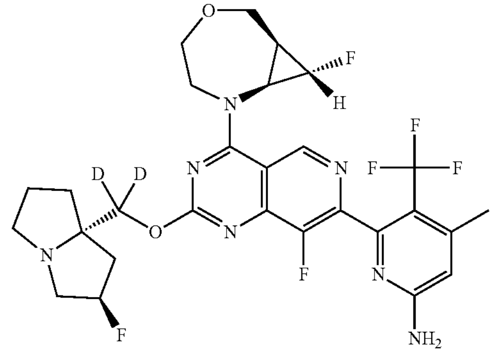 [SMILES: [2H]C([2H])(Oc1nc(N2CCOC[C@H]3[C@H](F)[C@H]32)c2cnc(-c3nc(N)cc(C)c3C(F)(F)F)c(F)c2n1)[C@@]12CCCN1C[C@H](F)C2] | 6-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-methyl-5-(trifluoromethpyridin-2-amine |
| 187 | 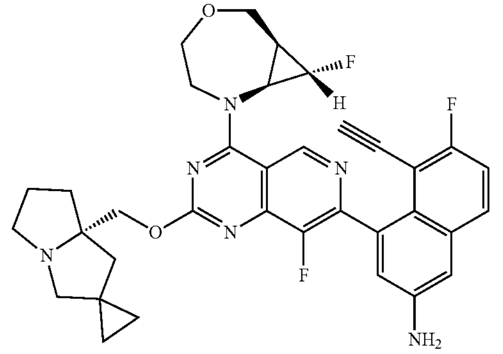 [SMILES: C#Cc1c(F)ccc2cc(N)cc(-c3ncc4c(N5CCOC[C@H]6[C@H](F)[C@H]65)nc(OC[C@@]56CCCN5CC5(CC5)C6)nc4c3F)c12] | 4-(2-(((S)-dihydro-1 'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 188 | 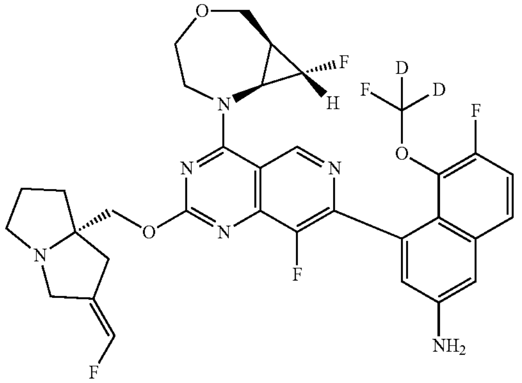 [SMILES: [2H]C([2H])(F)Oc1c(F)ccc2cc(N)cc(-c3ncc4c(N5CCOC[C@H]6[C@H](F)[C@H]65)nc(OC[C@@]56CCCN5C/C(=C\F)C6)nc4c3F)c12] | 6-fluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-methoxy)pyrido[4,3-d]pyrimidin-7-yl)-5-(fluoromethoxy-d2)naphthalen-2-amine |
| 189 | 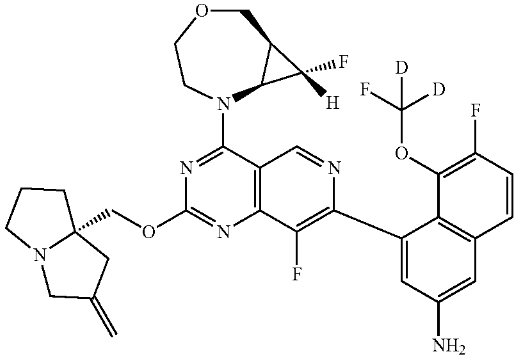 [SMILES: [2H]C([2H])(F)Oc1c(F)ccc2cc(N)cc(-c3ncc4c(N5CCOC[C@H]6[C@H](F)[C@H]65)nc(OC[C@@]56CCCN5CC(=C)C6)nc4c3F)c12] | 6-fluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-methoxy)pyrido[4,3-d]pyrimidin-7-yl)-5-(fluoromethoxy-d2)naphthalen-2-amine |

TABLE 1-continued

| Example No. | Structure | Name |
|---|---|---|
| 190 | 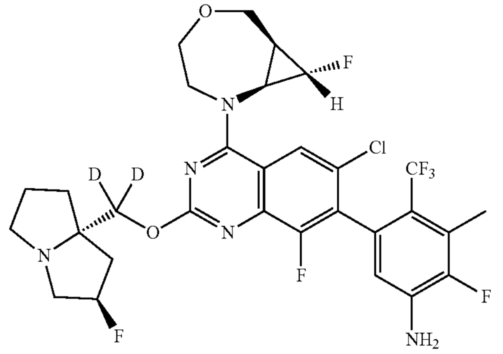 [SMILES: [2H]C([2H])(Oc1nc(N2CCOC[C@H]3[C@H](F)[C@H]32)c2cc(Cl)c(-c3cc(N)c(F)c(C)c3C(F)(F)F)c(F)c2n1)[C@@]12CCCN1C[C@H](F)C2] | 5-(6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-2-fluoro-3-methyl-4-(trifluoromethyl)aniline |
| 191 | 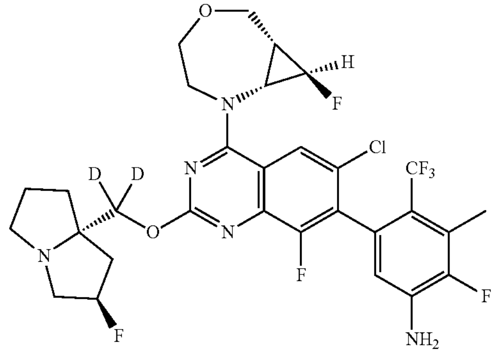 | 5-(6-chloro-8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-2-fluoro-3-methyl-4-(trifluoromethyl)aniline |
| 192 | 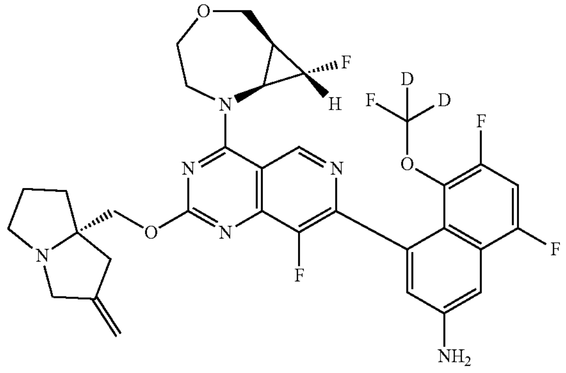 [SMILES: [2H]C([2H])(F)Oc1c(F)cc(F)c2cc(N)cc(-c3ncc4c(N5CCOC[C@H]6[C@H](F)[C@H]65)nc(OC[C@@]56CCCN5CC(=C)C6)nc4c3F)c12] | 6,8-difluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(methoxy-d3)naphthalen-2-amine |
| 193 | 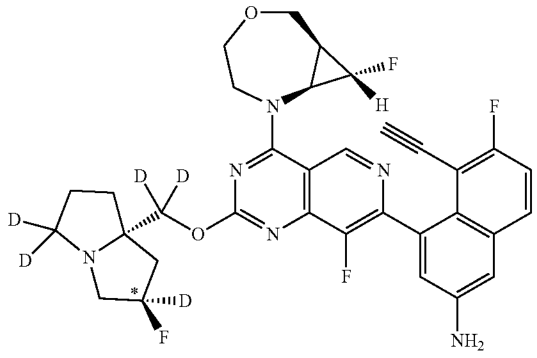 [SMILES: [2H]C1([2H])CC[C@@]2(C([2H])([2H])Oc3nc(N4CCOC[C@H]5[C@H](F)[C@H]54)c4cnc(-c5cc(N)cc6ccc(F)c(C#C)c56)c(F)c4n3)C[C@@]([2H])(F)CN12] | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl-2,5,5-d3)methoxy-d2)pyrido[4,3-d]pyrimidin-7-yl)naphthalen-2-amine |

TABLE 1-continued

| Example No. | Structure | Name |
|---|---|---|
| 194 | 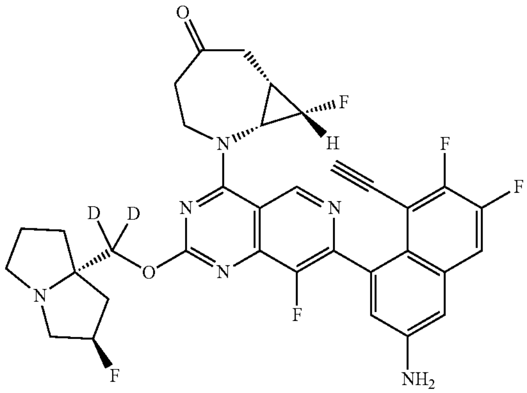 [SMILES: [2H]C([2H])(Oc1nc(N2CCC(=O)C[C@@H]3[C@H](F)[C@@H]32)c2cnc(-c3cc(N)cc4cc(F)c(F)c(C#C)c34)c(F)c2n1)[C@@]12CCCN1C[C@H](F)C2] | (1R,7S,8S)-2-(7-(3-amino-8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octan-5-one |
| 195 | 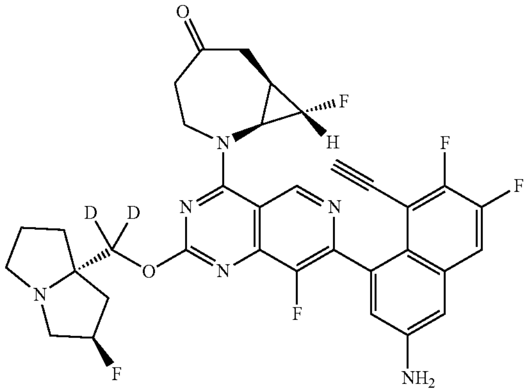 [SMILES: [2H]C([2H])(Oc1nc(N2CCC(=O)C[C@H]3[C@H](F)[C@H]32)c2cnc(-c3cc(N)cc4cc(F)c(F)c(C#C)c34)c(F)c2n1)[C@@]12CCCN1C[C@H](F)C2] | (1S,7R,8S)-2-(7-(3-amino-8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octan-5-one |
| 196 | 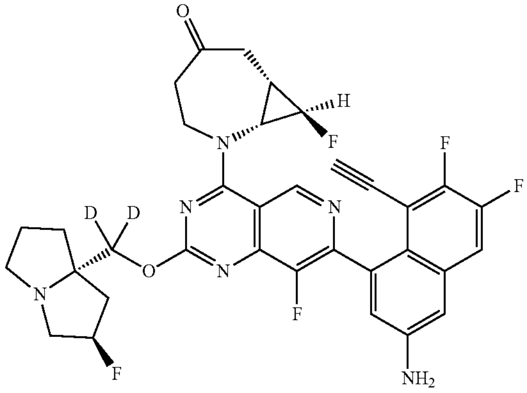 [SMILES: [2H]C([2H])(Oc1nc(N2CCC(=O)C[C@@H]3[C@@H](F)[C@@H]32)c2cnc(-c3cc(N)cc4cc(F)c(F)c(C#C)c34)c(F)c2n1)[C@@]12CCCN1C[C@H](F)C2] | (1R,7S,8R)-2-(7-(3-amino-8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octan-5-one |
| 197 | 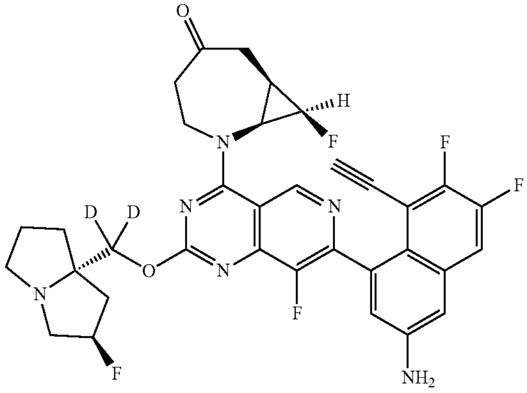 [SMILES: [2H]C([2H])(Oc1nc(N2CCC(=O)C[C@H]3[C@@H](F)[C@H]32)c2cnc(-c3cc(N)cc4cc(F)c(F)c(C#C)c34)c(F)c2n1)[C@@]12CCCN1C[C@H](F)C2] | (1S,7R,8R)-2-(7-(3-amino-8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octan-5-one |

TABLE 1-continued

| Example No. | Structure | Name |
|---|---|---|
| 198 | 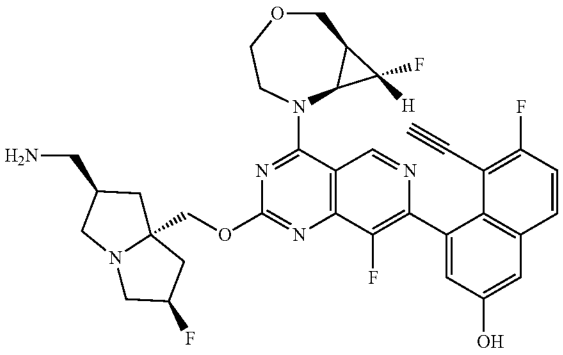 [SMILES: C#Cc1c(F)ccc2cc(O)cc(-c3ncc4c(N5CCOC[C@H]6[C@H](F)[C@H]65)nc(OC[C@]56C[C@@H](F)CN5C[C@@H](CN)C6)nc4c3F)c12] | 4-(2-(((2R,6R,7aS)-2-(aminomethyl)-6-fluorotetrahydro-1H-pyrrolizin-7a(5H)-yl)methoxy)-8-fluoro-4-((1S,7S,8S)-8-fluoro-5-oxa-2-azabicyclo[5.1.0]octan-2-pyrido[4,3-d]pyrimidin-7-yl)-5-ethynyl-6-fluoronaphthalen-2-ol |
| 199 | 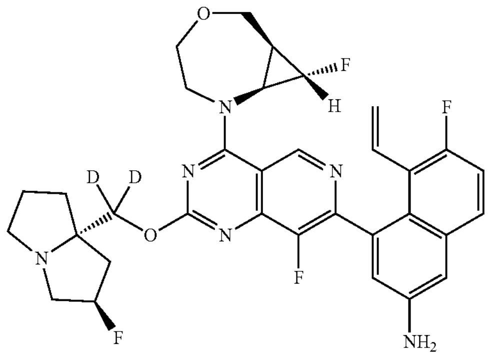 [SMILES: [2H]C([2H])(Oc1nc(N2CCOC[C@H]3[C@H](F)[C@H]32)c2cnc(-c3cc(N)cc4ccc(F)c(C=C)c34)c(F)c2n1)[C@@]12CCCN1C[C@H](F)C2] | 6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-vinyl)naphthalen-2-amine |
| 200 | 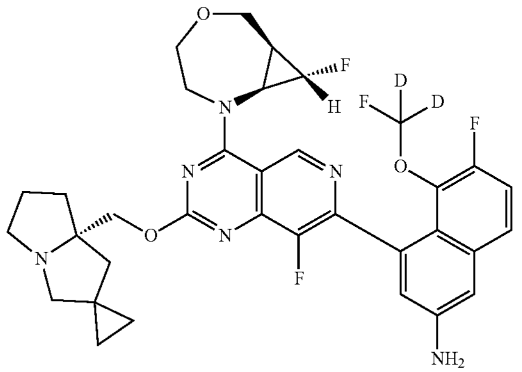 [SMILES: [2H]C([2H])(F)Oc1c(F)ccc2cc(N)cc(-c3ncc4c(N5CCOC[C@H]6[C@H](F)[C@H]65)nc(OC[C@@]56CCCN5CC5(CC5)C6)nc4c3F)c12] | 4-(2-(((S)-dihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine |
| 201 | 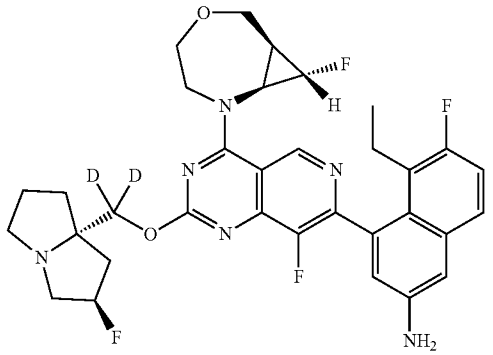 [SMILES: [2H]C([2H])(Oc1nc(N2CCOC[C@H]3[C@H](F)[C@H]32)c2cnc(-c3cc(N)cc4ccc(F)c(CC)c34)c(F)c2n1)[C@@]12CCCN1C[C@H](F)C2] | 5-ethyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
|---|---|---|
| 202 | 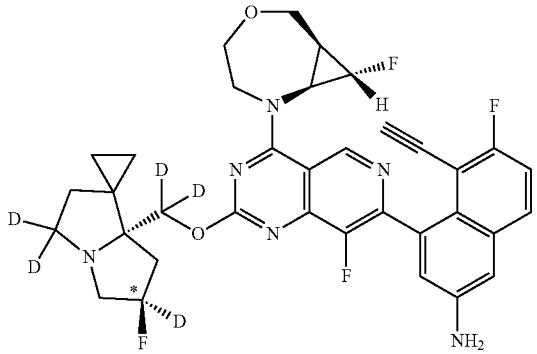 [SMILES: [2H]C1([2H])CC2(CC2)[C@@]2(C([2H])([2H])Oc3nc(N4CCOC[C@H]5[C@H](F)[C@H]54)c4cnc(-c5cc(N)cc6ccc(F)c(C#C)c56)c(F)c4n3)C[C@@]([2H])(F)CN12] | 5-ethynyl-6-fluoro-4-(8-fluoro-4-((1S,7S,8S)-8-fluoro-5-oxa-2-azabicyclo[5.1.0]octan-2-yl)-2-(((6'R,7a'R)-6'-fluorotetrahydrospiro[cyclopropane-1,1'-pyrrolizin]-7a'(5'H)-yl-3',3,6'd3)methoxy-d2)pyrido[4,3-d]pyrimidin-7-yl)naphthalen-2-amine |
| 203 | 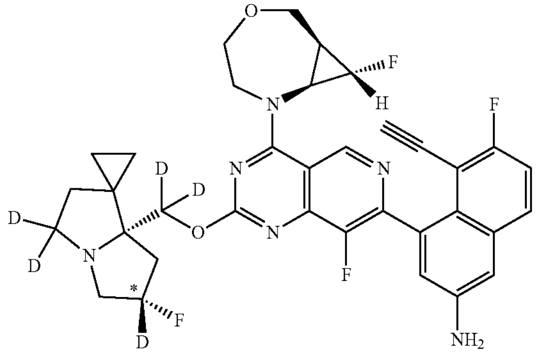 [SMILES: [2H]C1([2H])CC2(CC2)[C@@]2(C([2H])([2H])Oc3nc(N4CCOC[C@H]5[C@H](F)[C@H]54)c4cnc(-c5cc(N)cc6ccc(F)c(C#C)c56)c(F)c4n3)C[C@]([2H])(F)CN12] | 5-ethynyl-6-fluoro-4-(8-fluoro-4-((1S,7S,8S)-8-fluoro-5-oxa-2-azabicyclo[5.1.0]octan-2-yl)-2-(((6'S,7a'R)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine |
| 204 | 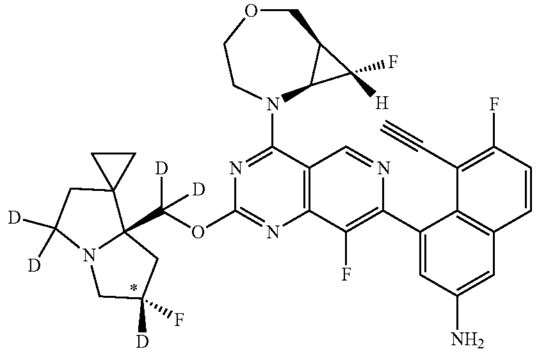 [SMILES: [2H]C1([2H])CC2(CC2)[C@]2(C([2H])([2H])Oc3nc(N4CCOC[C@H]5[C@H](F)[C@H]54)c4cnc(-c5cc(N)cc6ccc(F)c(C#C)c56)c(F)c4n3)C[C@]([2H])(F)CN12] | 5-ethynyl-6-fluoro-4-(8-fluoro-4-((1S,7S,8S)-8-fluoro-5-oxa-2-azabicyclo[5.1.0]octan-2-yl)-2-(((6'S,7a'S)-6'-fluorotetrahydrospiro[cyclopropane-1,1'-pyrrolizin]-7a'(5'H)-yl-3',3',6'-d3)methoxy-d2)pyrido[4,3-d]pyrimidin-7-y ])naphthalen-2-amine |
| 205 | 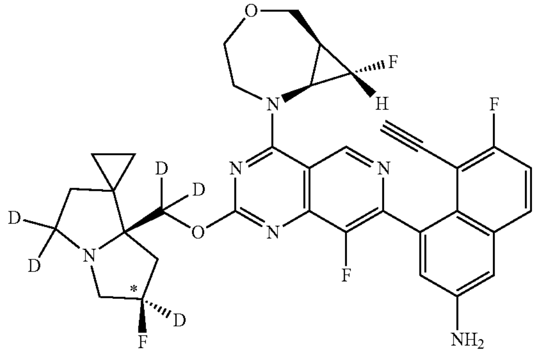 [SMILES: [2H]C1([2H])CC2(CC2)[C@]2(C([2H])([2H])Oc3nc(N4CCOC[C@H]5[C@H](F)[C@H]54)c4cnc(-c5cc(N)cc6ccc(F)c(C#C)c56)c(F)c4n3)C[C@@]([2H])(F)CN12] | 5-ethynyl-6-fluoro-4-(8-fluoro-4-((1S,7S,8S)-8-fluoro-5-oxa-2-azabicyclo[5.1.0]octan-2-yl)-2-(((6'R,7a'S)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine |

TABLE 1-continued

| Example No. | Structure | Name |
|---|---|---|
| 206 | 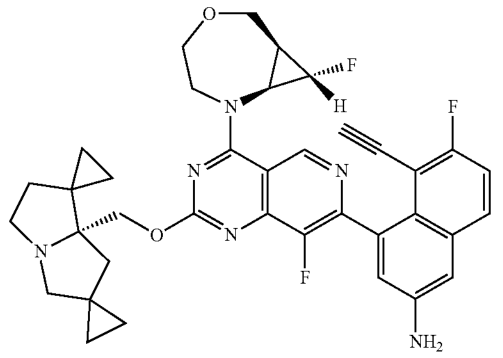 [SMILES: C#Cc1c(F)ccc2cc(N)cc(-c3ncc4c(N5CCOC[C@H]6[C@H](F)[C@H]65)nc(OC[C@]56CC7(CC7)CN5CCC65CC5)nc4c3F)c12] | 4-(2-(((R)-dihydro-5'H-dispiro[cyclopropane-1,1'-pyrrolizine-6',1''-cyclopropan]-7a'(7'H)-methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 207 | 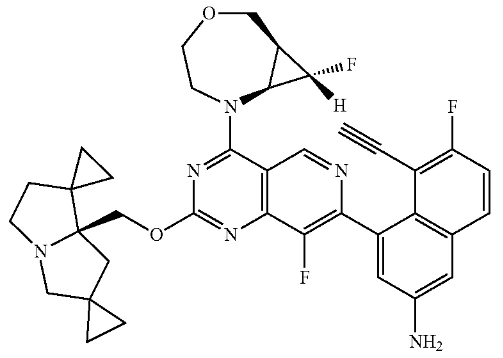 [SMILES: C#Cc1c(F)ccc2cc(N)cc(-c3ncc4c(N5CCOC[C@H]6[C@H](F)[C@H]65)nc(OC[C@@]56CC7(CC7)CN5CCC65CC5)nc4c3F)c12] | 4-(2-(((S)-dihydro-5'H-dispiro[cyclopropane-1,1'-pyrrolizine-6',1''-cyclopropan]-7a'(7'H)-methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 208 | 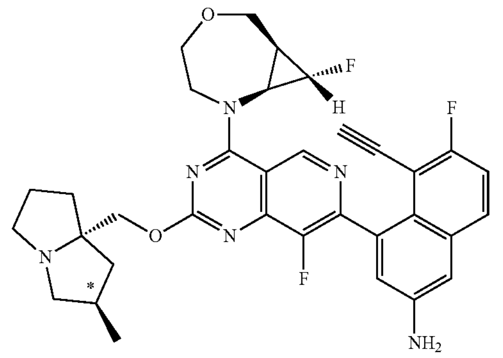 [SMILES: C#Cc1c(F)ccc2cc(N)cc(-c3ncc4c(N5CCOC[C@H]6[C@H](F)[C@H]65)nc(OC[C@@]56CCCN5C[C@H](C)C6)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-methyltetrahydro-1H-pyrrolizin-7a(5H)-yl)methoxy)pyrido[4,3-d]pyrimidin-7-yl)naphthalen-2-amine |
| 209 | 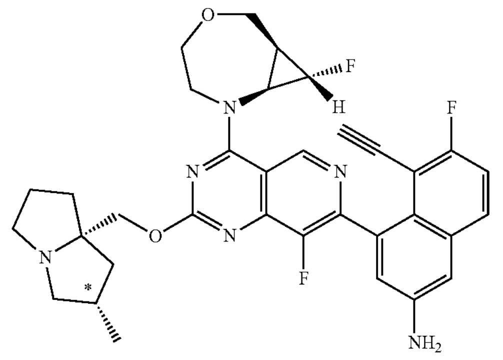 [SMILES: C#Cc1c(F)ccc2cc(N)cc(-c3ncc4c(N5CCOC[C@H]6[C@H](F)[C@H]65)nc(OC[C@@]56CCCN5C[C@@H](C)C6)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-((7aS)-2-methyltetrahydro-1H-pyrrolizin-7a(5H)-yl)methoxy)pyrido[4,3-d]pyrimidin-7-yl)naphthalen-2-amine |

TABLE 1-continued

| Example No. | Structure | Name |
|---|---|---|
| 210 | 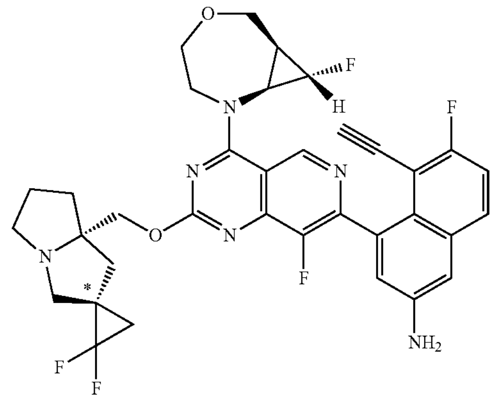 [SMILES: C#Cc1c(F)ccc2cc(N)cc(-c3ncc4c(N5CCOC[C@H]6[C@H](F)[C@H]65)nc(OC[C@@]56CCCN5C[C@]5(CC5(F)F)C6)nc4c3F)c12] | 4-(2-(((1R,7a'S)-2,2-difluorodihydro-1'H,3'H-spiro[cyclopropane-1,2'-pyrrolizin]-7a'(5'H)-methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 211 | 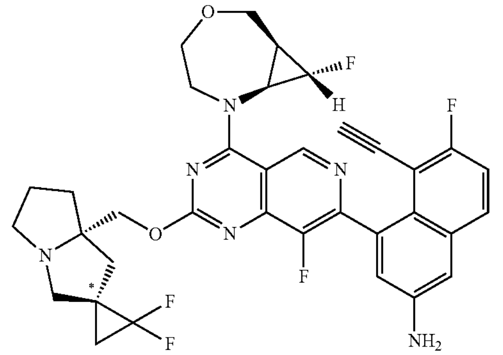 [SMILES: C#Cc1c(F)ccc2cc(N)cc(-c3ncc4c(N5CCOC[C@H]6[C@H](F)[C@H]65)nc(OC[C@@]56CCCN5C[C@@]5(CC5(F)F)C6)nc4c3F)c12] | 4-(2-(((1S,7a 'S)-2,2-difluorodihydro-1'H,3'H-spiro{cyclopropane-1,2'-pyrrolizin]-7a(5'H)-methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 212 | 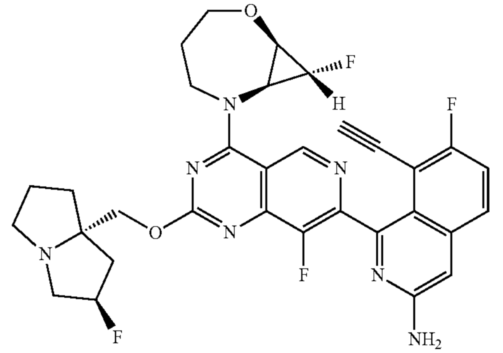 [SMILES: C#Cc1c(F)ccc2cc(N)nc(-c3ncc4c(N5CCCO[C@H]6[C@H](F)[C@H]65)nc(OC[C@@]56CCCN5C[C@H](F)C6)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy)pyrido[4,3-d]pyrimidin-7-yl)naphthalen-2-amine |
| 213 | 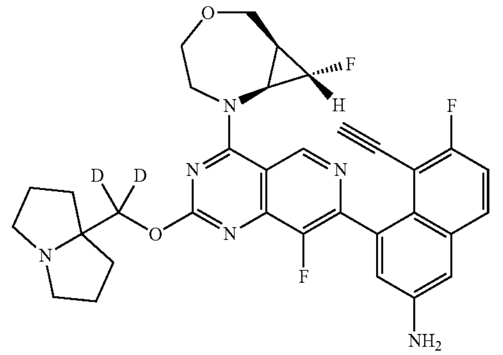 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)C12CCCN1CCC2] | 5-ethynyl-6-fluoro-4-(8-fluoro-4-((1S,7S,8S)-8-fluoro-5-oxa-2-azabicyclo[5.1.0]octan-2-yl)-2-((tetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
|---|---|---|
| 214 | 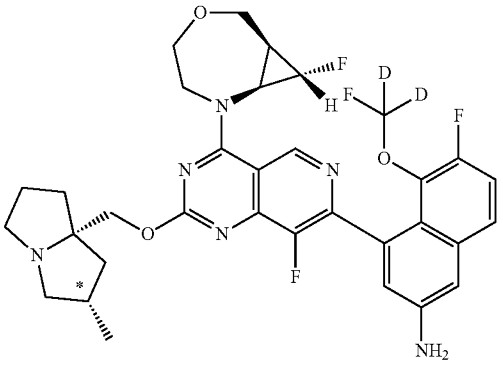 [SMILES: [2H]C([2H])(F)Oc1c(F)ccc2cc(N)cc(-c3ncc4c(N5CCOC[C@H]6[C@H](F)[C@H]65)nc(OC[C@@]56CCCN5C[C@@H](C)C6)nc4c3F)c12] | 6-fluoro-4-(8-fluoro-4-((1S,7S,8S)-8-fluoro-5-oxa-2-azabicyclo[5.1.0]octan-2-yl)-2-((7aS)-2-methyltetrahydro-1H-pyrrolizin-7a(5H)-yl)methoxy)pyrido[4,3-d]pyrimidin-7-yl)-5-(fluoromethoxy-d2)naphthalen-2-amine |
| 215 | 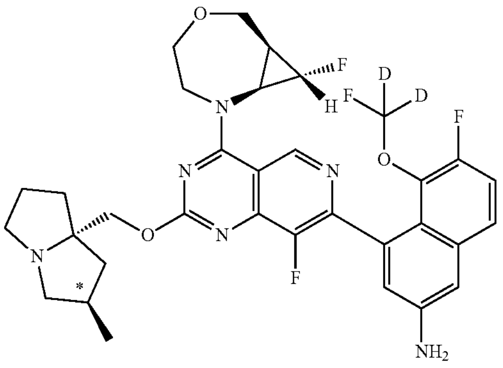 [SMILES: [2H]C([2H])(F)Oc1c(F)ccc2cc(N)cc(-c3ncc4c(N5CCOC[C@H]6[C@H](F)[C@H]65)nc(OC[C@@]56CCCN5C[C@H](C)C6)nc4c3F)c12] | 6-fluoro-4-(8-fluoro-4-((1S,7S,8S)-8-fluoro-5-oxa-2-azabicyclo[5.1.0]octan-2-yl)-2-(((2R,7aS)-2-methyltetrahydro-1H-pyrrolizin-7a(5H)-yl)methoxy)pyrido[4,3-d]pyrimidin-7-yl)-5-(fluoromethoxy-d2)naphthalen-2-amine |
| 216 | 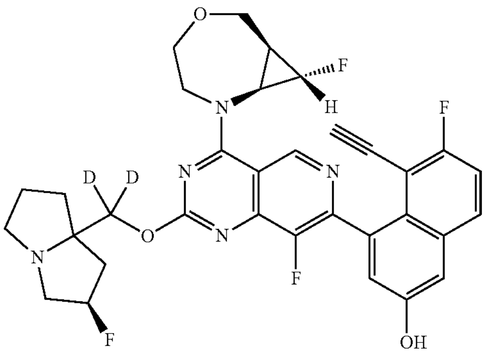 [SMILES: [2H]C([2H])(Oc1nc(N2CCOC[C@H]3[C@H](F)[C@H]32)c2cnc(-c3cc(O)cc4ccc(F)c(C#C)c34)c(F)c2n1)C12CCCN1C[C@H](F)C2] | 5-ethynyl-6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol |
| 217 | 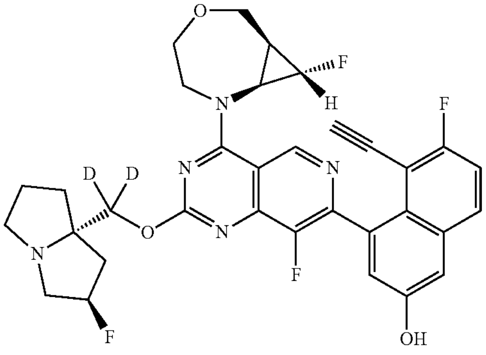 [SMILES: [2H]C([2H])(Oc1nc(N2CCOC[C@H]3[C@H](F)[C@H]32)c2cnc(-c3cc(O)cc4ccc(F)c(C#C)c34)c(F)c2n1)[C@@]12CCCN1C[C@H](F)C2] | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol |

TABLE 1-continued

| Example No. | Structure | Name |
|---|---|---|
| 218 | 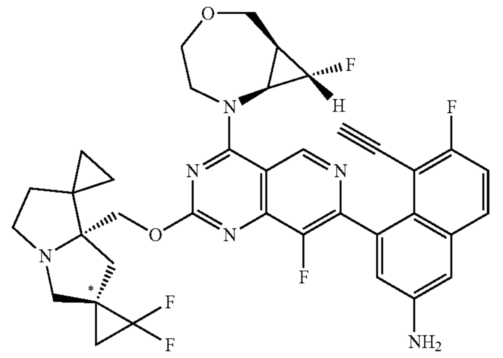 [SMILES: C#Cc1c(F)ccc2cc(N)cc(-c3ncc4c(N5CCOC[C@H]6[C@H](F)[C@H]65)nc(OC[C@]56C[C@@]7(CN5CCC65CC5)CC7(F)F)nc4c3F)c12] | 4-(2-(((6'S,7a'R)-2'',2''-difluorodihydro-5'H-dispiro[cyclopropane-1,1'-pyrrolizine-6',1''-cyclopropan]-7a'(7'H)-methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 219 | 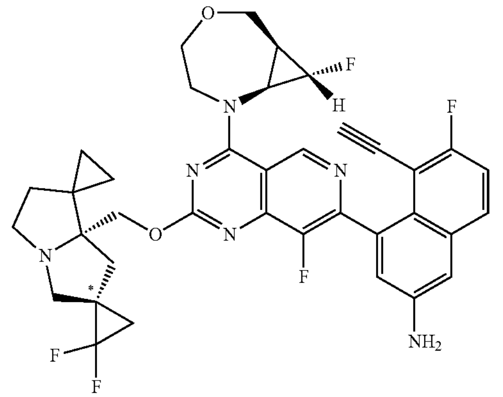 [SMILES: C#Cc1c(F)ccc2cc(N)cc(-c3ncc4c(N5CCOC[C@H]6[C@H](F)[C@H]65)nc(OC[C@]56C[C@]7(CN5CCC65CC5)CC7(F)F)nc4c3F)c12] | 4-(2-(((6'R,7a'R)-2'',2''-difluorodihydro-5'H-dispiro[cyclopropane-1,1'-pyrrolizine-6',1''-cyclopropan]-7a'(7'H)-methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 220 | 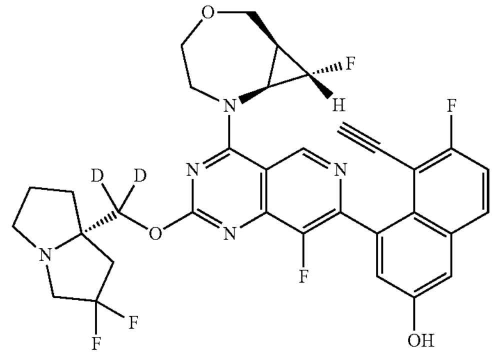 [SMILES: [2H]C([2H])(Oc1nc(N2CCOC[C@H]3[C@H](F)[C@H]32)c2cnc(-c3cc(O)cc4ccc(F)c(C#C)c34)c(F)c2n1)[C@@]12CCCN1CC(F)(F)C2] | 4-(2-(((S)-2,2-difluorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 221 | 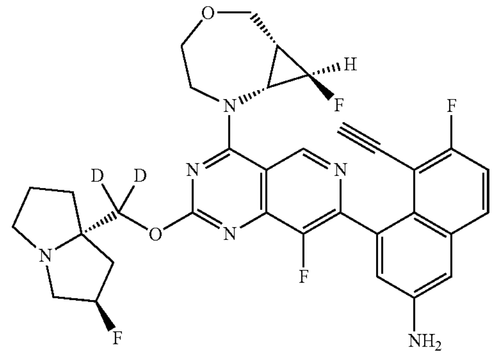 [SMILES: [2H]C([2H])(Oc1nc(N2CCOC[C@@H]3[C@@H](F)[C@@H]32)c2cnc(-c3cc(N)cc4ccc(F)c(C#C)c34)c(F)c2n1)[C@@]12CCCN1C[C@H](F)C2] | 5-ethynyl-6-fluoro-4-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
|---|---|---|
| 222 | 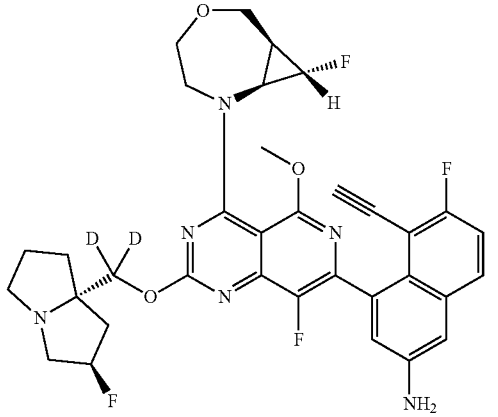 [SMILES: [2H]C([2H])(Oc1nc(N2CCOC[C@H]3[C@H](F)[C@H]32)c2c(OC)nc(-c3cc(N)cc4ccc(F)c(C#C)c34)c(F)c2n1)[C@@]12CCCN1C[C@H](F)C2] | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-5-methoxypyrido[4,3-d]pyrimidin-7-yl)naphthalen-2-amine |
| 223 | 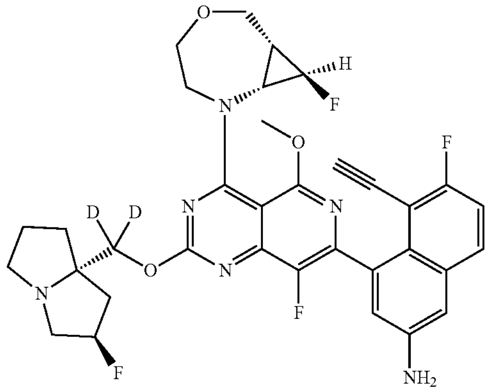 [SMILES: [2H]C([2H])(Oc1nc(N2CCOC[C@@H]3[C@@H](F)[C@@H]32)c2c(OC)nc(-c3cc(N)cc4ccc(F)c(C#C)c34)c(F)c2n1)[C@@]12CCCN1C[C@H](F)C2] | 5-ethynyl-6-fluoro-4-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-5-methoxypyrido[4,3-d]pyrimidin-7-yl)naphthalen-2-amine |
| 224 | 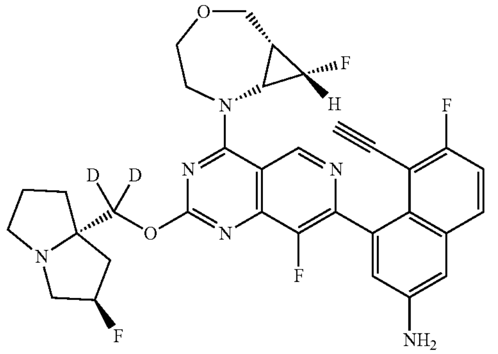 | 5-ethynyl-6-fluoro-4-(8-fluoro-4-((1R,7R,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 225 | 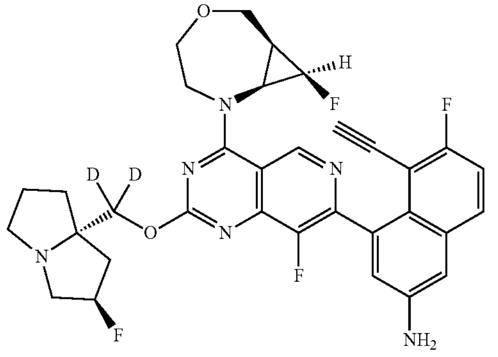 [SMILES: [2H]C([2H])(Oc1nc(N2CCOC[C@H]3[C@@H](F)[C@H]32)c2cnc(-c3cc(N)cc4ccc(F)c(C#C)c34)c(F)c2n1)[C@@]12CCCN1C[C@H](F)C2] | 5-ethynyl-6-fluoro-4-(8-fluoro-4-((1S,7S,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
| --- | --- | --- |
| 226 | 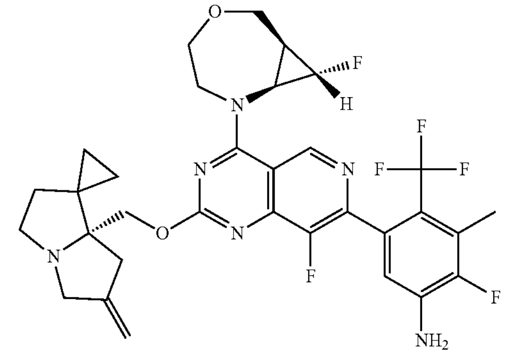 [SMILES: C=C1CN2CCC3(CC3)[C@@]2(COc2nc(N3CCOC[C@H]4[C@H](F)[C@H]43)c3cnc(-c4cc(N)c(F)c(C)c4C(F)(F)F)c(F)c3n2)C1] | 2-fluoro-5-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)~yl)methoxy)pyrido[4,3-d]pyrimidin-7-yl)-3-yl)methyl-4-(trifluoromethyl)aniline |
| 227 | 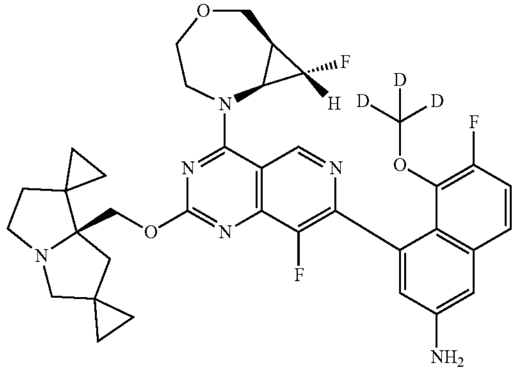 [SMILES: [2H]C([2H])([2H])Oc1c(F)ccc2cc(N)cc(-c3ncc4c(N5CCOC[C@H]6[C@H](F)[C@H]65)nc(OC[C@@]56CC7(CC7)CN5CCC65CC5)nc4c3F)c12] | 4-(2-(((S)-dihydro-5'H-dispiro[cyclopropane-1,1'-pyrrolizine-6',1''-cyclopropan]-7a'(7'H)-methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine |
| 228 | 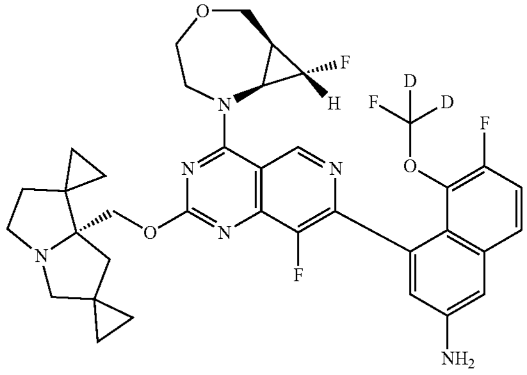 [SMILES: [2H]C([2H])(F)Oc1c(F)ccc2cc(N)cc(-c3ncc4c(N5CCOC[C@H]6[C@H](F)[C@H]65)nc(OC[C@]56CC7(CC7)CN5CCC65CC5)nc4c3F)c12] | 4-(2-(((R)-dihydro-5'H-dispiro[cyclopropane-1,1'-pyrrolizine-6',1''-cyclopropan]-7a'(7'H)-methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine |
| 229 | 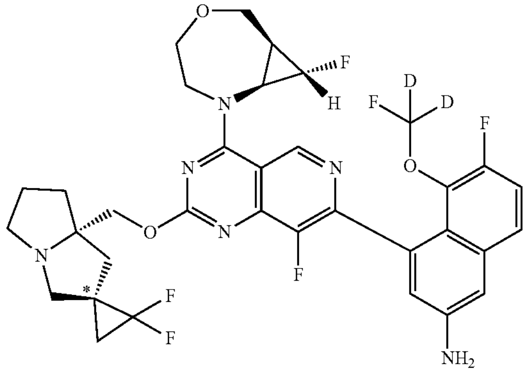 [SMILES: [2H]C([2H])(F)Oc1c(F)ccc2cc(N)cc(-c3ncc4c(N5CCOC[C@H]6[C@H](F)[C@H]65)nc(OC[C@@]56CCCN5C[C@@]5(CC5(F)F)C6)nc4c3F)c12] | 4-(2-(((1S,7a 'S)-2,2-difluorodihydro-1'H,3'H-spiro[cyclopropane-1,2'-pyrrolizin]-7a'(5'H)-methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine |

TABLE 1-continued

| Example No. | Structure | Name |
|---|---|---|
| 230 | 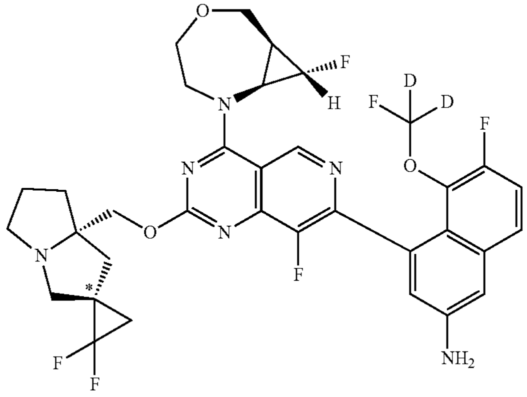 [SMILES: [2H]C([2H])(F)Oc1c(F)ccc2cc(N)cc(-c3ncc4c(N5CCOC[C@H]6[C@H](F)[C@H]65)nc(OC[C@@]56CCCN5C[C@]5(CC5(F)F)C6)nc4c3F)c12] | 4-(2-(((1R,7a'S)-2,2-difluorodihydro-1'H,3'H-spiro[cyclopropane-1,2'-pyrrolizin}-7a'(5'H)-methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine |
| 231 | 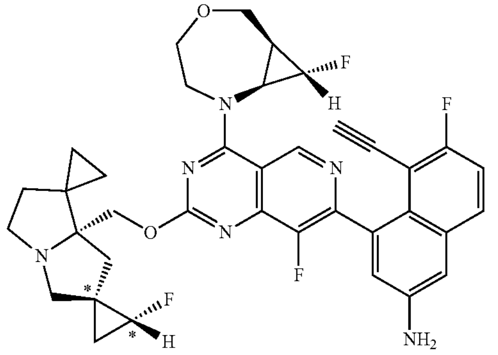 [SMILES: C#Cc1c(F)ccc2cc(N)cc(-c3ncc4c(N5CCOC[C@H]6[C@H](F)[C@H]65)nc(OC[C@]56C[C@]7(C[C@H]7F)CN5CCC65CC5)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((2"R,6'S,7a 'R)-2"-fluorodihydro-5'H-dispiro[cyclopropane-1,1'-pyrrolizine-6',]"-cyclopropan]-7a'(7'H)-yl)methoxy)pyrido[4,3-d]pyrimidin-7-yl)naphthalen-2-amine |
| 232 | 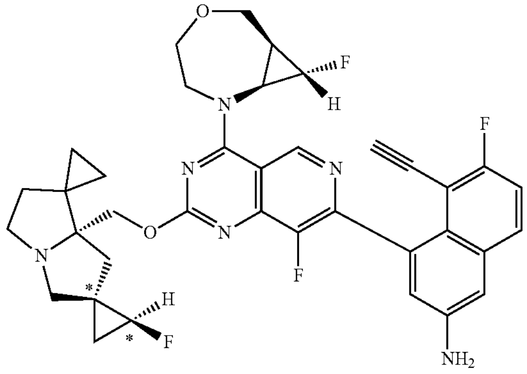 [SMILES: C#Cc1c(F)ccc2cc(N)cc(-c3ncc4c(N5CCOC[C@H]6[C@H](F)[C@H]65)nc(OC[C@]56C[C@]7(C[C@@H]7F)CN5CCC65CC5)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((2"S,6'S,7a'R)-2"-fluorodihydro-5'H-dispiro[cyclopropane-1,1'-pyrrolizine-6',]" cyclopropan]-7a'(7'H)-yl)methoxy)pyrido[4,3-d]pyrimidin-7-yl)naphthalen-2-amine |
| 233 | 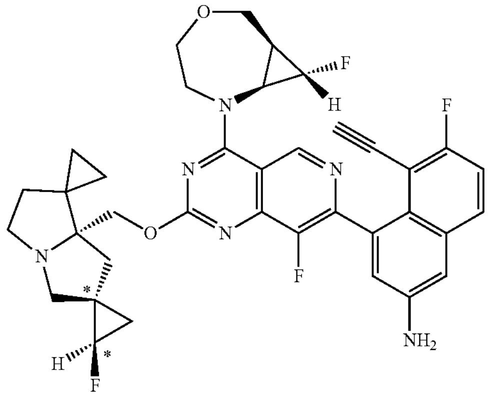 [SMILES: C#Cc1c(F)ccc2cc(N)cc(-c3ncc4c(N5CCOC[C@H]6[C@H](F)[C@H]65)nc(OC[C@]56C[C@@]7(C[C@H]7F)CN5CCC65CC5)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((2"R,6'R,7a'R)-2"-fluorodihydro-5'H-dispiro[cyclopropane-1,1'-pyrrolizine-6',1"-cyclopropan]-7a'(7'H)-yl)methoxy)pyrido[4,3-d]pyrimidin-7-yl)naphthalen-2-amine |

TABLE 1-continued

| Example No. | Structure | Name |
|---|---|---|
| 234 | 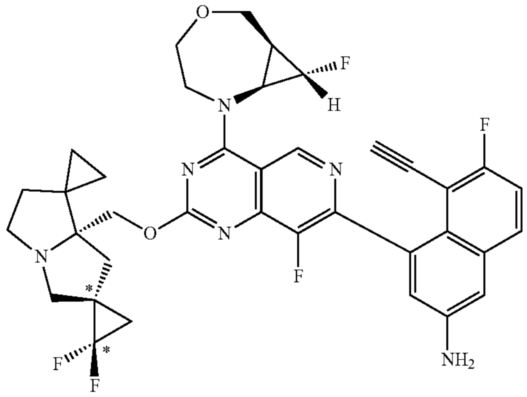 | 5-ethynyl-6-fluoro-4-(8~fluoro-4-((1S,7S,8S)-8-fluoro-5-oxa-2-azabicyclo[5.1.0]octan-2-yl)-2-(((2"S,6'R,7a'R)-2"-fluorodihydro-5'H-dispiro[cyclopropane-1,1'-pyrrolizine-6',1"-cyclopropan]-7a'(7'H)-methoxy)pyrido[4,3-d]pyrimidin-7-yl)naphthalen-2-amine |
| 235 | 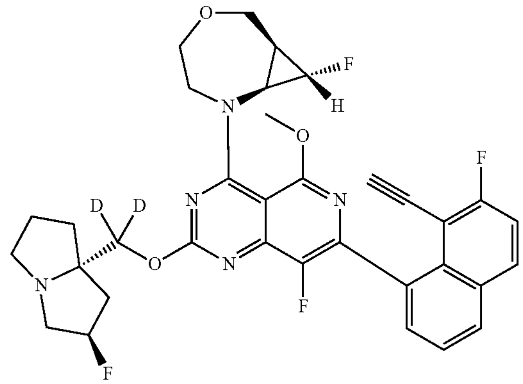 [SMILES: [2H]C([2H])(Oc1nc(N2CCOC[C@H]3[C@H](F)[C@H]32)c2c(OC)nc(-c3cccc4ccc(F)c(C#C)c34)c(F)c2n1)[C@@]12CCCN1C[C@H](F)C2] | (1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)-5-methoxypyrido[4,3-d]pyrimidin-4-yl)-8-fluoro-5-oxa-2-azabicyclo[5.1.0]octane |
| 236 | 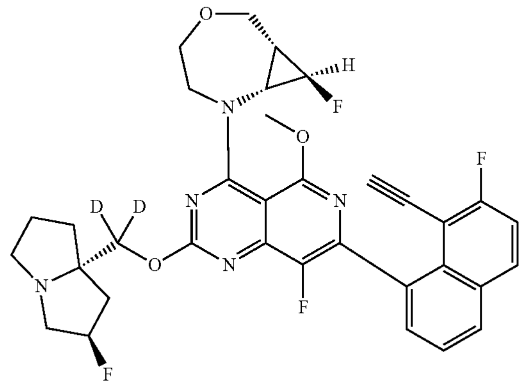 [SMILES: [2H]C([2H])(Oc1nc(N2CCOC[C@@H]3[C@@H](F)[C@@H]32)c2c(OC)nc(-c3cccc4ccc(F)c(C#C)c34)c(F)c2n1)[C@@]12CCCN1C[C@H](F)C2] | (1R,7R,8R)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)-5-methoxypyrido[4,3-d]pyrimidin-4-yl)-8-fluoro-5-oxa-2-azabicyclo[5.1.0]octane |
| 237 | 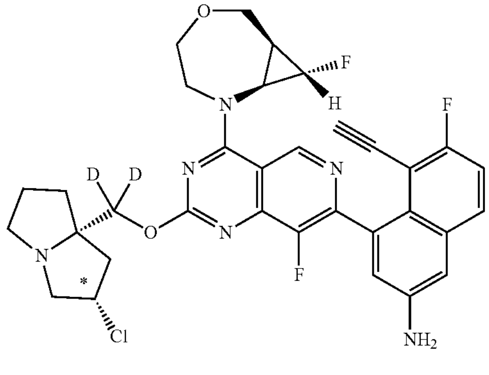 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1C[C@@H](Cl)C2] | 4-(2-((7aS)-2-chlorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |

TABLE 1-continued

| Example No. | Structure | Name |
| --- | --- | --- |
| 238 | 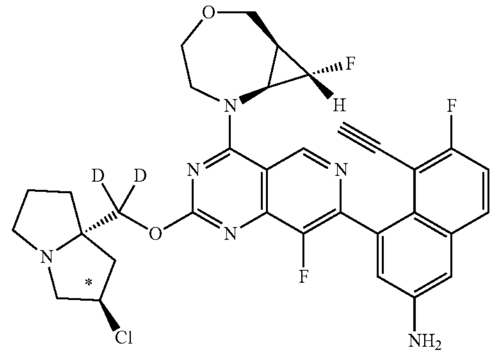 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1C[C@H](Cl)C2] | 4-(2-(((2R,7aS)-2-chlorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 239 | 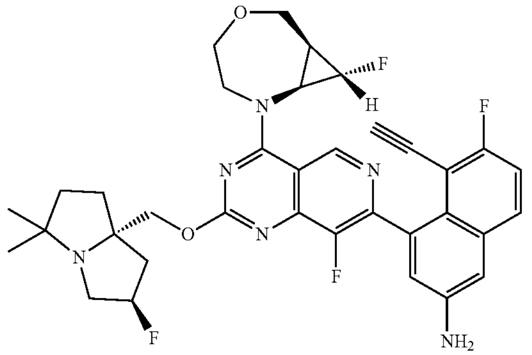 [SMILES: C#Cc1c(F)ccc2cc(N)cc(-c3ncc4c(N5CCOC[C@H]6[C@H](F)[C@H]65)nc(OC[C@@]56CCC(C)(C)N5C[C@H](F)C6)nc4c3F)c12] | 5-ethynyl-6-fluoro-4-(8-fluoro-2-(((2R,7aS)-2-fluoro-5,5-dim ethyltetrahydro-1H-pyrrolizin-7a(5H)-methoxy)-4-((1S,7S,8S)-8-fluoro-5-oxa-2-azabicyclo[5.1.0]octan-2-yl)pyrido[4,3-d]pyrimidin-7-yl)naphthalen-2-amine |
| 240 | 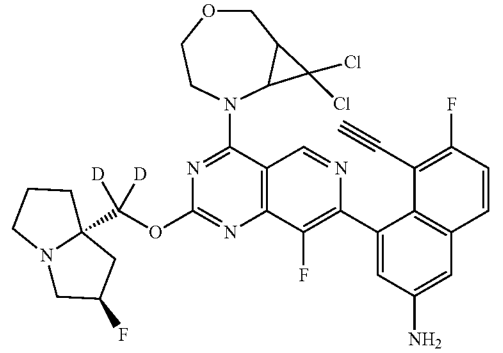 [SMILES: [2H]C([2H])(Oc1nc(N2CCOCC3C2C3(Cl)Cl)c2cnc(-c3cc(N)cc4ccc(F)c(C#C)c34)c(F)c2n1)[C@@]12CCCN1C[C@H](F)C2] | 4-(4-(8,8-dichloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 241 | 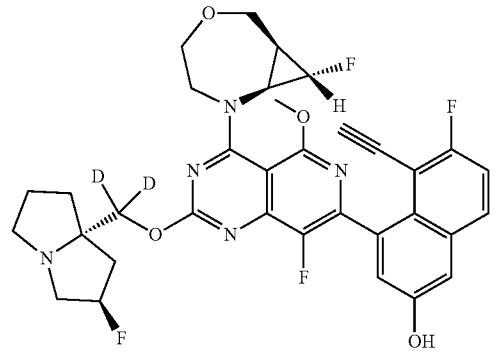 [SMILES: [2H]C([2H])(Oc1nc(N2CCOC[C@H]3[C@H](F)[C@H]32)c2c(OC)nc(-c3cc(O)cc4ccc(F)c(C#C)c34)c(F)c2n1)[C@@]12CCCN1C[C@H](F)C2] | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-5-methoxypyrido[4,3-d]pyrimidin-7-yl)naphthalen-2-ol |

TABLE 1-continued

| Example No. | Structure | Name |
| --- | --- | --- |
| 242 | 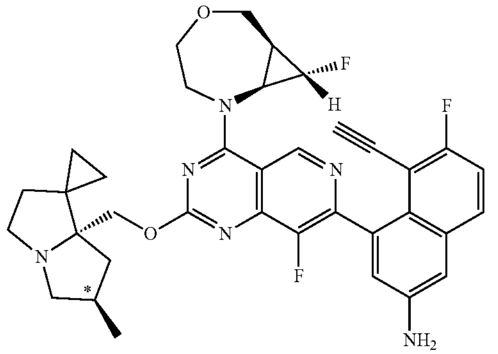 [SMILES: C#Cc1c(F)ccc2cc(N)cc(-c3ncc4c(N5CCOC[C@H]6[C@H](F)[C@H]65)nc(OC[C@]56C[C@@H](C)CN5CCC65CC5)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((6'R,7a'R)-6'-methyltetrahydrospiro[cyclopropane-1,1'-pyrrolizin]-7a'(5'H)-yl)methoxy)pyrido[4,3-d]pyrimidin-7-yl)naphthalen-2-amine |
| 243 | 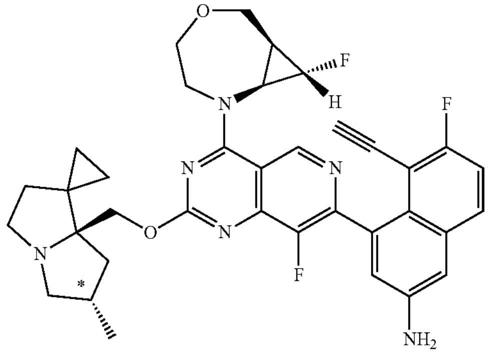 [SMILES: C#Cc1c(F)ccc2cc(N)cc(-c3ncc4c(N5CCOC[C@H]6[C@H](F)[C@H]65)nc(OC[C@@]56C[C@H](C)CN5CCC65CC5)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((6'S,7a'S)-6'-methyltetrahydrospiro[cyclopropane-1,1'-pyrrolizin]-7a'(5'H)-yl)methoxy)pyrido[4,3-d]pyrimidin-7-yl)naphthalen-2-amine |
| 244 | 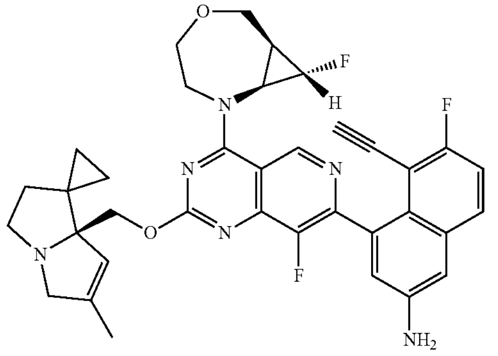 [SMILES: C#Cc1c(F)ccc2cc(N)cc(-c3ncc4c(N5CCOC[C@H]6[C@H](F)[C@H]65)nc(OC[C@@]56C=C(C)CN5CCC65CC5)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((S)-6'-methyl-2',3'-dihydrospiro[cyclopropane-1,1'-pyrrolizin]-7a'(5'H)-yl)methoxy)pyrido[4,3-d]pyrimidin-7-yl)naphthalen-2-amine |
| 245 | 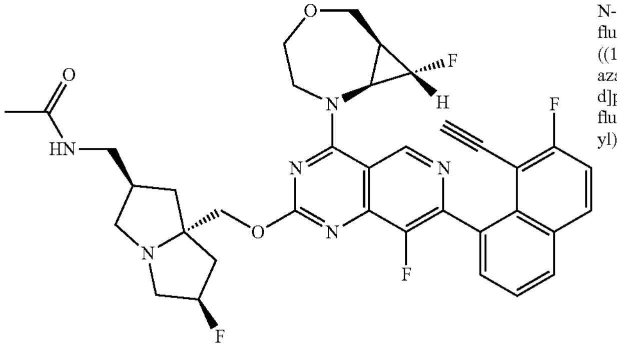 | N-(((2R,6R,7aS)-7a-(((7-(8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-oxy)methyl)-6-fluorohexahydro-1H-pyrrolizin-2-yl)methyl)acetamide |

TABLE 1-continued

| Example No. | Structure | Name |
| --- | --- | --- |
| 246 | 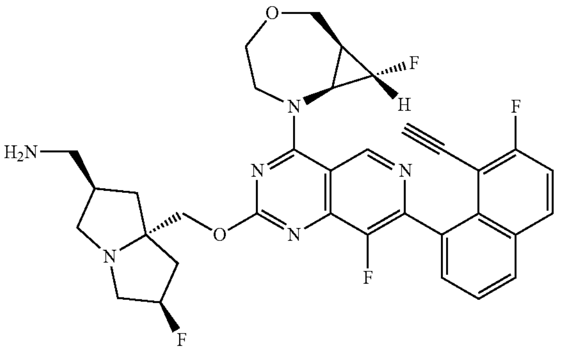 [SMILES: C#Cc1c(F)ccc2cccc(-c3ncc4c(N5CCOC[C@H]6[C@H](F)[C@H]65)nc(OC[C@]56C[C@@H](F)CN5C[C@@H](CN)C6)nc4c3F)c12] | ((2R,6R,7aS)-7a-(((7-(8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-oxy)methyl)-6-fluorohexahydro-1H-pyrrolizin-2-yl)methanamine |
| 247 | 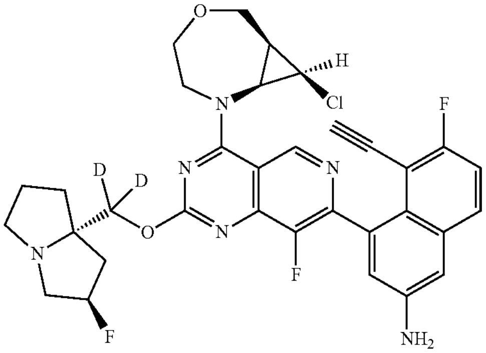 [SMILES: [2H]C([2H])(Oc1nc(N2CCOC[C@H]3[C@@H](Cl)[C@H]32)c2cnc(-c3cc(N)cc4ccc(F)c(C#C)c34)c(F)c2n1)[C@@]12CCCN1C[C@H](F)C2] | 4-(4-((1S,7S,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 248 | 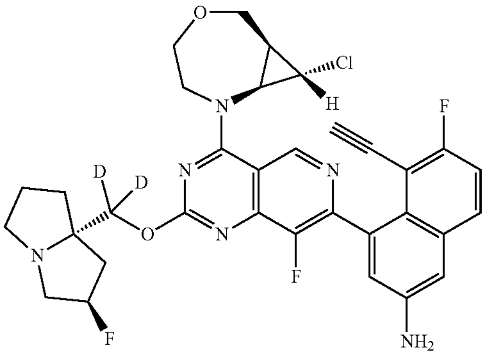 [SMILES: [2H]C([2H])(Oc1nc(N2CCOC[C@H]3[C@H](Cl)[C@H]32)c2cnc(-c3cc(N)cc4ccc(F)c(C#C)c34)c(F)c2n1)[C@@]12CCCN1C[C@H](F)C2] | 4-(4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 249 | 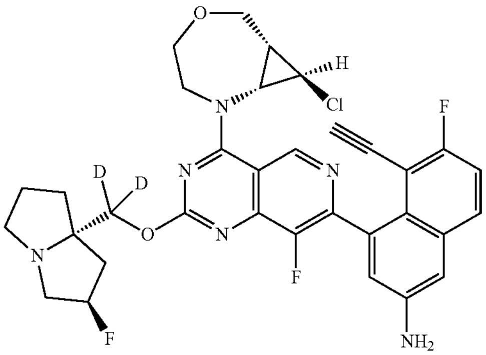 | 4-(4-((1R,7R,8R)-8-chloro-5-oxa-2-azabicyclo[5.1.0]octan-2-yl)-8-fluoro~2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |

TABLE 1-continued

| Example No. | Structure | Name |
|---|---|---|
| 250 | 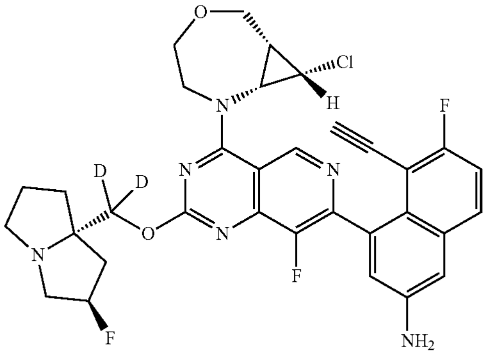 [SMILES: [2H]C([2H])(Oc1nc(N2CCOC[C@@H]3[C@@H](Cl)[C@@H]32)c2cnc(-c3cc(N)cc4ccc(F)c(C#C)c34)c(F)c2n1)[C@@]12CCCN1C[C@H](F)C2] | 4-(4-((1R,7R,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 251 | 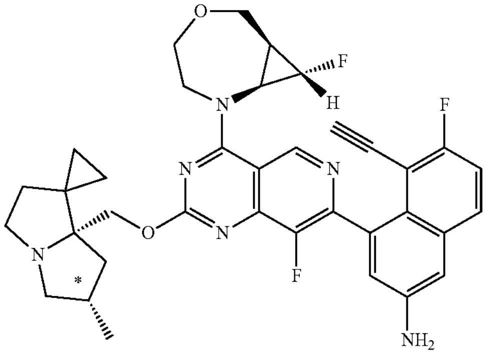 [SMILES: C#Cc1c(F)ccc2cc(N)cc(-c3ncc4c(N5CCOC[C@H]6[C@H](F)[C@H]65)nc(OC[C@]56C[C@H](C)CN5CCC65CC5)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((6'S,7a 'R)-6'-methyltetrahydrospiro[cyclopropane-1,1'-pyrrolizin]-7a'(5'H)-yl)methoxy)pyrido[4,3-d]pyrimidin-7-yl)naphthalen-2-amine |
| 252 | 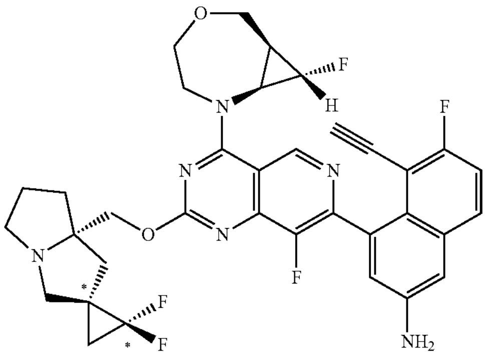 | 5-ethynyl-6-fluoro-4-(8-fluoro~4-((1S,7S,8S)-8-fluoro-5-oxa-2-azabicyclo[5.1.0]octan-2-yl)-2-(((1S,2S,7a 'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine |
| 253 | 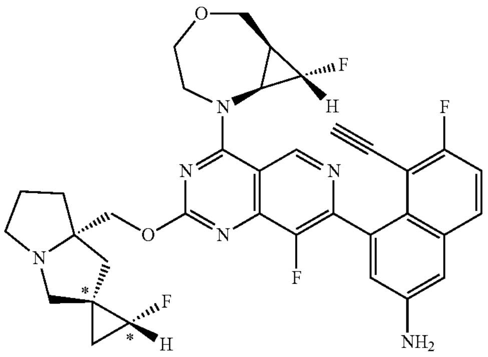 [SMILES: C#Cc1c(F)ccc2cc(N)cc(-c3ncc4c(N5CCOC[C@H]6[C@H](F)[C@H]65)nc(OC[C@@]56CCCN5C[C@@]5(C[C@H]5F)C6)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((1S,2R,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine |

TABLE 1-continued

| Example No. | Structure | Name |
| --- | --- | --- |
| 254 | 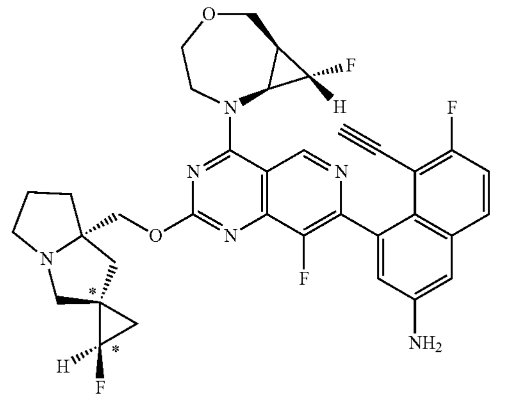 [SMILES: C#Cc1c(F)ccc2cc(N)cc(-c3ncc4c(N5CCOC[C@H]6[C@H](F)[C@H]65)nc(OC[C@@]56CCCN5C[C@]5(C[C@H]5F)C6)nc4c3F)c12] | 5-ethynyl-6-fluoro-4-(8-fluoro-4-((1S,7S,8S)-8-fluoro-5-oxa-2-azabicyclo[5.1.0]octan-2-y])-2-(((1R,2R,7a 'S)-2-fluorodihydro-1H,3'H-spiro[cyclopropane-1,2'-pyrrolizin]-7a'(5'H)-yl)methoxy)pyrido[4,3-d]pyrimidin-7-yl)naphthalen-2-amine |
| 255 | 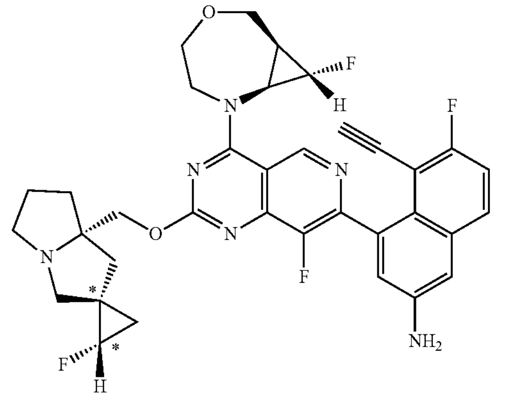 [SMILES: C#Cc1c(F)ccc2cc(N)cc(-c3ncc4c(N5CCOC[C@H]6[C@H](F)[C@H]65)nc(OC[C@@]56CCCN5C[C@]5(C[C@@H]5F)C6)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine |
| 256 | 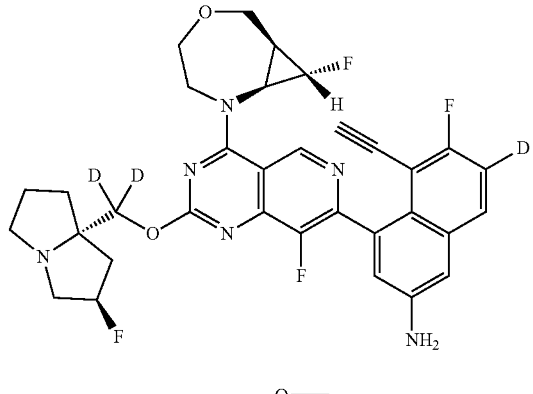 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-7-d-2-amine |
| 257 | 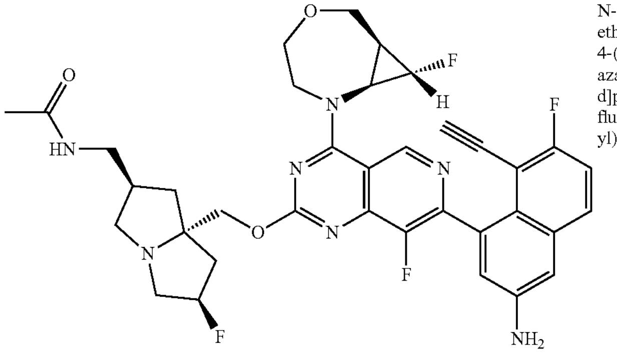 | N-(((2R,6R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yloxy)methyl)-6-fluorohexahydro-1H-pyrrolizin-2-yl)methyl)acetamide |

TABLE 1-continued

| Example No. | Structure | Name |
|---|---|---|
| 258 | 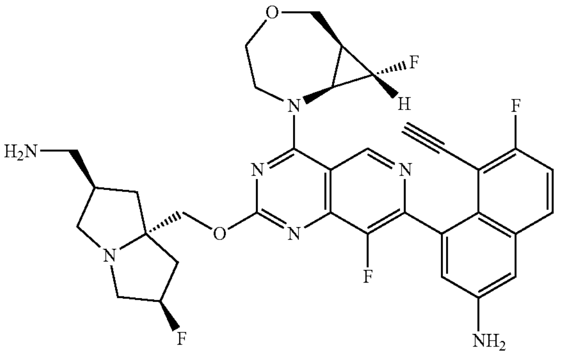 [SMILES: C#Cc1c(F)ccc2cc(N)cc(-c3ncc4c(N5CCOC[C@H]6[C@H](F)[C@H]65)nc(OC[C@]56C[C@@H](F)CN5C[C@@H](CN)C6)nc4c3F)c12] | 4-(2-(((2R,6R,7aS)-2-(aminomethyl)-6-fluorotetrahydro-1H-pyrrolizin-7a(5H)-yl)methoxy)-8-fluoro-4-((1S,7,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 259 | 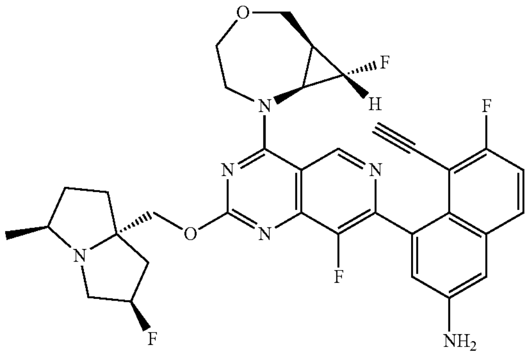 [SMILES: C#Cc1c(F)ccc2cc(N)cc(-c3ncc4c(N5CCOC[C@H]6[C@H](F)[C@H]65)nc(OC[C@@]56CC[C@H](C)N5C[C@H](F)C6)nc4c3F)c12] | 5-ethynyl-6-fluoro-4-(8-fluoro-2-(((2R,5S,7aS)-2-fluoro-5-methyltetrahydro-1H-pyrrolizin-7a(5H)-methoxy)-4-((1S,7S,8S)-8-fluoro-5-oxa-2-azabicyclo[5.1.0]octan-2-yl)pyrido[4,3-d]pyrimidin-7-yl)naphthalen-2-amine |
| 260 | 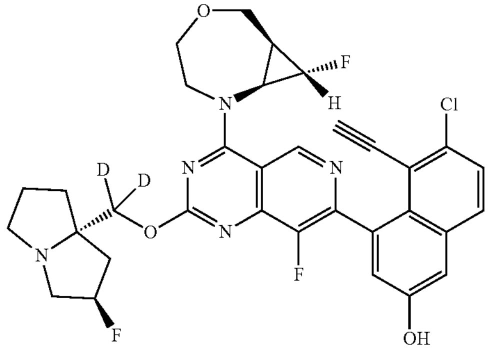 [SMILES: [2H]C([2H])(Oc1nc(N2CCOC[C@H]3[C@H](F)[C@H]32)c2cnc(-c3cc(O)cc4ccc(Cl)c(C#C)c34)c(F)c2n1)[C@@]12CCCN1C[C@H](F)C2] | 6-chloro-5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)ynaphthalen-2-ol |
| 261 | 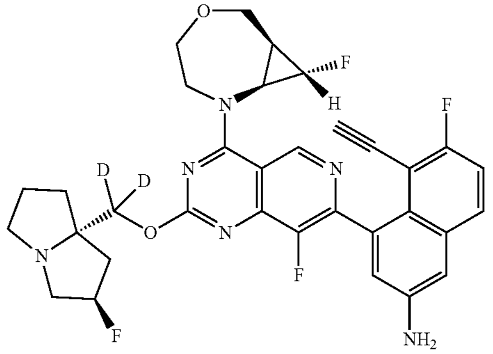 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1C[C@H](F)C2] | 5-ethynyl-6-fluoro-4-(4-((1S,7S,8S)-8-fluoro-5-oxa-2-azabicyclo[5.1.0]octan-2-yl)-2-(((2R.7aS)-2-fluorotetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
| --- | --- | --- |
| 262 | 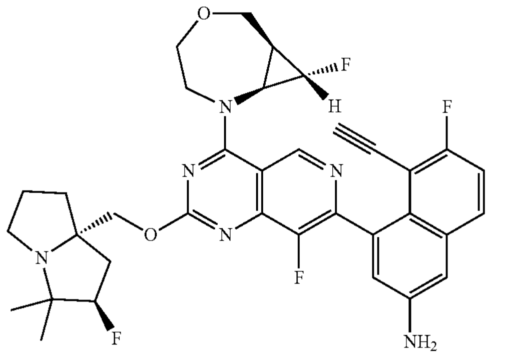 [SMILES: C#Cc1c(F)ccc2cc(N)cc(-c3ncc4c(N5CCOC[C@H]6[C@H](F)[C@H]65)nc(OC[C@@]56CCCN5C(C)(C)[C@H](F)C6)nc4c3F)c12] | 5-ethynyl-6-fluoro-4-(8-fluoro-2-(((2R,7aS)-2-fluoro-3,3-dimethyltetrahydro-1H-pyrrolizin-7a(5H)-methoxy)-4-((1S,7S,8S)-8-fluoro-5-oxa-2-azabicyclo[5.1.0]octan-2-yl)pyrido[4,3-d]pyrimidin-7-yl)naphthalen-2-amine |
| 263 | 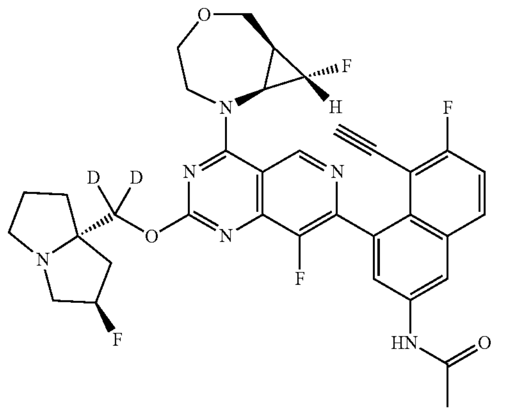 [SMILES: [2H]C([2H])(Oc1nc(N2CCOC[C@H]3[C@H](F)[C@H]32)c2cnc(-c3cc(NC(C)=O)cc4ccc(F)c(C#C)c34)c(F)c2n1)[C@@]12CCCN1C[C@H](F)C2] | N-(5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-yl)acetamide |
| 264 | 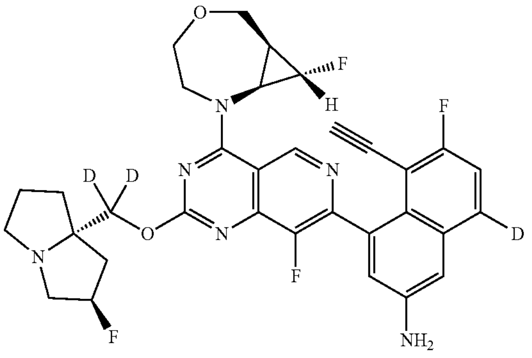 [SMILES: [2H]c1cc(F)c(C#C)c2c(-c3ncc4c(N5CCOC[C@H]6[C@H](F)[C@H]65)nc(OC([2H])([2H])[C@@]56CCCN5C[C@H](F)C6)nc4c3F)cc(N)cc12] | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-8-d-2-amine |
| 265 | 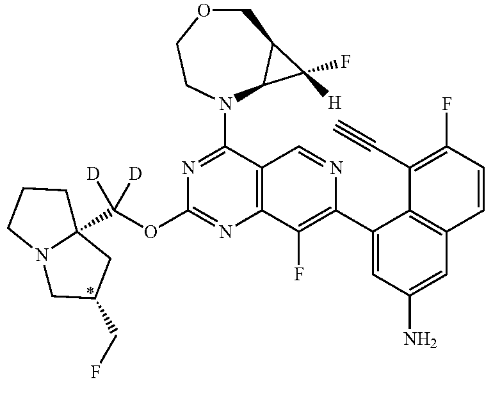 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1C[C@@H](CF)C2] | 5-ethynyl-6-fluoro-4-(8-fluoro-4-((1S,7S,8S)-8-fluoro-5-oxa-2-azabicyclo[5.1.0]octan-2-yl)-2-(((2S,7aS)-2-(fluoromethtetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
| --- | --- | --- |
| 266 | 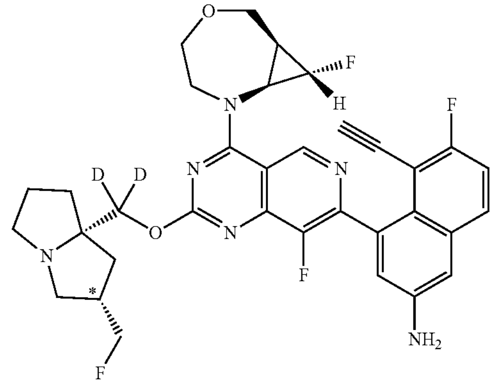 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1C[C@@H](CF)C2] | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-(fluoromethtetrahydro-1H-pyrrolizin-7a(5H)-yl)methoxy-d2)pyrido[4,3-d]pyrimidin-7-yl)naphthalen-2-amine |
| 267 | 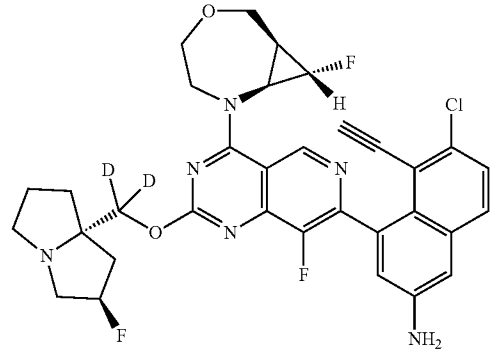 [SMILES: [2H]C([2H])(Oc1nc(N2CCOC[C@H]3[C@H](F)[C@H]32)c2cnc(-c3cc(N)cc4ccc(Cl)c(C#C)c34)c(F)c2n1)[C@@]12CCCN1C[C@H](F)C2] | 6-chloro-5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 268 | 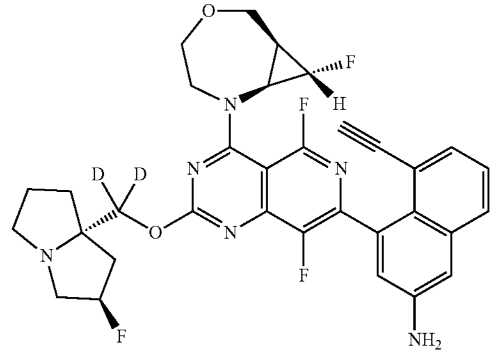 [SMILES: [2H]C([2H])(Oc1nc(N2CCOC[C@H]3[C@H](F)[C@H]32)c2c(F)nc(-c3cc(N)cc4cccc(C#C)c34)c(F)c2n1)[C@@]12CCCN1C[C@H](F)C2] | 5-ethynyl-4-(8-fluoro-4-(1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine |
| 269 | 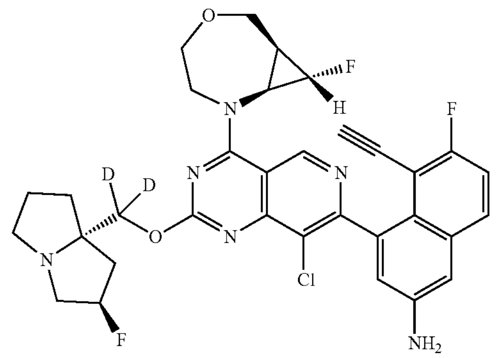 [SMILES: [2H]C([2H])(Oc1nc(N2CCOC[C@H]3[C@H](F)[C@H]32)c2cnc(-c3cc(N)cc4ccc(F)c(C#C)c34)c(Cl)c2n1)[C@@]12CCCN1C[C@H](F)C2] | 4-(8-chloro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |

TABLE 1-continued

| Example No. | Structure | Name |
|---|---|---|
| 270 | 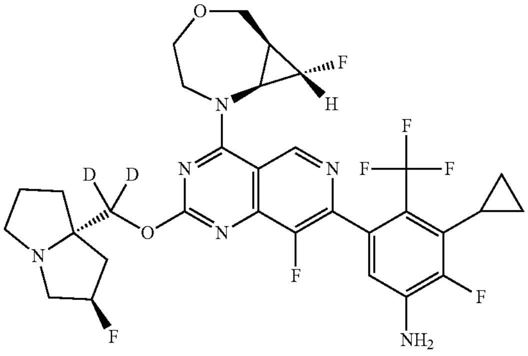 [SMILES: [2H]C([2H])(Oc1nc(N2CCOC[C@H]3[C@H](F)[C@H]32)c2cnc(-c3cc(N)c(F)c(C4CC4)c3C(F)(F)F)c(F)c2n1)[C@@]12CCCN1C[C@H](F)C2] | 3-cyclopropyl-2-fluoro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-(trifluoromethyl)aniline |
| 271 | 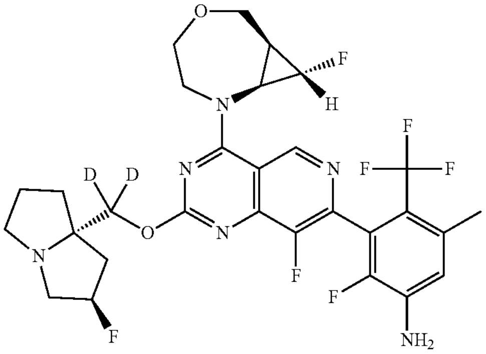 [SMILES: [2H]C([2H])(Oc1nc(N2CCOC[C@H]3[C@H](F)[C@H]32)c2cnc(-c3c(F)c(N)cc(C)c3C(F)(F)F)c(F)c2n1)[C@@]12CCCN1C[C@H](F)C2] | 2-fluoro-3-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-methyl-4-(trifluoromethyl)aniline |
| 272 | 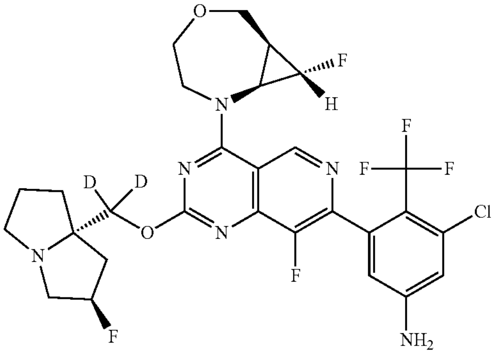 [SMILES: [2H]C([2H])(Oc1nc(N2CCOC[C@H]3[C@H](F)[C@H]32)c2cnc(-c3cc(N)cc(Cl)c3C(F)(F)F)c(F)c2n1)[C@@]12CCCN1C[C@H](F)C2] | 3-chloro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-(trifluoromethyl)aniline |
| 273 | 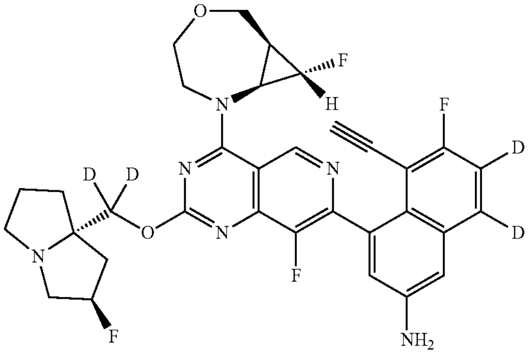 [SMILES: [2H]c1c(F)c(C#C)c2c(-c3ncc4c(N5CCOC[C@H]6[C@H](F)[C@H]65)nc(OC([2H])([2H])[C@@]56CCCN5C[C@H](F)C6)nc4c3F)cc(N)cc2c1[2H]] | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-7,8-d2-2-amine |

TABLE 1-continued

| Example No. | Structure | Name |
|---|---|---|
| 274 | 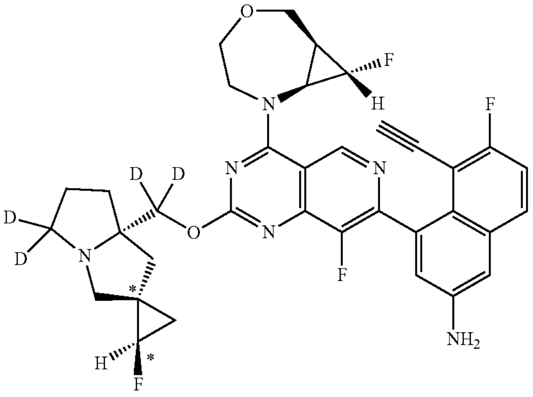 [SMILES: [2H]C1([2H])CC[C@@]2(C([2H])([2H])Oc3nc(N4CCOC[C@H]5[C@H](F)[C@H]54)c4cnc(-c5cc(N)cc6ccc(F)c(C#C)c56)c(F)c4n3)C[C@@]3(C[C@H]3F)CN12] | 5-ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl-5',5'-d2)methoxy-d2)pyrido[4,3-d]pyrimidin-7-yl)naphthalen-2-amine |
| 275 | 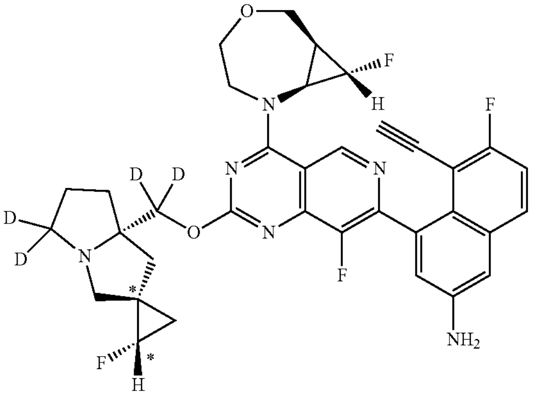 [SMILES: [2H]C1([2H])CC[C@@]2(C([2H])([2H])Oc3nc(N4CCOC[C@H]5[C@H](F)[C@H]54)c4cnc(-c5cc(N)cc6ccc(F)c(C#C)c56)c(F)c4n3)C[C@@]3(C[C@@H]3F)CN12] | 5-ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl-5',5'-d2)methoxy-d2)pyrido[4,3-d]pyrimidin-7-yl)naphthalen-2-amine |
| 276 | 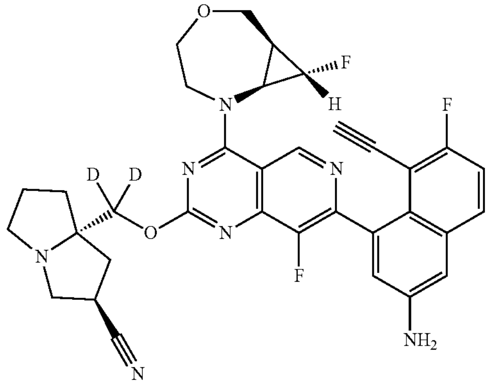 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1C[C@H](C#N)C2] | (2R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizine-2-carbonitrile |
| 277 | 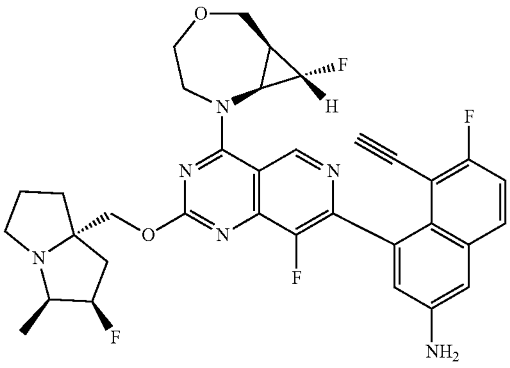 [SMILES: C#Cc1c(F)ccc2cc(N)cc(-c3ncc4c(N5CCOC[C@H]6[C@H](F)[C@H]65)nc(OC[C@@]56CCCN5[C@H](C)[C@H](F)C6)nc4c3F)c12] | 5-ethynyl-6-fluoro-4-(8-fluoro-2-(((2R,3R,7aS)-2-fluoro-3-methyltetrahydro-1H-pyrrolizin-7a(5H)-methoxy)-4-((1S,7S,8S)-8-fluoro-5-oxa-2-azabicyclo[5.1.0]octan-2-yl)pyrido[4,3-d]pyrimidin-7-yl)naphthalen-2-amine |

TABLE 1-continued

| Example No. | Structure | Name |
|---|---|---|
| 278 | 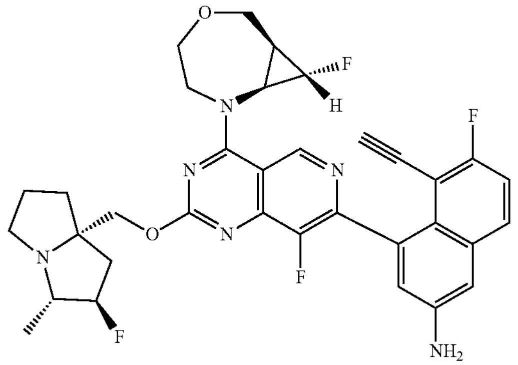 [SMILES: C#Cc1c(F)ccc2cc(N)cc(-c3ncc4c(N5CCOC[C@H]6[C@H](F)[C@H]65)nc(OC[C@@]56CCCN5[C@@H](C)[C@H](F)C6)nc4c3F)c12] | 5-ethynyl-6-fluoro-4-(8-fluoro-2-(((2R,3S,7aS)-2-fluoro-3-methyltetrahydro-1H-pyrrolizin-7a(5H)-methoxy)-4-((1S,7S,8S)-8-fluoro-5-oxa-2-azabicyclo[5.1.0]octan-2-yl)pyrido[4,3-d]pyrimidin-7-yl)naphthalen-2-amine |
| 279 | 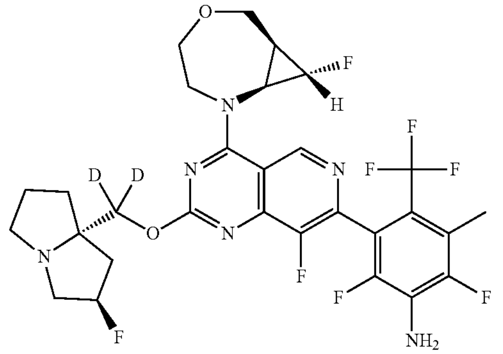 [SMILES: [2H]C([2H])(Oc1nc(N2CCOC[C@H]3[C@H](F)[C@H]32)c2cnc(-c3c(F)c(N)c(F)c(C)c3C(F)(F)F)c(F)c2n1)[C@@]12CCCN1C[C@H](F)C2] | 2,6-difluoro-3-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-methyl-4-(trifluoromethyl)aniline |
| 280 | 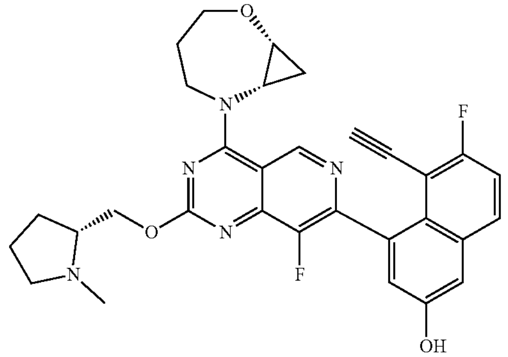 [SMILES: C#Cc1c(F)ccc2cc(O)cc(-c3ncc4c(N5CCCO[C@@H]6C[C@@H]65)nc(OC[C@H]5CCCN5C)nc4c3F)c12] | 4-(4-((1R,7S)-2-oxa-6-azabicyclo[5.1.0]octan-6-yl)-8-fluoro-2-(((R)-1-methylpyrrolidin-2-yl)methoxy)pyrido[4,3-d]pyrimidin-7-yl)-5-ethynyl-6-fluoronaphthalen-2-ol |
| 281 | 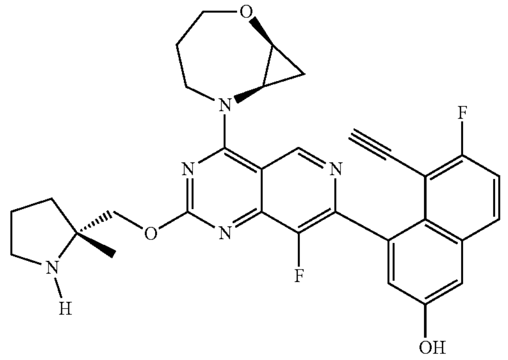 [SMILES: C#Cc1c(F)ccc2cc(O)cc(-c3ncc4c(N5CCCO[C@H]6C[C@H]65)nc(OC[C@@]5(C)CCCN5)nc4c3F)c12] | 4-(4-((1S,7R)-2-oxa-6-azabicyclo[5.1.0]octan-6-yl)-8-fluoro-2-(((R)-2-methylpyrrolidin-2-yl)methoxy)pyrido[4,3-d]pyrimidin-7-yl)-5-ethynyl-6-fluoronaphthalen-2-ol |

TABLE 1-continued

| Example No. | Structure | Name |
|---|---|---|
| 282 | 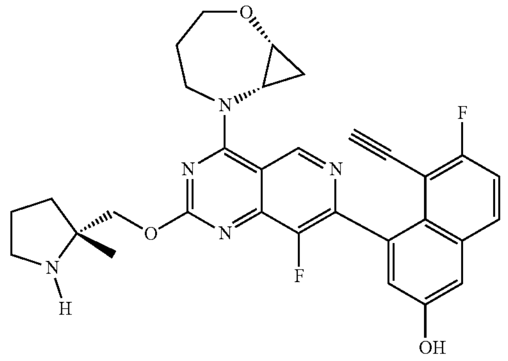 [SMILES: C#Cc1c(F)ccc2cc(O)cc(-c3ncc4c(N5CCCO[C@@H]6C[C@@H]65)nc(OC[C@@]5(C)CCCN5)nc4c3F)c12] | 4-(4-((1R,7S)-2-oxa-6-azabicyclo[5.1.0]octan-6-yl)-8-fluoro-2-(((R)-2-methylpyrrolidin-2-yl)methoxy)pyrido[4,3-d]pyrimidin-7-yl)-5-ethynyl-6-fluoronaphthalen-2-ol |
| 283 | 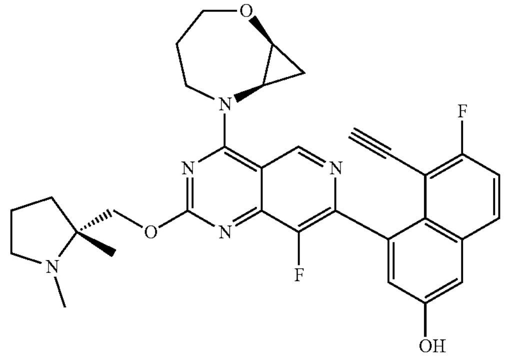 [SMILES: C#Cc1c(F)ccc2cc(O)cc(-c3ncc4c(N5CCCO[C@H]6C[C@H]65)nc(OC[C@@]5(C)CCCN5C)nc4c3F)c12] | 4-(4-((1S,7R)-2-oxa-6-azabicyclo[5.1.0]octan-6-yl)-2-(((R)-1,2-dimethylpyrrolidin-2-methoxy)-8-fluoropyrido[4,3-d]pyrimidin-7-yl)-5-ethynyl-6-fluoronaphthalen-2-ol |
| 284 | 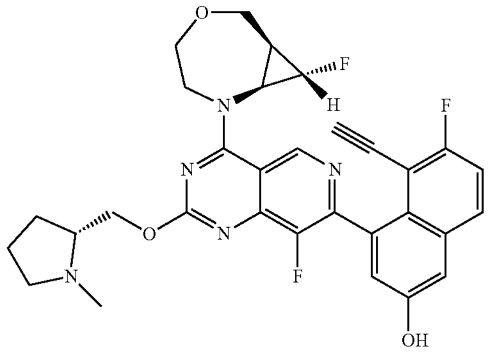 [SMILES: C#Cc1c(F)ccc2cc(O)cc(-c3ncc4c(N5CCOC[C@H]6[C@H](F)[C@H]65)nc(OC[C@H]5CCCN5C)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((R)-1-methylpyrrolidin-2-yl)methoxy)pyrido[4,3-d]pyrimidin-7-yljnaphthalen-2-ol |
| 285 | 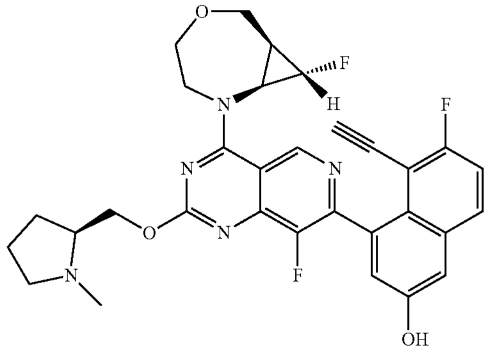 [SMILES: C#Cc1c(F)ccc2cc(O)cc(-c3ncc4c(N5CCOC[C@H]6[C@H](F)[C@H]65)nc(OC[C@@H]5CCCN5C)nc4c3F)c12] | 5-ethynyl-6-fluoro-4-(8-fluoro-4-((1S,7S.8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol |

TABLE 1-continued

| Example No. | Structure | Name |
| --- | --- | --- |
| 286 | 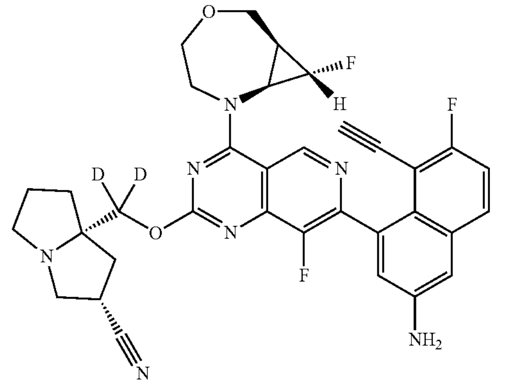 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1C[C@@H](C#N)C2] | 7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizine-2-carbonitrile |
| 287 | 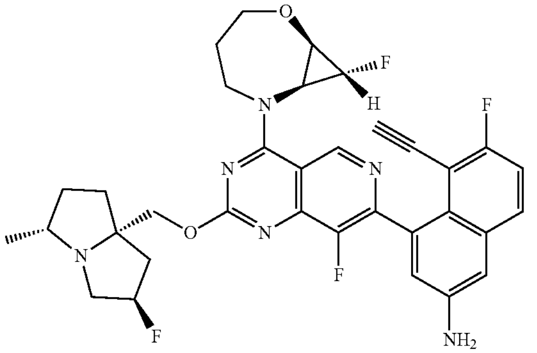 [SMILES: C#Cc1c(F)ccc2cc(N)cc(-c3ncc4c(N5CCCO[C@H]6[C@H](F)[C@H]65)nc(OC[C@@]56CC[C@@H](C)N5C[C@H](F)C6)nc4c3F)c12] | 5-ethynyl-6-fluoro-4-(8-fluoro-2-(((2R,5R,7aS)-2-fluoro-5-methyltetrahydro-1H-pyrrolizin-7a(5H)-methoxy)-4-((1S,7S,8S)-8-fluoro-5-oxa-2-azabicyclo[5.1.0]octan-2-yl)pyrido[4,3-d]pyrimidin-7-yl)naphthalen-2-amine |
| 288 | 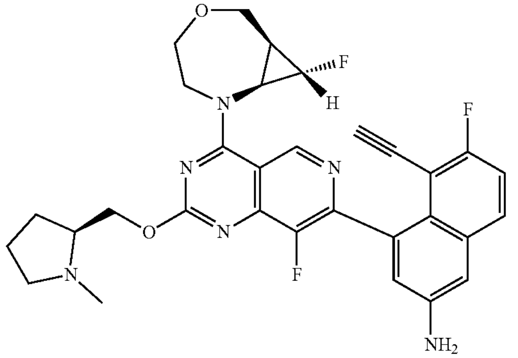 [SMILES: C#Cc1c(F)ccc2cc(N)cc(-c3ncc4c(N5CCOC[C@H]6[C@H](F)[C@H]65)nc(OC[C@@H]5CCCN5C)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-amine |
| 289 | 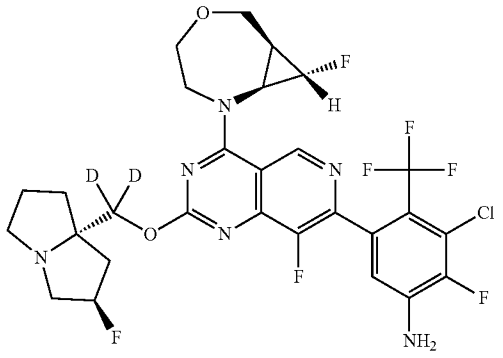 [SMILES: [2H]C([2H])(Oc1nc(N2CCOC[C@H]3[C@H](F)[C@H]32)c2cnc(-c3cc(N)c(F)c(Cl)c3C(F)(F)F)c(F)c2n1)[C@@]12CCCN1C[C@H](F)C2] | 3-chloro-2-fluoro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-(trifluoromethyl)aniline |

TABLE 1-continued

| Example No. | Structure | Name |
| --- | --- | --- |
| 290 | 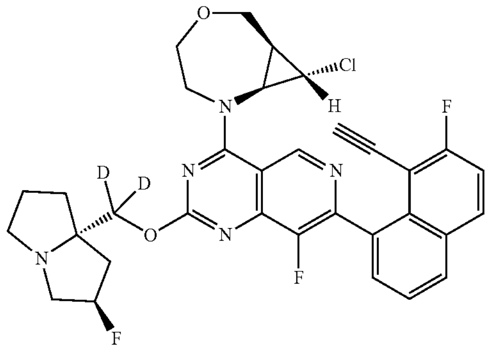 [SMILES: [2H]C([2H])(Oc1nc(N2CCOC[C@H]3[C@H](Cl)[C@H]32)c2cnc(-c3cccc4ccc(F)c(C#C)c34)c(F)c2n1)[C@@]12CCCN1C[C@H](F)C2] | (1S,7S,8S)-8-chloro-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane |
| 291 | 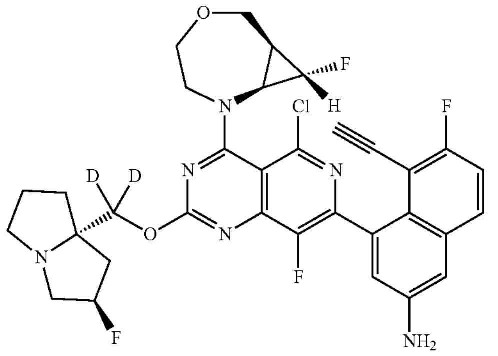 [SMILES: [2H]C([2H])(Oc1nc(N2CCOC[C@H]3[C@H](F)[C@H]32)c2c(Cl)nc(-c3cc(N)cc4ccc(F)c(C#C)c34)c(F)c2n1)[C@@]12CCCN1C[C@H](F)C2] | 4-(5-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 292 | 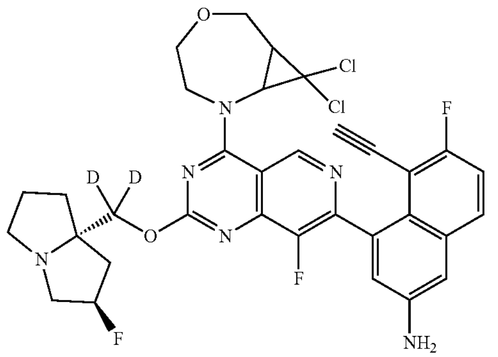 [SMILES: [2H]C([2H])(Oc1nc(N2CCOCC3C2C3(Cl)Cl)c2cnc(-c3cc(N)cc4ccc(F)c(C#C)c34)c(F)c2n1)[C@@]12CCCN1C[C@H](F)C2] | 4-(4-(8,8-dichloro-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 293 | 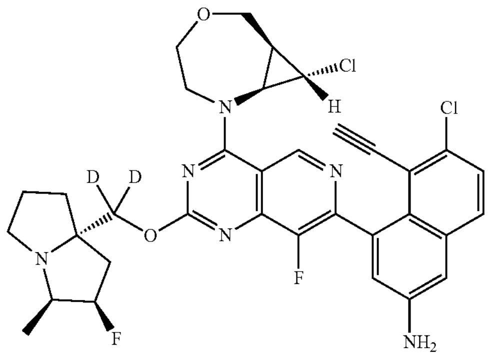 [SMILES: [2H]C([2H])(Oc1nc(N2CCOC[C@H]3[C@H](Cl)[C@H]32)c2cnc(-c3cc(N)cc4ccc(Cl)c(C#C)c34)c(F)c2n1)[C@@]12CCCN1[C@H](C)[C@H](F)C2] | 6-chloro-4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl)naphthalen-2-amine |

TABLE 1-continued

| Example No. | Structure | Name |
| --- | --- | --- |
| 294 | 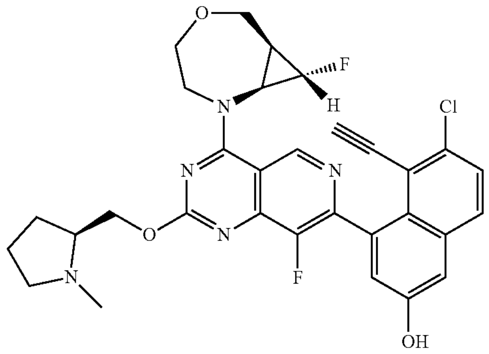 [SMILES: C#Cc1c(Cl)ccc2cc(O)cc(-c3ncc4c(N5CCOC[C@H]6[C@H](F)[C@H]65)nc(OC[C@@H]5CCCN5C)nc4c3F)c12] | 6-chloro-5-ethynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol |
| 295 | 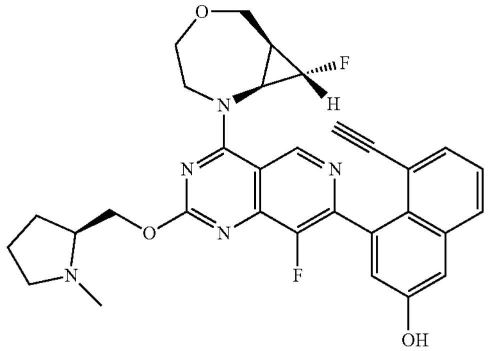 [SMILES: C#Cc1cccc2cc(O)cc(-c3ncc4c(N5CCOC[C@H]6[C@H](F)[C@H]65)nc(OC[C@@H]5CCCN5C)nc4c3F)c12] | 5-ethynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol |
| 296 | 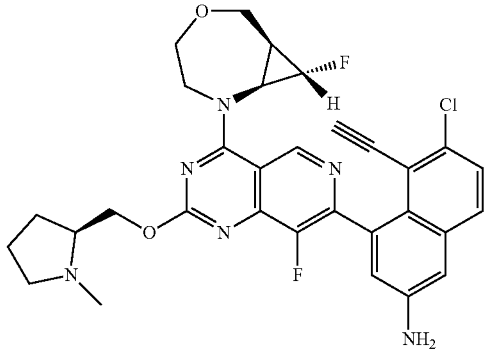 [SMILES: C#Cc1c(Cl)ccc2cc(N)cc(-c3ncc4c(N5CCOC[C@H]6[C@H](F)[C@H]65)nc(OC[C@@H]5CCCN5C)nc4c3F)c12] | 6-chloro-5-ethynyl-4-(8-fluoro-4-((1S,7S,8S)-8-fluoro-5-oxa-2-azabicyclo[5.1.0]octan-2-yl)-2-(((S)-1-methylpyrrolidin-2-methoxy)pyrido[4,3-d]pyrimidin-7-yl)naphthalen-2-amine |
| 297 | 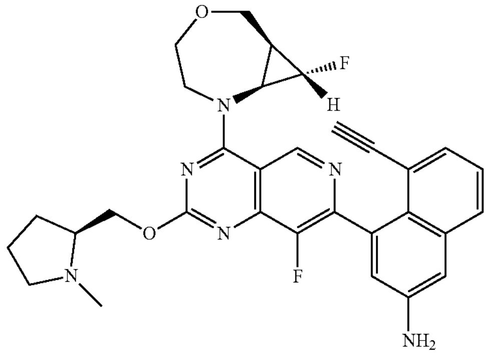 [SMILES: C#Cc1cccc2cc(N)cc(-c3ncc4c(N5CCOC[C@H]6[C@H](F)[C@H]65)nc(OC[C@@H]5CCCN5C)nc4c3F)c12] | 5-ethynyl-4-(8-fluoro-4-((1S,7S,8S)-8-fluoro-5-oxa-2-azabicyclo[5.1.0]octan-2-yl)-2-(((S)-1-methylpyrrolidin-2-methoxy)pyrido[4,3-d]pyrimidin-7-yl)naphthalen-2-amine |

TABLE 1-continued

| Example No. | Structure | Name |
| --- | --- | --- |
| 298 | 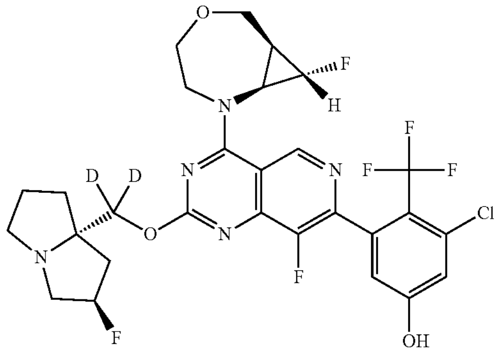 [SMILES: [2H]C([2H])(Oc1nc(N2CCOC[C@H]3[C@H](F)[C@H]32)c2cnc(-c3cc(O)cc(Cl)c3C(F)(F)F)c(F)c2n1)[C@@]12CCCN1C[C@H](F)C2] | 3-chloro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-(trifluoromethyl)phenol |
| 299 | 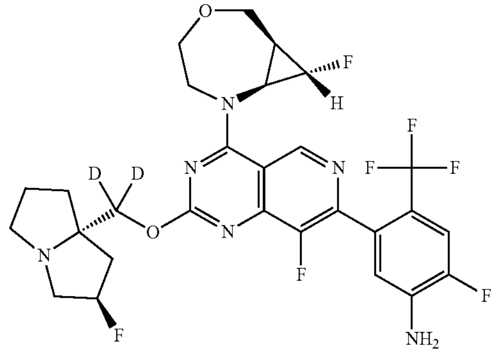 [SMILES: [2H]C([2H])(Oc1nc(N2CCOC[C@H]3[C@H](F)[C@H]32)c2cnc(-c3cc(N)c(F)cc3C(F)(F)F)c(F)c2n1)[C@@]12CCCN1C[C@H](F)C2] | 2-fluoro-5-(8-fluoro-4-((1S,7S,8S)-8-fluoro-5-oxa-2-azabicyclo[5.1.0]octan-2-yl)-yl)-2-(((2R,7aS)-2-fluorotetrahydro-1H-pyrrolizin-7a(5H)-yl)methoxy-d2)pyrido[4,3-d]pyrimidin-7-y ])-4-(trifluoromethyl)aniline |
| 300 | 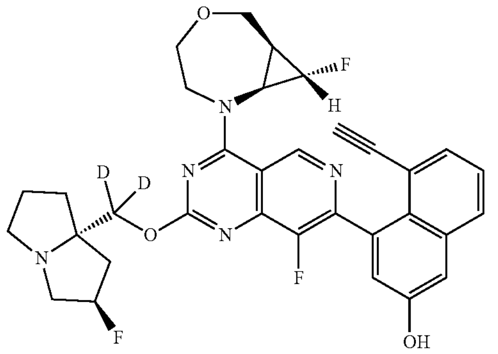 [SMILES: [2H]C([2H])(Oc1nc(N2CCOC[C@H]3[C@H](F)[C@H]32)c2cnc(-c3cc(O)cc4cccc(C#C)c34)c(F)c2n1)[C@@]12CCCN1C[C@H](F)C2] | 5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl])naphthalen-2-ol |
| 301 | 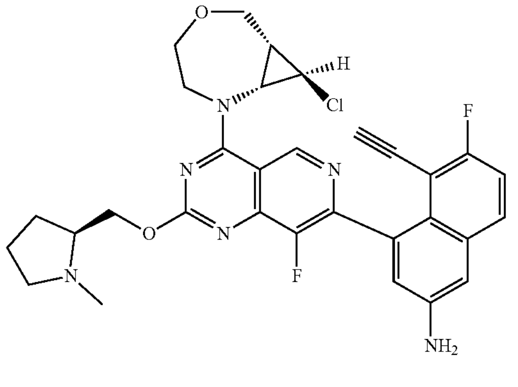 [SMILES: C#Cc1c(F)ccc2cc(N)cc(-c3ncc4c(N5CCOC[C@@H]6[C@@H](Cl)[C@@H]65)nc(OC[C@@H]5CCCN5C)nc4c3F)c12] | 4-(4-((1R,7R,8R)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-5-ethynyl-6-fluoronaphthalen-2-amine |

TABLE 1-continued

| Example No. | Structure | Name |
|---|---|---|
| 302 | 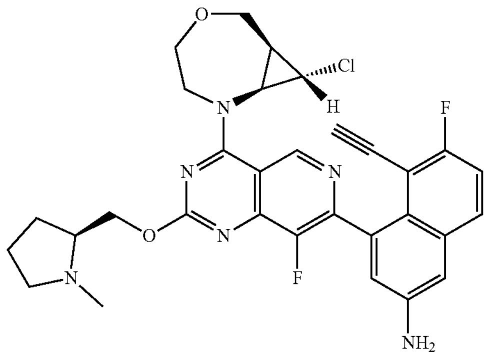 [SMILES: C#Cc1c(F)ccc2cc(N)cc(-c3ncc4c(N5CCOC[C@H]6[C@H](Cl)[C@H]65)nc(OC[C@@H]5CCCN5C)nc4c3F)c12] | 4-(4-((1S,7S,8S)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynyl-6-fluoronaphthalen-2-amine |
| 303 | 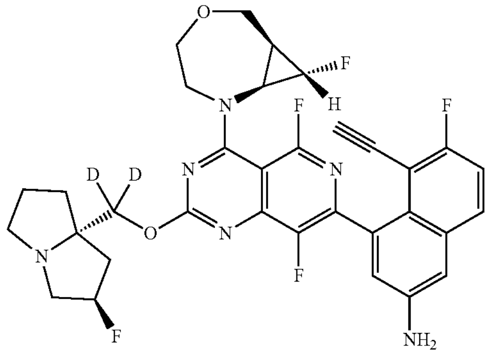 [SMILES: [2H]C([2H])(Oc1nc(N2CCOC[C@H]3[C@H](F)[C@H]32)c2c(F)nc(-c3cc(N)cc4ccc(F)c(C#C)c34)c(F)c2n1)[C@@]12CCCN1C[C@H](F)C2] | 4-(5,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethyny]-6-fluoronaphthalen-2-amine |
| 304 | 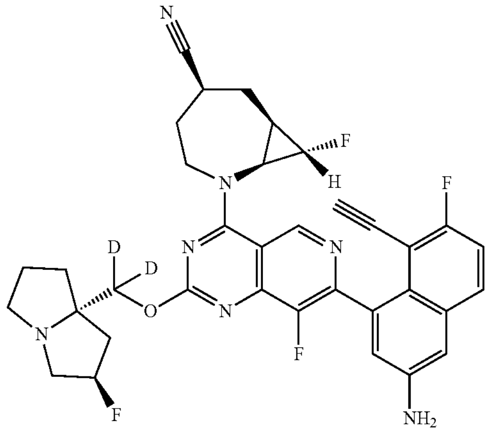 [SMILES: [2H]C([2H])(Oc1nc(N2CC[C@@H](C#N)C[C@H]3[C@H](F)[C@H]32)c2cnc(-c3cc(N)cc4ccc(F)c(C#C)c34)c(F)c2n1)[C@@]12CCCN1C[C@H](F)C2] | (1S,5S,7R,8S)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile |
| 305 | 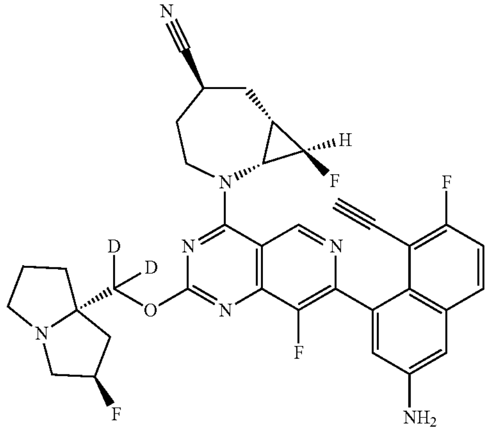 | (1R,5S,7S,8R)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile |

TABLE 1-continued

| Example No. | Structure | Name |
| --- | --- | --- |
| 306 | 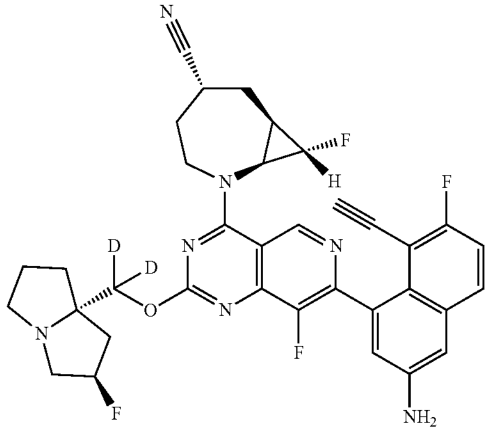 [SMILES: [2H]C([2H])(Oc1nc(N2CC[C@H](C#N)C[C@H]3[C@H](F)[C@H]32)c2cnc(-c3cc(N)cc4ccc(F)c(C#C)c34)c(F)c2n1)[C@@]12CCCN1C[C@H](F)C2] | (1S,5R,7R,8S)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile |
| 307 | 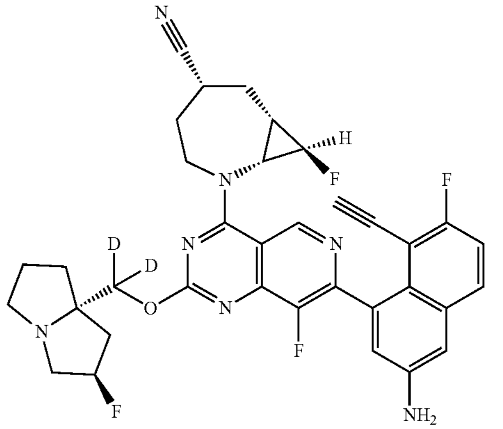 [SMILES: [2H]C([2H])(Oc1nc(N2CC[C@H](C#N)C[C@@H]3[C@@H](F)[C@@H]32)c2cnc(-c3cc(N)cc4ccc(F)c(C#C)c34)c(F)c2n1)[C@@]12CCCN1C[C@H](F)C2] | (1R,5R,7S,8R)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile |
| 308 | 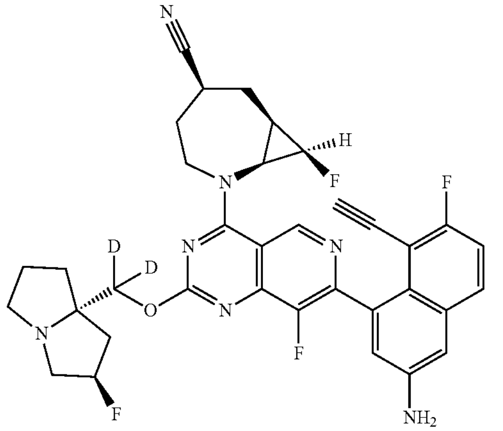 [SMILES: [2H]C([2H])(Oc1nc(N2CC[C@@H](C#N)C[C@H]3[C@@H](F)[C@H]32)c2cnc(-c3cc(N)cc4ccc(F)c(C#C)c34)c(F)c2n1)[C@@]12CCCN1C[C@H](F)C2] | (1S,5S,7R,8R)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile |

TABLE 1-continued

| Example No. | Structure | Name |
|---|---|---|
| 309 | 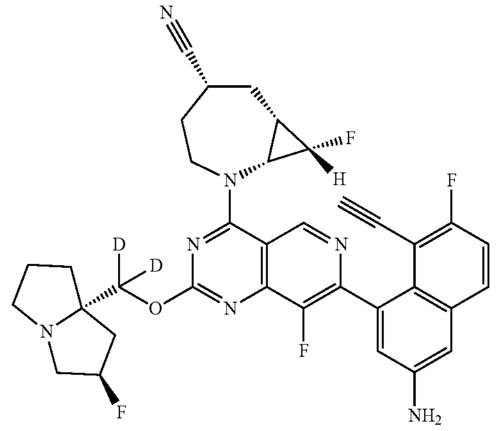 [SMILES: [2H]C([2H])(Oc1nc(N2CC[C@H](C#N)C[C@@H]3[C@H](F)[C@@H]32)c2cnc(-c3cc(N)cc4ccc(F)c(C#C)c34)c(F)c2n1)[C@@]12CCCN1C[C@H](F)C2] | (1R,5R,7S,8S)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile |
| 310 | 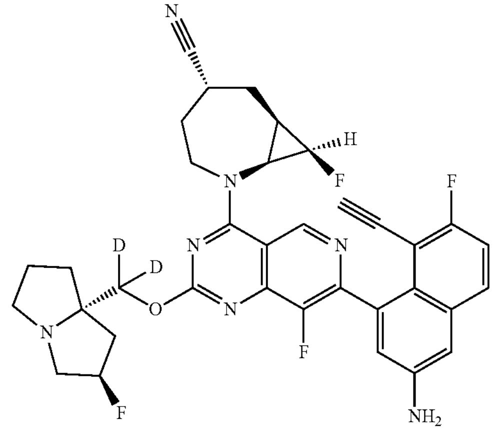 | (1S,5R,7R,8R)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile |
| 311 | 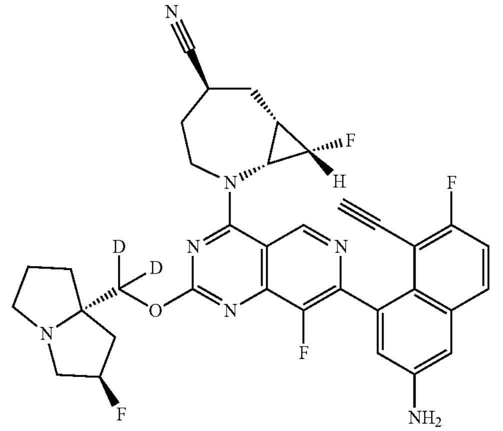 [SMILES: [2H]C([2H])(Oc1nc(N2CC[C@@H](C#N)C[C@@H]3[C@H](F)[C@@H]32)c2cnc(-c3cc(N)cc4ccc(F)c(C#C)c34)c(F)c2n1)[C@@]12CCCN1C[C@H](F)C2] | (1R,5S,7S,8S)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile |

TABLE 1-continued

| Example No. | Structure | Name |
| --- | --- | --- |
| 312 | 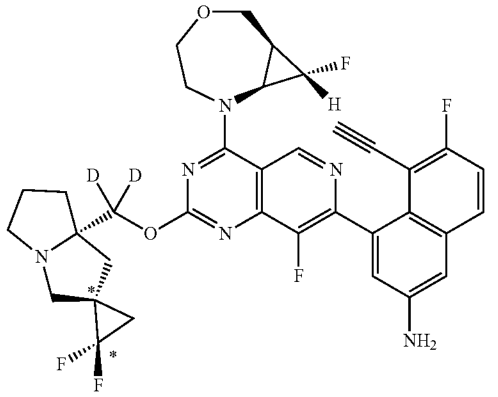 | 5-ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'pyrrolizin]-7a'(5H)-yl)methoxy-d2)pyrido[4,3-d]pyrimidin-7-yl)naphthalen-2-amine |
| 313 | 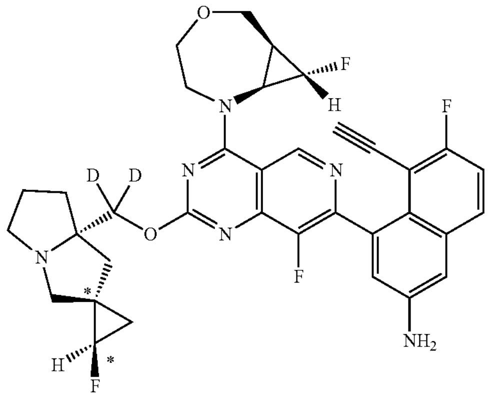 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1C[C@]1(C[C@H]1F)C2] | 5-ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a(5'H)-yl)methoxy-d2)pyrido[4,3-d]pyrimidin-7-yl)naphthalen-2-amine |
| 314 | 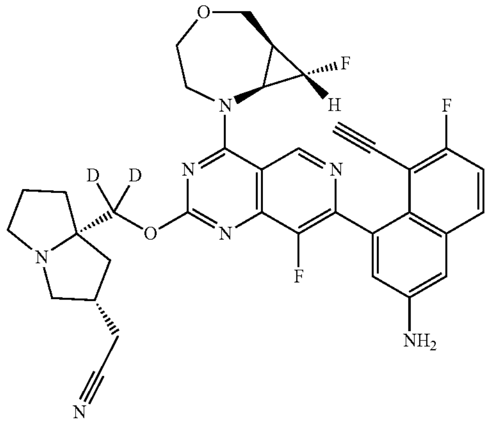 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1C[C@@H](CC#N)C2] | 2-((2R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizin-2-yl)acetonitrile |

TABLE 1-continued

| Example No. | Structure | Name |
| --- | --- | --- |
| 315 | 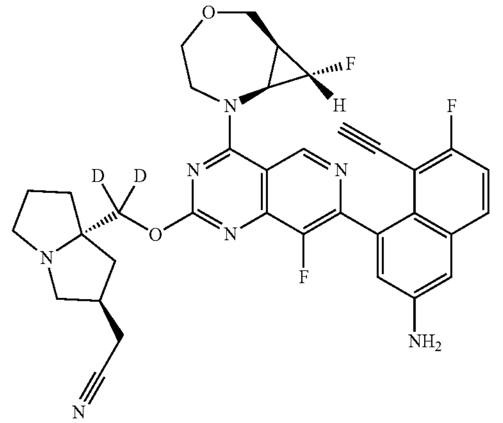 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1C[C@H](CC#N)C2] | 2-(7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-oxy)methyl-d2)hexahydro-1H-pyrrolizin-2-yl)acetonitrile |
| 316 | 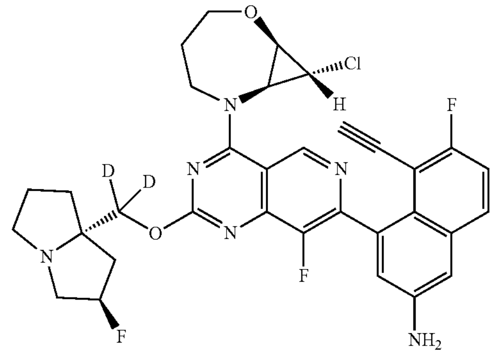 [SMILES: [2H]C([2H])(Oc1nc(N2CCCO[C@H]3[C@H](Cl)[C@H]32)c2cnc(-c3cc(N)cc4ccc(F)c(C#C)c34)c(F)c2n1)[C@@]12CCCN1C[C@H](F)C2] | 4-(4-((1R,7S,8R)-8-chloro-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 317 | 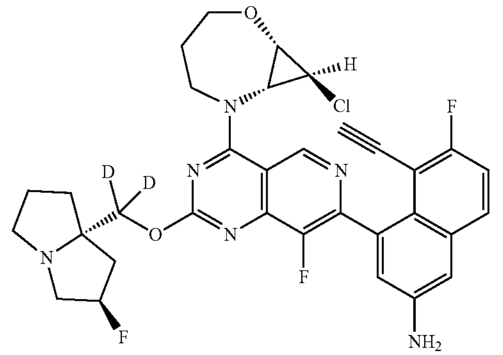 [SMILES: [2H]C([2H])(Oc1nc(N2CCCO[C@@H]3[C@@H](Cl)[C@@H]32)c2cnc(-c3cc(N)cc4ccc(F)c(C#C)c34)c(F)c2n1)[C@@]12CCCN1C[C@H](F)C2] | 4-(4-((1S,7R,&S)-8-chloro-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 318 | 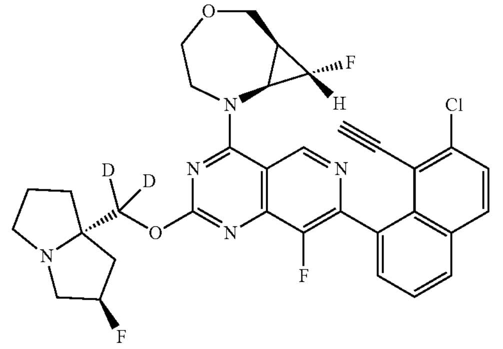 | (1S,7S,8S)-2-(7-(7-chloro-8-ethynyl)naphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane |

TABLE 1-continued

| Example No. | Structure | Name |
|---|---|---|
| 319 | 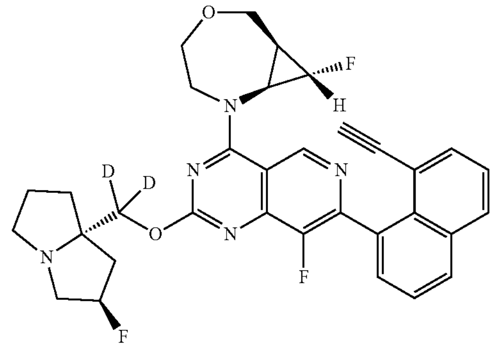 [SMILES: [2H]C([2H])(Oc1nc(N2CCOC[C@H]3[C@H](F)[C@H]32)c2cnc(-c3cccc4cccc(C#C)c34)c(F)c2n1)[C@@]12CCCN1C[C@H](F)C2] | (1S,7S,8S)-2-(7-(8-ethynylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane |
| 320 | 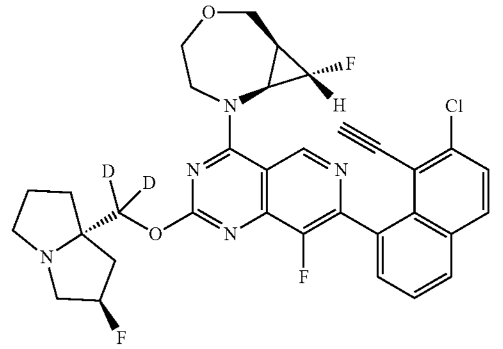 | (1S,7S,8S)-8-chloro-2-(7-(7-chloro-8-ethynylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane |
| 321 | 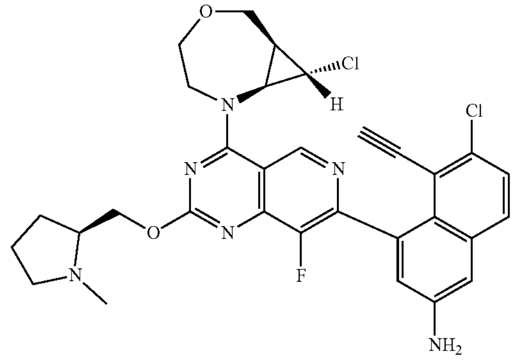 [SMILES: C#Cc1c(Cl)ccc2cc(N)cc(-c3ncc4c(N5CCOC[C@H]6[C@H](Cl)[C@H]65)nc(OC[C@@H]5CCCN5C)nc4c3F)c12] | 6-chloro-4-(4-((1S,7S,8S)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine |
| 322 | 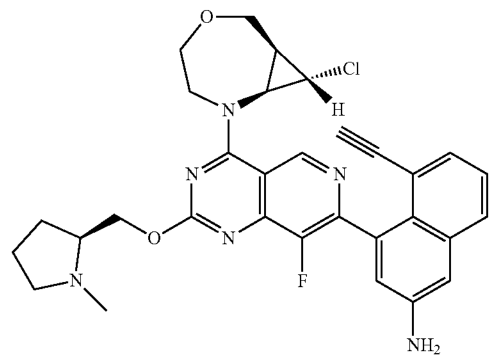 | 4-(4-((1S,7S,8S)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynyl)naphthalen-2-amine |

TABLE 1-continued

| Example No. | Structure | Name |
|---|---|---|
| 323 | 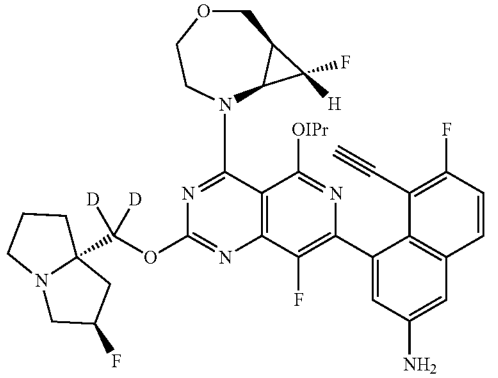 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-5-isopropoxypyrido[4,3-d]pyrimidin-7-yl)naphthalen-2-amine |
| 324 | 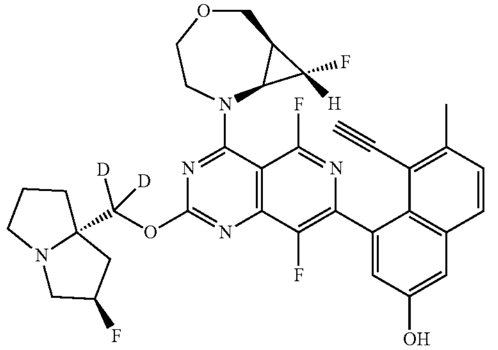 [SMILES: [2H]C([2H])(Oc1nc(N2CCOC[C@H]3[C@H](F)[C@H]32)c2c(F)nc(-c3cc(O)cc4ccc(C)c(C#C)c34)c(F)c2n1)[C@@]12CCCN1C[C@H](F)C2] | 5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-6-methylnaphthalen-2-ol |
| 325 | 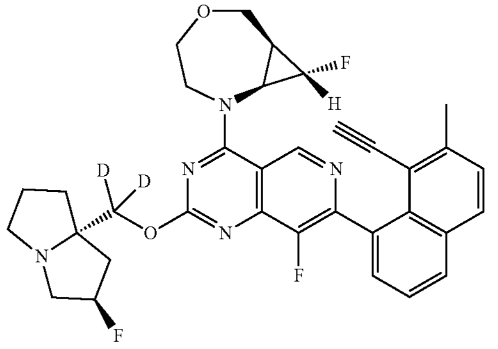 [SMILES: [2H]C([2H])(Oc1nc(N2CCOC[C@H]3[C@H](F)[C@H]32)c2cnc(-c3cccc4ccc(C)c(C#C)c34)c(F)c2n1)[C@@]12CCCN1C[C@H](F)C2] | (1S,7S,8S)-2-(7-(8-ethynyl-7-methyl)naphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane |
| 326 | 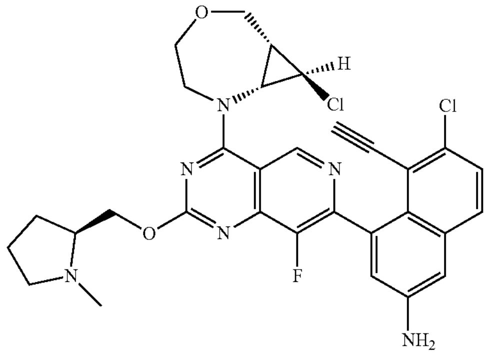 [SMILES: C#Cc1c(Cl)ccc2cc(N)cc(-c3ncc4c(N5CCOC[C@@H]6[C@@H](Cl)[C@@H]65)nc(OC[C@@H]5CCCN5C)nc4c3F)c12] | 6-chloro-4-(4-((1R,7R,8R)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynyl)naphthalen-2-amine |

TABLE 1-continued

| Example No. | Structure | Name |
| --- | --- | --- |
| 327 | 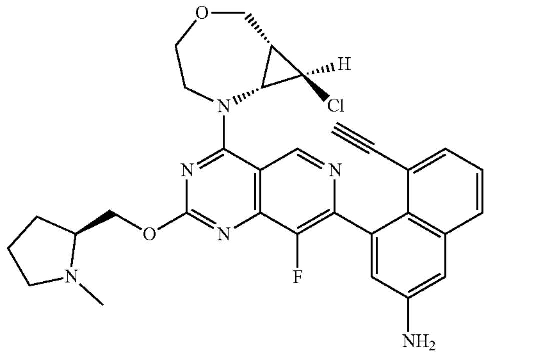 [SMILES: C#Cc1cccc2cc(N)cc(-c3ncc4c(N5CCOC[C@@H]6[C@@H](Cl)[C@@H]65)nc(OC[C@@H]5CCCN5C)nc4c3F)c12] | 4-(4-((1R,7R,8R)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynymnaphthalen-2-amine |
| 328 | 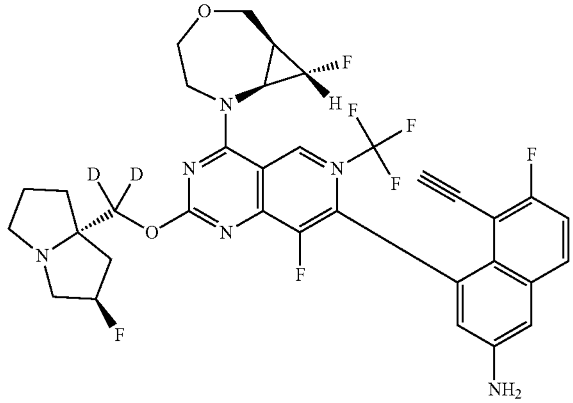 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-6-(trifluoromethyl)quinazolin-7-naphthalen-2-amine |
| 329 | 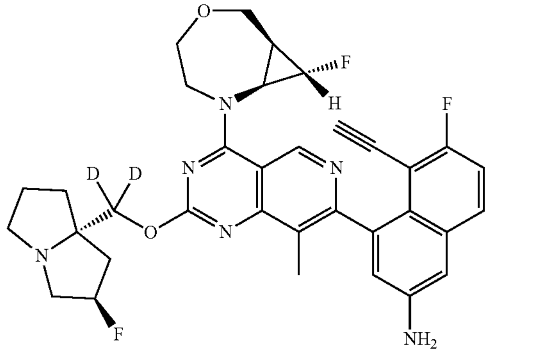 | 5-ethynyl-6-fluoro-4-(4-((1S,7,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-yl)naphthalen-2-amine |
| 330 | 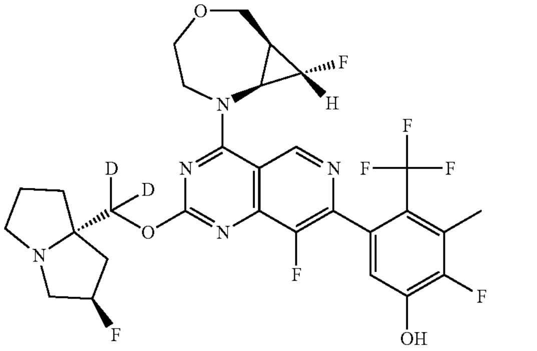 [SMILES: [2H]C([2H])(Oc1nc(N2CCOC[C@H]3[C@H](F)[C@H]32)c2cnc(-c3cc(O)c(F)c(C)c3C(F)(F)F)c(F)c2n1)[C@@]12CCCN1C[C@H](F)C2] | 2-fluoro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-3-methyl-4-(trifluoromethphenol |

TABLE 1-continued

| Example No. | Structure | Name |
| --- | --- | --- |
| 331 | 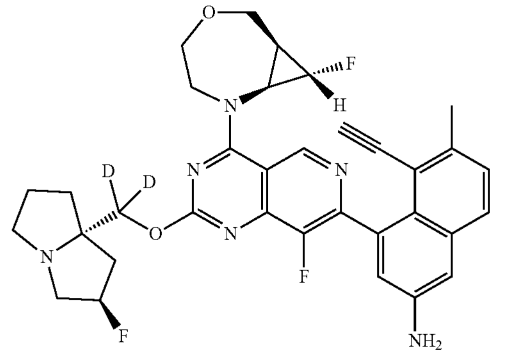 | 5-ethynyl-4-(8-fluoro-4-((1S,7,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-6-methylnaphthalen-2-amine |
| 332 | 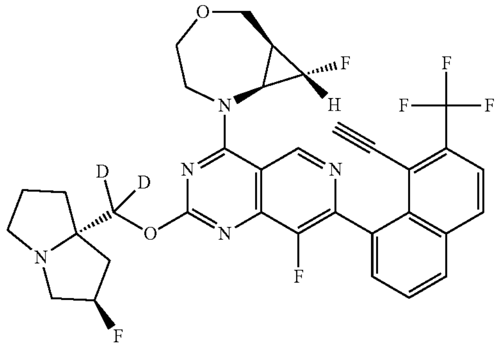 [SMILES: [2H]C([2H])(Oc1nc(N2CCOC[C@H]3[C@H](F)[C@H]32)c2cnc(-c3cccc4ccc(C(F)(F)F)c(C#C)c34)c(F)c2n1)[C@@]12CCCN1C[C@H](F)C2] | (1S,7S,8S)-2-(7-(8-ethynyl-7-(trifluoromethnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane |
| 333 | 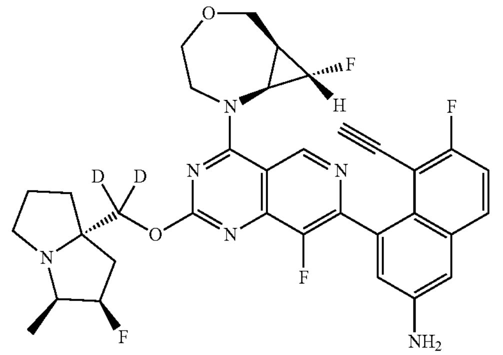 | 5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine |
| 334 | 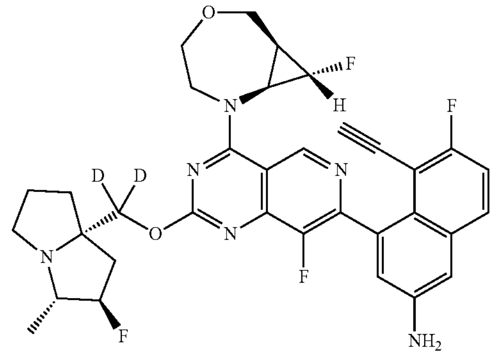 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1[C@@H](C)[C@H](F)C2] | 5-ethynyl-6-fluoro-4-(8-fluoro-2-(((2R,3S,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine |

TABLE 1-continued

| Example No. | Structure | Name |
|---|---|---|
| 335 | 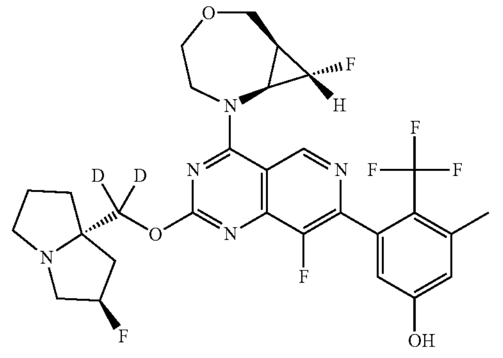 [SMILES: [2H]C([2H])(Oc1nc(N2CCOC[C@H]3[C@H](F)[C@H]32)c2cnc(-c3cc(O)cc(C)c3C(F)(F)F)c(F)c2n1)[C@@]12CCCN1C[C@H](F)C2] | 3-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-methyl-4-(trifluoromethphenol |
| 336 | 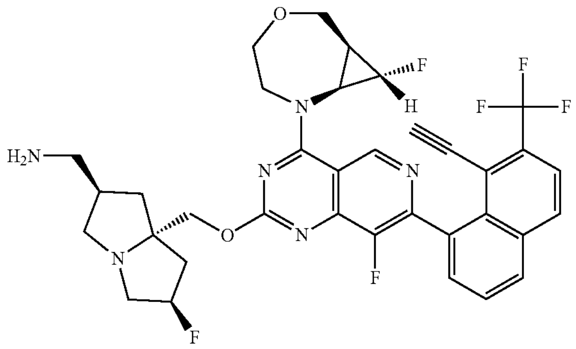 [SMILES: C#Cc1c(C(F)(F)F)ccc2cccc(-c3ncc4c(N5CCOC[C@H]6[C@H](F)[C@H]65)nc(OC[C@]56C[C@@H](F)CN5C[C@@H](CN)C6)nc4c3F)c12] | ((2R,6R,7aS)-7a-(((7-(8-ethynyl-7-(trifluoromethnaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-2-ylmethanamine |
| 337 | 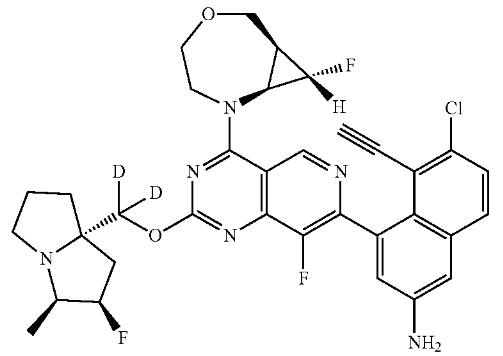 [SMILES: [2H]C([2H])(Oc1nc(N2CCOC[C@H]3[C@H](F)[C@H]32)c2cnc(-c3cc(N)cc4ccc(Cl)c(C#C)c34)c(F)c2n1)[C@@]12CCCN1[C@H](C)[C@H](F)C2] | 6-chloro-5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine |
| 338 | 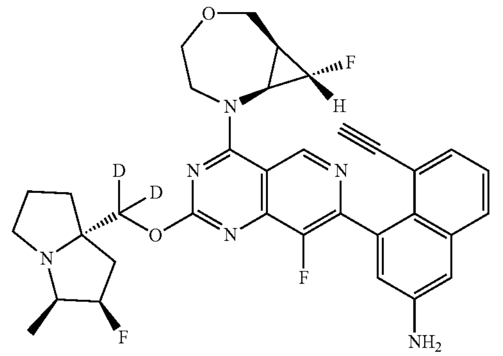 [SMILES: [2H]C([2H])(Oc1nc(N2CCOC[C@H]3[C@H](F)[C@H]32)c2cnc(-c3cc(N)cc4cccc(C#C)c34)c(F)c2n1)[C@@]12CCCN1[C@H](C)[C@H](F)C2] | 5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-pyrido[4,3-d]pyrimidin-7-yl)naphthalen-2-amine |

TABLE 1-continued

| Example No. | Structure | Name |
|---|---|---|
| 339 | 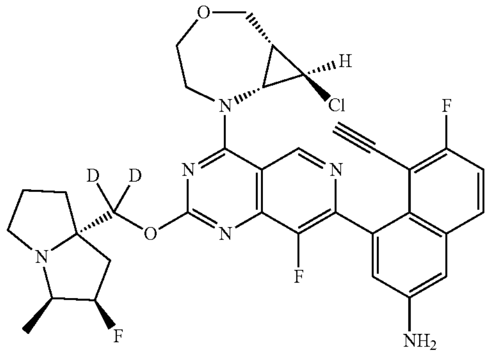 [SMILES: [2H]C([2H])(Oc1nc(N2CCOC[C@@H]3[C@@H](Cl)[C@@H]32)c2cnc(-c3cc(N)cc4ccc(F)c(C#C)c34)c(F)c2n1)[C@@]12CCCN1[C@H](C)[C@H](F)C2] | 4-(4-((1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-amine |
| 340 | 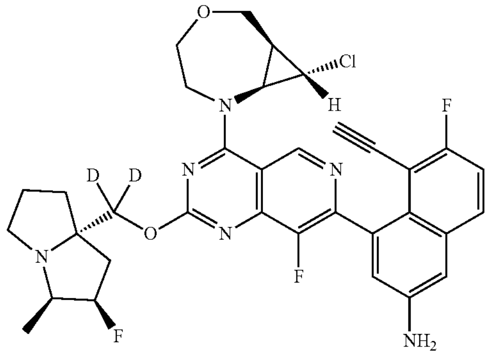 [SMILES: [2H]C([2H])(Oc1nc(N2CCOC[C@H]3[C@H](Cl)[C@H]32)c2cnc(-c3cc(N)cc4ccc(F)c(C#C)c34)c(F)c2n1)[C@@]12CCCN1[C@H](C)[C@H](F)C2] | 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-amine |
| 341 | 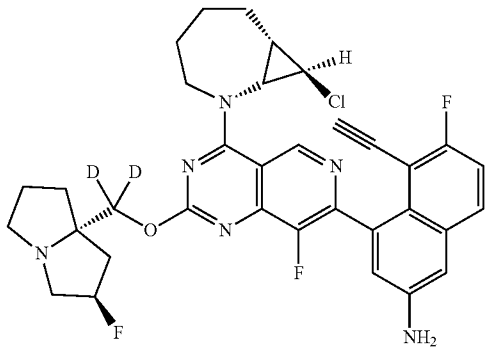 | 4-(4-((1R,7S,8R)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 342 | 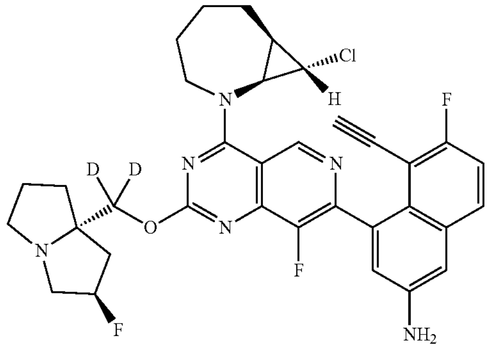 | 4-(4-((1S,7R,8S)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |

TABLE 1-continued

| Example No. | Structure | Name |
| --- | --- | --- |
| 343 | 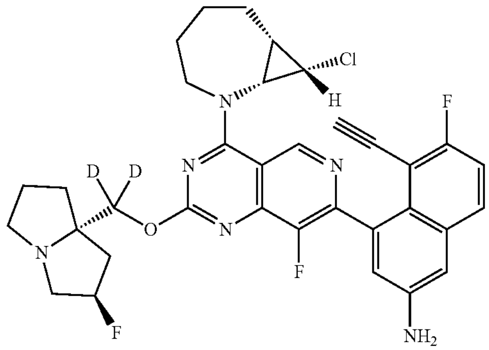 [SMILES: [2H]C([2H])(Oc1nc(N2CCCC[C@@H]3[C@H](Cl)[C@@H]32)c2cnc(-c3cc(N)cc4ccc(F)c(C#C)c34)c(F)c2n1)[C@@]12CCCN1C[C@H](F)C2] | 4-(4-((1R,7S,8S)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 344 | 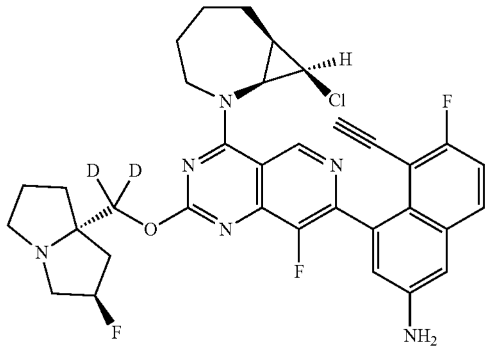 | 4-(4-((1S,7R,8R)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 345 | 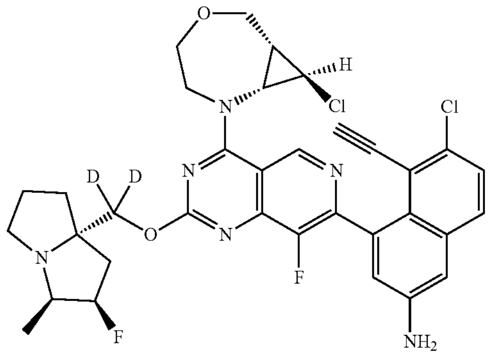 | 6-chloro-4-(4-((1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynylnaphthalen-2-amine |
| 346 | 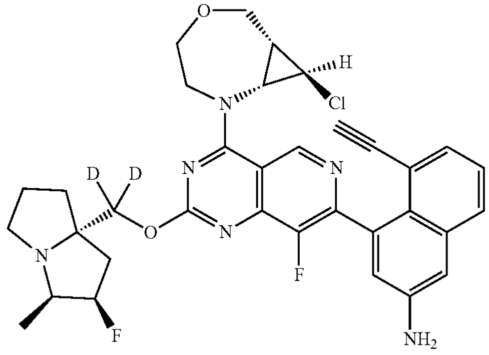 [SMILES: [2H]C([2H])(Oc1nc(N2CCOC[C@@H]3[C@@H](Cl)[C@@H]32)c2cnc(-c3cc(N)cc4cccc(C#C)c34)c(F)c2n1)[C@@]12CCCN1[C@H](C)[C@H](F)C2] | 4-(4-(1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynylna phthalen-2-amine |

TABLE 1-continued

| Example No. | Structure | Name |
|---|---|---|
| 347 | 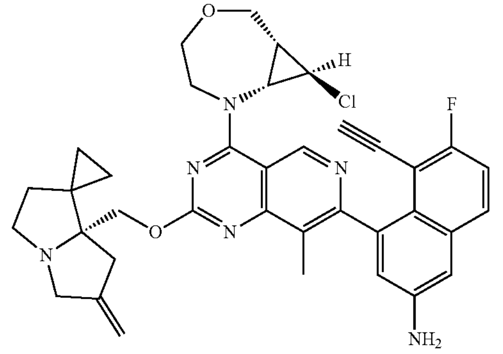 [SMILES: C#Cc1c(F)ccc2cc(N)cc(-c3ncc4c(N5CCOC[C@@H]6[C@@H](Cl)[C@@H]65)nc(OC[C@]56CC(=C)CN5CCC65CC5)nc4c3C)c12] | 4-(4-((1R,7R,8R)-8-chloro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy)pyrido[4,3-d]pyrimidin-7-yl)-5-ethynyl-6-fluoronaphthalen-2-amine |
| 348 | 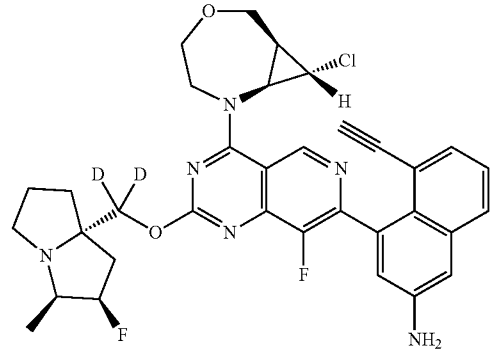 [SMILES: [2H]C([2H])(Oc1nc(N2CCOC[C@H]3[C@H](Cl)[C@H]32)c2cnc(-c3cc(N)cc4cccc(C#C)c34)c(F)c2n1)[C@@]12CCCN1[C@H](C)[C@H](F)C2] | 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynylnaphthalen-2-amine |
| 349 | 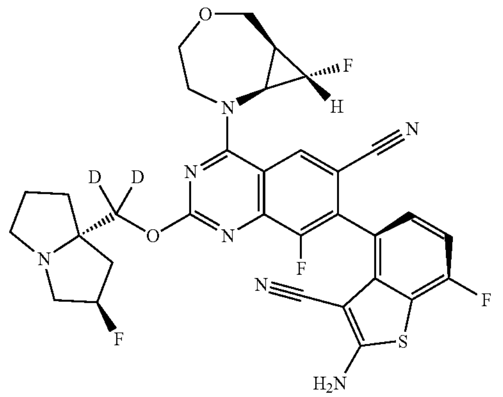 | (S)-7-(2-amino-3-cyano-7-fluorobenzo[b]thiophen-4-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazoline-6-carbonitrile |
| 350 | 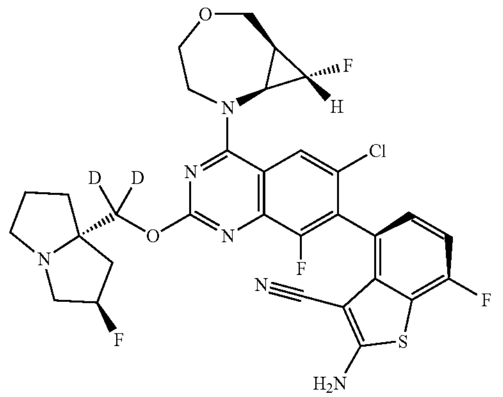 | 2-amino-4-((R)-6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-7-fluorobenzo[b]thiophene-3-carbonitrile |

TABLE 1-continued

| Example No. | Structure | Name |
| --- | --- | --- |
| 351 | 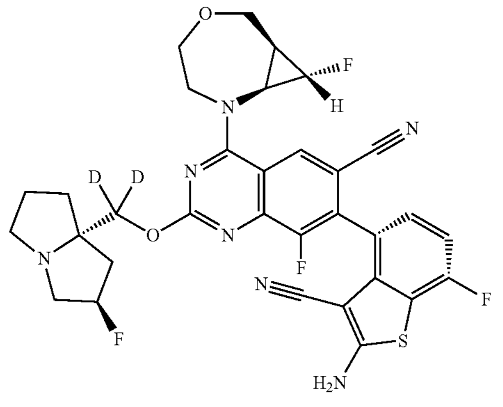 | (R)-7-(2-amino-3-cyano-7-fluorobenzo[b]thiophen-4-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-methoxy-d2)quinazoline-6-carbonitrile |
| 352 | 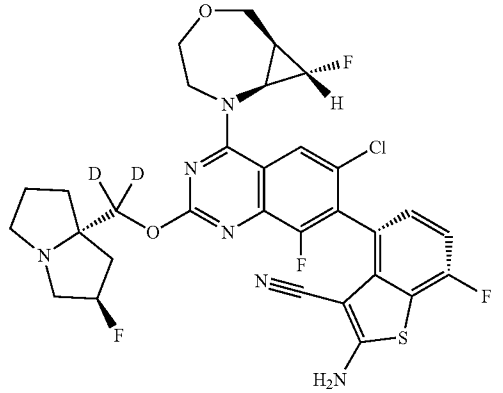 | 2-amino-4-((S)-6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-7-fluorobenzo[b]thiophene-3-carbonitrile |
| 353 | 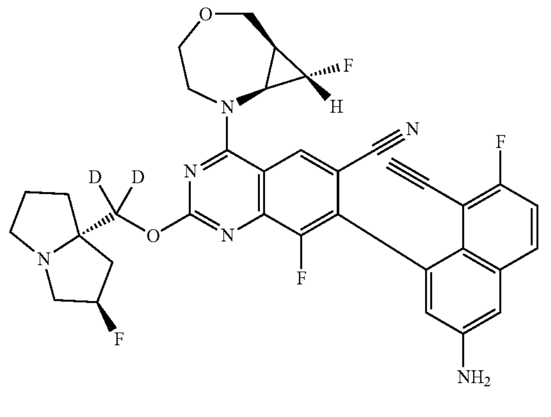 [SMILES: [2H]C([2H])(Oc1nc(N2CCOC[C@H]3[C@H](F)[C@H]32)c2cc(C#N)c(-c3cc(N)cc4ccc(F)c(C#C)c34)c(F)c2n1)[C@@]12CCCN1C[C@H](F)C2] | 7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazoline-6-carbonitrile |
| 354 | 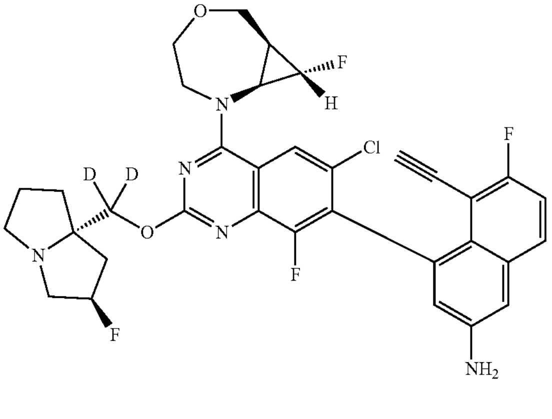 [SMILES: [2H]C([2H])(Oc1nc(N2CCOC[C@H]3[C@H](F)[C@H]32)c2cc(Cl)c(-c3cc(N)cc4ccc(F)c(C#C)c34)c(F)c2n1)[C@@]12CCCN1C[C@H](F)C2] | 4-(6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-amine |

TABLE 1-continued

| Example No. | Structure | Name |
|---|---|---|
| 355 | 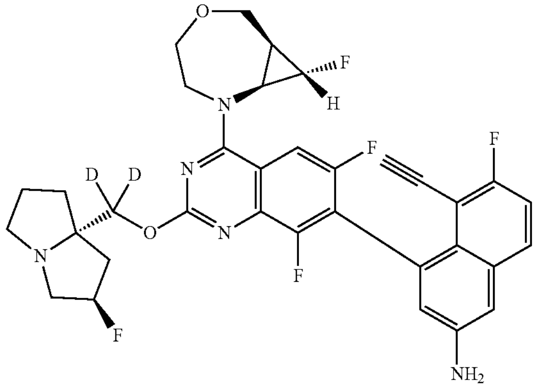 [SMILES: [2H]C([2H])(Oc1nc(N2CCOC[C@H]3[C@H](F)[C@H]32)c2cc(F)c(-c3cc(N)cc4ccc(F)c(C#C)c34)c(F)c2n1)[C@@]12CCCN1C[C@H](F)C2] | 4-(6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-amine |
| 356 | 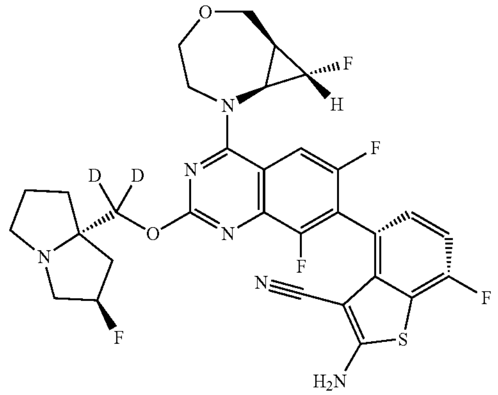 | 2-amino-4-((R)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-7-fluorobenzo[b]thiophene-3-carbonitrile |
| 357 | 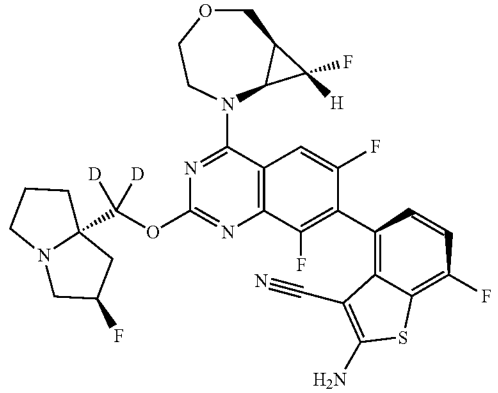 | 2-amino-4-((S)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-7-fluorobenzo[b]thiophene-3-carbonitrile |

TABLE 1-continued

| Example No. | Structure | Name |
|---|---|---|
| 358 | 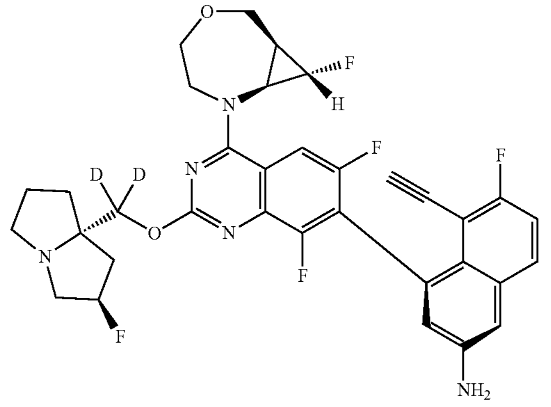 | (S)-7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-methoxy-d2)quinazoline-6-carbonitrile |
| 359 | 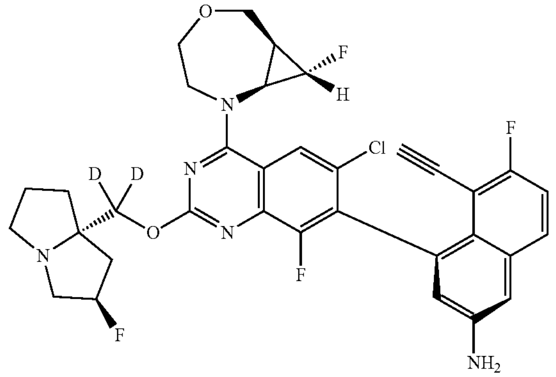 | 4-((R)-6-chloro-8-fluoro-4-((1S,7S,8S)-8-fluoro-5-oxa-2-azabicyclo[5.1.0]octan-2-2-(((2R,7aS)-2-fluorotetrahydro-1H-pyrrolizin-7a(5H)-yl)methoxy-d2)quinazolin-7-yl)-5-ethynyl-6-fluoronaphthalen-2-amine |
| 360 | 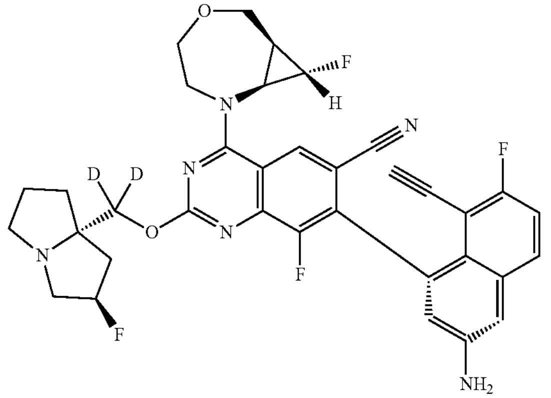 | (R)-7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazoline-6-carbonitrile |
| 361 | 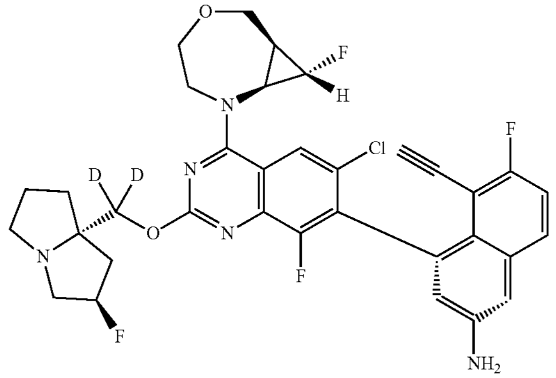 | 4-((S)-6-chloro-8-fluoro-4-((1S,7S,8S)-8-fluoro-5-oxa-2-azabicyclo[5.1.0]octan-2-2-(((2R,7aS)-2-fluorotetrahydro-1H-pyrrolizin-7a(5H)-yl)methoxy-d2)quinazolin-7-yl)-5-ethynyl-6-fluoronaphthalen-2-amine |

TABLE 1-continued

| Example No. | Structure | Name |
|---|---|---|
| 362 | 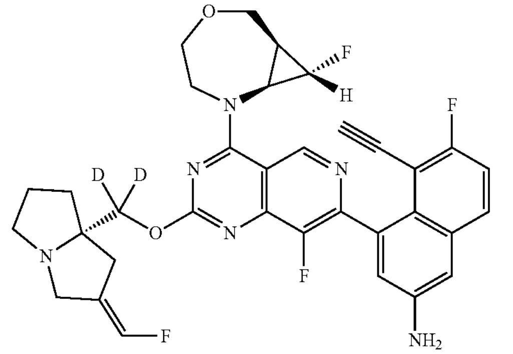 [SMILES: [2H]C([2H])(Oc1nc(N2CCOC[C@H]3[C@H](F)[C@H]32)c2cnc(-c3cc(N)cc4ccc(F)c(C#C)c34)c(F)c2n1)[C@@]12CCCN1C/C(=C/F)C2] | 5-ethynyl-6-fluoro-4-(8-fluoro-4-((1S,7S,8S)-8-fluoro-5-oxa-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-naphthalen-2-amine |
| 363 | 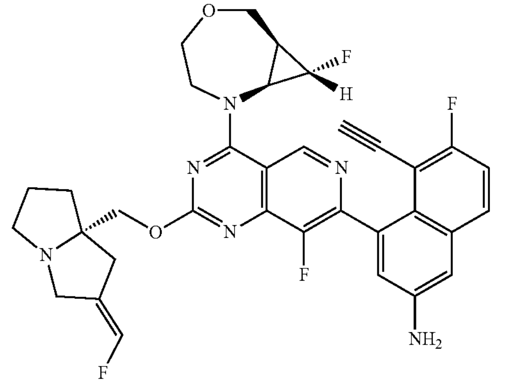 [SMILES: C#Cc1c(F)ccc2cc(N)cc(-c3ncc4c(N5CCOC[C@H]6[C@H](F)[C@H]65)nc(OC[C@@]56CCCN5C/C(=C\F)C6)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-methoxy)pyrido[4,3-d]pyrimidin-7-naphthalen-2-amine |
| 364 | 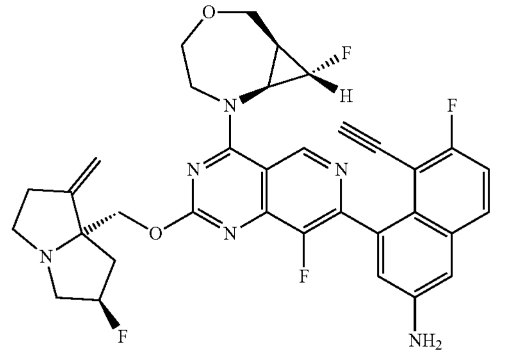 | 5-ethynyl-6-fluoro-4-(8-fluoro-2-(((6R,7a R)-6-fluoro-1-methylenetetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine |
| 365 | 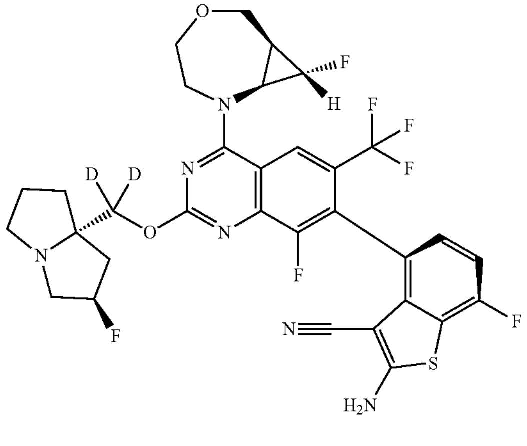 | 2-amino-7-fluoro-4-((S)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-6-(trifluoromethyl)quinazolin-7-benzo[b]thiophene-3-carbonitrile |

TABLE 1-continued

| Example No. | Structure | Name |
|---|---|---|
| 366 | 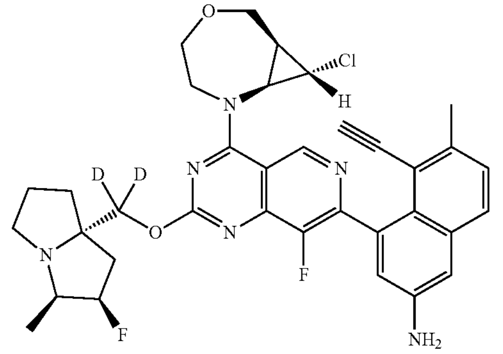 [SMILES: [2H]C([2H])(Oc1nc(N2CCOC[C@H]3[C@H](Cl)[C@H]32)c2cnc(-c3cc(N)cc4ccc(C)c(C#C)c34)c(F)c2n1)[C@@]12CCCN1[C@H](C)[C@H](F)C2] | 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-methyl)naphthalen-2-amine |
| 367 | 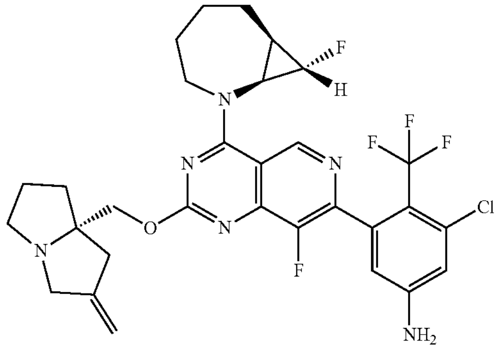 [SMILES: C=C1CN2CCC[C@@]2(COc2nc(N3CCCC[C@H]4[C@H](F)[C@H]43)c3cnc(-c4cc(N)cc(Cl)c4C(F)(F)F)c(F)c3n2)C1] | 3-chloro-5-(8-fluoro-4-((1S,7R,8S)-8-fluoro-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-4-(trifluoromethyl)aniline |
| 368 | 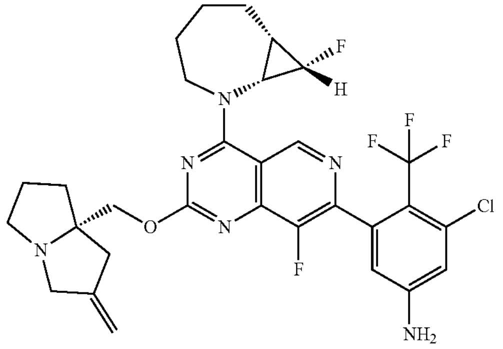 [SMILES: C=C1CN2CCC[C@@]2(COc2nc(N3CCCC[C@@H]4[C@H](F)[C@@H]43)c3cnc(-c4cc(N)cc(Cl)c4C(F)(F)F)c(F)c3n2)C1] | 3-chloro-5-(8-fluoro-4-((1R,7S,8R)-8-fluoro-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-4-(trifluoromethyl)aniline |
| 369 | 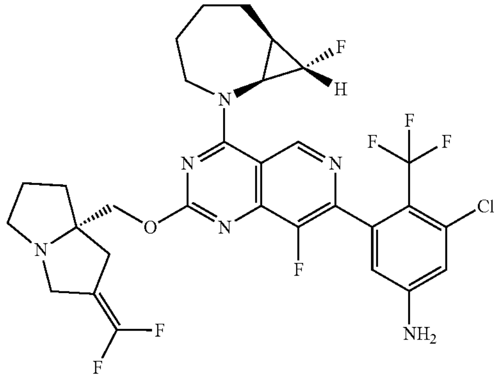 [SMILES: Nc1cc(Cl)c(C(F)(F)F)c(-c2ncc3c(N4CCCC[C@H]5[C@H](F)[C@H]54)nc(OC[C@@]45CCCN4CC(=C(F)F)C5)nc3c2F)c1] | 3-chloro-5-(2-(((S)-2-(difluoromethylene)tetrahydro-1H-pyrrolizin-7a(5H)-yl)methoxy)-8-fluoro-4-((1S,7R,8S)-8-fluoro-2-azabicyclo[5.1.0]octan-2-yl)pyrido[4,3-d]pyrimidin-7-yl)-4-(trifluoromethyl)aniline |

TABLE 1-continued

| Example No. | Structure | Name |
|---|---|---|
| 370 | 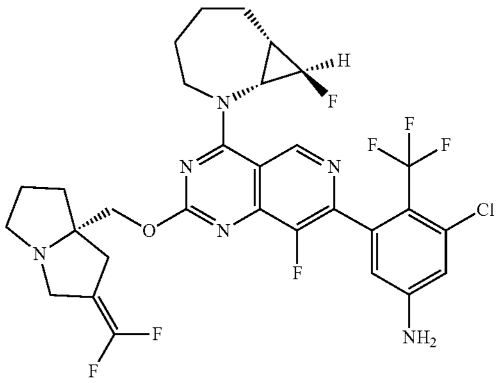 [SMILES: Nc1cc(Cl)c(C(F)(F)F)c(-c2ncc3c(N4CCCC[C@@H]5[C@@H](F)[C@@H]54)nc(OC[C@@]45CCCN4CC(=C(F)F)C5)nc3c2F)c1] | 3-chloro-5-(2-(((S)-2-(difluoromethylene)tetrahydro-1H-pyrrolizin-7a(5H)-yl)methoxy)-8-fluoro-4-((1R,7S,8R)-8-fluoro-2-azabicyclo[5.1.0]octan-2-yl)pyrido[4,3-d]pyrimidin-7-yl)-4-(trifluoromethyl)aniline |
| 371 | 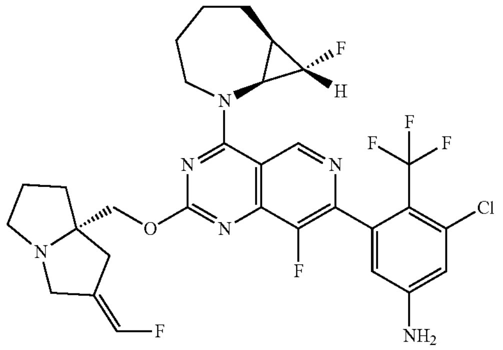 [SMILES: Nc1cc(Cl)c(C(F)(F)F)c(-c2ncc3c(N4CCCC[C@H]5[C@H](F)[C@H]54)nc(OC[C@@]45CCCN4C/C(=C/F)C5)nc3c2F)c1] | 3-chloro-5-(8-fluoro-4-((1S,7R,8S)-8-fluoro-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)-4-(trifluoromethyl)aniline |
| 372 | 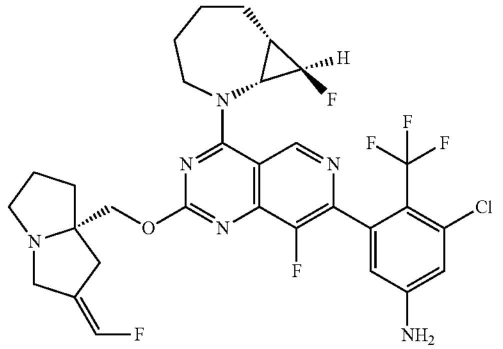 [SMILES: Nc1cc(Cl)c(C(F)(F)F)c(-c2ncc3c(N4CCCC[C@@H]5[C@@H](F)[C@@H]54)nc(OC[C@@]45CCCN4C/C(=C/F)C5)nc3c2F)c1] | 3-chloro-5-(8-fluoro-4-((1R,7S,8R)-8-fluoro-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)-4-(trifluoromethyl)aniline |
| 373 | 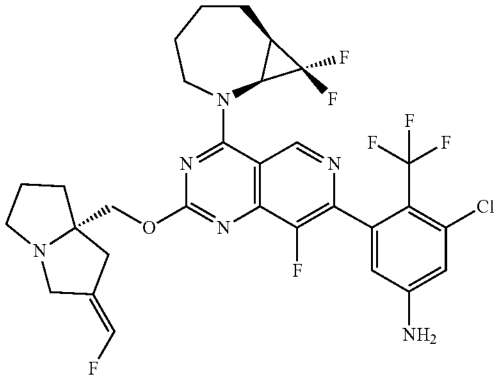 | 3-chloro-5-(8-fluoro-4-((1S,7R,8S)-8-fluoro-2-azabicyclo[5.1.0]octan-2-y])-2-(((S,Z)-2-(fluoromethylene)tetrahydro-1H-pyrrolizin-7a(5H)-yl)methoxy)pyrido[4,3-d]pyrimidin-7-yl)-4-(trifluoromethyl)aniline |

TABLE 1-continued

| Example No. | Structure | Name |
|---|---|---|
| 374 | 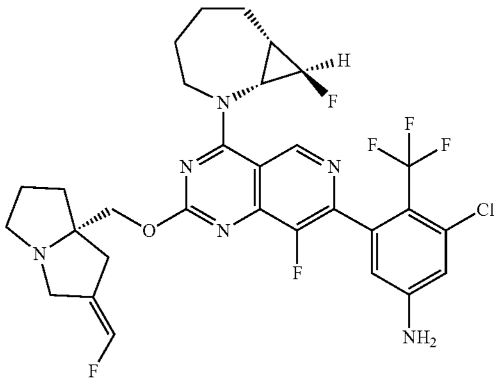 [SMILES: Nc1cc(Cl)c(C(F)(F)F)c(-c2ncc3c(N4CCCC[C@@H]5[C@@H](F)[C@@H]54)nc(OC[C@@]45CCCN4C/C(=C\F)C5)nc3c2F)c1] | 3-chloro-5-(8-fluoro-4-((1R,7S,8R)-8-fluoro-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-4-(trifluoromethyl)aniline |
| 375 | 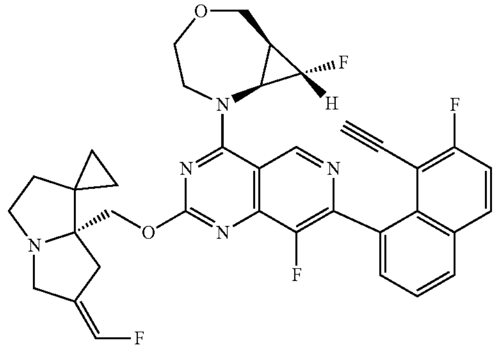 [SMILES: C#Cc1c(F)ccc2cccc(-c3ncc4c(N5CCOC[C@H]6[C@H](F)[C@H]65)nc(OC[C@]56C/C(=C\F)CN5CCC65CC5)nc4c3F)c12] | (1S,7S,8S)-2-(7-(8-ethynyl-7-fluoronaphthalen-1-yl)-8-fluoro-2-(((R,E)-6'-(fluoromethylene)tetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane |
| 376 | 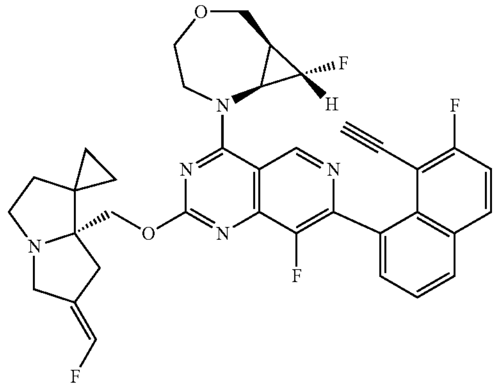 [SMILES: C#Cc1c(F)ccc2cccc(-c3ncc4c(N5CCOC[C@H]6[C@H](F)[C@H]65)nc(OC[C@]56C/C(=C/F)CN5CCC65CC5)nc4c3F)c12] | (1S,7S,8S)-2-(7-(8-ethynyl-7-fluoronaphthalen-1-yl)-8-fluoro-2-(((R,Z)-6'-(fluoromethylene)tetrahydrospiro[cyclopropane-1,1'pyrrolizin]-7a'(5'H)-yl)methoxy)pyrido[4,3-d]pyrimidin-4-yl)-8-fluoro-5-oxa-2-azabicyclo[5.1.0]octane |
| 377 | 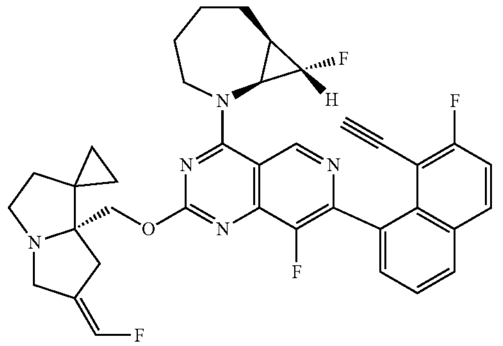 [SMILES: C#Cc1c(F)ccc2cccc(-c3ncc4c(N5CCCC[C@H]6[C@H](F)[C@H]65)nc(OC[C@]56C/C(=C\F)CN5CCC65CC5)nc4c3F)c12] | (R,E)-7a-(((7-(8-ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-oxy)methyl)-6'-(fluoromethylene)hexahydrospiro[cyclopropane-1,1'-pyrrolizine] |

TABLE 1-continued

| Example No. | Structure | Name |
|---|---|---|
| 378 | 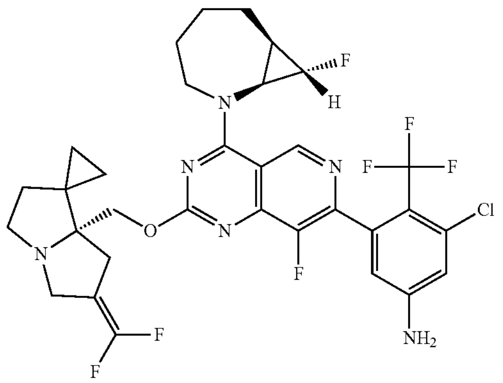 [SMILES: Nc1cc(Cl)c(C(F)(F)F)c(-c2ncc3c(N4CCCC[C@H]5[C@H](F)[C@H]54)nc(OC[C@]45CC(=C(F)F)CN4CCC54CC4)nc3c2F)c1] | 3-chloro-5-(8-fluoro-4-((1S,7R,8S)-8-fluoro-2-azabicyclo[5.1.0]octan-2-yl)-2-(((R,E)-6'-(fluoromethylene)tetrahydrospiro [cyclopropane-1,1'-pyrrolizin]-7a'(5'H)-methoxy)pyrido[4,3-d]pyrimidin-7-yl)-4-(trifluoromethyl)aniline |
| 379 | 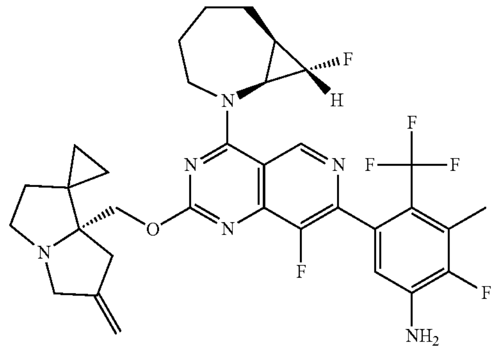 [SMILES: C=C1CN2CCC3(CC3)[C@@]2(COc2nc(N3CCCC[C@H]4[C@H](F)[C@H]43)c3cnc(-c4cc(N)c(F)c(C)c4C(F)(F)F)c(F)c3n2)C1] | 2-fluoro-5-(8-fluoro-4-((1S,7R,8S)-8-fluoro-2-azabicyclo [5.1.0]octan-2-yl)-2-(((R)-6'-methylenetetrahydrospiro[cyclopropane-1,1'-pyrrolizin]-7a'(5'H)-methoxy)pyrido[4,3-d]pyrimidin-7-yl)-3-methyl-4-(trifluoromethyl)aniline |
| 380 | 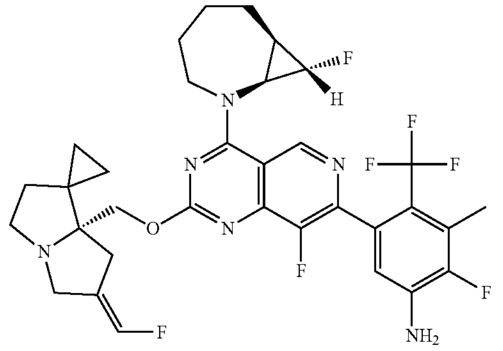 [SMILES: Cc1c(F)c(N)cc(-c2ncc3c(N4CCCC[C@H]5[C@H](F)[C@H]54)nc(OC[C@]45C/C(=C\F)CN4CCC54CC4)nc3c2F)c1C(F)(F)F] | 2-fluoro-5-(8-fluoro-4-((1S,7R,8S)-8-fluoro-2-azabicyclo[5.1.0]octan-2-yl)-2-(((R,E)-6'-(fluoromethylene)tetrahydrospiro [cyclopropane-1,1'-pyrrolizin]-7a'(5'H)-methoxy)pyrido[4,3-d]pyrimidin-7-yl)-3-methyl-4-(trifluoromethyl)aniline |
| 381 | 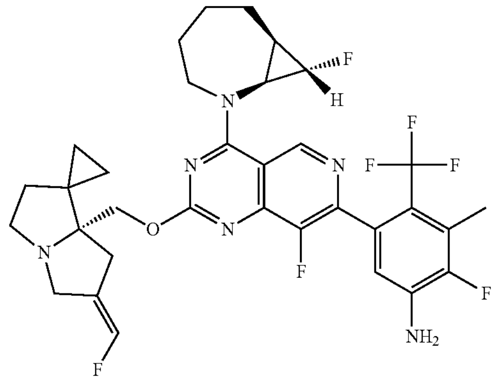 [SMILES: Cc1c(F)c(N)cc(-c2ncc3c(N4CCCC[C@H]5[C@H](F)[C@H]54)nc(OC[C@]45C/C(=C/F)CN4CCC54CC4)nc3c2F)c1C(F)(F)F] | 2-fluoro-5-(8-fluoro-4-((1S,7R,8S)-8-fluoro-2-azabicyclo[5.1.0]octan-2-yl)-2-(((R,Z)-6'-(fluoromethylene)tetrahydrospiro [cyclopropane-1,1'pyrrolizin]-7a'(5'H)-methoxy)pyrido[4,3-d]pyrimidin-7-yl)-3-methyl-4-(trifluoromethyl)aniline |

TABLE 1-continued

| Example No. | Structure | Name |
|---|---|---|
| 382 | 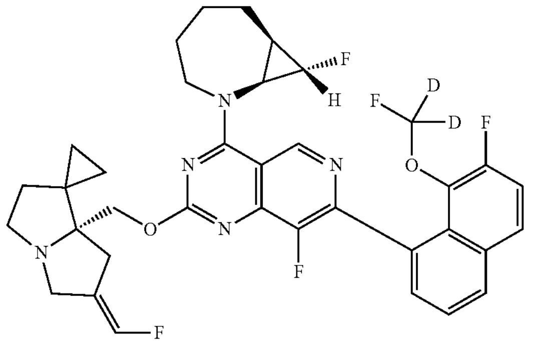 [SMILES: [2H]C([2H])(F)Oc1c(F)ccc2cccc(-c3ncc4c(N5CCCC[C@H]6[C@H](F)[C@H]65)nc(OC[C@]56C/C(=C\F)CN5CCC65CC5)nc4c3F)c12] | (R,E)-7a-(((8-fluoro-7-(7-fluoro-8-(fluoromethoxy-d2)naphthalen-1-yl)-4-((1S,7R,8S)-8-fluoro-2-azabicyclo[5.1.0]octan-2-yl)pyrido[4,3-d]pyrimidin-2-oxy)methyl)-6'-(fluoromethylene)hexahydrospiro [cyclopropane-1,1'-pyrrolizine] |
| 383 | 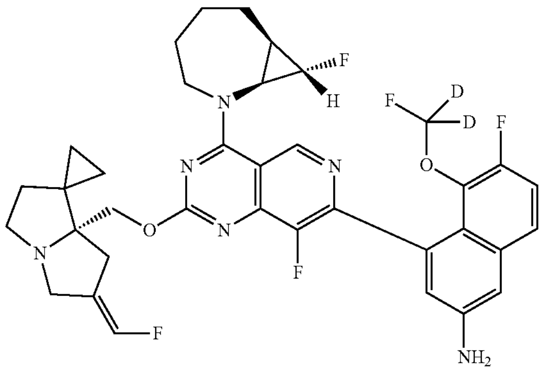 [SMILES: [2H]C([2H])(F)Oc1c(F)ccc2cc(N)cc(-c3ncc4c(N5CCCC[C@H]6[C@H](F)[C@H]65)nc(OC[C@]56C/C(=C\F)CN5CCC65CC5)nc4c3F)c12] | 6-fluoro-4-(8-fluoro-4-((1S,7R,8S)-8-fluoro-2-azabicyclo[5.1.0]octan-2-yl)-2-(((R,E)-6'-(fluoromethylene)tetrahydrospiro [cyclopropane-1,1'-pyrrolizin]-7a'(5'H)-methoxy)pyrido[4,3-d]pyrimidin-7-yl)-5-(fluoromethoxy-d2)naphthalen-2-amine |
| 384 | 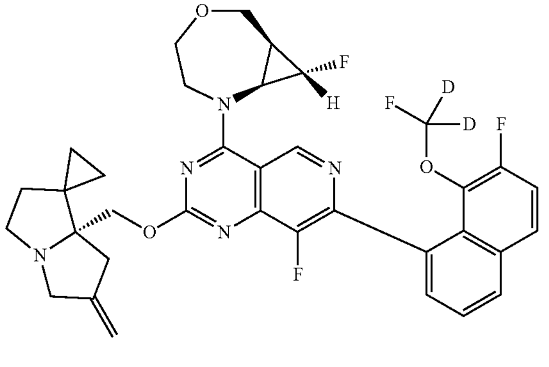 [SMILES: [2H]C([2H])(F)Oc1c(F)ccc2cccc(-c3ncc4c(N5CCOC[C@H]6[C@H](F)[C@H]65)nc(OC[C@]56CC(=C)CN5CCC65CC5)nc4c3F)c12] | (1S,7S,8S)-8-fluoro-2-(8-fluoro-7-(7-fluoro-8-(fluoromethoxy-d2)naphthalen-1-2-(((R)-6'-methylenetetrahydrospiro[cyclopropane-1,1'-pyrrolizin]-7a'(5'H)-yl)methoxy)pyrido[4,3-d]pyrimidin-4-yl)-5-oxa-2-azabicyclo[5.1.0]octane |
| 385 | 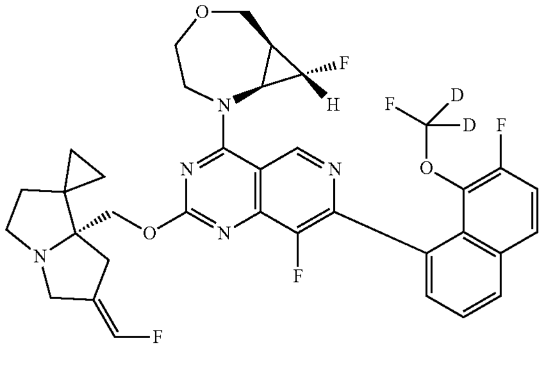 [SMILES: [2H]C([2H])(F)Oc1c(F)ccc2cccc(-c3ncc4c(N5CCOC[C@H]6[C@H](F)[C@H]65)nc(OC[C@]56C/C(=C\F)CN5CCC65CC5)nc4c3F)c12] | (1S,7S,8S)-8-fluoro-2-(8-fluoro-7-(7-fluoro-8-(fluoromethoxy-d2)naphthalen-1-2-(((R,E)-6'-(fluoromethylene)tetrahydrospiro [cyclopropane-1,1'-pyrrolizin]-7a'(5'H)-yl)methoxy)pyrido[4,3-d]pyrimidin-4-yl)-5-oxa-2-azabicyclo[5.1.0]octane |

TABLE 1-continued

| Example No. | Structure | Name |
|---|---|---|
| 386 | 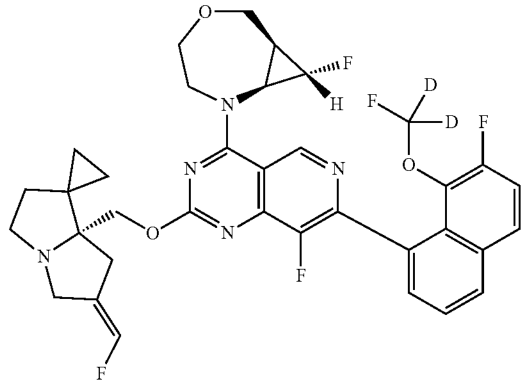 [SMILES: [2H]C([2H])(F)Oc1c(F)ccc2cccc(-c3ncc4c(N5CCOC[C@H]6[C@H](F)[C@H]65)nc(OC[C@]56C/C(=C/F)CN5CCC65CC5)nc4c3F)c12] | (1S,7S,8S)-8-fluoro-2-(8-fluoro-7-(7-fluoro-8-(fluoromethoxy-d2)naphthalen-1-2-(((R,Z)-6'-(fluoromethylene)tetrahydrospiro [cyclopropane-1,1'-pyrrolizin]-7a'(5'H)-yl)methoxy)pyrido[4,3-d]pyrimidin-4-yl)-5-oxa-2-azabicyclo[5.1.0]octane |
| 387 | 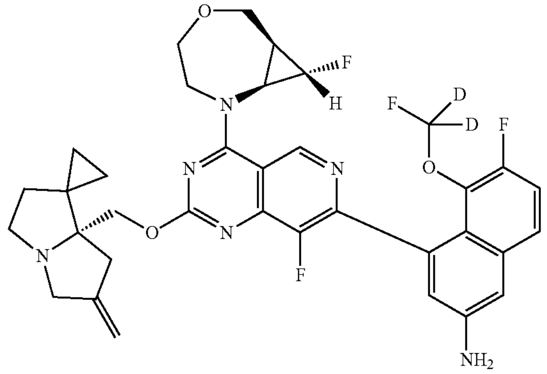 [SMILES: [2H]C([2H])(F)Oc1c(F)ccc2cc(N)cc(-c3ncc4c(N5CCOC[C@H]6[C@H](F)[C@H]65)nc(OC[C@]56CC(=C)CN5CCC65CC5)nc4c3F)c12] | 6-fluoro-4-(8-fluoro-4-((1S,7S,8S)-8-fluoro-5-oxa-2-azabicyclo[5.1.0]octan-2-2-(((R)-6'-methylenetetrahydrospiro[cyclopropane-1,1'pyrrolizin]-7a'(5'H)-yl)methoxy)pyrido[4,3-d]pyrimidin-7-yl)-5-(fluoromethoxy-d2)naphthalen-2-amine |
| 388 | 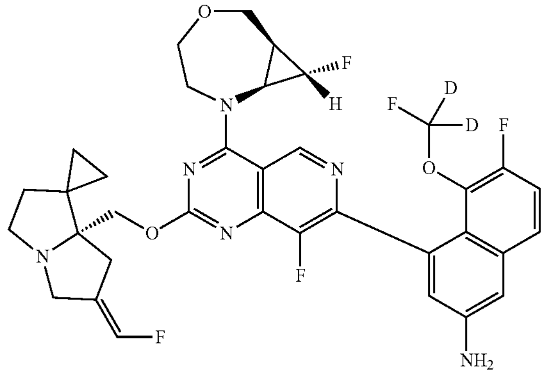 [SMILES: [2H]C([2H])(F)Oc1c(F)ccc2cc(N)cc(-c3ncc4c(N5CCOC[C@H]6[C@H](F)[C@H]65)nc(OC[C@]56C/C(=C\F)CN5CCC65CC5)nc4c3F)c12] | 6-fluoro-4-(8-fluoro-4-((1S,7S,8S)-8-fluoro-5-oxa-2-azabicyclo[5.1.0]octan-2-2-(((R,E)-6'-(fluoromethylene) tetrahydrospiro [cyclopropane-1,1'-pyrrolizin]-7a'(5'H)-yl)methoxy)pyrido[4,3-d]pyrimidin-7-yl)-5-(fluoromethoxy-d2)naphthalen-2-amine |
| 389 | 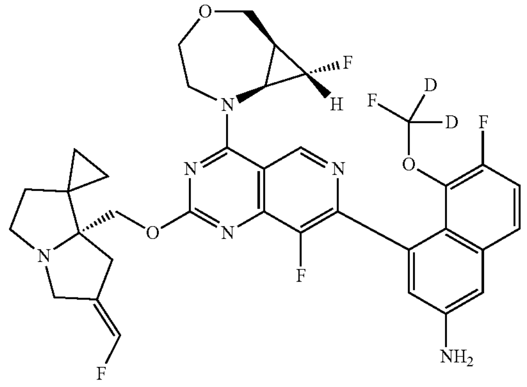 [SMILES: [2H]C([2H])(F)Oc1c(F)ccc2cc(N)cc(-c3ncc4c(N5CCOC[C@H]6[C@H](F)[C@H]65)nc(OC[C@]56C/C(=C/F)CN5CCC65CC5)nc4c3F)c12] | 6-fluoro-4-(8-fluoro-4-((1S,7,8S)-8-fluoro-5-oxa-2-azabicyclo[5.1.0]octan-2-2-(((R,Z)-6'-(fluoromethylene) tetrahydrospiro [cyclopropane-1,1'-pyrrolizin]-7a'(5'H)-yl)methoxy)pyrido[4,3-d]pyrimidin-7-yl)5-(fluoromethoxy-d2)naphthalen-2-amine |

TABLE 1-continued

| Example No. | Structure | Name |
|---|---|---|
| 390 | 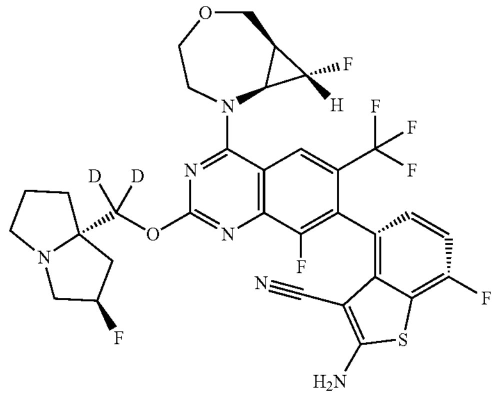 | 2-amino-7-fluoro-4-((R)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-6-(trifluoromethyl)quinazolin-7-yl)benzo[b]thiophene-3-carbonitrile |
| 391 | 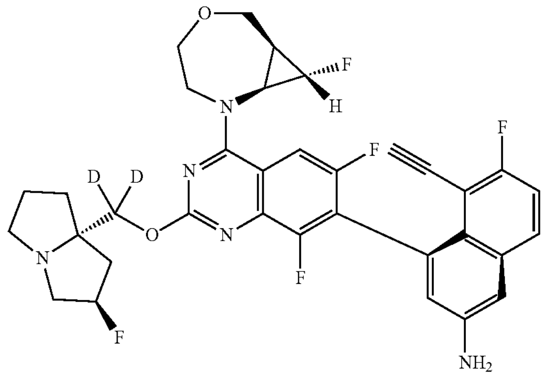 | 4-((R)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-amine |
| 392 | 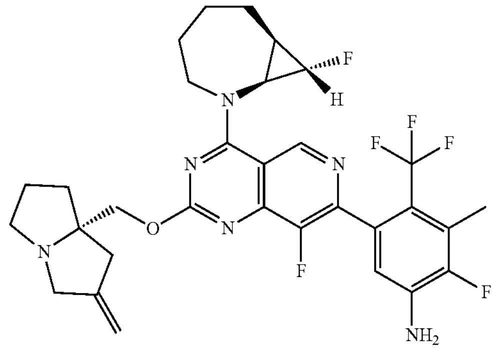 [SMILES: C=C1CN2CCC[C@@]2(COc2nc(N3CCCC[C@H]4[C@H](F)[C@H]43)c3cnc(-c4cc(N)c(F)c(C)c4C(F)(F)F)c(F)c3n2)C1] | 2-fluoro-5-(8-fluoro-4-((1S,7R,8S)-8-fluoro-2-azabicyclo[5.1.0]octan-2-yl)-2-(((S)-2-methylenetetrahydro-1H-pyrrolizin-7a(5H)-methoxy)pyrido[4,3-d]pyrimidin-7-yl)-3-methyl-4-(trifluoromethyl)aniline |
| 393 | 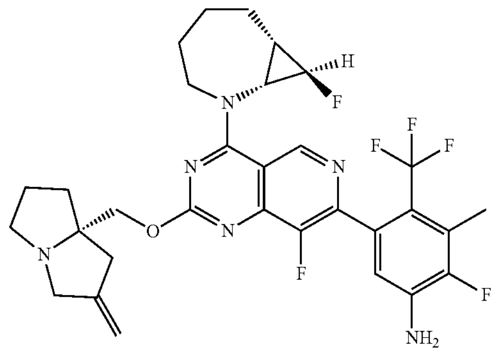 [SMILES: C=C1CN2CCC[C@@]2(COc2nc(N3CCCC[C@@H]4[C@@H](F)[C@@H]43)c3cnc(-c4cc(N)c(F)c(C)c4C(F)(F)F)c(F)c3n2)C1] | 2-fluoro-5-(8-fluoro-4-((1R,7S,8R)-8-fluoro-2-azabicyclo[5.1.0]octan-2-yl)-2-(((S)-2-methylenetetrahydro-1H-pyrrolizin-7a(5H)-methoxy)pyrido[4,3-d]pyrimidin-7-yl)-3-methyl-4-(trifluoromethyl)aniline |

TABLE 1-continued

| Example No. | Structure | Name |
|---|---|---|
| 394 | 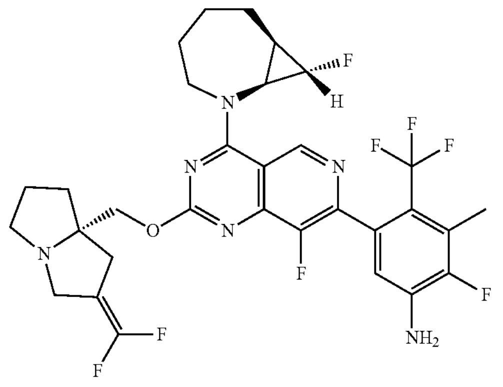 [SMILES: Cc1c(F)c(N)cc(-c2ncc3c(N4CCCC[C@H]5[C@H](F)[C@H]54)nc(OC[C@@]45CCCN4CC(=C(F)F)C5)nc3c2F)c1C(F)(F)F] | 5-(2-(((S)-2-(difluoromethylene)tetrahydro-1H-pyrrolizin-7a(5H)-methoxy)-8-fluoro-4-((1S,7R,8S)-8-fluoro-2-azabicyclo[5.1.0]octan-2-yl)pyrido[4,3-d]pyrimidin-7-yl)-2-fluoro-3-methyl-4-(trifluoromethyl)aniline |
| 395 | 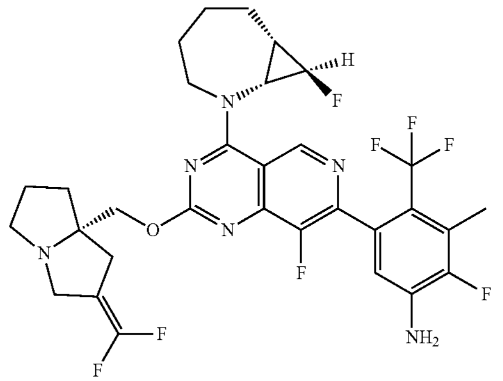 [SMILES: Cc1c(F)c(N)cc(-c2ncc3c(N4CCCC[C@@H]5[C@@H](F)[C@@H]54)nc(OC[C@@]45CCCN4CC(=C(F)F)C5)nc3c2F)c1C(F)(F)F] | 5-(2-(((S)-2-(difluoromethylene)tetrahydro-1H-pyrrolizin-7a(5H)-methoxy)-8-fluoro-4-((1R,7S,8R)-8-fluoro-2-azabicyclo[5.1.0]octan-2-yl)pyrido[4,3-d]pyrimidin-7-yl)-2-fluoro-3-methyl-4-(trifluoromethyl)aniline |
| 396 | 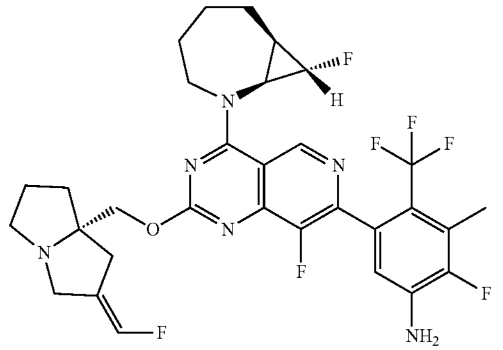 [SMILES: Cc1c(F)c(N)cc(-c2ncc3c(N4CCCC[C@H]5[C@H](F)[C@H]54)nc(OC[C@@]45CCCN4C/C(=C/F)C5)nc3c2F)c1C(F)(F)F] | 2-fluoro-5-(8-fluoro-4-((1S,7R,8S)-8-fluoro-2-azabicyclo[5.1.0]octan-2-yl)-2-(((S,E)-2-(fluoromethylene)tetrahydro-1H-pyrrolizin-7a(5H)-methoxy)pyrido[4,3-d]pyrimidin-7-yl)-3-methyl-4-(trifluoromethyl)aniline |
| 397 | 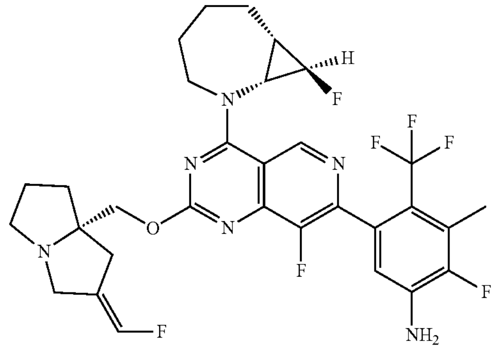 [SMILES: Cc1c(F)c(N)cc(-c2ncc3c(N4CCCC[C@@H]5[C@@H](F)[C@@H]54)nc(OC[C@@]45CCCN4C/C(=C/F)C5)nc3c2F)c1C(F)(F)F] | 2-fluoro-5-(8-fluoro-4-((1R,7S,8R)-8-fluoro-2-azabicyclo[5.1.0]octan-2-yl)-2-(((S,E)-2-(fluoromethylene)tetrahydro-1H-pyrrolizin-7a(5H)-methoxy)pyrido[4,3-d]pyrimidin-7-yl)-3-methyl-4-(trifluoromethyl)aniline |

TABLE 1-continued

| Example No. | Structure | Name |
|---|---|---|
| 398 | 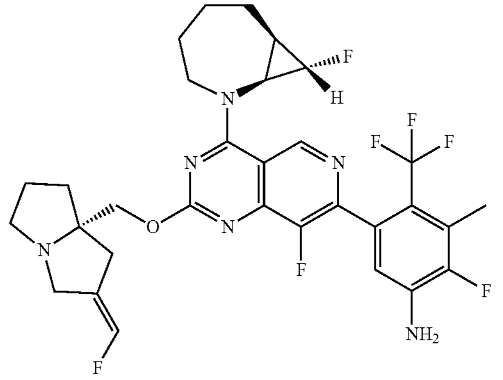 [SMILES: Cc1c(F)c(N)cc(-c2ncc3c(N4CCCC[C@H]5[C@H](F)[C@H]54)nc(OC[C@@]45CCCN4C/C(=C\F)C5)nc3c2F)c1C(F)(F)F] | 2-fluoro-5-(8-fluoro-4-((1S,7R,8S)-8-fluoro-2-azabicyclo[5.1.0]octan-2-yl)-2-(((S,Z)-2-(fluoromethylene)tetrahydro-1H-pyrrolizin-7a(5H)-methoxy)pyrido[4,3-d]pyrimidin-7-yl)-3-methyl-4-(trifluoromethyl)aniline |
| 399 | 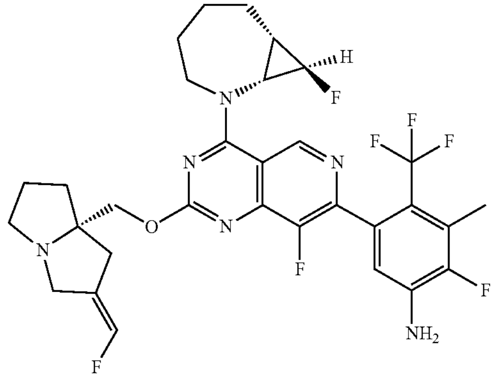 [SMILES: Cc1c(F)c(N)cc(-c2ncc3c(N4CCCC[C@@H]5[C@@H](F)[C@@H]54)nc(OC[C@@]45CCCN4C/C(=C\F)C5)nc3c2F)c1C(F)(F)F] | 2-fluoro-5-(8-fluoro-4-((1R,7S,8R)-8-fluoro-2-azabicyclo[5.1.0]octan-2-yl)-2-(((S,Z)-2-(fluoromethylene)tetrahydro-1H-pyrrolizin-7a(5H)-methoxy)pyrido[4,3-d]pyrimidin-7-yl)-3-methyl-4-(trifluoromethyl)aniline |
| 400 | 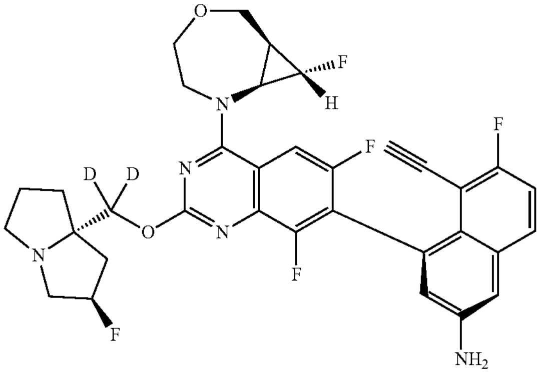 | 4-((S)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-amine |
| 401 | 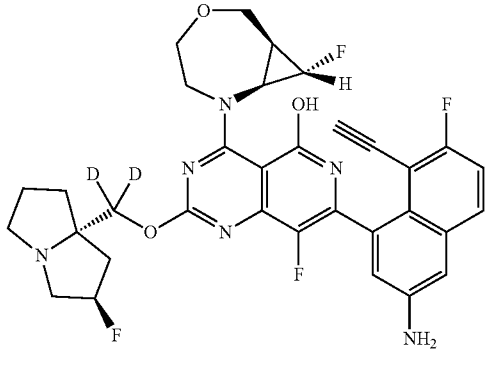 [SMILES: [2H]C([2H])(Oc1nc(N2CCOC[C@H]3[C@H](F)[C@H]32)c2c(O)nc(-c3cc(N)cc4ccc(F)c(C#C)c34)c(F)c2n1)[C@@]12CCCN1C[C@H](F)C2] | 7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-5-ol |

TABLE 1-continued

| Example No. | Structure | Name |
|---|---|---|
| 402 | 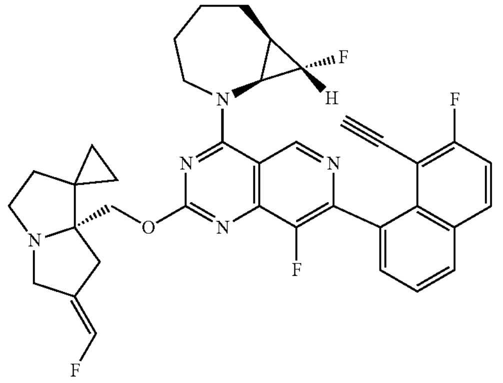 [SMILES: C#Cc1c(F)ccc2cccc(-c3ncc4c(N5CCCC[C@H]6[C@H](F)[C@H]65)nc(OC[C@]56C/C(=C/F)CN5CCC65CC5)nc4c3F)c12] | (R,Z)-7a-(((7-(8-ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yl)oxy)methyl)-6'-(fluoromethylene)hexahydrospiro[cyclopropane-1,1'-pyrrolizine] |
| 403 | 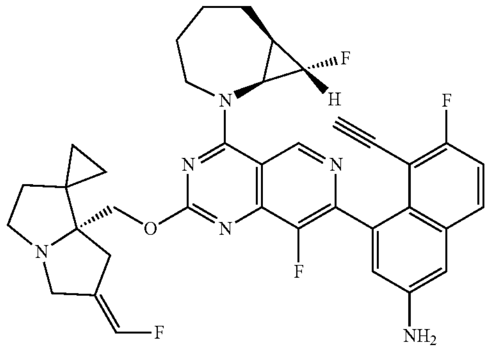 [SMILES: C#Cc1c(F)ccc2cc(N)cc(-c3ncc4c(N5CCCC[C@H]6[C@H](F)[C@H]65)nc(OC[C@]56C/C(=C\F)CN5CCC65CC5)nc4c3F)c12] | 5-ethynyl-6-fluoro-4-(8-fluoro-4-((1S,7R,8S)-8-fluoro-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine |
| 404 | 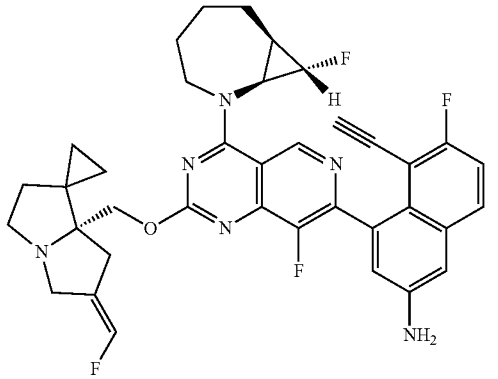 [SMILES: C#Cc1c(F)ccc2cc(N)cc(-c3ncc4c(N5CCCC[C@H]6[C@H](F)[C@H]65)nc(OC[C@]56C/C(=C/F)CN5CCC65CC5)nc4c3F)c12] | 5-ethynyl-6-fluoro-4-(8-fluoro-4-((1S,7R,8S)-8-fluoro-2-azabicyclo[5.1.0]octan-2-yl)-2-(((R,Z)-6'-(fluoromethylene)tetrahydrospiro[cyclopropane-1,1'-pyrrolizin]-7a'(5'H)-methoxy)pyrido[4,3-d]pyrimidin-7-yl)naphthalen-2-amine |
| 405 | 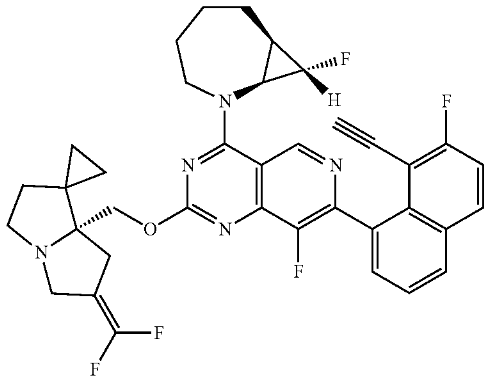 [SMILES: C#Cc1c(F)ccc2cccc(-c3ncc4c(N5CCCC[C@H]6[C@H](F)[C@H]65)nc(OC[C@]56CC(=C(F)F)CN5CCC65CC5)nc4c3F)c12] | (R)-6'-(difluoromethylene)-7a'-(((7-(8-ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yloxy)methhexahydrospiro[cyclopropane-1,1'-pyrrolizine] |

TABLE 1-continued

| Example No. | Structure | Name |
|---|---|---|
| 406 | 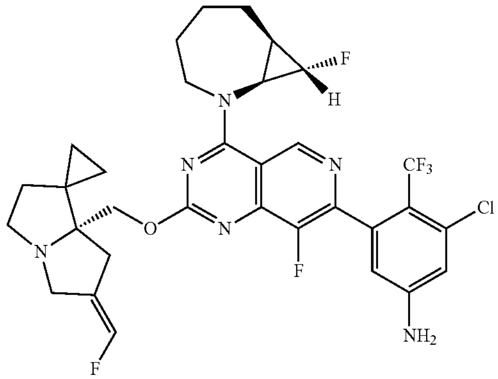 [SMILES: Nc1cc(Cl)c(C(F)(F)F)c(-c2ncc3c(N4CCCC[C@H]5[C@H](F)[C@H]54)nc(OC[C@]45C/C(=C/F)CN4CCC54CC4)nc3c2F)c1] | 3-chloro-5-(8-fluoro-4-((1S,7R,8S)-8-fluoro-2-azabicyclo[5.1.0]octan-2-yl)-2-(((R,Z)-6'-(fluoromethylene)tetrahydrospiro[cyclopropane-1,1'-pyrrolizin]-7a'(5'H)-methoxy)pyrido[4,3-d]pyrimidin-7-yl)-4-(trifluoromethyl)aniline |
| 407 | 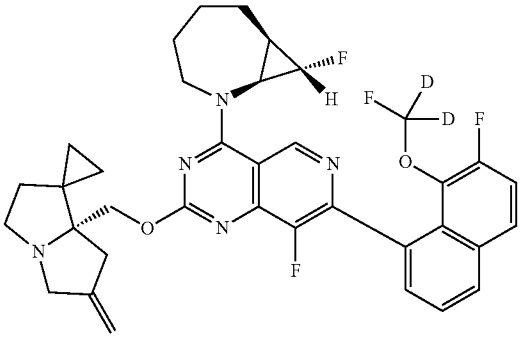 [SMILES: [2H]C([2H])(F)Oc1c(F)ccc2cccc(-c3ncc4c(N5CCCC[C@H]6[C@H](F)[C@H]65)nc(OC[C@]56CC(=C)CN5CCC65CC5)nc4c3F)c12] | (R)-7a'-(((8-fluoro-7-(7-fluoro-8-(fluoromethoxy-d2)naphthalen-1-yl)-4-((1S,7R,8S)-8-fluoro-2-azabicyclo[5.1.0]octan-2-yl)pyrido[4,3-d]pyrimidin-2-oxy)methyl)-6'-methylenehexahydrospiro[cyclopropane-1,1'-pyrrolizine] |
| 408 | 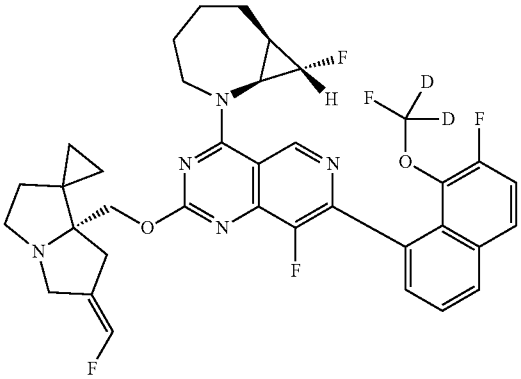 [SMILES: [2H]C([2H])(F)Oc1c(F)ccc2cccc(-c3ncc4c(N5CCCC[C@H]6[C@H](F)[C@H]65)nc(OC[C@]56C/C(=C/F)CN5CCC65CC5)nc4c3F)c12] | (R,Z)-7a'-(((8-fluoro-7-(7-fluoro-8-(fluoromethoxy-d2)naphthalen-1-yl)-4-((1S,7R,8S)-8-fluoro-2-azabicyclo[5.1.0]octan-2-yl)pyrido[4,3-d]pyrimidin-2-yl)oxy)methyl)-6'-(fluoromethylene)hexahydrospiro[cyclopropane-1,1'pyrrolizine] |
| 409 | 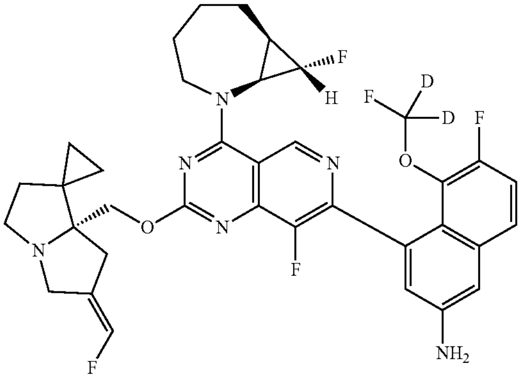 [SMILES: [2H]C([2H])(F)Oc1c(F)ccc2cc(N)cc(-c3ncc4c(N5CCCC[C@H]6[C@H](F)[C@H]65)nc(OC[C@]56C/C(=C/F)CN5CCC65CC5)nc4c3F)c12] | 6-fluoro-4-(8-fluoro-4-((1S,7R,8S)-8-fluoro-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine |

TABLE 1-continued

| Example No. | Structure | Name |
| --- | --- | --- |
| 410 | 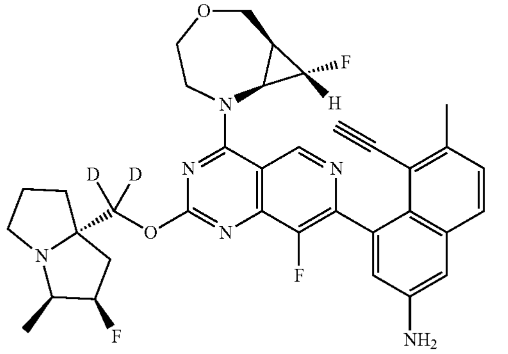 | 5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)-6-methyl)naphthalen-2-amine |
| 411 | 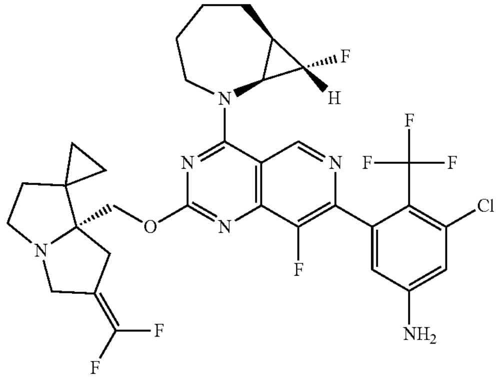 [SMILES: Nc1cc(Cl)c(C(F)(F)F)c(-c2ncc3c(N4CCCC[C@H]5[C@H](F)[C@H]54)nc(OC[C@]45CC(=C(F)F)CN4CCC54CC4)nc3c2F)c1] | 3-chloro-5-(2-(((R)-6'-(difluoromethylene)tetrahydrospiro[cyclopropane-1,1'-pyrrolizin]-7a'(5'H)-yl)methoxy)-8-fluoro-4-((1S,7R,8S)-8-fluoro-2-azabicyclo[5.1.0]octan-2-yl)pyrido[4,3-d]pyrimidin-7-yl)-4-(trifluoromethyl)aniline |
| 412 | 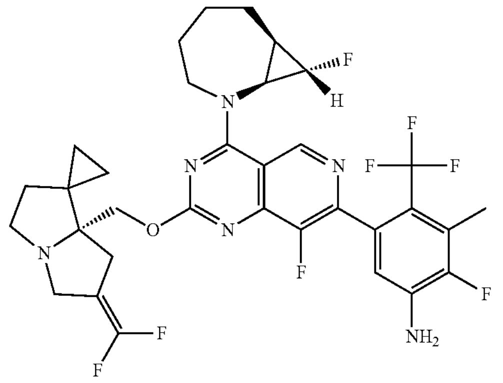 [SMILES: Cc1c(F)c(N)cc(-c2ncc3c(N4CCCC[C@H]5[C@H](F)[C@H]54)nc(OC[C@]45CC(=C(F)F)CN4CCC54CC4)nc3c2F)c1C(F)(F)F] | 5-(2-(((R)-6'-(difluoromethylene)tetrahydrospiro[cyclopropane-1,1'-pyrrolizin]-7a'(5'H)-yl)methoxy)-8-fluoro-4-((1S,7R,8S)-8-fluoro-2-azabicyclo[5.1.0]octan-2-yl)pyrido[4,3-d]pyrimidin-7-yl)-2-fluoro-3-methyl-4-(trifluoromethyl)aniline |
| 413 | 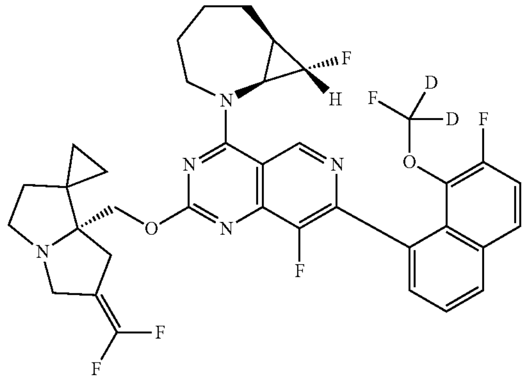 [SMILES: [2H]C([2H])(F)Oc1c(F)ccc2cccc(-c3ncc4c(N5CCCC[C@H]6[C@H](F)[C@H]65)nc(OC[C@]56CC(=C(F)F)CN5CCC65CC5)nc4c3F)c12] | (R)-6'-(difluoromethylene)-7a'-(((8-fluoro-7-(7-fluoro-8-(fluoromethoxy-d2)naphthalen-1-yl)-4-((1S,7R,8S)-8-fluoro-2-azabicyclo[5.1.0]octan-2-yl)pyrido[4,3-d]pyrimidin-2-yl)oxy)methhexahydrospiro[cyclopropane-1,1'-pyrrolizine] |

TABLE 1-continued

| Example No. | Structure | Name |
|---|---|---|
| 414 | 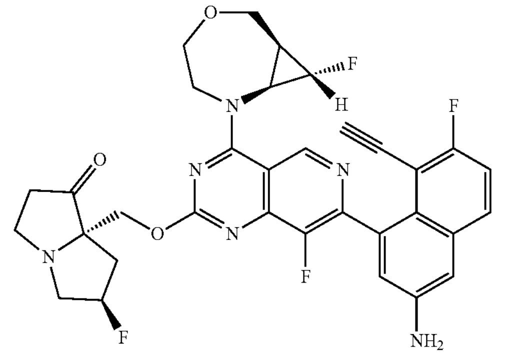 [SMILES: C#Cc1c(F)ccc2cc(N)cc(-c3ncc4c(N5CCOC[C@H]6[C@H](F)[C@H]65)nc(OC[C@]56C[C@@H](F)CN5CCC6=O)nc4c3F)c12] | (6R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-oxy)methyl)-6-fluorohexahydro-1H-pyrrolizin-1-one |
| 415 | 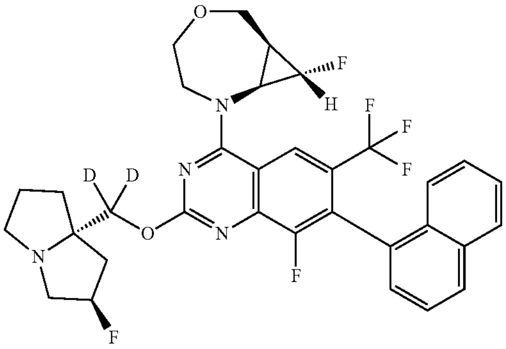 [SMILES: [2H]C([2H])(Oc1nc(N2CCOC[C@H]3[C@H](F)[C@H]32)c2cc(C(F)(F)F)c(-c3cccc4ccccc34)c(F)c2n1)[C@@]12CCCN1C[C@H](F)C2] | (1S,7S,8S)-8-fluoro-2-(8-fluoro-2-(((2R,7aS)-2-fluorotetrahydro-1H-pyrrolizin-7a(5H)-yl)methoxy-d2)-7-(naphthalen-1-yl)-6-(trifluoromethyl)quinazolin-4-yl)-5-oxa-2-azabicyclo[5.1.0]octane |
| 416 | 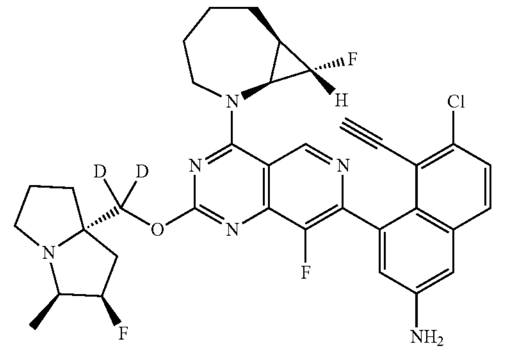 [SMILES: [2H]C([2H])(Oc1nc(N2CCCC[C@H]3[C@H](F)[C@H]32)c2cnc(-c3cc(N)cc4ccc(Cl)c(C#C)c34)c(F)c2n1)[C@@]12CCCN1[C@H](C)[C@H](F)C2] | 6-chloro-5-ethynyl-4-(8-fluoro-2-(((2R,3R,7aS)-2-fluoro-3-methyltetrahydro-1H-pyrrolizin-7a(5H)-yl)methoxy-d2)-4-((1S,7R,8S)-8-fluoro-2-azabicyclo[5.1.0]octan-2-yl)pyrido[4,3-d]pyrimidin-7-yl)naphthalen-2-amine |
| 417 | 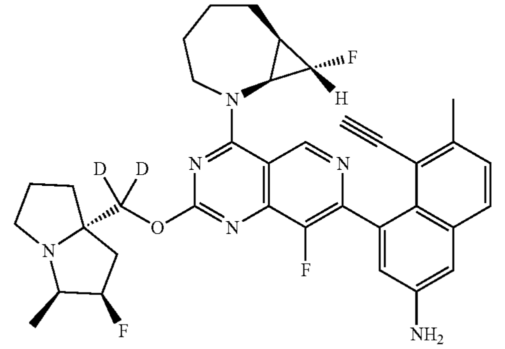 [SMILES: [2H]C([2H])(Oc1nc(N2CCCC[C@H]3[C@H](F)[C@H]32)c2cnc(-c3cc(N)cc4ccc(C)c(C#C)c34)c(F)c2n1)[C@@]12CCCN1[C@H](C)[C@H](F)C2] | 5-ethynyl-4-(8-fluoro-2-(((2R,3R,7aS)-2-fluoro-3-methyltetrahydro-1H-pyrrolizin-7a(5H)-yl)methoxy-d2)-4-((1S,7R,8S)-8-fluoro-2-azabicyclo[5.1.0]octan-2-yl)pyrido[4,3-d]pyrimidin-7-yl)-6-methyl)naphthalen-2-amine |

TABLE 1-continued

| Example No. | Structure | Name |
|---|---|---|
| 418 | 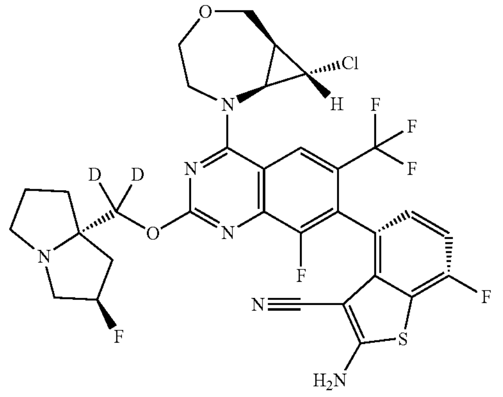 | 2-amino-4-((R)-4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)-6-(trifluoromethyl)quinazolin-7-yl)-7-fluorobenzo[b]thiophene-3-carbonitrile |
| 419 | 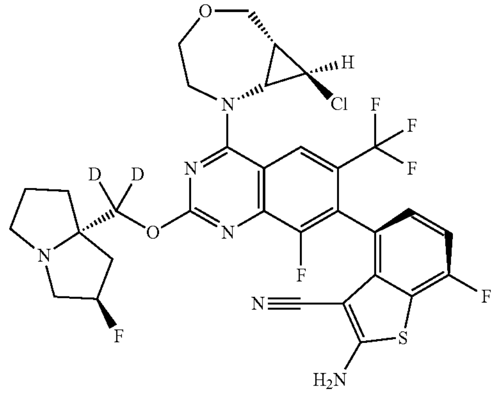 | 2-amino-4-((S)-4-((1R,7R,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)-6-(trifluoromethyl)quinazolin-7-yl)-7-fluorobenzo[b]thiophene-3-carbonitrile |
| 420 | 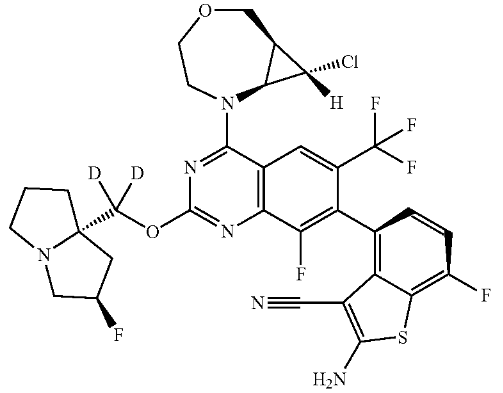 | 2-amino-4-((S)-4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)-6-(trifluoromethyl)quinazolin-7-yl)-7-fluorobenzo[b]thiophene-3-carbonitrile |
| 421 | 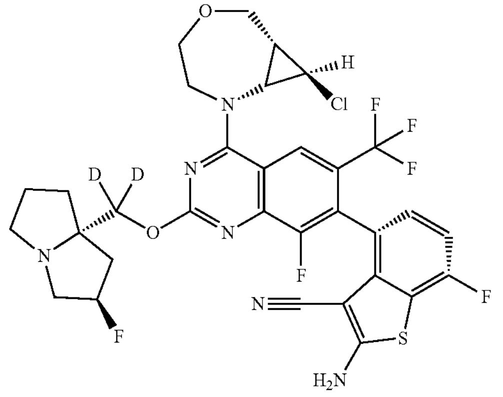 | 2-amino-4-((R)-4-((1R,7R,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)-6-(trifluoromethyl)quinazolin-7-yl)-7-fluorobenzo[b]thiophene-3-carbonitrile |

TABLE 1-continued

| Example No. | Structure | Name |
| --- | --- | --- |
| 422 | 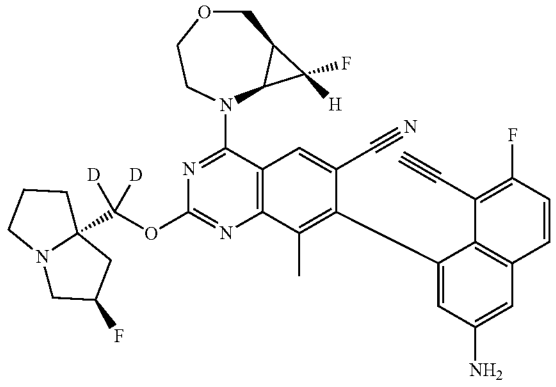 [SMILES: [2H]C([2H])(Oc1nc(N2CCOC[C@H]3[C@H](F)[C@H]32)c2cc(C#N)c(-c3cc(N)cc4ccc(F)c(C#C)c34)c(C)c2n1)[C@@]12CCCN1C[C@H](F)C2] | 7-(3-amino-8-ethynyl-7-fluoronaphthalen-1-yl)-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazoline-6-carbonitrile |
| 423 | 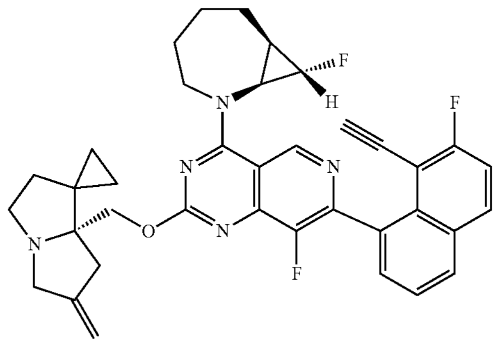 [SMILES: C#Cc1c(F)ccc2cccc(-c3ncc4c(N5CCCC[C@H]6[C@H](F)[C@H]65)nc(OC[C@]56CC(=C)CN5CCC65CC5)nc4c3F)c12] | (R)-7a'-(((7-(8-ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-oxy)methyl)-6'-methylenehexahydrospiro[cyclopropane-1,1'-pyrrolizine] |
| 424 | 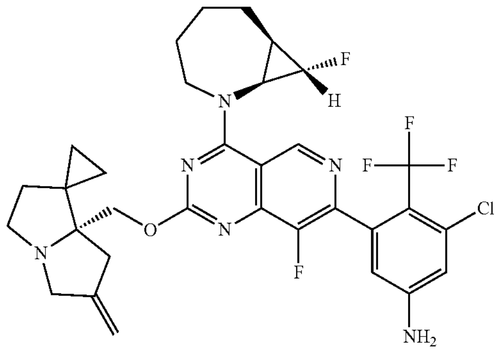 [SMILES: C=C1CN2CCC3(CC3)[C@@]2(COc2nc(N3CCCC[C@H]4[C@H](F)[C@H]43)c3cnc(-c4cc(N)cc(Cl)c4C(F)(F)F)c(F)c3n2)C1] | 3-chloro-5-(8-fluoro-4-((1S,7R,8S)-8-fluoro-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)-4-(trifluoromethyl)aniline |
| 425 | 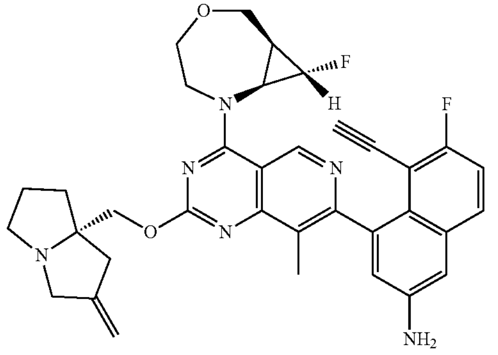 [SMILES: C#Cc1c(F)ccc2cc(N)cc(-c3ncc4c(N5CCOC[C@H]6[C@H](F)[C@H]65)nc(OC[C@@]56CCCN5CC(=C)C6)nc4c3C)c12] | 5-ethynyl-6-fluoro-4-(4-((1S,7S,8S)-8-fluoro-5-oxa-2-azabicyclo[5.1.0]octan-2-yl)-8-methyl-2-(((S)-2-methylenetetrahydro-1H-pyrrolizin-7a(5H)-yl)methoxy)pyrido[4,3-d]pyrimidin-7-yl)naphthalen-2-amine |

TABLE 1-continued

| Example No. | Structure | Name |
| --- | --- | --- |
| 426 | 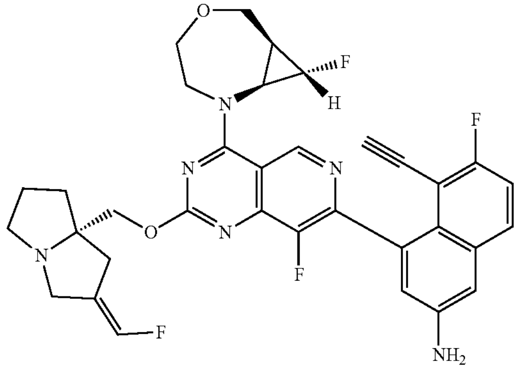 [SMILES: C#Cc1c(F)ccc2cc(N)cc(-c3ncc4c(N5CCOC[C@H]6[C@H](F)[C@H]65)nc(OC[C@@]56CCCN5C/C(=C/F)C6)nc4c3F)c12] | 5-ethynyl-6-fluoro-4-(4-(1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)-8-methylpyrido[4,3-d]pyrimidin-7-yl)naphthalen-2-amine |
| 427 | 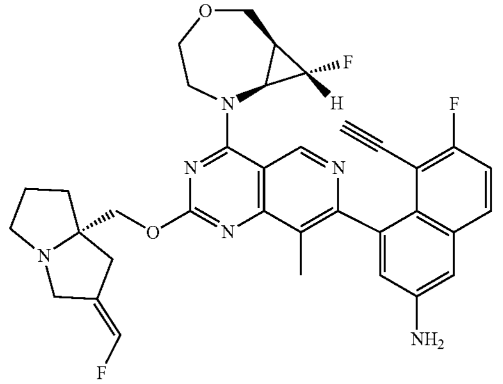 [SMILES: C#Cc1c(F)ccc2cc(N)cc(-c3ncc4c(N5CCOC[C@H]6[C@H](F)[C@H]65)nc(OC[C@@]56CCCN5C/C(=C\F)C6)nc4c3C)c12] | 5-ethynyl-6-fluoro-4-(4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)-8-methylpyrido[4,3-d]pyrimidin-7-yl)naphthalen-2-amine |
| 428 | 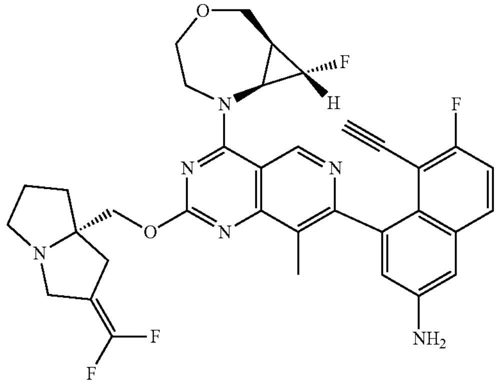 [SMILES: C#Cc1c(F)ccc2cc(N)cc(-c3ncc4c(N5CCOC[C@H]6[C@H](F)[C@H]65)nc(OC[C@@]56CCCN5CC(=C(F)F)C6)nc4c3C)c12] | 4-(2-(((S)-2-(difluoromethylene)tetrahydro-1H-pyrrolizin-7a(5H)-methoxy)-4-((1S,7S,8S)-8-fluoro-5-oxa-2-azabicyclo[5.1.0]octan-2-yl)-8-methylpyrido[4,3-d]pyrimidin-7-yl)-5-ethynyl-6-fluoronaphthalen-2-amine |
| 429 | 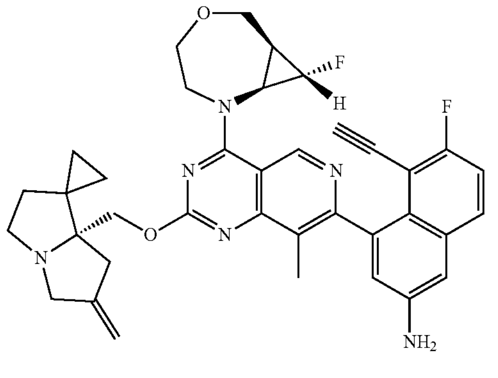 | 5-ethynyl-6-fluoro-4-(4-((1S,7S,8S)-8-fluoro-5-oxa-2-azabicyclo[5.1.0]octan-2-8-methyl-2-(((R)-6'-methylenetetrahydrospiro[cyclopropane-1,1'-pyrrolizin]-7a'(5'H)-yl)methoxy)pyrido[4,3-d]pyrimidin-7-yl)naphthalen-2-amine |

TABLE 1-continued

| Example No. | Structure | Name |
|---|---|---|
| 430 | 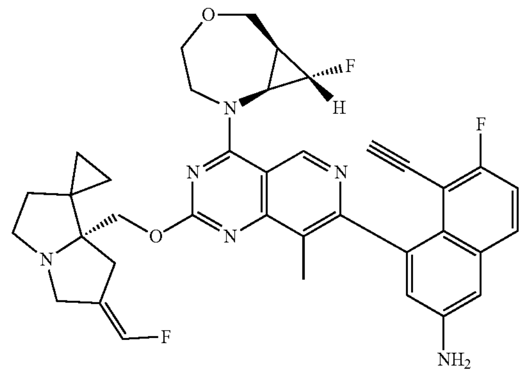 [SMILES: C#Cc1c(F)ccc2cc(N)cc(-c3ncc4c(N5CCOC[C@H]6[C@H](F)[C@H]65)nc(OC[C@]56C/C(=C\F)CN5CCC65CC5)nc4c3C)c12] | 5-ethynyl-6-fluoro-4-(4-((1S,7S,8S)-8-fluoro-5-oxa-2-azabicyclo[5.1.0]octan-2-2-(((R,E)-6'-(fluoromethylene)tetrahydrospiro [cyclopropane-1,1'-pyrrolizin]-7a'(5'H)-yl)methoxy)-8-methylpyrido[4,3-d]pyrimidin-7-yl)naphthalen-2-amine |
| 431 | 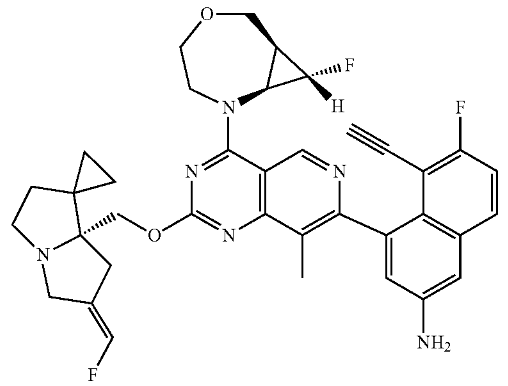 [SMILES: C#Cc1c(F)ccc2cc(N)cc(-c3ncc4c(N5CCOC[C@H]6[C@H](F)[C@H]65)nc(OC[C@]56C/C(=C/F)CN5CCC65CC5)nc4c3C)c12] | 5-ethynyl-6-fluoro-4-(4-((1S,7S,8S)-8-fluoro-5-oxa-2-azabicyclo[5.1.0]octan-2-2-(((R,Z)-6'-(fluoromethylene)tetrahydrospiro [cyclopropane-1,1'-pyrrolizin]-7a'(5'H)-methoxy)-8-methylpyrido[4,3-d]pyrimidin-7-naphthalen-2-amine |
| 432 | 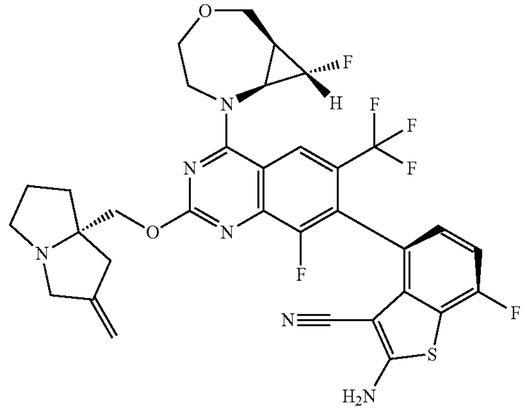 | 2-amino-7-fluoro-4-((S)-8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)-6-(trifluoromethyl)quinazolin-7-benzo[b]thiophene-3-carbonitrile |

TABLE 1-continued

| Example No. | Structure | Name |
|---|---|---|
| 433 | 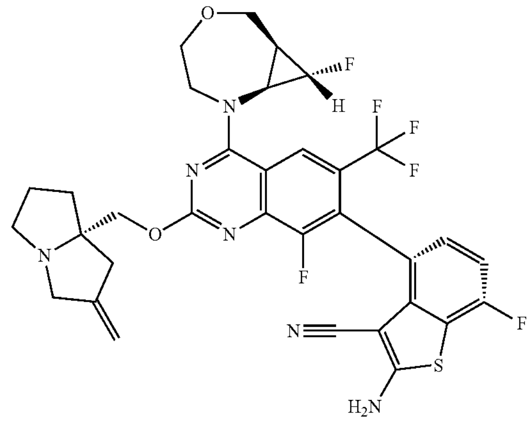 | 2-amino-7-fluoro-4-((R)-8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)-6-(trifluoromethyl)quinazolin-7-benzo[b]thiophene-3-carbonitrile |
| 434 | 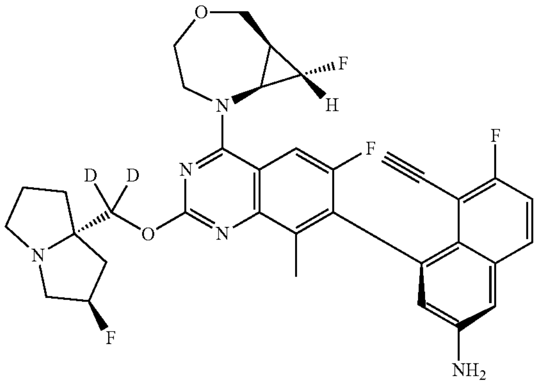 | 5-ethynyl-6-fluoro-4-((R)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)naphthalen-2-amine |
| 435 | 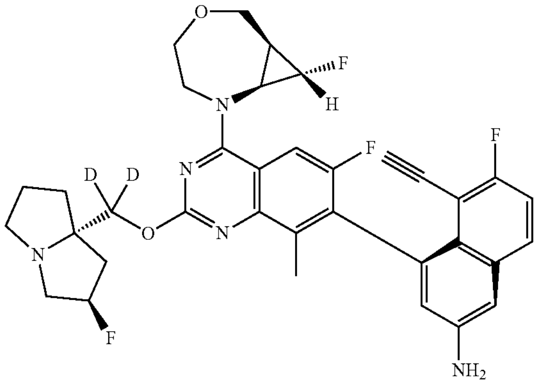 | 5-ethynyl-6-fluoro-4-((S)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)naphthalen-2-amine |
| 436 | 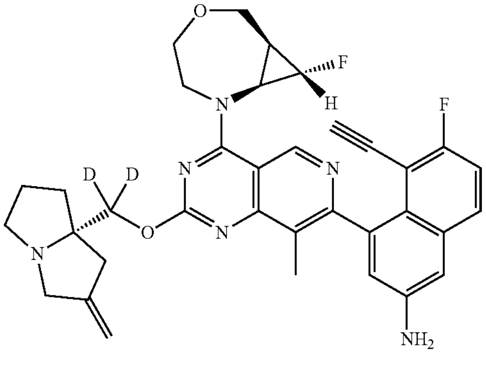 [SMILES: [2H]C([2H])(Oc1nc(N2CCOC[C@H]3[C@H](F)[C@H]32)c2cnc(-c3cc(N)cc4ccc(F)c(C#C)c34)c(C)c2n1)[C@@]12CCCN1CC(=C)C2] | 5-ethynyl-6-fluoro-4-(4-((1S,7S,8S)-8-fluoro-5-oxa-2-azabicyclo[5.1.0]octan-2-yl)-8-methyl-2-(((S)-2-methylenetetrahydro-1H-pyrrolizin-7a(5H)-yl)methoxy-d2)pyrido[4,3-d]pyrimidin-7-yl)naphthalen-2-amine |

TABLE 1-continued

| Example No. | Structure | Name |
|---|---|---|
| 437 | 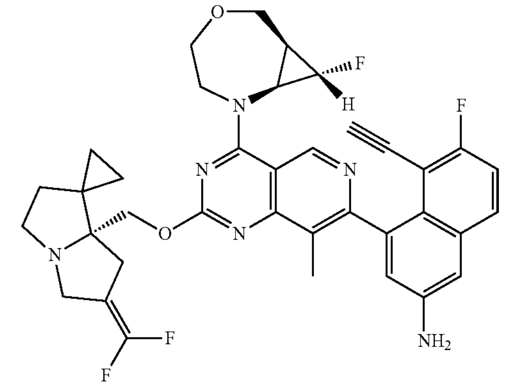 [SMILES: C#Cc1c(F)ccc2cc(N)cc(-c3ncc4c(N5CCOC[C@H]6[C@H](F)[C@H]65)nc(OC[C@]56CC(=C(F)F)CN5CCC65CC5)nc4c3C)c12] | 4-(2-(((R)-6'-(difluoromethylene)tetrahydrospiro[cyclopropane-1,1'-pyrrolizin]-7a'(5'H)-yl)methoxy)-4-((1S,7S,8S)-8-fluoro-5-oxa-2-azabicyclo[5.1.0]octan-2-yl)-8-methylpyrido[4,3-d]pyrimidin-7-yl)-5-ethynyl-6-fluoronaphthalen-2-amine |
| 438 | 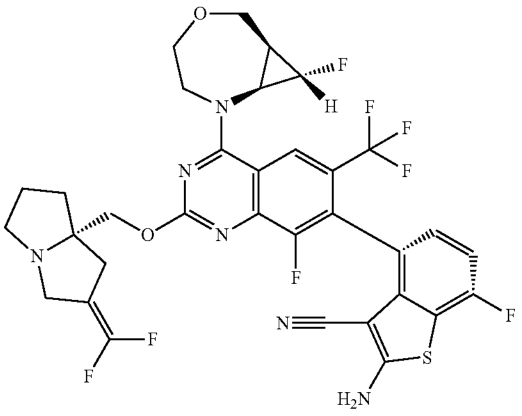 | 2-amino-4-((R)-2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)-6-(trifluoromethyl)quinazolin-7-yl)-7-fluorobenzo[b]thiophene-3-carbonitrile |
| 439 | 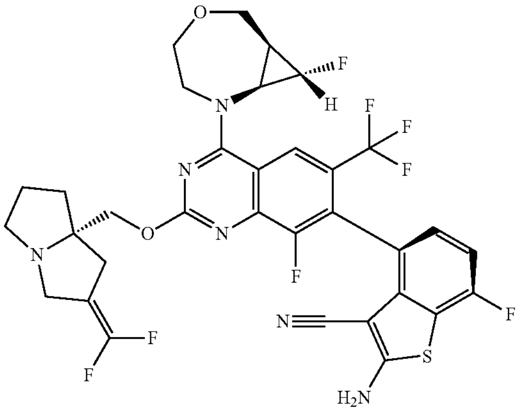 | 2-amino-4-((S)-2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)-6-(trifluoromethyl)quinazolin-7-yl)-7-fluorobenzo[b]thiophene-3-carbonitrile |

TABLE 1-continued

| Example No. | Structure | Name |
| --- | --- | --- |
| 440 | 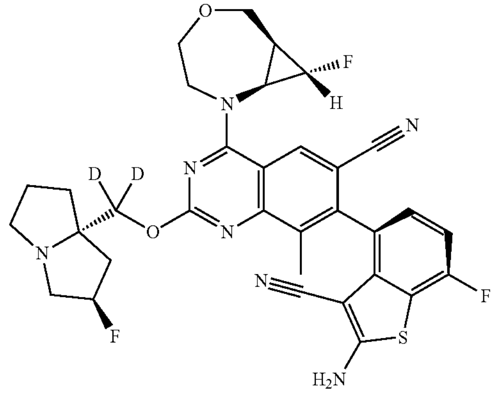 | (R)-7-(2-amino-3-cyano-7-fluorobenzo[b]thiophen-4-yl)-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazoline-6-carbonitrile |
| 441 | 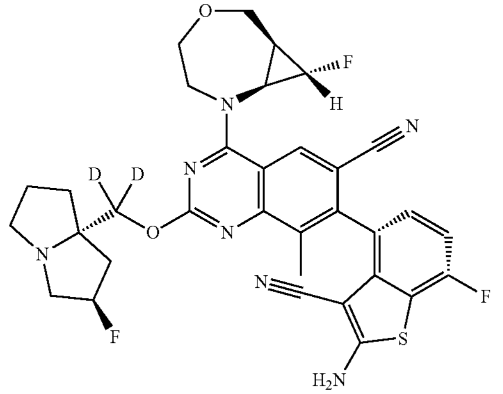 | (S)-7-(2-amino-3-cyano-7-fluorobenzo[b]thiophen-4-yl)-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazoline-6-carbonitrile |
| 442 | 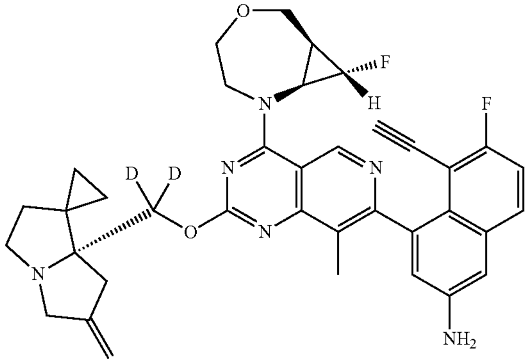 [SMILES: [2H]C([2H])(Oc1nc(N2CCOC[C@H]3[C@H](F)[C@H]32)c2cnc(-c3cc(N)cc4ccc(F)c(C#C)c34)c(C)c2n1)[C@]12CC(=C)CN1CCC21CC1] | 5-ethynyl-6-fluoro-4-(4-((1S,7S,8S)-8-fluoro-5-oxa-2-azabicyclo[5.1.0]octan-2-yl)-8-methyl-2-(((R)-6'methylenetetrahydrospiro[cyclopropane-1,1'pyrrolizin]-7a'(5'H)-yl)methoxy-d2)pyrido[4,3-d]pyrimidin-7-yl)naphthalen-2-amine |
| 443 | 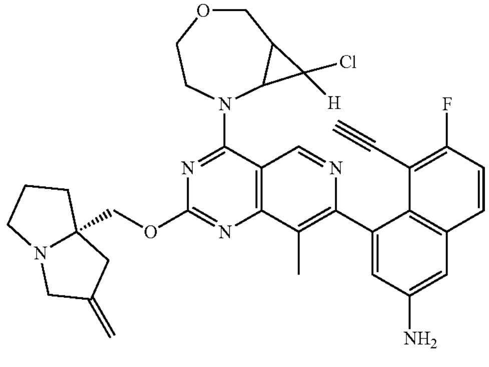 [SMILES: C#Cc1c(F)ccc2cc(N)cc(-c3ncc4c(N5CCOCC6C(Cl)C65)nc(OC[C@@]56CCCN5CC(=C)C6)nc4c3C)c12] | 4-(4-(8-chloro-5-oxa-2-azabicyclo[5.1.0]octan-2-yl)-8-methyl-2-(((S)-2-methylenetetrahydro-1H-pyrrolizin-7a(5H)-yl)methoxy)pyrido[4,3-d]pyrimidin-7-yl)-5-ethynyl-6-fluoronaphthalen-2-amine |

TABLE 1-continued

| Example No. | Structure | Name |
|---|---|---|
| 444 | 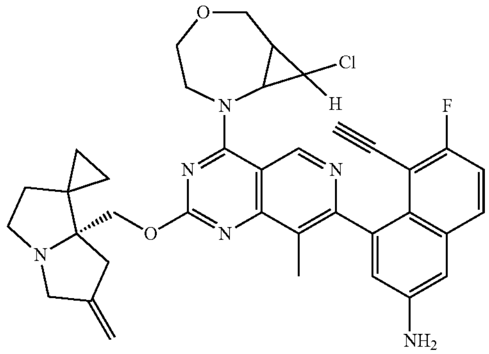 [SMILES: C#Cc1c(F)ccc2cc(N)cc(-c3ncc4c(N5CCOCC6C(Cl)C65)nc(OC[C@]56CC(=C)CN5CCC65CC5)nc4c3C)c12] | 4-(4-(8-chloro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy)pyrido[4,3-d]pyrimidin-7-yl)-5-ethynyl-6-fluoronaphthalen-2-amine |
| 445 | 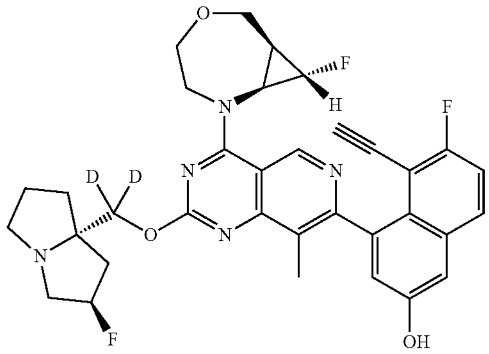 [SMILES: [2H]C([2H])(Oc1nc(N2CCOC[C@H]3[C@H](F)[C@H]32)c2cnc(-c3cc(O)cc4ccc(F)c(C#C)c34)c(C)c2n1)[C@@]12CCCN1C[C@H](F)C2] | 5-ethynyl-6-fluoro-4-(4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-naphthalen-2-ol |
| 446 | 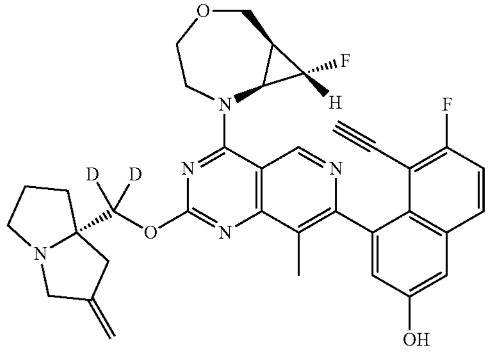 [SMILES: [2H]C([2H])(Oc1nc(N2CCOC[C@H]3[C@H](F)[C@H]32)c2cnc(-c3cc(O)cc4ccc(F)c(C#C)c34)c(C)c2n1)[C@@]12CCCN1CC(=C)C2] | 5-ethynyl-6-fluoro-4-(4-((1S,7,8S)-8-fluoro-5-oxa-2-azabicyclo[5.1.0]octan-2-yl)-8-methyl-2-(((S)-2-methylenetetrahydro-1H-pyrrolizin-7a(5H)-yl)methoxy-d2)pyrido[4,3-d]pyrimidin-7-yl)naphthalen-2-ol |
| 447 | 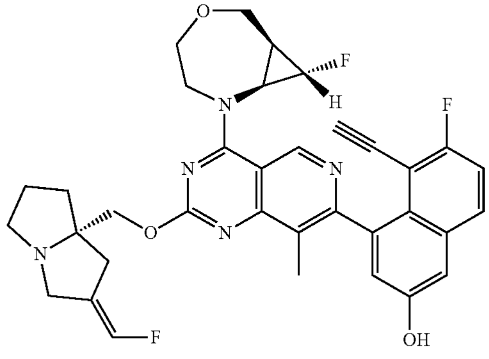 [SMILES: C#Cc1c(F)ccc2cc(O)cc(-c3ncc4c(N5CCOC[C@H]6[C@H](F)[C@H]65)nc(OC[C@@]56CCCN5C/C(=C/F)C6)nc4c3C)c12] | 5-ethynyl-6-fluoro-4-(4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)-8-methylpyrido[4,3-d]pyrimidin-7-yl)naphthalen-2-ol |

TABLE 1-continued

| Example No. | Structure | Name |
|---|---|---|
| 448 | 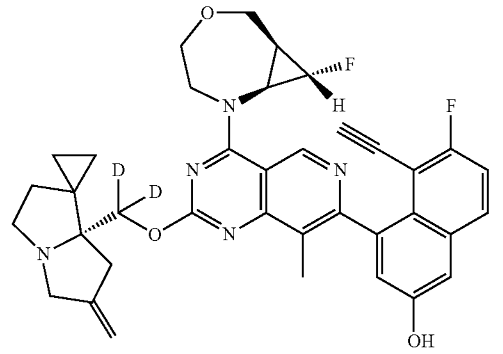 [SMILES: [2H]C([2H])(Oc1nc(N2CCOC[C@H]3[C@H](F)[C@H]32)c2cnc(-c3cc(O)cc4ccc(F)c(C#C)c34)c(C)c2n1)[C@]12CC(=C)CN1CCC21CC1] | 5-ethynyl-6-fluoro-4-(4-((1S,7S,8S)-8-fluoro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy-d2)pyrido[4,3-d]pyrimidin-7-yl)naphthalen-2-ol |
| 449 | 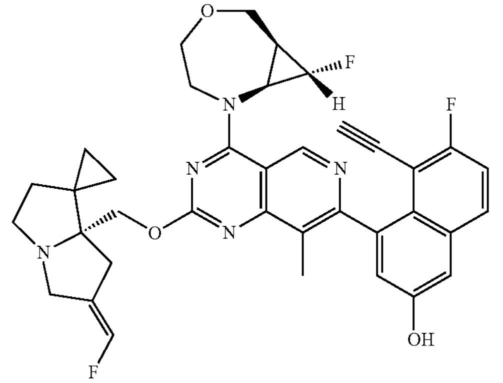 [SMILES: C#Cc1c(F)ccc2cc(O)cc(-c3ncc4c(N5CCOC[C@H]6[C@H](F)[C@H]65)nc(OC[C@]56C/C(=C/F)CN5CCC65CC5)nc4c3C)c12] | 5-ethynyl-6-fluoro-4-(4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)-8-methylpyrido[4,3-d]pyrimidin-7-yl)naphthalen-2-ol |
| 450 | 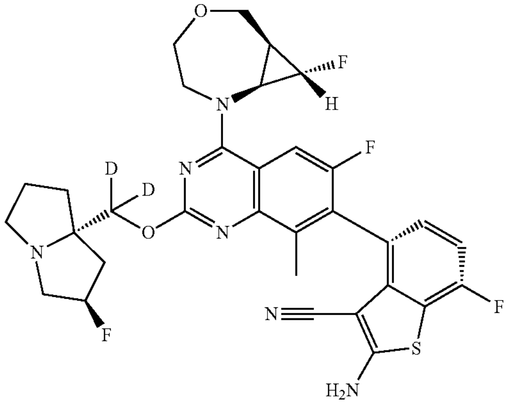 | 2-amino-7-fluoro-4-((S)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-benzo[b]thiophene-3-carbonitrile |
| 451 | 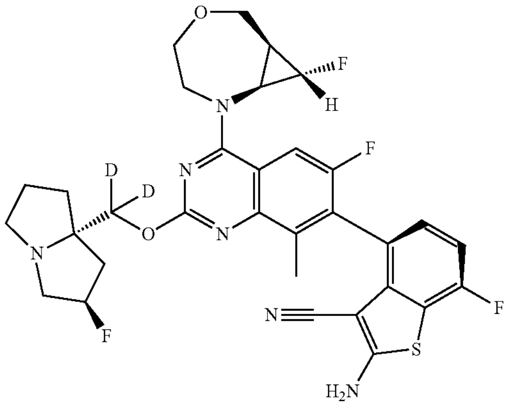 | 2-amino-7-fluoro-4-((R)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)benzo[b]thiophene-3-carbonitrile |

TABLE 1-continued

| Example No. | Structure | Name |
|---|---|---|
| 452 | 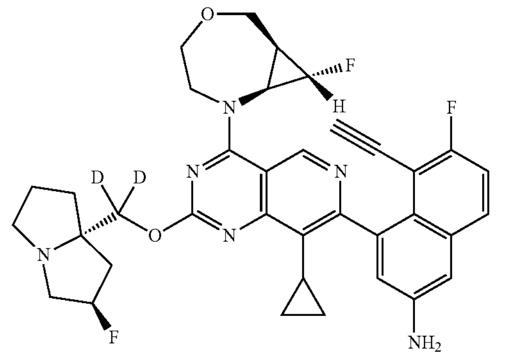 [SMILES: [2H]C([2H])(Oc1nc(N2CCOC[C@H]3[C@H](F)[C@H]32)c2cnc(-c3cc(N)cc4ccc(F)c(C#C)c34)c(C3CC3)c2n1)[C@@]12CCCN1C[C@H](F)C2] | 4-(8-cyclopropyl-4-((1S,7S,8S)-8-fluoro-5-oxa-2-azabicyclo[5.1.0]octan~2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 453 | 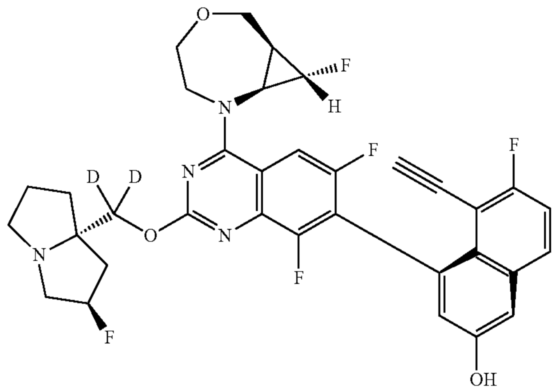 | 4-((R)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-ol |
| 454 | 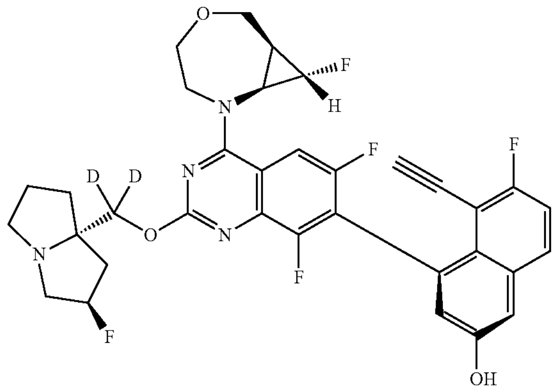 | 4-((S)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-ol |
| 455 | 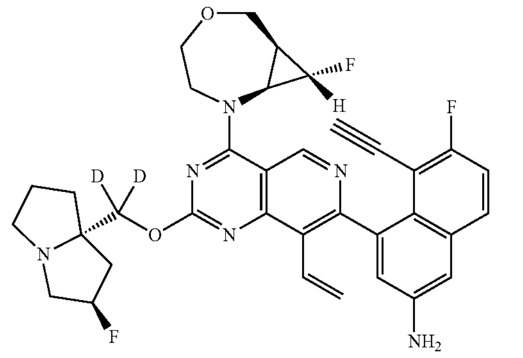 [SMILES: [2H]C([2H])(Oc1nc(N2CCOC[C@H]3[C@H](F)[C@H]32)c2cnc(-c3cc(N)cc4ccc(F)c(C#C)c34)c(C=C)c2n1)[C@@]12CCCN1C[C@H](F)C2] | 5-ethynyl-6-fluoro-4-(4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-vinylpyrido[4,3-d]pyrimidin-7-yl)naphthalen-2-amine |

TABLE 1-continued

| Example No. | Structure | Name |
|---|---|---|
| 456 | 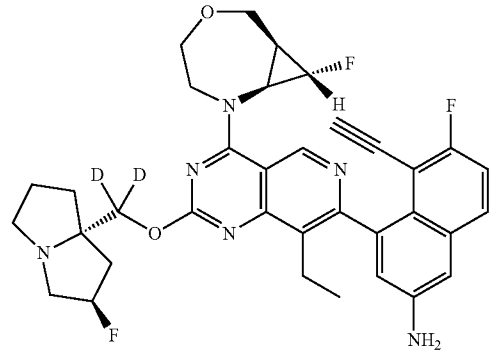 [SMILES: [2H]C([2H])(Oc1nc(N2CCOC[C@H]3[C@H](F)[C@H]32)c2cnc(-c3cc(N)cc4ccc(F)c(C#C)c34)c(CC)c2n1)[C@@]12CCCN1C[C@H](F)C2] | 4-(8-ethyl-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine |
| 457 | 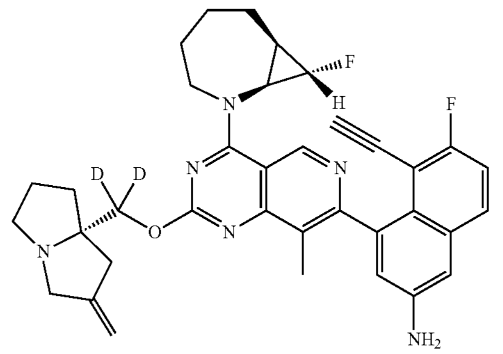 [SMILES: [2H]C([2H])(Oc1nc(N2CCCC[C@H]3[C@H](F)[C@H]32)c2cnc(-c3cc(N)cc4ccc(F)c(C#C)c34)c(C)c2n1)[C@@]12CCCN1CC(=C)C2] | 5-ethynyl-6-fluoro-4-(4-(1S,7R,8S)-8-fluoro-2-azabicyclo[5.1.0]octan-2-yl)-8-methyl-2-(((S)-2-methylenetetrahydro-1H-pyrrolizin-7a(5H)-yl)methoxy-d2)pyrido[4,3-d]pyrimidin-7-yl)naphthalen-2-amine |
| 458 | 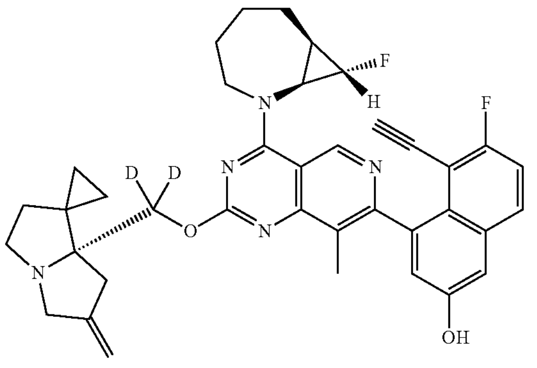 [SMILES: [2H]C([2H])(Oc1nc(N2CCCC[C@H]3[C@H](F)[C@H]32)c2cnc(-c3cc(O)cc4ccc(F)c(C#C)c34)c(C)c2n1)[C@]12CC(=C)CN1CCC21CC1] | 5-ethynyl-6-fluoro-4-(4-((1S,7R,8S)-8-fluoro-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy-d2)pyrido[4,3-d]pyrimidin-7-yl)naphthalen-2-amine |
| 459 | 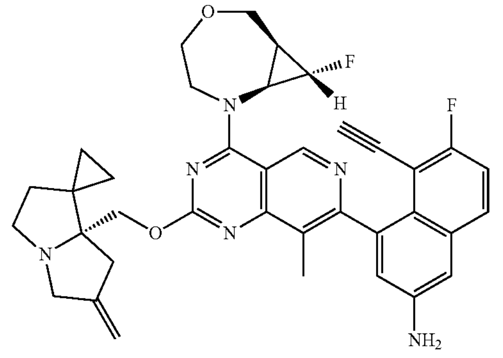 [SMILES: C#Cc1c(F)ccc2cc(N)cc(-c3ncc4c(N5CCOC[C@H]6[C@H](F)[C@H]65)nc(OC[C@]56CC(=C)CN5CCC65CC5)nc4c3C)c12] | 4-(4-((1S,7S,8S)-8-chloro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy)pyrido[4,3-d]pyrimidin-7-yl)-5-ethynyl-6-fluoronaphthalen-2-amine |

TABLE 1-continued

| Example No. | Structure | Name |
|---|---|---|
| 460 | 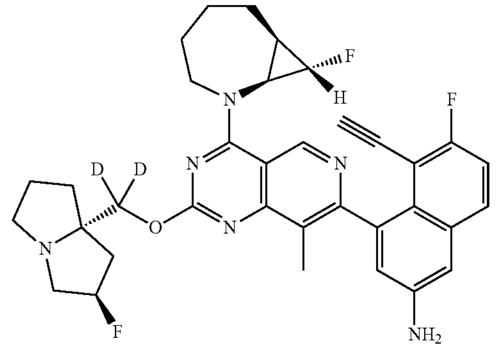 [SMILES: [2H]C([2H])(Oc1nc(N2CCCC[C@H]3[C@H](F)[C@H]32)c2cnc(-c3cc(N)cc4ccc(F)c(C#C)c34)c(C)c2n1)[C@@]12CCCN1C[C@H](F)C2] | 5-ethynyl-6-fluoro-4-(4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-naphthalen-2-amine |
| 461 | 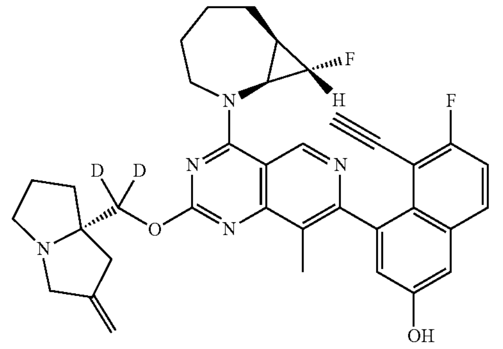 [SMILES: [2H]C([2H])(Oc1nc(N2CCCC[C@H]3[C@H](F)[C@H]32)c2cnc(-c3cc(O)cc4ccc(F)c(C#C)c34)c(C)c2n1)[C@@]12CCCN1CC(=C)C2] | 5-ethynyl-6-fluoro-4-(4-(1S,7R,8S)-8-fluoro-2-azabicyclo[5.1.0]octan-2-yl)-8-methyl-2-(((S)-2-methylenetetrahydro-1H-pyrrolizin-7a(5H)-yl)methoxy-d2)pyrido[4,3-d]pyrimidin-7-yl)naphthalen-2-ol |
| 462 | 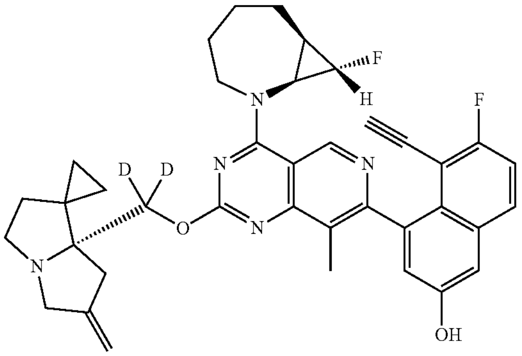 [SMILES: [2H]C([2H])(Oc1nc(N2CCCC[C@H]3[C@H](F)[C@H]32)c2cnc(-c3cc(O)cc4ccc(F)c(C#C)c34)c(C)c2n1)[C@]12CC(=C)CN1CCC21CC1] | 5-ethynyl-6-fluoro-4-(4-((1S,7R,8S)-8-fluoro-2-azabicyclo[5.1.0]octan-2-yl)-8-methyl-2-(((R)-6'-methylenetetrahydrospiro[cyclopropane-1.1'-pyrrolizin]-7a(5'H)-yl)methoxy-d2)pyrido[4,3-d]pyrimidin-7-yl)naphthalen-2-ol |
| 463 | 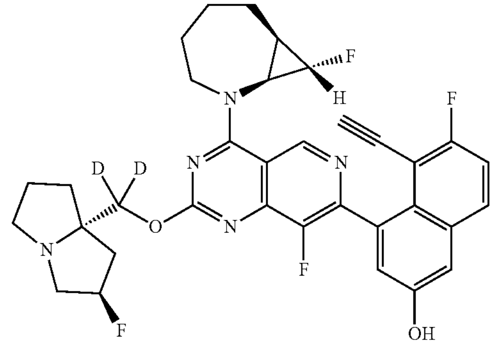 [SMILES: [2H]C([2H])(Oc1nc(N2CCCC[C@H]3[C@H](F)[C@H]32)c2cnc(-c3cc(O)cc4ccc(F)c(C#C)c34)c(F)c2n1)[C@@]12CCCN1C[C@H](F)C2] | 5-ethynyl-6-fluoro-4-(4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-yl)naphthalen-2-ol |

TABLE 1-continued

| Example No. | Structure | Name |
|---|---|---|
| 464 | 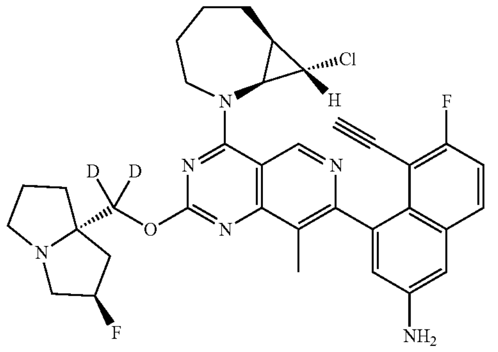 [SMILES: [2H]C([2H])(Oc1nc(N2CCCC[C@H]3[C@H](Cl)[C@H]32)c2cnc(-c3cc(N)cc4ccc(F)c(C#C)c34)c(C)c2n1)[C@@]12CCCN1C[C@H](F)C2] | 4-(4-((1S,7R,8S)-8-chloro-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-yl)-5-ethynyl-6-fluoronaphthalen-2-amine |
| 465 | 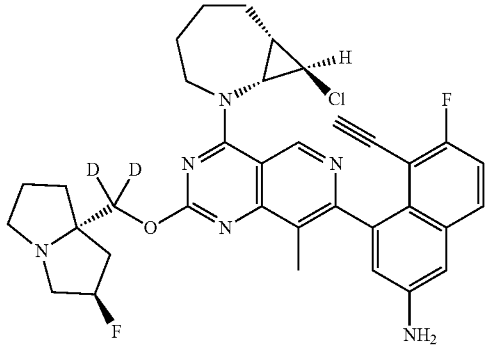 [SMILES: [2H]C([2H])(Oc1nc(N2CCCC[C@@H]3[C@@H](Cl)[C@@H]32)c2cnc(-c3cc(N)cc4ccc(F)c(C#C)c34)c(C)c2n1)[C@@]12CCCN1C[C@H](F)C2] | 4-(4-((1R,7S,8R)-8-chloro-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-yl)-5-ethynyl-6-fluoronaphthalen-2-amine |
| 466 | 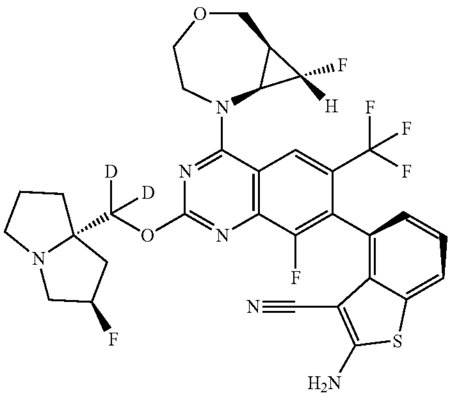 | 2-amino-4-((S)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-6-(trifluoromethyl)quinazolin-7-benzo[b]thiophene-3-carbonitrile |
| 467 | 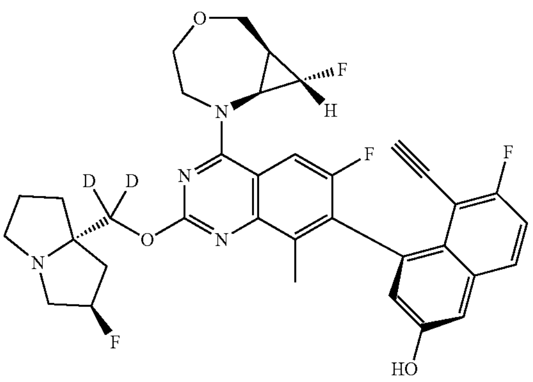 | 5-ethynyl-6-fluoro-4-((R)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)naphthalen-2-ol |

TABLE 1-continued

| Example No. | Structure | Name |
|---|---|---|
| 468 | 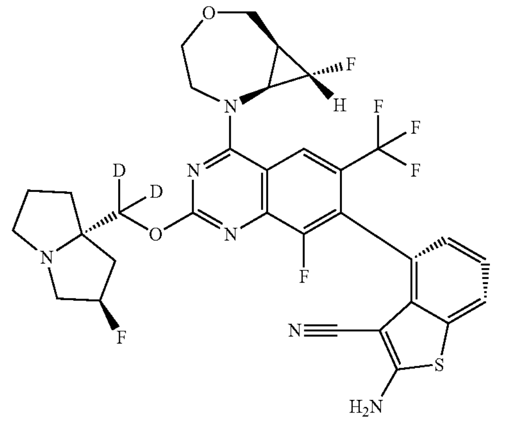 | 2-amino-4-((R)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-6-(trifluoromethyl)quinazolin-7-benzo[b]thiophene-3-carbonitrile |
| 469 | 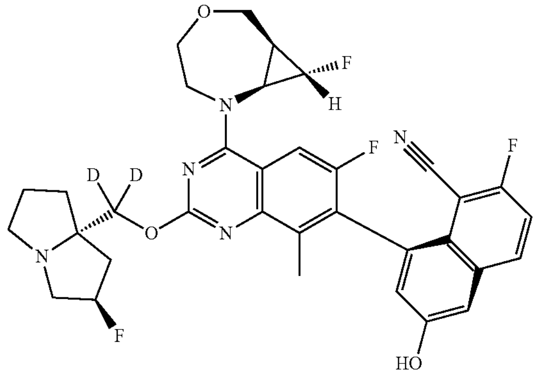 | 5-ethynyl-6-fluoro-4-((S)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)naphthalen-2-ol |
| 470 | 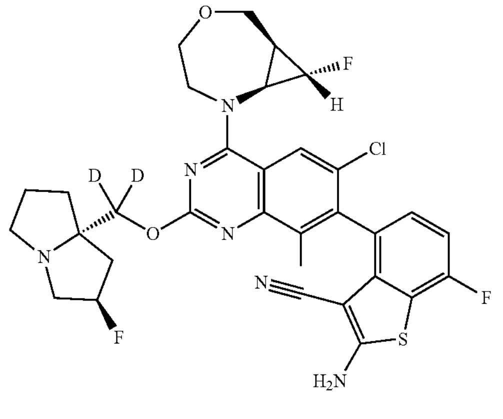 | 2-amino-4-(6-chloro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)-7-fluorobenzo[b]thiophene-3-carbonitrile |
| 471 | 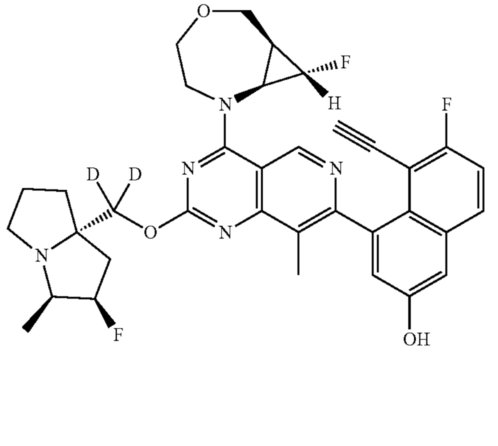 | 5-ethynyl-6-fluoro-4-(2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)-8-methylpyrido[4,3-d]pyrimidin-7-yl)naphthalen-2-ol |

TABLE 1-continued

| Example No. | Structure | Name |
|---|---|---|
| 472 | 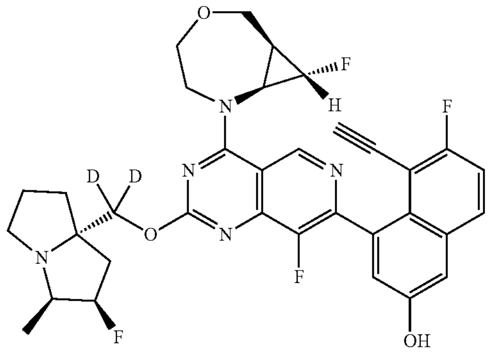 [SMILES: [2H]C([2H])(Oc1nc(N2CCOC[C@H]3[C@H](F)[C@H]32)c2cnc(-c3cc(O)cc4ccc(F)c(C#C)c34)c(C)c2n1)[C@@]12CCCN1[C@H](C)[C@H](F)C2] | 5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-ol |
| 473 | 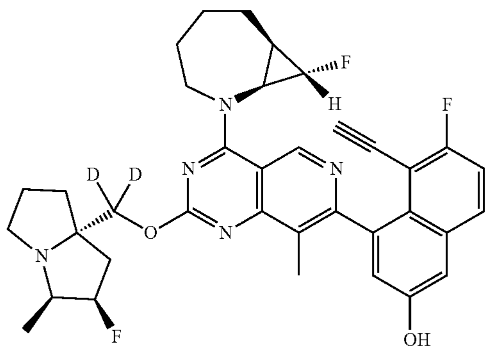 [SMILES: [2H]C([2H])(Oc1nc(N2CCCC[C@H]3[C@H](F)[C@H]32)c2cnc(-c3cc(O)cc4ccc(F)c(C#C)c34)c(C)c2n1)[C@@]12CCCN1[C@H](C)[C@H](F)C2] | 5-ethynyl-6-fluoro-4-(2-(((2R,3R,7aS)-2-fluoro-3-methyltetrahydro-1H-pyrrolizin-7a(5H)-yl)methoxy-d2)-4-((1S,7R,8S)-8-fluoro-2-azabicyclo[5.1.0]octan-2-yl)-8-methylpyrido[4,3-d]pyrimidin-7-yl)naphthalen-2-ol |
| 474 | 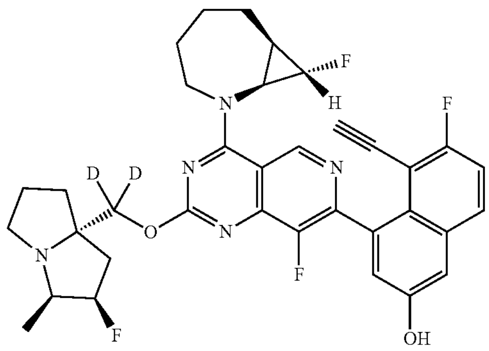 | 5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7R,8S)-8-fluoro-2-azabicyclo[5.1.0]octan-2-yl)pyrido[4,3-d]pyrimidin-7-yl)naphthalen-2-ol |
| 475 | 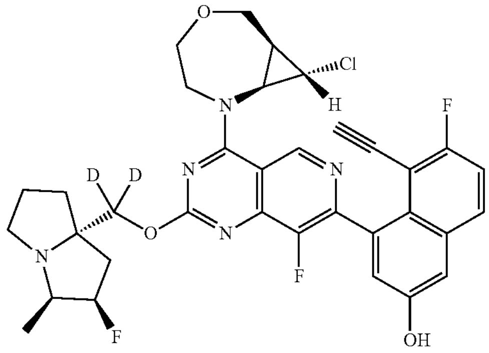 | 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-ol |

TABLE 1-continued

| Example No. | Structure | Name |
|---|---|---|
| 476 | 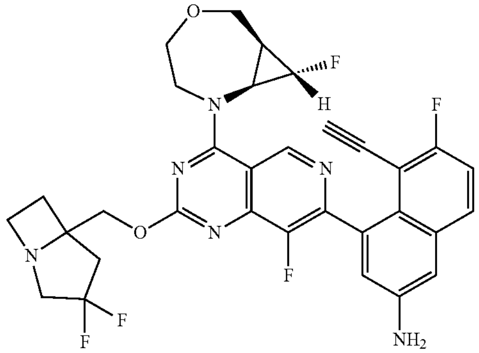 [SMILES: C#Cc1c(F)ccc2cc(N)cc(-c3ncc4c(N5CCOC[C@H]6[C@H](F)[C@H]65)nc(OCC56CCN5CC(F)(F)C6)nc4c3F)c12] | 4-(2-((3,3-difluoro-1-azabicyclo[3.2.0]heptan-5-methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine |
| 477 | 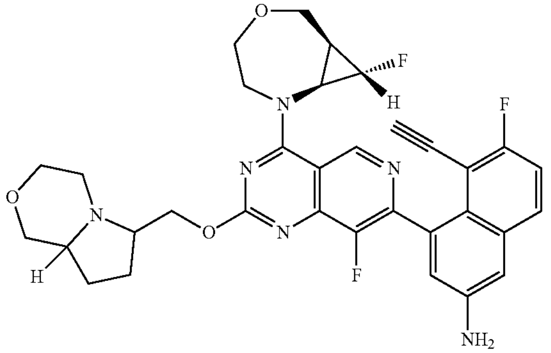 [SMILES: C#Cc1c(F)ccc2cc(N)cc(-c3ncc4c(N5CCOC[C@H]6[C@H](F)[C@H]65)nc(OCC5CCC6COCCN65)nc4c3F)c12] | 5-ethynyl-6-fluoro-4-(8-fluoro-4-((1S,7S,8S)-8-fluoro-5-oxa-2-azabicyclo[5.1.0]octan-2-yl)-2-(hexahydro-1H-pyrrolo[2,1-c][1,4]oxazin-6-yl)methoxy)pyrido[4,3-d]pyrimidin-7-yl)naphthalen-2-amine |

Figure 2:
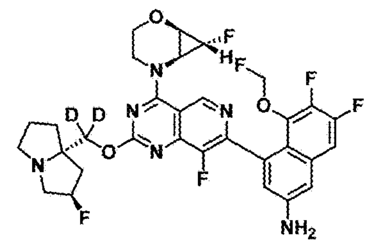
FIG. 2 provides additional structures of compounds of Formula (I)
Figure 2:
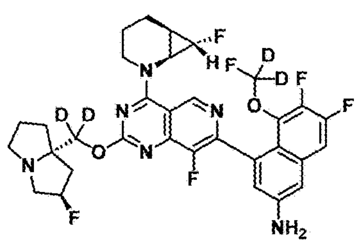
Figure 2:
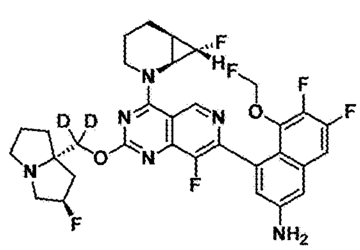
Figure 2:
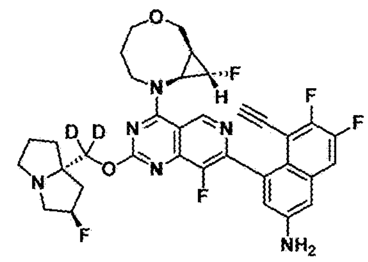
Figure 2:
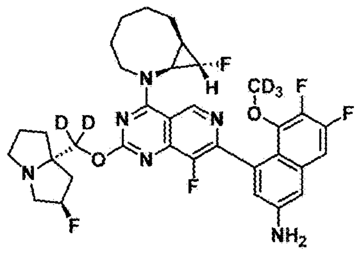
Figure 2:
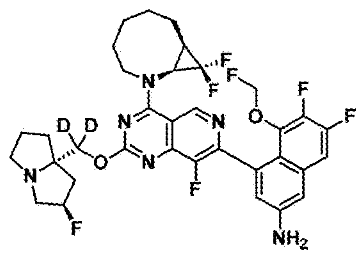
Figure 2:
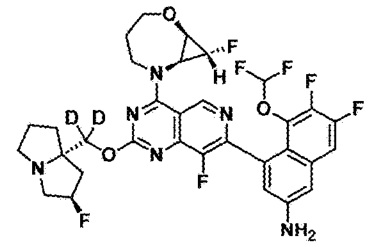
Figure 3:
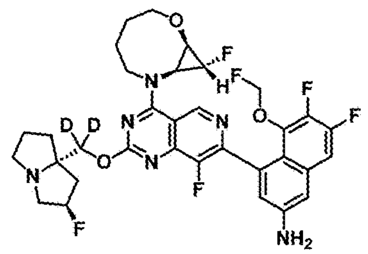
FIG. 3 provides additional structures of compounds of Formula (I)
Figure 3:
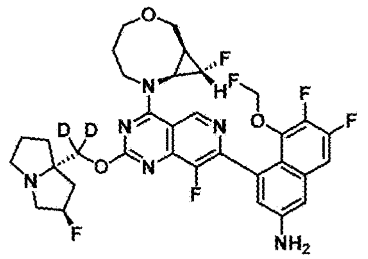
Figure 3:
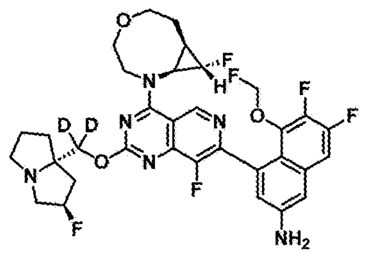
Figure 3:
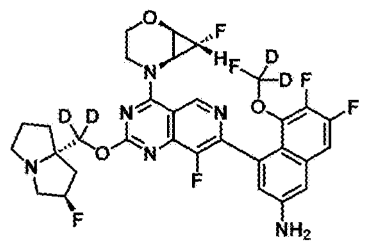
Figure 3:
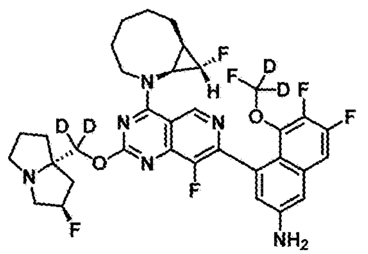
Figure 3:
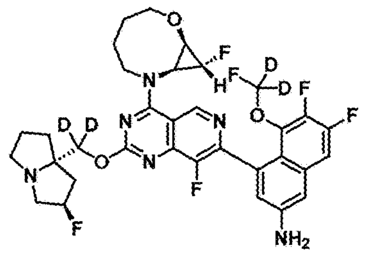
Figure 3:
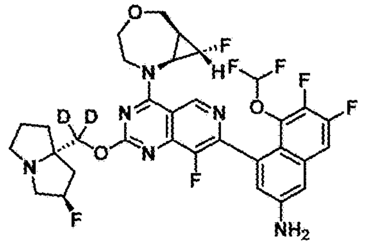
Figure 3:
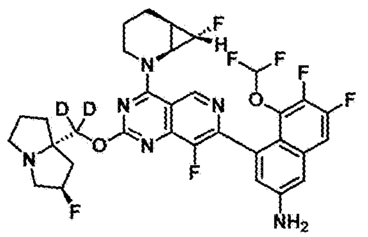
Figure 3:
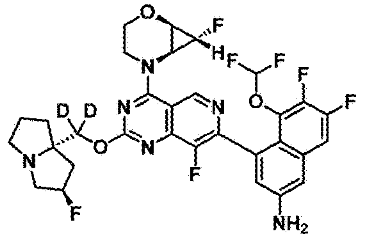
Figure 4:
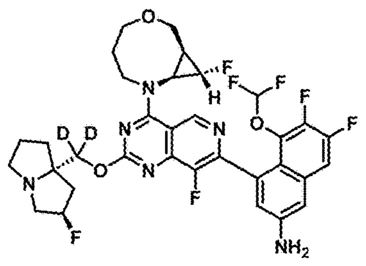
FIG. 4 provides additional structures of compounds of Formula (I)
Figure 4:
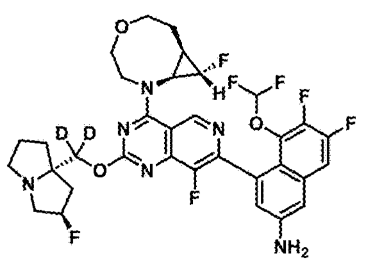
Figure 4:
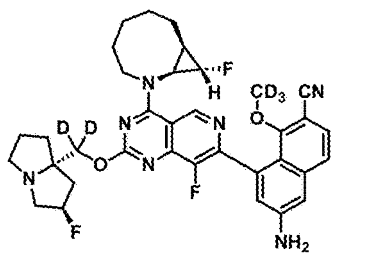
Figure 4:
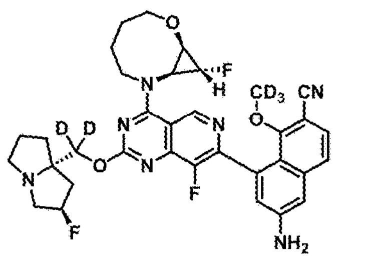
Figure 4:
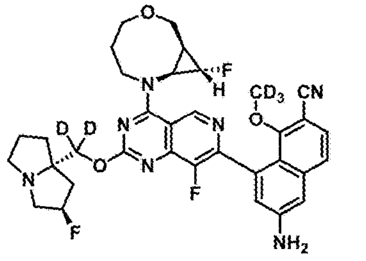
Figure 4:
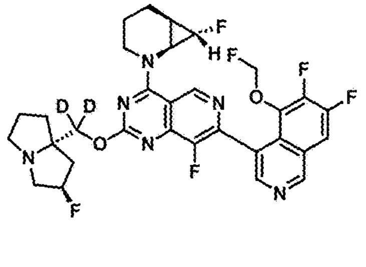
Figure 4:
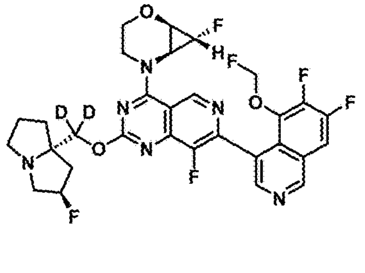
Figure 4:
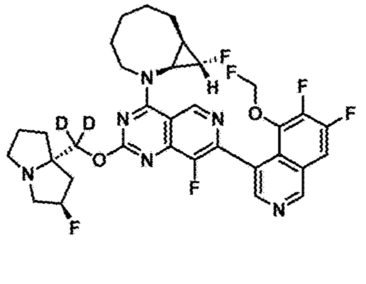
Figure 5:
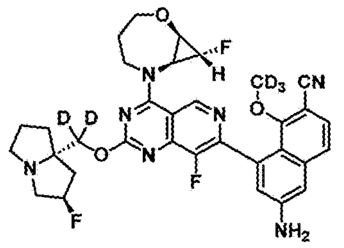
FIG. 5 provides additional structures of compounds of Formula (I)
Figure 5:
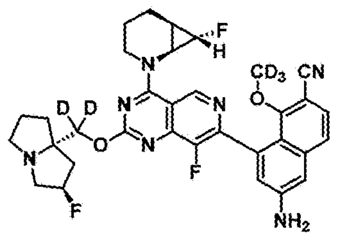
Figure 5:
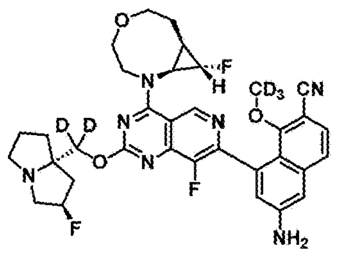
Figure 5:
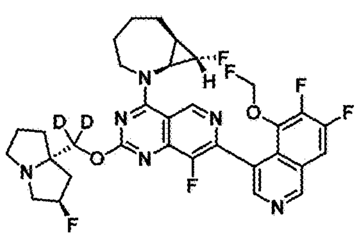
Figure 5:
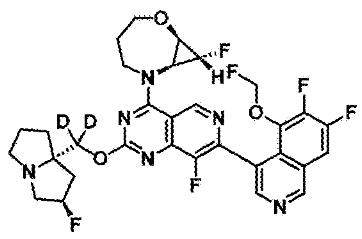
Figure 5:
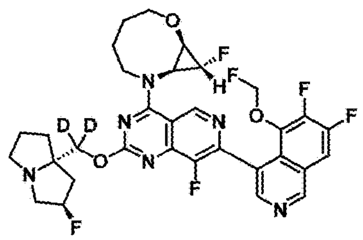
Figure 5:
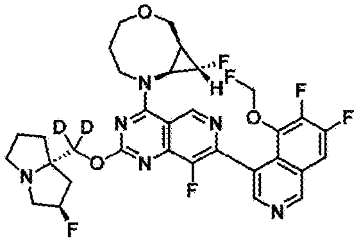
Figure 5:
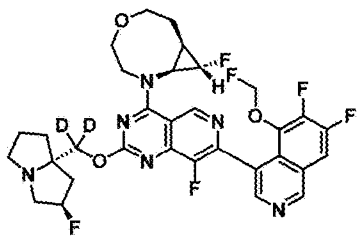
Figure 6:
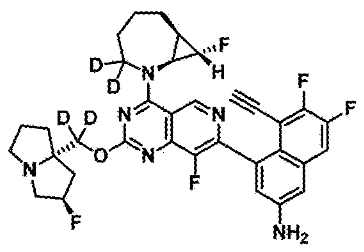
FIG. 6 provides additional structures of compounds of Formula (I)
Figure 6:
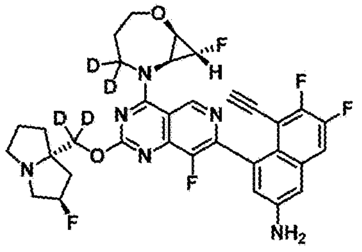
Figure 6:
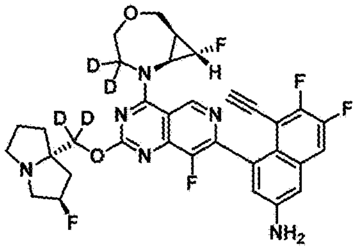
Figure 6:
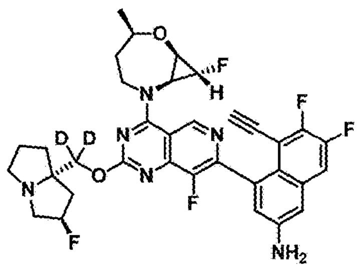
Figure 6:
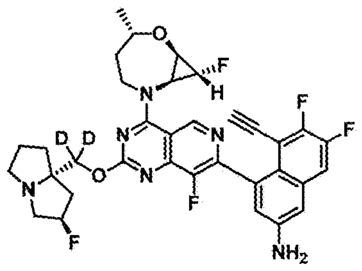
Figure 6:
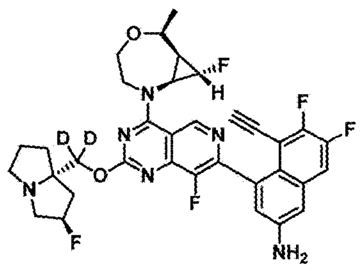
Figure 6:
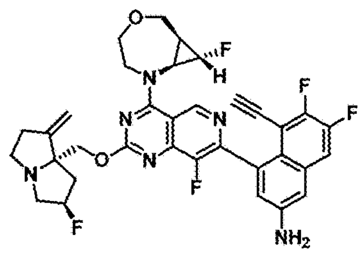
Figure 6:
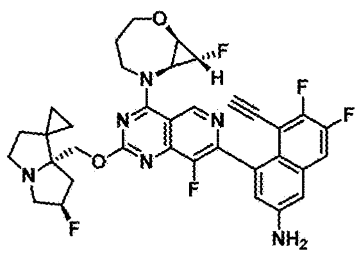
Figure 6:
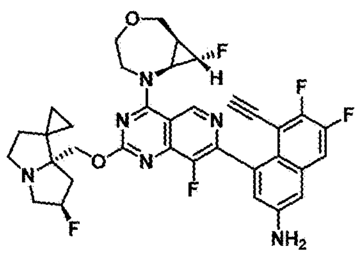
Figure 7:
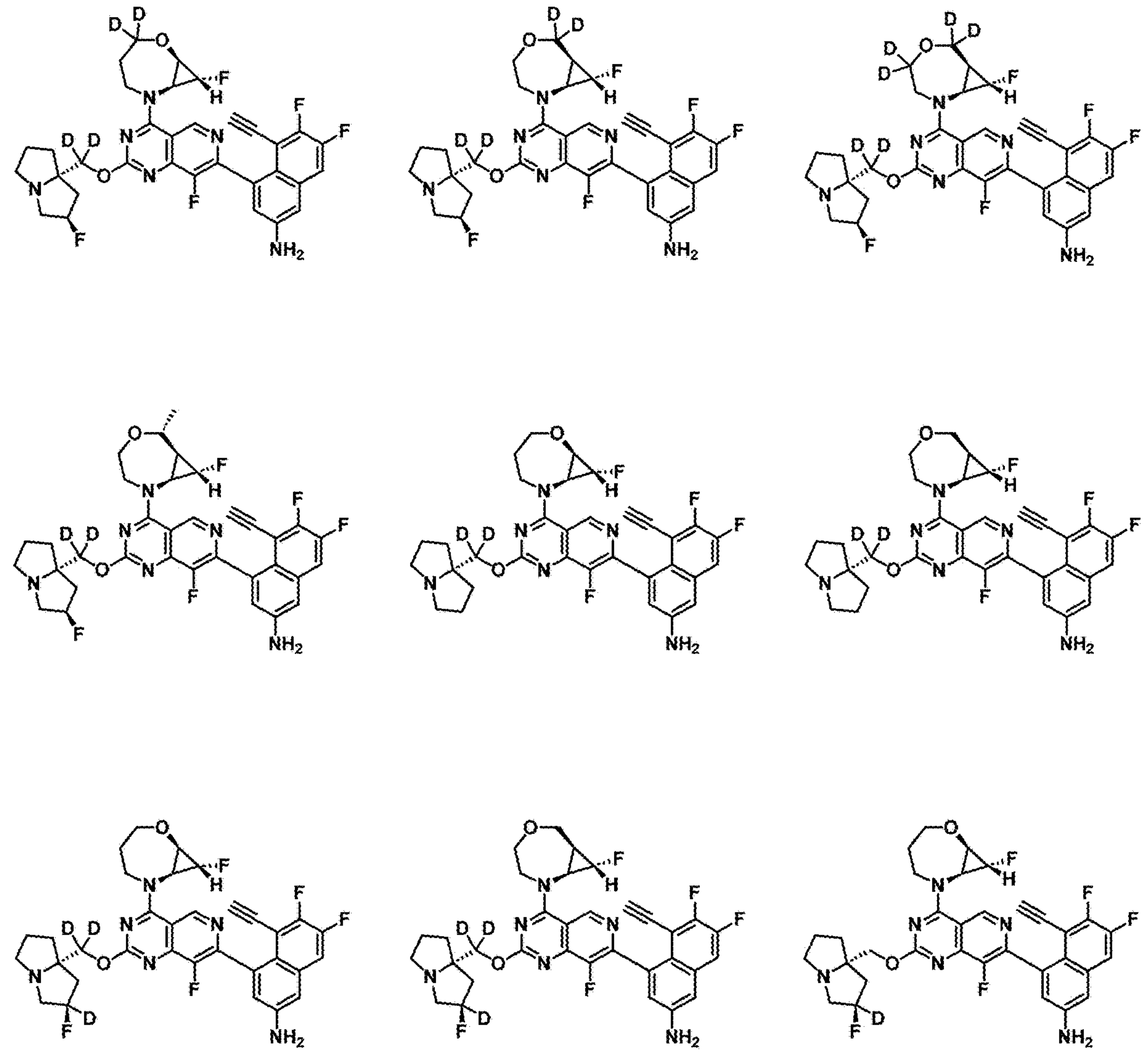
FIG. 7 provides additional structures of compounds of Formula (I)
Figure 8:
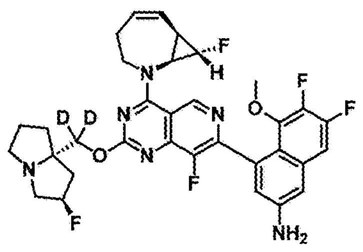
FIG. 8 provides additional structures of compounds of Formula (I)
Figure 8:
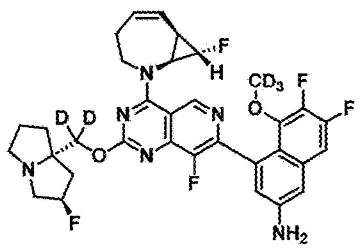
Figure 8:
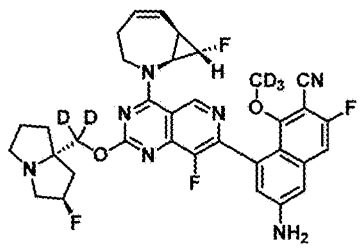
Figure 8:
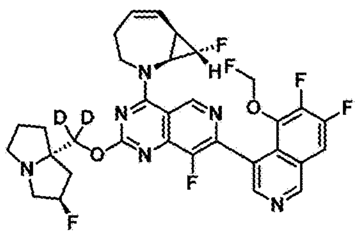
Figure 8:
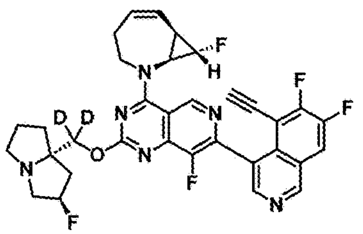
Figure 8:
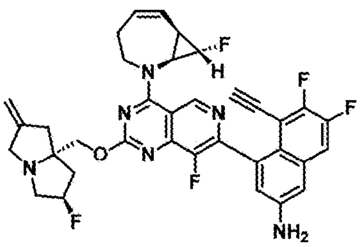
Figure 8:
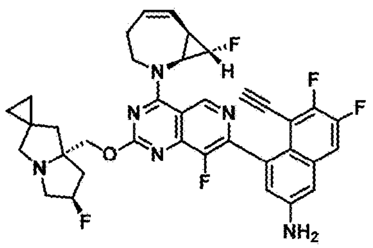
Figure 8:
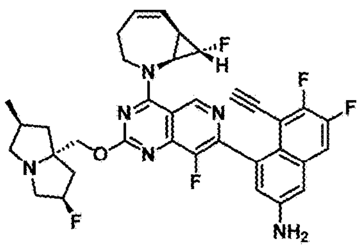
Figure 9:
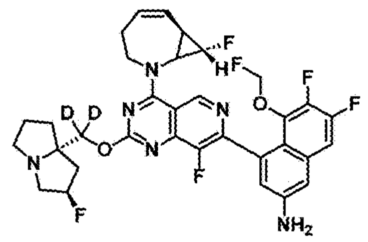
FIG. 9 provides additional structures of compounds of Formula (I)
Figure 9:
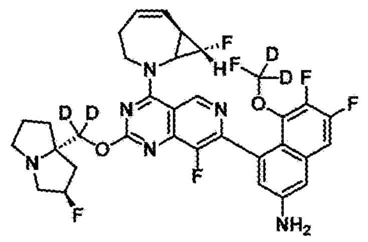
Figure 9:
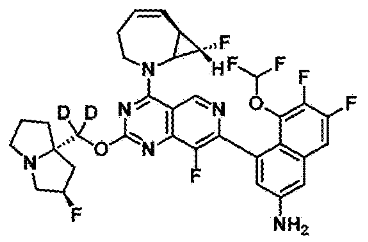
Figure 9:
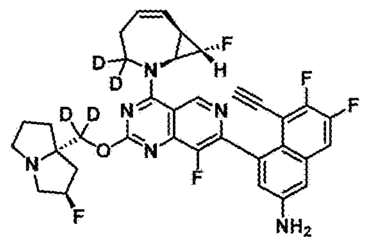
Figure 9:
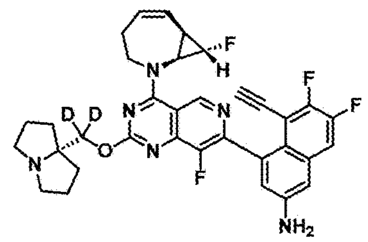
Figure 9:
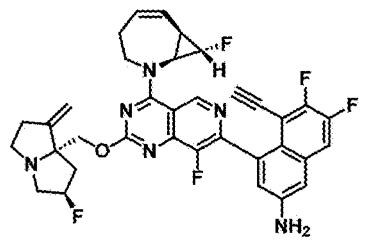
Figure 9:
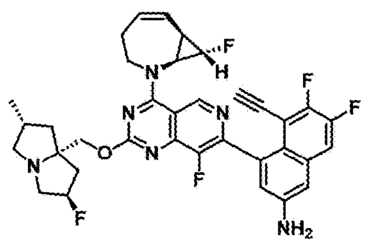
Figure 9:
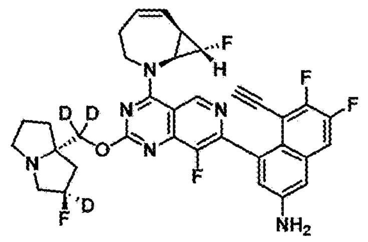
Figure 9:
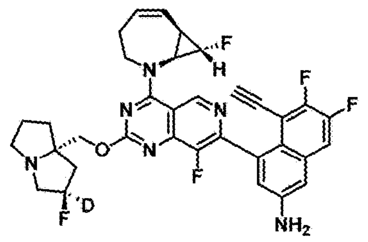
Figure 10:
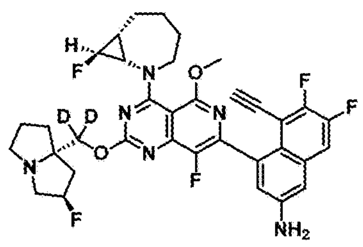
FIG. 10 provides additional structures of compounds of Formula (I)
Figure 10:
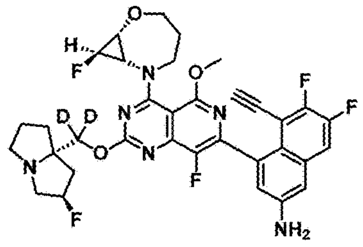
Figure 10:
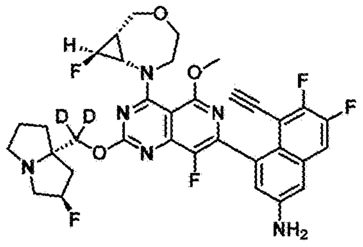
Figure 10:
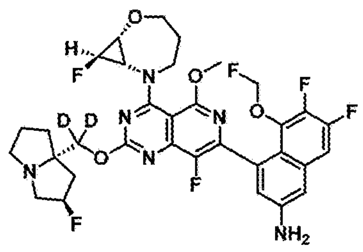
Figure 10:
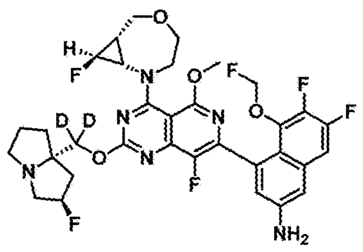
Figure 10:
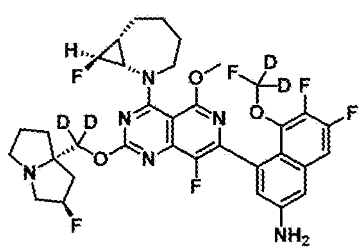
Figure 10:
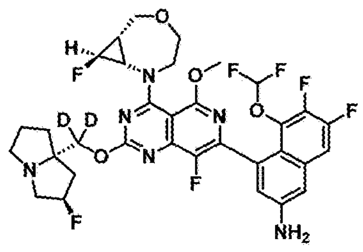
Figure 10:
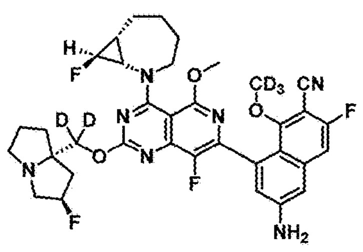
Figure 10:
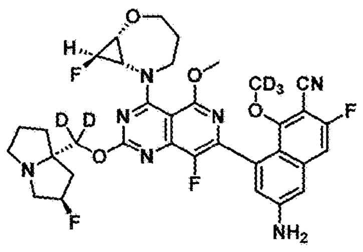
Figure 11:
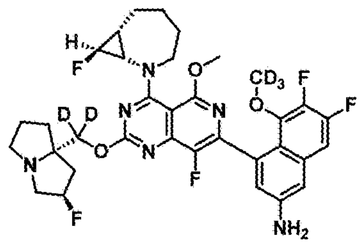
FIG. 11 provides additional structures of compounds of Formula (I)
Figure 11:
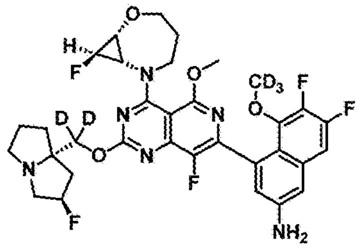
Figure 11:
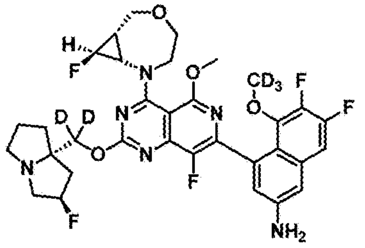
Figure 11:
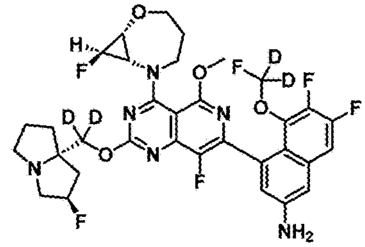
Figure 11:
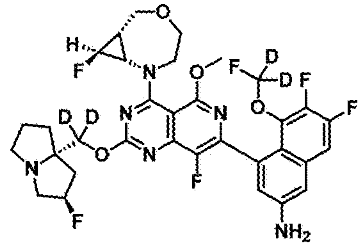
Figure 11:
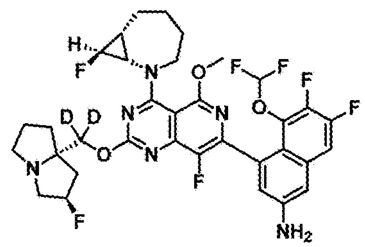
Figure 11:
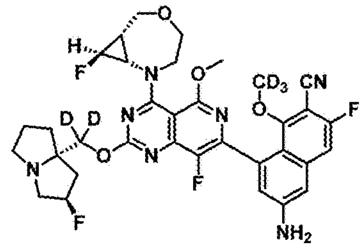
Figure 11:
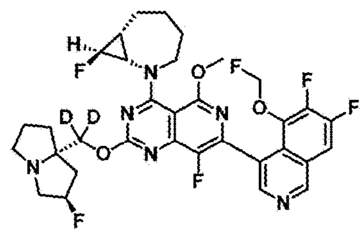
Figure 11:
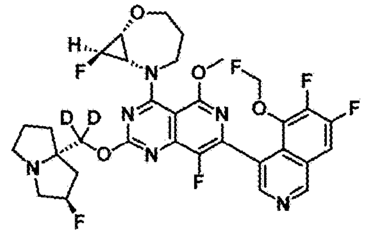
Figure 12:
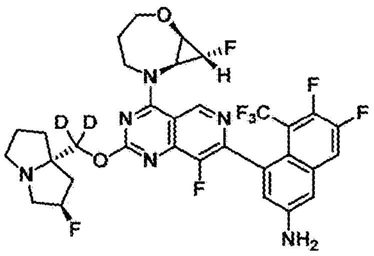
FIG. 12 provides additional structures of compounds of Formula (I)
Figure 12:
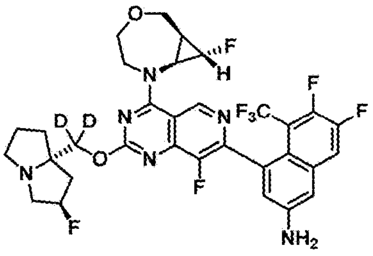
Figure 12:
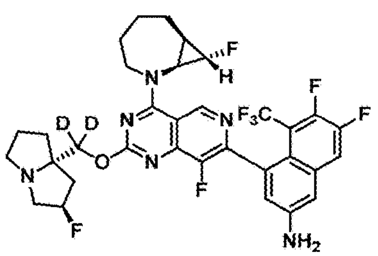
Figure 12:
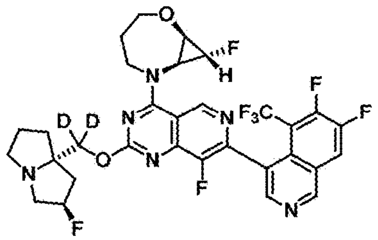
Figure 12:
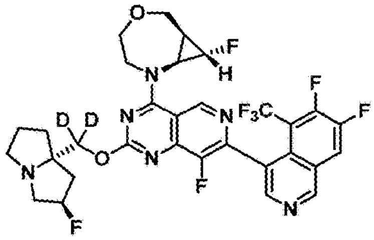
Figure 12:
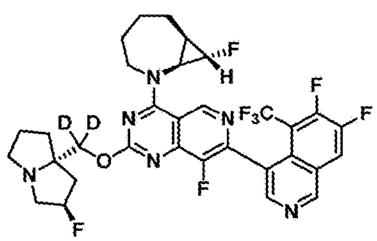
Figure 12:
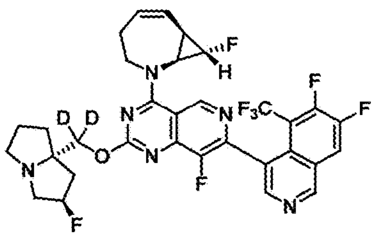
Figure 12:
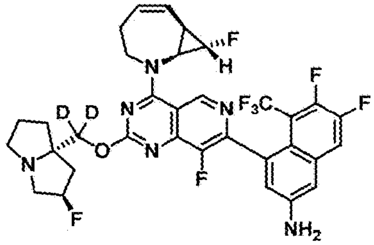
Figure 12:
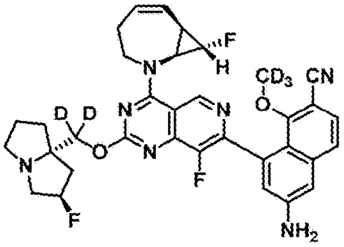
Figure 12:
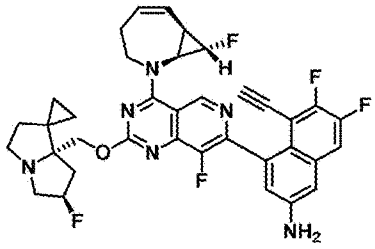
Figure 12:
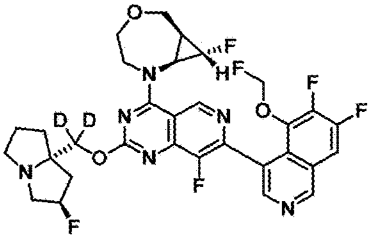
Figure 12:
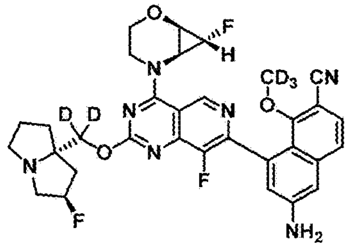
Figure 13:
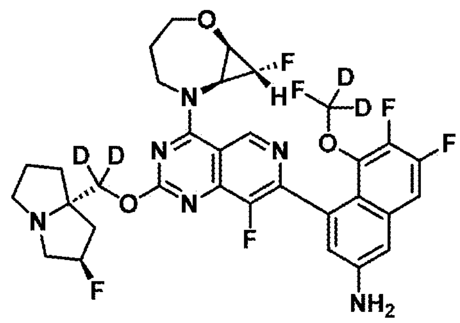
FIG. 13 provides additional structures of compounds of Formula (I)
Figure 13:
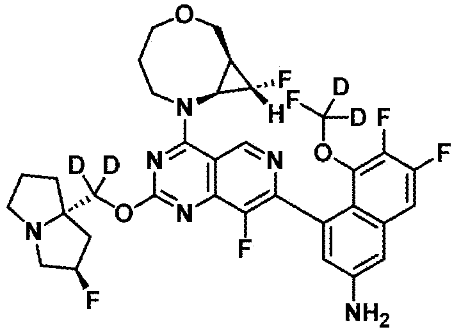
Figure 13:
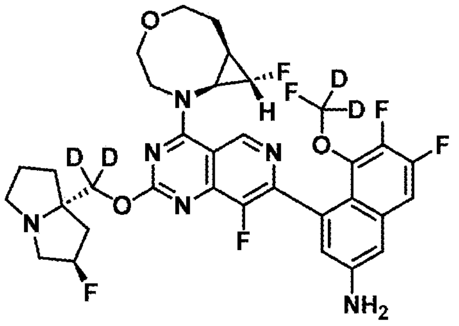
Figure 13:
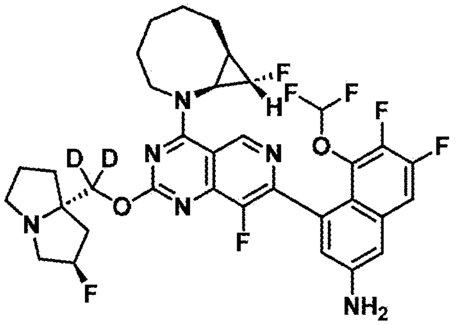
Figure 13:
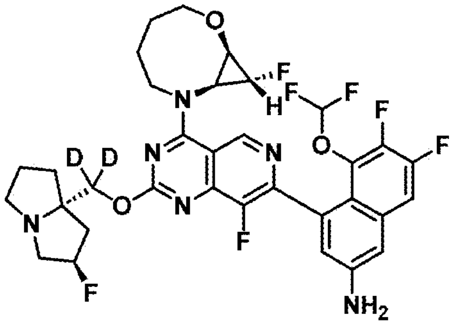
Figure 13:
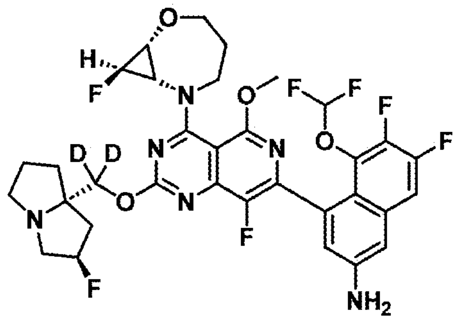
Figure 13:
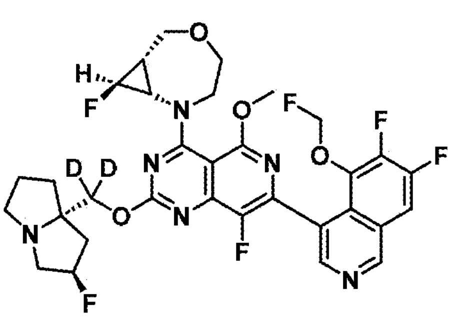
Figure 14:
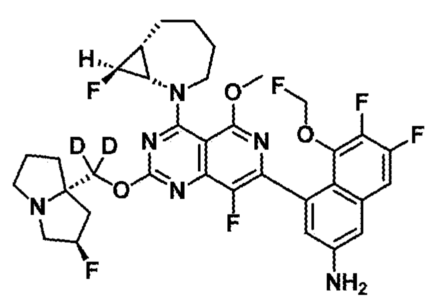
FIG. 14 provides additional structures of compounds of Formula (I)
Figure 14:
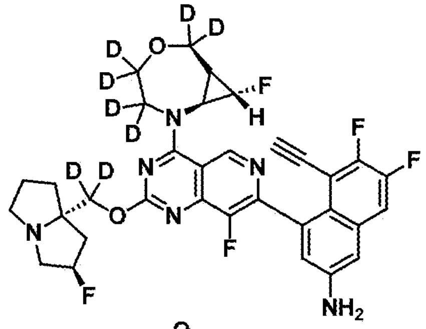
Figure 14:
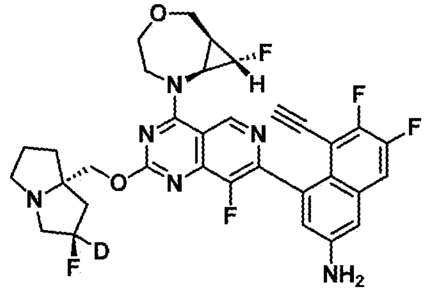
Figure 14:
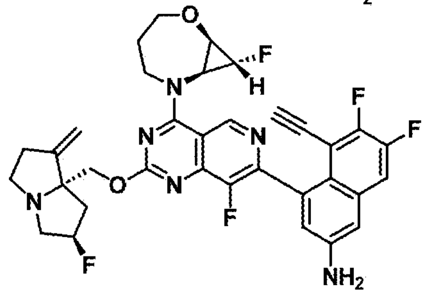
Figure 14:
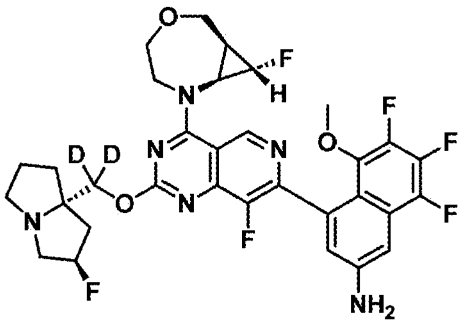
Figure 14:
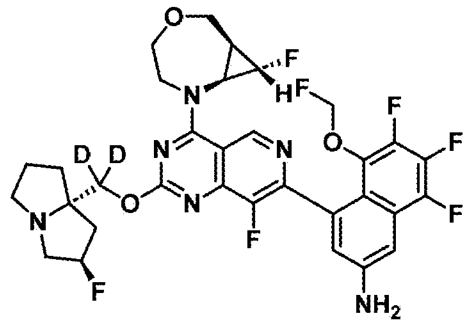
Figure 14:
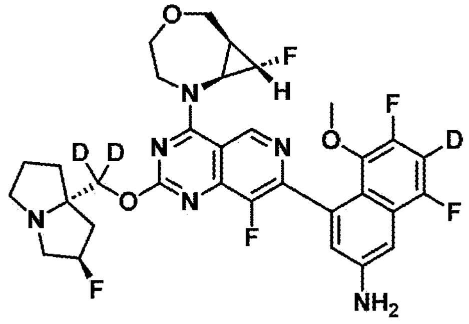
Figure 14:
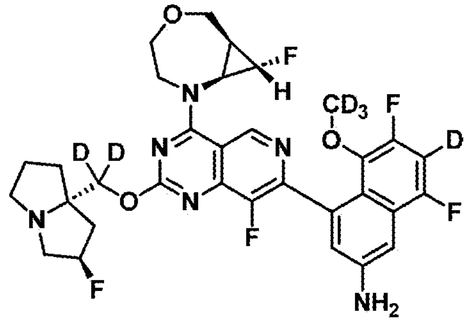
Figure 14:
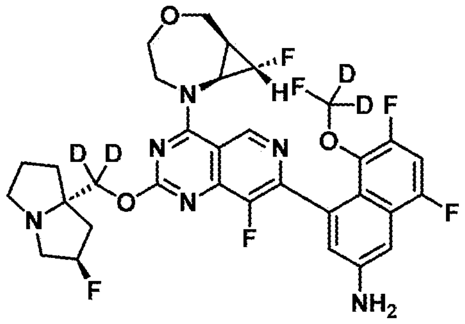
Figure 15:
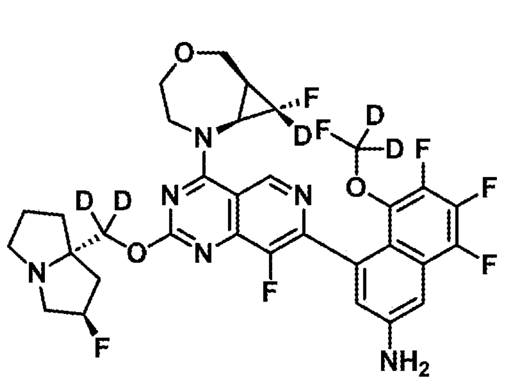
FIG. 15 provides additional structures of compounds of Formula (I)
Figure 15:
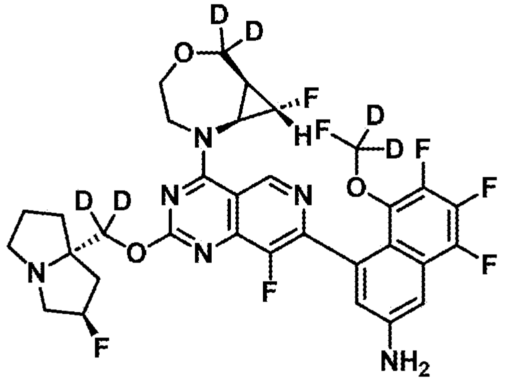
Figure 15:
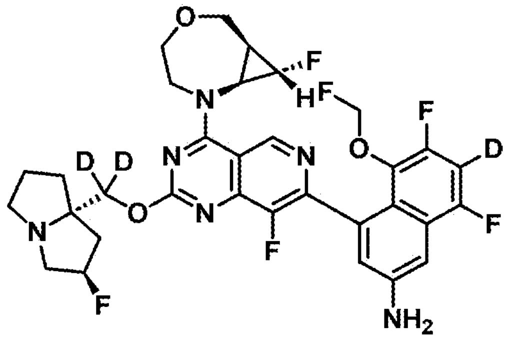
Figure 15:
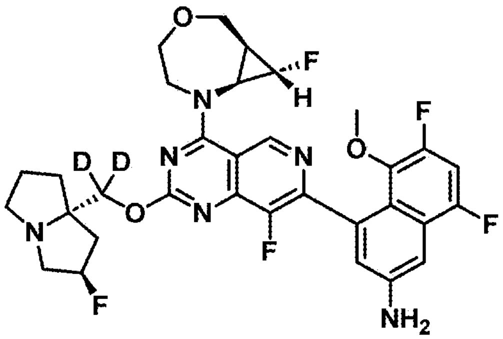
Figure 15:
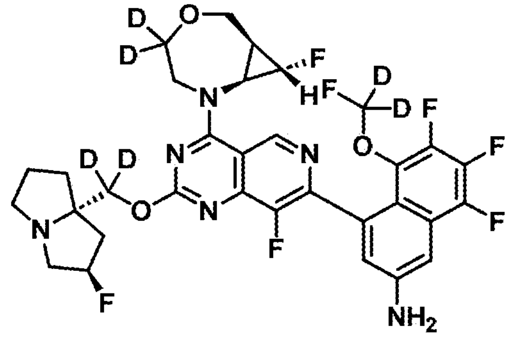
Figure 15:
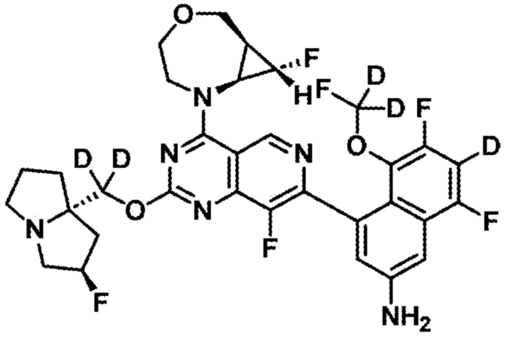
Figure 16:
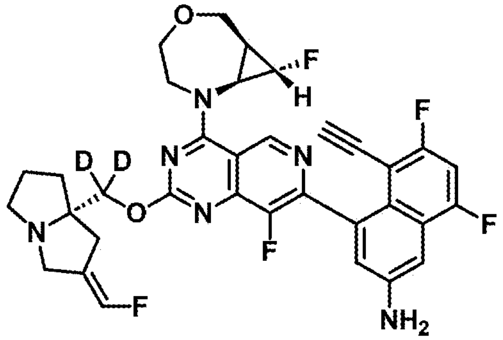
FIG. 16 provides additional structures of compounds of Formula (I)
Figure 16:
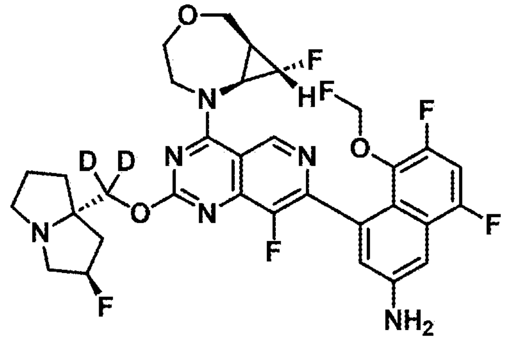
Figure 16:
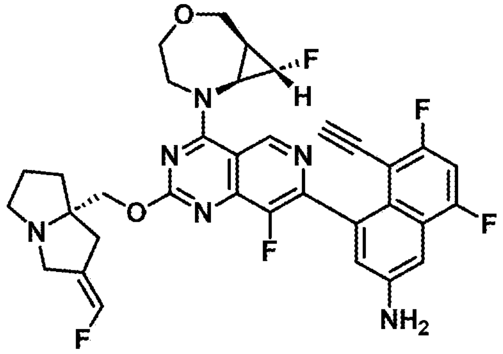
Figure 16:
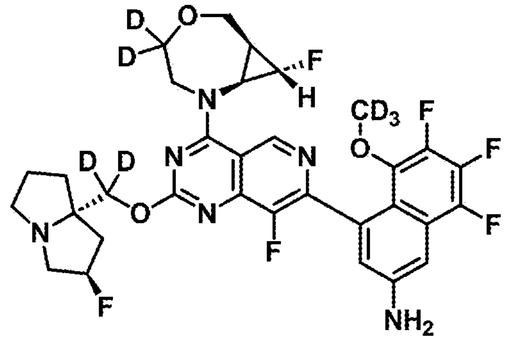
Figure 16:
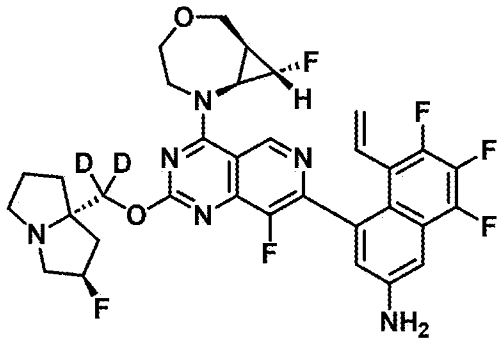
Figure 17:
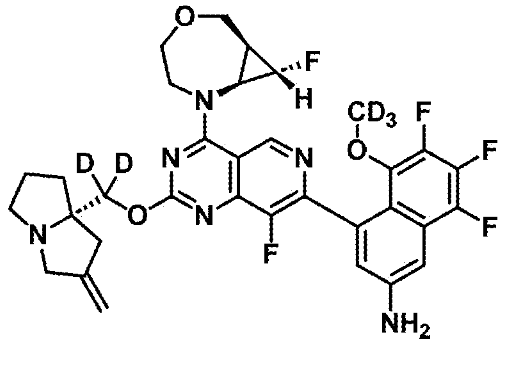
FIG. 17 provides additional structures of compounds of Formula (I)
Figure 17:
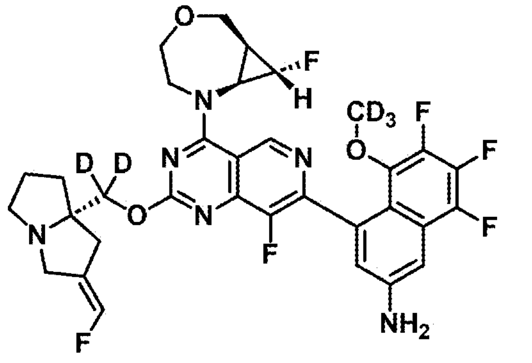
Figure 17:
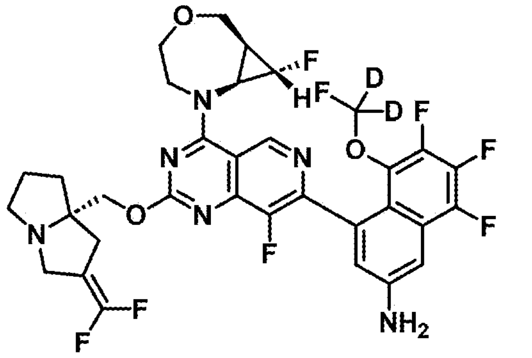
Figure 17:
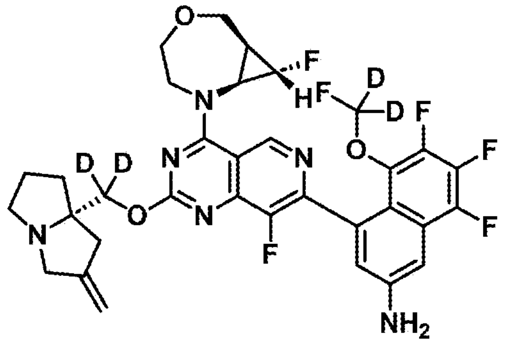
Figure 17:
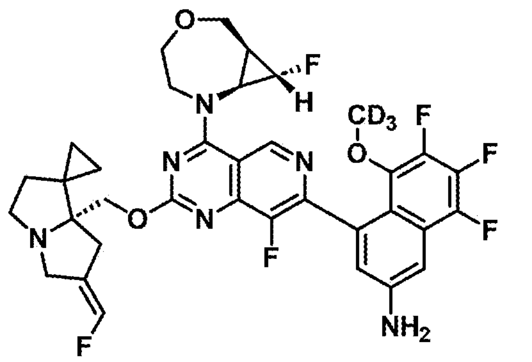
Figure 17:
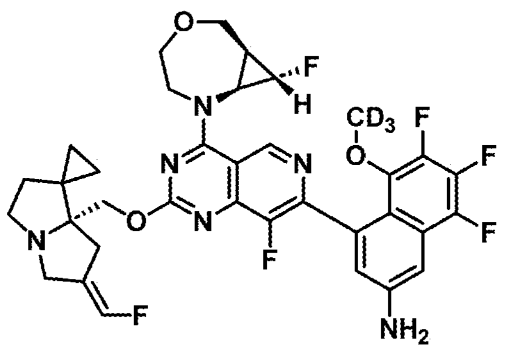
Figure 17:
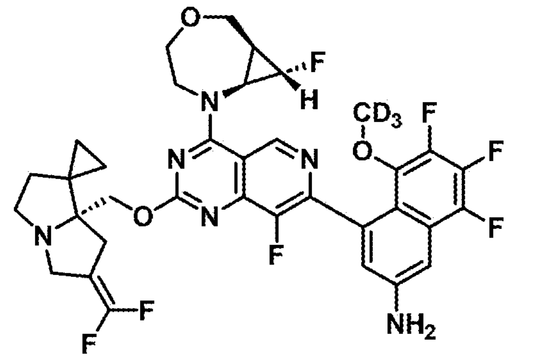
Figure 17:
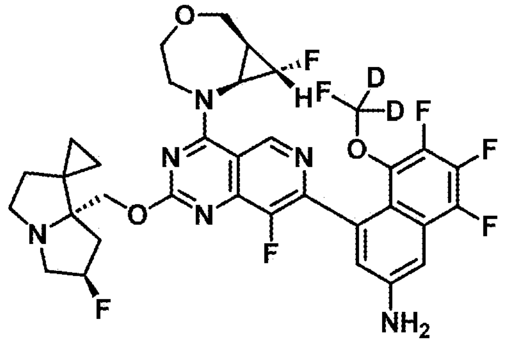
Figure 18:
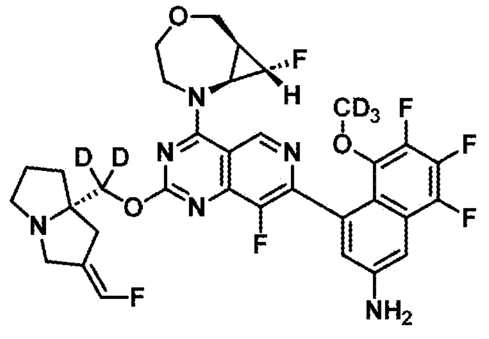
FIG. 18 provides additional structures of compounds of Formula (I)
Figure 18:
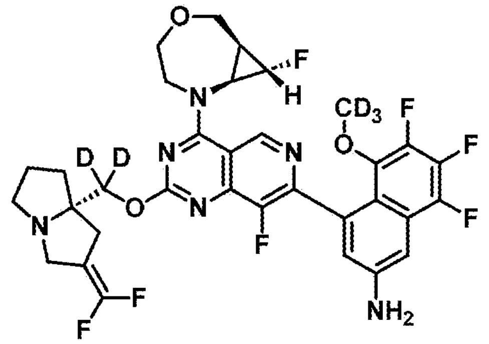
Figure 18:
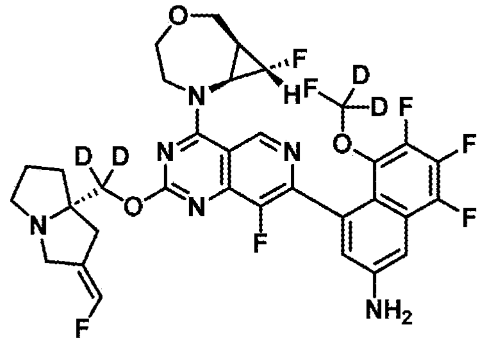
Figure 18:
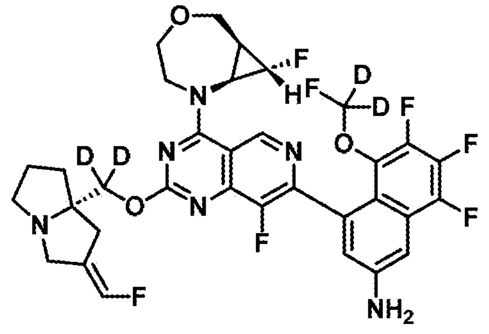
Figure 18:
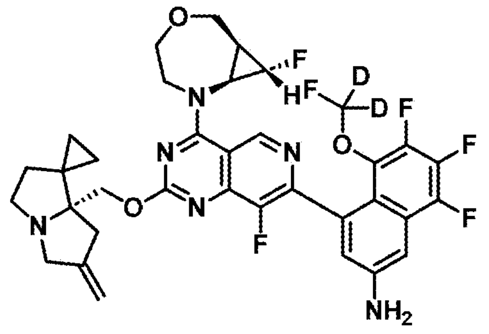
Figure 18:
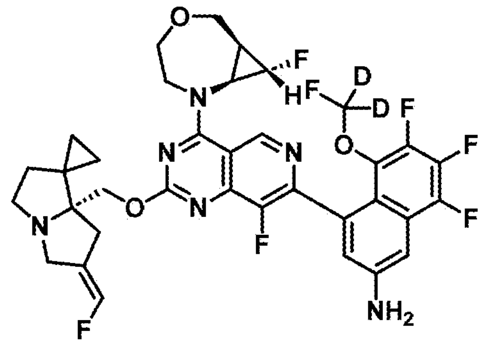
Figure 18:
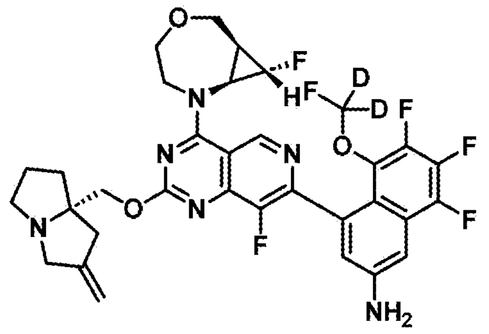
Figure 18:
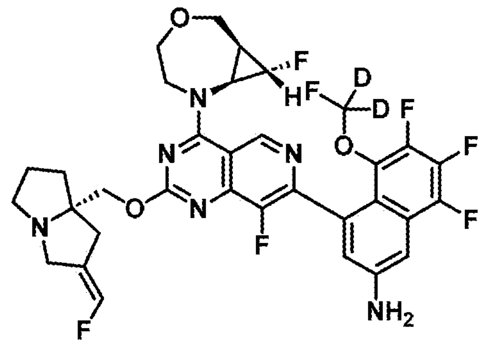
Figure 19:
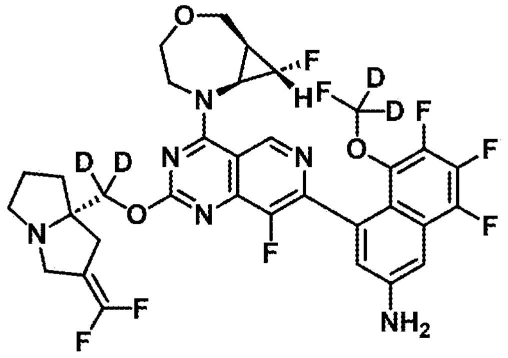
FIG. 19 provides additional structures of compounds of Formula (I)
Figure 19:
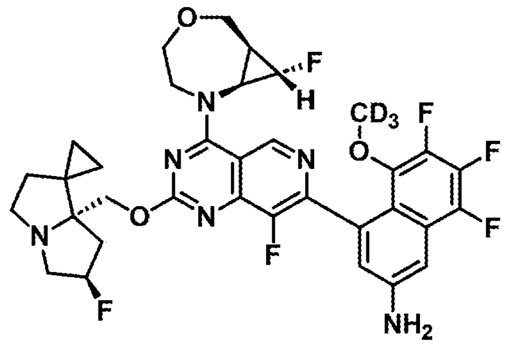
Figure 19:
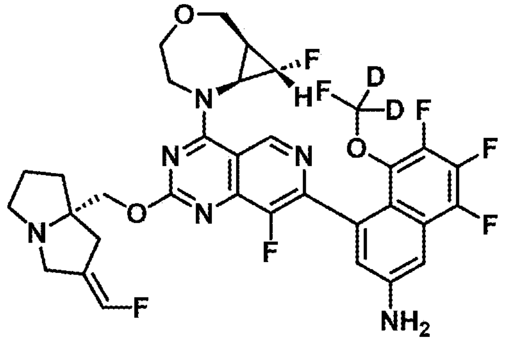
Figure 19:
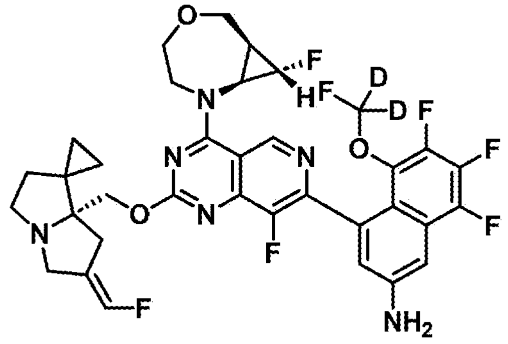
Figure 19:
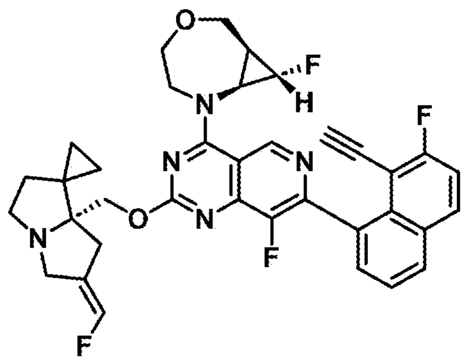
Figure 19:
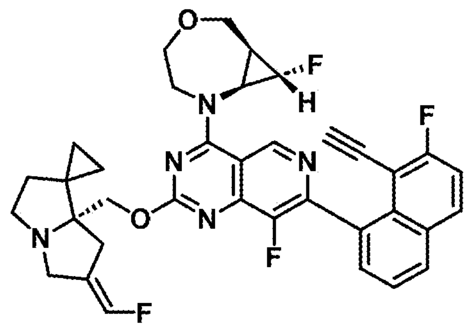
Figure 20:
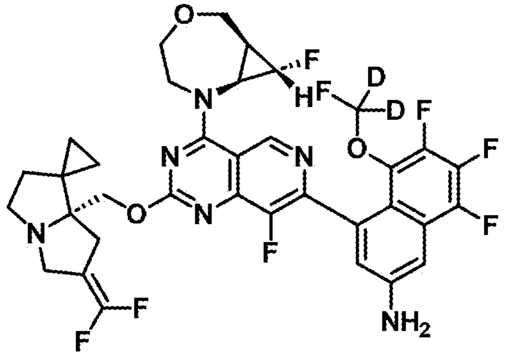
FIG. 20 provides additional structures of compounds of Formula (I)
Figure 20:
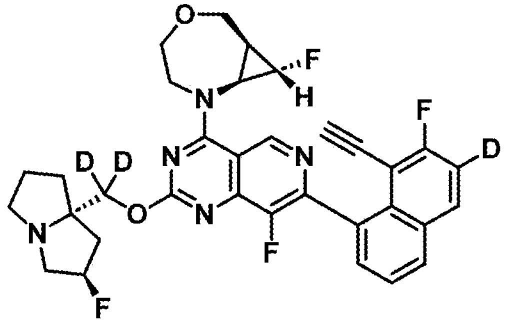
Figure 20:
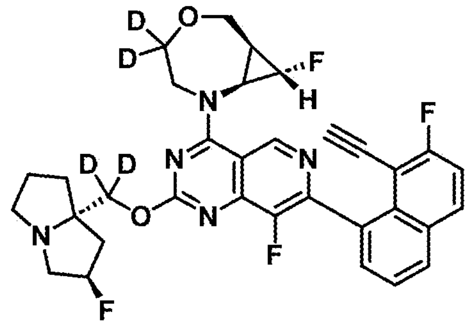
Figure 20:
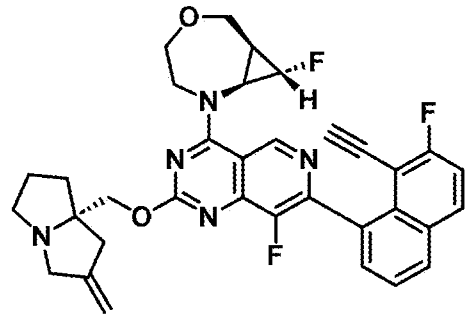
Figure 20:
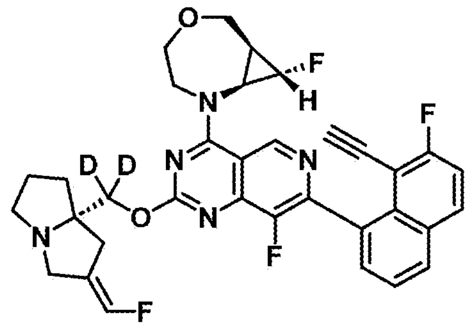
Figure 20:
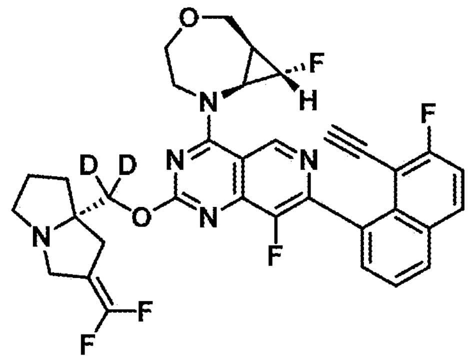
Figure 20:
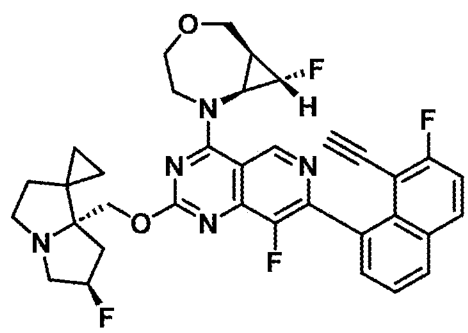
Figure 20:
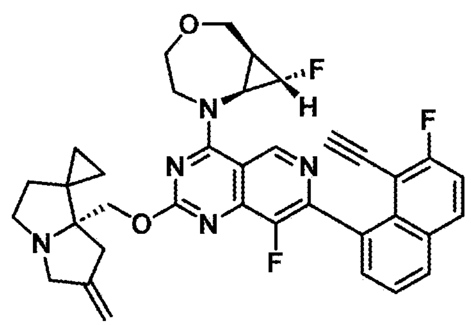
Figure 21:
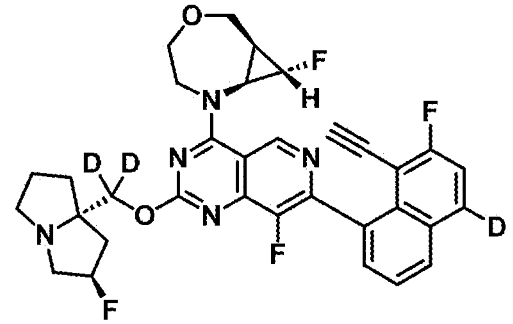
FIG. 21 provides additional structures of compounds of Formula (I)
Figure 21:
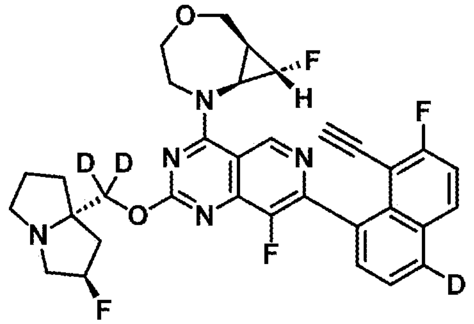
Figure 21:
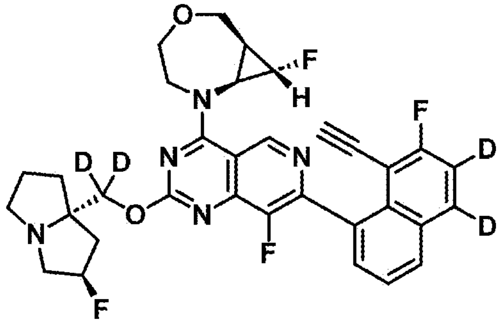
Figure 21:
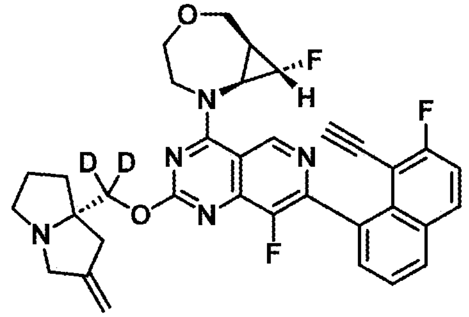
Figure 22:
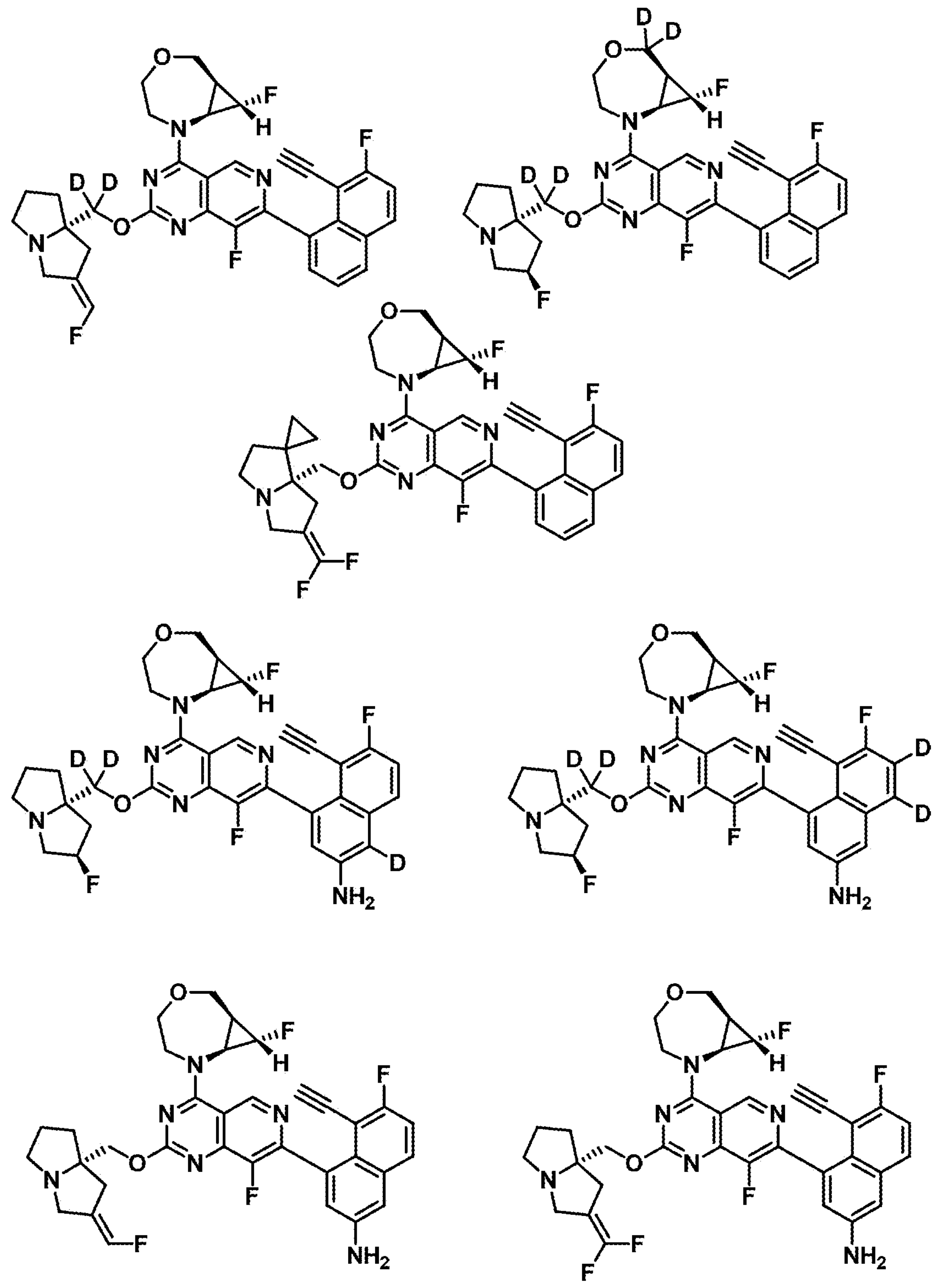
FIG. 22 provides additional structures of compounds of Formula (I)
Figure 23:
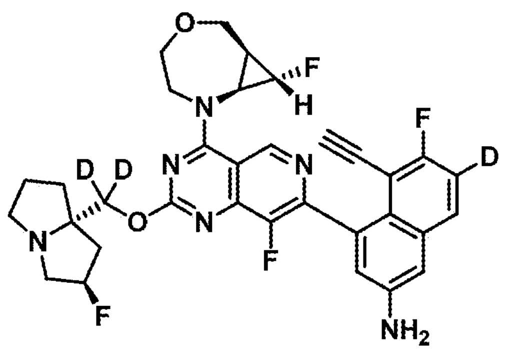
FIG. 23 provides additional structures of compounds of Formula (I)
Figure 23:
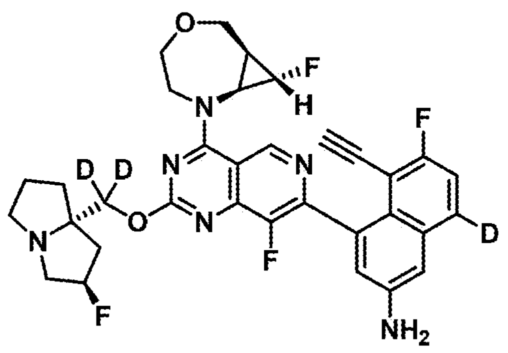
Figure 23:
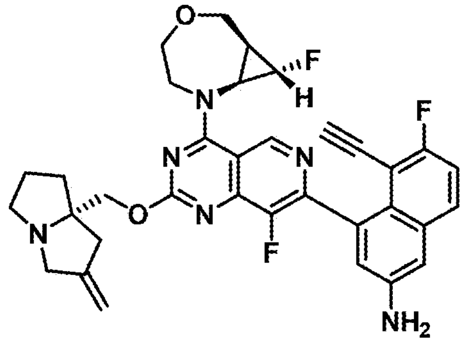
Figure 23:
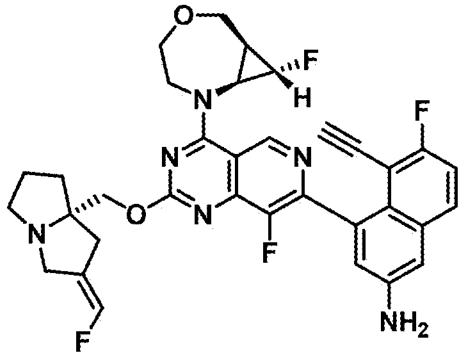
Figure 23:
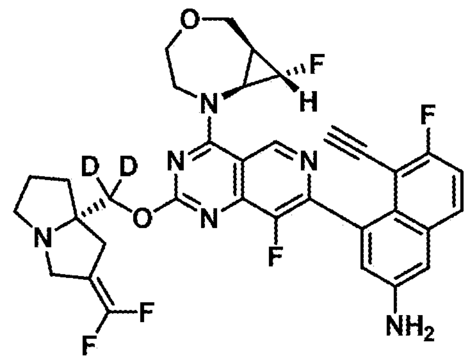
Figure 23:
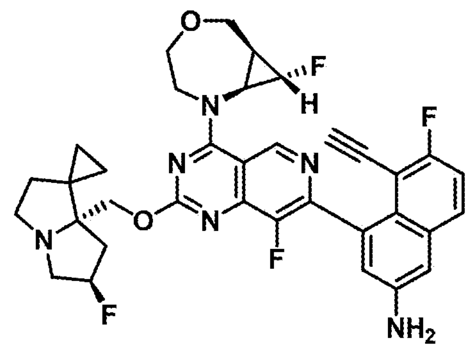
Figure 23:
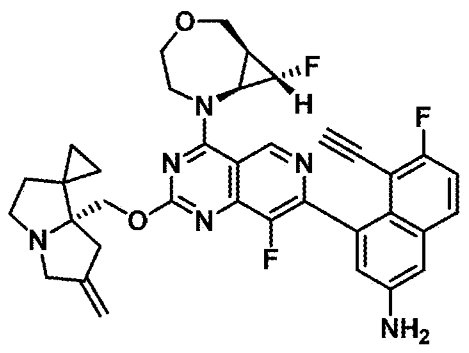
Figure 23:
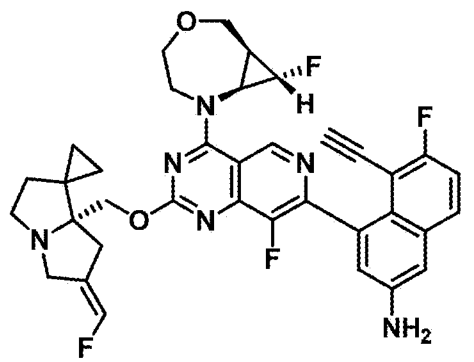
Figure 24:
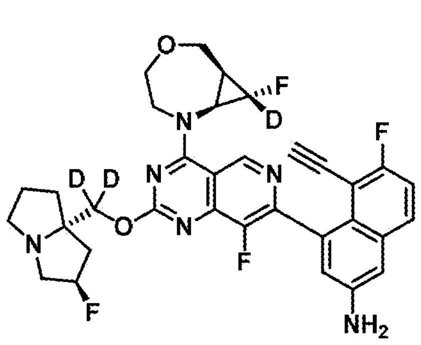
FIG. 24 provides additional structures of compounds of Formula (I)
Figure 24:
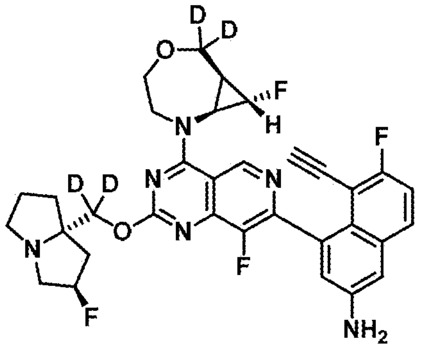
Figure 24:
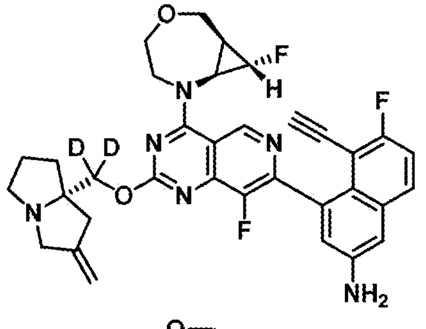
Figure 24:
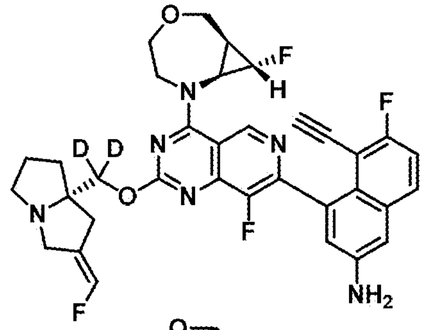
Figure 24:
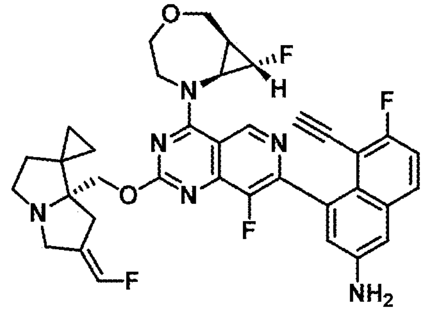
Figure 24:
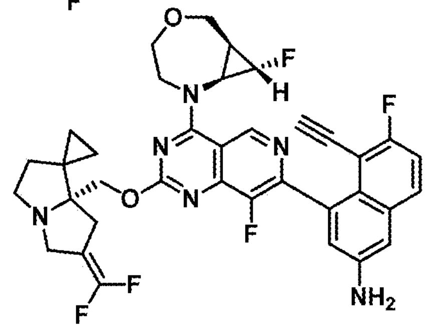
Figure 24:
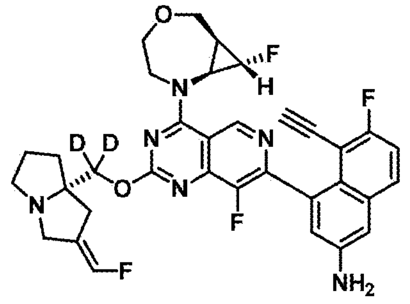
Figure 24:
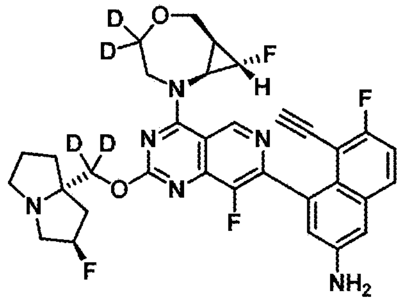
Figure 24:
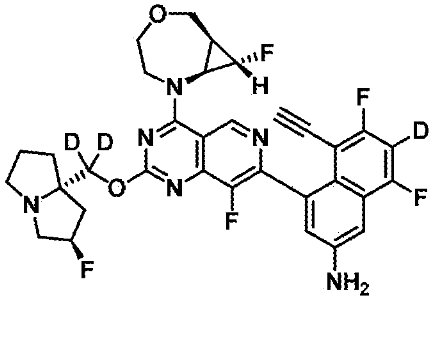
Figure 25:
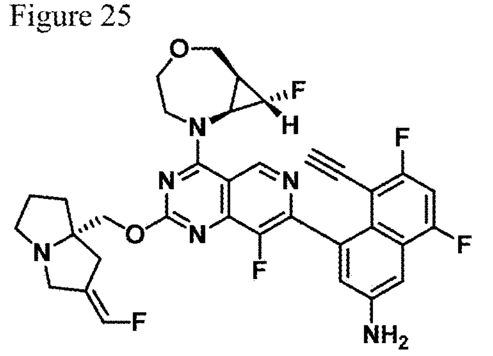
FIG. 25 provides additional structures of compounds of Formula (I)
Figure 25:
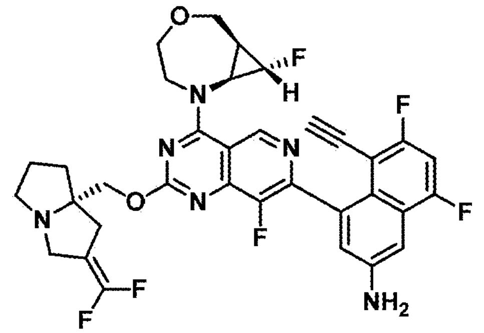
Figure 25:
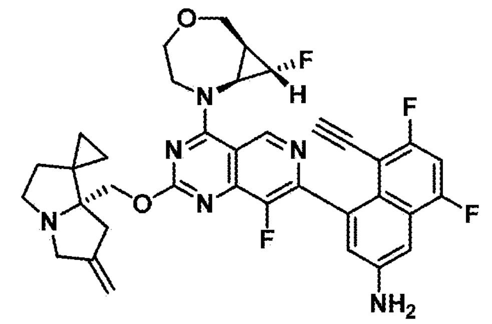
Figure 25:
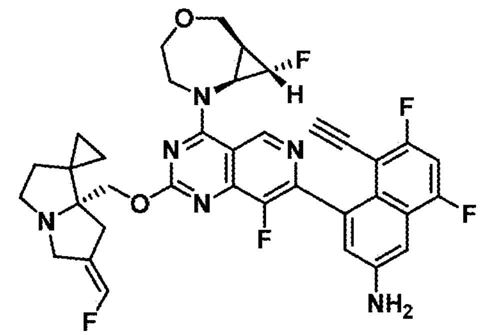
Figure 25:
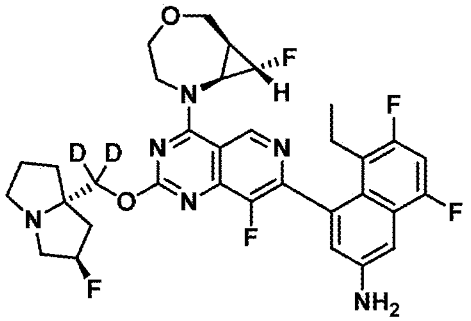
Figure 25:
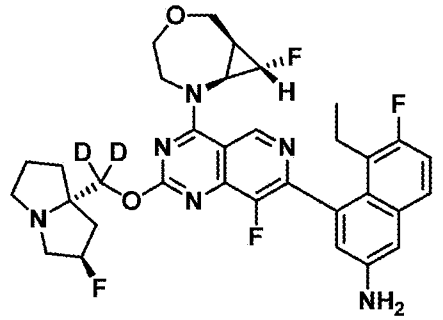
Figure 25:
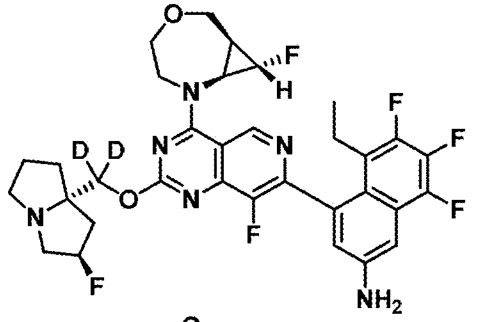
Figure 25:
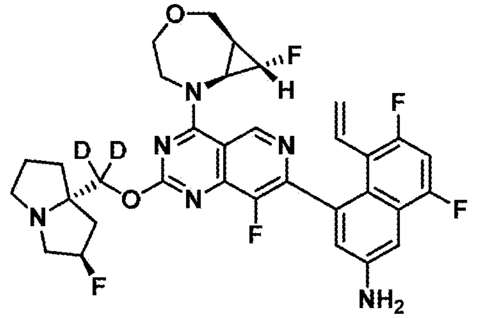
Figure 25:
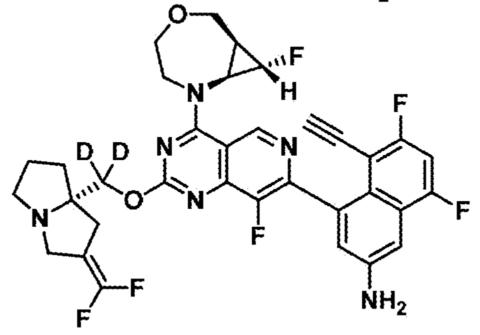
Figure 25:
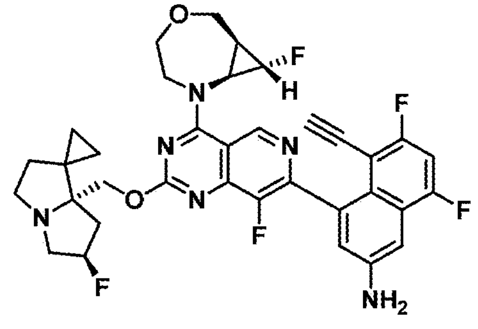
Figure 26:
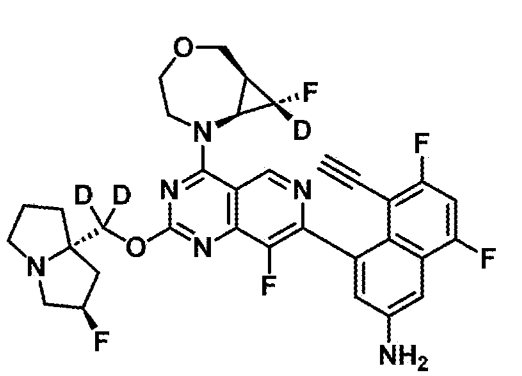
FIG. 26 provides additional structures of compounds of Formula (I).
Figure 26:
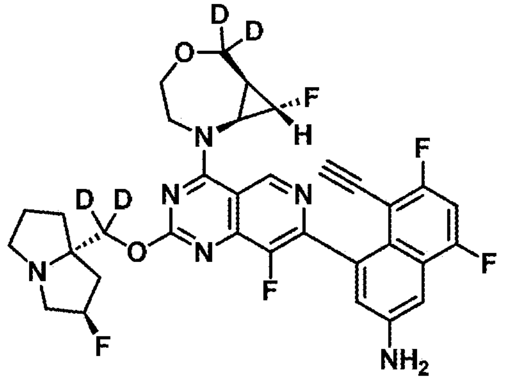
Figure 26:
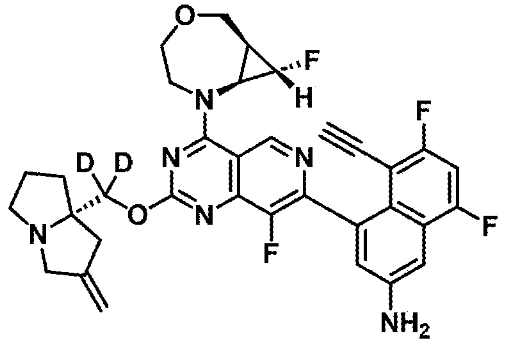
Figure 26:
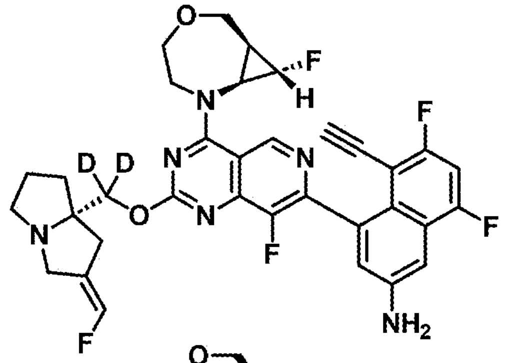
Figure 26:
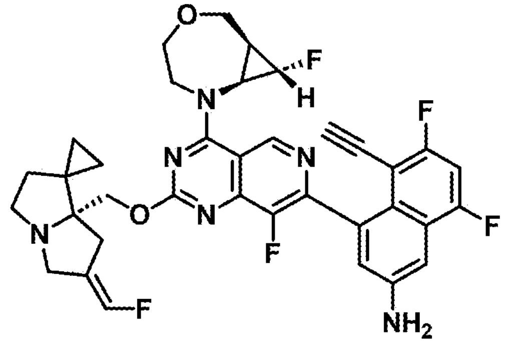
Figure 26:
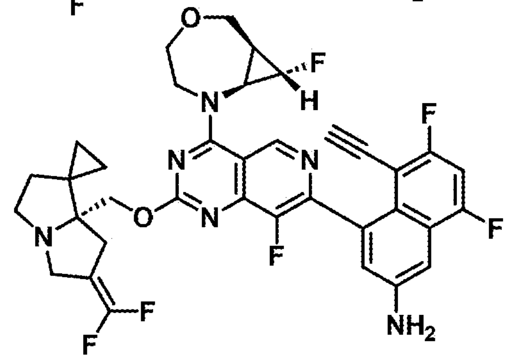
Figure 26:
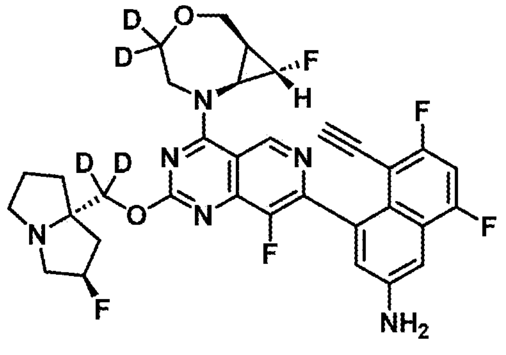
Figure 26:
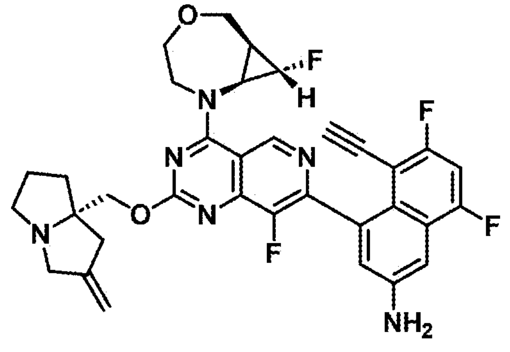

One embodiment provides a KRAS inhibitory compound, or a pharmaceutically acceptable salt or solvate thereof, having a structure presented in any one of FIGS. 1-26.

Preparation of Compounds

The compounds used in the synthetic chemistry reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Comwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCl America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R.V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J.C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the KRAS inhibitory compound described herein is administered as a pure chemical. In other embodiments, the KRAS inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, PA (2005)).

Provided herein is a pharmaceutical composition comprising at least one KRAS inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), or a pharmaceutically acceptable salt or solvate thereof.

One embodiment provides a method of preparing a pharmaceutical composition comprising mixing a compound of Formula (I), or a pharmaceutically acceptable salt or solvate thereof, and a pharmaceutically acceptable carrier.

In certain embodiments, the KRAS inhibitory compound as described by Formula (I), or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

One embodiment provides a pharmaceutical composition comprising a pharmaceutically acceptable excipient and a compound of Table 1, or a pharmaceutically acceptable salt or solvate thereof.

One embodiment provides a method of preparing a pharmaceutical composition comprising mixing a compound of Table 1, or a pharmaceutically acceptable salt or solvate thereof, and a pharmaceutically acceptable carrier.

In certain embodiments, the KRAS inhibitory compound as described by Table 1, or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose, or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21st Ed. Mack Pub. Co., Easton, PA (2005)).

In some embodiments, the KRAS inhibitory compound as described by Formula (I), Formula (Ia), or Table 1, or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one KRAS inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 0.01 mg to about 1000 mg, one to four times, or more, per day.

Methods of Treatment

One embodiment provides a compound of Formula (I), or a pharmaceutically acceptable salt or solvate thereof, for use in a method of treatment of the human or animal body. One embodiment provides a compound of Formula (Ia), or a pharmaceutically acceptable salt or solvate thereof, for use in a method of treatment of the human or animal body. One embodiment provides a compound of Formula (Ib), or a pharmaceutically acceptable salt or solvate thereof, for use in a method of treatment of the human or animal body. One embodiment provides a compound of Formula (Ic), or a pharmaceutically acceptable salt or solvate thereof, for use in a method of treatment of the human or animal body. One embodiment provides a compound of Formula (Id), or a pharmaceutically acceptable salt or solvate thereof, for use in a method of treatment of the human or animal body.

One embodiment provides a compound of Formula (I), or a pharmaceutically acceptable salt or solvate thereof, for use in a method of treating cancer. One embodiment provides a compound of Formula (Ia), or a pharmaceutically acceptable salt or solvate thereof, for use in a method of treating cancer.

One embodiment provides a compound of Formula (Ib), or a pharmaceutically acceptable salt or solvate thereof, for use in a method of treating cancer. One embodiment provides a compound of Formula (Ic), or a pharmaceutically acceptable salt or solvate thereof, for use in a method of treating cancer. One embodiment provides a compound of Formula (Id), or a pharmaceutically acceptable salt or solvate thereof, for use in a method of treating cancer. One embodiment provides the method of treating cancer wherein the cancer is lung adenocarcinoma.

One embodiment provides a use of a compound of Formula (I), or a pharmaceutically acceptable salt or solvate thereof, in the manufacture of a medicament for the treatment of cancer. One embodiment provides a use of a compound of Formula (Ia), or a pharmaceutically acceptable salt or solvate thereof, in the manufacture of a medicament for the treatment of cancer. One embodiment provides a use of a compound of Formula (Ib), or a pharmaceutically acceptable salt or solvate thereof, in the manufacture of a medicament for the treatment of cancer. One embodiment provides a use of a compound of Formula (Ic), or a pharmaceutically acceptable salt or solvate thereof, in the manufacture of a medicament for the treatment of cancer. One embodiment provides a use of a compound of Formula (Id), or a pharmaceutically acceptable salt or solvate thereof, in the manufacture of a medicament for the treatment of cancer. One embodiment provides the use wherein the cancer is lung adenocarcinoma.

In some embodiments is provided a method of treating cancer, in a patient in need thereof, comprising administering to the patient a compound of Formula (I), or a pharmaceutically acceptable salt or solvate thereof. In some embodiments is provided a method of treating cancer, in a patient in need thereof, comprising administering to the patient a pharmaceutical composition comprising a compound of Formula (I), or a pharmaceutically acceptable salt or solvate thereof, and a pharmaceutically acceptable excipient. One embodiment provides the method of treating cancer wherein the cancer is lung adenocarcinoma.

In some embodiments is provided a method of treating cancer, in a patient in need thereof, comprising administering to the patient a compound of Formula (Ia), or a pharmaceutically acceptable salt or solvate thereof. In some embodiments is provided a method of treating cancer, in a patient in need thereof, comprising administering to the patient a pharmaceutical composition comprising a compound of Formula (Ia), or a pharmaceutically acceptable salt or solvate thereof, and a pharmaceutically acceptable excipient. One embodiment provides the method of treating cancer wherein the cancer is lung adenocarcinoma.

In some embodiments is provided a method of treating cancer, in a patient in need thereof, comprising administering to the patient a compound of Formula (Ib), or a pharmaceutically acceptable salt or solvate thereof. In some embodiments is provided a method of treating cancer, in a patient in need thereof, comprising administering to the patient a pharmaceutical composition comprising a compound of Formula (Ib), or a pharmaceutically acceptable salt or solvate thereof, and a pharmaceutically acceptable excipient. One embodiment provides the method of treating cancer wherein the cancer is lung adenocarcinoma.

In some embodiments is provided a method of treating cancer, in a patient in need thereof, comprising administering to the patient a compound of Formula (Ic), or a pharmaceutically acceptable salt or solvate thereof. In some embodiments is provided a method of treating cancer, in a patient in need thereof, comprising administering to the patient a pharmaceutical composition comprising a compound of Formula (Ic), or a pharmaceutically acceptable salt or solvate thereof, and a pharmaceutically acceptable excipient. One embodiment provides the method of treating cancer wherein the cancer is lung adenocarcinoma.

In some embodiments is provided a method of treating cancer, in a patient in need thereof, comprising administering to the patient a compound of Formula (Id), or a pharmaceutically acceptable salt or solvate thereof. In some embodiments is provided a method of treating cancer, in a patient in need thereof, comprising administering to the patient a pharmaceutical composition comprising a compound of Formula (Id), or a pharmaceutically acceptable salt or solvate thereof, and a pharmaceutically acceptable excipient. One embodiment provides the method of treating cancer wherein the cancer is lung adenocarcinoma.

One embodiment provides a compound of Table 1, or a pharmaceutically acceptable salt or solvate thereof, for use in a method of treatment of the human or animal body.

One embodiment provides a compound of Table 1, or a pharmaceutically acceptable salt or solvate thereof, for use in a method of treating cancer. One embodiment provides the method of treating cancer wherein the cancer is lung adenocarcinoma.

In some embodiments is provided a method of treating cancer, in a patient in need thereof, comprising administering to the patient a compound of Table 1, or a pharmaceutically acceptable salt or solvate thereof. In some embodiments is provided a method of treating cancer, in a patient in need thereof, comprising administering to the patient a pharmaceutical composition comprising a compound of Table 1, or a pharmaceutically acceptable salt or solvate thereof, and a pharmaceutically acceptable excipient. One embodiment provides the method of treating cancer wherein the cancer is lung adenocarcinoma.

One embodiment provides a use of a compound of Table 1, or a pharmaceutically acceptable salt or solvate thereof, in the manufacture of a medicament for the treatment of cancer. One embodiment provides the use wherein the cancer is lung adenocarcinoma.

Provided herein is the method wherein the pharmaceutical composition is administered orally. Provided herein is the method wherein the pharmaceutical composition is administered by injection.

One embodiment provides a method of inhibiting KRAS protein activity comprising contacting the KRAS protein with a compound of Formula (I), Formula (Ia), Formula (Ib), Formula (Ic), Formula (Id), or Table 1. Another embodiment provides the method of inhibiting KRAS protein activity, wherein the KRAS protein is contacted in an in vivo setting. Another embodiment provides the method of inhibiting KRAS protein activity, wherein the KRAS protein is contacted in an in vitro setting.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the KRAS inhibitory compounds disclosed herein are synthesized according to the following examples. As used below, and throughout the description of the invention, the following abbreviations, unless otherwise indicated, shall be understood to have the following meanings:

ACN acetonitrile
° C. degrees Celsius
δH chemical shift in parts per million downfield from tetramethylsilane
DCM dichloromethane ($CH_2Cl_2$)
DIAD diisopropyl azodicarboxylate
DIEA diisopropylethylamine
DMF dimethylformamide
DMSO dimethylsulfoxide
EA ethyl acetate
EtOAc ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
μ micro
m multiplet (spectral); meter(s); milli
M molar
$M^+$ parent molecular ion
Me methyl
MsCl methanesulfonyl chloride
MHz megahertz
min minute(s)
mol mole(s); molecular (as in mol wt)
mL milliliter
MS mass spectrometry
nm nanometer(s)
NMR nuclear magnetic resonance
pH potential of hydrogen; a measure of the acidity or basicity of an aqueous solution
PE petroleum ether
RT room temperature
s singlet (spectral)
t triplet (spectral)
SFC Supercritical fluid chromatography
T temperature
TFA trifluoroacetic acid
THE tetrahydrofuran
TPP Triphenylphosphine Intermediate 1 & 2:
Benzyl 6,7-dihydro-5H-1,4-oxazepine-4-carboxylate & benzyl 3,7-dihydro-2H-1,4-oxazepine-4-carboxylate

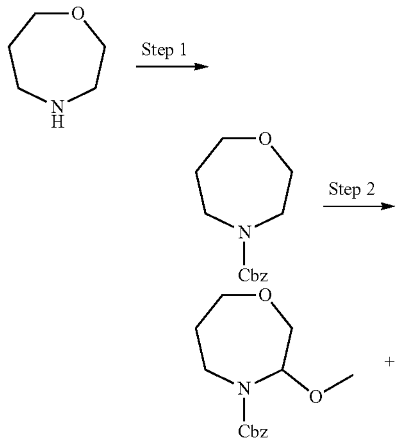

-continued

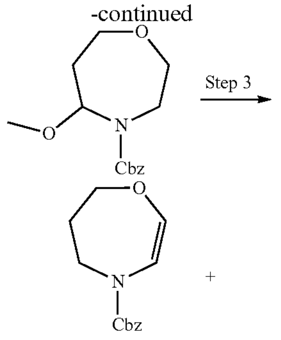

Intermediate 1

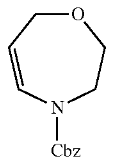

Intermediate 2

Step 1: Benzyl 1,4-oxazepane-4-carboxylate

To an ice-cooled mixture of 1,4-oxazepane (20 g, 197.73 mmol) and $K_2CO3$ (54.65 g, 395.45 mmol) in THF (200 mL) under nitrogen atmosphere was added Cbz-$C_1$ (40.47 g, 237.27 mmol) dropwise at room temperature. The ice bath was removed, and the resulting mixture was stirred at room temperature for 16 hours. The resulting mixture was quenched with saturated aq. $NaHCO_3$ (300 mL) and extracted with ethyl acetate (3×300 mL). The combined organic layers were washed with brine (500 mL), dried over anhydrous sodium sulfate, filtered, and concentrated under reduced pressure. The residue was purified by silica gel flash chromatography, eluted with 35% EA in PE to afford the title compound (44 g, 94% yield) as a colorless oil. MS: m/z=236.05 $[M+H]^+$. $^1$H NMR (400 MHz, Chloroform-d) δ 7.39-7.29 (m, 5H), 5.15 (s, 2H), 3.75-3.56 (m, 8H), 1.93-1.79 (m, 2H).

Step 2: Benzyl 3-methoxy-1,4-oxazepane-4-carboxylate & benzyl 5-methoxy-1,4-oxazepane-4-carboxylate To a solution of benzyl 1,4-oxazepane-4-carboxylate (40 g, 170.00 mmol) in MeOH (200 mL) was added tetraethylammonium tosylate (25.62 g, 85.00 mmol) at room temperature. The reaction mixture was electrolysis with C(+) I C(−) electrodes at constant current 200 mA. The resulting mixture was stirred at 20° C. for 72 hours. The resulting mixture was concentrated under reduced pressure. The residue was purified by silica gel flash chromatography, eluted 35% EA in PE to afford a mixture of the title compounds (37 g, 82.03%) as a light-yellow oil. $^1$H NMR (400 MHz, Chloroform-d) § 7.39-7.31 (m, 5H), 5.53-5.09 (m, 3H), 4.12-3.20 (m, 9H), 2.72-2.22 (m, 1H), 2.12-1.24 (m, 1H).

Step 3: Benzyl 6,7-dihydro-5H-1,4-oxazepine-4-carboxylate & benzyl 3,7-dihydro-2H-1,4-oxazepine-4-carboxylate To an ice-cooled solution of benzyl 3-methoxy-1,4-oxazepane-4-carboxylate and benzyl 5-methoxy-1,4-oxazepane-4-carboxylate (8.3 g, 31.28 mmol) in DCM (830 mL) were added DIEA (4.85 g, 37.54 mmol) and TMSOTf (8.34 g, 37.54 mmol 1.2) under nitrogen atmosphere. The reaction mixture was stirred in an ice bath for 0.5 hour. The solid was filtered out, and the filter cake was washed with hexane (1660 mL). The filtrate was concentrated under reduced pressure. The residue was purified by silica gel flash chromatography, cluted with 42% EA in PE to afford two peaks. The first eluting peak was collected and concentrated under reduced pressure to afford the title compound (Intermediate 1, 2.18 g, 29% yield) as a yellow solid. $^1$H NMR (400 MHz, Chloroform-d) § 7.40-7.29 (m, SH), 5.96-5.74 (m, 2H), 5.18 (s, 2H), 4.11-4.07 (m, 2H), 3.84-3.87 (m, 2H), 2.04-1.94 (m, 2H). The second eluting peak was collected and concentrated under reduced pressure to afford the title compound (Intermediate 2, 2.52 g, 34% yield) as a yellow solid. $^1$H NMR (400 MHZ, Chloroform-d) § 7.42-7.28 (m, 5H), 5.26-4.85 (m, 4H), 4.22-4.20 (m, 2H), 3.93-3.70 (m, 4H).

Intermediate 3: 6-(2,7-Dichloro-8-fluoropyrido[4,3-d] pyrimidin-4-yl)-2-oxa-6-azabicyclo[5.1.0]octane

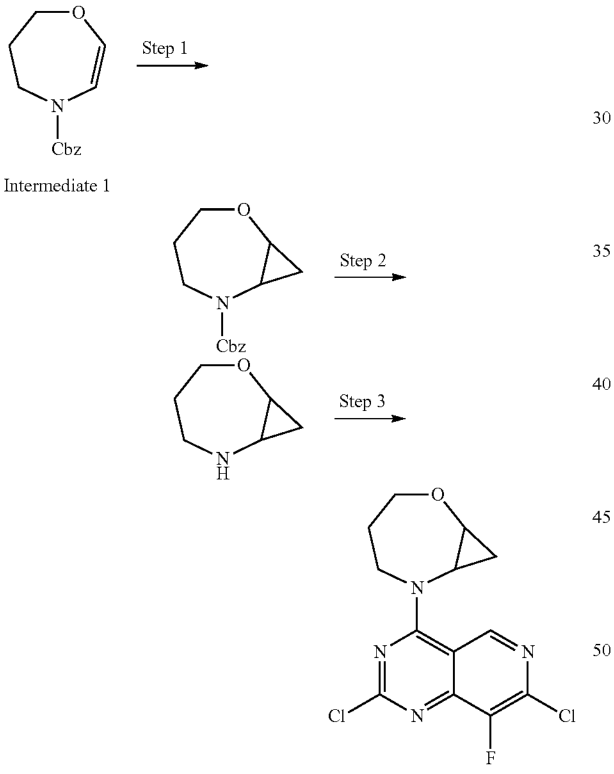

Intermediate 3

Step 1: Benzyl 2-oxa-6-azabicyclo[5.1.0]octane-6-carboxylate

To a solution of Intermediate 1 (2.18 g, 9.35 mmol) in DCM (25 mL) was added ZnEt2 (24.93 mL, 24.93 mmol, 1 M in n-hexane) at room temperature. The mixture was stirred at room temperature for 0.5 hours. A solution of diiodomethane (10.02 g, 37.40 mmol) in DCM (12 mL) was added to the mixture dropwise in an ice bath, and the mixture was stirred at room temperature for 12 hours. The resulting mixture was poured into cold saturated aq. $NH_4Cl$ (100 mL), extracted with DCM (3×100 mL), washed with brine (100 mL), dried with anhydrous Na2SO4, filtered and concentrated under reduced pressure. The residue was purified by silica gel flash chromatography, eluted with 40% EA in PE to afford the title compound (1.8 g, 77% yield) as a yellow oil. MS: m/z=248.10 [M+H]$^+$. $^1$H NMR (400 MHz, Chloroform-d) § 7.38-7.28 (m, 5H), 5.29-5.07 (m, 2H), 4.18-3.92 (m, 2H), 3.69-3.63 (m, 1H), 3.42-3.39 (m, 1H), 3.16-3.10 (m, 1H), 2.45-2.40 (m, 1H), 1.91-1.74 (m, 2H), 1.46-1.10 (m, 2H).

Step 2: 2-Oxa-6-azabicyclo[5.1.0]octane

To an ice-cooled solution of benzyl 2-oxa-6-azabicyclo[5.1.0]octane-6-carboxylate (4 g, 16.17 mmol) in MeOH (200 mL) was added Pd/C(1.3 g, 10 wt %) under nitrogen atmosphere. The resulting mixture was stirred in an ice bath for 40 min under hydrogen atmosphere. The resulting mixture was filtered and concentrated under reduced pressure to afford the title compound (1.55 g, crude used through) as a light yellow oil.

Step 3: 6-(2,7-Dichloro-8-fluoropyrido[4,3-d]pyrimidin-4-yl)-2-oxa-6-azabicyclo[5.1.0]octane To a stirred solution of 2,4,7-trichloro-8-fluoropyrido[4,3-d]pyrimidine (3.46 g, 13.70 mmol) and 2-oxa-6-azabicyclo[5.1.0]octane (1.55 g, crude) in DCM (40 mL) was added DIEA (5.31 g, 41.11 mmol) dropwise at −40° C. under nitrogen atmosphere. The resulting mixture was stirred for 1 hour at −40° C. The mixture was diluted with 10% citric solution (50 mL) and extracted with DCM (3×100 mL). The combined organic layers were washed with brine (100 mL), dried over anhydrous $Na_2SO_4$, filtered and concentrated under reduced pressure to afford the title compound (Intermediate 3, 4 g, crude) as a light-yellow solid. MS: m/z=329.00, 331.00 [M+H]$^+$.

Intermediate 4 & 5: (1R,7S)-6-(7-chloro-8-fluoro-2-(((2R,7aS)-2-fluorotetrahydro-1H-pyrrolizin-7a(5H)-yl)methoxy-d$_2$)pyrido[4,3-d]pyrimidin-4-yl)-2-oxa-6-azabicyclo[5.1.0]octane & (1S,7R)-6-(7-chloro-8-fluoro-2-(((2R,7aS)-2-fluorotetrahydro-1H-pyrrolizin-7a(5H)-yl)methoxy-d$_2$)pyrido[4,3-d]pyrimidin-4-yl)-2-oxa-6-azabicyclo[5.1.0]octane

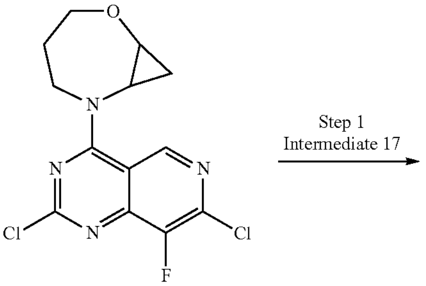

Intermediate 3

-continued

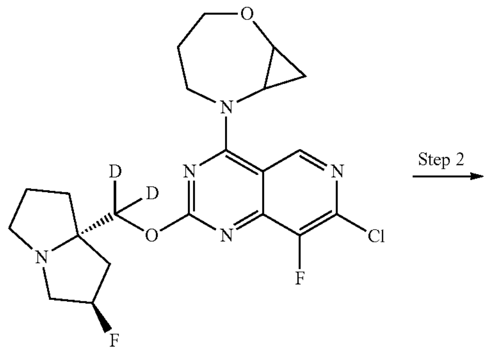

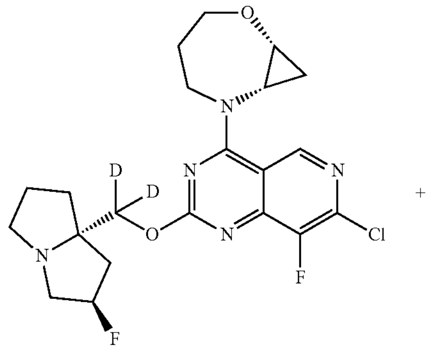

+

Intermediate 4

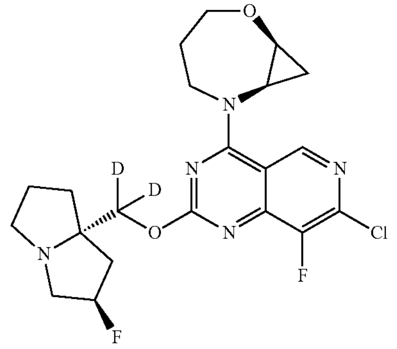

Intermediate 5

Step 1: 6-(7-Chloro-8-fluoro-2-(((2R,7aS)-2-fluoro-tetrahydro-1H-pyrrolizin-7a (5H)-yl) methoxy-d2) pyrido[4,3-d]pyrimidin-4-yl)-2-oxa-6-azabicyclo [5.1.0]octane To a stirred solution of Intermediate 3 (4 g, crude) in DMSO (40 mL) under nitrogen atmosphere were added KF (2.47 g, 42.53 mmol) and Intermediate 17 (3.13 g, 19.44 mmol) at room temperature. The resulting mixture was heated at 100° C. for 16 hours. The mixture was cooled to room temperature, diluted with water (50 mL), and extracted with DCM (3×100 mL). The combined organic layers were washed with brine (3×100 mL), dried over anhydrous $Na_2SO_4$, filtered and concentrated under reduced pressure. The residue was purified by silica gel flash chromatography, eluted with $CH_2Cl$/MeOH (10: 1) to afford the title compound (1.5 g, 20% yield for three steps) as a light yellow solid. MS: m/z=454.15 [M+H].

Step 2: (1R,7S)-6-(7-chloro-8-fluoro-2-(((2R,7aS)-2-fluorotetrahydro-1/-pyrrolizin-7a (5H)-yl) methoxy-d2)pyrido[4,3-d]pyrimidin-4-yl)-2-oxa-6-azabicyclo[5.1.0]octane & (1S,7R)-6-(7-chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-2-oxa-6-azabicyclo[5.1.0]octane The mixture of 6-(7-chloro-8-fluoro-2-(((2R,7aS)-2-fluorotetrahydro-1/-pyrrolizin-7a (5H)-yl) methoxy-d2)pyrido [4,3-d]pyrimidin-4-yl)-2-oxa-6-azabicyclo[5.1.0]octane (1.5 g, 3.30 mmol) was separated by Prep-SFC with the following conditions: Column: JW-Lux Cellulose-3, 4.6 x 50 mm, 3 um; Mobile Phase A: CO2; Mobile Phase B: MeOH; Flow rate: 100 mL/min; Gradient: isocratic 15% B; Back Pressure (bar): 100; RT1: 5.13 min; RT2: 7.47 min. The first eluting peak (RT1: 5.13 min) was concentrated and lyophilized to give the title compound (Intermediate 4, 495 mg, 33% yield) as a light yellow solid $^1$H NMR (400 MHZ, Chloroform-d) δ 9.10 (s, 1H), 5.36-5.23 (m, 1H), 4.68-4.65 (m, 1H), 4.02-3.99 (m, 1H), 3.78-3.72 (m, 2H), 3.55-3.49 (m, 1H), 3.36-3.22 (m, 3H), 3.13-2.99 (m, 2H), 2.43-2.17 (m, 4H), 1.99-1.70 (m, 4H), 1.39-1.33 (m, 1H), 0.79-0.75 (m, 1H). The second eluting peak (RT2: 7.47 min) was concentrated and lyophilized to give the title compound (Intermediate 5, 510 mg, 34% yield) as a light yellow solid. $^1$H NMR (400 MHz, Chloroform-d) δ 9.10 (s, 1H), 5.35-5.22 (m, 1H), 4.68-4.65 (m, 1H), 4.03-4.00 (m, 1H), 3.78-3.72 (m, 2H), 3.55-3.49 (m, 1H), 3.31-3.18 (m, 3H), 3.14-3.09 (m, 1H), 3.02-2.96 (m, 1H), 2.44-2.15 (m, 4H), 1.99-1.87 (m, 4H), 1.39-1.29 (m, 1H), 0.79-0.75 (m, 1H).

Intermediate 6: 4-(4-Azabicyclo[5.1.0]octan-4-yl)-2,7-dichloro-8-fluoropyrido[4,3-d]pyrimidine

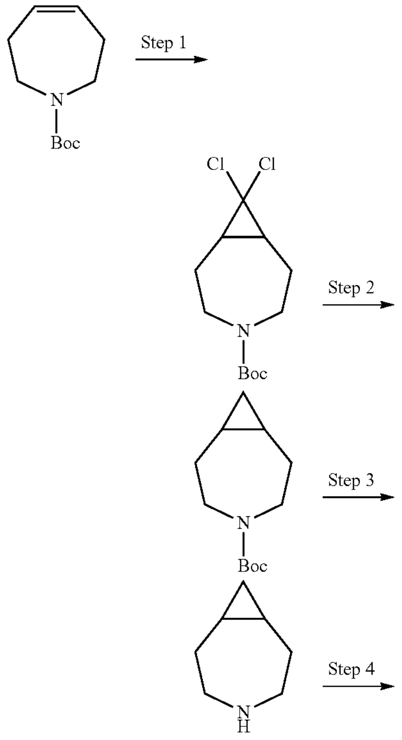

-continued

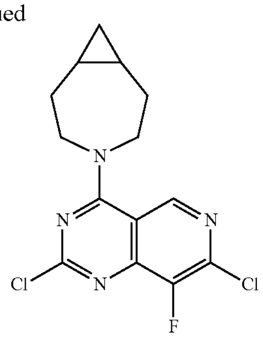

Intermediate 6

Step 1: tert-Butyl 8,8-dichloro-4-azabicyclo[5.1.0]octane-4-carboxylate

To a solution of tert-butyl 2,3,6,7-tetrahydro-1H-azepine-1-carboxylate (1 g, 5.07 mmol), benzyl (triethyl) ammonium chloride (23 mg, 101 umol) in $CHCl_3$ (12 mL) was added a solution of NaOH (661 mg, 16.5 mmol) in $H_2O$ (1.3 mL). The mixture was stirred at 35° C. for 16 h under $N_2$ atmosphere. The mixture was diluted with $H_2O$ (20 mL) and extracted with $CH_2C_{12}$ (10 mL×3). The combined organic layers were dried over $Na_2SO_4$, filtered and concentrated under reduced pressure. The residue was purified by silica gel flash chromatography (eluent: 0~3% of EtOAc in petroleum ether) to give the title compound (0.87 g, 88% yield) as a yellow oil. $^1$H NMR (400 MHZ, Chloroform-d) δ 4.07-3.81 (m, 2H), 3.02-2.82 (m, 2H), 2.35-2.25 (m, 2H), 1.87-1.74 (m, 2H), 1.67-1.60 (m, 2H), 1.44 (s, 9H).

Step 2: tert-Butyl 4-azabicyclo[5.1.0]octane-4-carboxylate

To a suspension of sodium debris (1.7 g, 76 mmol) in THF (15 mL) was degassed and purged with N2 three times. A solution of tert-butyl 8,8-dichloro-4-azabicyclo[5.1.0]octane-4-carboxylate (330 mg, 1.18 mmol) in MeOH (6 mL) and THF (6 mL) was added dropwise to the mixture at 25° C. to 40° C. under $N_2$. The reaction mixture was stirred at 25° C. for 2 h under $N_2$ atmosphere. The reaction mixture was quenched slowly with sat. $NH_4Cl$ aq. (50 mL) at 0° C. and extracted with EtOAc (30 mL×3). The combined organic layers were washed with saturate brine (80 mL), dried over $Na_2SO_4$, filtered and concentrated under reduced pressure. The residue was purified by silica gel flash chromatography (eluent: 0~4% of EtOAc in petroleum ether) to give the title compound (204 mg, 82% yield) as a colorless oil. $^1$H NMR (400 MHZ, Chloroform-d) δ 3.52 (s, 2H), 3.22-3.13 (m, 2H), 2.21 (s, 2H), 1.43 (s, 9H), 1.41-1.31 (m, 2H), 1.00-0.89 (m, 2H), 0.68-0.61 (m, 1H), 0.25-0.19 (m, 1H)

Step 3: 4-Azabicyclo[5.1.0]octane

To a solution of tert-butyl 4-azabicyclo[5.1.0]octane-4-carboxylate (204 mg, 965 umol) in HCl (2M in EtOAc, 4 mL) was stirred at 25° C. for 0.5 h. The reaction mixture was concentrated under reduced pressure to give the title compound (143 mg, crude, HCl) as a white solid, which was used in the next step without further purification.

Step 4: 4-(4-Azabicyclo[5.1.0]octan-4-yl)-2,7-dichloro-8-fluoropyrido[4,3-d]pyrimidine To a solution of 2,4,7-trichloro-8-fluoropyrido[4,3-d]pyrimidine (245 mg, 969 umol), DIPEA (674.80 μL, 3.87 mmol) in $CH_2Cl_2$ (5 mL) was added 4-azabicyclo[5.1.0]octane (143 mg, 969 umol, HCl) at −40° C. under $N_2$ atmosphere. The reaction mixture was stirred at −40° C. for 0.5 h under $N_2$ atmosphere. The reaction mixture was diluted with water (10 mL) and extracted with EtOAc (20 mL×2). The combined organic layers were washed with brine (20 mL×2), dried over anhydrous $Na_2SO_4$, filtered and concentrated under reduced pressure to give the compound title compound (Intermediate 6, 253 mg, crude) as a yellow solid, which was used in the next step without further purification. MS: m/z=327.0 $[M+H]^{+}$.

Intermediate 7: tert-Butyl 2,3,4,5-tetrahydro-1H-azepine-1-carboxylate

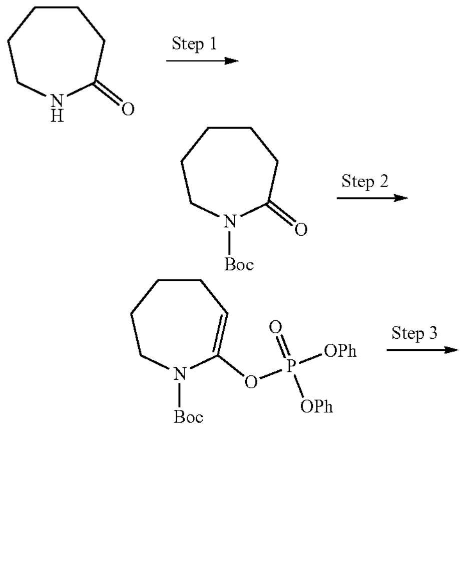

Intermediate 7

Step 1: tert-Butyl 2-oxoazepane-1-carboxylate

To a solution of azepan-2-one (40 g, 353 mmol) and $(Boc)_2O$ (84.9 g, 389 mmol) in dry THF (400 mL) was added DMAP (47.5 g, 389 mmol). The mixture was stirred at 25° C. for 3 h. TLC indicated that azepan-2-one was consumed completely and one new spot formed (PE/EA=3:1, Rf=0.5, color developing reagent: ninhydrin). The reaction mixture was diluted with water (500 mL) and extracted with EtOAc (300 mL×3). The combined organic layers were washed with brine (200 mL), dried over anhydrous $Na_2SO_4$, filtered and concentrated under reduced pressure. The residue was purified by silica gel flash chromatography (eluent: 0~30% EtOAc in Petroleum ether) to give the title compound (75 g, 99% yield) as an off-white oil. $^1$H NMR (400 MHz, CDCL) δ 3.76 (s, 2H), 2.67-2.60 (m, 2H), 1.80-1.68 (m, 6H), 1.51 (s, 9H).

Step 2: tert-Butyl 7-((diphenoxyphosphoryl)oxy)-2,3,4,5-tetrahydro-1/-azepine-1-carboxylate To a solution of tert-butyl 2-oxoazepane-1-carboxylate (68 g, 319 mmol) in THF (1500 mL) were added dropwise TMEDA (44.5 g, 383 mmol) and LDA (2 M, 191 mL) at −78° C. under $N_2$. The mixture was stirred at this temperature for 2 h. Diphenyl phosphorochloridate (103 g, 383 mmol) was added dropwise at −78° C. under $N_2$. The resulting mixture was stirred at −78° C. for 3 h. TLC indicated that tert-butyl 2-oxoazepane-1-carboxylate was consumed completely and one new spot formed (PE/EA=5: 1, Rr=0.76, color developing reagent: ninhydrin). The reaction mixture was diluted with sat. $NH_4Cl$ ag. (500 ml) and extracted with EtOAc (300 mL×3). The combined organic layers were washed with brine (200 mL), dried over anhydrous $Na_2SO_4$, filtered and concentrated under reduced pressure. The residue was purified by silica gel flash chromatography (cluent: 0~10% EtOAc in Petroleum ether) to give the title compound (85 g, 60% yield) as a yellow oil. $^1H$ NMR (400 MHZ, $CDCl_3$) δ 7.41-7.28 (m, 4H), 7.27-7.15 (m, 6H), 5.42 (t, J=2.8, 6.4 Hz, 1H), 3.93-3.07 (m, 2H), 2.14-1.99 (m, 2H), 1.73 (dd, J=5.6, 11.2 Hz, 2H), 1.58-1.48 (m, 2H), 1.41 (s, 9H).

Step 3: tert-Butyl 2,3,4,5-tetrahydro-1/-azepine-1-carboxylate

To a solution of tert-butyl 7-((diphenoxyphosphoryl)oxy)-2,3,4,5-tetrahydro-1/-azepine-1-carboxylate (58 g, 130 mmol) in DME (600 mL) were added triphenylphosphane (2.73 g, 10.4 mmol) and Pd $(OAc)_2$ (1.17 g, 5.21 mmol) at 25° C. under $N_2$. TEA (39.5 g, 391 mmol) and formic acid (5.99 g, 130 mmol) in DME (400 mL) were added dropwise to the mixture at 25° C. under $N_2$. The mixture was stirred at 84° C. for 40 min under $N_2$. TLC indicated one new spot formed (PE/EA=5: 1, R (=0.81, color developing reagent: ninhydrin). The reaction mixture was diluted with water (500 mL) and extracted with EtOAc (300 mL×3). The combined organic layers were washed with brine (200 mL), dried over anhydrous $Na_2SO_4$, filtered and concentrated under reduced pressure. The residue was purified by silica gel flash chromatography (eluent: 0~10% EtOAc in Petroleum ether) to give the title compound (Intermediate 7, 20 g, 78% yield) as an off-white oil. $^1H$ NMR (400 MHZ, $CDCl_3$) δ 6.65-6.26 (m, 1H), 5.05-4.81 (m, 1H), 3.61 (s, 2H), 2.22-2.07 (m, 2H), 1.77-1.63 (m, 4H), 1.45 (s, 9H).

Intermediate 8: 4-(2-Azabicyclo[5.1.0]octan-2-yl)-2,7-dichloro-8-fluoropyrido[4,3-d]pyrimidine

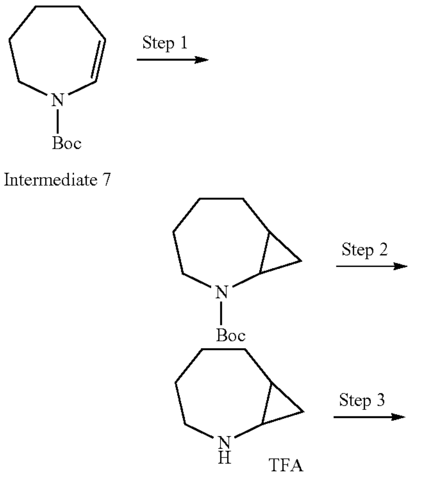

Intermediate 7

-continued

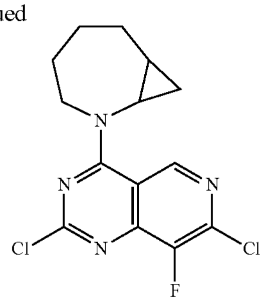

Intermediate 8

Step 1: tert-Butyl 2-azabicyclo[5.1.0]octane-2-carboxylate

To a solution of Intermediate 7 (160 mg, 760 μmol) in $CH_2Cl_2$ (3 mL) was added diethylzinc (1 M in n-hexane, 1.52 mL). The mixture was stirred at 0° C. for 0.5 h under $N_2$. A solution of $CH_2I_2$ (815 mg, 3.04 mmol) in $CH_2Cl_2$ (1.5 mL) was added to the mixture dropwise at 0° C. under $N_2$. The mixture was stirred at 20° C. for 2 h. The reaction mixture was diluted with sat $NH_4Cl$ aq (10 mL) and extracted with EtOAc (30 mL×3). The combined organic layers were washed with brine (20 mL), dried over anhydrous $Na_2SO_4$, filtered and concentrated under reduced pressure. The residue was purified by silica gel flash chromatography (eluent: 0~10% EtOAc in Petroleum ether) to give the title compound (120 mg, 75% yield) as a colorless oil. $^1H$ NMR (400 MHz, Dimethylsulfoxide-$d_6$) δ 3.86-3.72 (m, 1H), 2.92-2.76 (m, 2H), 2.22-2.11 (m, 1H), 1.72-1.58 (m, 2H), 1.38 (s, 11H), 0.99-0.88 (m, 3H), 0.55 (d, J=3.2 Hz, 1H)

Step 2: 2-Azabicyclo[5.1.0]octane

To a solution of tert-butyl 2-azabicyclo[5.1.0]octane-2-carboxylate (120 mg, 568 μmol) in $CH_2Cl_2$ (2 mL) was added TFA (2 mL) at 0° C. The mixture was stirred at 20° C. for 0.5 h. The mixture was concentrated under reduced pressure to give the title compound (100 mg, TFA salt) as a yellow oil, which was used in the next step without further purification.

Step 3: 4-(2-Azabicyclo[5.1.0]octan-2-yl)-2,7-dichloro-8-fluoropyrido[4,3-d]pyrimidine To a solution of 2,4,7-trichloro-8-fluoro-pyrido[4,3-d] pyrimidine (228 mg, 899 μmol) in $CH_2Cl_2$ (2 mL) were added DIPEA (581 g, 783 μL) and 2-azabicyclo[5.1.0] octane (100 mg, 899 μmol) at −40° C. under $N_2$. The mixture was stirred at −40° C. for 1 h. The reaction mixture was diluted with water (30 mL) and extracted with $CH_2Cl_2$ (30 mL×3). The combined organic layers were washed with brine (20 mL), dried over anhydrous $Na_2SO_4$, filtered and concentrated under reduced pressure to give the title compound (Intermediate 8, 150 mg, crude) as a yellow oil, which was used in the next step without further purification. MS: m/z=327.0 $[M+H]^{+\cdot}$ Intermediate 9: 7-Chloro-4-(8,8-difluoro-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidine

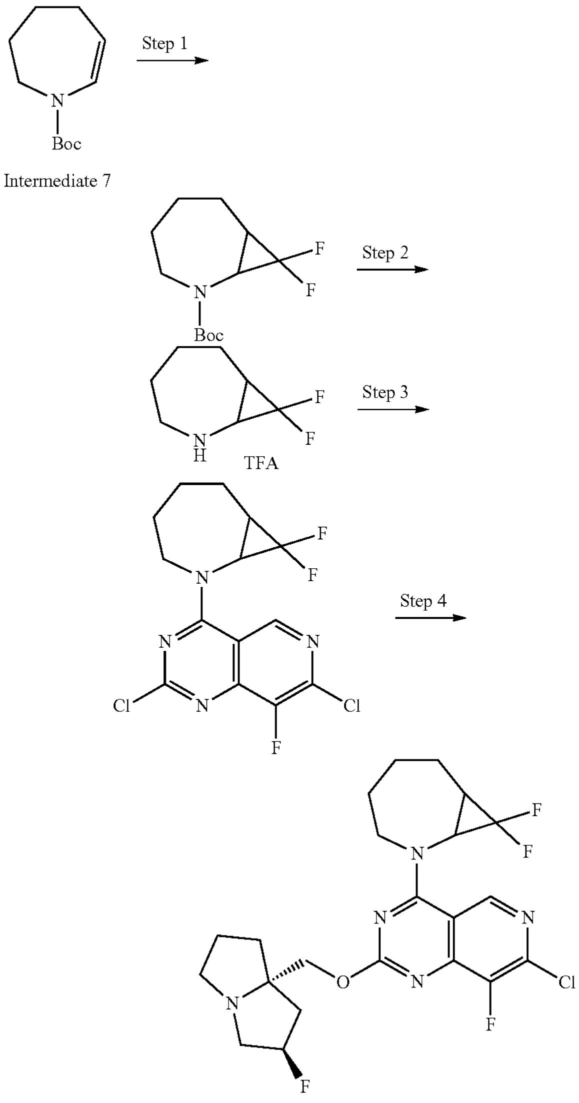

Intermediate 9

Step 1: terf-Butyl 8,8-difluoro-2-azabicyclo[5.1.0]octane-2-carboxylate

To a solution of Intermediate 7 (100 mg, 507 μmol) in THF (2 mL) were added NaI (760 mg, 5.07 mmol) and trimethyl (trifluoromethyl) silane (721 mg, 5.07 mmol). The mixture was stirred at 55° C. for 3 h. The reaction mixture was diluted with water (10 mL) and extracted with EtOAc (30 mL×3). The combined organic layers were washed with brine (20 mL), dried over anhydrous $Na_2SO_4$, filtered, and concentrated under reduced pressure. The residue was purified by silica gel flash chromatography (eluent: 0~10% EtOAc in Petroleum ether) to give the title compound (120 mg, 96% yield) as a colorless oil. $^1$H NMR (400 MHZ, Chloroform-d) δ 4.01 (d, J=11.2 Hz, 1H), 3.08-2.77 (m, 2H), 2.12-1.95 (m, 1H), 1.88-1.69 (m, 3H), 1.60-1.52 (m, 3H), 1.49-1.43 (m, 9H). $^{19}$F NMR (376 MHz, Chloroform-d) δ −127.71, −128.14, −149.06, −149.49.

Step 2: 8,8-Difluoro-2-azabicyclo[5.1.0]octane TFA salt

To a solution of tert-butyl 8,8-difluoro-2-azabicyclo[5.1.0]octane-2-carboxylate (600 mg, 2.43 mmol) in $CH_2Cl_2$ (15 mL) was added TFA (15 mL) at 0° C. The mixture was stirred at 20° C. for 0.5 h. The reaction mixture was concentrated under reduced pressure to give the title compound (600 mg, TFA, salt) as a yellow oil, which was used in the next step without further purification. $^1$H NMR (400 MHZ, Chloroform-d) δ 9.89-9.38 (m, 2H), 3.67 (d,)=13.2 Hz, 1H), 3.41 (t, J=10.0 Hz, 1H), 3.11 (t, J=12.8 Hz, 1H), 2.39-2.26 (m, 1H), 2.20-2.00 (m, 3H), 1.99-1.84 (m, 1H), 1.76-1.51 (m, 2H). $^{19}$F NMR (376 MHz, Chloroform-d) δ −126.76, −127.22, −148.98, −149.44.

Step 3: 2,7-Dichloro-4-(8,8-difluoro-2-azabicyclo[5.1.0]octan-2-yl)-8-fluoropyrido[4,3-d]pyrimidine To a solution of 2,4,7-trichloro-8-fluoro-pyrido[4,3-d]pyrimidine (580 mg, 2.30 mmol) in $CH_2Cl_2$ (10 mL) were added DIPEA (1.48 g, 2 mL) and 8,8-difluoro-2-azabicyclo[5.1.0]octane (600 mg, 2.30 mmol) at −40° C. under $N_2$. The mixture was stirred at −40° C. for 1 h. The reaction mixture was diluted with water (30 mL) and extracted with $CH_2Cl_2$ (30 mL×3). The combined organic layers were washed with brine (20 mL), dried over anhydrous $Na_2SO_4$, filtered and concentrated under reduced pressure to give the title compound (1 g, crude) as a yellow solid, which was used into the next step without further purification. MS: m/z=363.0 [M+H]$^+$. $^1$H NMR (400 MHz, Chloroform-d) & 9.20 (s, 1H), 4.54 (d, J=13.6 Hz, 1H), 3.86 (t, J=10.4 Hz, 1H), 3.44-3.33 (m, 1H), 2.33-2.15 (m, 2H), 2.07-2.04 (m, 1H), 1.90-1.84 (m, 1H), 1.68-1.51 (m, 2H), 1.50-1.46 (m, 1H), Step 4: 7-Chloro-4-(8,8-difluoro-2-azabicyclo[5.1.0]octan-2-yl)-8-fluoro-2-(((2R,7aS)-2-fluorotetrahydro-1/-pyrrolizin-7a (5H)-yl) methoxy)pyrido[4,3-d]pyrimidine To a solution of 2,7-dichloro-4-(8,8-difluoro-2-azabicyclo[5.1.0]octan-2-yl)-8-fluoropyrido[4,3-d]pyrimidine (1 g, 2.75 mmol) in 1,4-dioxane (10 mL) were added DIPEA (1.07 g, 1.44 mL) and ((2R,7aS)-2-fluorotetrahydro-1H-pyrrolizin-7a (5H)-yl) methanol (1.10 g, 6.88 mmol). The mixture was stirred at 110° C. for 16 hr. The mixture was concentrated under reduced pressure. The residue was purified by silica gel flash chromatography (eluent: 0~10% MeOH in $CH_2Cl_2$) to give the title compound (Intermediate 9, 880 mg, 62% yield over 3 steps) as a yellow solid. MS: m/z=486.2 [M+H]$^+$. $^1$H NMR (400 MHZ, Dimethylsulfoxide-$d_6$) δ 9.11 (s, 1H), 5.39-5.17 (m, 1H), 4.38-4.24 (m, 2H), 4.20-4.07 (m, 2H), 3.23-2.97 (m, 3H), 2.86-2.77 (m, 1H), 2.36-2.27 (m, 1H), 2.18-2.09 (m, 2H), 2.06-1.95 (m, 3H), 1.95-1.68 (m, 6H), 1.64-1.53 (m, 1H), 1.40-1.29 (m, 1H). $^{19}$F. NMR (376 MHz, Dimethylsulfoxide-$d_6$) δ−125.11, −136.40, −138.02, −145.97, −172.16.

Intermediate 10: 4-(3-Azabicyclo[5.1.0]octan-3-yl)-2,7-dichloro-8-fluoropyrido[4,3-d]pyrimidine

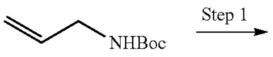

-continued

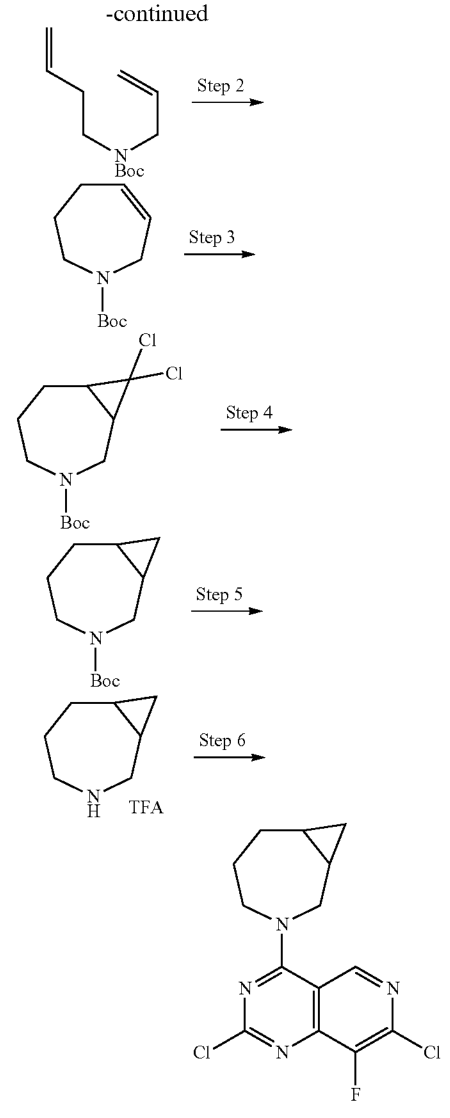

Intermediate 10

Step 1: ter-Butyl allyl (but-3-en-1-yl) carbamate

To a solution of NaH (3.82 g, 95.4 mmol, 60% purity) in DMF (65 mL) was added tert-butyl allylcarbamate (10 g, 63.6 mmol) in DMF (135 mL) dropwise at 0° C. under $N_2$. The mixture was stirred at 25° C. for 30 minutes, and 4-bromobut-1-ene (11.38 g, 76.3 mmol) in DMF (135 mL) was added dropwise to the mixture at 0° C. The reaction mixture was warmed to 25° C. and stirred at 25° C. for 0.5 h. The reaction mixture was quenched with sat. $NH_4Cl$ aq. (100 mL) at 0° C., warmed to 25° C. and stirred at 25° C. for 30 min. The reaction mixture was diluted with H2O (60 mL) and extracted with EtOAc (200 mL×3). The combined organic layers were washed with brine (400 mL), dried over $Na_2SO_4$, filtered and concentrated under reduced pressure. The residue was purified by silica gel flash chromatography (Eluent: 0~5% of EtOAc in petroleum ether) to give the title compound (15.6 g, 98% yield) as a colorless oil. $^1H$ NMR (400 MHz, Chloroform-d) δ 5.93-5.68 (m, 2H), 5.17-4.92 (m, 4H), 3.80 (s, 2H), 3.17 (s, 2H), 2.03 (q, J=6.8 Hz, 2H), 1.65-1.57 (m, 2H), 1.45 (s, 9H).

Step 2: tert-butyl 2,3,4,7-tetrahydro-1/-azepine-1-carboxylate

To a solution of tert-butyl allyl (but-3-en-1-yl) carbamate (10 g, 44.4 mmol) in $CH_2Cl_2$ (1500 mL) was added Grubb's II (3.77 g, 4.44 mmol) at 40° C. under $N_2$. The mixture was stirred at 40° C. for 2 h under $N_2$ atmosphere. The reaction mixture was concentrated under reduced pressure. The residue was purified by silica gel flash chromatography (Eluent: 0~10% of EtOAc in petroleum ether) to give the title compound (7.1 g, 81% yield) as a brown oil. $^1H$ NMR (400 MHz, Chloroform-d) δ 5.83-5.63 (m, 2H), 3.98-3.78 (m, 1H), 3.57-3.37 (m, 4H), 2.37-2.14 (m, 4H), 1.47-1.44 (m, 9H).

Step 3: tert-Butyl 8,8-dichloro-3-azabicyclo[5.1.0] octane-3-carboxylate

To a solution of tert-butyl 2,3,4,7-tetrahydro-1/-azepine-1-carboxylate (500 mg, 2.53 mmol) and BnNEtsCl (16 mg, 50.7 μmol) in CHCls (10 mL) was added a solution of NaOH (1.27 g, 31.7 mmol) in $H_2O$ (2.43 mL) dropwise at 25° C. The reaction mixture was stirred at 45° C. for 16 h. The mixture was diluted with sat. $NH_4Cl$ aq. (30 mL) and extracted with EtOAc (30 mL×3). The combined organic layers were dried over $Na_2SO_4$, filtered and concentrated under reduced pressure. The residue was purified by silica gel flash chromatography (Eluent: 0~7% of EtOAc in petroleum ether) to give the title compound (780 mg, 60% yield) as a colorless oil. $^1H$ NMR (400 MHz, Chloroform-d) δ 4.09-3.76 (m, 2H), 3.03-2.79 (m, 2H), 2.40-2.20 (m, 2H), 1.88-1.75 (m, 2H), 1.73-1.58 (m, 2H), 1.44 (s, 9H).

Step 4: tert-Butyl 3-azabicyclo[5.1.0]octane-3-carboxylate

To a suspension of sodium debris (1.56 g, 67.9 mmol) in THF (10 mL) was addded a solution of ter-butyl 8,8-dichloro-3-azabicyclo[5.1.0]octane-3-carboxylate (250 mg, 892 μmol) in MeOH (1 mL) dropwise at 0° C. under $N_2$ atmosphere. During the addition, the temperature was controlled between 0° C. and 25° C. The mixture was stirred at 25° C. for 3 h under $N_2$ atmosphere. MeOH was slowly added dropwise until the sodium metal disappearred completely while the temperature was controlled between 25° C. and 40° C. The reaction mixture was quenched with sat. $NH_4Cl$ aq. (50 mL) slowly at 0° C. and extracted with EtOAc (30 mL×3). The combined organic layers were washed with brine (80 mL), dried over $Na_2SO_4$, filtered and concentrated under reduced pressure. The residue was purified by silica gel flash chromatography (Eluent: 0~6% of EtOAc in petroleum ether) to give the title compound (130 mg, 69% yield) as a colorless oil. $^1H$ NMR (400 MHz, Chloroform-d) δ 3.69-3.40 (m, 2H), 3.28-3.10 (m, 2H), 2.26-2.16 (m, 2H), 1.49-1.39 (m, 11H), 1.02-0.90 (m, 2H), 0.71-0.60 (m, 1H), 0.22 (q, J=5.2 Hz, 1H).

Step 5: 3-Azabicyclo[5.1.0]octane, TFA salt

To a solution of tert-butyl 3-azabicyclo[5.1.0]octane-3-carboxylate (130 mg, 615 μmol) in $CH_2Cl_2$ (3 mL) was added TFA (0.5 mL, 6.73 mmol). The mixture was stirred at 25° C. for 1 h. The reaction mixture was concentrated under reduced pressure to give the title compound (138 mg, TFA salt) as a yellow gum.

Step 6: 4-(3-Azabicyclo[5.1.0]octan-3-yl)-2,7-dichloro-8-fluoropyrido[4,3-d]pyrimidine To solution of 2,4,7-trichloro-8-fluoropyrido[4,3-d]pyrimidine (139 mg, 550 μmol, 0.9 eq) and DIPEA (320 μL, 1.83 mmol) in $CH_2Cl_2$ (5 mL) at −40° C. was added 3-azabicyclo[5.1.0]octane (138 mg, 612 μmol, TFA salt). The mixture was stirred at −40° C. for 15 min. The reaction mixture was diluted with $H_2O$ (20 mL) and extracted with EtOAc (20 mL×2). The combined organic layers were washed with brine (20 mL), dried over $Na_2SO_4$, filtered and concentrated under reduced pressure to give the title compound (Intermediate 10, 170 mg, 62% yield over 2 steps) as a yellow solid. MS: m/z=326.8 $[M+H]^{+.}$ Intermediate 11 & 12: tert-Butyl 8-fluoro-2-azabicyclo[5.1.0]octane-2-carboxylate (trans mixture) & tert-butyl 8-fluoro-2-azabicyclo[5.1.0]octane-2-carboxylate (cis mixture)

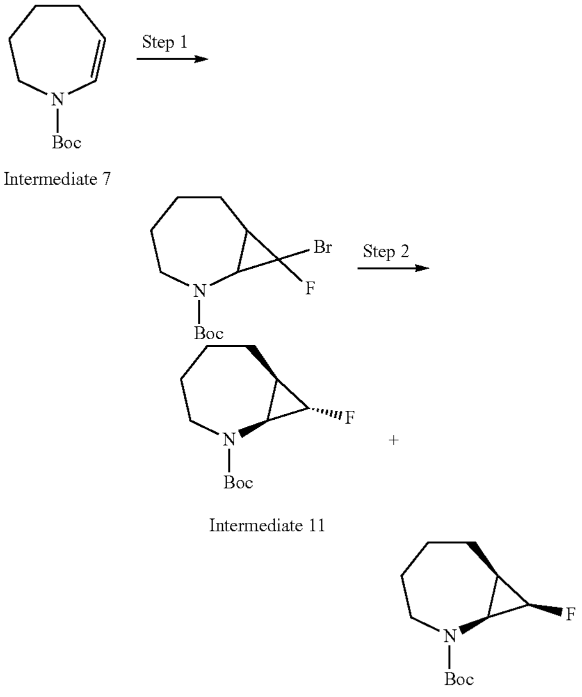

Intermediate 7

Intermediate 11

Intermediate 12

Step 1: tert-Butyl 8-bromo-8-fluoro-2-azabicyclo[5.1.0]octane-2-carboxylate

To a solution of NaOEt (7.93 g, 117 mmol) in $CH_2Cl_2$ (50 mL) was added dropwise a solution of tert-butyl 2,3,4,5-tetrahydro-1/-azepine-1-carboxylate (10 g, 50.7 mmol) and ethyl 2,2-dibromo-2-fluoroacetate (26.8 g, 101 mmol) in $CH_2Cl_2$ (50 mL) at 0° C. under $N_2$. The reaction mixture was stirred at 25° C. for 12 h. TLC indicated one new spot formed (PE/EA=5: 1, Rf=0.60, color developing reagent: ninhydrin). The residue was concentrated under reduced pressure. The residue was purified by silica gel flash chromatography (eluent: 0~10% EtOAc in Petroleum ether) to give the title compound (9 g, 58% yield) as a yellow oil. $^1H$ NMR (400 MHz, $CDCl_3$) δ 4.02-3.79 (m, 1H), 3.03-2.82 (m, 2H), 2.29-2.07 (m, 1H), 1.84-1.69 (m, 3H), 1.58-1.42 (m, 12H). $^{19}F$. NMR (376 MHZ, $CDCl_3$)-127.11, −157.44.

Step 2: tert-Butyl 8-fluoro-2-azabicyclo[5.1.0]octane-2-carboxylate (trans mixture) & tert-butyl 8-fluoro-2-azabicyclo[5.1.0]octane-2-carboxylate (cis mixture)

To a suspension of sodium debris (8.59 g, 374 mmol) in THF (40 mL) was added a solution of tert-butyl 8-bromo-8-fluoro-2-azabicyclo[5.1.0]octane-2-carboxylate (4 g, 13 mmol) in THF (20 mL) and MeOH (20 mL) at 25° C. under $N_2$ atmosphere. During the addition, the temperature was controlled between 25° C. and 40° C. Then the suspension was stirred at 25° C. for 3 h. MeOH was added dropwise till the sodium metal disappeared completely while the temperature was controlled between 25° C. and 40° C. TLC indicated two spots formed (PB: EA=10: 1, Rt=0.60 with FNMR=-205 and R. 0.55 with FNMR=-232, color developing reagent: ninhydrin). The reaction mixture was quenched slowly with sat. NHACl aq. (200 mL) at 0° C. and extracted with EtOAc (200 mL×3). The combined organic layers were washed with brine (60 mL), dried over anhydrous $Na_2SO_4$, filtered, and concentrated under reduced pressure. The residue was purified by silica gel flash chromatography (eluent: 0~10% EtOAc in Petroleum ether) to give the title compound (trans mixture) (Intermediate 11, 1.2 g, 40% yield) as an off-white oil and the title compound (cis mixture) (Intermediate 12, 900 mg, 30% yield) as an off-white oil. Spectra for Intermediate 11: $^1H$ NMR (400 MHZ, $CDCl_3$) δ=4.44 (s, 1H), 3.97 (s, 1H), 2.81 (dd, J=9.2, 18.8 Hz, 2H), 2.37-2.20 (m, 1H), 1.76-1.66 (m, 2H), 1.58-1.39 (m, 12H), 1.13-0.95 (m, 1H). $^{19}F$. NMR (376 MHz, $CDCl_3$) δ −205.16. Spectra for Intermediate 12: $^1H$ NMR (400 MHZ, CDCL) δ 4.59-4.23 (m, 1H), 3.95 (s, 1H), 3.02-2.83 (m, 1H), 2.42 (s, 1H), 1.95-1.86 (m, 1H) 1.84-1.67 (m, 3H), 1.63-1.54 (m, 2H), 1.45 (s, 9H), 1.14-1.03 (m, 1H). $^{19}F$ NMR (376 MHz, $CDCl_3$) δ −233.29.

Intermediate 13 & 14: 2,7-Dichloro-8-fluoro-4-((1R,7S,8R)-8-fluoro-2-azabicyclo[5.1.0]octan-2-yl)pyrido[4,3-d]pyrimidine & 2,7-dichloro-8-fluoro-4-((1S,7R,8S)-8-fluoro-2-azabicyclo[5.1.0]octan-2-yl)pyrido[4,3-d]pyrimidine

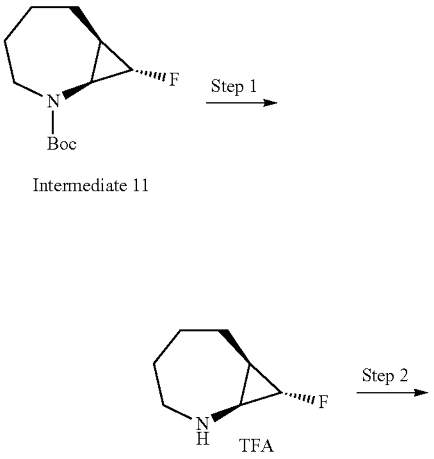

Intermediate 11

-continued

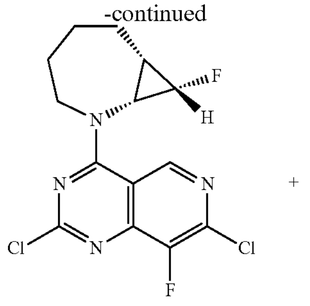

Intermediate 13

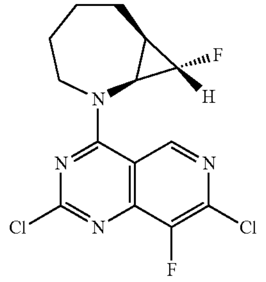

Intermediate 14

Step 1: 8-Fluoro-2-azabicyclo[5.1.0]octane TFA salt (trans mixture)

To a solution of fert-butyl 8-fluoro-2-azabicyclo[5.1.0] octane-2-carboxylate (trans mixture) (500 mg, 568 μmol) in $CH_2Cl$ (5 mL) was added TFA (S mL) at 0° C. The mixture was stirred at 20° C. for 0.5 h. The residue was concentrated under reduced pressure to give the title compound (500 mg, TFA salt) as a yellow oil, which was used in the next step without further purification.

Step 2: 2,7-Dichloro-8-fluoro-4-((1R,7S,8R)-8-fluoro-2-azabicyclo[5.1.0]octan-2-yl)pyrido[4,3-d] pyrimidine & 2,7-dichloro-8-fluoro-4-((1S,7R,8S)-8-fluoro-2-azabicyclo[5.1.0]octan-2-yl)pyrido[4,3-d] pyrimidine To a solution of 2,4,7-trichloro-8-fluoro-pyrido[4,3-d] pyrimidine (586 mg, 2.32 mmol) in $CH_2Cl_2$ (5 mL) were added DIPEA (1.5 g, 2.02 mL) and 8-fluoro-2-azabicyclo [5.1.0]octane TFA salt (trans mixture) (500 mg, 2.32 mmol, TFA salt) at −40° C. under $N_2$. The mixture was stirred at −40° C. for 1 h. The reaction mixture was diluted with water (50 mL) and extracted with $CH_2Cl$ (30 mL×3). The combined organic layers were washed with brine (20 mL), dried over anhydrous $Na_2SO_4$, filtered, and concentrated under reduced pressure. The residue was separated by SFC(column: DAICEL CHIRALCEL OJ (250 mm×30 mm, 10 μm); mobile phase: [$CO_2$-EtOH (0.1% $NH_3$ $H_2O$)]; B %: 40%, isocratic elution mode) to give the title compound (Intermediate 13, 200 mg, 25% yield, SFC peak 1: 1.126 min) as a yellow solid and the title compound (Intermediate 14, 200 mg, 25% yield, SFC peak 2: 1.546 min) as a yellow solid. Spectra for Intermediate 13: MS: m/z=345.0 $[M+H]^+$. $^1H$ NMR (400 MHZ, Chloroform-d) δ 9.31 (s, 1H), 4.60 (d, J=13.6 Hz, 1H), 4.23-3.94 (m, 1H), 3.76-3.62 (m, 1H), 3.42-3.28 (m, 1H), 2.49-2.35 (m, 1H), 2.12-1.90 (m, 3H), 1.85-1.72 (m, 1H), 1.64-1.59 (m, 1H), 1.12-0.94 (m, 1H). $^{19}F$ NMR. (376 MHz, Chloroform-d) δ-132.27, −203.94, −203.97. Spectra for Intermediate 14: MS: m/z=345.0 $[M+H]^+$. $^1H$ NMR (400 MHZ, Chloroform-d) δ 9.30 (s, 1H), 4.60 (d, J=13.6 Hz, 1H), 4.23-3.97 (m, 1H), 3.79-3.61 (m, 1H), 3.44-3.27 (m, 1H), 2.48-2.36 (m, 1H), 2.14-1.89 (m, 3H), 1.85-1.72 (m, 1H), 1.66-1.58 (m, 1H), 1.13-0.94 (m, 1H)$_{19}$F NMR (376 MHz, Chloroform-d) δ-132.29, −203.891, −203.951.

Intermediate 15 & 16: 2,7-Dichloro-8-fluoro-4-((1S,7R,8R)-8-fluoro-2-azabicyclo[5.1.0]octan-2-yl)pyrido[4,3-d]pyrimidine & 2,7-dichloro-8-fluoro-4-((1R,7S,8S)-8-fluoro-2-azabicyclo[5.1.0]octan-2-yl)pyrido[4,3-d]pyrimidine

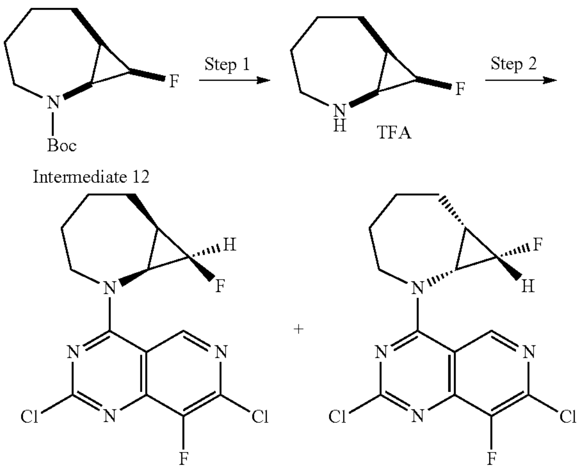

Intermediate 12

Intermediate 15 + Intermediate 16

Step 1: 8-Fluoro-2-azabicyclo[5.1.0]octane TFA salt (cis mixture)

To a solution of tert-butyl 8-fluoro-2-azabicyclo[5.1.0] octane-2-carboxylate (cis mixture) (500 mg, 2.18 mmol) in $CH_2Cl_2$ (5 mL) was added TFA (486 μL, 6.54 mmol). The mixture was stirred at 25° C. for 2 h. The reaction mixture was concentrated under reduced pressure to give the title compound (cis mixture, TFA salt) (280 mg, TFA salt) as a colorless oil, which was used in the next step without further purification.

Step 2: 2,7-Dichloro-8-fluoro-4-((1S,7R,8R)-8-fluoro-2-azabicyclo[5.1.0]octan-2-yl)pyrido[4,3-d] pyrimidine & 2,7-dichloro-8-fluoro-4-((1R,7S,8S)-8-fluoro-2-azabicyclo[5.1.0]octan-2-yl)pyrido[4,3-d] pyrimidine To a solution of 2,4,7-trichloro-8-fluoropyrido[4,3-d]pyrimidine (547 mg, 2.17 mmol) in $CH_2Cl$ (10 mL) were added DIPEA (2.27 mL, 13.0 mmol) and 8-fluoro-2-azabicyclo[5.1.0]octane TFA salt (cis mixture) (280 mg, 2.17 mmol, TFA salt) at −40° C. under $N_2$. The mixture was stirred at −40° C. for 0.5 h. The reaction mixture was diluted with water (15 mL) and extracted with EtOAc (20 mL×3). The combined organic layers were washed with brine (20 mL×2), dried over anhydrous $Na_2SO_4$, filtered and concentrated under reduced pressure. The residue was purified by silica gel flash chromatography (eluent: 0~20% of EtOAc in Petroleum ether) to give a mixture. The mixture was separated by SFC: DAICEL CHIRALPAK IK (250 mm×30 mm, 10 µm); mobile phase: [$CO_2$-i-PrOH (0.1% $NH_3H_2O$)]; B %: 40%, isocratic elution mode) to give the title compound (Intermediate 15, 150 mg, 20% yield over 2 steps, SFC Peak1: 1.898 min) as a white solid and the title compound (Intermediate 16, 150 mg, 20% yield over 2 steps, SFC Peak2: 2.263 min) as a white solid. Spectra for Intermediate 15: MS: m/z=344.8 $[M+H]^+$. $^1H$ NMR (400 $MHI_2$, Dimethylsulfoxide-d6) § 9.62 (s, 1H), 5.10-4.82 (m, 1H), 4.41 (d,)=13.2 Hz, 1H), 3.68-3.60 (m, 1H), 3.46 (t, J=12.4 Hz, 1H), 2.03-1.92 (m, 2H), 1.86-1.75 (m, 2H), 1.68-1.56 (m, 2H), 1.36-1.21 (m, 1H). Spectra for Intermediate 16: MS: m/z=344.8 $[M+H]^+$. $^1H$ NMR (400 MHZ, Dimethylsulfoxide-$d_6$) δ 9.62 (s, 1H), 5.06-4.85 (m, 1H), 4.41 (d, J=13.2 Hz, 1H), 3.70-3.61 (m, 1H), 3.46 (t,)=12.4 Hz, 1H), 2.03-1.94 (m, 2H), 1.86-1.77 (m, 2H), 1.67-1.57 (m, 2H), 1.32-1.22 (m, 1H).

Intermediate 17: ((2R,7aS)-2-fluorotetrahydro-1H-pyrrolizin-7a(5H)-yl)methan-$d_2$-ol

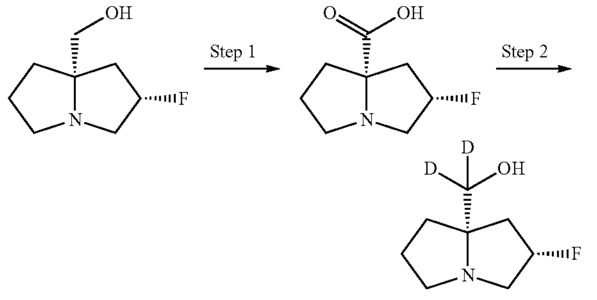

Intermediate 17

Step 1: (2R,7aS)-2-Fluoro-hexahydropyrrolizine-7a-carboxylic acid

To a stirred solution of ((2R,7aS)-2-fluorotetrahydro-1H-pyrrolizin-7a (5H)-yl) methanol (500 mg, 3.141 mmol) and RuCls.$H_2O$ (35.40 mg, 0.157 mmol) in CC14 (4 mL), MeCN (4 mL) and $H_2O$ (6 mL) under nitrogen atmosphere was added $NaIO_4$ (2686.99 mg, 12.564 mmol) at room temperature. The reaction mixture was stirred at room temperature for 5 hours. The resulting mixture was filtered and concentrated under reduced pressure. The residue was purified by silica gel flash chromatography, eluted with $CH_2Cl_2$ (25% AcOH)/MeOH (5: 1) to afford the title compound (200 mg, 36% yield) as a brown-yellow semi-solid. MS: m/z=174.10 $[M+H]^{+\cdot}$

Step 2: ((2R,7aS)-2-Fluorotetrahydro-1H-pyrrolizin-7a (5H)-yl) methan-dz-ol

To an ice-cooled solution of (2R,7aS)-2-fluoro-hexahydropyrrolizine-7a-carboxylic acid (200 mg, 1.155 mmol) in Me-THF (2 mL) under nitrogen atmosphere was added $LiAlD_4$ (2.43 mL, 2.425 mmol, 1M in THF) dropwise. The ice bath was removed, and the reaction mixture was heated at 90° C. for 2 hours. The reaction mixture was cooled and quenched with MeOH (5 mL) in an ice bath. The resulting mixture was concentrated under reduced pressure. The residue was purified by silica gel flash chromatography, eluted with 1-20% methanol in dichloromethane to afford the title compound (Intermediate 17, 100 mg, 53% yield) as a yellow oil. MS: m/z=162.15 $[M+H]^{+\cdot}$ Intermediate 18: N-(6,7-Difluoro-4-(4,4,5,5-tetramethyl-1,3,2-dioxaborolan-2-yl)-5-((triisopropylsilyl)ethynyl)naphthalen-2-yl)-1,1-diphenylmethanimine

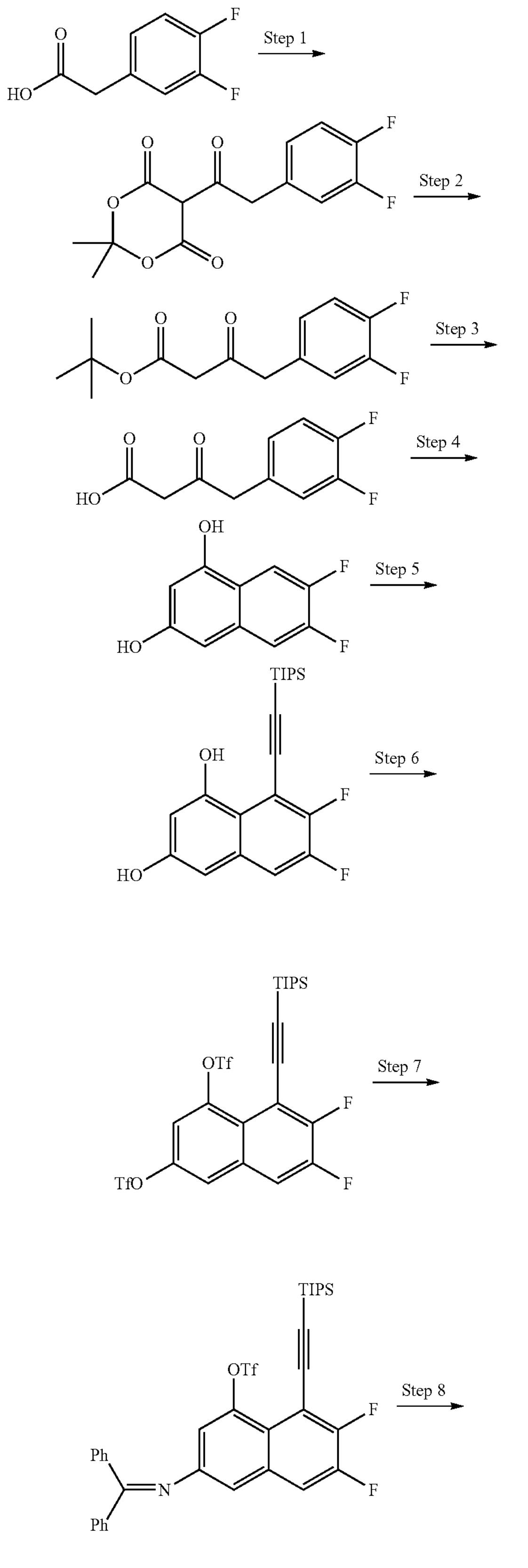

-continued

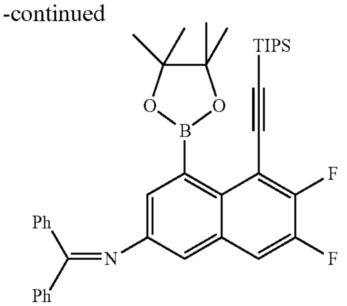

Intermediate 18

Step 1: 5-(2-(3,4-Difluorophenyl) acetyl)-2,2-dimethyl-1,3-dioxane-4,6-dione

To an ice cooled mixture of (3,4-difluorophenyl) acetic acid (7 g, 40.667 mmol), DMAP (5.47 g, 44.734 mmol) and Meldrum's acid (5.86 g, 40.667 mmol) in DCM (71.79 mL) under nitrogen atmosphere was added DCC(9.23 g, 44.734 mmol) dropwise. The reaction mixture was stirred at 0° C. with an ice bath for 16 hours. The resulting mixture was filtered, and the filter cake was washed with DCM (3×100 mL). The resulting mixture was washed with 1 M $NaHSO_4$ (3×100 mL) and brine (3×100 mL), dried over anhydrous sodium sulfate, filtered and concentrated under reduced pressure to give the title compound (8 g, crude used through) as a yellow oil. MS: m/z=297.10 $[M-H]^{+\cdot}$ Step 2: tert-Butyl 4-(3,4-difluorophenyl)-3-oxobutanoate A solution 5-(2-(3,4-difluorophenyl) acetyl)-2,2-dimethyl-1,3-dioxane-4,6-dione (8 g, crude) in 1-BuOH (80 mL) under nitrogen atmosphere was heated at 88° C. for 5 hours. The resulting mixture was cooled to room temperature, concentrated under reduced pressure. The residue was purified by silica gel flash chromatography, eluted with 0-15% EA in PE to afford the title compound (7 g, 65% yield for two steps) as a light-yellow oil. MS: m/z=269.05 $[M-H]^-$. 1H NMR (300 MHz, Chloroform-d) δ 7.26-7.00 (m, 2H), 6.93-6.91 (m, 1H), 3.80 (s, 2H), 3.40 (s, 2H), 1.47 (s, 9H).

Step 3: 4-(3,4-Difluorophenyl)-3-oxobutanoic acid

To an ice cooled solution of tert-butyl 4-(3,4-difluorophenyl)-3-oxobutanoate (7 g, 25.899 mmol) in DCM (70 mL) under nitrogen atmosphere was added TFA (70 mL, 863.994 mmol) dropwise. The ice bath was removed, and the resulting mixture was stirred at room temperature for 4 hours. The resulting mixture was co-evaporated with toluene (70 mL×6) to give the title compound (6 g, crude used through) as a yellow solid. MS: m/z=213.00 [M-H]

Step 4: 6,7-Difluoronaphthalene-1,3-diol

A solution of 4-(3,4-difluorophenyl)-3-oxobutanoic acid (6 g, crude) in $CF_3SO_3H$ (180 mL) under nitrogen atmosphere was stirred at room temperature for 16 hours. The resulting mixture was diluted with EtOAc (800 mL), washed with water (4×300 mL) and brine (400 mL). The organic layer was dried over anhydrous $Na_2SO_4$, filtered, and concentrated under reduced pressure. The residue was purified by silica gel flash chromatography, eluted with 0-50% EA in PE to afford the title compound (1.7 g, 34% yield for two steps) as a black oil. MS: m/z=195.10 $[M-H]^-$. $^1H$ NMR (400 MHZ, DMSO-d6) δ 10.35 (s, 1H), 9.71 (s, 1H), 7.78-7.72 (m, 1H), 7.63-7.58 (m, 1H), 6.62-6.53 (m, 2H).

Step 5: 6,7-Difluoro-8-((triisopropylsilyl) ethynyl) naphthalene-1,3-diol

To a stirred solution of 6,7-difluoronaphthalene-1,3-diol (520 mg, 2.65 mmol) and (2-bromoethynyl)triisopropylsilane (761.91 mg, 2.91 mmol) in 1,4-dioxane (6 mL) under nitrogen atmosphere were added [Ru (p-cymene)$Cl_2]_2$ (162.34 mg, 0.26 mmol) and KOAc (520.35 mg, 5.30 mmol) at room temperature. The resulting mixture was heated at 110° C. for 2 hours. The resulting mixture was cooled to room temperature, filtered and concentrated under reduced pressure. The residue was purified by silica gel flash chromatography, eluted with 0-50% EA in PE to afford the title compound (600 mg, 60% yield) as a brown solid. MS: m/z=377.00 $[M+H]^{+\cdot}$ Step 6: 6,7-Difluoro-8-((triisopropylsilyl) ethynyl) naphthalene-1,3-diyl bis(trifluoromethanesulfonate)

To a stirred solution of 6,7-difluoro-8-((triisopropylsilyl) ethynyl) naphthalene-1,3-diol (1.8 g, 4.781 mmol) in DCM (18 mL) were added DIEA (3.7 g, 28.686 mmol) and Tf2O (4.4 g, 14.343 mmol) at −40° C. under nitrogen atmosphere. The resulting mixture was stirred at −40° C. for 3 hours. The resulting mixture was quenched with aq. $NaHCO_3$ (50 mL), extracted with $CH_2Cl$ (3×100 mL), washed with brine (100 mL), dried over anhydrous $Na_2SO_4$, and concentrated under reduced pressure to afford the title compound (3 g, crude used through) as a brown oil. MS: m/z=638.95 $[M-H]^{-\cdot}$ Step 7: 3-((Diphenylmethylene)amino)-6,7-difluoro-8-((triisopropylsilyl) ethynyl) naphthalen-1-yl trifluoromethanesulfonate To a stirred mixture of 6,7-difluoro-8-((triisopropylsilyl) ethynyl) naphthalene-1,3-diyl bis(trifluoromethanesulfonate) (3 g, crude), Pd2 (dba): (428.83 mg, 0.468 mmol), XantPhos (812.90 mg, 1.405 mmol) and $Cs2CO_3$ (3051.55 mg, 9.366 mmol) in toluene (30 mL) under nitrogen atmosphere was added diphenylmethanimine (933.59 mg, 5.151 mmol) at room temperature. The resulting mixture was heated at 100° C. for 2 hours. The resulting mixture was cooled to room temperature, filtered, and concentrated under reduced pressure. The residue was purified by silica gel flash chromatography, eluted with PE/EA (10: 1) to afford the title compound (3 g, 93% yield for two steps) as a yellow oil. MS: m/z=672.20 $[M+H]^{+\cdot}$ Step 8: N-(6,7-difluoro-4-(4,4,5,5-tetramethyl-1,3,2-dioxaborolan-2-yl)-5-((triisopropylsilyl) ethynyl) naphthalen-2-yl)-1,1-diphenylmethanimine To a stirred solution of 3-((diphenylmethylene)amino)-6,7-difluoro-8-((triisopropylsilyl) ethynyl) naphthalen-1-yl trifluoromethanesulfonate (2 g, 2.977 mmol) and 4,4,4',4',5,5,5',5'-octamethyl-2,2'-bi (1,3,2-dioxaborolane) (B2Pin2, 1.512 g, 5.954 mmol) in 1,4-dioxane (20 mL) under nitrogen atmosphere were added KOAc (876.53 mg, 8.931 mmol) and Pd (dppf)$C_{12}$.$CH_2Cl_2$ (12.13 mg, 0.015 mmol) at room temperature. The reaction mixture was heated at 110° C. for 3 hours. The resulting mixture was cooled to room temperature, filtered, and concentrated under reduced pressure. The residue was purified by silica gel flash chromatography, eluted with 0-20% EA in PE to afford the title compound (Intermediate 18, 1.2 g, 62% yield) as a yellow solid. MS: m/z=650.65 $[M+H]^+$. $^1H$ NMR (400 MHZ, DMSO-$d_6$) δ 7.86-7.83 (m, 1H), 7.70-7.68 (m, 2H), 7.59-7.55 (m, 1H), 7.51-7.48 (m, 2H), 7.31-7.29 (m, 4H), 7.19-7.17 (m, 2H), 7.09-7.08 (m, 1H), 1.27 (s, 12H), 1.13-1.07 (m, 21H).

Intermediate 19 & 20: N-(6-Fluoro-4-(4,4,5,5-tetramethyl-1,3,2-dioxaborolan-2-yl)-5-((triisopropylsilyl)ethynyl)naphthalen-2-yl)-1,1-diphenylmethanimine & 6-Fluoro-4-(4,4,5,5-tetramethyl-1,3,2-dioxaborolan-2-yl)-5-((triisopropylsilyl)ethynyl)naphthalen-2-amine

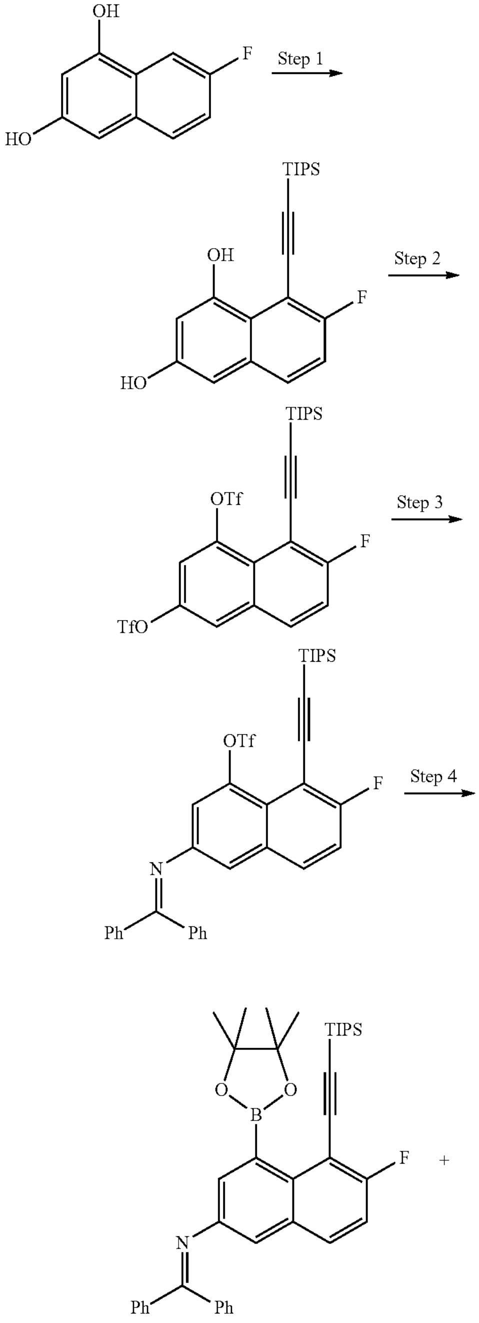

Intermediate 19

-continued

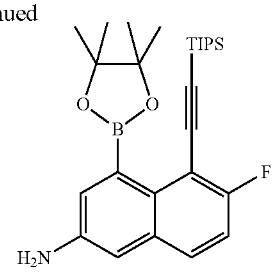

Intermediate 20

Step 1: 7-Fluoro-8-((triisopropylsilyl) ethynyl) naphthalene-1,3-diol

To a solution of 7-fluoronaphthalene-1,3-diol (50 g, 281 mmol) and 2-bromoethynyl (triisopropyl) silane (77 g, 295 mmol) in 1,4-dioxane (334 mL) were added KOAc (55.1 g, 561 mmol) and dichlororuthenium: 1-isopropyl-4-methyl-benzene (17.2 g, 28.1 mmol). The mixture was stirred at 110° C. for 2 h under $N_2$ atmosphere. The reaction mixture was filtered and concentrated under reduced pressure. The residue was purified by silica gel flash chromatography (Eluent: 0~5% of EtOAc in petroleum ether) to give the title compound (70 g, 194 mmol, 69% yield) as a brown solid. MS: m/z=359.1 $[M+H]^+$. $^1H$ NMR (400 MHZ, Chloroform-d) δ 9.15 (s, 1H), 7.59 (dd, J=5.6, 9.2 Hz, 1H), 7.17 (t, J=8.8 Hz, 1H), 6.77-6.62 (m, 2H), 1.21-1.15 (m, 21H). $^{19}F$ NMR (376 MHz, Chloroform-d) δ −112.51.

Step 2: 7-Fluoro-8-((triisopropylsilyl) ethynyl) naphthalene-1,3-diyl bis(trifluoromethanesulfonate)

To a solution of 7-fluoro-8-((triisopropylsilyl) ethynyl) naphthalene-1,3-diol (140 g, 390 mmol) and DIPEA (408 mL, 2.34 mol) in $CH_2Cl_2$ (3.5 L) was added Tf2O (258 ml, 1.56 mol) dropwise under $N_2$ atmosphere at 0° C. The mixture was stirred at 0° C. under $N_2$ atmosphere for 2 h. The reaction mixture was partitioned between $CH_2Cl_2$ (500 mL) and $H_2O$ (2 L). The organic phase was separated, washed with brine (500 mL), dried over $Na_2SO_4$, filtered and concentrated under reduced pressure. The residue was purified by silica gel flash chromatography (Eluent: 0~3% of EtOAc in petroleum ether) to give the title compound (218 g, 340 mmol, 87% yield) as a brown solid. $^1H$ NMR (400 MHZ, Chloroform-d) δ 7.87 (dd, J=5.2, 9.2 Hz, 1H), 7.80 (d, J=2.4 Hz, 1H), 7.54-7.47 (m, 2H), 1.26-1.21 (m, 3H), 1.19-1.15 (m, 18H)

Step 3: 3-((Diphenylmethylene)amino)-7-fluoro-8-((triisopropylsilyl) ethynyl) naphthalen-1-yl trifluoromethanesulfonate A mixture of 7-fluoro-8-((triisopropylsilyl) ethynyl) naphthalene-1,3-diylbis (trifluoromethanesulfonate) (94 g, 151 mmol), diphenylmethanimine (54.7 g, 302 mmol, 50.7 mL), (5-diphenylphosphanyl-9,9-dimethyl-xanthen-4-yl)-diphenyl-phosphane (17.5 g, 30.2 mmol), Pd2 $(dba)_3$ (6.91 g, 7.55 mmol) and $Cs2CO_3$ (148 g, 453 mmol) in toluene (1800 mL) was degassed, purged with $N_2$ three times, and stirred at 100° C. under $N_2$ atmosphere for 2 h. The reaction mixture was filtered and concentrated under reduced pressure. The residue was purified by silica gel flash chromatography (Eluent: 0~3% of EtOAc in petroleum ether) to give the crude product (80 g) as a brown solid. The crude was triturated with MeOH (150 mL) at 25° C. for 20 min and filtered. The filter cake was dried under reduced pressure to give the title compound (70 g, 94.2 mmol, 62% yield) as a yellow solid. MS: m/z=654.3 $[M+H]^+$. $^1H$ NMR (400 MHz, Chloroform-d) δ 7.78 (d, J=8.0 Hz, 2H), 7.57-7.51 (m, 2H), 7.48-7.41 (m, 2H), 7.27 (s, 2H), 7.26-7.19 (m, 2H), 7.17-7.01 (m, 4H), 1.22-1.13 (m, 21H). $^{19}F$ NMR (376 MHz, Dimethylsulfoxide-d6) δ −71.40, −104.22.

Step 4: N-(6-fluoro-4-(4,4,5,5-tetramethyl-1,3,2-dioxaborolan-2-yl)-5-((triisopropylsilyl) ethynyl) naphthalen-2-yl)-1,1-diphenylmethanimine & 6-Fluoro-4-(4,4,5,5-tetramethyl-1,3,2-dioxaborolan-2-yl)-5-((triisopropylsilyl) ethynyl) naphthalen-2-amine A mixture of 3-((diphenylmethylene)amino)-7-fluoro-8-((triisopropylsilyl) ethynyl) naphthalen-1-yl trifluoromethanesulfonate (50 g, 76.5 mmol), 4,4,5,5-tetramethyl-2-(4,4,5,5-tetramethyl-1,3,2-dioxaborolan-2-yl)-1,3,2-dioxaborolane (39 g, 153 mmol), KOAc (30 g, 306 mmol), and Pd (dppf)$Cl_2$ (11.2 g, 15.3 mmol) in 1,4-dioxane (600 mL) was degassed, purged with $N_2$ three times, and stirred at 100° C. under $N_2$ atmosphere for 16 h. The reaction mixture was filtered and concentrated under reduced pressure. The residue was purified by silica gel flash chromatography (Bluent: 0~100% of EtOAc in petroleum ether) to give the title compound (Intermediate 19, 9 g, 14.3 mmol, 19% yield) as a yellow solid and the title compound (Intermediate 20, 10 g, 21.4 mmol, 28% yield) as a brown oil. Spectra for Intermediate 19: MS: m/z=632.4 $[M+H]^+$. H NMR (400 MHZ, Dimethylsulfoxide-d6) δ 7.86-7.79 (m, 1H), 7.72-7.67 (m, 2H), 7.60-7.53 (m, 1H), 7.53-7.47 (m, 2H), 7.42 (t, J=9.2 Hz, 1H), 7.34-7.27 (m, 4H), 7.22-7.16 (m, 2H), 7.14-7.10 (m, 1H), 1.27 (s, 12H), 1.14-1.08 (m, 21H), $^{19}F$. NMR (376 MHz, Dimethylsulfoxide-d6) δ −106.71. Spectra for Intermediate 20: MS: m/z=468.3 $[M+H]^+$. $^1H$ NMR (400 MHz, Dimethylsulfoxide-d6) δ 7.67-7.57 (m, 1H), 7.27 (t, J=9.0 Hz, 1H), 7.23-7.17 (m, 1H), 6.89 (d, J=2.4 Hz, 1H), 5.48 (s, 2H), 1.33 (s, 12H), 1.17-1.11 (m, 21H). $^{19}F$ NMR (376 MHz, Dimethylsulfoxide-$d_6$) δ-112.20.

Intermediate 21 & 22: (1R,7R)-2-(7-Chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-8,8-difluoro-5-oxa-2-azabicyclo[5.1.0]octane & (1S,7S)-2-(7-chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-8,8-difluoro-5-oxa-2-azabicyclo[5.1.0]octane

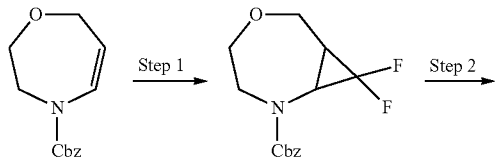

Intermediate 2

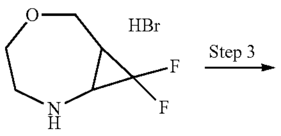

-continued

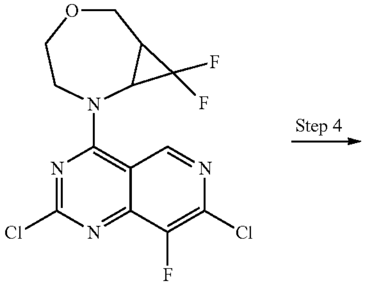

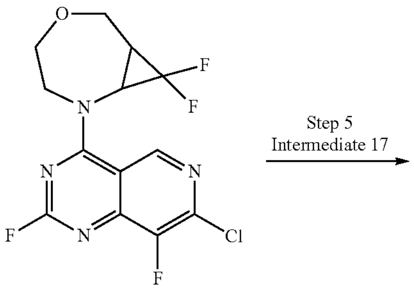

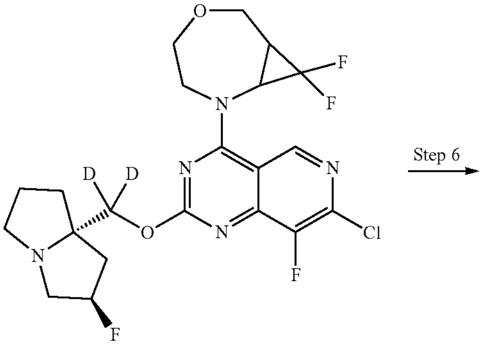

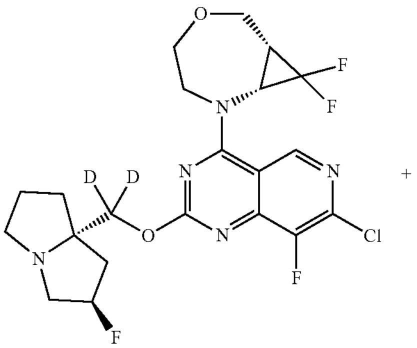

Intermediate 21
Structure tentatively assigned

-continued

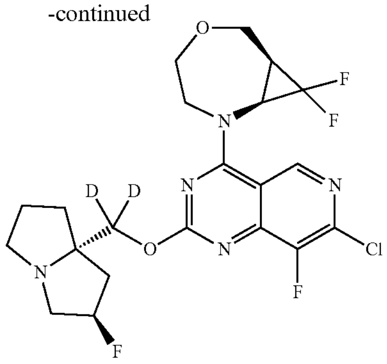

Intermediate 22
Structure tentatively assigned

Step 1: Benzyl 8,8-difluoro-5-oxa-2-azabicyclo[5.1.0]octane-2-carboxylate To a stirred mixture of Intermediate 2 (5 g, 21.43 mmol) and NaI (1.61 g, 10.71 mmol) in THE (50 mL) was added trimethyl (trifluoromethyl) silane (12.19 g, 85.74 mmol) dropwise at room temperature under nitrogen atmosphere. The reaction mixture was heated at 65° C. for 16 hours. The resulting mixture was cooled to room temperature, diluted with water (100 mL) and extracted with EtOAc (3x200 mL). The combined organic layers were washed with brine (200 mL), dried over anhydrous $Na_2SO_4$, filtered and concentrated under reduced pressure. The residue was purified by silica gel flash chromatography, eluted with PE/EA (10: 1) to afford the title compound (5.1 g, 83% yield) as a light yellow solid. MS: m/z=284.00 $[M+H]^+$. $^1H$ NMR (400 MHZ, Chloroform-d) § 7.42-7.30 (m, 5H), 5.18 (s, 2H), 4.35-4.29 (m, 1H), 4.16 (d, J=14.4 Hz, 1H), 3.97 (d, J=12.8 Hz, 1H), 3.60-3.48 (m, 2H), 3.30-3.23 (m, 2H), 2.28-2.17 (m, 1H). $^{19}F$ NMR (376 MHz, Chloroform-d) δ −125.47--126.24 (m, IF), −147.36--148.73 (m, 1F).

Step 2: 8,8-Difluoro-5-oxa-2-azabicyclo[5.1.0]octane hydrobromide

A solution of benzyl 8,8-difluoro-5-oxa-2-azabicyclo[5.1.0]octane-2-carboxylate (2.3 g, 8.11 mmol) in 33 wt % HBr in AcOH (23 mL) was stirred in an ice bath for 1 hour under nitrogen atmosphere. The resulting mixture was concentrated under reduced pressure. The residue was triturated with hexane (3x50 mL) to afford the compound (1.5 g, crude used through) as a light yellow solid.

Step 3: 2-(2,7-Dichloro-8-fluoropyrido[4,3-d]pyrimidin-4-yl)-8,8-difluoro-5-oxa-2-azabicyclo[5.1.0]octane To a stirred solution of 2,4,7-trichloro-8-fluoropyrido[4,3-d]pyrimidine (2.54 g, 10.05 mmol) and 8,8-difluoro-5-oxa-2-azabicyclo[5.1.0]octane hydrobromide (1.5 g, crude) in DCM (40 mL) was added DIEA (3.90 g, 30.17 mmol) dropwise at −40° C. under nitrogen atmosphere. The reaction mixture was stirred at −40° C. for 1 hour. The resulting mixture was diluted with 10% citric solution (50 mL) and extracted with DCM (3x50 mL). The combined organic layers were washed with brine (50 mL), dried over anhydrous $Na_2SO_4$, filtered and concentrated under reduced pressure. The residue was purified by silica gel flash chromatography, eluted with PE/EA (1: 1) to afford the title compound (1.9 g, 51% yield) as a light yellow solid. MS: m/z=365.05, 367.05 [M+H].

Step 4: 2-(7-Chloro-2,8-difluoropyrido[4,3-d]pyrimidin-4-yl)-8,8-difluoro-5-oxa-2-azabicyclo[5.1.0]octane To a stirred solution of 2-{2,7-dichloro-8-fluoropyrido[4,3-d]pyrimidin-4-yl}-8,8-difluoro-5-oxa-2-azabicyclo[5.1.0]octane (1.9 g, 5.20 mmol) in DMSO (40 mL) was added KF (604.61 mg, 10.40 mmol) at room temperature under nitrogen atmosphere. The reaction mixture was heated at 80° C. for 16 hours. The resulting mixture was cooled to room temperature, diluted with water (100 mL), extracted with EtOAc (3x100 mL). The combined organic layers were washed with brine (100 mL), dried over anhydrous $Na_2SO_4$, filtered and concentrated under reduced pressure. The residue was purified by silica gel flash chromatography, eluted with PE/EA (1: 1) to afford the title compound (1.6 g, 88% yield) as a light yellow solid. MS: m/z=349.10 $[M+H]^{+\cdot}$ Step 5: 2-(7-Chloro-8-fluoro-2-(((2R,7aS)-2-fluoro-tetrahydro-1/-pyrrolizin-7a (5H)-yl) methoxy-d2) pyrido[4,3-d]pyrimidin-4-yl)-8,8-difluoro-5-oxa-2-azabicyclo[5.1.0]octane To an ice-cooled stirred mixture of Intermediate 17 (443.86 mg, 2.75 mmol) in THF (8 mL) was added NaH (110.12 mg, 2.75 mmol, 60% dispersion in mineral oil) under nitrogen atmosphere. The mixture was stirred an an ice bath for 30 min. To the above mixture was added 2-(7-chloro-2,8-difluoropyrido[4,3-d]pyrimidin-4-yl)-8,8-difluoro-5-oxa-2-azabicyclo[5.1.0]octane (800 mg, 2.29 mmol). The ice bath was removed, and the reaction mixture was stirred at room temperature for 1 hour. The resulting mixture was quenched with saturated aq. $NH_4Cl$ (50 mL) in an ice bath and extracted with $CH_2Cl_2$ (3x50 mL). The combined organic layers were washed with brine (50 mL), dried over anhydrous $Na_2SO_4$, filtered and concentrated under reduced pressure. The residue was purified by silica gel flash chromatography, eluted with $CH_2CL$/MeOH (10: 1) to afford the title compound (480 mg, 42% yield) as a light yellow solid. MS: m/z=490.35 $[M+H]^{+\cdot}$ Step 6: (1R,7R)-2-(7-chloro-8-fluoro-2-(((2R,7aS)-2-fluorotetrahydro-1H-pyrrolizin-7a (5H)-yl) methoxy-d2) pyrido[4,3-d]pyrimidin-4-yl)-8,8-difluoro-5-oxa-2-azabicyclo[5.1.0]octane & (1S,7S)-2-(7-chloro-8-fluoro-2-(((2R,7aS)-2-fluorotetrahydro-1H-pyrrolizin-7a (5H)-yl) methoxy-d2)pyrido[4,3-d]pyrimidin-4-yl)-8,8-difluoro-5-oxa-2-azabicyclo[5.1.0]octane 2-(7-Chloro-8-fluoro-2-(((2R,7aS)-2-fluorotetrahydro-1H-pyrrolizin-7a (5H)-yl) methoxy-dz) pyrido[4,3-d]pyrimidin-4-yl)-8,8-difluoro-5-oxa-2-azabicyclo[5.1.0]octane (480 mg, 0.98 mmol) was separated by Prep-CHIRAL-HPLC with the following conditions: Column: CHIRALPAK IF 2x25 cm, 5 μm; Mobile Phase A: Hex (0.5% 2 M $NH_3$-MeOH); Mobile Phase B: EtOH; Flow rate: 20 mL/min; Gradient: isocratic 30% B; Detector: UV 220 & 254 nm; RT1: 8.655 min; RT2: 11.221 min. The first eluting peak (RT1: 8.655 min) was concentrated and lyophilized to give the title compound (Intermediate 21, 180 mg, 37% yield, structure tentatively assigned) as a light yellow solid. MS: m/z=490.15 $[M+H]^+$. The second eluting peak (RT2: 11.221 min) was concentrated and lyophilized to give the title compound (Intermediate 22, 90 mg, 18% yield, structure tentatively assigned) as a light yellow solid. MS: m/z=490.15 $[M+H]^{+\cdot}$ Intermediate 23 & 24: 8-Fluoro-2-oxa-6-azabicyclo[5.1.0]octane hydrobromide (trans mixture) & 8-fluoro-2-oxa-6-azabicyclo[5.1.0]octane hydrobromide (cis mixture)

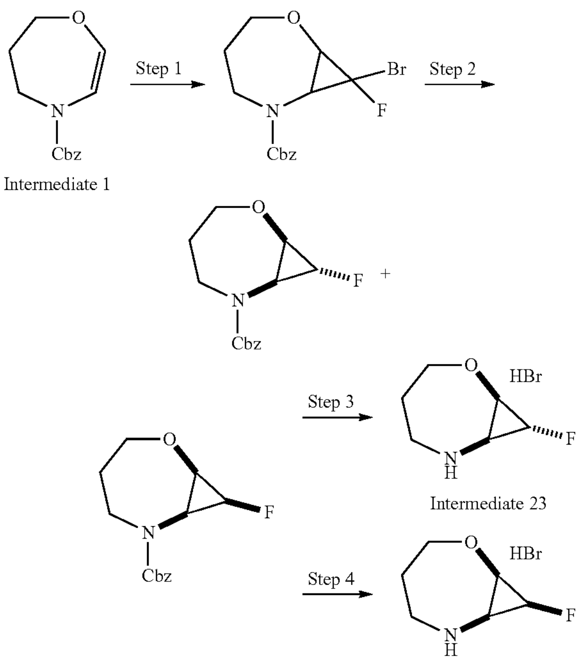

Intermediate 1

Intermediate 23

Intermediate 24

Step 1: Benzyl 8-bromo-8-fluoro-2-oxa-6-azabicyclo[5.1.0]octane-6-carboxylate

To an ice-cooled solution of Intermediate 1 (5.0 g, 21.45 mmol) and TBAI (1.62 g, 4.40 mmol) in DCM (50 mL) were added 50% aq. NaOH (50 mL) and dibromofluoromethane (12.35 g, 64.35 mmol) dropwise. The ice bath was removed, and the reaction mixture was stirred at room temperature for 16 hours. The resulting mixture was diluted with iced water (100 mL) and extracted with DCM (3×100 mL). The combined organic layers were washed with brine (100 mL), dried over anhydrous $Na_2SO_4$, filtered, concentrated under reduced pressure. The residue was purified by silica gel flash chromatography, eluted with 0-30% EA in PE to afford the title compound (2.6 g, 35% yield) as an off-white semi-solid. MS: m/z=361.10, 363.10 $[M+NH_4]^{+\cdot}$ Step 2: Benzyl 8-fluoro-2-oxa-6-azabicyclo[5.1.0]octane-6-carboxylate (trans mixture) and benzyl 8-fluoro-2-oxa-6-azabicyclo[5.1.0]octane-6-carboxylate (cis mixture)

To a stirred mixture of benzyl 8-bromo-8-fluoro-2-oxa-6-azabicyclo[5.1.0]octane-6-carboxylate (2.6 g, 7.58 mmol) in EtOH (25 mL) under nitrogen atmosphere were added $NH_4Cl$ (2.10 g, 68.22 mmol) and Zn (2.53 g, 68.22 mmol) at room temperature. The reaction mixture was stirred at 10° C. for 16 hours. The resulting mixture was filtered and concentrated under reduced pressure. The residue was purified by silica gel flash chromatography, eluted with 0-20% EA in PE to afford two mixtures. The first eluting peak was collected and concentrated under reduced pressure to give the title compound (trans mixture, F-NMR=−211) (233 mg, 12% yield) as an off-white semi-solid. $^1$H-NMR (400 MHZ, Chloroform-d) δ 7.32-7.24 (m, 5H), 5.16-5.12 (m, 2H), 4.66-4.55 (m, 1H), 4.10-3.65 (m, 4H), 3.00-2.90 (m, 1H), 2.87-2.80 (m, 1H), 1.79-1.48 (m, 2H). $^{19}$F. NMR (376 MHz, Chloroform-d) δ −211.30 (s, IF). The second eluting peak was collected and concentrated under reduced pressure to give the title compound (cis mixture, F-NMR=−239) (1.0 g, 50% yield) as an off-white semi-solid. $^{19}$F NMR (376 MHZ, Chloroform-d) δ −239.8 (s, IF)

Step 3: 8-Fluoro-2-oxa-6-azabicyclo[5.1.0]octane hydrobromide (trans mixture)

A solution of benzyl 8-fluoro-2-oxa-6-azabicyclo[5.1.0]octane-6-carboxylate (trans mixture) (233 mg, 1.78 mmol) in 33 wt % HBr in AcOH (2 mL) was stirred in an ice bath for 1 hour. The resulting mixture was concentrated under reduced pressure. The residue was triturated with hexane (3×8 mL) to afford the title compound (trans mixture, HBr salt) (Intermediate 23, 130 mg, crude used through) as a brown solid. MS: m/z=132.10 $[M+H]^+$. $^1$H NMR (300 MHZ, Deuterium Oxide) δ 5.13-4.93 (m, 1H), 4.14-3.97 (m, 2H), 3.80-3.72 (m, 1H), 3.48-3.38 (m, 1H), 3.33-3.24 (m, 2H), 1.94-1.88 (m, 2H). $^{19}$F NMR (282 MHz, Deuterium Oxide) δ −211.86 (s, IF).

Step 4: 8-Fluoro-2-oxa-6-azabicyclo[5.1.0]octane hydrobromide (cis mixture)

A solution of benzyl 8-fluoro-2-oxa-6-azabicyclo[5.1.0]octane-6-carboxylate (cis mixture) (1.00 g, 7.63 mmol) in 33 wt % HBr in AcOH (10 mL) was stirred in an ice bath for 1 hour. The resulting mixture was concentrated under reduced pressure. The residue was triturated with hexane (3×20 mL) to afford the title compound (cis mixture) (Intermediate 24, 600 mg, HBr salt, crude used through) as a brown solid. MS: m/z=132.10 $[M+H]^+$. $^1$H NMR (300 MHZ, Deuterium Oxide) δ 4.85-4.65 (m, 1H), 4.14-3.86 (m, 2H), 3.65-3.35 (m, 3H), 2.94-2.89 (m, 1H), 2.16-1.99 (m, 2H). $^{19}$F. NMR (282 MHz, Deuterium Oxide) δ −240.77 (s, 1F)

Intermediate 25 & 26: (1S,7R,8R)-6-(7-Chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-8-fluoro-2-oxa-6-azabicyclo[5.1.0]octane & (1R,7S,8S)-6-(7-chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-8-fluoro-2-oxa-6-azabicyclo[5.1.0]octane

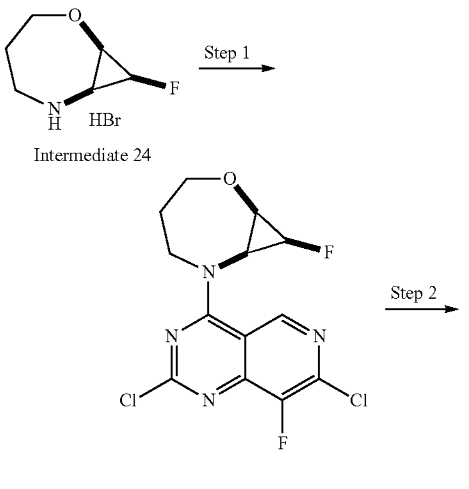

Intermediate 24

-continued

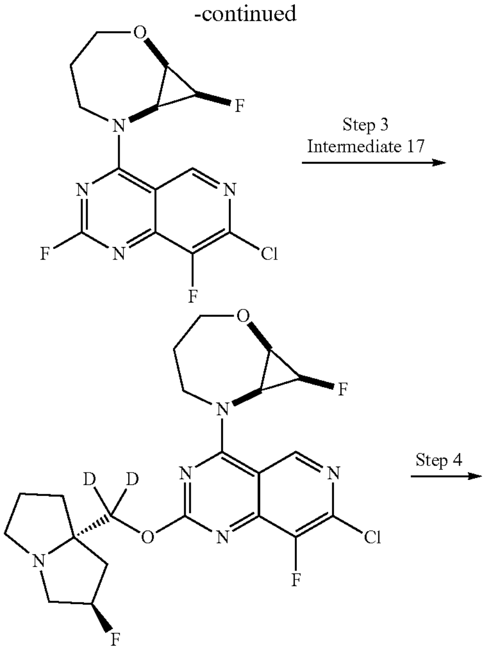

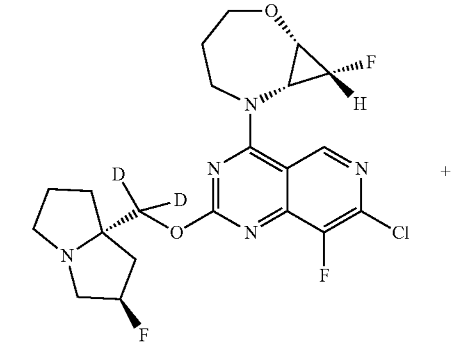

Intermediate 25

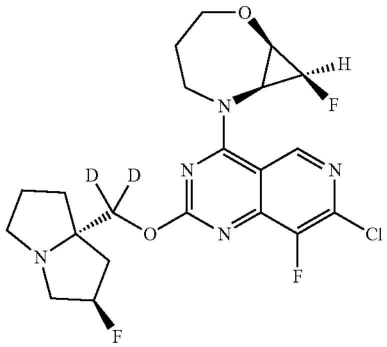

Intermediate 26

Step 1: 6-(2,7-Dichloro-8-fluoropyrido[4,3-d]pyrimidin-4-yl)-8-fluoro-2-oxa-6-azabicyclo[5.1.0] octane (cis mixture)

A solution of 2,4,7-trichloro-8-fluoropyrido[4,3-d]pyrimidine (481 mg, 1.90 mmol) and 4A molecular sieves in DCM (34 mL) was stirred at room temperature for 30 min, and then DIEA (738.77 mg, 5.71 mmol) and Intermediate 24 (340 mg, crude) were added at −40° C. The reaction mixture was stirred at −40° C. for 1 hour. The resulting mixture was diluted with 10% citric solution (50 mL) and extracted with DCM (3×50 mL). The combined organic layers were washed with brine (50 mL), dried over anhydrous $Na_2SO_4$, filtered and concentrated under reduced pressure. The residue was purified by silica gel flash chromatography, eluted with DCM/EA (5: 1) to afford the title compound (cis mixture) (530 mg, 80% yield) as a light yellow solid. MS: m/z=347.00, 349.00 $[M+H]^{+\cdot}$ Step 2: 6-(7-Chloro-2,8-difluoropyrido[4,3-d]pyrimidin-4-yl)-8-fluoro-2-oxa-6-azabicyclo[5.1.0] octane (cis mixture)

To a stirred solution of 6-(2,7-dichloro-8-fluoropyrido[4,3-d]pyrimidin-4-yl)-8-fluoro-2-oxa-6-azabicyclo[5.1.0]octane (cis mixture) (460 mg, 1.32 mmol) in DMSO (28 mL) was added KF (153.97 mg, 2.65 mmol) at room temperature under nitrogen atmosphere. The reaction mixture was stirred at 80° C. for 16 hours. The resulting mixture was cooled to room temperature, diluted with water (100 mL), and extracted with EtOAc (3×100 mL). The combined organic layers were washed with brine (3×50 mL), dried over anhydrous $Na_2SO_4$, filtered and concentrated under reduced pressure. The residue was purified by silica gel flash chromatography, eluted with DCM/EA (5: 1) to afford the title compound (cis mixture) (180 mg, 41% yield) as a light yellow solid. MS: m/z=330.65 $[M+H]^{+\cdot}$ Step 3: 6-(7-Chloro-8-fluoro-2-(((2R,7aS)-2-fluoro-tetrahydro-1/-pyrrolizin-7a (5H)-yl) methoxy-d2) pyrido[4,3-d]pyrimidin-4-yl)-8-fluoro-2-oxa-6-azabicyclo[5.1.0]octane (cis mixture)

To an ice-cooled stirred mixture of Intermediate 17 (105.30 mg, 0.65 mmol) in THF (18 mL) was added NaH (26.12 mg, 0.65 mmol, 60% dispersion in mineral oil) under nitrogen atmosphere. After stirring in an ice bath for 30 min, Intermediate 17 (cis mixture) (180 mg, 0.54 mmol) was added to the above mixture. The ice bath was removed, and the resulting mixture was stirred at room temperature for 1 hour. The resulting mixture was quenched with sat. aq. $NH_4Cl$ (100 mL), extracted with $CH_2Cl_2$ (3×100 mL). The combined organic layers were washed with brine (100 mL), dried over anhydrous $Na_2SO_4$, filtered and concentrated under reduced pressure. The residue was purified by silica gel flash chromatography, eluted with $CH_2Cl_2$/MeOH (10: 1) to afford the title compound (cis mixture) (100 mg, 38% yield) as a light yellow solid. MS: m/z=471.80 $[M+H]^{+\cdot}$ Step 4: (1S,7R,8R)-6-(7-chloro-8-fluoro-2-(((2R,7aS)-2-fluorotetrahydro-1/-pyrrolizin-7a (5H)-yl) methoxy-d2) pyrido[4,3-d]pyrimidin-4-yl)-8-fluoro-2-oxa-6-azabicyclo [5.1.0]octane & (1R,75,8S)-6-(7-chloro-8-fluoro-2-(((2R, 7aS)-2-fluorotetrahydro-1/-pyrrolizin-7a (5/f)-yl) methoxy-d2)pyrido[4,3-d]pyrimidin-4-yl)-8-fluoro-2-oxa-6-azabicyclo[5.1.0]octane 6-(7-Chloro-8-fluoro-2-(((2R,7aS)-2-fluorotetrahydro-1/-pyrrolizin-7a (5H)-yl) methoxy-d2) pyrido[4,3-d]pyrimidin-4-yl)-8-fluoro-2-oxa-6-azabicyclo [5.1.0]octane (cis mixture) (100 mg, 0.21 mmol) was separated by Prep-CHIRAL-HPLC with the following conditions: Column: CHIRAL ART Cellulose-SZ 250×20 mm, 5 μm; Mobile Phase A: Hex (0.5% 2 M $NH_3$-MeOH); Mobile Phase B: EtOH; Flow rate: 20 mL/min; Gradient: isocratic 30%; Detector: UV 220 & 254 nm; RT1: 10.147 min; RT2: 15.476 min. The first eluting peak (RT1: 10.147 min) was concentrated and lyophilized to give the title compound (Intermediate 25, 40 mg, 40% yield) as a light yellow solid. MS: m/z=472.20 $[M+H]^+$. The second eluting peak (RT2: 15.476 min) was concentrated and lyophilized to give the title compound (Intermediate 26, 40 mg, 40% yield) as a light yellow solid. MS: m/z=472.20 $[M+H]^{+\cdot}$ Intermediate 27 & 28: (1S,7R,8S)-6-(7-Chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-8-fluoro-2-oxa-6-azabicyclo[5.1.0]octane & (1R,7S,8R)-6-(7-chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-8-fluoro-2-oxa-6-azabicyclo[5.1.0]octane

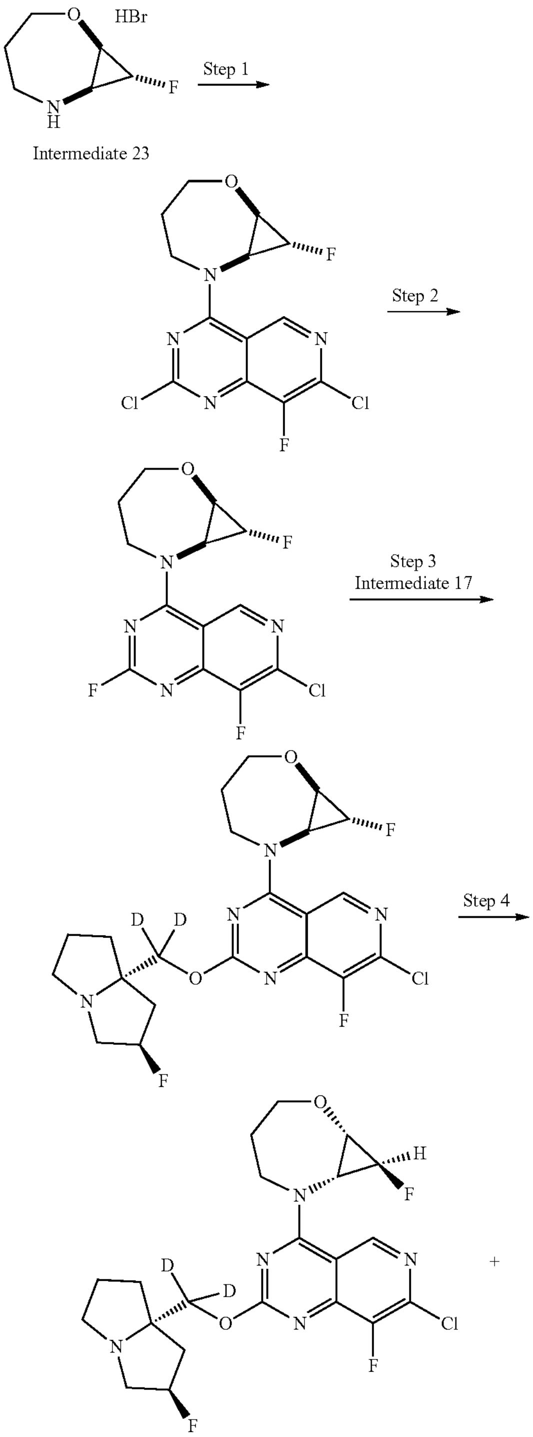

Intermediate 23

Intermediate 27

-continued

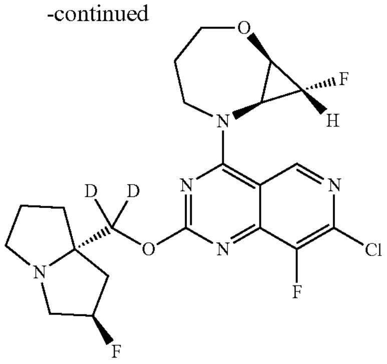

Intermediate 28

Step 1: 6-(2,7-Dichloro-8-fluoropyrido[4,3-d]pyrimidin-4-yl)-8-fluoro-2-oxa-6-azabicyclo[5.1.0]octane (trans mixture)

A solution of 2,4,7-trichloro-8-fluoropyrido[4,3-d]pyrimidine (260 mg, 1.03 mmol) and 4A molecular sieves in DCM (13 mL) was stirred at room temperature for 30 min, and then DIEA (399.34 mg, 3.09 mmol) and Intermediate 23 (trans mixture) (130 mg, crude) were added at −40° C. The reaction mixture was stirred at −40° C. for 1 hour. The resulting mixture was diluted with 10% citric solution (50 mL) and extracted with DCM (3×50 mL). The combined organic layers were washed with brine (50 mL), dried over anhydrous $Na_2SO_4$, filtered and concentrated under reduced pressure. The residue was purified by silica gel flash chromatography, eluted with DCM/EA (5: 1) to afford the title compound (trans mixture) (160 mg, 44% yield) as a light yellow solid. MS: m/z=346.95, 348.95 $[M+H]^{+\cdot}$ Step 2: 6-(7-Chloro-2,8-difluoropyrido[4,3-d]pyrimidin-4-yl)-8-fluoro-2-oxa-6-azabicyclo[5.1.0]octane (trans mixture)

To a stirred solution of 6-(2,7-dichloro-8-fluoropyrido[4,3-d]pyrimidin-4-yl)-8-fluoro-2-oxa-6-azabicyclo[5.1.0]octane (trans mixture) (250 mg, 0.72 mmol) in DMSO (25 mL) was added KF (83.68 mg, 1.44 mmol) at room temperature under nitrogen atmosphere. The reaction mixture was heated at 80° C. for 16 hours. The resulting mixture was cooled to room temperature, diluted with water (100 mL), extracted with EtOAc (3×100 mL). The combined organic layers were dried over anhydrous $Na_2SO_4$, filtered and concentrated under reduced pressure. The residue was purified by silica gel flash chromatography, eluted with DCM/EA (5: 1) to afford the title compound (trans mixture) (100 mg, 41% yield) as a light yellow solid. MS: m/z=331.00 $[M+H]^{+\cdot}$ Step 3: 6-(7-chloro-8-fluoro-2-(((2R,7aS)-2-fluoro-tetrahydro-1H-pyrrolizin-7a (5H)-yl) methoxy-d2) pyrido[4,3-d]pyrimidin-4-yl)-8-fluoro-2-oxa-6-azabicyclo[5.1.0]octane (trans mixture)

To an ice-cooled stirred mixture of Intermediate 17 (58.50 mg, 0.36 mmol) in THF (9 mL) was added NaH (14.51 mg, 60% dispersion in mineral oil) under nitrogen atmosphere. After stirring with an ice bath for 30 min, 6-(7-chloro-2,8-difluoropyrido[4,3-d]pyrimidin-4-yl)-8-fluoro-2-oxa-6-azabicyclo[5.1.0]octane (trans mixture) (100 mg, 0.30 mmol) was added to the above mixture. The ice bath was removed, and the reaction mixture was stirred at room temperature for an hour. The resulting mixture was quenched with sat. aq. $NH_4Cl$ (50 mL) and extracted with $CH_2Cl_2$ (3×50 mL). The combined organic layers were dried over anhydrous $Na_2SO_4$, filtered and concentrated under reduced pressure. The residue was purified by silica gel flash chromatography, eluted with $CH_2Cl_2$/MeOH (10: 1) to afford the title compound (trans mixture) (65 mg, 45% yield) as a light yellow solid. MS: m/z=472.10 $[M+H]^{+\cdot}$ Step 3: (1S,7R,8S)-6-(7-Chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-8-fluoro-2-oxa-6-azabicyclo[5.1.0]octane & (1R,7S,8R)-6-(7-chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-8-fluoro-2-oxa-6-azabicyclo[5.1.0]octane 6-(7-Chloro-8-fluoro-2-(((2R,7aS)-2-fluorotetrahydro-1H-pyrrolizin-7a (SH)-yl) methoxy-$d_2$)pyrido[4,3-d]pyrimidin-4-yl)-8-fluoro-2-oxa-6-azabicyclo[5.1.0]octane (trans mixture) (65 mg, 0.14 mmol) was separated by Prep-CHIRAL-HPLC with the following conditions: Column: CHIRALPAK IF, 2*25 cm, 5 μm; Mobile Phase A: Hex (0.5% 2M $NH_3$-MeOH), Mobile Phase B: EtOH; Flow rate: 20 mL/min; Gradient: isocratic 25; Wave Length: 220/254 nm; RT1: 14.707 min; RT2: 18.946 min. The first eluting peak (RT1: 14.707 min) was concentrated and lyophilized to give the title compound (Intermediate 27, 26 mg, 40% yield) as a light yellow solid. The second eluting peak (RT2: 18.946 min) was concentrated and lyophilized to give the title compound (Intermediate 28, 27 mg, 41% yield) as a light yellow solid.

Intermediate 29 & 30: (1S,7R)-6-(7-Chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-2-oxa-6-azabicyclo[5.1.0]octane-5,5-$d_2$ & (1R,7S)-6-(7-chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-2-oxa-6-azabicyclo[5.1.0]octane-5,5-$d_2$

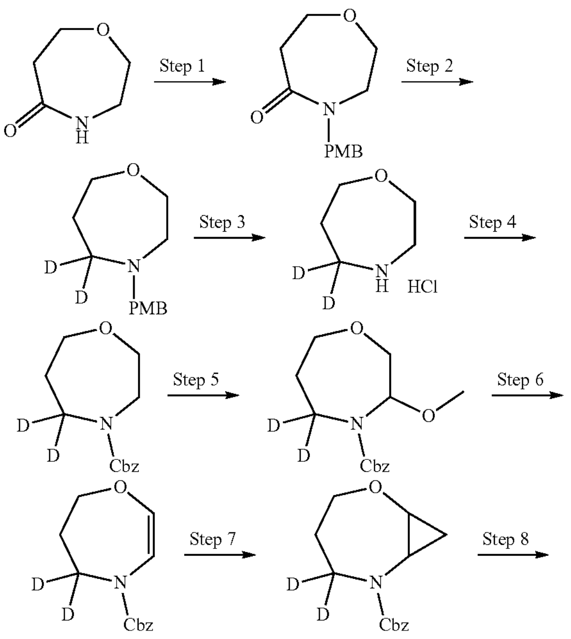

-continued

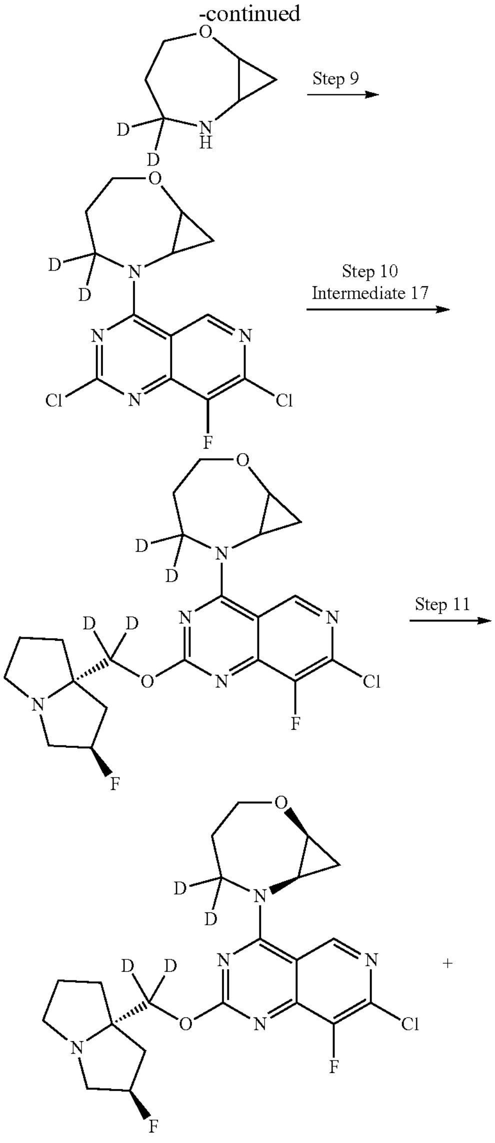

Intermediate 29

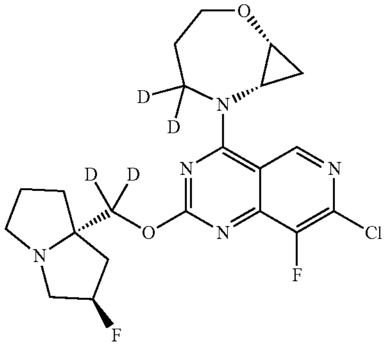

Intermediate 30

Step 1: 4-[(4-Methoxyphenyl)methyl]-1,4-oxazepan-5-one

To an ice-cooled solution of 1,4-oxazepan-5-one (30 g, 260.57 mmol) in DMF (300 mL) was added NaH (12.51 g, 312.68 mmol, 60% dispersion in mineral oil) under nitrogen atmosphere. After stirring with an ice bath for 15 min, PMBCl (44.89 g, 286.63 mmol) was added dropwise. The ice bath was removed, and the reaction mixture was stirred at room temperature for 3 hours. The resulting mixture was quenched with sat. aq. $NH_4Cl$ (1000 mL) and extracted with EA (4×800 mL). The combined organic layers were washed with brine (800 mL), dried over $Na_2SO_4$, filtered and concentrated under reduced pressure. The residue was purified by silica gel flash chromatography, eluted with 4% MeOH in DCM to the title compound (52 g, 84% yield) as a colorless oil. 1H-NMR (300 MHz, DMSO-$d_6$) δ7.21-7.16 (m, 2H), 6.91-6.86 (m, 2H), 4.44 (s, 2H), 3.73 (s, 3H), 3.66-3.63 (m, 2H), 3.50-3.38 (m, 4H), 2.73-2.67 (m, 2H).

Step 2: 4-(4-Methoxybenzyl)-1,4-oxazepane-5,5-$d_2$

To an ice-cooled solution of 4-[(4-methoxyphenyl) methyl]-1,4-oxazepan-5-one (24 g, 102.00 mmol) in THF (240 mL) under nitrogen atmosphere was added $LiAlD_4$ (306.01 mL, 306.01 mmol, 1 M in THF) dropwise. The ice bath was removed, and the reaction mixture was stirred at room temperature for 16 hours. The resulting mixture was quenched with water (11.6 mL), 15% aq. NaOH (34.8 mL) and water (11.6 mL) with an ice bath. The resulting mixture was stirred at room temperature for 15 min, then filtered and concentrated under reduced pressure. The residue was purified by silica gel flash chromatography, eluted with 3% MeOH in DCM to afford the title compound (18.9 g, 82% yield) as a colorless oil. 1H-NMR (400 MHZ, Chloroform-d) § 7.26-7.24 (m, 2H), 6.88-6.84 (m, 2H), 3.83-3.76 (m, 5H), 3.74-3.70 (m, 2H), 3.60 (s, 2H), 2.68-2.63 (m, 2H), 1.89-1.86 (m, 2H).

Step 3: 1,4-oxazepane-5,5-$d_2$ hydrochloride

To an ice-cooled solution of 4-(4-methoxybenzyl)-1,4-oxazepane-5,5-$d_2$ (18.9 g, 84.63 mmol) in DCE (380 mL) under nitrogen atmosphere was added 1-chloroethyl carbonochloridate (30.25 g, 211.59 mmol). The ice bath was removed, and the reaction mixture was heated at 85° C. for 16 hours. The resulting mixture was cooled to room temperature and concentrated under reduced pressure. The residue was dissolved in MeOH (190 mL) and heated at 65° C. for 3 hours. The resulting mixture was cooled to room temperature and HCl (4 N in 1,4-dioxane, 21.16 mL, 84.64 mmol) was added. The resulting mixture was concentrated under reduced pressure. The residue was triturated with Et20 (3×50 mL) to afford the title compound (11.2 g, crude) as a yellow solid.

Step 4: Benzyl 1,4-oxazepane-4-carboxylate-5,5-$d_2$

To an ice-cooled mixture of 1,4-oxazepane-5,5-$d_2$ hydrochloride (10 g, 71.62 mmol) and $K_2CO_3$ (27.77 g, 214.87 mmol) in THF (100 mL) under nitrogen atmosphere was added Cbz-$C_1$ (14.66 g, 85.95 mmol) dropwise. The ice bath was removed, and the resulting mixture was stirred at room temperature for 16 hours. The resulting mixture was quenched with $H_2O$ (300 mL) and extracted with ethyl acetate (3×300 mL). The combined organic layers were washed with brine (500 mL), dried over anhydrous sodium sulfate, filtered and concentrated under reduced pressure. The residue was purified by silica gel flash chromatography, eluted with 35% EA in PE to afford benzyl 1,4-oxazepane-4-carboxylate-5,5-$d_2$ (13 g, 76% yield) as a colorless oil. 1H NMR (400 MHz, Chloroform-d) δ 7.37-7.29 (m, 5H), 5.15 (s, 2H), 3.81-3.69 (m, 4H), 3.62-3.56 (m, 2H), 1.93-1.86 (m, 2H).

Step 5: Benzyl 3-methoxy-1,4-oxazepane-4-carboxylate-5,5-$d_2$ & benzyl 5-methoxy-1,4-oxazepane-4-carboxylate-5-d To a solution of benzyl 1,4-oxazepane-4-carboxylate-5,5-$d_2$ (13 g, 54.78 mmol) in MeOH (150 mL) was added tetraethylammonium tosylate (8.26 g, 27.39 mmol) at room temperature. The reaction mixture was electrolyzed at room temperature for 20 hours using C(+)/C(−) electrodes at constant current 200 mA. The resulting mixture was concentrated under reduced pressure. The residue was purified by silica gel flash chromatography, eluted 35% EA in PE to afford the title compounds (12 g, 82% yield) as a light-yellow oil. 1H-NMR (400 MHZ, Chloroform-d) δ crude H-NMR showed two isomers.

Step 6: Benzyl 6,7-dihydro-1,4-oxazepine-4 (5H)-carboxylate-5,5-$d_2$

To an ice-cooled solution of benzyl 3-methoxy-1,4-oxazepane-4-carboxylate-5,5-$d_2$ & benzyl 5-methoxy-1,4-oxazepane-4-carboxylate-5-d (11.7 g, 43.76 mmol) in DCM (120 mL) were added DIEA (5.26 g, 40.66 mmol) and TMSOTf (8.34 g, 37.54 mmol) under nitrogen atmosphere. The resulting mixture was stirred in an ice bath for 30 min, quenched with saturated aq. $NaHCO_3$ (100 mL), and extracted with ethyl acetate (3×100 mL). The combined organic layers were washed with brine (100 mL), dried over anhydrous sodium sulfate, filtered and concentrated under reduced pressure. The residue was purified by silica gel flash chromatography, eluted with 42% EA in PE to afford two isomers. The first eluting peak was collected and concentrated under reduced pressure to afford the title compound (5.0 g, 48% yield) as a yellow oil. $^1H$ NMR (300 MHz, Chloroform-d) δ 7.41-7.29 (m, 5H), 5.94-5.74 (m, 2H), 5.18 (s, 2H), 4.10-4.07 (m, 2H), 2.04-1.96 (m, 2H).

Step 7: Benzyl 2-oxa-6-azabicyclo[5.1.0]octane-6-carboxylate-5,5-$d_2$

To a solution of benzyl 6,7-dihydro-1,4-oxazepine-4 (5/)-carboxylate-5,5-$d_2$ (5.0 g, 21.25 mmol) in DCM (50 mL) was added ZnEt2 (53.13 mL, 53.13 mmol, 1 M in n-hexane) at room temperature. After stirring at room temperature for 0.5 hour, a solution of $CH_2I_2$ (22.77 g, 85.00 mmol) in DCM (12 mL) was added to the mixture dropwise with an ice bath. The reaction mixture was stirred at room temperature for 12 hours. The resulting mixture was poured into cold sat. aq. $NH_4Cl$ (100 mL) and extracted with DCM (3×100 mL). The combined organic layers were washed with brine (100 mL), dried with anhydrous $Na_2SO_4$, filtered and concentrated under reduced pressure. The residue was purified by silica gel flash chromatography, eluted with 35% EA in PE to afford the title compound (4.0 g, 75% yield) as a yellow oil. MS: m/z=250.10 $[M+H]^+$. $^1H$ NMR (400 MHZ, Chloroform-d) 6 7.39-7.29 (m, 5H), 5.20-5.10 (m, 2H), 3.97-3.92 (m, 1H), 3.69-3.63 (m, 1H), 3.43-3.39 (m, 1H), 2.45-2.42 (m, 1H), 1.91-1.64 (m, 2H), 1.26-1.10 (m, 2H).

Step 8: 2-Oxa-6-azabicyclo[5.1.0]octane-5,5-$d_2$

To an ice-cooled solution of benzyl 2-oxa-6-azabicyclo [5.1.0]octane-6-carboxylate-5,5-$d_2$ (2 g, 8.02 mmol) in MeOH (100 mL) was added Pd/C(667 mg, 10 wt %) under nitrogen atmosphere. The reaction mixture was stirred in an ice bath for 40 min under hydrogen atmosphere. The resulting mixture was filtered and concentrated under reduced pressure to afford the title compound (580 mg, crude used through) as a light yellow oil.

Step 9: 6-(2,7-dichloro-8-fluoropyrido[4,3-d]pyrimidin-4-yl)-2-oxa-6-azabicyclo[5.1.0]octane-5,5-$d_2$ To a stirred solution of 2,4,7-trichloro-8-fluoropyrido[4,3-d]pyrimidine (1.27 g, 5.03 mmol) and 2-oxa-6-azabicyclo[5.1.0]octane-5,5-$d_2$ (580 mg, crude) in DCM (13 mL) was added DIEA (1.95 g, 15.10 mmol) dropwise at −40° C. under nitrogen atmosphere. The reaction mixture was stirred at −40° C. for 1 hour. The resulting mixture was quenched with 10% citric solution (50 mL) and extracted with DCM (3×80 mL). The combined organic layers were washed with brine (100 mL), dried over anhydrous $Na_2SO_4$, filtered and concentrated under reduced pressure to afford the title compound (1.1 g, crude used through) as a light yellow solid. MS: m/z=331.10, 333.10 [M+H].

Step 10: 6-(7-Chloro-8-fluoro-2-(((2R,7aS)-2-fluorotetrahydro-1H-pyrrolizin-7a (5H)-yl) methoxy-$d_2$) pyrido[4,3-d]pyrimidin-4-yl)-2-oxa-6-azabicyclo [5.1.0]octane-5,5-d2

To a stirred solution of 6-(2,7-dichloro-8-fluoropyrido[4,3-d]pyrimidin-4-yl)-2-oxa-6-azabicyclo[5.1.0]octane-5,5-$d_2$ (1.1 g, 3.32 mmol) in DMSO (11 mL) under nitrogen atmosphere were added KF (675.40 mg, 11.62 mmol) and Intermediate 17 (856.79 mg, 5.31 mmol) at room temperature. The reaction mixture was heated at 100° C. for 16 hours. The resulting mixture was cooled to room temperature, diluted with water (60 mL), and extracted with DCM (3×60 mL). The combined organic layers were washed with brine (3×50 mL), dried over anhydrous Na2$SO_4$, filtered and concentrated under reduced pressure. The residue was purified by silica gel flash chromatography, eluted with $CH_2Cl_2$/MeOH (10: 1) to afford the title compound (670 mg, 29% yield for two steps) as a light yellow solid. MS: m/z=456.30 $[M+H]^{+\cdot}$ Step 11: (1S,7R)-6-(7-Chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-2-oxa-6-azabicyclo[5.1.0]octane-5,5-$d_2$ & (1R,7S)-6-(7-chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-2-oxa-6-azabicyclo[5.1.0]octane-5, 5-da 6-(7-Chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-2-oxa-6-azabicyclo[5.1.0]octane-5,5-$d_2$ (900 mg, 1.97 mmol) was separated by Prep-SFC with the following conditions: Column: Enantiocel $C_9$-5, 30×250 mm, 5.0 μm; Mobile Phase A: $CO_2$, Mobile Phase B: IPA; Flow rate: 100 mL/min; Gradient: isocratic 50% B; Back Pressure (bar): 100; Detector: UV 220 nm; RT1: 3.9 min; RT2: 6.4 min; Sample Solvent: MeOH: DCM=2: 1. The first eluting peak (RT1: 3.9 min) was concentrated and lyophilized to give the title compound (Intermediate 29, 350 mg, 38% yield) as a light yellow solid. MS: m/z=456.30 $[M+H]^+$. The second eluting peak (RT2: 6.4 min) was concentrated and lyophilized to give the title compound (Intermediate 30, 350 mg, 38% yield) as a light yellow solid. MS: m/z=456.30 $[M+H]^{+\cdot}$ Intermediate 31 & 32: Benzyl 8-fluoro-5-oxa-2-azabicyclo[5.1.0]octane-2-carboxylate (trans mixture) & Benzyl 8-fluoro-5-oxa-2-azabicyclo[5.1.0]octane-2-carboxylate (cis mixture)

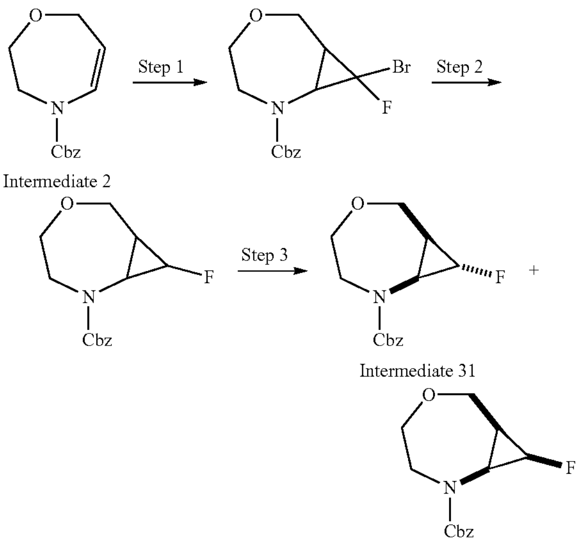

Intermediate 2

Intermediate 31

Intermediate 32

Step 1: Benzyl 8-bromo-8-fluoro-5-oxa-2-azabicyclo[5.1.0]octane-2-carboxylate

To an ice-cooled solution of Intermediate 2 (2.0 g, 8.58 mmol) and TBAI (0.65 g, 1.76 mmol) in DCM (10 mL) under nitrogen atmosphere were added 33 wt % aq. NaOH solution (20 mL) and dibromofluoromethane (4.94 g, 25.74 mmol). The ice bath was removed, and the reaction mixture was stirred at room temperature for 16 hours. The resulting mixture was diluted with iced water (50 mL), extracted with DCM (3×50 mL). The combined organic layers were washed with brine (50 mL), dried over anhydrous $Na_2SO_4$, filtered, and concentrated under reduced pressure. The residue was purified by silica gel flash chromatography, eluted with 0-30% EA in PE to afford the title compound (2.4 g, 82% yield) as an off-white semi-solid. MS: m/z=361.10, 363.10 $[M+NH_4]^{+\cdot}$ Step 2 & 3: Benzyl 8-fluoro-5-oxa-2-azabicyclo[5.1.0]octane-2-carboxylate (trans mixture) & Benzyl 8-fluoro-5-oxa-2-azabicyclo[5.1.0]octane-2-carboxylate (cis mixture)

To a stirred mixture of benzyl 8-bromo-8-fluoro-5-oxa-2-azabicyclo[5.1.0]octane-2-carboxylate (2.4 g, 7.00 mmol) in EtOH (25 mL) under nitrogen atmosphere were added $NH_4Cl$ (3.37 g, 63.00 mmol) and Zn (4.12 g, 63.00 mmol) at room temperature. The reaction mixture was heated at 70° C. for 16 hours. The resulting mixture was cooled to room temperature, filtered and concentrated under reduced pressure. The residue was purified by silica gel flash chromatography, eluted with 0-20% EA in PE to afford two mixtures. The first eluting mixtures were collected and concentrated under reduced pressure to give the title compound (trans mixture) (Intermediate 31, 700 mg, 38% yield) as an off-white semi-solid. MS: m/z=283.20 $[M+NH_4]^+$. $^1H$ NMR (300 MHz, Chloroform-d) & 7.39-7.32 (m, 5H), 5.30-5.21 (m, 2H), 4.72-4.52 (m, 1H), 4.41-4.35 (m, 1H), 4.06-4.01 (m, 1H), 3.85-3.80 (m, 1H), 3.49-3.30 (m, 1H), 3.25-3.14 (m, 3H), 2.05-1.92 (m, 1H). $^{19}F$ NMR (282 MHz, Chloroform-d) δ −207.85 (s, 1F). The second eluting mixtures were collected and concentrated under reduced pressure to give the title compound (cis mixture) (Intermediate 32, 360 mg, 19% yield) as a yellow oil. MS: m/z=283.20 $[M+NH_4]^+$. $^1H$ NMR (300 MHz, Chloroform-d) δ 7.38-7.30 (m, 5H), 5.15 (s, 2H), 4.67-4.46 (m, 1H), 4.33-4.26 (m, 1H), 4.19-4.14 (m, 1H) 4.02-3.91 (m, 1H), 3.69-3.55 (m, 2H), 3.37-3.29 (m, 1H), 2.74-2.72 (m, 1H)1.64-1.51 (m, 1H). $^{19}F$ NMR (282 MHz, Chloroform-d) δ −232.23 (s, 1F).

Intermediate 33 & 34: (1R,7R,8R)-2-(7-Chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-8-fluoro-5-oxa-2-azabicyclo[5.1.0]octane & (1S,7S,8S)-2-(7-chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-8-fluoro-5-oxa-2-azabicyclo[5.1.0]octane

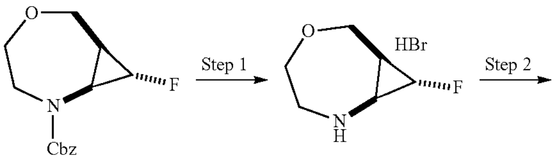

Intermediate 31

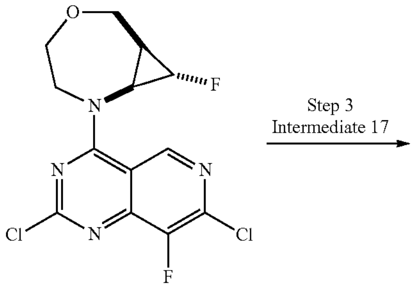

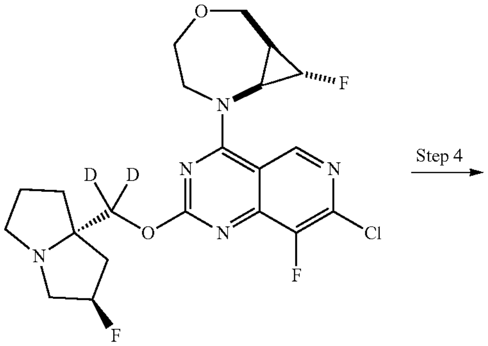

-continued

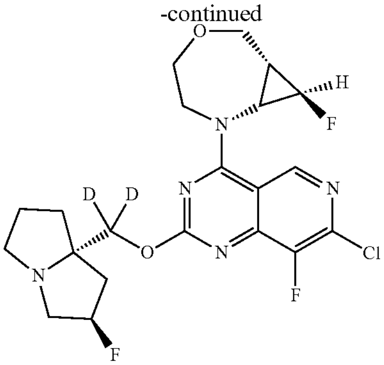

+

Intermediate 33

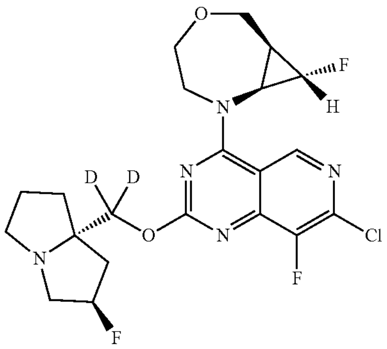

Intermediate 34

Step 1: 8-Fluoro-5-oxa-2-azabicyclo[5.1.0]octane hydrobromide (trans mixture)

Intermediate 31 (trans mixture) (2.6 g, 9.81 mmol) in 33 wt % HBr in AcOH (26 mL) under nitrogen atmosphere was stirred in an ice bath for 1 hour. The resulting mixture was concentrated under reduced pressure. The residue was trituration with hexane (3×50 mL) to afford the title compound (trans mixture, HBr salt) (1.9 g, crude used through) as a light yellow solid.

Step 2: 2-(2,7-Dichloro-8-fluoropyrido[4,3-d]pyrimidin-4-yl)-8-fluoro-5-oxa-2-azabicyclo[5.1.0]octane (trans mixture)

To a stirred solution of 8-fluoro-5-oxa-2-azabicyclo[5.1.0]octane hydrobromide (trans mixture) (600 mg, crude) and 2,4,7-trichloro-8-fluoropyrido[4,3-d]pyrimidine (1154.94 mg, 4.57 mmol) in DCM (11 mL) was added DIEA (1773.88 mg, 13.72 mmol) dropwise at −40° C. under nitrogen atmosphere. The reaction mixture was stirred at −40° C. for 1 hour. The resulting mixture was diluted with 10% citric solution (50 mL) and extracted with DCM (3×50 mL). The combined organic layers were washed with brine (50 mL.), dried over anhydrous $Na_2SO_4$, filtered and concentrated under reduced pressure. The residue was purified by silica gel flash chromatography, cluted with $CH_2Cl_2$/EA (5: 1) to afford the title compound (trans mixture) (800 mg, 50% yield) as a light yellow solid. MS: m/z=347.10, 349.10 [M+H].

Step 3: 2-(7-Chloro-8-fluoro-2-(((2R,7aS)-2-fluoro-tetrahydro-1/-pyrrolizin-7a (5)-yl) methoxy-$d_2$) pyrido[4,3-d]pyrimidin-4-yl)-8-fluoro-5-oxa-2-azabicyclo[5.1.0]octane (trans mixture)

To a stirred solution of 2-(2,7-dichloro-8-fluoropyrido[4,3-d]pyrimidin-4-yl)-8-fluoro-5-oxa-2-azabicyclo[5.1.0]octane (trans mixture) (800 mg, 2.30 mmol) in DMSO (8 mL) under nitrogen atmosphere were added KF (468.59 mg, 8.06 mmol) and Intermediate 17 (594.43 mg, 3.68 mmol) at room temperature. The resulting mixture was heated at 100° C. for 16 hours. The resulting mixture was cooled to room temperature, diluted with water (50 mL) and extracted with DCM (3×100 mL). The combined organic layers were washed with brine (50 mL), dried over anhydrous $Na_2SO_4$, filtered and concentrated under reduced pressure. The residue was purified by silica gel flash chromatography, eluted with $CH_2Cl_2$/MeOH (10: 1) to afford the title compound (trans mixture) (400 mg, 36% yield) as a light yellow solid. MS: m/z=472.25 $[M+H]^{+\cdot}$ Step 4: (1R,7R,8R)-2-(7-Chloro-8-fluoro-2-(((2R,7aS)-2-fluorotetrahydro-1H-pyrrolizin-7a (5H)-yl) methoxy-$d_2$) pyrido[4,3-d]pyrimidin-4-yl)-8-fluoro-5-oxa-2-azabicyclo [5.1.0]octane & (1S,7S,8S)-2-(7-chloro-8-fluoro-2-(((2R, 7aS)-2-fluorotetrahydro-1/-pyrrolizin-7a (5H)-yl) methoxy-$d_2$)pyrido[4,3-d]pyrimidin-4-yl)-8-fluoro-5-oxa-2-azabicyclo[5.1.0]octane 2-(7-Chloro-8-fluoro-2-(((2R,7aS)-2-fluorotetrahydro-1/-pyrrolizin-7a (5H)-yl) methoxy-$d_2$) pyrido[4,3-d]pyrimidin-4-yl)-8-fluoro-5-oxa-2-azabicyclo [5.1.0]octane (trans mixture) (400 mg, 0.84 mmol) was separated by Prep-SFC with the following conditions: Column: (S, S)-Whelk-O 1 5 μm Kromasil, 3×25 cm, 5 μm; Mobile Phase A: $CO_2$; Mobile Phase B: MeCN: MeOH=1: 1 (1% 2 M $NH_3$-MeOH); Flow rate: 100 mL/min; Gradient: isocratic 50% B; Back Pressure (bar): 100; Detector: UV 220 nm; RT1: 3.3 min; RT2: 6.1 min, Sample Solvent: MeOH. The first eluting peak (RT1: 3.3 min) was concentrated and lyophilized to give the title compound (Intermediate 33, 150 mg, 37%) as a light yellow solid. MS: m/z=472.10 $[M+H]^+$. $^1$H NMR (400 MHz, Chloroform-d) δ 9.21 (s, 1H), 5.41-5.16 (m, 1H), 4.69-4.55 (m, 1H), 4.50-4.21 (m, 2H), 4.03-3.79 (m, 3H), 3.70-3.55 (m, 1H), 3.33-3.15 (m, 3H), 3.05-2.94 (m, 1H), 2.40-1.74 (m, 8H). $^{19}$F. NMR (376 MHz, $CDCl_3$) δ −134.22 (s, IF), —173.15 (s, IF), —207.66 (s, IF). The second eluting peak (RT2: 6.1 min) was concentrated and lyophilized to give the title compound (Intermediate 34, 200 mg, 50%) as a light yellow solid. MS: m/z=472.10 $[M+H]^+$: $^1$H NMR (400 MHZ, Chloroform-d) δ 9.22 (s, 1H), 5.37-5.16 (m, 1H), 4.68-4.58 (m, 1H), 4.49-4.22 (m, 2H), 4.02-3.81 (m, 3H), 3.71-3.57 (m, 1H), 3.31-3.12 (m, 3H), 3.05-2.91 (m, 1H), 2.40-1.77 (m, 8H). $^{19}$F. NMR (376 MHz, $CDCl_3$) δ −134.20 (s, IF), —173.11 (s, IF), —207.61 (s, IF).

Intermediate 35 & 36: (1R,7R,8S)-2-(7-Chloro-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane & (1S,7S,8R)-2-(7-chloro-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane

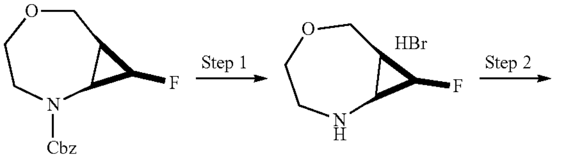

Intermediate 32

-continued

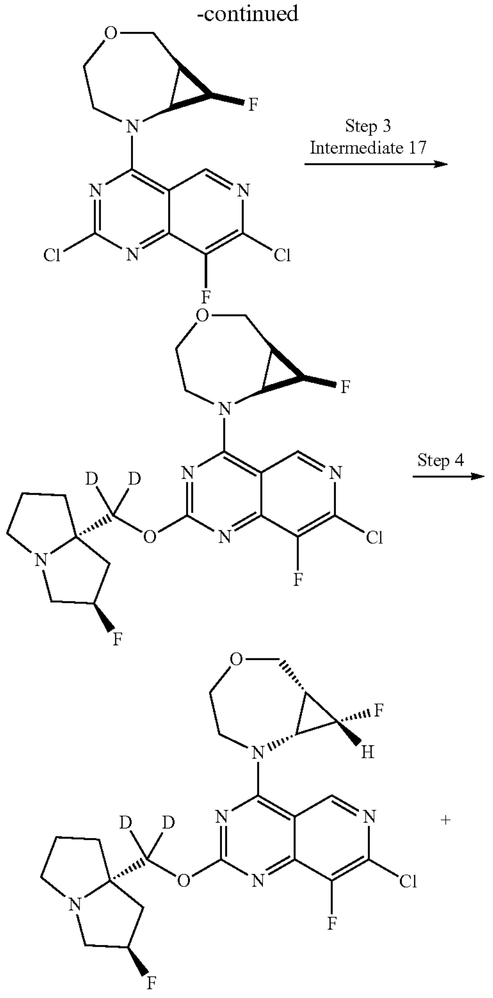

Intermediate 35

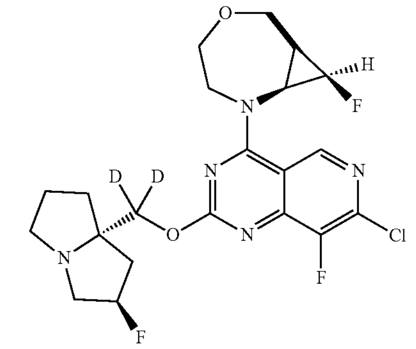

Intermediate 36

Step 1: 8-fluoro-5-oxa-2-azabicyclo[5.1.0]octane hydrobromide (cis mixture)

A solution of Intermediate 32 (600 mg, 2.26 mmol) in 33 wt % HBr in AcOH (6 mL) under nitrogen atmosphere was stirred in an ice bath for 1 hour. The resulting mixture was concentrated under reduced pressure. The residue was purified by trituration with hexane (3×50 mL) to afford the title compound (cis mixture, HBr salt) (470 mg, crude used through) as a light yellow solid.

Step 2: 2-(2,7-dichloro-8-fluoropyrido[4,3-d]pyrimidin-4-yl)-8-fluoro-5-oxa-2-azabicyclo[5.1.0]octane (cis mixture)

To a stirred solution of 2,4,7-trichloro-8-fluoropyrido[4,3-d]pyrimidine (866.20 mg, 3.43 mmol) and 8-fluoro-5-oxa-2-azabicyclo[5.1.0]octane hydrobromide (cis mixture) (450 mg, crude) in DCM (18 mL) was added DIEA (1.33 g, 10.29 mmol) dropwise at −40° C. under nitrogen atmosphere. The reaction mixture was stirred at −40° C. for 1 hour. The resulting mixture was diluted with 10% citric solution (50 mL) and extracted with DCM (3x50 mL). The combined organic layers were washed with brine (50 mL), dried over anhydrous $Na_2SO_4$, filtered and concentrated under reduced pressure. The residue was purified by silica gel flash chromatography, eluted with PE/EA (1: 1) to afford the title compound (cis mixture) (260 mg, 21% yield) as a light yellow solid. MS: m/z=347.05, 349.05 $[M+H]^{+\cdot}$ Step 3: 2-(7-Chloro-8-fluoro-2-(((2R,7aS)-2-fluorotetrahydro-1H-pyrrolizin-7a (5H)-yl) methoxy-$d_2$) pyrido[4,3-d]pyrimidin-4-yl)-8-fluoro-5-oxa-2-azabicyclo[5.1.0]octane (cis mixture)

To a stirred solution of 2-(2,7-dichloro-8-fluoropyrido[4,3-d]pyrimidin-4-yl)-8-fluoro-5-oxa-2-azabicyclo[5.1.0]octane (cis mixture) (250 mg, 0.72 mmol) in DMSO (2.5 mL) under nitrogen atmosphere were added KF (146.43 mg, 2.52 mmol) and Intermediate 17 (185.76 mg, 1.15 mmol) at room temperature. The reaction mixture was heated at 100° C. for 16 hours. The resulting mixture was cooled to room temperature, diluted with water (20 mL), extracted with DCM (3x30 mL). The combined organic layers were washed with brine (3x20 mL), dried over anhydrous $Na_2SO_4$, filtered and concentrated under reduced pressure. The residue was purified by silica gel flash chromatography, eluted with $CH_2Cl_2$/MeOH (10: 1) to afford 2-(7-chloro-8-fluoro-2-(((2R,7aS)-2-fluorotetrahydro-1H-pyrrolizin-7a (5H)-yl) methoxy-$d_2$) pyrido[4,3-d]pyrimidin-4-yl)-8-fluoro-5-oxa-2-azabicyclo [5.1.0]octane (cis mixture) (100 mg, 29% yield) as a light yellow solid. MS: m/z=472.30 $[M+H]^{+\cdot}$ Step 4: (1R, 7R,8S)-2-(7-Chloro-8-fluoro-2-(((2R,7aS)-2-fluorotetrahydro-1H-pyrrolizin-7a (5H)-yl) methoxy-$d_2$) pyrido[4,3-d]pyrimidin-4-yl)-8-fluoro-5-oxa-2-azabicyclo [5.1.0]octane & (IS, 7S,8R)-2-(7-chloro-8-fluoro-2-(((2R, 7aS)-2-fluorotetrahydro-1H-pyrrolizin-7a (5H)-yl) methoxy-$d_2$)pyrido[4,3-d]pyrimidin-4-yl)-8-fluoro-5-oxa-2-azabicyclo[5.1.0]octane 2-(7-Chloro-8-fluoro-2-(((2R, 7aS)-2-fluorotetrahydro-1/-pyrrolizin-7a (5H)-yl) methoxy-$d_2$)pyrido[4,3-d]pyrimidin-4-yl)-8-fluoro-5-oxa-2-azabicyclo[5.1.0]octane (cis mixture) (100 mg, 0.21 mmol) was separated by Prep-CHIRAL-HPLC with the following conditions: Column: CHIRALPAK IF, 2x25 cm, 5 μm; Mobile Phase A: Hex (0.5% 2 M $NH_3$-MeOH), Mobile Phase B: EtOH; Flow rate: 20 mL/min; Gradient: isocratic 20%; Detector: UV 220 & 254 nm; RT1: 14.255 min; RT2: 16.335 min. The first eluting peak (RT1: 14.225 min) was concentrated and lyophilized to give the title compound (Intermediate 35, 35 mg, 35% yield) as a light yellow solid. MS: m/z=471.85 $[M+H]^+$. The second eluting peak (RT2: 16.335 min) was concentrated and lyophilized to give the title compound (Intermediate 36, 35 mg, 35% yield) as a light yellow solid. MS: m/z=471.80 $[M+H]^{+\cdot}$ Intermediate 37 & 38: (1R,6S)-5-(7-Chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-2-oxa-5-azabicyclo[4.1.0]heptane. & (1S,6R)-5-(7-chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-2-oxa-5-azabicyclo[4.1.0]heptane

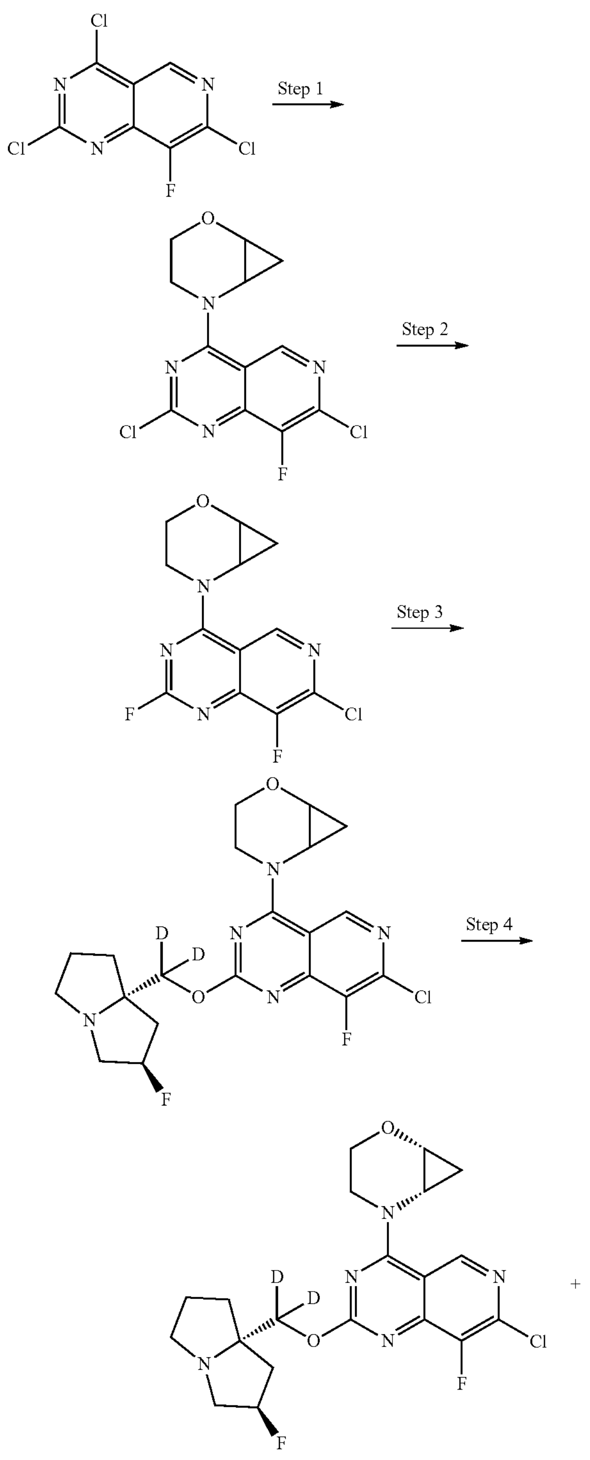

Intermediate 37

-continued

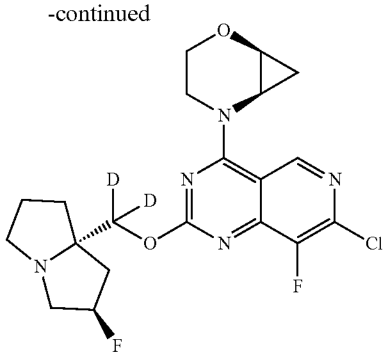

Intermediate 38

Step 1: 5-(2,7-Dichloro-8-fluoropyrido[4,3-d]pyrimidin-4-yl)-2-oxa-5-azabicyclo[4.1.0]heptane To a mixture of 2,4,7-trichloro-8-fluoropyrido[4,3-d]pyrimidine (2 g, 7.92 mmol) and 2-oxa-5-azabicyclo[4.1.0]heptane hydrochloride (1.07 g, 7.92 mmol) in DCM (40 mL) under nitrogen atmosphere was added DIEA (3.07 g, 23.76 mmol) dropwise at −40° C. The reaction mixture was stirred at −40° C. for 1 hour. The resulting mixture was diluted with water (150 mL) and extracted with DCM (3×100 mL). The combined organic layers were dried over anhydrous $Na_2SO_4$, filtered and concentrated under reduced pressure. The residue was purified by silica gel flash chromatography, eluted with 5% methanol in dichloromethane to afford the title compound (2 g, 80% yield) as a yellow solid. MS: m/z=314.95, 316.95 $[M+H]^{+\cdot}$ Step 2: 5-(7-Chloro-2,8-difluoropyrido[4,3-d]pyrimidin-4-yl)-2-oxa-5-azabicyclo[4.1.0]heptane To a stirred solution of 5-(2,7-dichloro-8-fluoropyrido[4,3-d]pyrimidin-4-yl)-2-oxa-5-azabicyclo[4.1.0]heptane (2 g, 6.34 mmol) in DMSO (40 mL) under nitrogen atmosphere was added KF (0.66 g, 11.42 mmol) at room temperature. The reaction mixture was heated at 80° C. for 16 hours. The resulting mixture was cooled to room temperature, diluted with EtOAc (300 mL), and washed with brine (3×80 mL). The organic layer was dried over anhydrous $Na_2SO_4$, filtered and concentrated under reduced pressure. The residue was purified by silica gel flash chromatography, eluted with 5% methanol in dichloromethane to afford the title compound (1.5 g, 79% yield) as a yellow solid. MS: m/z=299.00 $[M+H]^{+\cdot}$ Step 3: 5-(7-Chloro-8-fluoro-2-(((2R,7aS)-2-fluoro-tetrahydro-1H-pyrrolizin-7a (5H)-yl) methoxy-$d_2$) pyrido[4,3-d]pyrimidin-4-yl)-2-oxa-5-azabicyclo [4.1.0]heptane To an ice-cooled solution of Intermediate 17 (0.97 g, 6.02 mmol) in THF (40 mL) under nitrogen atmosphere was added NaHI (0.24 g, 6.02 mmol, 60% dispersion in mineral oil). After stirring in an ice bath for 0.5 hours, 5-(7-chloro-2,8-difluoropyrido[4,3-d]pyrimidin-4-yl)-2-oxa-5-azabicyclo[4.1.0]heptane (1.5 g, 5.02 mmol) was added to the above mixture. The ice bath was removed, and the reaction mixture was stirred at room temperature for 1 hour. The resulting mixture was quenched with saturated aq. $NH_4Cl$ (100 mL) and extracted with ethyl acetate (3×80 mL). The combined organic layers were washed with brine (50 mL), dried over anhydrous sodium sulfate, filtered and concentrated under reduced pressure. The residue was purified by RP-Flash directly with the following conditions: Column, $C_{18}$, Mobile phase A: 5 mM aq. $NH_4HCO3$; Mobile phase B: MeCN;

Gradient: 5% B-95% B in 40 min, 57% B hold 3 mins; Flow rate: 40 mL/min; Detector UV: 254 & 210 nm. The collected fractions were combined, concentrated and then lyophilized overnight to give the title compound (500 mg, 22% yield) as a yellow solid. MS: m/z=440.25 $[M+H]^{+\cdot}$ Step 4: (1R,6S)-5-(7-Chloro-8-fluoro-2-(((2R,7aS)-2-fluorotetrahydro-1H-pyrrolizin-7a (5H)-yl) methoxy-$d_2$) pyrido[4,3-d]pyrimidin-4-yl)-2-oxa-5-azabicyclo[4.1.0] heptane. & (15,6R)-5-(7-chloro-8-fluoro-2-(((2R,7aS)-2-fluorotetrahydro-1/-pyrrolizin-7a (5H)-yl) methoxy-$d_2$) pyrido[4,3-d]pyrimidin-4-yl)-2-oxa-5-azabicyclo[4.1.0] heptane 5-(7-Chloro-8-fluoro-2-(((2R,7aS)-2-fluorotetrahydro-1H-pyrrolizin-7a (SH)-yl) methoxy-$d_2$) pyrido[4,3-d]pyrimidin-4-yl)-2-oxa-5-azabicyclo[4.1.0] heptane (500 mg, 1.13 mmol) was separated by Prep-Chiral-HPLC with following conditions: Column: CHIRALPAK IF, 2×25 cm, 5 μm; Mobile Phase A: MTBE (0.5% 2 M $NH_3$-MeOH)-HPLC; Mobile Phase B: EtOH-HPLC; Flow rate: 20 mL/min; Gradient: isocratic 30%; Detected: UV 220 & 254 nm; RT1: 7.032 min; RT2: 8.72 min. The first eluting isomer (RT1: 7.032 min) was concentrated and lyophilized overnight to give the title compound (Intermediate 37, 150 mg, 30% yield) as a yellow lyophilized powder. MS: m/z=440.20 $[M+H]^+$. The second eluting isomer (RT2: 8.72 min) was concentrated and lyophilized overnight to give the title compound (Intermediate 38, 190 mg, 38% yield) as a yellow lyophilized powder. MS: m/z=440.15 $[M+H]^{+\cdot}$ Intermediate 39 & 40: (1R,7S)-6-(7-Chloro-8-fluoro-2-(((2R,7aS)-2-fluorotetrahydro-1H-pyrrolizin-7a(5H)-yl)methoxy-$d_2$)-5-methoxypyrido[4,3-d]pyrimidin-4-yl)-2-oxa-6-azabicyclo[5.1.0]octane & (1S,7R)-6-(7-chloro-8-fluoro-2-(((2R,7aS)-2-fluorotetrahydro-1H-pyrrolizin-7a(5H)-yl)methoxy-$d_2$)-5-methoxypyrido[4,3-d]pyrimidin-4-yl)-2-oxa-6-azabicyclo[5.1.0]octane

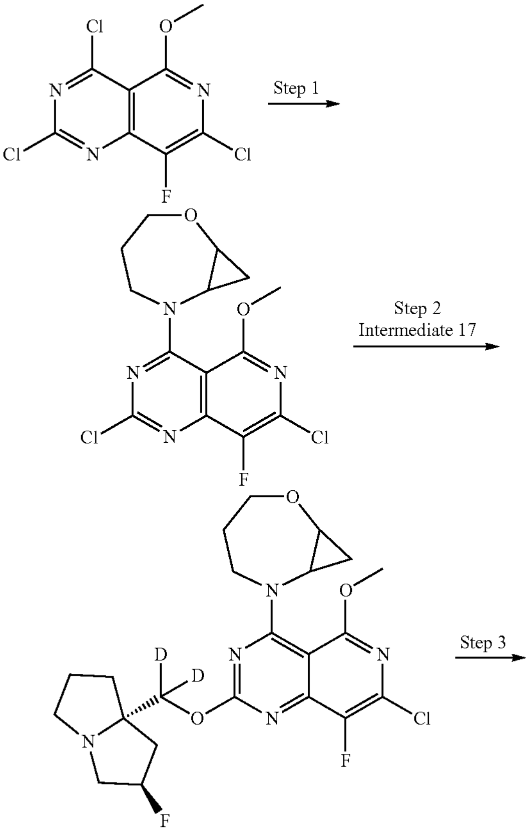

-continued

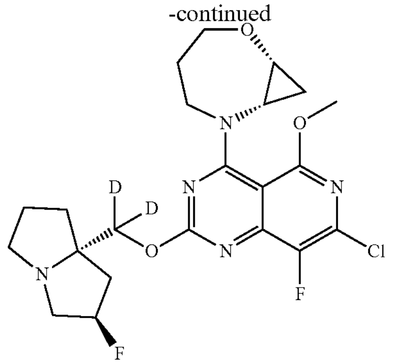

+

Intermediate 39

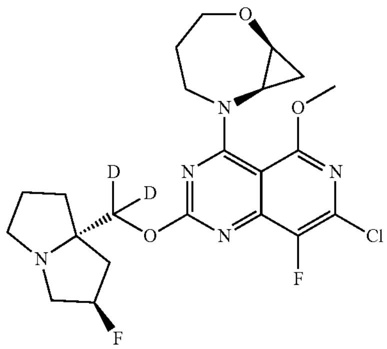

Intermediate 40

Step 1: 6-(2,7-Dichloro-8-fluoro-5-methoxypyrido[4,3-d]pyrimidin-4-yl)-2-oxa-6-azabicyclo[5.1.0]octane To a stirred solution of 2,4,7-trichloro-8-fluoro-5-methoxypyrido[4,3-d]pyrimidine (1.0 g, 3.54 mmol, refer to Intermediate 132 for detail procedures) and 2-oxa-6-azabicyclo[5.1.0]octane (0.40 g, 3.54 mmol, refer to Intermediate 3 for detail procedures) in DCM (20 mL) was added DIEA (0.92 g, 7.08 mmol) dropwise at −40° C. under nitrogen atmosphere. The reaction mixture was stirred at −40° C. for 1 hour. The resulting mixture was diluted with 10% citric acid solution (50 mL) and extracted with DCM (3×50 mL). The combined organic layers were washed with brine (50 mL), dried over anhydrous $Na_2SO_4$, filtered and concentrated under reduced pressure to afford the title compound (0.9 g, crude used through) as a light yellow solid. MS: m/z=359.10, 361.10 $[M+H]^{+\cdot}$ Step 2: 6-(7-Chloro-8-fluoro-2-(((2R,7aS)-2-fluorotetrahydro-1H-pyrrolizin-7a (5H)-yl) methoxy-$d_2$)-5-methoxypyrido[4,3-d]pyrimidin-4-yl)-2-oxa-6-azabicyclo[5.1.0]octane To a stirred solution of 6-(2,7-dichloro-8-fluoro-5-methoxypyrido[4,3-d]pyrimidin-4-yl)-2-oxa-6-azabicyclo[5.1.0]octane (0.9 g, crude) in DMSO (9 mL) under nitrogen atmosphere were added KF (0.51 g, 8.77 mmol) and Intermediate 17 (0.65 g, 4.01 mmol) at room temperature. The reaction mixture was heated at 100° C. for 16 hours. The resulting mixture was cooled to room temperature, diluted with water (30 mL), extracted with DCM (3×30 mL). The combined organic layers were washed with brine (3×30 mL), dried over anhydrous $Na_2SO_4$, filtered and concentrated under reduced pressure. The residue was purified by silica gel flash chromatography, eluted with $CH_2Cl_2$/MeOH (10: 1) to afford the title compound (440 mg, 25% yield for two steps) as a light yellow solid. MS: m/z=484.20 $[M+H]^{+\cdot}$ Step 3: (1R,7S)-6-(7-chloro-8-fluoro-2-(((2R,7aS)-2-fluorotetrahydro-1H-pyrrolizin-7a (5H)-yl) methoxy-$d_2$)-5-methoxypyrido[4,3-d]pyrimidin-4-yl)-2-oxa-6-azabicyclo[5.1.0]octane & (1S,7R)-6-(7-chloro-8-fluoro-2-(((2R,7aS)-2-fluorotetrahydro-1/-pyrrolizin-7a (5H)-yl) methoxy-$d_2$)-5-methoxypyrido[4,3-d]pyrimidin-4-yl)-2-oxa-6-azabicyclo[5.1.0]octane 6-(7-Chloro-8-fluoro-2-(((2R,7aS)-2-fluorotetrahydro-1H-pyrrolizin-7a (5H)-yl) methoxy-$d_2$)-5-methoxypyrido[4,3-d]pyrimidin-4-yl)-2-oxa-6-azabicyclo[5.1.0]octane (440 mg, 0.81 mmol) was separated by Prep-CHIRAL-HPLC with the following conditions: Column: CHIRALPAK IF 2×25 cm, 5 μm; Mobile Phase A: Hexane (0.5% 2 M $NH_3$-McOH), Mobile Phase B: EtOH; Flow rate: 20 mL/min; Gradient: isocratic 30% B; Detector: UV 220 nm & 254 nm; RTI: 10.889 min; RT2: 14.542 min. The first eluting peak (RT1: 10.889 min) was concentrated and lyophilized to give the title compound (Intermediate 39, 120 mg, 30% yield) as an off-white solid. MS: m/z=484.25 $[M+H]^+$. The second eluting peak (RT2: 14.542 min) was concentrated and lyophilized to give the title compound (Intermediate 40, 120 mg, 30% yield) as an off-white solid. MS: m/z=484.2 $[M+H]^{+\cdot}$ Intermediate 41 & 42: Benzyl-7-fluoro-2-oxa-5-azabicyclo[4.1.0]heptane-5-carboxylate (trans mixture) & benzyl 7-fluoro-2-oxa-5-azabicyclo[4.1.0]heptane-5-carboxylate (cis mixture)

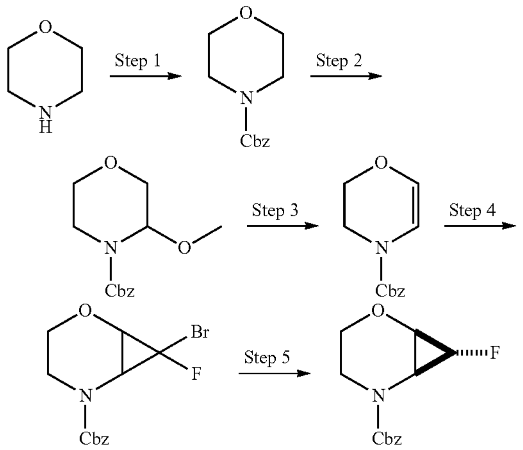

+

Intermediate 41

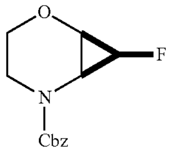

Intermediate 42

Step 1: Benzyl morpholine-4-carboxylate

To an ice-cooled mixture of morpholine (5 g, 57.39 mmol) and $K_2CO_3$ (23.80 g, 172.17 mmol) in THF (50 mL) under nitrogen atmosphere was added CbzCl (11.75 g, 68.86 mmol) dropwise. The ice bath was removed, and the reaction mixture was stirred at room temperature for 16 hours. The resulting mixture was quenched with sat. aq. $NaHCO_3$ (500 mL) and extracted with EA (3×300 mL). The combined organic layers were washed with brine (200 mL), dried over anhydrous sodium sulfate, filtered and concentrated under reduced pressure. The residue was purified by silica gel flash chromatography, eluted with 35% EA in PE to afford the title compound (11 g, 86% yield) as a colorless oil. 1H-NMR (400 MHz, Chloroform-d) δ 7.39-7.31 (m, 5H), 5.15 (s, 2H), 3.66-3.49 (m, 8H).

Step 2: Benzyl 3-methoxymorpholine-4-carboxylate

To a solution of benzyl morpholine-4-carboxylate (10 g, 45.19 mmol) in MeOH (200 mL) was added tetraethylammonium tosylate (6.81 g, 22.59 mmol) at room temperature. The reaction mixture was electrolyzed at 20° C. for 28 hours using C(+)/C(−) electrodes at constant current 200 mA. The resulting mixture was concentrated under reduced pressure. The residue was purified by silica gel flash chromatography, eluted 35% EA in PE to afford the title compound (8 g, 70% yield) as a light-yellow oil. 1H-NMR (400 MHz, Chloroform-d) $7.40-7.32 (m, 5H), 5.34-5.04 (m, 3H), 4.20-3.16 (m, 10H).

Step 3: Benzyl 2,3-dihydro-4H-1,4-oxazine-4-carboxylate

To an ice-cooled solution of benzyl 3-methoxymorpholine-4-carboxylate (8 g, 31.83 mmol) in DCM (90 mL) were added DIEA (5.35 g, 41.38 mmol) and TMSOTf (8.49 g, 38.20 mmol) under nitrogen atmosphere. The reaction mixture was stirred in an ice bath for 0.5 hour. The resulting mixture was diluted with hexane (200 mL), filtered and concentrated under reduced pressure. The residue was purified by silica gel flash chromatography, eluted with 42% EA in PE to afford the title compound (5 g, 71% yield). $^1$H-NMR (400 MHZ, Chloroform-d) δ 7.57-7.32 (m, SH), 6.34-6.20 (m, 1H), 6.03-5.75 (m, 1H), 5.19 (d, J=4.0 Hz, 2H), 4.10-4.02 (m, 2H), 3.84-3.73 (m, 2H).

Step 4: Benzyl 7-bromo-7-fluoro-2-oxa-5-azabicyclo [4.1.0]heptane-5-carboxylate To an ice-cooled solution of benzyl 2,3-dihydro-4/7-1,4-oxazine-4-carboxylate (5 g, 22.80 mmol) in DCM (15 mL) were added NaOH (25 mL, 50% aq.) and dibromofluoromethane (13124.32 mg, 68.41 mmol). The ice bath was removed, and the reaction mixture was stirred at room temperature for 16 hours. The resulting mixture was diluted with water (100 mL) and extracted with DCM (3×50 mL). The combined organic layers were washed with brine (70 mL), dried over anhydrous sodium sulfate, filtered and concentrated under reduced pressure. The residue was purified by silica gel flash chromatography, eluted with 38% EA in PE to afford the title compound (6 g, 79% yield) as a yellow oil. 1H-NMR (300 MHz, Chloroform-d) δ 7.45-7.33 (m, 5H), 5.31-5.19 (m, 2H), 4.26-3.79 (m, 2H), 3.75-3.60 (m, 1H), 3.50-3.29 (m, 3H).

Step 5: Benzyl-7-fluoro-2-oxa-5-azabicyclo[4.1.0] heptane-5-carboxylate (trans mixture) & benzyl 7-fluoro-2-oxa-5-azabicyclo[4.1.0]heptane-5-carboxylate (cis mixture)

To a stirred solution of benzyl 7-bromo-7-fluoro-2-oxa-5-azabicyclo[4.1.0]heptane-5-carboxylate (5 g, 15.14 mmol) and $NH_4Cl$ (7290.71 mg, 136.29 mmol) in EtOH (23 mL) was added Zn (8911.32 mg, 136.29 mmol) at room temperature. The reaction mixture was stirred at 10° C. for 20 hours. The resulting mixture was filtered and concentrated under reduced pressure. The residue was purified by silica gel flash chromatography, eluted with 43% EA in PE to give two mixtures. The first eluting peak was concentrated to give the title compound (trans mixture) (Intermediate 41, 2.02 g, 53% yield) as a light yellow oil. JH NMR (400 MHZ, Chloroform-d) δ 7.42-7.31 (m, 5H), 5.28-5.16 (m, 2H), 4.59-4.43 (m, 1H), 4.06-3.96 (m, 1H), 3.73-3.61 (m, 2H), 3.34-3.19 (m, 3H). $^{19}$F.-NMR (376 MHz, Chloroform-d) à-215.72-~216.69 (m, F). The second eluting peak was concentrated to give the title compound (cis mixture) (Intermediate 42, 1.28 g, 33% yield) as a yellow oil. JH-NMR (400 MHz, Chloroform-d) δ 7.40-7.32 (m, 5H), 5.30-5.17 (m, 2H), 4.45-4.19 (m, 1H), 3.94-3.79 (m, 1H), 3.70-3.30 (m, 4H), 2.90-2.80 (m, 1H). $^{19}$F-NMR (376 MHz, Chloroform-d) δ −240.93-−242.11 (m, 1F)

Intermediate 43 & 44: (1S,6R,7S)-5-(7-Chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-7-fluoro-2-oxa-5-azabicyclo[4.1.0]heptane & (1R,6S,7R)-5-(7-chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-7-fluoro-2-oxa-5-azabicyclo[4.1.0]heptane

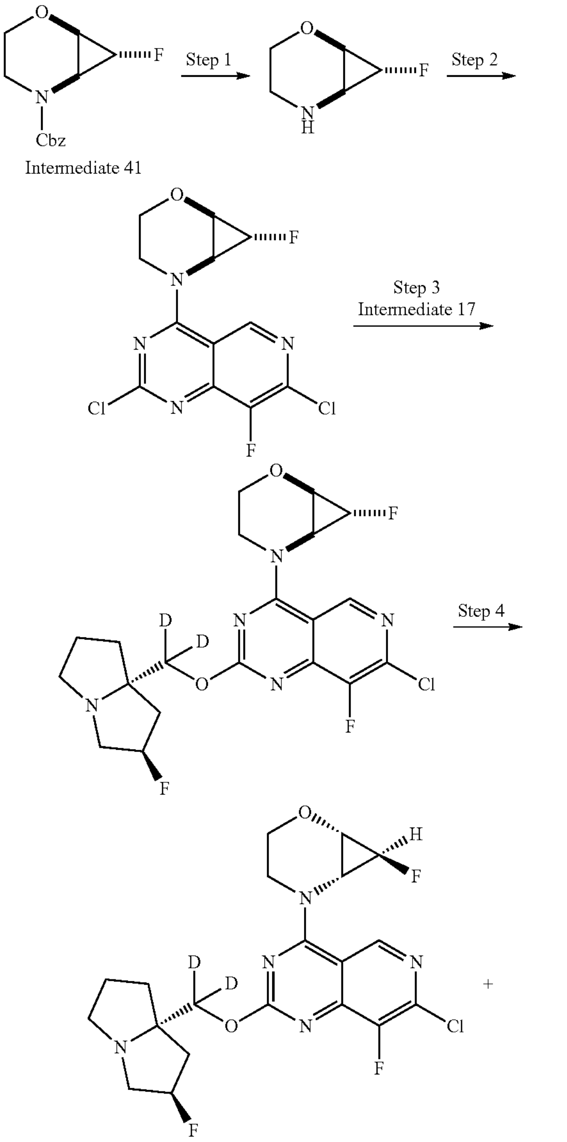

Intermediate 43

-continued

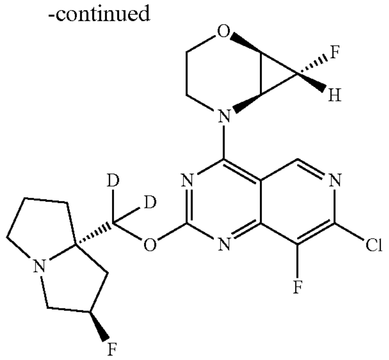

Intermediate 44

Step 1: 7-Fluoro-2-oxa-5-azabicyclo[4.1.0]heptane (trans mixture)

To an ice-cooled solution of Intermediate 41 (2.0 g, 7.96 mmol) in MeOH (100 mL) was added Pd/C(771.01 mg, 10% wt) under nitrogen atmosphere. The reaction mixture was stirred in an ice bath for 40 min under hydrogen atmosphere using a hydrogen balloon. The resulting mixture was filtered through a Celite pad and concentrated under reduced pressure to afford the title compound (trans mixture) (750 mg, 80% yield, assumed 100% purity) as a light yellow oil.

Step 2: 5-(2,7-Dichloro-8-fluoropyrido[4,3-d]pyrimidin-4-yl)-7-fluoro-2-oxa-5-azabicyclo[4.1.0]heptane (trans mixture)

To a stirred solution of 7-fluoro-2-oxa-5-azabicyclo[4.1.0]heptane (trans mixture) (750 mg, crude) and 2,4,7-trichloro-8-fluoropyrido[4,3-d]pyrimidine (1616.57 mg, 6.40 mmol) in DCM (16 mL) was added DIEA (2482.91 mg, 19.21 mmol) dropwise at −40° C. under nitrogen atmosphere. The reaction mixture was stirred at −40° C. for 1 hour. The resulting mixture was diluted with 10% citric solution (50 mL) and extracted with DCM (3×60 mL). The combined organic layers were washed with brine (50 mL), dried over anhydrous $Na_2SO_4$, filtered and concentrated under reduced pressure. The residue was purified by silica gel flash chromatography, eluted with PE/EA (1: 1) to afford the title compound (trans mixture) (1.1 g, 51% yield) as a light yellow solid. MS: m/z=332.65 $[M+H]^{+\cdot}$ Step 2: 5-(7-Chloro-8-fluoro-2-(((2R,7aS)-2-fluorotetrahydro-1/-pyrrolizin-7a (5H)-yl) methoxy-$d_2$) pyrido[4,3-d]pyrimidin-4-yl)-7-fluoro-2-oxa-5-azabicyclo[4.1.0]heptane (trans mixture)

To a stirred solution of 5-(2,7-Dichloro-8-fluoropyrido[4,3-d]pyrimidin-4-yl)-7-fluoro-2-oxa-5-azabicyclo[4.1.0]heptane (trans mixture) (1.1 g, 3.30 mmol) in DMSO (11 mL) under nitrogen atmosphere were added KF (671.45 mg, 11.55 mmol) and Intermediate 17 (532.36 mg, 3.30 mmol) at room temperature. The reaction mixture was heated at 100° C. for 16 hours. The resulting mixture was cooled to room temperature, diluted with water (80 mL), and extracted with DCM (3×100 mL). The combined organic layers were washed with brine (3×50 mL), dried over anhydrous $Na_2SO_4$, filtered and concentrated under reduced pressure. The residue was purified by silica gel flash chromatography, eluted with $CH_2Cl_2$/MeOH (10: 1) to afford the title compound (trans mixture) (600 mg, 39% yield) as a light yellow solid. MS: m/z=457.80 $[M+H]^{+\cdot}$ Step 3: (IS,6R, 7S)-5-(7-Chloro-8-fluoro-2-(((2R,7aS)-2-fluorotetrahydro-1/-pyrrolizin-7a (5/)-yl) methoxy-$d_2$) pyrido[4,3-d]pyrimidin-4-yl)-7-fluoro-2-oxa-5-azabicyclo[4.1.0]heptane & (1R,65,7R)-5-(7-chloro-8-fluoro-2-(((2R,7aS)-2-fluorotetrahydro-LH-pyrrolizin-7a (5H)-yl) methoxy-$d_2$)pyrido[4,3-d]pyrimidin-4-yl)-7-fluoro-2-oxa-5-azabicyclo[4.1.0]heptane 5-(7-Chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-7-fluoro-2-oxa-5-azabicyclo[4.1.0]heptane (trans mixture) (600 mg, 1.31 mmol) was separated by Prep-SFC Column: CHIRAL ART Cellulose-SJ, 3×25 cm, 5 μm, Mobile Phase A: $CO_2$; Mobile Phase B: IPA (0.1% DEA); Flow rate: 100 mL/min; Gradient: isocratic 45% B; Back Pressure (bar): 100; Detector: UV 220 nm; RT1: 2.8 min; RT2: 4.7 min. The first eluting peak (RT1: 2.8 min) was concentrated and lyophilized to give the title compound (Intermediate 43, 110 mg, 18% yield) as a light yellow solid. MS: m/z=458.20 $[M+H]^{+}$. The second eluting peak (RT2: 4.7 min) was concentrated and lyophilized to give the title compound (Intermediate 44, 110 mg, 18% yield) as a light yellow solid. MS: m/z=458.20 $[M+H]^{+\cdot}$ Intermediate 45: ((2,3-Difluoro-8-(4,4,5,5-tetramethyl-1,3,2-dioxaborolan-2-yl)naphthalen-1-yl)ethylnyl)triisopropylsilane

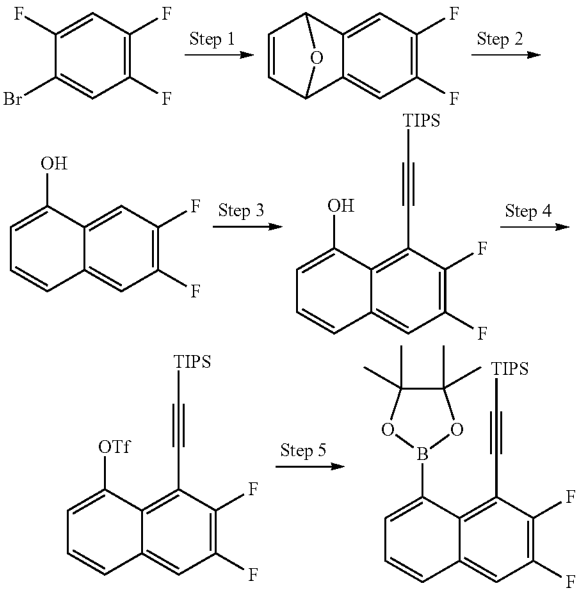

Intermediate 45

Step 1: 6,7-Difluoro-1,4-dihydro-1,4-epoxynaphthalene

To a stirred solution of 1-bromo-2,4,5-trifluorobenzene (1.0 g, 4.74 mmol) in anhydrous EtzO (10 mL) was added n-BuLi (2.5 M in n-hexane, 2.27 mL, 5.69 mmol) dropwise at −78° C. The reaction mixture was stirred at −78° C. for 0.5 hours. To the above mixture was added furan (3.2 g, 47.40 mmol) at −78° C., then stirred at −78° C. for 2 hours and additional 16 hours at room temperature. The resulting mixture was quenched with water (20 mL), extracted with ethyl acetate (3×50 mL). The combined organic layers were washed with brine (50 mL), dried over anhydrous sodium sulfate, filtered and concentrated under reduced pressure. The residue was purified by silica gel flash chromatography, eluted with EA/PE (1/5) to afford the title compound (300 mg, 34% yield) as a yellow oil. MS: m/z=180.95 $[M+H]^+$. $^1$H NMR (300 MHz, $CD_3CN$) δ 7.21-7.13 (m, 2H), 7.05-7.03 (m, 2H), 5.70-5.69 (m, 2H). $^{19}$F NMR (282 MHz, $CD_3CN)_6$-144.99 (s, 2F).

Step 2: 6,7-Difluoronaphthalen-1-ol

To an ice-cooled solution of 6,7-difluoro-1,4-dihydro-1,4-epoxynaphthalene (1.3 g, 7.22 mmol) in anhydrous DCM (15 mL) was added boron trifluoride diethyl etherate (1.07 g, 7.58 mmol). The ice bath was removed, and the reaction mixture was stirred at room temperature for 2 hours. The resulting mixture was concentrated under reduced pressure. The residue was purified by RP-Flash with the following conditions: column: C-18; Mobile phase A: Water; Mobile phase B: MeCN; Gradient: 10% B to 50% B in 20 min; Detector: UV 254 nm. The collected fractions were combined, concentrated, and then lyophilized overnight to afford the title compound (1.0 g, 76% yield) as a light yellow solid. MS: m/z=179.04 $[M-H]^+$. JH NMR (400 MHZ, Chloroform-d) δ 7.96-7.91 (m, 1H), 7.54-7.52 (m, 1H), 7.36-7.37 (m, 2H), 6.80-6.78 (m, 1H), 5.24 (bs, 1H). $^{19}$F NMR (376 MHz, Chloroform-d) δ −136.83--137.48 (m, 2F).

Step 3: 6,7-Difluoro-8-((triisopropylsilyl) ethynyl) naphthalen-1-ol

To a stirred solution of 6,7-difluoronaphthalen-1-ol (1.0 g, 5.55 mmol) in anhydrous 1,4-dioxane (10 mL) were added dichloro (p-cymene) ruthenium (II) dimer (336.80 mg, 0.55 mmol), (2-bromoethynyl)triisopropylsilane (1.52 g, 5.83 mmol) and KOAc (1.08 g, 11.10 mmol) at room temperature under argon atmosphere. The reaction mixture was heated at 110° C. for 2 hours. The resulting mixture was cooled to room temperature and concentrated under reduced pressure. The residue was purified by silica gel flash chromatography, eluted with EA/PE (1/5) to afford the title compound (1.3 g, 65% yield) as a light yellow solid. MS: m/z=359.10 $[M-H]^+$, $^1$H NMR (300 MHz, Chloroform-d) δ 8.98 (s, 1H), 7.55-7.49 (m, 1H), 7.41-7.38 (m, 1H), 7.35-7.27 (m, 1H), 7.00-6.97 (m, 1H), 1.29-1.16 (m, 21H). $^{19}$F. NMR (282 MHZ, Chloroform-d) δ −131.53--131.67 (m, 1F), −137.55--137.63 (m, 1F).

Step 4: 6,7-Difluoro-8-((triisopropylsilyl) ethynyl) naphthalen-1-yl trifluoromethanesulfonate To a stirred solution of 6,7-difluoro-8-((triisopropylsilyl) ethynyl) naphthalen-1-ol (1.57 g, 4.36 mmol) in DCM (16 mL) were added N-ethyl-N-isopropylpropan-2-amine (2.25 g, 17.44 mmol) and trifluoromethanesulfonic anhydride (1.84 g, 6.54 mmol) at −40° C. under argon atmosphere. The reaction mixture was stirred at −40° C. for 1 hour. The resulting mixture was quenched with saturated aq. $NaHCO_3$ (80 mL) and extracted with DCM (3×100 mL). The combined organic layers were washed with brine (100 mL), dried over anhydrous sodium sulfate, filtered and concentrated under reduced pressure. The residue was purified by silica gel flash chromatography, eluted with 0-30% ethyl acetate in petroleum ether to afford the title compound (1.6 g, 0.65 mmol, 76% yield) as a light yellow solid. $^1$H NMR (300 MHz, Chloroform-d) δ 7.79-7.76 (m, 1H), 7.62-7.46 (m, 3H), 1.25-1.15 (m, 21H). $^{19}$F. NMR (282 MHZ, Chloroform-d) δ −71.20 (s, 3F), −124.63--124.71 (d, 1F), −134.16--134.24 (d, 1F).

Step 5: ((2,3-Difluoro-8-(4,4,5,5-tetramethyl-1,3,2-dioxaborolan-2-yl) naphthalen-1-yl) ethynyl)triisopropylsilane To a stirred mixture of 6,7-difluoro-8-((triisopropylsilyl) ethynyl) naphthalen-1-yl trifluoromethanesulfonate (2.2 g, 4.46 mmol) and 4,4,5,5-tetramethyl-2-(4,4,5,5-tetramethyl-1,3,2-dioxaborolan-2-yl)-1,3,2-dioxaborolane (3.40 g, 13.39 mmol) in 1,4-dioxane (44 mL) were added Pd (dppf) $C_{12}{\cdot}CH_2Cl_2$ (363.83 mg, 0.44 mmol) and KOAc (1.75 g, 17.86 mmol) at room temperature under nitrogen atmosphere. The reaction mixture was heated at 110° C. for 16 hours. The resulting mixture was cooled to room temperature, filtered and concentrated under reduced pressure. The residue was purified by silica gel flash chromatography, eluted with 0-10% ethyl acetate in petroleum ether to afford the title compound (Intermediate 45,1.2 g, 57% yield) as a light yellow solid. $^1$H NMR (400 MHZ, Chloroform-d) δ 7.78-7.74 (m, 2H), 7.54-7.42 (m, 2H), 1.43 (s, 12H), 1.27-1.13 (m, 21H).

Intermediate 46: 2-(7-Fluoro-8-(methoxy-d3)naphthalen-1-yl)-4,4,5,5-tetramethyl-1,3,2-dioxaborolane

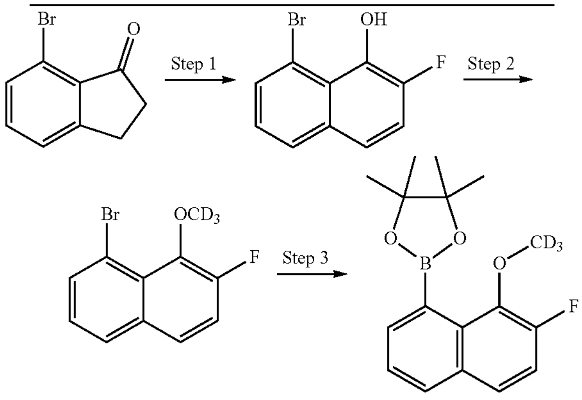

Intermediate 46

Step 1: 8-Bromo-2-fluoronaphthalen-1-ol

To a stirred solution of 7-bromo-2,3-dihydro-1/-inden-1-one (3.5 g, 16.58 mmol) and TBAB (534.5 mg, 1.65 mmol) in toluene (40 mL) was added (bromodifluoromethyl)trimethylsilane (10.1 g, 49.74 mmol) at room temperature under nitrogen atmosphere. The reaction mixture was heated at 110° C. for 16 hours. To the above solution was added TBAF (1 M in THE, 3.31 mL, 3.31 mmol) at room temperature, and then the mixture was stirred at room temperature for 1 hour. The resulting mixture was quenched with $H_2O$ (50 mL) and extracted with ethyl acetate (3×80 mL). The combined organic layers were washed with water (80 mL) and brine (80 mL), dried over anhydrous sodium sulfate, filtered and concentrated under reduced pressure. The residue was purified by silica gel flash chromatography, eluted with PE/EA (5: 1) to afford the title compound (2.8 g, 70% yield) as an off-white solid. MS: m/z=238.65, 240.65 $[M-H]^+$. 1H NMR (300 MHz, DMSO-$d_6$) δ 10.11-10.10 (m, 1H), 7.90-7.86 (m, 1H), 7.78-7.75 (m, 1H), 7.54-7.45 (m, 2H), 7.30-7.24 (m, 1H). $^{19}F$ NMR (282 MHz, DMSO-$d_6$) δ −135.81−−136.21 (m, 1 F).

Step 2: 8-Bromo-2-fluoro-1-(methoxy-$d_3$) naphthalene

To a solution of 8-bromo-2-fluoronaphthalen-1-ol (1.5 g, 6.22 mmol) in acetone (20 mL) were added $K_2CO_3$ (1.28 g, 9.33 mmol) and iodomethane-$d_3$ (1.35 g, 9.33 mmol) at room temperature under nitrogen atmosphere. The reaction mixture was heated at 80° C. for 2 hours. The resulting mixture was cooled to room temperature, filtered and concentrated under reduced pressure. The residue was purified by silica gel flash chromatography, eluted with PE/EA (5: 1) to afford the title compound (1.5 g, 93% yield) as a yellow semi-solid. $^1H$ NMR (300 MHZ, DMSO-$d_6$) δ 8.02-7.99 (m, 1H), 7.90-7.83 (m, 2H), 7.65-7.58 (m, 1H), 7.39-7.34 (m, 1H). $^{19}F$ NMR (282 MHz, DMSO-$d_6$) δ-129.64 (s, 1F).

Step 3: 2-(7-Fluoro-8-(methoxy-$d_3$) naphthalen-1-yl)-4,4,5,5-tetramethyl-1,3,2-dioxaborolane To a stirred solution of 8-bromo-2-fluoro-1-(methoxy-$d_3$) naphthalene (500 mg, 1.93 mmol) and 4,4,4',4',5,5,5',5'-octamethyl-2,2'-bi (1,3,2-dioxaborolane) (983.86 mg, 3.87 mmol) in 1,4-dioxane (5 mL) were added Pd (dppf) $Cl_2$.DCM (155.16 mg, 0.19 mmol) and KOAc (570.29 mg, 5.811 mmol) at room temperature under nitrogen atmosphere. The reaction mixture was heated at 80° C. for 3 hours. The resulting mixture was cooled to room temperature and concentrated under reduced pressure. The residue was purified by silica gel flash chromatography, eluted with PE/EA (7: 1) to afford the title compound (Intermediate 46, 510 mg, 86% yield) as a yellow solid. 3H NMR (300 MHz, DMSO-$d_6$) δ 7.96-7.93 (m, 1H), 7.74-7.69 (m, 1H), 7.54-7.45 (m, 3H), 1.37 (s, 12H). $^{19}F$ NMR (282 MHz, DMSO-$d_6$) δ −132.64 (s, 1F), Intermediate 47: 6-Amino-1-(methoxy-$d_3$)-8-(4,4,5,5-tetramethyl-1,3,2-dioxaborolan-2-yl)-2-naphthonitrile

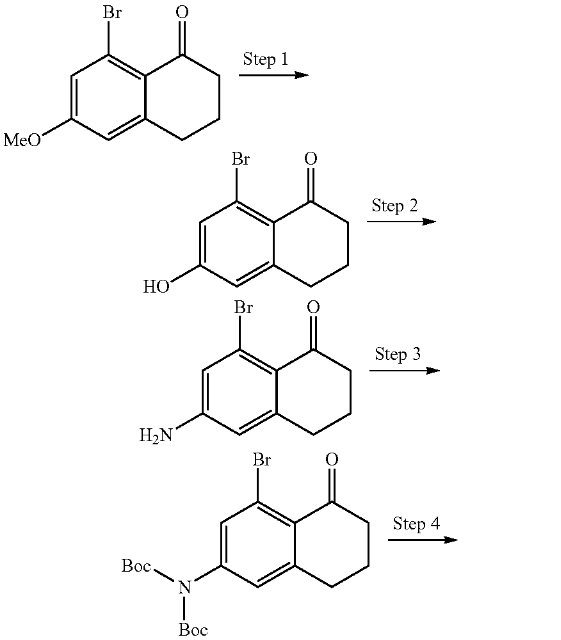

-continued

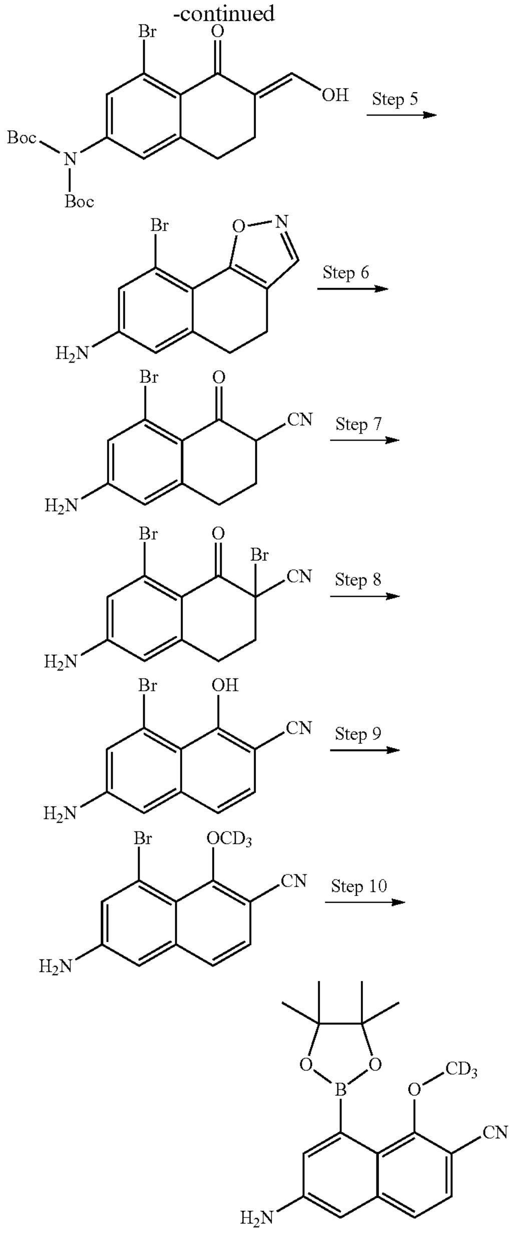

Intermediate 47

Step 1: 8-Bromo-6-hydroxy-3,4-dihydronaphthalen-1 (2H)-one

To a solution of 8-bromo-6-methoxy-3,4-dihydronaphthalen-1 (2H)-one (30 g, 117 mmol) in toluene (400 mL) was added AlCl (39.2 g, 293 mmol). The mixture was stirred at 100° C. for 1 hr. After the reaction was cooled to 25° C., the mixture was poured into cold water (500 mL), and extracted with EtOAc (200 mL×3). The combined organic layers were washed with brine (100 mL×2), dried over $Na_2SO_4$, filtered and concentrated under reduced pressure. After purification by silica gel flash chromatography (Eluent of 0~30% EtOAc in petroleum ether), the title compound (27.3 g, yield: 92%) was obtained as a yellow solid. MS: m/z=240.8, 242.8 $[M+H]^+$. $^1H$ NMR (400 MHZ, Dimethylsulfoxide-$d_6$) δ

10.67 (br s, 1H), 6.96 (d,)=2.4 Hz, 1H), 6.69 (d, J=2.4 Hz, 1H), 2.86 (t, J=6.0 Hz, 2H), 2.55-2.51 (m, 2H), 1.98-1.87 (m, 2H).

Step 2: 6-Amino-8-bromo-3,4-dihydronaphthalen-1 (2H)-one

To a solution of 8-bromo-6-hydroxy-3,4-dihydronaphthalen-1 (2H)-one (27.3 g, 113 mmol) in DMA (300 mL) was added NaOH (13.5 g, 339 mmol). The mixture was stirred at 20° C. for 1 hr. 2-Bromo-2-methylpropanamide (56.4 g, 339 mmol) was added, and the reaction mixture was stirred at 20° C. for 16 hr. Then NaOH (45.2 g, 1.13 mol) was added, and the resulting mixture was stirred at 50° C. for 3 hr. Then $H_2O$ (170 mL, 9.44 mol) was added, and the reaction mixture was stirred at 100° C. for another 2 hr. After the reaction was cooled to 25° C., the mixture was diluted with $H_2O$ (400 mL) and extracted with EtOAc (200 mL×2). The combined organic layers were washed with $H_2O$ (200 mL), dried over $Na_2SO_4$, filtered and concentrated under reduced pressure. After purification by silica gel flash chromatography (Eluent of 0~50% EtOAc in petroleum ether), the title compound (30 g, yield: 68%) was obtained as a yellow oil. MS: m/z=239.9, 241.9 $[M+H]^+$. $^1H$ NMR (400 MHZ, Dimethylsulfoxide-$d_6$) δ 6.73 (s, 1H), 6.36 (s, 1H), 6.22 (br s, 2H), 2.77-2.73 (m, 2H), 2.43 (t, J=6.4 Hz, 2H), 1.90-1.85 (m, 2H).

Step 3: tert-Butyl N-(8-bromo-1-oxo-tetralin-6-yl)-N-tert-butoxycarbonyl-carbamate To a solution of 6-amino-8-bromo-3,4-dihydronaphthalen-1 (2H)-one (30 g, 124 mmol) in THE (500 mL) were added DMAP (1.53 g, 12.4 mmol) and BoczO (86 mL, 374 mmol). The mixture was stirred at 65° C. for 16 hr. The mixture was diluted with $H_2O$ (200 mL) and extracted with EtOAc (200 mL×2). The combined organic layers were washed with $H_2O$ (200 mL), dried over $Na_2SO_4$, filtered and concentrated under reduced pressure. After purification by silica gel flash chromatography (Eluent of 0~5% EtOAc in petroleum ether), the title compound (16.2 g, yield: 28%) was obtained as a yellow oil. MS: m/z=461.9, 463.9 $[M+Na]^+$. $^1H$ NMR (400 MHz, Dimethylsulfoxide-$d_6$) δ 7.47 (d, J=1.6 Hz, 1H), 7.26 (d, J=1.6 Hz, 1H), 2.96 (t, J=6.0 Hz, 2H), 2.64 (t, J=6.4 Hz, 2H), 2.02-1.97 (m, 2H), 1.42 (s, 18H).

Step 4: tert-Butyl N-[(2E)-8-bromo-2-(hydroxymethylene)-1-oxo-tetralin-6-yl]-N-tert-butoxycarbonyl-carbamate To a solution of tert-butyl N-(8-bromo-1-oxo-tetralin-6-yl)-N-tert-butoxycarbonyl-carbamate (5 g, 11.3 mmol) in THF (80 mL) was added NaH (908 mg, 22.7 mmol, 60% purity in oil) at 0° C. The mixture was stirred at 0° C. for 1 hr. Then HCOOEt (8 mL, 99.4 mmol) was added dropwise. The resulting mixture was stirred at 45° C. for 3 hr. The reaction mixture was quenched with saturated $NH_4Cl$ (30 mL) at 0° C. The resulting mixture was carefully neutralized with HCl (3 M) and the pH was adjusted to about 7. The mixture was extracted with EtOAc (50 mL×2). The combined organic layers were washed with brine (50 mL×2), dried over $Na_2SO_4$, filtered and concentrated under reduced pressure. The title compound (5 g, crude) was obtained as a yellow solid. MS: m/z=367.9, 369.9 $[M-100+H]^+$. 3H NMR (400 MHZ, Dimethylsulfoxide-$d_6$) δ 9.86-9.73 (m, 1H), 7.77-7.65 (m, 2H), 7.42-7.36 (m, 1H), 2.76-2.72 (m, 2H), 2.58-2.50 (m, 2H), 1.48 (s, 18H).

Step 5: 9-Bromo-4,5-dihydronaphtho[2,1-d]isoxazol-7-amine

To a solution of tert-butyl N-[(2E)-8-bromo-2-(hydroxymethylene)-1-oxo-tetralin-6-yl]-N-tert-butoxycarbonyl-carbamate (5.5 g, 11.7 mmol) in AcOH (50 mL) was added $NH_2OH.HCl$ (1.63 g, 23.4 mmol). The mixture was stirred at 80° C. for 2 hr. The pH of the reaction was adjusted to about 7 with saturated $NaHCO_3$. The mixture was extracted with EtOAc (30 mL×2). The combined organic layers were washed with brine and dried over $Na_2SO_4$, filtered and concentrated under reduced pressure. The title compound (4 g, crude) was obtained as a brown solid. MS: m/z=264.8, 266.8 $[M+H]^{+.}$ Step 6: 6-Amino-8-bromo-1-oxo-1,2,3,4-tetrahydronaphthalene-2-carbonitrile To a solution of 9-bromo-4,5-dihydronaphtho[2,1-d]isoxazol-7-amine (4 g, 7.54 mmol) in THF (30 mL) was added MeONa (1.63 g, 30.1 mmol). The mixture was stirred at 25° C. for 1 hr. The pH of the reaction mixture was adjusted to about 7 with HCl (IM). The mixture was extracted with EtOAc (40 mL×2). The combined organic layers were washed with brine (30 mL×2) and dried over $Na_2SO_4$, filtered and concentrated under reduced pressure. After purification by silica gel flash chromatography (Eluent of 0~70% EtOAc in petroleum ether), the title compound (1.7 g, yield: 42% for three steps) was obtained as a yellow solid. MS: m/z=264.8, 266.8 $[M+H]^+$. $^1H$ NMR (400 MHZ, Dimethylsulfoxide-$d_6$) δ 6.79 (d, J=2.0 Hz, 1H), 6.50 (s, 2H), 6.36 (d, J=2.0 Hz, 1H), 4.29-4.23 (m, 1H), 2.97-2.87 (m, 1H), 2.86-2.78 (m, 1H), 2.37-2.29 (m, 1H), 2.26-2.14 (m, 1H).

Step 7: 6-Amino-2,8-dibromo-1-oxo-1,2,3,4-tetrahydronaphthalene-2-carbonitrile

To a solution of 6-amino-8-bromo-1-oxo-1,2,3,4-tetrahydronaphthalene-2-carbonitrile (1.7 g, 6.41 mmol) in ACN (90 mL) was added PyBr3 (2.26 g, 7.05 mmol). The mixture was stirred at 70° C. for 0.5 hrs. The mixture was diluted with $H_2O$ (50 mL) and extracted with EtOAc (60 mL×2). The combined organic layers were dried over $Na_2SO_4$, filtered and concentrated under reduced pressure. The title compound (2.2 g, crude) was obtained as a brown solid. MS: m/z=342.6, 344.6, 346.6 $[M+H]^{+.}$ Step 8: 6-Amino-8-bromo-1-hydroxy-2-naphthonitrile To a solution of 6-amino-2,8-dibromo-1-oxo-1,2,3,4-tetrahydronaphthalene-2-carbonitrile (2.2 g, 6.40 mmol) in DMF (30 mL) was added LiBr (1.22 g, 14 mmol). The mixture was stirred at 100° C. for 1 hr. The mixture was diluted with $H_2O$ (50 mL) and extracted with EtOAc (60 mL×2). The combined organic layers were dried over $Na_2SO_4$, filtered and concentrated under reduced pressure. After purification by silica gel flash chromatography (Eluent of 0~30% EtOAc in petroleum ether), the title compound (320 mg, yield: 18% for two steps) was obtained as a yellow solid. MS: m/z=262.8, 264.8 $[M+H]^+$. $^1H$ NMR (400 MHZ, Dimethylsulfoxide-$d_6$) 10.66 (br s, 1H), 7.31-7.23 (m, 2H), 7.12 (d, J=8.8 Hz, 1H), 6.76 (d, J=2.4 Hz, 1H), 6.03 (br s, 2H).

Step 9: 6-Amino-8-bromo-1-(methoxy-$d_3$)-2-naphthonitrile

To a solution of 6-amino-8-bromo-1-hydroxy-2-naphthonitrile (300 mg, 1.14 mmol) in DMF (5 mL) was added $K_2CO_3$ (315 mg, 2.28 mmol) and $CD_3I$ (85.2 mL, 1.37 mmol) at 0° C. The mixture was stirred at 20° C. for 1 hr. The reaction mixture was diluted with $H_2O$ (50 mL) and extracted with EtOAc (60 mL×2). The combined organic layers were dried over $Na_2SO_4$, filtered and concentrated under reduced pressure. After purification by silica gel flash chromatography (Eluent of 0~17% EtOAc in petroleum ether), the title compound (267 mg, yield: 78%) was obtained as a yellow solid. MS: m/z=279.8, 281.8 $[M+H]^+$. $^1H$ NMR (400 MHz, Dimethylsulfoxide-$d_6$) δ 7.47-7.38 (m, 3H), 6.86 (d, J=2.0 Hz, 1H), 6.18 (br s, 2H).

Step 10: 6-Amino-1-(methoxy-$d_3$)-8-(4,4,5,5-tetramethyl-1,3,2-dioxaborolan-2-yl)-2-naphthonitrile To a solution of 6-amino-8-bromo-1-(methoxy-$d_3$)-2-naphthonitrile (257 mg, 917 μmol) and 4,4,5,5-tetramethyl-2-(4,4,5,5-tetramethyl-1,3,2-dioxaborolan-2-yl)-1,3,2-dioxaborolane (349 mg, 1.38 mmol) in 1,4-dioxane (4 mL) were added Cy3PPdGs (67.4 mg, 92 μmol) and KOAc (270 mg, 2.75 mmol). The mixture was degassed and purged with $N_2$ three times. The mixture was stirred at 100° C. for 1 hr under $N_2$. The mixture was concentrated under reduced pressure. After purification by silica gel flash chromatography (Eluent of 100% $CH_2Cl_2$), the title compound (Intermediate 47, 145 mg, yield: 46%) was obtained. MS: m/z=328.0 $[M+H]^+$. 1H NMR (400 MHZ, Dimethylsulfoxide-$d_6$) δ 7.37 (d, J=8.4 Hz, 1H), 7.30 (d, J=8.4 Hz, 1H), 6.98 (d, J=2.0 Hz, 1H), 6.81 (d, J=2.0 Hz, 1H), 5.99 (br s, 2H), 1.35 (s, 12H).

Intermediate 48: 6-((Diphenylmethylene)amino)-3-fluoro-1-(methoxy-d3)-8-(4,4,5,5-tetramethyl-1,3,2-dioxaborolan-2-yl)naphthonitrile

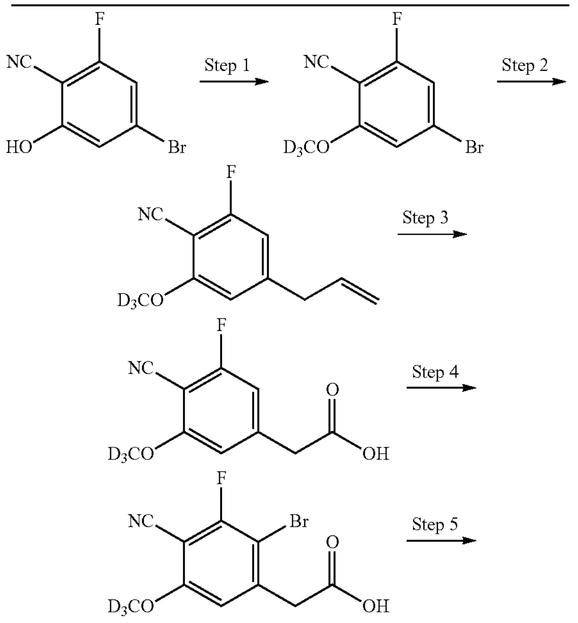

-continued

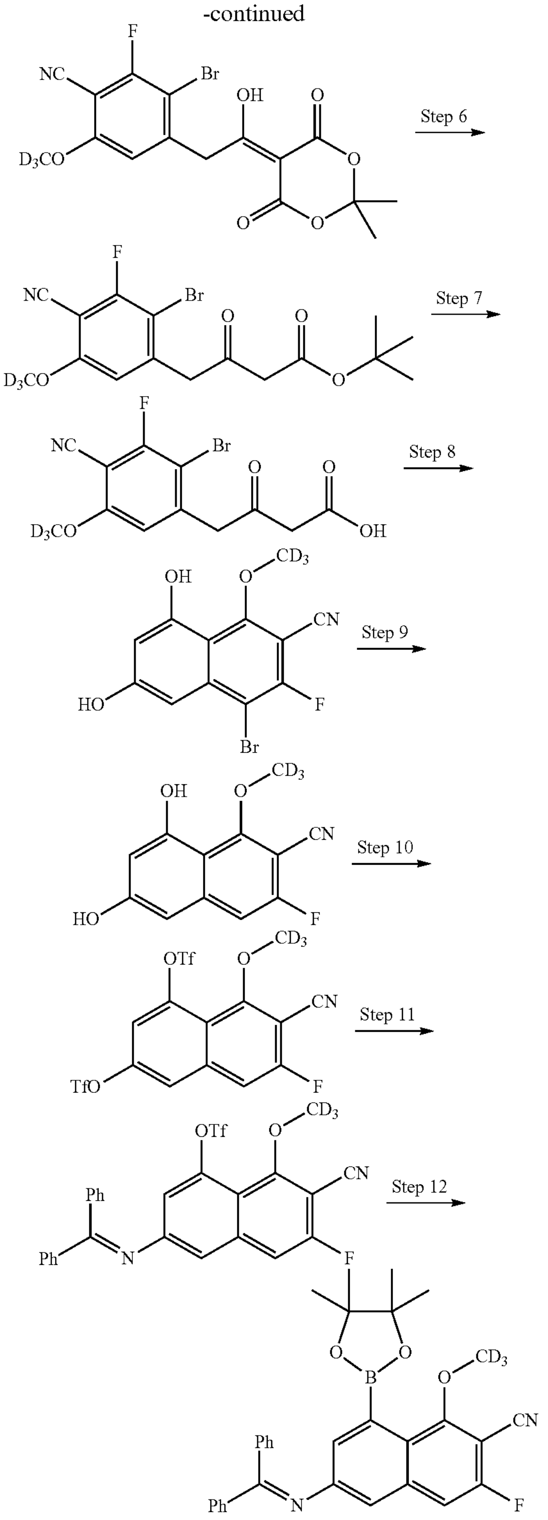

Intermediate 48

Step 1: 4-Bromo-2-fluoro-6-(methoxy-$d_3$)benzonitrile

To a solution of 4-bromo-2-fluoro-6-hydroxybenzonitrile (7 g, 32.4 mmol) in MeCN (70 mL) were added $K_2CO_3$ (8.9 g, 64.8 mmol) and $CD_3I$ (9.2 g, 64.8 mmol) at 25° C. The mixture was stirred at 50° C. for 3 hr under $N_2$. The reaction mixture was filtered concentrated under reduced pressure. The title compound (7 g, yield: 93%) was obtained as a white solid. MS: m/z=232.9, 234.9 $[M+H]^+$. 3H NMR (400 MHZ, Dimethylsulfoxide-$d_6$) δ 7.48 (dd, J=8.8, 1.6 Hz, 1H), 7.40 (d, J=1.6 Hz, 1H). $^{19}F$ NMR (376 MHz, Dimethylsulfoxide-$d_6$) δ −106.22.

Step 2: 4-Allyl-2-fluoro-6-(methoxy-$d_3$)benzonitrile

To a solution of 4-bromo-2-fluoro-6-(methoxy-$d_3$)benzonitrile (10 g, 42.9 mmol) and 2-allyl-4,4,5,5-tetramethyl-1,3,2-dioxaborolane (8.6 g, 51.5 mmol) in THF (750 mL) were added Pd $(PPh_3)_4$ (5.0 g, 4.3 mmol) and CsF (20.0 g, 129 mmol). The mixture was degassed and purged with $N_2$ three times and stirred at 75° C. for 16 hr under $N_2$. The reaction mixture was concentrated under reduced pressure. After purification by silica gel flash chromatography (eluent of 0~5% of EtOAc in petroleum ether), the title compound (5.77 g, yield: 69%) was obtained as an off white solid. $^1H$ NMR (400 MHZ, Dimethylsulfoxide-$d_6$) δ 6.97 (s, 1H), 6.91 (d, J=10.0 Hz, 1H), 6.02-5,90 (m, 1H), 5.20-5.04 (m, 2H), 3.45 (d, J=6.8 Hz, 2H). $^{19}F$ NMR (376 MHZ, Dimethylsulfoxide-$d_6$) δ −108.36.

Step 3: 2-(4-Cyano-3-fluoro-5-(methoxy-$d_3$)phenyl) acetic acid

To a solution of 4-allyl-2-fluoro-6-(methoxy-$d_3$)benzonitrile (5 g, 25.7 mmol) in ACN (100 mL), $H_2O$ (150 mL) and EtOAc (100 mL) was added RuCl (0.5 g, 2.6 mmol) at 0° C. Then $NaIO_4$ (8.3 g, 38.6 mmol) was added in batches at 0° C. over 0.5 hr. The reaction mixture was stirred at 0° C. for 0.5 hr under $N_2$ atmosphere. The reaction mixture was poured into $H_2O$ (100 mL). The resulting mixture washed with EtOAc (500 mL×2). The pH of the combined aqueous phase was adjusted to 6 with 2 M HCl. The mixture was extracted with EtOAc (100 mL×2). The combined organic layers were dried over anhydrous $Na_2SO_4$, filtered and concentrated under reduced pressure. The title compound (1.0 g, yield: 18%) was obtained as an off white solid. MS: m/z=423.1 $[2M-H]^-$. $^1H$ NMR (400 MHZ, Dimethylsulfoxide-$d_6$) δ 12.63 (s, 1H), 7.06 (s, 1H), 7.01 (d, J=10.0 Hz, 1H), 3.72 (s, 2H). $^{19}F$ NMR (376 MHz, Dimethylsulfoxide-$d_6$) δ −108.78.

Step 4: 2-(2-Bromo-4-cyano-3-fluoro-5-(methoxy-$d_3$)phenyl) acetic acid

To a solution of 2-(4-cyano-3-fluoro-5-(methoxy-$d_3$)phenyl) acetic acid (1 g, 4.7 mmol) and KBr (2.8 g, 23.6 mmol) in $H_2O$ (10 mL) was added Br2 (0.6 mL, 11.8 mmol). The mixture was stirred at 50° C. for 2 hr. The reaction mixture was filtered, and the filter cake was washed with water (50 mL) and dried under reduced pressure. The title compound (900 mg, yield: 63%) was obtained as an off white solid. MS: m/z=579.0, 581.0, 583.0 $[2M-H]^-$. $^1H$ NMR (400 MHZ, Dimethylsulfoxide-$d_6$) δ 7.24 (s, 1H), 3.76 (s, 2H). $^{19}F$ NMR (376 MHz, Dimethylsulfoxide-$d_6$) δ−99.87,99.94.

Step 5: 3-Bromo-4-(2-(2,2-dimethyl-4,6-dioxo-1,3-dioxan-5-ylidene)-2-hydroxyethyl)-2-fluoro-6-(methoxy-$d_3$)benzonitrile To a solution of 2-(2-bromo-4-cyano-3-fluoro-5-(methoxy-$d_3$)phenyl) acetic acid (850 mg, 2.9 mmol) in ACN (8 mL) were added 2,2-dimethyl-1,3-dioxane-4,6-dione (463 mg, 3.2 mmol), DMAP (36 g, 293 μmol) and DIPEA (1.1 mL, 6.4 mmol). Then 1-BuCOCl (0.36 mL, 2.9 mmol) was added dropwise at 0° C. under $N_2$. The resulting mixture was stirred at 25° C. for 1 hr under N2. The reaction mixture was quenched with 2M HCl (10 mL) at 0° C., and the precipitate was filtered and washed with water and dried under reduced pressure. The title compound (1.01 g, yield: 69%) was obtained as an off white solid. MS: m/z=414.9, 416.9 $[M-H]^-$. $^1H$ NMR (400 MHz, Dimethylsulfoxide-$d_6$) δ 7.23 (s, 1H), 4.56 (s, 2H), 4.03-3.95 (m, 1H), 1.65 (s, 6H). $^{19}F$ NMR (376 MHz, Dimethylsulfoxide-$d_6$) δ −99.76.

Step 6: tert-Butyl 4-(2-bromo-4-cyano-3-fluoro-5-(methoxy-da)phenyl)-3-oxobutanoate A solution of 3-bromo-4-(2-(2,2-dimethyl-4,6-dioxo-1,3-dioxan-5-ylidene)-2-hydroxyethyl)-2-fluoro-6-(methoxy-$d_3$)benzonitrile (1.0 g, 2.4 mmol) in/-BuOH (25 mL) was stirred at 90° C. for 2 hr. The reaction mixture was concentrated under reduced pressure to afford the title compound (950 mg, yield: 88%) as an off white solid. MS: m/z=386.8, 388.8 $[M-H]^-$. 1H NMR (400 MHz, Dimethylsulfoxide-$d_6$) δ 7.20 (s, 1H), 4.19 (s, 2H), 3.64 (s, 2H), 1.42 (s, 9H). $^{19}F$. NMR (376 MHz, Dimethylsulfoxide-$d_6$) δ −99.35.

Step 7: 4-(2-Bromo-4-cyano-3-fluoro-5-(methoxy-da)phenyl)-3-oxobutanoic acid

To a solution of ter-butyl 4-(2-bromo-4-cyano-3-fluoro-5-(methoxy-da)phenyl)-3-oxobutanoate (950 mg, 2.4 mmol) in $CH_2Cl_2$ (3 mL) was added TFA (3.6 mL). The mixture was stirred at 25° C. for 1 hr. The reaction mixture was concentrated under reduced pressure to give the title compound (800 mg crude) as an off white solid. MS: m/z=330.9, 332.9 $[M-H]^-$. $^1H$ NMR (400 MHZ, Dimethylsulfoxide-$d_6$)δ 7.20 (s, 1H), 4.22 (s, 2H), 3.65 (s, 2H). $^{19}F$. NMR (376 MHz, Dimethylsulfoxide-$d_6$) δ −99.35.

Step 8: 4-Bromo-3-fluoro-6,8-dihydroxy-1-(methoxy-$d_3$)-2-naphthonitrile

A solution of 4-(2-bromo-4-cyano-3-fluoro-5-(methoxy-$d_3$)phenyl)-3-oxobutanoic acid (800 mg, 2.4 mmol) in $CF_3SO_3H$ (8 mL) was stirred at 25° C. for 16 hr. The reaction mixture was poured into ice water (10 mL). The precipitate was filtered, and the filter cake was washed with water (50 mL) and dried under reduced pressure. The title compound (410 mg, yield: 47%) was obtained as a yellow solid. MS: m/z=313.0, 315.0 $[M-H]^-$. $^1H$ NMR (400 MHZ, Dimethylsulfoxide-$d_6$) δ 11.57-9.97 (m, 2H), 6.97 (d, J=2.0 Hz, 1H), 6.60 (d,)=2.0 Hz, 1H). $^{19}F$. NMR (376 MHz, Dimethylsulfoxide-$d_6$) δ −102.48.

Step 9: 3-Fluoro-6,8-dihydroxy-1-(methoxy-$d_3$)-2-naphthonitrile

To a solution of 4-bromo-3-fluoro-6,8-dihydroxy-1-(methoxy-da)-2-naphthonitrile (400 mg, 1.27 mmol) in MeOH (10 mL) was added Pd/C(135 mg, 10% purity). The mixture was degassed and purged with $H_2$ three times, and the mixture was stirred at 25° C. for 2 hr under $H_2$ atmosphere (15 psi). The mixture was filtered, and the filter cake was washed with MeOH (100 mL). The filtrate was concentrated under reduced pressure to give the title compound (300 mg) as an off white solid. MS: m/z=235.0 $[M-H]^-$. $^1H$ NMR (400 MHZ, Dimethylsulfoxide-$d_6$) δ 10.46 (s, 1H), 10.35 (s, 1H), 7.37 (d,)=11.2 Hz, 1H), 6.67 (d,)=2.0 Hz, 1H), 6.53 (d, J=2.0 Hz, 1H). $^{19}F$ NMR (376 MHz, Dimethylsulfoxide-$d_6$) δ −114.93.

Step 10: 7-Cyano-6-fluoro-8-(methoxy-$d_3$) naphthalene-1,3-diyl bis(trifluoromethanesulfonate)

To a solution of 3-fluoro-6,8-dihydroxy-1-(methoxy-$d_3$)-2-naphthonitrile (270 mg, 1.1 mmol) and 1,1,1-trifluoro-N-phenyl-N-((trifluoromethyl) sulfonyl) methanesulfonamide (837 mg, 2.3 mmol) in DMF (6 mL) were added DMAP (4 mg, 34 μmol) and TEA (256 mg, 2.5 mmol) at 0° C. The mixture was stirred at 0° C. under $N_2$ for 0.5 hr. The reaction mixture was diluted with $H_2O$ (50 mL) and extracted with EtOAc (50 mL×3). The combined organic layers were dried over anhydrous $Na_2SO_4$, filtered and concentrated under reduced pressure. The title compound (450 mg crude) was obtained as an off white solid. MS: m/z=498.9 $[M-H]^-$. $^1H$ NMR (400 MHz, Dimethylsulfoxide-$d_6$) 8.47 (d,)=2.0 Hz, 1H), 8.16 (d, J=2.0 Hz, 1H), 8.09 (d, J=10.0 Hz, 1H).

Step 11: 7-Cyano-3-((diphenylmethylene)amino)-6-fluoro-8-(methoxy-$d_3$) naphthalen-1-yl trifluoromethanesulfonate To a solution of 7-cyano-6-fluoro-8-(methoxy-$d_3$) naphthalene-1,3-diyl bis(trifluoromethanesulfonate) (450 mg, 899 μmol) in 1,4-dioxane (40 mL) were added diphenylmethanimine (163 mg, 899 μmol), $CszCO_3$ (879 mg, 2.7 mmol) and XantPhosPdG3 (85 mg, 90 μmol). The mixture was stirred at 90° C. under $N_2$ for 2 hr. The reaction mixture was concentrated under reduced pressure. After purification by silica gel flash chromatography (eluent of 0~20% EtOAc in petroleum ether), the title compound (300 mg, yield: 45%) was obtained as a yellow oil. MS: m/z=532.0 $[M+H]^+$. $^1H$ NMR (400 MHZ, Dimethylsulfoxide-$d_6$) δ 7.79-7.64 (m, 3H), 7.64-7.45 (m, 4H), 7.43-7.39 (m, 1H), 7.37-7.27 (m, 3H), 7.25-7.19 (m, 2H). $^{19}F$. NMR (376 MHz, Dimethylsulfoxide-$d_6$) δ −73.03, −110.67.

Step 12: 6-((Diphenylmethylene)amino)-3-fluoro-1-(methoxy-$d_3$)-8-(4,4,5,5-tetramethyl-1,3,2-dioxaborolan-2-yl)-2-naphthonitrile To a solution of 7-cyano-3-((diphenylmethylene)amino)-6-fluoro-8-(methoxy-$d_3$) naphthalen-1-yl trifluoromethanesulfonate (280 mg, 527 μmol) in 1,4-dioxane (6 mL) were added 4,4,4',4',5,5,5',5'-octamethyl-2,2'-bi (1,3,2-dioxaborolane) (160 mg, 632 μmol), KOAc (155 mg, 1.6 mmol) and Cy3PPdG3 (34 mg, 52.7 μmol). The mixture was stirred at 100° C. under $N_2$ for 1 hr. The reaction mixture was concentrated under reduced pressure. After purification by silica gel flash chromatography (eluent of 0~15% EtOAc in petroleum ether), the title compound (Intermediate 48, 135 mg, yield: 34%) was obtained as an off white solid. MS: m/z=510.2 $[M+H]^+$.

Intermediate 49: 4-(2-Azabicyclo[4.1.0]heptan-2-yl)-7-chloro-8-fluoro-2-(((2R,7aS)-2-fluorotetrahydro-1H-pyrrolizin-7a(5H)-yl)methoxy-d2)pyrido[4,3-d]pyrimidine

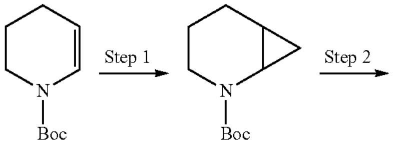

-continued

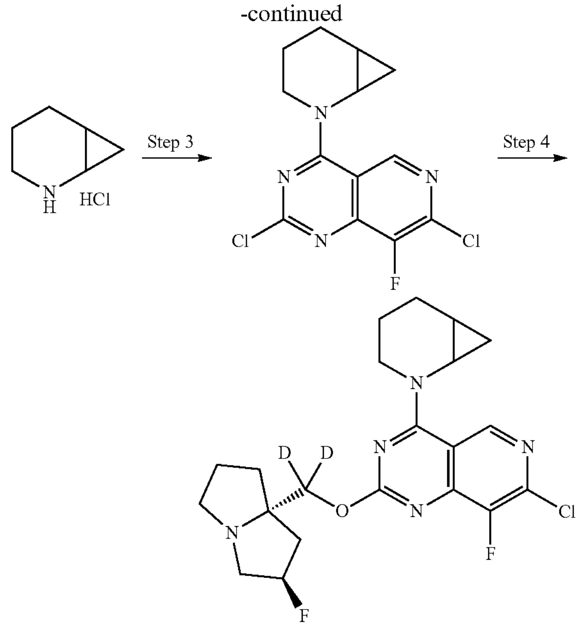

Intermediate 49

Step 1: tert-Butyl 2-azabicyclo[4.1.0]heptane-2-carboxylate

To a solution of tert-butyl 3,4-dihydropyridine-1 (2H)-carboxylate (5.4 g, 29.5 mmol) in $CH_2Cl_2$ (80 mL) was added diethylzinc (59.0 mL, 1 M in n-hexane) at 0° C. under $N_2$. The mixture was stirred at 0° C. for 0.5 h under $N_2$. A solution of $CH_2I_2$ (31.6 g, 39.2 mmol) in $CH_2Cl_2$ (30 mL) was added dropwise to the mixture at 0° C. under $N_2$, and the mixture was stirred at 20° C. for 3.5 h. The reaction mixture was quenched with sat. $NH_4Cl$ aq. (200 mL). The organic phase was separated and extracted with EtOAc (200 mL×3). The combined organic layers were washed with brine (200 mL), dried over anhydrous $Na_2SO_4$, filtered and concentrated under reduced pressure. The residue was purified by silica gel flash chromatography (eluent: 0~6% EtOAc in Petroleum ether) to give the title compound (3 g, 52% yield) as a colorless oil. $^1H$ NMR (400 MHz, Chloroform-d) δ 3.82-3.55 (m, 1H), 2.90-2.70 (m, 1H), 2.68-2.44 (m, 1H), 1.87-1.71 (m, 211), 1.60-1.52 (m, 1H), 1.52-1.42 (m, 9H), 1.30-1.12 (m, 2H), 0.89-0.69 (m, 1H), 0.34-0.18 (m, 1H).

Step 2: 2-Azabicyclo[4.1.0]heptane (HCl salt)

To a solution of tert-butyl 2-azabicyclo[4.1.0]heptane-2-carboxylate (1.4 g, 568 μmol) in $CH_2Cl_2$ (20 mL) was added HCl (10 mL, 2M in EtOAc) at 0° C. The mixture was stirred at 20° C. for 0.5 h. The mixture was concentrated under reduced pressure to give the title compound (900 mg, HCl salt) as a white solid, which was used in the next step without further purification.

Step 3: 4-(2-Azabicyclo[4.1.0]heptan-2-yl)-2,7-dichloro-8-fluoropyrido[4,3-d]pyrimidine To a solution of 2,4,7-trichloro-8-fluoro-pyrido[4,3-d] pyrimidine (1.70 g, 6.74 mmol) and DIPEA (3.52 mL, 20.21 mmol) in $CH_2Cl$ (20 mL) was added 2-azabicyclo[4.1.0] heptane (900 mg, 6.74 mmol, HCl salt) at −40° C. under $N_2$.

The mixture was stirred at −40° C. for 0.5 h under N2. The reaction mixture was diluted with water (30 mL) and extracted with $CH_2Cl$ (30 mL×3). The combined organic layers were washed with brine (20 mL), dried over anhydrous $Na_2SO_4$, filtered and the filtrate was concentrated under reduced pressure to give the title compound (2.1 g, crude) as a yellow solid, which was used in the next step without further purification. MS: m/z=313.0 $[M+H]^{+.}$ Step 4: 4-(2-Azabicyclo[4.1.0]heptan-2-yl)-7-chloro-8-fluoro-2-(((2R,7aS)-2-fluorotetrahydro-1H-pyrrolizin-7a (5H)-yl) methoxy-$d_2$)pyrido[4,3-d] pyrimidine To a solution of 4-(2-azabicyclo[4.1.0]heptan-2-yl)-2,7-dichloro-8-fluoropyrido[4,3-d]pyrimidine (1.2 g, 3.83 mmol) and DIPEA (2.00 mL, 11.5 mmol) in 1,4-dioxane (15 mL) was added Intermediate 17 (1.11 g, 6.9 mmol). The mixture was stirred at 110° C. for 16 h. The mixture was concentrated under reduced pressure. The residue was purified by silica gel flash chromatography (eluent: 0~5% MeOH in $CH_2Cl_2$) to give the title compound (Intermediate 49, 1.57 g, 89% yield over 3 steps) as a yellow solid. MS: m/z=438.1 $[M+H]^+$. $^1H$ NMR (400 MHz, Chloroform-d) & 9.64-9.58 (m, 1H), 5.53-5.21 (m, 2H), 4.68 (d, J=14.0 Hz, 1H), 4.04-3.93 (m, 1H), 3.29-3.10 (m, 4H), 2.04-1.92 (m, 5H), 1.70-1.57 (m, 5H), 1.27-1.13 (m, 2H), 0.78-0.73 (m, 1H).

Intermediate 50 & 51: tert-Butyl 7-fluoro-2-azabicyclo[4.1.0]heptane-2-carboxylate (cis mixture) & tert-butyl 7-fluoro-2-azabicyclo[4.1.0]heptane-2-carboxylate (trans mixture)

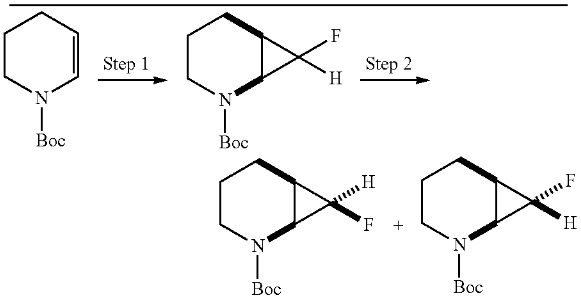

Intermediate 50 Intermediate 51

Step 1: tert-Butyl 7-bromo-7-fluoro-2-azabicyclo [4.1.0]heptane-2-carboxylate

To a solution of NaOEt (854 mg, 12.6 mmol) in $CH_2Cl_2$ (10 mL) were added tert-butyl 3,4-dihydropyridine-1 (2H)-carboxylate (1 g, 5.46 mmol) and ethyl 2,2-dibromo-2-fluoroacetate (2.88 g, 10.9 mmol). The mixture was stirred at 25° C. for 16 h under $N_2$. The reaction mixture was diluted with $H_2O$ (50 mL) and extracted with $CH_2Cl_2$ (30 mL×2). The combined organic layers were washed with brine (50 mL), dried over anhydrous $Na_2SO_4$, filtered and concentrated under reduced pressure. The residue was purified by silica gel flash chromatography (eluent: 0~6% of EtOAc in petroleum ether) to give the title compound (1.15 g, 74% yield) as a light-yellow oil. $^1H$ NMR (400 MHZ, Chloroform-d)δ 3.86-3.53 (m, 1H), 3.37-3.17 (m, 1H), 2.85-2.56 (m, 1H), 2.02-1.81 (m, 3H), 1.80-1.59 (m, 2H), 1.52 (d, J=2.4 Hz, 9H). $^{19}F$ NMR (376 MHz, Chloroform-d) δ −130.36, −161.24.

Step 2: tert-Butyl 7-fluoro-2-azabicyclo[4.1.0]heptane-2-carboxylate (cis mixture) & tert-butyl 7-fluoro-2-azabicyclo[4.1.0]heptane-2-carboxylate (trans mixture)

To a suspension of Na (1.80 g, 78.2 mmol) in THF (15 mL) was added a solution of tert-butyl-7-bromo-7-fluoro-2-azabicyclo[4.1.0]heptane-2-carboxylate (1.15 g, 3.91 mmol) in MeOH (5 mL) slowly at 0° C. under $N_2$. During the addition, the reaction temperature was kept between 25° C. and 40° C. And the mixture was stirred at 25° C. for 2 h under $N_2$. The reaction was quenched slowly with MeOH until the sodium metal disappeared completely. The temperature was maintained between 25° C. and 40° C. The reaction mixture was quenched with sat. $NH_4Cl$ aq. (50 mL) slowly at 0° C. and extracted with EtOAc (50 mL×3). The combined organic layers were washed with brine (50 mL), dried over anhydrous $Na_2SO_4$, filtered, and concentrated under reduced pressure. The residue was purified by silica gel flash chromatography (eluent: 0-4% of EtOAc in petroleum ether) to give the title compound (cis mixture) (Intermediate 50, 220 mg, 26% yield) as a colorless oil and the title compound (trans mixture) (Intermediate 51, 388 mg, 46% yield) as a colorless oil. Spectra for Example 50: 1H NMR (400 MHZ, Chloroform-d) δ 4.33-4.07 (m, 1H), 3.78-3.54 (m, 1H), 3.29-3.09 (m, 1H), 2.64-2.36 (m, 1H), 1,94-1.87 (m, 1H), 1.64-1.59 (m, 3H), 1.51-1.47 (m, 9H), 1.10-0.99 (m, 1H). $^{19}F$ NMR (376 MHZ, Chloroform-d) δ −208.77. Spectra for Intermediate 51: 1H NMR (400 MHz, Chloroform-d) δ 4.67-4.30 (m, 1H), 3.81-3.49 (m, 1H), 2.65 (s, 2H), 1.95-1.69 (m, 2H), 1.55-1.49 (m, 2H), 1.48 (s, 9H), 1.27-1.09 (m, 1H). $^{19}F$ NMR (376 MHz, Chloroform-d) δ −236.05, −236.30.

Intermediate 52 & 53: 2,7-Dichloro-8-fluoro-4-((1R,6S,7R)-7-fluoro-2-azabicyclo[4.1.0]heptan-2-yl)pyrido[4,3-d]pyrimidine & 2,7-dichloro-8-fluoro-4-((1S,6R,7S)-7-fluoro-2-azabicyclo[4.1.0] heptan-2-yl)pyrido [4,3-d]pyrimidine

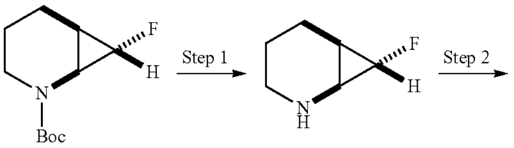

Intermediate 51

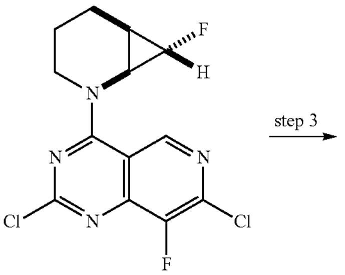

-continued

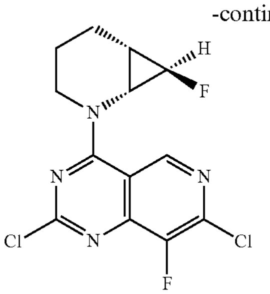

Intermediate 52

+

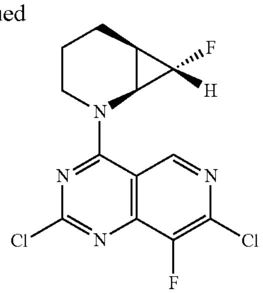

Intermediate 53

Step 1: 7-Fluoro-2-azabicyclo[4.1.0]heptane (trans mixture)

To a solution of Intermediate 51 (trans mixture) (388 mg, 1.80 mmol) in $CH_2Cl$ (2 mL) was added HCl (2 mL, 2M in EtOAc). The mixture was stirred at 20° C. for 2 h under $N_2$. The reaction mixture was concentrated under reduced pressure to give the title compound (trans mixture) (200 mg, 96% yield) as a yellow oil.

Step 2: 2,7-Dichloro-8-fluoro-4-((trans)-7-fluoro-2-azabicyclo[4.1.0]heptan-2-yl)pyrido[4,3-d]pyrimidine To a solution of 2,4,7-trichloro-8-fluoro-pyrido[4,3-d]pyrimidine (482 mg, 1.91 mmol) and DIPEA (1.2 mL, 898 mmol) in $CH_2Cl_2$ (5 mL) was added 7-fluoro-2-azabicyclo[4.1.0]heptane (trans mixture) (200 mg, 1.74 mmol) at −40° C. under $N_2$. The mixture was stirred at −40° C. for 0.5 h. The reaction mixture was concentrated under reduced pressure. The residue was purified by silica gel flash chromatography (eluent: 0~20% of EtOAc in petroleum ether) to give the title compound (trans mixture) (450 mg, 74% yield) as a yellow solid. MS: m/z=330.7 $[M+H]^{+\cdot}$ Step 3: 2,7-Dichloro-8-fluoro-4-((1R,6S,7R)-7-fluoro-2-azabicyclo[4.1.0]heptan-2-yl)pyrido[4,3-d]pyrimidine & 2,7-Dichloro-8-fluoro-4-((1S,6R,7S)-7-fluoro-2-azabicyclo[4.1.0]heptan-2-yl)pyrido[4,3-d]pyrimidine 2,7-Dichloro-8-fluoro-4-(7-fluoro-2-azabicyclo[4.1.0]heptan-2-yl)pyrido[4,3-d]pyrimidine (400 mg, 1.21 mmol) was separated by SFC(column: DAICEL CHIRALCEL OJ (250 mm×30 mm, 10 μm); mobile phase: [$CO_2$-MeOH (0.1% $NH_3H_2O$)]; B %: 25%, isocratic elution mode) to give the title compound (Intermediate 52, 150 mg, 37% yield, SFC Peak1: 1.524 min) as a yellow solid and the title compound (Intermediate 53, 120 mg, 30% yield, SFC Peak2: 1.631 min) as a yellow solid. Spectra for Intermediate 52: MS: m/z=330.7 $[M+H]^+$. $^1H$ NMR (400 MHz, Dimethylsulfoxide-$d_6$) δ 9.51 (s, 1H), 4.72 (d, J=13.2 Hz, 1H), 4.68-4.49 (m, 1H), 3.61 (t, J=10.4 Hz, 1H), 2.81 (t, J=12.8 Hz, 1H), 2.19-1.83 (m, 4H), 1.31-1.24 (m, 1H), $^{19}F$ NMR (376 MHz, Dimethylsulfoxide-$d_6$) δ −131.70, −209.75. Spectra for Intermediate 53: MS: m/z=330.8 $[M+H]^+$. $^1H$ NMR (400 MHZ, Dimethylsulfoxide-$d_6$) & 9.51 (s, 1H), 4.72 (d, J=13.2 Hz, 1H), 4.67-4.49 (m, 1H), 3.62 (t, J=10.4 Hz, 1H), 2.87-2.76 (m, 1H), 2.17-1.90 (m, 4H), 1.32-1.25 (m, 1H). $^{19}F$. NMR (376 MHz, Dimethylsulfoxide-$d_6$) δ −131.69, −209.73.

Intermediate 54: 4-(2-Azabicyclo[6.1.0]nonan-2-yl)-2,7-dichloro-8-fluoropyrido[4,3-d]pyrimidine

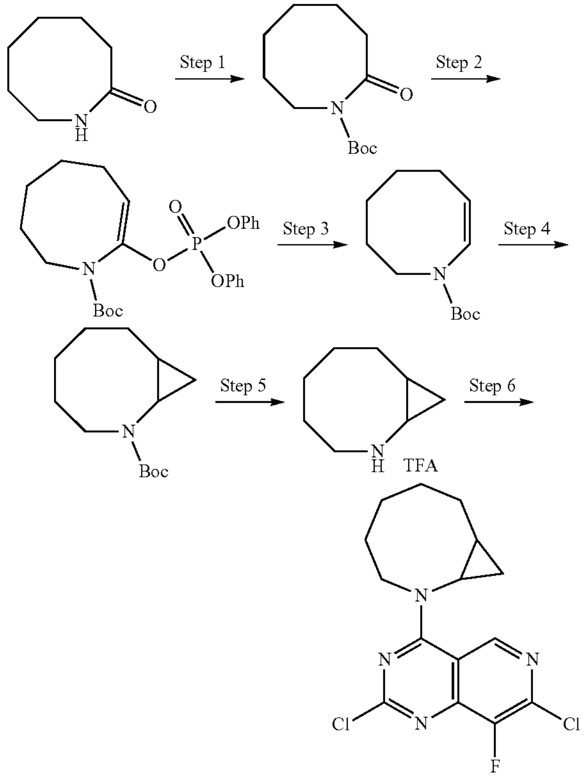

Intermediate 54

Step 1: tert-Butyl 2-oxoazocane-1-carboxylate

To a solution of azocan-2-one (15 g, 118 mmol) and $(Boc)_2O$ (28.3 g, 130 mmol) in dry THF (200 mL) was added DMAP (15.9 g, 130 mmol). The mixture was stirred at 25° C. for 3 h. The reaction mixture was diluted with water (500 mL) and extracted with EtOAc (300 mL×3). The combined organic layers were washed with brine (200 mL), dried over anhydrous $Na_2SO_4$, filtered and concentrated under reduced pressure. The residue was purified by silica gel flash chromatography (eluent: 0~30% EtOAc in petroleum ether) to give the title compound (18 g, 67% yield) as a yellow oil. $^1H$ NMR (400 MHZ, Chloroform-d)δ 3.84-3.70 (m, 2H), 2.64-2.50 (m, 2H), 1.82-1.78 (m, 2H), 1.77-1.67 (m, 2H), 1.61-1.43 (m, 13H).

Step 2: tert-Butyl (E)-8-((diphenoxyphosphoryl)oxy)-3,4,5,6-tetrahydroazocine-1 (2/f)-carboxylate To a solution of tert-butyl 2-oxoazocane-1-carboxylate (18 g, 79.2 mmol) and diphenyl phosphorochloridate (31.92 g, 118.8 mmol) in THF (200 mL) was added dropwise KHMDS (95.04 mL, 1 M in THF) at −78° C. under $N_2$. After addition, the mixture was stirred at −78° C. for 1 h under $N_2$. The reaction mixture was diluted with sat. $NH_4Cl$ aq. (100 mL) and extracted with EtOAc (200 mL×3). The combined organic layers were washed with brine (100 mL), dried over anhydrous $Na_2SO_4$, filtered and concentrated under reduced pressure. The residue was purified by silica gel flash chromatography (eluent: 0~10% EtOAc in petroleum ether) to give the title compound (31 g, 85% yield) as a yellow oil. $^1H$ NMR (400 MHZ, Chloroform-d)$_8$ $_{7.37}$-7.30 (m, 4H), 7.26-7.15 (m, 6H), 5.65-5.45 (m, 1H), 2.10-2.04 (m, 2H), 1.70-1.55 (m, 7H), 1.49-1.38 (m, 10H).

Step 3: tert-Butyl (Z)-3,4,5,6-tetrahydroazocine-1 (2H)-carboxylate

To a solution of tert-butyl (E)-8-((diphenoxyphosphoryl) oxy)-3,4,5,6-tetrahydroazocine-1 (2H)-carboxylate (20 g, 43.5 mmol) in DME (100 mL) were added triphenylphosphane (913 mg, 3.48 mmol) and Pd $(OAc)_2$ (391 mg, 1.74 mmol) at 25° C. under $N_2$, and then a solution of TEA (13.2 g, 131 mmol) and formic acid (2.0 g, 43.5 mmol) in DME (60 mL) was added dropwise to the mixture at 25° C. under $N_2$. The mixture was stirred at 85° C. for 40 min under $N_2$. The reaction mixture was diluted with water (300 mL) and extracted with EtOAc (200 mL×3). The combined organic layers were washed with brine (100 mL), dried over anhydrous $Na_2SO_4$, filtered and concentrated under reduced pressure. The residue was purified by silica gel flash chromatography (eluent: 0~10% EtOAc in petroleum ether) to give the title compound (8 g, 87% yield) as a brown oil. $^1$H NMR (400 MHz, Chloroform-d) δ 6.78-6.51 (m, 1H), 4.85-4.63 (m, 1H), 3.78-3.68 (m, 2H), 2.35-2.27 (m, 2H), 1.81-1.72 (m, 2H), 1.66-1.55 (m, 4H), 1.47 (s, 9H).

Step 4: tert-Butyl 2-azabicyclo[6.1.0]nonane-2-carboxylate

To a solution of tert-butyl (Z)-3,4,5,6-tetrahydroazocine-1 (2H)-carboxylate (1 g, 4.73 mmol) in $CH_2Cl_2$ (18 mL) was added diethylzinc (9.47 mL, 1 M in n-hexane). The mixture was stirred at 0° C. for 0.5 h under $N_2$. A solution of $CH_2I_2$ (5.07 g, 18.9 mmol) in $CH_2Cl_2$ (9 mL) was added to the mixture dropwise at 0° C. under $N_2$. The mixture was stirred at 20° C. for 2 h under $N_2$. The reaction mixture was diluted with sat. $NH_4Cl$ aq. (50 mL) and extracted with EtOAc (60 mL×3). The combined organic layers were washed with brine (30 mL), dried over anhydrous $Na_2SO_4$, filtered and concentrated under reduced pressure. The residue was purified by silica gel flash chromatography (eluent: 0~10% EtOAc in petroleum ether) to give the title compound (160 mg, 15% yield) as a colorless oil. $^1$H NMR (400 MHz, Chloroform-d) 4.09-3.95 (m, 1H), 2.80-2.67 (m, 1H), 2.22-2.13 (m, 1H), 2.03-1.93 (m, 1H), 1.83-1.70 (m, 1H), 1.69-1.63 (m, 1H), 1.61 (d, J=3.6 Hz, 1H), 1.50-1.41 (m, 12H), 1.04-0.97 (m, 1H), 0.92-0.77 (m, 2H), 0.72-0.62 (m, 1H).

Step 5: 2-Azabicyclo[6.1.0]nonane TFA, salt

To a solution of tert-butyl 2-azabicyclo[6.1.0]nonane-2-carboxylate (160 mg, 710 μmol) in $CH_2Cl_2$ (2 mL) was added TFA (2 mL) at 0° C. The mixture was stirred at 20° C. for 0.5 h. The mixture was concentrated under reduced pressure to give the title compound (90 mg, TFA salt) as a yellow oil, which was used in the next step without further purification.

Step 6: 4-(2-Azabicyclo[6.1.0]nonan-2-yl)-2,7-dichloro-8-fluoropyrido[4,3-d]pyrimidine To a solution of 2,4,7-trichloro-8-fluoro-pyrido[4,3-d]pyrimidine (181 mg, 719 μmol) in $CH_2Cl_2$ (2 mL) was added DIPEA (626 μL, 3.59 mmol) and 2-azabicyclo[6.1.0]nonane (90 mg, 719 μmol) at −40° C. under $N_2$. The mixture was stirred at −40° C. for 1 h. The reaction mixture was diluted with water (30 mL) and extracted with $CH_2Cl_2$ (30 mL×3). The combined organic layers were washed with brine (20 mL), dried over anhydrous $Na_2SO_4$, filtered and concentrated under reduced pressure to give the title compound (Intermediate 54, 270 mg, crude) as a yellow solid, which was used in the next step without further purification. MS: m/z=341.0 [M+H]$^{+\cdot}$ Intermediate 55 & 56: tert-Butyl 9-fluoro-2-azabicyclo[6.1.0]nonane-2-carboxylate (trans mixture) & tert-butyl 9-fluoro-azabicyclo[6.1.0]nonane-2-carboxylate (cis mixture)

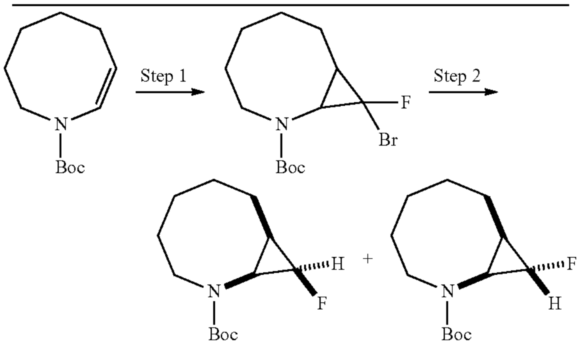

Intermediate 55

Intermediate 56

Step 1: tert-Butyl 9-bromo-9-fluoro-2-azabicyclo [6.1.0]nonane-2-carboxylate

A mixture of NaOEt (3.70 g, 54.4 mmol) in $CH_2Cl_2$ (70 mL) was degassed and purged with $N_2$ three times, then a solution of tert-butyl (Z)-3,4,5,6-tetrahydroazocine-1 (2H)-carboxylate (5 g, 23.7 mmol) in $CH_2Cl_2$ (15 mL) was added dropwise into the reaction vessel at 0° C. under $N_2$. Then a solution of ethyl 2,2-dibromo-2-fluoroacetate (6.56 g, 24.9 mmol) in $CH_2Cl_2$ (15 mL) was added dropwise into the reaction vessel at 0° C. under $N_2$, and then the mixture was stirred at 25° C. for 4 h under $N_2$ atmosphere. The reaction mixture was quenched with sat. $NH_4Cl$ aq. (200 mL) at 0° C. and extracted with EtOAc (200 mL×2). The combined organic layers were washed with brine (100 mL), dried over anhydrous $Na_2SO_4$, filtered and the filtrate was concentrated under reduced pressure to give a residue. The residue was purified by silica gel flash chromatography (eluent: 0~5% of EtOAc in Petroleum ether) to give the title compound (4.3 g, 51% yield) as a yellow oil. $^1$H NMR (400 MHz, Chloroform-d) & 3.52-3.38 (m, 2H), 3.17-3.02 (m, 1H), 1.71-1.59 (m, 6H), 1.52-1.50 (m, 9H), 1.48-1.47 (m, 2H), 0.91-0.79 (m, 1H). $^{19}$F NMR (376 MHz, Chloroform-d) δ −116.52, −117.00, −126.14, −126.25, −126.36, −126.38, −126.50, −156.61.

Step 2: tert-Butyl 9-fluoro-2-azabicyclo[6.1.0] nonane-2-carboxylate (trans mixture) & fert-butyl 9-fluoro-2-azabicyclo[6.1.0]nonane-2-carboxylate (cis mixture)

To a solution of Na (8.81 g, 383 mmol) in THF (100 mL) was added dropwise tert-butyl 9-bromo-9-fluoro-2-azabicyclo[6.1.0]nonane-2-carboxylate (3.8 g, 11.8 mmol) in THE (20 mL) and MeOH (20 mL) at 25° C. under $N_2$. Then MeOH (20 mL) was added dropwise at 35° C. under $N_2$. The mixture was stirred at 40° C. for 2 h under $N_2$. The reaction mixture was quenched with sat. $NH_4Cl$ aq. (200 mL) at 0° C. and extracted with EtOAc (300 mL×2). The combined organic layers were washed with brine (200 mL), dried over anhydrous $Na_2SO_4$, filtered and concentrated under reduced pressure. The residue was purified by silica gel flash chromatography (eluent: 0~5% of EtOAc in Petroleum ether) to give the title compound (trans mixture) (Intermediate 55, 1.2 g, 42% yield) as a yellow oil and the title compound (cis mixture) (Intermediate 56, 980 mg, 34% yield) as a yellow oil. Spectra for Intermediate 55: 1H NMR (400 MHz, Chloroform-d) δ 4.78-4.51 (m, 1H), 4.01-3.89 (m, 1H), 2.78-2.68 (m, 1H), 2.61-2.48 (m, 1H), 2.10-1.98 (m, 1H), 1.80-1.58 (m, 3H), 1.56-1.52 (m, 1H), 1.50-1.48 (m, 1H), 1.47 (s, 9H), 1.43-1.38 (m, 1H), 1.30-1.19 (m, 1H), 0.93-0.78 (m, 1H). $^{19}$F NMR (376 MHz, Chloroform-d) δ −206.13, −206.23, −206.26. Spectra for Intermediate 56: 3H NMR (400 MHZ, Chloroform-d)δ 5.33-5.03 (m, 1H), 4.04-3.89 (m, 1H), 3.51-3.34 (m, 1H), 3.03-2.95 (m, 1H), 2.25-2.10 (m, 1H), 1.81-1.74 (m, 3H), 1.60-1.54 (m, 3H), 1.45-1.43 (m, 9H), 1.40-1.39 (m, 1H), 0.91-0.76 (m, 1H), $^{19}$F. NMR (376 MHz, Chloroform-d) δ −233.86.

Intermediate 57 & 58: 2,7-Dichloro-8-fluoro-4-((1R,6S,7R)-9-fluoro-2-azabicyclo[6.1.0]nonan-2-yl)pyrido[4,3-d]pyrimidine & 2,7-dichloro-8-fluoro-4-((1S,8R,9S)-9-fluoro-2-azabicyclo[6.1.0]nonan-2-yl)pyrido[4,3-d]pyrimidine

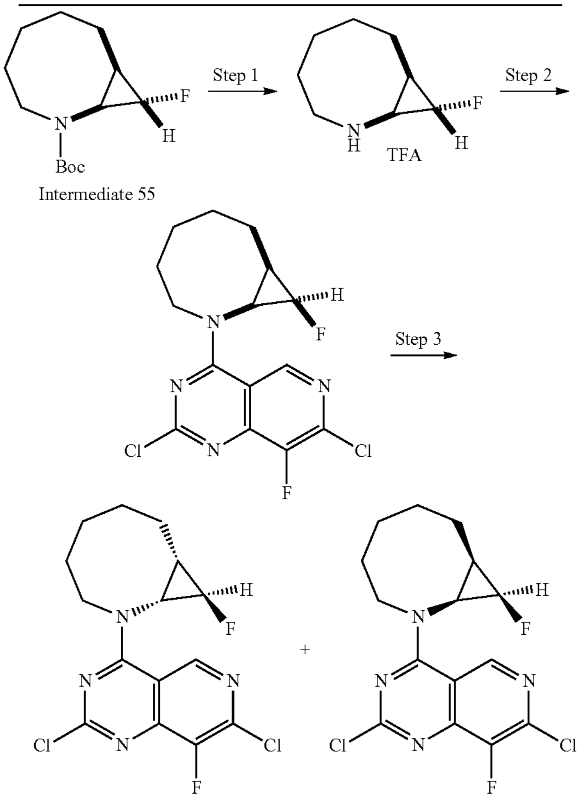

Intermediate 55

Intermediate 57

Intermediate 58

Step 1: 9-Fluoro-2-azabicyclo[6.1.0]nonane TFA salt (trans mixture)

To a solution of tert-butyl 9-fluoro-2-azabicyclo[6.1.0]nonane-2-carboxylate (trans mixture) (1.1 g, 4.52 mmol) in $CH_2Cl_2$ (15 mL) was added TFA (6 mL, 81.4 mmol) at 0° C. The mixture was stirred at 20° C. for 0.1 h. The residue was concentrated under reduced pressure to give the title compound (trans mixture) (1.1 g, TFA salt) as a yellow oil, which was used in the next step without further purification. $^1$H NMR (400 MHZ, Chloroform-d)δ 4.79-4.41 (m, 1H), 3.43-3.28 (m, 1H), 3.18-3.03 (m, 1H), 2.98-2.80 (m, 1H), 2.44-2.34 (m, 1H), 2.00-1.78 (m, 3H), 1.77-1.64 (m, 2H), 1.61-1.43 (m, 2H), 1.26-1.10 (m, 1H). $^{19}$F NMR (376 MHz, Chloroform-d) δ −76.00, −209.31.

Step 2: 2,7-Dichloro-8-fluoro-4-(9-fluoro-2-azabicyclo[6.1.0]nonan-2-yl)pyrido[4,3-d]pyrimidine To a solution of 2,4,7-trichloro-8-fluoro-pyrido[4,3-d]pyrimidine (1.08 g, 4.28 mmol) in $CH_2Cl_2$ (6 mL) were added DIPEA (3.72 mL, 21.4 mmol) and 9-fluoro-2-azabicyclo[6.1.0]nonane (trans mixture) (1.1 g, 4.28 mmol, TFA salt) at −40° C. under $N_2$. The mixture was stirred at −40° C. for 1 h under $N_2$. The reaction mixture was diluted with water (60 mL) and extracted with EtOAc (50 mL×2). The combined organic layers were washed with brine (60 mL), dried over anhydrous $Na_2SO_4$, filtered and concentrated under reduced pressure. The residue was purified by silica gel flash chromatography (eluent: 0~20% of EtOAc in Petroleum ether) to give the title compound (865 mg, 54% yield).

Step 3: 2,7-Dichloro-8-fluoro-4-((1R,85,9R)-9-fluoro-2-azabicyclo[6.1.0]nonan-2-yl)pyrido[4,3-d]pyrimidine & 2,7-dichloro-8-fluoro-4-((1S,8R,9S)-9-fluoro-2-azabicyclo[6.1.0]nonan-2-yl)pyrido[4,3-d]pyrimidine 2,7-Dichloro-8-fluoro-4-(9-fluoro-2-azabicyclo[6.1.0]nonan-2-yl)pyrido[4,3-d]pyrimidine (trans mixture) (300 mg) was separated by SFC(column: DAICEL CHIRALCEL OJ (250 mm×30 mm, 10 μm); mobile phase: [$CO_2$-i-PrOH (0.1% $NH_3$ $H_2O$)]; B %: 35%, isocratic elution mode) to give the title compound (Intermediate 57, 123 mg, SFC peak 1: 1.253 min) as a yellow solid and the title compound (Intermediate 58, 122 mg, SFC peak 2: 1.618 min) as a yellow solid. Spectra for Intermediate 57: MS: m/z=359.0 $[M+H]^+$. Spectra for Intermediate 57: MS: m/z=358.9 $[M+H]^+$. $^1$H NMR (400 MHz, Dimethylsulfoxide-$d_6$) δ 9.19 (s, 1H), 4.49-4.31 (m, 2H), 3.96-3.77 (m, 1H), 3.32-3.28 (m, 1H), 2.00-1.48 (m, 7H), 1.43-1.33 (m, 1H), 0.84-0.69 (m, 1H). $^{19}$F NMR (376 MHz, Dimethylsulfoxide-$d_6$)-135.87, −208.10. Spectra for Intermediate 58: MS: m/z=359.0 $[M+H]^+$. $^1$H NMR (400 MHz, Dimethylsulfoxide-$d_6$) δ 9.19 (s, 1H), 4.51-4.38 (m, 1H), 4.34-4.27 (m, 1H), 3.93-3.81 (m, 1H), 3.31-3.26 (m, 1H), 1.96-1.51 (m, 7H), 1.43-1.31 (m, 1H), 0.84-0.68 (m, 1H). $^{19}$F NMR (376 MHz, Dimethylsulfoxide-$d_6$) −135.87, −208.09.

Intermediate 59 & 60: 2,7-Dichloro-8-fluoro-4-((1S,6R,7R)-7-fluoro-2-azabicyclo[4.1.0]heptan-2-yl)pyrido[4,3-d]pyrimidine & 2,7-Dichloro-8-fluoro-4-((1R,6S,7S)-7-fluoro-2-azabicyclo[4.1.0]heptan-2-yl)pyrido[4,3-d]pyrimidine

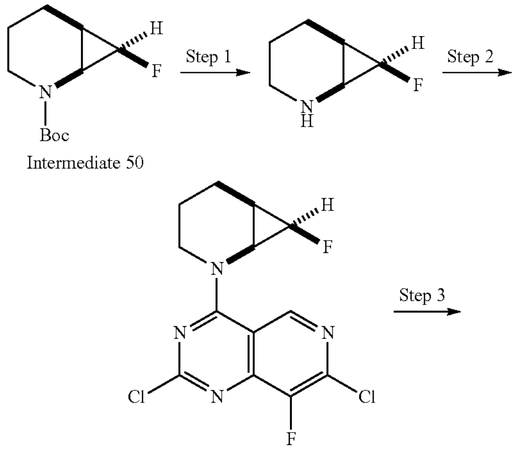

Intermediate 50

-continued

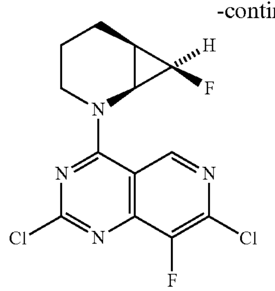

Intermediate 59

+

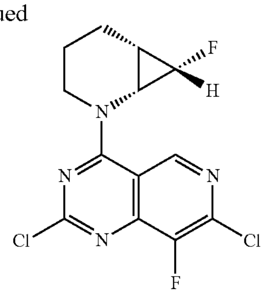

Intermediate 60

Step 1: 7-fluoro-2-azabicyclo[4.1.0]heptane (cis mixture)

To a mixture of tert-butyl 7-fluoro-2-azabicyclo[4.1.0]heptane-2-carboxylate (cis mixture) (220 mg, 1.02 mmol) in $CH_2Cl_2$ (2 mL) was added HCl (2 mL, 2M in EtOAc). The mixture was stirred at 25° C. for 0.5 h. The reaction mixture was concentrated under reduced pressure to give the title compound (cis mixture) (117 mg, HCl salt) as a white solid, which was used in the next step without further purification.

Step 2: 2,7-Dichloro-8-fluoro-4-((cis)-7-fluoro-2-azabicyclo[4.1.0]heptan-2-yl)pyrido[4,3-d]pyrimidine (cis mixture)

To a solution of 2,4,7-trichloro-8-fluoro-pyrido[4,3-d]pyrimidine (282 mg, 1.12 mmol) and DIPEA (708 μL, 4.06 mmol) in $CH_2Cl_2$ (5 mL) was added 7-fluoro-2-azabicyclo[4.1.0]heptane (cis mixture) (117 mg, 1.02 mmol) at −40° C. under $N_2$. The mixture was stirred at −40° C. for 0.5 h. The reaction mixture was concentrated under reduced pressure. The residue was purified by silica gel flash chromatography (eluent: 0~24% of EtOAc in petroleum ether) to give the title compound (cis mixture) (260 mg, 77% yield over 2 steps) as a yellow solid. MS: m/z=331.0 $[M+H]^{+.}$

Step 3: 2,7-Dichloro-8-fluoro-4-((1S,6R,7R)-7-fluoro-2-azabicyclo[4.1.0]heptan-2-yl)pyrido[4,3-d]pyrimidine & 2,7-Dichloro-8-fluoro-4-((1R,6S,7S)-7-fluoro-2-azabicyclo[4.1.0]heptan-2-yl)pyrido[4,3-d]pyrimidine 2,7-Dichloro-8-fluoro-4-(7-fluoro-2-azabicyclo[4.1.0]heptan-2-yl)pyrido[4,3-d]pyrimidine (cis mixture) (260 mg, 785 μmol) was separated by SFC(column: DAICEL CHIRALPAK AD (250 mm×30 mm, 10 μm); mobile phase: [$CO_2$-MeOH (0.1% $NH_3$ $H_2O$)]; B %: 40%, isocratic elution mode) to give the title compound (Intermediate 59, 90 mg, 35% yield, SFC Peak 1; 1.819 min) as a yellow solid and the title compound (Intermediate 60, 70 mg, 27% yield, SFC Peak 2: 2.174 min) as a yellow solid. Spectra for Intermediate 59: MS: m/z=330.9 $[M+H]^+$. $^1$HNMR (400 MHz, Dimethylsulfoxide-$d_6$) δ 9.74 (s, 1H), 5.19-4.92 (m, 1H), 4.73-4.57 (m, 1H), 3.81-3.64 (m, 1H), 3.14-2.94 (m, 1H), 2.17-2.02 (m, 1H), 1.84-1.63 (m, 3H), 1.50-1.35 (m, 1H). $^{19}$F NMR (376 MHz, Dimethylsulfoxide-$d_6$) δ −134.36, −232.37. Spectra for Intermediate 60: MS: m/z=330.8 $[M+H]^+$. $^1$HNMR (400 MHZ, Dimethylsulfoxide-$d_6$) δ 9.74 (s, 1H), 5.17-4.94 (m, 1H), 4.74-4.55 (m, 1H), 3.81-3.65 (m, 1H), 3.13-2.94 (m, 1H), 2.17-1.99 (m, 1H), 1.84-1.66 (m, 3H), 1.51-1.36 (m, 1H). $^{19}$F NMR (376 MHZ, Dimethylsulfoxide-$d_6$) δ −134.36, −232.38.

Intermediate 61: 6,7-Difluoro-5-(fluoromethoxy)-4-(4,4,5,5-tetramethyl-1,3,2-dioxaborolan-2-yl)naphthalen-2-amine

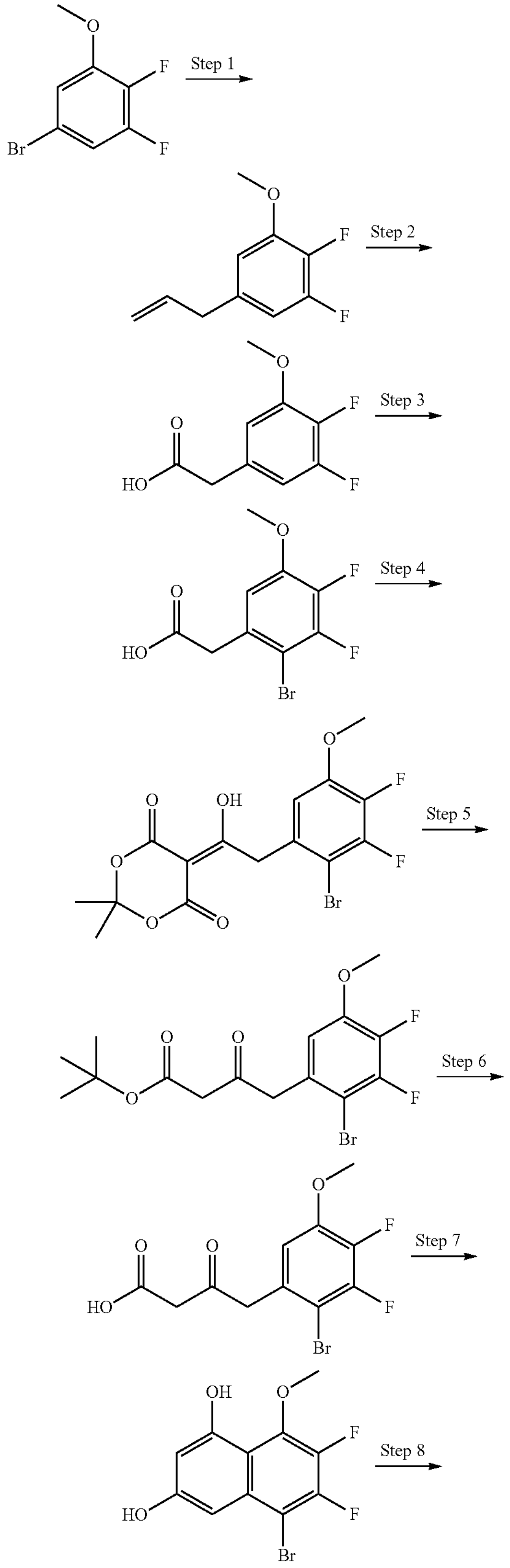

-continued

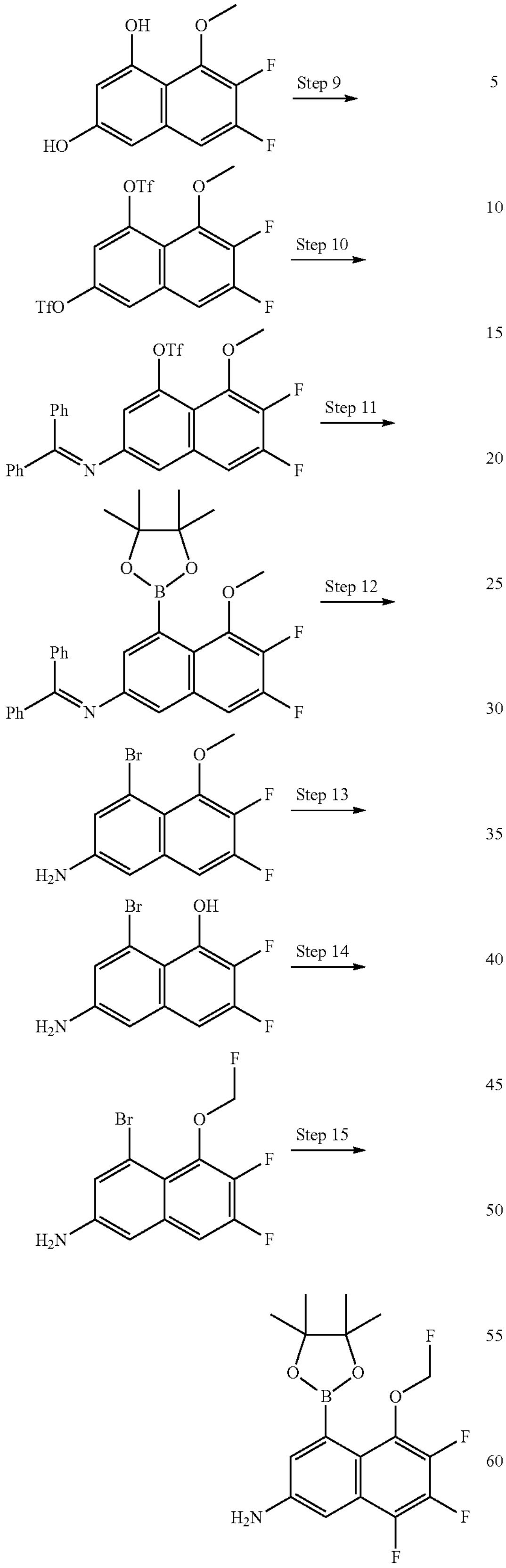

Intermediate 61

Step 1: 5-Allyl-1,2-difluoro-3-methoxybenzene

To a solution of 5-bromo-1,2-difluoro-3-methoxybenzene (20 g, 89.7 mmol), 2-allyl-4,4,5,5-tetramethyl-1,3,2-dioxaborolane (30.1 g, 179 mmol) in THF (2 L) were added Pd $(PPh_3)_4$ (10.36 g, 8.97 mmol) and CsF (40.9 g, 269 mmol). The mixture was degassed, purged with $N_2$ three times, and stirred at 75° C. for 16 h under $N_2$. The reaction mixture concentrated under reduced pressure. The residue was purified by silica gel flash chromatography (eluent: 0~10% of EtOAc in Petroleum ether) to give the title compound (35 g, 71% yield) as a colorless oil. $^1$H NMR (400 MHZ, Dimethylsulfoxide-$d_6$) δ 6.65-6.53 (m, 2H), 5.97-5.82 (m, 1H), 5.17-5.03 (m, 2H), 3.91-3.88 (m, 3H), 3.32 (d, J=6.4 Hz, 2H).

Step 2: 2-(3,4-Difluoro-5-methoxyphenyl) acetic acid

To a solution of 5-allyl-1,2-difluoro-3-methoxybenzene (28 g, 152 mmol) in ACN (380 mL), $H_2O$ (540 mL) and EtOAc (380 mL) was added RuCl (6.31 g, 30.4 mmol) at 0° C. under $N_2$ atmosphere. Then $NaIO_4$ (130 g, 608 mmol) was added in batches at 0° C. under $N_2$ atmosphere over 1 h. The reaction mixture was stirred at 0° C. for 1 h under $N_2$ atmosphere, filtered and the filter cake was washed with EtOAc (500 mL). The filtrate was extracted with EtOAc (500 mL×3). The combined organic phases were washed with NazS2O3 (100 mL) and brine (500 mL), dried over anhydrous $Na_2SO_4$, filtered and concentrated under reduced pressure to give the title compound (21 g, 68% yield) as a brown solid. $^1$H NMR (400 MHZ, Dimethylsulfoxide-$d_6$) δ 12.57-12.26 (m, 1H), 6.97-6.81 (m, 2H), 3.85 (s, 3H), 3.58 (s, 2H).

Step 3: 2-(2-Bromo-3,4-difluoro-5-methoxyphenyl) acetic acid

To a solution of 2-(3,4-difluoro-5-methoxyphenyl) acetic acid (21 g, 104 mmol) in acetic acid (80 mL) was added bromine (7.49 mL, 145.3 mmol). The mixture was stirred at 25° C. for 2 h. The reaction mixture was diluted with water (300 mL) and quenched with sat. NazS203 aq. (50 mL). The precipitate was filtered. The filter cake was washed with water (300 mL) and dried under reduced pressure to give the title compound (28.59 g, 98% yield) as a light yellow solid. $^1$H NMR (400 MHz, Dimethylsulfoxide-$d_6$) δ 12.6 (br s, 1H), 7.27-7.16 (m, 1H), 3.87 (s, 3H), 3.75 (s, 2H).

Step 4: 5-(2-(2-Bromo-3,4-difluoro-5-methoxyphenyl)-1-hydroxyethylidene)-2,2-dimethyl-1,3-dioxane-4,6-dione To a solution of 2-(2-bromo-3,4-difluoro-5-methoxyphenyl) acetic acid (28.6 g, 101.7 mmol) in ACN (200 mL) were added 2,2-dimethyl-1,3-dioxane-4,6-dione (16.1 g, 111.9 mmol), DMAP (1.24 g, 10.1 mmol) and DIPEA (39.0 mL, 223.8 mmol). Then f-BuCOCl (12.5 mL, 101.7 mmol) was added dropwise at 0° C. under $N_2$. The mixture was stirred at 25° C. for 3 h under $N_2$. The reaction mixture was quenched with 2N HCl (400 mL), and the precipitate was filtered and washed with water and dried under reduced pressure to give the title compound (28.5 g, 69% yield) as a brown solid. $^1$H NMR (400 MHZ, Dimethylsulfoxide-$d_6$) δ 7.23-7.15 (m, 1H), 4.52 (s, 2H), 3.87 (s, 3H), 1.69 (s, 6H).

Step 5: tert-Butyl 4-(2-bromo-3,4-difluoro-5-methoxyphenyl)-3-oxobutanoate

A solution of 5-(2-(2-bromo-3,4-difluoro-5-methoxyphenyl)-1-hydroxyethylidene)-2,2-dimethyl-1,3-dioxane-4,6-dione (28.5 g, 70.0 mmol) in/-BuOH (300 mL) was stirred at 90° C. for 2 h. The reaction mixture was concentrated under reduced pressure to give the title compound (26 g, crude) as a brown solid. MS: m/z=377.0 $[M-H]^{-}$.

Step 6: 4-(2-Bromo-3,4-difluoro-5-methoxyphenyl)-3-oxobutanoic acid

To a solution of tert-butyl 5-(2-(2-bromo-3,4-difluoro-5-methoxyphenyl)-1-hydroxyethylidene)-2,2-dimethyl-1,3-dioxane-4,6-dione (26 g, 68.6 mmol) in $CH_2Cl_2$ (50 mL) was added TFA (50 mL). The mixture was stirred at 25° C. for 2 h. The reaction mixture was concentrated under reduced pressure to give the title compound (22 g, crude) as a brown solid. $^1$H NMR (400 MHZ, Dimethylsulfoxide-$d_6$) δ 12.9 (br s, 1H), 7.11 (d, J=7.2 Hz, 1H), 4.08 (s, 2H), 3.86 (s, 3H), 3.60 (s, 2H).

Step 7: 5-Bromo-6,7-difluoro-8-methoxynaphthalene-1,3-diol

A solution of 4-(2-bromo-3,4-difluoro-5-methoxyphenyl)-3-oxobutanoic acid (22 g, 68.1 mmol) in $CF_3SO_3H$ (50 mL) was stirred at 25° C. for 16 h. The reaction mixture was poured into ice water (500 mL). The precipitate was filtered. The filter cake was washed with water (200 mL) and dried under reduced pressure to give the title compound (19 g, crude) as a brown solid. $^1$H NMR (400 MHz, Dimethylsulfoxide-$d_6$) δ 10.11 (s, 1H), 10.03 (s, 1H), 6.91 (d, J=2.0 Hz, 1H), 6.54 (d, J=2.4 Hz, 1H), 3.96 (s, 3H).

Step 8: 6,7-Difluoro-8-methoxynaphthalene-1,3-diol

To a solution of 5-bromo-6,7-difluoro-8-methoxynaphthalene-1,3-diol (19 g, 62.28 mmol) in MeOH (100 mL) was added Pd/C(2.65 g, 12.46 mmol, 10% purity). The mixture was degassed, purged with $H_2$ three times, and stirred at 25° C. for 2 h under Hz atmosphere (15 psi). The mixture was filtered, and the filter cake was washed with EtOAc (200 mL). The filtrate was concentrated under reduced pressure. The residue was purified by silica gel flash chromatography (eluent: 0~13% EtOAc in Petroleum ether) to give the title compound (10 g, 67% yield over 4 steps) as a white solid. MS: m/z=224.9 $[M-H]^{-}$. $^1$H NMR (400 MHZ, Dimethylsulfoxide-$d_6$) δ 9.70 (d, J=14 Hz, 2H), 7.36 (dd, J=7.6, 12 Hz, 1H), 6.62-6.42 (m, 2H), 3.96 (s, 3H). $^{19}$F. NMR (376 MHz, Dimethylsulfoxide-$d_6$) δ −137.25, −137.31, −162.68, −162.74.

Step 9: 6,7-Difluoro-8-methoxynaphthalene-1,3-diyl bis(trifluoromethanesulfonate)

To a solution of 6,7-difluoro-8-methoxynaphthalene-1,3-diol (5 g, 22.1 mmol) and DIPEA (17.1 g, 132 mmol) in $CH_2Cl_2$ (50 mL) was added Tf2O (24.9 g, 88.4 mmol) at 0° C. The mixture was stirred at 0° C. under $N_2$ for 0.5 h. The reaction mixture was diluted with $H_2O$ (50 mL) and extracted with EtOAc (50 mL×3). The combined organic layers were dried over anhydrous $Na_2SO_4$, filtered and concentrated under reduced pressure. The residue was purified by silica gel flash chromatography (eluent: 0~1% EtOAc in petroleum ether) to give the title compound (9.65 g, 88% yield) as a white solid. MS: m/z=489.0 $[M-H]^{-}$. $^1$H NMR (400 MHZ, Dimethylsulfoxide-$d_6$) δ 8.39 (d, J=2.4 Hz, 1H), 8.13-8.08 (m, 1H), 8.01 (s, 1H), 4.07 (d, J=2.0 Hz, 3H). $^{19}$F NMR (376 MHz, Dimethylsulfoxide-$d_6$) δ −72.38, −72.87, −130.44, −130.49, −149.38, −149.43.

Step 10: 3-((Diphenylmethylene)amino)-6,7-difluoro-8-methoxynaphthalen-1-yl trifluoromethanesulfonate To a solution of 6,7-difluoro-8-methoxynaphthalene-1,3-diyl bis(trifluoromethanesulfonate) (9.65 g, 19.6 mmol) in 1,4-dioxane (80 mL) were added diphenylmethanimine (3.57 g, 19.6 mmol), $Cs_2CO_3$ (19.2 g, 59.0 mmol) and XantPhosPdG3 (1.87 g, 1.97 mmol). The mixture was stirred at 80° C. under $N_2$ for 1 h. The reaction mixture was diluted with $H_2O$ (100 mL) and extracted with EtOAc (100 mL×3). The combined organic layers were washed with brine (100 mL), dried over anhydrous $Na_2SO_4$, filtered and concentrated under reduced pressure. The residue was purified by silica gel flash chromatography (eluent: 0~2% EtOAc in petroleum ether) to give the title compound (7.67 g, 12.3 mmol, 63% yield) as a yellow oil. MS: m/z=522.4 $[M+H]^{+}$. $^1$H NMR (400 MHZ, Dimethylsulfoxide-$d_6$)δ 7.76-7.66 (m, 4H), 7.61-7.47 (m, 4H), 7.32-7.31 (m, 2H), 7.21-7.20 (m, 2H), 7.08 (s, 1H), 3.99 (d, J=1.6 Hz, 3H). $^{19}$F. NMR (376 MHz, Dimethylsulfoxide-$d_6$) δ −73.17, −133.48, −154.36, −154.42.

Step 11: N-(6,7-difluoro-5-methoxy-4-(4,4,5,5-tetramethyl-1,3,2-dioxaborolan-2-yl) naphthalen-2-yl)-1,1-diphenylmethanimine To a solution of 3-((diphenylmethylene)amino)-6,7-difluoro-8-methoxynaphthalen-1-yl trifluoromethanesulfonate (7.67 g, 14.7 mmol) in DMA (60 mL) were added 4,4,5,5-tetramethyl-2-(4,4,5,5-tetramethyl-1,3,2-dioxaborolan-2-yl)-1,3,2-dioxaborolane (4.48 g, 17.6 mmol), AcOK (4.33 g, 44.1 mmol) and CysPPdG3 (956 mg, 1.47 mmol). The mixture was stirred at 100° C. under $N_2$ for 1 h. The reaction mixture was diluted with $H_2O$ (100 mL) and extracted with EtOAc (100 mL×3). The combined organic layers were dried over anhydrous $Na_2SO_4$, filtered and concentrated under reduced pressure. The residue was purified by silica gel flash chromatography (eluent: 0~2% EtOAc in petroleum ether) to give the title compound (5.88 g, 78% yield) as a yellow solid. MS: m/z=500.0 $[M+H]^{+}$. $^1$H NMR (400 MHZ, Dimethylsulfoxide-$d_6$) δ 7.71-7.66 (m, 2H), 7.58-7.53 (m, 1H), 7.51-7.41 (m, 3H), 7.31-7.30 (m, 3H), 7.21-7.14 (m, 3H), 6.91 (s, 1H), 4.03 (d, J=2.0 Hz, 3H), 1.31 (s, 12H). $^{19}$F NMR (376 MHz, Dimethylsulfoxide-$d_6$) δ −136.65, −157.78.

Step 12; 4-Bromo-6,7-difluoro-5-methoxynaphthalen-2-amine

To a solution of N-(6,7-difluoro-5-methoxy-4-(4,4,5,5-tetramethyl-1,3,2-dioxaborolan-2-yl) naphthalen-2-yl)-1,1-diphenylmethanimine (2 g, 4.01 mmol) in 1,4-dioxane (200 mL) was added a solution of CuBrz (894 mg, 4.01 mmol) in $H_2O$ (100 mL). The mixture was stirred at 100° C. under $N_2$ for 4 h. The reaction mixture was diluted with $H_2O$ (100 mL) and extracted with EtOAc (300 mL×3). The combined organic layers were washed with brine (300 mL), dried over anhydrous $Na_2SO_4$, filtered and concentrated under reduced pressure. The residue was purified by silica gel flash chromatography (eluent: 0~10% EtOAc in petroleum ether) to give the title compound (760 mg, 56% yield) as a brown solid. MS: m/z=287.9 $[M+H]^+$. 1H NMR (400 MHz, Dimethylsulfoxide-$d_6$) $7.40-7.35 (m, 1H), 7.31 (d, J=2.0 Hz, 1H), 6.81 (d, J=2.0 Hz, 1H), 5.72 (s, 2H), 3.89 (s, 3H). $^{19}F$ NMR (376 MHZ, Dimethylsulfoxide-$d_6$) δ −136.22, −136.28, −160.13, −160.19.

Step 13: 6-Amino-8-bromo-2,3-difluoronaphthalen-1-ol

BBr3 (S mL, 2 M in $CH_2Cl_2$) was added to 4-bromo-6,7-difluoro-5-methoxynaphthalen-2-amine (760 mg, 2.64 mmol) at 0° C. under $N_2$. The mixture was stirred at 25° C. under $N_2$ for 1 h. The reaction mixture was quenched with $H_2O$ (50 mL) at 25° C. and extracted with EtOAc (50 mL×3). The combined organic layers were washed with brine (50 mL), dried over anhydrous $Na_2SO_4$, filtered and concentrated under reduced pressure to give the title compound (708 mg, 88% yield) as a brown solid. MS: m/z=273.8 $[M+H]^+$. $^1H$ NMR (400 MHZ, Dimethylsulfoxide-$d_6$) § 10.38 (s, 1H), 7.20 (d, J=1.6 Hz, 1H), 7.03-6.98 (m, 1H), 6.71 (d, J=2.0 Hz, 1H), 6.05-5.13 (br d, 2H). $^{19}F$ NMR (376 MHz, Dimethylsulfoxide-$d_6$) δ −136.93, −166.53, −166.59.

Step 14: 4-Bromo-6,7-difluoro-5-(fluoromethoxy) naphthalen-2-amine

To a solution of 6-amino-8-bromo-2,3-difluoronaphthalen-1-ol (290 mg, 1.06 mmol) in ACN (30 mL) were added $Cs2CO_3$ (1.03 g, 3.17 mmol) and bromo (fluoro) methane (119 mg, 1.06 mmol) at 0° C. The mixture was stirred at 25° C. for 1 h. The reaction mixture was diluted with $H_2O$ (50 mL) and extracted with EtOAc (50 mL×3). The combined organic layers were dried over anhydrous $Na_2SO_4$, filtered and concentrated under reduced pressure. The residue was purified by silica gel flash chromatography (eluent: 0~8% EtOAc in petroleum ether) to give the title compound (236 mg, 66% yield) as a white solid. MS: m/z=305.8 $[M+H]^+$. $^1H$ NMR (400 MHZ, Dimethylsulfoxide-$d_6$) δ 7.57-7.52 (m, 1H), 7.36 (d, J=2.0 Hz, 1H), 6.85 (d, J=2.0 Hz, 1H), 5.85 (s, 1H), 5.80 (s, 2H), 5.71 (s, 1H). $^{19}F$ NMR (376 MHz, Dimethylsulfoxide-$d_6$) 6-136.10, —136.16, −151.06, −151.10, −157.09, −157.15.

Step 15: 6,7-Difluoro-S-(fluoromethoxy)-4-(4,4,5,5-tetramethyl-1,3,2-dioxaborolan-2-yl) naphthalen-2-amine To a solution of 4-bromo-6,7-difluoro-5-(fluoromethoxy) naphthalen-2-amine (225 mg, 735 μmol) in 1,4-dioxane (4 mL) were added 4,4,5,5-tetramethyl-2-(4,4,5,5-tetramethyl-1,3,2-dioxaborolan-2-yl)-1,3,2-dioxaborolane (224 mg, 882 μmol), K3PO4 (468 mg, 2.21 mmol) and Cy3PPdG3 (47 mg, 73.5 μmol). The mixture was stirred at 100° C. under $N_2$ for 16 h. The reaction mixture was concentrated under reduced pressure. The residue was purified by silica gel flash chromatography (eluent: 0~10% EtOAc in petroleum ether) to give the title compound (Intermediate 61, 200 mg, 49% yield) as a brown oil. MS: m/z=353.8 $[M+H]^+$. 1H NMR (400 MHz, Dimethylsulfoxide-$d_6$) & 7.39 (dd, J=7.6, 12.0 Hz, 1H), 6.98 (d, J=1.6 Hz, 1H), 6.81 (d, J=2.0 Hz, 1H), 5.86 (s, 1H), 5.73 (s, 1H), 5.60 (s, 2H), 1.34 (s, 12H). $^{19}F$. NMR (376 MHz, Dimethylsulfoxide-$d_6$) δ −137.84, −137.90, −148.28, −162.18, −162.24.

Intermediate 62: 5-(Difluoromethoxy)-6,7-difluoro-4-(4,4,5,5-tetramethyl-1,3,2-dioxaborolan-2-yl)naphthalen-2-amine

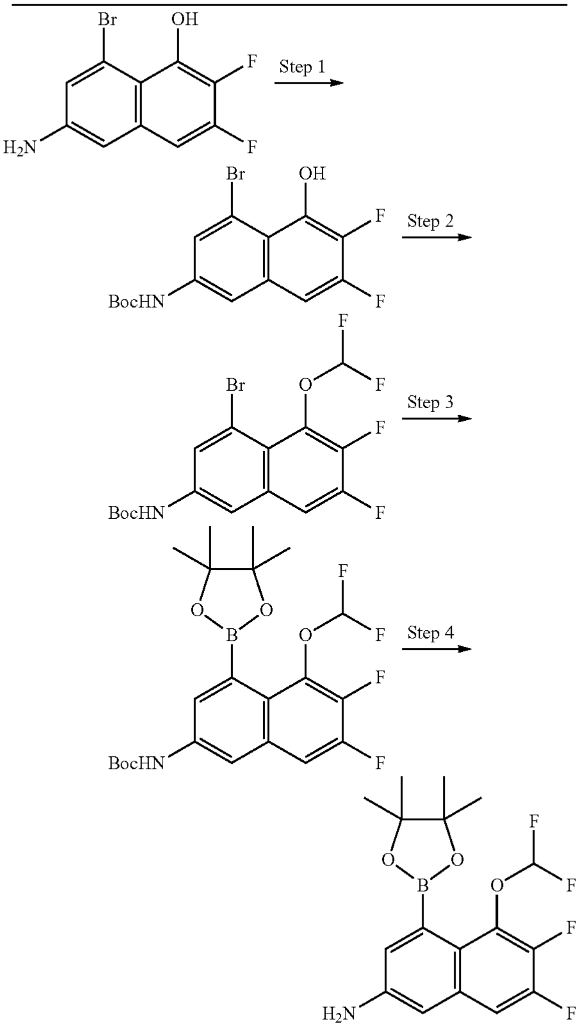

Intermediate 62

Step 1: tert-Butyl (4-bromo-6,7-difluoro-5-hydroxynaphthalen-2-yl) carbamate

To a solution of 6-amino-8-bromo-2,3-difluoronaphthalen-1-ol (300 mg, 1.09 mmol, refer to Intermediate 61 for detail procedures) in MeOH (3 mL) was added BoczO (360 mg, 1.64 mmol) at 25° C. The mixture was stirred at 70° C. for 1 h under $N_2$ atmosphere. The reaction mixture was diluted with water (50 mL) and extracted with EtOAc (50 mL×3). The combined organic layers were washed with brine (50 mL×2), dried over anhydrous $Na_2SO_4$, filtered and concentrated under reduced pressure. The residue was purified by silica gel flash chromatography (eluent: 0~4% of EtO Ac in petroleum ether) to give the title compound (400 mg, 84% yield) as a brown solid. MS: m/z=317.8 $[M+H-Bu]^+$. $^1H$ NMR (400 MHZ, Dimethylsulfoxide-$d_6$) 10.75 (s, 1H), 9.67 (s, 1H), 7.97 (s, 1H), 7.80 (d,.J=1.6 Hz, 1H), 7.34 (dd, J=7.6, 11.2 Hz, 1H), 1.49 (s, 9H). $^{19}F$ NMR (376 MHz, Dimethylsulfoxide-$d_6$) δ −135.57, −162.03.

Step 2: tert-Butyl (4-bromo-5-(difluoromethoxy)-6,7-difluoronaphthalen-2-yl) carbamate To a solution of tert-butyl (4-bromo-6,7-difluoro-S-hydroxynaphthalen-2-yl) carbamate (300 mg, 802 μmol) in DMF (1 mL) were added $K_2CO_3$ (167 mg, 1.20 mmol) and sodium $(I)_2$-chloro-2,2-difluoroacetate (135 mg, 882 μmol) at 25° C. under $N_2$ atmosphere. The mixture was stirred at 70° C. for 1 h. The reaction mixture was diluted with water (50 mL) and extracted with EtOAc (50 mL×3). The combined organic layers were washed with brine (50 mL×2), dried over anhydrous $Na_2SO_4$, filtered and concentrated under reduced pressure to give a residue. The residue was purified by silica gel flash chromatography (eluent: 0~4% EtOAc in petroleum ether) to give the title compund (220 mg, 63% yield) as a yellow oil. MS: m/z=325.8 [M+H-Boc]$^+$. JH NMR (400 MHZ, Dimethylsulfoxide-$d_6$) δ 9.86 (s, 1H), 8.20 (s, 1H), 8.04 (dd, J=8.0, 11.2 Hz, 1H), 7.98 (d, J=1.6 Hz, 1H), 7.28 (t, J=72.8 Hz, 1H), 1.51 (s, 9H). $^{19}$F NMR (376 MHz, Dimethylsulfoxide-$d_6$) δ −82.54, −134.56, −134.63, −149.89, −149.92.

Step 3: tert-Butyl (5-(difluoromethoxy)-6,7-difluoro-4-(4,4,5,5-tetramethyl-1,3,2-dioxaborolan-2-yl) naphthalen-2-yl) carbamate A mixture of tert-butyl (4-bromo-5-(difluoromethoxy)-6,7-difluoronaphthalen-2-yl) carbamate (210 mg, 495 μmol), 4,4,4',4',5,5,5',5'-octamethyl-2,2'-bi (1,3,2-dioxaborolane) (151 mg, 595 μmol), Cy3P-Pd-G3 (33 mg, 49.5 μmol) and $K_3PO_4$ (316 mg, 1.49 mmol) in 1,4-dioxane (2 mL) was degassed and purged with $N_2$ three times. The mixture was stirred at 100° C. for 16 h under N2 atmosphere. The reaction mixture was concentrated under reduced pressure. The residue was purified by silica gel flash chromatography (eluent: 0~3% EtOAc in petroleum ether) to give the title compound (140 mg, 59% yield) as a yellow solid. MS: m/z=494.0 [M+Na]$^+$. $^1$H NMR (400 MHZ, Dimethylsulfoxide-$d_6$) δ 9.71 (s, 1H), 8.23 (d, J=1.2 Hz, 1H), 7.90 (dd, J=8.0, 11.6 Hz, 1H), 7.64 (d, J=2.0 Hz, 1H), 7.26 (t, J=71.2 Hz, 1H), 1.50 (s, 9H), 1.35 (s, 12H). $^{19}$F. NMR (376 MHz, Dimethylsulfoxide-$d_6$) δ −80.36, −80.39, −136.38, −136.44, −154.38, −154.40

Step 4: 5-(Difluoromethoxy)-6,7-difluoro-4-(4,4,5,5-tetramethyl-1,3,2-dioxaborolan-2-yl) naphthalen-2-amine To a mixture of tert-butyl (5-(difluoromethoxy)-6,7-difluoro-4-(4,4,5,5-tetramethyl-1,3,2-dioxaborolan-2-yl) naphthalen-2-yl) carbamate (120 mg, 255 μmol) in HCl (2M in EtOAc, 2 mL) was stirred at 25° C. for 0.5 h. The reaction mixture was concentrated under reduced pressure to give the title compound (Intermediate 62, 95 mg, crude) as a yellow oil, which was used in the next step without further purification. MS: m/z=371.8 [M+H]$^+$.

Intermediate 63: 6,7-Difluoro-5-(methoxy-$d_3$)-4-(4,4,5,5-tetramethyl-1,3,2-dioxaborolan-2-yl)naphthalen-2-amine

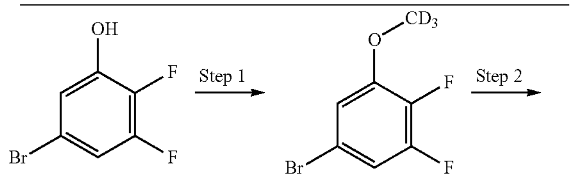

-continued

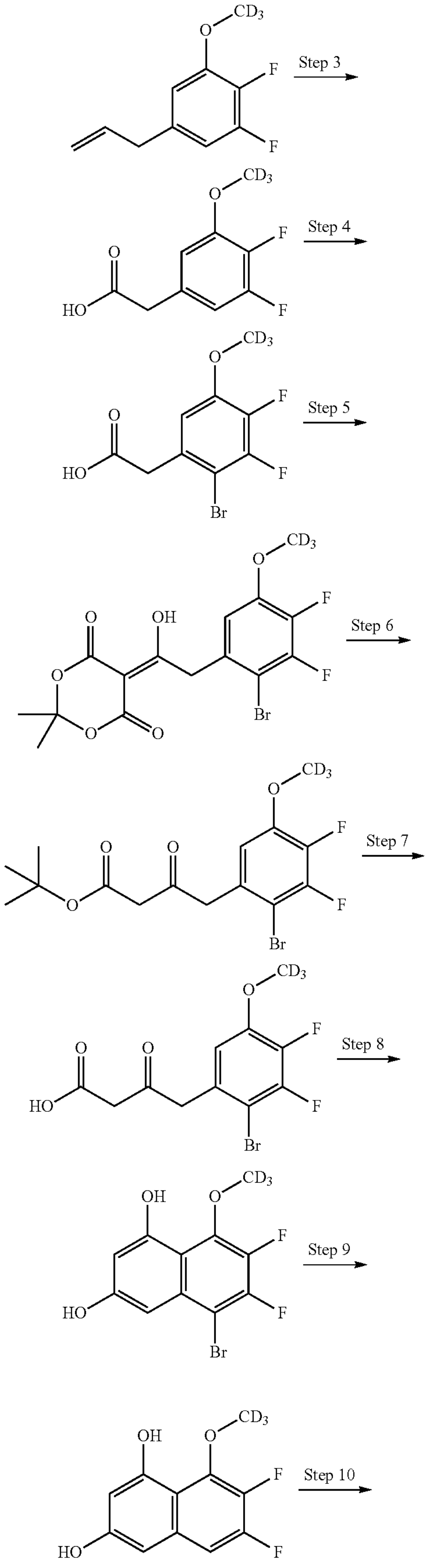

-continued

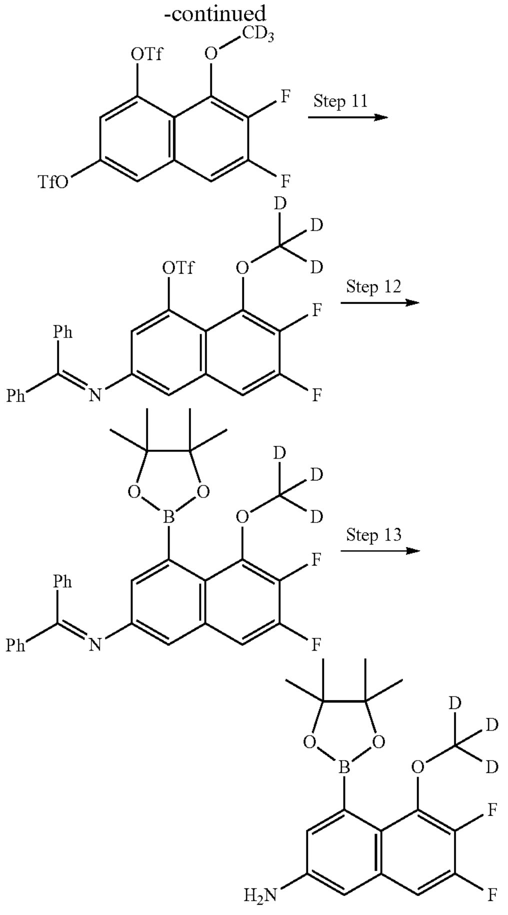

Intermediate 63

Step 1: 5-Bromo-1,2-difluoro-3-(methoxy-$d_3$)benzene

To a solution of 5-bromo-2,3-difluorophenol (20 g, 95.7 mmol) in DMF (200 mL) was added K2CO3 (40 g, 287 mmol) at 0° C. under $N_2$. Then trideuterio (iodo) methane (6.42 mL, 105 mmol) in DMF (200 mL) was added dropwise at 0° C. under $N_2$. The mixture was stirred at 0° C. for 2 h under $N_2$. The mixture was diluted with $H_2O$ (200 mL) and extracted with EtOAc (100 mL×2). The combined organic layers were washed with brine (100 mL×2), dried over anhydrous $Na_2SO_4$ and concentrated under reduced pressure. The residue was purified by silica gel flash chromatography (eluent: 0~2% of EtOAc in petroleum ether) to give the title compound (33.2 g, 77% yield) as a colorless oil. $^1$H NMR (400 MHZ, Dimethylsulfoxide-$d_6$)$_{8\ 7.37}$-7.30 (m, 1H), 7.28-7.23 (m, 1H). $^{19}$F. NMR (376 MHz, Dimethylsulfoxide-$d_6$) δ −136.30,-136.97, −161.52, −161.58.

Step 2: 5-Allyl-1,2-difluoro-3-(methoxy-$d_3$)benzene

A mixture of 5-bromo-1,2-difluoro-3-(methoxy-$d_3$)benzene (33.2 g, 147 mmol), 2-allyl-4,4,5,5-tetramethyl-1,3,2-dioxaborolane (49 g, 294 mmol), CsF (67 g, 441 mmol) and Pd (PPb3)$_4$ (7.49 g, 7.35 mmol) in THF (2500 mL) was degassed and purged with $N_2$ three times, and then the mixture was refluxed for 16 h under $N_2$ atmosphere. The mixture was diluted with $H_2O$ (500 mL) and extracted with EtOAc (300 mL×2). The combined organic layers were washed with brine (300 mL), dried over anhydrous $Na_2SO_4$ and concentrated under reduced pressure. The residue was purified by silica gel flash chromatography (eluent: 0~2% of EtO Ac in petroleum ether) to give the title compound (24.6 g, 89% yield) as a yellow oil. $^1$H NMR (400 MHZ, Dimethylsulfoxide-$d_6$) δ 6.88-6.75 (m, 2H), 6.01-5.87 (m, 1H), 5.16-5.03 (m, 2H), 3.33-3.31 (m, 2H), $^{19}$F NMR (376 MHz, Dimethylsulfoxide-$d_6$) δ −138.91, −138.97, −164.48, −164.54.

Step 3: 2-(3,4-Difluoro-5-(methoxy-$d_3$)phenyl) acetic acid

To a solution of 5-allyl-1,2-difluoro-3-(methoxy-$d_3$)benzene (24.58 g, 131 mmol) in ACN (320 mL), EtOAc (320 mL) and $H_2O$ (520 mL) was added RuCl (5.45 g, 26.3 mmol) at 0° C. Then $NaIO_4$ (98 g, 458 mmol) was added slowly over 1 h while the reaction temperature was maintained between 0 and 10° C. The resulting mixture was stirred at 0° C. for 1 h. The reaction mixture was filtered, and the filter cake was washed with EtOAc (200 mL). The filtrate was quenched with sat. NazS2O3 aq. (200 mL) and extracted with EtOAc (200 mL×2). The combined organic phases were washed with brine (800 mL), dried over anhydrous $Na_2SO_4$, filtered and concentrated under reduced pressure. The residue was triturated with petroleum ether (500 mL) at 25° C. for 10 min and filtered. The filter cake was washed with petroleum ether (100 mL), dried under reduced pressure to give the title compound (19.8 g, 74% yield) as a black brown solid. JH NMR (400 MHz, Dimethylsulfoxide-$d_6$) δ 12.51 (br s, 1H), 7.05-6.77 (m, 2H), 3.57 (s, 2H). $^{19}$F NMR (376 MHz, Dimethylsulfoxide-$d_6$) δ −139.27, −139.32, −163.80, −163.86.

Step 4: 2-(2-Bromo-3,4-difluoro-S-(methoxy-$d_3$) phenyl) acetic acid

To a solution of 2-(3,4-difluoro-5-(methoxy-$d_3$)phenyl) acetic acid (18 g, 87.7 mmol) in acetic acid (80 mL) was added Brz (6 mL, 116 mmol) at 0° C. The mixture was stirred at 20° C. for 3 h. The reaction mixture was quenched with water (160 mL) and sat. NazS2O3 aq. (15 mL) at 25° C. The precipitate was filtered, and the filter cake was washed with water (100 mL) and dried under reduced pressure to give the title compound (18 g, 66% yield, confirmed by 2D-NMR) as an off-white solid. $^1$H NMR (400 MHZ, Dimethylsulfoxide-$d_6$) δ 12.57 (br s, 1H), 7.21-7.17 (m, 1H), 3.74 (s, 2H). $^{19}$F NMR (376 MHz, Dimethylsulfoxide-$d_6$) δ −129.18, −129.24, −158.38, −158.43.

Step 5: 5-(2-(2-Bromo-3,4-difluoro-5-(methoxy-$d_3$) phenyl)-1-hydroxyethylidene)-2,2-dimethyl-1,3-dioxane-4,6-dione To a solution of 2-(2-bromo-3,4-difluoro-5-(methoxy-$d_3$) phenyl) acetic acid (18 g, 63.4 mmol) in ACN (180 mL) were added 2,2-dimethyl-1,3-dioxane-4,6-dione (10 g, 69.7 mmol), DMAP (774 mg, 6.34 mmol) and DIPEA (24 mL, 139 mmol). Then/-BuCOCl (7.80 mL, 63.4 mmol) was added dropwise at 0° C. under $N_2$. The mixture was stirred at 20° C. for 3 h under $N_2$. The reaction mixture was quenched with HCl (200 mL, IN in water) at 0° C. The precipitate was filtered, and the filter cake was washed with water (50 mL) and dried under reduced pressure to give the title compound (21.3 g, 80% yield) as a white solid. MS: m/z=409.9 $[M-H]^-$. $^1$H NMR (400 MHz, Chloroform-d) δ

15.50 (br s, 1H), 6.79-6.72 (m, 1H), 4.58 (s, 2H), 1.77 (s, 6H). $^{19}$F NMR. (376 MHz, Chloroform-d) δ −125.87, ~125.93, −155.82, −155,87.

Step 6: tert-Butyl 4-(2-bromo-3,4-difluoro-5-(methoxy-$d_3$)phenyl)-3-oxobutanoate A mixture of 5-(2-(2-bromo-3,4-difluoro-5-(methoxy-$d_3$) phenyl)-1-hydroxyethylidene)-2,2-dimethyl-1,3-dioxane-4,6-dione (21.3 g, 43.1 mmol) in t-BuOH (500 mL) was degassed and purged with $N_2$ three times. The mixture was stirred at 90° C. for 2 h under $N_2$ atmosphere. The reaction mixture was concentrated to give the title compound (18 g, crude) as a brown solid, which was used in the next step without further purification. MS: m/z=380.0, 382.0 [M−H]$^-$.

Step 7: 4-(2-Bromo-3,4-difluoro-5-(methoxy-$d_3$) phenyl)-3-oxobutanoic acid

To a solution of tert-butyl 4-(2-bromo-3,4-difluoro-5-(methoxy-$d_3$)phenyl)-3-oxobutanoate (18 g, 41.4 mmol) in $CH_2Cl_2$ (50 mL) was added TFA (66.0 mL, 888 mmol). The mixture was stirred at 25° C. for 0.5 h. The reaction mixture was concentrated under reduced pressure to give the title compound (18 g, crude) as a black brown solid, which was used in the next step without further purification. MS: m/z=279.7 [M-COOH].

Step 8: 5-Bromo-6,7-difluoro-8-(methoxy-$d_3$) naphthalene-1,3-diol

A solution of 4-(2-bromo-3,4-difluoro-5-(methoxy-$d_3$) phenyl)-3-oxobutanoic acid (18 g, 55.2 mmol) in trifluoromethanesulfonic acid (150 mL) was stirred at 20° C. for 16 h. The reaction mixture was poured into ice water (200 mL) slowly. The precipitate was filtered, and the filter cake was washed with water (50 ml×3), sat. $NaHCO_3$ aq. (50 mL), water (50 ml) in sequence, dried under reduced pressure to give the title compound (12 g, 65% yield over 3 steps) as a black brown solid. MS: m/z=307.8 [M−H]$^-$. $^1$H NMR (400 MHZ, Dimethylsulfoxide-$d_6$) & 10.12 (s, 1H), 10.03 (s, 1H), 6.91 (d, J=2 Hz, 1H), 6.55 (d, J=2 Hz, 1H). $^{19}$F NMR (376 MHZ, Dimethylsulfoxide-$d_6$) δ −124.36, −124.42, −160.23, −160.29.

Step 9: 6,7-Difluoro-8-(methoxy-$d_3$) naphthalene-1,3-diol

To a solution of 5-bromo-6,7-difluoro-8-(methoxy-$d_3$) naphthalene-1,3-diol (12 g, 38.9 mmol) in MeOH (120 mL) was added Pd/C(4.15 g, 3.89 mmol, 10% purity) under $N_2$. The mixture was degassed, purged with Hz three times, and stirred at 25° C. for 2 h under Hz atmosphere (15 psi). The mixture was filtered, washed with MeOH (100 mL), and concentrated. The residue was purified by silica gel flash chromatography (eluent: 0~20% of EtO Ac in petroleum ether) to give the title compound (7.6 g, 77% yield) as a white solid. MS: m/z=227.9 [M−H]$^-$. $^1$H NMR (400 MHz, Dimethylsulfoxide-$d_6$) δ 9.71 (s, 2H), 7.39-7.32 (m, 1H), 6.59 (d, J=2 Hz, 1H), 6.46 (d,.J=1.6 Hz, 1H). $^{19}$F NMR (376 MHz, Dimethylsulfoxide-$d_6$) δ −137.25, −137.30, −162.73, −162.79.

Step 10: 6,7-Difluoro-8-(methoxy-$d_3$) naphthalene-1,3-diyl bis(trifluoromethanesulfonate)

To a solution of 6,7-difluoro-8-(trideuteriomethoxy) naphthalene-1,3-diol (7.6 g, 33.16 mmol) and DIPEA (35 mL, 199 mmol) in $CH_2Cl_2$ (140 mL) was added dropwise Tf2O (22 mL, 133 mmol) at 0° C. under $N_2$. The mixture was stirred at 0° C. for 1 h under $N_2$ atmosphere. The reaction mixture was quenched with $H_2O$ (140 mL) and extracted with $CH_2Cl_2$ (140 mL×3). The combined organic layers were washed with brine (280 mL), dried over $Na_2SO_4$, filtered and concentrated under reduced pressure. The residue was purified by silica gel flash chromatography (eluent: 0~4% of $CH_2Cl_2$ in petroleum ether) to give the title compound (14.9 g, 91% yield) as a yellow solid. MS: m/z=491.7 [M−H]$^-$. $^1$H NMR (400 MHZ, Dimethylsulfoxide-$d_6$) δ 8.39 (d,.J=2.4 Hz, 1H), 8.13-8.06 (m, 1H), 8.01 (d, J=1.6 Hz, 1H). $^{19}$F NMR (376 MHz, Dimethylsulfoxide-$d_6$)$_6$-72.45, −72.95, −130.51, −130.56, −149.54, −149.60.

Step 11: 3-((Diphenylmethylene)amino)-6,7-difluoro-8-(methoxy-$d_3$) naphthalen-1-yl trifluoromethanesulfonate A solution of 6,7-difluoro-8-(methoxy-d'3) naphthalene-1,3-diyl bis(trifluoromethanesulfonate) (9.3 g, 18.9 mmol), diphenylmethanimine (3.16 mL, 18.9 mmol), $Cs_2CO_3$ (18.4 g, 56.56 mmol) and XantPhosPdG3 (900 mg, 0.95 mmol) in 1,4-dioxane (180 mL) was degassed and purged with $N_2$ three times, and then the mixture was stirred at 80° C. under $N_2$ for 2 h. The reaction mixture was concentrated under reduced pressure. The residue was purified by silica gel flash chromatography (cluent: 0~4% of EtOAc in petroleum ether) to give the title compound (4 g, 70% yield) as a yellow oil. MS: m/z=525.1 [M+H]$^+$. $^1$H NMR (400 MHZ, Dimethylsulfoxide-$d_6$) δ 7.77-7.63 (m, 4H), 7.63-7.47 (m, 4H), 7.35 (d, J=2.0 Hz, 1H), 7.33-7.31 (m, 2H), 7.22-7.19 (m, 1H), 7.09 (s, 1H). $^{19}$F NMR (376 MHz, Dimethylsulfoxide-$d_6$) δ −73.20, −133.44, −133.49, −154.47, −154.52.

Step 12: N-(6,7-difluoro-5-(methoxy-$d_3$)-4-(4,4,5,5-tetramethyl-1,3,2-dioxaborolan-2-yl) naphthalen-2-yl)-1,1-diphenylmethanimine A solution of 3-((diphenylmethylene)amino)-6,7-difluoro-8-(methoxy-$d_3$) naphthalen-1-yl trifluoromethanesulfonate (4 g, 7.63 mmol), 4,4,4',4',5,5,5',5'-octamethyl-2,2'-bi (1,3,2-dioxaborolane) (2.32 g, 9.15 mmol), AcOK (2.25 g, 22.9 mmol), and Cy3PPdG3 (496 mg, 763 μmol) in DMA (50 mL) was degassed and purged with $N_2$ three times, and then the mixture was stirred at 100° C. under $N_2$ for 1 h. The reaction mixture was diluted with $H_2O$ (150 mL) and extracted with EtOAc (50 mL×3). The combined organic layers were washed with brine (75 mL), dried over anhydrous $Na_2SO_4$, filtered and concentrated under reduced pressure to give the title compound (8 g, crude) as a black brown oil, which was used into the next step without further purification. MS: m/z=502.9 [M+H].

Step 13: 6,7-Difluoro-5-(methoxy-$d_3$)-4-(4,4,5,5-tetramethyl-1,3,2-dioxaborolan-2-yl) naphthalen-2-amine To a solution of N-(6,7-difluoro-5-(methoxy-$d_3$)-4-(4,4,5,5-tetramethyl-1,3,2-dioxaborolan-2-yl) naphthalen-2-yl)-1,1-diphenylmetbanimine (18 g, 16.1 mmol) in EtOH (135 mL) were added hydroxylamine hydrochloride (2.24 g, 32.3 mmol) and AcOK (4.75 g, 48.4 mmol). The mixture was stirred at 25° C. for 0.5 h. The reaction mixture was concentrated. The residue was purified by silica gel flash chromatography (eluent: 0~20% of EtOAc in petroleum ether) to give the title compound (Intermediate 63, 4.4 g, 76% yield over 2 steps) as a yellow solid. MS: m/z=338.8 $[M+H]^+$. $^1H$ NMR (400 MHZ, Dimethylsulfoxide-$d_6$) δ 7.27-7.19 (m, 1H), 6.90 (d, J=1.6 Hz, 1H), 6.76 (d, J=2 Hz, 1H), 5.51 (s, 2H), 1.34 (s, 12H). $^{19}F$ NMR (376 MHZ, Dimethylsulfoxide-$d_6$) δ −138.12, −138.18, −163.21, −163.26.

Intermediate 64: 6,7,8-Trifluoro-4-(4,4,5,5-tetramethyl-1,3,2-dioxaborolan-2-yl)-5-((triisopropylsilyl)ethynyl)naphthalen-2-amine

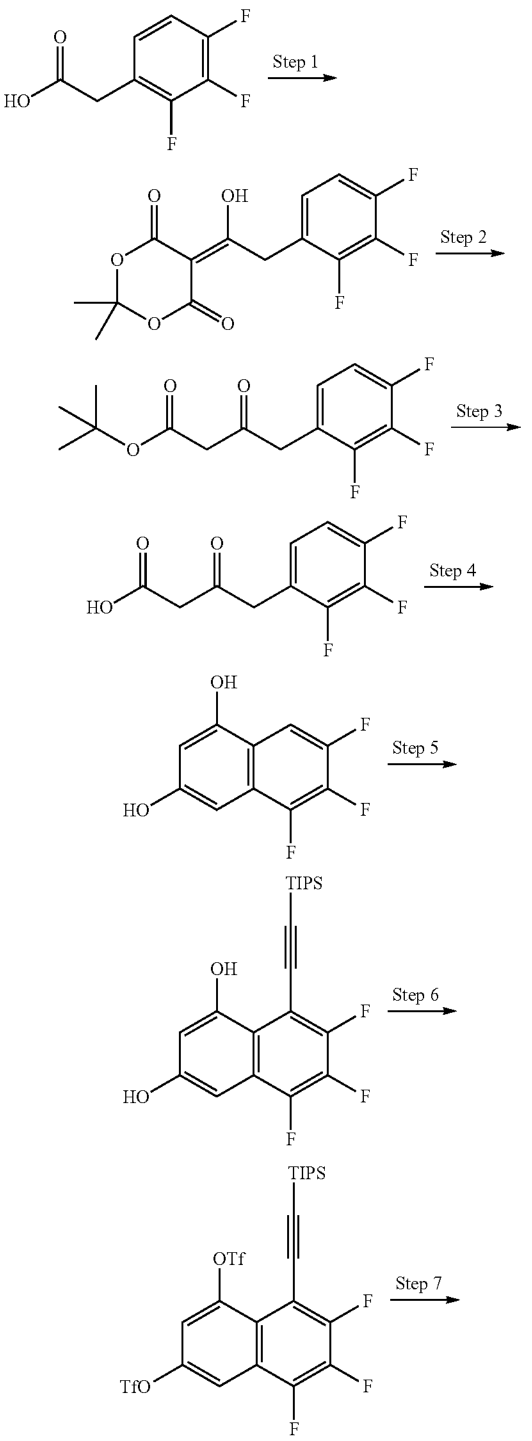

-continued

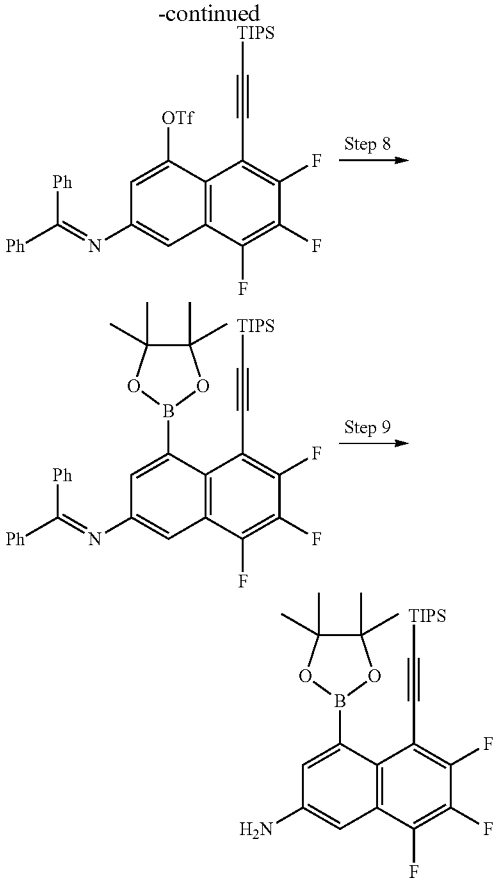

Intermediate 64

Step 1: 5-(1-Hydroxy-2-(2,3,4-trifluorophenyl)ethylidene)-2,2-dimethyl-1,3-dioxane-4,6-dione To a solution of 2-(2,3,4-trifluorophenyl) acetic acid (25 g, 131.50 mmol) in ACN (250 mL) were added 2,2-dimethyl-1,3-dioxane-4,6-dione (20.9 g, 145 mmol), DMAP (1.61 g, 13.2 mmol) and DIPEA (50.4 mL, 289 mmol). Then/-BuCOCl (16.2 mL, 132 mmol) was added dropwise at 0° C. The mixture was stirred at 20° C. for 1 h. IN HCl (800 mL) was added dropwise to the mixture until a lot of solid appeared. Then the precipitate was filtered, washed with water (800 mL) and dried under reduced pressure to give the title compound (38 g, 91% yield) as an off-white solid, which was used in the next step without further purification. 1H NMR (400 MHz, Chloroform-d) δ 15.51 (s, 1H), 7.10-6.87 (m, 2H), 4.49 (s, 2H), 1.76 (s, 6H). $^{19}F$ NMR (376 MHz, Chloroform-d) δ −134.69, −136.10, −159.75, −159.81.

Step 2: ter-Butyl 3-oxo-4-(2,3,4-trifluorophenyl) butanoate

A mixture of 5-(1-hydroxy-2-(2,3,4-trifluorophenyl)ethylidene)-2,2-dimethyl-1,3-dioxane-4,6-dione (38 g, 120 mmol) in t-BuOH (350 mL) and toluene (50 mL) was stirred at 90° C. for 1 h. The reaction mixture was concentrated to dryness to give the title compound (28 g, 59% yield) as a yellow oil, which was used into the next step without further purification. $^1H$ NMR (400 MHz, Chloroform-d) δ 7.04-6.80

(m, 2H), 3.92-3.70 (m, 2H), 3.45 (s, 2H), 1.47 (d, J=3.2, 9H). $^{19}$F. NMR (376 MHz, Chloroform-d) δ −135.23, −135.28, −136.85, −160.11, −160.16.

Step 3: 3-Oxo-4-(2,3,4-trifluorophenyl) butanoic acid

To a solution of tert-butyl 3-oxo-4-(2,3,4-trifluorophenyl) butanoate (28 g, 97.1 mmol) in $CH_2Cl_2$ (150 mL) was added TFA (144 mL, 1.94 mol). The mixture was stirred at 20° C. for 1 h. The reaction mixture was concentrated under reduced pressure to give the title compound (22 g, 80% yield) as a light yellow solid, which was used in the next step without further purification. $^1$H NMR (400 MHZ, Dimethylsulfoxide-d$_6$) δ 7.35-7.22 (m, 1H), 7.16-7.05 (m, 1H), 4.02 (d, J=4.8, 2H), 3.62 (s, 2H). $^{19}$F NMR (376 MHz, Dimethylsulfoxide-d$_6$) δ −136.99, −137.06, −137.48, −137.52, −162.37, −162.43.

Step 4: 5,6,7-Trifluoronaphthalene-1,3-diol

A mixture of 3-oxo-4-(2,3,4-trifluorophenyl) butanoic acid (21 g, 90.5 mmol) in $CF_3SO_3H$ (168 mL) was stirred at 100° C. for 0.5 h. The reaction mixture was cooled to 0° C., and slowly poured into ice-water (500 mL). The precipitate was filtered and washed with water (200 mL) to give the title compound (17.2 g, 89% yield) as a light yellow solid, which was used in the next step without further purification. $^1$H NMR (400 MHZ, Dimethylsulfoxide-d$_6$) δ 10.66 (br s, 1H), 7.73-7.56 (m, 1H), 6.71-6.57 (m, 2H). $^{19}$F NMR (376 MHz, Dimethylsulfoxide-d$_6$) δ −142.75, −146.83, −146.89, −162.67, −162.72.

Step 5: 5,6,7-Trifluoro-8-((triisopropylsilyl) ethynyl) naphthalene-1,3-diol

A mixture of 5,6,7-trifluoronaphthalene-1,3-diol (16.2 g, 75.65 mmol), (bromoethynyl)triisopropylsilane (21.74 g, 83.22 mmol), KOAc (14.85 g, 151.30 mmol) and dichloro (p-cymene) ruthenium (II) dimer (4.63 g, 7.57 mmol) in 1,4-dioxane (160 mL) was degassed, purged with $N_2$ three times, and stirred at 110° C. for 2 h under $N_2$ atmosphere. The reaction mixture was concentrated under reduced pressure. The residue was purified by silica gel flash chromatography (eluent: 0~10% of EtOAc in petroleum ether) to give the title compound (17.5 g, 56% yield) as a black brown solid. MS: m/z=393.0 [M−H]$^-$. JH NMR (400 MHz, Dimethylsulfoxide-d$_6$) 10.56 (s, 1H), 10.11 (s, 1H), 6.72-6.55 (m, 2H), 1.16-1.06 (m, 21H). $^{19}$F NMR (376 MHz, Dimethylsulfoxide-d$_6$) δ −136.05, −143.53, −143.60, −161.90, −161.97.

Step 6: 5,6,7-Trifluoro-8-((triisopropylsilyl) ethynyl) naphthalene-1,3-diyl bis(trifluoromethanesulfonate)

To a solution of 5,6,7-trifluoro-8-((triisopropylsilyl) ethynyl) naphthalene-1,3-diol (17.5 g, 44.36 mmol) in $CH_2Cl_2$ (200 mL) were added DIPEA (38.6 mL, 221.80 mmol) and THO (21.96 mL, 133.08 mmol) at 0° C. under $N_2$. The mixture was stirred at 0° C. for 1 h under $N_2$. The reaction mixture was quenched with $H_2O$ (500 mL) and extracted with $CH_2Cl$ (600 mL×3). The combined organic layers were washed with brine (600 mL), dried over anhydrous $Na_2SO_4$, filtered and concentrated under reduced pressure. The residue was purified by silica gel flash chromatography (eluent: 0~1% of EtOAc in petroleum ether) to give the title compound (19.5 g, 67% yield) as a yellow oil. MS: m/z=657.0 [M−H]$^-$. $^1$H NMR (400 MHz, Chloroform-d) δ 8.02 (d, J=2.4 Hz, 1H), 7.58-7.48 (m, 1H), 1.17-1.14 (m, 21H). $^{19}$F NMR (376 MHz, Chloroform-d) δ −70.96, −72.30, −119.11, −119.20, −138.20, −153.71, −153.82.

Step 7: 3-((Diphenylmethylene)amino)-5,6,7-trifluoro-8-((triisopropylsilyl) ethynyl) naphthalen-1-yl trifluoromethanesulfonate A solution of 3-((diphenylmethylene)amino)-5,6,7-trifluoro-8-((triisopropylsilyl) ethynyl) naphthalen-1-yl trifluoromethanesulfonate (19.5 g, 29.6 mmol), diphenylmethanimine (5.9 g, 32.6 mmol), $Cs_2CO_3$ (28.9 g, 88.8 mmol) and XantPhosPdG3 (2.81 g, 2.96 mmol) in 1,4-dioxane (200 mL) was degassed, purged with $N_2$ three times, and stirred at 80° C. for 1 h under $N_2$. The reaction mixture was concentrated under reduced pressure. The residue was purified by silica gel flash chromatography (eluent: 0~2% of EtOAc in petroleum ether) to give the title compound (12 g, 59% yield) as a yellow solid. MS: m/z=690.5 [M+H]$^+$. $^1$H NMR (400 MHZ, Chloroform-d)δ 7.79-7.75 (m, 2H), 7.60-7.40 (m, 3H), 7.34-7.27 (m, 4H), 7.18-7.08 (m, 3H), 1.24-1.09 (m, 21H). $^{19}$F. NMR (376 MHz, Chloroform-d) δ −71.24, −71.31, −124.77, −124.86, −140.84, −157.70, −157.76, −157.82.

Step 8: 1,1-Diphenyl-N-(6,7,8-trifluoro-4-(4,4,5,5-tetramethyl-1,3,2-dioxaborolan-2-yl)-5-((triisopropylsilyl) ethynyl) naphthalen-2-yl) methanimine A solution of 3-((diphenylmethylene)amino)-5,6,7-trifluoro-8-((triisopropylsilyl) ethynyl) naphthalen-1-yl trifluoromethanesulfonate (310 mg, 449 μmol), 4,4,4',4',5,5,5',5'-octamethyl-2,2'-bi (1,3,2-dioxaborolane) (285 mg, 1.12 mmol), KOAc (132 mg, 1.35 mmol) and Pd (dppf)$Cl_2$ (37 mg, 44.9 μmol) in tolune (3 mL) was degassed, purged with $N_2$ three times, and stirred at 120° C. for 1 h under $N_2$. The reaction mixture was concentrated under reduced pressure to give the title compound (300 mg, crude) as a yellow oil.

Step 9: 6,7,8-Trifluoro-4-(4,4,5,5-tetramethyl-1,3,2-dioxaborolan-2-yl)-5-((triisopropylsilyl) ethynyl) naphthalen-2-amine To a solution of 1,1-diphenyl-N-(6,7,8-trifluoro-4-(4,4,5,5-tetramethyl-1,3,2-dioxaborolan-2-yl)-5-((triisopropylsilyl) ethynyl) naphthalen-2-yl) methanimine (300 mg, 449 μmol) in EtOH (3 mL) were added NaOAc (55 mg, 674 μmol) and $NH_2OH$ HCl (37 mg, 539 μmol). The mixture was stirred at 20° C. for 2 h. The reaction mixture was concentrated under reduced pressure. The residue was purified by silica gel flash chromatography (eluent: 0~20% of EtOAc in petroleum ether) to give the title compound (Intermediate 64, 100 mg, 42% yield over 2 steps) as a yellow solid. MS: m/z=504.1 [M+H]$^+$. $^1$H NMR (400 MHZ, Dimethylsulfoxide-d$_6$) δ 7.25 (d, J=2.0 Hz, 1H), 6.94 (d, J=2.0 Hz, 1H), 5.93 (s, 2H), 1.33 (s, 12H), 1.12-1.07 (m, 21H). IF NMR (376 MHz, Dimethylsulfoxide-d$_6$) δ −135.37, −135.45, −145.08, −162.32, −163.37.

Intermediate 65: 6,7-Difluoro-5-(fluoromethoxy-$d_2$)-4-(4,4,5,5-tetramethyl-1,3,2-dioxaborolan-2-yl)naphthalen-2-amine

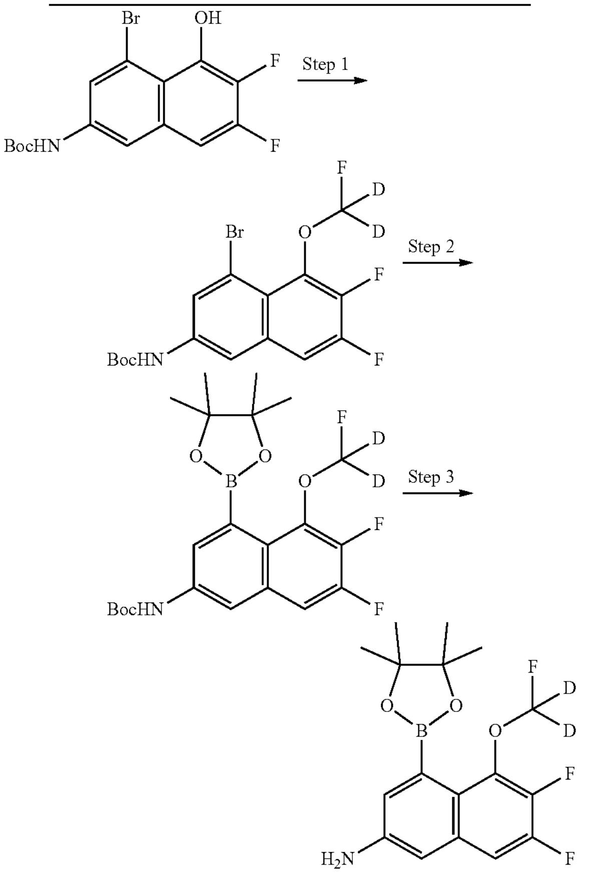

Intermediate 65

Step 1: tert-Butyl (4-bromo-6,7-difluoro-5-(fluoromethoxy-$d_2$) naphthalen-2-yl) carbamate To a mixture of tert-butyl (4-bromo-6,7-difluoro-5-hydroxynaphthalen-2-yl) carbamate (1.04 g, 2.77 mmol, refer to Intermediate 62 for detail procedures) in DMF (20 mL) were added $K_2CO_3$ (697 mg, 5.04 mmol) and fluoromethyl-$d_2$ 4-methylbenzenesulfonate (520 mg, 2.52 mmol). The mixture was stirred at 80° C. for 2 h under $N_2$. The reaction mixture was diluted with water (500 mL) and extracted with EtOAc (200 mL×3). The combined organic layers were washed with brine (300 mL×2), dried over anhydrous $Na_2SO_4$, filtered and concentrated under reduced pressure. The residue was purified by silica gel flash chromatography (eluent: 0~10% of EtOAc in petroleum ether) to give the title compound (900 mg, 79% yield) as a white solid. MS: m/z=307.9 [M+H-Boc]$^+$. $^1$H NMR (400 MHz, Dimethylsulfoxide-$d_6$) δ 9.81 (s, 1H), 8.18-7.93 (m, 2H), 7.87-7.47 (m, 1H), 1.50 (s, 9H). $^{19}$F NMR (376 MHz, Dimethylsulfoxide-$d_6$) δ −134.64, −152.11, −152.17, −152.54, −152.55.

Step 2: ter-Butyl (6,7-difluoro-5-(fluoromethoxy-2)-4-(4,4,5,5-tetramethyl-1,3,2-dioxaborolan-2-yl) naphthalen-2-yl) carbamate To a mixture of ter-butyl (4-bromo-6,7-difluoro-5-(fluoromethoxy-$d_2$) naphthalen-2-yl) carbamate (290 mg, 710 μmol) in 1,4-dioxane (10 mL) were added K3PO4 (452 mg, 2.13 mmol), 4,4,4',4',5,5,5',5'-octamethyl-2,2'-bi (1,3,2-dioxaborolane) (216 mg, 852 μmol) and Cy3PPdGs (46 mg, 71 μmol). The mixture was stirred at 100° C. for 16 h under $N_2$. The reaction mixture was concentrated under reduced pressure. The residue was purified by silica gel flash chromatography (eluent: 0~4% of EtOAc in petroleum ether) to the title compound (160 mg, 67% yield) as a white solid. MS: m/z=478.2 [M+Na]. 3H NMR (400 MHZ, Dimethylsulfoxide-$d_6$) δ 9.64 (s, 1H), 8.17 (br s, 1H), 7.79-7.69 (m, 1H), 7.55 (s, 1H), 1.49 (s, 9H), 1.35 (s, 12H). $^{19}$F NMR (376 MHz, Dimethylsulfoxide-$d_6$) δ −136.38, −136.43, −149.69, −149.72, −157.49, −157.54.

Step 3: 6,7-Difluoro-5-(fluoromethoxy-$d_2$)-4-(4,4,5,5-tetramethyl-1,3,2-dioxaborolan-2-yl) naphthalen-2-amine To a solution of tert-butyl (6,7-difluoro-5-(fluoromethoxy-$d_2$)-4-(4,4,5,5-tetramethyl-1,3,2-dioxaborolan-2-yl) naphthalen-2-yl) carbamate (160 mg, 351 μmol) in HCl (10 mL, 2M in EtOAc). The mixture was stirred at 25° C. for 2 h. The reaction mixture was concentrated under reduced pressure to give the title compound (Intermediate 65, 124 mg, crude) as a white solid, which was used into the next step without further purification. MS: m/z=356.2 [M+H].

Intermediate 66: 2-(7-Fluoro-8-(fluoromethoxy-$d_2$)napthalen-1-yl)-4,4,5,5-tetramethyl-1,3,2-dioxaborolane

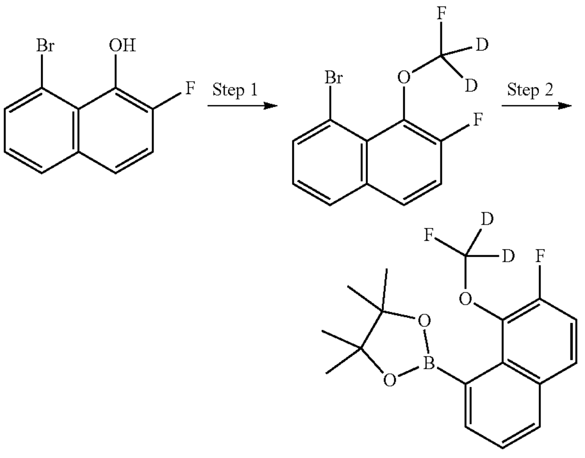

Intermediate 66

Step 1: 8-Bromo-2-fluoro-1-(fluoromethoxy-dz) naphthalene

To a mixture of 8-bromo-2-fluoronaphthalen-1-ol (500 mg, 2.07 mmol, refer to Intermediate 46 for detail procedures) in DMF (10 mL) were added $K_2CO_3$ (573 mg, 4.15 mmol) and fluoromethyl-$d_2$ 4-methylbenzenesulfonate (385 mg, 1.87 mmol). The mixture was stirred at 80° C. for 2 h under $N_2$. The reaction mixture was diluted with water (80 mL) and extracted with EtOAc (80 mL×3). The combined organic layers were washed with brine (100 mL×2), dried over anhydrous $Na_2SO_4$, filtered and concentrated under reduced pressure. The residue was purified by silica gel flash chromatography (eluent: 0~1% of EtOAc in petroleum ether) to give the title compound (560 mg, 98% yield) as a white solid. $^{1}H$ NMR (400 MHZ, Dimethylsulfoxide-$d_6$) δ 8.06 (d, J=8.4 Hz, 1H), 8.01-7.92 (m, 2H), 7.67 (t, J=9.2 Hz, 1H), 7.41 (t, J=7.6 Hz, 1H). $^{19}F$ NMR (376 MHz, Dimethylsulfoxide-$d_6$) δ −126.85, −126.89, −152.93, −152.95.

Step 2: 2-(7-Fluoro-8-(fluoromethoxy-$d_2$) naphthalen-1-yl)-4,4,5,5-tetramethyl-1,3,2-dioxaborolane A mixture of 8-bromo-2-fluoro-1-(fluoromethoxy-$d_2$) naphthalene (500 mg, 1.82 mmol), 4,4,4',4',5,5,5',5'-octamethyl-2,2'-bi (1,3,2-dioxaborolane) (508 mg, 2.00 mmol), KOAc (535 mg, 5.45 mmol) and CysPPdG3 (118 mg, 182 μmol) in 1,4-dioxane (5 mL) was degassed, purged with $N_2$ three times, and stirred at 100° C. for 1 h under $N_2$ atmosphere. The reaction mixture was concentrated under reduced pressure. The residue was purified by silica gel flash chromatography (eluent: 0~2% of EtOAc in Petroleum ether) to give the title compound (Intermediate 66, 350 mg, 60% yield) as a white solid. $^{1}$HNMR (400 MHz, Dimethylsulfoxide-$d_6$) δ 8.03-7.97 (m, 1H), 7.89-7.81 (m, 1H), 7.61-7.49 (m, 3H), 1.36 (s, 12H). $^{19}$F. NMR (376 MHz, Dimethylsulfoxide-$d_6$) δ −132.07, −132.13, −150.04.

Intermediate 67: 2-(7-Fluoro-8-(fluoromethoxy)napthalen-1-yl)-4,4,5,5-tetramethyl-1,3,2-dioxaborolane

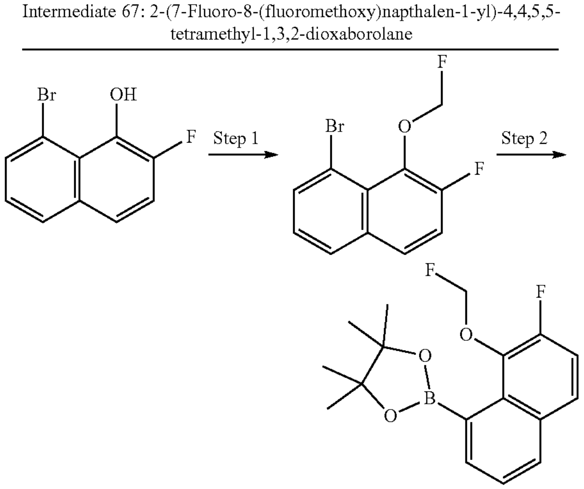

Intermediate 67

Step 1: 8-Bromo-2-fluoro-1-(fluoromethoxy) naphthalene

To a mixture of 8-bromo-2-fluoronaphthalen-1-ol (1 g, 4.15 mmol) and Cs2$CO_3$ (3.38 g, 10.4 mmol) in ACN (10 mL) was added bromo (fluoro) methane (1.40 g, 12.4 mmol) at 0° C. under $N_2$. The mixture was stirred at 0° C. for 1h $N_2$ atmosphere. The reaction mixture was diluted with water (50 mL) and extracted with EtOAc (50 mL×3). The combined organic layers were washed with brine (50 mL×2), dried over anhydrous $Na_2SO_4$, filtered and concentrated under reduced pressure to give the title compound (1.1 g, 97% yield) as a black solid. $^{1}$HNMR (400 MHz, Dimethylsulfoxide-$d_6$) δ 8.05 (d, J=8.0 Hz, 1H), 8.00-7.92 (m, 2H), 7.66 (t, J=9.6 Hz, 1H), 7.41 (t, J=8.0 Hz, 1H), 5.90-5.72 (d, J=53.6 Hz, 2H), $^{19}F$ NMR (376 MHZ, Dimethylsulfoxide-$d_6$) δ −126.82, −126.86, −151.63, −151.68.

Step 2: 2-(7-Fluoro-8-(fluoromethoxy) naphthalen-1-yl)-4,4,5,5-tetramethyl-1,3,2-dioxaborolane A mixture of 8-bromo-2-fluoro-1-(fluoromethoxy) naphthalene (1 g, 3.66 mmol), 4,4,4',4',5,5,5',5'-octamethyl-2,2'-bi (1,3,2-dioxaborolane) (1.02 g, 4.03 mmol), $K_3PO_4$ (2.33 g, 11.0 mmol) and $Cy_3PPdG_3$ (269 mg, 366 μmol) in 1,4-dioxane (10 mL) was degassed, purged with $N_2$ three times, and stirred at 100° C. for 1 h under $N_2$ atmosphere. The reaction mixture was concentrated under reduced pressure. The residue was purified by silica gel flash chromatography (eluent: 0~2% of EtOAc in petroleum ether) to give the title compound (Intermediate 67, 388 mg, 30% yield) as a yellow solid. $^{1}$HNMR (400 MHZ, Dimethylsulfoxide-$d_6$) δ 8.04-7.96 (m, 1H), 7.89-7.82 (m, 1H), 7.62-7.50 (m, 3H), 5.92-5.72 (d, J=53.6 Hz, 2H), 1.36 (s, 12H). $^{19}F$ NMR (376 MHz, Dimethylsulfoxide-$d_6$) δ −132.00, −132.03, −148.73, −148.77.

Intermediate 68: 7-Bromo-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidine

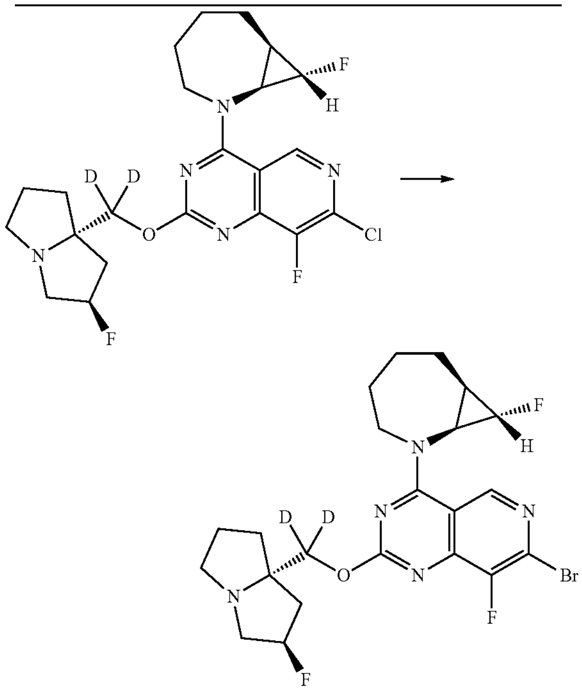

Intermediate 68

To a solution of 7-chloro-8-fluoro-4-((1S,7R,8S)-8-fluoro-2-azabicyclo[5.1.0]octan-2-yl)-2-(((2R,7aS)-2-fluorotetrahydro-1/-pyrrolizin-7a (5H)-yl) methoxy-$d_2$)pyrido[4,3-d]pyrimidine (200 mg, 426 μmol, refer to Example 16 for detail procedures) in MeCN (100 mL) was added TMSBr (326 mg, 2.1 mmol) at 25° C. The mixture was stirred at 80° C. for 12 hr. The mixture was added to saturated $NaHCO_3$ (200 mL) and extracted with $CH_2Cl_2$ (100 mL×2). The combined organic layers was dried over $Na_2SO_4$, filtered and concentrated under reduced pressure. After purification by silica gel flash chromatography (Eluent of 0~6% MeOH in CH: $Cl_2$), the title compound (Intermediate 68, 200 mg, yield: 90%) was obtained as a yellow solid. MS: m/z=514.0, 516.0 $[M+H]^+$. $^{1}H$ NMR (400 MHZ, Dimethylsulfoxide-$d_6$) δ 9.14 (s, 1H), 5.39-5.15 (m, 1H), 4.68-4.49 (m, 1H), 4.37 (d, J=13.2 Hz, 1H), 4.06-3.95 (m, 1H), 3.12-2.98 (m, 3H), 2.87-2.78 (m, 1H), 2.26-2.19 (m, 1H), 2.14-2.09 (m, 1H), 2.06-1.93 (m, 3H), 1.90-1.70 (m, 6H), 1.68-1.62 (m, 1H), 1.52-1.42 (m, 1H), 1.10-0.97 (m, 1H). $^{19}F$ NMR (400 MHZ, Dimethylsulfoxide-$d_6$) δ −130.33, −132.27, −172.15.

Intermediate 69: 5-Chloro-6-fluoro-4-(trimethylstannyl)isoquinoline

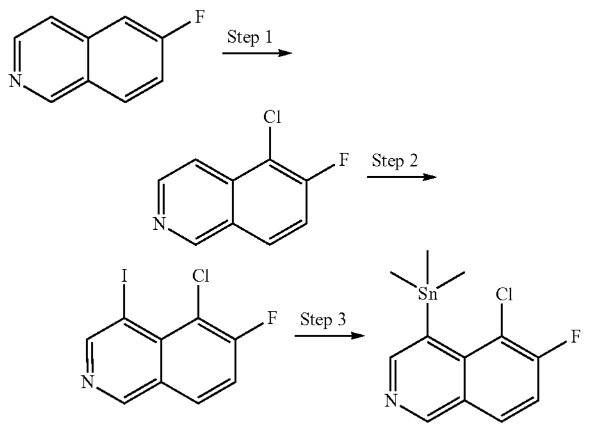

Intermediate 69

Step 1: 5-Chloro-6-fluoroisoquinoline

To a solution of 6-fluoroisoquinoline (5 g, 33.9 mmol) in $H_2SO_4$ (50 mL) was added NCS (9.0 g, 67.9 mmol) at 0° C. The mixture was stirred at 25° C. for 16 hr. Then the mixture was stirred at 80° C. for another 24 hr. The reaction mixture was poured into ice and neutralized with saturated $NaHCO_3$ (pH about 8) and extracted with EtOAc (500 mL×2). The combined organic layers were washed with brine (500 mL×2), dried over $Na_2SO_4$, filtered and concentrated under reduced pressure. After purification by silica gel flash chromatography (Eluent of 0~15% EtOAc in petroleum ether), the title compound (4.3 g, yield: 47%) was obtained as a light yellow solid. MS: m/z=181.9 $[M+H]^+$. $^1H$ NMR (400 MHZ, Chloroform-d) δ 9.27 (s, 1H), 8.67 (d, J=5.6 Hz, 1H), 8.04 (d, J=5.6 Hz, 1H), 7.96 (dd, J=9.2, 5.2 Hz, 1H), 7.48 (t, J=8.8 Hz, 1H). $^{19}F$ NMR (400 MHZ, Chloroform-d) δ −106.43.

Step 2: 5-Chloro-6-fluoro-4-iodoisoquinoline

To a solution of 5-chloro-6-fluoroisoquinoline (4.3 g, 23.7 mmol) in ACN (40 mL) were added 12 (9.0 g, 35.5 mmol) and TBHP (18.2 mL, 189 mmol, 70% purity in $H_2O$). The mixture was stirred at 80° C. for 16 hr under $N_2$ atmosphere. The reaction mixture was diluted with $H_2O$ (300 mL) and extracted with EtOAc (300 mL×2). The combined organic layers were washed with brine (300 mL), dried over $Na_2SO_4$, filtered and concentrated under reduced pressure. After purification by silica gel flash chromatography (Eluent of 0~9% EtOAc in petroleum ether) and triturated with petroleum ether: EtOAc=10: 1 at 25° C. for 10 min, the title compound (1.38 g, yield: 17%) was obtained as an off-white solid. MS: m/z=307.7 $[M+H]^+$. JH NMR (400 MHZ, Chloroform-d) δ 9.18 (s, 1H), 9.12 (s, 1H), 7.93 (dd, J=8.8, 5.6 Hz, 1H), 7.53 (t, J=8.8 Hz, 1H). $^{19}F$. NMR (400 MHZ, Chloroform-d) δ −98.67.

Step 3: 5-Chloro-6-fluoro-4-(trimethylstannyl) isoquinoline

To a solution of 5-chloro-6-fluoro-4-iodoisoquinoline (1.38 g, 4.49 mmol) in toluene (20 mL) were added SnzMes (5.3 mL, 25.8 mmol) and Pd $(PPh_3)_4$ (519 mg, 449 μmol). The mixture was stirred at 100° C. for 20 hr under $N_2$ atmosphere. The reaction mixture was quenched with KF (10 mL) at 25° C., diluted with $H_2O$ (100 mL), and extracted with EtOAc (100 mL×3). The combined organic layers were washed with brine (100 mL), dried over $Na_2SO_4$, filtered and concentrated under reduced pressure. After purification by silica gel flash chromatography (Eluent of 0~10% EtOAc in petroleum ether) and reversed-phase HPLC(40% ACN in $H_2O$), the title compound (Intermediate 69, 400 mg, yield: 25%) was obtained as an off-white solid. MS: m/z=345.8 $[M+H]^+$. $^1H$ NMR (400 MHZ, Chloroform-d) δ 9.19 (s, 1H), 8.72 (s, 1H), 7.97-7.91 (m, 1H), 7.52-7.45 (m, 1H), 0.53-0.45 (m, 9H). $^{19}F$. NMR (400 MHZ, Chloroform-d) δ −104.13.

Intermediate 70: 6,7-Difluoro-5-methoxy-4-(trimethylstannyl)isoquinoline

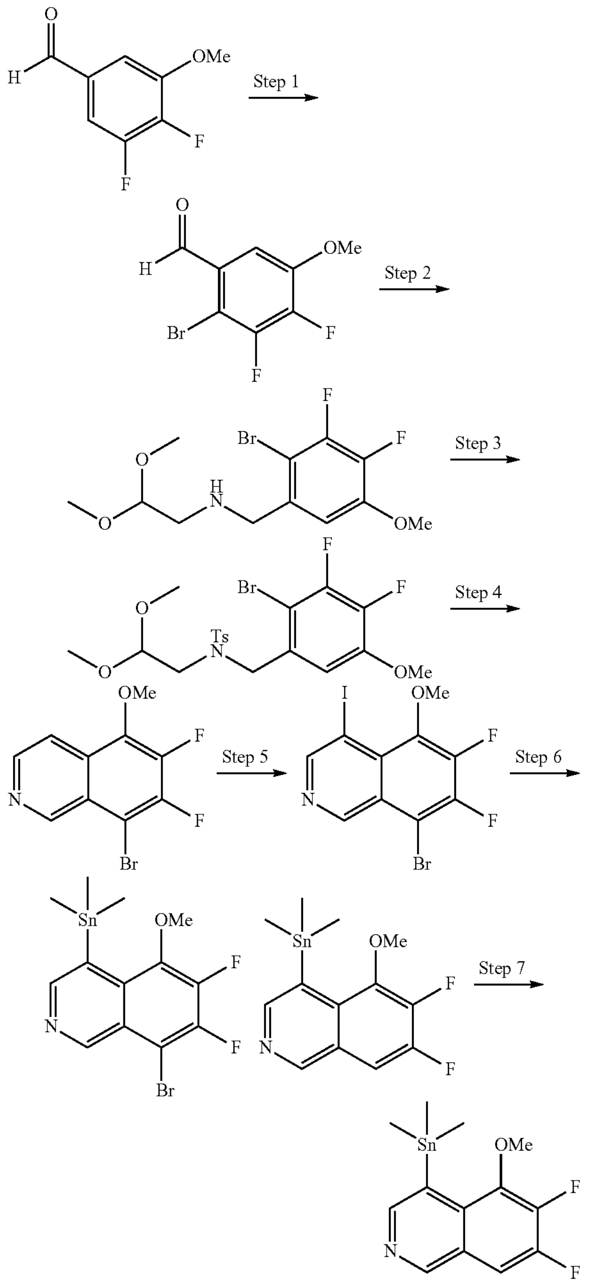

Intermediate 70

Step 1:
2-Bromo-3,4-difluoro-5-methoxybenzaldehyde

To a solution of 3,4-difluoro-5-methoxy-benzaldehyde (12.9 g, 74.9 mmol) in $H_2O$ (135 mL) were added KBr (44.6 g, 375 mmol) and Brz (225 mmol, 11.6 mL). The mixture was stirred at 25° C. for 48 hr. The mixture was filtered, and the wet cake was washed with $H_2O$ (100 mL×3). Then the wet cake was concentrated to give the title compound (17.9 g, yield: 95%) as a white solid. $^1$H NMR (400 MHz, Chloroform-d) δ 10.27 (s, 1H), 7.39 (dd, J=8.0, 2.0 Hz, 1H), 3.97 (s, 3H). $^{19}$F. NMR (400 MHz, Chloroform-d) δ −127.555, −127.608, −144.810, −144.862.

Step 2: N-(2-Bromo-3,4-difluoro-5-methoxybenzyl)-2,2-dimethoxyethan-1-amine

To a solution of 2-bromo-3,4-difluoro-5-methoxybenzaldehyde (2.0 g, 7.97 mmol) and 2,2-dimethoxyethanamine (1.0 g, 9.56 mmol) in $CH_2Cl_2$ (50 mL) was added NaBH$(OAc)_3$ (5.0 g, 23.9 mmol) at 0° C. The mixture was stirred at 25° C. for 16 hr under $N_2$ atmosphere. The reaction mixture was quenched with saturated NaHCOs (100 mL) at 0° C. and extracted with EtOAc (100 mL×2). The combined organic layers were washed with brine (100 mL), dried over $Na_2SO_4$, filtered and concentrated under reduced pressure. After purification by silica gel flash chromatography (Eluent of 0~8% MeOH in $CH_2Cl_2$), the title compound (2.6 g, yield: 95%) was obtained as a white solid. MS: m/z=339.9, 341.9 $[M+H]^+$. $^1$H NMR (400 MHZ, Chloroform-d)δ 6.93 (dd, J=8.0, 2.0 Hz, 1H), 4.49 (t, J=5.6 Hz, 1H), 3.91 (s, 3H), 3.85 (s, 2H), 3.38 (s, 6H), 2.75 (d,)=5.6 Hz, 2H). $^{19}$F NMR (400 MHz, Chloroform-d) δ −127.495, −127.548, −157.321, −157.381.

Step 3: N-(2-Bromo-3,4-difluoro-5-methoxybenzyl)-N-(2,2-dimethoxyethyl)-4-methylbenzenesulfonamide To a solution of N-(2-bromo-3,4-difluoro-5-methoxybenzyl)-2,2-dimethoxyethan-1-amine (2.2 g, 6.47 mmol) in $CH_2Cl_2$ (25 mL) were added Py (1.6 mL, 19.4 mmol) and TsCl (1.5 g, 7.76 mmol). The mixture was stirred at 25° C. for 16 hr. The reaction mixture was diluted with $H_2O$ (50 mL) and extracted with $CH_2Cl_2$ (50 mL×2). The combined organic layers were washed with brine (50 mL), dried over $Na_2SO_4$, filtered and concentrated under reduced pressure. After purification by silica gel flash chromatography (Eluent of 0~2% MeOH in $CH_2Cl_2$), the title compound (2.6 g, yield: 95%) was obtained as a white solid. MS: m/z=516.0, 517.9 $[M+Na]^+$. $^1$H NMR (400 MHz, Chloroform-d) δ 7.72 (d, J=8.4 Hz, 2H), 7.33 (d, J=8.4 Hz, 2H), 7.02 (dd, J=8.0, 2.0 Hz, 1H), 4.47 (s, 2H), 4.37 (t, J=5.6 Hz, 1H), 3.86 (s, 3H), 3.28 (d, J=5.6 Hz, 2H), 3.24 (s, 6H), 2.44 (s, 3H). $^{19}$F NMR (400 MHZ, Chloroform-d) δ −127.803, −127.856, −156.781, −156.841.

Step 4:
8-Bromo-6,7-difluoro-5-methoxyisoquinoline

To N-(2-bromo-3,4-difluoro-5-methoxybenzyl)-2,2-dimethoxyethanamine (20 g, 40.5 mmol) was added ClSO3H (10 mL) at 0° C. The mixture was stirred at 90° C. for 10 min. The reaction mixture was poured into ice and neutralized with $NaHCO_3$, and extracted with EtOAc (100 mL×2). The combined organic layers were washed with brine (100 mL), dried over $Na_2SO_4$, filtered and concentrated under reduced pressure. After purification by silica gel flash chromatography (Eluent of 0~30% EtOAc in petroleum ether), the title compound (6 g, yield: 52%) was obtained as a white solid. MS: m/z=273.9, 275.8 $[M+H]^+$. $^1$H NMR (400 MHZ, Chloroform-d)δ 9.51 (s, 1H), 8.62 (d, J=5.6 Hz, 1H), 7.93 (d, J=5.6 Hz, 1H), 4.23 (d, J=3.6 Hz, 3H). $^{19}$F. NMR (400 MHz, Chloroform-d) δ −122.497, −122.549, −148.007, −148.060.

Step 5:
8-Bromo-6,7-difluoro-4-iodo-5-methoxyisoquinoline

To a solution of 8-bromo-6,7-difluoro-5-methoxyisoquinoline (1.5 g, 5.47 mmol) and $I_2$ (1.7 g, 6.57 mmol) in ACN (15 mL) was added TBHP (6.00 mL, 43.8 mmol, 70% purity in $H_2O$). The mixture was stirred at 90° C. for 16 hr. The reaction mixture was diluted with $H_2O$ (50 mL) and extracted with EtOAc (50 mL×2). The combined organic layers were washed with brine (50 mL), dried over $Na_2SO_4$, filtered, and concentrated under reduced pressure. After purification by silica gel flash chromatography (Eluent of 0~10% EtOAc in petroleum ether), the title compound (1.6 g, yield: 71%) was obtained as a white solid. MS: m/z=399.7, 401.7 $[M+H]^+$. $^1$H NMR (400 MHZ, Chloroform-d)δ 9.48 (s, 1H), 9.07 (s, 1H), 4.11 (d, J=3.6 Hz, 3H). $^{19}$F NMR (400 MHZ, Chloroform-d) δ −119.713, −119.773, −142.513, −142.573.

Step 6: 8-Bromo-6,7-difluoro-5-methoxy-4-(trimethylstannyl) isoquinoline

A mixture of 8-bromo-6,7-difluoro-4-iodo-5-methoxyisoquinoline (1.0 g, 2.50 mmol), Sn2Me6 (2.2 mL, 10.5 mmol) and Pd $(PPh_3)_4$ (289 mg, 250 μmol) in 1,4-dioxane (10 mL) was degassed, purged with $N_2$ three times, and stirred at 90° C. for 30 hr under Na atmosphere. The reaction mixture was quenched with saturated KF (20 mL) at 25° C., diluted with $H_2O$ (50 mL), and extracted with $CH_2Cl_2$ (50 mL×3). The combined organic layers were washed with brine (50 mL), dried over $Na_2SO_4$, filtered and concentrated under reduced pressure. After purification by silica gel flash chromatography (Eluent of 0~8% EtOAc in petroleum ether), the title compound (200 mg, yield: 16%) was obtained as a white solid and 6,7-difluoro-5-methoxy-4-(trimethylstannyl) isoquinolinewas (25 mg, yield: 2%) was obtained as a white solid. MS: m/z=437.9 $[M+H]^+$. $^1$H NMR (400 MHZ, Chloroform-d)δ 9.56 (s, 1H), 8.58 (s, 1H), 4.35-4.31 (m, 3H), 0.50-0.37 (m, 9H).

Step 7: 6,7-Difluoro-5-methoxy-4-(trimethylstannyl) isoquinoline

To a solution of 8-bromo-6,7-difluoro-5-methoxy-4-(trimethylstannyl) isoquinoline (120 mg, 275 μmol) in THF (1.5 mL) was degassed and purged with $N_2$ three times, and then the mixture was stirred at −40° C. for 5 min under $N_2$ atmosphere. Then i-PrMgCl (2 M, 412 μL) was added dropwise at −40° C. The resulting mixture was stirred at −40° C. for 30 min. The reaction mixture was quenched with 1 M HCl (5 mL) at 0° C. and extracted with EtOAc (10 mL×2). The combined organic layers were washed with brine (20 mL), dried over $Na_2SO_4$, filtered and concentrated under reduced pressure. After purification by silica gel flash chromatography (Eluent of 0~30% EtOAc in petroleum ether), the title compound (Intermediate 70, 68 mg, yield: 58%) was obtained as a white solid. MS: m/z=359.8

$[M+H]^+$. $^1H$ NMR (400 MHZ, Chloroform-d) § 9.12 (s, 1H), 8.50 (s, 1H), 7.41 (dd, J=9.2, 7.2 Hz, 1H), 4.31 (d, J=5.6 Hz, 3H), 0.47-0.33 (m, 9H).

Intermediate 71: 6,7-Difluoro-4-(4,4,5,5-tetramethyl-1,3,2-dioxaborolan-2-yl)-5-((triisopropylsilyl)ethynyl)naphthalen-2-amine

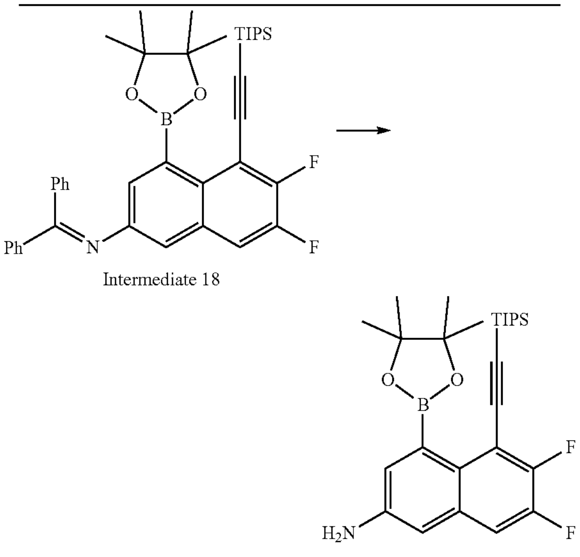
Intermediate 18
Intermediate 71

To a solution of Intermediate 18 (4,300 g, crude) in EtOH (15 L) at room temperature were added NaOAc (1,085.87 g, 13,236.878 mmol) and $NH_2OH.HCl$ (919.83 g, 13,236.878 mmol) at room temperature. The resulting mixture was stirred for 8 h at room temperature. Additional NaOAc (1,085.87 g, 13,236.878 mmol) and $NH_2OH.HCl$ (919.83 g, 13,236.878 mmol) were added at room temperature. The resulting mixture was stirred for additional 16 h at room temperature. The resulting mixture was diluted with MTBE (15 L). The resulting mixture was washed with of brine (30 L). The aqueous layer was extracted with MTBE (1x2 L). The combined organic layers were dried over anhydrous $Na_2SO_4$, filtered and concentrated under reduced pressure. The residue was purified by silica gel flash chromatography, eluted with PE/EA (5: 1) to afford the title compound (Intermediate 71, 560 g, 52.8%) as a yellow solid. MS: m/z=527.3 $[M+H]^+$. 1H-NMR: (400 MHz, DMSO-$d_6$) δ 7.64 (dd, J=11.8, 8.3 Hz, 1H), 7.19 (d, J=2.3 Hz, 1H), 6.85 (d, J=2.3 Hz, 1H), 5.66 (s, 2H), 1.33 (s, 12H), 1.10 (d, J=4.4 Hz, 21H). $^{19}F$-NMR: (400 MHz, DMSO-$d_6$)$_6$-136.79 (d, J=23.5 Hz), —139.06 (d, J=23.5 Hz).

Intermediate 72 &73: (1R,7S)-2-(7-Chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-5-oxa-2-azabicyclo[5.1.0]octane & (1S,7R)-2-(7-chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-5-oxa-2-azabicyclo[5.1.0]octane

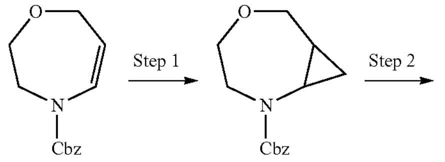

Intermediate 2

-continued

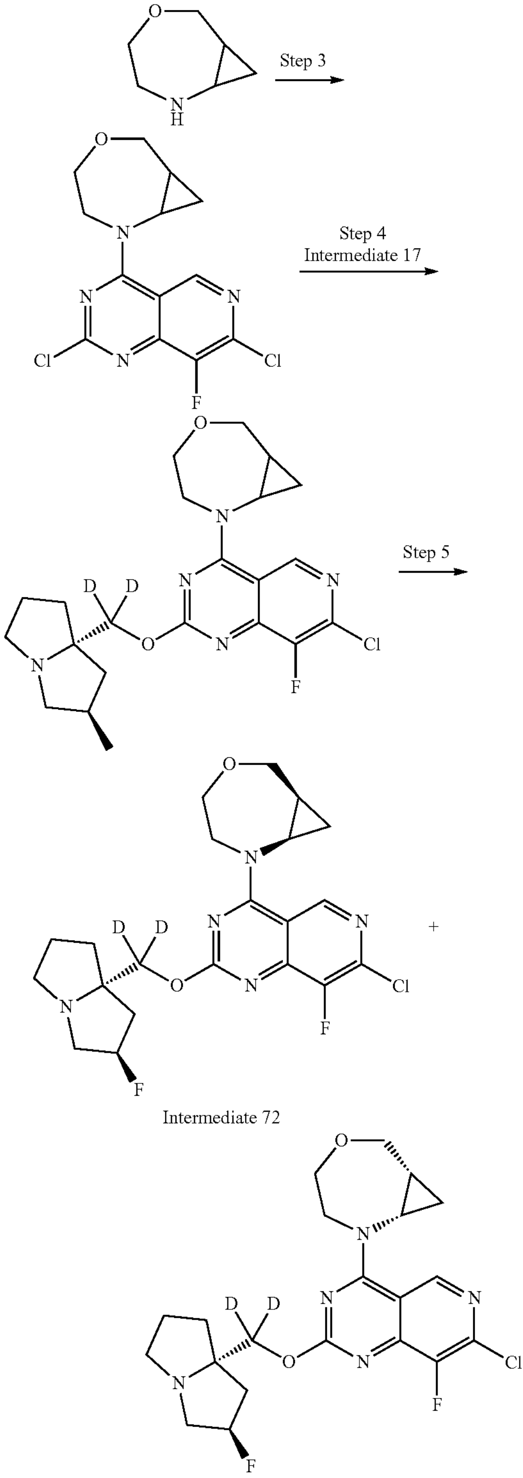

Intermediate 72
Intermediate 73

Step 1: Benzyl 5-oxa-2-azabicyclo[5.1.0]octane-2-carboxylate

To a solution of Intermediate 2 (16 g, 68.59 mmol) in DCM (160 mL) under nitrogen atmosphere was added $ZnEt_2$ (171.48 mL, 171.48 mmol, 1 M in n-hexane) at room temperature. After stirring at room temperature for 0.5 hours, a solution of $CH_2I_2$ (73.48 g, 274.36 mmol) in DCM (20 mL) was added to the above mixture dropwise with an ice bath. The ice bath was removed, and the reaction was stirred at room temperature for 12 hours. The resulting mixture was poured into cold saturated aq. $NH_4Cl$ (300 mL) and extracted with DCM (3×300 mL). The combined organic layers were washed with brine (300 mL), dried with anhydrous $Na_2SO_4$, filtered and concentrated under reduced pressure. The residue was purified by silica gel flash chromatography, eluted with 42% EA in PE to afford the title compound (12.3 g, 72% yield) as a yellow oil. $^1$H NMR (400 MHZ, Chloroform-d)δ 7.38-7.29 (m, 5H), 5.21-5.11 (m, 2H), 4.43-4.39 (m, 1H), 4.13-3.72 (m, 2H), 3.52-3.46 (m, 1H), 3.33-3.26 (m, 1H), 3.10-3.04 (m, 1H), 3.52-3.46 (m, 1H), 1.48-1.38 (m, 1H), 1.20-0.88 (m, 2H).

Step 2: 5-oxa-2-azabicyclo[5.1.0]octane

To an ice-cooled solution of benzyl 5-oxa-2-azabicyclo[5.1.0]octane-2-carboxylate (5 g, 20.21 mmol) in MeOH (250 mL) was added Pd/C(1.67 g, 10% wt) under nitrogen atmosphere. The reaction mixture was stirred in an ice bath for 40 min under hydrogen atmosphere. The resulting mixture filtered and concentrated under reduced pressure to afford the title compound (2.0 g, crude used through) as a light-yellow oil.

Step 3: 2-(2,7-Dichloro-8-fluoropyrido[4,3-d]pyrimidin-4-yl)-5-oxa-2-azabicyclo[5.1.0]octane To a solution of 2,4,7-trichloro-8-fluoropyrido[4,3-d]pyrimidine (4.46 g, 17.674 mmol) and 5-oxa-2-azabicyclo[5.1.0]octane (2.0 g, crude) in DCM (40 mL) under nitrogen atmosphere was added DIEA (6.85 g, 53.022 mmol) dropwise at −40° C. The reaction mixture was stirred at −40° C. for 1 hour. The resulting mixture was diluted with 10% aq. citric acid (100 mL) and extracted with DCM (3×100 mL). The combined organic layers were washed with brine (100 mL), dried over anhydrous $Na_2SO_4$, filtered and concentrated under reduced pressure to afford the title compound (4 g, crude used through) as a light yellow solid. MS: m/z=329.10, 331.10 $[M+H]^{+\cdot}$ Step 4: 2-(7-Chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-S-oxa-2-azabicyclo[5.1.0]octane To a solution of 2-(2,7-dichloro-8-fluoropyrido[4,3-d]pyrimidin-4-yl)-5-oxa-2-azabicyclo[5.1.0]octane (4 g, crude) in DMSO (40 mL) under nitrogen atmosphere were added KF (2.47 g, 42.52 mmol) and Intermediate 17 (3.13 g, 19.44 mmol) at room temperature. The reaction mixture was heated at 100° C. for 16 hours. The resulting mixture was cooled to room temperature, diluted with water (100 mL) and extracted with DCM (3×100 mL). The combined organic layers were washed with brine (3×100 mL), dried over anhydrous $Na_2SO_4$, filtered and concentrated under reduced pressure. The residue was purified by silica gel flash chromatography, eluted with $CH_2Cl$/MeOH (10: 1) to afford the title compound (750 mg, 9.3% yield for three steps) as a light yellow solid. MS: m/z=454.20 $[M+H]^{+\cdot}$ Step 5: (1R,7S)-2-(7-Chloro-8-fluoro-2-(((2R,7aS)-2-fluorotetrahydro-1H-pyrrolizin-7a (5/I)-yl) methoxy-$d_2$)pyrido[4,3-d]pyrimidin-4-yl)-5-oxa-2-azabicyclo[5.1.0]octane & (1S,7R)-2-(7-chloro-8-fluoro-2-(((2R,7aS)-2-fluorotetrahydro-1H-pyrrolizin-7a (5H)-yl) methoxy-$d_2$)pyrido[4,3-d]pyrimidin-4-yl)-5-oxa-2-azabicyclo[5.1.0]octane 2-(7-Chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-5-oxa-2-azabicyclo[5.1.0]octane (900 mg, 1.98 mmol) was separated by Prep-SFC with the following conditions: Column: OptiChiral-$C_9$-5 3×25 cm, 5 μm; Mobile Phase A: $CO_2$, Mobile Phase B: IPA (0.1% DEA); Flow rate: 100 mL/min; Gradient: isocratic 30% B; Back Pressure (bar): 100; Detector: UV 220 nm; RT1: 7.9 min; RT2: 11.3 min; Sample Solvent: MEOH; Injection Volume: 1.2 mL. The first eluting peak (RT1: 7.9 min) was concentrated and lyophilized to give the title compound (Intermediate 72, 320 mg, 35% yield) as a light yellow solid. MS: m/z=454.15 $[M+H]^+$. The second eluting peak (RT2: 11.3 min) was concentrated and lyophilized to give the title compound (Intermediate 73, 310 mg, 34% yield) as a light yellow solid. MS: m/z=454.20 [M+H].

Intermediate 74: 6,7,8-Trifluoro-5-(methoxy-$d_3$)-4-(4,4,5,5-tetramethyl-1,3,2-dioxaborolan-2-yl)naphthalen-2-amine

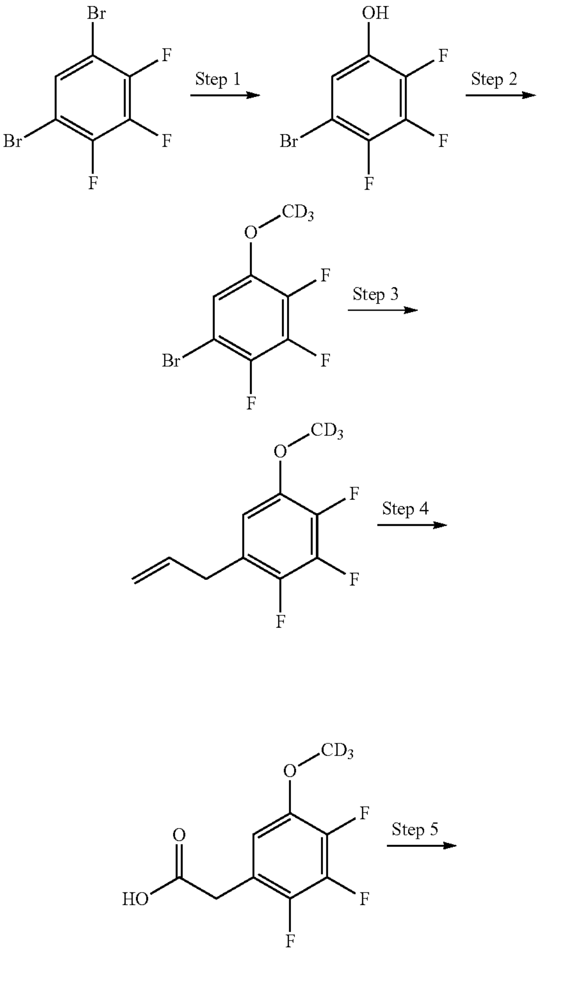

-continued

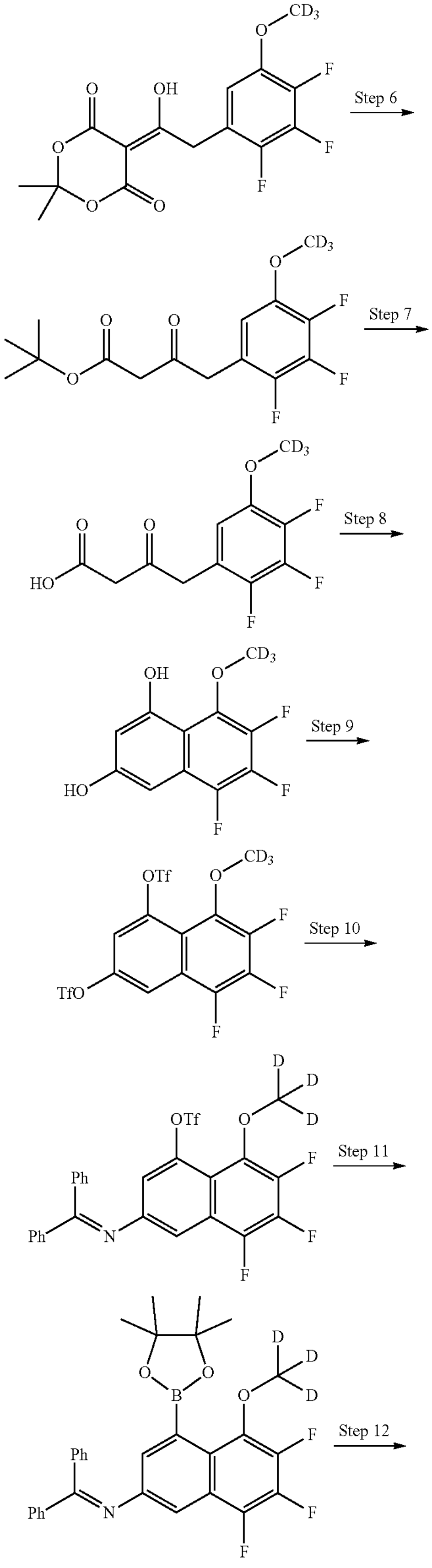

-continued

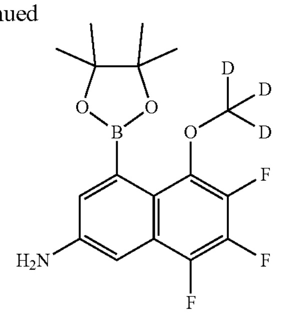

Intermediate 74

Step 1: 5-Bromo-2,3,4-trifluorophenol

To a solution of 1,5-dibromo-2,3,4-trifluoro-benzene (80 g, 276 mmol) in THE (2.7 L) was added dropwise i-PrMgCl (152 mL, 2 M in THF) at −20° C. under $N_2$, and the reaction mixture was warmed to 0° C. and stirred for 0.5 h under $N_2$. Trimethyl borate (34.4 g, 331.2 mmol) in THF (200 mL) was added dropwise at 0° C. under $N_2$, then the mixture was warmed to 20° C. and stirred for 1 h under $N_2$. The solution was cooled to −20° C., and peracetic acid (177 g, 372.6 mmol, 16% purity) in THF (400 mL) was added dropwise. The solution was stirred for 0.5 h at 20° C. under $N_2$. The reaction mixture was quenched with sat. $NH_4Cl$ (1 L) aq. and sat. $Na_2SO_3$ aq. (1 L) in sequence at 20° C. The mixture was then diluted with $H_2O$ (2 L) and extracted with EtOAc (2 L×3). The combined organic layers were washed with brine (1.6 L), dried over anhydrous $Na_2SO_4$, filtered and concentrated under reduced pressure. The residue was purified by silica gel flash chromatography (eluent: 0~5% of EtOAc in petroleum ether) to give the title compound (42 g, 56% yield) as a yellow oil. $^1H$ NMR (400 MHZ, Chloroform-d)δ 7.07-6.96 (m, 1H), 5.75 (br s, 1H). $^{19}F$. NMR (376 MHz, Chloroform-d) δ −136.76, −136.82, −155.27, −158.39.

Step 2: 1-Bromo-2,3,4-trifluoro-5-(methoxy-$d_3$) benzene

To a solution of 5-bromo-2,3,4-trifluorophenol (10 g, 44.1 mmol) in DMF (80 mL) was added $K_2CO_3$ (18.3 g, 132 mmol). Then trideuterio (iodo) methane (2.95 mL, 48.5 mmol) in DMF (20 mL) was added dropwise to the mixture at 0° C. under $N_2$. The mixture was stirred at 0° C. for 2 h under $N_2$. The mixture was diluted with $H_2O$ (500 mL) and extracted with EtOAc (500 mL×3). The combined organic layers were washed with brine (300 mL×2), dried over anhydrous $Na_2SO_4$ and concentrated under reduced pressure. The residue was purified by silica gel flash chromatography (eluent: 0~5% of EtOAc in petroleum ether) to give the title compound (9.8 g, 91% yield) as a colorless oil. $^1H$ NMR (400 MHZ, Dimethylsulfoxide-$d_6$)δ 7.48-7.38 (m, 1H). $^{19}F$. NMR (376 MHz, Dimethylsulfoxide-$d_6$) δ −138.15, −138.21, −155.58, −155.61, −156.48-156.53, −156.55, −156.60.

Step 3: 1-Allyl-2,3,4-trifluoro-5-(methoxy-$d_3$)benzene

A mixture of 1-bromo-2,3,4-trifluoro-5-(methoxy-$d_3$)benzene (30 g, 123 mmol), 2-allyl-4,4,5,5-tetramethyl-1,3,2-dioxaborolane (41.3 g, 246 mmol), $Cs_2CO_3$ (80.1 g, 246 mmol) and Pd $(PPh_3)_4$ (14.2 g, 12.3 mmol) in 1,4-dioxane (300 mL) and $H_2O$ (60 mL) was degassed, purged with $N_2$ three times, and stirred at 90° C. for 3 h under $N_2$. The mixture was diluted with $H_2O$ (500 mL) and extracted with EtOAc (300 mL×3). The combined organic layers were washed with brine (300 mL), dried over anhydrous $Na_2SO_4$ and concentrated under reduced pressure. The residue was purified by silica gel flash chromatography (eluent: 0~1% of EtOAc in petroleum ether) to give the title compound (24 g, 95% yield) as a colorless oil. $^1H$ NMR (400 MHZ, Chloroform-d) δ 6.58-6.46 (m, 1H), 5.97-5.82 (m, 1H), 5.19-5.05 (m, 2H), 3.37 (d, J=6.8 Hz, 2H). $^{19}F$ NMR (376 MHz, Chloroform-d) δ −149.08, −149.13, −158.06, −158.97, −159.02.

Step 4: 2-(2,3,4-Trifluoro-5~(methoxy-$d_3$)phenyl) acetic acid

To a solution of 1-allyl-2,3,4-trifluoro-5-(methoxy-$d_3$) benzene (6.0 g, 29.2 mmol) in ACN (100 mL) and $H_2O$ (100 mL) was added RuCl (606 mg, 2.92 mmol) at 0° C. Then $NaIO_4$ (32 g, 146 mmol) was added slowly over 1 h, and the reaction temperature was maintained at 0~10° C. The resulting mixture was stirred at 0° C. for 1 h. The reaction mixture was filtered, and the filter cake was washed with EtOAc (200 mL). The filtrate was quenched with sat. NazSzO3 aq. (200 mL) and extracted with EtOAc (200 mL×2). The combined organic phases were washed with brine (800 mL), dried over anhydrous $Na_2SO_4$, filtered and concentrated under reduced pressure. The residue was purified by silica gel flash chromatography (eluent: 0~2% of MeOH in $CH_2Cl_2$) to give the title compound (6.2 g, 86% yield) as a yellow oil. $^1H$ NMR (400 MHZ, Dimethylsulfoxide-$d_6$) δ 12.63 (br s, 1H), 7.10-7.00 (m, 1H), 3.69-3.65 (m, 2H). IF NMR (376 MHz, Dimethylsulfoxide-$d_6$) δ −143.32, −157.96, −158.01, −160.64, −160.70, −160.76.

Step 5: 5-(1-Hydroxy-2-(2,3,4-trifluoro-5-(methoxy-$d_3$)phenyl)ethylidene)-2,2-dimethyl-1,3-dioxane-4,6-dione To a solution of 2-(2,3,4-trifluoro-5-(methoxy-$d_3$)phenyl) acetic acid (6.2 g, 27.8 mmol) in ACN (30 mL) were added 2,2-dimethyl-1,3-dioxane-4,6-dione (4.4 g, 30.6 mmol), DMAP (340 mg, 2.78 mmol) and DIPEA (11 mL, 61.2 mmol). Then/-BuCOCl (3.42 mL, 27.8 mmol) was added dropwise at 0° C. under $N_2$. The mixture was stirred at 20° C. for 3 h under $N_2$. The reaction mixture was quenched with HCl aq. (200 mL, IN in water) at 0° C. The precipitate was filtered, and the filter cake was washed with water (100 mL), dried under reduced pressure to give the title compound (9.2 g, 88% yield) as a yellow solid. MS: m/z=347.9 $[M-H]^-$. $^1H$ NMR (400 MHz, Dimethylsulfoxide-$d_6$) δ 7.03-6.97 (m, 1H), 4.40 (s, 2H), 1.67 (s, 6H). $^{19}F$ NMR (376 MHz, Dimethylsulfoxide-$d_6$) δ −147.80, −147.86, −157.82, −160.64, −160.70.

Step 6: tert-Butyl 3-oxo-4-(2,3,4-trifluoro-5-(methoxy-$d_3$)phenyl) butanoate

A mixture of 5-(1-hydroxy-2-(2,3,4-trifluoro-5-(methoxy-$d_3$)phenyl)ethylidene)-2,2-dimethyl-1,3-dioxane-4,6-dione (9.2 g, 26.3 mmol) in t-BuOH (100 mL) was degassed, purged with $N_2$ three times, and stirred at 90° C. for 2 h under $N_2$ atmosphere. The reaction mixture was concentrated under reduced pressure to give the title compound (8.2 g, crude) as a yellow oil, which was used in the next step without further purification. MS: m/z=320.1 $[M-H]^-$. 1H NMR (400 MHz, Chloroform-d) δ 6.59-6.44 (m, 1H), 3.85 (s, 2H), 3.45 (s, 2H), 1.48 (s, 9H). $^{19}F$ NMR (376 MHz, Chloroform-d) δ −147.16, −147.22, −155.63, −155.69, −158.16, −158.21.

Step 7: 3-Oxo-4-(2,3,4-trifluoro-5-(methoxy-$d_3$) phenyl) butanoic acid

To a solution of tert-butyl 3-oxo-4-(2,3,4-trifluoro-5-(methoxy-$d_3$)phenyl) butanoate (8.0 g, 24.9 mmol) in $CH_2Cl_2$ (30 mL) was added TFA (30 mL, 404 mmol). The mixture was stirred at 20° C. for 1 h. The reaction mixture was concentrated under reduced pressure to give the title compound (6.4 g, crude) as a black brown oil, which was used in the next step without further purification. MS: m/z=220.1 [M-COOH]. $^1H$ NMR (400 MHZ, Dimethylsulfoxide-$d_6$) δ 6.99-6.89 (m, 1H), 4.00 (s, 2H), 3.62 (s, 2H). $^{19}F$ NMR (376 MHz, Dimethylsulfoxide-$d_6$) δ −147.90,-147.96, −157.72, −160.64, −160.70.

Step 8: 5,6,7-Trifluoro-8-(methoxy-$d_3$) naphthalene-1,3-diol

A solution of 3-oxo-4-(2,3,4-trifluoro-5-(methoxy-$d_3$) phenyl) butanoic acid (6.4 g, 24.2 mmol) in trifluoromethanesulfonic acid (10 mL) was stirred at 25° C. for 16 h. The reaction mixture was poured into ice water (200 mL) slowly, and the precipitate was filtered. The filter cake was washed with water (50 ml×3), sat. $NaHCO_3$ aq. (50 mL), and water (50 ml) in sequence, dried under reduced pressure to give the title compound (5.4 g, 64% yield over 3 steps) as a black brown solid. MS: m/z=246.0 $[M-H]^-$. 3H NMR (400 MHZ, Dimethylsulfoxide-$d_6$) δ 10.43-9.70 (m, 2H), 6.65 (d, J=2.4 Hz, 1H), 6.55 (d, J=2.4 Hz, 1H). $^{19}F$ NMR (376 MHZ, Dimethylsulfoxide-$d_6$) δ −152.32, −152.37, −160.81, −160.86, −161.65.

Step 9: 5,6,7-Trifluoro-8-(methoxy-d'3) naphthalene-1,3-diyl bis(trifluoromethanesulfonate)

To a solution of 5,6,7-trifluoro-8-(methoxy-$d_3$) naphthalene-1,3-diol (5.4 g, 21.9 mmol) and DIPEA (23 mL, 131 mmol) in $CH_2Cl_2$ (30 mL) was added Tf2O (15 mL, 87.4 mmol) dropwise at 0° C. under $N_2$. The mixture was stirred at 0° C. for 2 h under $N_2$. The reaction mixture was quenched with $H_2O$ (200 mL) and extracted with $CH_2Cl_2$ (300 mL×3). The combined organic layers were washed with brine (300 mL), dried over anhydrous $Na_2SO_4$, filtered and concentrated under reduced pressure. The residue was purified by silica gel flash chromatography (eluent: 0~1% of $CH_2Cl_2$ in petroleum ether) to give the title compound (8.2 g, 67% yield) as a yellow solid. MS: m/z=509.9 $[M-H]^-$. $^1H$ NMR (400 MHZ, Chloroform-d)$_{8\ 8.00}$ (d, J=1.6 Hz, 1H), 7.31 (s, 1H). $^{19}F$ NMR (376 MHz, Chloroform-d) δ −72.31, −72.77, −146.25, −146.31, −146.93,~146.99-152.12, −152.17.

Step 10: 3-((Diphenylmethylene)amino)-5,6,7-trifluoro-8-(methoxy-d'3) naphthalen-1-yl trifluoromethanesulfonate A solution of 5,6,7-trifluoro-8-(methoxy-$d_3$) naphthalene-1,3-diyl bis(trifluoromethanesulfonate) (8.0 g, 15.7 mmol), diphenylmethanimine (2.7 mL, 15.7 mmol), $Cs_2CO_3$ (15.3 g, 47.0 mmol) and XantPhosPdG$_3$ (742 mg, 0.78 mmol) in 1,4-dioxane (150 mL) was degassed, purged with $N_2$ three times, and stirred at 80° C. under $N_2$ for 2 h. The reaction mixture was concentrated under reduced pressure. The residue was purified by silica gel flash chromatography (eluent: 0~2% of EtOAc in petroleum ether) to give the title compound (5.2 g, 44% yield) as a brown oil. MS: m/z=543.2 $[M+H]^+$. $^1H$ NMR (400 MHz, Chloroform-d) δ 7.86-7.76 (m, 5H), 7.59 (s, 1H), 7.51-7.44 (m, 5H), 7.14-7.12 (m, 1H). $^{19}F$ NMR (376 MHz, Chloroform-d) δ −72.66, −73.20, −149.64,~151.60, −151.66, −156.22, −156.27.

Step 11: 1,1-Diphenyl-N-(6,7,8-trifluoro-5-(methoxy-$d_3$)-4-(4,4,5,5-tetramethyl-1,3,2-dioxaborolan-2-yl) naphthalen-2-yl) methanimine A solution of 3-((diphenylmethylene)amino)-5,6,7-trifluoro-8-(methoxy-$d_3$) naphthalen-1-yl trifluoromethanesulfonate (5 g, 9.22 mmol), 4,4,4',4',5,5,5',5'-octamethyl-2,2'-bi (1,3,2-dioxaborolane) (2.81 g, 11.1 mmol), AcOK (2.71 g, 27.7 mmol) and CysPPdG3 (600 mg, 922 μmol) in DMA (50 mL) was degassed and purged with $N_2$ three 3 times, and the mixture was stirred at 100° C. under $N_2$ for 2 h. The reaction mixture was diluted with $H_2O$ (400 mL) and extracted with EtOAc (500 mL×3). The combined organic layers were washed with brine (500 mL), dried over anhydrous $Na_2SO_4$, filtered and concentrated under reduced pressure to give the title compound (5 g, crude) as a black brown oil, which was used in the next step without further purification. MS: m/z=521.0 $[M+H]^{+\cdot}$ Step 12: 6,7,8-Trifluoro-5-(methoxy-$d_3$)-4-(4,4,5,5-tetramethyl-1,3,2-dioxaborolan-2-yl) naphthalen-2-amine To a solution of 1,1-diphenyl-N-(6,7,8-trifluoro-5-(methoxy-$d_3$)-4-(4,4,5,5-tetramethyl-1,3,2-dioxaborolan-2-yl) naphthalen-2-yl) methanimine (5.0 g, 9.61 mmol) in EtOH (10 mL) were added hydroxylamine hydrochloride (1.34 g, 19.2 mmol) and AcOK (2.83 g, 28.8 mmol). The mixture was stirred at 20° C. for 2 h. The reaction mixture was concentrated and purified by silica gel flash chromatography (eluent: 0~8% of EtOAc in petroleum ether) to give the title compound (Intermediate 74, 3.0 g, 76% yield over 2 steps, confirmed by 2D-NMR) as a brown solid. MS: m/z=356.7 $[M+H]^+$. $^1H$ NMR (400 MHz, Dimethylsulfoxide-$d_6$) δ 6.98 (d, J=1.6 Hz, 1H), 6.87 (d, J=2.0 Hz, 1H), 5.80 (s, 2H), 1.34 (s, 12H). $^{19}F$ NMR (376 MHZ, Dimethylsulfoxide-$d_6$) δ −155.94, −156.00, −162.09, −162.15, −162.28, −162.33.

Intermediate 75: 4-Bromo-8-chloro-6-fluoro-5-(methoxy-$d_3$)isoquinoline

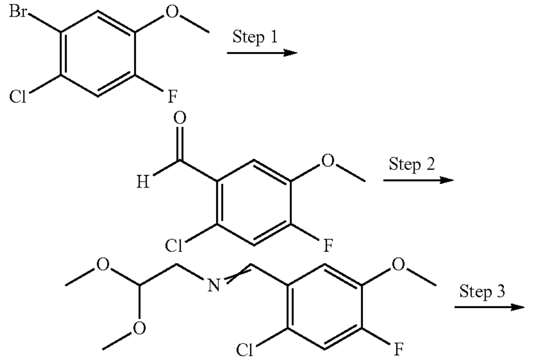

-continued

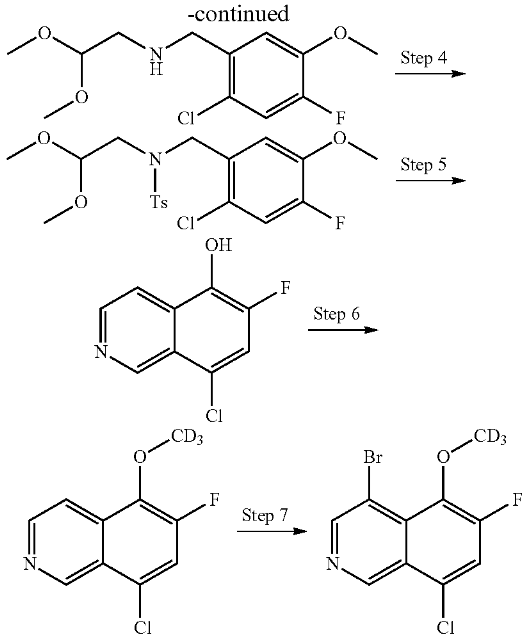

Intermediate 75

Step 1: 2-Chloro-4-fluoro-5-methoxybenzaldehyde

To an ice-cooled solution of 1-bromo-2-chloro-4-fluoro-5-methoxybenzene (13.4 g, 55.96 mmol) in THE (135 mL) under nitrogen atmosphere was added isopropylmagnesium chloride (56 mL, 111.91 mmol, 2 M in THF) dropwise for 1 hour, then followed by the addition of DMF (20.45 g, 279.79 mmol) dropwise in portions with an ice bath. The ice bath was removed, and the reaction mixture was stirred at room temperature for 1 hour. The resulting mixture was quenched with sat. aq. $NH_4Cl$ (100 mL) in an ice bath and extracted with EtOAc (3×100 mL). The combined organic layers were washed with brine (100 mL), dried over anhydrous $Na_2SO_4$, filtered and concentrated under reduced pressure. The residue was purified by silica gel flash chromatography, eluted with PE/EA (6: 1) to afford the title compound (10.9 g, 83% yield) as a light yellow solid. $^1H$ NMR (300 MHz, Chloroform-d) & 10.37 (s, 1H), 7.53-7.50 (m, 1H), 7.22-7.18 (m, 1H), 3.94 (s, 3H). $^{19}F$ NMR (282 MHz, Chloroform-d) δ −121.55 (s, 1F).

Step 2: 1-(2-Chloro-4-fluoro-5-methoxyphenyl)-N-(2,2-dimethoxyethyl) methanimine To a solution of 2-chloro-4-fluoro-5-methoxybenzaldehyde (5 g, 26.51 mmol) in toluene (50 mL) were added 4-methylbenzenesulfonic acid (0.46 g, 2.65 mmol) and 2,2-dimethoxyethanamine (3.07 g, 29.16 mmol) at room temperature. The reaction mixture was heated at 130° C. for 3 hours. The resulting mixture was cooled to room temperature, neutralized to pH 8 with sat. a. $NaHCO_3$, and then extracted with EtOAc (3×100 mL). The combined organic layers were washed with brine (100 mL), dried over anhydrous sodium sulfate, filtered and concentrated under reduced pressure to afford the title compound (7.3 g, 99% yield) as an orange oil. MS: m/z=276.05 $[M+H]^+$. $^1H$ NMR (300 MHz, Chloroform-d) δ 8.63-8.62 (m, 1H), 7.67-7.64 (m, 1H), 7.18-7.10 (m, 1H), 4.72-4.68 (m, 1H), 3.94 (s, 3H), 3.83-3.80 (m, 2H), 3.43 (s, 6H).

Step 3: N-(2-Chloro-4-fluoro-5-methoxybenzyl)-2,2-dimethoxyethan-1-amine

To an ice-cooled solution of 1-(2-chloro-4-fluoro-5-methoxyphenyl)-N-(2,2-dimethoxyethyl) methanimine (1 g, 3.62 mmol) in EtOH (10 mL) was added NaBH4 (0.17 g, 4.53 mmol). The ice bath was removed, and the reaction mixture was stirred at room temperature for 4 hours. The resulting mixture was quenched with acetic acid in an ice bath and concentrated under reduced pressure. The residue was diluted with DCM (10 mL), neutralized to pH 8 with sat. aq. $NaHCO_3$ and extracted with DCM (3×20 mL). The combined organic layers were washed with brine (40 mL), dried over anhydrous sodium sulfate, filtered and concentrated under reduced pressure to afford the title compound (1 g, crude used through) as a brown oil. MS: m/z=278.10 $[M+H]^+$. $^1H$ NMR (300 MHz, Chloroform-d) δ 7.18-7.05 (m, 2H), 4.52-4.48 (m, 1H), 3.88 (s, 3H), 3.84 (s, 2H), 3.38 (s, 6H), 2.76 (d,)=5.4 Hz, 2H).

Step 4: N-(2-Chloro-4-fluoro-5-methoxybenzyl)-N-(2,2-dimethoxyethyl)-4-methylbenzenesulfonamide To an ice-cooled solution of N-(2-chloro-4-fluoro-5-methoxybenzyl)-2,2-dimethoxyethan-1-amine (1.0 g, crude) in DCM (12 mL) were added pyridine (1.0 g, 12.60 mmol) and 4-methylbenzenesulfonyl chloride (858 mg, 4.50 mmol). The ice bath was removed, and the reaction mixture was stirred at room temperature for 3 hours. The resulting mixture was diluted with DCM (50 mL), washed with HCl (1.5 M in $H_2O$, 15 mL), sat. aq. $NaHCO_3$ (15 mL), and brine (15 mL). The organic layer was dried over anhydrous $Na_2SO_4$, filtered and concentrated under reduced pressure to afford the title compound (1.5 g, 96% yield for two steps) as a brown oil. $^1H$ NMR (400 MHZ, Chloroform-d)δ 7.76-7.68 (m, 2H), 7.36-7.28 (m, 2H), 7.15-7.13 (m, 1H), 7.06-7.03 (m, 1H), 4.47 (s, 2H), 4.41-4.32 (m, 1H), 3.83 (s, 3H), 3.28-3.24 (m, 8H), 2.43 (s, 3H).

Step 5: 8-Chloro-6-fluoroisoquinolin-5-ol

To an ice-cooled solution of N-(2-chloro-4-fluoro-5-methoxybenzyl)-N-(2,2-dimethoxyethyl)-4-methylbenzenesulfonamide (3 g, 6.94 mmol) in DCM (30 mL) under nitrogen atmosphere was added aluminium chloride (4.63 g, 34.73 mmol). The ice bath was removed, and the reaction mixture was heated at 50° C. for 3 hours. The resulting mixture was cooled to room temperature and concentrated under reduced pressure. The residue was purified by silica gel flash chromatography, eluted with DCM/MeOH (10: 1) to afford 1.7 g crude product. The crude product (1.7 g) was triturated with sat. aq. NaHICO3 (30 mL) and filtered. The filter-cake was washed with water (3×5 mL) and dried under reduced pressure to afford the title compound (1.1 g, 80% yield) as a grey solid. MS: m/z=198.00 $[M+H]^+$. $^1H$ NMR (300 MHz, DMSO-$d_6$) δ 9.41 (s, 1H), 8.60-8.58 (m, 1H), 8.08 (s, 1H), 7.86-7.82 (m, 1H).

Step 6: 8-Chloro-6-fluoro-5-(methoxy-da) isoquinoline

To a mixture of triphenylphosphine (15.92 mg, 6.07 mmol) in THF (10 mL) under nitrogen atmosphere was added diisopropyl azodicarboxylate (1.43 g, 7.08 mmol) at room temperature. After stirring for 5 min, 8-chloro-6-fluoroisoquinolin-5-ol (1.0 g, 5.06 mmol) and $CD_3OD$ (219.0 mg, 6.07 mmol) were added at room temperature. The reaction mixture was stirred at room temperature for 4 hours. The resulting mixture was concentrated under reduced pressure. The residue was purified by silica gel flash chromatography, eluted with PE/EA (3: 1) to afford the title compound (680 mg, 62% yield) as a light yellow solid. MS: m/z=215.05 $[M+H]^+$. $^1H$ NMR (300 MHz, Chloroform-d) & 9.55 (s, 1H), 8.63-8.60 (m, 1H), 7.99-7.97 (m, 1H), 7.47-7.43 (m, 1H).

Step 7: 4-Bromo-8-chloro-6-fluoro-5-(methoxy-$d_3$) isoquinoline

To a mixture of 8-chloro-6-fluoro-5-(methoxy-$d_3$) isoquinoline (700 mg, 3.26 mmol) in MeCN (7 mL) was added N-bromosuccinimide (870.7 mg, 4.89 mmol) at room temperature. The reaction mixture was heated at 60° C. for 5 hours. The resulting mixture was cooled to room temperature and concentrated under reduced pressure. The residue was purified by silica gel flash chromatography, eluted with PE/EA (10: 1) to afford the title compound (Intermediate 75, 130 mg, 13% yield) as an off-white solid. MS: m/z=292.90, 294.90 $[M+H]^+$. $^1H$ NMR (300 MHZ, Chloroform-d)δ 9.57 (s, 1H), 8.78 (s, 1H), 7.67-7.63 (m, 1H), $^{19}F$ NMR (282 MHZ, Chloroform-d) δ −118.48 (s, IF).

Intermediate 76: (1S,7S,8S)-2-(7-Bromo-8-fluoro-2-(((2R,7aS)-2-fluorotetrahydro-1H-pyrrolizin-7a(5H)-yl)methoxy-$d_2$)pyrido[4,3-d]pyrimidin-4-yl)-8-fluoro-5-oxa-2-azabicyclo[5.1.0]octane

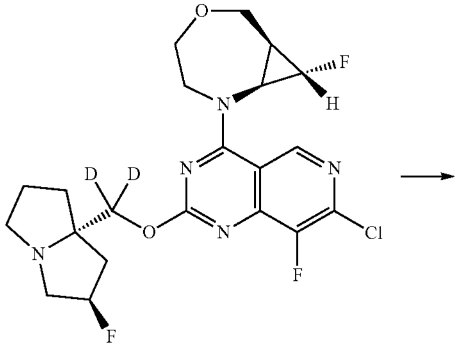

Intermediate 34

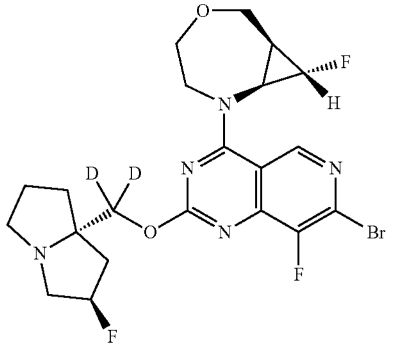

Intermediate 76

To a solution of Intermediate 34 (500 mg, 1.1 mmol) in MeCN (500 mL) was added TMSBr (811 mg, 5.3 mmol) at 25° C. The mixture was stirred at 80° C. for 3 hr. The mixture was added to saturated NaHCOs (500 mL) and extracted with $CH_2Cl_2$ (200 mL×2). The combined organic layers was dried over $Na_2SO_4$, filtered and concentrated under reduced pressure. After purification by silica gel flash chromatography (Eluent of 0~6% MeOH in $CH_2Cl_2$), the title compound (Intermediate 76, 510 mg, yield: 90%) was obtained as a yellow solid. MS: m/z=516.0, 518.0 $[M+H]^+$. $^1H$ NMR (400 MHZ, Dimethylsulfoxide-$d_6$) δ 9.19 (s, 1H), 5.40-5.18 (m, 1H), 4.88-4.67 (m, 1H), 4.46 (d, J=13.2 Hz, 1H), 4.36-4.25 (m, 2H), 4.01-3.91 (m, 1H), 3.68-3.54 (m, 2H), 3.17-3.00 (m, 4H), 2.90-2.79 (m, 1H), 2.38-2.28 (m, 1H), 2.19-2.04 (m, 2H), 2.02-1.95 (m, 1H), 1.93-1.76 (m, 3H). $^{19}F$ NMR (400 MHZ, Dimethylsulfoxide-$d_6$) δ −130.07, −172.22.

Intermediate 77: 6-Fluoro-5-(fluoromethoxy)-4-(trimethylstannyl)isoquinoline

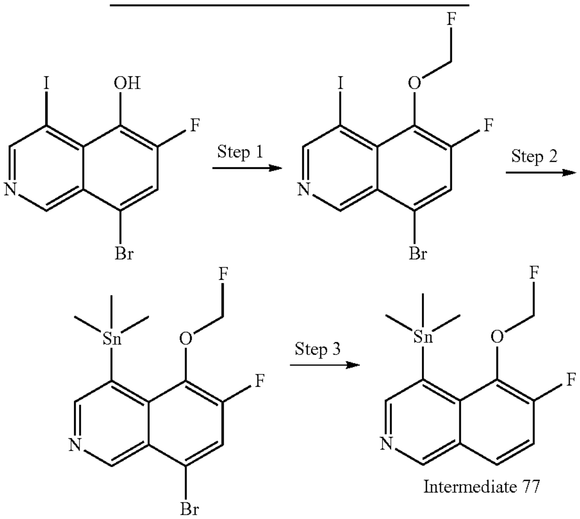

Intermediate 77

Step 1: 8-Bromo-6-fluoro-5-(fluoromethoxy)-4-iodoisoquinoline

To a solution of 8-bromo-6-fluoro-4-iodoisoquinolin-5-ol (900 mg, 2.45 mmol, HBr salt) in DMF (20 mL) were added $K_2CO_3$ (1 g, 7.34 mmol) and $CH_2FBr$ (276 mg, 2.45 mmol). The mixture was stirred at 50° C. for 2 hr. The reaction mixture was diluted with $H_2O$ (40 mL) and extracted with EtOAc (40 mL×2). The combined organic layers were washed with brine (50 mL×2), dried over $Na_2SO_4$, filtered and concentrated under reduced pressure. After purification by silica gel flash chromatography (Eluent of 0~7% EtOAc in petroleum ether), the title compound (660 mg, yield: 67%) was obtained as an off-white solid. MS: m/z=399.6, 401.7 $[M+H]^+$. $^1$HNMR (400 MHZ, Chloroform-d) δ 9.51 (s, 1H), 9.14 (s, 1H), 7.81 (d, J=9.6 Hz, 1H), 5.79 (d, J=52.8 Hz, 2H). $^{19}$F. NMR (400 MHz, Chloroform-d) δ −119.592, −119.630, −152.488.

Step 2: 8-Bromo-6-fluoro-5-(fluoromethoxy)-4-(trimethylstannyl) isoquinoline

A mixture of 8-bromo-6-fluoro-5-(fluoromethoxy)-4-jodoisoquinoline (660 mg, 1.65 mmol), $Sn_2Me_6$ (3.46 mL, 16.0 mmol) and Pd $(PPh_3)_4$ (190 mg, 165 μmol) in 1,4-dioxane (10 mL) was degassed and purged with $N_2$ three times, then the mixture was stirred at 90° C. for 20 hr under $N_2$ atmosphere. Another SnzMe6 (1.31 mL, 6.32 mmol) and Pd $(PPh_3)_4$ (190 mg, 165 μmol) were added, and the mixture was degassed and purged with $N_2$ three times. The mixture was stirred at 90° C. for another 20 hr under $N_2$ atmosphere. The reaction mixture was quenched with saturated KF (10 mL) at 25° C., diluted with $H_2O$ (100 mL), and extracted with EtOAc (50 mL×3). The combined organic layers were washed with brine (100 mL), dried over $Na_2SO_4$, filtered and concentrated under reduced pressure. After purification by silica gel flash chromatography (Eluent of 0~3% EtOAc in petroleum ether), the title compound (200 mg, yield: 25%) was obtained as an off-white solid. MS: m/z=437.7, 439.8 $[M+H]^+$. $^1$HNMR (400 MHZ, Chloroform-d) δ 9.51 (s, 1H), 8.73-8.64 (m, 1H), 7.70 (d, J=12.0 Hz, 1H), 5.98 (d, J=52.8 Hz, 2H), 0.40 (s, 9H). $^{19}$F NMR (400 MHz, Chloroform-d) δ −127.057, −150.704, −150.749.

Step 3: 6-Fluoro-5-(fluoromethoxy)-4-(trimethylstannyl) isoquinoline

A solution of 8-bromo-6-fluoro-5-(fluoromethoxy)-4-(trimethylstannyl) isoquinoline (200 mg, 457 μmol) in THE (4 mL) was degassed and purged with $N_2$ three times, and the mixture was stirred at −40° C. for 5 min under $N_2$ atmosphere. Then i-PrMgCl (1.4 mL, 2 M) was added dropwise at −40° C. The resulting mixture was stirred at −40° C. for 2 hr under $N_2$ atmosphere. The reaction mixture was quenched with saturated $NH_4Cl$ aqueous solution (5 mL) at 0° C. and extracted with EtOAc (30 mL×2). The combined organic layers were washed with brine (20 mL), dried over $Na_2SO_4$, filtered and concentrated under reduced pressure. After purification by silica gel flash chromatography (Eluent of 0~5% EtOAc in petroleum ether), the title compound (Intermediate 77, 100 mg, yield: 57%) was obtained as an off-white solid. MS: m/z=357.8 $[M+H]^+$. $^1$HNMR (400 MHZ, Chloroform-d) δ 9.15 (s, 1H), 8.60 (s, 1H), 7.74 (dd, J=9.2, 5.2 Hz, 1H), 7.43 (dd, J=12.4, 9.2 Hz, 1H), 6.00 (d, J=52.0 Hz, 2H), 0.40 (s, 9H). $^{19}$F NMR (400 MHz, Chloroform-d) 6-127.405, −150.461.

Intermediate 78: 6-Fluoro-5-methoxy-4-(trimethylstannyl)isoquinoline

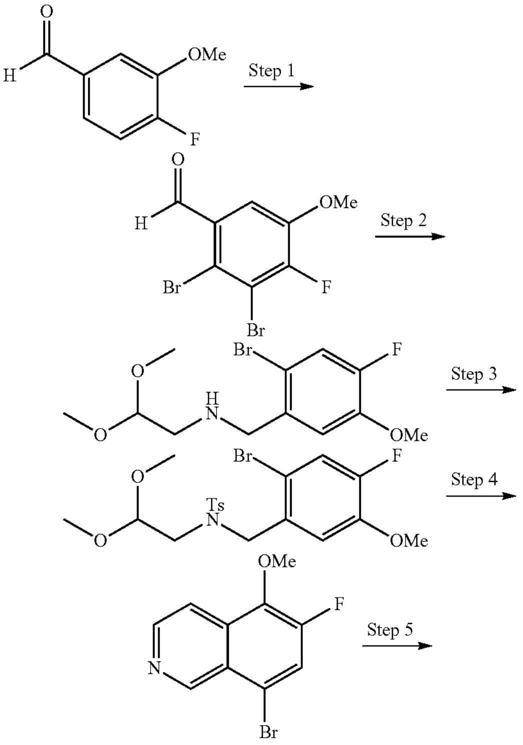

-continued

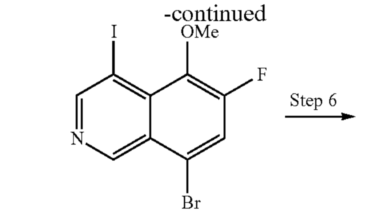

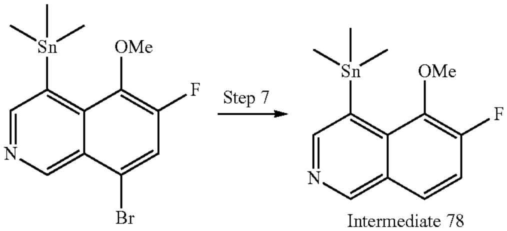

Intermediate 78

Step 1: 2-Bromo-4-fluoro-5-methoxybenzaldehyde

To a solution of 4-fluoro-3-methoxybenzaldehyde (4.3 g, 27.9 mmol) in $H_2O$ (45 mL) were added KBr (16.6 g, 139 mmol) and Brz (69.9 mmol, 3.6 mL). The mixture was stirred at 25° C. for 16 hr. The mixture was filtered, and the wet cake washed with $H_2O$ (50 mL×3). Then the wet cake was dried to give the title compound (6.4 g, yield: 98%) as a white solid. $^1$H NMR (400 MHz, Chloroform-d) δ 10.24 (s, 1H), 7.53 (d, J=9.2 Hz, 1H), 7.38 (d, J=10.0 Hz, 1H), 3.94 (s, 3H). $^{19}$F NMR (400 MHz, Chloroform-d) δ −121.761.

Step 2: N-(2-Bromo-4-fluoro-5-methoxybenzyl)-2,2-dimethoxyethan-1-amine

To a solution of 2-bromo-4-fluoro-5-methoxybenzaldehyde (36 g, 154 mmol) and 2,2-dimethoxyethanamine (19.5 g, 185 mmol) in $CH_2Cl_2$ (500 mL) was added NaBH $(OAc)_3$ (98.2 g, 463 mmol) at 0° C. The mixture was stirred at 25° C. for 16 hr under $N_2$ atmosphere. The reaction mixture was quenched with saturated $NaHCO_3$ (500 mL) at 0° C. and extracted with EtOAc (500 mL×2). The combined organic layers were washed with brine (300 mL), dried over $Na_2SO_4$, filtered and concentrated under reduced pressure. After purification by silica gel flash chromatography (Eluent of 0~100% EtOAc in petroleum ether), the title compound (18.4 g, yield: 69%) was obtained as a yellow oil. MS: m/z=321.9, 323.9 $[M+H]^+$. $^1$H NMR (400 MHz, Chloroform-d) δ 7.24 (d, J=4.8 Hz, 1H), 7.06 (d, J=8.8 Hz, 1H), 4.50 (t, J=5.2 Hz, 1H), 3.87 (s, 3H), 3.83 (s, 2H), 3.64 (br s, 1H), 3.36 (s, 6H), 2.75 (d, J=5.2 Hz, 2H). $^{19}$F. NMR (400 MHz, Chloroform-d) δ −134.569.

Step 3: N-(2-Bromo-4-fluoro-5-methoxybenzyl)-N-(2,2-dimethoxyethyl)-4-methylbenzenesulfonamide To a solution of N-(2-bromo-4-fluoro-5-methoxybenzyl)-2,2-dimethoxyethan-1-amine (16 g, 49.7 mmol) in $CH_2Cl$ (500 mL) were added Py (12 mL, 149 mmol) and TsCl (11.4 g, 59.6 mmol) at 0° C. The mixture was stirred at 25° C. for 16 hr. The reaction mixture was diluted with $H_2O$ (500 mL) and extracted with $CH_2Cl_2$ (500 mL×2). The combined organic layers were washed with brine (500 mL), dried over $Na_2SO_4$, filtered and concentrated under reduced pressure. After purification by silica gel flash chromatography (Eluent of 0~100% EtOAc in petroleum ether), the title compound (22.6 g, yield: 93%) was obtained as a white solid. MS: m/z=497.8, 499.8 $[M+Na]^+$. $^1$H NMR (400 MHZ, Chloroform-d)δ 7.73 (d, J=8.0 Hz, 2H), 7.33 (d, J=8.0 Hz, 2H), 7.21 (d,.J=10.4 Hz, 1H), 7.16 (d,.J=8.8 Hz, 1H), 4.45 (s, 2H), 4.37 (t, J=5.2 Hz, 1H), 3.83 (s, 3H), 3.28 (d, J=5.6 Hz, 2H), 3.23 (s, 6H), 2.44 (s, 3H). $^{19}$F. NMR (400 MHz, Chloroform-d) δ −134.509.

Step 4: 8-Bromo-6-fluoro-5-methoxyisoquinoline

N-(2-bromo-4-fluoro-5-methoxybenzyl)-N-(2,2-dimethoxyethyl)-4-methylbenzenesulfonamide (19 g, 39.9 mmol) was added in ClSO3H (20 mL) at 0° C., then the mixture was stirred at 90° C. for 5 min. The reaction mixture was poured onto ice, neutralized with NaHICOs, and extracted with EtOAc (100 mL×2). The combined organic layers were washed with brine (100 mL), dried over $Na_2SO_4$, filtered and concentrated under reduced pressure. After purification by silica gel flash chromatography (Eluent of 0~10% EtOAc in petroleum ether), the title compound (7.1 g, yield: 69%) was obtained as a white solid. MS: m/z=256.0, 258.0 $[M+H]^+$. $^1$H NMR (400 MHz, Chloroform-d) δ 9.51 (s, 1H), 8.61 (d, J=5.6 Hz, 1H), 7.98 (d, J=6.0 Hz, 1H), 7.66 (d, J=11.2 Hz, 1H), 4.16 (d, J=2.8 Hz, 3H). $^{19}$F NMR (400 MHZ, Chloroform-d) δ −125.589.

Step 5: 8-Bromo-6-fluoro-4-iodo-S-methoxyisoquinoline

To a solution of 8-bromo-6-fluoro-5-methoxyisoquinoline (2.6 g, 10.15 mmol) and $I_2$ (3.09 g, 12.18 mmol) in ACN (30 mL) was added TBHP (11 mL, 81.2 mmol, 70% purity in $H_2O$). The mixture was stirred at 90° C. for 16 hr under $N_2$ atmosphere. The reaction mixture was diluted with $H_2O$ (100 mL) and extracted with EtOAc (100 mL×2). The combined organic layers were washed with brine (100 mL), dried over $Na_2SO_4$, filtered and concentrated under reduced pressure. After purification by silica gel flash chromatography (Eluent of 0~10% EtOAc in petroleum ether), the title compound (3.2 g, yield: 80%) was obtained as a yellow solid. MS: m/z=381.9, 383.8 $[M+H]^+$. $^1$H NMR (400 MHz, Chloroform-d) δ 9.49 (s, 1H), 9.07 (s, 1H), 7.78 (d, J=10.4 Hz, 1H), 4.05 (d, J=0.8 Hz, 3H). $^{19}$F. NMR (400 MHz, Chloroform-d) δ −120.516.

Step 6: 8-Bromo-6-fluoro-5-methoxy-4-(trimethylstannyl)isoquinoline

A mixture of 8-bromo-6-fluoro-4-iodo-5-methoxyisoquinoline (1.7 g, 4.45 mmol), SnzMe6 (5.49 mL, 26.5 mmol) and Pd $(PPh_3)_4$ (514 mg, 445 μmol) in 1,4-dioxane (30 mL) was degassed and purged with $N_2$ three times, then the mixture was stirred at 90° C. for 16 hr under $N_2$ atmosphere. The reaction mixture was quenched with sat. KF solution (20 mL) at 25° C., and diluted with $H_2O$) (50 mL), and extracted with $CH_2Cl_2$ (50 mL×3). The combined organic layers were washed with brine (50 mL), dried over $Na_2SO_4$, filtered and concentrated under reduced pressure. After purification by silica gel flash chromatography (Eluent of 0~10% EtOAc in petroleum ether), the title compound (500 mg, yield: 18%) was obtained as a white solid. MS: m/z=418.0, 420.0, 422.0 $[M+H]^+$. $^1$H NMR (400 MHz, Chloroform-d) δ 9.48 (s, 1H), 8.63 (s, 1H), 7.65 (d,.J=12.4 Hz, 1H), 4.21 (d,.J=5.2 Hz, 3H), 0.38 (s, 9H). $^{19}$F NMR (400 MHZ, Chloroform-d) δ −121.611.

Step 7: 6-Fluoro-5-methoxy-4-(trimethylstannyl) isoquinoline

A solution of 8-bromo-6-fluoro-5-methoxy-4-(trimethylstannyl) isoquinoline (450 mg, 1.07 mmol) in THE (5 mL) was degassed and purged with $N_2$ three times, then the mixture was stirred at −40° C. for 10 min under $N_2$ atmosphere. Then i-PrMgCl (2 M, 3.22 mL) was added dropwise at −40° C. The resulting mixture was stirred at −40° C. for 30 min. The reaction mixture was quenched with 1 M HCl (5 mL) at 0° C. and extracted with EtOAc (10 mL×2). The combined organic layers were washed with brine (20 mL), dried over $Na_2SO_4$, filtered and concentrated under reduced pressure. After purification by silica gel flash chromatography (Eluent of 0~30% EtOAc in petroleum ether), the title compound (Intermediate 78, 130 mg, yield: 35%) was obtained as a white solid. MS: m/z=342.1 $[M+H]^+$. $^1$H NMR (400 MHZ, Chloroform-d)δ 9.12 (s, 1H), 8.55 (s, 1H), 7.58 (dd, J=8.8, 4.8 Hz, 1H), 7.36 (dd, J=13.2, 9.2 Hz, 1H), 4.21 (d, J=5.2 Hz, 3H), 0.37 (s, 9H). $^{19}$F NMR (400 MHZ, Chloroform-d) δ −127.751.

Intermediate 79: 6-Fluoro-5-(fluoromethoxy-d2)-4-(trimethylstannyl)isoquinoline

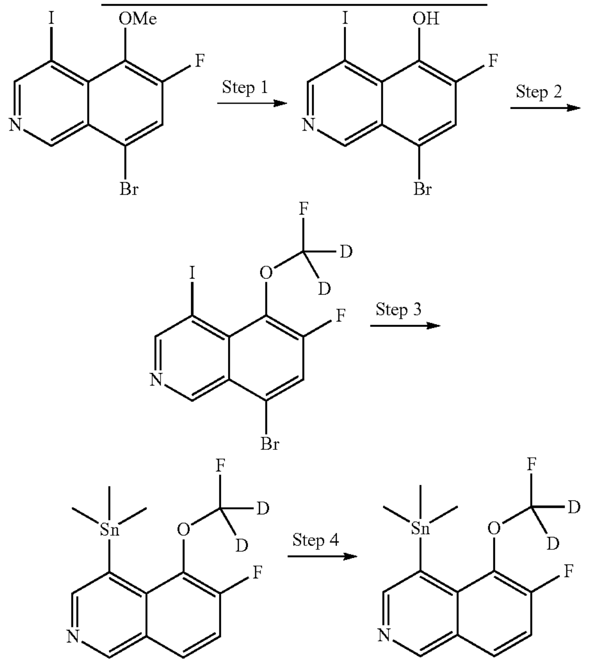

Intermediate 79

Step 1: 8-Bromo-6-fluoro-4-iodoisoquinolin-5-ol

To a solution of 8-bromo-6-fluoro-4-iodo-5-methoxyisoquinoline (5 g, 13.1 mmol) in HBr (50 mL, 40% in $H_2O$) was degassed and purged with $N_2$ three times. The mixture was stirred at 120° C. for 16 hr under $N_2$ atmosphere. The reaction mixture was filtered, and the wet cake was concentrated under reduced pressure. The title compound (3.98 g, HBr salt, yield: 82%) was obtained as a yellow solid. MS: m/z=367.9, 369.9 $[M+H]^+$. $^1$H NMR (400 MHZ, Dimethylsulfoxide-$d_6$) § 11.2 (br s, 1H), 9.33 (s, 1H), 8.98 (s, 1H), 8.16 (d, J=10.4 Hz, 1H). $^{19}$F NMR (400 MHz, Dimethylsulfoxide-$d_6$) ¿-127.200.

Step 2: 8-Bromo-6-fluoro-5-(fluoromethoxy-$d_2$)-4-iodoisoquinoline

To a solution of 8-bromo-6-fluoro-4-iodo-isoquinolin-5-ol (2 g, 4.46 mmol, HBr salt) in DMF (50 mL) was added $K_2CO_3$ (1.9 g, 13.3 mmol). After addition, the mixture was stirred at 25° C. for 1 hr, and then fluoromethyl-$d_{2}$ $_4$-methylbenzenesulfonate (918 mg, 4.46 mmol) was added at 25° C. The resulting mixture was stirred at 70° C. for 15 hr. The reaction mixture was diluted with $H_2O$) (200 mL) and extracted with EtOAc (50 mL×2). The combined organic layers were washed with brine (100 mL), dried over $Na_2SO_4$, filtered and concentrated under reduced pressure. After purification by silica gel flash chromatography (Eluent of 0~10% EtOAc in petroleum ether), the title compound (1.3 g, yield: 72%) was obtained as a white solid. MS: m/z=401.7, 403.7 $[M+H]^+$. HNMR (400 MHZ, Chloroform-d)δ 9.51 (s, 1H), 9.14 (s, 1H), 7.80 (d, J=9.6 Hz, 1H). $^{19}$F. NMR (400 MHZ, Chloroform-d) δ −119.713, −153.749, −153.771.

Step 3: 6-Fluoro-5-(fluoromethoxy-$d_2$)-4-(trimethylstannyl) isoquinoline

A mixture of 8-bromo-6-fluoro-5-(fluoromethoxy-$d_2$)-4-iodoisoquinoline (1.3 g, 3.23 mmol), $Sn_2Me_6$ (4.0 mL, 19.4 mmol) and Pd $(PPb_3)_4$ (373 mg, 323 μmol) in 1,4-dioxane (15 mL) was degassed and purged with $N_2$ three times, and the mixture was stirred at 90° C. for 20 hr under $N_2$ atmosphere. $Sn_2Me_6$ (4.05 mL, 19.5 mmol) and $Pd(PPh_3)_4$ (373 mg, 323 μmol) were added. The mixture was degassed and purged with $N_2$ three times. The mixture was stirred at 90° C. for another 20 hr under $N_2$ atmosphere. The reaction mixture was quenched with sat. KF solution (10 mL) at 25° C., diluted with $H_2O$ (100 mL), and extracted with EtOAc (50 mL×3). The combined organic layers were washed with brine (100 mL), dried over $Na_2SO_4$, filtered and concentrated under reduced pressure. After purification by silica gel flash chromatography (Eluent of 0~6% EtOAc in petroleum ether), the title compound (Intermediate 79, 200 mg, yield: 16%) was obtained as an off-white solid. MS: m/z=361.9 $[M+H]^+$. $^1$HNMR (400 MHZ, Chloroform-d)δ 9.19 (s, 1H), 8.60-8.50 (m, 1H), 8.06-8.01 (m, 1H), 7.58-7.51 (m, 1H), 0.50 (s, 9H). $^{19}$F NMR (400 MHz, Chloroform-d) δ −128.178, −149.276, −149.298.

Intermediate 80 & 81: N-(6-Fluoro-5-(methoxy-d3)-4-(4,4,5,5-tetramethyl-1,3,2-dioxaborolan-2-yl)naphthalen-2-yl)-1,1-diphenylmethanimine & 6-fluoro-5-(methoxy-d3)-4-(4,4,5,5-tetramethyl-1,3,2-dioxaborolan-2-yl)naphthalen-2-amine

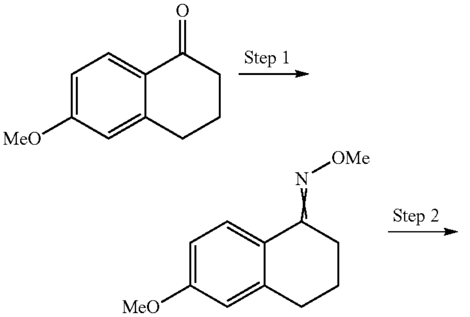

-continued

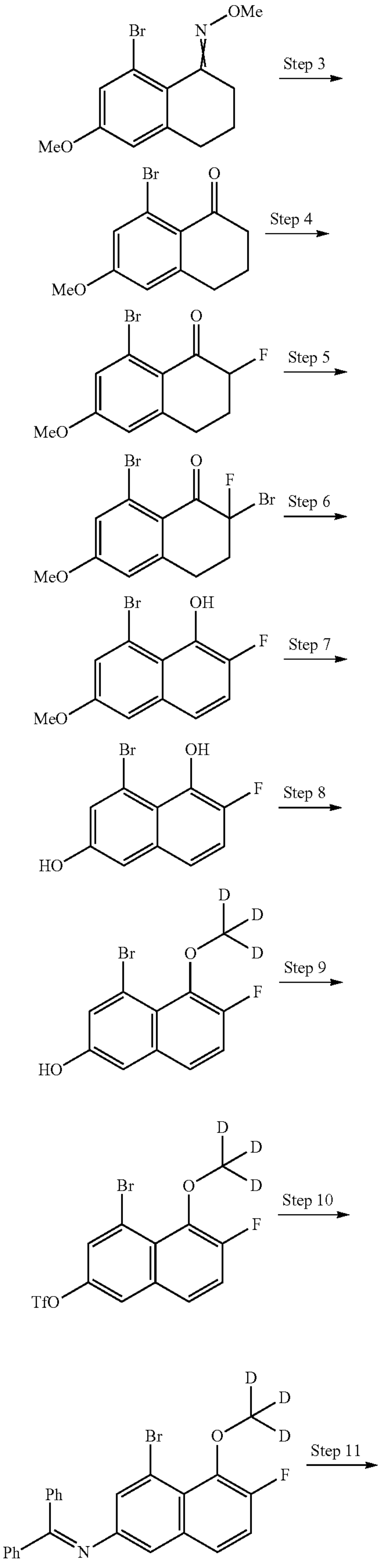

-continued

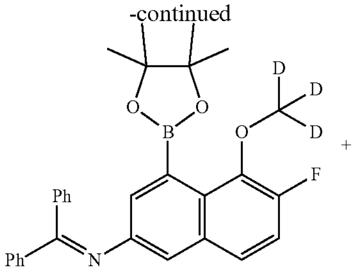

Intermediate 80

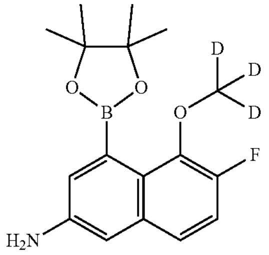

Intermediate 81

Step 1: (S)-7-(hydroxymethyl) azepan-4-one O-methyl oxime

To a solution of 6-methoxy-3,4-dihydronaphthalen-1 (2H)-one (100 g, 567.5 mmol) and O-methylhydroxylamine hydrochloride (56.9 g, 681 mmol) in EtOH (1.5 L) was added pyridine (68.7 mL, 851 mmol) dropwise at 20° C. The mixture was stirred at 20° C. for 16 h. The reaction mixture was concentrated under reduced pressure. The residue was diluted with $H_2O$ (800 mL) and extracted with EtOAc (800 mL×3). The combined organic layers were washed with brine (500 mL), dried over anhydrous $Na_2SO_4$, filtered and concentrated under reduced pressure to give the title compound (110 g, 98% purity) as a brown oil, which was used in the step without further purification. MS: m/z=206.0 $[M+H]^+$. $^1H$ NMR (400 MHz, Chloroform-d) δ 7.91 (d, J=8.8 Hz, 1H), 6.75 (dd, J=2.8, 8.8 Hz, 1H), 6.64 (d, J=2.4 Hz, 1H), 3.96 (s, 3H), 3.81 (s, 3H), 2.71 (t, J=6.4 Hz, 4H), 1.90-1.75 (m, 2H).

Step 2: 8-Bromo-6-methoxy-3,4-dihydronaphthalen-1 (2H)-one O-methyl oxime

To a solution of 6-methoxy-3,4-dihydronaphthalen-1 (2H)-one O-methyl oxime (48 g, 234 mmol) in AcOH (2 L) were added NBS (41.62 g, 234 mmol) and Pd $(OAc)_2$ (5.25 g, 23.4 mmol). The mixture was stirred at 60° C. for 1 h under $N_2$. The reaction mixture was concentrated under reduced pressure, diluted with $H_2O$ (1 L), and extracted with EtOAc (1 L×3). The combined organic layers were washed with brine (1 L), dried over anhydrous $Na_2SO_4$, filtered and concentrated under reduced pressure to give the title compound (130 g, 88% purity) as a black-brown solid, which used in the next step without further purification. MS: m/z=283.9 $[M+H]^+$. $^1H$ NMR (400 MHZ, Dimethylsulfoxide-$d_6$)δ 7.09 (d, J=2.0 Hz, 1H), 6.86 (d, J=2.0 Hz, 1H), 6.64 (d,.J=2.4 Hz, 1H), 3.89 (s, 3H), 3.78 (s, 3H), 2.67-2.55 (m, 6H).

Step 3: 8-Bromo-6-methoxy-3,4-dihydronaphthalen-1 (2H)-one

To a solution of 8-bromo-6-methoxy-3,4-dihydronaphthalen-1 (2H)-one O-methyl oxime (29 g, 102.06 mmol) in 1,4-dioxane (300 mL) was added HCl (6 M in water, 290 mL). The mixture was stirred at 90° C. for 2 h. The reaction mixture was quenched with sat. $Na_2CO$saq. (300 mL) at 0° C. and extracted with EtOAc (300 mL×3). The combined organic layers were washed with brine (300 mL), dried over anhydrous $Na_2SO_4$, filtered and concentrated under reduced pressure. The residue was purified by silica gel flash chromatography (eluent: 0~7% of EtOAc in Petroleum ether) to give the title compound (17.6 g, 61% yield for 3 step) as a yellow solid. MS: m/z=254.9, 256.9 $[M+H]^+$. $^1$H NMR (400 MHZ, Dimethylsulfoxide-$d_6$) δ 7.14 (d, J=2.4 Hz, 1H), 6.95 (d, J=2.4 Hz, 1H), 3.84 (s, 3H), 2.94 (t, J=6.0 Hz, 2H), 2.56 (t, J=6.4 Hz, 2H), 2.01-1.92 (m, 2H).

Step 4: 8-Bromo-2-fluoro-6-methoxy-3,4-dihydronaphthalen-1 (2H)-one

To a solution of 8-bromo-6-methoxy-3,4-dihydronaphthalen-1 (2H)-one (48 g, 188 mmol) in MeOH (480 mL) was added $H_2SO_4$ (3.36 mL, 63.03 mmol) and SelectFluor (80 g, 225.8 mmol). The mixture was stirred at 50° C. for 5 h. The reaction mixture was concentrated under reduced pressure, diluted with $H_2O$ (400 mL) and extracted with EtOAc (400 mL×3). The combined organic layers were washed with brine (500 mL), dried over anhydrous $Na_2SO_4$, filtered and concentrated under reduced pressure to give the title compound (48 g, 86% yield) as a brown solid, which was used in the next step without further purification. MS: m/z=272.9 $[M+H]^+$. $^1$H NMR (400 MHZ, Chloroform-d)δ 7.15 (d, J=2.4, 1H), 7.79 (d, J=2.4, 1H), 5.13-4.97 (m, 1H), 3.86 (s, 3H), 3.14-3.09 (m, 2H), 2.54-2.46 (m, 1H), 2.36-2.30 (m, 1H). $^{19}$F. NMR (376 MHz, Chloroform-d) δ −188.61.

Step 5: 2,8-Dibromo-2-fluoro-6-methoxy-3,4-dihydronaphthalen-1 (2H)-one

To a solution of 8-bromo-2-fluoro-6-methoxy-3,4-dihydronaphthalen-1 (2H)-one (47 g, 173.6 mmol) in ACN (470 mL) was added PyBr3 (60.54 g, 189.3 mmol). The mixture was stirred at 70° C. for 2 h under $N_2$. The reaction mixture was quenched with $H_2O$ (500 mL) at 25° C. and extracted with EtOAc (500 mL×3). The combined organic layers were washed with brine (500 mL×2), dried over anhydrous $Na_2SO_4$, filtered and concentrated under reduced pressure. The residue was triturated with mixture solvents (Petroleum ether/Ethyl acetate=10/1, 200 mL) at 25° C. for 30 min to give the title compound (55 g, 90% yield) as a brown solid. MS: m/z=352.8 $[M+H]^+$. $^1$H NMR (400 MHZ, Chloroform-d) & 7.22 (s, 1H), 6.72 (d, J=1.6 Hz, 1H), 3.89 (s, 3H), 3.38-3.30 (m, 1H), 3.13-3.07 (m, 1H), 2.85-2.79 (m, 1H), 2.67-2.57 (m, 1H). $^{19}$F NMR (376 MHz, Chloroform-d) δ −111.58.

Step 6: 8-Bromo-2-fluoro-6-methoxynaphthalen-1-ol

To a solution of 2,8-dibromo-2-fluoro-6-methoxy-3,4-dihydronaphthalen-1 (2H)-one (54 g, 153.4 mmol) in DMF (540 mL) was added LiBr (29.3 g, 337.5 mmol). The mixture was stirred at 100° C. for 1 h. The reaction mixture was quenched with $H_2O$ (500 mL) at 25° C. and extracted with EtOAc (300 mL×3). The combined organic layers were washed with brine (400 mL×2), dried over anhydrous $Na_2SO_4$, filtered and concentrated under reduced pressure. The residue was triturated with mixture solvents (Petroleum ether/Ethyl acetate=10/1, 200 mL) at 25° C. for 30 min to give the title compound (40.17 g, 96% yield) as a brown solid. $^1$H NMR (400 MHz, Chloroform-d) δ 7.43 (d, J=2.4, 1H), 7.33-7.29 (m, 1H), 7.25-7.23 (m, 1H), 7.11-7.10 (m, 1H), 7.06-7.05 (m, 1H). $^{19}$F NMR (376 MHz, Dimethylsulfoxide-$d_6$) δ −141.77.

Step 7: 8-Bromo-2-fluoronaphthalene-1,6-diol

To a solution of 8-bromo-2-fluoro-6-methoxynaphthalen-1-ol (6 g, 22.13 mmol) in $CH_2Cl_2$ (6.5 mL) was added BBr3 (6.40 mL, 66.40 mmol) at 0° C. The mixture was stirred at 25° C. for 0.5 h. The reaction mixture was quenched with $H_2O$ (100 mL) dropwise at 25° C. The pH of the mixture was adjusted to 7 with sat. $NaHCO_3$ aq. The mixture was extracted with EtOAc (100 mL×3). The combined organic layers were washed with brine (200 mL), dried over anhydrous $Na_2SO_4$, filtered and concentrated under reduced pressure. The residue was triturated with $CH_2Cl_2$ (10 mL) at 25° C. for 0.5 h to give the title compound (4.86 g, 86% yield) as a white solid. $^1$H NMR (400 MHz, Dimethylsulfoxide-$d_6$) δ 9.94-9.90 (m, 2H), 7.37-7.32 (m, 2H), 7.23-7.19 (m, 1H), 7.09-7.08 (m, 1H). $^{19}$F NMR (376 MHz, Dimethylsulfoxide-$d_6$) δ −141.22.

Step 8: 4-Bromo-6-fluoro-5-(methoxy-$d_3$) naphthalen-2-ol

To a solution of 8-bromo-2-fluoronaphthalene-1,6-diol (2 g, 7.78 mmol) in DMF (12 mL) was added $K_2CO_3$ (3.23 g, 23.3 mmol). Then iodomethane-$d_3$ (1.21 g, 8.56 mmol) was added dropwise at 0° C. under $N_2$. The mixture was stirred at 0° C. for 2 h under $N_2$. The reaction mixture was quenched with $H_2O$ (80 mL) at 0° C. and extracted with EtOAc (50 mL×3). The combined organic layers were washed with brine (50 mL), dried over anhydrous $Na_2SO_4$, filtered and concentrated under reduced pressure. The residue was purified by silica gel flash chromatography (eluent: 0~6% of EtOAc in Petroleum ether) to give the title compound (1.65 g, 77% yield) as a yellow oil. MS: m/z=271.8, 273.8 $[M-H]^-$. 3H NMR (400 MHZ, Chloroform-d)δ 7.44 (d,)=2.4 Hz, 1H), 7.37-7.30 (m, 1H), 7.25-7.20 (m, 1H), 7.08-7.03 (m, 1H), 5.45-5.18 (m, 1H). 1F NMR (376 MHz, Chloroform-d) δ −133.58.

Step 9: 4-Bromo-6-fluoro-5-(methoxy-$d_3$) naphthalen-2-yl trifluoromethanesulfonate To a solution of 4-bromo-6-fluoro-5-(methoxy-$d_3$) naphthalen-2-ol (1.65 g, 6.02 mmol) in $CH_2Cl_2$ (60 mL) was added DIPEA (3.15 mL, 18.1 mmol). Then Tf2O (1.19 mL, 7.22 mmol) was added dropwise at 0° C. under $N_2$. The mixture was stirred at 0° C. for 0.5 h under $N_2$. The reaction mixture was quenched with $H_2O$ (50 mL) and extracted with EtOAc (100 mL×2). The combined organic layers were washed with brine (50 mL), dried over anhydrous $Na_2SO_4$, filtered and concentrated under reduced pressure. The residue was purified by silica gel flash chromatography (eluent: 0~15% of EtOAc in Petroleum ether) to give the title compound (2.3 g, 94% yield) as a yellow oil. $^1$H NMR (400 MHz, Chloroform-d) δ 7.77-7.66 (m, 2H), 7.64-7.58 (m, 1H), 7.50-7.42 (m, 1H), $^{19}$F. NMR (376 MHz, Chloroform-d) 6-72.65, −127.40.

Step 10: N-(4-bromo-6-fluoro-5-(methoxy-$d_3$) naphthalen-2-yl)-1,1-diphenylmethanimine A mixture of 4-bromo-6-fluoro-5-(methoxy-$d_3$) naphthalen-2-yl trifluoromethanesulfonate (2.2 g, 5.42 mmol), diphenylmethanimine (982 mg, 5.42 mmol), XantPhosPdG3 (514 mg, 542 μmol) and $Cs_2CO_3$ (5.29 g, 16.3 mmol) in 1,4-dioxane (30 mL) was degassed, purged with $N_2$ three times, and stirred at 80° C. for 8 h under $N_2$ atmosphere. The reaction mixture was concentrated under reduced pressure. The residue was purified by silica gel flash chromatography (eluent: 0~2% of EtOAc in Petroleum ether) to give the title compound (900 mg, 36% yield) as a yellow oil. $^1H$ NMR (400 MHz, Chloroform-d) & 7.79-7.74 (m, 2H), 7.53-7.48 (m, 1H), 7.45-7.40 (m, 2H), 7.33-7.27 (m, 5H), 7.24-7.18 (m, 1H), 7.17-7.12 (m, 2H), 7.02 (d,.J=1.6 Hz, 1H). $^{19}F$ NMR (376 MHz, Chloroform-d) δ −132.05.

Step 11: N-(6-Fluoro-5-(methoxy-$d_3$)-4-(4,4,5,5-tetramethyl-1,3,2-dioxaborolan-2-yl) naphthalen-2-yl)-1,1-diphenylmethanimine & 6-fluoro-5-(methoxy-$d_3$)-4-(4,4,5,5-tetramethyl-1,3,2-dioxaborolan-2-yl) naphthalen-2-amine A mixture of N-(4-bromo-6-fluoro-5-(methoxy-$d_3$) naphthalen-2-yl)-1,1-diphenylmethanimine (850 mg, 1.94 mmol), 4,4,4',4',5,5,5',5'-octamethyl-2,2'-bi (1,3,2-dioxaborolane) (592 mg, 2.33 mmol), CysPPdG3 (159 mg, 194 μmol) and KOAc (572 mg, 5.83 mmol) in 1,4-dioxane (18 mL) was degassed, purged with $N_2$ three times, and stirred at 100° C. for 1 h under $N_2$ atmosphere. The reaction mixture was concentrated under reduced pressure. The residue was purified by silica gel flash chromatography (eluent: 0~100% of EtOAc in Petroleum ether) to give the title compound (Intermediate 80, 400 mg, 41% yield) as a yellow solid and the title compound (Intermediate 81, 400 mg, 51% yield) as a yellow solid. Spectrum for Intermediate 80: MS: m/z=485.3 $[M+H]^+$. $^1H$ NMR (400 MHZ, Chloroform-d)δ 7.77 (d, J=7.6, 2H), 7.50-7.37 (m, 3H), 7.25-7.17 (m, 4H), 7.17-7.07 (m, 4H), 6.95 (s, 1H), 1.38 (s, 12H). $^{19}F$ NMR (376 MHz, Chloroform-d) δ −134.96. Spectrum for Intermediate 81: MS: m/z=321.1 $[M+H]^+$. $^1H$ NMR (400 MHz, Chloroform-d) δ 7.24-7.20 (m, 1H), 7.17-7.11 (m, 1H), 6.99 (s, 1H), 6.95-6.92 (m, 1H), 1.24 (s, 12H). $^{19}F$ NMR (376 MHz, Chloroform-d) δ −137.97.

Intermediate 82 and 83: Ethyl (1R, 7a′S)-2-bromo-2-fluoro-5′-oxodihydro-1′H,3′H-spiro[cyclopropane-1,2′-pyrrolizine]-7a′(5′H)-carboxylate & ethyl (1S,7a′S)-2-bromo-2-fluoro-5′-oxodihydro-1′H,3′H-spiro[cyclopropane-1,2′-pyrrolizine]-7a′(5′H)-carboxylate

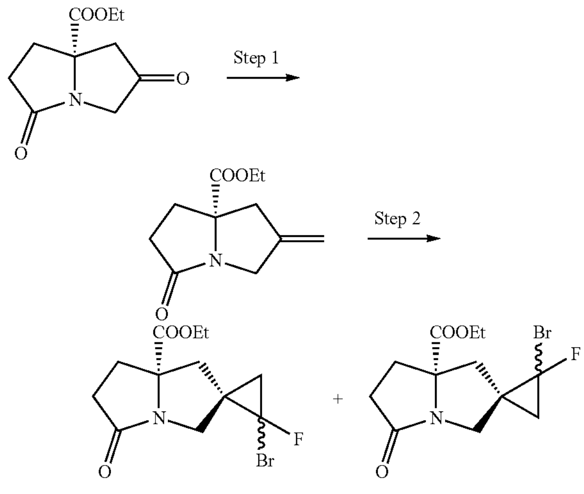

Intermediate 82

Intermediate 83

Step 1: Ethyl(S)-2-methylene-5-oxotetrahydro-1H-pyrrolizine-7a (5H)-carboxylate

To a solution of methyl (triphenyl)phosphonium bromide (37.21 g, 104.16 mmol) in THF (200 mL) was added dropwise t-BuOK (94.69 mL, 1 M in THF) at 0° C. under $N_2$. The reaction mixture was stirred at 60° C. for 1 h. The reaction mixture was cooled to 25° C. A solution of ethyl (S)-2,5-dioxotetrahydro-1/-pyrrolizine-7a (5H)-carboxylate (10 g, 47.4 mmol) in THF (200 mL) was added dropwise to the above mixture at 25° C. The mixture was stirred for another 1 h at the same temperature. The reaction mixture was quenched with sat. NHACl aq. (300 mL) and extracted with EtOAc (300 mL×3). The combined organic layers were washed with brine (100 mL), dried over anhydrous $Na_2SO_4$, filtered and concentrated under reduced pressure. The residue was purified by silica gel flash chromatography (eluent: 20~50% EtOAc in petroleum ether) to give the title compound (6.9 g, 18% yield) as a yellow oil. MS: m/z=210.1 $[M+H]^+$. 3H NMR (400 MHZ, Chloroform-d)δ 5.16-4.95 (m, 2H), 4.29 (d, J=15.6 Hz, 1H), 4.20 (q, J=7.2 Hz, 2H), 3.72 (d, J=15.6 Hz, 1H), 3.05 (d, J=16.0 Hz, 1H), 2.85-2.71 (m, 1H), 2.66-2.56 (m, 1H), 2.53-2.39 (m, 2H), 2.12 (td, J=10.4, 12.8 Hz, 1H), 1.27 (,)=7.2 Hz, 3H).

Step 2: Ethyl (1R,7a'S)-2-bromo-2-fluoro-5'-oxodihydro-1'H,3'H-spiro[cyclopropane-1,2'-pyrrolizine]-7a'(5'H)-carboxylate & ethyl (15,7a'S)-2-bromo-2-fluoro-5'-oxodihydro-1'H,3'H-spiro[cyclopropane-1,2'-pyrrolizine]-7a'(5'H)-carboxylate A mixture of ethyl(S)-2-methylene-5-oxotetrahydro-1/-pyrrolizine-7a (5H)-carboxylate (6.9 g, 33.0 mmol), dibromo (fluoro) methane (18.7 g, 97.5 mmol, 11.0 mL) and benzyl (triethyl) ammonium chloride (740 mg, 3.25 mmol) in $CH_2Cl_2$ (100 mL) and NaOH (20 mL, 50% in water) was degassed, purged with $N_2$ three times, and stirred at 40° C. for 16 h under $N_2$ atmosphere. The reaction mixture was diluted with water (200 mL) and extracted with EtOAc (200 mL×3). The combined organic layers were washed with brine (100 mL), dried over anhydrous $Na_2SO_4$, filtered and concentrated under reduced pressure. The residue was purified by silica gel flash chromatography (eluent: 20%~60% EtOAc in petroleum ether) to give the title compound (Intermediate 82, 2.0 g, 19% yield, the first peak) as a yellow oil and the title compound (Intermediate 83, 1.2 g, 12% yield, the second peak) as a yellow oil. Spectra for Intermediate 82: MS: m/z=319.9, 321.9 $[M+H]^+$. $^1H$ NMR (400 MHZ, Chloroform-d)δ 4.25 (qd, J=1.2, 7.2 Hz, 2H), 4.14-4.01 (m, 1H), 3.19-2.96 (m, 1H), 2.89-2.74 (m, 1H), 2.63-2.45 (m, 2H), 2.36-2.12 (m, 3H), 1.72-1.58 (m, 1H), 1.45-1.33 (m, 1H), 1.30 (t, J=7.2 Hz, 3H). $^{19}F$. NMR (376 MHz, Chloroform-d) δ −134.78, −135.52. Spectra for Intermediate 83: MS: m/z=320.0, 322.0 $[M+H]^+$. 3H NMR (400 MHz, Chloroform-d) δ 4.36-4.20 (m, 2H), 3.79-3.63 (m, 1H), 3.48 (t, J=11.8 Hz, 1H), 2.86-2.67 (m, 2H), 2.62-2.44 (m, 2H), 2.21-1.97 (m, 2H), 1.66 (dd, J=8.4, 17.2 Hz, 1H), 1.46-1.37 (m, 1H), 1.34 (td, J=3.2, 7.2 Hz, 3H). $^{19}F$ NMR (376 MHz, Chloroform-d) δ −136.09, −136.57.

Intermediate 84 & 85: Ethyl (1S, 2S, 7a'S)-2-fluoro-5'-oxodihydro-1'H,3'H-spiro[cyclopropane-1,2'-pyrrolizine]-7a'(5'H)-carboxylate & ethyl (1S, 2R, 7a'S)-2-fluoro-5'-oxodihydro-1'H,3'H-spiro[cyclopropane-1,2'-pyrrolizine]-7a'(5'H)-carboxylate

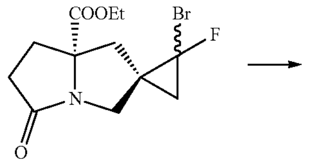

Intermediate 83

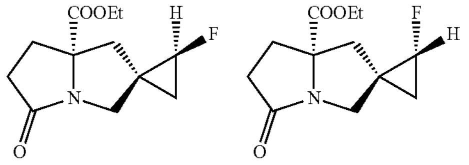

Intermediate 84 Intermediate 85

To a solution of Intermediate 83 (1.20 g, 3.75 mmol) in EtOH (24 mL) were added $NH_4Cl$ (4.01 g, 75.0 mmol) and Zn (2.21 g, 33.73 mmol) in batches. The mixture was stirred at 80° C. for 6 h under $N_2$. The reaction mixture was filtered and concentrated under reduced pressure. The residue was purified by prep-HPLC(column: $CD_{02}$-Waters Xbidge BEH $C_{18\ 150\times25}$ x 10 μm, mobile phase: [water ($NH_3$ $H_2O$)-ACN]; gradient: 16%~36% B over 13 min) to give the title compound (Intermediate 84, $^{19}$FNMR: −211.68 ppm, 250 mg, 28% yield, LCMS peak 1, retention time: 1.122 min) as a yellow oil and the title compound (Intermediate 85, 19FNMR: −210.32 ppm, 340 mg, 38% yield, LCMS peak 2, retention time: 1.178 min) as a yellow oil. Spectra for Intermediate 84: MS: m/z=242.1 $[M+H]^+$. $^1$H NMR (400 MHz, Chloroform-d) δ 4.49-4.18 (m, 3H), 3.69 (d, J=11.6 Hz, 1H), 3.32 (d, J=11.6 Hz, 1H), 2.92-2.76 (m, 1H), 2.60-2.42 (m, 2H), 2.20-1.97 (m, 2H), 1.85 (dd, J=7.2, 12.8 Hz, 1H), 1.31 (t, J=7.2 Hz, 3H), 1.07-0.88 (m, 2H), $^{19}$F. NMR (376 MHz, Chloroform-d) δ −211.68. Spectra for Intermediate 85: MS: m/z=242.1 $[M+H]^+$. $^1$H NMR (400 MHZ, Chloroform-d) δ 4.50-4.28 (m, 1H), 4.28-4.16 (m, 2H), 3.55 (dd, J=5.6, 11.2 Hz, 1H), 2.98 (d,J=11.2 Hz, 1H), 2.85-2.72 (m, 1H), 2.69-2.57 (m, 1H), 2.54-2.42 (m, 2H), 2.24-2.11 (m, 1H), 2.02 (d, J=12.8 Hz, 1H), 1.30 (t, J=7.2 Hz, 3H), 1.11-0.91 (m, 2H). $^{19}$F NMR (376 MHz, Chloroform-d) δ −210.32.

Intermediate 86: ((1S, 2S, 7a'S)-2-Fluorodihydro-1'H,3'H-spiro[cyclopropane-1,2'-pyrrolizin]-7a'(5'H)-yl)methanol

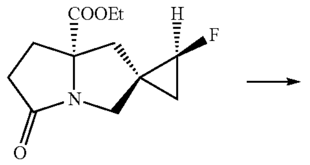

Intermediate 84

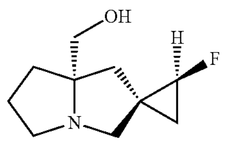

Intermediate 86

To a solution of Intermediate 84 (150 mg, 622 μmol) in THF (5 mL) was added dropwise LiAlH4 (1.24 mL, 2.5 M in THF) at 0° C. under $N_2$. The mixture was stirred at 65° C. for 2 h under $N_2$. The reaction mixture was quenched with $Na_2SO_4\cdot10H_2O$ (300 mg) slowly. The organic layer was dried over anhydrous $Na_2SO_4$, filtered and concentrated under reduced pressure. The residue was purified by silica gel flash chromatography (eluent: 0~15% MeOH in $CH_2Cl_2$) to give the title compound (Intermediate 86, 95 mg, 82% yield, structure tentatively assigned) as a yellow oil. MS: m/z=185.8 $[M+H]^+$. $^1$H NMR (400 MHZ, Chloroform-d)δ 4.64-4.32 (m, 1H), 3.46-3.30 (m, 2H), 3.25 (d, J=10.8 Hz, 1H), 3.13-3.04 (m, 1H), 2.88-2.77 (m, 2H), 2.02-1.77 (m, 4H), 1.75-1.67 (m, 2H), 1.01-0.78 (m, 2H). $^{19}$F NMR (376 MHZ, Chloroform-d) δ −213.17.

Intermediate 87: ((1S, 2R, 7a'S)-2-fluorodihydro-1'H,3'H-spiro[cyclopropane-1,2'-pyrrolizin]-7a'(5'H)-yl)methanol

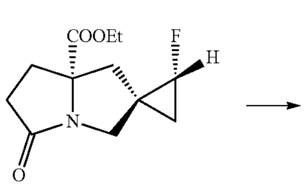

Intermediate 85

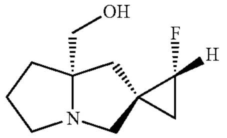

Intermediate 87

Intermediate 87 (structure tentatively assigned) was prepared in a manner similar to Intermediate 86. MS: m/z=185.8 $[M+H]^+$. $^1$H NMR (400 MHZ, Chloroform-d) 4.56-4.33 (m, 1H), 3.47-3.33 (m, 2H), 3.11-3.03 (m, 1H), 2.90-2.62 (m, 4H), 2.01-1.83 (m, 5H), 1.80-1.72 (m, 1H), 0.99-0.80 (m, 2H). $^{19}$F NMR (376 MHz, Chloroform-d) δ −210.87.

Intermediate 88 & 89: Ethyl (1R, 2R, 7a'S)-2-fluoro-5'-oxodihydro-1'H,3'H-spiro[cyclopropane-1,2'-pyrrolizine]-7a'(5'H)-carboxylate & ethyl (1R, 2S, 7a'S)-2-fluoro-5'-oxodihydro-1'H,3'H-spiro[cyclopropane-1,2'-pyrrolizine]-7a'(5'H)-carboxylate

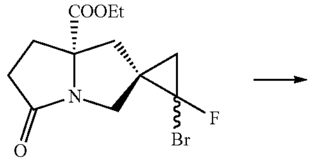

Intermediate 82

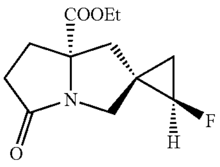

+

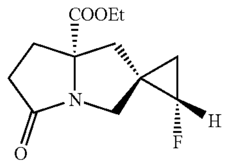

Intermediate 88 Intermediate 89

To a solution of Intermediate 82 (2.05 g, 6.40 mmol) in EtOH (40 mL) were added Zn (2.09 g, 32.0 mmol) and $NH_4Cl$ (3.08 g, 57.63 mmol) slowly under $N_2$. The mixture was stirred at 70° C. for 8 h under $N_2$. The reaction mixture was filtered, diluted with $H_2O$ (50 mL), and extracted with $CH_2Cl_2$ (100 mL×2). The combined organic layers were washed with brine (200 mL), dried over anhydrous $Na_2SO_4$, filtered and the filtrate was concentrated under reduced pressure. The residue was purified by silica gel flash chromatography (eluent: 0~40% of ethyl acetate in petroleum ether) to give crude product. Then the crude product was purified by prep-HPLC (column: CD06-Waters Xbidge C18 150×40×10 μm; mobile phase: [water ($NH_3$ $H_2O$)-ACN];

gradient: 15%~45% B over 10 min) to give the title compound (Intermediate 88, 19F NMR: −211.75 ppm, 600 mg, 31% yield) and the title compound (Intermediate 89, 1° F. NMR: −211.09 ppm, 595 mg, 37% yield). Spectra for Intermediate 88: MS: m/z=242.0 $[M+H]^+$. 1H NMR (400 MHZ, Chloroform-d)δ 4.63-4.37 (m, 1H), 4.23 (q, J=7.2 Hz, 2H), 3.98 (d, J=12.0 Hz, 1H), 3.10 (d, J=12.0 Hz, 1H), 2.87-2.69 (m, 1H), 2.59-2.39 (m, 2H), 2.18-1.93 (m, 3H), 1.29 (t, J=7.2 Hz, 3H), 1.05-0.85 (m, 2H). $^{19}$F. NMR (376 MHz, Chloroform-d)δ −211.75. Spectra for Intermediate 89: MS: m/z=242.1 $[M+H]^+$. $^1$H NMR (400 MHZ, Chloroform-d)δ 4.67-4.40 (m, 1H), 4.25 (q,)=7.2 Hz, 2H), 3.65 (dd, J=2.0, 11.6 Hz, 1H), 2.91 (dd, J=6.0, 11.6 Hz, 1H), 2.83-2.72 (m, 1H), 2.66-2.57 (m, 1H), 2.50-2.41 (m, 1H), 2.36 (d, J=13.2 Hz, 1H), 2.19-2.07 (m, 2H), 1.31 (t, J=7.2 Hz, 3H), 1.09-0.98 (m, 1H), 0.93-0.84 (m, 1H). $^{19}$F NMR (376 MHz, Chloroform-d) 6-211.09.

Intermediate 90: ((1R, 2R, 7a'S)-2-fluorodihydro-1'H,3'H-spiro[cyclopropane-1,2'-pyrrolizin]-7a'(5'H)-yl)methanol

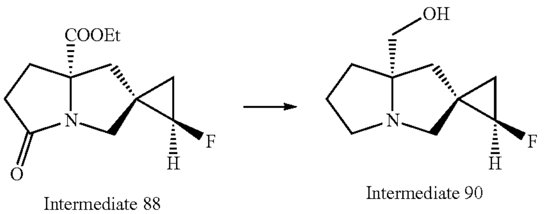

Intermediate 88

Intermediate 90

To a solution of Intermediate 88 (300 mg, 1.24 mmol) in THF (6 mL) was added dropwise LiAIH4 (2.49 mL, 2.5 M in THF) at 0° C. under $N_2$. The mixture was stirred at 0° C. for 0.5 h under $N_2$. Then the mixture was stirred at 70° C. for 2.5 h under $N_2$. The reaction mixture was quenched with $Na_2SO_4$. $10H_2O$) (3 g) slowly, filtered and the filter cake was washed with EtOAc (80 mL). The combined organic layers were dried over anhydrous $Na_2SO_4$, filtered and concentrated under reduced pressure. The residue was purified by silica gel flash chromatography (cluent: 0~15% of MeOH in $CH_2Cl_2$) to give the title compound (Intermediate 90, 178 mg, 77% yield, structure tentatively assigned) as an off-white solid. $^1$H NMR (400 MHz, Chloroform-d) & 4.61-4.33 (m, 1H), 3.43-3.26 (m, 2H), 3.21-3.11 (m, 2H), 2.85 (d, J=12.0 Hz, 1H), 2.78-2.66 (m, 1H), 1.92-1.71 (m, 5H), 1.48 (d, J=13.2 Hz, 1H), 0.94-0.76 (m, 2H). $^{19}$F NMR (376 MHz, Chloroform-d) δ −207.27.

Intermediate 91: ((1R, 2S, 7a'S)-2-fluorodihydro-1'H,3'H-spiro[cyclopropane-1,2'-pyrrolizin]-7a'(5'H)-yl)methanol

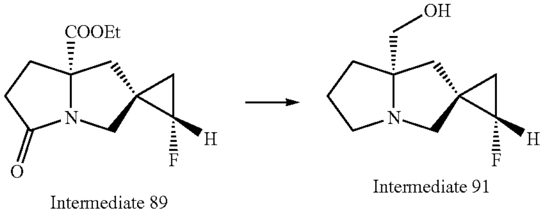

Intermediate 89

Intermediate 91

To a solution of Intermediate 89 (300 mg, 1.24 mmol) in THF (6 mL) was added dropwise $LiAlH_4$ (2.5 M in THE, 2.49 mL) at 0° C. under $N_2$. The mixture was stirred at 0° C. for 0.5 h under $N_2$, and then at 70° C. for 2.5 h under $N_2$. The reaction mixture was quenched with $Na_2SO_4 \cdot 10 \cdot H_2O$ (3 g) slowly and washed with EtOAc (80 mL). The combined organic layers were dried over anhydrous $Na_2SO_4$, filtered and concentrated under reduced pressure. The residue was purified by silica gel flash chromatography (eluent: 0~20% of MeOH in $CH_2Cl_2$) to give the title compound (Intermediate 91, 200 mg, 87% yield, structure tentatively assigned) as a colorless gum. MS: m/z=185.8 $[M+H]^+$. $^1$H NMR (400 MHZ, Chloroform-d)δ 4.66-4.36 (m, 1H), 3.46-3.41 (m, 1H), 3.40-3.33 (m, 1H), 3.21-3.14 (m, 1H), 3.00 (dd, J=7.2, 12.0 Hz, 1H), 2.82-2.74 (m, 1H), 2.47 (d, J=11.6 Hz, 1H), 2.04-1.98 (m, 1H), 1.94-1.84 (m, 3H), 1.83-1.68 (m, 2H), 0.94-0.83 (m, 1H), 0.79-0.71 (m, 1H). $^{19}$F. NMR (376 MHZ, Chloroform-d) δ −209.92.

Intermediate 92: 2-Fluoro-N,N-bis(4-methoxybenzyl)-3-methyl-5-(4,4,5,5-tetramethyl-1,3,2-dioxaborolan-2-yl)-4-(trifluoromethyl)aniline

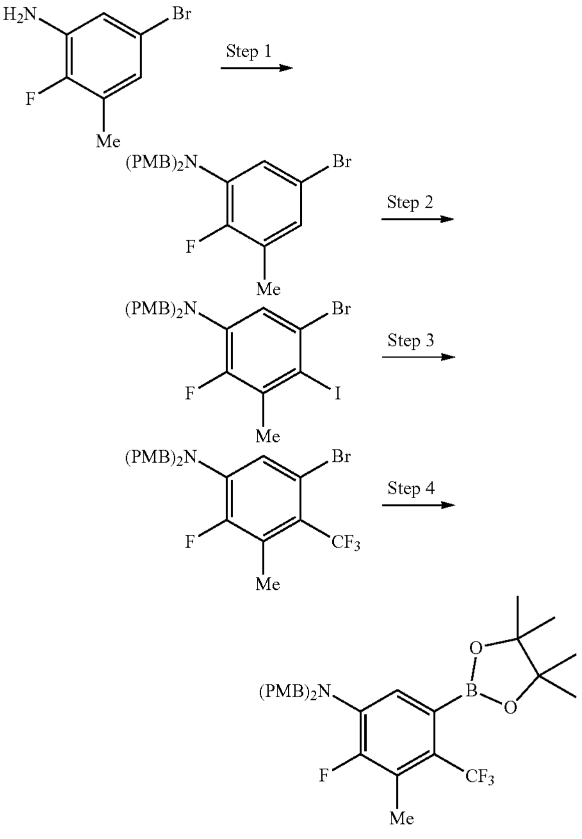

Intermediate 92

Step 1: 5-Bromo-2-fluoro-N,N-bis(4-methoxybenzyl)-3-methylaniline

To an ice-cooled solution of 5-bromo-2-fluoro-3-methylaniline (2 g, 9.80 mmol) in DMF (16.7 mL) was added NaH (0.71 g, 29.40 mmol, 60% dispersion in mineral oil) under nitrogen atmosphere. After stirring in an ice bath for 30 min, PMBCl (3.07 g, 19.60 mmol) was added to the above mixture in an ice bath. The ice bath was removed, and the reaction mixture was stirred at room temperature for an additional 2 hours. The resulting mixture was quenched with sat. aq. $NH_4Cl$ (50 mL) in an ice bath and extracted with EtOAc (4×50 mL). The combined organic layers were washed with brine (100 mL), dried over anhydrous $Na_2SO_4$, filtered and concentrated under reduced pressure. The residue was purified by silica gel flash chromatography, eluted with PE/EA (10: 1) to afford the title compound (3.7 g, 84% yield) as a light yellow oil. MS: m/z=443.90, 445.90 $[M+H]^+$. $^1H$ NMR (400 MHz, Chloroform-d) δ 7.18-7.16 (m, 4H), 6.88-6.81 (m, 6H), 4.19 (s, 4H), 3.79 (s, 6H), 3.79 (s, 6H), 2.24 (d, J=2.8 Hz, 3H). $^{19}F$ NMR (376 MHz, Chloroform-d) δ −128.45 (s, 1F).

Step 2: 5-Bromo-2-fluoro-4-iodo-N,N-bis(4-methoxybenzyl)-3-methylaniline

To an ice-cooled solution of 5-bromo-2-fluoro-N,N-bis (4-methoxybenzyl)-3-methylaniline (2.7 g, 6.07 mmol) in acetic acid (22 mL) was added NIS (1.50 g, 6.68 mmol) under nitrogen atmosphere. The ice bath was removed, and the reaction mixture was stirred at room temperature for 1.5 hours. The resulting mixture was quenched with sat. aq. NazS2O3 (15 mL) in an ice bath, diluted with EtOAc (150 mL), and washed with water (4×30 mL). The organic layer was dried over anhydrous $Na_2SO_4$, filtered, and concentrated under reduced pressure. The residue was purified by silica gel flash chromatography, eluted with PE/EA (10: 1) to afford the title compound (2.7 g, 77% yield) as a light yellow oil. MS: m/z=570.10, 572.10 $[M+H]^+$. $^1H$ NMR (400 MHz, Chloroform-d) δ 7.17-7.00 (m, 5H), 6.85-6.81 (m, 4H), 4.23 (s, 4H), 3.79 (s, 6H), 2.47 (d, J=3.6 Hz, 3H), $^{19}F$ NMR (376 MHz, Chloroform-d) δ −119.22-−119.30 (d, 1F).

Step 3: 5-Bromo-2-fluoro-N,N-bis(4-methoxybenzyl)-3-methyl-4-(trifluoromethyl) aniline To a stirred solution of 5-bromo-2-fluoro-4-iodo-N,N-bis (4-methoxybenzyl)-3-methylaniline (900 mg, 1.57 mmol) and CuI (3.00 g, 15.78 mmol) in DMF (9 mL) was added methyl 2,2-difluoro-2-(fluorosulfonyl)acetate (2.91 g, 15.14 mmol) at room temperature under nitrogen atmosphere. The reaction mixture was heated at 75° C. for 4 hours. The resulting mixture was cooled to room temperature, diluted with water (30 mL) and extracted with EtOAc (3×30 mL). The combined organic layers were washed with brine (30 mL), dried over anhydrous $Na_2SO_4$, filtered and concentrated under reduced pressure. The residue was purified by silica gel flash chromatography, eluted with 0-10% EA in PE to afford the title compound (700 mg, 86% yield) as a colorless oil. MS: m/z=512.10, 514.10 $[M+H]^+$. $^1H$ NMR (400 MHZ, Chloroform-d)δ 7.18-6.83 (m, 9H), 4.33 (s, 4H), 3.80 (s, 6H), 2.42-2.35 (m, 3H). $^{19}F$ NMR (376 MHZ, Chloroform-d) δ −53.01-−54.40 (m, 3F), −138.23 (s, IF).

Step 4: 2-Fluoro-N,N-bis(4-methoxybenzyl)-3-methyl-5-(4,4,5,5-tetramethyl-1,3,2-dioxaborolan-2-yl)-4-(trifluoromethyl) aniline To a stirred solution of 5-bromo-2-fluoro-N,N-bis [(4-methoxyphenyl)methyl]-3-methyl-4-(trifluoromethyl) aniline (700 mg, 1.36 mmol) and bis (pinacolato)diboron (693.90 mg, 2.732 mmol) in 1,4-dioxane (7.0 mL) were added Pd (dppf)$Cl_2$-DCM (222.60 mg, 0.27 mmol) and KOAc (402.27 mg, 4.09 mmol) at room temperature under nitrogen atmosphere. The reaction mixture was heated at 110° C. for 2 hours. The resulting mixture was cooled to room temperature, diluted with EtOAc (30 mL), washed with brine (2×15 mL), dried over anhydrous $Na_2SO_4$, filtered and concentrated under reduced pressure. The residue was purified by silica gel flash chromatography, eluted with PE/EA (10: 1) to afford the title compound (Intermediate 92, 300 mg, 39% yield) as a colorless oil. MS: m/z=560.40 $[M+H]^{+}$ Intermediate 93: ((7a'S)-2,2-Difluorodihydro-1'H,3'H-spiro[cyclopropane-1,2'-pyrrolizin]-7a'(5'H)-yl)methanol

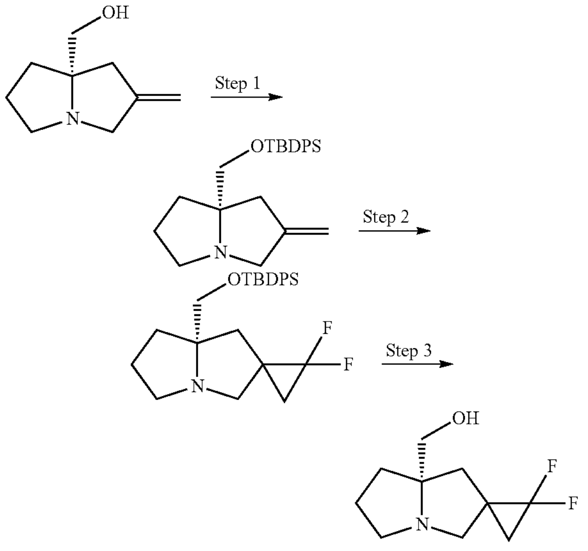

Intermediate 93

Step 1: (S)-7a-(((tert-Butyldiphenylsilyl)oxy)methyl)-2-methylenehexahydro-1H-pyrrolizine To an ice-cooled mixture of(S)-(2-methylenetetrahydro-1H-pyrrolizin-7a (5H)-yl) methanol (3 g, 19.57 mmol) and imidazole (3327.31 mg, 48.94 mmol) in DMF (30 mL) under nitrogen atmosphere was added TBDPSCl (6457.80 mg, 23.49 mmol). The ice bath was removed, and the reaction mixture was stirred at room temperature for 16 hours. The resulting mixture was diluted with EA (500 mL), washed with water (3×100 mL) and brine (100 mL). The organic layer was concentrated under reduced pressure. The residue was purified by silica gel flash chromatography, eluted with 3% MeOH in DCM to afford the title compound (6.5 g, 84% yield) as a yellow oil. MS: m/z=392.20 $[M+H]^{+}$ Step 2: (7a'S)-7a'-(((tert-Butyldiphenylsilyl)oxy)methyl)-2,2-difluorotetrahydro-1',3'H-spiro[cyclopropane-1,2'-pyrrolizine]

To a solution of(S)-7a-(((tert-butyldiphenylsilyl)oxy)methyl)-2-methylenehexahydro-1H-pyrrolizine (4 g, 10.21 mmol) and NaI (765.49 mg, 5.10 mmol) in THF (50 mL) under nitrogen atmosphere was added TMSCF3 (5083.23 mg, 35.74 mmol) at room temperature. The reaction mixture was heated at 65° C. for 2.5 hours. The resulting mixture was cooled to room temperature, diluted with DCM (500 mL), washed with sat. aq. NazS2O3 (3×100 mL), dried over with $Na_2SO_4$, filtered and concentrated under reduced pressure. The residue was purified by silica gel flash chromatography, eluted with 5% MeOH in DCM to afford the title compound (1.0 g, 22% yield) as a brown oil. MS: m/z=442.15 $[M+H]^{+}$ Step 3: ((7a'S)-2,2-Difluorodihydro-1'H,3'H-spiro [cyclopropane-1,2'-pyrrolizin]-7a'(5'H)-yl) methanol To a solution of (7a'S)-7a'-(((tert-butyldiphenylsilyl)oxy) methyl)-2,2-difluorotetrahydro-l'H,3'H-spiro[cyclopropane-1,2'-pyrrolizine](1.0 g, 2.26 mmol) in MeOH (10 mL) under nitrogen atmosphere was added $NH_4F$ (3354.51 mg, 90.56 mmol) at room temperature. The reaction mixture was heated at 65° C. for 4 hours. The resulting mixture was cooled to room temperature and concentrated under reduced pressure. The residue was purified by silica gel flash chromatography, eluted with 15% MeOH in DCM to afford the title compound (Intermediate 93, 450 mg, crude) as a yellow oil. MS: m/z=204.10 $[M+H]^+$.

Intermediate 94 & 95: Ethyl (6'R,7a'R)-6'-fluoro-3'oxotetrahydrospiro [cyclopropane-1,1'-pyrrolizine]-7a'(5'H)-carboxylate-6'-d & ethyl (6'S,7a'R)-6'-fluoro-3'-oxotetrahydrospiro[cyclopropane-1,1'-pyrrolizine]-7a'(5'H)-carboxylate-6'-d

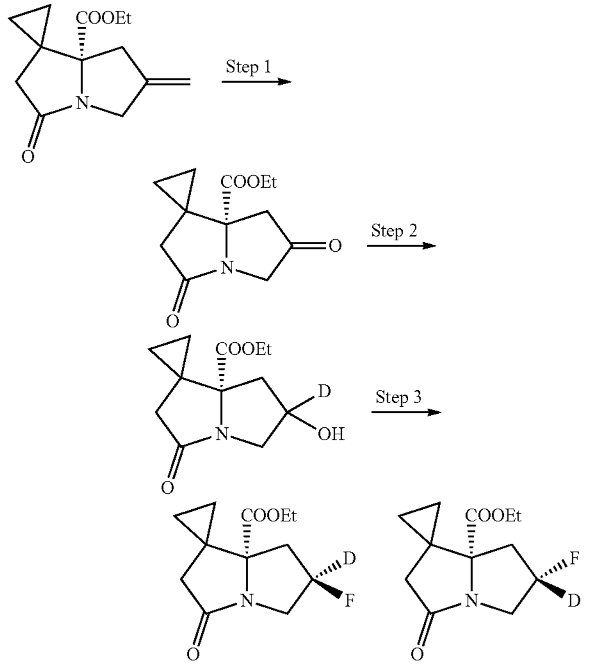

Intermediate 94 Intermediate 95

Step 1: Ethyl (R)-3',6'-Dioxotetrahydrospiro[cyclopropane-1,1'-pyrrolizine]-7a'(5'H)-carboxylate To a solution of ethyl (R)-6'-methylene-3'-oxotetrahydrospiro[cyclopropane-1,1'-pyrrolizine]-7a (5'H)-carboxylate (1.8 g, 7.65 mmol) and RuCl (60 mg, 268 μmol) in $CH_2Cl$ (20 mL), ACN (20 mL) and $H_2O$ (20 mL) was added $NaIO_4$ (9.82 g, 45.9 mmol) at 0° C. The mixture was stirred at 25° C. for 1 h. The reaction mixture was filtered and extracted with EtOAc (500 mL). The combined organic layers were washed with 50% $Na_2S_2O_3$ aq. (200 mL) and washed with brine (100 mL×2), dried over anhydrous $Na_2SO_4$, filtered and concentrated under reduced pressure. The residue was purified by silica gel flash chromatography (eluent: 25~50% of EtOAc in petroleum ether) to give the title compound (1.66 g, 82% yield) as a white solid. MS: m/z=238.0 $[M+H]^+$. $^1H$ NMR (400 MHZ, Chloroform-d)δ 4.39-4.14 (m, 3H), 3.45 (d, J=18.8 Hz, 1H), 3.13 (d, J=16.8 Hz, 1H), 2.91 (d, J=17.6 Hz, 1H), 2.38 (d, J=17.6 Hz, 1H), 2.19 (d, J=16.8 Hz, 1H), 1.30 (t, J=7.2 Hz, 3H), 0.94-0.68 (m, 4H).

Step 2: Ethyl (7a'R)-6'-hydroxy-3'-oxotetrahydrospiro[cyclopropane-1,1'-pyrrolizine]-7a'(5'H)-carboxylate-6'-d To a solution of ethyl (R)-3',6'-dioxotetrahydrospiro[cyclopropane-1,1'-pyrrolizine]-7a'(5'H)-carboxylate (1.66 g, 7.00 mmol) in EtOH (20 mL) was added NaBD4 (80 mg, 2.10 mmol) at 0° C. under $N_2$. The mixture was stirred at 0° C. for 15 min under $N_2$. The reaction mixture was quenched with 1N HCl (0.5 mL) at 0° C. The mixture was concentrated under reduced pressure. The residue was purified by silica gel flash chromatography (eluent: 0~70% of EtOAc in petroleum ether) to give the title compound (1.6 g, 90% yield) as a colorless oil. MS: m/z=240.9 $[M+H]^+$. $^1H$ NMR (400 MHZ, Dimethylsulfoxide-$d_6$) δ 5.12 (m, 1H), 4.96 (s, 1H), 4.22~4.04 (m, 2H), 3.69-2.77 (m, 3H), 2.29-2.02 (m, 2H), 1.67-1.51 (m, 1H), 1.26-1.13 (m, 3H), 0.92-0.56 (m, 4H).

Step 3: Ethyl (6'R,7a'R)-6'-fluoro-3'-oxotetrahydrospiro[cyclopropane-1,1'-pyrrolizine]-7a'(5'H)-carboxylate-6'-d & ethyl (6'S,7a'R)-6'-fluoro-3'-oxotetrahydrospiro[cyclopropane-1,1'-pyrrolizine]-7a'(5'H)-carboxylate-6'-d To a mixture of ethyl (7a'R)-6'-hydroxy-3'-oxotetrahydrospiro[cyclopropane-1,1'-pyrrolizine]-7a'(5'H)-carboxylate-6'-d (2.0 g, 8.32 mmol) in $CH_2Cl_2$ (30 mL) was added DAST (2.2 mL, 16.7 mmol) at −70° C. under $N_2$. The mixture was stirred at 25° C. for 5 h under $N_2$. The reaction mixture was quenched with MeOH (10 mL) at 25° C. The mixture was concentrated under reduced pressure. The residue was purified by silica gel flash chromatography (eluent: 0~35% of EtOAc in petroleum ether) to give the title compound (Intermediate 94, 400 mg, 19% yield) and (eluent: 35~42% of EtOAc in petroleum ether) to give the title compound (Intermediate 95, 700 mg, 33% yield) as a white solid. Spectra for Intermediate 94: MS: m/z=243.1 $[M+H]^+$. $^1$HNMR (400 MHZ, Dimethylsulfoxide-$d_6$) δ 4.22-4.10 (m, 2H), 4.05-3.90 (m, 1H), 3.18-3.02 (m, 1H), 2.94 (d, J=16.8 Hz, 1H), 2.47-2.34 (m, 1H), 2.09-1.95 (m, 2H), 1.25-1.19 (m, 3H), 1.00-0.92 (m, 1H), 0.74-0.57 (m, 3H). $^{19}F$ NMR. (376 MHz, Dimethylsulfoxide-$d_6$) δ −176.26, −176.29. Spectra for Intermediate 95: MS: m/z=243.0 $[M+H]^+$. $^1$HNMR (400 MHZ, Dimethylsulfoxide-$d_6$) δ 4.21-4.09 (m, 2H), 4.00-3.83 (m, 1H), 3.21-3.06 (m, 1H), 2.95-2.86 (m, 1H), 2.44-2.33 (m, 1H), 2.15 (d, J=16.8 Hz, 1H), 2.00-1.78 (m, 1H), 1.19 (t, J=7.2 Hz, 3H), 0.88-0.80 (m, 1H), 0.73-0.60 (m, 3H). $^{19}F$ NMR (376 MHZ, Dimethylsulfoxide-$d_6$)$_8$-169.86.

Intermediate 96: ((6'R,7a'R)-6'-Fluorotetrahydrospiro [cyclopropane-1,1'-pyrrolizin]-7a'(5'H)-yl-3',3',6'-$d_3$)methan-$d_2$-ol

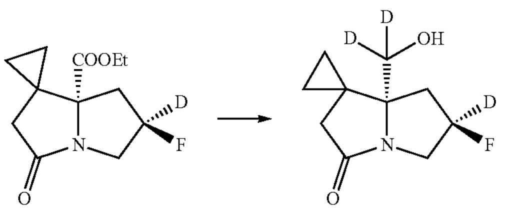

Intermediate 94 Intermediate 96

To a solution of Intermediate 94 (200 mg, 826 μmmol) in THF (10 mL) was added $LiAlD_4$ (95 mg, 2.06 mmol) at 0° C. under $N_2$. The mixture was stirred at 65° C. for 2 h. Then $D_2O$ (0.5 mL) was added to the reaction at 0° C. And then 15 wt % NaOH (0.5 mL) was added dropwise followed by addition of water (1.5 mL). The mixture was stirred at 20° C. for 0.5 h, dried over anhydrous $MgSO_4$, filtered and concentrated under reduced pressure. The residue was purified by silica gel flash chromatography ($CH_2Cl$/McOH (0.5% $NH_3$)=10/1 to 5/1) to give the title compound (210 mg, 64% yield) as a brown solid. $^1H$ NMR (400 MHz, Dimethylsulfoxide-$d_6$)δ: 3. 24-3.12 (m, 2H), 2.09-1.94 (m, 1H), 1.87-1.68 (m, 3H), 0.75-0.66 (m, 1H), 0.64-0.54 (m, 1H), 0.50-0.40 (m, 2H). $^{19}F$. NMR (376 MHz, Dimethylsulfoxide-$d_6$) δ −173.27.

Intermediate 97: ((6′S,7a′R)-6′-Fluorotetrahydrospiro [cyclopropane-1,1′-pyrrolizin]-7a′(5′H)-yl-3′,3′,6′-$d_3$)methan-$d_2$-ol

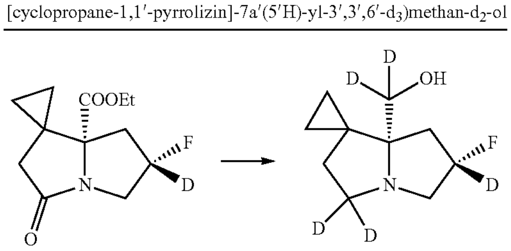

Intermediate 95 Intermediate 97

Intermediate 97 was prepared in a manner similar to Intermediate 96. JH NMR (400 MHZ, Chloroform-d)δ 4.54-4.05 (m, 1H), 3.23-3.12 (m, 1H), 2.97-2.82 (m, 1H), 2.07-1.95 (m, 1H), 1.84-1.49 (m, 3H), 0.94-0.85 (m, 1H), 0.50-0.31 (m, 3H). $^{19}F$ NMR (376 MHZ, Chloroform-d) δ −. 173.62, −173.63.

Intermediate 98: 2-Amino-7-fluoro-4-(4,4,5,5-tetramethyl-1,3,2-dioxaborolan-2-yl)benzo[b]thiophene-3-carbonitrile

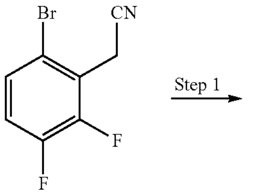

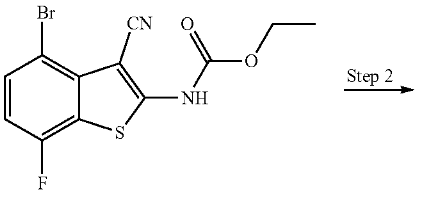

-continued

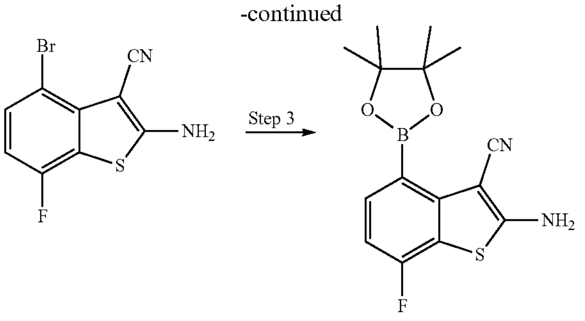

Intermediate 98

Step 1: Ethyl (4-bromo-3-cyano-7-fluorobenzo[b] thiophen-2-yl) carbamate

To a solution of 2-(6-bromo-2,3-difluorophenyl) acetonitrile (49 g, 211 mmol) in DMF (500 mL) was added/-BuOK (26 g, 232 mmol) at −10° C. and stirred for 30 min, then O-ethyl carbonisothiocyanatidate (27 mL, 229 mmol) was added at −10° C. The mixture was stirred at 100° C. for 2 h. The resulting mixture was added to water (500 mL), filtered and the filter cake was dried to give the title compound (67 g, crude) as a yellow solid, which was used in the next step without further purification.

Step 2: 2-Amino-4-bromo-7-fluorobenzo[b]thiophene-3-carbonitrile

To a solution of ethyl (4-bromo-3-cyano-7-fluorobenzo [b]thiophen-2-yl) carbamate (31 g, 90.3 mmol) in MeOH (115 mL) was added NaOH (19.9 g, 497 mmol) in Water (95 mL), then stirred at 65° C. for 18 h. The resulting mixture was added to water (300 mL), filtered to give a residue. The residue was purified by silica gel flash chromatography (eluent: 0~80% of EtOAc in petroleum ether) to give the title compound (29 g, 54% yield for two steps) as a yellow solid. 1H NMR (400 MHZ, Dimethylsulfoxide-$d_6$) δ 8.22 (s, 2H), 7.55-7.44 (m, 1H), 7.02-6.92 (m, 1H). $^{19}F$ NMR (376 MHZ, Dimethylsulfoxide-$d_6$) δ −118.10.

Step 3: 2-Amino-7-fluoro-4-(4,4,5,5-tetramethyl-1,3,2-dioxaborolan-2-yl)benzo[b]thiophene-3-carbonitrile To a solution of 2-amino-4-bromo-7-fluorobenzo[b]thiophene-3-carbonitrile (8 g, 29.5 mmol), 4,4,4',4',5,5,5',5'-octamethyl-2,2'-bi (1,3,2-dioxaborolane) (14.9 g, 59 mmol), Pd $(PPh_3)_4$ (4.09 g, 3.54 mmol) and KOAc (11.6 g, 118 mmol) in 1,4-dioxane (200 mL) was stirred at 95° C. for 6 h under nitrogen atmosphere. The reaction mixture was concentrated under reduced pressure to give a residue. The residue was purified by silica gel flash chromatography (eluent: 0~60% of EtOAc in petroleum ether) to give the title compound (3.8 g, 28% yield) as a yellow solid. 1H NMR (400 MHz, Dimethylsulfoxide-$d_6$) δ 8.10 (s, 2H), 7.50-7.46 (m, 1H), 7.00-6.95 (m, 1H), 1.33 (s, 12H). $^{19}F$ NMR (376 MHz, Dimethylsulfoxide-$d_6$) δ −113.79.

Intermediate 99: (6′-Methylenetetrahydrospiro[cyclopropane-1,1′-pyrrolizin]-7a′(5′H)-yl)methanol

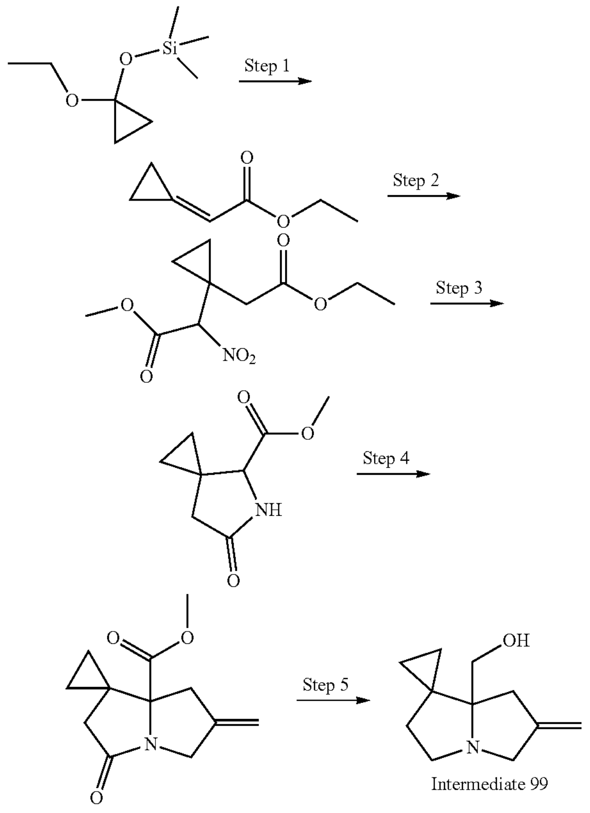

Intermediate 99

Step 1: Ethyl 2-cyclopropylideneacetate

To a solution of (1-ethoxycyclopropoxy)trimethylsilane (10 g, 28.68 mmol) in 2,5,8,11,14-pentaoxapentadecane (20 mL) under nitrogen atmosphere was added acetic acid (0.86 g, 14.34 mmol) at room temperature. The mixture was heated at 100° C. Ethyl 2-(triphenyl-lambda5-phosphanylidene)acetate (8.99 g, 25.81 mmol) in DCM (30 mL) was added dropwise at 100° C. for 2 hours. The reaction mixture was heated at 100° C. for 1 hour. The resulting mixture was purified by distillation under reduced pressure (0.1 atm) and the fraction was collected at 100° C. to afford the title compound (1.3 g, 18% yield) as a colorless oil. MS: m/z=127.05 $[M+H]^+$. $^1$H NMR (300 MHz, Chloroform-d) δ 6.23-6.22 (m, 1H), 4.25-4.18 (m, 2H), 1.49-1.41 (m, 2H), 1.32-1.19 (m, 5H).

Step 2: Methyl 2-(1-(2-ethoxy-2-oxoethyl)cyclopropyl)-2-nitroacetate

To a stirred solution of ethyl 2-cyclopropylideneacetate (1.3 g, 10.30 mmol) in THF (30 mL) under nitrogen atmosphere were added $K_2CO_3$ (1.63 g, 11.85 mmol) and methyl 2-nitroacetate (1.41 g, 11.85 mmol) at room temperature. The reaction mixture was heated at 65° C. for 16 hours. The resulting mixture was cooled to room temperature. The precipitated solids were collected by filtration and washed with EtOAc (3x30 mL). The filtrate was concentrated under reduced pressure. The residue was purified by silica gel column chromatography, eluted with PE/EA (4: 1) to afford the title compound (1.2 g, 47% yield) as a colorless oil. MS: m/z=246.00 $[M+H]^+$. JH NMR (300 MHz, Chloroform-d) δ 5.00 (s, 1H), 4.15-4.08 (m, 2H), 3.81 (s, 3H), 2.70-2.51 (m, 2H), 1.28-1.23 (m, 3H), 1.06-0.79 (m, 4H).

Step 3: Methyl 6-oxo-5-azaspiro[2.4]heptane-4-carboxylate

To a stirred solution of methyl 2-(1-(2-ethoxy-2-oxoethyl) cyclopropyl)-2-nitroacetate (1.2 g, 4.89 mmol) in acetic acid (0.6 mL) and methanol (12 mL) was added zinc (3.20 g, 48.93 mmol) at room temperature under nitrogen atmosphere. The reaction mixture was heated at 80° C. for 3 hours. The resulting mixture was cooled to room temperature, filtered and concentrated under reduced pressure. The residue was purified by silica gel flash chromatography, eluted with DCM/EtOAc (1: 3) to afford the title compound (0.45 g, 54% yield) as a white solid. MS: m/z=170.00 $[M+H]^+$. H NMR (300 MHz, DMSO-$d_6$) δ 8.11 (s, 1H), 3.74 (s, 1H), 3.67 (s, 3H), 2.44-2.39 (m, 1H), 2.02-1.96 (m, 1H), 0.84-0.55 (m, 4H).

Step 4: Methyl 6'-methylene-3'-oxotetrahydrospiro [cyclopropane-1,1'-pyrrolizine]-7a'(5' #)-carboxylate To a stirred solution of methyl 6-oxo-5-azaspiro[2.4] heptane-4-carboxylate (450 mg, 2.66 mmol) and 3-chloro-2-(chloromethyl) prop-1-ene (1.33 g, 10.64 mmol) in THF (6 mL) under nitrogen atmosphere was added LiHMDS (1 M in THF, 5.58 mL, 5.58 mmol) dropwise at −40° C. for 30 minutes. The reaction mixture was warmed to room temperature and stirred for 16 hours. The resulting mixture was quenched with sat. aq. NHACl (20 mL) and extracted with EtOAc (3x20 mL). The combined organic layers were washed with water (10 mL), dried over anhydrous $Na_2SO_4$, filtered and concentrated under reduced pressure. The residue was purified by silica gel flash chromatography, eluted with $CH_2Cl_2$/EA (1: 1) to afford the title compound (170 mg, 28% yield) as a colorless oil. MS: m/z=222.00 $[M+H]^+$. $^1$H NMR (300 MHZ, Acetonitrile-$d_3$) δ 5.07-5.00 (m, 2H), 4.26-4.20 (m, 1H), 3.70 (s, 3H), 3.59-3.54 (m, 1H), 2.94-2.77 (m, 2H), 2.49-2.48 (m, 1H), 2.18-2.12 (m, 1H), 0.90-0.87 (m, 1H), 0.71-0.64 (m, 3H).

Step 5: (6'-Methylenetetrahydrospiro[cyclopropane-1,1'-pyrrolizin]-7a'(5'H)-yl) methanol To an ice-cooled solution of methyl 6'-methylene-3'-oxotetrahydrospiro[cyclopropane-1,1'-pyrrolizine]-7a'(5'H)-carboxylate (170 mg, 0.76 mmol) in THF (2 mL) under nitrogen atmosphere was added LiAlH4 (0.77 mL, 1.536 mmol, 2 M in THF) dropwise. The ice bath was removed, and the reaction mixture was heated at 65° C. for 2 hours. The resulting mixture was cooled and quenched with water (0.05 mL), NaOH (0.05 mL, 15% in $H_2O$), and water (0.15 mL) in an ice bath. The resulting mixture was filtered and concentrated under reduced pressure. The residue was purified by silica gel flash chromatography, eluted with $CH_2Cl_2$/MeOH (10% $NH_4OH$) (1: 4) to afford the title compound (Intermediate 99, 90 mg, 65% yield) as a colorless oil. MS: m/z=180.05 $[M+H]^+$. JH NMR (300 MHz, Methanol-$d_4$) δ 4.96-4.93 (m, 2H), 3.77-3.64 (m, 1H), 3.43-3.35 (m, 3H), 3.19-3.09 (m, 1H), 2.84-2.72 (m, 1H), 2.50-2.41 (m, 1H), 2.31-2.23 (m, 1H), 2.04-1.91 (m, 1H), 1.87-1.74 (m, 1H), 0.92-0.81 (m, 1H), 0.61-0.48 (m, 3H).

Intermediate 100 & 101: (1S, 7S, 8S)-2-(7-Chloro-8-fluoro-2-(((S)-6′-methylenetetrahydrospiro[cyclopropane-1,1′-pyrrolizin]-7a′(5′H)-yl) methoxy)pyrido[4,3-d]pyrimidin-4-yl)-8-fluoro-5-oxa-2-azabicyclo [5.1.0]octane & (1S, 7S, 8S)-2-(7-chloro-8-fluoro-2-(((R)-6′-methylenetetrahydrospiro[cyclopropane-1,1′-pyrrolizin]-7a′(5′H)-yl) methoxy)pyrido[4,3-d]pyrimidin-4-yl)-8-fluoro-5-oxa-2-azabicyclo [5.1.0]octane

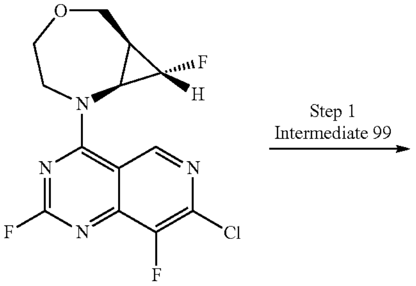

Intermediate 112

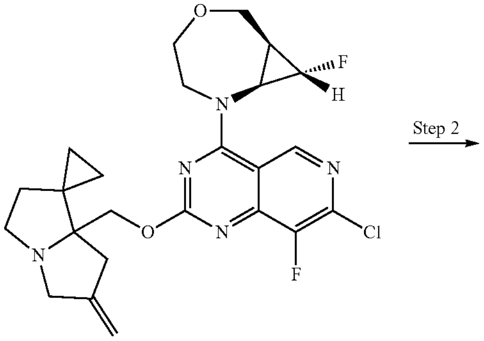

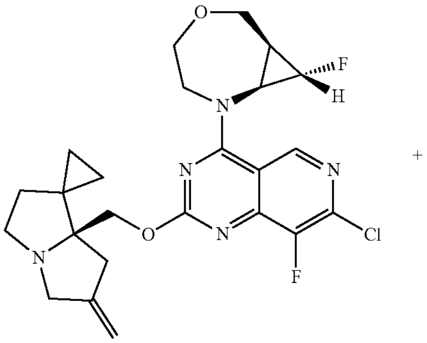

Intermediate 100

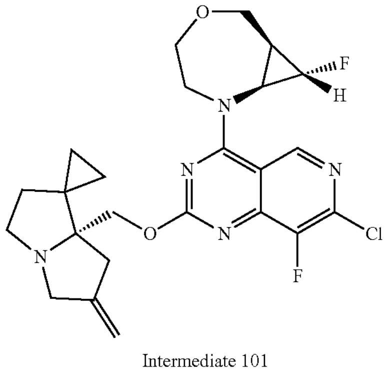

Intermediate 101

Step 1: (1S,7S,8S)-2-(7-Chloro-8-fluoro-2-((6'-methylenetetrahydrospiro[cyclopropane-1,1'-pyrrolizin]-7a'(5'/)-yl) methoxy)pyrido[4,3-d]pyrimidin-4-yl)-8-fluoro-5-oxa-2-azabicyclo[5.1.0]octane To an ice-cooled solution of Intermediate 99 (195.15 mg, 1.08 mmol) in THF (3 mL) under nitrogen atmosphere was added NaH (43.54 mg, 1.088 mmol, 60% dispersion in mineral oil). After stirring at ice bath for 30 min, Intermediate 112 (300 mg, 0.90 mmol) was added to the above mixture. The ice bath was removed, and the reaction mixture was stirred at room temperature for 2 hours. The resulting mixture was quenched with sat. aq. $NH_4Cl$ (50 mL) in an ice bath and extracted with EtOAc (3×50 mL). The combined organic layers were washed with brine (50 mL), dried over anhydrous $Na_2SO_4$, filtered and concentrated under reduced pressure. The residue was purified by Prep-TLC($CH_2Cl_2$/MeOH 15: 1) to afford the title compound (230 mg, 51% yield) as a light yellow solid. MS: m/z=490.15 $[M+H]^{+\cdot}$ Step 2: (15,7S,8S)-2-(7-chloro-8-fluoro-2-(((S)-6'-methylenetetrahydrospiro[cyclopropane-1,1'-pyrrolizin]-7a'(5'H)-yl) methoxy)pyrido[4,3-d]pyrimidin-4-yl)-8-fluoro-5-oxa-2-azabicyclo[5.1.0]octane & (1S,7S,8S)-2-(7-chloro-8-fluoro-2-(((R)-6'-methylenetetrahydrospiro[cyclopropane-1,1'-pyrrolizin]-7a'(5'/)-yl) methoxy)pyrido[4,3-d]pyrimidin-4-yl)-8-fluoro-5-oxa-2-azabicyclo[5.1.0]octane The mixture of (1S,7S,8S)-2-(7-chloro-8-fluoro-2-((6'-methylenetetrahydrospiro[cyclopropane-1,1'-pyrrolizin]-7a'(5'/)-yl) methoxy)pyrido[4,3-d]pyrimidin-4-yl)-8-fluoro-5-oxa-2-azabicyclo[5.1.0]octane (230 mg, 0.46 mmol) was separated by Prep-Chiral-HPLC with the following conditions: Column: CHIRALPAK IE, 2×25 cm, 5 μm; Mobile Phase A: MTBE (0.5% 2 M $NH_3$-MeOH)-HPLC; Mobile Phase B: EtOH-HPLC; Flow rate: 20 mL/min; Gradient: isocratic 10% B; Detector: UV 220 & 254 nm; RT1: 10.423 min; RT2: 13.104 min.

The first eluting peak (RTI: 10.423 min) was concentrated and lyophilized to give the title compound (Intermediate 100, 80 mg, 34% yield) as an off-white lyophilized powder. MS: m/z=490.25 $[M+H]^+$. $^1$H NMR (400 MHZ, Chloroform-d)δ 9.22 (s, 1H), 4.94 (s, 2H), 4.67-4.63 (m, 1H), 4.42-4.22 (m, 4H), 3.94-3.79 (m, 4H), 3.66-3.59 (m, 1H), 3.42-3.30 (m, 3H), 2.87-2.55 (m, 2H), 2.41-2.08 (m, 3H), 1.73 (s, 1H), 0.88-0.46 (m, 4H). $^{19}$F. NMR (376 MHZ, Chloroform-d) δ −133.82–−134.52 (m, 1F), −208.48 (s, IF). The second eluting peak (RT2: 13.104 min) was concentrated and lyophilized to give the title compound (Intermediate 101, 85 mg, 36% yield) as a light-yellow lyophilized powder. MS: m/z=490.25 $[M+H]^+$. $^1$H NMR (400 MHz, Chloroform-d) δ 9.22 (s, 1H), 4.92 (s, 2H), 4.66-4.61 (m, 1H), 4.43-4.22 (m, 4H), 3.94-3.79 (m, 4H), 3.65-3.58 (m, 1H), 3.40-3.15 (m, 3H), 2.77-2.55 (m, 2H), 2.36-2.10 (m, 3H), 1.73-1.67 (m, 1H), 0.94-0.47 (m, 4H). $^{19}$F NMR (376 MHz, Chloroform-d) δ −133.81–−134.52 (m, 1F), −208.47 (s, 1F).

Intermediate 102 & 103: (1S,7S,8S)-2-(7-Chloro-2-(((S)-dihydro-5′H-dispiro[cyclopropane-1,1′-pyrrolizine-6′,1″-cyclopropan]-7a′(7′H)-yl)methoxy)-8-fluoropyrido[4,3-d]pyrimidin-4-yl)-8-fluoro-5-oxa-2-azabicyclo[5.1.0]octane & (1S,7S,8S)-2-(7-chloro-2-(((R)-dihydro-5′H-dispiro[cyclopropane-1,1′-pyrrolizine-6′,1″-cyclopropan]-7a′(7′H)-yl)methoxy)-8-fluoropyrido[4,3-d]pyrimidin-4-yl)-8-fluoro-5-oxa-2-azabicyclo[5.1.0]octane

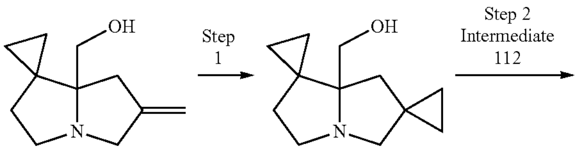

Intermediate 99

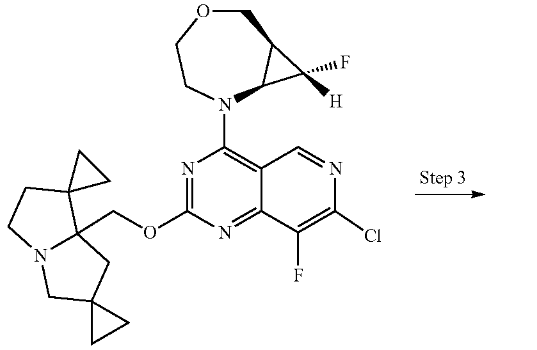

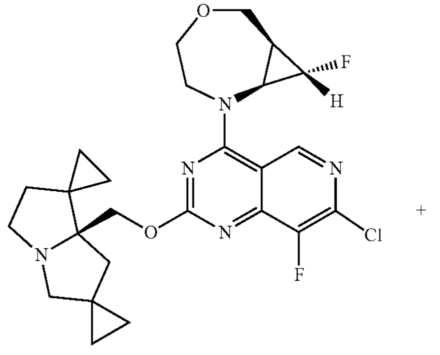

Intermediate 102

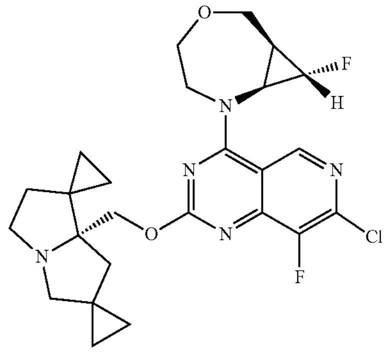

Intermediate 103

Step 1: (Dihydro-S'H-dispiro[cyclopropane-1, l'-pyrrolizine-6',1"-cyclopropan]-7a'(7'H)-yl) methanol To a solution of Intermediate 99 (150 mg, 0.84 mmol) in DCM (2.0 mL) were added diethylzinc (4.2 mL, 1 M in hexane, 4.19 mmol) and diiodomethane (1.01 g, 3.77 mmol) at −40° C. under nitrogen atmosphere. The reaction mixture was warmed to room temperature and stirred at room temperature for 2 hours. The pH of the resulting mixture was adjusted to 7 with sat. aq. $NH_4Cl$, and the mixture was concentrated under reduced pressure. The residue was purified by silica gel flash chromatography, eluted with $CH_2Cl_2$/MeOH/NHs.$H_2O$ (4: 1: 0.1) to afford the title compound (130 mg, 80% yield) as a yellow oil. MS: m/z=194.20 $[M+H]^+$. $^1H$ NMR (400 MHz, Chloroform-d) δ 3.97-3.65 (m, 5H), 3.21-3.03 (m, 1H), 2.89-2.85 (m, 1H), 2.34-2.23 (m, 1H), 2.07-2.00 (m, 2H), 1.62-1.59 (m, 1H), 0.90-0.50 (m, 8H).

Step 2: (1S,7S,8S)-2-(7-Chloro-2-((dihydro-5'H-dispiro[cyclopropane-1,1'-pyrrolizine-6',1"-cyclopropan]-7a'(TH)-yl) methoxy)-8-fluoropyrido[4,3-d]pyrimidin-4-yl)-8-fluoro-5-oxa-2-azabicyclo[5.1.0]octane To an ice-cooled solution of (dihydro-5'W-dispiro[cyclopropane-1, l'-pyrrolizine-6',1"-cyclopropan]-7a'(7'H)-yl) methanol (200 mg, 1.04 mmol) in THF (5.0 mL) was added NaH (40 mg, 1.04 mmol, 60% dispersion in mineral oil) under nitrogen atmosphere. After stirring in an ice bath for 30 minutes, a solution of Intermediate 112 (308 mg, 0.93 mmol) in THF (5.0 mL) was added to the above mixture dropwise in an ice bath. The ice bath was removed, and the reaction mixture was stirred at room temperature for 2 hours. The resulting mixture was quenched with sat. aq. $NH_4Cl$ (20 mL) in an ice bath and extracted with ethyl acetate (3×30 mL). The combined organic layers were washed with brine (30 mL), dried over anhydrous sodium sulfate, filtered, and concentrated under reduced pressure. The residue was purified by silica gel flash chromatography, eluted with $CH_2Cl_2$/MeOH (10: 1) to afford the title compound (300 mg, 57% yield) as a yellow oil. MS: m/z=504.15 $[M+H]^+$. $^1H$ NMR (400 MHz, Methanol-$d_4$) δ 9.32 (s, 1H), 4.71-4.50 (m, 4H), 4.43-4.38 (m, 1H), 4.21-4.12 (m, 1H), 3.97-3.93 (m, 1H), 3.84-3.63 (m, 3H), 3.47-3.34 (m, 3H), 2.40-1.97 (m, 6H), 0.91-0.74 (m, 8H).

Step 3: (1S,7S,8S)-2-(7-Chloro-2-(((S)-dihydro-5'H-dispiro[cyclopropane-1,1'-pyrrolizine-6',1"-cyclopropan]-7a (7'H)-yl) methoxy)-8-fluoropyrido[4,3-d]pyrimidin-4-yl)-8-fluoro-5-oxa-2-azabicyclo[5.1.0]octane & (15,7S,8S)-2-(7-chloro-2-(((R)-dihydro-S'H-dispiro[cyclopropane-1,l'-pyrrolizine-6',1"-cyclopropan]-7a'(7'/)-yl) methoxy)-8-fluoropyrido[4,3-d]pyrimidin-4-yl)-8-fluoro-5-oxa-2-azabicyclo[5.1.0]octane (1S,7S,8S)-2-(7-Chloro-2-((dihydro-5'H-dispiro[cyclopropane-1, l'-pyrrolizine-6',1"-cyclopropan]-7a'(7H)-yl) methoxy)-8-fluoropyrido[4,3-d]pyrimidin-4-yl)-8-fluoro-5-oxa-2-azabicyclo[5.1.0]octane (300 mg, 0.60 mmol) was separated by Prep-SFC with the following condition: Column: CHIRALPAK IG 2×25 cm, 5 μm; Mobile Phase A: Hex (0.5% 2 M $NH_3$.MeOH); Mobile Phase B: EtOH; Flow rate: 20 mL/min; Gradient: isocratic 40%; Detector: UV 220 & 254 nm; RT1: 11.89 min; RT2: 15.00 min. The first eluting peak (RT1: 11.89 min) was combined and concentrated to give the title compound (Intermediate 102, 100 mg, 33% yield) as a yellow oil. MS: m/z=504.20 $[M+H]^+$. The second eluting peak (RT2: 15.00 min) was combined and concentrated to give the title compound (Intermediate 103, 100 mg, 33% yield) as a yellow oil. MS: m/z=504.15 $[M+H]^+$ Intermediate 104 & 105: Benzyl 8-fluoro-6-azaspiro[bicyclo[5.1.0]octane- 3,2'-[1,3]dioxolane]-6-carboxylate (trans mixture) and benzyl 8-fluoro-6-azaspiro[bicyclo[5.1.0]octane- 3,2'-[1,3]dioxolane]-6-carboxylate (cis mixture)

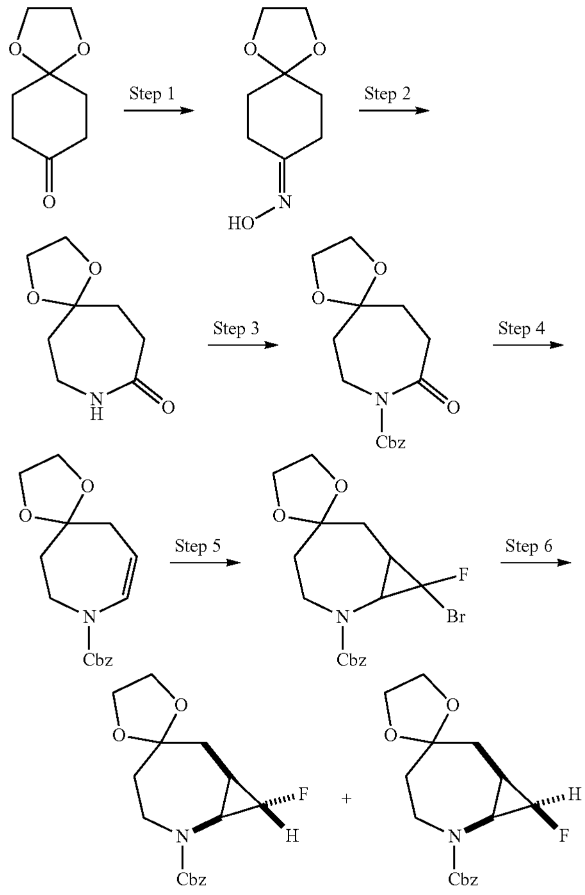

Intermediate 104 Intermediate 105

Step 1: 1,4-Dioxaspiro[4.5]decan-8-one oxime

To a solution of 1,4-dioxaspiro[4.5]decan-8-one (190 g, 1.22 mol) and hydroxylamine hydrochloride (338 g, 4.86 mol) in $H_2O$ (2000 mL) was added $Na_2CO_3$ (387 g, 3.65 mol) in batches and stirred at 25° C. for 1 h. The reaction mixture was extracted with EtOAc (1000 mL×3). The combined organic layers were washed with brine (500 mL×3), dried over anhydrous $Na_2SO_4$, filtered and the concentrated under reduced pressure to give the title compound (200 g, crude) as a white solid, which was used in the next step without further purification. $^1$HI NMR (400 MHz, Chloroform-d) δ 3.98 (d, J=1.6 Hz, 4H), 2.72-2.63 (m, 2H), 2.46-2.34 (m, 2H), 1.84-1.74 (m, 4H).

Step 2: 1,4-Dioxa-8-azaspiro[4.6]undecan-9-one

To a solution of 1,4-dioxaspiro[4.5]decan-8-one oxime (180 g, 1.05 mol) in acetone (1.8 L) was added NaOH (525 mL, 4 M in $H_2O$) and then 4-methylbenzenesulfonyl chloride (200 g, 1.05 mol) in acetone (1.8 L) was added dropwise to the mixture at 25° C. under $N_2$. The resulting mixture was stirred at 25° C. for 2 h. Then the reaction mixture was concentrated under reduced pressure. The residue was diluted with $H_2O$ (200 mL), and the pH of the mixture was adjusted with HCl (4 M in $H_2O$) to around 7. The reaction mixture was stirred at 25° C. for 16 h. After rearrangement, the reaction mixture was extracted with $CH_2Cl_2$ (5× 200 mL). The combined organic layers were dried over anhydrous $Na_2SO_4$, filtered and concentrated under reduced pressure. The residue was dissolved with toluene (100 mL), and then, n-hexane (200 mL) was added to give a precipitate. The precipitate was filtered, washed with n-hexane (100 mL), and dried under reduced pressure to give the title compound (43 g, 20% yield over 2 steps) as a yellow oil. MS: m/z=171.9 $[M+H]^{+\cdot}$ Step 3: Benzyl 9-oxo-1,4-dioxa-8-azaspiro[4.6]undecane-8-carboxylate To a solution of 1,4-dioxa-8-azaspiro[4.6]undecan-9-one (43 g, 251 mmol) in THF (1100 mL) was added n-BuLi (100 mL, 2.5 M in hexanes) dropwise at −78° C. under $N_2$. The mixture was stirred−78° C. for 1 h, and then CbzCl (35 ml, 251 mmol) in THF (110 mL) was added dropwise at −78° C. under $N_2$. The resulting mixture was stirred at 20° C. for 2 h under $N_2$. The reaction mixture was quenched with sat. $NH_4Cl$ aq. (500 mL) at 0° C. and extracted with EtOAc (300 mL×2). The combined organic layers were washed with brine (200 mL×2), dried over anhydrous $Na_2SO_4$, filtered and concentrated under reduced pressure. The residue was purified by silica gel flash chromatography (eluent: 0~50% EtOAc in petroleum ether) to give the title compound (66 g, 87% yield) as a brown oil. $^1$H NMR (400 MHZ, Chloroform-d)δ 7.45-7.28 (m, 5H), 5.28 (s, 2H), 3.96 (s, 4H), 3.94-3.88 (m, 2H), 2.79-2.72 (m, 2H), 1.94-1.85 (m, 4H).

Step 4: Benzyl 1,4-dioxa-8-azaspiro[4.6]undec-9-ene-8-carboxylate

To a solution of benzyl 9-oxo-1,4-dioxa-8-azaspiro[4.6]undecane-8-carboxylate (66 g, 216 mmol) in toluene (1.2 L) was added Lithium triethylborohydride (238 mL, 1 M in THF) dropwise at −70° C. under $N_2$ and stirred at −70° C. for 1 h. DMAP (264 mg, 2.16 mmol) was added in one portion. DIPEA (215 mL, 1.23 mol) and TFAA (45 mL, 324 mmol) were added dropwise by syringe in sequence while maintaining the temperature below-55° C. under $N_2$. The cooling bath was removed, and the reaction mixture was allowed to warm to 25° C. and stirred for 2 h under $N_2$. The reaction mixture was quenched with water (600 mL) slowly at 0° C. while keeping the temperature below 15° C. The combined organic layers were washed with brine (300 mL×2), dried over anhydrous $Na_2SO_4$, filtered and concentrated under reduced pressure. The residue was purified by silica gel flash chromatography (eluent: 0~20% EtOAc in petroleum ether) to give benzyl 1,4-dioxa-8-azaspiro[4.6]undec-9-ene-8-carboxylate (33.6 g, 58% yield) as a colorless oil. MS: m/z=289.9 $[M+H]^+$. $^1$H NMR (400 MHz, Chloroform-d) δ 7.39-7.34 (m, 5H), 8 6.72-6.49 (m, 1H), 5.18 (s, 2H), 5.02-4.87 (m, 1H), 3.92 (s, 4H), 3.80-3.73 (m, 2H), 2.46 (d, J=6.4 Hz, 2H), 2.08-2.01 (m, 2H).

Step 5: Benzyl 8-bromo-8-fluoro-6-azaspiro[bicyclo[5.1.0]octane-3,2'-[1,3]dioxolane]-6-carboxylate A solution of benzyl 1,4-dioxa-8-azaspiro[4.6]undec-9-ene-8-carboxylate (30 g, 104 mmol), Bu4NI (128 mg, 10.4 mmol) in $CH_2Cl_2$ (36 mL) and 50% (w %) NaOH aqueous (36 mL) was degassed and purged with $N_2$ three times. Dibromofluoromethane (60 g, 311 mmol) was added using a syringe, and the mixture was stirred at 35° C. for 7 h under $N_2$. The reaction mixture was quenched with sat. $NH_4Cl$ aq. (600 mL) and extracted with EtOAc (400 mL×2). The combined organic layers were washed with brine (500 mL), dried over anhydrous $Na_2SO_4$, filtered and concentrated under reduced pressure to give the title compound (37.2 g, crude) as a yellow solid, which was used into the next step without further purification. MS: m/z=421.8, 423.8 $[M+Na]^+$. $^1H$ NMR (400 MHZ, Chloroform-d) δ 7.45-7.21 (m, 5H), 6 5.25-5.03 (m, 2H), 3.94-3.82 (s, 4H), 3.64-2.98 (m, 3H), 2.34-2.09 (m, 1H), 1.89-1.69 (m, 4H). $^{19}F$. NMR (376 MHz, Chloroform-d) δ −128.56, −157.95.

Step 6: Benzyl 8-fluoro-6-azaspiro[bicyclo[5.1.0] octane-3,2'-[1,3]dioxolane]-6-carboxylate (trans mixture) and benzyl 8-fluoro-6-azaspiro[bicyclo [5.1.0]octane-3,2'-[1,3]dioxolane]-6-carboxylate (cis mixture)

To a solution of benzyl 8-bromo-8-fluoro-6-azaspiro[bicyclo[5.1.0]octane-3,2'-[1,3]dioxolane]-6-carboxylate (28 g, 70 mmol) in EtOH (280 mL) was added Zn (18.1 g, 275 mmol) and $NH_4Cl$ (34 g, 630 mmol) at 20° C. The mixture was stirred at 70° C. for 3 h under $N_2$. The reaction mixture was filtered and concentrated under reduced pressure. The residue was purified by silica gel flash chromatography (eluent: 0~30% EtOAc in petroleum ether) to give the title compound (trans mixture) (Intermediate 104, 15.5 g, 62% yield over 2 steps, the first peak) as a yellow oil and the title compound (cis mixture) (Intermediate 105, 3.5 g, 14% yield over 2 steps, the second peak) as a yellow oil. Spectra for Intermediate 104: MS: m/z=321.9 $[M+H]^+$. 1H NMR (400 MHz, Chloroform-d) δ 7.43-7.28 (m, 5H), 5.27-5.09 (m, 2H), 4.59-4.29 (m, 1H), 3.99-3.90 (m, 4H), 3.17-3.07 (m, 4H), 2.97 (dd, J=9.2, 18 Hz, 1H), 2.41-2.30 (m, 1H), 1.91-1.54 (m, 4H), 1.42-1.30 (m, 1H). $^{19}F$ NMR (376 MHz, Chloroform-d) δ −204.23. Spectra for Intermediate 105: MS: m/z=321.9 $[M+H]^+$. 3H NMR (400 MHZ, Chloroform-d)δ 7.41-7.28 (m, 5H), 5.13 (s, 2H), 4.66-4.39 (m, 1H), 4.00-3.94 (m, 4H), 3.36-3.23 (m, 1H), 2.55 (s, 1H), 2.03-1.89 (m, 4H), 1.27-1.23 (m, 1H). $^{19}F$. NMR (376 MHz, Chloroform-d) 6-232.90.

Intermediate 106 & 107: Benzyl 8-fluoro-2-azabicyclo[5.1.0]oct-5-ene-2-carboxylate (trans mixture) & benzyl 8-fluoro-2-azabicyclo[5.1.0]oct-4-ene-2-carboxylate (trans mixture)

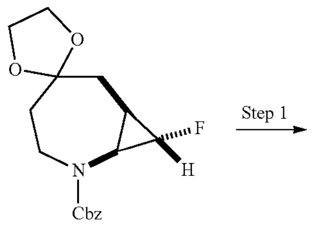

Intermediate 104

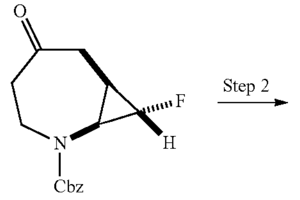

-continued

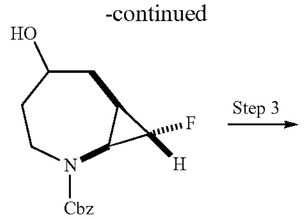

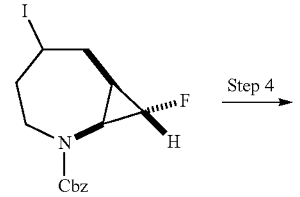

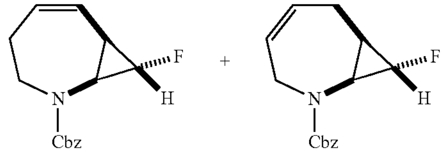

Intermediate 106 Intermediate 107

Step 1: Benzyl 8-fluoro-5-oxo-2-azabicyclo[5.1.0] octane-2-carboxylate (trans mixture)

To a solution of Intermediate 104 (14 g, 43.6 mmol) in acetone (112 mL) was added dropwise con. HCl (56 mL, 12 M in $H_2O$) at 20° C. and stirred at 50° C. for 1 h. The reaction mixture was quenched with sat. NaHCOsaq. (200 mL) at 0° C. and extracted with EtOAc (300 mL×2). The combined organic layers were dried over anhydrous $Na_2SO_4$, filtered and concentrated under reduced pressure. The residue was purified by silica gel flash chromatography (petroleum ether/Ethyl acetate=I/O to 1/1) to give the title compound (11.4 g, 78% yield) as a yellow oil. MS: m/z=299.8 $[M+Na]^+$. $^1H$ NMR (400 MHz, Chloroform-d) δ 7.44-7.28 (m, 5H), 5.30-5.18 (m, 2H), 4.66-4.27 (m, 1H), 4.07-3.92 (m, 1H), 3.28-3.05 (m, 2H), 2.99 (dd, J=6.0, 13.6 Hz, 1H), 2.66-2.60 (m, 1H), 2.58-2.47 (m, 1H), 2.31-2.21 (m, 1H), 1.76-1.64 (m, 1H). $^{19}F$. NMR (376 MHz, Chloroform-d) δ −203.83.

Step 2: Benzyl 8-fluoro-5-hydroxy-2-azabicyclo [5.1.0]octane-2-carboxylate (trans mixture)

To a solution of benzyl 8-fluoro-5-oxo-2-azabicyclo [5.1.0]octane-2-carboxylate (trans mixture) (11.4 g, 41.1 mmol) in MeOH (80 mL) was added NaBH4 (2.97 g, 78.5 mmol) at 0° C. The mixture was stirred at 0° C. for 1 h. The reaction mixture was quenched with sat. $NH_4Cl$ aq. (230 mL) at 0° C. The reaction mixture was diluted with water (400 mL) and extracted with ethyl acetate (3× 500 mL). The combined organic phases were dried over anhydrous $Na_2SO_4$, filtered and concentrated under reduced pressure to give the title compound (10.6 g, crude) as a white solid, which was used in the next step without further purification. MS: m/z=301.9 $[M+Na]^+$. $^1H$ NMR (400 MHz, Chloroform-d) δ 7.41-7.30 (m, 5H), 5.25-5.10 (m, 2H), 4.62-4.26 (m, 1H), 4.20-4.11 (m, 1H), 4.07-3.92 (m, 1H), 3.66-3.29 (m, 2H), 3.05-2.82 (m, 1H), 2.56-2.42 (m, 1H), 1.90-1.60 (m, 1H), 1.73-1.61 (m, 2H). $^{19}F$ NMR (376 MHz, Chloroform-d) ô-203.94, −204.37, −204.45.

Step 3: Benzyl 8-fluoro-5-iodo-2-azabicyclo[5.1.0] octane-2-carboxylate (trans mixture)

A mixture of benzyl 8-fluoro-5-hydroxy-2-azabicyclo [S.1.0]octane-2-carboxylate (trans mixture) (10.5 g, 37.6), imidazole (5.12 g, 75.2 mmol), $PPh_3$ (14.8 g, 56.4 mmol) and I2 (14.3 g, 56.4 mmol) in toluene (160 mL) was degassed, purged with $N_2$ three times, and stirred at 105° C. for 1 h under $N_2$. The reaction mixture was filtered and concentrated under reduced pressure to give the title compound (13 g, crude) as a brown oil, which was used in the next step without further purification.

Step 4: Benzyl 8-fluoro-2-azabicyclo[5.1.0]oct-5-ene-2-carboxylate (trans mixture) & benzyl 8-fluoro-2-azabicyclo[5.1.0]oct-4-ene-2-carboxylate (trans mixture)

A mixture of benzyl 8-fluoro-5-iodo-2-azabicyclo[5.1.0] octane-2-carboxylate (trans mixture) (13 g, 33.4 mmol) and DBU (40 mL, 265 mmol) in toluene (160 mL) was stirred at 105° C. for 2 h under $N_2$ atmosphere. The reaction mixture was filtered and concentrated under reduced pressure. The residue was purified by silica gel flash chromatography (cluent: 0~10% EtOAc in petroleum ether) to give the title compound (Intermediate 106, 2.5 g, 25% yield over 3 steps, the first peak) and benzyl 8-fluoro-2-azabicyclo[5.1.0]oct-5-ene-2-carboxylate (trans mixture) (Intermediate 107, 5.7 g, 56% yield over 3 steps, the second peak). Spectra for Intermediate 106: 1H NMR (400 MHZ, Chloroform-d) δ 7.46-7.28 (m, 5H), 5.81-5.69 (m, 1H), 5.45-5.33 (m, 1H), 5.26-5.10 (m, 2H), 4.57-4.26 (m, 1H), 4.02-3.83 (m, 1H), 3.40-3.24 (m, 2H), 2.44-2.15 (m, 2H), 2.09-1.96 (m, 1H). 1F NMR (376 MHz, Chloroform-d) δ −204.30, −204.63. Spectra for Intermediate 107: 1H NMR (400 MHz, Chloroform-d) δ 7.44-7.28 (m, 5H), 5.80-5.35 (m, 2H), 5.28-5.10 (m, 2H), 4.76-4.52 (m, 1H), 4.05-3.77 (m, 1H), 3.57-3.49 (m, 1H), 3.04-2.47 (m, 1H), 2.36-2.06 (m, 2H), 1.95-1.77 (m, 1H). $^{19}F$ NMR (376 MHz, Chloroform-d) δ −206.68.

Intermediate 108 & 109: 2,7-Dichloro-8-fluoro-4-((1R,7S,8R)-8-fluoro-2-azabicyclo[5.1.0]oct-5-en-2-yl)pyrido[4,3-d]pyrimidine & 2,7-Dichloro-8-fluoro-4-((1S,7R,8S)-8-fluoro-2-azabicyclo[5.1.0]oct-5-en-2-yl)pyrido[4,3-d]pyrimidine

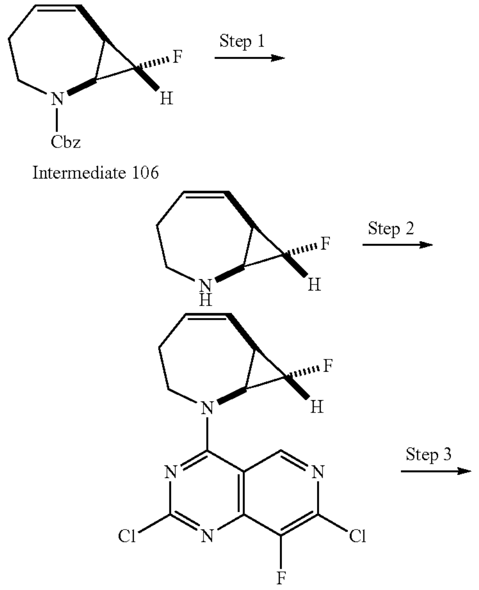

Intermediate 106

-continued

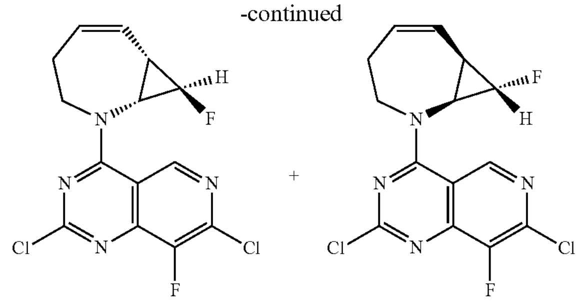

Intermediate 108 Intermediate 109

Step 1: 8-Fluoro-2-azabicyclo[5.1.0]oct-5-ene (trans mixture)

To a solution of Intermediate 106 (1.50 g, 5.74 mmol) in $CH_2Cl$ (16 mL) was added HBr (4 mL, 33% in AcOH) at 0° C. The reaction mixture was stirred at 25° C. for 1 h. The reaction mixture was concentrated under reduced pressure to give the title compound (1.15 g, HBr salt) as a colorless oil, which was used in the next step without further purification. MS: m/z=127.9 $[M+H]^+$. $^1H$ NMR (400 MHz, Chloroform-d) δ 10.57-10.04 (m, 1H), 9.53-9.04 (m, 1H), 5.91-5.83 (m, 1H), 5.69-5.59 (m, 1H), 5.41-5.15 (m, 1H), 3.54-3.26 (m, 3H), 2.80-2.62 (m, 2H), 2.40-2.20 (m, 1H), $^{19}F$ NMR (376 MHz, Chloroform-d) δ −205.15.

Step 2: 2,7-Dichloro-8-fluoro-4-((1S,7R,8S)-8-fluoro-2-azabicyclo[5.1.0]oct-5-en-2-yl)pyrido[4,3-d]pyrimidine (trans mixture)

To a solution of 2,4,7-trichloro-8-fluoropyrido[4,3-d]pyrimidine (1.40 g, 5.35 mmol), DIPEA (4.81 mL, 27.6 mmol) in $CH_2Cl_2$ (5 mL) was added a solution of 8-fluoro-2-azabicyclo[5.1.0]oct-5-ene (trans) (1.15 g, 5.35 mmol, HBr salt) in $CH_2Cl_2$ (3 mL) at −40° C. under $N_2$ atmosphere. The reaction mixture was stirred at −40° C. for 0.5 h under $N_2$ atmosphere. The reaction mixture was diluted with water (50 mL) and extracted with EtOAc (100 mL×2). The combined organic layers were washed with brine (100 mL), dried over anhydrous $Na_2SO_4$, filtered and concentrated under reduced pressure. The residue was dissolved with EtOAc (10 mL) to give a precipitate. The solid was filtered, and the filter cake was washed with EtOAc (5 mL), dried under reduced pressure to give the title compound (1.80 g, 90% yield over 2 steps) as a yellow solid.

Step 3: 2,7-Dichloro-8-fluoro-4-((1R,7S,8R)-8-fluoro-2-azabicyclo[5.1.0]oct-5-en-2-yl)pyrido[4,3-d]pyrimidine & 2,7-Dichloro-8-fluoro-4-((1S,7R,8S)-8-fluoro-2-azabicyclo[5.1.0]oct-5-en-2-yl)pyrido[4,3-d]pyrimidine 2,7-Dichloro-8-fluoro-4-((1S,7R,8S)-8-fluoro-2-azabicyclo[5.1.0]oct-5-en-2-yl)pyrido[4,3-d]pyrimidine (trans mixture) was separated by SFC(column: DAICEL CHIRALPAK IC(250 mm×3 0 mm, 10 μm); mobile phase: [$CO_2$-EtOH (0.1% $NH_3$·$H_2O$)]; B %: 30%, isocratic elution mode) to give the title compound (Intermediate 108, 500 mg, 26% yield, SFC peak 1 retention time: 1.839 min) as a yellow solid and the title compound (Intermediate 109, 1.00 g, 47% yield, SFC peak 2 retention time: 2.193 min) as a yellow solid. Spectra for Intermediate 108: MS: m/z=342.9 $[M+H]^+$. $^1H$ NMR (400 MHZ, Dimethylsulfoxide-$d_6$) δ 9.29

(s, 1H), 5.80-5.38 (m, 2H), 4.75-4.35 (m, 3H), 3.85-3.70 (m, 1H), 2.90-2.74 (m, 1H), 2.63-2.52 (m, 1H), 2.41-2.30 (m, 1H). $^{19}F$ NMR (376 MHz, Dimethylsulfoxide-$d_6$) δ −135.46, −205.06. Spectra for Intermediate 109: MS: m/z=342.8 $[M+H]^+$. $^1H$ NMR (400 MHZ, Dimethylsulfoxide-$d_6$) δ 9.29 (s, 1H), 5.79-5.37 (m, 2H), 4.67-4.40 (m, 3H), 3.85-3.70 (m, 1H), 2.78-2.74 (m, 1H), 2.57-2.52 (m, 1H), 2.40-2.31 (m, 1H). $^{19}F$ NMR (376 MHZ, Dimethylsulfoxide-$d_6$) δ −135.46, −205.06.

Intermediate 110: 7-Chloro-8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a(5H)-yl)methoxy-$d_2$)pyrido[4,3-d]pyrimidine

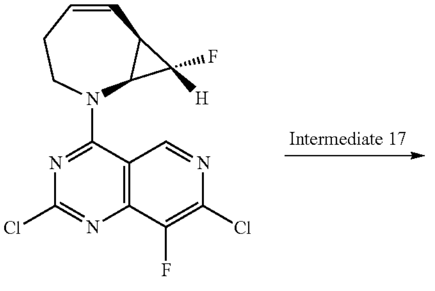

Intermediate 109

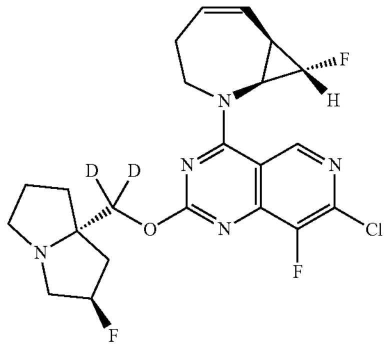

Intermediate 110

To a solution of Intermediate 109 (1.00 g, 2.91 mmol), DIPEA (1.52 mL, 8.74 mmol) and Intermediate 17 (845 mg, 5.25 mmol) in 1,4-dioxane (4 mL) was stirred at 105° C. under $N_2$ for 12 h. The reaction mixture was concentrated under reduced pressure. The residue was purified by silica gel flash chromatography (eluent: 0~3% of MeOH in $CH_2Cl_2$) to give the title compound (Intermediate 110, 1.00 g, 68% yield) as a yellow solid. MS: m/z=468.2 $[M+H]^+$. $^1H$ NMR (400 MHz, Dimethylsulfoxide-$d_6$) δ 9.16 (s, 1H), 5.76-5.70 (m, 1H), 5.76-5.70 (m, 1H), 5.47-5.38 (m, 1H), 4.70-4.60 (m, 1H), 4.55-4.39 (m, 3H), 3.85-3.65 (m, 1H), 3.09-2.99 (m, 3H), 2.86-2.76 (m, 2H), 2.39-2.30 (m, 1H), 2.10-1.98 (m, 3H), 1.84-1.73 (m, 3H). $^{19}F$. NMR (376 MHz, Dimethylsulfoxide-$d_6$) δ −137.06, −172.13, −204.65.

Intermediate 111 & 112: (1R,7R,8R)-2-(7-chloro-2,8-difluoropyrido[4,3-d]pyrimidin-4-yl)-8-fluoro-5-oxa-azabicyclo[5.1.0]octane & (1S,7S,8S)-2-(7-chloro-2,8-difluoropyrido[4,3-d]pyrimidin-4-yl)-8-fluoro-5-oxa-azabicyclo[5.1.0]octane

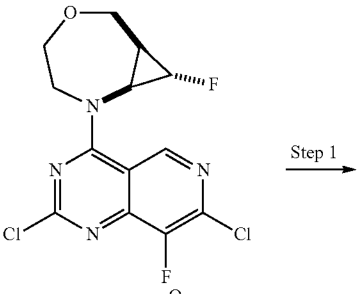

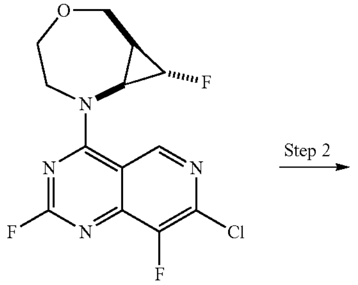

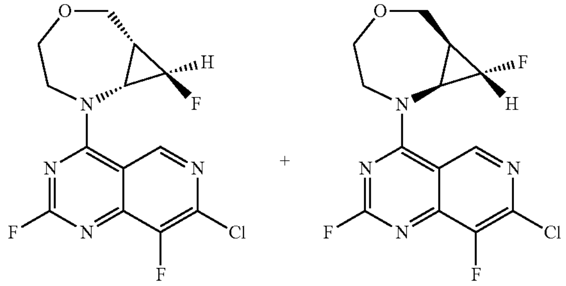

Intermediate 111 Intermediate 112

Step 1: 2-(7-Chloro-2,8-difluoropyrido[4,3-d]pyrimidin-4-yl)-8-fluoro-5-oxa-2-azabicyclo[5.1.0]octane (trans mixture)

To a stirred solution of 2-(2,7-dichloro-8-fluoropyrido[4,3-d]pyrimidin-4-yl)-8-fluoro-5-oxa-2-azabicyclo[5.1.0]octane (trans mixture) (4.8 g, 13.82 mmol, refer to Intermediate 33 &34 for detail procedures) in DMSO (96 mL) was added KF (1.45 g, 24.88 mmol) at room temperature under nitrogen atmosphere. The reaction mixture was stirred at 80° C. for 16 hours. The resulting mixture was cooled to room temperature, diluted with water (300 mL), and extracted with EtOAc (3x300 mL). The combined organic layers were washed with brine (3x300 mL), dried over anhydrous $Na_2SO_4$, filtered and concentrated under reduced pressure. The residue was purified by silica gel flash chromatography, eluted with DCM/EA (5: 1) to afford the title compound (2 g, 43% yield) as a light-yellow solid. MS: m/z=331.05 $[M+H]^+$.

Step 2: (1R,7R,8R)-2-(7-chloro-2,8-difluoropyrido[4,3-d]pyrimidin-4-yl)-8-fluoro-5-oxa-2-azabicyclo[5.1.0]octane & (1S,7S,8S)-2-(7-chloro-2,8-difluoropyrido[4,3-d]pyrimidin-4-yl)-8-fluoro-5-oxa-2-azabicyclo[5.1.0]octane 2-(7-Chloro-2,8-difluoropyrido[4,3-d]pyrimidin-4-yl)-8-fluoro-5-oxa-2-azabicyclo[5.1.0]octane (trans mixture) (2.7 g, 8.16 mmol, two batches) was separated by Prep-SFC with the following conditions: Column: CHIRAL ART Cellulose-SB 5×25 cm, 5 μm; Mobile Phase A: $CO_2$, Mobile Phase B: MeOH (0.1% 2 M $NH_3$-MeOH); Flow rate: 140 mL/min; Gradient: isocratic 40% B; RT1: 8 min; RT2: 9.5 min. The first eluting peak (RT1: 8 min) was concentrated and lyophilized to give the title compound (Intermediate 111, 1 g, 37% yield) as a light yellow solid. MS: m/z=331.10 $[M+H]^+$. The second eluting peak (RT2: 9.5 min) was concentrated and lyophilized to give the title compound (Intermediate 112, 970 mg, 35% yield) as a light yellow solid. MS: m/z=331.10 $[M+H]^{+\cdot}$ Intermediate 113: N-(6-Chloro-4-(4,4,5,5-tetramethyl-1,3,2-dioxaborolan-2-yl)-5-((triisopropylsilyl)ethynyl)naphthalen-2-yl)-1,1-diphenylmethanimine

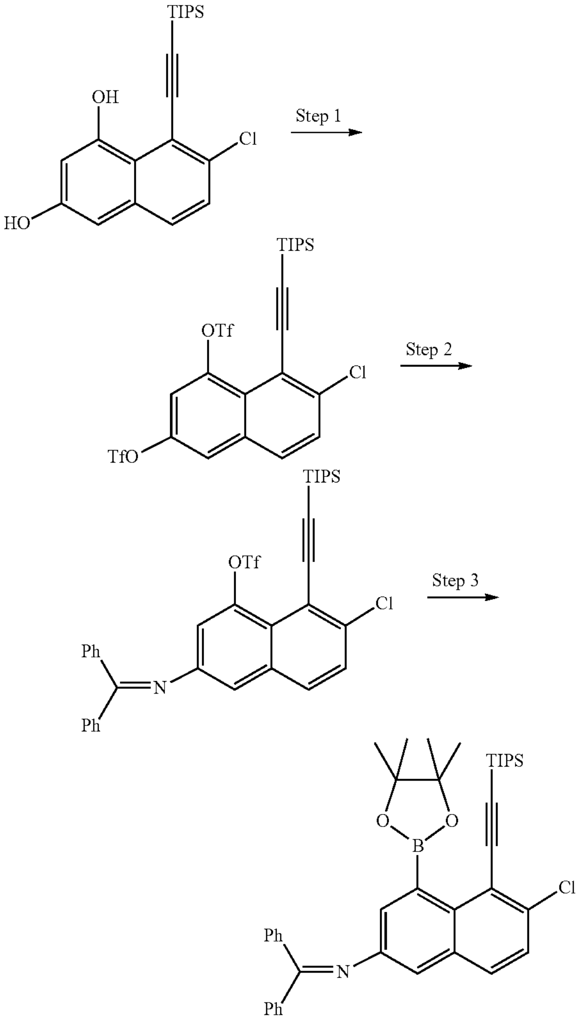

Intermediate 113

Step 1: 7-Chloro-8-((triisopropylsilyl) ethynyl) naphthalene-1,3-diyl bis(trifluoromethanesulfonate)

To an ice-cooled solution of 7-chloro-8-((triisopropylsilyl) ethynyl) naphthalene-1,3-diol (4.6 g, 12.26 mmol) in DCM (46 mL) under nitrogen atmosphere was added DIEA (9.53 g, 73.72 mmol) and (trifluoromethane) sulfonyl trifluoromethanesulfonate (13.88 g, 49.19 mmol). The reaction mixture was stirred in an ice bath for 2 hours. The resulting mixture was diluted with $H_2O$ (150 mL) and extracted with DCM (3×200 mL). The combined organic layers were washed with brine (200 mL), dried over anhydrous sodium sulfate, filtered and concentrated under reduced pressure. The residue was purified by silica gel flash chromatography, eluted with PE to afford the title compound (7 g, 89% yield) as a brown oil. MS: m/z=637.15 $[M-H]^-$ Step 2: 7-Chloro-3-((diphenylmethylene)amino)-8-((triisopropylsilyl) ethynyl) naphthalen-1-yl trifluoromethanesulfonate To a solution of 7-chloro-8-((triisopropylsilyl) ethynyl) naphthalene-1,3-diyl bis(trifluoromethanesulfonate) (2.44 g, 13.47 mmol) in toluene (70 mL) under nitrogen atmosphere were added XantPhos (380.27 mg, 0.65 mmol), Pd2 $(dba)_3$ (100.30 mg, 0.11 mmol) and Cs2$CO_3$ (7.14 g, 21.90 mmol) under nitrogen atmosphere. The reaction mixture was heated at 100° C. for 2 hours. The resulting mixture was cooled to room temperature, filtered and concentrated under reduced pressure. The residue was triturated with MeOH (3×30 mL) to afford the title compound (3.5 g, 48% yield) as a yellow solid. MS: m/z=670.15 $[M+H]^{+\cdot}$ Step 3: N-(6-Chloro-4-(4,4,5,5-tetramethyl-1,3,2-dioxaborolan-2-yl)-5-((triisopropylsilyl) ethynyl) naphthalen-2-yl)-1,1-diphenylmethanimine To a solution of 7-chloro-3-((diphenylmethylene)amino)-8-((triisopropylsilyl) ethynyl) naphthalen-1-yl trifluoromethanesulfonate (3.5 g, 5.22 mmol) and bis (pinacolato) diboron (3.33 g, 13.10 mmol) in 1,4-dioxane (35 mL) under nitrogen atmosphere were added Pd (dppf)$C_1$>>$CH_2Cl_2$ (111.14 mg, 1.04 mmol) and KOAc (2.07 g, 21.04 mmol) at room temperature. The reaction mixture was heated at 100° C. for 3 hours. The resulting mixture was cooled to room temperature, filtered and concentrated under reduced pressure. The residue was purified by silica gel flash chromatography, eluted with 3% EA in PE to afford the title compound (Intermediate 113, 1.21 g, 36% yield) as a yellow solid. MS: m/z=648.45 $[M+H]^+$. $^1H$ NMR (400 MHZ, Chloroform-d) δ 7.79-7.75 (m, 2H), 7.56-7.36 (m, 6H), 7.25-7.14 (m, 6H), 1.29-1.27 (m, 12H), 1.17-1.12 (m, 21H).

Intermediate 114 & 115: Benzyl 8-chloro-5-oxa-2-azabicyclo[5.1.0]octane-2-carboxylate (trans mixture) & benzyl 8-chloro-5-oxa-2-azabicyclo[5.1.0]octane-2-carboxylate (cis mixture)

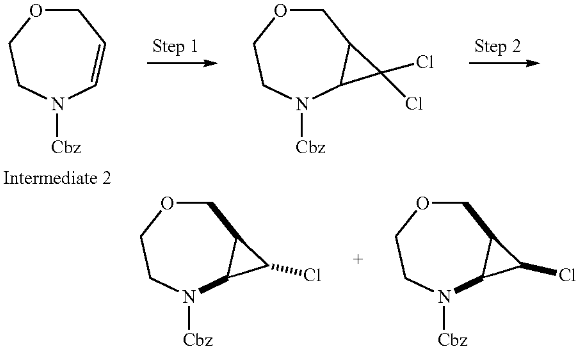

Intermediate 2

Intermediate 114

Intermediate 115

Step 1: Benzyl 8,8-dichloro-5-oxa-2-azabicyclo[5.1.0]octane-2-carboxylate

To an ice-cooled solution of Intermediate 2 (20 g, 85.73 mmol) and TBAI (6.33 g, 17.14 mmol) in DCM (100 mL) and NaOH (200 mL, 50% aq.) under nitrogen atmosphere was added chloroform (30.70 g, 257.21 mmol) dropwise. The ice bath was removed, and the reaction mixture was stirred at room temperature for 12 hours. The resulting mixture was diluted with water (100 mL) and extracted with DCM (3×100 mL). The combined organic layers were washed with brine (100 mL), dried over anhydrous sodium, filtered and concentrated under reduced pressure. The residue was purified by silica gel flash chromatography, eluted with PE/EA (3: 1) to afford the title compound (22 g, 73% yield) as a light yellow solid. MS: m/z=316.00, 318.00 $[M+H]^+$. $^1H$ NMR (400 MHZ, Chloroform-d)δ 7.50-7.31 (m, 5H), 5.29-5.16 (m, 2H), 4.56-4.50 (m, 1H), 4.14-3.93 (m, 2H), 3.64-3.50 (m, 2H), 3.34-3.28 (m, 2H), 2.28-2.16 (m, 1H).

Step 2: Benzyl 8-chloro-5-oxa-2-azabicyclo[5.1.0]octane-2-carboxylate (trans mixture) & benzyl 8-chloro-5-oxa-2-azabicyclo[5.1.0]octane-2-carboxylate (cis mixture)

To a stirred mixture of benzyl 8,8-dichloro-5-oxa-2-azabicyclo[5.1.0]octane-2-carboxylate (10 g, 31.62 mmol) in EtOH (100 mL) under nitrogen atmosphere were added ammonium chloride (15.23 g, 284.65 mmol) and Zn (18.61 g, 284.65 mmol) at room temperature. The reaction mixture was heated at 70° C. for 16 hours. The resulting mixture was cooled to room temperature, filtered and concentrated under reduced pressure. The residue was purified by silica gel flash chromatography, eluted with 0-20% EA in PE to afford two mixtures. The first eluting mixtures were collected and concentrated under reduced pressure to give benzyl 8-chloro-5-oxa-2-azabicyclo[5.1.0]octane-2-carboxylate (trans mixture) (Intermediate 114, 4.8 g, 53% yield) as an off-white semi-solid. MS: m/z=282.05 $[M+H]^+$. JH NMR (300 MHZ, Chloroform-d) δ 7.46-7.29 (m, 5H), 5.29-5.14 (m, 2H), 4.40-4.34 (m, 1H), 4.05-3.78 (m, 2H), 3.51-3.06 (m, 5H), 1.87-1.78 (m, 1H). The second eluting mixtures were collected and concentrated under reduced pressure to give the title compound (Intermediate 115, 2.2 g, 24% yield) as a yellow oil. $^1H$ NMR (300 MHz, Chloroform-d) δ 7.41-7.30 (m, 5H), 5.23-5.08 (m, 2H), 4.43-4.36 (m, 1H), 4.14-3.97 (m, 2H), 3.77-3.57 (m, 2H) 3.40-3.32 (m, 2H), 2.97-2.92 (m, H), 1.74-1.63 (m, 1H).

Intermediate 116 & 117: (1S,7S,8S)-8-Chloro-2-(7-chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-5-oxa-2-azabicyclo[5.1.0]octane & (1R,7R,8R)-8-chloro-2-(7-chloro-8-fluoro-2-(((2R,7aS)-2-fluorotetrahydro-1H-pyrrolizin-7a(5H)-yl)methoxy-$d_2$)pyrido[4,3-d]pyrimidin-4-yl)-5-oxa-2-azabicyclo[5.1.0]octane

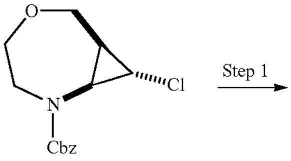

Intermediate 114

-continued

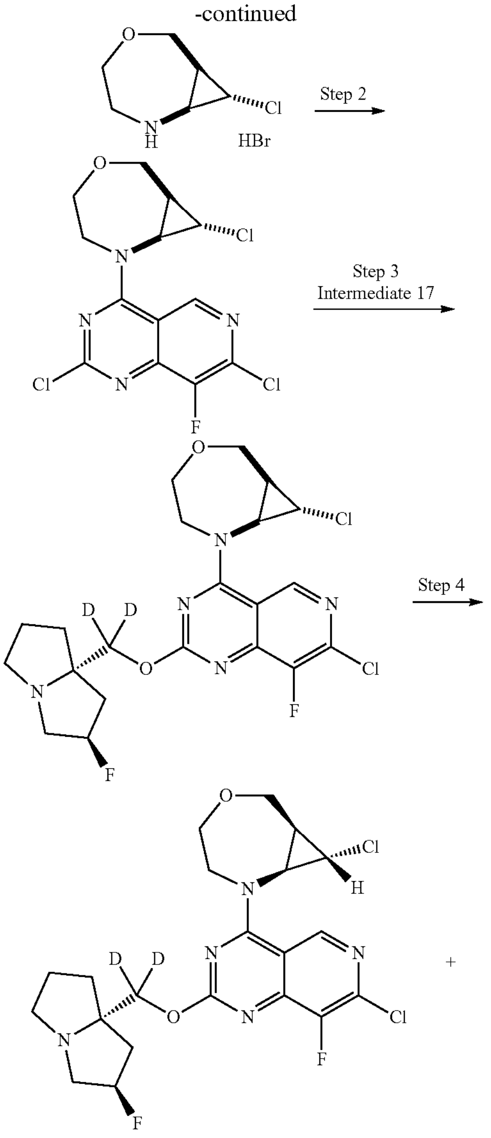

Intermediate 116

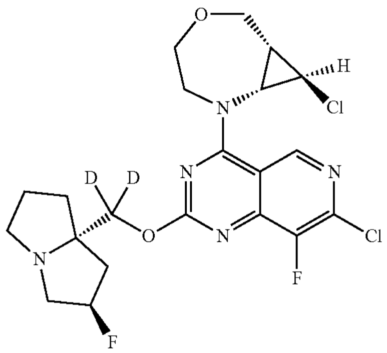

Intermediate 117

Step 1: 8-Chloro-5-oxa-2-azabicyclo[5.1.0]octane hydrobromide (trans mixture)

A mixture of Intermediate 114 (1.8 g, 6.39 mmol) in HBr (33 wt % in AcOH, 18 mL) under nitrogen atmosphere was stirred in an ice bath for 1 hour. The resulting mixture was concentrated under reduced pressure. The residue was triturated with hexane (3×50 mL) to afford the title compound (1.2 g, crude used through) as a yellow solid.

Step 2: 8-Chloro-2-(2,7-dichloro-8-fluoropyrido[4,3-d]pyrimidin-4-yl)-5-oxa-2-azabicyclo[5.1.0]octane (trans mixture)

To a solution of 2,4,7-trichloro-8-fluoropyrido[4,3-d]pyrimidine (1027.43 mg, 4.07 mmol) in DCM (10 mL) under nitrogen atmosphere were added DIEA (1578.05 mg, 12.21 mmol) and 8-Chloro-5-oxa-2-azabicyclo[5.1.0]octane hydrobromide (trans mixture) (930 mg, crude) at −40° C. The reaction mixture was stirred at −40° C. for 1 hour. The resulting mixture was quenched with water (50 mL) and extracted with DCM (3×50 mL). The combined organic layers were washed with brine (30 mL), dried over anhydrous sodium sulfate, filtered and concentrated under reduced pressure. The residue was purified by silica gel flash chromatography, eluted with 30% EA in PE to give the title compound (1.4 g, 94% yield) as a light yellow solid. MS: m/z=362.90, 364.90 $[M+H]^{+\cdot}$ Step 3: 8-Chloro-2-(7-chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-5-oxa-2-azabicyclo[5.1.0]octane (trans mixture)

To a stirred solution of 8-chloro-2-(2,7-dichloro-8-fluoropyrido[4,3-d]pyrimidin-4-yl)-5-oxa-2-azabicyclo[5.1.0] octane (trans mixture) (1.4 g, 3.85 mmol) in DMSO (10 mL) were added KF (782.93 mg, 13.48 mmol) and Intermediate 17 (0.99 g, 6.16 mmol) at room temperature under nitrogen atmosphere. The reaction mixture was stirred at 100° C. for 16 hours. The resulting mixture was cooled to room temperature, diluted with water (50 mL), extracted with DCM (3×100 mL). The combined organic layers were washed with brine (3×80 mL), dried over anhydrous $Na_2SO_4$, filtered and concentrated under reduced pressure. The residue was purified by silica gel flash chromatography, eluted with 9% MeOH in DCM to afford the title compound (1.1 g, 54% yield) as a yellow solid. MS: m/z=488.15 $[M+H]^{+\cdot}$ Step 4: (15,7S,8S)-8-Chloro-2-(7-chloro-8-fluoro-2-(((2R,7aS)-2-fluorotetrahydro-1H-pyrrolizin-7a (5H)-yl) methoxy-$d_2$)pyrido[4,3-d]pyrimidin-4-yl)-5-oxa-2-azabicyclo[5.1.0]octane & (IR,7R,8R)-8-chloro-2-(7-chloro-8-fluoro-2-(((2R,7aS)-2-fluorotetrahydro-1H-pyrrolizin-7a (5/1)-yl) methoxy-$d_2$)pyrido[4,3-d]pyrimidin-4-yl)-5-oxa-2-azabicyclo[5.1.0]octane 8-Chloro-2-(7-chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-5-oxa-2-azabicyclo[5.1.0]octane (trans mixture) (490 mg, 0.96 mmol) was separated by Prep-Chiral-HPLC with the following conditions: Column: CHIRALPAK IA 2×25 cm, 5 μm; Mobile Phase A: Hex (0.5% 2 M $NH_3$-MeOH); Mobile Phase B: EtOH; Flow rate: 20 mL/min; Gradient: isocratic 25% B; Detector: UV 220 & 254 nm; RTI: 14.80 min; RT2: 19.68 min. The first eluting peak (RT1: 14.80 min) was concentrated and lyophilized to give the title compound (Intermediate 116, 170 mg, 34% yield) as a yellow solid. MS: m/z=488.15 $[M+H]^+$. $^1$H NMR (300 MHz, Chloroform-d) δ 9.19 (s, 1H), 5.38-5.20 (m, 1H), 4.62-4.57 (m, 1H), 4.44-4.40 (m, 1H), 3.98-3.80 (m, 2H), 3.77-3.61 (m, 2H), 3.50-3.13 (m, 4H), 3.10-2.95 (m, 2H), 2.20-1.80 (m, 7H). The second eluting peak (RT2: 19.68 min) was concentrated and lyophilized to give the title compound (Intermediate 117, 170 mg, 31% yield) as a light-yellow solid. MS: m/z=488.15 $[M+H]^+$. 1H NMR (300 MHz, Chloroform-d) δ 9.19 (s, 1H), 5.38-5.21 (m, 1H), 4.62-4.57 (m, 1H), 4.45-4.39 (m, 1H), 3.98-3.90 (m, 2H), 3.78-3.61 (m, 2H), 3.50-3.22 (m, 4H), 3.03-2.94 (m, 2H), 2.30-1.80 (m, 7H).

Intermediate 118: 4-(2,8-Difluoro-4-((1S,7S,8S)-8-fluoro-5-oxa-2-azabicyclo[5.1.0]octan-2-yl)pyrido[4,3-d]pyrimidin-7-yl)-6-fluoro-5-((triisopropylsilyl)ethynyl)naphthalen-2-amine

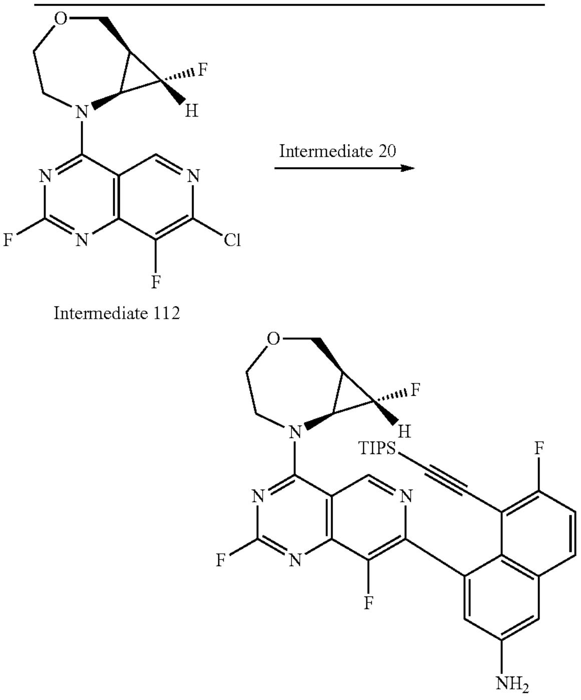

Intermediate 112

Intermediate 118

A mixture of Intermediate 112 (12 g, 36.28 mmol), Intermediate 20 (36.58 g, 72.58 mmol, HCl), AdanBuP-Pd-G3 (cataCXiumAPdG3) (5.28 g, 7.26 mmol), and KsPO4 (23.1 g, 108.86 mmol) in THF (240 mL) and $H_2O$ (48 mL) was degassed, purged with $N_2$ three times, and the mixture was stirred at 80° C. for 5 h under $N_2$ atmosphere. The reaction mixture was concentrated under reduced pressure. The residue was purified by silica gel flash chromatography (eluent: 0~5% of MeOH in $CH_2Cl_2$) to give the crude product. The crude was purified by prep-HPLC(column: XPT C18 250×70×7 μm; mobile phase: [water (ammonia hydroxide v/v)-ACN], gradient: 65%~95% B over 23 min) to give the title compound (Intermediate 118, 13.239 g, 60% purity) as a yellow solid. MS: m/z=636.3 $[M+H]^+$. $^1$H NMR (400 MHZ, Dimethylsulfoxide-$d_6$) δ 9.56 (s, 1H), 7.84-7.76 (m, 1H), 7.41-7.32 (m, 1H), 7.15-6.97 (m, 2H), 5.69 (s, 2H), 5.14-4.87 (m, 1H), 4.50-4.27 (m, 3H), 4.07-3.96 (m, 1H), 3.75-3.59 (m, 2H), 3.26-3.07 (m, 1H), 2.48-2.29 (m, 1H), 0.85-0.79 (m, 18H), 0.53-0.36 (m, 3H). $^{19}$F. NMR (376 MHz, Dimethylsulfoxide-$d_6$) δ −41.05, −41.78, −110.77, −111.09, −138.96, −207.86.

Intermediate 119 & 120: (R)-7a′-(((tert-Butyldiphenylsilyl)oxy)methyl)-6′-methylenehexahydrospiro[cyclopropane-1,1′-pyrrolizine] & (S)-7a′-(((tert-butyldiphenylsilyl)oxy)methyl)-6′-methylenehexahydrospiro[cyclopropane-1,1′-pyrrolizine]

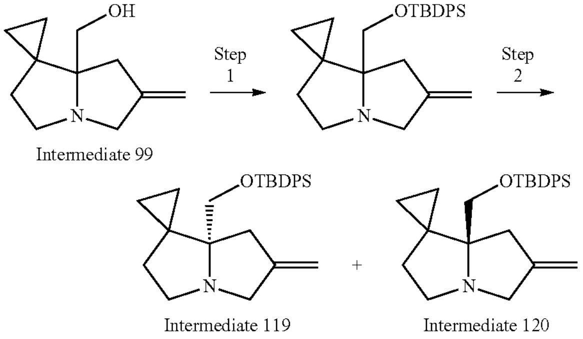

Step 1: 7a'-((((ert-Butyldiphenylsilyl)oxy)methyl)-6'-methylenehexahydrospiro[cyclopropane-1,1'-pyrrolizine]

To a mixture of Intermediate 99 (570 mg, 3.18 mmol) in N,N-dimethylformamide (5.5 mL) were added 1H-imidazole (439 mg, 6.46 mmol) and tert-butyl (chloro)diphenylsilane (961 mg, 3.50 mmol) at 25° C. under nitrogen atmosphere. The resulting mixture was stirred for 16 hours at 25° C. under nitrogen atmosphere. The reaction was monitored by TLC and LCMS. The mixture was quenched with sat. aq. $NH_4Cl$ (0.2 mL). The mixture was filtered, and the filtrate was directly purified by reversed-phase flash chromatography with the following conditions: column, C18 silica gel; mobile phase, MeCN in Water (0.1% $NH_3 \cdot H_2O$), 2% to 100% gradient in 20 min; detector, UV 254 nm & 210 nm. The product-containing fractions were collected and concentrated to afford the title compound (1.2 g, 90%) as an off-white oil. MS: m/z=418.20 $[M+H]^+$. $^1H$ NMR (400 MHZ, Chloroform-d) δ 7.68-7.57 (m, 4H), 7.46-7.29 (m, 6H), 4.85 (s, 2H), 3.70-3.04 (m, 5H), 2.73-2.55 (m, 2H), 2.30 (d, J=15.8 Hz, 1H), 1.96-1.67 (m, 2H), 1.12 (s, 1H), 1.05 (s, 9H), 0.66-0.59 (m, 1H), 0.53-0.39 (m, 2H).

Step 2: (R)-7a'-(((tert-Butyldiphenylsilyl)oxy)methyl)-6'-methylenehexahydrospiro [cyclopropane-1,1'-pyrrolizine]& (S)-7a-(( (iert-butyldiphenylsilyl)oxy)methyl)-6'-methylenehexahydrospiro[cyclopropane-1,1'-pyrrolizine]7a-(((tert-Butyldiphenylsilyl)oxy)methyl)-6'-methylenehexahydrospiro[cyclopropane-1,1'-pyrrolizine](2.8 g, 6.7 mmol) was separated by Prep-SFC with the following conditions: Column: CHIRAL ART Cellulose-SZ, 3*25 cm, 5 μm; Mobile Phase A: $CO_2$, Mobile Phase B: MeOH (0.1% 7M $NH_3$. MeOH); Flow rate: 100 mL/min; Gradient: isocratic 18% B; Wave Length: 220 nm; RT1 (min): 8.1; RT2 (min): 11.3; Injection Volume: 0.5 mL; Number Of Runs: 40. The first eluting peak was combined and concentrated to give the title compound (Intermediate 119, 1.34 g, 47%) as an off-white oil. MS: m/z=418.25 $[M+H]^+$. $^1H$ NMR (400 MHz, Chloroform-d) δ 7.76-7.54 (m, 4H), 7.45-7.30 (m, 6H), 4.85 (s, 2H), 3.73-3.01 (m, 5H), 2.77-2.56 (m, 2H), 2.30 (d, J=15.8 Hz, 1H), 1.82 (d, J=48.4 Hz, 2H), 1.12 (s, 1H), 1.05 (s, 9H), 0.67-0.58 (m, 1H), 0.56-0.35 (m, 2H). The second eluting peak was combined and concentrated to give the title compound (Intermediate 120, 1.26 g, 45%). MS: m/z=418.20 $[M+H]^+$. $^1H$ NMR (400 MHZ, Chloroform-d)δ 7.70-7.59 (m, 4H), 7.47-7.32 (m, 6H), 4.86 (s, 2H), 3.75-3.01 (m, 5H), 2.76-2.55 (m, 2H), 2.30 (d, J=15.9 Hz, 1H), 1.82 (d, J=57.4 Hz, 2H), 1.12 (s, 1H), 1.05 (s, 9H), 0.68-0.58 (m, 1H), 0.56-0.38 (m, 2H).

Intermediate 121: ((7a′R)-2″,2″-Difluorodihydro-5′H-dispiro[cyclopropane-1,1′-pyrrolizine-6′,1″-cyclopropane]-7a′(7′H)-yl)methanol

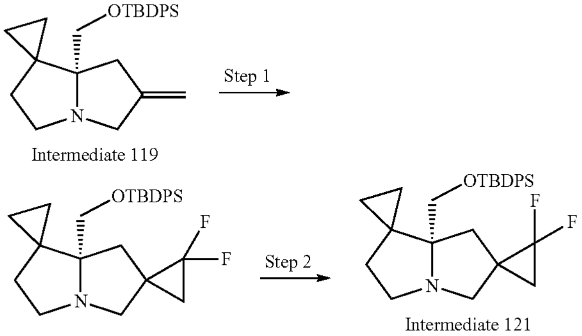

Step 1: (7a'R)-7a'-(((tert-Butyldiphenylsilyl)oxy) methyl)-2",2"-difluorotetrahydro-5'//-dispiro[cyclopropane-1,1'-pyrrolizine-6',1"-cyclopropane]

To a stirred solution of Intermediate 119 (850 mg, 2.03 mmol) in toluene (3 mL) were added tetrabutylammonium bromide (19.7 mg, 0.06 mmol) and (bromodifluoromethyl) trimethylsilane (620 mg, 3.05 mmol) under argon atmosphere at 25° C. The resulting mixture was heated at 110° C. for 2 hours under argon atmosphere. The reaction progress was monitored by TLC and LCMS. After completion of the reaction, the mixture was concentrated under reduced pressure. The residue was purified by silica gel flash chromatography with the following conditions: column, $C_{18}$ column, 40 g, 20-35 μm, 100 A; mobile phase A: water; mobile phase B: MeOH, 2% to 98% gradient in 25 min; detector, UV 254 & 210 nm. The fractions containing desired product were combined and concentrated under reduced pressure to afford the title compound (320 mg, 34%) as a colorless oil. MS: m/z=468.25 $[M+H]^+$. $^1H$ NMR (400 MHZ, Acetonitrile-3) δ 7.78-7.62 (m, 4H), 7.55-7.32 (m, 6H), 3.55-3.31 (m, 2H), 3.15-2.96 (m, 2H), 2.90-2.58 (m, 2H), 1.90-1.71 (m, 3H), 1.68-1.59 (m, 1H), 1.07-0.98 (m, 9H), 0.96-0.78 (m, 3H), 0.68-0.57 (m, 1H), 0.54-0.41 (m, 2H). $^{19}F$. NMR (376 MHz, CD: CN) δ −134.83−−136.56 (m, 1F), —136.59−−139.32 (m, IF).

Step 2: ((7a'R)-2",2"-Difluorodihydro-5'H-dispiro [cyclopropane-1,1'-pyrrolizine-6',1"-cyclopropan]-7a'(7H)-yl) methanol To a stirred solution of (Ta'R)-7a'-(((tert-butyldiphenylsilyl)oxy)methyl)-2",2"-difluorotetrahydro-5'H-dispiro[cyclopropane-1,1'-pyrrolizine-6',1"-cyclopropane](246 mg, 0.53 mmol) in methanol (4 mL) was added amine hydrofluoride (780 mg, 21.0 mmol) under argon atmosphere at room temperature. The resulting mixture was stirred at room temperature for 12 hours under the argon atmosphere. The reaction progress was monitored by TLC and LCMS. After completion of the reaction, the resulting mixture was concentrated under reduced pressure. The residue was purified by silica gel flash chromatography, eluted with $MeOH/NH_3$-$H_2O/CH_2Cl_2$ (1: 0.1: 9) to afford the title compound (Intermediate 121, 105 mg, 87%) as a colorless oil. MS: m/z=230.05 $[M+H]^+$. $^1H$ NMR (400 MHZ, Acetonitrile-$d_3$) δ 4.16-3.32 (m, 1H), 3.31-3.08 (m, 4H), 3.02-2.71 (m, 2H), 1.92-1.68 (m, 4H), 1.46-1.25 (m, 2H), 0.77-0.44 (m, 4H). $^{19}F$ NMR (376 MHZ, $CD_3CN$) δ −135.20-−136.54 (m, IF), —137.26-−139.45 (m, IF).

Intermediate 122 & 123: Ethyl (6′R,7a′R)-2″-bromo-2″-fluoro-3′-oxodihydro-5′H-dispiro[cyclopropane-1,1′-pyrrolizine-6′,1″-cyclopropane]-7a′(7′H)-carboxylate & ethyl (6′S,7a′R)-2″-bromo-2″-fluoro-3′-oxodihydro-5′H-dispiro[cyclopropane-1,1′-pyrrolizine-6′,1″-cyclopropane]-7a′(7′H)-carboxylate

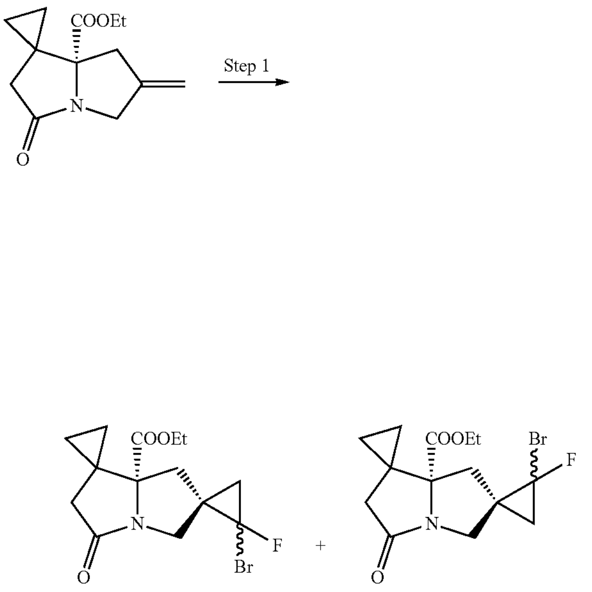

Intermediate 122 Intermediate 123

A mixture of ethyl (R)-6'-methylene-3'-oxotetrahydrospiro[cyclopropane-1, l'-pyrrolizine]-7a'(5'H)-carboxylate (4 g, 17.0 mmol), dibromo (fluoro) methane (9.78 g, 51.0 mmol, 5.78 mL) and benzyl (triethyl) ammonium; chloride (387 mg, 1.70 mmol) in $CH_2Cl_2$ (80 mL) and NaOH (16 mL, 50% in water) was degassed and purged with $N_2$ three times, and the mixture was stirred at 40° C. for 16 h under $N_2$ atmosphere. The reaction mixture was diluted with water (300 mL) and extracted with EtOAc (300 mL×3). The combined organic layers were washed with brine (200 mL), dried over anhydrous $Na_2SO_4$, filtered and concentrated under reduced pressure. The residue was purified by silica gel flash chromatography (eluent: 30%~60% of EtOAc in petroleum ether) to give the title compound (Intermediate 122, 1.20 g, 19% yield, the first peak) as a yellow oil and the title compound (Intermediate 123, 1.07 g, 17% yield, the second peak) as a yellow oil. Spectra for Intermediate 122: 1H NMR (400 MHZ, Chloroform-d)δ 4.33-4.04 (m, 3H), 3.13-2.87 (m, 2H), 2.32-1.95 (m, 3H), 1.71-1.50 (m, 2H), 1.30 (t, J=7.2 Hz, 3H), 0.96-0.86 (m, 1H), 0.83-0.74 (m, 1H), 0.73-0.65 (m, 2H). $^{19}F$. NMR (376 MHz, Chloroform-d) ô-135.15, −136.17. Spectra for Intermediate 123: 1H NMR (400 MHz, Chloroform-d) δ 4.38-4.19 (m, 2H), 3.84-3.70 (m, 1H), 3.44-3.33 (m, 1H), 3.11-2.97 (m, 1H), 2.43-2.18 (m, 2H), 2.06-1.59 (m, 3H), 1.35-1.28 (m, 3H), 1.03-0.81 (m, 2H), 0.73-0.61 (m, 2H). $^{19}F$. NMR (376 MHz, Chloroform-d) δ −135.59, −136.44.

Intermediate 124 & 125: Ethyl (2″R,6′R,7a′R)-2″-fluoro-3′-oxodihydro-5′H-dispiro[cyclopropane-1,1′-pyrrolizine-6′,1″-cyclopropane]-7a′(7′H)-carboxylate & ethyl (2″S,6′R,7a′R)-2″-fluoro-3′-oxodihydro-5′H-dispiro[cyclopropane-1,1′-pyrrolizine-6′,1″-cyclopropane]-7a′(7′H)-carboxylate

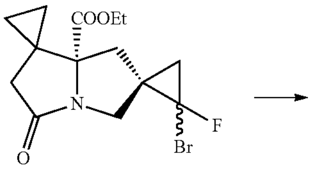

Intermediate 122

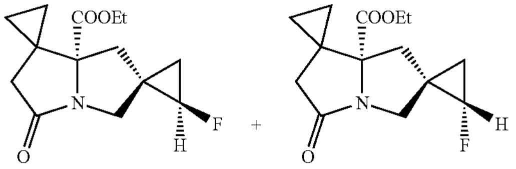

Intermediate 124 Intermediate 125

To a solution of Intermediate 122 (1.20 g, 3.47 mmol) in EtOH (28 mL) was added $NH_4Cl$ (1.67 g, 31.2 mmol) and Zn (1.18 g, 18.0 mmol) in batches. The mixture was stirred at 70° C. for 3 h under $N_2$. The reaction mixture was filtered and concentrated under reduced pressure. The residue was purified by silica gel flash chromatography (eluent: 30%~50% of EtOAc in petroleum ether) to give the title compound (Intermediate 124, $^{19}F$NMR: −213.19 ppm, 388 mg, 42% yield, the first peak) as a yellow oil and the title compound (Intermediate 125, 19FNMR: −212.77 ppm, 156 mg, 17% yield, the second peak) as a yellow oil. Spectra for Intermediate 124: 1H NMR (400 MHz, Chloroform-d) δ 4.67-4.42 (m, 1H), 4.34-4.18 (m, 2H), 4.06 (d, J=11.6 Hz, 1H), 3.14-3.01 (m, 2H), 2.28-2.18 (m, 1H), 1.99-1.91 (m, 1H), 1.80-1.82 (m, 1H), 1.30 (t, J=7.2 Hz, 3H), 1.00-0.74 (m, 4H), 0.70-0.62 (m, 2H). $^{19}F$ NMR (376 MHz, Chloroform-d) δ −213.19. Spectra for Intermediate 125: $^1H$ NMR (400 MHz, Chloroform-d) δ 4.68-4.44 (m, 1H), 4.34-4.19 (m, 2H), 3.84-3.74 (m, 1H), 3.12-3.04 (m, 1H), 2.81-2.72 (m, 1H), 2.26-2.01 (m, 3H), 1.31 (t, J=7.2 Hz, 3H), 1.08-0.96 (m, 1H), 0.96-0.89 (m, 1H), 0.85-0.76 (m, 2H), 0.72-0.61 (m, 2H), $^{19}F$ NMR (376 MHz, Chloroform-d) δ −212.77.

Intermediate 126: (2″R,6′R,7a′R)-2″-Fluorodihydro-5′H-dispiro[cyclopropane-1,1′-pyrrolizine-6′,1″-cyclopropan]-7a′(7′H)-yl) methanol

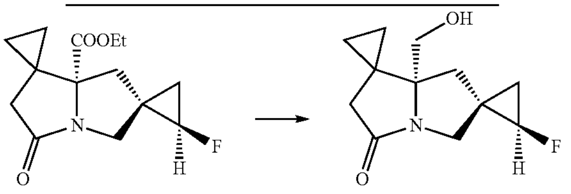

Intermediate 124 Intermediate 126

To a solution of Intermediate 124 (288 mg, 1.08 mmol) in THF (3 mL) was added LiAlH4 (2.15 mL, 2.5 M in THF) dropwise at 0° C. under $N_2$ atmosphere. The mixture was stirred at 0° C. for 0.5 h under $N_2$, warmed to 65° C., and stirred at 65° C. for 1.5 h. The reaction mixture was quenched with $Na_2SO_4\$10H_2O$ (1.74 g) slowly. The reaction mixture dried over anhydrous $Na_2SO_4$, filtered and concentrated under reduced pressure to give the title compound (Intermediate 126, 184 mg, crude) as a yellow solid. $^1$H NMR (400 MHZ, Dimethylsulfoxide-d6) δ 4.78-4.56 (m, 1H), 4.32-4.15 (m, 1H), 3.24-3.13 (m, 2H), 3.05 (d, J=11.2 Hz, 1H), 3.00-2.93 (m, 1H), 2.71 (d, J=11.6 Hz, 1H), 2.64-2.57 (m, 1H), 1.85-1.77 (m, 1H), 1.64-1.54 (m, 2H), 1.37-1.27 (m, 1H), 0.85-0.69 (m, 3H), 0.51-0.44 (m, 1H), 0.43-0.36 (m, 2H). $^{19}$F. NMR (376 MHz, Dimethylsulfoxide-$d_6$)$_6$-206.69.

Intermediate 127 & 128: (2R,5S,7aS)-7a-(((tert-Butyldiphenylsilyl)oxy)methyl)-2-fluoro-5-methylhexahydro-1H-pyrrolizine & (2R,7aS)-7a-(((tert-butyldiphenylsilyl)oxy)methyl)-2-fluoro-5,5-dimethylhexahydro-1H-pyrrolizine

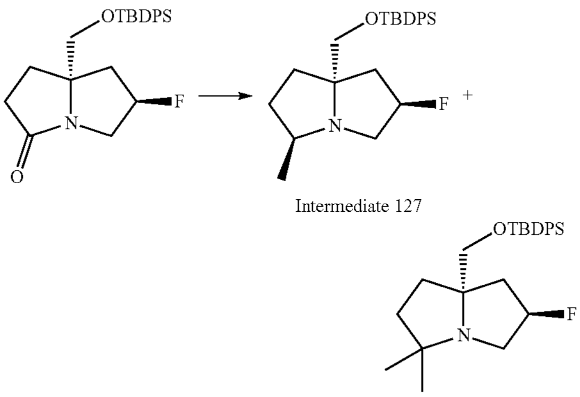

Intermediate 127

Intermediate 128

To a stirred solution of (6R,7aS)-7a-(((tert-butyldiphenylsilyl)oxy)methyl)-6-fluorohexahydro-3H-pyrrolizin-3-one (4.0 g, 9.71 mmol) and 2,6-di-tert-butyl-4-methylpyridine (2394.74 mg, 11.66 mmol) in DCM (40 mL) was added (trifluoromethane) sulfonyl trifluoromethanesulfonate (3290.21 mg, 11.66 mmol) dropwise at −78° C. under nitrogen atmosphere. After stirring at −78° C. for 45 min, MeMgBr (3 M in THF, 3.24 mL, 9.71 mmol) was added to the above mixture. The dry ice bath was removed, and the reaction mixture was stirred at room temperature for 1 hour. NaBH4 (1102.94 mg, 29.15 mmol) was added to the above mixture. The resulting mixture was stirred at room temperature for another an hour. The resulting mixture was diluted with 20% sodium hydroxide aqueous solution (80 mL) and extracted with DCM (3×100 mL). The combined organic layers were washed with brine (80 mL), dried over anhydrous $Na_2SO_4$, filtered and concentrated under reduced pressure. The residue was purified by silica gel flash chromatography, eluted with PE/EA (5: 1) to give two peaks. The first eluting peak was collected and concentrated under reduced pressure to give the title compound (Intermediate 127, 1.0 g, 25% yield) as a light-yellow oil. MS: m/z=412.35 $[M+H]^+$. $^1$H NMR (400 MHZ, Chloroform-d) δ 7.73-7.63 (m, 4H), 7.44-7.35 (m, 6H), 5.30-5.17 (m, 1H), 3.55-2.82 (m, 4H), 2.18-1.98 (m, 3H), 1.92-1.32 (m, 4H), 1.10-1.02 (m, 12H). $^{19}$F NMR (376 MHZ, CDCl) δ −173.43 (s, 1F). The second eluting peak was collected and concentrated under reduced pressure to give the title compound (Intermediate 128, 380 mg, 9% yield) as a light-yellow oil. MS: m/z=426.35 $[M+H]^+$. $^1$H NMR (400 MHZ, Chloroform-d)δ 7.67-7.60 (m, 4H), 7.37-7.28 (m, 6H), 5.25-5.00 (m, 1H), 3.40-3.10 (m, 3H), 3.03-2.85 (m, 1H), 2.37-2.25 (m, 1H), 1.80-1.59 (m, 5H), 1.09-0.92 (m, 15H). $^{19}$F NMR (376 MHz, CDCl) δ −171.79 (s, IF).

Intermediate 129: ((2R,5S,7aS)-2-fluoro-5-methyltetrahydro-1H-pyrrolizin-7a(5H)-yl)methanol

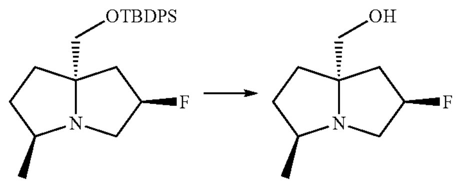

Intermediate 127 Intermediate 129

To a mixture of Intermediate 127 (1.04 g, 2.52 mmol) in methanol (10 mL) was added ammonium fluoride (3742.97 mg, 101.08 mmol) under nitrogen atmosphere. The reaction mixture was heated at 60° C. for 16 hours. The resulting mixture was cooled to room temperature, filtered and concentrated under reduced pressure. The residue was purified by silica gel flash chromatography, eluted with 15% MeOH in DCM to afford the title compound (Intermediate 129, 250 mg, 57% yield) as a yellow oil. $^1$H NMR (400 MHZ, DMSO-$d_6$) δ 5.32-5.17 (m, 1H), 4.50 (bs, 1H), 3.17-2.91 (m, 4H), 2.87-2.77 (m, 1H), 2.03-1.77 (m, 4H), 1.67-1.59 (m, 1H), 1.38-1.23 (m, 1H), 1.01-1.00 (d, J=6.0 Hz, 3H). $^{19}$F NMR (376 MHz, DMSO-$d_6$) δ−170.21 (s, IF).

Intermediate 130: ((1R,2R,7a'S)-2-fluorodihydro-1'H,3'H-spiro[cyclopropane-1,2'-pyrrolizin]-7a'(5'H)-yl-5',5'-$d_2$)methan-$d_2$-ol

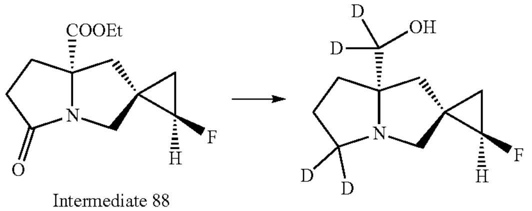

Intermediate 88

Intermediate 130

To a slurry of $LiAlD_4$ (143 mg, 3.11 mmol) in THF (5 mL) was added Intermediate 88 (150 mg, 624 μmol) at 0° C. under $N_2$. The mixture was stirred at 0° C. for 0.5 h under $N_2$. The mixture was then stirred at 70° C. for 1.5 h under $N_2$. The reaction mixture was quenched with $D_2O$ (0.14 mL) slowly. 15% w/NaOH aq. (0.14 mL) was added dropwise, followed by addition of $H_2O$ (0.42 mL). The mixture was filtered, and the filter cake was washed with EtOAc (40 mL). The combined organic layers were dried over anhydrous $Na_2SO_4$, filtered and concentrated under reduced pressure. The residue was purified by silica gel flash chromatography (eluent: 0~15% of MeOH in $CH_2Cl$) to give the title compound (Intermediate 130, 92 mg, 78% yield) as a yellow oil. $^1$H NMR (400 MHZ, Chloroform-d) δ 4.62-4.32 (m, 1H), 3.16 (d,)=12.0 Hz, 1H), 2.84 (d, J=12.0 Hz, 1H), 1.94-1.64 (m, 6H), 1.48 (d, J=13.4 Hz, 1H), 0.90-0.77 (m, 2H). $^{19}$F NMR (376 MHz, Chloroform-d) δ −207.35.

Intermediate 131: ((1R,2S,7a'S)-2-fluorodihydro-1'H,3'H-spiro[cyclopropane-1,2'-pyrrolizin]-7a'(5'H)-yl-5',5'-$d_2$)methan-$d_2$-ol

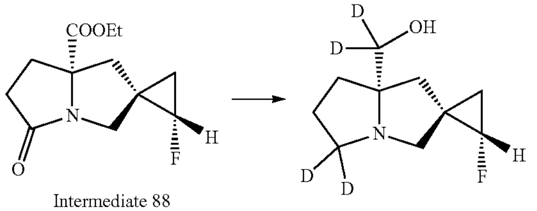

Intermediate 88

Intermediate 130

Intermediate 131 was prepared in a manner similar to Intermediate 130. MS: m/z=189.9 $[M+H]^+$. HJ+. $^1H$ NMR (400 MHZ, Chloroform-d) δ 4.66-4.38 (m, 1H), 3.29-3.15 (m, 1H), 2.53 (d, J=12.0 Hz, 1H), 2.23-2.14 (m, 1H), 2.03-1.73 (m, 5H), 1.02-0.77 (m, 2H). $^{19}F$ NMR. (376 MHz, Chloroform-d) δ −210.05.

Intermediate 132: (1S,7S,8S)-2-(2,7-Dichloro-8-fluoro-5-methoxypyrido[4,3-d]pyrimidin-4-yl)-8-fluoro-5-oxa-2-azabicyclo[5.1.0]octane

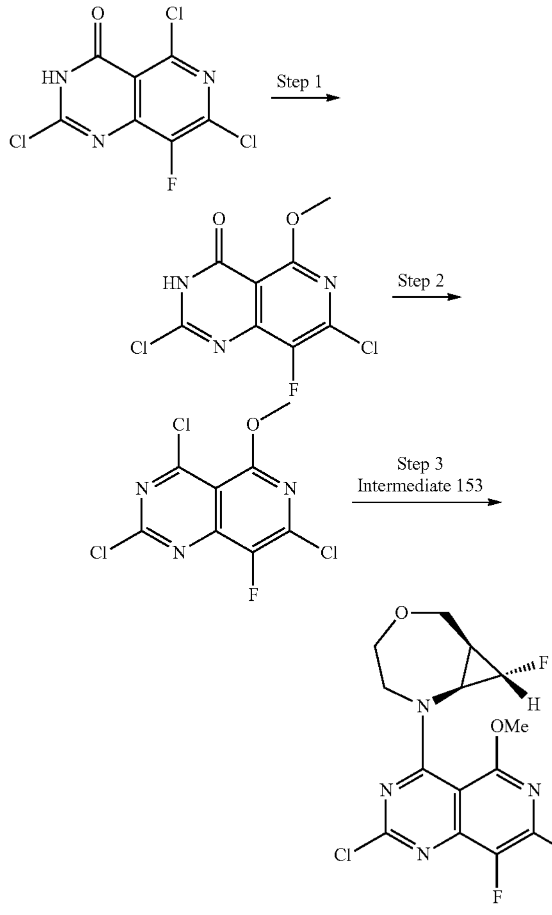

Intermediate 132

Step 1: 2,7-Dichloro-8-fluoro-5-methoxypyrido[4,3-d]pyrimidin-4 (3H)-one

To a suspension of NaH (596 mg, 14.9 mmol) in THF (10 mL) was added MeOH (241 μL, 5.96 mmol) dropwise at 0° C. under $N_2$. The mixture was stirred at 0° C. under $N_2$ for 0.5 h. The mixture was added to a solution of 2,5,7-trichloro-8-fluoropyrido[4,3-d]pyrimidin-4 (3H)-one (2 g, 7.45 mmol) in THF (10 mL) dropwise at 0° C. The resulting mixture was stirred at the same temperature for another 1 h under $N_2$. The reaction mixture was quenched with sat. $NH_4CL$. aq. (20 mL) at 0° C., and then the pH of the mixture was adjusted to around 3 with HCl aq. (10 mL, 6 M in $H_2O$). The mixture was diluted with $H_2O$ (50 mL) and extracted with EtOAc (50 mL×3). The combined organic layers were washed with brine (50 mL), dried over anhydrous $Na_2SO_4$, filtered and concentrated under reduced pressure to give the title compound (2 g, crude) as a yellow solid. MS: m/z=263.8 $[M+H]^{+\cdot}$ Step 2: 2,4,7-Trichloro-8-fluoro-5-methoxypyrido[4,3-d]pyrimidine To a solution of 2,7-dichloro-8-fluoro-5-methoxypyrido[4,3-d]pyrimidin-4 (3H)-one (2 g, 7.57 mmol) in $CH_2Cl_2$ (20 mL) was added DIPEA (7.83 g, 60.6 mmol) and $POCl_3$ (4.65 g, 30.3 mmol) at 0° C. under $N_2$. The mixture was stirred at 0° C. for 1 h under $N_2$. The reaction mixture was concentrated under reduced pressure to give the title compound (2.14 g, crude) as a black-brown oil. MS: m/z=281.9 $[M+H]^{+\cdot}$ Step 3: (1S,7S,8S)-2-(2,7-Dichloro-8-fluoro-S-methoxypyrido[4,3-d]pyrimidin-4-yl)-8-fluoro-5-oxa-2-azabicyclo[5.1.0]octane To a solution of 2,4,7-trichloro-8-fluoro-5-methoxypyrido[4,3-d]pyrimidine (2.14 g, 7.58 mmol) in $CH_2Cl_2$ (20 mL) was added DIPEA (2.94 g, 22.7 mmol) and Intermediate 153 (1.61 g, 7.58 mmol, HBr) at −40° C. under $N_2$ and stirred at the same temperature for 1 h under $N_2$. The reaction mixture was quenched with $H_2O$ (50 mL) and extracted with $CH_2Cl_2$ (50 mL×3). The combined organic layers were washed with brine (50 mL), dried over anhydrous $Na_2SO_4$, filtered and concentrated under reduced pressure to give the title compound (Intermediate 132, 2.8 g, crude) as a black-brown oil. MS: m/z=376.9 $[M+H]^{+\cdot}$ Intermediate 133& 134: (1R,7R,8R)-2-(7-bromo-6-chloro-8-fluoro-2-(((2R,7aS)-2-fluorotetrahydro-1H-pyrrolizin-7a(5H)-yl)methoxy-$d_2$)quinazolin-4-yl)-8-fluoro-5-oxa-2-azabicyclo[5.1.0]octane & (1S,7S,8S)-2-(7-bromo-6-chloro-8-fluoro-2-(((2R,7aS)-2-fluorotetrahydro-1H-pyrrolizin-7a(5H)-yl)methoxy-$d_2$)quinazolin-4-yl)-8-fluoro-5-oxa-2-azabicyclo[5.1.0]octane

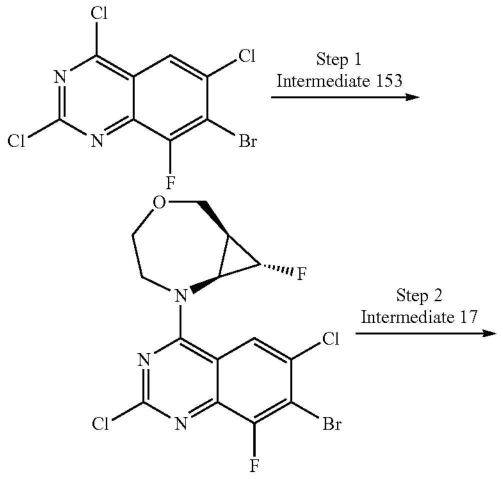

-continued

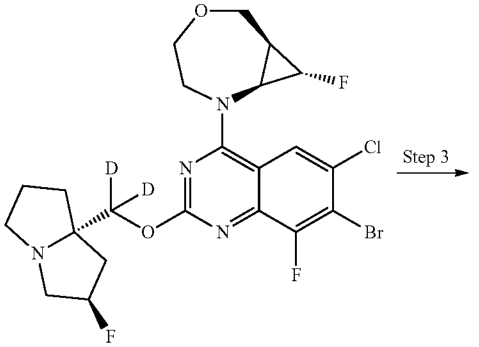

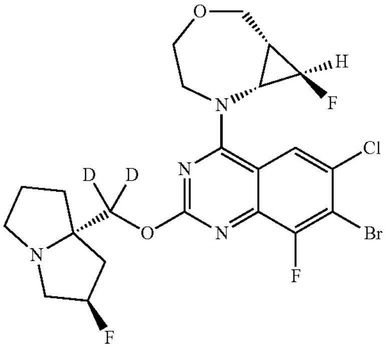

+

Intermediate 133

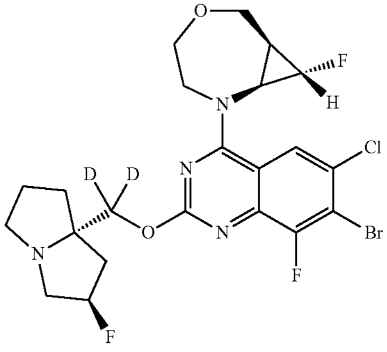

Intermediate 134

Step 1: 2-(7-Bromo-2,6-dichloro-8-fluoroquinazolin-4-yl)-8-fluoro-5-oxa-2-azabicyclo[5.1.0]octane To an ice-cooled mixture of 7-bromo-2,4,6-trichloro-8-fluoroquinazoline (7.00 g, 21.19 mmol) in DCM (70 mL) were added DIEA (8.22 g, 63.57 mmol) and Intermediate 153 (4.47 g, 21.19 mmol, refer to Intermediate 33 & 34 for detail procedures) under nitrogen atmosphere. The reaction mixture was cooled to −40° C. and stirred for 2 hours. The mixture was warmed up to room temperature and concentrated under reduced pressure. The residue was purified by silica gel flash chromatography, eluted with 45% EA in PE to afford the title compound (6.9 g, 76%) as a yellow oil. MS: m/z=424.15, 426.15, 428.15 $[M+H]^+$. $^1H$ NMR (400 MHZ, Chloroform-d)δ 8.35 (s, 1H), 4.63-4.53 (m, 1H), 4.48-4.37 (m, 1H), 4.37-4.16 (m, 1H), 4.02-3.85 (m, 3H), 3.70-3.59 (m, 1H), 3.45-3.07 (m, 1H), 2.40-2.21 (m, 1H).

Step 2: 2-(7-Bromo-6-chloro-8-fluoro-2-(((2R,7aS)-2-fluorotetrahydro-1H-pyrrolizin-7a (5H)-yl) methoxy-$d_2$) quinazolin-4-yl)-8-fluoro-5-oxa-2-azabicyclo[5.1.0]octane To an ice-cooled mixture of 2-(7-bromo-2,6-dichloro-8-fluoroquinazolin-4-yl)-8-fluoro-5-oxa-2-azabicyclo[5.1.0] octane (6.9 g, 16.23 mmol) in DMSO (70 mL) were added Intermediate 17 (4.19 g, 25.97 mmol) and potassium fluoride (3.30 g, 56.82 mmol) under nitrogen atmosphere. The reaction mixture was heated at 100° C. for 16 hours. The mixture was cooled down to room temperature. The resulting mixture was extracted with EA (3×200 mL), washed with $H_2O$ (1×200 mL), dried over anhydrous $Na_2SO_4$, filtered, and concentrated under reduced pressure. The residue was purified by silica gel flash chromatography, eluted with $CH_2Cl_2$/MeOH (10: 1) to afford the title compound (3.4 g, 38%) as a white solid. MS: m/z=549.05, 551.05 $[M+H]^{+\cdot}$ Step 3: (1R,7R,8R)-2-(7-bromo-6-chloro-8-fluoro-2-(((2R,7aS)-2-fluorotetrahydro-1H-pyrrolizin-7a (5H)-yl) methoxy-$d_2$) quinazolin-4-yl)-8-fluoro-5-oxa-2-azabicyclo[5.1.0]octane & (1S,7S,8S)-2-(7-bromo-6-chloro-8-fluoro-2-(((2R,7aS)-2-fluorotetrahydro-1H-pyrrolizin-7a (5H)-yl) methoxy-$d_2$) quinazolin-4-yl)-8-fluoro-5-oxa-2-azabicyclo[5.1.0] octane 2-(7-Bromo-6-chloro-8-fluoro-2-(((2R,7aS)-2-fluorotetrahydro-1H-pyrrolizin-7a (5H)-yl) methoxy-$d_2$) quinazolin-4-yl)-8-fluoro-5-oxa-2-azabicyclo[5.1.0]octane (3.4 g, 6.2 mmol) was separated by Prep-SFC with the following conditions: Column: CHIRALPAK IH, 7*25 cm, 10 μm; Mobile Phase A: IPA (0.1% 7M $NH_3$-MeOH), Mobile Phase B: $CO_2$; Flow rate: 240 mL/min; Gradient: isocratic 50% B; Back Pressure (bar): 100; Wave Length: 220 nm; RT1 (min): 11.05; RT2 (min): 12.92; Injection Volume: 10 mL. The first eluting peak (RT1: 11.05 min) was concentrated and lyophilized to give the title compound (Intermediate 133, 800 mg, 23% yield) as a white solid. MS: m/z=549.10, 551.10 $[M+H]^+$, $^1H$ NMR. (400 MHZ, DMSO-$d_6$) δ 8.40 (s, 1H), 5.37-5.18 (m, 1H), 4.82-4.59 (m, 1H), 4.43-4.21 (m, 3H), 3.95 (d, J=12.2 Hz, 1H), 3.72-3.62 (m, 1H), 3.58-3.46 (m, 1H), 3.16-2.99 (m, 4H), 2.88-2.79 (m, 1H), 2.36~2.20 (m, 1H), 2.14-2.09 (m, 1H), 2.06-1.95 (m, 2H), 1.89-1.71 (m, 3H). $^{19}F$ NMR (376 MHZ, DMSO-$d_6$) δ −112.72 (IF), ~172.18 (IF), —207.84 (1F). The second eluting peak (RT2: 12.92 min) was concentrated and lyophilized to give the title compound (Intermediate 134, 1.1 g, 32% yield) as a light yellow solid. MS: m/z=549.10, 551.00 $[M+H]^+$. $^1H$ NMR (400 MHZ, DMSO-$d_6$) δ 8.40 (s, 1H), 5.39-5.19 (m, 1H), 4.81-4.61 (m, 1H), 4.44-4.21 (m, 3H), 3.95 (d, J=12.2 Hz, 1H), 3.73-3.63 (m, 1H), 3.58-3.48 (m, 1H), 3.19-2.99 (m, 4H), 2.91-2.80 (m, 1H), 2.37-2.22 (m, 1H), 2.19-1.95 (m, 3H), 1.90-1.69 (m, 3H). $^{19}F$. NMR (376 MHZ, DMSO-$d_6$) δ −112.70 (1F), —172.18 (IF), —207.87 (IF).

Intermediate 135 & 136: Ethyl (S,E)-2-(fluoromethylene)-5-oxotetrahydro-1H-pyrrolizine-7a(5H)-carboxylate & ethyl (S,Z)-2-(fluoromethylene)-5-oxotetrahydro-1H-pyrrolizine-7aH(5H)-carboxylate

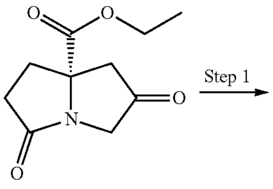

-continued

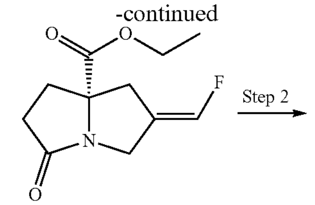

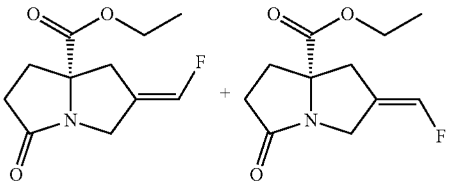

Intermediate 135 Intermediate 136

Step 1: Ethyl(S)-2-(fluoromethylene)-5-oxotetrahydro-1H-pyrrolizine-7a (5H)-carboxylate To a solution of 2-fluoromethanesulfonylpyridine (4.40 g, 25.09 mmol) in THF (200 mL) was added KHMDS (1 M in THF, 29.83 mL, 29.83 mmol) dropwise at −78° C. under argon atmosphere. After stirring at −78° C. for 0.5 hour, a solution of ethyl (7aS)-2,5-dioxo-tetrahydropyrrolizine-7a-carboxylate (5 g, 23.67 mmol) in THF (20 mL) was added dropwise to the above mixture at −78° C. The resulting mixture was warmed to room temperature and stirred for 16 hours. The resulting mixture was quenched with sat. aq. $NH_4Cl$ (200 mL) and extracted with ethyl acetate (3×200 mL). The combined organic layers were washed with brine (200 mL), dried over anhydrous sodium sulfate, filtered and concentrated under reduced pressure. The residue was purified by silica gel flash chromatography, eluted with 0-60% ethyl acetate in petroleum ether to afford the title compound (2 g, 18% yield) as a light-yellow oil. MS: m/z=228.00 $[M+H]^+$. $^1H$ NMR (300 MHz, Chloroform-d) § 6.70-6.45 (m, 1H), 4.40-4.32 (m, 1H), 4.23-4.21 (m, 2H), 3.91-3.70 (m, 1H), 3.33-3.01 (m, 1H), 2.86-2.56 (m, 2H), 2.52-2.40 (m, 2H), 2.18-2.10 (m, 1H), 1.31-1.27 (m, 3H).

Step 2: Ethyl (S,E)-2-(fluoromethylene)-5-oxotetrahydro-1/-pyrrolizine-7a (5H)-carboxylate & ethyl (S,Z)-2-(fluoromethylene)-5-oxotetrahydro-1H-pyrrolizine-7a (5H)-carboxylate Ethyl(S)-2-(fluoromethylene)-5-oxotetrahydro-1/-pyrrolizine-7a (5H)-carboxylate (550 mg) was separated by Achiral-Prep-SFC with the following conditions: Column: GreenSep Nitro, 30× 150 mm 5 μm; Mobile Phase A: $CO_2$; Mobile Phase B: IPA (20 mM $NH_3$); Flow rate: 60 mL/min; Gradient: isocratic 12% B; Column Temperature (° C.): 35; Back Pressure (bar): 100; Detector: UV 220 nm; RT1: 3.22 min; RT2: 4.50 min. The first eluting peak (RT1: 3.22 min) was combined and concentrated under reduced pressure to give the title compound (Intermediate 135, 164 mg, 29% yield) as a colorless oil. MS: m/z=228.00 $[M+H]^+$. $^1H$ NMR (300 MHZ, Chloroform-d) § 6.74-6.45 (m, 1H), 4.36-4.31 (m, 1H), 4.26-4.19 (m, 2H), 3.74-3.69 (m, 1H), 3.33-3.28 (m, 1H), 2.82-2.62 (m, 2H), 2.51-2.40 (m, 2H), 2.19-2.08 (m, 1H), 1.29 (t, J=7.2 Hz, 3H). $^{19}F$. NMR (282 MHz, Chloroform-d) δ -128.69 (s, IF). The second eluting peak (RT1: 4.50 min) was combined and concentrated under reduced pressure to give the title compound (Intermediate 136, 140 mg, 25% yield) as a colorless oil. MS: m/z=228.00 $[M+H]^+$. $^1H$ NMR (300 MHz, Chloroform-d) δ 6.69-6.41 (m, 1H), 4.41-4.36 (m, 1H), 4.26-4.18 (m, 2H), 3.91-3.86 (m, 1H), 3.05-3.00 (m, 1H), 2.84-2.75 (m, 1H), 2.63-2.34 (m, 3H), 2.20-2.01 (m, 1H), 1.28 (t,)=7.2 Hz, 3H). $^{19}F$. NMR (282 MHz, Chloroform-d) d-127.96 (s, IF).

Intermediate 137: (S,Z)-(2-(fluoromethylene)tetrahydro-1H-pyrrolizin-7a(5H)-yl)methanol

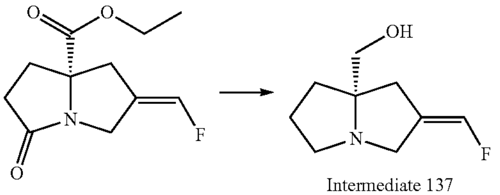

Intermediate 136 Intermediate 137

To an ice-cooled solution of Intermediate 136 (164 mg, 0.72 mmol) in THF (13 mL) was added DIBAL-H (1 M in hexane, 7.33 mL, 7.33 mmol) under argon atmosphere. The ice bath was removed, and the reaction mixture was stirred at room temperature for 1 hour. The resulting mixture was quenched with sat. aq. NaOH (0.29 mL) and concentrated under reduced pressure. The residue was purified by silica gel flash chromatography, eluted with 0-20% methanol (10% $NH_3$ $H_2O$) in dichloromethane to afford the title compound (Intermediate 137, 91.6 mg, 74% yield) as a light-yellow oil. MS: m/z=172.00 $[M+H]^+$. $^1H$ NMR (300 MHz, Chloroform-d) δ 6.65-6.35 (m, 1H), 3.80-3.75 (m, 1H), 3.49-3.43 (m, 1H), 3.37-3.29 (m, 2H), 3.20-3.13 (m, 2H), 2.71-2.65 (m, 1H), 2.47-2.41 (m, 1H), 2.30-2.22 (m, 1H), 1.94-1.67 (m, 4H). $^{19}F$ NMR (282 MHz, Chloroform-d) 6-129.94 (s, 1F).

Intermediate 138: (1D,7S,8S)-2-(7-chloro-8-fluoro-2-((S,Z)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane

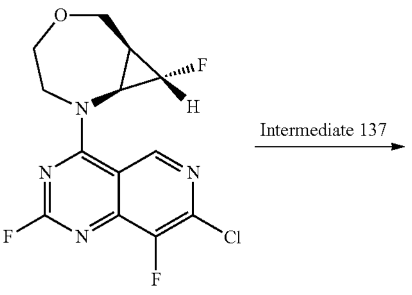

Intermediate 112

-continued

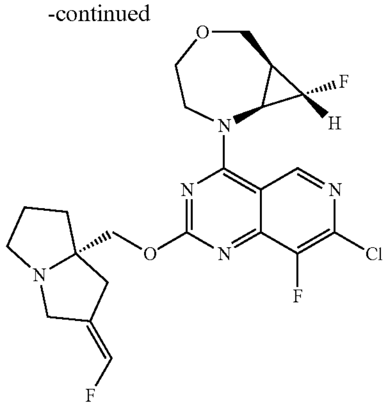

Intermediate 138

To an ice-cooled solution of Intermediate 137 (116.49 mg, 0.68 mmol) in THF (3 mL) under nitrogen atmosphere was added 1-BuOK (61.08 mg, 0.54 mmol). After stirring in an ice bath for 30 min, Intermediate 112 (150 mg, 0.45 mmol) was added to the above mixture in portions. The ice bath was removed, and the reaction mixture was stirred at room temperature for 1 hour. The resulting mixture was quenched with sat. aq. $NH_4Cl$ (20 mL) and extracted with DCM (3×30 mL). The combined organic layers were washed with brine (50 mL), dried over anhydrous $Na_2SO_4$, filtered and concentrated under reduced pressure. The residue was purified by Prep-TLC($CH_2Cl_2$/MeOH 10: 1) to afford the title compound (Intermediate 138, 210 mg, 96% yield) as a light yellow solid. MS: m/z=482.05 $[M+H]^{+}$.

Intermediate 139 & 140: (2R,5S,7aS)-7a-(((tert-Butyldiphenylsilyl)oxy)methyl)-2-fluoro-5-methylhexahydro-1H-pyrrolizine & (2R,5R,7aS)-7a-(((tert-butyldiphenylsilyl)oxy)methyl)-2-fluoro-5-methylhexahydro-1H-pyrrolizine

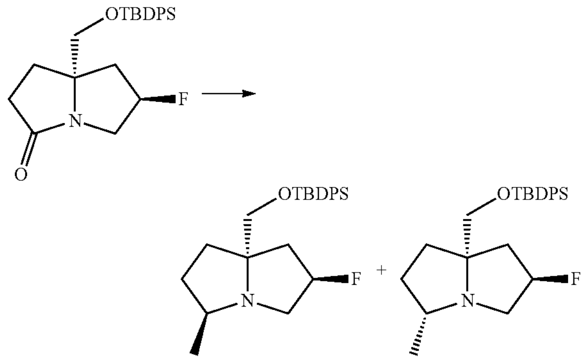

Intermediate 139 Intermediate 140

Structure tentatively assigned

To a mixture of (6R,7aS)-7a-(((tert-butyldiphenylsilyl)oxy)methyl)-6-fluorohexahydro-3H-pyrrolizin-3-one (2 g, 4.85 mmol) and chloroiridium; methanidylidyneoxidanium; bis(triphenylphosphane) (0.08 g, 0.09 mmol) in DCM (30 mL) under $N_2$ was added 1,1,3,3-tetramethyldisiloxane (1.31 g, 9.71 mmol) at room temperature. The mixture was stirred at room temperature for 0.5 hours. Methylmagnesium bromide (1.0 M in THE, 9.72 mL, 9.72 mmol) was added dropwise at −70° C. The reaction mixture was stirred at room temperature for 4 hours. The resulting mixture was quenched with aq. $NH_4Cl$ (100 mL) in an ice bath and extracted with ethyl acetate (3×80 mL). The combined organic layers were dried over anhydrous sodium sulfate, filtered and concentrated under reduced pressure. The residue was purified by silica gel flash chromatography, eluted with PE/EA (7: 1) to give two isomers. The first eluting isomer was concentrated to give the title compound (Intermediate 139, 200 mg, 10% yield) as a light-yellow oil. MS: m/z=412.20 $[M+H]^{+}$. $^{1}$H NMR (400 MHz, Chloroform-d)δ 7.73-7.67 (m, 4H), 7.44-7.35 (m, 6H), 5.30-5.17 (m, 1H), 3.45-2.75 (m, 5H), 2.27-1.67 (m, 6H), 1.10-1.00 (m, 12H). $^{19}$F NMR (376 MHz, Chloroform-d) d-171.79 (s, IF). The second eluting isomer was concentrated to give the other title compound (Intermediate 140, 1500 mg, 74% yield) as a light-yellow oil. MS: m/z=412.15 $[M+H]^{+}$. $^{1}$H NMR (400 MHZ, Chloroform-d)δ 7.72-7.67 (m, 4H), 7.44-7.34 (m, 6H), 5.30-5.17 (m, 1H), 3.43 (s, 2H), 3.13-3.06 (m, 3H), 2.44-2.34 (m, 1H), 1.94-1.59 (m, 5H), 1.18 (d, J=6.4 Hz, 3H), 1.06 (s, 9H). $^{19}$F NMR (376 MHz, Chloroform-d) δ −172.76-179.88 (m, 1F).

Intermediate 141: ((2R,5R,7aS)-2-fluoro-5-methyltetrahydro-1H-pyrrolizin-7a(5H)-yl)methanol

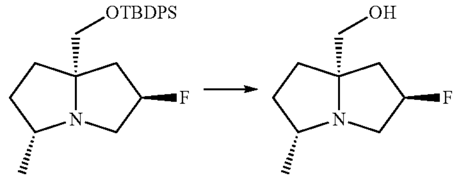

Intermediate 140 Intermediate 141

To a solution of Intermediate 140 (1.5 g, 3.64 mmol) in methanol (20 mL) was added $NH_4F$ (5.40 g, 145.76 mmol) at room temperature. The reaction mixture was heated at 60° C. for 16 hours. The resulting mixture was cooled to room temperature, filtered and concentrated under reduced pressure. The residue was purified by silica gel flash chromatography (eluted with $CH_2Cl_2$/MeOH (8: 1)) to afford the title compound (Intermediate 141, 400 mg, 63% yield) as a light-yellow oil. MS: m/z=174.05 $[M+H]^{+}$. $^{1}$H NMR (400 MHZ, DMSO-$d_6$) & 5.18-5.01 (m, 1H), 4.52 (s, 1H), 3.13-2.91 (m, 5H), 1.70-1.50 (m, 5H), 1.09 (d, J=6.8 Hz, 3H). $^{19}$F NMR (376 MHz, DMSO-$d_6$)$_6$-171.42-178.74 (m, IF).

Intermediate 142: (1S,7S,8S)-2-(7-Chloro-2-(((2R,7aS)-2-fluorotetrahydro-1H-pyrrolizin-7a(5H)-yl)methoxy-$d_2$)-8-methylpyrido[4,3-d]pyrimidin-4-yl)-8-fluoro-5-oxa-2-azabicyclo[5.1.0]octane

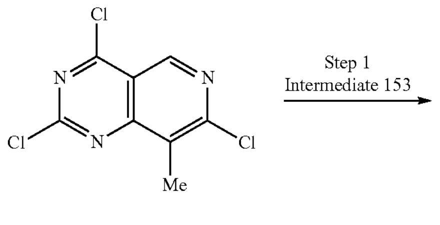

-continued

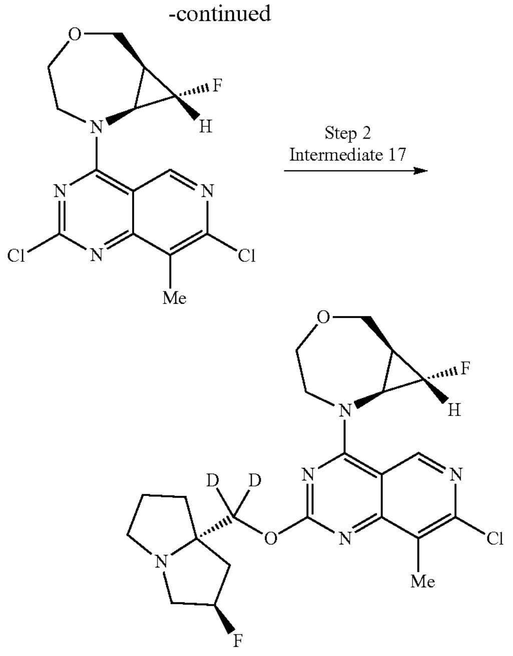

Intermediate 142

Step 1: (1S,7S,8S)-2-(2,7-Dichloro-8-methylpyrido[4,3-d]pyrimidin-4-yl)-8-fluoro-5-oxa-2-azabicyclo[5.1.0]octane To a stirred solution of 2,4,7-trichloro-8-methylpyrido[4,3-d]pyrimidine (200 mg, 0.81 mmol) and Intermediate 153 (170.68 mg, 0.81 mmol, refer to Intermediate 33 & 34 for detail procedures) in DCM (5 mL) was added DIEA (312.08 mg, 2.42 mmol) dropwise at −40° C. under nitrogen atmosphere. The reaction mixture was stirred at −40° C. for 1 hour. The resulting mixture was diluted with water (30 mL) and extracted with DCM (3x30 mL). The combined organic layers were washed with brine (50 mL), dried over anhydrous $Na_2SO_4$, filtered and concentrated under reduced pressure. The residue was purified by Prep-TLC(PE/EA 3: 1) to afford the title compound (200 mg, 72% yield) as a light yellow solid. MS: m/z=343.05, 345.05 $[M+H]^+$. $^1H$ NMR (400 MHZ, Chloroform-d) & 9.40 (s, 1H), 4.67-4.62 (m, 1H), 4.43-4.22 (m, 2H), 3.96-3.82 (m, 3H), 3.69-3.62 (m, 1H), 3.28 (s, 1H), 2.67 (s, 3H), 2.35-2.30 (m, 1H).

Step 2: (1S,7S,8S)-2-(7-Chloro-2-(((2R,7aS)-2-fluorotetrahydro-1H-pyrrolizin-7a (5H)-yl) methoxy-$d_2$)-8-methylpyrido[4,3-d]pyrimidin-4-yl)-8-fluoro-5-oxa-2-azabicyclo[5.1.0]octane To a stirred solution of (1S,7S,8S)-2-(2,7-dichloro-8-methylpyrido[4,3-d]pyrimidin-4-yl)-8-fluoro-5-oxa-2-azabicyclo[5.1.0]octane (200 mg, 0.58 mmol) in DMSO (2.0 mL) under $N_2$ were added KF (118.50 mg, 2.04 mmol) and Intermediate 17 (150.33 mg, 0.93 mmol) at room temperature. The reaction mixture was heated at 100° C. for 16 hours. The resulting mixture was cooled to room temperature, diluted with water (30 mL) and extracted with DCM (3x30 mL). The combined organic layers were washed with brine (50 mL), dried over anhydrous $Na_2SO_4$, filtered and concentrated under reduced pressure. The residue was purified by Prep-TLC($CH_2Cl_2$/MeOH 15: 1) to afford the title compound (Intermediate 142, 220 mg, 80% yield) as a light yellow solid. MS: m/z=468.15 $[M+H]^{+.}$ Intermediate 143 & 144: (6R,7aS)-7a-(((tert-Butyldiphenylsilyl)oxy)methyl-$d_2$)-6-fluorohexahydro-3H-pyrrolizin-3-one & (2R,7aS)-7a-(((tert-butyldiphenylsilyl)oxy)methyl-$d_2$)-2-fluorohexahydro-3H-pyrrolizin-3-one

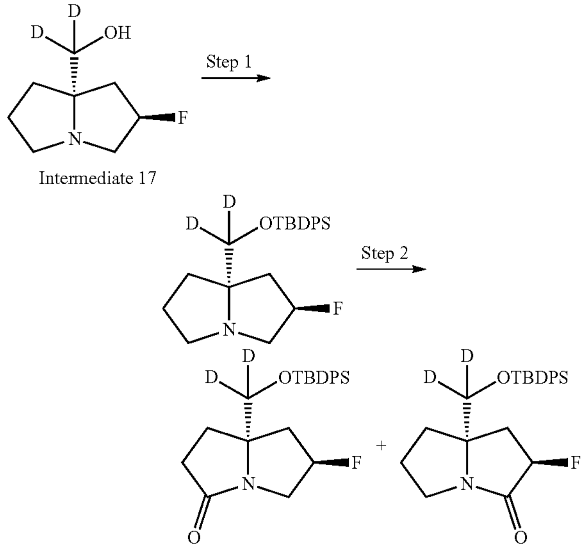

Intermediate 17

Intermediate 143

Intermediate 144

Step 1: (2R,7aS)-7a-(((tert-butyldiphenylsilyl)oxy)methyl-$d_2$)-2-fluorohexahydro-1H-pyrrolizine To an ice-cooled solution of Intermediate 17 (30 g, 186.08 mmol) and Imidazole (25.34 g, 372.17 mmol) in DMF (300 mL) under $N_2$ was added tert-butyl (chloro)diphenylsilane (61.38 g, 223.30 mmol). The ice bath was removed, and the reaction mixture was stirred at room temperature for 2 hours. The resulting mixture was diluted with $CH_2Cl_2$ (1000 mL), washed with water (3x300 mL) and brine (300 mL), dried over anhydrous $Na_2SO_4$, filtered and concentrated under reduced pressure. The residue was purified by silica gel flash chromatography, eluted with 0-20% EA in PE to afford the title compound (60 g, 80% yield) as a light-yellow oil. MS: m/z=400.15 $[M+H]^+$. $^1H$ NMR (400 MHZ, Chloroform-d)δ 7.73-7.65 (m, 4H), 7.44-7.35 (m, 6H), 5.26-5.11 (m, 1H), 3.15-3.08 (m, 2H), 2.95-2.88 (m, 3H), 2.15-1.63 (m, 5H), 1.07 (s, 9H).

Step 2: (6R,7aS)-7a-(((tert-Butyldiphenylsilyl)oxy)methyl-$d_2$)-6-fluorohexahydro-3/-pyrrolizin-3-one & (2R,7aS)-7a-(((tert-butyldiphenylsilyl)oxy)methyl-$d_2$)-2-fluorohexahydro-3H-pyrrolizin-3-one To an ice-cooled solution of (2R,7aS)-7a-(((tert-butyldiphenylsilyl)oxy)methyl-$d_2$)-2-fluorohexahydro-1/-pyrrolizine (60 g, 150.14 mmol) and trichlororuthenium hydrate (16.92 g, 75.07 mmol) in CC14 (300 mL) and $H_2O$ (300 mL) was added $NaIO_4$ (160.57 g, 750.71 mmol). The ice bath was removed, and the reaction mixture was stirred at room temperature for 30 min. The resulting mixture was filtered, and then extracted with DCM (3x100 mL). The combined organic layers were dried over anhydrous $Na_2SO_4$, filtered and concentrated under reduced pressure. The residue was purified by silica gel flash chromatography, eluted with 0-20% EA in PE to afford 60 g mixture of two isomers as a light-yellow solid. The mixture was purified by Prep-Achiral-SFC with the following conditions: Column: XA-GreenSep Naphthyl, 3×25 cm, 5 μm; Mobile Phase A: $CO_2$; Mobile Phase B: IPA (0.1% 7 M $NH_3$"MeOH); Flow rate: 200 mL/min; Gradient: isocratic 20% B; Detector: UV 220 nm; RT1=4.30 min; RT2: 6.07 min. The first eluting peak (RT1: 4.30 min) was concentrated and lyophilized to give the title compound (Intermediate 143, 40 g, 66% yield) as a yellow solid. MS: m/z=414.30 $[M+H]^+$. $^1H$ NMR (400 MHZ, Chloroform-d)δ 7.64-7.61 (m, 4H), 7.47-7.38 (m, 6H), 5.34-5.20 (m, 1H), 4.23-4.07 (m, 1H), 3.19-2.99 (m, 1H), 2.81-2.65 (m, 1H), 2.43-2.12 (m, 3H), 2.05-1.97 (m, 2H), 1.04 (s, 9H). $^{19}F$ NMR (376 MHz, Chloroform-d) δ −173.04 (s, 1F). The second eluting peak (RT2: 6.07 min) was concentrated and lyophilized to give the title compound (Intermediate 144, 12 g, 20% yield) as a yellow solid. MS: m/z=414.30 $[M+H]^+$. $^1H$ NMR (400 MHz, Chloroform-d) δ 7.65-7.58 (m, 4H), 7.47-7.37 (m, 6H), 5.74-5.51 (m, 1H), 3.84-3.72 (m, 1H), 2.94-2.86 (m, 2H), 2.10-1.71 (m, 4H), 1.66-1.55 (m, 1H), 1.05 (s, 9H). $^{19}F$ NMR (376 MHz, Chloroform-d) 6-184.21 (s, 1F).

Intermediate 145 & 146: (2R,3S,7aS)-7a-(((tert-Butyldiphenylsilyl)oxy)methyl-$d_2$)-2-fluoro-3-methylhexahydro-1H-pyrrolizine. & (2R,3R,7aS)-7a-(((tert-butyldiphenylsilyl)oxy)methyl-$d_2$)-2-fluoro-3-methylhexahydro-1H-pyrrolizine

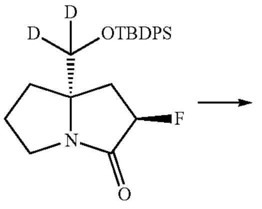

Intermediate 144

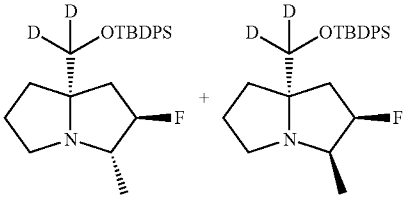

Intermediate 145 Intermediate 146

To a mixture of Intermediate 144 (3.6 g, 8.70 mmol) and chloroiridium; methanidylidyneoxidanium; bis(triphenylphosphane) (0.14 g, 0.17 mmol) in DCM (36 mL) under $N_2$ was added 1,1,3,3-tetramethyldisiloxane (2.34 g, 17.40 mmol) at room temperature. The mixture was stirred at room temperature for 0.5 hours. Methylmagnesium bromide (1.0 M in THF, 17.41 mL, 17.40 mmol) was added to the above mixture at −70° C. The resulting mixture was stirred at room temperature for 4 hours. The resulting mixture was quenched with sat. $NH_4Cl$ aq. (100 mL) in an ice bath and extracted with ethyl acetate (3×80 mL). The combined organic layers were dried over anhydrous sodium sulfate, filtered and concentrated under reduced pressure. The residue was purified by silica gel flash chromatography, eluted with PE/EA (7: 1) to give two isomers. The first eluting isomer was concentrated to give the title compound (Intermediate 145, 0.6 g, 16% yield) as a light-yellow oil. MS: m/z=414.20 $[M+H]^+$. $^1H$ NMR (400 MHZ, Chloroform-d) δ 7.71-7.57 (m, 4H), 7.43-7.35 (m, 6H), 4.78-4.63 (m, 1H), 3.16-2.70 (m, 3H), 2.39-2.31 (m, 1H), 2.03-1.78 (m, 3H), 1.75-1.62 (m, 2H), 1.08-1.06 (m, 12H). $^{19}F$ NMR (376 MHz, Chloroform-d) δ −182.46 (s, 1F). The second eluting isomer was concentrated to give the title compound (Intermediate 146, 1.8 g, 49% yield) as a light-yellow oil. MS: m/z=414.25 $[M+H]^+$. $^1H$ NMR (400 MHz, Chloroform-d) & 7.68-7.64 (m, 4H), 7.43-7.34 (m, 6H), 5.00-4.85 (m, 1H), 3.19-2.79 (m, 3H), 2.23-1.95 (m, 3H), 1.82-1.63 (m, 3H), 1.32 (d, J=7.2 Hz, 3H), 1.06 (s, 9H). $^{19}F$ NMR (376 MHz, Chloroform-d) δ −187.10 (s, 1F).

Intermediate 147: ((2R,3R,7aS)-2-fluoro-3-methyltetrahydro-1H-pyrrolizin-7a(5H)-yl)methan-$d_2$-ol

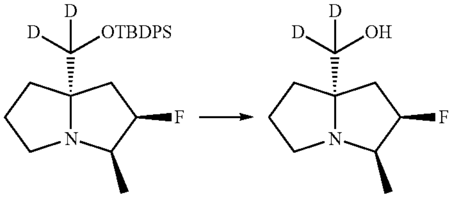

Intermediate 146 Intermediate 147

To a solution of Intermediate 146 (400 mg, 0.97 mmol) in methanol (4.0 mL) was added $NH_4F$ (1.43 g, 38.61 mmol) at room temperature. The reaction mixture was heated at 65° C. for 4 hours. The resulting mixture was cooled to room temperature, filtered and concentrated under reduced pressure. The residue was purified by Prep-TLC(DCM: MeOH=10: 1) to afford the title compound (Intermediate 147, 110 mg, 64% yield) as a yellow oil. MS: m/z=176.05 $[M+H]^+$. $^1HI$ NMR (400 MHz, DMSO-$d_6$) δ 5.11-4.96 (m, 1H), 3.26-2.24 (m, 1H), 3.17-2.87 (m, 2H), 2.18-1.54 (m, 6H), 1.25-1.19 (m, 3H). $^{19}F$ NMR (376 MHz, DMSO-$d_6$) δ −186.00 (s, 1F).

Intermediate 148: ((1*R*, 2*R*, 7a'*S*)-2-Fluorodihydro-1'*H*,3'*H*-spiro[cyclopropane-1,2'-pyrrolizin]-7a'(5'*H*)-ylmethan-*d*$_2$-ol

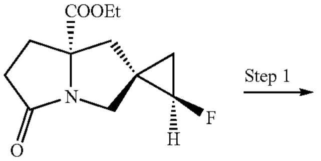

Intermediate 88

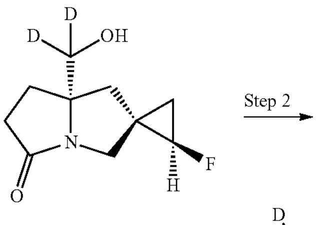

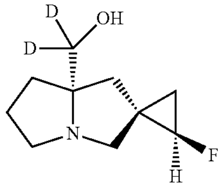

Intermediate 148

Step 1: (1R,2R,7a'S)-2-fluoro-7a'-(hydroxymethyl-$d_2$)tetrahydro-3'H,5'H-spiro[cyclopropane-1,2'-pyrrolizin]-5'-one To a solution of Intermediate 88 (170 mg, 705 μmol) in $CD_3OD$ (5 mL) was added NaBD4 (133 mg, 3.52 mmol) at 0° C. under $N_2$. The mixture was stirred at 25° C. for 16 h under $N_2$ and quenched with $D_2O$ (0.5 mL) and IN HCl (0.5 mL) at 0° C. The mixture was concentrated under reduced pressure. The residue was purified by silica gel flash chromatography (eluent: 0~4% of MeOH in dichloromethane) to give the title compound (120 mg, 84% yield) as a colorless oil. MS: m/z=202.2 $[M+H]^{+\cdot}$ Step 2: ((1R,2R,7a'S)-2-Fluorodihydro-1'H,3'H-spiro[cyclopropane-1,2'-pyrrolizin]-7a'(5'H)-yl) methan-$d_2$-ol To a solution of (1R,2R,7a'S)-2-fluoro-7a'-(hydroxymethyl-dz)tetrahydro-3'H,5'H-spiro[cyclopropane-1,2'-pyrrolizin]-5'-one (120 mg, 596 μmol) in THE (2 mL) was added LiAlH4 (715 μL, 2.5 M in THF) dropwise at 0° C. under $N_2$. The mixture was stirred at 65° C. for 2 h under $N_2$. The reaction mixture was cooled to 0° C. and quenched with $H_2O$ (0.1 mL), 15 wt % NaOH aq. (0.1 mL) and $H_2O$ (0.3 mL). The reaction mixture was diluted with THE (10 mL) and extracted with dichloromethane (50 mL×3). The combined organic layers were dried over $Na_2SO_4$, filtered and concentrated under reduced pressure. The residue was purified by silica gel flash chromatography (Dichloromethane: MeOH=5: 1) to give the title compound (Intermediate 148, 80 mg, 72% yield) as a colorless oil. MS: m/z=188.2 [M+H].

Intermediate 149: (1*S*, 7*S*, 8*S*)-2-(5, 7-Dichloro-8-fluoro-2-(((2*R*, 7a*S*)-2-fluorotetrahydro-1*H*-pyrrolizin-7a(5*H*)-yl)methoxy-*d*2)pyrido[4, 3-*d*]pyrimidin-4-yl)-8-fluoro-5-oxa-2-azabicyclo[5.10]ocatne

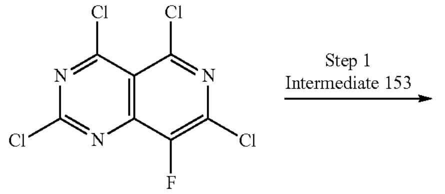

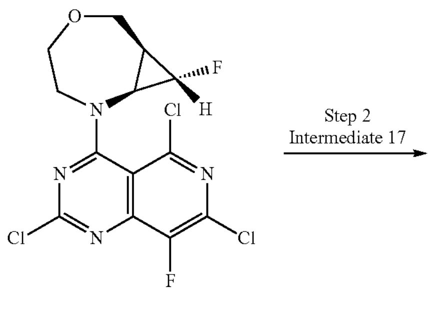

-continued

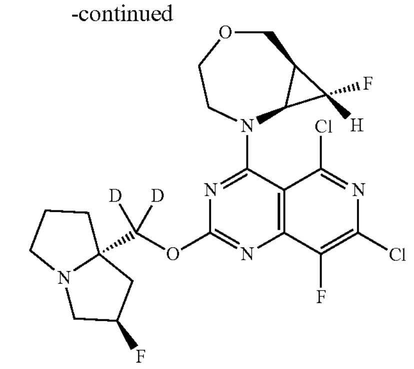

Intermediate 149

Step 1: (1S,7S,8S)-8-Fluoro-2-(2,5,7-trichloro-8-fluoropyrido[4,3-d]pyrimidin-4-yl)-5-oxa-2-azabicyclo[5.1.0]octane To a solution of 2,5,7-trichloro-8-fluoropyrido[4,3-d]pyrimidin-4 (3H)-one (2.14 g. 7.47 mmol) and DIPEA (3.94 mL, 22.64 mmol) in ACN (5 mL) was added a solution of Intermediate 153 (1.6 g, 7.55 mmol, HBr salt) in ACN (5 mL) at 0° C. under $N_2$. The mixture was stirred at 0° C. for 0.5 h under $N_2$. The reaction mixture was quenched with $H_2O$ (100 mL) and extracted with $CH_2Cl_2$ (100 mL×2). The combined organic layers were washed with brine (100 mL), dried over anhydrous $Na_2SO_4$, filtered and concentrated under reduced pressure. The residue was purified by silica gel flash chromatography (eluent: 0~3% of MeOH in $CH_2Cl_2$) to give the title compound (1.4 g, 41% yield over 2 steps) as a yellow solid. MS: m/z=381.0 $[M+H]^{+\cdot}$ Step 2: (15,7S,8S)-2-(5,7-Dichloro-8-fluoro-2-(((2R, 7aS)-2-fluorotetrahydro-1/-pyrrolizin-7a (5H)-yl) methoxy-$d_2$)pyrido[4,3-d]pyrimidin-4-yl)-8-fluoro-5-oxa-2-azabicyclo[5.1.0]octane A mixture of (1S,7S,8S)-8-fluoro-2-(2,5,7-trichloro-8-fluoropyrido[4,3-d]pyrimidin-4-yl)-5-oxa-2-azabicyclo [5.1.0]octane (1.3 g, 2.86 mmol), Intermediate 17 (923 mg, 5.72 mmol) and DIPEA (1.50 mL, 8.59 mmol) in 1,4-dioxane (20 mL) was degassed and purged with $N_2$ three times. The mixture was stirred at 110° C. for 16 h under $N_2$ atmosphere. The reaction mixture was concentrated under reduced pressure. The residue was purified by silica gel flash chromatography (eluent: 0~5% of MeOH in $CH_2Cl_2$) to give a crude product. The crude product was further purified by reversed-phase column (column: $C_{18}$; mobile phase: [water (0.1% $NH_3{\cdot}H_2O$)-ACN]; B %: 0%~74%, 40 min) to give the title compound (Intermediate 149, 770 mg, 53% yield) as a yellow solid. MS: m/z=506.1 $[M+H]^+$. $^1H$ NMR (400 MHZ, Dimethylsulfoxide-$d_6$) δ 5.41-5.15 (m, 1H), 4.52-4.21 (m, 4H), 4.02-3.88 (m, 1H), 3.69-3.56 (m, 2H), 3.11-2.96 (m, 3H), 2.84-2.67 (m, 2H), 2.23-1.72 (m, 7H). $^{19}F$ NMR (376 MHZ, Dimethylsulfoxide-$d_6$) δ −139.60, −172.20, −206.10.

Intermediate 150: (1*S*, 7*S*, 8*S*)-2-(7-Bromo-2,6-difluoro-8-methylquinazolin-4-yl)-8-fluoro-5-oxa-2-azabicyclo[5.1.0]octane

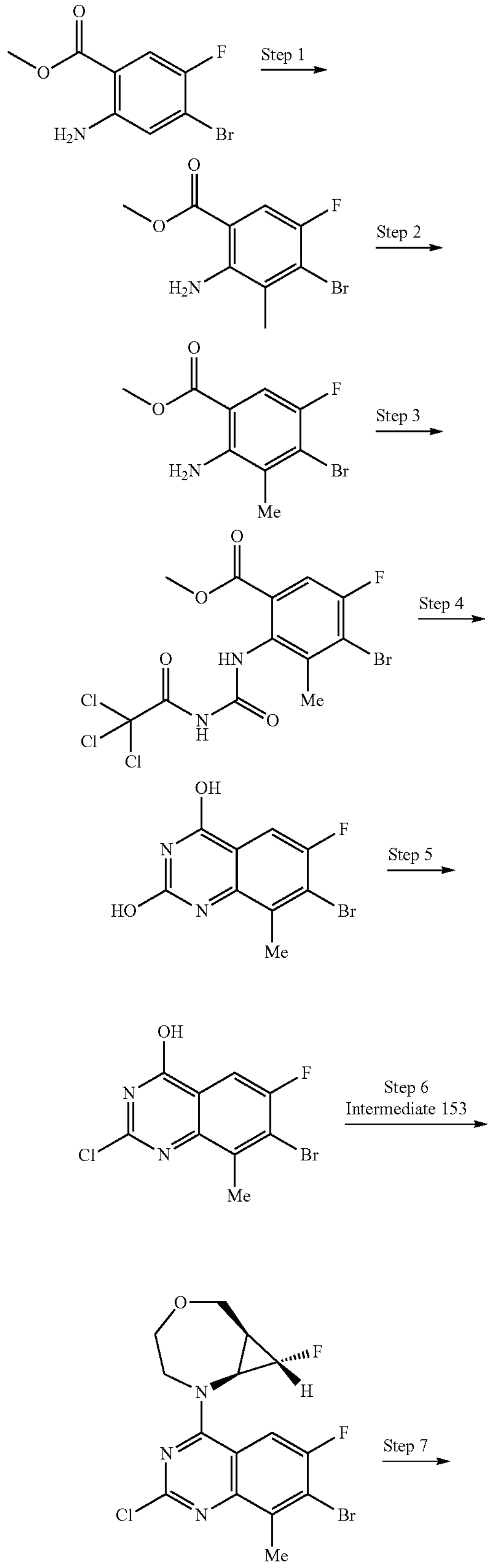

-continued

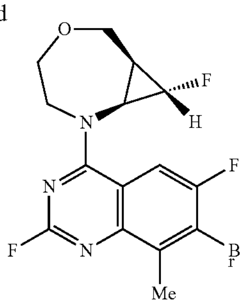

Step 1: methyl 2-amino-4-bromo-5-fluoro-3-iodobenzoate

To a stirred solution of methyl 2-amino-4-bromo-5-fluorobenzoate (4.5 g, 18.14 mmol) and Ag2$SO_4$ (9.05 g, 29.02 mmol) in methanol (43.2 mL) and $H_2O$ (36 mL) was added dropwise a solution of iodine (7.37 g, 29.02 mmol) in THF (43.2 mL) at room temperature. The reaction mixture was stirred at room temperature for 0.5 hour. The resulting mixture was concentrated under reduced pressure to remove MeOH & THF, filtered and extracted with EtOAc (3×150 mL). The combined organic layers were washed with brine (150 mL), dried over anhydrous $Na_2SO_4$, filtered and concentrated under reduced pressure. The residue was purified by silica gel flash chromatography (eluted with PE/EA (15: 1)) to afford the title compound (6.2 g, 91% yield) as an off-white solid. MS: m/z=373.95, 375.95 $[M+H]^+$. $^1H$ NMR (400 MHZ, Chloroform-d) § 7.72-7.75 (m, 1H), 3.90 (s, 3H). $^{19}F$ NMR (376 MHz, Chloroform-d) δ −111.95 (s, 1F).

Step 2: Methyl 2-amino-4-bromo-5-fluoro-3-methylbenzoate

To a stirred solution of methyl 2-amino-4-bromo-5-fluoro-3-iodobenzoate (6 g, 16.04 mmol) and methylboronic acid (5762.73 mg, 96.27 mmol) in 1,2-dimethoxyethane (87.6 mL) and $H_2O$ (15 mL) were added Pd $(PPh_3)_2Cl_2$ (1126.20 mg, 1.60 mmol) and $K_2CO_3$ (4.43 g, 32.09 mmol) at room temperature under $N_2$. The reaction mixture was heated at 90° C. for 16 hours. The resulting mixture was cooled to room temperature, diluted with water (100 mL), and extracted with EtOAc (3×60 mL). The combined organic layers were washed with brine (60 mL), dried over anhydrous $Na_2SO_4$, filtered and concentrated under reduced pressure. The residue was purified by silica gel flash chromatography (eluted with PE/EA (15: 1)) to afford the title compound (2.2 g, 52% yield) as an off-white solid. MS: m/z=261.95, 263.95 $[M+H]^+$. 1II NMR (400 MHz, Chloroform-d) δ 7.55-7.53 (m, 1H), 3.88 (s, 3H), 2.33 (s, 3H). $^{19}F$ NMR (376 MHz, Chloroform-d) δ −118.82 (s, IF).

Step 3: Methyl 4-bromo-5-fluoro-3-methyl-2-(3-(2,2,2-trichloroacetyl) ureido)benzoate To a stirred solution of methyl 2-amino-4-bromo-5-fluoro-3-methylbenzoate (2 g, 7.63 mmol) in THF (25 mL) was added trichloroethanecarbonyl isocyanate (2.16 g, 11.44 mmol) at room temperature under $N_2$. The reaction mixture was stirred at room temperature for 30 min. The resulting mixture was concentrated under reduced pressure. The residue was triturated with MTBE (3×25 mL) to give the title compound (3.5 g, crude) as an off-white solid. MS: m/z=470.75 and 472.75 $[M+Na]^{+\cdot}$ Step 4:
7-Bromo-6-fluoro-8-methylquinazoline-2,4-diol To a stirred solution of methyl 4-bromo-5-fluoro-3-methyl-2-(3-(2,2,2-trichloroacetyl) ureido)benzoate (3.5 g, crude) in methanol (120 mL) was added $NH_3$ MeOH (7 M in MeOH, 3.11 mL, 21.75 mmol) dropwise at room temperature. The reaction mixture was stirred at room temperature for 1 hour. The resulting mixture was concentrated under reduced pressure. The residue was triturated with MTBE (3x40 mL) to give the title compound (1.9 g, crude) as an off-white solid. MS: m/z=272.85, 274.85 $[M+H]^{+\cdot}$ Step 5:
7-Bromo-2,4-dichloro-6-fluoro-8-methylquinazoline To a stirred solution of POCl (665.36 mg, 4.33 mmol) and DIEA (3.08 g, 23.80 mmol) was added 7-bromo-6-fluoro-8-methylquinazoline-2,4-diol (1.3 g, crude) in an ice bath under $N_2$. The reaction mixture was heated at 110° C. for 16 hours. The resulting mixture was cooled to room temperature and concentrated under reduced pressure. The residue was quenched with sat. $NaHCO_3$ aq. (15 mL) in an ice bath, diluted with water (100 mL), and extracted with EtOAc (3x50 mL). The combined organic layers were washed with brine (30 mL), dried over anhydrous $Na_2SO_4$, filtered and concentrated under reduced pressure. The residue was purified by silica gel flash chromatography (eluted with PE/EA (10: 1)) to afford the title compound (700 mg, 43% yield for three steps) as an off-white solid. $^1H$ NMR (300 MHz, Chloroform-d) δ 7.82-7.79 (m, 1H), 2.89 (d, J=0.6 Hz, 3H). $^{19}F$ NMR (282 MHz, Chloroform-d) δ −97.76 (s, 1F).

Step 6: (15,7S,8S)-2-(7-Bromo-2-chloro-6-fluoro-8-methylquinazolin-4-yl)-8-fluoro-5-oxa-2-azabicyclo [5.1.0]octane To a stirred solution of 7-bromo-2,4-dichloro-6-fluoro-8-methylquinazoline (300 mg, 0.96 mmol) and Intermediate 153 (205.25 mg, 0.96 mmol) in DCM (5 mL) was added DIEA (375.29 mg, 2.90 mmol) dropwise at room temperature under $N_2$. The reaction mixture was stirred at room temperature for 1 hour. The resulting mixture was concentrated under reduced pressure. The residue was purified by Prep-TLC(PE/EA 5: 1) to afford the title compound (300 mg, 76% yield) as an off-white solid. MS: m/z=403.90, 405.90 $[M+H]^+$. $^1H$ NMR (300 MHZ, Chloroform-d)δ 7.94-7.91 (m, 1H), 4.54-4.39 (m, 2H), 4.29-4.08 (m, 1H), 3.99-3.96 (m, 2H), 3.89-3.80 (m, 1H), 3.66-3.57 (m, 1H), 3.23-3.07 (m, 1H), 2.82 (s, 3H), 2.35-2.23 (m, 1H). $^{19}F$ NMR (282 MHz, Chloroform-d) δ −104.30 (s, 1F), —207.16 (s, IF).

Step 7: (1S,7S,8S)-2-(7-Bromo-2,6-difluoro-8-methylquinazolin-4-yl)-8-fluoro-5-oxa-2-azabicyclo [5.1.0]octane To a solution of (IS,7S,85)-2-(7-bromo-2-chloro-6-fluoro-8-methylquinazolin-4-yl)-8-fluoro-5-oxa-2-azabicyclo[5.1.0]octane (320 mg, 0.79 mmol) in DMSO (0.5 mL) under $N_2$ was added KF (321.61 mg, 5.53 mmol) at room temperature. The reaction mixture was heated at 120° C. for 16 hours. The resulting mixture was cooled to room temperature, diluted with water (10 mL), and extracted with EtOAc (3x30 mL). The combined organic layers were washed with brine (30 mL), dried over anhydrous $Na_2SO_4$, filtered and concentrated under reduced pressure. The residue was purified by Prep-TLC(PE/EA 6: 1) to afford the title compound (Intermediate 150, 170 mg, 55% yield) as an off-white solid. MS: m/z=388.00, 390.00 $[M+H]^+$. $^1H$ NMR (400 MHZ, Chloroform-d)δ 8.00-7.98 (m, 1H), 4.53-4.41 (m, 2H), 4.30-4.15 (m, 1H), 3.98-3.83 (m, 3H), 3.67-3.60 (m, 1H), 3.23-3.07 (m, 1H), 2.80 (s, 3H), 2.35-2.26 (m, 1H). $^{19}F$ NMR (376 MHz, Chloroform-d) δ −46.78 (s, IF), —106.04 (s, IF), —207.06 (s, 1F).

Intermediate 151: (1*S*, 7*S*, 8*S*)-2-(2, 7-Dichloro-8-iodopyrido[4, 3-d]pyrimidin-4-yl)-8-fluoro-5-oxa-2-azabicyclo[5.1.0]octane

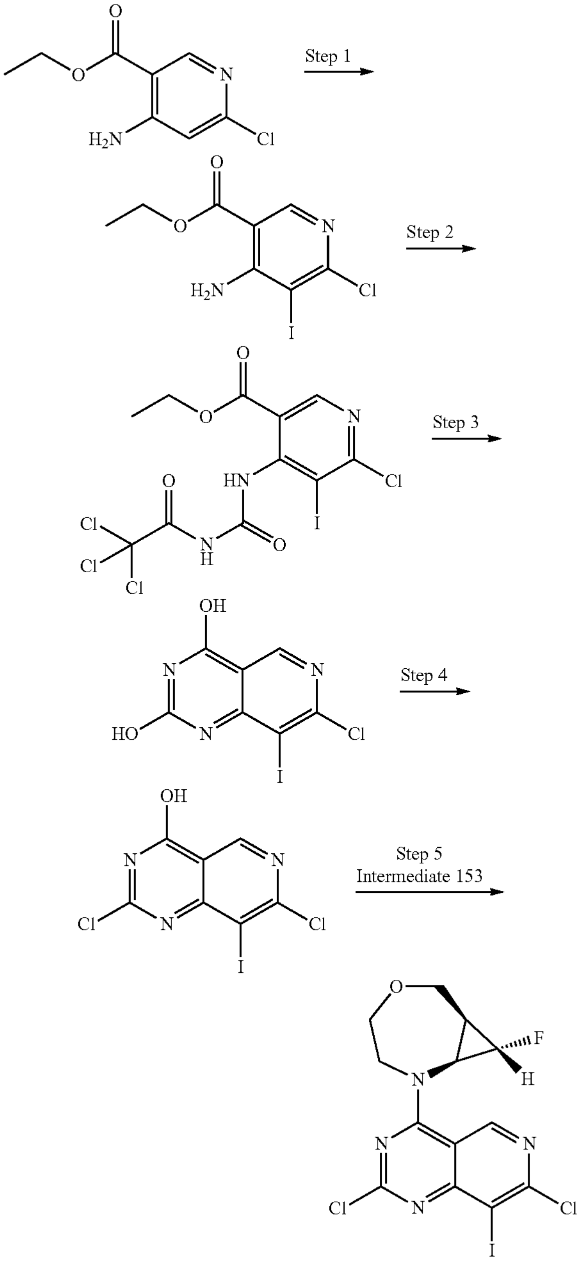

Intermediate 151

Step 1: Ethyl 4-amino-6-chloro-5-iodonicotinate

To a stirred solution of ethyl 4-amino-6-chloronicotinate (80 g, 398.76 mmol) and Ag2$SO_4$ (198.93 g, 638.02 mmol) in MeOH (768 mL) and $H_2O$ (640 mL) was added a solution of iodine (323.8 g, 1.27 mol) in THF (768 mL) at room temperature. The reaction mixture was heated at 65° C. for 16 hours. The resulting mixture was cooled to room temperature, filtered and concentrated under reduced pressure. The resulting mixture was diluted with DCM (600 mL), poured into cold sat. NaHISOs aq. (1800 mL), and extracted with DCM (3×800 mL). The combined organic layers were washed with brine (400 mL), dried over anhydrous $Na_2SO_4$, filtered and concentrated under reduced pressure. The residue was triturated with EA (80 mL). The precipitated solids were collected by filtration and washed with EA (3×20 mL) to give the title compound (80 g, 245.0 mmol, 61% yield) as a light yellow solid. MS: m/z=326.85 $[M+H]^+$. $^1H$ NMR (400 MHz, Chloroform-d) δ 8.48 (s, 1H), 4.35-4.29 (m, 2H), 1.32 (t, J=7.2 Hz, 3H).

Step 2: Ethyl 6-chloro-5-iodo-4-(3-(2,2,2-trichloroacetyl) ureido) nicotinate

To a stirred solution of ethyl 4-amino-6-chloro-5-iodonicotinate (10 g, 30.62 mmol) in THE (100 mL) under $N_2$ was added trichloroethanecarbonyl isocyanate (5.77 g, 30.62 mmol) at room temperature. The reaction mixture was stirred at room temperature for 30 min. The resulting mixture was concentrated under reduced pressure. The residue was triturated with MTBE (80 mL). The precipitated solids were collected by filtration and washed with MTBE (20 mL) to give the title compound (12 g, 76% yield) as an off-white solid. MS: m/z=513.95, 515.95 $[M+H]^{+\cdot}$ Step 3: 7-Chloro-8-iodopyrido[4,3-d]pyrimidine-2, 4-diol To a stirred solution of ethyl 6-chloro-5-iodo-4-(3-(2,2,2-trichloroacetyl) ureido) nicotinate (12 g, 23.30 mmol) in methanol (180 mL) was added $NH_3{}^a$MeOH (7 M in MeOH, 9.32 mL, 65.25 mmol) at room temperature. The reaction mixture was stirred at room temperature for 1 hour. The resulting mixture was concentrated under reduced pressure. The residue was triturated with MTBE (150 mL) to give the title compound (10 g, crude used through) as an off-white solid. 1H NMR (400 MHZ, DMSO-$d_6$) δ 8.35 (s, 1H).

Step 4: 2,4,7-Trichloro-8-iodopyrido[4,3-d]pyrimidine

To an ice-cooled stirred solution of $POCl_3$ (100 mL) and DIEA (19.98 g, 154.57 mmol) was added 7-chloro-8-iodopyrido[4,3-d]pyrimidine-2,4-diol (10 g, crude) under nitrogen atmosphere. The ice bath was removed, and the reaction mixture was heated at 110° C. for 16 hours. The resulting mixture was cooled to room temperature and concentrated under reduced pressure. The residue was diluted EA (50 mL), poured into cold sat. $NaHCO_3$ aq. (100 mL) slowly, and extracted with EtOAc (3×200 mL). The combined organic layers were washed water (100 mL) and brine (100 mL), dried over anhydrous $Na_2SO_4$, filtered and concentrated under reduced pressure. The residue was purified by silica gel flash chromatography (eluted with PE/BA (25: 1)) to afford the title compound (6.5 g, 77% yield for two steps) as a light yellow solid. 1H NMR (400 MHz, Chloroform-d) δ 9.32 (s, 1H).

Step 5: (15,75,8S)-2-(2,7-Dichloro-8-iodopyrido[4,3-d]pyrimidin-4-yl)-8-fluoro-5-oxa-2-azabicyclo[5.1.0]octane To a stirred solution of 2,4,7-trichloro-8-iodopyrido[4,3-d]pyrimidine (2.5 g, 6.93 mmol) and DIEA (2.689 g, 20.81 mmol) in DCM (30 mL) was added Intermediate 153 (1.471 g, 6.93 mmol) dropwise at −40° C. under $N_2$. The reaction mixture was stirred at −40° C. for 1 hour. The resulting mixture was diluted with 10% citric solution (50 mL) and extracted with DCM (3×50 mL). The combined organic layers were washed with brine (50 mL), dried over anhydrous $Na_2SO_4$, filtered and concentrated under reduced pressure. The residue was purified by silica gel flash chromatography (eluted with 20% DCM in EA) to afford the title compound (Intermediate 151, 2.1 g, 66% yield) as a light yellow solid. MS: m/z=454.85, 456.85 $[M+H]^{+\cdot}$ Intermediate 152: 7-Bromo-8-fluoro-4-((1*S*, 7*S*, 8*S*)-8-fluoro-5-oxa-2-azabicyclo[5.1.0]octan-2-yl)-2-(methylsulfonyl)quinazoline-6-carbonitrile

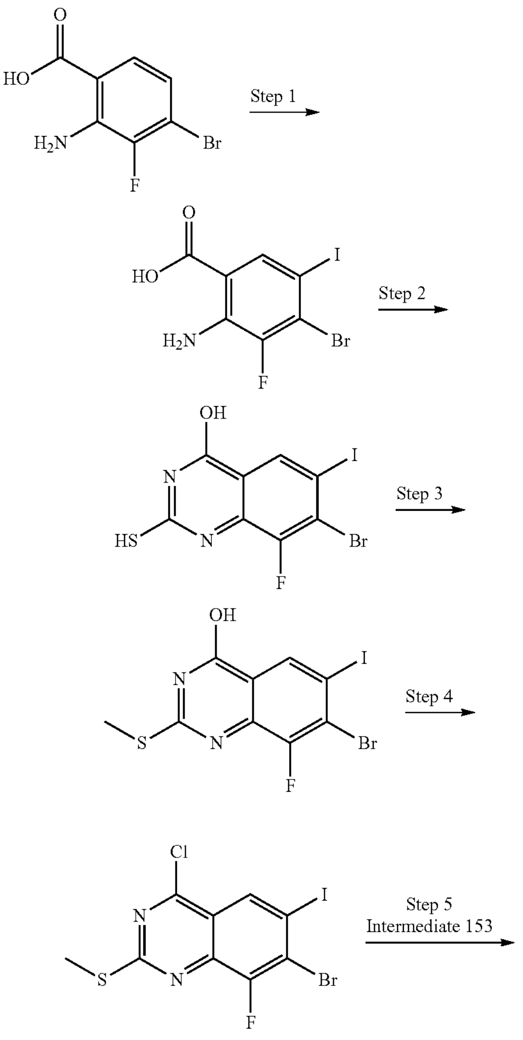

-continued

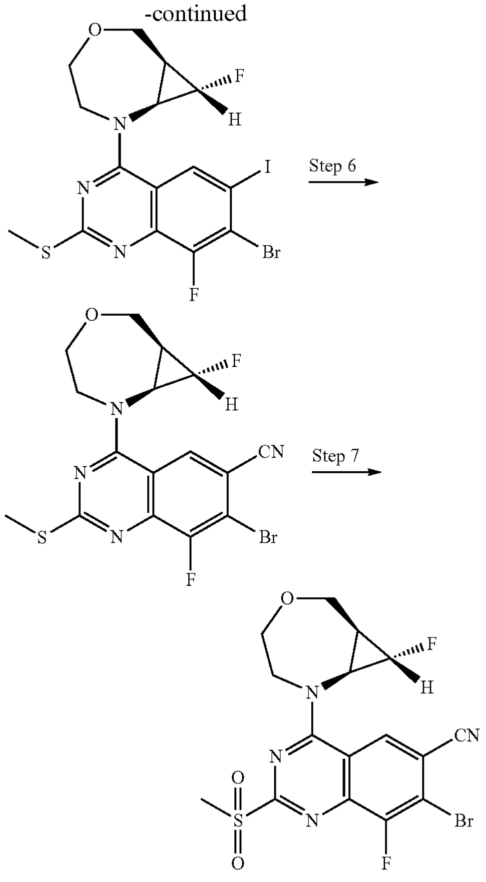

Intermediate 152

Step 1: 2-Amino-4-bromo-3-fluoro-5-iodobenzoic acid

To a stirred solution of 2-amino-4-bromo-3-fluorobenzoic acid (20 g, 85.46 mmol) in DMF (200 mL) was added 1-iodopyrrolidine-2,5-dione (28.84 g, 128.19 mmol) at room temperature under $N_2$. The reaction mixture was heated at 80° C. for 2 hours. The resulting mixture was cooled to room temperature and poured into water. The precipitate was filtered and washed with water and MeCN to afford the title compound (28 g, 93% yield) as a yellow solid. $^1$H NMR (400 MHz, DMSO-$d_6$) δ 13.34 (s, 1H), 7.99 (m, 1H), 6.91 (bs, 2H). $^{19}$F NMR (376 MHz, DMSO-$d_6$) δ −116.19 (s, IF).

Step 2: 7-Bromo-8-fluoro-6-iodo-2-mercaptoquinazolin-4-ol

A solution of 2-amino-4-bromo-3-fluoro-5-iodobenzoic acid (28 g, 77.79 mmol) in $SOCl_2$ (360 mL) was heated at 50° C. for 3 hours. The resulting mixture was cooled to room temperature and concentrated under reduced pressure. The residue was dissolved in acetone (140 mL). The resulting solution was added dropwise to a solution of ammonium sulfurothioate (12.68 g, 85.58 mmol) in acetone (140 mL). The mixture was stirred at room temperature for 1 hour and then filtered. The filter cake was washed with water and dissolved in 10% aq. NaOH. The resulting mixture was filtered. The pH of the filtrate was adjusted to about 2 with 1 M aq. HCl. The precipitate was filtered and washed with methanol to afford the title compound (30 g, crude, 96% yield) as a yellow solid. MS: m/z=400.75, 402.75 [M+H]$^+$. $^1$H NMR (400 MHZ, DMSO-$d_6$) § 12.91 (s, 1H), 12.73 (s, 1H), 8.13 (s, 1H). $^{19}$F NMR (376 MHz, DMSO-$d_6$) δ −108.34 (s, 1F).

Step 3: 7-Bromo-8-fluoro-6-iodo-2-(methylthio) quinazolin-4-ol

To a solution of 7-bromo-8-fluoro-6-iodo-2-mercaptoquinazolin-4-ol (20 g, 49.88 mmol) in methanol (500 mL) was added a solution of NaOH (3.99 g, 99.75 mmol) and iodomethane (14.46 g, 99.75 mmol) in $H_2O$ (400 mL). The reaction mixture was stirred at room temperature for 2 hours. The resulting mixture was filtered. The filter cake was washed with water and then dissolved in 10% aq. NaOH. The resulting mixture was filtered. The pH of the filtrate was adjusted to about 6 with 1 M aq. HCl. The resulting mixture was filtered again and the filter cake was washed with methanol to afford the title compound (15 g, crude) as a yellow solid. MS: m/z=414.65, 416.65 [M+H]$^{+.}$ Step 4: 7-Bromo-4-chloro-8-fluoro-6-iodo-2-(methylthio) quinazoline To a solution of 7-bromo-8-fluoro-6-iodo-2-(methylthio) quinazolin-4-ol (15 g, crude) in POC13 (150 mL) was added DIEA (12.59 mL, 72.28 mmol) at room temperature. The reaction mixture was heated at 100° C. for 2 hours. The resulting mixture was cooled to room temperature and concentrated under reduced pressure. The residue was diluted with ethyl acetate (150 mL) and washed with water (70 mL) and brine (3×50 mL). The organic layer was dried over anhydrous $Na_2SO_4$, filtered and concentrated under reduced pressure. The residue was purified by silica gel flash chromatography (eluted with 10% EA in PE) to give the title compound (12 g, crude) as a light-yellow solid. MS: m/z=432.85, 434.85 [M+H].

Step 5: (1S,7S,8S)-2-(7-Bromo-8-fluoro-6-iodo-2-(methylthio) quinazolin-4-yl)-8-fluoro-5-oxa-2-azabicyclo[5.1.0]octane To a stirred solution of 7-bromo-4-chloro-8-fluoro-6-iodo-2-(methylthio) quinazoline (12 g, crude) in DMSO (120 mL) under $N_2$ were added DIEA (10.73 g, 83.05 mmol) and Intermediate 153 (7044.92 mg, 33.22 mmol) at room temperature. The reaction mixture was stirred at room temperature for 1 hour. The resulting mixture was diluted with $H_2O$ (300 mL) and extracted with EA (3×300 mL). The combined organic layers were washed with brine (300 mL), dried over anhydrous $Na_2SO_4$, filtered and concentrated under reduced pressure. The residue was purified by silica gel flash chromatography (eluted with 20% EA in PE) to afford the title compound (13 g, 49% yield for three steps) as a light-yellow solid. MS: m/z=528.00, 530.00 [M+H]$^+$, $^1$H NMR (300 MHz, Chloroform-d) δ 8.45 (s, 1H), 4.62-4.57 (m, 1H), 4.52-4.11 (m, 2H), 4.08-3.85 (m, 3H), 3.68-3.59 (m, 3H), 3.33-3.13 (m, 1H), 2.58 (s, 3H), 2.43-2.24 (m, 1H).

Step 6: 7-Bromo-8-fluoro-4-((1S,7S,8S)-8-fluoro-5-oxa-2-azabicyclo[5.1.0]octan-2-yl)-2-(methylthio) quinazoline-6-carbonitrile To a stirred solution of (15,7S,8S)-2-(7-bromo-8-fluoro-6-iodo-2-(methylthio) quinazolin-4-yl)-8-fluoro-5-oxa-2-azabicyclo[5.1.0]octane (10 g, 18.93 mmol) in DMF (100 mL) was added CuCN (3.39 g, 37.87 mmol) at room temperature under $N_2$. The reaction mixture was heated at 100° C. for 16 hours. The resulting mixture was cooled to room temperature, diluted with EA (1500 mL), washed with $H_2O$ (3×500 mL) and brine (500 mL), dried over anhydrous $Na_2SO_4$, filtered and concentrated under reduced pressure. The residue was purified by silica gel column chromatography (eluted with 25% EA in PE) to afford the title compound (6 g, 74% yield) as a light yellow solid. MS: m/z=426.95, 428.95 $[M+H]^{+}$.

Step 7: 7-Bromo-8-fluoro-4-((15,7S,8S)-8-fluoro-5-oxa-2-azabicyclo[5.1.0]octan-2-yl)-2-(methylsulfonyl) quinazoline-6-carbonitrile To an ice-cooled solution of 7-bromo-8-fluoro-4-((15,75,8S)-8-fluoro-5-oxa-2-azabicyclo[5.1.0]octan-2-yl)-2-(methylthio) quinazoline-6-carbonitrile (5 g, 11.70 mmol) in DCM (50 mL) was added 3-chlorobenzene-1-carboperoxoic acid (5.05 g, 29.26 mmol). The reaction mixture was stirred in an ice bath for 1 hour. The resulting mixture was diluted with ethyl acetate (10 mL) and washed with water (10 mL) and brine (10 mL). The organic layer was dried over anhydrous $Na_2SO_4$, filtered and concentrated under reduced pressure. The residue was purified by silica gel flash chromatography (eluted with 30% EA in PE) to afford the title compound (Intermediate 152, 4 g, 74% yield) as a yellow solid. MS: m/z=459.00, 461.00 $[M+H]^{+}$.

Intermediate 153: (1*S*, 7*S*, 8*S*)-8-Fluoro-5-oxa-2-azabicyclo[5.1.0]ocatne

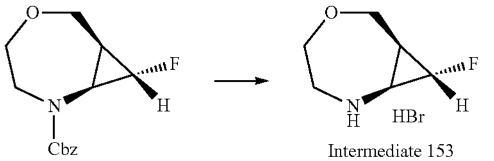

Intermediate 153

A mixture of benzyl (15,7S,8S)-8-fluoro-S-oxa-2-azabicyclo[5.1.0]octane-2-carboxylate (2.0 g, 102 mmol, refer to Intermediate 31 and 32 for detail procedures) and HBr (10 mL, 30% in AcOH) was stirred at 0° C. for 1 h. The reaction mixture was concentrated under reduced pressure to give the title compound (1.6 g, HBr salt) as a yellow solid, which was used in the next step without further purification.

Intermediate 154: 6-Chloro-4-(4, 4, 5, 5-tetramethyl-1, 3, 2-dioxaborolan-2-yl)-5-((triisopropylsilyl)ethynyl)naphthalen-2-amine hydrochloride

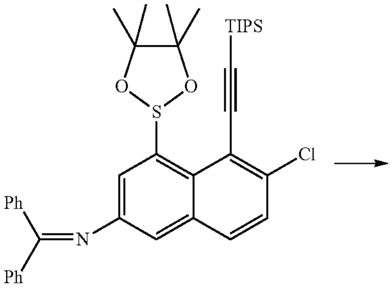

Intermediate 113

-continued

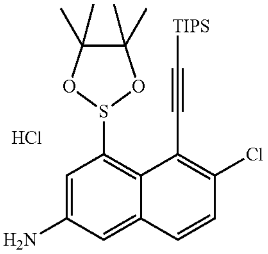

Intermediate 155

To a solution of Intermediate 113 (3 g, 4.628 mmol) in EtOH (30 mL) were added NaOAc (760 mg, 9.264 mmol) and Hydroxylamine hydrochloride (643 mg, 9.253 mmol) at room temperature. The reaction mixture was stirred at room temperature for 1 hour. The resulting mixture was quenched with sat. $NaHCO_3$ aq. (40 mL) and extracted with ethyl acetate (60 mL×3). The combined organic layers were washed with brine (60 mL), dried over anhydrous sodium sulfate, filtered and concentrated under reduced pressure. The residue was purified by silica gel flash chromatography (eluted with 78% EA in PE) to afford a crude product (2 g). The crude product was dissolved in EA (1.4 mL), and HCl (1.0 M in EA, 8.8 mL, 8.800 mmol) was added in an ice bath. The resulting mixture was stirred in an ice bath for 30 min. The solid was collected by filtration, washed with hexane (4×50 mL), dried under reduced pressure to afford the title compound (Intermediate 154, 1.05 g, 47% yield) as an off-white solid. MS: m/z=484.20 $[M+H]^{+}$. JH NMR (400 MHz, Methanol-$d_4$) δ 8.04-7.86 (m, 2H), 7.78-7.53 (m, 2H), 1.43 (d, J=5.6 Hz, 12H), 1.24-1.14 (m, 21H).

Intermediate 156: (1*S*, 7*S*, 8*S*)-2-(7-Chloro-2-fluoro-8-methylpyrido[4, 3-*d*]pyrimidin-4-yl)-8-fluoro-5-oxa-2-azabicyclo[5.1.0]octane

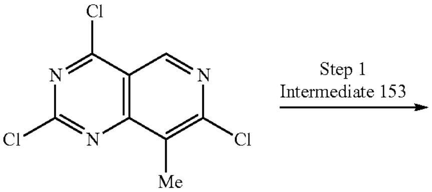

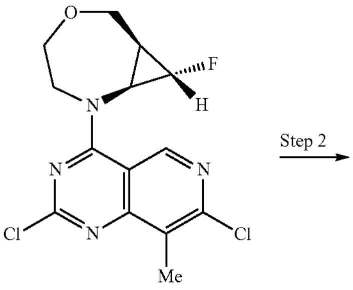

-continued

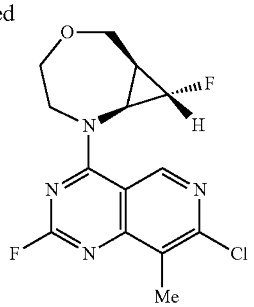

Intermediate 156

Step 1: (15,7S,8S)-2-(2,7-Dichloro-8-methylpyrido[4,3-d]pyrimidin-4-yl)-8-fluoro-5-oxa-2-azabicyclo[5.1.0]octane To a solution of Intermediate 153 (1.62 g, 7.65 mmol, HBr salt) in $CH_2Cl_2$ (20 mL) was added DIPEA (5.61 mL, 32.2 mmol) and 2,4,7-trichloro-8-methylpyrido[4,3-d]pyrimidine (2 g, 8.05 mmol) at −78° C. under $N_2$. The mixture was stirred at −78° C. for 0.5 h. The reaction mixture was diluted with water (50 mL) and extracted with EtOAc (50 mL×2). The combined organic layers were washed with brine (50 mL), dried over anhydrous $Na_2SO_4$, filtered and concentrated under reduced pressure. The residue was purified by silica gel flash chromatography (eluent: 0~15% of EtOAc in petroleum ether) to give the title compound (2.7 g, 98% yield) as a yellow solid. MS: m/z=342.9 $[M+H]^+$. $^1H$ NMR (400 MHZ, Chloroform-d)δ 9.40 (s, 1H), 4.70-4.61 (m, 1H), 4.47-4.19 (m, 2H), 4.00-3.84 (m, 3H), 3.70-3.60 (m, 1H), 3.41-3.14 (m, 1H), 2.67 (s, 3H), 2.39-2.25 (m, 1H).

Step 2: (1S,7S,8S)-2-(7-chloro-2-fluoro-8-methylpyrido[4,3-d]pyrimidin-4-yl)-8-fluoro-5-oxa-2-azabicyclo[5.1.0]octane To a solution of (1S,7S,8S)-2-(2,7-dichloro-8-methylpyrido[4,3-d]pyrimidin-4-yl)-8-fluoro-5-oxa-2-azabicyclo[5.1.0]octane (2.6 g, 7.58 mmol) in DMSO (26 mL) was added KF (1.32 g, 22.7 mmol) under $N_2$ at 25° C. The mixture was stirred at 80° C. for 16 h. The reaction mixture was diluted with $H_2O$ (300 mL) and extracted with EtOAc (200 mL×2). The combined organic layers were washed with brine (300 mL), dried over anhydrous $Na_2SO_4$, filtered and concentrated under reduced pressure. The residue was purified by silica gel flash chromatography (eluent: 0~20% of EtOAc in petroleum ether) to give the title compound (Intermediate 156, 2 g, 81% yield) as a yellow solid. MS: m/z=327.1 $[M+H]^+$. $^1H$ NMR (400 MHz, Chloroform-d) δ 9.42 (s, 1H), 4.72-4.54 (m, 1H), 4.48-4.22 (m, 2H), 4.03-3.83 (m, 3H), 3.72-3.60 (m, 1H), 3.45-3.13 (m, 1H), 2.64 (s, 3H), 2.44-2.25 (m, 1H).

Intermediate 157: 6-Fluoro-4-(2-fluoro-4-((1*S*, 7*S*, 8*S*)-8-fluoro-5-oxa-2-azabicyclo[5.1.0]octan-2-yl)-8-methylpyrido[4, 3-*d*]pyrimidin-7-yl)-5-((triisopropylsilyl)ethynyl)naphthalen-2-amine

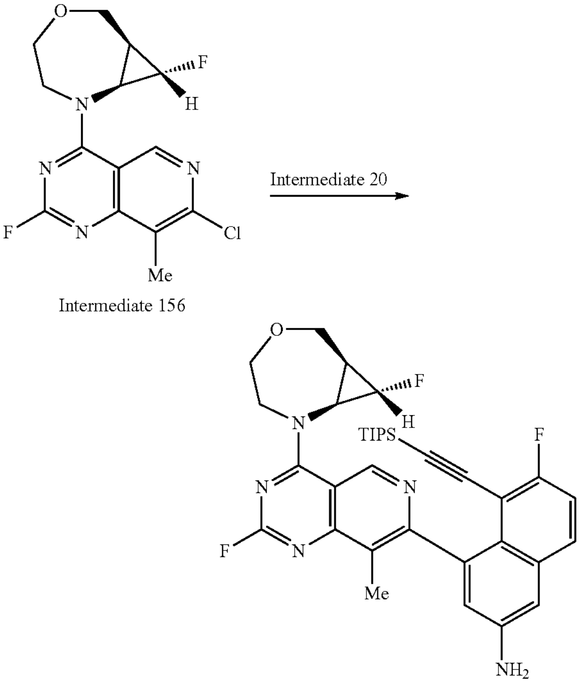

Intermediate 156

Intermediate 157

To a solution of Intermediate 156 (2.6 g, 7.58 mmol) in DMSO (26 mL) was added KF (1.32 g, 22.7 mmol) under $N_2$ at 25° C. The mixture was stirred at 80° C. for 16 h. The reaction mixture was diluted with $H_2O$ (300 mL) and extracted with EtOAc (200 mL×2). The combined organic layers were washed with brine (300 mL), dried over anhydrous $Na_2SO_4$, filtered and concentrated under reduced pressure. The residue was purified by silica gel flash chromatography (eluent: 0~20% of EtOAc in petroleum ether) to give the title compound (Intermediate 157, 2 g, 81% yield) as a yellow solid. MS: m/z=327.1 $[M+H]^+$. $^1H$ NMR (400 MHz, Chloroform-d) δ 9.42 (s, 1H), 4.72-4.54 (m, 1H), 4.48-4.22 (m, 2H), 4.03-3.83 (m, 3H), 3.72-3.60 (m, 1H), 3.45-3.13 (m, 1H), 2.64 (s, 3H), 2.44-2.25 (m, 1H).

Intermediate 158 & 159: Ethyl (*S*)-6′-methylene-3′-oxotetrahydrospiro[cyclopropane-1, 1′-pyrrolizine]-7a′(5′*H*)-carboxylate & ethyl (*R*)-6′-methylene-3′-oxotetrahydrospiro[cyclopropane-1, 1′-pyrrolizine]-7a′(5′*H*)-carboxylate

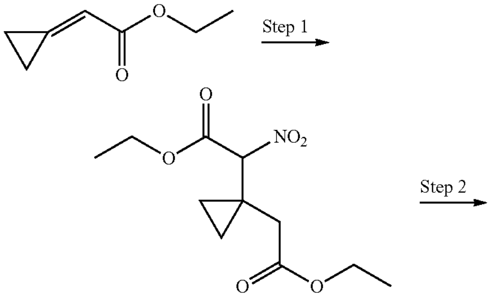

-continued

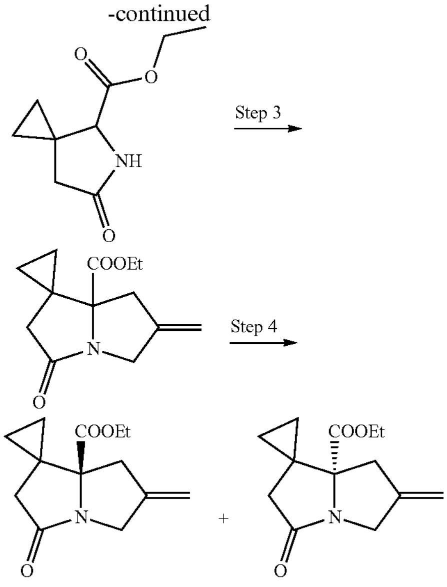

Example 158 Example 159

Step 1: Ethyl 2-(1-(2-ethoxy-2-oxoethyl)cyclopropyl)-2-nitroacetate

A mixture of ethyl 2-cyclopropylideneacetate (150 g, 1.19 mol), ethyl 2-nitroacetate (152 mL, 1.37 mol) and $K_2CO_3$ (189 g, 1.37 mol) in THF (3000 mL) was degassed, purged with $N_2$ three times, and stirred at 80° C. for 3 h under $N_2$. The reaction mixture was concentrated under reduced pressure. The residue was diluted with $H_2O$ (1000 mL). The pH of the mixture was adjusted to around 3 with HCl aq. (1 L, 6 M in $H_2O$). The mixture was extracted with $CH_2Cl_2$ (1000 mLx3). The combined organic layers were washed with brine (1000 mL), dried over anhydrous $Na_2SO_4$, filtered and concentrated under reduced pressure to give the title compound (308 g, crude) as a yellow liquid, which was used in the next step without further purification. $^1$H NMR (400 MHZ, Chloroform-d)δ 5.02 (s, 1H), 4.30-4.20 (m, 2H), 4.15-4.06 (m, 2H), 2.64-2.53 (m, 1H), 1.32-1.27 (m, 3H), 1.27-1.20 (m, 3H), 1.07-0.99 (m, 1H), 0.94-0.77 (m, 3H).

Step 2: Ethyl 6-oxo-5-azaspiro[2.4]heptane-4-carboxylate

To a solution of ethyl 2-(1-(2-ethoxy-2-oxoethyl)cyclopropyl)-2-nitroacetate (39.5 g, 152 mmol) in AcOH (400 mL) and EtOH (800 mL) was added Zn (99 g, 1.52 mol) in batches at 25° C. under $N_2$. The mixture was stirred at 100° C. for 16 h under $N_2$. The reaction mixture was filtered and concentrated under reduced pressure. The residue was diluted with sat. NaHCOsaq. (500 mL) (pH was adjusted to around 8) and extracted with EtOAc (500 mLx3). The combined organic layers were washed with brine (500 mL), dried over anhydrous $Na_2SO_4$, filtered and concentrated under reduced pressure. The residue was purified by silica gel flash chromatography (cluent: 0~1% of MeOH in $CH_2Cl_2$) to give the title compound (31.6 g, 56% yield) as a white solid. MS: m/z=184.0 [M+H]$^+$. $^1$H NMR (400 MHZ, Dimethylsulfoxide-d$_6$) δ 8.11 (s, 1H), 4.16-4.09 (m, 2H), 3.70 (s, 1H), 2.42 (d, J=16.8 Hz, 1H) 2.01-1.95 (m, 1H), 1.20 (t, J=7.2 Hz, 3H), 0.84-0.77 (m, 1H), 0.74-0.66 (m, 1H), 0.66-0.58 (m, 2H).

Step 3: Ethyl 6'-methylene-3'-oxotetrahydrospiro [cyclopropane-1,1'-pyrrolizine]-7a'(5'H)-carboxylate To a solution of ethyl 6-oxo-5-azaspiro[2.4]heptane-4-carboxylate (20 g, 109 mmol) and 3-chloro-2-(chloromethyl) prop-1-ene (51 mL, 437 mmol) in THF (1000 mL) was added dropwise LiHMDS (229 mL, 1 M in THF) at −40° C. over 50 min under $N_2$. The mixture was stirred at this temperature for 30 min, and continued to stir at 25° C. for 15.5 h under $N_2$. The reaction mixture was quenched with sat. $NH_4Cl$ aq. (1000 mL) at 25° C. and extracted with EtOAc (1000 mLx3). The combined organic layers were washed with brine (2000 mL), dried over anhydrous $Na_2SO_4$, filtered and concentrated under reduced pressure. The residue was purified by silica gel flash chromatography (eluent: 0~35% of EtOAc in petroleum ether) to give the title compound (6.5 g, 25% yield) as a yellow oil. MS: m/z=236.1 [M+H]$^{+.}$ Step 4: Ethyl(S)-6'-methylene-3'-oxotetrahydrospiro [cyclopropane-1, l'-pyrrolizine]-7a'(5'H)-carboxylate & ethyl (R)-6'-methylene-3'-oxotetrahydrospiro[cyclopropane-1,1'-pyrrolizine]-7a'(S'H)-carboxylate Ethyl 6'-methylene-3'-oxotetrahydrospiro[cyclopropane-1,1'-pyrrolizine]-7a'(5'H)-carboxylate (30 g) was separated by SFC(column: DAICEL CHIRALPAK AS (250 mm×50 mm, 10 μm); mobile phase: [$CO_2$-i-PrOH (0.1% $NH_3$ $H_2O$)]; gradient: 45%~50% B over 2.5 min) to give the title compound (Intermediate 158, 13.77 g, 46% yield, SFC peak 1, retention time: 1.216 min) as a yellow oil and the other title compound (Intermediate 159, 14.4 g, 48% yield, SFC peak 1, retention time: 1.542 min) as a yellow oil. Spectra for Intermediate 158: MS: m/z=236.0 [M+H]$^+$. $^1$H NMR (400 MHZ, Chloroform-d)δ 5.10-4.98 (m, 2H), 4.34 (br d, J=16 Hz, 1H), 4.28-4.13 (m, 2H), 3.65 (br d, J=15.6 Hz, 1H), 3.07 (d, J=16.8 Hz, 1H), 2.84 (br d, J=14.8 Hz, 1H), 2.36 (br d, J=14.8 Hz, 1H), 2.20 (d, J=16.8 Hz, 1H), 1.27 (t, J=7.2 Hz, 3H), 0.92-0.77 (m, 2H), 0.71-0.60 (m, 2H). Spectra for Intermediate 159: MS: m/z=236.0 [M+H]$^+$, $^1$H NMR (400 MHZ, Chloroform-d) δ 5.09-4.98 (m, 2H), 4.34 (br d, J=15.6 Hz, 1H), 4.27-4.13 (m, 2H), 3.70-3.60 (m, 1H), 3.07 (d, J=16.8 Hz, 1H), 2.84 (dd, J=0.8, 14.4 Hz, 1H), 2.40-2.32 (m, 1H), 2.19 (d, J=16.8 Hz, 1H), 1.26 (t, J=7.2 Hz, 3H), 0.91-0.78 (m, 2H), 0.70-0.61 (m, 2H).

Intermediate 160: (*R*)-(6′-Methylenetetrahydrospiro[cyclopropane-1, 1′-pyrrolizin]-7a′(5′*H*)-yl)methan-*d*$_2$-ol

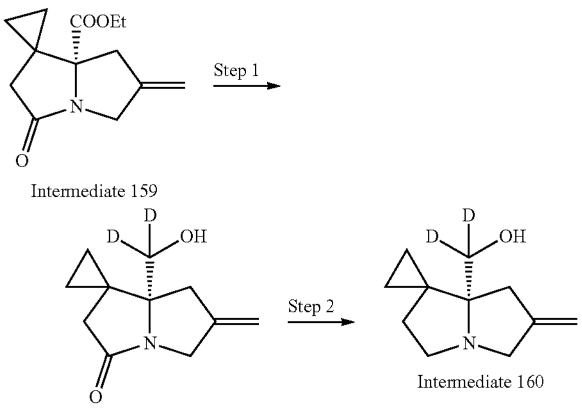

Intermediate 159

Intermediate 160

Step 1: (R)-Ta'-(Hydroxymethyl-$d_2$)-6'-methylenetetrahydrospiro[cyclopropane-1,1'-pyrrolizin]-3'(2'H)-one To a solution of Intermediate 159 (500 mg, 2.13 mmol) in $CD_3OD$ (10 mL) was added NaBD4 (402 mg, 10.6 mmol) under $N_2$. The mixture was stirred at 25° C. for 16 h under $N_2$. The reaction mixture was quenched with HCl (5 mL, 1 M in $H_2O$) and concentrated under reduced pressure. The residue was purified by silica gel flash chromatography (eluent: 0~8% MeOH in $CH_2Cl_2$) to give the title compound (390 mg, 94% yield) as an off-white solid. MS: m/z=196.2 $[M+H]^{+\cdot}$ Step 2: (R)-(6'-Methylenetetrahydrospiro[cyclopropane-1,1'-pyrrolizin]-7a'(5'H)-yl) methan-$d_2$-ol To a solution of (R)-Ta'-(hydroxymethyl-$d_2$)-6'-methylenetetrahydrospiro[cyclopropane-1,1'-pyrrolizin]-3'(2'H)-one (340 mg, 1.74 mmol) in THF (15 mL) was added LiAlH4 (3.48 mL, 2.5 M in THF) at 0° C. under $N_2$. The mixture was stirred at 70° C. for 3 h under $N_2$, quenched with $Na_2SO_4$\$$10H_2O$ (3 g) at 0° C. under $N_2$, filtered and concentrated under reduced pressure. The residue was purified by silica gel flash chromatography (eluent: 0~30% MeOH in $CH_2Cl_2$) to give the title compound (Intermediate 160, 230 mg, 69% yield) as a yellow oil, MS: m/z=182.2 $[M+H]^+$. $^1H$ NMR (400 MHZ, Chloroform-d) δ 4.98-4.83 (m, 2H), 3.74 (d, J=14.4 Hz, 1H), 3.37 (d, J=14.8 Hz, 1H), 3.24-3.15 (m, 1H), 2.80-2.70 (m, 1H), 2.26-2.17 (m, 2H), 2.05-1.95 (m, 1H), 1.78-1.69 (m, 1H), 0.65-0.55 (m, 2H), 0.54-0.45 (m, 2H).

Intermediate 161 &162: Benzyl (1*R*, 7*R*, 8*R*)-8-chloro-5-oxa-2-azabicyclo[5.1.0]octane-2-carboxylate & Benzyl (1*S*, 7*S*, 8*S*)-8-chloro-5-oxa-2-azabicyclo[5.1.0]octane-2-carboxylate

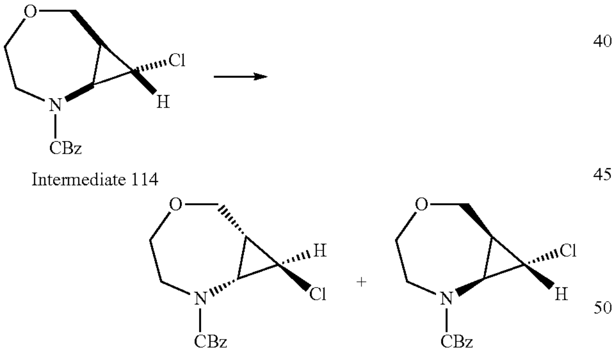

Intermediate 161 + Intermediate 162

Intermediate 114 (40 g) was purified by SFC(column: DAICEL CHIRALPAK IG (250 mm×30 mm, 10 μm); mobile phase: [$CO_2$-EtOH (0.1% $NH_3.H_2O$)]; B %: 25%, isocratic elution mode) to give the title compound (Intermediate 161, SFC peak 1: 1.240 min, 20.7 g, 51% yield) as a white solid and the other title compound (Intermediate 162, SFC peak 2: 1.442 min, 17.1 g, 42% yield) as a white solid. Spectra for Intermediate 161: MS: m/z=282.1 $[M+H]^+$. $^1H$ NMR (400 MHZ, Chloroform-d)δ 7.51-7.29 (m, 5H), 5.30-5.12 (m, 2H), 4.42-4.32 (m, 1H), 4.11-3.93 (m, 1H), 3.85-3.76 (m, 1H), 3.50-3.42 (m, 1H), 3.36-3.18 (m, 3H), 3.13-3.02 (m, 1H), 1.88-1.78 (m, 1H). Spectra for Intermediate 162: MS: m/z=282.2 $[M+H]^+$. $^1H$ NMR (400 MHz, Chloroform-d) δ 7.50-7.28 (m, 5H), 5.27-5.10 (m, 2H), 4.41-4.32 (m, 1H), 4.09-3.94 (m, 1H), 3.86-3.77 (m, 1H), 3.51-3.42 (m, 1H), 3.37-3.17 (m, 3H), 3.12-3.00 (m, 1H), 1.89-1.78 (m, 1H).

Intermediate 163: (1*S*, 7*S*, 8*S*)-8-chloro-2-(7-chloro-2-fluoro-8-methylpyrido[4, 3-*d*]pyrimidin-4-yl)-5-oxa-2-azabicyclo[5.1.0]octane

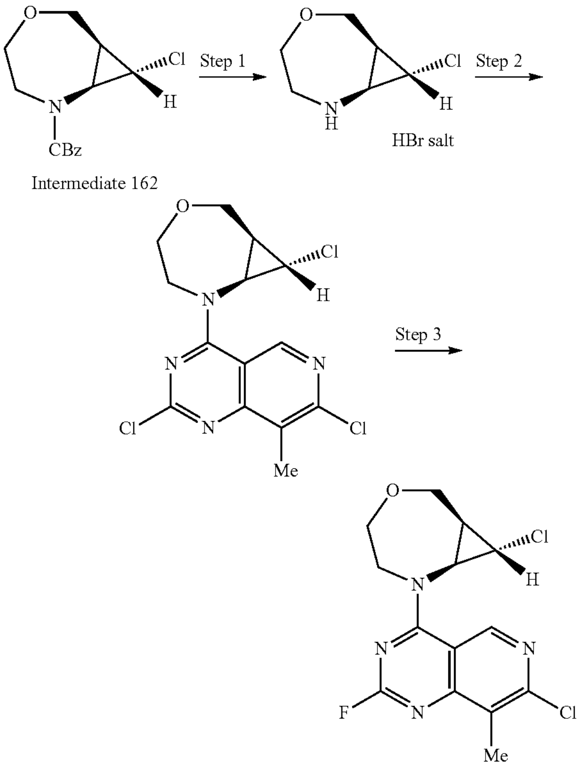

Intermediate 163

Step 1: (1S,7S,8S)-8-Chloro-5-oxa-2-azabicyclo[5.1.0]octane

To a solution of Intermediate 162 (500 mg, 1.76 mmol) was added HBr (5 mL, 30% in AcOH). The mixture was stirred at 25° C. for 1 h. The reaction mixture was concentrated under reduced pressure to give the title compound (402 mg, HBr salt) as a brown solid, which was used into the next step without further purification.

Step 2: (1S,7S,8S)-8-chloro-2-(2,7-dichloro-8-methylpyrido[4,3-d]pyrimidin-4-yl)-5-oxa-2-azabicyclo[5.1.0]octane A mixture of (1S,7S,8S)-8-chloro-5-oxa-2-azabicyclo[5.1.0]octane (402 mg, 1.76 mmol, HBr salt), 2,4,7-trichloro-8-methylpyrido[4,3-d]pyrimidine (460 mg, 1.85 mmol) in $CH_2Cl_2$ (8 mL) was added DIPEA (1.61 mL, 9.26 mmol) at −78° C. under $N_2$. The mixture was stirred at −78° C. for 1 h under $N_2$. The reaction mixture was quenched with $H_2O$ (7 mL) at 0° C. and extracted with $CH_2Cl_2$ (10 mL×3). The combined organic layers were washed with brine (5 mL), dried over anhydrous $Na_2SO_4$, filtered and concentrated under reduced pressure. The residue was purified by silica gel flash chromatography (eluent: 0~30% of EtOAc in petroleum ether) to give the title compound (500 mg, 73% yield) as a yellow solid. MS: m/z=358.9, 360.9 $[M+H]^{+\cdot}$ Step 3: (1S,75,8S)-8-chloro-2-(7-chloro-2-fluoro-8-methylpyrido[4,3-d]pyrimidin-4-yl)-5-oxa-2-azabicyclo[5.1.0]octane To a solution of (1S,7S,8S)-8-chloro-2-(2,7-dichloro-8-methylpyrido[4,3-d]pyrimidin-4-yl)-5-oxa-2-azabicyclo[5.1.0]octane (400 mg, 1.09 mmol) in DMSO (4 mL) was added KF (315 mg, 5.43 mmol) under $N_2$. The mixture was stirred at 100° C. for 6 h. The reaction mixture was added water (8 mL) at 25° C. and extracted with EtOAc (10 mL×3). The combined organic layers were washed with brine (10 mL), dried over anhydrous $Na_2SO_4$, filtered and concentrated under reduced pressure. The residue was purified by silica gel flash chromatography (eluent: 100% of $CH_2Cl_2$) to give the title compound (Intermediate 163, 320 mg, 79% yield) as a yellow solid. MS: m/z=342.9 $[M+H]^{+\cdot}$ Intermediate 164 & 165: Benzyl (1*R*, 7*S*, 8*R*)-8-fluoro-2-azabicyclo[5.1.0]octane-2-carboxylate & Benzyl (1*S*, 7*R*, 8*S*)-8-fluoro-2-azabicyclo[5.1.0]octane-2-carboxylate

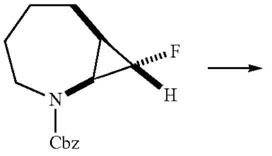

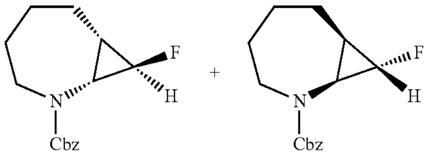

Intermediate 164 Intermediate 165

Benzyl-8-fluoro-2-azabicyclo[5.1.0]octane-2-carboxylate (trans) (35 g) was separated by SFC (column: DAICEL CHIRALPAK IG (250 mm×30 mm, 10 μm); mobile phase: [$CO_2$-MeOH (0.1% $NH_3$*$H_2O$)]; B %: 20%, isocratic elution mode) to give the title compound (Intermediate 164, SFC peak 2, retention time: 1.236 min, 13.7 g, 39% yield) as a colorless oil and the other title compound (Intermediate 165, SFC peak 1, retention time: 1.002 min, 14.0 g, 40% yield) as a colorless oil. Spectra for Intermediate 164: $^1H$ NMR (400 MHZ, Chloroform-d) δ 7.45-7.28 (m, 5H), 5.27-5.08 (m, 2H), 4.74-4.30 (m, 1H), 4.13-3.90 (m, 1H), 2.99-2.84 (m, 2H), 2.37-2.19 (m, 1H), 1.80-1.67 (m, 2H), 1.66-1.53 (m, 1H), 1.59-1.53 (m, 2H), 1.12-0.98 (m, 1H). $^{19}F$ NMR (376 MHz, Chloroform-d) δ −203.93, −204.35. Spectra for Intermediate 165: MS: m/z=264.1 $[M+H]^+$. $^1H$ NMR (400 MHZ, Chloroform-d) δ 7.47-7.28 (m, 5H), 5.28-5.06 (m, 2H), 4.75-4.32 (m, 1H), 4.15-3.90 (m, 1H), 2.99-2.82 (m, 2H), 2.35-2.22 (m, 1H), 1.81-1.68 (m, 2H), 1.67-1.58 (m, 1H), 1.51-1.37 (m, 2H), 1.12-0.97 (m, 1H). $^{19}F$ NMR (376 MHZ, Chloroform-d) δ −204.36.

Intermediate 166: 7-Chloro-2, 8-difluoro-4-((1*S*, 7*R*, 8*S*)-8-fluoro-2-azabicyclo[5.1.0]octan-2-yl)pyrido[4, 3-*d*]pyrimidine

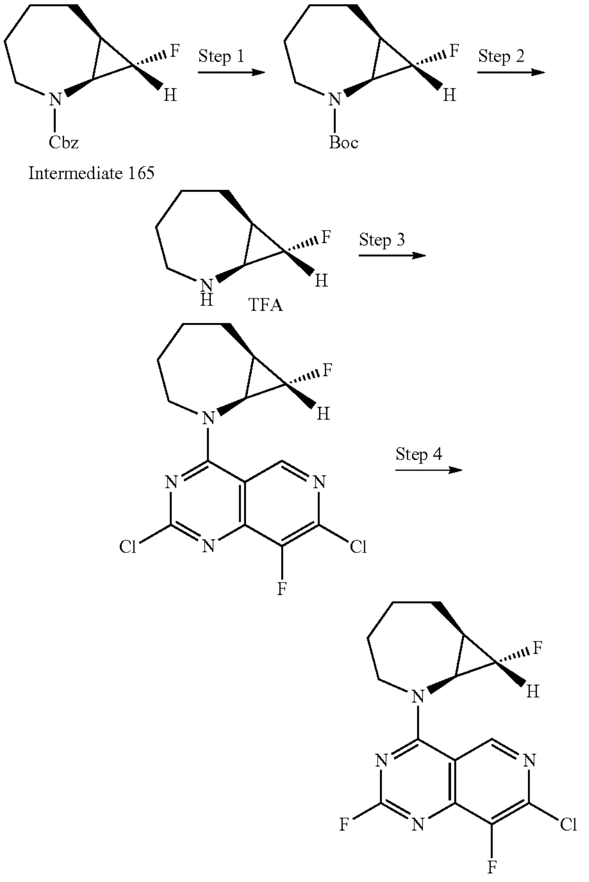

Intermediate 165

Intermediate 166

Step 1: tert-Butyl (1S,7R,8S)-8-fluoro-2-azabicyclo[5.1.0]octane-2-carboxylate

To a solution of Intermediate 165 (10 g, 37.9 mmol) in MeOH (110 mL) was added wet Pd/C (4.04 g, 10% purity) and BoczO (10.5 mL, 45.5 mmol) under Ar. The suspension was degassed and purged with $H_2$ three 3 times. The mixture was stirred under $H_2$ (15 psi) at 25° C. for 16 h. Pd/C was filtered off and washed with MeOH (100 mL×3). The combined organic phases were evaporated. The residue was purified by silica gel flash chromatography (eluent: 0~5% of ethyl acetate in petroleum ether) to give the title compound (8.4 g, 96% yield) as a colorless oil. MS: m/z=174.2 $[M+H\text{-}t\text{-}Bu]^+$. $^1H$ NMR (400 MHZ, Chloroform-d)δ 4.51-4.24 (m, 1H), 4.04-3.87 (m, 1H), 2.90-2.70 (m, 2H), 2.34-2.19 (m, 1H), 1.80-1.64 (m, 2H), 1.53-1.37 (m, 12H), 1.13-0.99 (m, 1H). $^{19}F$ NMR (376 MHz, Chloroform-d) δ −204.12, −205.16.

Step 2: (1S,7R,8S)-8-fluoro-2-azabicyclo[5.1.0]octane

To a solution of tert-butyl (1S,7R,8S)-8-fluoro-2-azabicyclo[5.1.0]octane-2-carboxylate (9,4 g, 41.0 mmol) in $CH_2Cl_2$ (50 mL) was added TFA (23.5 mL, 316 mmol) at 0° C. The mixture was stirred at 0° C. for 1 h. The reaction mixture was concentrated under reduced pressure to give the title compound (9.97 g, TFA salt) as a yellow oil. $^1$H NMR (400 MHZ, Chloroform-d)δ 9.14 (s, 1H), 8.08 (s, 1H), 4.99-4.72 (m, 1H), 3.61 (m, 1H), 3.28-2.96 (m, 2H), 2.60-2.44 (m, 1H), 2.10-1.82 (m, 3H), 1.74-1.50 (m, 2H), 1.38-1.17 (m, 1H). [19]F. NMR (376 MHz, Chloroform-d) 6-204.00.

Step 3: 2,7-Dichloro-8-fluoro-4-((1S,7R,8S)-8-fluoro-2-azabicyclo[5.1.0]octan-2-yl)pyrido[4,3-d]pyrimidine To a solution of 2,4,7-trichloro-8-fluoropyrido[4,3-d]pyrimidine (2.08 g, 8.22 mmol) in $CH_2C_{12}$ (10 mL) was added DIPEA (7.2 mL, 41.1 mmol) at −40° C. under $N_2$. A solution of (1S,7R,8S)-8-fluoro-2-azabicyclo[5.1.0]octane (2 g, 8.22 mmol, TFA salt) in $CH_2Cl_2$ (10 mL) was added dropwise and then the mixture was stirred at −40° C. for 1 h under $N_2$. The reaction mixture was quenched with water (50 mL) and extracted with EtOAc (50 mL×3). The combined organic layers were washed with brine (50 mL×2), dried over anhydrous $Na_2SO_4$, filtered and concentrated under reduced pressure. The residue was purified by silica gel flash chromatography (eluent: 0~5% of ethyl acetate in petroleum ether) to give the title compound (2.6 g, 92% yield) as a yellow solid. MS: m/z=345.0 $[M+H]^+$. $^1$H NMR (400 MHZ, Dimethylsulfoxide-$d_6$) δ 9.30 (s, 1H), 4.78-4.50 (m, 1H), 4.39 (d, J=13.2 Hz, 1H), 4.18-4.07 (m, 1H), 3.45-3.37 (m, 1H), 2.30-2.19 (m, 1H), 2.10-1.94 (m, 1H), 1.91-1.62 (m, 3H), 1.55-1.36 (m, 1H), 1.11-0.97 (m, 1H). $^{19}$F NMR (376 MHz, Dimethylsulfoxide-$d_6$) δ −135.80, −205.38.

Step 4: 7-Chloro-2,8-difluoro-4-((1S,7R,8S)-8-fluoro-2-azabicyclo[5.1.0]octan-2-yl)pyrido[4,3-d]pyrimidine To a solution of 2,7-dichloro-8-fluoro-4-((1S,7R,8S)-8-fluoro-2-azabicyclo[5.1.0]octan-2-yl)pyrido[4,3-d]pyrimidine (2.7 g, 7.82 mmol) in DMSO (10 mL) was added KF (2.27 g, 39.1 mmol). The mixture was stirred at 100° C. for 1 h under $N_2$. The reaction mixture was diluted with water (100 mL) and extracted with EtOAc (30 mL×3). The combined organic layers were washed with brine (50 mL), dried over anhydrous $Na_2SO_4$, filtered and concentrated under reduced pressure. The residue was purified by silica gel flash chromatography (eluent: 100% of dichloromethane) to give the title compound (Intermediate 166, 2 g, 71% yield) as a yellow solid. MS: m/z=329.0 $[M+H]^+$. $^1$H NMR (400 MHZ, Dimethylsulfoxide-$d_6$) δ 9.31 (s, 1H), 4.76-4.52 (m, 1H), 4.37 (d, J=13.6 Hz, 1H), 4.21-4.05 (m, 1H), 3.33-3.25 (m, 1H), 2.31~2.18 (m, 1H), 2.12-2.00 (m, 1H), 1.93-1.57 (m, 3H), 1.54-1.34 (m, 1H), 1.12-0.91 (m, 1H). $^{19}$F NMR (376 MHz, Dimethylsulfoxide-$d_6$) δ −40.87, −136.17, −205.36.

Intermediate 167 & 168: Benzyl-8-chloro-2-azabicyclo[5.1.0]octane-2-carboxylate (cis) & benzyl-8-chloro-2-azabicyclo[5.1.0]octane-2-carboxylate (trans)

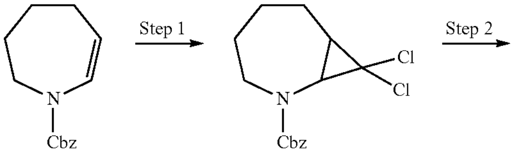

-continued

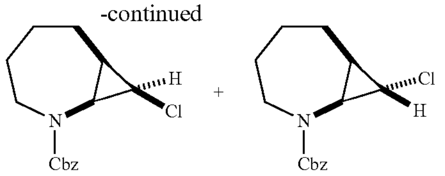

Intermediate 167 Intermediate 168

Step 1: Benzyl 8,8-dichloro-2-azabicyclo[5.1.0]octane-2-carboxylate

To a solution of benzyl 2,3,4,5-tetrahydro-1/-azepine-1-carboxylate (11.5 g, 49.7 mmol) and TEBAC(227 mg, 994 μmol) in $CHCl_3$ (180 mL) was added dropwise a solution of NaOH (24.7 g, 622 mmol) in $H_2O$ (45 mL) at 20° C. under $N_2$. The reaction mixture was stirred at 35° C. for 16 h. The reaction mixture was quenched with $H_2O$ (200 mL) and extracted with $CH_2Cl_2$ (100 mL×3). The combined organic layers were washed with brine (100 mL), dried over anhydrous $Na_2SO_4$, filtered and concentrated under reduced pressure. The residue was purified by silica gel flash chromatography (eluent: 0~4% EtOAc in Petroleum ether) to give the title compound (12 g, 76% yield) as a yellow solid. $^1$H NMR (400 MHZ, Chloroform-d)δ 7.61-7.28 (m, 5H), 5.29-5.11 (m, 2H), 3.92-3.81 (m, 1H), 3.18-3.07 (m, 2H), 2.31-2.22 (m, 1H), 1.88-1.76 (m, 3H), 1.63-1.52 (m, 3H).

Step 2: Benzyl-8-chloro-2-azabicyclo[5.1.0]octane-2-carboxylate (cis) & benzyl-8-chloro-2-azabicyclo[5.1.0]octane-2-carboxylate (trans)

To a solution of benzyl 8,8-dichloro-2-azabicyclo[5.1.0]octane-2-carboxylate (12 g, 38.2 mmol) in EtOH (150 mL) was added Zn (25 g, 382 mmol) and $NH_4Cl$ (20.4 g, 382 mmol) at 25° C. in sequence under $N_2$. The reaction mixture was stirred at 100° C. for 16 h under $N_2$. The reaction mixture was filtered and concentrated under reduced pressure. The residue was purified by silica gel flash chromatography (eluent: 0~5% EtOAc in Petroleum ether) to give the title compound (Intermdiate 167, 4.7 g, 44% yield, spot 2 with more polarity) as a yellow oil and the other title compound (Intermediate 168, 4.8 g, 45% yield, spot 1 with less polarity) as a yellow solid.

Spectra for Intermdiate 167: MS: m/z=280.1 $[M+H]^+$. $^1$H NMR (400 MHZ, Chloroform-d)$_8$ $_{7.48}$-7.28 (m, 5H), 5.29-4.97 (m, 2H), 4.05-3.75 (m, 1H), 3.42-3.07 (m, 2H), 2.85-2.65 (m, 1H), 2.07-1.97 (m, 1H), 1.90-1.77 (m, 2H), 1.70-1.60 (m, 3H), 1.36-1.27 (m, 1H). Spectra for Intermediate 168: MS: m/z=280.2 $[M+H]^+$. 3H NMR (400 MHZ, Chloroform-d) δ 7.54-7.28 (m, 5H), 5.25-5.10 (m, 2H), 4.15-3.95 (m, 1H), 3.23-2.79 (m, 3H), 2.43-2.27 (m, 1H), 1.78-1.67 (m, 2H), 1.53-1.40 (m, 3H), 1.19-1.08 (m, 1H).

Intermediate 169: 2,7-Dichloro-4-((1S,7R,8S)-8-chloro-2-azabicyclo[5.1.0]octan-2-yl)-8-methylpyrido[4,3-d]pyrimidine

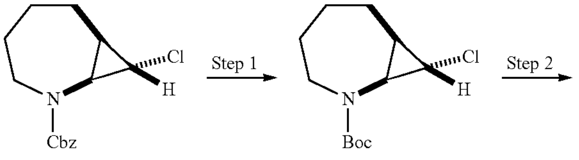

Intermediate 168

-continued

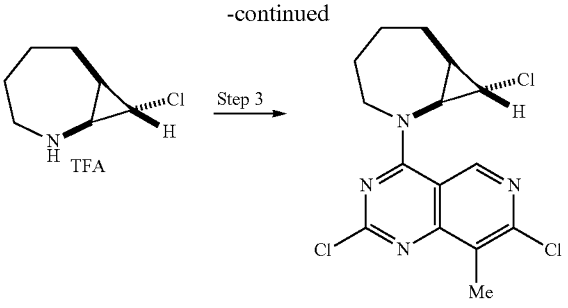

Intermediate 169

Step 1: tert-Butyl (1S,7R,8S)-8-chloro-2-azabicyclo[5.1.0]octane-2-carboxylate To a solution of Pd/C(129 mg, 122 μmol, 10% purity) in MeOH (2 mL) was added Intermediate 168 (170 mg, 608 μmol) at 25° C. under Ar. The reaction mixture was degassed, purged with $H_2$ three times, and stirred at 25° C. under $H_2$ for 2 h. The reaction mixture was filtered and concentrated under reduced pressure. The residue was purified by silica gel flash chromatography (eluent: 0~10% EtOAc in Petroleum ether) to give the title compound (94% yield) as a yellow oil. $^1$H NMR (400 MHZ, Chloroform-d) & 4.07-3.83 (m, 1H), 3.05-2.64 (m, 3H), 2.47-2.25 (m, 1H), 1.79-1.63 (m, 2H), 1.53-1.42 (m, 12H), 1.21-1.09 (m, 1H).

Step 2: (1S,7R,8S)-8-chloro-2-azabicyclo[5.1.0]octane (TFA salt)

To a solution of tert-butyl (1S,7R,8S)-8-chloro-2-azabicyclo[5.1.0]octane-2-carboxylate (140 mg, 570 μmol) in $CH_2Cl_2$ (2 mL) was added TFA (1.27 mL, 17.1 mmol) at 25° C. The reaction mixture was stirred at 25° C. for 0.5 h. The reaction mixture was concentrated under reduced pressure to give the title compound (100 mg, TFA salt) as a yellow oil, which was used in the next step without further purification.

Step 3: 2,7-Dichloro-4-((1S,7R,8S)-8-chloro-2-azabicyclo[5.1.0]octan-2-yl)-8-methylpyrido[4,3-d]pyrimidine To a solution of 2,4,7-trichloro-8-methylpyrido[4,3-d]pyrimidine (142 mg, 570 μmol) and DIPEA (496 AL, 2.85 mmol) in $CH_2Cl_2$ (5 mL) was added a solution of (1S,7R,85)-8-chloro-2-azabicyclo[5.1.0]octane (100 mg, 385 μmol, TFA salt) in $CH_2Cl_2$ (2 mL) at −40° C. under $N_2$. The reaction mixture was stirred at −40° C. for 1 h under $N_2$. The reaction mixture was diluted with water (50 mL) and extracted with EtOAc (60 mL×2). The combined organic layers were washed with brine (50 mL×2), dried over anhydrous $Na_2SO_4$, filtered and concentrated under reduced pressure. The residue was purified by silica gel flash chromatography (eluent: 0~3% of MeOH in $CH_2Cl_2$) to give the title compound (Intermediate 169, 200 mg, crude) as a yellow solid, which was used in the next step without further purification. MS: m/z=356.9, 358.9 [M+H]$^{+\cdot}$

Intermediate 170: 7-Chloro-2-fluoro-4-((1S,7R,8S)-8-fluoro-2-azabicyclo[5.1.0]octan-2-yl)-8-methylpyrido[4,3-d]pyridine

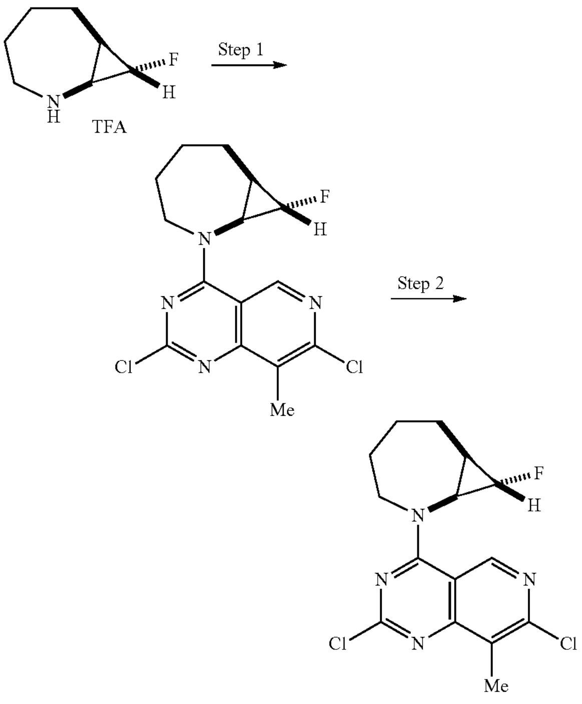

Intermediate 170

Step 1: 2,7-Dichloro-4-((1S,7R,8S)-8-fluoro-2-azabicyclo[5.1.0]octan-2-yl)-8-methylpyrido[4,3-d]pyrimidine To a solution of 2,4,7-trichloro-8-methylpyrido[4,3-d]pyrimidine (800 mg, 3.22 mmol) in $CH_2Cl_2$ (16 mL) were added DIPEA (1.66 g, 12.9 mmol) and (1S,7R,8S)-8-fluoro-2-azabicyclo[5.1.0]octane) (900 mg, 2.96 mmol, TFA salt) at −40° C. under $N_2$. The reaction mixture was stirred at −40° C. for 1 h, then diluted with water (20 mL) and extracted with EtOAc (10 mL×3). The combined organic layers were washed with brine (30 mL), dried over anhydrous $Na_2SO_4$, filtered and the filtrate was concentrated under reduced pressure to give a residue. The residue was purified by flash silica gel chromatography (eluent: 0~15% ethyl acetate in petroleum ether) to give 2,7-dichloro-4-((1S,7R,8S)-8-fluoro-2-azabicyclo[5.1.0]octan-2-yl)-8-methylpyrido[4,3-d]pyrimidine (1.1 g, crude) as a yellow solid. MS: m/z=341.1 [M+H]$^{+\cdot}$

Step 2: 7-Chloro-2-fluoro-4-((1S,7R,8S)-8-fluoro-2-azabicyclo[5.1.0]octan-2-yl)-8-methylpyrido[4,3-d]pyrimidine To a solution of 2,7-dichloro-4-((1S,7R,8S)-8-fluoro-2-azabicyclo[5.1.0]octan-2-yl)-8-methylpyrido[4,3-d]pyrimidine (1.1 g, 3.22 mmol) in DMSO (15 mL) was added KF (1.0 g, 17.6 mmol) at 25° C. under $N_2$. The mixture was stirred at 100° C. for 10 h. The reaction mixture was quenched with $H_2O$ (50 mL) and EtOAc (20 mL×3). The combined layers were dried over $Na_2SO_4$, filtered and concentrated under reduced pressure. The residue was purified by silica gel flash chromatography (eluent: 0~7% ethyl acetate in petroleum ether) to give the title compound (Intermediate 170, 800 mg, 76% yield for two steps) as a yellow solid. MS: m/z=325.1 $[M+H]^{+\cdot}$ Intermediate 171: (S)-(2-Methylenetetrahydro-1H-pyrrolizin-7a(5H)-yl) methan-$d_2$-ol

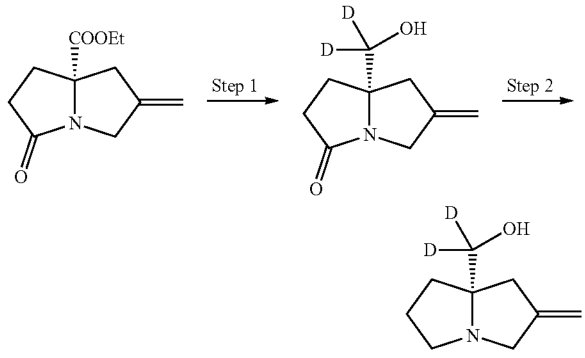

Intermediate 171

Step 1: (S)-7a-(hydroxymethyl-$d_2$)-6-methylene-hexahydro-3/-pyrrolizin-3-one To a solution of ethyl(S)-2-methylene-5-oxotetrahydro-1/-pyrrolizine-7a (5H)-carboxylate (1 g, 4.78 mmol) in $CD_3OD$ (20 mL) was added NaBD4 (904 mg, 23.9 mmol) at 0° C. under $N_2$. The mixture was stirred at 25° C. for 16 h. The reaction mixture was quenched with HCl (0.8 mL, 1M in $H_2O$) at 25° C. and concentrated under reduced pressure. The residue was purified by silica gel flash chromatography (eluent: 0~5% of MeOH in $CH_2Cl_2$) to give the title compound (735 mg, 91% yield) as a yellow oil. MS: m/z=170.3 $[M+H]^+$. $^1H$ NMR (400 MHZ, Dimethylsulfoxide-$d_6$) δ 5.07-4.93 (m, 3H), 4.10-3.99 (m, 1H), 3.56-3.45 (m, 1H), 2.69-2.53 (m, 2H), 2.31-2.24 (m, 1H), 2.23-2.14 (m, 2H), 1.92-1.80 (m, 1H).

Step 2: (S)-(2-Methylenetetrahydro-1//-pyrrolizin-7a (5H)-yl) methan-$d_2$-ol To a solution of(S)-7a-(hydroxymethyl-$d_2$)-6-methylene-hexahydro-3H-pyrrolizin-3-one (735 mg, 4.34 mmol) in THF (10 mL) was added $LiAlH_4$ (8.69 mL, 2.5 M in THF) dropwise at 0° C. under $N_2$. The mixture was stirred at 70° C. for 4 h. The reaction mixture was slowly quenched with $Na_2SO_4 \cdot 10H_2O$ (15 g) at 0° C. The organic layers were dried over $Na_2SO_4$, filtered and concentrated under reduced pressure. The residue was purified by silica gel flash chromatography (eluent: 0~20% of MeOH in $CH_2Cl_2$) to give the title compound (Intermediate 171, 430 mg, 64% yield) as a yellow oil. MS: m/z=156.3 $[M+H]^+$. $^1H$ NMR (400 MHZ, Dimethylsulfoxide-$d_6$) 4.89-4.80 (m, 2H), 3.49-3.48 (m, 1H), 3.16-3.11 (m, 1H), 2.95-2.87 (m, 1H), 2.53-2.52 (m, 1H), 2.49-2.46 (m, 1H), 2.21-2.12 (m, 1H), 1.89-1.82 (m, 1H), 1.81-1.73 (m, 1H), 1.72-1.60 (m, 1H), 1.53-1.43 (m, 1H).

Intermediate 172 & 173: (1S, 7R, 8S)-8-Chloro-6-(7-chloro-8-fluoro-2-(((2R,7aS)-2-fluorotetrahydro-1H-pyrrolizin-7a(5H)-yl)methoxy-$d_2$) pyrido[4,3-d]pyrimidin-4-yl)-2-oxa-6-azabicyclo[5.1.]octane & (1R, 7S, 8R)-8-chloro-6-(7-chloro-8-fluoro-2-(((2R, 7aS)-2-fluorotetrahydro-1H-pyrrolizin-7a(5H)-yl)methoxy-$d_2$)pyrido[4,3-d] pyrimidin-4-yl)-2-oxa-6-azabicyclo[5.1.0]octane

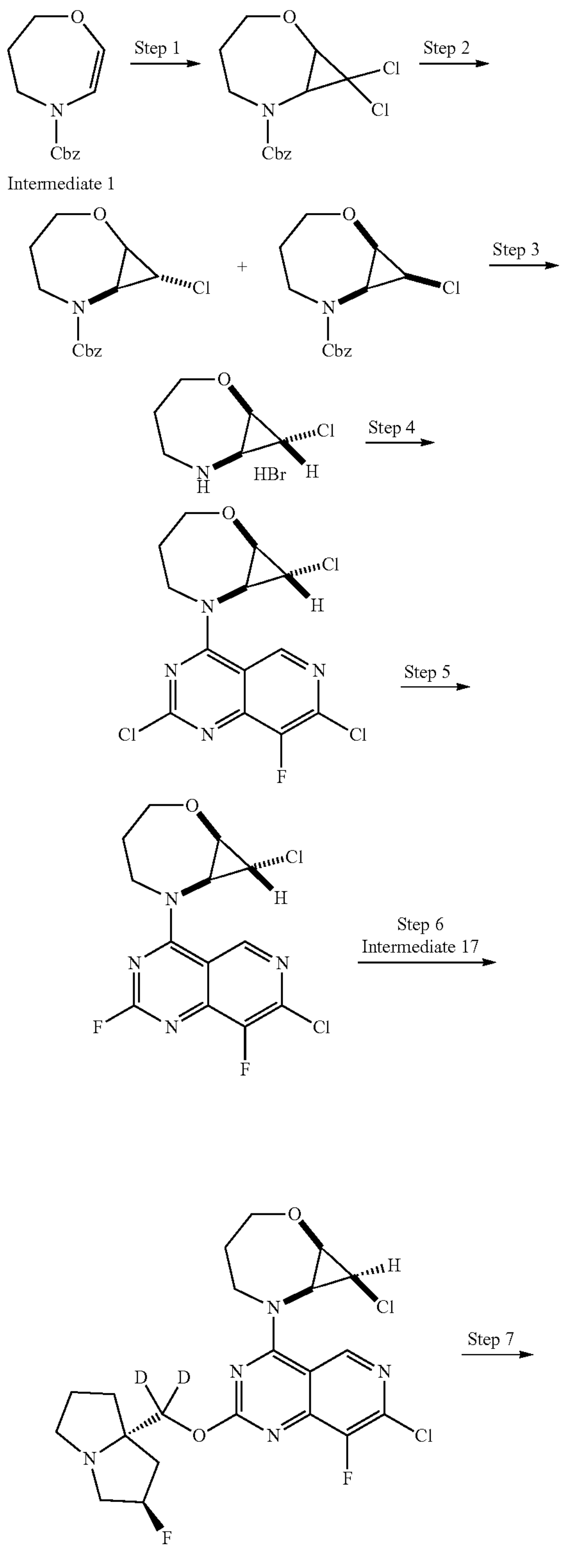

-continued

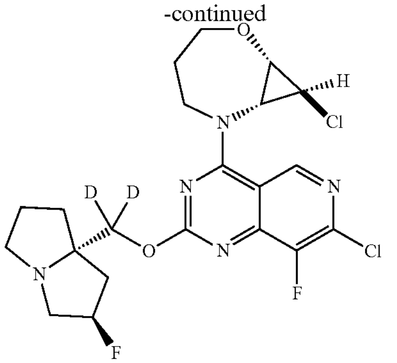

+

Intermediate 172

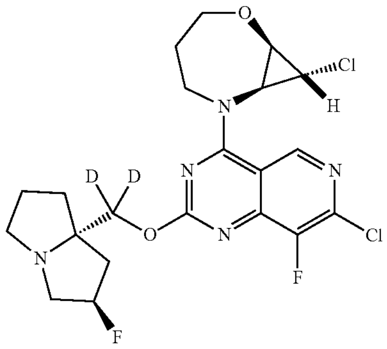

Intermediate 173

Step 1: benzyl 8,8-dichloro-2-oxa-6-azabicyclo [5.1.0]octane-6-carboxylate

To an ice-cooled solution of Intermediate 1 (10 g, 42.87 mmol) and tetrabutylazanium iodide (3.17 g, 8.57 mmol) in DCM (50 mL) and NaOH (100 mL, 50% aq.) under $N_2$ was added chloroform (15.35 g, 128.61 mmol) dropwise. The ice bath was removed, and the reaction mixture was stirred at room temperature for 12 hours. The resulting mixture was diluted with water (100 mL) and extracted with $CH_2Cl_2$ (3×100 mL). The combined organic layers were washed with brine (100 mL), dried over anhydrous sodium, filtered and concentrated under reduced pressure. The residue was purified by silica gel flash chromatography (eluted with 20% EA in PE) to afford the title compound (12 g, 88% yield) as a light yellow solid. $^1$H NMR (400 MHz, Chloroform-d) δ 7.52-7.29 (m, 5H), 5.25-5.16 (m, 2H), 4.00-3.73 (m, 4H), 3.44-3.39 (m, 1H), 3.08-3.07 (m, 1H), 1.99-1.93 (m, 2H).

Step 2: Benzyl 8-chloro-2-oxa-6-azabicyclo[5.1.0] octane-6-carboxylate (trans mixture)

To a stirred mixture of benzyl 8,8-dichloro-2-oxa-6-azabicyclo[5.1.0]octane-6-carboxylate (12 g, 37.95 mmol) and ammonium chloride (18.27 g, 341.58 mmol) in EtOH (120 mL) was added Zn (22.33 g, 341.58 mmol) at room temperature under $N_2$. The resulting mixture was heated for 16 hours at 70° C. under $N_2$. The resulting mixture was filtered, and the filter cake was washed with EtOH (3×100 mL). The filtrate was concentrated under reduced pressure. The residue was purified by silica gel flash chromatography (eluted with 30% EA in PE) to give two peaks. The first eluting peak was collected and concentrated under reduced pressure to give benzyl 8-chloro-2-oxa-6-azabicyclo[5.1.0]octane-6-carboxylate (trans mixture) (4 g, 37% yield) as a light yellow solid. $^1$H NMR (300 MHz, Chloroform-d) δ 7.42-7.31 (m, 5H), 5.21-5.16 (m, 2H), 4.23-3.83 (m, 2H), 3.76-3.04 (m, 4H), 2.79-2.76 (m, 1H), 1.86-1.77 (m, 2H). The second eluting peak was collected and concentrated under reduced pressure to give benzyl 8-chloro-2-oxa-6-azabicyclo[5.1.0]octane-6-carboxylate (cis mixture) (450 mg, crude, 4% yield) as a light yellow oil. $^1$H NMR (300 MHz, Chloroform-d) δ 7.46-7.27 (m, 5H), 5.22-4.90 (m, 2H), 4.42-2.72 (m, 7H), 1.36-1.11 (m, 2H).

Step 3: 8-Chloro-2-oxa-6-azabicyclo[5.1.0]octane hydrobromide (trans mixture)

A solution of benzyl 8-chloro-2-oxa-6-azabicyclo[5.1.0]octane-6-carboxylate (trans mixture) (3.7 g, 13.13 mmol) in hydrogen bromide (37 mL, 33 wt % in acetic acid) was stirred in an ice bath for 1 hour. The resulting mixture was concentrated under reduced pressure. The residue was triturated with hexane (3×50 mL) to afford the title compound (2.8 g, 94% yield) as a light yellow solid.

Step 4: 8-Chloro-6-(2,7-dichloro-8-fluoropyrido[4,3-d]pyrimidin-4-yl)-2-oxa-6-azabicyclo[5.1.0]octane (trans mixture)

To a solution of 2,4,7-trichloro-8-fluoropyrido[4,3-d]pyrimidine (3.0 g, 11.88 mmol) in DCM (30 mL) under nitrogen atmosphere were added DIEA (4.61 g, 35.65 mmol) and 8-chloro-2-oxa-6-azabicyclo[5.1.0]octane hydrobromide (trans mixture) (2.72 g, 11.88 mmol) at −40° C. The reaction mixture was stirred at −40° C. for 1 hour. The resulting mixture was quenched with water (50 mL) and extracted with DCM (3×50 mL). The combined organic layers were washed with brine (30 mL), dried over anhydrous sodium sulfate, filtered and concentrated under reduced pressure. The residue was purified by silica gel flash chromatography (eluted with 30% EA in PE) to the title compound (3.0 g, 69% yield) as a light yellow solid. MS: m/z=363.00, 365.00 $[M+H]^{+.}$ Step 5: 8-chloro-6-(7-chloro-2,8-difluoropyrido[4,3-d]pyrimidin-4-yl)-2-oxa-6-azabicyclo[5.1.0]octane (trans mixture)

To a stirred solution of 8-chloro-6-(2,7-dichloro-8-fluoropyrido[4,3-d]pyrimidin-4-yl)-2-oxa-6-azabicyclo[5.1.0]octane (trans mixture) (500 mg, 1.37 mmol) in DMSO (5.0 mL) under $N_2$ were added KF (103.86 mg, 1.79 mmol) at room temperature. The reaction mixture was heated at 80° C. for 16 hours. The resulting mixture was cooled to room temperature, diluted with water (10 mL) and extracted with DCM (3×30 mL). The combined organic layers were washed with brine (10 mL), dried over anhydrous $Na_2SO_4$, filtered and concentrated under reduced pressure. The residue was purified by TCL ($CH_2Cl_2$: MeOH=10: 1) to afford the title compound (340 mg, 71% yield) as a light yellow solid. MS: m/z=347.05, 349.05 $[M+H]^{+.}$ Step 6: 8-chloro-6-(7-chloro-8-fluoro-2-(((2R,7aS)-2-fluorotetrahydro-1/-pyrrolizin-7a (5H)-yl) methoxy-$d_2$)pyrido[4,3-d]pyrimidin-4-yl)-2-oxa-6-azabicyclo[5.1.0]octane (trans mixture)

To an ice-cooled solution of ((2R,7aS)-2-fluorotetrahydro-1H-pyrrolizin-7a (5H)-yl) methan-dz-ol (189.48 mg, 1.18 mmol) in THF (5.0 mL) under $N_2$ was added 1-BuOK (131.88 mg, 1.18 mmol). The mixture was stirred in an ice bath for 30 min. 8-Chloro-6-(7-chloro-2,8-difluoropyrido[4,3-d]pyrimidin-4-yl)-2-oxa-6-azabicyclo[5.1.0]octane (trans mixture) (340 mg, 0.98 mmol) was added to the above mixture. The ice-bath was removed, and the reaction mixture was stirred at room temperature for 1 hour. The resulting mixture was quenched with sat. $NH_4Cl$ aq. (10 mL) in an ice bath and extracted with EA (3x30 mL). The combined organic layers were washed with brine (30 mL), dried over anhydrous $Na_2SO_4$, filtered and concentrated under reduced pressure. The residue was purified by silica gel flash chromatography (eluted with 20% EA in PE) to afford the title compound (300 mg, 67% yield) as a yellow solid. MS: m/z=488.25, 490.25 $[M+H]^{+\cdot}$ Step 7: (1S,7R,8S)-8-chloro-6-(7-chloro-8-fluoro-2-(((2R,7aS)-2-fluorotetrahydro-1H-pyrrolizin-7a (5H)-yl) methoxy-$d_2$)pyrido[4,3-d]pyrimidin-4-yl)-2-oxa-6-azabicyclo[5.1.0]octane & (1R,7S,8R)-8-chloro-6-(7-chloro-8-fluoro-2-(((2R,7aS)-2-fluorotetrahydro-1H-pyrrolizin-7a (5H)-yl) methoxy-$d_2$) pyrido[4,3-d]pyrimidin-4-yl)-2-oxa-6-azabicyclo [5.1.0]octane 8-Chloro-6-(7-chloro-8-fluoro-2-(((2R,7aS)-2-fluorotetrahydro-1H-pyrrolizin-7a (5H)-yl) methoxy-$d_2$)pyrido[4,3-d]pyrimidin-4-yl)-2-oxa-6-azabicyclo[5.1.0]octane (trans mixture) (300 mg, 0.61 mmol) was separated by Prep-Chiral-HPLC with the following conditions: Column: CHIRALPAK IA 2x25 cm, 5 μm; Mobile Phase A: Hex (0.5% 2 M $NH_3$-MeOH); Mobile Phase B: EtOH; Flow rate: 20 mL/min; Gradient: isocratic 40%; Detector: UV 220 & 254 nm; RTI: 9.636 min; RT2: 12.755 min. The first eluting peak (RTI: 9.636 min) was concentrated and lyophilized to give the title compound (Intermediate 172, 105 mg, 35% yield) as a light yellow solid. MS: m/z=488.25, 490.25 $[M+H]^+$. $^1H$ NMR (300 MHz, Chloroform-d)δ 9.02 (s, 1H), 5.40-5.22 (m, 1H), 4.64-4.60 (m, 1H), 4.08-4.04 (m, 1H), 3.92-3.90 (m, 1H), 3.82-3.73 (m, 1H), 3.55-3.22 (m, 5H), 3.10-2.95 (m, 2H), 2.50-1.80 (m, 8H). $^{19}F$ NMR (282 MHz, Chloroform-d) δ −134.37 (s, 1F)-−173.03 (s, 1F). The second eluting peak (RT2: 12.755 min) was concentrated and lyophilized to give the other title compound (Intermediate 173, 105 mg, 35% yield) as a light yellow solid. MS: m/z=488.25, 490.25 $[M+H]^+$. $^1H$ NMR (300 MHz, Chloroform-d) δ 9.02 (s, 1H), 5.39-5.21 (m, 1H), 4.65-4.60 (m, 1H), 4.09-4.04 (m, 1H), 3.92-3.90 (m, 1H), 3.81-3.74 (m, 1H), 3.55-3.10 (m, SH), 3.05-2.92 (m, 2H), 2.50-1.85 (m, 8H). $^{19}F$ NMR (282 MHz, Chloroform-d) δ −134.39 (s, IF), —172.95 (s, IF).

Intermediate 174: 6-Fluoro-5-(fluoromethoxy-$d_2$)-4-(4,4,5,5-tetramethyl-1,3,2-dioxaborolan-2-yl)naphthalen-2-amine

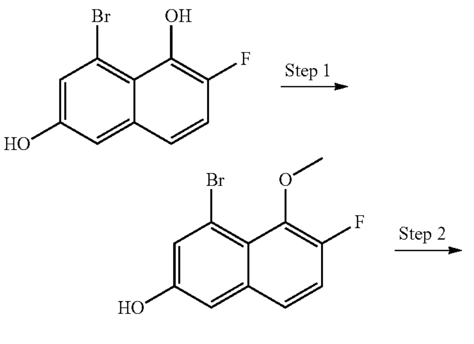

-continued

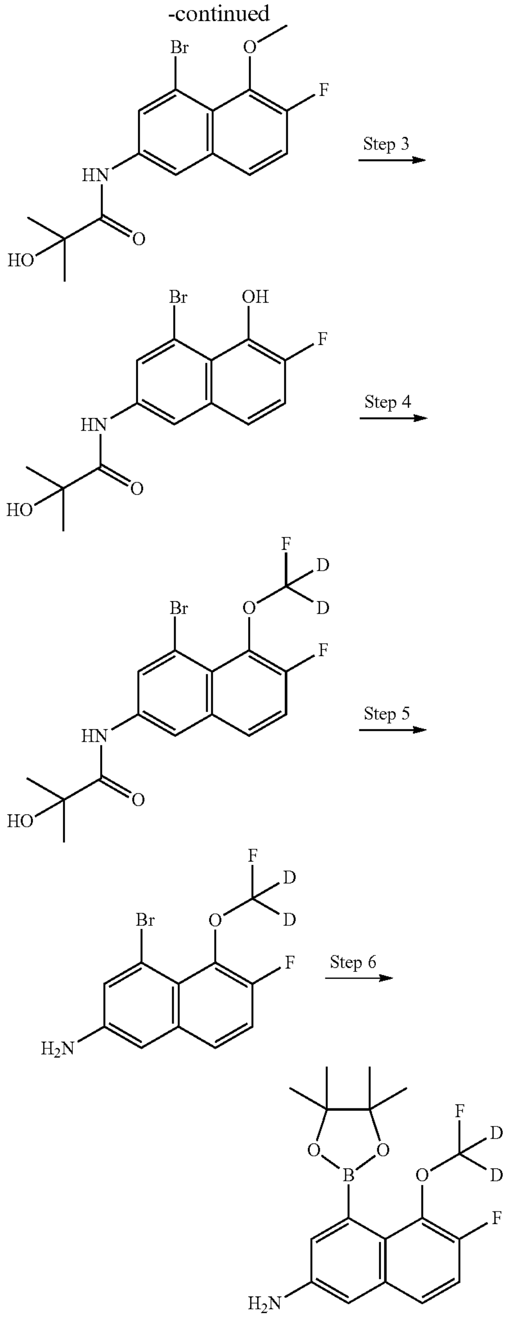

Intermediate 174

Step 1: 4-Bromo-6-fluoro-5-methoxynaphthalen-2-ol

To a solution of 8-bromo-2-fluoronaphthalene-1,6-diol (5 g, 19.5 mmol) and $K_2CO_3$ (8.06 g, 58.4 mmol) in DMF (50 mL) was added $CH_3I$ (1.21 mL, 19.5 mmol) dropwise at 0° C. under $N_2$. The mixture was stirred at 0° C. for 2 h under $N_2$. The reaction mixture was quenched with $H_2O$ (200 mL) at 0° C. and extracted with EtOAc (100 mLx3). The combined organic layers were washed with brine (200 mL), dried over $Na_2SO_4$, filtered and concentrated under reduced pressure. The residue was purified by silica gel flash chromatography (eluent: 0~8% of EtOAc in petroleum ether) to give the title compound (4.7 g, 88% yield) as a brown oil. MS: m/z=268.9, 270.9 [M−H]$^-$. $^1$H NMR (400 MHZ, Chloroform-d)δ 10.29-9.98 (m, 1H), 7.58 (dd, J=5.4, 9.2 Hz, 1H), 7.53-7.38 (m, 2H), 7.25-7.19 (m, 1H), 3.87 (s, 3H). $^{19}$F NMR (400 MHZ, Chloroform-d) δ −134.77.

Step 2: N-(4-Bromo-6-fluoro-5-methoxynaphthalen-2-yl)-2-hydroxy-2-methylpropanamide To a solution of 4-bromo-6-fluoro-5-methoxynaphthalen-2-ol (4.6 g, 17.0 mmol) in DMA (10 mL) was added 2-bromo-2-methylpropanamide (8.45 g, 50.9 mmol) and NaOH (6.11 g, 152.7 mmol) at 20° C. under $N_2$. The mixture was stirred at 50° C. for 6 h. The reaction mixture was quenched with $H_2O$ (200 mL) at 0° C. and extracted with EtOAc (100 mL×3). The combined organic layers were washed with brine (200 mL), dried over $Na_2SO_4$, filtered and concentrated under reduced pressure. The residue was purified by silica gel flash chromatography (eluent: 0~20% of EtOAc in petroleum ether) to give the title compound (5.96 g, 87% yield) as a yellow oil. MS: m/z=354.0, 356.0 [M−H]$^-$. $^1$H NMR (400 MHZ, Dimethylsulfoxide-$d_6$) δ 9.95 (s, 1H), 8.51-8.25 (m, 2H), 7.70 (dd, J=5.6, 9.2 Hz, 1H), 7.57-7.51 (m, 1H), 5.78 (s, 1H), 3.90 (s, 3H), 1.38 (s, 6H). $^{19}$F NMR (376 MHz, Dimethylsulfoxide-$d_6$) δ −131.96.

Step 3: N-(4-Bromo-6-fluoro-5-hydroxynaphthalen-2-yl)-2-hydroxy-2-methylpropanamide To a solution of N-(4-bromo-6-fluoro-5-methoxynaphthalen-2-yl)-2-hydroxy-2-methylpropanamide (5.86 g, 16.5 mmol) in $CH_2Cl_2$ (0.5 mL) was added BBr3 (10 mL, 2 M in $CH_2Cl_2$) at 0° C. under $N_2$. The mixture was stirred at 25° C. for 2 h. The reaction mixture was quenched with $H_2O$ (100 mL) at 0° C. and extracted with EtOAc (100 mL×3). The combined organic layers were washed with brine (100 mL), dried over $Na_2SO_4$, filtered and concentrated under reduced pressure. The residue was purified by silica gel flash chromatography (eluent: 0~100% of EtOAc in petroleum ether) to give the title compound (3.03 g, 54% yield) as an off-white solid. MS: m/z=342.1, 344.1 [M+H]$^+$. JH NMR (400 MHZ, Dimethylsulfoxide-$d_6$) 10.04 (s, 1H), 9.85 (s, 1H), 8.32 (s, 1H), 8.20 (s, 1H), 7.43 (t, J=9.6 Hz, 1H), 7.37-7.30 (m, 1H), 5.75 (s, 1H), 1.37 (s, 6H). $^{19}$F NMR (376 MHz, Dimethylsulfoxide-$d_6$) δ −138.38, −139.06.

Step 4: N-(4-Bromo-6-fluoro-5-(fluoromethoxy-$d_2$) naphthalen-2-yl)-2-hydroxy-2-methylpropanamide To a solution of fluoromethyl-$d_2$ $_4$-methylbenzenesulfonate (1.22 g, 5.9 mmol) and N-(4-bromo-6-fluoro-5-hydroxynaphthalen-2-yl)-2-hydroxy-2-methylpropanamide (3.03 g, 8.9 mmol) in DMF (25 mL) was added $K_2CO_3$ (2.45 g, 17.7 mmol). The mixture was stirred at 80° C. for 4 h. The reaction mixture was quenched with $H_2O$ (100 mL) at 0° C. and extracted with EtOAc (100 mL×3). The combined organic layers were washed with brine (300 mL), dried over $Na_2SO_4$, filtered and concentrated under reduced pressure. The residue was purified by silica gel flash chromatography (eluent: 0~30% of EtOAc in petroleum ether) to give the title compound (2.35 g, 99% yield) as a light yellow solid. MS: m/z=376.0, 378.0 [M+H]$^+$. $^1$H NMR (400 MHZ, Dimethylsulfoxide-$d_6$) δ 9.99 (s, 1H), 8.50 (d,)=2.0 Hz, 1H), 8.37 (d, J=2.0 Hz, 1H), 7.83 (dd, J=5.6, 9.2 Hz, 1H), 7.64-7.55 (m, 1H), 5.79 (s, 1H), 1.38 (s, 6H). $^{19}$F NMR (376 MHZ, Dimethylsulfoxide-$d_6$) δ −129.42, −152.72, −152.74.

Step 5: 4-Bromo-6-fluoro-5-(fluoromethoxy-$d_2$) naphthalen-2-amine

To a solution of N-(4-bromo-6-fluoro-5-(fluoromethoxy-$d_2$) naphthalen-2-yl)-2-hydroxy-2-methylpropanamide (2.35 g, 6.25 mmol) in EtOH (10 mL) was added NaOH (8.45 mL, 5 M in $H_2O$). The mixture was stirred at 100° C. for 16 h. The reaction mixture was concentrated under reduced pressure. The residue was purified by silica gel flash chromatography (eluent: 0~15% of EtOAc in petroleum ether) to give the title compound (1.42 g, 75% yield) as a yellow solid. MS: m/z=289.9, 290.9 [M+H]$^+$. $^1$H NMR (400 MHZ, Dimethylsulfoxide-$d_6$) δ 7.50 (dd, J=5.6, 9.2 Hz, 1H), 7.43-7.34 (m, 2H), 6.90 (d, J=2.0 Hz, 1H), 5.64 (s, 2H). $^{19}$F NMR (376 MHz, Dimethylsulfoxide-$d_6$)$_6$-134.98, −152.39.

Step 6: 6-Fluoro-5-(fluoromethoxy-$d_2$)-4-(4,4,5,5-tetramethyl-1,3,2-dioxaborolan-2-yl) naphthalen-2-amine A mixture of 4-bromo-6-fluoro-5-(fluoromethoxy-$d_2$) naphthalen-2-amine (1.4 g, 4.83 mmol), 4,4,4',4',5,5,5',5'-octamethyl-2,2'-bi (1,3,2-dioxaborolane) (3.68 g, 14.5 mmol), CysPPdG3 (471 mg, 724 μmol) and $K_3PO_4$ (3.07 g, 14.5 mmol) in 1,4-dioxane (10 mL) was degassed and purged with $N_2$ for 3 times. The mixture was stirred at 100° C. for 16 h under $N_2$. The reaction mixture was concentrated under reduced pressure. The residue was purified by flash silica gel chromatography (eluent: 0~35% of EtOAc in petroleum ether) to give the title compound (Intermediate 174, 681 mg, 71% yield) as a yellow solid. MS: m/z=337.9 [M+H]$^+$. $^1$H NMR (400 MHz, Dimethylsulfoxide-$d_6$) δ 7.38 (dd, J=5.2, 9.2 Hz, 1H), 7.32-7.25 (m, 1H), 7.02 (d, J=2.0 Hz, 1H), 6.85 (d, J=2.4 Hz, 1H), 5.44 (s, 2H), 1.34 (s, 12H), $^{19}$F. NMR (376 MHz, Dimethylsulfoxide-$d_6$) δ −139.70, −149.68, −149.72.

Example 1 & 2: 4-(4-((15,7R)-2-Azabicyclo[5.1.0] octan-2-yl)-8-fluoro-2-(((2R,7aS)-2-fluorotetrahydro-1H-pyrrolizin-7a (5/)-yl) methoxy)pyrido[4,3-d]pyrimidin-7-yl)-5-ethynyl-6-fluoronaphthalen-2-ol & 4-(4-((1R,7S)-2-azabicyclo[5.1.0]octan-2-yl)-8-fluoro-2-(((2R,7aS)-2-fluorotetrahydro-1H-pyrrolizin-7a (5H)-yl) methoxy)pyrido[4,3-d] pyrimidin-7-yl)-5-ethynyl-6-fluoronaphthalen-2-ol

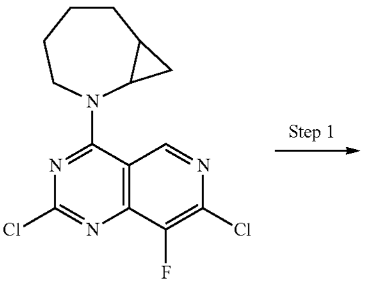

Intermediate 7

-continued

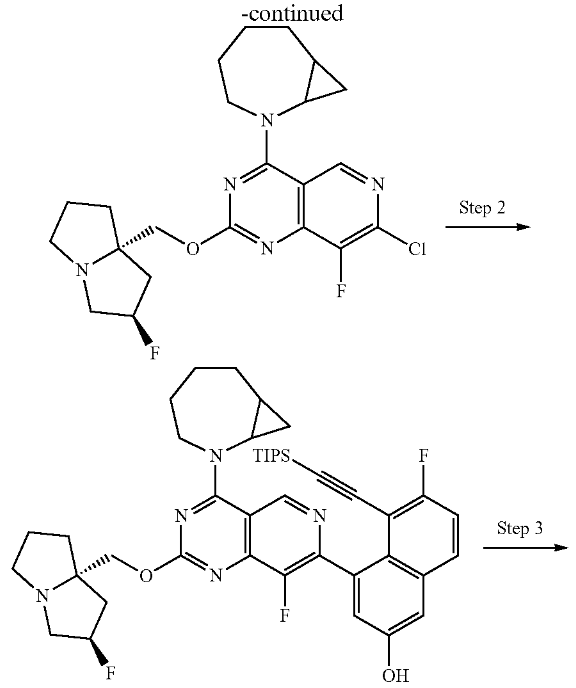

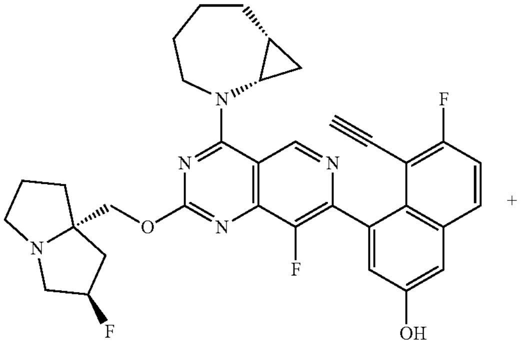

Example 1

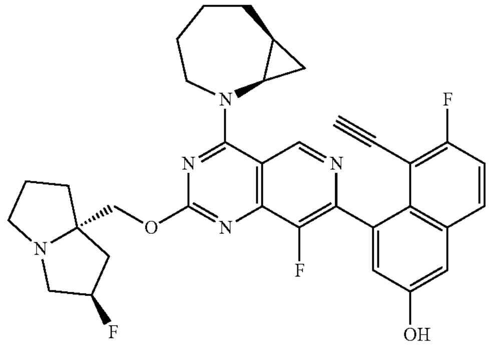

Example 2

Step 1: 4-(2-Azabicyclo[5.1.0]octan-2-yl)-7-chloro-8-fluoro-2-(((2R,7aS)-2-fluorotetrahydro-1H-pyrrolizin-7a (5H)-yl) methoxy)pyrido[4,3-d]pyrimidine To a solution of Intermediate 7 (150 mg, 458 μmol) in 1,4-dioxane (2 mL) were added DIPEA (178 mg, 240 L) and ((2R,7aS)-2-fluorotetrahydro-1H-pyrrolizin-7a (5H)-yl) methanol (182 mg, 1.15 mmol). The mixture was stirred at 110° C. for 16 h. The mixture was concentrated under reduced pressure. The residue was purified by silica gel flash chromatography (eluent: 0~10% MeOH in $CH_2Cl_2$) to give the title compound (130 mg, 50% yield) as a yellow solid. MS: m/z=450.2 $[M+H]^{+\cdot}$ Step 2: 4-(4-(2-Azabicyclo[5.1.0]octan-2-yl)-8-fluoro-2-(((2R,7aS)-2-fluorotetrahydro-1H-pyrrolizin-7a (5H)-yl) methoxy)pyrido[4,3-d]pyrimidin-7-yl)~6-fluoro-5-((triisopropylsilyl) ethynyl) naphthalen-2-ol A mixture of 4-(2-azabicyclo[5.1.0]octan-2-yl)-7-chloro-8-fluoro-2-(((2R,7aS)-2-fluorotetrahydro-1H-pyrrolizin-7a (5H)-yl) methoxy)pyrido[4,3-d]pyrimidine (400 mg, 890 μmol), 6-fluoro-4-(4,4,5,5-tetramethyl-1,3,2-dioxaborolan-2-yl)-5-((triisopropylsilyl) ethynyl) naphthalen-2-ol (500 mg, 1.07 mmol), AdanBuP-Pd-G3 (cataCXiumAPdG3) (65 mg, 89 μmol), $K_3PO_4$ (566 mg, 2.67 mmol) in $H_2O$ (1 mL) and 1,4-dioxane (5 mL) was degassed, purged with $N_2$ three times, and stirred at 100° C. for 2 h under $N_2$ atmosphere. The reaction mixture was concentrated under reduced pressure. The residue was purified by silica gel flash chromatography (eluent: 0~10% MeOH in $CH_2Cl_2$) to give the title compound (450 mg, 63% yield) as a yellow solid. MS: m/z=756.4 $[M+H]^+$. $^1H$ NMR (400 MHz, Dimethylsulfoxide-$d_6$) δ 10.10 (s, 1H), 9.51 (d, J=1.6 Hz, 1H), 7.96 (dd, J=6.0, 9.2 Hz, 1H), 7.46 (t, J=8.8 Hz, 1H), 7.38 (d, J=2.4 Hz, 1H), 7.16 (d, J=2.4 Hz, 1H), 5.42-5.15 (m, 1H), 4.36 (d, J=13.2 Hz, 1H), 4.14-4.05 (m, 1H), 3.97 (t, J=10.0 Hz, 1H), 3.47-3.35 (m, 2H), 3.13-3.00 (m, 3H), 2.88-2.79 (m, 1H), 2.37-2.17 (m, 2H), 2.14-2.00 (m, 3H), 1.95-1.65 (m, 7H), 1.56-1.40 (m, 2H), 0.83 (dd, J=7.6, 9.6 Hz, 18H), 0.73-0.62 (m, 1H), 0.49-0.43 (m, 3H), $^{19}F$ NMR. (376 MHz, Dimethylsulfoxide-$d_6$) δ −108.89, −141.33, −172.33.

Step 3: 4-(4-((1S,7R)-2-Azabicyclo[5.1.0]octan-2-yl)-8-fluoro-2-(((2R,7aS)-2-fluorotetrahydro-1/-pyrrolizin-7a (5/)-yl) methoxy)pyrido[4,3-d]pyrimidin-7-yl)-5-ethynyl-6-fluoronaphthalen-2-ol & 4-(4-((1R,7S)-2-azabicyclo[5.1.0]octan-2-yl)-8-fluoro-2-(((2R,7aS)-2-fluorotetrahydro-1H-pyrrolizin-7a (5H)-yl) methoxy)pyrido[4,3-d]pyrimidin-7-yl)-5-ethynyl-6-fluoronaphthalen-2-ol To a solution of 4-(4-(2-azabicyclo[5.1.0]octan-2-yl)-8-fluoro-2-(((2R,7aS)-2-fluorotetrahydro-1H-pyrrolizin-7a (5/)-yl) methoxy)pyrido[4,3-d]pyrimidin-7-yl)-6-fluoro-5-((triisopropylsilyl) ethynyl) naphthalen-2-ol (450 mg, 595 μmol) in DMSO (4 mL) was added CsF (271 mg, 1.79 mmol). The mixture was stirred at 25° C. for 1 h. The reaction mixture was diluted with water (50 mL) and extracted with EtOAc (60 mL×2). The combined organic layers were washed with brine (30 mL), dried over anhydrous $Na_2SO_4$, filtered and concentrated under reduced pressure. The residue was purified by silica gel flash chromatography (eluent: 0~10% MeOH in $CH_2Cl_2$) to give 4-(4-(2-azabicyclo[5.1.0]octan-2-yl)-8-fluoro-2-(((2R,7aS)-2-fluorotetrahydro-1H-pyrrolizin-7a (5H)-yl) methoxy) pyrido[4,3-d]pyrimidin-7-yl)-5-ethynyl-6-fluoronaphthalen-2-ol (350 mg). The mixture was separated by SFC (column: DAICEL CHIRALCEL OJ (250 mm×30 mm, 10 μm); mobile phase: [$CO_2$-MeOH (0.1% $NH_3$ $H_2O$)]; B %: 40%, isocratic elution mode) to give the title compound (Example 1, 90 mg, 25% yield, SFC peak 1: 1.138 min) as a yellow solid. MS: m/z=600.3 $[M+H]^+$. $^1H$ NMR (400 MHZ, Dimethylsulfoxide-$d_6$) δ 10.18-10.04 (m, 1H), 9.56-9.39 (m, 1H), 7.97 (dd, J=6.0, 9.2 Hz, 1H), 7.50-7.42 (m, 1H), 7.38 (d, J=2.4 Hz, 1H), 7.20-7.14 (m, 1H), 5.38-5.17 (m, 1H), 4.44 (d, J=12.8 Hz, 1H), 4.15-3.86 (m, 3H), 3.52-3.36 (m, 2H), 3.13-2.99 (m, 3H), 2.87-2.77 (m, 1H), 2.30-2.18 (m, 1H), 2.13-2.03 (m, 2H), 1.93-1.66 (m, 6H), 1.56-1.42 (m, 2H), 1.21-0.94 (m, 3H), 0.63-0.40 (m, 1H). $^{19}$F NMR (376 MHZ, Dimethylsulfoxide-$d_6$) δ −110.76, −110.88, −140.73, −141.17, −172.07, −172.17. And the title compound (Example 2, 65 mg, 17% yield, SFC peak 2: 1.491 min) was obtained as a yellow solid. MS: m/z=600.3 $[M+H]^+$. 1H NMR (400 MHz, Dimethylsulfoxide-$d_6$) δ 10.19-10.01 (m, 1H), 9.57-9.37 (m, 1H), 7.97 (dd, J=6.0, 9.2 Hz, 1H), 7.46 (t, J=9.2 Hz, 1H), 7.38 (d, J=2.4 Hz, 1H), 7.20-7.14 (m, 1H), 5.40-5.15 (m, 1H), 4.43 (d, J=13.2 Hz, 1H), 4.14-3.86 (m, 3H), 3.53-3.36 (m, 2H), 3.13-2.98 (m, 3H), 2.88-2.78 (m, 1H), 2.29-2.18 (m, 1H), 2.16-2.03 (m, 2H), 1.98-1.73 (m, 6H), 1.55-1.39 (m, 2H), 1.30-0.83 (m, 3H), 0.64-0.40 (m, 1H). $^{19}$F NMR (376 MHz, Dimethylsulfoxide-$d_6$) δ −110.76, −110.86,~140.68, −141.17, −172.06, −172.16.

Example 3: 4-(4-(4-Azabicyclo[5.1.0]octan-4-yl)-8-fluoro-2-(((2R,7aS)-2-fluorotetrahydro-1/-pyrrolizin-7a (5H)-yl) methoxy)pyrido[4,3-d]pyrimidin-7-yl)-5-ethynyl-6-fluoronaphthalen-2-ol

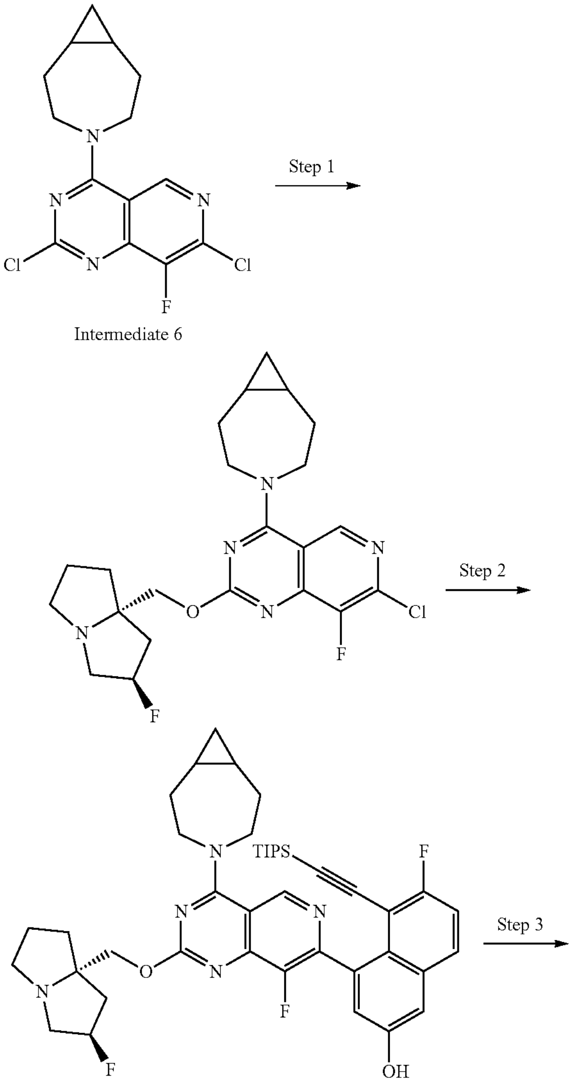

-continued

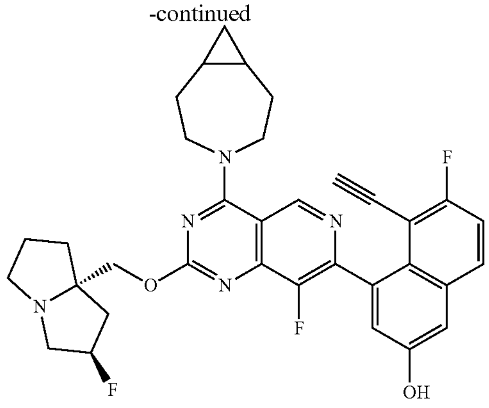

Example 3

Step 1: 4-(4-Azabicyclo[5.1.0]octan-4-yl)-7-chloro-8-fluoro-2-(((2R,7aS)-2-fluorotetrahydro-1H-pyrrolizin-7a (5H)-yl) methoxy)pyrido[4,3-d]pyrimidine To a solution of Intermediate 6 (100 mg, 306 μmol), DIPEA (160 μL, 917 μmol) and ((2R,7aS)-2-fluorotetrahydro-1H-pyrrolizin-7a (5H)-yl) methanol (97 mg, 611 μmol) in 1,4-dioxane (4 mL) was stirred at 110° C. under $N_2$ for 16 h. The reaction mixture was concentrated under reduced pressure. The residue was purified by silica gel flash chromatography (eluent: 0~5% of MeOH in $CH_2Cl_2$) to give the title compound (127 mg, 91% yield) as a yellow solid. MS: m/z=450.2 $[M+H]^+$. $^1$H NMR (400 MHZ, Dimethylsulfoxide-$d_6$) δ 8.77 (s, 1H), 5.35-5.19 (m, 1H), 4.13-4.01 (m, 4H), 3.85-3.79 (m, 2H), 3.11-3.00 (m, 3H), 2.86-2.78 (m, 1H), 2.18-1.54 (m, 10H), 1.03-0.97 (m, 2H), 0.72-0.65 (m, 1H), 0.37-0.31 (m, 1H). $^{19}$F NMR (376 MHZ, Dimethylsulfoxide-$d_6$) δ −136.89, −172.14.

Step 2: 4-(4-(4-Azabicyclo[5.1.0]octan-4-yl)-8-fluoro-2-(((2R,7aS)-2-fluorotetrahydro-1H-pyrrolizin-7a (5H)-yl) methoxy)pyrido[4,3-d]pyrimidin-7-yl)-6-fluoro-5-((triisopropylsilyl) ethynyl) naphthalen-2-ol A mixture of 4-(4-azabicyclo[5.1.0]octan-4-yl)-7-chloro-8-fluoro-2-(((2R,7aS)-2-fluorotetrahydro-1H-pyrrolizin-7a (5/)-yl) methoxy)pyrido[4,3-d]pyrimidine (127 mg, 282 μmol), 6-fluoro-4-(4,4,5,5-tetramethyl-1,3,2-dioxaborolan-2-yl)-5-((triisopropylsilyl) ethynyl) naphthalen-2-ol (132 mg, 282 μmol), $K_3PO_4$ (180 mg, 847 μmol) and AdanBuP-Pd-Gs (cataCXiumAPdGs) (21 mg, 28 μmol) in 1,4-dioxane (5 mL) and $H_2O$ (1 mL) was degassed and purged with $N_2$ three times, and stirred at 110° C. under $N_2$ for 2 h. The reaction mixture was concentrated under reduced pressure. The residue was purified by silica gel flash chromatography (eluent: 0~7% of MeOH in $CH_2Cl_2$) to give the title compound (86 mg, 40% yield) as a yellow solid. MS: m/z=756.4 $[M+H]^{+}$.

Step 3: 4-(4-(4-Azabicyclo[5.1.0]octan-4-yl)-8-fluoro-2-(((2R,7aS)-2-fluorotetrahydro-1H-pyrrolizin-7a (5H)-yl) methoxy)pyrido[4,3-d]pyrimidin-7-yl)-5-ethynyl-6-fluoronaphthalen-2-ol To a solution of 4-(4-(4-azabicyclo[5.1.0]octan-4-yl)-8-fluoro-2-(((2R,7aS)-2-fluorotetrahydro-1H-pyrrolizin-7a (5H)-yl) methoxy)pyrido[4,3-d]pyrimidin-7-yl)-6-fluoro-5-((triisopropylsilyl) ethynyl) naphthalen-2-ol (86 mg, 114 μmol) in DMSO (1 mL) was added CsF (52 mg, 341 μmol). The mixture was stirred at 20° C. for 0.5 h. The reaction mixture was diluted with water (10 mL) and extracted with EtOAc (20 mL×2). The combined organic layers were washed with brine (40 mL), dried over $Na_2SO_4$, filtered and concentrated under reduced pressure. The residue was purified by silica gel chromatography (eluent: 0~7% of MeOH in $CH_2Cl_2$) to give the title compound (Example 3, 44.9 mg, 65% yield) as a yellow solid. MS: m/z=600.3 $[M+H]^+$. $^1H$ NMR (400 MHZ, Dimethylsulfoxide-$d_6$) δ 10.15 (s, 1H), 8.93 (s, 1H), 8.02-7.91 (m, 1H), 7.50-7.42 (m, 1H), 7.41-7.36 (m, 1H), 7.20-7.15 (m, 1H), 5.40-5.15 (m, 1H), 4.32-4.21 (m, 1H), 4.16-4.00 (m, 3H), 3.99-3.96 (m, 1H), 3,95-3.86 (m, 1H), 3.80-3.68 (m, 1H), 3.10-3.01 (m, 3H), 2.86-2.79 (m, 1H), 2.18-1.58 (m, 10H), 1.11-1.01 (m, 2H), 0.76-0.67 (m, 1H), 0.44-0.35 (m, 1H). $^{19}F$ NMR (376 MHZ, Dimethylsulfoxide-$d_6$) δ −110.77, −140.04, −140.06, −172.07, −172.17.

Example 4 & 5: 4-(4-((15,7R)-2-azabicyclo[5.1.0]octan-2-yl)-8-fluoro-2-(((2R,7aS)-2-fluorotetrahydro-1/-pyrrolizin-7a (5H)-yl) methoxy)pyrido[4,3-d]pyrimidin-7-yl)-5-ethynyl-6-fluoronaphthalen-2-amine & 4-(4-((1R,7S)-2-azabicyclo[5.1.0]octan-2-yl)-8-fluoro-2-(((2R,7aS)-2-fluorotetrahydro-1H-pyrrolizin-7a (5H)-yl) methoxy)pyrido[4,3-d]pyrimidin-7-yl)-5-ethynyl-6-fluoronaphthalen-2-amine

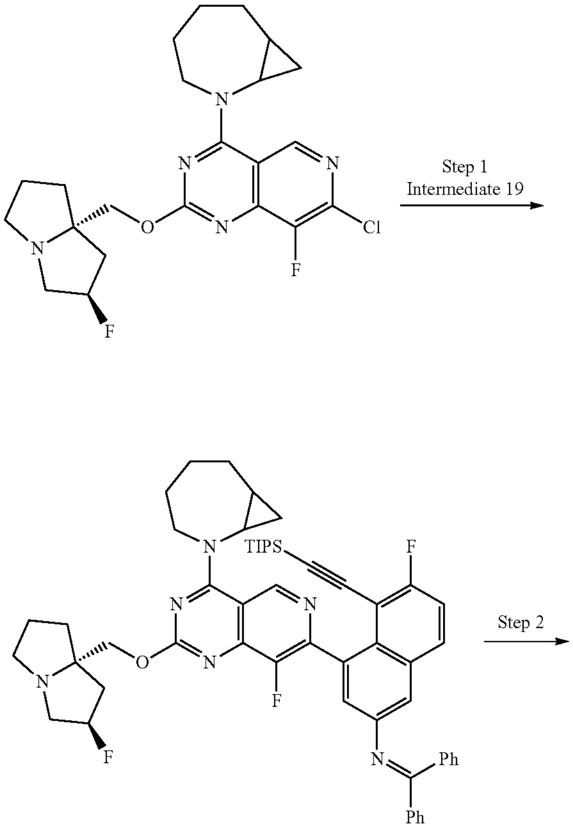

-continued

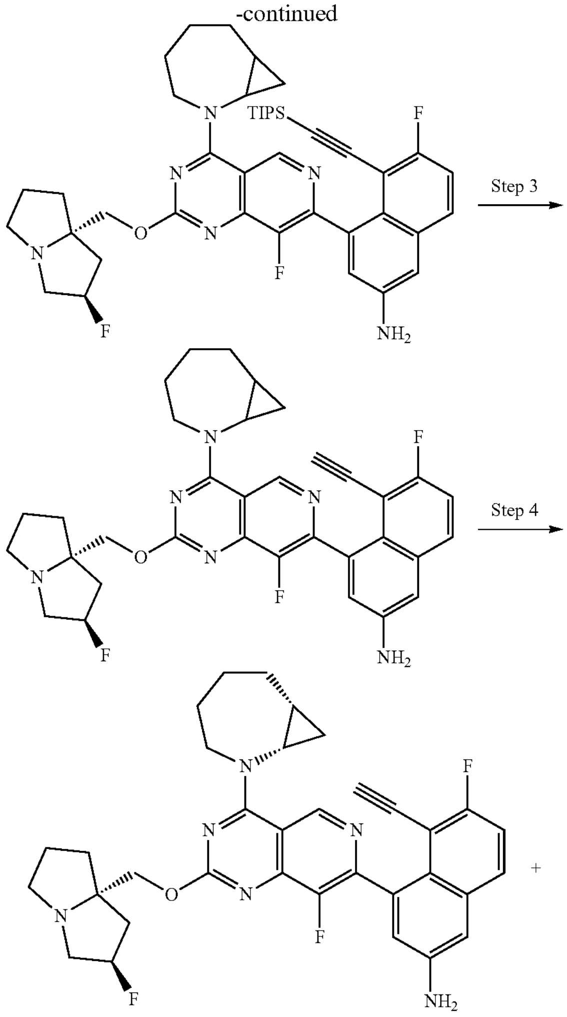

Example 4

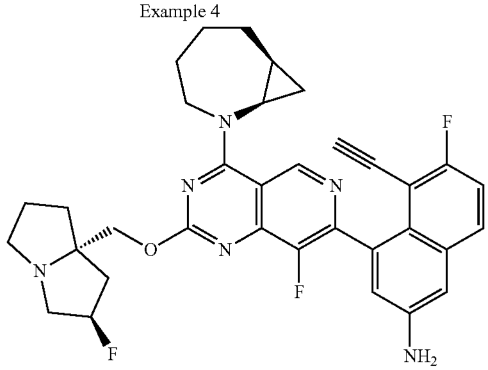

Example 5

Step 1: N-(4-(4-(2-azabicyclo[5.1.0]octan-2-yl)-8-fluoro-2-(((2R,7aS)-2-fluorotetrahydro-1H-pyrrolizin-7a (SH)-yl) methoxy)pyrido[4,3-d]pyrimidin-7-yl)-6-fluoro-5-((triisopropylsilyl) ethynyl) naphthalen-2-yl)-1,1-diphenylmethanimine A mixture of 4-(2-azabicyclo[5.1.0]octan-2-yl)-7-chloro-8-fluoro-2-(((2R,7aS)-2-fluorotetrahydro-1H-pyrrolizin-7a (5)-yl) methoxy)pyrido[4,3-d]pyrimidine (refer to Example 1 for detail procedures, 125 mg, 278 μmol), Intermediate 19 (211 mg, 333 μmol), AdanBuP-Pd-G3 (cataCXiumAPdG3)

(20 mg, 28 μmol), and KsPO4 (177 mg, 833 μmol) in $H_2O$ (0.5 mL) and 1,4-dioxane (2.5 mL) was degassed, purged with $N_2$ three times, and stirred at 100° C. for 2 h under $N_2$ atmosphere. The reaction mixture was concentrated under reduced pressure. The residue was purified by silica gel flash chromatography (eluent: 0~10% MeOH in $CH_2Cl_2$) to give the title compound (160 mg, 63% yield) as a yellow solid. MS: m/z=919.5 $[M+H]^+$. $^1H$ NMR (400 MHz, Dimethylsulfoxide-$d_6$) δ 9.62-9.40 (m, 1H), 7.96-1.92 (m, 1H), 7.73-7.69 (m, 2H), 7.57-7.53 (m, 1H), 7.49 (t, J=8.4 Hz, 3H), 7.43 (t, J=2.4 Hz, 1H), 7.35-7.31 (m, 3H), 7.25-7.21 (m, 2H), 7.08-7.03 (m, 1H), 5.39-5.20 (m, 1H), 4.38-4.32 (m, 1H), 4.15-4.06 (m, 1H), 4.00-3.93 (m, 1H), 3.45-3.34 (m, 2H), 3.14-3.02 (m, 3H), 2.88-2.80 (m, 1H), 2.28-2.11 (m, 3H), 2.09-2.00 (m, 2H), 1.92-1.88 (m, 3H), 1.82-1.71 (m, 3H), 1.60-1.42 (m, 3H), 0.84-0.79 (m, 18H), 0.48-0.39 (m, 4H). $^{19}F$ NMR (376 MHz, Dimethylsulfoxide-$d_6$) δ −106.14, −106.17, −141.32, −172.24, −172.36, −172.37.

Step 2: 4-(4-(2-Azabicyclo[5.1.0]octan-2-yl)-8-fluoro-2-(((2R,7aS)-2-fluorotetrahydro-1H-pyrrolizin-7a (5H)-yl) methoxy)pyrido[4,3-d]pyrimidin-7-yl)-6-fluoro-5-((triisopropylsilyl) ethynyl) naphthalen-2-amine To a solution of N-(4-(4-(2-azabicyclo[5.1.0]octan-2-yl)-8-fluoro-2-(((2R,7aS)-2-fluorotetrahydro-1H-pyrrolizin-7a (5H)-yl) methoxy)pyrido[4,3-d]pyrimidin-7-yl)-6-fluoro-5-((triisopropylsilyl) ethynyl) naphthalen-2-yl)-1,1-diphenylmethanimine (160 mg, 174 μmol) in EtOH (3 mL) were added NaOAc (29 mg, 348 μmol) and $NH_2OH$ HCl (24 mg, 348 μmol). The mixture was stirred at 25° C. for 1.5 h. The reaction mixture was concentrated under reduced pressure. The residue was purified by silica gel flash chromatography (eluent: 0~10% MeOH in $CH_2Cl_2$) to give the title compound (70 mg, 53% yield) as a yellow solid. MS: m/z=755.5 $[M+H]^+$. $^1H$ NMR (400 MHZ, Dimethylsulfoxide-$d_6$) δ 9.65-9.40 (m, 1H), 7.81-7.73 (m, 1H), 7.39-7.29 (m, 1H), 7.09-7.69 (m, 2H), 5.76-5.57 (m, 2H), 5.45-5.20 (m, 1H), 4.41-4.32 (m, 1H), 4.26-3.96 (m, 2H), 3.47-3.41 (m, 1H), 3.39-3.36 (m, 1H), 3.18-2.72 (m, 4H), 2.28-1.66 (m, 12H), 1.54-1.42 (m, 2H), 0.88-0.78 (m, 18H), 0.55-0.39 (m, 4H). $^{19}F$ NMR (376 MHz, Dimethylsulfoxide-$d_6$) δ −111.40, −141.17, −172.25, −172.35, −172.39.

Step 3: 4-(4-(2-Azabicyclo[5.1.0]octan-2-yl)-8-fluoro-2-(((2R,7aS)-2-fluorotetrahydro-1H-pyrrolizin-7a (5H)-yl) methoxy)pyrido[4,3-d]pyrimidin-7-yl)-5-ethynyl-6-fluoronaphthalen-2-amine To a solution of 4-(4-(2-azabicyclo[5.1.0]octan-2-yl)-8-fluoro-2-(((2R,7aS)-2-fluorotetrahydro-1H-pyrrolizin-7a (5/)-yl) methoxy)pyrido[4,3-d]pyrimidin-7-yl)-6-fluoro-5-((triisopropylsilyl) ethynyl) naphthalen-2-amine (70 mg, 93 μmol) in DMSO (2 mL) was added CsF (42 mg, 278 μmol). The mixture was stirred at 25° C. for 1 h. The reaction mixture was diluted with water (20 mL) and extracted with EtOAc (30 mL×2). The combined organic layers were washed with brine (20 mL), dried over anhydrous $Na_2SO_4$, filtered, and concentrated under reduced pressure. The residue was purified by silica gel flash chromatography (eluent: 0~10% MeOH in $CH_2Cl_2$) to give the title compound (31.2 mg, 51% yield) as a yellow solid.

Step 4: 4-(4-((1S,7R)-2-azabicyclo[5.1.0]octan-2-yl)-8-fluoro-2-(((2R,7aS)-2-fluorotetrahydro-1H-pyrrolizin-7a (5H)-yl) methoxy)pyrido[4,3-d]pyrimidin-7-yl)-5-ethynyl-6-fluoronaphthalen-2-amine & 4-(4-((1R,7S)-2-azabicyclo[5.1.0]octan-2-yl)-8-fluoro-2-(((2R,7aS)-2-fluorotetrahydro-1/-pyrrolizin-7a (5/)-yl) methoxy)pyrido[4,3-d]pyrimidin-7-yl)-5-ethynyl-6-fluoronaphthalen-2-amine 4-(4-(2-Azabicyclo[5.1.0]octan-2-yl)-8-fluoro-2-(((2R,7aS)-2-fluorotetrahydro-1/-pyrrolizin-7a (5H)-yl) methoxy) pyrido[4,3-d]pyrimidin-7-yl)-5-ethynyl-6-fluoronaphthalen-2-amine (350 mg) was purified by SFC(column: DAICEL CHIRALPAK IC(250 mm×30 mm, 10 μm); mobile phase: [Hexane-EtOH (0.1% IPAm)]; B %: 30%, isocratic elution mode) to give the title compound (Example 4, 120 mg, 32% yield, SFC peak 1: 1.824 min) as a yellow solid. MS: m/z=599.3 $[M+H]^+$. $^1H$ NMR (400 MHZ, Dimethylsulfoxide-$d_6$) δ 9.56-9.39 (m, 1H), 7.77 (dd, J=6.0, 9.2 Hz, 1H), 7.41-7.27 (m, 1H), 7.04 (s, 2H), 5.63 (s, 2H), 5.39-5.14 (m, 1H), 4.43 (d, J=13.2 Hz, 1H), 4.16-4.07 (m, 1H), 4.05-3.79 (m, 2H), 3.57-3.38 (m, 2H), 3.16-3.05 (m, 2H), 3.01 (s, 1H), 2.87-2.79 (m, 1H), 2.23 (dd, J=6.0, 13.6 Hz, 1H), 2.16-1.62 (m, 10H), 1.54-1.39 (m, 2H), 1.21-1.11 (m, 1H), 0.63-0.39 (m, 1H). $^{19}F$ NMR (376 MHZ, Dimethylsulfoxide-$d_6$) δ −113.39, −141.24, −172.18. And the title compound (Example 5, 110 mg, 30% yield, SFC peak 2: 5.426 min) was obtained as a yellow solid. MS: m/z=599.3 $[M+H]^+$. $^1H$ NMR (400 MHZ, Dimethylsulfoxide-$d_6$) δ 9.60-9.34 (m, 1H), 7.77 (dd, J=6.0, 9.2 Hz, 1H), 7.33 (t, J=9.2 Hz, 1H), 7.04 (s, 2H), 5.63 (s, 2H), 5.42-5.14 (m, 1H), 4.43 (d, J=13.2 Hz, 1H), 4.15-3.76 (m, 3H), 3.55-3.38 (m, 2H), 3.14-2.99 (m, 3H), 2.88-2.77 (m, 1H), 2.30-1.59 (m, 11H), 1.56-1.37 (m, 2H), 1.16 (d,)=7.2, 13.6 Hz, 1H), 0.59 (d, J=4.8 Hz, 1H). $^{19}F$ NMR (376 MHz, Dimethylsulfoxide-$d_6$) δ −113.40, −113.49, −141.25, −172.06, −172.16.

Example 6: 4-(4-(8,8-Difluoro-2-azabicyclo[5.1.0]octan-2-yl)-8-fluoro-2-(((2R,7aS)-2-fluorotetrahydro-1/-pyrrolizin-7a (5H)-yl) methoxy)pyrido[4,3-d]pyrimidin-7-yl)-5-ethynyl-6-fluoronaphthalen-2-ol

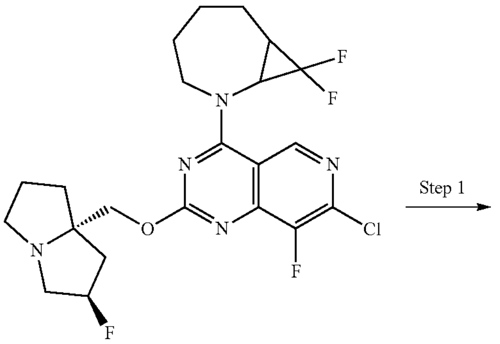

Intedrmediate 9

-continued

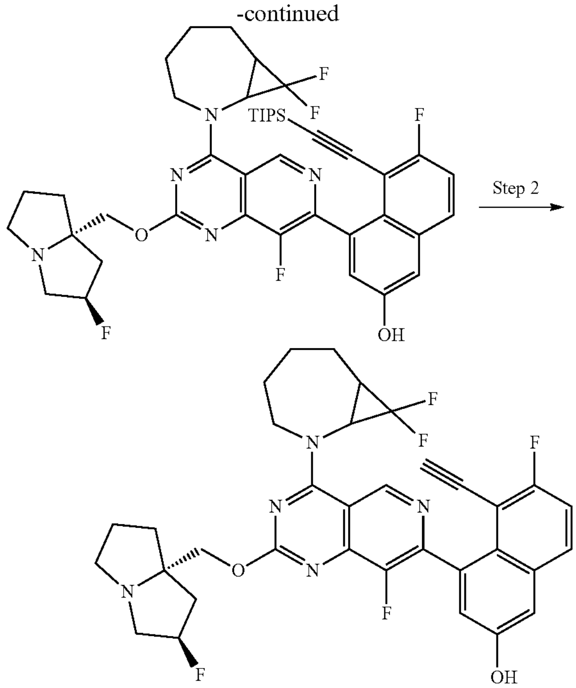

Example 6

Step 1: 4-(4-(8,8-Difluoro-2-azabicyclo[5.1.0]octan-2-yl)-8-fluoro-2-(((2R,7aS)-2-fluorotetrahydro-1/-pyrrolizin-7a (5H)-yl) methoxy)pyrido[4,3-d]pyrimidin-7-yl)-6-fluoro-5-((triisopropylsilyl) ethynyl) naphthalen-2-ol A mixture of Intermediate 9 (100 mg, 206 μmol), 6-fluoro-4-(4,4,5,5-tetramethyl-1,3,2-dioxaborolan-2-yl)-5-((triisopropylsilyl) ethynyl) naphthalen-2-ol (116 mg, 247 μmol), AdanBuP-Pd-G3 (cataCXiumAPdG3) (15 mg, 28 μmol), and $K_3PO_4$ (131 mg, 617 μmol) in $H_2O$ (0.5 mL) and 1,4-dioxane (2.5 mL) was degassed, purged with $N_2$ three times, and stirred at 100° C. for 2 h under $N_2$ atmosphere. The reaction mixture was concentrated under reduced pressure. The residue was purified by silica gel flash chromatography (eluent: 0~10% MeOH in $CH_2Cl_2$) to give the title compound (100 mg, yield: 60%) as a yellow solid. MS: m/z=792.4 $[M+H]^+$. $^1H$ NMR (400 MHZ, Dimethylsulfoxide-$d_6$) δ 10.12 (s, 1H), 9.23-9.06 (m, 1H), 7.98 (dd,)=6.0, 9.2 Hz, 1H), 7.48 (t, J=8.8 Hz, 1H), 7.39 (d, J=2.4 Hz, 1H), 7.13 (d, J=2.0 Hz, 1H), 5.41-5.20 (m, 1H), 4.42-4.29 (m, 2H), 4.21-4.06 (m, 2H), 3.52-3.42 (m, 2H), 3.17-3.02 (m, 3H), 2.92-2.79 (m, 1H), 2.26-1.81 (m, 12H), 0.81 (t, J=7.6 Hz, 18H), 0.46 (m, 3H). $^{19}F$. NMR (376 MHz, Dimethylsulfoxide-$d_6$)-110.64, −110.79, −125.53, −139.70, −148.43, −148.50, −172.10,-172.22.

Step 2: 4-(4-(8,8-Difluoro-2-azabicyclo[5.1.0]octan-2-yl)-8-fluoro-2-(((2R,7aS)-2-fluorotetrahydro-1/-pyrrolizin-7a (5H)-yl) methoxy)pyrido[4,3-d]pyrimidin-7-yl)-5-ethynyl-6-fluoronaphthalen-2-ol To a solution of 4-(4-(8,8-difluoro-2-azabicyclo[5.1.0]octan-2-yl)-8-fluoro-2-(((2R,7aS)-2-fluorotetrahydro-1/-pyrrolizin-7a (5H)-yl) methoxy)pyrido[4,3-d]pyrimidin-7-yl)-6-fluoro-5-((triisopropylsilyl) ethynyl) naphthalen-2-ol (100 mg, 126 μmol) in DMSO (2 mL) was added CsF (58 mg, 379 μmol). The mixture was stirred at 25° C. for 1 h. The reaction mixture was diluted with water (20 mL) and extracted with EtOAc (30 mL×2). The combined organic layers were washed with brine (20 mL), dried over anhydrous $Na_2SO_4$, filtered, and concentrated under reduced pressure. The residue was purified by silica gel flash chromatography (eluent: 0~10% MeOH in $CH_2Cl_2$) to give the title compound (Example 6, 39.9 mg, yield: 49%) was obtained as a yellow solid. MS: m/z=636.2 $[M+H]^+$. 3H NMR (400 MHZ, Dimethylsulfoxide-$d_6$) δ 10.23-10.05 (m, 1H), 9.39-9.11 (m, 1H), 7.99 (dd, J=6.0, 8.8 Hz, 1H), 7.53-7.37 (m, 2H), 7.23-7.13 (m, 1H), 5.38-5.17 (m, 1H), 4.43-4.32 (m, 1H), 4.17-4.06 (m, 2H), 3.95-3.67 (m, 1H), 3.53-3.34 (m, 2H), 3.12-2.99 (m, 3H), 2.88-2.77 (m, 1H), 2.33-2.25 (m, 1H), 2.23-2.11 (m, 2H), 2.06-1.76 (m, 8H), 1.68-1.56 (m, 1H), 1.50-1.36 (m, 1H). $^{19}F$ NMR (376 MHz, Dimethylsulfoxide-$d_6$) δ −110.60, −110.75, −125.15, 125.27, −139.40, −139.60, −148.20, −171.98, −172.08, −172.10.

Example 7 & 8: 4-(4-((1S,7R)-2-Azabicyclo[5.1.0]octan-2-yl)-8-fluoro-2-(((2R,7aS)-2-fluorotetrahydro-1H-pyrrolizin-7a (5/)-yl) methoxy-$d_2$)pyrido[4,3-d]pyrimidin-7-yl)-5-ethynyl-6,7-difluoronaphthalen-2-amine & 4-(4-((1R,7S)-2-azabicyclo[5.1.0]octan-2-yl)-8-fluoro-2-(((2R,7aS)-2-fluorotetrahydro-1/-pyrrolizin-7a (5H)-yl) methoxy-$d_2$)pyrido[4,3-d]pyrimidin-7-y1)-5-ethynyl-6,7-difluoronaphthalen-2-amine

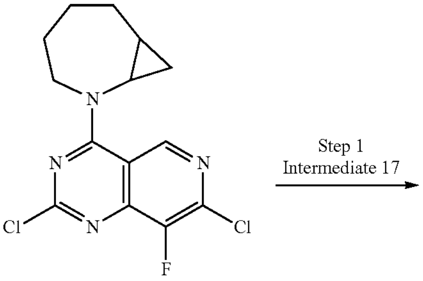

Intermediate 8

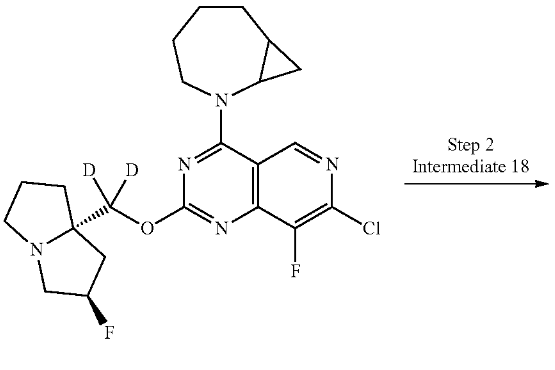

-continued

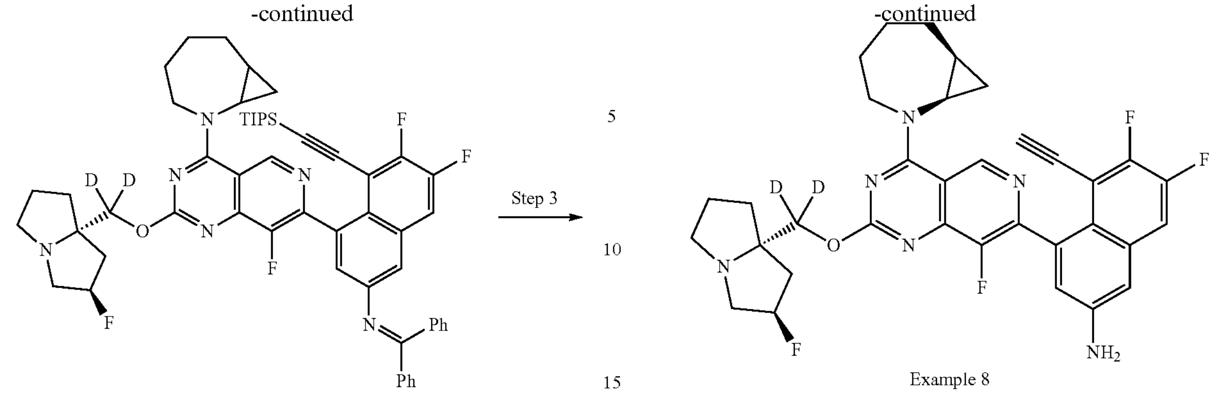

Example 8

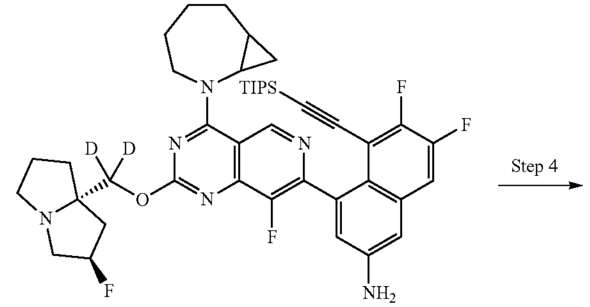

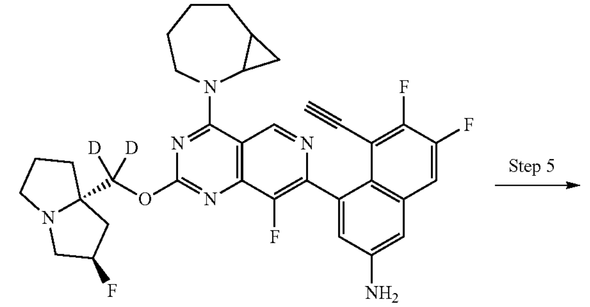

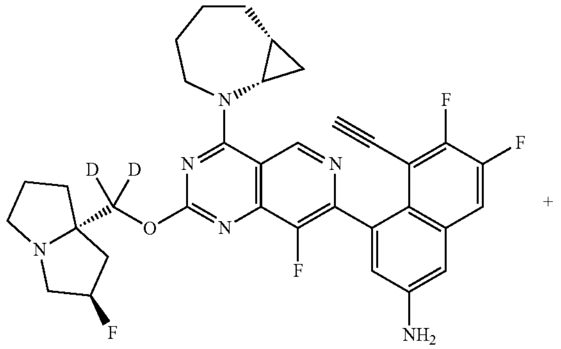

Example 7

Step 1: 4-(2-Azabicyclo[5.1.0]octan-2-yl)-7-chloro-8-fluoro-2-(((2R,7aS)-2-fluorotetrahydro-1//-pyrrolizin-7a (5H)-yl) methoxy-$d_2$)pyrido[4,3-d]pyrimidine A mixture of Intermediate 8 (700 mg, 2.14 mmol), Intermediate 17 (621 mg, 3.85 mmol), DIPEA (1.12 mL, 6.42 mmol) and CsF (975 mg, 6.42 mmol) in 1,4-dioxane (8 mL) was degassed, purged with $N_2$ three times, and stirred at 100° C. for 12 h under $N_2$ atmosphere. The reaction mixture was filtered and concentrated under reduced pressure. The residue was purified by silica gel flash chromatography (cluent: 0~4% of MeOH in $CH_2Cl_2$) to give the title compound (680 mg, 69% yield) as a yellow oil. MS: m/z=452.2 $[M+H]^+$. $^1H$ NMR (400 MHz, Dimethylsulfoxide-$d_6$) δ 9.22 (s, 1H), 5.35-5.16 (m, 1H), 4.57-4.47 (m, 1H), 3.41-3.33 (m, 1H), 3.27-3.12 (m, 4H), 2.98-2.93 (m, 1H), 2.37-2.24 (m, 2H), 2.21-2.09 (m, 2H), 1.97-1.89 (m, 3H), 1.78-1.68 (m, 1H), 1.64-1.56 (m, 1H), 1.55-1.44 (m, 2H), 1.31-1.22 (m, 2H), 0.97-0.84 (m, 1H), 0.36-0.29 (m, 1H), $^{19}F$ NMR (376 MHz, Dimethylsulfoxide-$d_6$) δ −135.53, −173.17.

Step 2: N-(4-(4-(2-Azabicyclo[5.1.0]octan-2-yl)-8-fluoro-2-(((2R,7aS)-2-fluorotetrahydro-1H-pyrrolizin-7a (SH)-yl) methoxy-$d_2$)pyrido[4,3-d]pyrimidin-7-yl)-6,7-difluoro-5-((triisopropylsilyl) ethynyl) naphthalen-2-yl)-1,1-diphenylmethanimine A mixture of 4-(2-azabicyclo[5.1.0]octan-2-yl)-7-chloro-8-fluoro-2-(((2R,7aS)-2-fluorotetrahydro-1H-pyrrolizin-7a (5H)-yl) methoxy-$d_2$)pyrido[4,3-d]pyrimidine (250 mg, 553 μmol), Intermediate 18 (647 mg, 996 μmol), $K_3PO_4$ (704 mg, 3.32 mmol) and AdanBuP-Pd-G3 (cataCXiumAPdGs) (81 mg, 111 μmol) in THF (5 mL) and $H_2O$ (1 mL) was degassed, purged with $N_2$ three times, and stirred at 80° C. for 2 h under $N_2$ atmosphere. The reaction mixture was concentrated under reduced pressure. The residue was purified by silica gel flash chromatography (eluent: 0~4% of MeOH in $CH_2Cl_2$) to give the title compound (500 mg, 84% yield) as a yellow solid. MS: m/z=939.6 [M+H].

Step 3: 4-(4-(2-Azabicyclo[5.1.0]octan-2-yl)-8-fluoro-2-(((2R,7aS)-2-fluorotetrahydro-1H-pyrrolizin-7a (5H)-yl) methoxy-$d_2$)pyrido[4,3-d]pyrimidin-7-yl)-6,7-difluoro-S-((triisopropylsilyl) ethynyl) naphthalen-2-amine To a solution of N-(4-(4-(2-azabicyclo[5.1.0]octan-2-yl)-8-fluoro-2-(((2R,7aS)-2-fluorotetrahydro-1/-pyrrolizin-7a (5H)-yl) methoxy-$d_2$)pyrido[4,3-d]pyrimidin-7-yl)-6,7-difluoro-5-((triisopropylsilyl) ethynyl) naphthalen-2-yl)-1,1-diphenylmethanimine (500 mg, S32 µmol) in Ethanol (10 mL) were added NaOAc (87 mg, 1.06 mmol) and hydroxylamine hydrochloride (74 mg, 1.06 mmol). The mixture was stirred at 25° C. for 2 h. The reaction mixture was concentrated under reduced pressure. The residue was purified by silica gel flash chromatography (eluent: 0~7% of MeOH in $CH_2Cl_2$) to give the title compound (359 mg, 87% yield) as a yellow solid. MS: m/z=775.5 $[M+H]^+$. $^1$H NMR (400 MHZ, Dimethylsulfoxide-$d_6$) 6 9.67-9.50 (m, 1H), 7.78 (dd, J=8.4, 11.6 Hz, 1H), 7.09-6.88 (m, 2H) 5.88-5.66 (m, 2H), 5.53-5.31 (m, 1H), 4.39-4.34 (m, 1H), 3.48-3.36 (m, SH), 3.12-2.99 (m, 1H), 2.36-2.22 (m, 3H), 2.18-2.10 (m, 1H), 2.00-1.92 (m, 3H), 1.88-1.80 (m, 1H), 1.73-1.42 (m, 4H), 1.28-1.20 (m, 2H), 0.86-0.79 (m, 18H), 0.54-0.40 (m, 4H). $^{19}$F NMR (376 MHZ, Dimethylsulfoxide-$d_6$) δ −135.99, −136.06, −138.56, −138.59, −141.05, −172.57, −172.68.

Step 4: 4-(4-(2-Azabicyclo[5.1.0]octan-2-yl)-8-fluoro-2-(((2R,7aS)-2-fluorotetrahydro-1H-pyrrolizin-7a (SH)-yl) methoxy-$d_2$)pyrido[4,3-d]pyrimidin-7-yl)-5-ethynyl-6,7-difluoronaphthalen-2-amine To a solution of 4-(4-(2-azabicyclo[5.1.0]octan-2-yl)-8-fluoro-2-(((2R,7aS)-2-fluorotetrahydro-1/-pyrrolizin-7a (5H)-yl) methoxy-$d_2$)pyrido[4,3-d]pyrimidin-7-yl)-6,7-difluoro-5-((triisopropylsilyl) ethynyl) naphthalen-2-amine (346 mg, 446 µmol) in DMSO (2 mL) was added CsF (203 mg, 1.34 mmol). The mixture was stirred at 25° C. for 1 h. The reaction mixture was diluted with water (100 mL) and extracted with EtOAc (100 mL×2). The combined organic layers were washed with brine (100 mL×2), dried over anhydrous $Na_2SO_4$, filtered and concentrated under reduced pressure to give the title compound (256 mg, crude) as a brown solid. MS: m/z=619.3 $[M+H]^+$.

Step 5: 4-(4-((1S,7R)-2-Azabicyclo[5.1.0]octan-2-yl)-8-fluoro-2-(((2R,7aS)-2-fluorotetrahydro-1/4-pyrrolizin-7a (5H)-yl) methoxy-$d_2$)pyrido[4,3-d] pyrimidin-7-yl)-5-ethynyl-6,7-difluoronaphthalen-2-amine & 4-(4-((1R,7S)-2-azabicyclo[5.1.0]octan-2-yl)-8-fluoro-2-(((2R,7aS)-2-fluorotetrahydro-1/-pyrrolizin-7a (5H)-yl) methoxy-$d_2$)pyrido[4,3-d] pyrimidin-7-yl)-5-ethynyl-6,7-difluoronaphthalen-2-amine 4-(4-(2-Azabicyclo[5.1.0]octan-2-yl)-8-fluoro-2-(((2R,7aS)-2-fluorotetrahydro-1/-pyrrolizin-7a (5H)-yl) methoxy-$d_2$)pyrido[4,3-d]pyrimidin-7-yl)-5-ethynyl-6,7-difluoronaphthalen-2-amine (256 mg) was purified by SFC (column: (s,s) WHELK-01 (250 mm×30 mm, 10 µm); mobile phase: [$CO_2$-EtOH (0.1% $NH_3H_2O$)]; B %: 40%, isocratic elution mode) to give the title compound (Example 7, 84 mg, 32% yield over 2 steps, SFC Peak 1: 0.371 min) as a brown solid. MS: m/z=619.3 $[M+H]^+$. $^1$H NMR (400 MHz, Dimethylsulfoxide-$d_6$) δ 9.51-9.42 (m, 1H), 7.78 (dd, J=8.4, 11.6 Hz, 1H), 7.03-6.96 (m, 2H) 5.78 (s, 2H), 5.35-5.19 (m, 1H), 4.48-4.37 (m, 1H), 4.23-3.97 (m, 1H), 3.53-3.41 (m, 2H), 3.12-3.05 (m, 2H), 3.03-2.99 (m, 1H), 2.86-2.78 (m, 1H), 2.28-2.19 (m, 1H), 2.14-1.95 (m, 4H), 1.92-1.75 (m, 5H), 1.53-1.40 (m, 2H), 1.19-1.05 (m, 2H), 0.60-0.41 (m, 1H). $^{19}$F NMR (376 MHz, Dimethylsulfoxide-$d_6$)$_8$-137.78, −138.67, −138.73, −140.79, −172.07, −172.17. And the title compound (Example 8, 53 mg, 20% yield over 2 steps, SFC Peak 2: 0.966 min) was obtained as a brown solid. MS: m/z=619.3 $[M+H]^+$. $^1$H NMR (400 MHz, Dimethylsulfoxide-$d_6$) δ 9.53-9.41 (m, 1H), 7.78 (dd, J=8.4, 11.6 Hz, 1H), 7.03-6.96 (m, 2H) 5.77 (s, 2H), 5.36-5.19 (m, 1H), 4.47-4.40 (m, 1H), 4.23-3,98 (m, 1H), 3.52-3.38 (m, 2H), 3.12-3.05 (m, 2H), 3.02-2.99 (m, 1H), 2.87-2.79 (m, 1H), 2.28-2.19 (m, 1H), 2.14-1.89 (m, 5H), 1.87-1.69 (m, 4H), 1.54-1.39 (m, 2H), 1.22-1.03 (m, 2H), 0.61-0.41 (m, 1H). $^{19}$F NMR (376 MHz, Dimethylsulfoxide-$d_6$) δ −137.79, −138.69, −140.73, −141.30, −172.06, −172.16.

Example 9: 4-(4-(4-Azabicyclo[5.1.0]octan-4-yl)-8-fluoro-2-(((2R,7aS)-2-fluorotetrahydro-1/-pyrrolizin-7a (5H)-yl) methoxy-$d_2$)pyrido[4,3-d]pyrimidin-7-yl)-5-ethynyl-6,7-difluoronaphthalen-2-amine

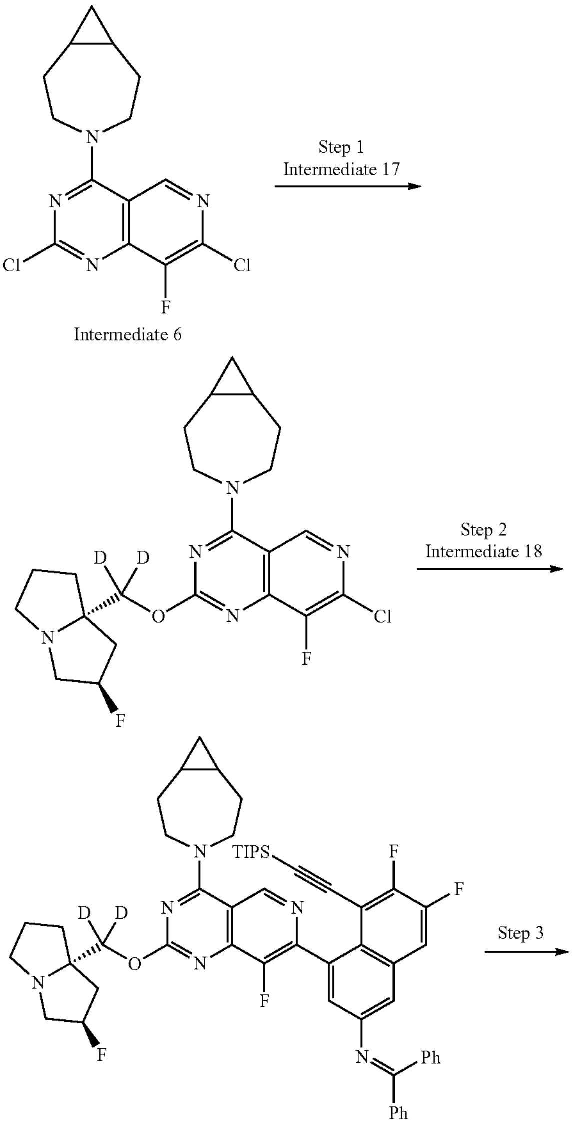

-continued

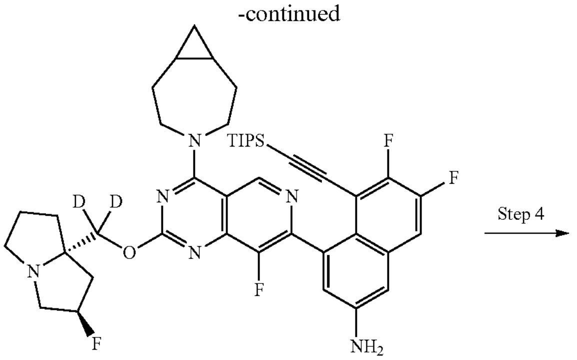

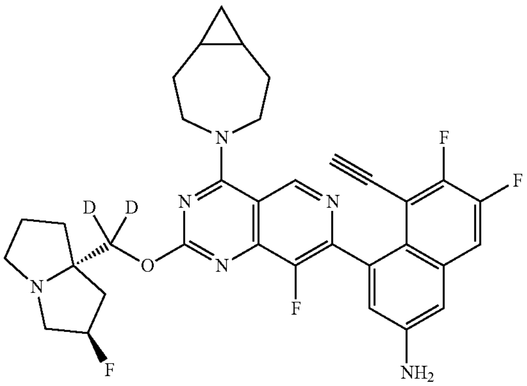

Example 9

Step 1: 4-(4-Azabicyclo[5.1.0]octan-4-yl)-7-chloro-8-fluoro-2-(((2R,7aS)-2-fluorotetrahydro-1H-pyrrolizin-7a (5H)-yl) methoxy-$d_2$)pyrido[4,3-d]pyrimidine A mixture of Intermediate 6 (200 mg, 611 μmol), Intermediate 17 (177 mg, 1.1 mmol), DIPEA (319 AL, 1.83 mmol) and CsF (279 mg, 1.83 mmol) in 1,4-dioxane (8 mL) was degassed and purged with $N_2$ three times, and then the mixture was stirred at 100° C. for 16 h under $N_2$ atmosphere. The reaction mixture was filtered and concentrated under reduced pressure. The residue was purified by silica gel flash chromatography (eluent: 0~6% of MeOH in $CH_2Cl_2$) to give 4-(4-azabicyclo[5.1.0]octan-4-yl)-7-chloro-8-fluoro-2-(((2R,7aS)-2-fluorotetrahydro-1H-pyrrolizin-7a (5H)-yl) methoxy-$d_2$)pyrido[4,3-d]pyrimidine (280 mg, 73% yield) as a yellow solid. MS: m/z=452.2 $[M+H]^{+\cdot}$ Step 2: N-(4-(4-(4-Azabicyclo[5.1.0]octan-4-yl)-8-fluoro-2-(((2R,7aS)-2-fluorotetrahydro-1/-pyrrolizin-7a (5H)-yl) methoxy-$d_2$)pyrido[4,3-d]pyrimidin-7-yl)-6,7-difluoro-5-((triisopropylsilyl) ethynyl) naphthalen-2-yl)-1,1-diphenylmethanimine A mixture of 4-(4-azabicyclo[5.1.0]octan-4-yl)-7-chloro-8-fluoro-2-(((2R,7aS)-2-fluorotetrahydro-1H-pyrrolizin-7a (5/)-yl) methoxy-$d_2$)pyrido[4,3-d]pyrimidine (230 mg, 509 μmol), Intermediate 18 (595 mg, 916 μmol), KsPO4 (324 mg, 1.53 mmol) and AdanBuP-Pd-G3 (cataCXiumAPdG3) (37 mg, 51 μmol) in 1,4-dioxane (5 mL) and $H_2O$ (1 mL) was degassed, purged with $N_2$ three times, and stirred at 110° C. for 2 h under $N_2$ atmosphere. The reaction mixture was concentrated under reduced pressure. The residue was purified by silica gel flash chromatography (eluent: 0~5% of MeOH in $CH_2Cl_2$) to give the title compound (600 mg, 85% yield) as a yellow solid. MS: m/z=939.5 $[M+H]^{+\cdot}$ Step 3: 4-(4-(4-Azabicyclo[5.1.0]octan-4-yl)-8-fluoro-2-(((2R,7aS)-2-fluorotetrahydro-1H-pyrrolizin-7a (5H)-yl) methoxy-$d_2$)pyrido[4,3-d]pyrimidin-7-yl)-6,7-difluoro-5-((triisopropylsilyl) ethynyl) naphthalen-2-amine To a solution of N-(4-(4-(4-azabicyclo[5.1.0]octan-4-yl)-8-fluoro-2-(((2R,7aS)-2-fluorotetrahydro-1/-pyrrolizin-7a (5H)-yl) methoxy-$d_2$)pyrido[4,3-d]pyrimidin-7-yl)-6,7-difluoro-5-((triisopropylsilyl) ethynyl) naphthalen-2-yl)-1,1-diphenylmethanimine (600 mg, 434 μmol) in Ethanol (6 mL) were added NaOAc (71 mg, 869 μmol) and hydroxylamine hydrochloride (60 mg. 869 μmol). The mixture was stirred at 25° C. for 1 h. The reaction mixture was concentrated under reduced pressure. The residue was purified by silica gel flash chromatography (eluent: 0~7% of MeOH in $CH_2Cl_2$) to give the title compound (214 mg, 62% yield) as a yellow solid. MS: m/z=775.3 $[M+H]^{+\cdot}$ Step 4: 4-(4-(4-Azabicyclo[5.1.0]octan-4-yl)-8-fluoro-2-(((2R,7aS)-2-fluorotetrahydro-1H-pyrrolizin-7a (5H)-yl) methoxy-$d_2$)pyrido[4,3-d]pyrimidin-7-yl)-5-ethynyl-6,7-difluoronaphthalen-2-amine To a solution of 4-(4-(4-azabicyclo[5.1.0]octan-4-yl)-8-fluoro-2-(((2R,7aS)-2-fluorotetrahydro-1H-pyrrolizin-7a (5H)-yl) methoxy-$d_2$)pyrido[4,3-d]pyrimidin-7-yl)-6,7-difluoro-5-((triisopropylsilyl) ethynyl) naphthalen-2-amine (214 mg, 276 μmol) in DMSO (1 mL) was added CsF (126 mg, 828 μmol). The mixture was stirred at 25° C. for 1 h. The reaction mixture was diluted with water (10 mL) and extracted with EtOAc (10 mL×2). The combined organic layers were washed with brine (10 mL×2), dried over anhydrous $Na_2SO_4$, filtered and concentrated under reduced pressure. The residue was purified by silica gel flash chromatography (cluent: 0~8% of MeOH in $CH_2Cl_2$) to give the title compound (Example 9, 50.8 mg, 28% yield) as a yellow solid. MS: m/z=619.1 $[M+H]^+$. $^1H$ NMR (400 MHZ, Dimethylsulfoxide-$d_6$) δ 8.92 (s, 1H), 7.78 (dd, J=8.4, 11.6 Hz, 1H) 7.20-6.96 (m, 2H), 5.78 (s, 2H), 5.37-5.19 (m, 1H), 4.30-4.20 (m, 1H), 4.12-4.00 (m, 2H), 3.94-3.71 (m, 2H), 3.16-3.02 (m, 3H), 2.86-2.79 (m, 1H), 2.17-1.62 (m, 10H), 1.11-1.02 (m, 2H), 0.76-0.68 (m, 1H), 0.43-0.35 (m, 1H), $^{19}F$. NMR (376 MHz, Dimethylsulfoxide-$d_6$) δ −137.75, −137.81, −138.62, −138.68, −140.13, −140.16, −172.07, −172.17.

Example 10: 4-(4-((1S,7R)-2-Oxa-6-azabicyclo[5.1.0]octan-6-yl)-8-fluoro-2-(((2R,7aS)-2-fluorotetrahydro-1H-pyrrolizin-7a (5H)-yl) methoxy-$d_2$) pyrido[4,3-d]pyrimidin-7-yl)-5-ethynyl-6-fluoronaphthalen-2-ol

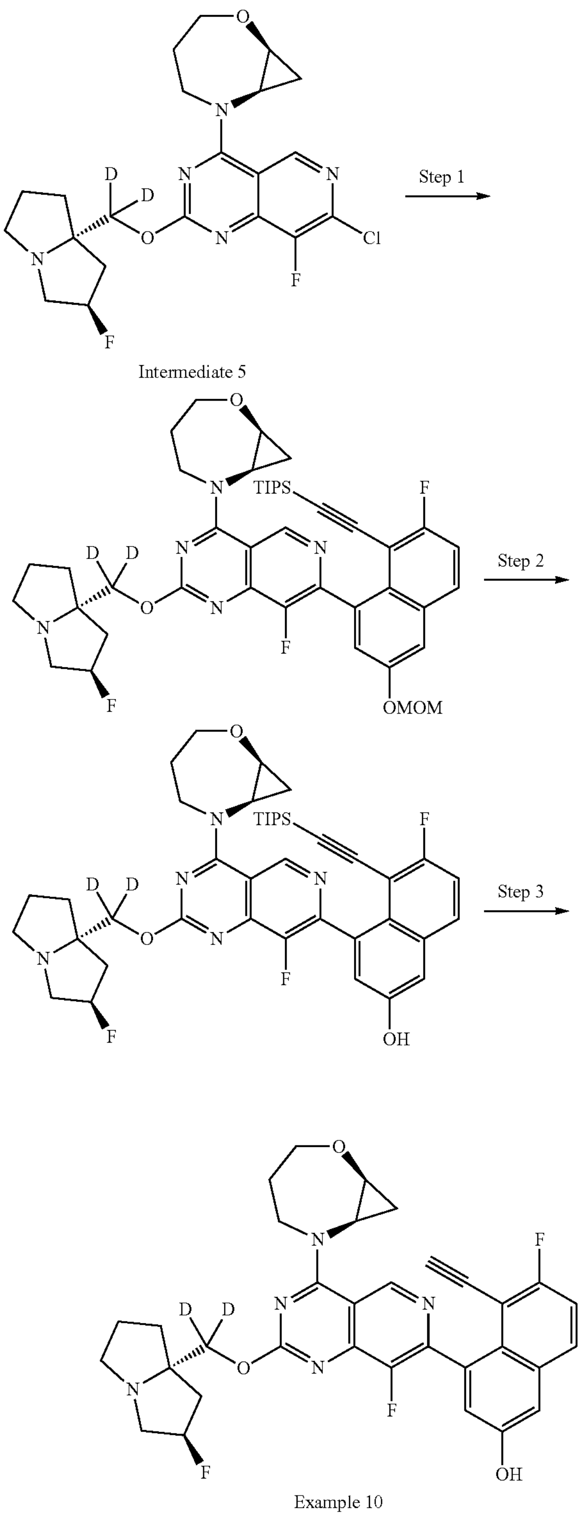

Intermediate 5

Example 10

Step 1: (1S,7R)-6-(8-Fluoro-7-(7-fluoro-3-(methoxymethoxy)-8-((triisopropylsilyl) ethynyl) naphthalen-1-yl)-2-(((2R,7aS)-2-fluorotetrahydro-1/-pyrrolizin-7a (5/1)-yl) methoxy-$d_2$)pyrido[4,3-d] pyrimidin-4-yl)-2-oxa-6-azabicyclo[5.1.0]octane To a stirred mixture of Intermediate 5 (200 mg, 0.44 mmol) and ((2-fluoro-6-(methoxymethoxy)-8-(4,4,5,5-tetramethyl-1,3,2-dioxaborolan-2-yl) naphthalen-1-yl) ethynyl)triisopropylsilane (338.74 mg, 0.66 mmol) in toluene (10 mL) and $H_2O$ (2 mL) under nitrogen atmosphere were added CataCXium A Pd G3 (38.51 mg, 0.05 mmol) and Cs2$CO_3$ (473.74 mg, 1.45 mmol) at room temperature. The reaction mixture was heated at 100° C. for 16 hours. The resulting mixture was cooled to room temperature, filtered and concentrated under reduced pressure. The residue was purified by Prep-TLC($CH_2Cl_2$/McOH 10: 1) to afford the title compound (295 mg, 83% yield) as a light yellow solid. MS: m/z=804.35 $[M+H]^{+\cdot}$ Step 2: 4-(4-((1S,7R)-2-Oxa-6-azabicyclo[5.1.0]octan-6-yl)-8-fluoro-2-(((2R,7aS)-2-fluorotetrahydro-1/-pyrrolizin-7a (5H)-yl) methoxy-$d_2$)pyrido[4,3-d]pyrimidin-7-yl)-6-fluoro-5-((triisopropylsilyl) ethynyl) naphthalen-2-ol To an ice-cooled stirred solution of (1S,7R)-6-(8-fluoro-7-(7-fluoro-3-(methoxymethoxy)-8-((triisopropylsilyl) ethynyl) naphthalen-1-yl)-2-(((2R,7aS)-2-fluorotetrahydro-1H-pyrrolizin-7a (5H)-yl) methoxy-$d_2$)pyrido[4,3-d]pyrimidin-4-yl)-2-oxa-6-azabicyclo[5.1.0]octane (265 mg, 0.33 mmol) in MeCN (15 mL) was added HCl (4 M in 1,4-dioxane, 2.88 mL, 11.55 mmol) dropwise. The resulting mixture was stirred in an ice bath for 1 hour. The resulting mixture was quenched with sat. aq. NaHICO3 (30 mL) in an ice bath and extracted with DCM (3×50 mL). The combined organic layers were washed with brine (50 mL), dried over anhydrous $Na_2SO_4$, filtered and concentrated under reduced pressure to afford the title compound (250 mg, crude used through) as a light yellow solid. MS: m/z=760.50 $[M+H]^{+\cdot}$ Step 3: 4-(4-((1S,7R)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6-fluoronaphthalen-2-ol To a stirred solution of 4-(4-((15,7R)-2-oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-6-fluoro-5-((triisopropylsilyl) ethynyl) naphthalen-2-ol (250 mg, crude) in DMF (3 mL) was added CsF (935.43 mg, 6.16 mmol) at room temperature. The reaction mixture was stirred at room temperature for 3 hours. The resulting mixture was filtered and purified by RP-Flash directly with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 2% B to 2% B in 3 min, 2% B to 55% B in 15 min, 55% B to 55% B in 5 min, 55% B to 95% B in 4 min; Detector: UV 254 & 210 nm. The collected fractions were combined, concentrated and then lyophilized overnight to give the title compound (Example 10, 101.9 mg, 51% yield for two steps) as a yellow lyophilized powder. MS: m/z=604.20 $[M+H]^+$. $^1H$ NMR (400 MHZ, DMSO-$d_6$) δ 10.13-10.11 (m, 1H), 9.41-9.37 (m, 1H), 7.99-7.96 (m, 1H), 7.49-7.45 (m, 1H), 7.39-7.38 (m, 1H), 7.19-7.17 (m, 1H), 5.35-5.22 (m, 1H), 4.55-4.41 (m, 1H), 4.18--3.89 (m, 2H), 3.78-3.72 (m, 2H), 3.65-3.55 (m, 1H), 3.50-3.40 (m, 1H), 3.19-3.01 (m, 3H), 2.90-2.81 (m, 1H), 2.20-1.70 (m, 8H), 1.32-1.23 (m, 1H), 0.96-0.65 (m, 1H). $^{19}$F NMR (376 MHz, DMSO-$d_6$) δ −110.83--110.84 (d, 1F), −140.40--140.75 (d, 1F), −172.03--172.15 (d, 1F).

Example 11: 4-(4-((1R,7S)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6-fluoronaphthalen-2-ol

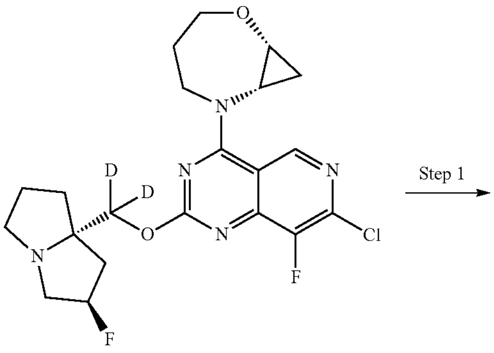

Intermediate 4

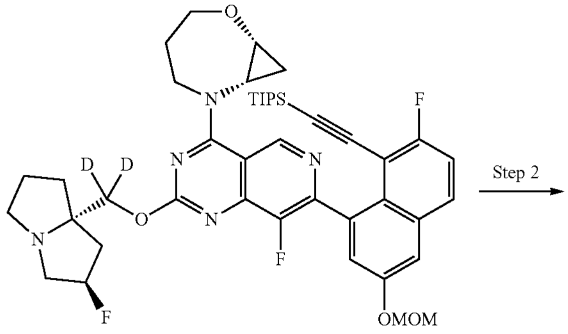

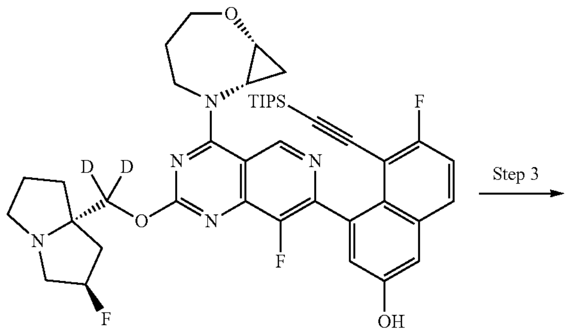

-continued

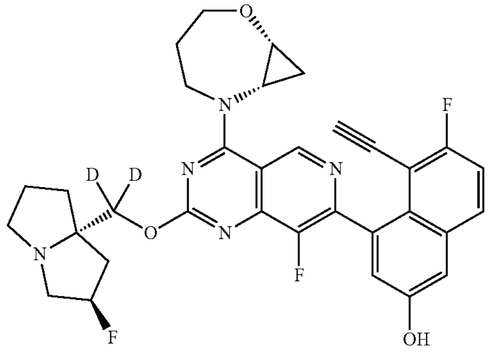
Example 11

Example 11 was prepared in a manner similar to Example 10. MS: m/z=604.35 [M+H]$^+$. $^1$H NMR (400 MHZ, DMSO-$d_6$) δ 10.14-10.12 (m, 1H), 9.42-9.37 (m, 1H), 7.99-7.96 (m, 1H), 7.49-7.45 (m, 1H), 7.39-7.38 (m, 1H), 7.19-7.16 (m, 1H), 5.35-5.21 (m, 1H), 4.57-4.42 (m, 1H), 4.18-3.89 (m, 2H), 3.77-3.70 (m, 2H), 3.68-3.58 (m, 1H), 3.50-3.38 (m, 1H), 3.12-3.01 (m, 3H), 2.89-2.80 (m, 1H), 2.20-1.72 (m, 8H), 1.39-1.20 (m, 1H), 1.00-0.61 (m, 1H). $^{19}$F NMR. (376 MHz, DMSO-$d_6$) δ −110.81--110.86 (d, 1F), −140.44--140.73 (d, 1F), −172.08--172.20 (d, 1F).

Example 12: 4-(4-(3-Azabicyclo[5.1.0]octan-3-yl)-8-fluoro-2-(((2R,7aS)-2-fluorotetrahydro-1H-pyrrolizin-7a (5H)-yl)methoxy)pyrido[4,3-d]pyrimidin-7-yl)-5-ethynyl-6-fluoronaphthalen-2-ol

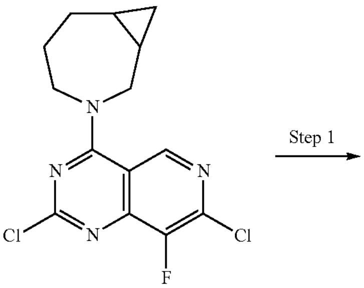

Intermediate 9

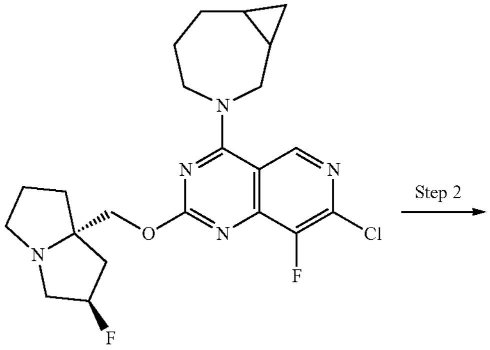

-continued

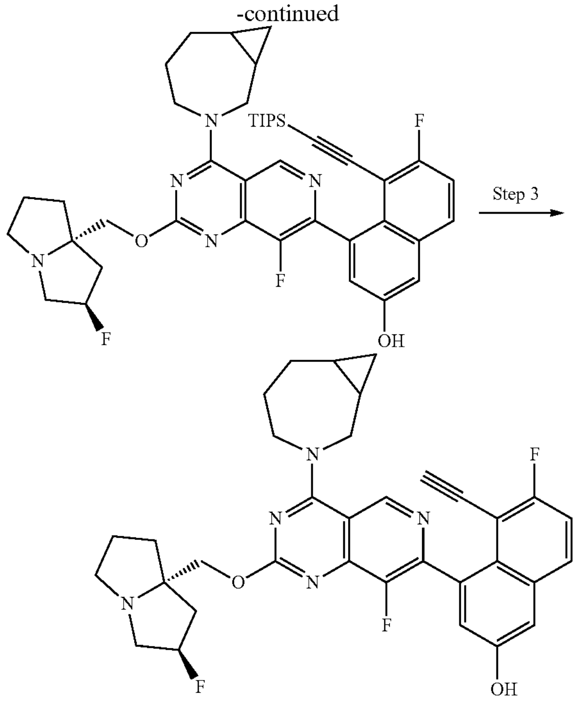

Example 12

Step 1: 4-(3-Azabicyclo[5.1.0]octan-3-yl)-7-chloro-8-fluoro-2-(((2R,7aS)-2-fluorotetrahydro-1H-pyrrolizin-7a (5H)-yl)methoxy)pyrido[4,3-d]pyrimidine To a solution of Intermediate 9 (170 mg, 519 μmol) in 1,4-dioxane (6 mL) were added DIPEA (272 μL, 1.56 mmol) and ((2R,7aS)-2-fluorotetrahydro-1H-pyrrolizin-7a (5H)-yl) methanol (165 mg, 1.04 mmol). The mixture was stirred at 110° C. for 16 h. The mixture was concentrated under reduced pressure. The residue was purified by silica gel flash chromatography (Eluent: 0~5% of MeOH in $CH_2Cl_2$) to give the title compound (41 mg, 14% yield) as a yellow solid. MS: m/z=450.0 $[M+H]^+$. $^1H$ NMR (400 MHZ, Chloroform-d) δ 8.76-8.63 (m, 1H), 5.42-5.08 (m, 1H), 4.33-4.02 (m, 4H), 3.86-3.70 (m, 2H), 3.64-3.11 (m, 3H), 3.07-2.92 (m, 1H), 2.63-2.41 (m, 2H), 2.32-2.10 (m, 3H), 2.00-1.81 (m, 3H), 1.50-1.34 (m, 2H), 1.17-0.99 (m, 2H), 0.91-0.78 (m, 1H), 0.30 (q, J=5.2 Hz, 1H). $^{19}F$ NMR (376 MHz, Chloroform-d) 8-134.61, −172.01, −173.18.

Step 2: (4-(4-(3-Azabicyclo[5.1.0]octan-3-yl)-8-fluoro-2-(((2R,7aS)-2-fluorotetrahydro-1H-pyrrolizin-7a (5H)-yl)methoxy)pyrido[4,3-d]pyrimidin-7-yl)-6-fluoro-5-((triisopropylsilyl) ethynyl) naphthalen-2-ol A mixture of 4-(3-azabicyclo[5.1.0]octan-3-yl)-7-chloro-8-fluoro-2-(((2R,7aS)-2-fluorotetrahydro-1H-pyrrolizin-7a (5H)-yl)methoxy)pyrido[4,3-d]pyrimidine (41 mg, 88.9 μmol), 6-fluoro-4-(4,4,5,5-tetramethyl-1,3,2-dioxaborolan-2-yl)-5-((triisopropylsilyl) ethynyl)naphthalen-2-ol (54 mg, 112 μmol), $Ad_2nBuP$-Pd-$G_3$ (cataCXiumAPdGs) (6 mg, 8.89 μmol), and $K_3PO_4$ (52 mg, 267 μmol) in 1,4-dioxane (5 mL) and $H_2O$ (0.5 mL) was degassed, purged with $N_2$ three times, and stirred at 100° C. for 2 h under $N_2$ atmosphere. The reaction mixture was concentrated under reduced pressure. The residue was purified by silica gel flash chromatography (Eluent: 0~5% of MeOH in $CH_2Cl_2$) to give the title compound (48 mg, 57% yield) as a yellow solid. MS: m/z=756.6 $[M+H]^{+\cdot}$ Step 3: 4-(4-(3-Azabicyclo[5.1.0]octan-3-yl)-8-fluoro-2-(((2R,7aS)-2-fluorotetrahydro-1H-pyrrolizin-7a (5H)-yl)methoxy)pyrido[4,3-d]pyrimidin-7-yl)-5-ethynyl-6-fluoronaphthalen-2-ol To a solution of (4-(4-(3-azabicyclo[5.1.0]octan-3-yl)-8-fluoro-2-(((2R,7aS)-2-fluorotetrahydro-1H-pyrrolizin-7a (5H)-yl)methoxy)pyrido[4,3-d]pyrimidin-7-yl)-6-fluoro-5-((triisopropylsilyl) ethynyl)naphthalen-2-ol (48 mg, 63.5 μmol) in DMSO (2 mL) was added CsF (29 mg, 190 μmol). The mixture was stirred at 25° C. for 20 min. The reaction mixture was diluted with $H_2O$ (20 mL) and extracted with EtOAc (20 mL×2). The combined organic layers were washed with brine (20 mL), dried over $Na_2SO_4$, filtered and concentrated under reduced pressure. The residue was purified by silica gel flash chromatography (eluent: 0~10% of MeOH in $CH_2Cl_2$) to give the title compound (Example 12, 12.3 mg, 32% yield) as a yellow solid. MS: m/z=600.3 $[M+H]^+$. $^1H$ NMR (400 MHZ, Dimethylsulfoxide-$d_6$) δ 10.16 (s, 1H), 8.93 (s, 1H), 7.97 (dd, J=6.0, 9.2 Hz, 1H), 7.46 (t, J=8.8 Hz, 1H), 7.41-7.36 (m, 1H), 7.17 (s, 1H), 5.52-5.13 (m, 1H), 4.35-4.21 (m, 1H), 4.16-3.97 (m, 4H), 3.95-3.84 (m, 1H), 3.81-3.69 (m, 1H), 3.14-3.07 (m, 2H), 3.05-2.99 (m, 1H), 2.90-2.77 (m, 1H), 2.21-1.94 (m, 4H), 1.89-1.60 (m, 6H), 1.10-1.01 (m, 2H), 0.78-0.67 (m, 1H), 0.44-0.34 (m, 1H). $^{19}F$ NMR (376 MHz, Dimethylsulfoxide-$d_6$) δ −110.77, −140.03, −140.06, −172.08, −172.17.

Example 13: 5-Ethynyl-6,7-difluoro-4-(8-fluoro-4-((1S,7R,8R)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine

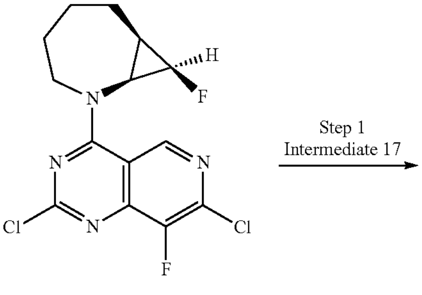

Intermediate 15

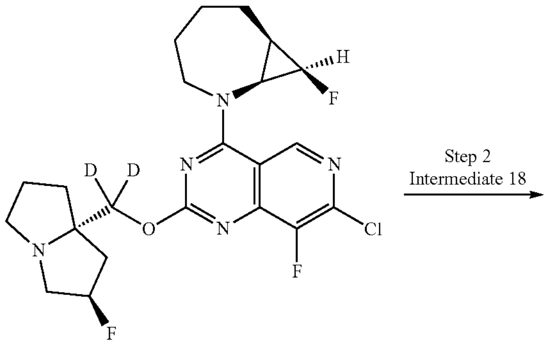

-continued

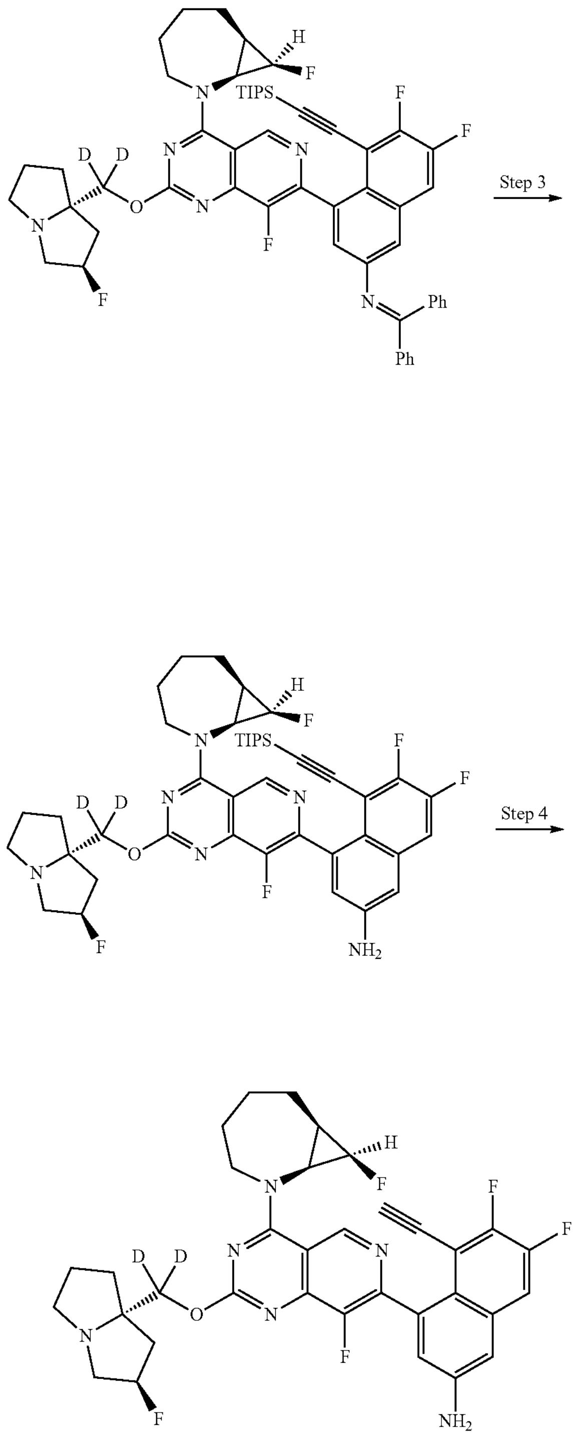

Example 13

Example 13 was prepared in a manner similar to Example 9. MS: m/z=637.2 $[M+H]^+$. $^1H$ NMR (400 MHZ, Dimethylsulfoxide-$d_6$) δ 9.69-9.49 (m, 1H), 7.85-7.75 (m, 1H), 7.05-6.96 (m, 2H), 5.85-5.74 (m, 2H), 5.37-5.20 (m, 1H), 5.04-4.81 (m, 1H), 4.49-4.35 (m, 1H), 4.05-3.51 (m, 2H), 3.49-3.42 (m, 1H), 3.15-2.99 (m, 3H), 2.88-2.78 (m, 1H), 2.18-2.09 (m, 1H), 2.09-1.93 (m, 5H), 1.88-1.74 (m, 4H), 1.68-1.54 (m, 2H), 1.47-1.34 (m, 1H). $^{19}F$ NMR (376 MHz, Dimethylsulfoxide-$d_6$) δ −137.61, −137.67, −137.80, −137.86, −138.61, −138.67, −140.27, −140.33, −172.05, −172.14, −230.66.

Example 14: 5-Ethynyl-6,7-difluoro-4-(8-fluoro-4-((1R,7S,8S)-8-fluoro-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine

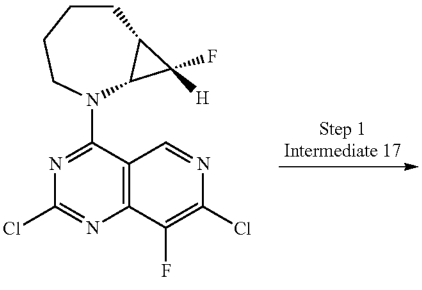

Intermediate 16

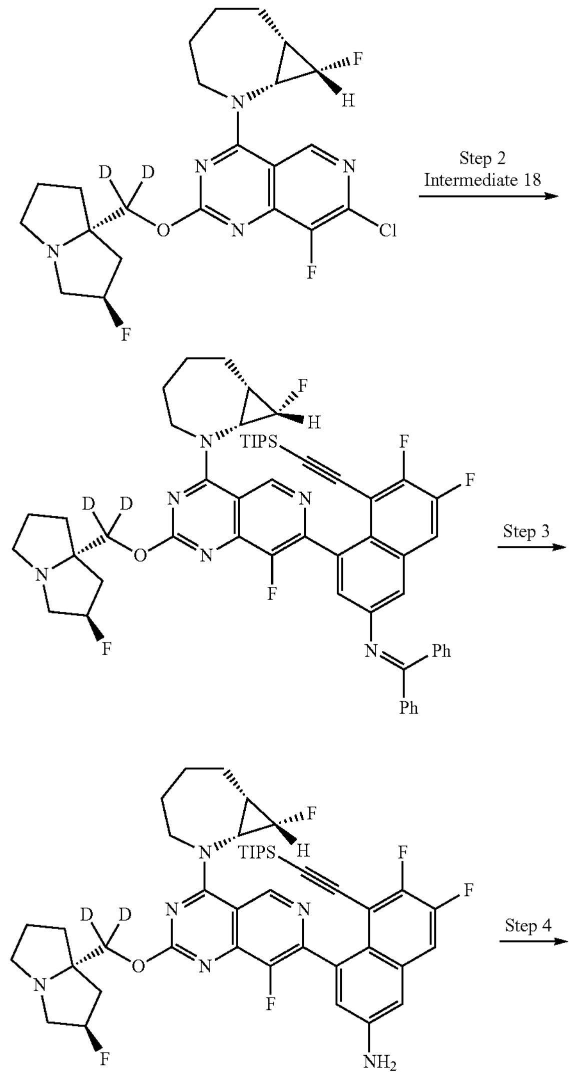

-continued

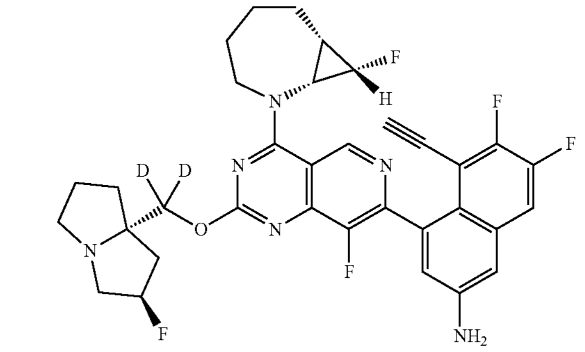

Example 14

Example 14 was prepared in a manner similar to Example 9. MS: m/z=637.2 $[M+H]^+$. $^1H$ NMR (400 MHZ, Dimethylsulfoxide-$d_6$) δ 9.70-9.49 (m, 1H), 7.84-7.73 (m, 1H), 7.06-6.93 (m, 2H), 5.79 (d, J=7.6 Hz, 2H), 5.40-5.16 (m, 1H), 5.04-4.78 (m, 1H), 4.50-4.34 (m, 1H), 4.07-3.51 (m, 2H), 3.49-3.41 (m, 1H), 3.16-2.99 (m, 3H), 2.87-2.78 (m, 1H), 2.17-2.09 (m, 1H), 2.05-1.75 (m, 9H), 1.68-1.53 (m, 2H), 1.48-1,33 (m, 1H). $^{19}F$ NMR (376 MHZ, Dimethylsulfoxide-$d_6$) δ −137.60, −137.66, −137.81, −137.87, −138.60, −138.64, −140.31, −172.09, ~172.18, −230.67.

Example 15: 5-Ethynyl-6,7-difluoro-4-(8-fluoro-4-((1R,7S,8R)-8-fluoro-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine

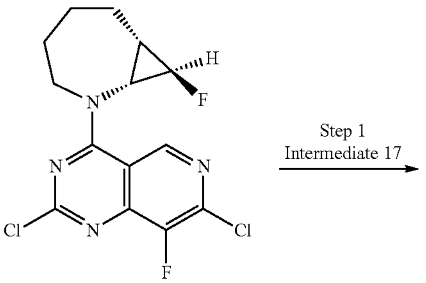

Intermediate 13

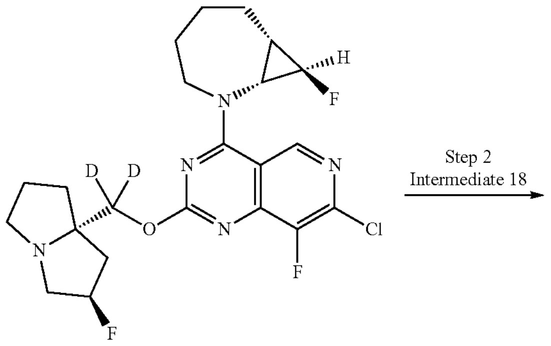

-continued

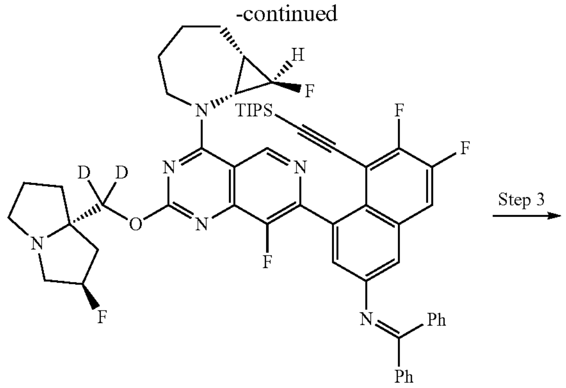

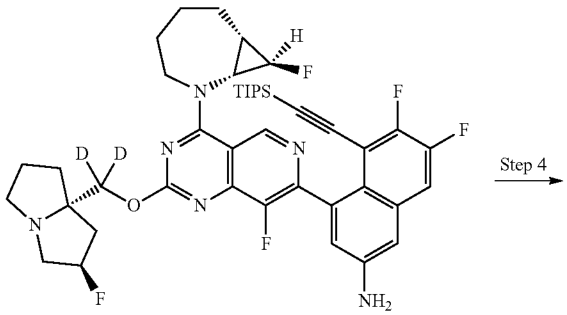

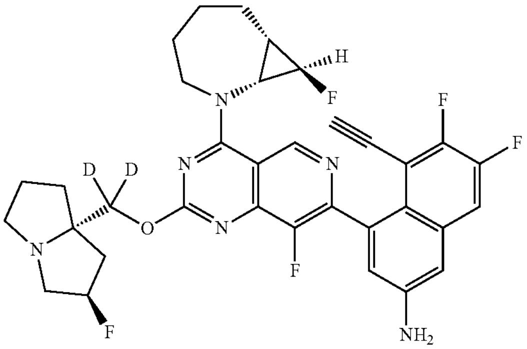

Example 15

Example 15 was prepared in a manner similar to Example 9. MS: m/z=637.2 $[M+H]^+$. $^1H$ NMR (400 MHz, Dimethylsulfoxide-$d_6$) δ 9.41-9.30 (m, 1H), 7.82-7.73 (m, 1H), 7.00 (s, 2H), 5.83-5.73 (m, 2H), 5.36-5.19 (m, 1H), 4.74-4.48 (m, 1H), 4.46-4.35 (m, 1H), 4.27 (s, 1H), 4.10-3.97 (m, 1H), 3.23-2.95 (m, 4H), 2.85-2.80 (m, 1H), 2.34-2.21 (m, 1H), 2.15-1.97 (m, 4H), 1.91-1.69 (m, 6H), 1.56-1.43 (m, 1H), 1.15-0.78 (m, 1H). $^{19}F$ NMR (376 MHz, Dimethylsulfoxide-$d_6$) δ −137.70, −137.75, −138.68, −140.20, −140.65, −172.09, −172.19, −204.68,-205.00.

Example 16: 5-Ethynyl-6,7-difluoro-4-(8-fluoro-4-((1S,7R,8S)-8-fluoro-2-azabicyclo[5.1.0]octan-2-yl)-2-(((2R,7aS)-2-fluorotetrahydro-LH-pyrrolizin-7a (5H)-yl)methoxy-$d_2$)pyrido[4,3-d]pyrimidin-7-yl) naphthalen-2-amine

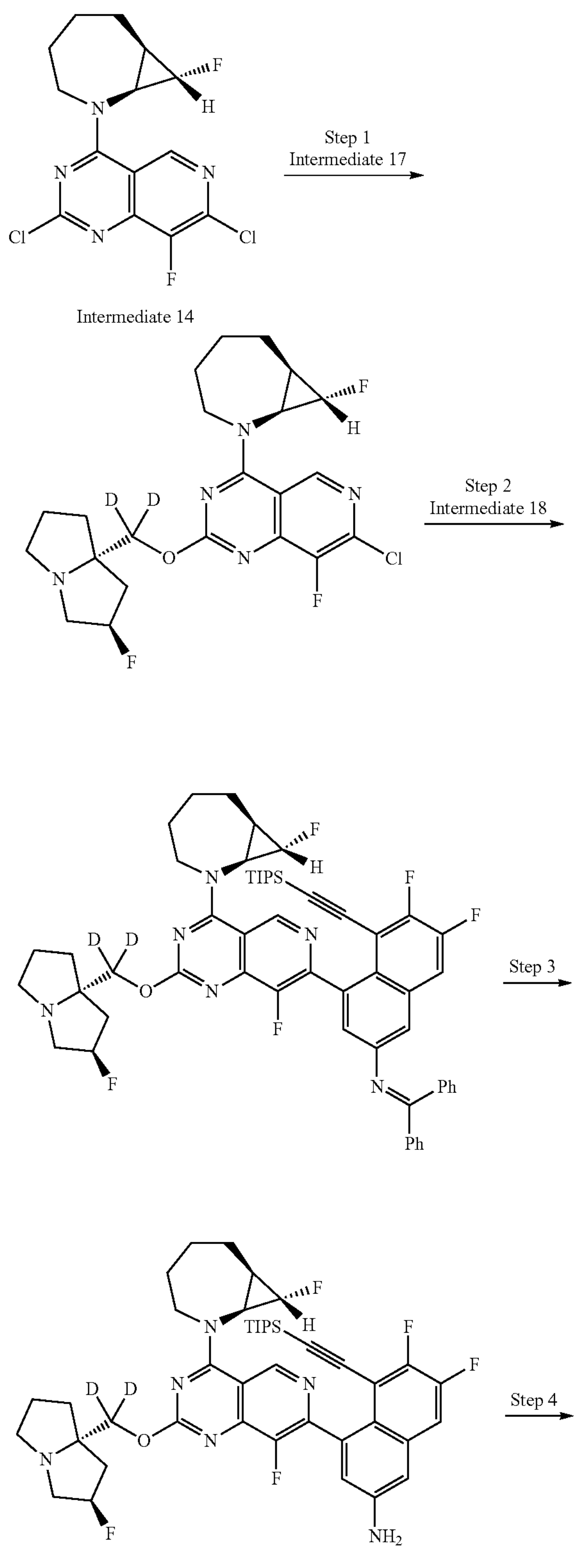

-continued

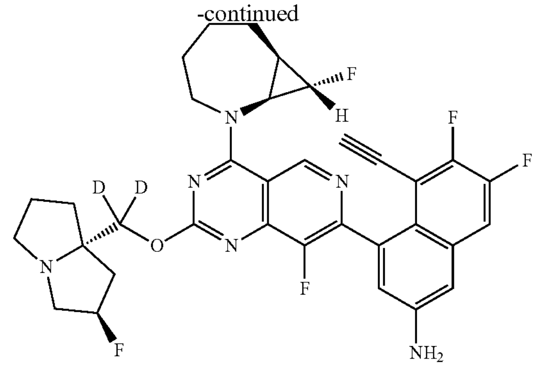

Example 16

Step 1: 7-Chloro-8-fluoro-4-((1S,7R,8S)-8-fluoro-2-azabicyclo[5.1.0]octan-2-yl)-2-(((2R,7aS)-2-fluoro-tetrahydro-1H-pyrrolizin-7a (5H)-yl)methoxy-$d_2$) pyrido[4,3-d]pyrimidine To a solution of Intermediate 14 (100 mg, 290 μmol) in 1,4-dioxane (2 mL) were added DIPEA (112 mg, 151 μL) and Intermediate 17 (84 mg, 521 μmol) and CsF (132 mg, 869 μmol). The mixture was stirred at 110° C. for 5 h. The residue was concentrated under reduced pressure to give a residue. The residue was purified by silica gel flash chromatography (eluent: 0~10% MeOH in $CH_2Cl_2$) to give the title compound (70 mg, 51% yield) as a yellow solid. MS: m/z=470.2 $[M+H]^+$. $^1$H NMR (400 MHZ, Chloroform-d) δ 9.15 (s, 1H), 5.40-5.13 (m, 1H), 4.51 (d, J=13.6 Hz, 1H), 4.24-3.97 (m, 1H), 3.60 (dd, J=9.2, 16.0 Hz, 1H), 3.47-3.37 (m, 1H), 3.28-3.18 (m, 2H), 3.06-3.00 (m, 1H), 2.86-2.78 (m, 1H), 2.47-2.33 (m, 1H), 2.26-2.06 (m, 3H), 2.00-1.76 (m, 7H), 1.59-1.52 (m, 1H), 1.10-0.96 (m, 1H) $^{19}$F NMR (376 MHZ, Chloroform-d) −134.66, −173.05, −204.08.

Step 2: N-(6,7-Difluoro-4-(8-fluoro-4-((15,7R,8S)-8-fluoro-2-azabicyclo[5.1.0]octan-2-yl)-2-(((2R, 7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-yl)-1,1-diphenylmethanimine A mixture of 7-chloro-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d] pyrimidine (70 mg, 149 μmol), Intermediate 18 (145 mg, 223 μmol), AdanBuP-Pd-Gs (cataCXiumAPdG$_3$) (22 mg, 30 μmol), and $K_3PO_4$ (190 mg, 894 μmol) in $H_2O$ (1 mL) and THF (5 mL) was degassed and purged with $N_2$ three times, and then the mixture was stirred at 80° C. for 2 h under $N_2$ atmosphere. The reaction mixture was concentrated under reduced pressure. The residue was purified by silica gel flash chromatography (eluent: 0~10% MeOH in $CH_2Cl_2$) to give the title compound (130 mg, 84% yield) as a yellow solid. MS: m/z=957.5 $[M+H]^{+\cdot}$ Step 3: 6,7-Difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine To a solution of N-(6,7-difluoro-4-(8-fluoro-4-((1S,7R, 8S)-8-fluoro-2-azabicyclo[5.1.0]octan-2-yl)-2-(((2R,7aS)-

2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-yl)-1,1-diphenylmethanimine (130 mg, 136 μmol) in EtOH (2 mL) were added NaOAc (17 mg, 204 μmol) and $NH_2OH$ HCl (14 mg, 204 μmol). The mixture was stirred at 25° C. for 1.5 h. The reaction mixture was concentrated under reduced pressure. The residue was purified by silica gel flash chromatography (eluent: 0~10% MeOH in $CH_2Cl_2$) to give the title compound (100 mg, 91% yield) as a yellow solid. MS: m/z=793.4 $[M+H]^{+\cdot}$ Step 4: 5-Ethynyl-6, 7-difluoro-4-(8-fluoro-4-((1S, 7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine To a solution of 6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-amine (100 mg, 126 μmol) in DMSO (2 mL) was added CsF (57 mg, 378 μmol). The mixture was stirred at 25° C. for 1 h. The reaction mixture was diluted with water (20 mL) and extracted with EtOAc (30 mL×2). The combined organic layers were washed with brine (20 mL), dried over anhydrous $Na_2SO_4$, filtered, and concentrated under reduced pressure. The residue was purified by silica gel flash chromatography (eluent: 0~10% MeOH in $CH_2Cl_2$) to give the title compound (Example 16, 46.4 mg, 57% yield) as a yellow solid. MS: m/z=637.2 $[M+H]^+$. $^1H$ NMR (400 MHZ, Dimethylsulfoxide-$d_6$) δ 9.44-9.23 (m, 1H), 7.79 (dd, J=8.8, 11.6 Hz, 1H), 7.10-6.89 (m, 2H), 5.88-5.69 (m, 2H), 5.44-5.14 (m, 1H), 4.75-4.48 (m, 1H), 4.41 (d, J=13.2 Hz, 1H), 4.34-3.91 (m, 2H), 3.56-3.39 (m, 1H), 3.17-2.97 (m, 3H), 2.84 (d,J=2.0 Hz, 1H), 2.31-2.22 (m, 1H), 2.15-1.95 (m, 4H), 1.91-1.67 (m, 6H), 1.55-1.45 (m, 1H), 0.86 (d, J=7.6 Hz, 1H). $^{19}F$ NMR (376 MHZ, Dimethylsulfoxide-$d_6$) δ −137.51, −137.78, −137.84, −138.54, −138.65, −140.16, −140.57, −140.67, ~172.07, −172.19, −205.07.

Example 17: 4-(4-((1S,7R)-2-Oxa-6-azabicyclo [5.1.0]octan-6-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-5-ethynyl-6,7-difluoronaphthalen-2-amine

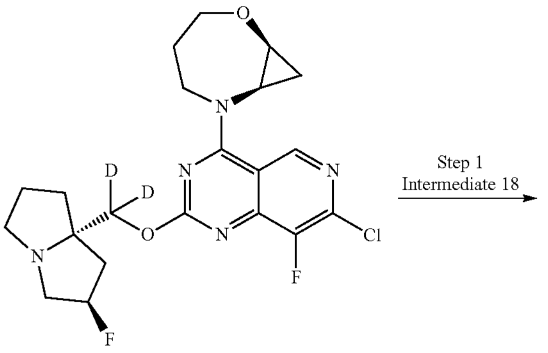

Intermediate 5

-continued

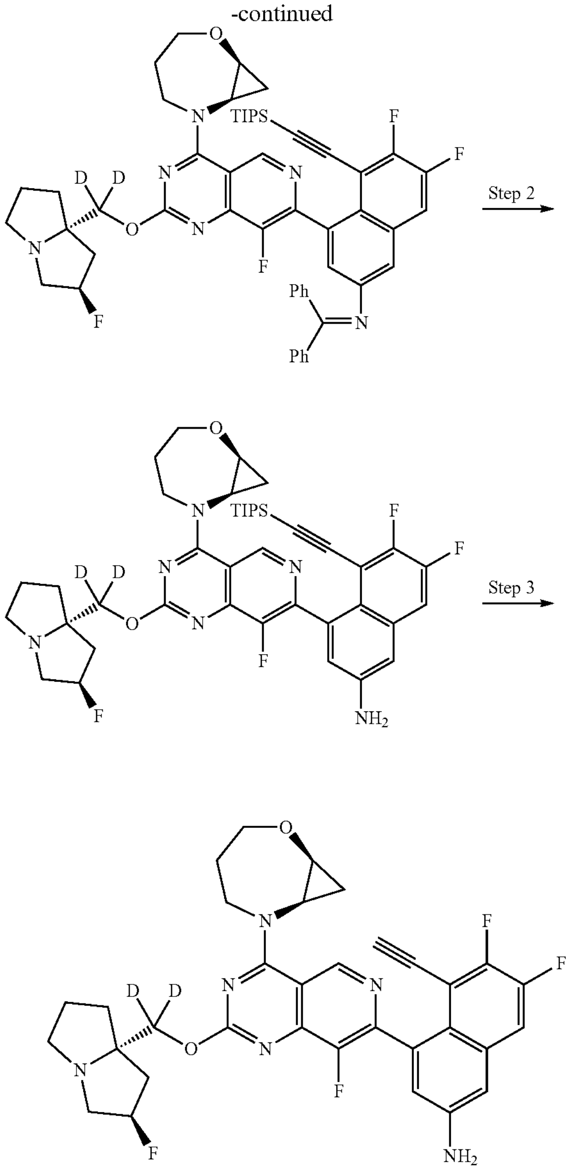

Example 17

Step 1: N-(4-(4-((1S,7R)-2-Oxa-6-azabicyclo[5.1.0] octan-6-yl)-8-fluoro-2-(((2R,7aS)-2-fluorotetrahydro-1H-pyrrolizin-7a (5H)-yl)methoxy-$d_2$)pyrido [4,3-d]pyrimidin-7-yl)-6,7-difluoro-5-((triisopropylsilyl) ethynyl)naphthalen-2-yl)-1,1-diphenylmethanimine To a stirred mixture of Intermediate 5 (260 mg, 0.57 mmol) and Intermediate 18 (558.21 mg, 0.85 mmol) in toluene (13 mL) and $H_2O$ (2.6 mL) under nitrogen atmosphere were added CataCXium A Pd G3 (50.06 mg, 0.06 mmol) and $CszCO_3$ (615.86 mg, 1.89 mmol) at room temperature. The reaction mixture was heated at 100° C. for 16 hours. The resulting mixture was cooled to room temperature, filtered and concentrated under reduced pressure. The residue was purified by Prep-TLC ($CH_2Cl_2$/MeOH=10: 1) to afford the title compound (350 mg, 64% yield) as a light yellow solid. MS: m/z=941.50 $[M+H]^{+\cdot}$ Step 2: 4-(4-((1S,7R)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-6,7-difluoro-S-((triisopropylsilyl) ethynyl)naphthalen-2-amine To a solution of N-(4-(4-((1S,7R)-2-oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-6,7-difluoro-5-((triisopropylsilyl) ethynyl)naphthalen-2-yl)-1,1-diphenylmethanimine (350 mg, 0.37 mmol) in EtOH (4 mL) under nitrogen atmosphere were added NaOAc (61.01 mg, 0.74 mmol) and $NH_2OH$ HCl (51.68 mg, 0.74 mmol) at room temperature. The resulting mixture was stirred at room temperature for 1 hour. The resulting mixture was filtered and concentrated under reduced pressure. The residue was purified by silica gel flash chromatography, eluted with 10% MeOH in DCM to afford the title compound (270 mg, 93% yield) as a yellow solid. MS: m/z=777.50 $[M+H]^{+.}$ Step 3: 4-(4-((1S,7R)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6,7-difluoronaphthalen-2-amine To a stirred solution of 4-(4-((15,7R)-2-oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-6,7-difluoro-5-((triisopropylsilyl) ethynyl)naphthalen-2-amine (270 mg, 0.34 mmol) in DMF (3 mL) was added CsF (299.81 mg, 1.97 mmol) at room temperature. The reaction mixture was stirred at room temperature for 1 hour. The resulting mixture was purified by RP-Flash with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 2% B to 2% B in 3 min, 2% B to 55% B in 15 min, 55% B to 55% B in 4 min, 55% B to 95% B in 4 min; Detector: UV 254 & 210 nm. The collected fractions were combined, concentrated, and lyophilized overnight to give the title compound (Example 17, 147 mg, 68% yield) as a yellow lyophilized powder. MS: m/z=621.35 $[M+H]^+$. $^1H$ NMR (400 MHZ, DMSO-$d_6$) δ 9.42-9.36 (m, 1H), 7.81-7.76 (m, 1H), 7.03-6.99 (m, 2H), 5.79 (s, 2H), 5.35-5.22 (m, 1H), 4.55-4.49 (m, 1H), 4.30-4.01 (m, 1H), 3.95-3.89 (m, 1H), 3.85-3.72 (m, 2H), 3.63-3.56 (m, 1H), 3.50-3.35 (m, 1H), 3.10-3.01 (m, 3H), 2.90-2.82 (m, 1H), 2.18-1.77 (m, 8H), 1.30-1.26 (m, 1H), 0.94-0.60 (m, 1H). $^{19}F$ NMR (376 MHz, DMSO-$d_6$) δ −137.79--138.70 (m, 2F), −140.45--140.87 (m, 1F), −172.04--172.15 (m, 1F).

Example 18: 4-(4-((1R,7S)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6,7-difluoronaphthalen-2-amine

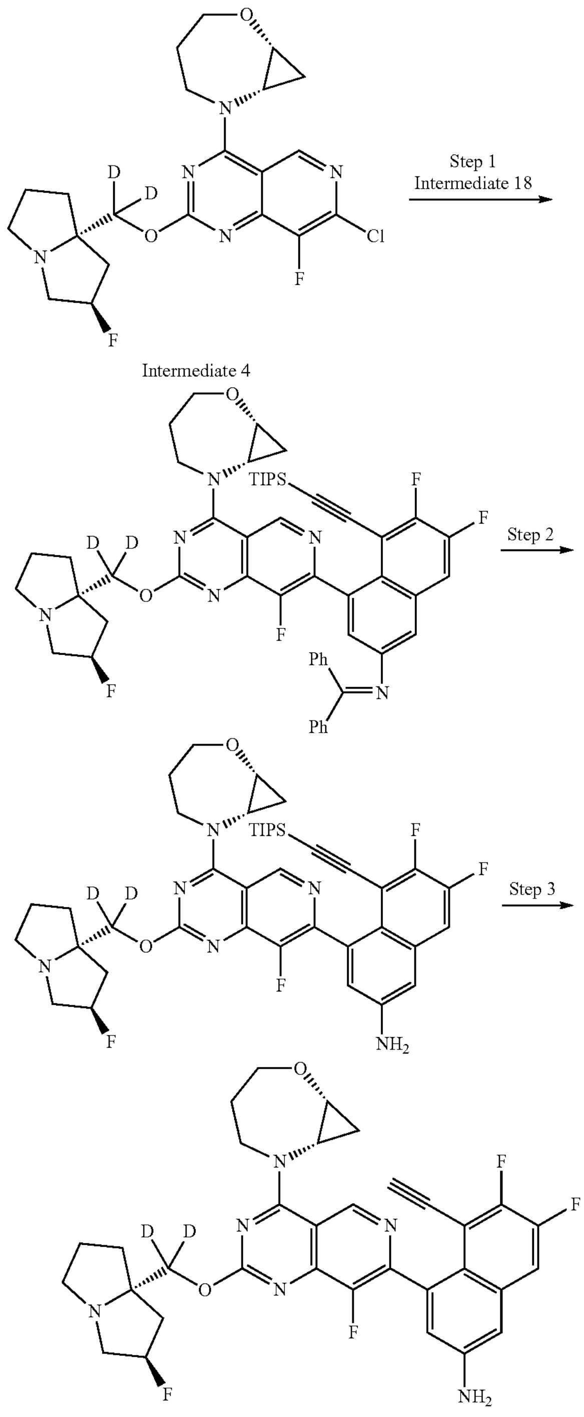

Example 18

Example 18 was prepared in a manner similar to Example 17. MS: m/z=621.25 $[M+H]^+$. $^1H$ NMR (400 MHZ, DMSO-$d_6$) δ 9.45-9.33 (m, 1H), 7.84-7.76 (m, 1H), 7.03-6.99 (m, 2H), 5.79 (s, 2H), 5.35-5.21 (m, 1H), 4.52-4.45 (m, 1H), 4.29-4.01 (m, 1H), 3.95-3.85 (m, 1H), 3.84-3.71 (m, 2H), 3.63-3.57 (m, 1H), 3.44-3.38 (m, 1H), 3.10-3.01 (m, 3H), 2.87-2.80 (m, 1H), 2.18-1.69 (m, 8H), 1.34-1.21 (m, 1H), 0.94-0.56 (m, 1H). $^{19}$F NMR (376 MHZ, DMSO-$d_6$) δ −137.78--137.90 (m, 1F), −138.62--138.71 (m, 1F), −140.51--140.85 (m, 1F), −172.09-172.21 (d, 1F).

Example 19: 4-(4-((1S,7S)-8,8-Difluoro-5-oxa-2-azabicyclo[5.1.0]octan-2-yl)-8-fluoro-2-(((2R,7aS)-2-fluorotetrahydro-1H-pyrrolizin-7a (5H)-yl) methoxy-$d_2$)pyrido[4,3-d]pyrimidin-7-yl)-5-ethynyl-6,7-difluoronaphthalen-2-amine

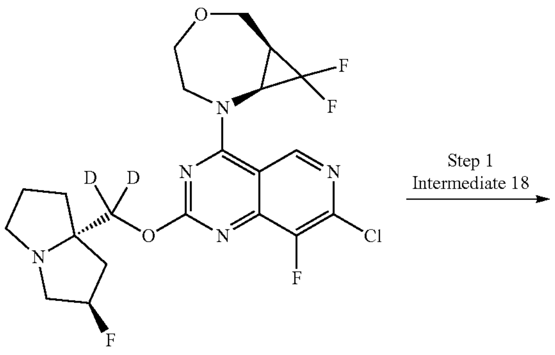

Intermediate 22

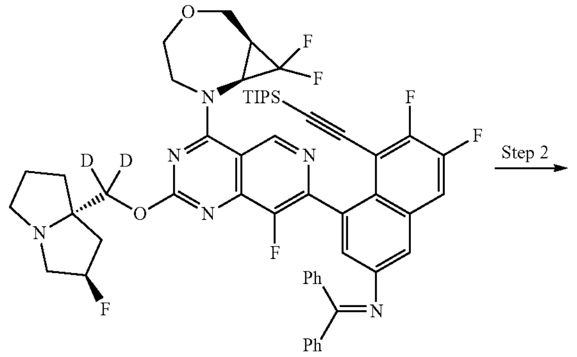

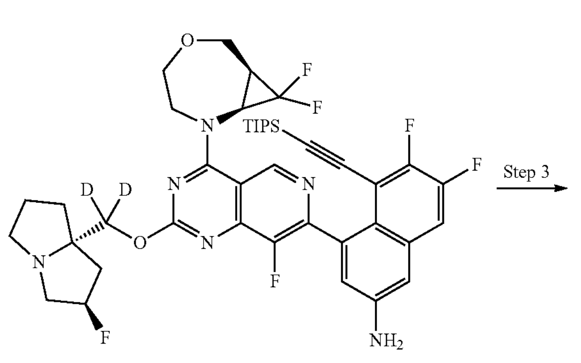

-continued

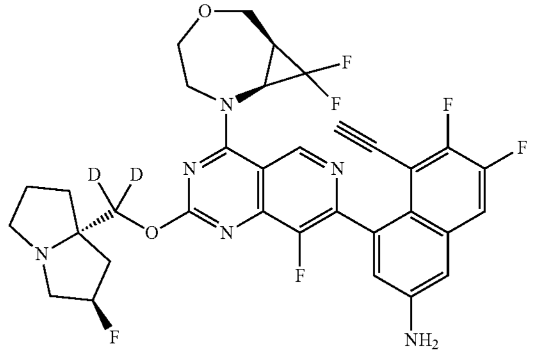

Example 19

Example 19 was prepared in a manner similar to Example 17. MS: m/z=657.35. 1H NMR (400 MHz, DMSO-$d_6$) δ 9.40-9.21 (m, 1H), 7.84-7.79 (m, 1H), 7.04-7.00 (m, 2H), 5.83-5.81 (m, 2H), 5.35-5.22 (m, 1H), 4.80-4.30 (m, 3H), 4.16-4.11 (m, 1H), 4.02-3.78 (m, 2H), 3.75-3.68 (m, 1H), 3.60-3.50 (m, 1H), 3.09-3.01 (m, 3H), 2.90-2.70 (m, 2H), 2.20-1.94 (m, 3H), 1.94-1.72 (m, 3H). $^{19}$F NMR (376 MHz, DMSO-$d_6$) δ −123.39--123.41 (m, 1F), −137.49--137.77 (m, 1F), −138.51--139.57 (m, 2F), −144.57--145.02 (m, 1F), −172.10--172.14 (d, 1F).

Example 20: 4-(4-((1R,7R)-8,8-Difluoro-S-oxa-2-azabicyclo[5.1.0]octan-2-yl)-8-fluoro-2-(((2R,7aS)-2-fluorotetrahydro-1H-pyrrolizin-7a (5H)-yl) methoxy-$d_2$)pyrido[4,3-d]pyrimidin-7-yl)-5-ethynyl-6,7-difluoronaphthalen-2-amine

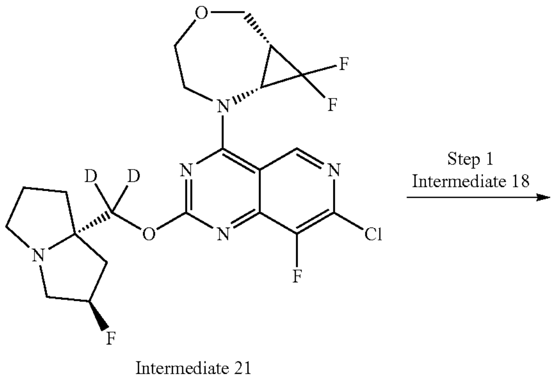

Intermediate 21

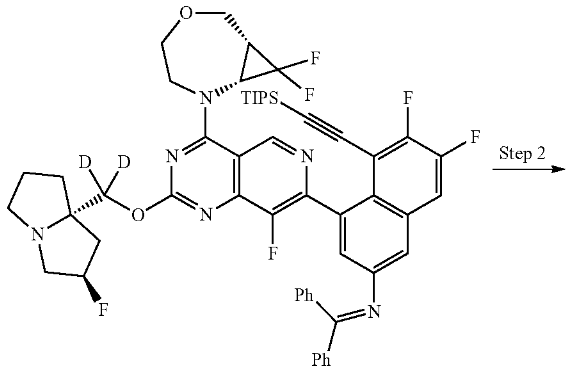

-continued

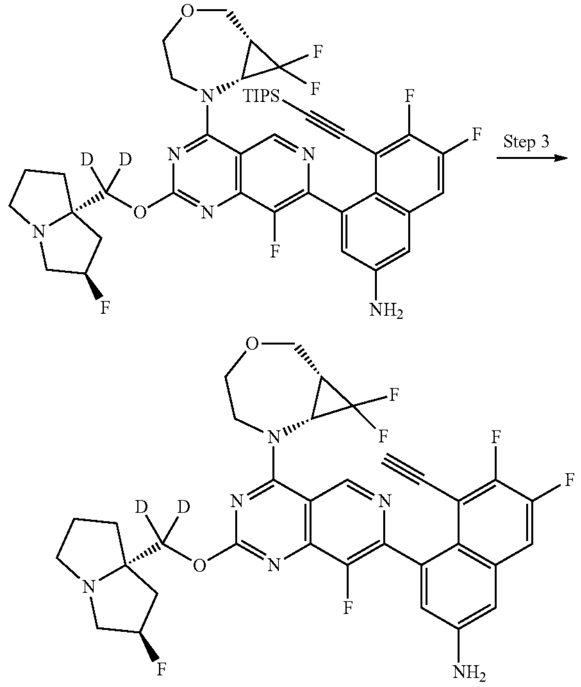

Example 20

-continued

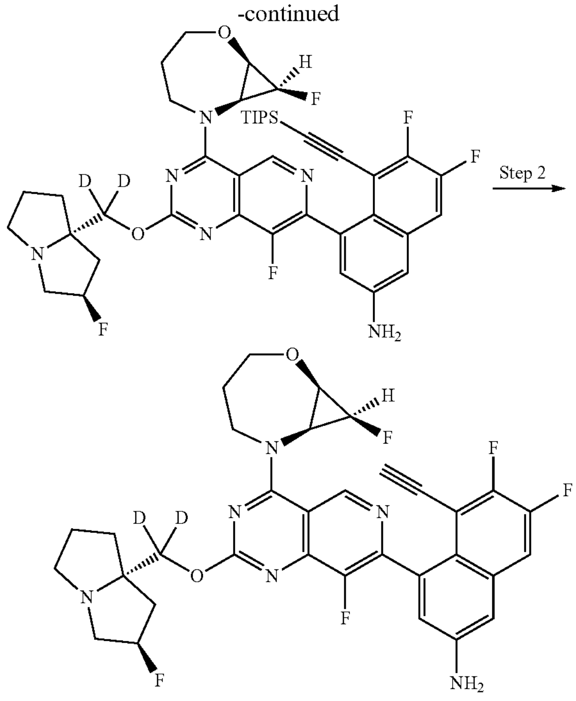

Example 21

Example 20 was prepared in a manner similar to Example 17. MS: m/z=657.25 $[M+H]^+$. $^1H$ NMR (400 MHZ, DMSO-$d_6$) δ 9.37-9.21 (m, 1H), 7.84-7.79 (m, 1H), 7.03-7.01 (m, 2H), 5.82-5.80 (m, 2H), 5.35-5.21 (m, 1H), 4.73-4.37 (m, 3H), 4.19-4.11 (m, 1H), 4.02-3.72 (m, 31), 3.68-3.45 (m, 1H), 3.09-3.01 (m, 3H), 2.83-2.71 (m, 2H), 2.14-1.94 (m, 3H), 1.88-1.70 (m, 3H). $^{19}F$ NMR (376 MHz, DMSO-$d_6$) δ −123.39-−124.41 (m, 1F), −137.48-−139.54 (m, 3F), −144.54, −144.94 (m, 1F), −172.09-−172.19 (m, 1F).

Example 21: 5-Ethynyl-6,7-difluoro-4-(8-fluoro-4-((1R,7S,8S)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$)pyrido[4,3-d]pyrimidin-7-yl)naphthalen-2-amine

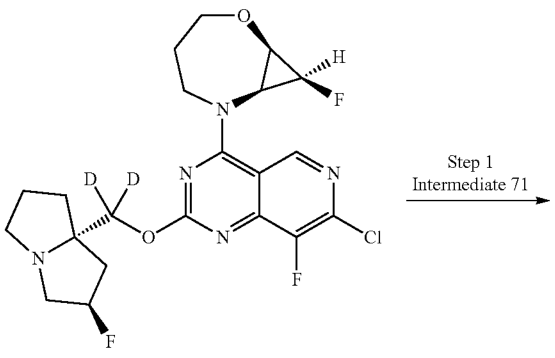

Intermediate 26

Step 1: 6,7-Difluoro-4-(8-fluoro-4-((1R,7S,8S)-8-fluoro-2-oxa-6-azabicyclo[5.1.0]octan-6-yl)-2-(((2R,7aS)-2-fluorotetrahydro-1H-pyrrolizin-7a (5H)-yl)methoxy-2)pyrido[4,3-d]pyrimidin-7-yl)-5-((triisopropylsilyl) ethynyl)naphthalen-2-amine To a solution of Intermediate 26 (32 mg, 0.06 mmol) and Intermediate 71 (59.26 mg, 0.12 mmol) in THF (0.2 mL) and $H_2O$ (0.04 mL) were added $K_3PO_4$ (86.36 mg, 0.40 mmol) and CataCXium A Pd G3 (9.88 mg, 0.01 mmol) at room temperature under nitrogen atmosphere. The reaction mixture was irradiated with microwave radiation at 60° C. for 1 hour. The resulting mixture was cooled to room temperature, diluted with $H_2O$ (10 mL) and extracted with ethyl acetate (3×10 mL). The combined organic layers were washed with brine (10 mL), dried over anhydrous sodium sulfate, filtered and concentrated under reduced pressure. The residue was purified by Prep-TLC ($CH_2Cl_2$/MeOH 10: 1) to afford the title compound (26 mg, 48% yield) as a brown yellow solid. MS: m/z=795.05 $[M+H]^+$.

Step 2: 5-Ethynyl-6,7-difluoro-4-(8-fluoro-4-((1R,7S,8S)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$)pyrido[4,3-d]pyrimidin-7-yl)naphthalen-2-amine To a stirred solution of 6,7-difluoro-4-(8-fluoro-4-((1R,7S,8S)-8-fluoro-2-oxa-6-azabicyclo[5.1.0]octan-6-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine (26 mg, 0.03 mmol) in DMF (0.5 mL) was added CsF (49.68 mg, 0.33 mmol) at room temperature. The reaction mixture was stirred at room temperature for 16 hours. The resulting mixture was purified by RP-Flash directly with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 62% B in 15 min, 62% B to 62% B in 3 min, 62% B to 95% B in 4 min; Detector: UV 254 & 210 nm. The collected fractions were combined, concentrated and lyophilized overnight to give the title compound (Example 21, 6.8 mg, 30% yield) as a yellow solid. MS: m/z=639.35 $[M+H]^+$. $^1$H NMR (400 MHz, Methanol-$d_4$) δ 9.54-9.52 (m, 1H), 7.58-7.53 (m, 1H), 7.10 (s, 2H), 5.38-5.25 (m, 1H), 4.75-4.60 (m, 2H), 4.11-3.98 (m, 2H), 3.78-3.66 (m, 2H), 3.50-3.00 (m, 6H), 2.50-1.80 (m, 8H). $^{19}$F NMR (376 MHz, Methanol-$d_4$) δ −137.77-140.39 (m, 3F), −173.68--173.76 (d, 1F).

Example 22: 5-Ethynyl-6,7-difluoro-4-(8-fluoro-4-((1S,7R,8R)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$)pyrido[4,3-d] pyrimidin-7-yl)naphthalen-2-amine

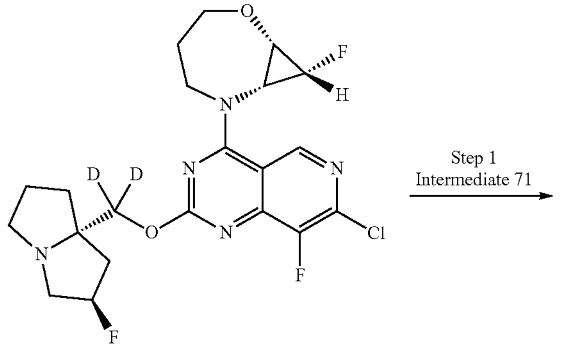

Intermediate 25

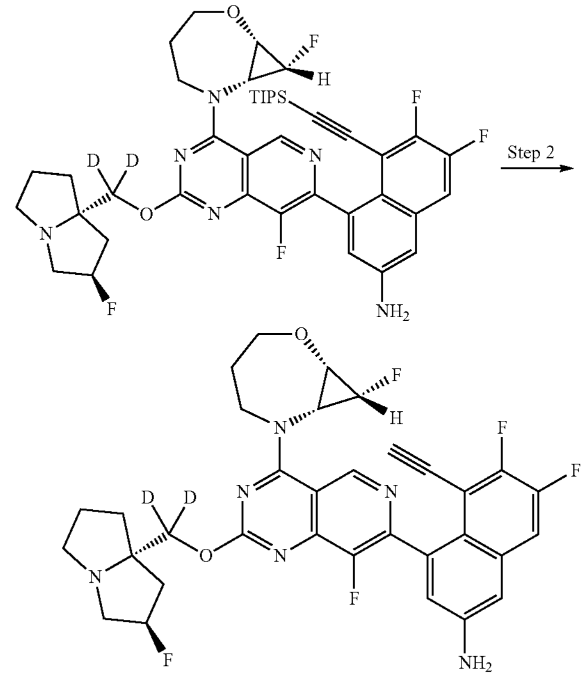

Example 22

Example 22 was prepared in a manner similar to Example 21. MS: m/z=639.30 $[M+H]^+$. $^1$H NMR (400 MHZ, Methanol-$d_4$) δ 9.54-9.51 (m, 1H), 7.58-7.53 (m, 1H), 7.10 (s, 2H), 5.38-5.24 (m, 1H), 4.87-4.65 (m, 2H), 4.08-3.90 (m, 2H), 3.80-3.60 (m, 2H), 3.49-3.44 (m, 1H), 3.40-3.16 (m, 4H), 3.10-2.95 (m, 1H), 2.40-1.80 (m, 8H). $^{19}$F NMR (376 MHz, Methanol-$d_4$) δ −137.76--137.81 (d, 1F), −139.52--140.36 (m, 2F), −173.65--173.68 (d, 1F).

Example 23: 5-Ethynyl-6, 7-difluoro-4-(8-fluoro-4-((1S,7R,8S)-8-fluoro-2-oxa-6-azabicyclo[5.1.0]octan-6-yl)-2-(((2R,7aS)-2-fluorotetrahydro-LH-pyrrolizin-7a (5H)-yl)methoxy-$d_2$)pyrido[4,3-d] pyrimidin-7-yl)naphthalen-2-amine

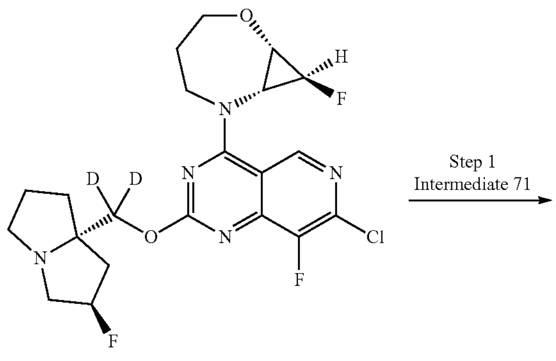

Intermediate 27

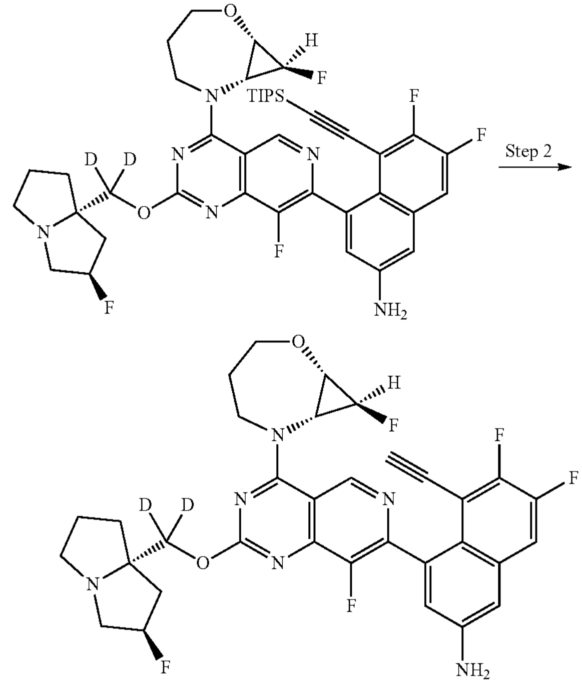

Example 23

Example 23 was prepared in a manner similar to Example 21. MS: m/z=639.15 $[M+H]^+$. $^1$H NMR (400 MHZ, DMSO-$d_6$) δ 9.31-9.28 (m, 1H), 7.82-7.77 (m, 1H), 7.00 (s, 2H), 5.80 (s, 2H), 5.35-5.21 (m, 1H), 4.97-4.83 (m, 1H), 4.48-3.78 (m, 6H), 3.60-3.54 (m, 1H), 3.11-2.96 (m, 3H), 2.86-2.80 (m, 1H), 2.20-1.70 (m, 8H). $^{19}$F NMR (376 MHz, DMSO-$d_6$) δ −137.84--140.27 (m, 3F), −172.11--172.24 (d, 1F), −211.86--212.70 (d, 1F).

Example 24: 5-Ethynyl-6,7-difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$)pyrido[4,3-d]pyrimidin-7-yl)naphthalen-2-amine

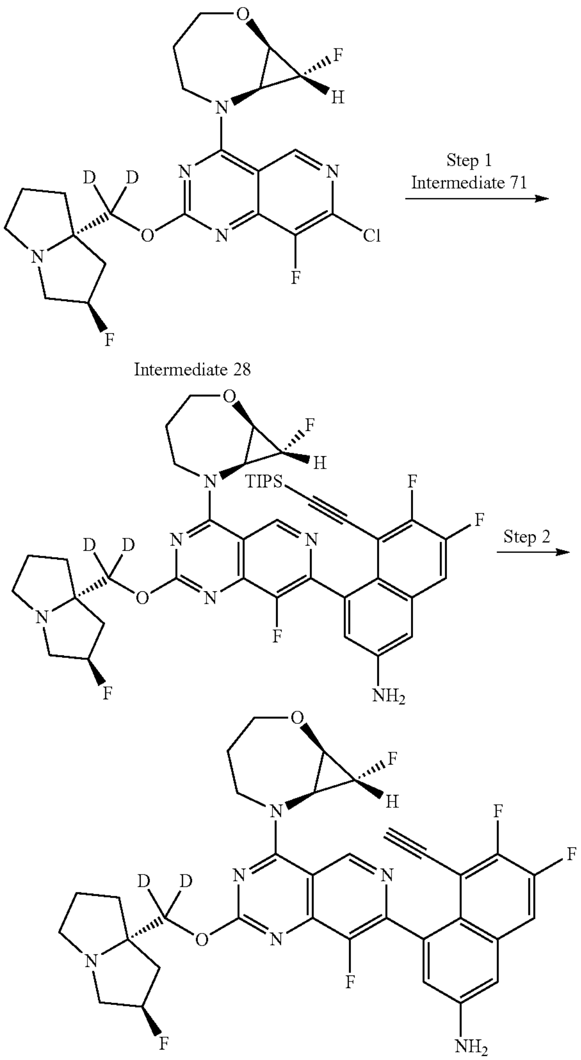

Example 24

Step 1: 6,7-Difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$)pyrido[4,3-d]pyrimidin-7-yl)-5-((triisopropylsilyl) ethynyl)naphthalen-2-amine To a solution of Intermediate 28 (27 mg, 0.05 mmol) and Intermediate 71 (55.56 mg, 0.11 mmol) in THF (1 mL) and $H_2O$ (0.2 mL) were added $K_3PO_4$ (72.87 mg, 0.34 mmol) and CataCXium A Pd G3 (8.33 mg, 0.01 mmol) at room temperature under nitrogen atmosphere. The reaction mixture was irradiated with microwave radiation at 60° C. for 1 hour. The resulting mixture was cooled to room temperature, diluted with $H_2O$ (10 mL) and extracted with ethyl acetate (3×10 mL). The combined organic layers were washed with brine (10 mL), dried over anhydrous sodium sulfate, filtered and concentrated under reduced pressure. The residue was purified by Prep-TLC ($CH_2Cl_2$/MeOH 10: 1) to afford the title compound (32 mg, 70% yield) as a brown yellow solid. MS: m/z=795.05 $[M+H]^{+}$.

Step 2: 5-Ethynyl-6,7-difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine To a stirred solution of 6,7-difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine (32 mg, 0.04 mmol) in DMF (0.5 mL) was added CsF (61.14 mg, 0.40 mmol) at room temperature. The reaction mixture was stirred at room temperature for 16 hours. The resulting mixture was purified by RP-Flash directly with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 60% B in 15 min, 60% B to 60% B in 3 min, 60% B to 95% B in 4 min; Detector: UV 254 & 210 nm. The collected fractions were combined, concentrated and lyophilized overnight to give the title compound (Example 24, 13.5 mg, 51% yield) as a yellow lyophilized powder. MS: m/z=639.15 $[M+H]^{+}$. $^{1}H$ NMR (400 MHZ, DMSO-$d_6$) δ 9.31-9.28 (m, 1H), 7.82-7.77 (m, 1H), 7.00 (s, 2H), 5.81-5.79 (m, 2H), 5.35-5.22 (m, 1H), 4.98-4.83 (m, 1H), 4.48-4.37 (m, 2H), 4.21-4.06 (m, 2H), 3.99-3.81 (m, 2H), 3.64-3.49 (m, 1H), 3.19-2.95 (m, 3H), 2.90-2.80 (m, 1H), 2.20-1.70 (m, 8H). $^{19}F$ NMR (376 MHz, DMSO-$d_6$) δ −137.85−−140.28 (m, 3F), −172.04−−172.16 (d, 1F).

Example 25: 4-(4-((1S,7R)-2-Oxa-6-azabicyclo[5.1.0]octan-6-yl-5,5-$d_2$)-8-fluoro-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6,7-difluoronaphthalen-2-amine

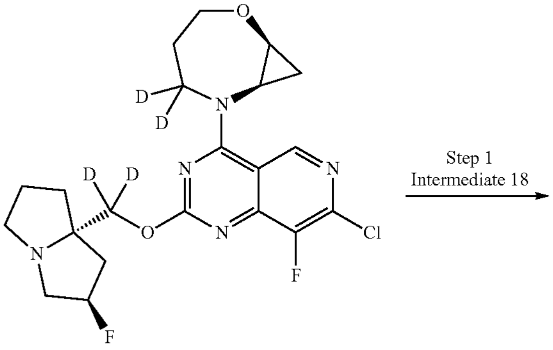

Intermediate 29

-continued

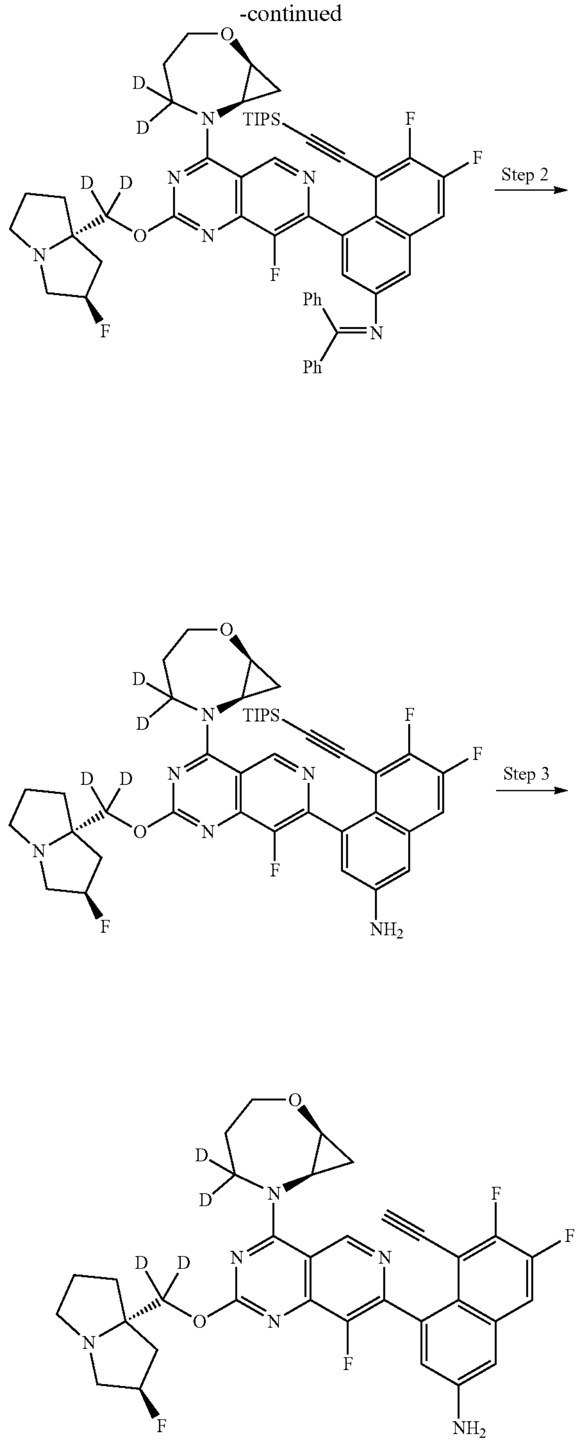

Example 25

Example 25 was prepared in a manner similar to Example 17. MS: m/z=623.25 $[M+H]^+$. $^1H$ NMR (400 MHZ, DMSO-$d_6$) δ 9.40-9.36 (m, 1H), 7.82-7.77 (m, 1H), 7.03-6.98 (m, 2H), 5.80 (s, 2H), 5.35-5.22 (m, 1H), 4.30-4.01 (m, 1H), 3.90-3.85 (m, 1H), 3.82-3.72 (m, 2H), 3.50-3.33 (m, 1H), 3.09-3.01 (m, 3H), 2.86-2.80 (m, 1H), 2.18-1.76 (m, 8H), 1.30-1.20 (m, 1H), 0.94-0.60 (m, 1H). $^{19}F$ NMR (376 MHz, DMSO-$d_6$) δ −137.80-−140.89 (m, 3F), −172.04-−172.15 (m, 1F).

Example 26: 4-(4-((1R,7S)-2-Oxa-6-azabicyclo[5.1.0]octan-6-yl-5,5-$d_2$)-8-fluoro-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6,7-difluoronaphthalen-2-amine

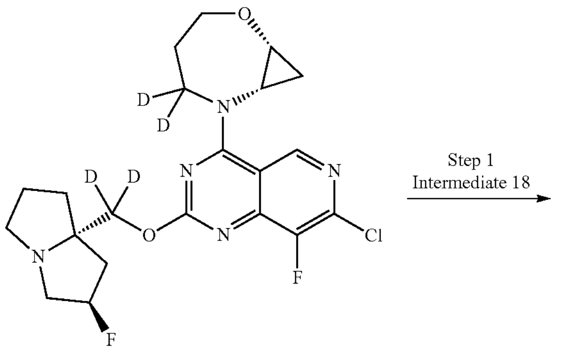

Intermediate 30

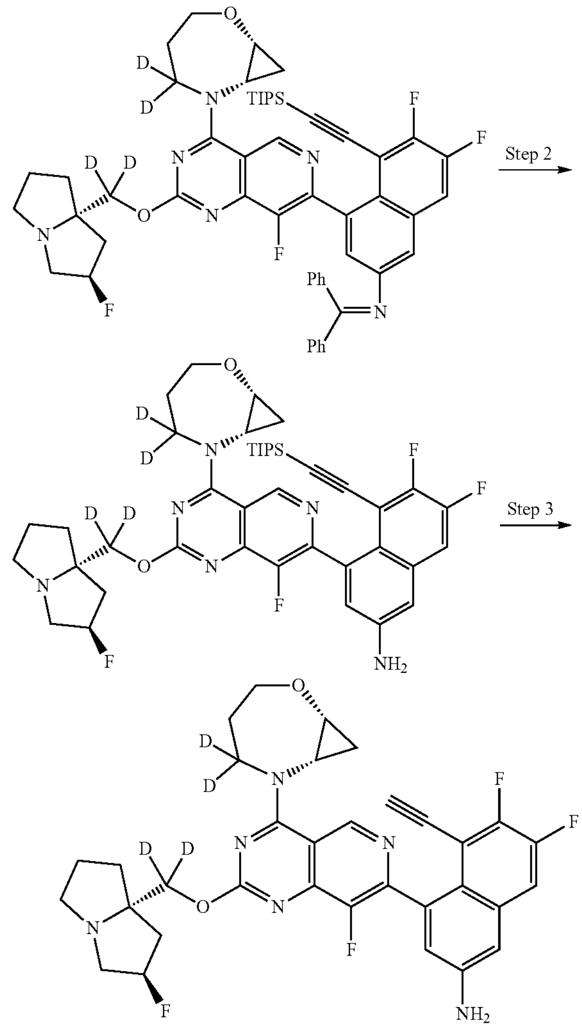

Example 26

Example 26 was prepared in a manner similar to Example 17. MS: m/z=623.20 $[M+H]^+$. $^1H$ NMR (400 MHZ, DMSO-$d_6$) δ 9.42-9.36 (m, 1H), 7.82-7.77 (m, 1H), 7.03-6.99 (m, 2H), 5.80 (s, 2H), 5.35-5.21 (m, 1H), 4.30-4.02 (m, 1H), 3.93-3.85 (m, 1H), 3.82-3.82 (m, 2H), 3.44-3.34 (m, 1H), 3.12-3.01 (m, 3H), 2.84-2.82 (m, 1H), 2.20-1.77 (m, 8H), 1.33-1.26 (m, 1H), 0.94-0.65 (m, 1H). $^{19}$F NMR (376 MHz, DMSO-$d_6$) δ −137.79--137.90 (m, 1F), −138.62--140.87 (m, 2F), −172.09--172.22 (d, 1F).

Example 27: 5-Ethynyl-6,7-difluoro-4-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)naphthalen-2-amine

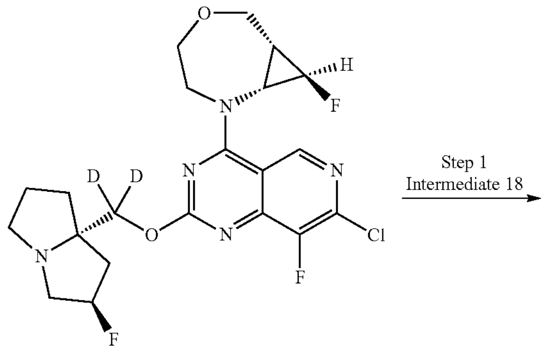

Intermediate 33

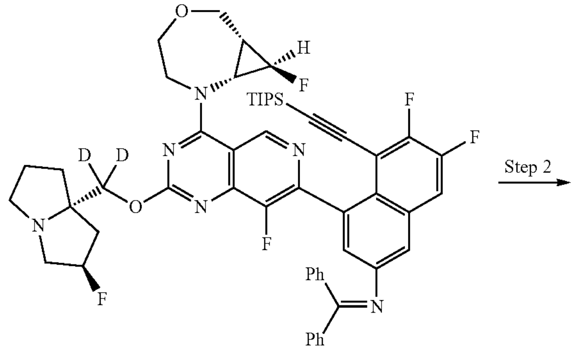

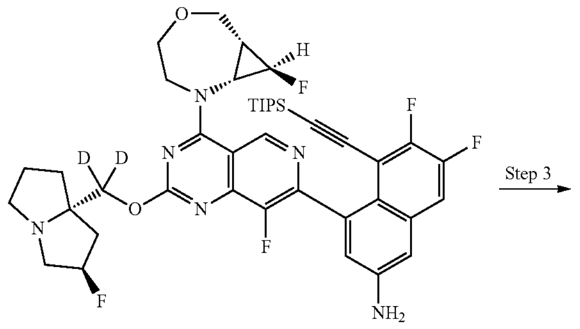

-continued

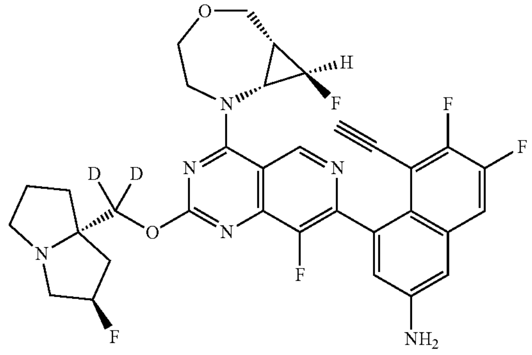

Example 27

Example 27 was prepared in a manner similar to Example 17. MS: m/z=639.40 [M+H]$^+$. $^1$H NMR (400 MHZ, DMSO-$d_6$) δ 9.49-9.32 (m, 1H), 7.83-7.78 (m, 1H), 7.02-7.00 (m, 2H), 5.82-5.81 (m, 2H), 5.34-5.21 (m, 1H), 4.95-4.73 (m, 1H), 4.51-4.02 (m, 5H), 3.74-3.57 (m, 2H), 3.32-2.95 (m, 4H), 2.85-2.82 (m, 1H), 2.40-2.30 (m, 1H), 2.17-1.96 (m, 3H), 1.91-1.70 (m, 3H). $^{19}$F NMR (376 MHz, DMSO-$d_6$) δ −137.67--140.51 (m, 3F), −172.10--172.21 (d, 1F), −207.8 (s, 1F).

Example 28: 5-Ethynyl-6,7-difluoro-4-(8-fluoro-4-((15,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)naphthalen-2-amine

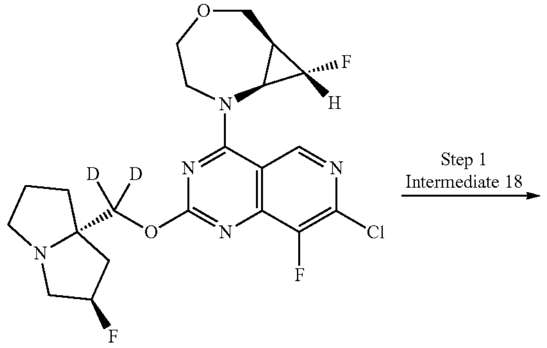

Intermediate 34

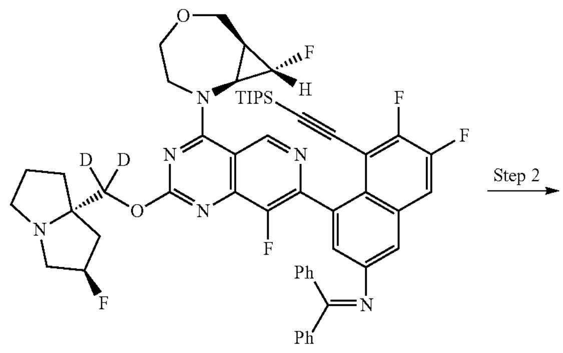

-continued

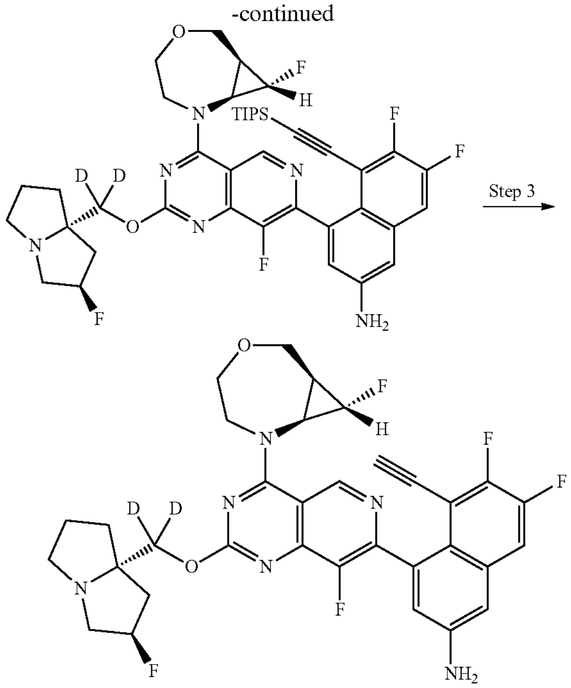

Example 28

Step 1: N-(6,7-Difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-yl)-1,1-diphenylmethanimine To a stirred mixture of Intermediate 34 (90 mg, 0.19 mmol) and Intermediate 18 (223.03 mg, 0.344 mmol) in THF (4 mL) and $H_2O$ (0.8 mL) were added CataCXium A Pd G3 (27.78 mg, 0.038 mmol) and $K_3PO_4$ (242.89 mg, 1.14 mmol) at room temperature under nitrogen atmosphere. The reaction mixture was heated at 80° C. for 3 hours. The resulting mixture was cooled to room temperature, diluted with $H_2O$ (20 mL) and extracted with DCM (3x30 mL). The combined organic layers were washed with brine (30 mL), dried over anhydrous $Na_2SO_4$, filtered and concentrated under reduced pressure. The residue was purified by Prep-TLC ($CH_2Cl$/MeOH 10: 1) to afford the title compound (180 mg, 98% yield) as a light yellow solid. MS: m/z=959.40 $[M+H]^{+\cdot}$ Step 2: 6,7-Difluoro-4-(8-fluoro-4-((15,75,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine To a solution of N-(6,7-difluoro-4-(8-fluoro-4-((15,75,8S)-8-fluoro-5-oxa-2-azabicyclo[5.1.0]octan-2-yl)-2-(((2R,7aS)-2-fluorotetrahydro-LH-pyrrolizin-7a (5H)-yl) methoxy-$d_2$)pyrido[4,3-d]pyrimidin-7-yl)-5-((triisopropylsilyl) ethynyl)naphthalen-2-yl)-1,1-diphenylmethanimine (195 mg, 0.20 mmol) in EtOH (2 mL) were added NaOAc (33.35 mg, 0.40 mmol) and $NH_2OH$·HCl (28.25 mg, 0.40 mmol) at room temperature. The reaction mixture was stirred at room temperature for 2 hours. The resulting mixture was diluted with brine (50 mL), extracted with ethyl acetate (3x70 mL). The combined organic layers were dried over anhydrous sodium sulfate, filtered and concentrated under reduced pressure. The residue was purified by silica gel flash chromatography, eluted with 4% MeOH in DCM to afford the title compound (135 mg, 83% yield) as a yellow solid. MS: m/z=795.40 $[M+H]^{+\cdot}$ Step 3: 5-Ethynyl-6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine To a stirred solution of 6,7-difluoro-4-(8-fluoro-4-((1S,75,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine (135 mg, 0.17 mmol) in DMF (1 mL) was added CsF (386.93 mg, 2.55 mmol) at room temperature. The reaction mixture was stirred at room temperature for 3 hours. The resulting mixture was filtered and purified by RP-Flash directly with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 54% B in 15 min, 54% B to 54% B in 3 min, 54% B to 95% B in 4 min; Detector: UV 254 & 210 nm. The collected fractions were combined, concentrated and then lyophilized overnight to give the title compound (Example 28, 78.9 mg, 72% yield) as a yellow lyophilized powder. MS: m/z=639.15 $[M+H]^+$. JH NMR (400 MHZ, DMSO-$d_6$) δ 9.43-9.37 (m, 1H), 7.83-7.78 (m, 1H), 7.03-7.00 (m, 2H), 5.82-5.81 (m, 2H), 5.35-5.21 (m, 1H), 4.88-4.73 (m, 1H), 4.51-4.47 (m, 1H), 4.41-4.32 (m, 2H), 4.24-4.01 (m, 2H), 3.75-3.60 (m, 2H), 3.30-2.95 (m, 4H), 2.86-2.81 (m, 1H), 2.42-2.26 (m, 1H), 2.10-1.64 (m, 6H). $^{19}F$ NMR (376 MHz, DMSO-$d_6$) δ −137.66−−140.51 (m, 3F), −172.06−−172.18 (d, 1F), 207.72 (s, 1F).

Example 29: 5-Ethynyl-6,7-difluoro-4-(8-fluoro-4-((1R,7R,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d] pyrimidin-7-yl)naphthalen-2-amine

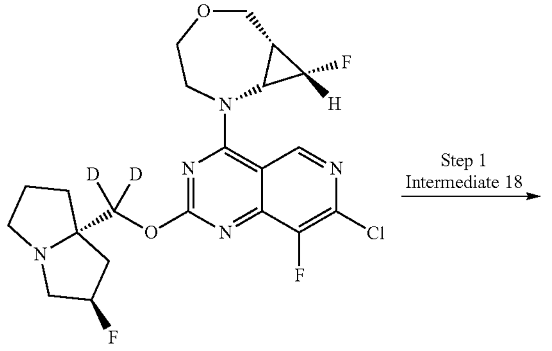

Intermediate 35

-continued

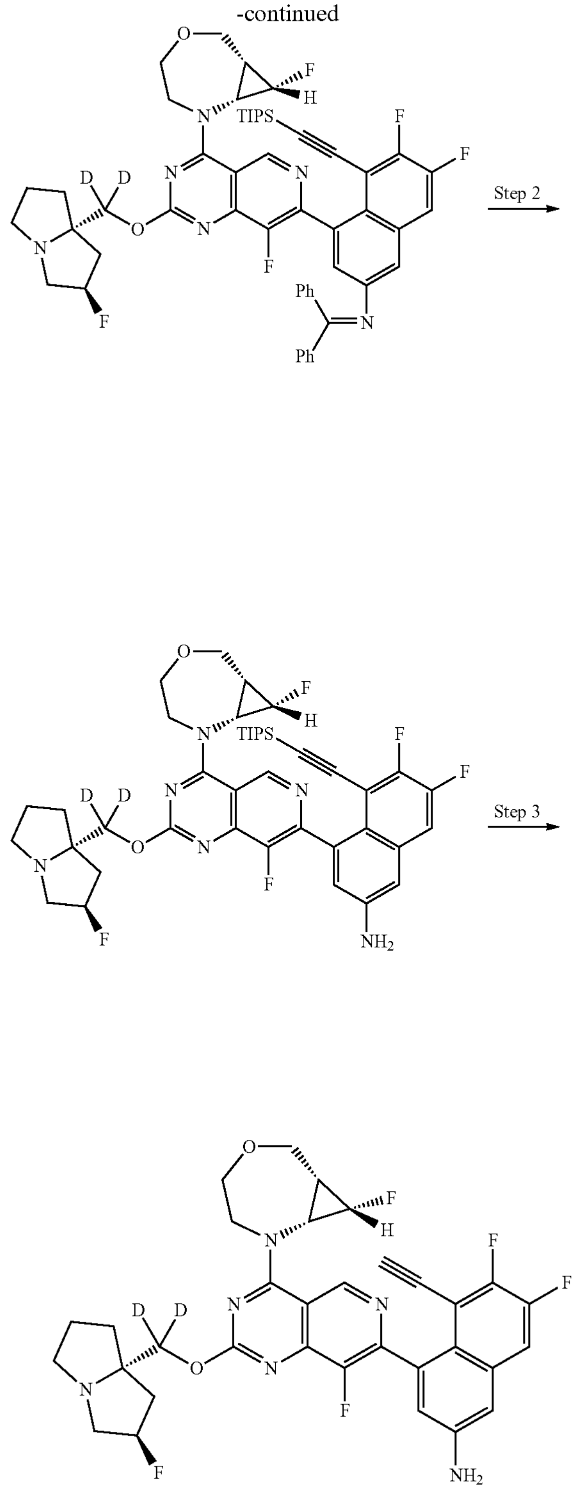

Example 29

Example 29 was prepared in a manner similar to Example 28. MS: m/z=639.15 $[M+H]^+$. $^1H$ NMR (400 MHZ, DMSO-$d_6$) δ 9.73-9.57 (m, 1H), 7.84-7.79 (m, 1H), 7.03-6.93 (m, 2H), 5.82-5.80 (m, 2H), 5.35-5.21 (m, 1H), 5.14-4.97 (m, 1H), 4.64-4.50 (m, 1H), 4.32-4.12 (m, 2H), 4.04-3.33 (m, 5H), 3.17-2.95 (m, 3H), 2.89-2.76 (m, 1H), 2.38-1.69 (m, 7H). $^{19}F$ NMR (376 MHz, DMSO-$d_6$) δ −137.55-−140.11 (m, 3F), −172.09-−172.17 (d, 1F).

Example 30: 5-Ethynyl-6, 7-difluoro-4-(8-fluoro-4-((1S,7S,8R)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)naphthalen-2-amine

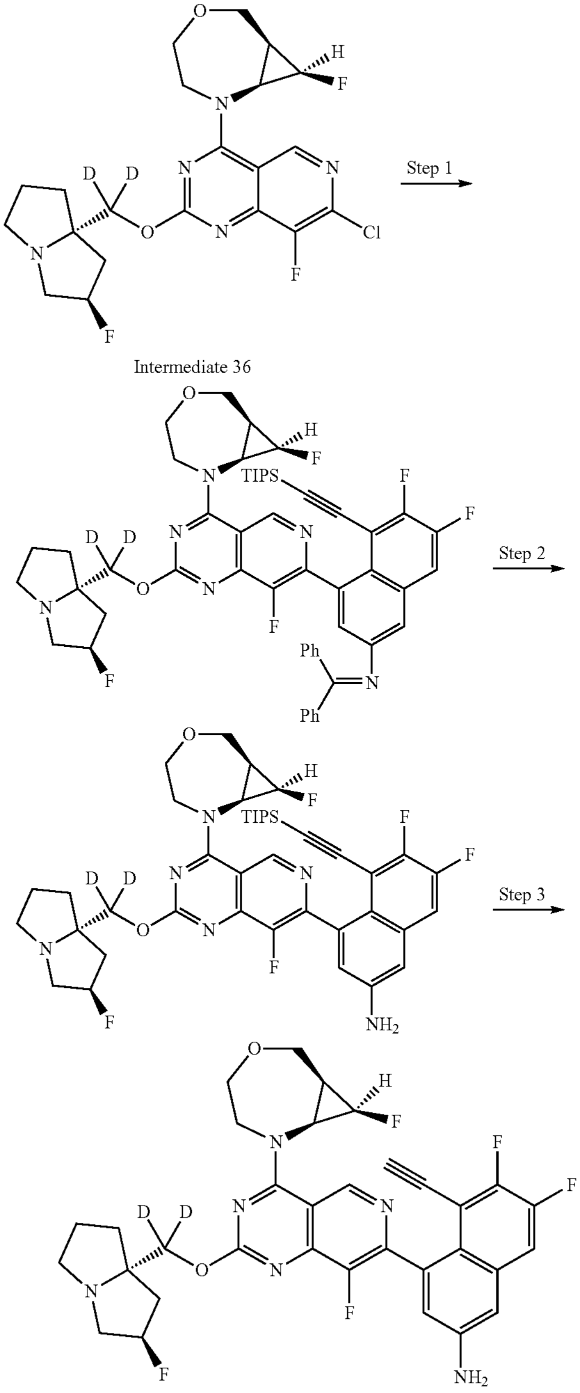

Example 30

Example 29 was prepared in a manner similar to Example 28. MS: m/z=639.10 $[M+H]^+$. $^1H$ NMR (400 MHZ, DMSO-$d_6$) δ 9.73-9.57 (m, 1H), 7.83-7.79 (m, 1H), 7.03-7.00 (m, 2H), 5.83-5.80 (m, 2H), 5.36-5.23 (m, 1H), 5.14-4.97 (m, 1H), 4.55-4.51 (m, 1H), 4.32-4.24 (m, 1H), 4.19-4.10 (m, 1H), 4.02-3.33 (m, 5H), 3.21-2.96 (m, 3H), 2.90-2.82 (m, 1H), 2.27-1.68 (m, 7H). $^{19}F$ NMR (376 MHz, DMSO-$d_6$) δ −137.54--140.11 (m, 3F), −172.08--172.18 (d, 1F). (missing F).

Example 31: 4-(4-((1R,6S)-2-Oxa-5-azabicyclo[4.1.0]heptan-5-yl)-8-fluoro-2-(((2R,7aS)-2-fluoro-tetrahydro-1H-pyrrolizin-7a (5H)-yl)methoxy-$d_2$)pyrido[4,3-d]pyrimidin-7-yl)-5-ethynyl-6,7-difluoronaphthalen-2-amine

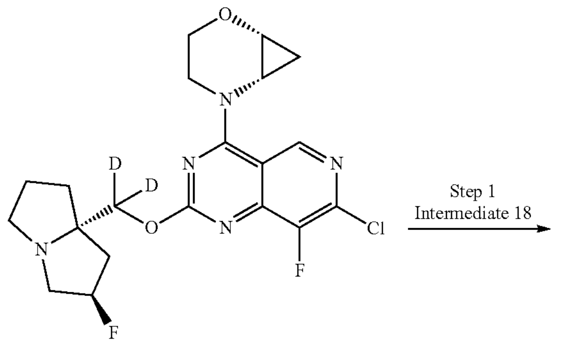

Intermediate 37

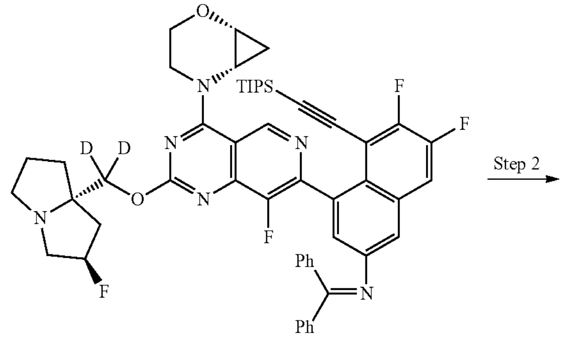

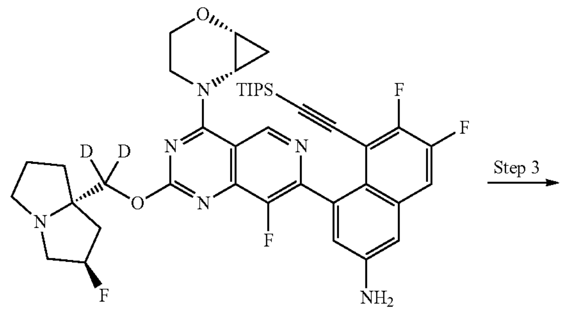

-continued

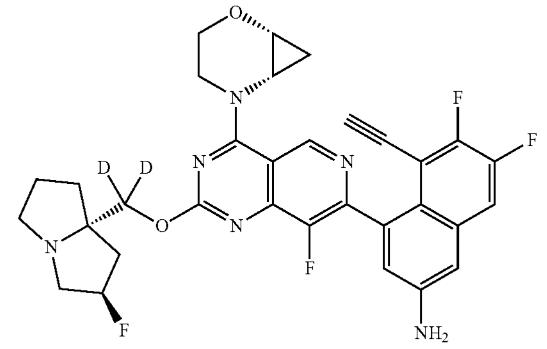

Example 31

Example 31 was prepared in a manner similar to Example 28. MS: m/z=607.20 [M+H]$^+$. $^1H$ NMR (400 MHZ, DMSO-$d_6$) δ 9.72-9.68 (m, 1H), 7.81-7.76 (m, 1H), 7.04-6.99 (m, 2H), 5.80 (s, 2H), 5.35-5.21 (m, 1H), 4.17-3.86 (m, 5H), 3.50-3.33 (m, 2H), 3.10-3.02 (m, 3H), 2.86-2.80 (m, 1H), 2.12-2.00 (m, 3H), 1.90-1.76 (m, 3H), 1.26-1.09 (m, 2H). $^{19}F$ NMR (376 MHz, DMSO-$d_6$) δ −137.72--137.89 (m, 1F), −138.59--138.67 (m, 1F), −139.74--139.92 (m, 1F), −172.10--172.21 (m, 1F).

Example 32: 4-(4-((15,6R)-2-Oxa-5-azabicyclo[4.1.0]heptan-5-yl)-8-fluoro-2-(((2R,7aS)-2-fluoro-tetrahydro-1H-pyrrolizin-7a (5H)-yl)methoxy-$d_2$)pyrido[4,3-d]pyrimidin-7-yl)-5-ethynyl-6,7-difluoronaphthalen-2-amine

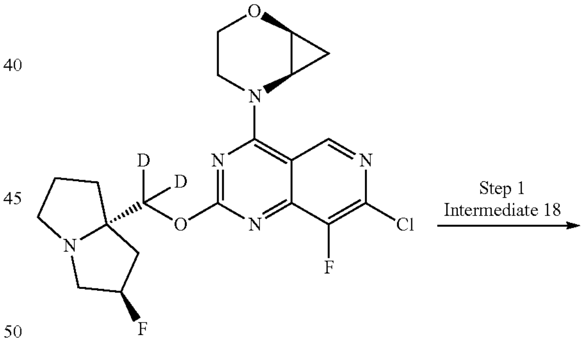

Intermediate 38

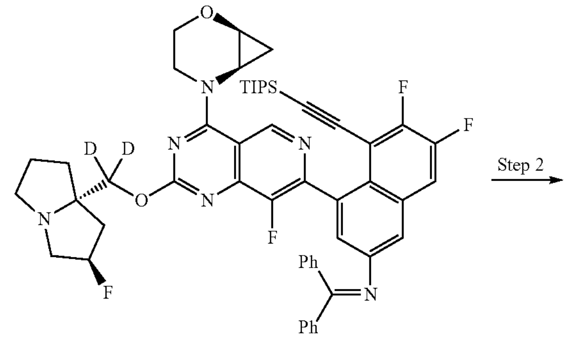

-continued

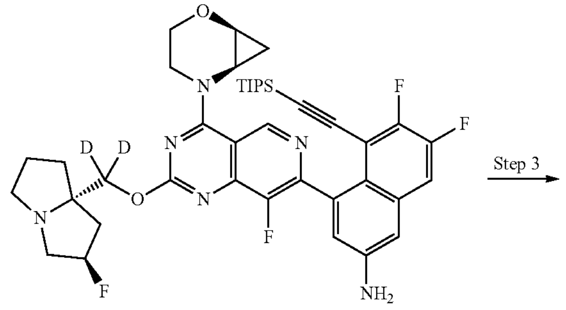

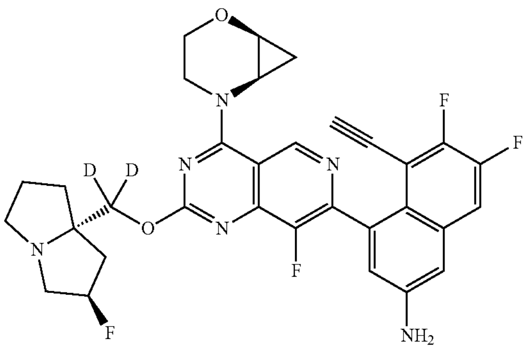

Example 32

Example 32 was prepared in a manner similar to Example 28. MS: m/z=607.20 $[M+H]^+$. $^1H$ NMR (400 MHZ, DMSO-$d_6$) δ 9.74-9.68 (m, 1H), 7.82-7.77 (m, 1H), 7.04-6.99 (m, 2H), 5.80 (s, 2H), 5.35-5.21 (m, 1H), 4.22-3.84 (m, 5H), 3.50-3.34 (m, 2H), 3.16-3.01 (m, 3H), 2.84-2.82 (m, 1H), 2.12-1.95 (m, 3H), 1.91-1.72 (m, 3H), 1.26-1.09 (m, 2H). $^{19}F$ NMR (376 MHz, DMSO-$d_6$) δ −137.74--137.88 (m, 1F), −138.59--139.96 (m, 2F), −172.08--172.21 (d, 1F).

Example 33: 4-(4-((1R,7S)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)-5-methoxypyrido[4,3-d]pyrimidin-7-yl)-5-ethynyl-6,7-difluoronaphthalen-2-amine

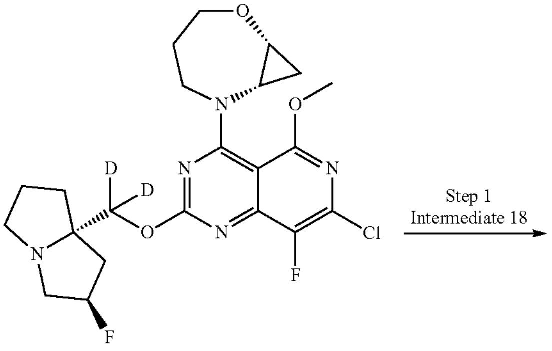

Intermediate 39

-continued

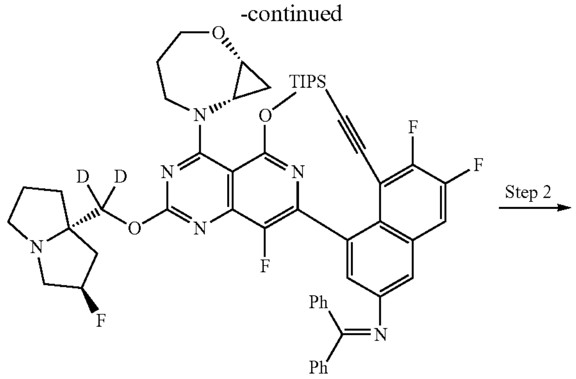

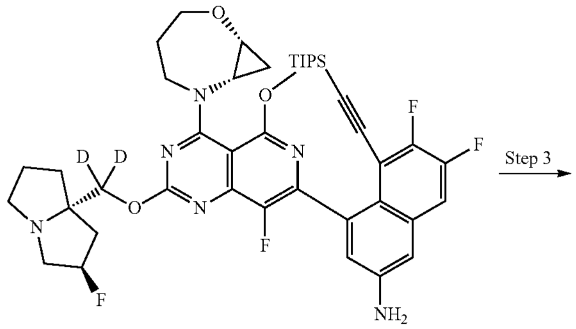

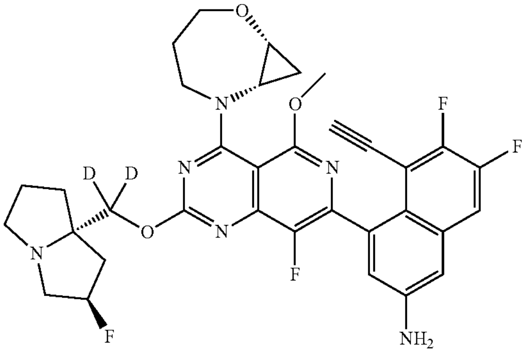

Example 33

Example 33 was prepared in a manner similar to Example 28. MS: m/z=651.30 $[M+H]^+$. $^1H$ NMR (400 MHZ, DMSO-$d_6$) δ 7.81-7.76 (m, 1H), 7.07-6.98 (m, 2H), 5.79 (s, 2H), 5.34-5.21 (m, 1H), 4.58-4.15 (m, 2H), 3.89-3.85 (m, 4H), 3.75-3.65 (m, 1H), 3.60-3.51 (m, 2H), 3.19-3.00 (m, 4H), 2.87-2.80 (m, 1H), 2.40-2.25 (m, 1H), 2.14-1.95 (m, 3H), 1.91-1.72 (m, 4H), 0.94-0.80 (m, 1H), 0.50-0.15 (m, 1H). $^{19}F$ NMR (376 MHz, DMSO-$d_6$) δ −137.46--137.60 (m, 1F), −138.63--138.70 (m, 1F), −149.38--150.75 (m, 1F), −172.08--172.17 (m, 1F).

Example 34: 4-(4-((1S,7R)-2-Oxa-6-azabicyclo[5.1.0]octan-6-yl)-8-fluoro-2-(((2R,7aS)-2-fluorotetrahydro-1/H-pyrrolizin-7a (5H)-yl)methoxy-$d_2$)-5-methoxypyrido[4,3-d]pyrimidin-7-yl)-5-ethynyl-6,7-difluoronaphthalen-2-amine

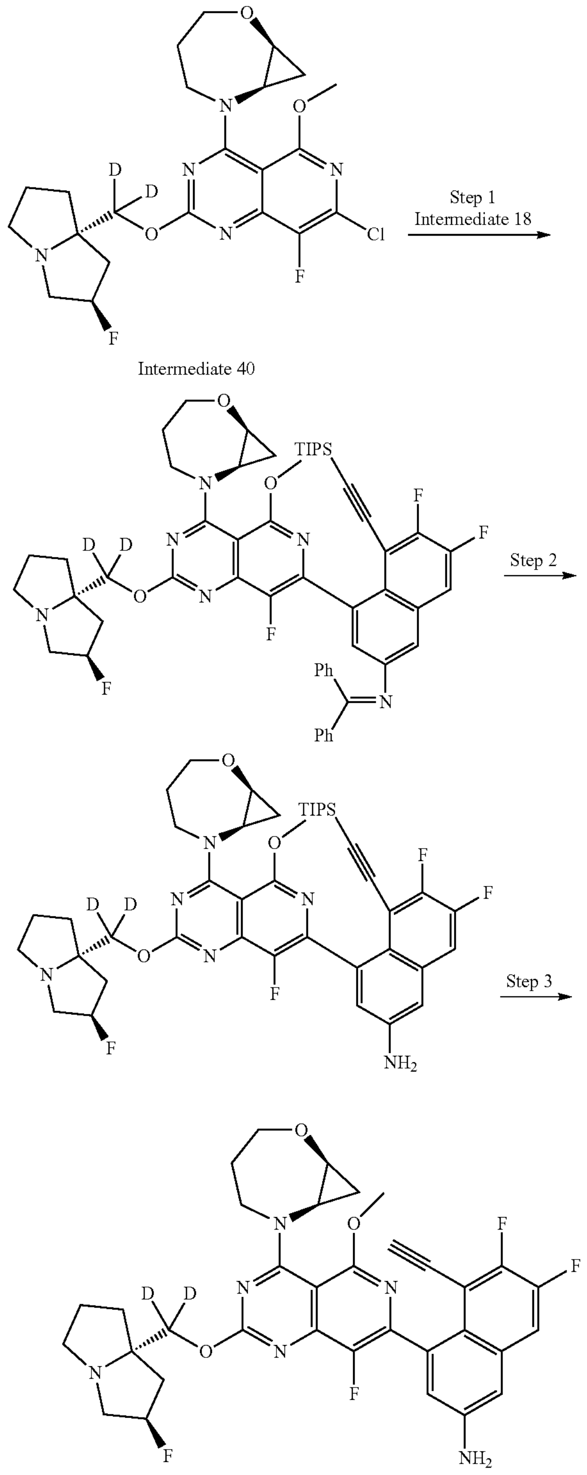

Example 34

Step 1: N-(4-(4-((1S,7R)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)-5-methoxypyrido[4,3-d]pyrimidin-7-yl)-6,7-difluoro-5-((triisopropylsilyl) ethynyl)naphthalen-2-yl)-1,1-diphenylmethanimine To a mixture of Intermediate 40 (70 mg, 0.14 mmol) and Intermediate 18 (206.75 mg, 0.31 mmol) in THF (3.5 mL) and $H_2O$ (0.7 mL) were added CataCXium A Pd G3 (21.07 mg, 0.03 mmol) and $K_3PO_4$ (184.22 mg, 0.87 mmol) at room temperature under nitrogen atmosphere. The reaction mixture was heated at 80° C. for 3 hours. The resulting mixture was cooled to room temperature, filtered and concentrated under reduced pressure. The residue was purified by silica gel flash chromatography, eluted with 4% methanol in dichloromethane to afford the title compound (90 mg, 64% yield) as a yellow solid. MS: m/z=971.45 $[M+H]^{+\cdot}$ Step 2: 4-(4-((1S,7R)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)-5-methoxypyrido[4,3-d]pyrimidin-7-yl)-6,7-difluoro-S-((triisopropylsilyl) ethynyl)naphthalen-2-amine To a solution of N-(4-(4-((1S,7R)-2-oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)-5-methoxypyrido[4,3-d]pyrimidin-7-yl)-6,7-difluoro-5-((triisopropylsilyl) ethynyl)naphthalen-2-yl)-1,1-diphenylmethanimine (85 mg, 0.08 mmol) in EtOH (2 mL) were added NaOAc (14.36 mg, 0.17 mmol) and $NH_2OH{\cdot}HCl$ (12.16 mg, 0.17 mmol) at room temperature under nitrogen atmosphere. The reaction mixture was stirred at room temperature for 1 hour. The resulting mixture was diluted with water (20 mL), and extracted with BA (3x30 mL). The combined organic layers were dried over anhydrous $Na_2SO_4$, filtered and concentrated under reduced pressure. The residue was purified by silica gel flash chromatography, eluted with 9% methanol in dichloromethane to afford the title compound (50 mg, 70% yield) as a yellow solid. MS: m/z=807.35 $[M+H]^{+\cdot}$ Step 3: 4-(4-((1S,7R)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)-5-methoxypyrido[4,3-d]pyrimidin-7-yl)-5-ethynyl-6,7-difluoronaphthalen-2-amine To a stirred solution of 4-(4-((1S,7R)-2-oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)-5-methoxypyrido[4,3-d]pyrimidin-7-yl)-6,7-difluoro-5-((triisopropylsilyl) ethynyl)naphthalen-2-amine (50 mg, 0.06 mmol) in DMF (2 mL) was added CsF (141.17 mg, 0.93 mmol) at room temperature. The reaction mixture was stirred at room temperature for 1 hour. The resulting mixture was filtered and purified by RP-Flash directly with the following conditions: Column, C18; Mobile phase A: 5 mM aq. $NH_4HCO_3$; Mobile phase B: MeCN; Gradient: 5% B~95% B in 40 min, 63% B hold 3 min; Flow rate: 20 mL/min; Detector UV: 254 & 210 nm. The collected fractions were combined, concentrated and then lyophilized overnight to give the title compound (Example 34, 19.2 mg, 46% yield) as a yellow lyophilized powder. MS: m/z=651.10 $[M+H]^+$. $^1H$ NMR (400 MHz, DMSO-$d_6$) δ 7.81-7.76 (m, 1H), 7.08-6.98 (m, 2H), 5.79 (s, 2H), 5.36-5.23 (m, 1H), 4.47-4.40 (m, 1H), 4.27-4.13 (m, 1H), 3.91-3.85 (m, 4H), 3.72-3.68 (m, 1H), 3.58-3.52 (m, 2H), 3.18-3.04 (m, 4H), 2.90-2.80 (m, 1H), 2.33-1.75 (m, 8H), 0.94-0.85 (m, 1H), 0.55-0.15 (m, 1H). $^{19}F$ NMR (376 MHz, DMSO-$d_6$) δ −137. 46−−137.58 (m, 1F), −138. 63−−138.71 (m, 1F), −149.36−−150.69 (d, 1F), −172.07−−172.17 (d, 1F).

Example 35: 4-(4-((1R,7S)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)-5-methoxypyrido[4,3-d]pyrimidin-7-yl)-5-ethynyl-6-fluoronaphthalen-2-ol

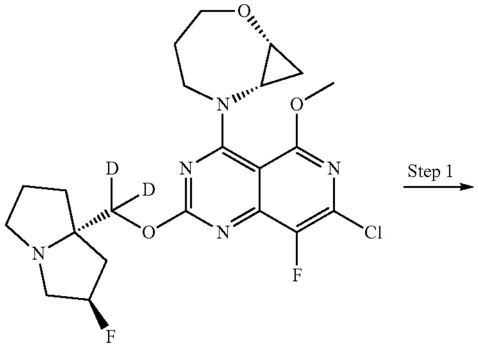

Intermediate 39

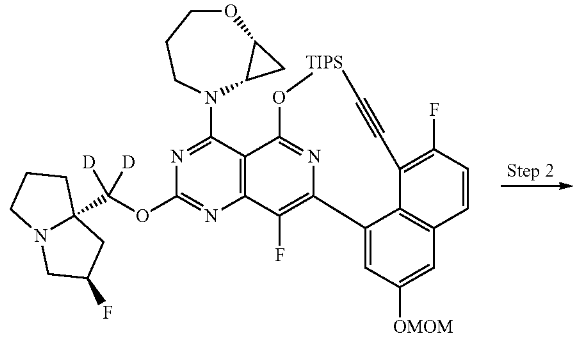

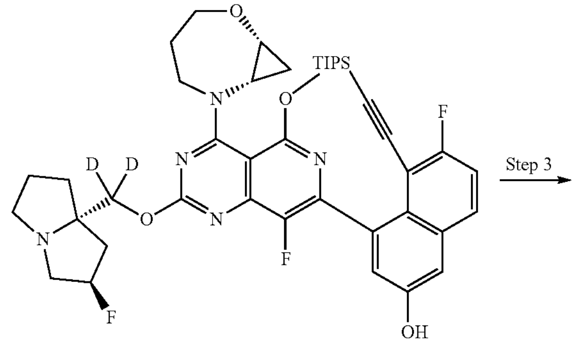

-continued

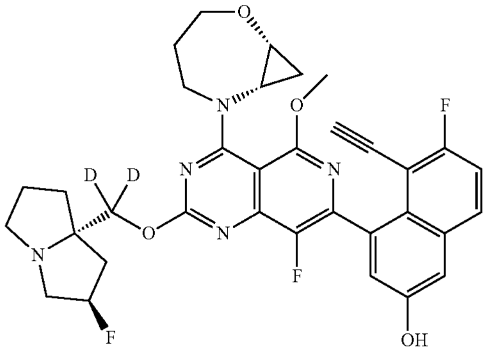

Example 35

Example 35 was prepared in a manner similar to Example 34. MS: m/z=634.30 [M+H]$^+$. $^1H$ NMR (400 MHZ, Methanol-$d_4$) δ 7.85-7.81 (m, 1H), 7.33-7.14 (m, 3H), 5.40-5.27 (m, 1H), 4.70-4.60 (m, 1H), 4.10-3.91 (m, 4H), 3.89-3.70 (m, 1H), 3.60-3.20 (m, 5H), 3.16-3.00 (m, 1H), 2.55-2.10 (m, 4H), 2.10-1.87 (m, 3H), 1.81-1.62 (m, 1H), 1.10-0.80 (m, 2H), 0.62-0.28 (m, 1H). $^{19}F$ NMR (376 MHz, Methanol-$d_4$) δ −111.74−−111.99 (m, 1F), −115.65−−115.75 (m, 1F), −173.62−−173.80 (m, 1F).

Example 36: 4-(4-((1S,7R)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)-5-methoxypyrido[4,3-d]pyrimidin-7-yl)-5-ethynyl-6-fluoronaphthalen-2-ol

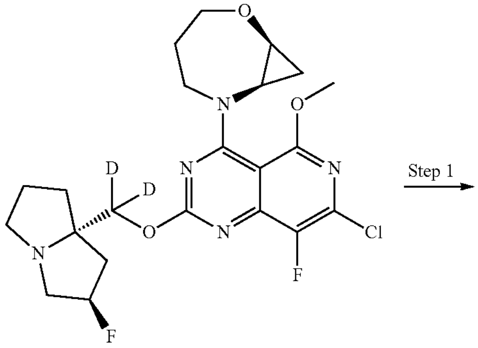

Intermediate 40

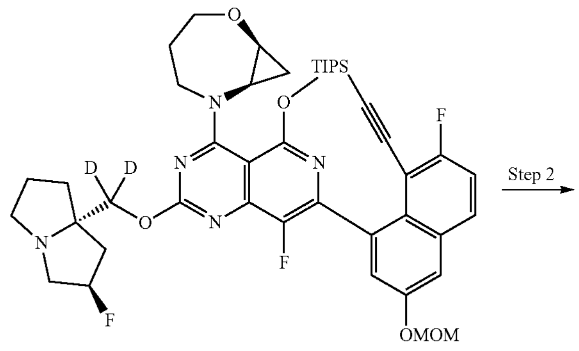

-continued

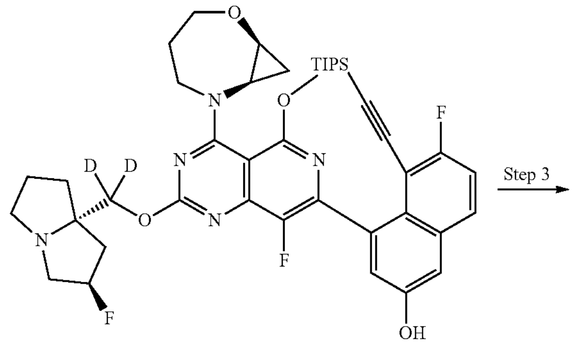

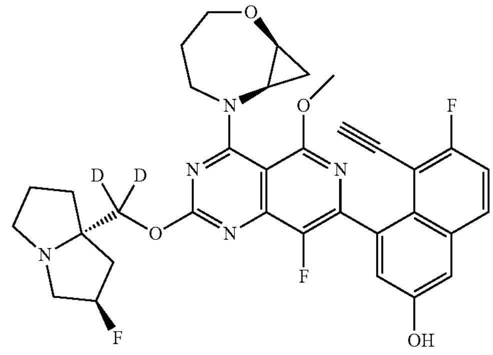

Example 36

Example 36 was prepared in a manner similar to Example 34. MS: m/z=634.15 $[M+H]^+$. $^1H$ NMR (400 MHZ, DMSO-$d_6$) δ 10.19-10.10 (m, 1H), 8.00-7.96 (m, 1H), 7.50-7.45 (m, 1H), 7.38-7.16 (m, 2H), 5.35-5.21 (m, 1H), 4.50-4.47 (m, 1H), 4.14-4.02 (m, 1H), 3.88-3.82 (m, 4H), 3.74-3.68 (m, 1H), 3.58-3.51 (m, 2H), 3.18-3.01 (m, 4H), 2.86-2.82 (m, 1H), 2.45-2.30 (m, 1H), 2.20-2.04 (m, 3H), 1.90-1.72 (m, 4H), 1.00-0.90 (m, 1H), 0.48-0.24 (m, 1H). $^{19}F$ NMR (376 MHz, DMSO-$d_6$) δ −110.52-−110.57 (m, 1F), −149.26, −150.68 (d, 1F), −172.04-−172.15 (d, 1F).

Example 37: 5-Ethynyl-6,7-difluoro-4-(8-fluoro-4-((15,6R,7S)-7-fluoro-2-oxa-5-azabicyclo[4.1.0]heptan-5-yl)-2-(((2R,7aS)-2-fluorotetrahydro-1H-pyrrolizin-7a (5H)-yl)methoxy-$d_2$)pyrido[4,3-d] pyrimidin-7-yl)naphthalen-2-amine

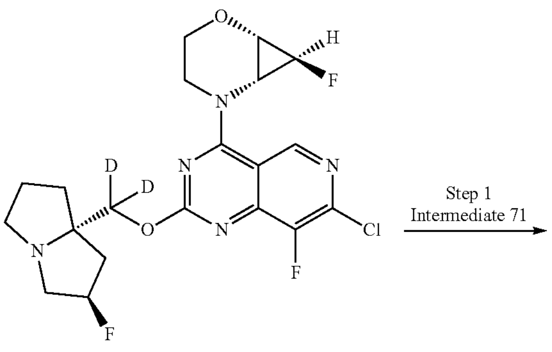

Intermediate 43

-continued

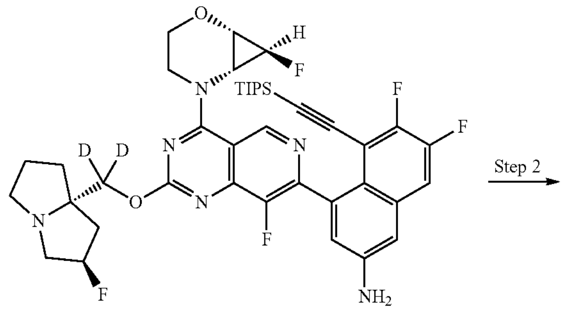

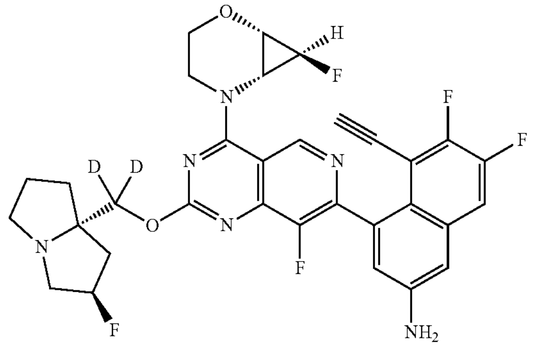

Example 37

Example 37 was prepared in a manner similar to Example 21. MS: m/z=625.20 $[M+H]^+$. $^1H$ NMR (400 MHZ, DMSO-$d_6$) δ 9.49 (s, 1H), 7.83-7.78 (m, 1H), 7.04-7.00 (m, 2H), 5.82 (s, 2H), 5.47-5.17 (m, 2H), 4.47-4.41 (m, 1H), 4.24-4.00 (m, 3H), 3.88-3.85 (m, 2H), 3.46-3.43 (m, 1H), 3.21-2.80 (m, 4H), 2.15-1.99 (m, 3H), 1.91-1.75 (m, 3H). $^{19}F$ NMR (376 MHz, DMSO-$d_6$) δ −137.66-−137.81 (m, 1F), −138.55-−138.62 (m, 1F), −139.35-−139.55 (d, 1F), −172.16-−172.27 (d, 1F), −217.73-−218.34 (m, 1F).

Example 38: 5-Ethynyl-6, 7-difluoro-4-(8-fluoro-4-((1R,65,7R)-7-fluoro-2-oxa-5-azabicyclo[4.1.0]heptan-5-yl)-2-(((2R,7aS)-2-fluorotetrahydro-1H-pyrrolizin-7a (5H)-yl)methoxy-$d_2$)pyrido[4,3-d] pyrimidin-7-yl)naphthalen-2-amine

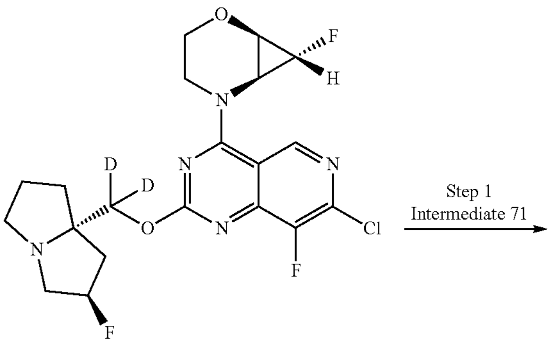

Intermediate 44

-continued

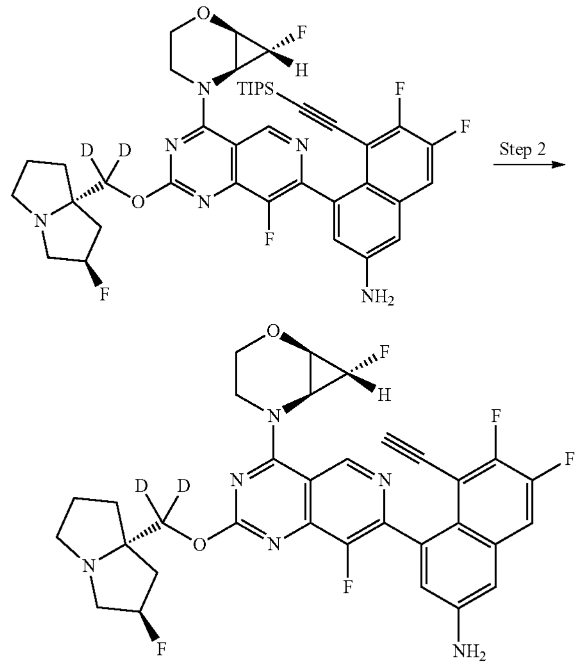

Example 38

Example 38 was prepared in a manner similar to Example 21. MS: m/z=625.20 $[M+H]^+$. $^1H$ NMR (400 MHZ, DMSO-$d_6$) δ 9.48 (s, 1H), 7.83-7.78 (m, 1H), 7.04-7.00 (m, 2H), 5.81 (s, 2H), 5.47-5.17 (m, 2H), 4.44-4.41 (m, 1H), 4.30-4.00 (m, 3H), 3.88-3.85 (m, 2H), 3.46-3.40 (m, 1H), 3.10-3.01 (m, 3H), 2.88-2.82 (m, 1H), 2.20-1.76 (m, 6H). $^{19}F$ NMR (376 MHz, DMSO-$d_6$) δ −137.80--137.68 (m, 1F), −138.56--138.62 (d, 1F), −139.34--139.59 (d, 1F), −172.09--172.21 (d, 1F), −217.74--218.35 (d, 1F).

Example 39: 4-(4-((1S,7R)-2-Oxa-6-azabicyclo [5.1.0]octan-6-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-2-amino-7-fluorobenzo [b]thiophene-3-carbonitrile

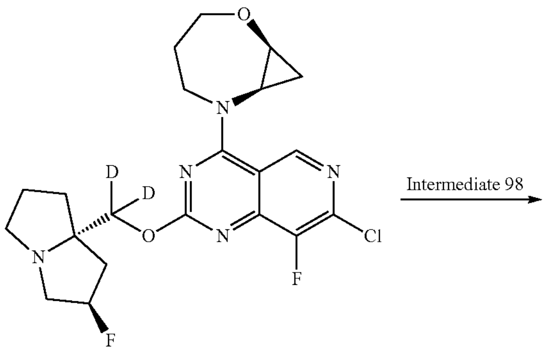

Intermediate 5

-continued

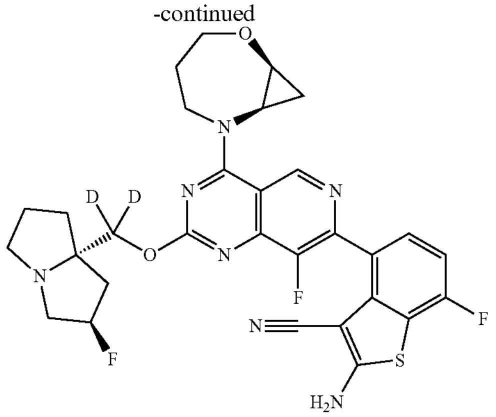

Example 39

To a stirred mixture of Intermediate 5 (150 mg, 0.33 mmol) and 2-amino-7-fluoro-4-(4,4,5,5-tetramethyl-1,3,2-dioxaborolan-2-yl)-1-benzothiophene-3-carbonitrile (136.68 mg, 0.42 mmol) in toluene (7.5 mL) and $H_2O$ (1.5 mL) were added $[AMPhosPdCl_2]_2$ (29.26 mg, 0.03 mmol) and $Cs_2CO_3$ (215.34 mg, 0.66 mmol) at room temperature under nitrogen atmosphere. The reaction mixture was heated at 95° C. for 16 hours. The resulting mixture was cooled to room temperature, filtered and concentrated under reduced pressure. The residue was purified by silica gel flash chromatography, eluted with DCM/MeOH (15: 1) to afford crude product. The crude product was purified by RP-Flash with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 54% B in 15 min, 54% B to 54% B in 3 min, 54% B to 95% B in 4 min; Detector: UV 254 & 210 nm. The collected fractions were combined, concentrated and lyophilized overnight to give the title compound (Example 39, 31.1 mg, 15% yield) as an off-white lyophilized powder. MS: m/z=610.20 $[M+H]^+$. $^1H$ NMR (400 MHz, DMSO-$d_6$) δ 9.40 (s, 1H), 8.09 (s, 2H), 7.44-7.40 (m, 1H), 7.17-7.12 (m, 1H), 5.35-5.22 (m, 1H), 4.56-4.51 (m, 1H), 3.88-3.83 (m, 1H), 3.81-3.70 (m, 2H), 3.60-3.51 (m, 1H), 3.45-3.43 (m, 1H), 3.10-3.01 (m, 3H), 2.86-2.80 (m, 1H), 2.20-1.70 (m, 8H), 1.32-1.23 (m, 1H), 0.60-0.58 (m, 1H). $^{19}F$ NMR (400 MHZ, DMSO-$d_6$) δ −116.27 (s, 1F), −140.90 (s, 1F), −172.08 (s, 1F).

Example 40: 4-(4-((1R,7S)-2-Oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-2-amino-7-fluorobenzo[b]thiophene-3-carbonitrile

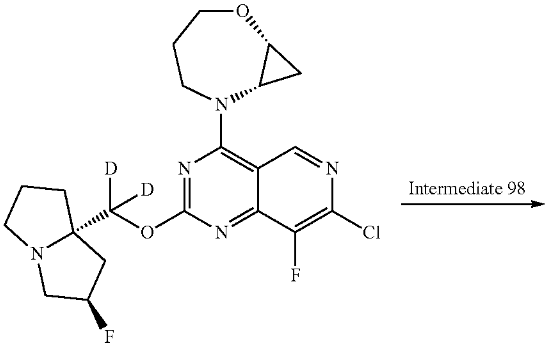

Intermediate 4

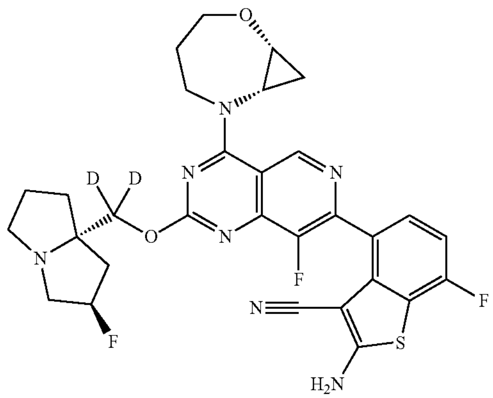

Example 40

Example 40 was prepared in a manner similar to Example 39. MS: m/z=610.20 $[M+H]^+$. $^1H$ NMR (400 MHZ, DMSO-$d_6$) δ 9.40 (s, 1H), 8.09 (s, 2H), 7.43-7.40 (m, 1H), 7.17-7.12 (m, 1H), 5.35-5.21 (m, 1H), 4.54-4.50 (m, 1H), 3.90-3.86 (m, 1H), 3.82-3.69 (m, 2H), 3.63-3.58 (m, 1H), 3.45-3.43 (m, 1H), 3.10-3.02 (m, 3H), 2.85-2.80 (m, 1H), 2.20-1.99 (m, 4H), 1.91-1.76 (m, 4H), 1.32-1.30 (m, 1H), 0.60-0.58 (m, 1H). $^{19}F$ NMR (400 MHz, DMSO-$d_6$) δ −116.27 (s, 1F), −140.92 (s, 1F), −172.13 (s, 1F).

Example: 41: 6,7,8-Trifluoro-4-(8-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-(methoxy-$d_3$)naphthalen-2-amine

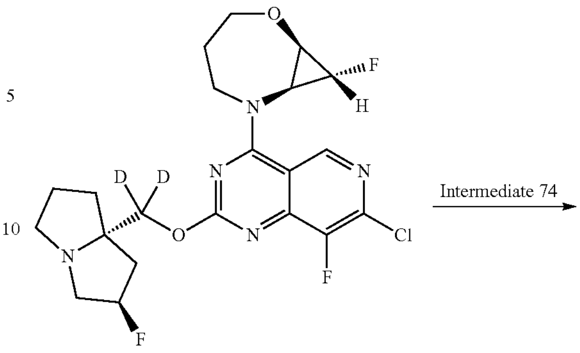

Intermediate 34

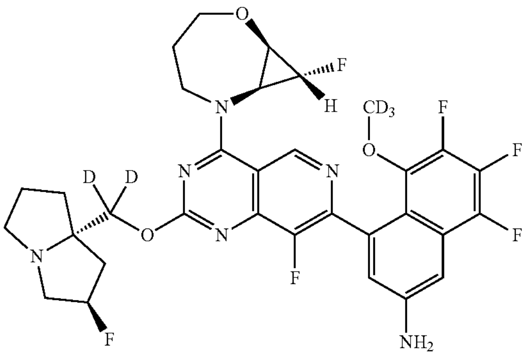

Example 41

To a mixture of Intermediate 34 (120 mg, 0.25 mmol) and Intermediate 74 (181.14 mg, 0.50 mmol) in THE (5 mL) and $H_2O$ (1 mL) under nitrogen atmosphere were added Cat-aCXium A Pd G3 (37.04 mg, 0.05 mmol) and $K_3PO_4$ (323.86 mg, 1.52 mmol) at room temperature. The reaction mixture was heated at 80° C. for 3 hours. The resulting mixture was cooled to room temperature, filtered, and concentrated under reduced pressure. The residue was purified by silica gel flash chromatography, eluted with 10% MeOH in DCM to afford a crude product. The crude product was purified by RP-Flash with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 61% B in 15 min, 61% B to 61% B in 3 min, 61% B to 95% B in 4 min; Detector: UV 254 & 210 nm. The collected fractions were combined, concentrated and lyophilized overnight to give the title compound (Example 41, 40.3 mg, 23% yield) as an off-white lyophilized powder. MS: m/z=666.20 $[M+H]^+$. JH NMR (400 MHz, DMSO-$d_6$) δ 9.45-9.40 (m, 1H), 7.05-6.98 (m, 2H), 6.03-6.00 (m, 2H), 5.35-5.21 (m, 1H), 4.96-4.77 (m, 1H), 4.52-4.29 (m, 3H), 4.02-3.99 (m, 1H), 3.73-3.59 (m, 2H), 3.33-3.24 (m, 1H), 3.09-3.00 (m, 3H), 2.85-2.81 (m, 1H), 2.42-2.30 (m, 1H), 2.20-1.92 (m, 3H), 1.90-1.74 (m, 3H). $^{19}F$ NMR (376 MHZ, DMSO-$d_6$) δ −140.61−-140.92 (m, 2F), −154.09−-154.18 (m, 1F), −160.99−-161.06 (m, 1F), −172.12−-172.17 (d, 1F), −207.63−-208.00 (m, 1F).

Example 42: (1S,75,8S)-2-(7-(8-Ethynyl-6,7-difluoronaphthalen-1-yl)-8-fluoro-2-(((2R,7aS)-2-fluorotetrahydro-1H-pyrrolizin-7a (5H)-yl)methoxy-$d_2$) pyrido[4,3-d]pyrimidin-4-yl)-8-fluoro-5-oxa-2-azabicyclo[5.1.0]octane

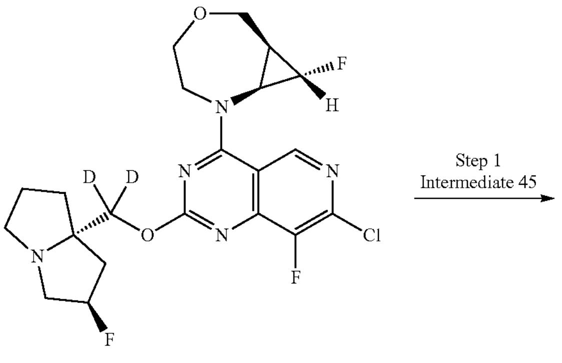

Intermediate 34

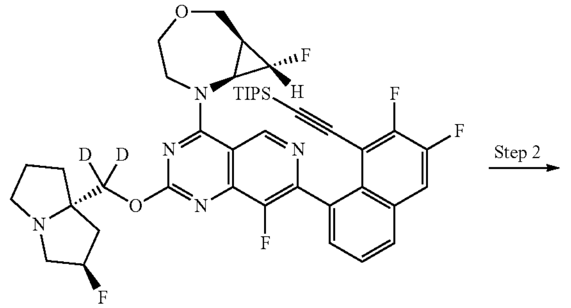

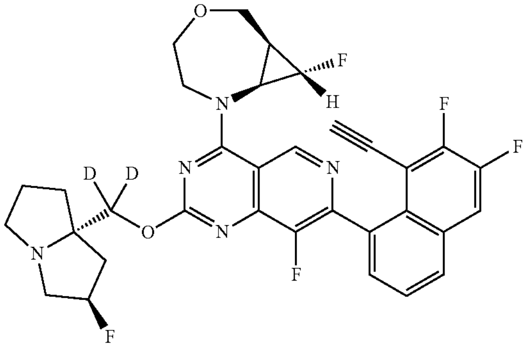

Example 42

Step 1: (15,7S,8S)-2-(7-(6,7-difluoro-8-((triisopropylsilyl) ethynyl)naphthalen-1-yl)-8-fluoro-2-(((2R, 7aS)-2-fluorotetrahydro-1H-pyrrolizin-7a (5H)-yl) methoxy-$d_2$)pyrido[4,3-d]pyrimidin-4-yl)-8-fluoro-5-oxa-2-azabicyclo[5.1.0]octane To a stirred mixture of Intermediate 34 (80 mg, 0.17 mmol) and Intermediate 45 (199.39 mg, 0.42 mmol) in THF (2 mL) and $H_2O$) (0.4 mL) were added CataCXium A Pd G3 (24.69 mg, 0.03 mmol) and $K_3PO_4$ (215.90 mg, 1.02 mmol) at room temperature under nitrogen atmosphere. The reaction mixture was heated at 80° C. for 3 hours. The resulting mixture was cooled to room temperature, filtered and concentrated under reduced pressure. The residue was purified by Prep-TLC ($CH_2Cl_2$/MeOH 10: 1) to afford the title compound (100 mg, 75% yield) as a light yellow solid. MS: m/z=780.30 $[M+H]^{+\cdot}$ Step 2: (15,7S,8S)-2-(7-(8-ethynyl-6,7-difluoronaphthalen-1-yl)-8-fluoro-2-(((2R,7aS)-2-fluorotetrahydro-1H-pyrrolizin-7a (5H)-yl)methoxy-$d_2$) pyrido[4,3-d]pyrimidin-4-yl)-8-fluoro-5-oxa-2-azabicyclo[5.1.0]octane To a stirred solution of (1S,7S,8S)-2-(7-(6,7-difluoro-8-((triisopropylsilyl) ethynyl)naphthalen-1-yl)-8-fluoro-2-(((2R,7aS)-2-fluorotetrahydro-1H-pyrrolizin-7a (5H)-yl) methoxy-$d_2$)pyrido[4,3-d]pyrimidin-4-yl)-8-fluoro-5-oxa-2-azabicyclo[5.1.0]octane (100 mg, 0.12 mmol) in DMF (0.8 mL) was added CsF (292.13 mg, 1.92 mmol) at room temperature. The reaction mixture was stirred at room temperature for 3 hours. The resulting mixture was filtered and purified by RP-Flash directly with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 54% B in 15 min, 54% B to 54% B in 3 min, 54% B to 95% B in 4 min; Detector: UV 254 & 210 nm. The collected fractions were combined, concentrated, and lyophilized overnight to give the title compound (Example 42, 60.7 mg, 75% yield) as a yellow lyophilized powder. MS: m/z=624.45 $[M+H]^+$. $^1H$ NMR (300 MHZ, DMSO-$d_6$) δ 9.45-9.40 (m, 1H), 8.31-8.25 (m, 1H), 8.19-8.16 (m, 1H), 7.78-7.62 (m, 2H), 5.38-5.20 (m, 1H), 4.92-4.72 (m, 1H), 4.52-4.19 (m, 4H), 4.05-3.95 (m, 1H), 3.72-3.61 (m, 2H), 3.30-3.00 (m, 4H), 2.90-2.80 (m, 1H), 2.40-2.24 (m, 1H), 2.20-1.70 (m, 6H). $^{19}F$ NMR (282 MHZ, DMSO-$d_6$) δ −129.42--129.65 (m, 1F), −137.11--137.20 (m, 1F), −139.91--140.02 (m, 1F), −172.09--172.20 (d, 1F), −207.70--208.00 (m, 1F).

Example 43: (1S,7S,8S)-8-Fluoro-2-(8-fluoro-7-(7-fluoro-8-(methoxy-$d_3$)naphthalen-1-yl)-2-(((2R, 7aS)-2-fluorotetrahydro-1H-pyrrolizin-7a (5H)-yl) methoxy-$d_2$)pyrido[4,3-d]pyrimidin-4-yl)-5-oxa-2-azabicyclo[5.1.0]octane

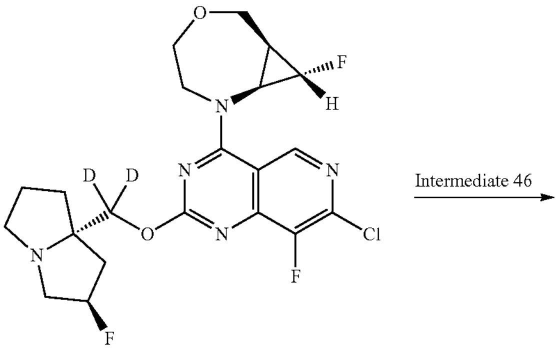

Intermediate 34

-continued

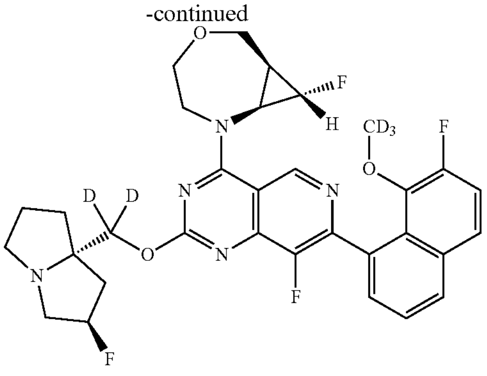

Example 43

-continued

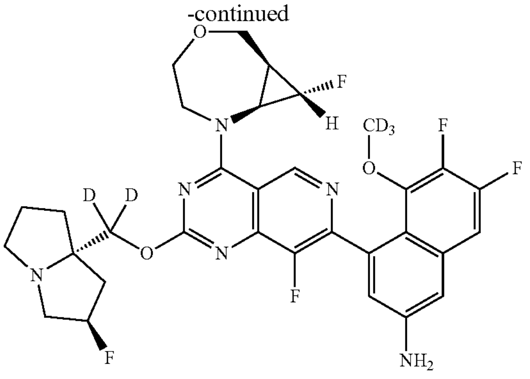

Example 44

To a stirred solution of Intermediate 34 (95 mg, 0.20 mmol) and Intermediate 46 (122.87 mg, 0.40 mmol) in THF (4 mL) and $H_2O$ (0.8 mL) were added CataCXium A Pd G3 (29.32 mg, 0.04 mmol) and $K_3PO_4$ (256.39 mg, 1.20 mmol) at room temperature under nitrogen atmosphere. The reaction mixture was irradiated with microwave radiation at 80° C. for 1 hour. The resulting mixture was cooled to room temperature, filtered and concentrated under reduced pressure. The residue was purified by Prep-TLC ($CH_2Cl_2$/MeOH 15: 1) to afford a crude product (100 mg). The crude product was purified by RP-flash with the following conditions: column, C18; Mobile phase A: 5 mM aq $NH_4HCO_3$; Mobile phase B: MeCN; Gradient 2% B to 60% B in 20 min; Detector: UV 254 nm. The collected fractions were combined, concentrated and then lyophilized overnight to give the title compound (Example 43, 61.6 mg, 49% yield) as an off-white lyophilized powder. MS: m/z=615.15 $[M+H]^+$. $^1H$ NMR (400 MHZ, DMSO-$d_6$) δ 9.47-9.43 (m, 1H), 8.14-8.11 (m, 1H), 7.91-7.87 (m, 1H), 7.66-7.49 (m, 3H), 5.35-5.22 (m, 1H), 4.96-4.78 (m, 1H), 4.52-4.49 (m, 1H), 4.39-4.30 (m, 2H), 4.02-3.99 (m, 1H), 3.74-3.60 (m, 2H), 3.32-3.01 (m, 4H), 2.86-2.81 (m, 1H), 2.41-2.33 (m, 1H), 2.12-1.90 (m, 3H), 1.86-1.70 (m, 3H). $^{19}F$ NMR (376 MHz, DMSO-$d_6$) δ −131.22--131.29 (d, 1F), −140.64--140.80 (d, 1F), −172.12--172.17 (d, 1F), −207.73 (s, 1F).

Example 44: 6,7-Difluoro-4-(8-fluoro-4-((15,7S, 8S)-8-fluoro-5-oxa-2-azabicyclo[5.1.0]octan-2-yl)-2-(((2R,7aS)-2-fluorotetrahydro-LH-pyrrolizin-7a (5H)-yl)methoxy-dr)pyrido[4,3-d]pyrimidin-7-yl)-5-(methoxy-$d_3$)naphthalen-2-amine To a solution of Intermediate 34 (200 mg, 0.42 mmol) and Intermediate 63 (214.99 mg, 0.63 mmol) in THF (8.5 mL) and $H_2O$ (1.7 mL) were added $K_3PO_4$ (539.76 mg, 2.54 mmol) and CataCXium A Pd G3 (61.73 mg, 0.08 mmol) at room temperature under nitrogen atmosphere. The reaction mixture was heated at 80° C. for 3 hours. The resulting mixture was cooled to room temperature, filtered and concentrated under reduced pressure. The residue was purified by Prep-TLC ($CH_2Cl_2$/MeOH 15: 1) to afford a crude product. The crude product was purified by RP-Flash with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 60% B in 15 min, 60% B to 60% B in 3 min, 60% B to 95% B in 4 min; Detector: UV 254 & 210 nm. The collected fractions were combined, concentrated and lyophilized overnight to give the title compound (Example 44, 183.0 mg, 66% yield) as an off-white lyophilized powder. MS: m/z=648.35 $[M+H]^+$. $^1H$ NMR (400 MHZ, DMSO-$d_6$) δ 9.45-9.40 (m, 1H), 7.44-7.40 (m, 1H), 6.94-6.89 (m, 2H), 5.74-5.72 (m, 2H), 5.36-5.22 (m, 1H), 4.96-4.77 (m, 1H), 4.52-4.48 (m, 1H), 4.38-4.30 (m, 2H), 4.02-3.99 (m, 1H), 3.73-3.56 (m, 2H), 3.30-3.00 (m, 4H), 2.86-2.80 (m, 1H), 2.42-2.27 (m, 1H), 2.20-1.70 (m, 6H). $^{19}F$ NMR (376 MHz, DMSO-$d_6$) δ −137.38--137.47 (m, 1F), −140.71--141.03 (d, 1F), −161.90-161.96 (m, 1F), −172.14--172.19 (d, 1F), −207.73 (s, 1F).

Example 45: (15,7S,8S)-2-(7-(8-Ethynyl-7-fluoronaphthalen-1-yl)-8-fluoro-2-(((2R,7aS)-2-fluorotetrahydro-1H-pyrrolizin-7a (5H)-yl)methoxy-$d_2$) pyrido[4,3-d]pyrimidin-4-yl)-8-fluoro-S-oxa-2-azabicyclo[5.1.0]octane

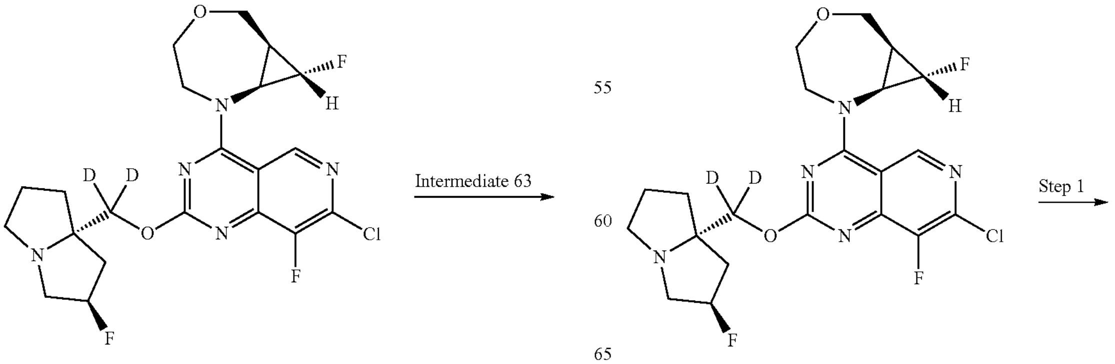

Intermediate 34

Intermediate 3$

-continued

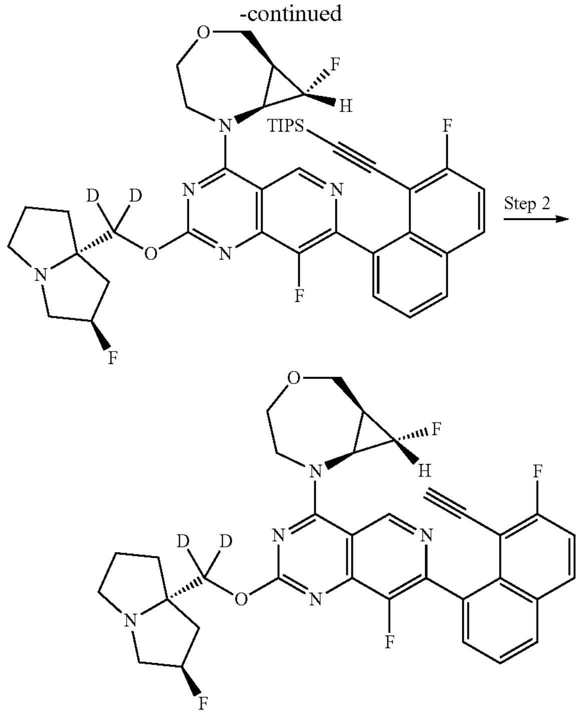

Example 45

Step 1: (1S,7S,8S)-8-Fluoro-2-(8-fluoro-7-(7-fluoro-8-((triisopropylsilyl) ethynyl)naphthalen-1-yl)-2-(((2R,7aS)-2-fluorotetrahydro-1H-pyrrolizin-7a (5H)-yl)methoxy-$d_2$)pyrido[4,3-d]pyrimidin-4-yl)-5-oxa-2-azabicyclo[5.1.0]octane To a solution of Intermediate 34 (150 mg, 0.31 mmol) and ((2-fluoro-8-(4,4,5,5-tetramethyl-1,3,2-dioxaborolan-2-yl) naphthalen-1-yl) ethynyl) triisopropylsilane (287.65 mg, 0.63 mmol) in THF (6.5 mL) and $H_2O$ (1.3 mL) were added $K_3PO_4$ (404.82 mg, 1.90 mmol) and CataCXium A Pd G3 (46.30 mg, 0.06 mmol) at room temperature under nitrogen atmosphere. The reaction mixture was heated at 80° C. for 3 hours. The resulting mixture was cooled to room temperature, filtered and concentrated under reduced pressure. The residue was purified by Prep-TLC ($CH_2Cl_2$/MeOH 10: 1) to afford the title compound (200 mg, 82% yield) as a brown yellow solid. MS: m/z=762.35 $[M+H]^{+}$.

Step 2: (1S,75,8S)-2-(7-(8-Ethynyl-7-fluoronaphthalen-1-yl)-8-fluoro-2-(((2R,7aS)-2-fluorotetrahydro-1H-pyrrolizin-7a (5H)-yl)methoxy-$d_2$)pyrido[4,3-d] pyrimidin-4-yl)-8-fluoro-5-oxa-2-azabicyclo[5.1.0] octane To a stirred solution of (1S,7S,8S)-8-fluoro-2-(8-fluoro-7-(7-fluoro-8-((triisopropylsilyl) ethynyl)naphthalen-1-yl)-2-(((2R,7aS)-2-fluorotetrahydro-1H-pyrrolizin-7a (5H)-yl) methoxy-$d_2$)pyrido[4,3-d]pyrimidin-4-yl)-5-oxa-2-azabicyclo[5.1.0]octane (200 mg, 0.26 mmol) in DMF (2 mL) was added CsF (398.71 mg, 2.62 mmol) at room temperature. The reaction mixture was stirred at room temperature for 3 hours. The resulting mixture was filtered and purified by RP-Flash directly with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 61% B in 15 min, 61% B to 61% B in 3 min, 61% B to 95% B in 4 min; Detector: UV 254 & 210 nm. The collected fractions were combined, concentrated and lyophilized overnight to give the title compound (Example 45, 71.3 mg, 44% yield) as an off-white lyophilized powder. MS: m/z=606.20 $[M+H]^{+}$. $^{1}H$ NMR (400 MHZ, DMSO-$d_6$) δ 9.45-9.39 (m, 1H), 8.26-8.20 (m, 2H), 7.72-7.60 (m, 3H), 5.35-5.21 (m, 1H), 4.90-4.75 (m, 1H), 4.52-4.33 (m, 3H), 4.22-3.98 (m, 2H), 3.72-3.61 (m, 2H), 3.30-3.20 (m, 1H), 3.09-3.01 (m, 3H), 2.88-2.81 (m, 1H), 2.43-2.30 (m, 1H), 2.12-1.76 (m, 6H). $^{19}F$ NMR (376 MHZ, DMSO-$d_6$) δ −105.71--105.83 (d, 1F), −139.88--140.33 (d, 1F), −172.07--172.17 (d, 1F), −207.79 (s, 1F).

Example 46: (1R,7R,8R)-2-(7-(8-ethynyl-7-fluoronaphthalen-1-yl)-8-fluoro-2-(((2R,7aS)-2-fluorotetrahydro-1H-pyrrolizin-7a (5H)-yl)methoxy-$d_2$) pyrido[4,3-d]pyrimidin-4-yl)-8-fluoro-5-oxa-2-azabicyclo [5.1.0]octane

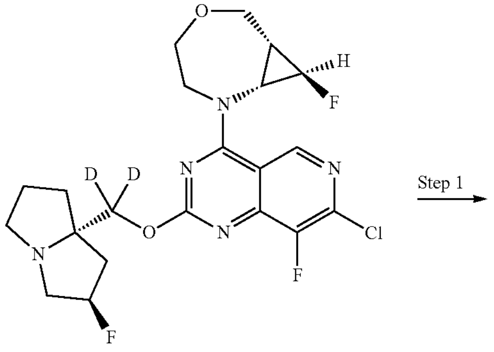

Intermediate 33

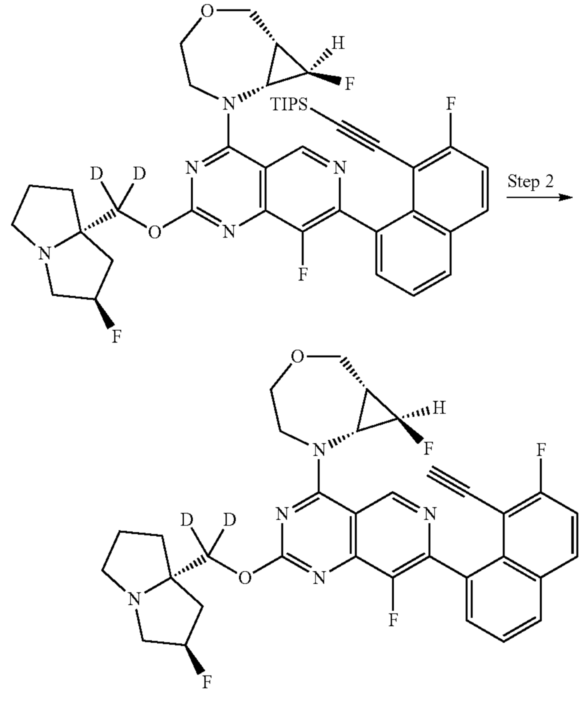

Example 46

Example 46 was prepared in a manner similar to Example 45. MS: m/z=606.20 $[M+H]^+$. $^1$H NMR (400 MHZ, DMSO-$d_6$) δ 9.50-9.39 (m, 1H), 8.26-8.20 (m, 2H), 7.72-7.60 (m, 3H), 5.34-5.20 (m, 1H), 4.90-4.75 (m, 1H), 4.52-4.48 (m, 1H), 4.40-4.34 (m, 2H), 4.22-3.98 (m, 2H), 3.72-3.60 (m, 2H), 3.33-3.20 (m, 1H), 3.15-3.00 (m, 3H), 2.86-2.81 (m, 1H), 2.45-2.30 (m, 1H), 2.11-1,99 (m, 3H), 1.99-1.76 (m, 3H). $^{19}$F NMR (376 MHZ, DMSO-$d_6$) δ −105.71--105.85 (m, 1F), −139.94--140.33 (m, 1F), −172.09--172.19 (m, 1F), −207.70--207.81 (m, 1F).

Example 47: 4-(4-((1S,7R)-5-Oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-2-amino-7-fluorobenzo[b]thiophene-3-carbonitrile

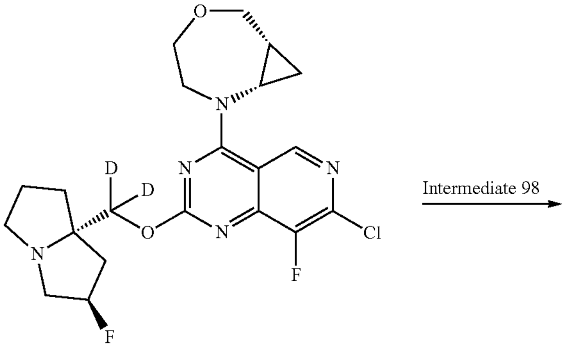

Intermediate 73

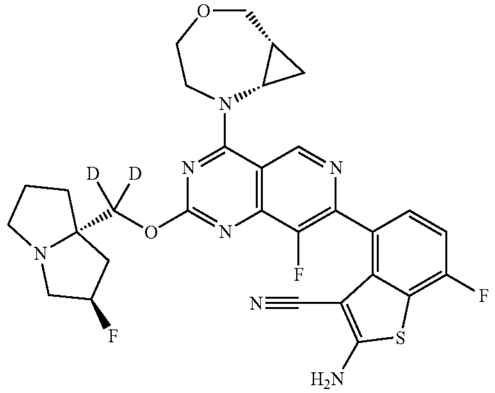

Example 48

Example 47 was prepared in a manner similar to Example 39. MS: m/z=610.15 $[M+H]^+$. $^1$H NMR (400 MHZ, DMSO-$d_6$) à 9.53 (s, 1H), 8.09 (s, 2H), 7.43-7.39 (m, 1H), 7.17-7.12 (m, 1H), 5.34-5.20 (m, 1H), 4.50 (d, J=13.2 Hz, 1H), 4.35-4.30 (m, 1H), 4.06-4.03 (m, 1H), 3.75-3.65 (m, 3H), 3.10-2.80 (m, 4H), 2.10-1.70 (m, 8H), 1.28-1.23 (m, 1H), 0.64-0.61 (m, 1H). $^{19}$F NMR (376 MHz, DMSO-$d_6$) 0-116.21 (s, 1F), −140.94 (s, 1F), −172.09 (s, 1F).

Example 48, 4-(4-((1R,7S)-5-Oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-2-amino-7-fluorobenzo[b]thiophene-3-carbonitrile

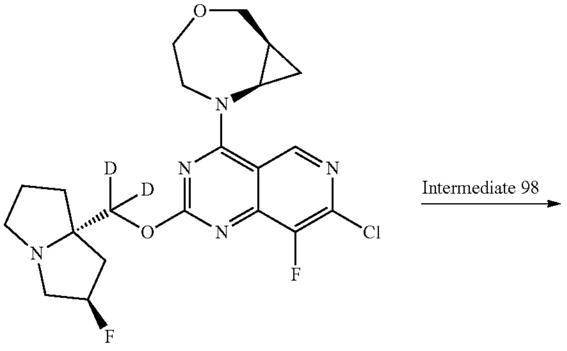

Intermediate 72

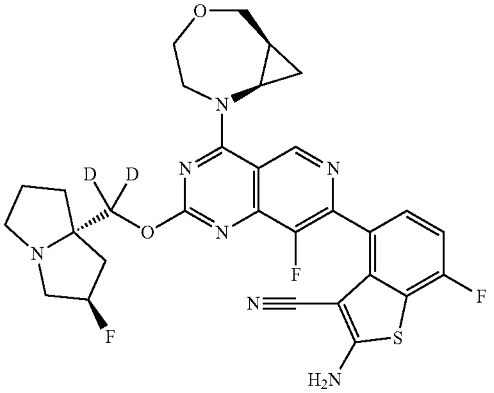

Example 48

Example 48 was prepared in a manner similar to Example 39. MS: m/z=610.15 $[M+H]^+$. H NMR (400 MHz, DMSO-$d_6$) δ 9.54 (s, 1H), 8.09 (s, 2H), 7.43-7.39 (m, 1H), 7.17-7.12 (m, 1H), 5.35-5.21 (m, 1H), 4.49 (d, J=13.2 Hz, 1H), 4.35-4.30 (m, 1H), 4.06-4.03 (m, 1H), 3.80-3.60 (m, 3H), 3.10-2.70 (m, 4H), 2.20-1.70 (m, 8H), 1.28-1.23 (m, 1H), 0.65-0.62 (m, 1H). $^{19}$F NMR (376 MHZ, DMSO-$d_6$) δ −116.21 (s, 1F), −140.90 (s, 1F), −172.11 (s, 1F).

Example 49: 6-Amino-8-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-1-(methoxy-$d_3$)-2-naphthonitrile

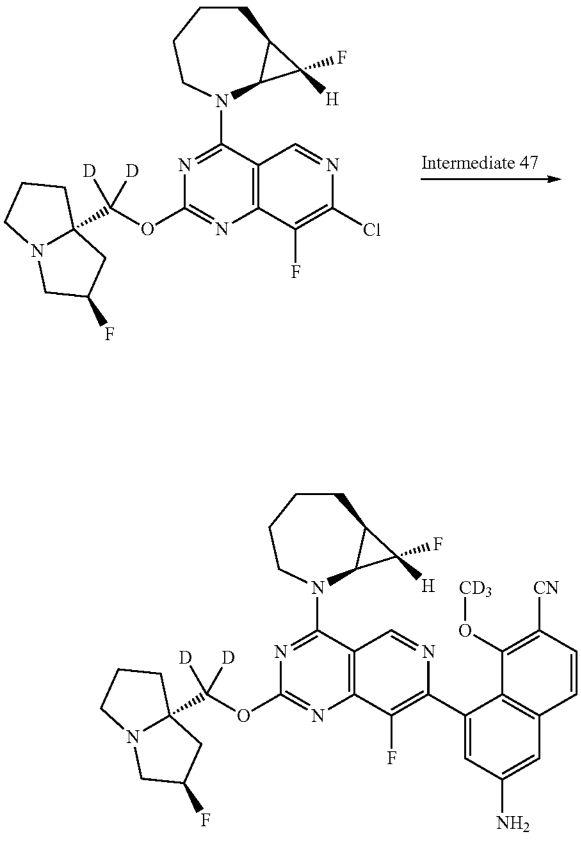

Example 49

A mixture of 7-chloro-8-fluoro-4-((15,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine (160 mg, 340 μmol, refer to Example 16 for detail procedures), Intermediate 47 (133 mg, 408 μmol), CataCXium A Pd G3 (25 mg, 34.0 μmol) and $Cs_2CO_3$ (333 mg, 1.02 mmol) in 1,4-dioxane (3 mL) and $H_2O$ (0.6 mL) was degassed and purged with $N_2$ three times, then the mixture was stirred at 80° C. for 1 hr under Na atmosphere. The reaction mixture was concentrated under reduced pressure. After purification by silica gel flash chromatography (eluent of 0~4% MeOH in $CH_2Cl_2$), the title compound (Example 49, 71 mg, yield: 30%) was obtained as a yellow solid. MS: m/z=635.2 $[M+H]^+$. JH NMR (400 MHZ, Dimethylsulfoxide-$d_6$) δ 9.47-9.37 (m, 1H), 7.56-7.35 (m, 2H), 7.08-6.94 (m, 2H), 6.26-6.16 (m, 2H), 5.37-5.19 (m, 1H), 4.80-4.54 (m, 1H), 4.49-4.38 (m, 1H), 4.11-4.01 (m, 1H), 3.40-3.34 (m, 1H), 3.13-3.05 (m, 2H), 3.05-2.95 (m, 1H), 2.88-2.79 (m, 1H), 2.28-2.21 (m, 1H), 2.16-2.10 (m, 1H), 2.06-2.03 (m, 1H), 2.01-1.94 (m, 2H), 1.87-1.68 (m, 6H), 1.54-1.45 (m, 1H), 1.19-1.06 (m, 1H). $^{19}F$ NMR (376 MHz, Dimethylsulfoxide-$d_6$) δ −140.638, −140.894, −172.096.

Example 50: 6-Amino-3-fluoro-8-(8-fluoro-4-((1S,7R,8S)-8-fluoro-2-azabicyclo[5.1.0]octan-2-yl)-2-(((2R,7aS)-2-fluorotetrahydro-LH-pyrrolizin-7a (5H)-yl)methoxy-$d_2$)pyrido[4,3-d]pyrimidin-7-yl)-1-(methoxy-$d_3$)-2-naphthonitrile

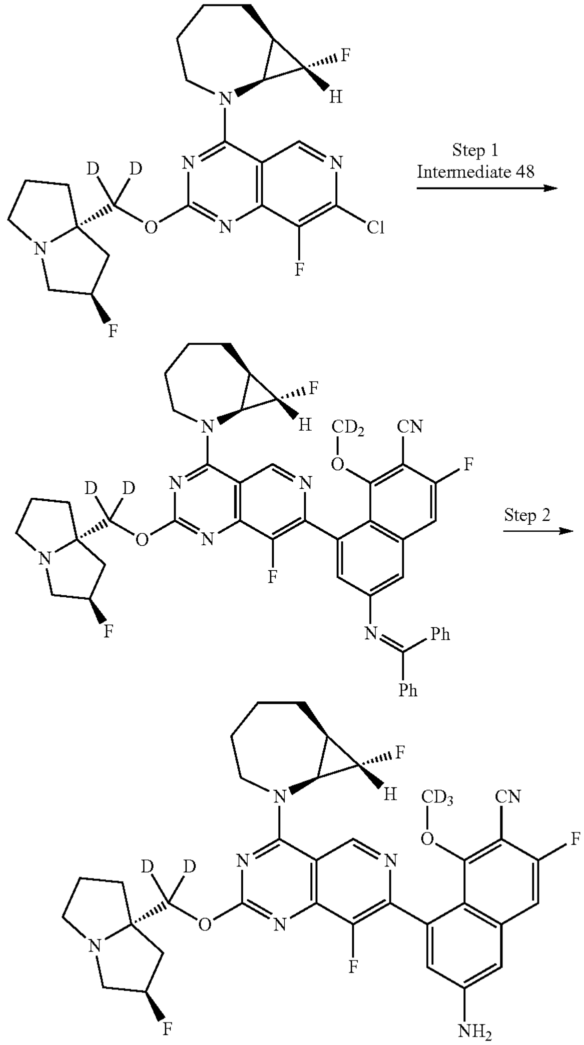

Example 50

Step 1: 6-((Diphenylmethylene) amino)-3-fluoro-8-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-1-(methoxy-$d_3$)-2-naphthonitrile To a solution of 7-chloro-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido [4,3-d]pyrimidine (90 mg, 192 μmol, refer to Example 16 for detail procedures) in 1,4-dioxane (2 mL) and $H_2O$ (0.4 mL) were added Intermediate 48 (107 mg, 211 μmol), $Cs_2CO_3$ (187 mg, 575 μmol) and CataCXium A Pd G3 (14 mg, 19 μmol). The mixture was degassed and purged with $N_2$ three times and stirred at 80° C. under $N_2$ for 1 hr. The reaction mixture was concentrated under reduced pressure to give the title compound (130 mg crude) was obtained as a yellow solid. MS: m/z=817.6 $[M+H]^{+\cdot}$ Step 2: 6-Amino-3-fluoro-8-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-1-(methoxy-$d_3$)-2-naphthonitrile To a solution of 6-((diphenylmethylene) amino)-3-fluoro-8-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-1-(methoxy-$d_3$)-2-naphthonitrile (130 mg, 159 μmol) in EtOH (2 mL) were added KOAc (47 mg, 477 μmol) and $NH_2OH{\cdot}HCl$ (22 mg, 318 μmol). The mixture was stirred at 25° C. under $N_2$ for 0.5 hr. The reaction mixture was concentrated under reduced pressure. After purification by silica gel flash chromatography (eluent of 0~10% MeOH in $CH_2Cl_2$), the title compound (Example 50, 23.5 mg, yield: 23%) was obtained as a yellow solid. MS: m/z=653.7 $[M+H]^+$. $^1$H NMR (400 MHZ, Dimethylsulfoxide-$d_6$) δ 9.46-9.36 (m, 1H), 7.41 (d, J=10.8 Hz, 1H), 6.99-6.88 (m, 2H), 6.44-6.34 (m, 2H), 5.52-5.22 (m, 1H), 4.79-4.53 (m, 1H), 4.49-4.37 (m, 1H), 4.14-3.97 (m, 1H), 3.54-3.44 (m, 1H), 3.22-2.80 (m, 3H), 2.31-2.21 (m, 2H), 2.12-1.68 (m, 10H), 1.53-1.46 (m, 1H), 1.20-1.12 (m, 1H). $^{19}$F NMR (376 MHz, Dimethylsulfoxide-$d_6$) δ −114.59, −140.83, −172.14, −204.53, −205.01.

-continued

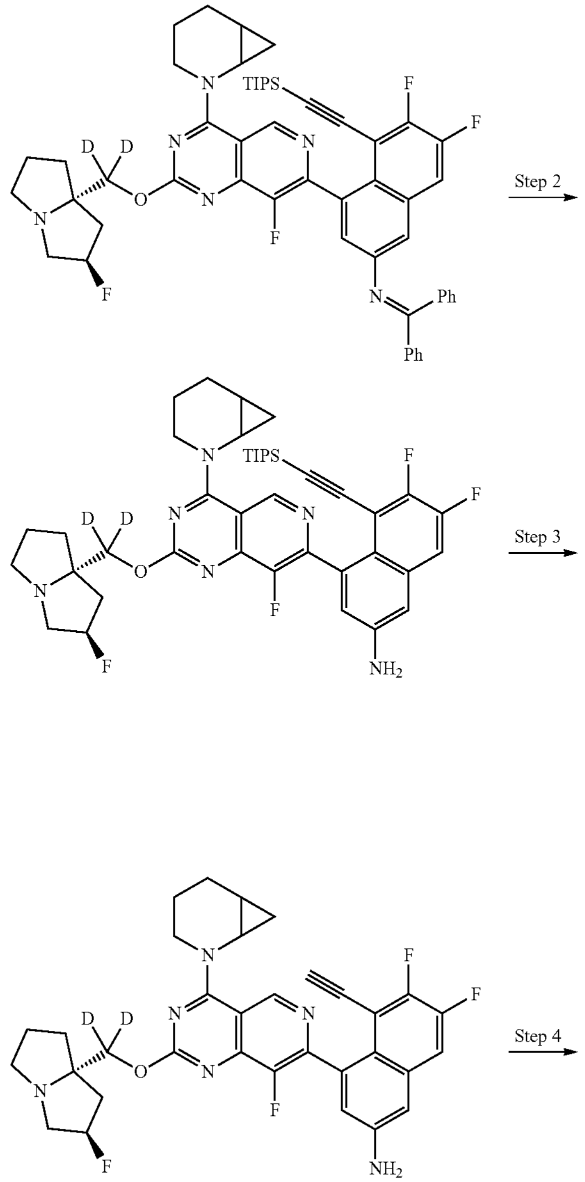

Example 51 & 52: 4-(4-((1S,6R)-2-Azabicyclo[4.1.0]heptan-2-yl)-8-fluoro-2-(((2R,7aS)-2-fluoro-tetrahydro-1H-pyrrolizin-7a (5H)-yl)methoxy-$d_2$) pyrido[4,3-d]pyrimidin-7-yl)-5-ethynyl-6,7-difluoronaphthalen-2-amine & 4-(4-((1R,6S)-2-azabicyclo[4.1.0]heptan-2-yl)-8-fluoro-2-(((2R,7aS)-2-fluorotetrahydro-1H-pyrrolizin-7a (5H)-yl) methoxy-$d_2$)pyrido[4,3-d]pyrimidin-7-yl)-5-ethynyl-6,7-difluoronaphthalen-2-amine

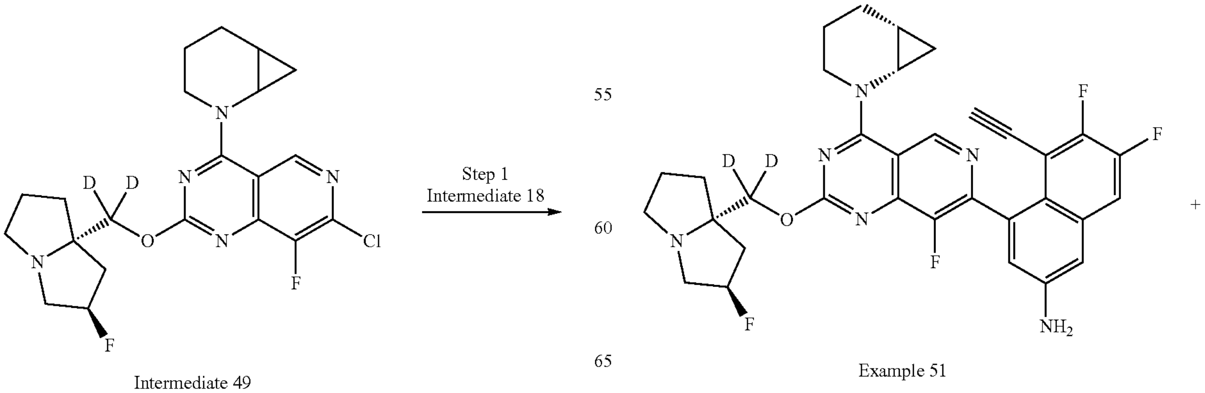

Intermediate 49

Example 51

-continued

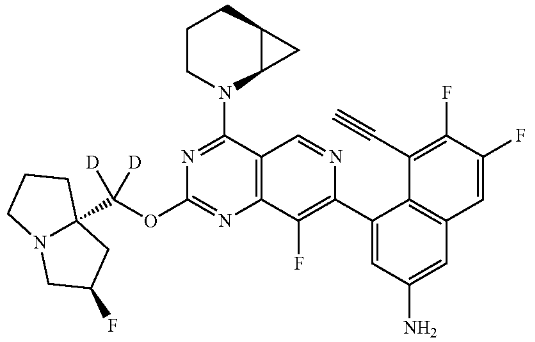

Example 52

Example 51 and 52 were prepared in a manner similar to Example 4 and 5. Spectra for Example 51: MS: m/z=605.2 $[M+H]^+$. $^1H$ NMR (400 MHZ, Dimethylsulfoxide-$d_6$) δ 9.75 (d, J=10.8, 1H), 7.78 (t, J=9.6, 1H), 7.06-6.96 (m, 2H), 5.78 (s, 2H), 5.44-5.15 (m, 1H), 4.69-4.50 (m, 1H), 4.22-4.00 (m, 1H), 3.55-3.45 (m, 1H), 3.13-3.01 (m, 3H), 2.89-2.77 (m, 2H), 2.14-2.04 (m, 2H), 2.03-1.88 (m, 2H), 1.89-1.71 (m, 5H), 1.64-1.44 (m, 2H), 1.21-1.10 (m, 1H), 0.85-0.71 (m, 1H). $^{19}F$ NMR (376 MHz, Dimethylsulfoxide-$d_6$) δ −137.78, −137.85, −137.92, −138-62, −138.71, −140.10, −140.22, −172.11, −172.21. Spectra for Example 52: MS: m/z=605.2 $[M+H]^+$. $^1H$ NMR (400 MHZ, Dimethylsulfoxide-$d_6$) δ 9.85-9.68 (m, 1H), 7.79-7.68 (m, 1H), 7.07-6.97 (m, 2H), 5.80-5.75 (s, 2H), 5.40-5.19 (m, 1H), 4.69-4.51 (m, 1H), 4.18-4.01 (m, 1H), 3.54-3.40 (m, 1H), 3.19-2.99 (m, 3H), 2.92-2.80 (m, 2H), 2.15-1.93 (m, 5H), 1.90-1.77 (m, 4H), 1.66-1.57 (m, 1H), 1.51-1.43 (m, 1H), 1.21-1.10 (m, 1H), 0.84-0.74 (m, 1H). $^{19}F$ NMR (376 MHz, Dimethylsulfoxide-$d_6$) δ −137.79, ~137.85, −137.91, −138.66, −138.72, −140.18, −172.10, −172.24.

Example 53: 5-Ethynyl-6,7-difluoro-4-(8-fluoro-4-((1R,6S,7R)-7-fluoro-2-azabicyclo[4.1.0]heptan-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine

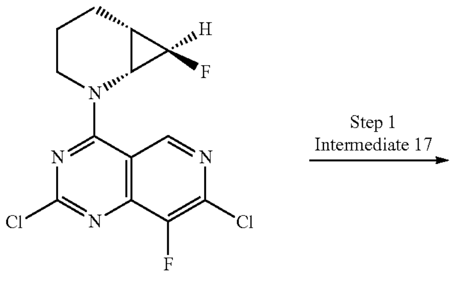

Intermediate 52

-continued

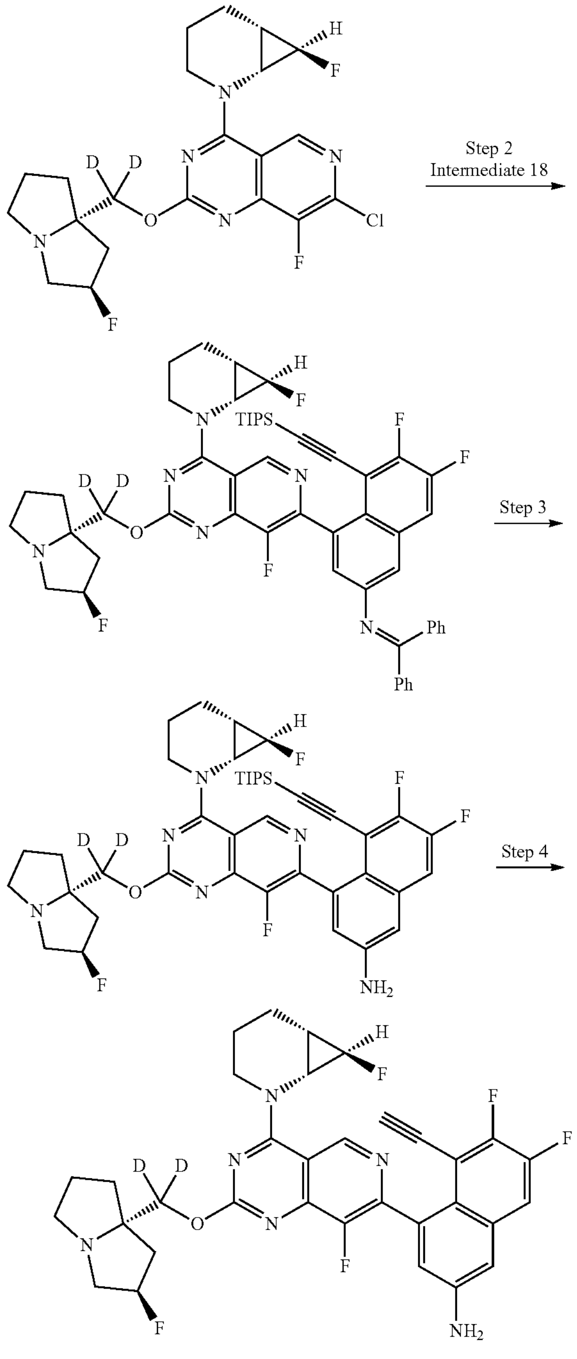

Example 53

Example 53 was prepared in a manner similar to Example 54. MS: m/z=623.2 $[M+H]^+$. $^1HNMR$ (400 MHz, Dimethylsulfoxide-$d_6$) δ 9.51 (d, J=12.4 Hz, 1H), 7.85-7.74 (m, 1H), 7.08-6.97 (m, 2H), 5.79 (s, 2H), 5.36-5.19 (m, 1H), 5.16-4.86 (m, 1H), 4.58-4.41 (m, 1H), 4.18-3.81 (m, 2H), 3.11-2.98 (m, 3H), 2.85-2.73 (m, 2H), 2.13-1.94 (m, 5H), 1.89-1.74 (m, 5H), 1.37-1.24 (m, 1H). $^{19}F$ NMR (376 MHz, Dimethylsulfoxide-$d_6$) δ −137.74, −137.84, −138.67, −139.73, −139.96, −172.08, −172.19, −209.24, −209.75.

Example 54: 5-Ethynyl-6,7-difluoro-4-(8-fluoro-4-((15,6R,7S)-7-fluoro-2-azabicyclo[4.1.0]heptan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine

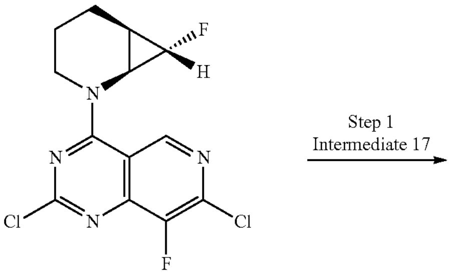

Intermediate 53

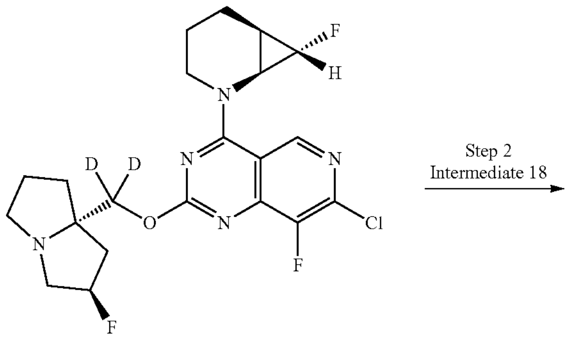

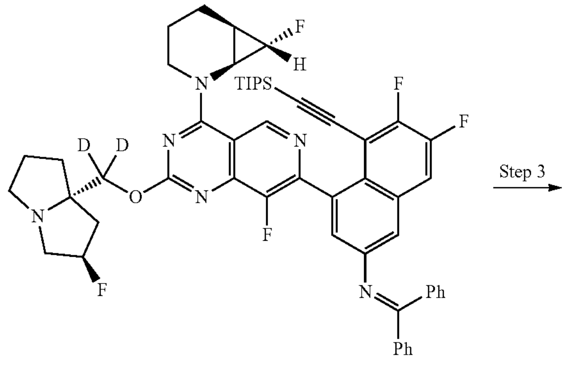

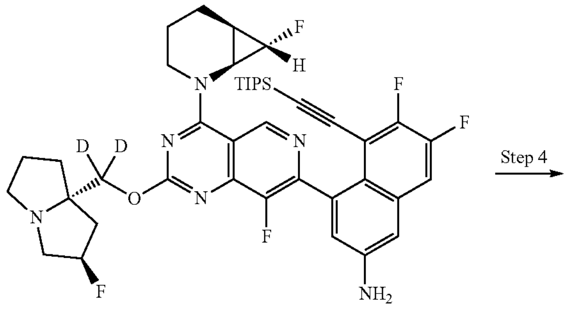

-continued

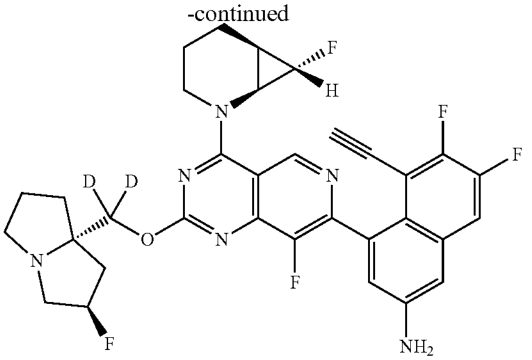

Example 54

Step 1: 7-Chloro-8-fluoro-4-((1S,6R,7S)-7-fluoro-2-azabicyclo[4.1.0]heptan-2-yl)-2-(((2R,7aS)-2-fluoro-tetrahydro-1H-pyrrolizin-7a (5H)-yl)methoxy-$d_2$) pyrido[4,3-d]pyrimidine A mixture of Intermediate 53 (120 mg, 362 μmol), Intermediate 17 (88 mg, 544 μmol) and DIPEA (189 AL, 1.09 mmol) in 1,4-dioxane (2 mL) was degassed and purged with $N_2$ three times, and then the mixture was stirred at 100° C. for 16 h under $N_2$ atmosphere. The reaction mixture was concentrated under reduced pressure. The residue was purified by silica gel flash chromatography (eluent: 0~3% of $CH_2Cl_2$ in MeOH) to give the title compound (88 mg, 52% yield) as a white solid. MS: m/z=456.0 $[M+H]^+$. $^1$HNMR (400 MHZ, Chloroform-d) δ 9.38 (s, 1H), 5.34-5.18 (m, 1H), 4.69-4.46 (m, 2H), 3.57 (t, J=10.0 Hz, 1H), 3.29-3.13 (m, 3H), 3.01-2.93 (m, 1H), 2.81-2.73 (m, 1H), 2.28-2.08 (m, 4H), 2.06-1.83 (m, 6H), 1.30-1.23 (m, 1H), $^{19}$F NMR (376 MHz, Chloroform-d) 8-134.21, −173.27, −209.60.

Step 2: N-(6,7-Difluoro-4-(8-fluoro-4-((15,6R,7S)-7-fluoro-2-azabicyclo[4.1.0]heptan-2-yl)-2-(((2R, 7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-yl)-1,1-diphenylmethanimine A mixture of 7-chloro-8-fluoro-4-((1S,6R,7S)-7-fluoro-2-azabicyclo[4.1.0]heptan-2-yl)-2-(((2R,7aS)-2-fluorotetrahydro-1H-pyrrolizin-7a (5H)-yl)methoxy-$d_2$)pyrido[4,3-d] pyrimidine (88 mg, 193 μmol), Intermediate 18 (150 mg, 232 μmol), $K_3PO_4$ (123 mg, 579 μmol) and $Ad_2nBuP$-Pd-G3 (cataCXiumAPd$G_3$) (14 mg, 19 μmol) in 1,4-dioxane (1 mL) and $H_2O$ (0.2 mL) was degassed and purged with $N_2$ three times, and then the mixture was stirred at 100° C. for 1 h under $N_2$ atmosphere. The reaction mixture was concentrated under reduced pressure to give a residue. The residue was purified by flash silica gel chromatography (eluent: 0~3% of MeOH in $CH_2Cl_2$) to give the title compound (158 mg, 82% yield) as a brown solid. MS: m/z=943.5 $[M+H]^{+}$.

Step 3: 6,7-Difluoro-4-(8-fluoro-4-((1S,6R,7S)-7-fluoro-2-azabicyclo[4.1.0]heptan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine To a solution of N-(6,7-difluoro-4-(8-fluoro-4-((1S,6R, 7S)-7-fluoro-2-azabicyclo[4.1.0]heptan-2-yl)-2-(((2R,7aS)-

2-fluorotetrahydro-1H-pyrrolizin-7a (5H)-yl)methoxy-$d_2$) pyrido[4,3-d]pyrimidin-7-yl)-S-((triisopropylsilyl) ethynyl) naphthalen-2-yl)-1,1-diphenylmethanimine (158 mg, 168 μmol) in EtOH (2 mL) was added NaOAc (27 mg, 335 μmol) and $NH_2OH$ HCl (15 mg, 218 μmol). The mixture was stirred at 25° C. for 0.5 h. The reaction mixture was concentrated under reduced pressure. The residue was purified by silica gel flash chromatography (eluent: 0~6% of MeOH in $CH_2Cl_2$) to give the title compound (100 mg, 83% yield) as a yellow solid. MS: m/z=779.6 $[M+H]^{+\cdot}$ Step 4: 5-Ethynyl-6,7-difluoro-4-(8-fluoro-4-((1S,6R,7S)-7-fluoro-2-azabicyclo[4.1.0]heptan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine To a solution of 6,7-difluoro-4-(8-fluoro-4-((1S,6R,7S)-7-fluoro-2-azabicyclo[4.1.0]heptan-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-amine (100 mg, 128 μmol) in DMSO (2 mL) was added CsF (20 mg, 128 μmol). The mixture was stirred at 20° C. for 0.5 h. The reaction mixture was diluted with water (50 mL) and extracted with EtOAc (50 mL×3). The combined organic layers were washed with brine (50 mL×2), dried over anhydrous $Na_2SO_4$, filtered and the filtrate was concentrated under reduced pressure. The residue was purified by reversed-phase column chromatography (column: C18; mobile phase: [Water ($NH_4HCO_3$)-MeOH); B %: 5%-65%, 30 min) to give the title compound (Example 54, 57.8 mg, 71% yield) as a yellow solid. MS: m/z=623.2 $[M+H]^+$. $^1$HNMR (400 MHZ, Dimethylsulfoxide-$d_6$) δ 9.51 (d, J=12.4 Hz, 1H), 7.82-7.74 (m, 1H), 7.05-6.97 (m, 2H), 5.79 (s, 2H), 5.36-5.19 (m, 1H), 5.15-4.86 (m, 1H), 4.58-4.40 (m, 1H), 4.16-3.84 (m, 2H), 3.10-2.99 (m, 3H), 2.85-2.74 (m, 2H), 2.14-1.97 (m, 5H), 1.87-1.74 (m, 5H), 1.35-1.25 (m, 1H). $^{19}$F NMR (376 MHz, Dimethylsulfoxide-$d_6$) δ −137.76, −137.83, −138.59, −138.67, −139.77, −139.93, −172.07, −172.18, −209.23, −209.74.

Example 55 & 56: 4-(4-((15,8R)-2-azabicyclo [6.1.0]nonan-2-yl)-8-fluoro-2-(((2R,7aS)-2-fluoro-tetrahydro-1H-pyrrolizin-7a (5H)-yl)methoxy-$d_2$) pyrido[4,3-d]pyrimidin-7-yl)-5-ethynyl-6,7-difluoronaphthalen-2-amine & 4-(4-((1R,8S)-2-azabicyclo[6.1.0]nonan-2-yl)-8-fluoro-2-(((2R,7aS)-2-fluorotetrahydro-1H-pyrrolizin-7a (5H)-yl) methoxy-$d_2$)pyrido[4,3-d]pyrimidin-7-yl)-5-ethynyl-6,7-difluoronaphthalen-2-amine

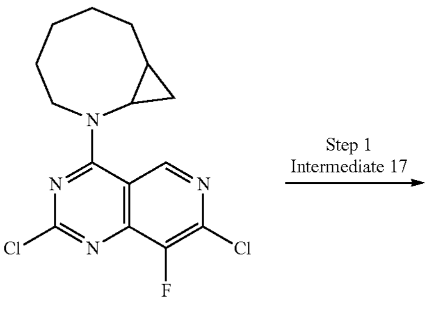

Intermediate 54

-continued

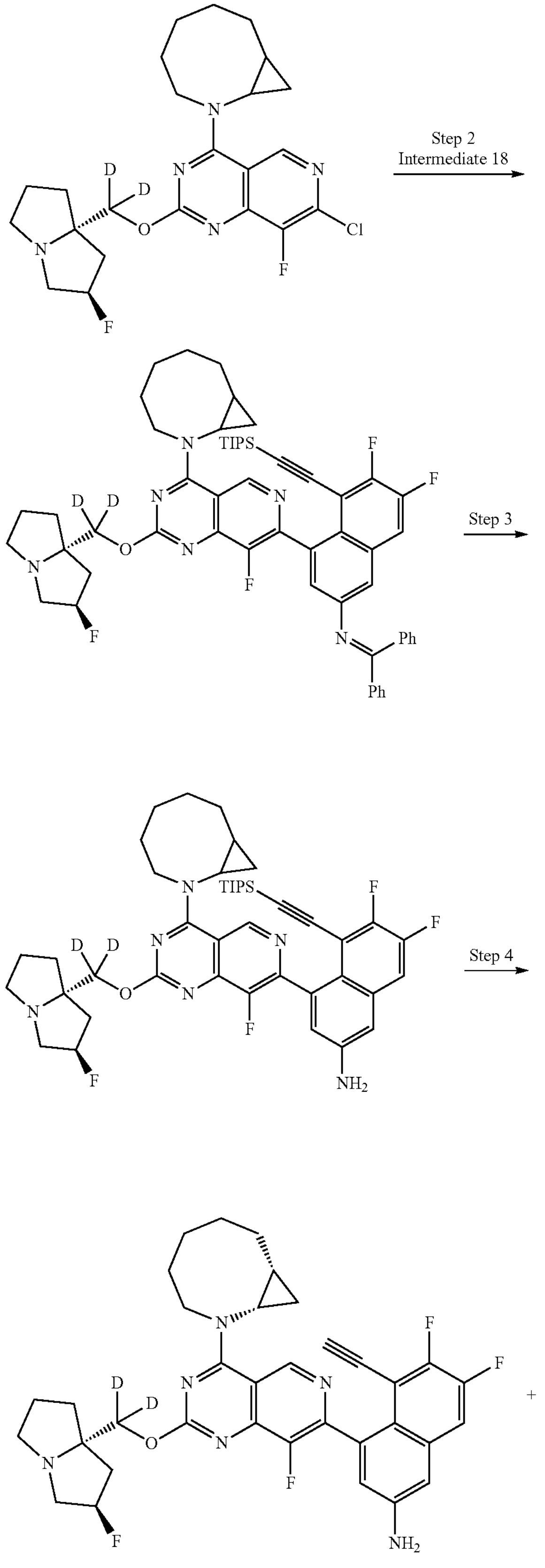

Example 55

-continued

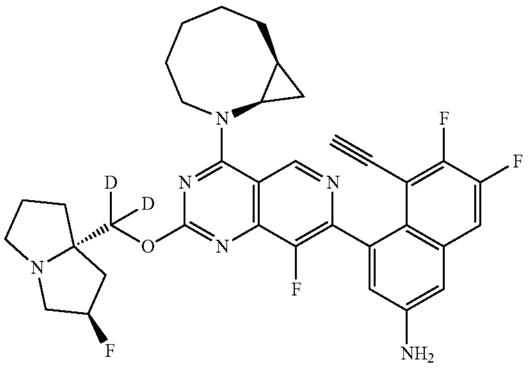

Example 56

Example 55 and 56 were prepared in a manner similar to Example 4 and 5. Spectra for Example 55: MS: m/z=633.2 [M+H]$^{+}$. $^{1}$H NMR (400 MHZ, Dimethylsulfoxide-$d_6$) δ 9.29 (d, J=16.4 Hz, 1H), 7.87-7.69 (m, 1H), 7.05-6.91 (m, 2H), 5.85-5.71 (m, 2H), 5.40-5.14 (m, 1H), 4.47-4.33 (m, 1H), 4.26-3.94 (m, 1H), 3.32-3.21 (m, 2H), 3.12-2.98 (m, 3H), 2.86-2.78 (m, 1H), 2.17-2.09 (m, 1H), 2.15-2.09 (m, 1H), 2.01-1.70 (m, 9H), 1.63-1.52 (m, 1H), 1.48-1.38 (m, 1H), 1.17-1.06 (m, 2H), 0.93-0.74 (m, 1H), 0.29-0.04 (m, 1H). $^{19}$F NMR (376 MHz, Dimethylsulfoxide-$d_6$) δ −137.67, −137.74, −137.88, −138.62, −138.70, −140.83, −141.16, −172.08, −172.17. Spectra for Example 56: MS: m/z=633.2 [M+H]$^{+}$. $^{1}$H NMR (400 MHZ, Dimethylsulfoxide-$d_6$) δ 9.29 (d, J=16.4 Hz, 1H), 7.86-7.71 (m, 1H), 7.04-6.94 (m, 2H), 5.86-5.70 (s, 2H), 5.40-5.17 (m, 1H), 4.25-3.92 (m, 1H), 4.26-3.92 (m, 1H), 3.30-3.16 (m, 2H), 3.12-2.98 (m, 3H), 2.88-2.78 (m, 1H), 2.16-2.03 (m, 2H), 2.00-1.70 (m, 9H), 1.63-1.52 (m, 1H), 1.49-1.37 (m, 1H), 1.17-1.06 (m, 2H), 0.94-0.74 (m, 1H), 0.31-0.04 (m, 1H). $^{19}$F NMR (376 MHz, Dimethylsulfoxide-$d_6$) δ −137.67, −137.74, −138.64, −138.70, −140.75, −141.14, 172.05, −172.14.

Example 57: 4-(4-(8,8-Difluoro-2-azabicyclo[5.1.0]octan-2-yl)-8-fluoro-2-(((2R,7aS)-2-fluorotetrahydro-1H-pyrrolizin-7a (5H)-yl)methoxy)pyrido[4,3-d]pyrimidin-7-yl)-5-ethynyl-6-fluoronaphthalen-2-amine -continued

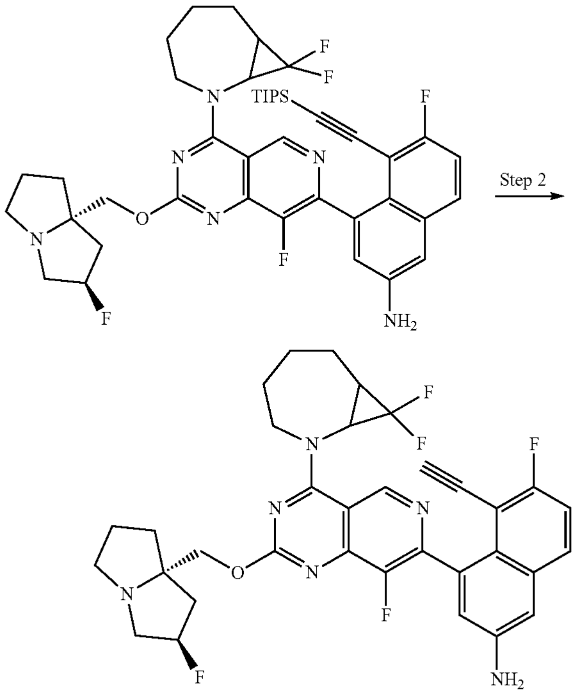

Example 57

Example 57 was prepared in a manner similar to Example 21. MS: m/z=635.2 [M+H]$^{+}$. $^{1}$H NMR (400 MHZ, Dimethylsulfoxide-$d_6$) δ 9.39-9.12 (m, 1H), 7.82-7.73 (m, 1H), 7.34 (t, J=9.2 Hz, 1H), 7.10-7.01 (m, 2H), 5.64 (d, J=6.4 Hz, 2H), 5.39-5.19 (m, 1H), 4.45-4.06 (m, 4H), 3.83-3.62 (m, 1H), 3.51-3.40 (m, 1H), 3.12-2.99 (m, 3H), 2.83 (d, J=6.0 Hz, 1H), 2.36-2.29 (m, 1H), 2.21-2.10 (m, 2H), 2.08-1.94 (m, 4H), 1.90-1.75 (m, 4H), 1.67-1.57 (m, 1H), 1.52-1.37 (m, 1H) $^{19}$F NMR (376 MHz, Dimethylsulfoxide-$d_6$) δ −113.24, −113.41, −124.61, −125.03, −139.51, −139.67, −146.15, −171.98, 172.08.

Example 58: 6-Fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-(methoxy-$d_3$)naphthalen-2-amine

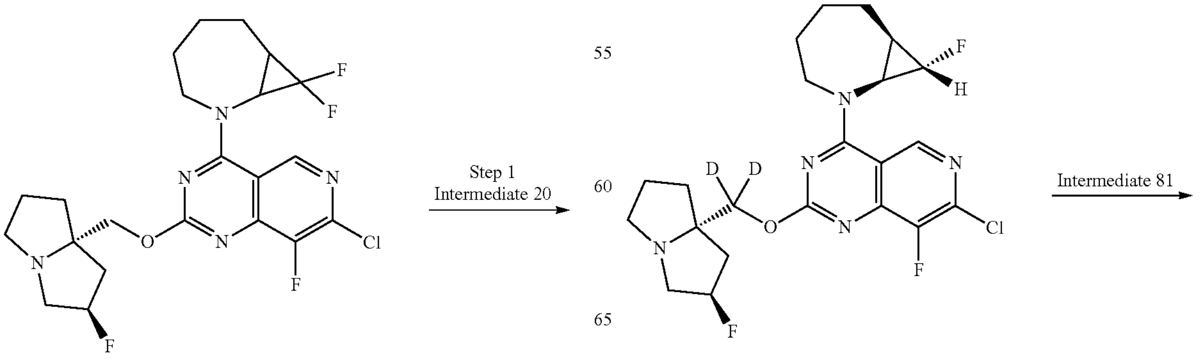

-continued

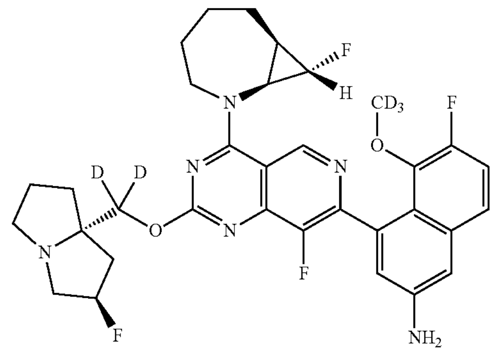

Example 58

A mixture of 7-chloro-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine (80 mg, 170 μmol, refer to Example 16 for detail procedures), Intermediate 81 (65 mg, 204 μmol), AdanBuP-Pd G3 (cataCXiumAPdG$_3$) (12 mg, 17 μmol) and $K_3PO_4$ (108 mg, 511 μmol) in $H_2O$ (0.4 mL) and 1,4-dioxane (2 mL) was degassed and purged with $N_2$ three times, and then the mixture was stirred at 105° C. for 2 h under $N_2$ atmosphere. The reaction mixture was concentrated under reduced pressure. The residue was purified by silica gel flash chromatography (eluent: 0~10% MeOH in $CH_2Cl_2$) to give the title compound (Example 58, 48.9 mg, 46% yield) as a yellow solid. MS: m/z=628.3 $[M+H]^+$. $^1H$ NMR (400 MHZ, Dimethylsulfoxide-$d_6$) δ 9.38 (d,J=16.4 Hz, 1H), 7.48-7.18 (m, 2H), 7.04-6.82 (m, 2H), 5.55 (d, J=10.8 Hz, 2H), 5.41-5.16 (m, 1H), 4.80-4.49 (m, 1H), 4.46-4.37 (m, 1H), 4.05 (dd, J=9.6, 17.2 Hz, 1H), 3.38-3.36 (m, 1H), 3.15-2.96 (m, 3H), 2.83 (d, J=6.0 Hz, 1H), 2.29-2.20 (m, 1H), 2.14-1.72 (m, 10H), 1.56-1.46 (m, 1H), 1.23-1.11 (m, 1H). $^{19}F$ NMR (376 MHZ, Dimethylsulfoxide-$d_6$) δ −138.58, −138.77, −140.60, −140.74, −141.06, −172.11, −172.16, −205.03.

Example 59: 5-Ethynyl-6,7-difluoro-4-(8-fluoro-4-((1R,8S,9R)-9-fluoro-2-azabicyclo[6.1.0]nonan-2-yl)-2-(((2R,7aS)-2-fluorotetrahydro-1H-pyrrolizin-7a (5H)-yl)methoxy-$d_2$)pyrido[4,3-d]pyrimidin-7-yl)naphthalen-2-amine

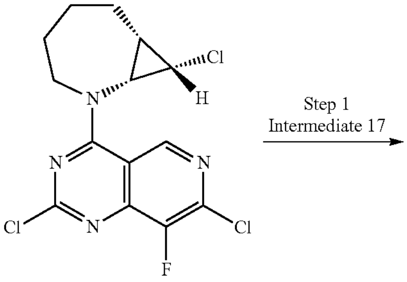

Intermediate 57

-continued

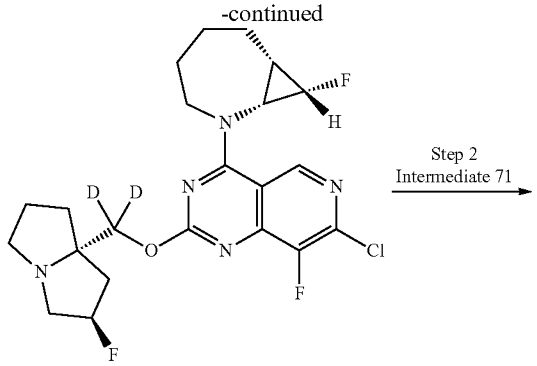

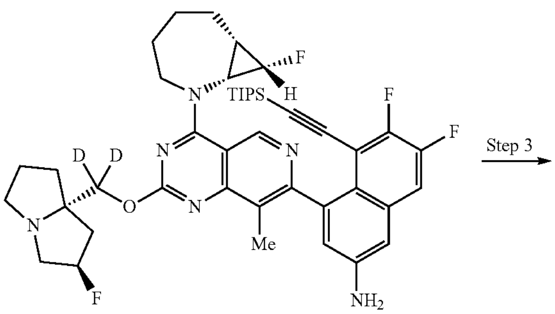

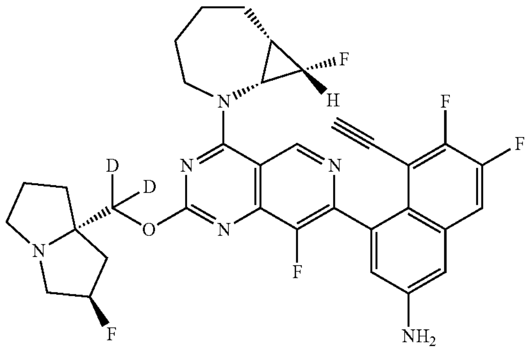

Example 59

Example 59 was prepared in a manner similar to Example 60. MS: m/z=651.2 $[M+H]^+$. $^1H$ NMR (400 MHz, Dimethylsulfoxide-$d_6$) δ 9.23-9.05 (m, 1H), 7.85-7.70 (m, 1H), 7.00 (s, 2H), 5.90-5.70 (m, 2H), 5.41-5.14 (m, 1H), 4.49-3.95 (m, 3H), 3.73-3.54 (m, 1H), 3,30-3.23 (m, 1H), 3.14-3.03 (m, 2H), 3.01 (s, 1H), 2.87-2.77 (m, 1H), 2.13 (m, 1H), 2.02-1.89 (m, 4H), 1.87-1.75 (m, 3H), 1.74-1.64 (m, 3H), 1.63-1.54 (m, 1H), 1.51-1.39 (m, 1H), 1.02-0.91 (m, 2H). $^{19}F$ NMR (376 MHz, Dimethylsulfoxide-$d_6$) −137.68, −137.74, −137.83, −138.59, −138.65, −140.13, −140.48, −172.08, −172.16, −207.83.

Example 60: 5-Ethynyl-6,7-difluoro-4-(8-fluoro-4-((1S,8R,9S)-9-fluoro-2-azabicyclo[6.1.0]nonan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine

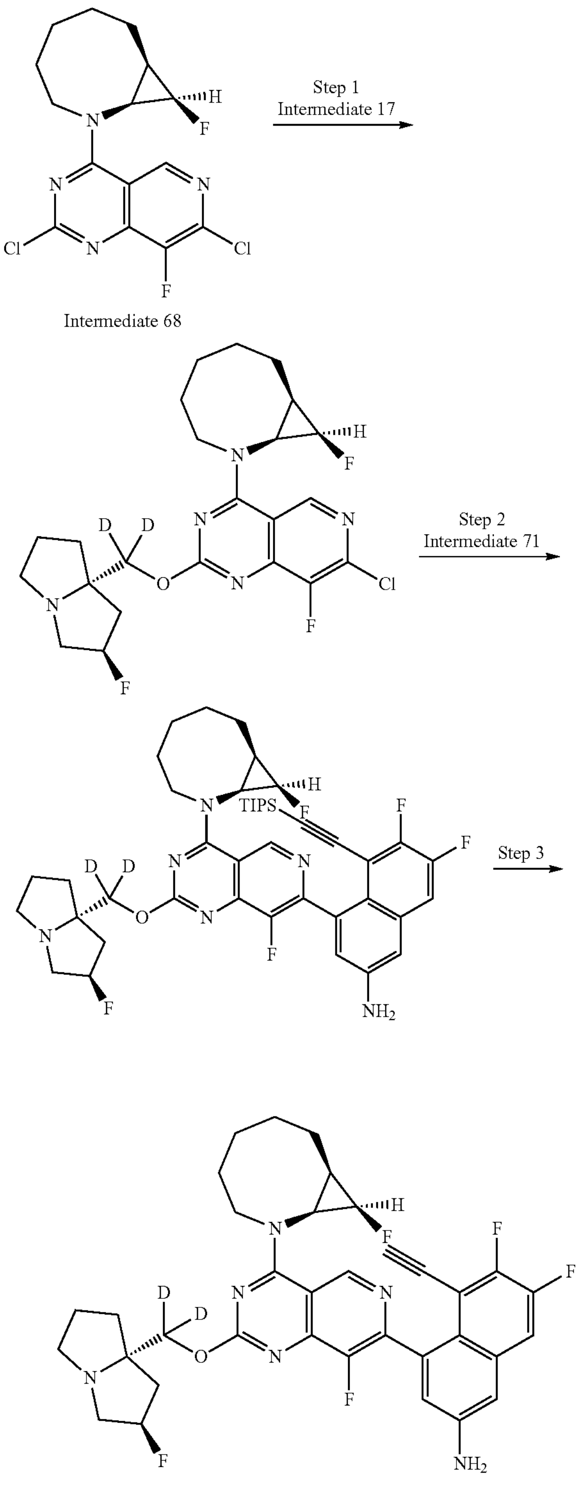

Intermediate 68

Example 60

Step 1: 7-Chloro-8-fluoro-4-((15,8R,9S)-9-fluoro-2-azabicyclo[6.1.0]nonan-2-yl)-2-(((2R,7aS)-2-fluoro-tetrahydro-1H-pyrrolizin-7a (5H)-yl)methoxy-$d_2$) pyrido[4,3-d]pyrimidine A mixture of Intermediate 58 (122 mg, 340 μmol), Intermediate 17 (99 mg, 611 μmol), DIPEA (177 μL, 1.02 mmol) in 1,4-dioxane (2 mL) was degassed and purged with $N_2$ three times, and then the mixture was stirred at 100° C. for 4 h under $N_2$ atmosphere. The reaction mixture was concentrated under reduced pressure. The residue was purified by silica gel flash chromatography (eluent: 0~6% of MeOH in $CH_2Cl_2$) to give the title compound (122 mg, 74% yield) as a yellow solid. MS: m/z=484.1 $[M+H]^{+\cdot}$ Step 2: 6,7-Difluoro-4-(8-fluoro-4-((15,8R,9S)-9-fluoro-2-azabicyclo[6.1.0]nonan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine A mixture of 7-chloro-8-fluoro-4-((1S,8R,9S)-9-fluoro-2-azabicyclo[6.1.0]nonan-2-yl)-2-(((2R,7aS)-2-fluorotetrahydro-1H-pyrrolizin-7a (5H)-yl)methoxy-$d_2$)pyrido[4,3-d] pyrimidine (121 mg, 250 μmol), Intermediate 71 (146 mg, 300 μmol), $K_3PO_4$ (159 mg, 750 μmol) and AdanBuP-Pd-$G_3$ (cataCXiumAPdG$_3$) (18 mg, 25 μmol) in 1,4-dioxane (S mL) and $H_2O$ (1 mL) was degassed, purged with $N_2$ three times, and stirred at 100° C. for 0.5 h under $N_2$ atmosphere. The reaction mixture was concentrated under reduced pressure. The residue was purified by silica gel flash chromatography (eluent: 0~5% of MeOH in $CH_2Cl_2$) to give the title compound (168 mg, 82% yield) as a yellow solid. MS: m/z=807.3 $[M+H]^{+\cdot}$ Step 3: 5-Ethynyl-6, 7-difluoro-4-(8-fluoro-4-((1S, 8R,9S)-9-fluoro-2-azabicyclo[6.1.0]nonan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine To a solution of 6,7-difluoro-4-(8-fluoro-4-((18,8R,9S)-9-fluoro-2-azabicyclo[6.1.0]nonan-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-amine (165 mg, 204 μmol) in DMSO (2 mL) was added CsF (124 mg, 818 μmol). The mixture was stirred at 25° C. for 0.5 h. The reaction mixture was diluted with water (30 mL) and extracted with EtOAc (30 mL×2). The combined organic layers were washed with brine (30 mL×2), dried over anhydrous $Na_2SO_4$, filtered and concentrated under reduced pressure. The residue was purified by reversed-phase HPLC (column: C18; mobile phase: [water ($NH_3$ $H_2O$)-ACN]; B %: 0%~60%, 25 min) to give the title compound (Example 60, 73.2 mg, 52% yield) as a yellow solid. MS: m/z=651.2 $[M+H]^+$. $^1H$ NMR (400 MHz, Dimethylsulfoxide-$d_6$) 9.22-9.05 (m, 1H), 7.85-7.70 (m, 1H), 7.00 (s, 2H), 5.80 (s, 2H), 5.39-5.16 (m, 1H), 4.48-3.92 (m, 3H), 3.74-3.55 (m, 1H), 3.29-3.26 (m, 1H), 3.15-3.05 (m, 2H), 3.03-2.98 (m, 1H), 2.90-2.75 (m, 1H), 2.17-2.09 (m, 1H), 2.00-1.81 (m, 5H), 1.79-1.54 (m, 6H), 1.51-1.40 (m, 1H), 1.08-0.85 (m, 2H). $^{19}F$ NMR (376 MHz, Dimethylsulfoxide-$d_6$) −137.68, −137.74, −138.58, −138.65, −140.08, −140.51, −171.98, −172.11, −207.80.

Example 61: 4-(4-((1S,7R)-5-Oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-5-ethynyl-6,7-difluoronaphthalen-2-amine

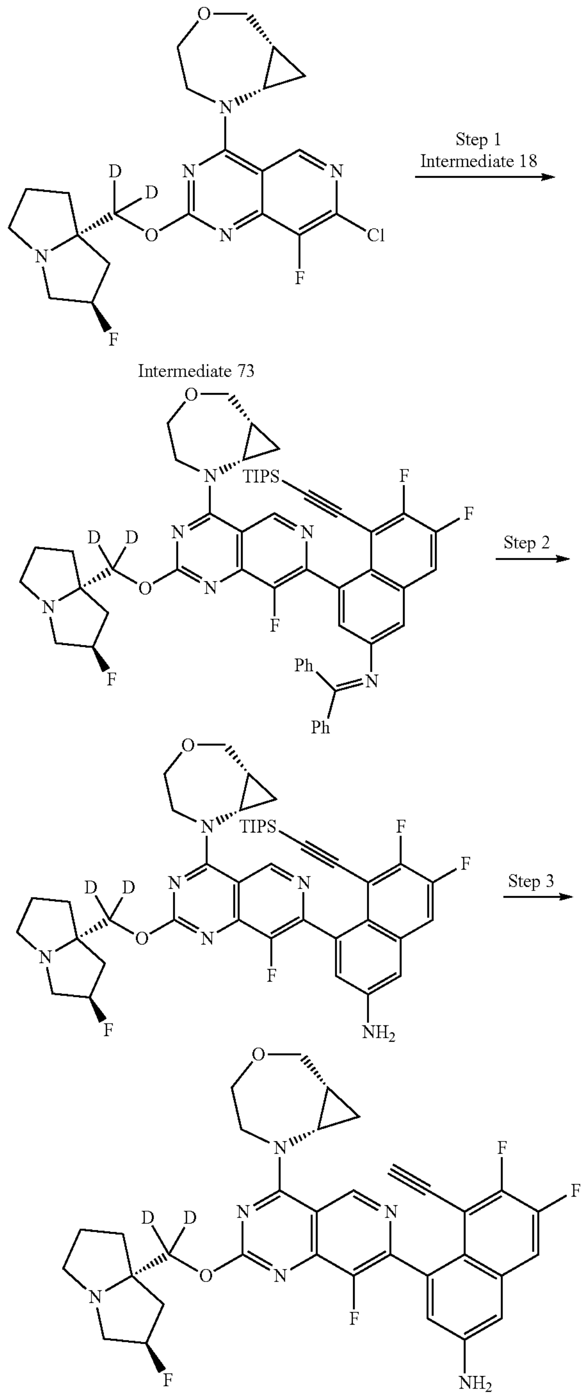

Intermediate 73

Example 61

Example 61 was prepared in a manner similar to Example 62. MS: m/z=621.25 $[M+H]^+$. $^1$H NMR (400 MHZ, DMSO-$d_6$) δ 9.56-9.46 (m, 1H), 7.82-7.77 (m, 1H), 7.02-6.99 (m, 2H), 5.79 (s, 2H), 5.38-5.25 (m, 1H), 4.52-4.48 (m, 1H), 4.37-4.32 (m, 1H), 4.20-4.00 (m, 2H), 3.78-3.65 (m, 3H), 3.26-2.78 (m, 5H), 2.20-2.00 (m, 3H), 1.91-1.76 (m, 4H), 1.26-1.22 (m, 1H), 0.87-0.72 (m, 1H), $^{19}$F NMR (376 MHz, DMSO-$d_6$) δ −137.64-−137.84 (m, 1F), −138.62-−138.69 (m, 1F), 140.51-−141.09 (m, 1F), −172.30 (s, 1F).

Example 62: 4-(4-((1R,7S)-5-oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-5-ethynyl-6,7-difluoronaphthalen-2-amine

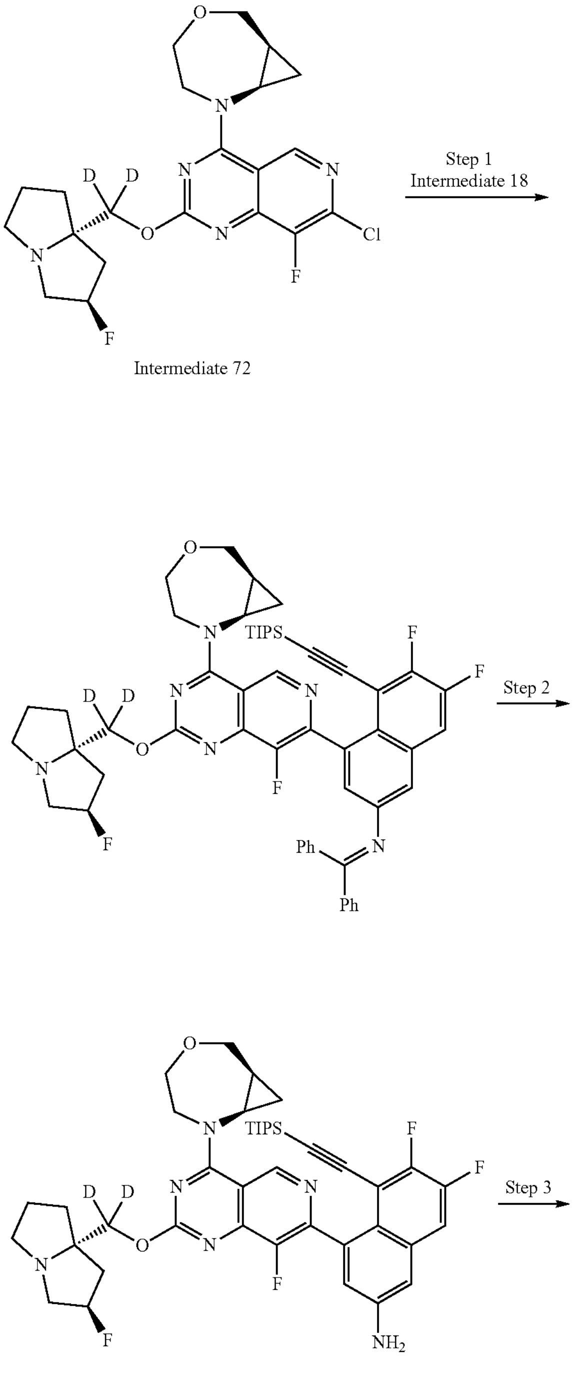

Intermediate 72

-continued

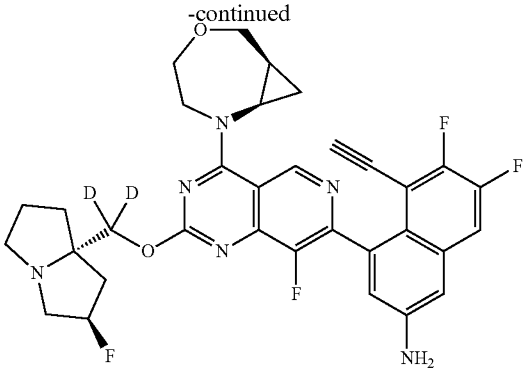

Example 62

Step 1: N-(4-(4-((1R,7S)-5-oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-6,7-difluoro-5-((triisopropylsilyl) ethynyl)naphthalen-2-yl)-1,1-diphenylmethanimine To a solution of Intermediate 72 (150 mg, 0.33 mmol) and Intermediate 18 (322.04 mg, 0.49 mmol) in toluene (2.0 mL) and water (0.4 mL) were added $Cs_2CO_3$ (355.31 mg, 1.08 mmol) and CataCXium A Pd G3 (28.88 mg, 0.04 mmol) at room temperature under nitrogen atmosphere. The reaction mixture was heated at 100° C. for 16 hours. The resulting mixture was cooled to room temperature, diluted with water (50 mL) and extracted with DCM (3×80 mL). The combined organic layers were washed with brine (2×50 mL), dried over anhydrous $Na_2SO_4$, filtered, and concentrated under reduced pressure. The residue was purified by silica gel flash chromatography, eluted with DCM/MeOH (10: 1) to afford the title compound (250 mg, 80% yield) as a yellow solid. MS: m/z=941.35 $[M+H]^{+\cdot}$ Step 2: 4-(4-((1R,7S)-5-oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-6,7-difluoro-5-((triisopropylsilyl) ethynyl)naphthalen-2-amine To a solution of N-(4-(4-((1R,7S)-S-oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-6,7-difluoro-5-((triisopropylsilyl) ethynyl)naphthalen-2-yl)-1,1-diphenylmethanimine (250 mg, 0.26 mmol) in EtOH (3.0 mL) were added $NH_2OH \cdot HCl$ (36.92 mg, 0.53 mmol) and NaOAc (43.58 mg, 0.53 mmol) at room temperature and then stirred at this temperature for 2 hours. The resulting mixture was filtered and concentrated under reduced pressure. The residue was purified by silica gel flash chromatography, eluted with DCM/MeOH (10: 1) to afford the title compound (170 mg, 82% yield) as a yellow solid. MS: m/z=777.30 $[M+H]^{+\cdot}$ Step 3: 4-(4-((1R,7S)-5-oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6,7-difluoronaphthalen-2-amine A solution of 4-(4-((1R,7S)-5-oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-6,7-difluoro-S-((triisopropylsilyl) ethynyl)naphthalen-2-amine (150 mg, 0.19 mmol) and CsF (586.51 mg, 3.86 mmol) in DMF (2.0 mL) was stirred at room temperature for 2 hours. The resulting mixture was filtered and purified by RP-Flash with the following conditions: Column: AQ-C18 Column (40 g); Mobile Phase A: 5 mM aq. $NH_4HCO_3$; Mobile Phase B: MeCN; Gradient: 0% B ~100% B within 40 min; Flow rate: 60 mL/min; Detector: UV 254 & 210 nm. The collected fractions were combined, concentrated and then lyophilized overnight to give the title compound (Example 62, 102.4 mg, 85% yield) as a yellow lyophilized powder. MS: m/z=621.20 $[M+H]^+$. $^1H$ NMR (400 MHZ, DMSO-$d_6$) δ 9.53-9.45 (m, 1H), 7.82-7.76 (m, 1H), 7.03-6.99 (m, 2H), 5.79 (s, 2H), 5.35-5.21 (m, 1H), 4.51-4.48 (m, 1H), 4.35-4.32 (m, 1H), 4.21-4.01 (m, 2H), 3.80-3.60 (m, 3H), 3.09-3.01 (m, 4H), 2.86-2.82 (m, 1H), 2.13-1.76 (m, 7H), 1.25-1.21 (m, 1H), 0.90-0.70 (m, 1H). $^{19}F$ NMR (376 MHz, DMSO-$d_6$) δ −137.69--137.86 (m, 1F), −138.63--138.70 (m, 1F), −140.52--141.16 (m, 1F), −172.07--172.17 (m, 1F).

Example 63: 5-Ethynyl-6, 7-difluoro-4-(8-fluoro-4-((1R,65,7S)-7-fluoro-2-azabicyclo[4.1.0]heptan-2-yl)-2-(((2R,7aS)-2-fluorotetrahydro-1H-pyrrolizin-7a (5H)-yl)methoxy-$d_2$)pyrido[4,3-d]pyrimidin-7-yl)naphthalen-2-amine

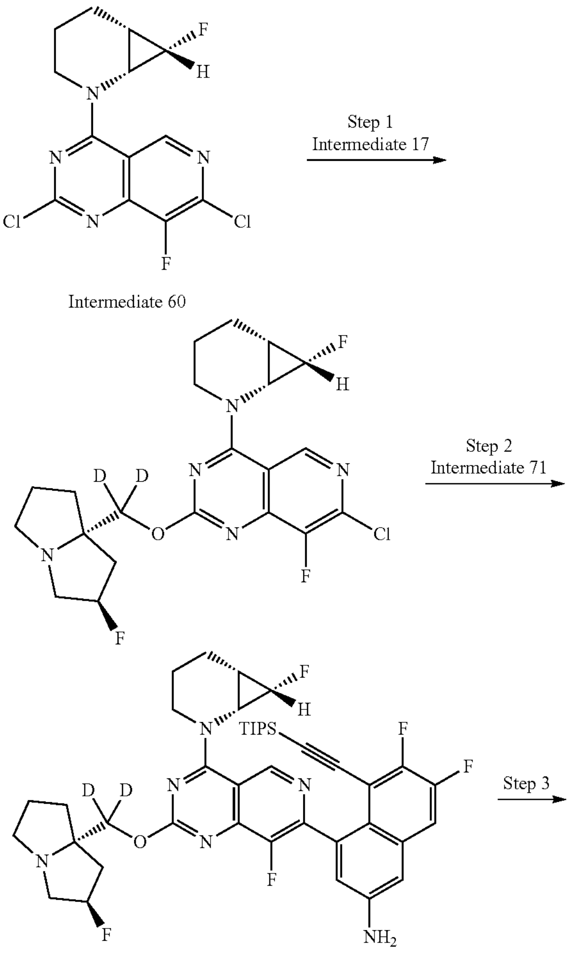

-continued

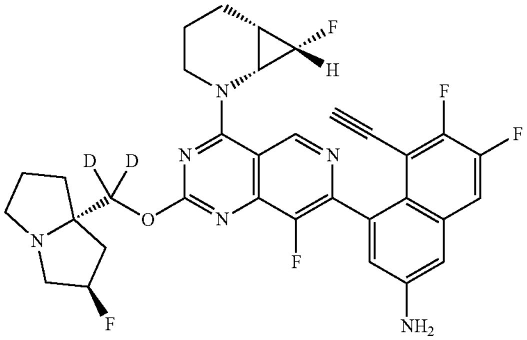

Example 63

Example 63 was prepared in a manner similar to Example 60. MS: m/z=623.2 $[M+H]^+$. $^1$HNMR (400 MHz, Dimethylsulfoxide-$d_6$) δ 9.73 (d, J=14.0 Hz, 1H), 7.85-7.71 (m, 1H), 7.08-6.89 (m, 2H), 5.78 (d, J=6.0 Hz, 2H), 5.36-5.19 (m, 1H), 5.12-4.88 (m, 1H), 4.73-4.64 (m, 1H), 4.10-3.61 (m, 2H), 3.11-3.00 (m, 4H), 2.86-2.78 (m, 1H), 2.15-1.99 (m, 4H), 1.88-1.52 (m, 7H). $^{19}$F NMR (376 MHz, Dimethylsulfoxide-$d_6$) δ −137.57, −137.64, −137.83, −137.89,-138.56, −138.62, −139.63, −139.82, −172.06, −172.17, −232.35, −233.32.

Example 64: 5-Ethynyl-6,7-difluoro-4-(8-fluoro-4-((1S,6R,7R)-7-fluoro-2-azabicyclo[4.1.0]heptan-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine

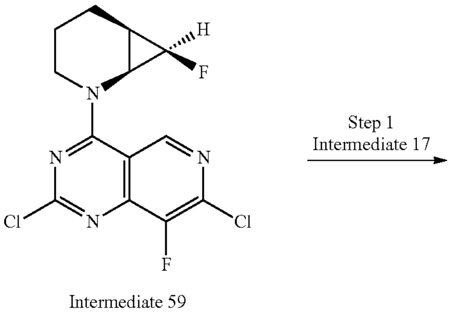

Intermediate 59

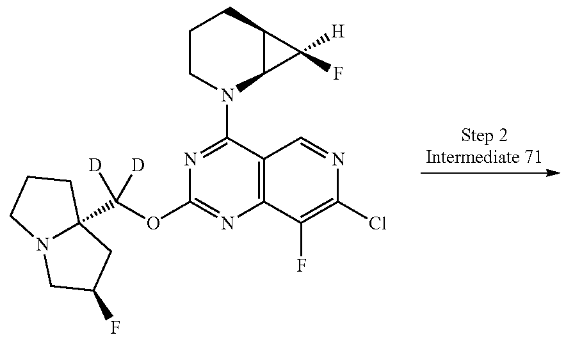

-continued

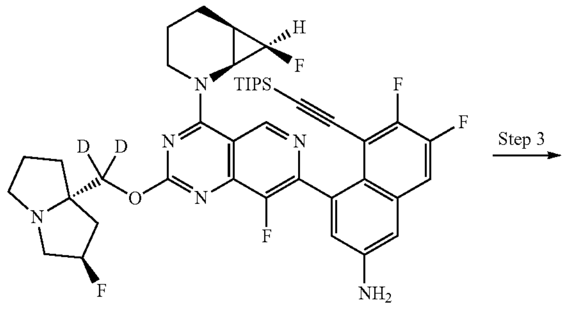

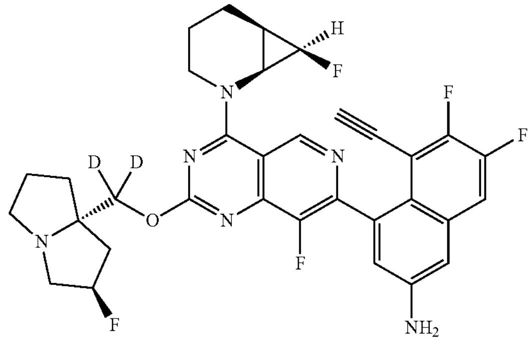

Example 64

Example 64 was prepared in a manner similar to Example 60. MS: m/z=623.2 $[M+H]^+$. $^1$HNMR (400 MHz, Dimethylsulfoxide-$d_6$) δ 9.78-9.67 (m, 1H), 7.86-7.71 (m, 1H), 7.10-6.94 (m, 2H), 5.79-5.75 (m, 2H), 5.37-5.16 (m, 1H), 5.12-4.85 (m, 1H), 4.74-4.62 (m, 1H), 4.15-3.43 (m, 2H), 3.11-3.05 (m, 2H), 3.03-2.99 (m, 2H), 2.87-2.79 (m, 1H), 2.14-2.00 (m, 4H), 1.88-1.75 (m, 5H), 1.68-1.47 (m, 2H). $^{19}$F NMR (376 MHz, Dimethylsulfoxide-$d_6$) δ −137.56, −137.84, −137.90, −138.56, −138.63, −139.66, −139.77, −172.10, −172.19, -232.37, -232.36.

Example 65: 6,7-Difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-(methoxy-$d_3$)naphthalen-2-amine

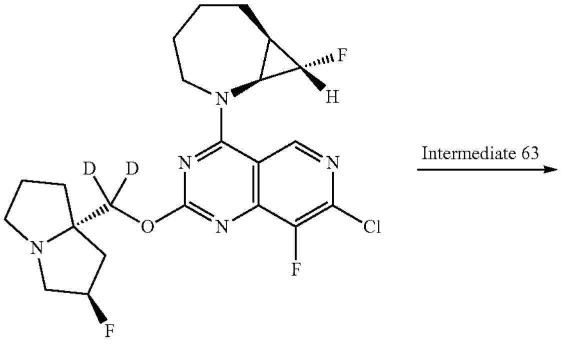

-continued

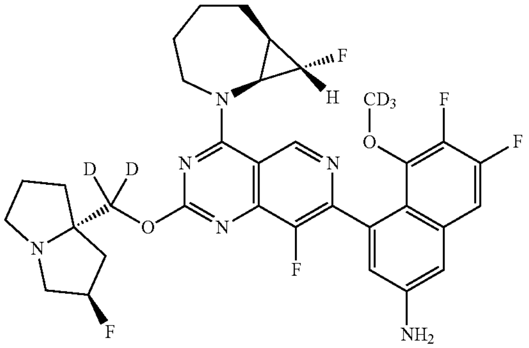

Example 65

A mixture of 7-chloro-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d] pyrimidine (200 mg, 426 μmol, refer to Example 16 for detail procedures), Intermediate 63 (201 mg, 596 μmol), $K_3PO_4$ (271 mg, 1.28 mmol) and $Ad_2nBuPPdG_3$ (cataCXium-mAPdG$_3$) (31 mg, 42 μmol) in 1,4-dioxane (5 mL) and $H_2O$ (1 mL) was degassed and purged with $N_2$ three times, and then the mixture was stirred at 100° C. for 1 h under $N_2$ atmosphere. The reaction mixture was concentrated under reduced pressure. The residue was purified by reversed-phase column chromatography (column: C18; mobile phase: [water ($NH_4HCO_3$)-ACN]; B %: 5%~65%, 25 min) to give the compound (Example 65, 155 mg, 53% yield) as a purple solid. MS: m/z=646.3 $[M+H]^+$. $^1H$ NMR (400 MHZ, Dimethylsulfoxide-$d_6$) δ 9.46-9.31 (m, 1H), 7.41 (dd, J=7.6, 11.6 Hz, 1H), 6.96-6.86 (m, 2H), 5.78-5.65 (m, 2H), 5.38-5.18 (m, 1H), 4.77-4.50 (m, 1H), 4.47-4.36 (m, 1H), 4.12-3.98 (m, 1H), 3.50-3.42 (m, 1H), 3.12-2.99 (m, 3H), 2.89-2.76 (m, 1H), 2.30-2.20 (m, 1H), 2.16-2.10 (m, 1H), 2.03-1.64 (m, 9H), 1.56-1.44 (m, 1H), 1.25-1.09 (m, 1H). $^{19}F$ NMR (376 MHz, Dimethylsulfoxide-$d_6$)-137.42, −137.46, −137.48, −137.51, −140.94, −141.23, −161.93, −161.99, −172.10, −172. 15, −204.66, −205.07.

Example 66: 6,7-Difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-(fluoromethoxy)naphthalen-2-amine

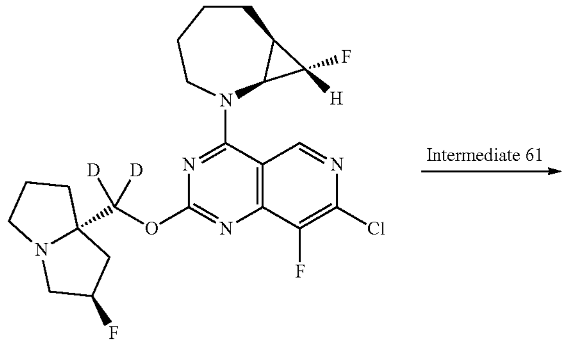

-continued

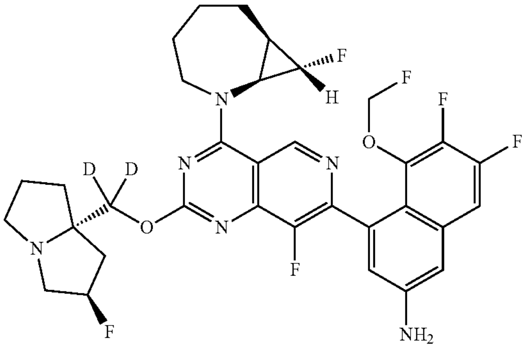

Example 66

To a solution of 7-chloro-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido [4,3-d]pyrimidine (40 mg, 85.1 μmol, refer to Example 16 for detail procedures) in 1,4-dioxane (2.5 mL) and $H_2O$ (0.5 mL) were added Intermediate 61 (60 mg, 170 μmol), $K_3PO_4$ (54 mg, 255 μmol) and AdanBuP-Pd-$G_3$ (cataCXium-mAPdG$_3$) (6 mg, 8.51 μmol). The mixture was stirred at 100° C. under $N_2$ for 1 h. The reaction mixture was concentrated under reduced pressure. The residue was purified by reversed-phase column chromatography (column: C18; mobile phase: [Water ($NH_3$ $H_2O$)-ACN)]; B %: 15%-50%, 30 min) to give the title compound (Example 66, 22.3 mg, 39% yield) as a yellow solid. MS: m/z=661.2 $[M+H]^+$. $^1H$ NMR (400 MHZ, Dimethylsulfoxide-$d_6$) δ 9.44-9.31 (m, 1H), 7.61-7.56 (m, 1H), 7.05-6.92 (m, 2H), 5.90-5.71 (m, 2H), 5.41-5.20 (m, 1H), 5.13-5.00 (m, 1H), 4.99-4.86 (m, 1H), 4.78-4.56 (m, 1H), 4.42 (d, J=13.2 Hz, 1H), 4.07-4.00 (m, 1H), 3.24-2.99 (m, 4H), 2.86 (br s, 1H), 2.30-2.21 (m, 1H), 2.17-1.95 (m, 4H), 1.89-1.66 (m, 6H), 1.55-1.44 (m, 1H), 1.20-1.05 (m, 1H). $^{19}F$ NMR (376 MHZ, Dimethylsulfoxide-$d_6$) δ −137.20, −137.28, −140.40, −140.48, −149.19, −149.24, −149.70, −159.24,-159.30, −159.56, −159.62, −172.13, −172.22.

Example 67: 5-(Difluoromethoxy)-6,7-difluoro-4-(8-fluoro-4-((1S,7R,8S)-8-fluoro-2-azabicyclo[5.1.0] octan-2-yl)-2-(((2R,7aS)-2-fluorotetrahydro-1H-pyrrolizin-7a (5H)-yl)methoxy-$d_2$)pyrido[4,3-d] pyrimidin-7-yl)naphthalen-2-amine

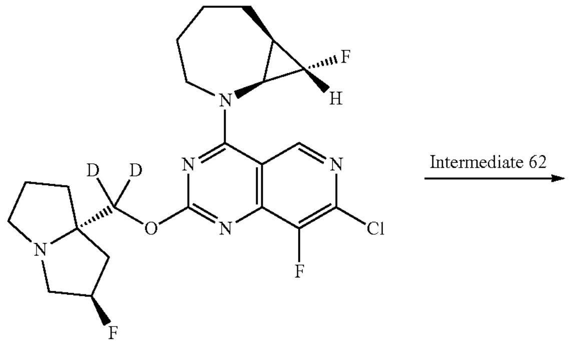

-continued

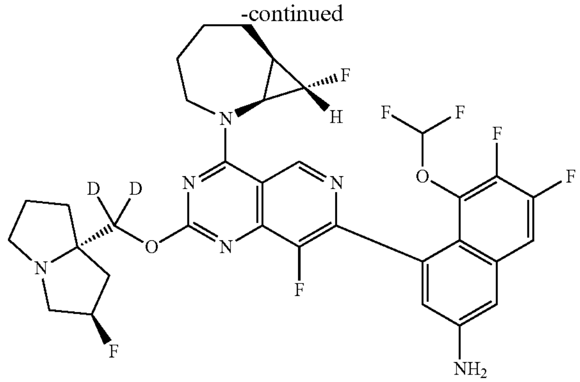

Example 67

-continued

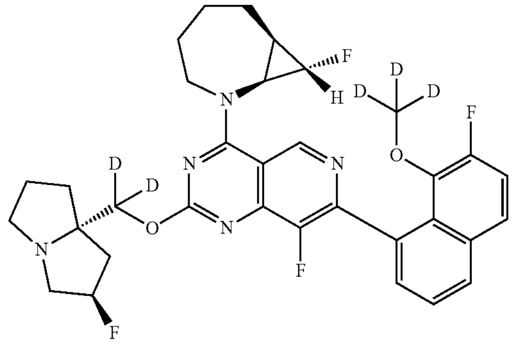

Example 68

A mixture of Intermediate 62 (64 mg, 170 μmol), 7-chloro-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine (40 mg, 85.1 μmol, refer to Example 16 for detail procedures), AdanBuP-Pd-$G_3$ (cataCXiumAPdG$_3$) (7 mg, 8.51 μmol) and $K_3PO_4$ (55 mg, 255 μmol) in 1,4-dioxane (2.5 mL) and $H_2O$ (0.5 mL) was degassed, purged with $N_2$ three times, and stirred at 100° C. for 2 h under $N_2$ atmosphere. The reaction mixture was concentrated under reduced pressure. The residue was purified by reversed-phase column chromatography (column: C18; mobile phase: [Water ($NH_3$ $H_2O$)-ACN)]; B %: 5%-50%, 35 min) to give the title compound (Example 67, 22.2 mg, 37% yield over 2 steps) as a white solid. MS: m/z=679.2 $[M+H]^+$. $^1H$ NMR (400 MHZ, Dimethylsulfoxide-$d_6$) δ 9.45-9.30 (m, 1H), 7.69 (dd, J=7.6, 11.2 Hz, 1H), 7.12-6.96 (m, 2H), 6.62 (dt, J=5.2, 72.8 Hz, 1H), 5.87 (d, J=10.0 Hz, 2H), 5.40-5.15 (m, 1H), 4.75-4.22 (m, 2H), 4.05 (td, J=10.8, 17.2 Hz, 1H), 3.30-3.20 (m, 1H), 3.12-2.99 (m, 3H), 2.86-2.77 (m, 1H), 2.34-2.22 (m, 1H), 2.15-1.95 (m, 4H), 1.91-1.69 (m, 6H), 1.57-1.45 (m, 1H), 1.18-0.99 (m, 1H). $^{19}F$ NMR (376 MHz, Dimethylsulfoxide-$d_6$) δ −81.16, −81.35, −81.62, −81.78, −82.02, −82.02, −82.39, −82.42, −82.84, −136.98, −137.09, −137.22, −137.28,-137.45, −140.40, −140.52, −140.68, −157.28, −157.40, −157.53, −157.57, −158.04, −158.10, −171.88, −171.94, −172.03, −172.37, −204.50, −205.64, −204.67.

Example 68: 8-Fluoro-7-(7-fluoro-8-(methoxy-$d_3$)naphthalen-1-yl)-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine A mixture of 7-chloro-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidine (200 mg, 426 μmol, refer to Example 16 for detail procedures), Intermediate 46 (233 mg, 766 μmol), $K_3PO_4$ (271 mg, 1.28 mmol) and AdanBuP-Pd-$G_3$ (cataCXiumAPdG$_3$) (31 mg, 42 μmol) in 1,4-dioxane (10 mL) and $H_2O$ (2 mL) was degassed, purged with $N_2$ three times, and stirred at 110° C. for 0.5 h under $N_2$ atmosphere. The reaction mixture was concentrated under reduced pressure. The residue was purified by silica gel flash chromatography (eluent: 0~2% of MeOH in $CH_2Cl_2$) to give 8-fluoro-7-(7-fluoro-8-(methoxy-$d_3$)naphthalen-1-yl)-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine (Example 68, 117.4 mg, 45% yield) as a yellow solid. MS: m/z=613.3 $[M+H]^+$. $^1H$ NMR (400 MHZ, Dimethylsulfoxide-$d_6$) δ 9.48-9.29 (m, 1H), 8.20-8.04 (m, 1H), 7.92-7.82 (m, 1H), 7.72-7.41 (m, 3H), 5.41-5.12 (m, 1H), 4.78-4.50 (m, 1H), 4.47-4.33 (m, 1H), 4.13-3.97 (m, 1H), 3.44-3.38 (m, 1H), 3.12-2.96 (m, 3H), 2.87-2.78 (m, 1H), 2.30-2.19 (m, 1H), 2.14-2.07 (m, 1H), 2.02-1.67 (m, 9H), 1.54-1.45 (m, 1H), 1.25-1.10 (m, 1H). $^{19}F$ NMR (376 MHz, Dimethylsulfoxide-$d_6$) δ −131.33, −140.86, −140.98, −172.09, −172.14, −205.07.

Example 69: 6,7,8-Trifluoro-4-(8-fluoro-4-((1S,7R,8S)-8-fluoro-2-azabicyclo[5.1.0]octan-2-yl)-2-(((2R,7aS)-2-fluorotetrahydro-LH-pyrrolizin-7a (5H)-yl)methoxy-$d_2$)pyrido[4,3-d]pyrimidin-7-yl)-5-(methoxy-$d_3$)naphthalen-2-amine

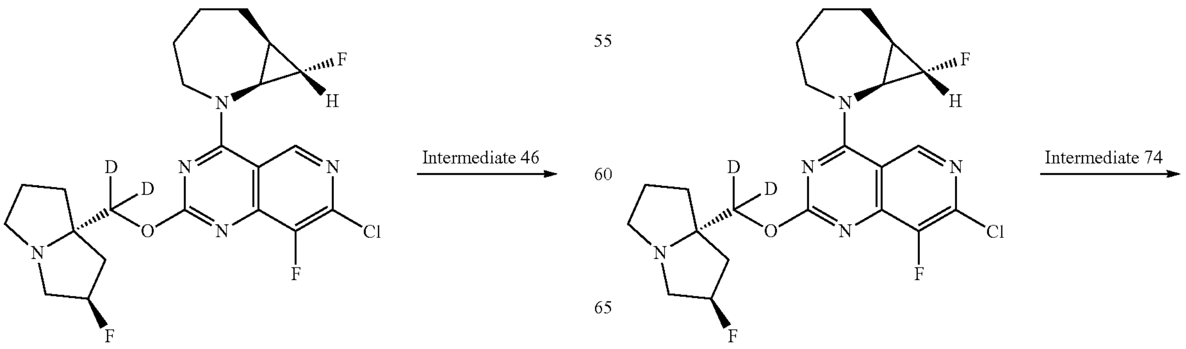

-continued

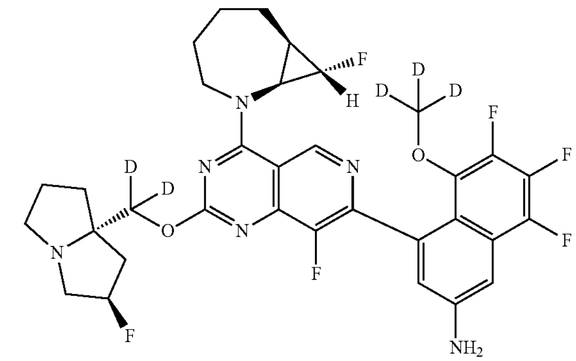

Example 69

Example 69 was prepared in a manner similar to Example 41. MS: m/z=664.2 $[M+H]^+$. $^1$H NMR (400 MHZ, Dimethylsulfoxide-$d_6$) δ 9.38 (d, J=15.6 Hz, 1H), 7.04 (s, 1H), 6.97 (dd, J=2.0, 5.6 Hz, 1H), 6.00 (d, J=10.4 Hz, 2H), 5.37-5.17 (m, 1H), 4.78-4.50 (m, 1H), 4.46-4.37 (m, 1H), 4.11-3.98 (m, 1H), 3.40-3.35 (m, 1H), 3.12-3.04 (m, 2H), 3.02-2.97 (m, 1H), 2.86-2.78 (m, 1H), 2.29-2.20 (m, 1H), 2.18-2.09 (m, 1H), 2.07-2.02 (m, 1H), 2.02-1.93 (m, 2H), 1.90-1.70 (m, 6H), 1.54-1.44 (m, 1H), 1.24-1.09 (m, 1H). $^{19}$F NMR (376 MHZ, Dimethylsulfoxide-$d_6$) δ −140.83, −141.12, −154.10, −154.16, −160.97, −161.07, −161.16, −172.10,-172.16, −204.63, −205.18.

Example 70: 5-Ethynyl-6,7,8-trifluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine

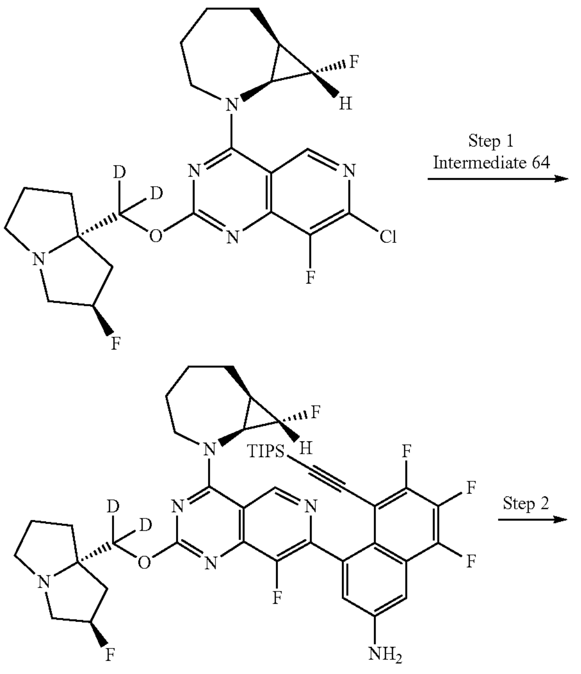

-continued

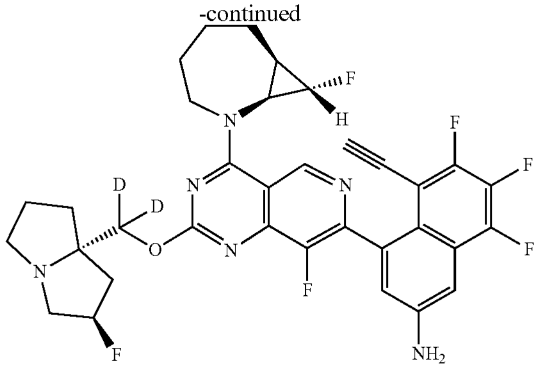

Example 70

Step 1: 6,7,8-Trifluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine A mixture of 7-chloro-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d] pyrimidine (50 mg, 106 μmol, refer to Example 16 for detail procedures), Intermediate 64 (80 mg, 160 μmol), $K_3PO_4$ (68 mg, 319 μmol) and $Ad_2nBuP$-Pd-$G_3$ (cataCXiumAPd$G_3$) (8 mg, 10.6 μmol) in 1,4-dioxane (1 mL) and $H_2O$ (0.2 mL) was degassed, purged with $N_2$ three times, and stirred at 110° C. for 1 h under $N_2$ atmosphere. The reaction mixture was concentrated under reduced pressure to give a residue. The residue was purified by flash silica gel chromatography (eluent: 0~5% of MeOH in $CH_2Cl$) to give the title compound (50 mg, 54% yield) as a yellow solid. MS: m/z=811.4 $[M+H]^{+\cdot}$ Step 2: 5-Ethynyl-6,7,8-trifluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine To a solution of 6,7,8-trifluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-amine (48 mg, 59 μmol) in DMSO (1 mL) was added CsF (27 mg, 178 μmol). The mixture was stirred at 20° C. for 0.5 h. The reaction mixture was diluted with water (50 mL) and extracted with EtOAc (50 mL×3). The combined organic layers were washed with brine (50 mL×2), dried over anhydrous $Na_2SO_4$, filtered and concentrated under reduced pressure. The residue was purified by reversed-phase column chromatography (column: C18; mobile phase: [water ($NH_4HCO_3$)-MeOH]; B %: 5%-65%, 30 min) to give the title compound (Example 70, 9.2 mg, 23% yield) as a brown solid. MS: m/z=655.1 $[M+H]^+$. $^1$HNMR (400 MHZ, Dimethylsulfoxide-$d_6$) δ 9.42-9.29 (m, 1H), 7.16-7.02 (m, 2H), 6.16-6.03 (m, 2H), 5.36-5.18 (m, 1H), 4.75-4.48 (m, 1H), 4.46-4.39 (m, 1H), 4.30-3.97 (m, 2H), 3.25-3.15 (m, 3H), 3.04-2.99 (m, 1H), 2.86-2.80 (m, 1H), 2.38-2.31 (m, 1H), 2.15-2.09 (m, 1H), 2.03-1.92 (m, 3H), 1.88-1.72 (m, 6H), 1.56-1.50 (m, 1H), 1.27-1.18 (m, 1H). $^{19}$F NMR (376 MHz, Dimethylsulfoxide-$d_6$) δ

−136.44, −136.58, −137.39, −140.13, −140.62, −144.20, −161.82, −161.88, −172.07, −172.17, −205.09.

Example 71: 6,7-Difluoro-4-(8-fluoro-4-((1S,7R, 8S)-8-fluoro-2-azabicyclo[5.1.0]octan-2-yl)-2-(((2R, 7aS)-2-fluorotetrahydro-1H-pyrrolizin-7a (5H)-yl) methoxy-$d_2$)pyrido[4,3-d]pyrimidin-7-yl)-5-(fluoromethoxy-$d_2$)naphthalen-2-amine

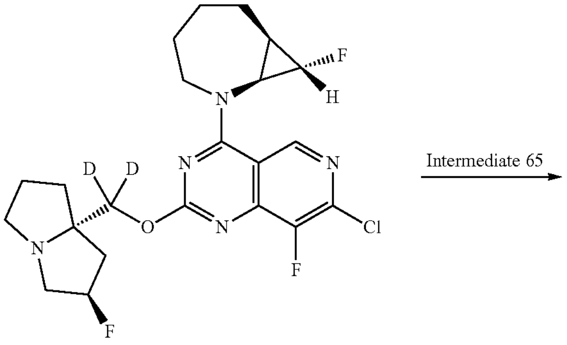

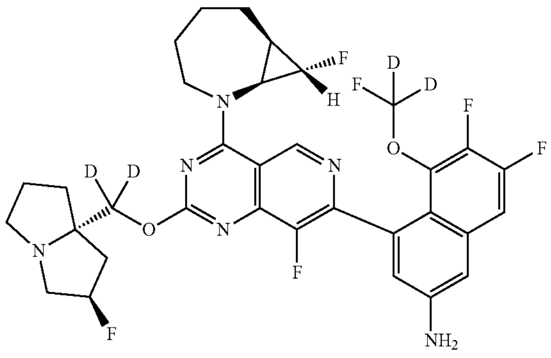

Example 71

A mixture of 7-chloro-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d] pyrimidine (117 mg, 249 μmol, refer to Example 16 for detail procedures), Intermediate 65 (124 mg, 349 μmol), $K_3PO_4$ (211 mg, 997 μmol) and AdanBuP-Pd-$G_3$ (cataCXium-mAPd$G_3$) (18 mg, 25 μmol) in 1,4-dioxane (5 mL) and $H_2O$ (1 mL) was degassed and purged with $N_2$ three times, and then the mixture was stirred at 110° C. for 1 h under $N_2$ atmosphere. The reaction mixture was concentrated under reduced pressure. The residue was purified by flash silica gel chromatography (eluent: 0~4% of MeOH in $CH_2Cl_2$) to give the title compound (Example 71, 51.5 mg, 31% yield over 2 steps) as a yellow solid. MS: m/z=663.2 $[M+H]^+$. $^1H$ NMR (400 MHz, Dimethylsulfoxide-$d_6$) δ 9.47-9.30 (d, J=21.6 Hz, 1H), 7.66-7.45 (m, 1H), 7.08-6.90 (m, 2H), 5.87-5.74 (m, 2H), 5.41-5.12 (m, 1H), 4.79-4.54 (m, 1H), 4.47-4.35 (m, 1H), 4.08-3.95 (m, 1H), 3.33-3.24 (m, 1H), 3.13-2.96 (m, 3H), 2.87-2.77 (m, 1H), 2.31-2.20 (m, 1H), 2.16-2.10 (m, 1H), 2.06-1.94 (m, 3H), 1.89-1.66 (m, 6H), 1.53-1.43 (m, 1H), 1.18-1.13 (m, 1H). $^{19}F$ NMR (376 MHz, Dimethylsulfoxide-$d_6$) δ −137.23, −137.30, −140.44, −140.50, −150.49, −150.97, −159.29, −159.66, −159.70, −172.08, −172.14, −204.66, −205.53.

Example 72: 8-Fluoro-7-(7-fluoro-8-(fluoromethoxy-$d_2$)naphthalen-1-yl)-4-((1S,7R,8S)-8-fluoro-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidine

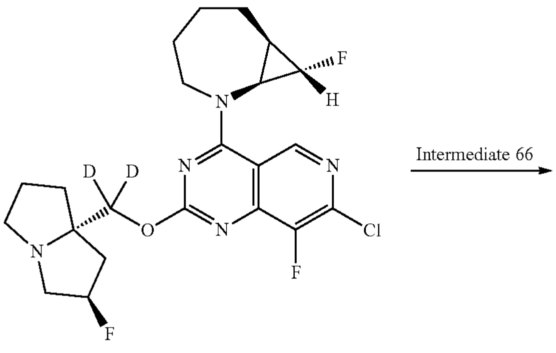

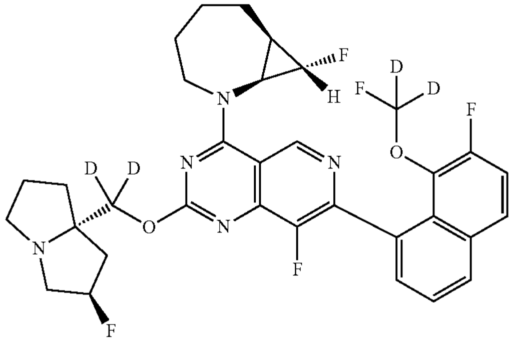

Example 72

Example 72 was prepared in a manner similar to Example 71. MS: m/z=630.2 $[M+H]^+$. $^1H$ NMR (400 MHZ, Dimethylsulfoxide-$d_6$) δ 9.44-9.35 (m, 1H), 8.22-8.19 (m, 1H), 8.04-7.97 (m, 1H), 7.72-7.56 (m, 3H), 5.40-5.16 (m, 1H), 4.80-4.56 (m, 1H), 4.49-4.37 (m, 1H), 4.12-3.98 (m, 1H), 3.40-3.35 (m, 1H), 3.25-3.15 (m, 2H), 3.03-2.98 (m, 1H), 2.87-2.77 (m, 1H), 2.38-2.30 (m, 1H), 2.17-2.09 (m, 1H), 2.03-1.90 (m, 3H), 1.89-1.63 (m, 6H), 1.56-1.44 (m, 1H), 1.22-1.08 (m, 1H). $^{19}F$ NMR (376 MHz, Dimethylsulfoxide-$d_6$) δ −129.08, −129.54, −140.41, −150.97, −151.55, −172.01, −172.14, −205.61, −205.45.

Example 73: 8-Fluoro-7-(7-fluoro-8-(fluoromethoxy)naphthalen-1-yl)-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$) pyrido[4,3-d]pyrimidine

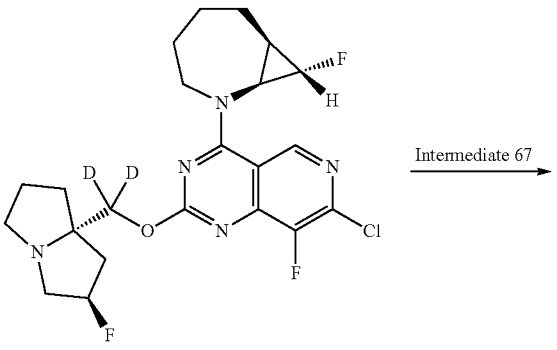

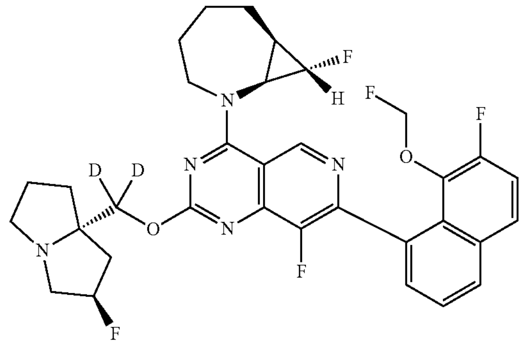

Example 73

Example 73 was prepared in a manner similar to Example 71. MS: m/z=628.1 $[M+H]^+$. $^1$HNMR (400 MHz, Dimethylsulfoxide-$d_6$) δ 9.45-9.33 (m, 1H), 8.21-8.14 (m, 1H), 8.07-7.99 (m, 1H), 7.72-7.55 (m, 3H), 5.37-5.18 (m, 1H), 5.16-4.89 (m, 2H), 4.79-4.57 (m, 1H), 4.42 (d, J=12.8 Hz, 1H), 4.09-3.97 (m, 1H), 3.40-3.35 (m, 1H), 3.12-3.04 (m, 2H), 3.00 (s, 1H), 2.87-2.77 (m, 1H), 2.31-2.20 (m, 1H), 2.17-2.08 (m, 1H), 2.06-1.94 (m, 3H), 1.89-1.69 (m, 6H), 1.56-1.45 (m, 1H), 1.22-1.10 (m, 1H), $^{19}$F NMR (376 MHz, Dimethylsulfoxide-$d_6$) δ −129.06, −129.44, −140.41, −149.67, −149.71, −150.23, −172.08, −172.14, −205.41.

Example 74: 6,7-Difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$)pyrido[4,3-d]pyrimidin-7-yl)-5-(methoxy-$d_3$)naphthalen-2-amine

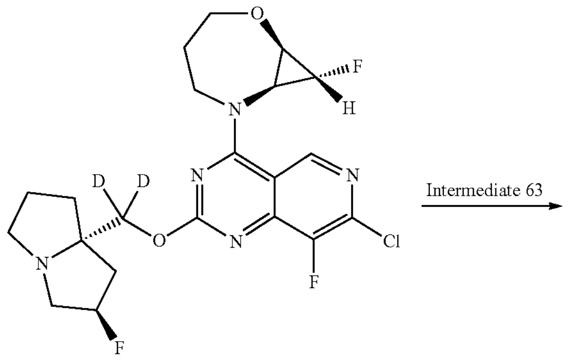

Intermediate 28

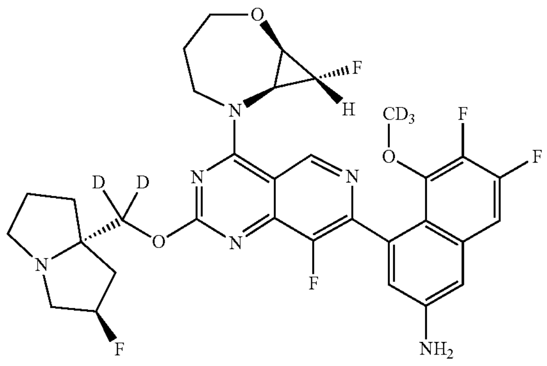

Example 74

Example 74 was prepared in a manner similar to Example 71. MS: m/z=648.30 $[M+H]^+$. $^1$H NMR (400 MHZ, DMSO-$d_6$) δ 9.33-9.30 (m, 1H), 7.44-7.39 (m, 1H), 6.93-6.90 (m, 2H), 5.73-5.71 (m, 2H), 5.35-5.22 (m, 1H), 4.88-4.69 (m, 1H), 4.51-4.48 (m, 1H), 4.18-4.09 (m, 2H), 3.95-3.93 (m, 1H), 3.84-3.81 (m, 1H), 3.59-3.53 (m, 1H), 3.10-3.01 (m, 3H), 2.86-2.81 (m, 1H), 2.16-1.77 (m, 8H). $^{19}$F NMR (376 MHz, DMSO-$d_6$) δ −137.41-−137.48 (m, 1F), −140.69-−140.80 (d, 1F), −161.92-−161.98 (d, 1F), −172.08-−172.14 (d, 1F), −211.81-−211.36 (d, 1F).

Example 75: (1R,7S,8R)-6-(7-(8-Ethynyl-7-fluoronaphthalen-1-yl)-8-fluoro-2-(((2R,7aS)-2-fluorotetrahydro-1H-pyrrolizin-7a (5H)-yl)methoxy-$d_2$)pyrido[4,3-d]pyrimidin-4-yl)-8-fluoro-2-oxa-6-azabicyclo[5.1.0]octane

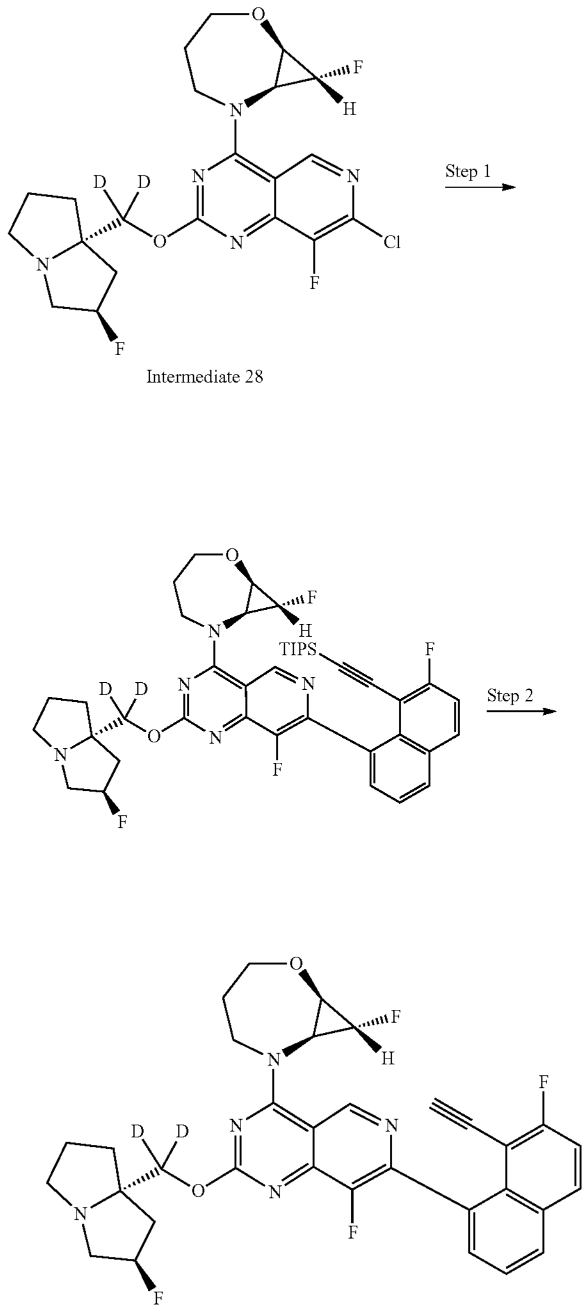

Example 75

Example 75 was prepared in a manner similar to Example 45. 1H NMR (400 MHZ, DMSO-$d_6$) δ 9.33-9.31 (m, 1H), 8.25-8.19 (m, 2H), 7.72-7.59 (m, 3H), 5.35-5.22 (m, 1H), 5.00-4.82 (m, 1H), 4.53-4.43 (m, 1H), 4.36 (s, 1H), 4.22-4.11 (m, 2H), 3.96-3.81 (m, 2H), 3.60-3.54 (m, 1H), 3.10-3.01 (m, 3H), 2.89-2.78 (m, 1H), 2.21-1.69 (m, 8H). $^{19}$F NMR (376 MHZ, DMSO-de) 8-105.86--105.90 (d, 1F), −139.86--140.10 (d, 1F), −172.03--172.15 (d, 1F), −211.77--212.63 (d, 1F).

Example 76: (1R,7S,8R)-6-(7-(8-Ethynyl-6,7-difluoronaphthalen-1-yl)-8-fluoro-2-(((2R,7aS)-2-fluorotetrahydro-1H-pyrrolizin-7a (5H)-yl)methoxy-$d_2$)pyrido[4,3-d]pyrimidin-4-yl)-8-fluoro-2-oxa-6-azabicyclo[5.1.0]octane

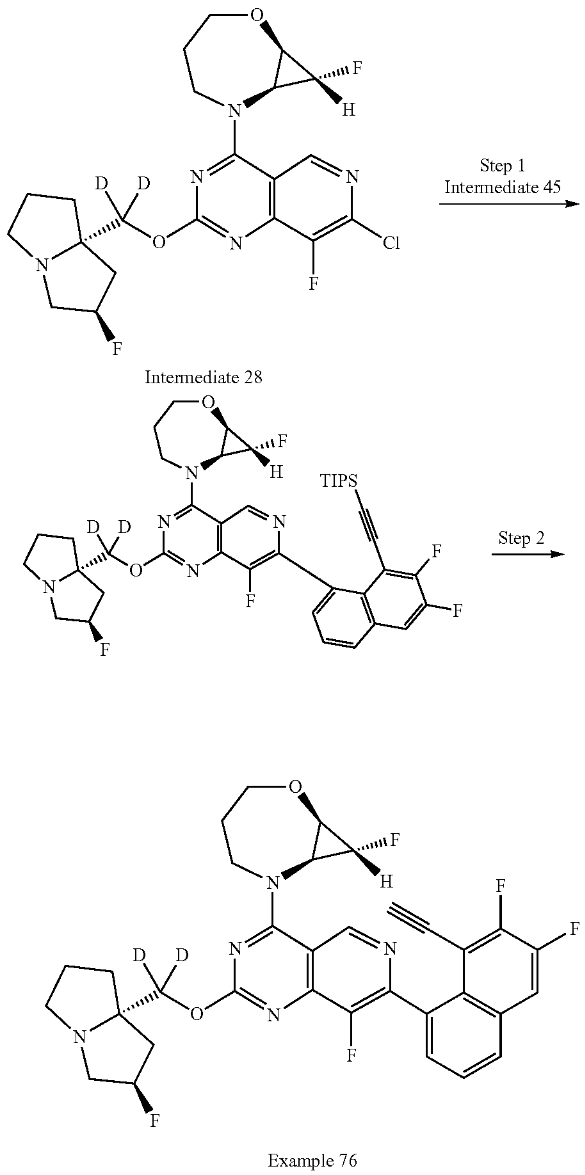

Example 76

Example 76 was prepared in a manner similar to Example 42. MS: m/z=624.20 [M+H]$^+$. $^1$H NMR (400 MHZ, DMSO-$d_6$) δ 9.33-9.31 (m, 1H), 8.30-8.25 (m, 1H), 8.18-8.16 (m, 1H), 7.76-7.72 (m, 1H), 7.65-8.63 (m, 1H), 5.35-5.22 (m, 1H), 5.00-4.70 (m, 1H), 4.54-4.47 (m, 2H), 4.23-4.12 (m, 2H), 3.95-4.81 (m, 2H), 3.60-3.54 (m, 1H), 3.14-3.01 (m, 3H), 2.87-2.82 (m, 1H), 2.21-1.69 (m, 8H). $^{19}$F NMR (376 MHz, DMSO-$d_6$) δ −129.63--129.71 (m, 1F), −137.16--137.24 (m, 1F), −139.91--140.12 (m, 1F), −172.05--172.16 (d, 1F), −211.80--212.75 (d, 1F)

Example 77: 6,7,8-Trifluoro-4-(8-fluoro-4-((1R,75,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-$d_2$)pyrido[4,3-d]pyrimidin-7-yl)-5-(methoxy-$d_3$)naphthalen-2-amine

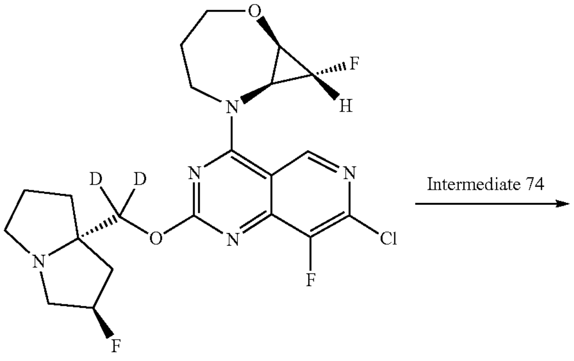

Intermediate 28

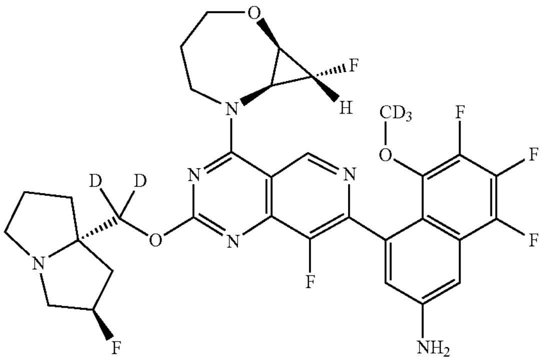

Example 77

Example 77 was prepared in a manner similar to Example 41. MS: m/z=666.20 $[M+H]^+$. $^1H$ NMR (400 MHZ, DMSO-$d_6$) δ 9.33-9.30 (m, 1H), 7.05-6.98 (m, 2H), 6.03-6.00 (m, 2H), 5.35-5.22 (m, 1H), 4.88-4.70 (m, 1H), 4.51-4.48 (m, 1H), 4.22-4.09 (m, 2H), 3.95-3.93 (m, 1H), 3.84-3.78 (m, 1H), 3.59-3.53 (m, 1H), 3.09-3.01 (m, 3H), 2.85-2.80 (m, 1H), 2.20-1.70 (m, 8H). $^{19}F$ NMR (376 MHz, DMSO-$d_6$) &-140.58--140.68 (d, 1F), −154.14--154.23 (m, 1F), −160.96--161.11 (m, 2F), −172.09--172.15 (d, 1F), −211.83--212.45 (d, 1F)

Example 78: 7-(8-Ethynyl-7-fluoronaphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine

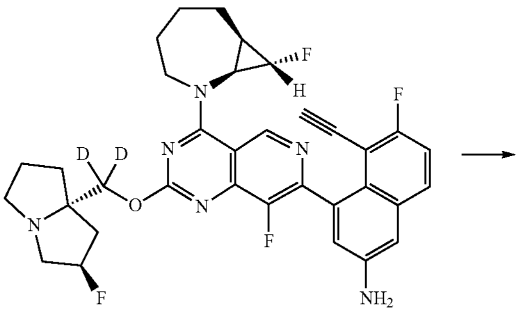

Example 82

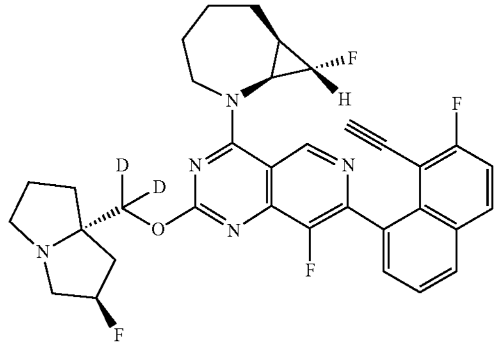

Example 78

To a solution of Example 82 (60 mg, 96.9 μmol) in EtOH (5 mL) was added HCl (600 AL, 6 M in $H_2O$) and $NaNO_2$ (17 mg, 242 μmol) at 0° C. The mixture was stirred at 0° C. for 30 min.

Then $H_3PO_2$ (63 mg, 969 μmol) was added, and the mixture was stirred at 20° C. for 2.5 h. The reaction mixture was quenched with $NaHCO_3$ (6 mL) at 25° C., diluted with $H_2O$ (10 mL) and extracted with EtOAc (20 mL×3). The combined organic layers were washed with brine (20 mL), dried over anhydrous $Na_2SO_4$, filtered and concentrated under reduced pressure. The residue was purified by silica gel flash chromatography (eluent: 0~5% of MeOH in $CH_2Cl_2$) to give the title compound (Example 78, 28.8 mg, 49% yield) as a yellow solid. MS: m/z=604.4 $[M+H]^+$. JH NMR (400 MHZ, Dimethylsulfoxide-$d_6$) δ 9.43-9.33 (m, 1H), 8.28-8.17 (m, 2H), 7.73-7.56 (m, 3H), 5.38-5.18 (m, 1H), 4.76-4.49 (m, 1H), 4.46-4.37 (m, 1H), 4.28-3.93 (m, 2H), 3.41-3.37 (m, 1H), 3.14-2.99 (m, 3H), 2.88-2.79 (m, 1H), 2.34-2.23 (m, 1H), 2.16-2.09 (m, 1H), 2.06-1.73 (m, 9H), 1.57-1.48 (m, 1H), 1.22-1.06 (m, 1H). $^{19}F$ NMR (376 MHz, Dimethylsulfoxide-$d_6$) δ −105.78, −105.87, −140.10, −140.50, −172.09, −172.19, -204.97, -205.04.

Example 79: 7-(8-Ethynyl-6,7-difluoronaphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine

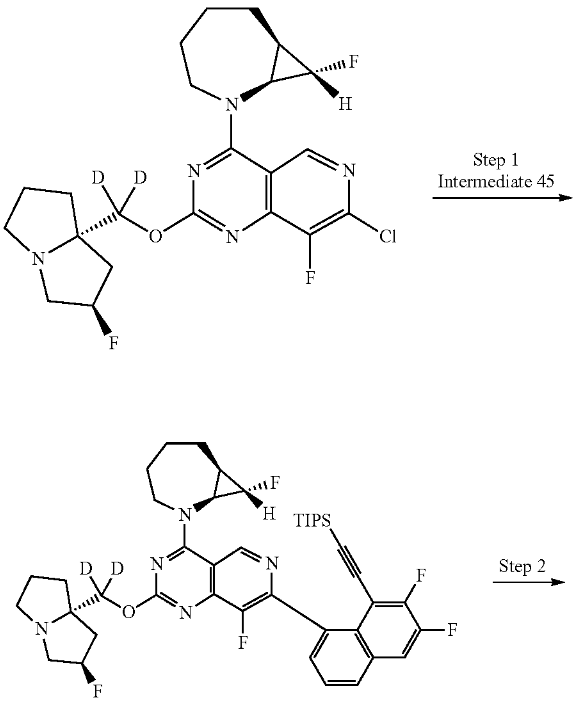

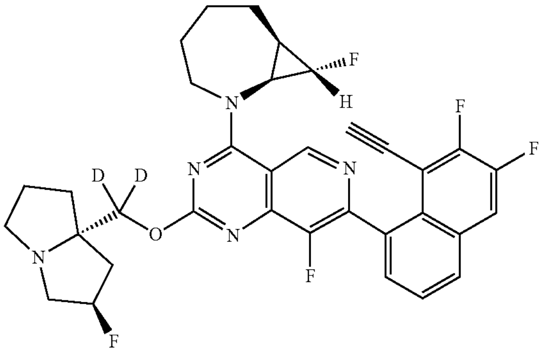

Example 79

Example 79 was prepared in a manner similar to Example 42. MS: m/z=622.35 $[M+H]^+$. $^1H$ NMR (400 MHZ, DMSO-$d_6$) δ 9.41-9.36 (m, 1H), 8.30-8.25 (m, 1H), 8.18-8.16 (m, 1H), 7.77-7.73 (m, 1H), 7.66-7.60 (m, 1H), 5.35-5.21 (m, 1H), 4.67-4.52 (m, 1H), 4.45-4.18 (m, 2H), 4.09-4.05 (m, 1H), 3.35-3.33 (m, 1H), 3.09-3.01 (m, 3H), 2.86-2.81 (m, 1H), 2.25-2.28 (m, 1H), 2.12-1.76 (m, 10H), 1.81-1.72 (m, 1H), 1.53-1.50 (m, 1H), 1.25-1.10 (m, 1H). $^{19}F$ NMR. (376 MHz, DMSO-$d_6$) δ −129.50--129.69 (m, 1F), −137.16-−137.25 (m, 1F), −140.17--140.52 (d, 1F), −172.07--172.17 (d, 1F), −204.65--204.07 (m, 1F).

Example 80: (15,7S,8S)-8-Fluoro-2-(8-fluoro-7-(7-fluoro-8-(fluoromethoxy-$d_2$)naphthalen-1-yl)-2-(((2R,7aS)-2-fluorotetrahydro-1H-pyrrolizin-7a (5H)-yl)methoxy-$d_2$)pyrido[4,3-d]pyrimidin-4-yl)-5-oxa-2-azabicyclo[5.1.0]octane

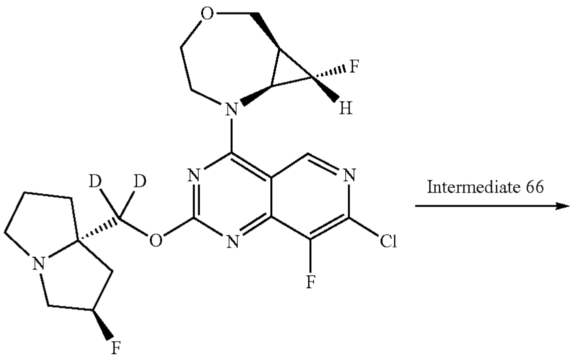

Intermediate 34

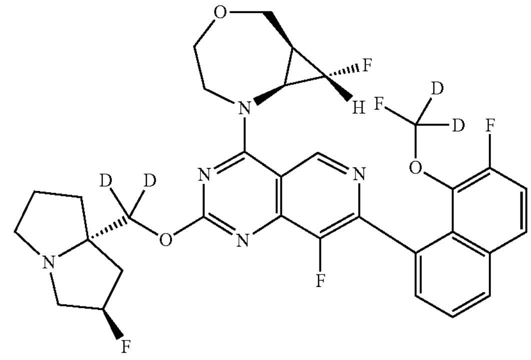

Example 80

To a solution of Intermediate 34 (100 mg, 0.21 mmol) and Intermediate 66 (102.40 mg, 0.31 mmol) in THF (4.24 mL) and $H_2O$ (0.84 mL) were added $K_3PO_4$ (269.88 mg, 1.27 mmol) and CataCXium A Pd G3 (30.87 mg, 0.04 mmol) at room temperature under nitrogen atmosphere. The reaction mixture was heated at 80° C. for 3 hours. The resulting mixture was cooled to room temperature, diluted with $H_2O$ (5 mL), and extracted with ethyl acetate (3×10 mL). The combined organic layers were washed with brine (8 mL), dried over anhydrous sodium sulfate, filtered and concentrated under reduced pressure. The residue was purified by Prep-TLC ($CH_2Cl_2$/MeOH 15: 1) to afford a crude product. The crude product was purified by RP-Flash directly with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 56% B in 15 min, 56% B to 56% B in 3 min, 56% B to 95% B in 4 min; Detector: UV 254 & 210 nm. The collected fractions were combined, concentrated and lyophilized overnight to give the title compound (Example 80, 50.0 mg, 36% yield) as an off-white lyophilized powder. MS: m/z=632.25 $[M+H]^+$. JH NMR (400 MHZ, DMSO-$d_6$) δ 9.52-9.38 (m, 1H), 8.20-8.18 (m, 1H), 8.06-8.03 (m, 1H), 7.72-7.58 (m, 3H), 5.34-5.21 (m, 1H), 4.98-4.83 (m, 1H), 4.53-4.49 (m, 1H), 4.40-4.28 (m, 2H), 4.03-4.00 (m, 1H), 3.81-3.63 (m, 2H), 3.32-3.00 (m, 4H), 2.87-2.80 (m, 1H), 2.45-2.25 (m, 1H), 2.21-1.70 (m, 6H). $^{19}F$ NMR (376 MHz, DMSO-$d_6$) δ −129.07-−129.53 (m, 1F), −140.24 (s, 1F), −151.01-−151.43 (d, 1F), −172.09-−172.15 (d, 1F), −208.15-−208.25 (m, 1F).

Example 81: 6-Amino-8-(8-fluoro-4-((15,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-1-(methoxy-$d_3$)-2-naphthonitrile

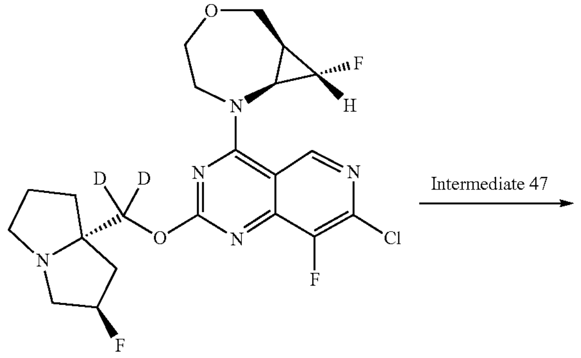

Intermediate 34

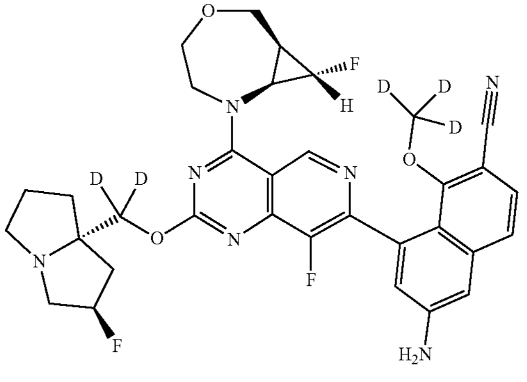

Example 81

Example 81 was prepared in a manner similar to Example 49. MS: m/z=637.40 $[M+H]^+$. $^1H$ NMR (400 MHz, DMSO-$d_6$) δ 9.46-9.41 (m, 1H), 7.50-7.45 (m, 2H), 7.05-6.99 (m, 2H), 6.21-6.19 (m, 2H), 5.34-5.21 (m, 1H), 4.94-4.79 (m, 1H), 4.52-4.49 (m, 1H), 4.39-4.30 (m, 2H), 4.03-4.00 (m, 1H), 3.71-3.59 (m, 2H), 3.22-3.17 (m, 1H), 3.12-3.00 (m, 3H), 2.87-2.81 (m, 1H), 2.41-2.20 (m, 1H), 2.12-1.97 (m, 3H), 1.85-1.76 (m, 3H). $^{19}F$ NMR (376 MHz, DMSO-$d_6$) δ −140.44-−140.71 (d, 1F), −172.09-−172.14 (d, 1F), −208.06-−209.00 (m, 1F).

Example 82: 5-Ethynyl-6-fluoro-4-(8-fluoro-4-((1S,7R,8S)-8-fluoro-2-azabicyclo[5.1.0]octan-2-yl)-2-(((2R,7aS)-2-fluorotetrahydro-LH-pyrrolizin-7a (5H)-yl)methoxy-$d_2$)pyrido[4,3-d]pyrimidin-7-yl) naphthalen-2-amine

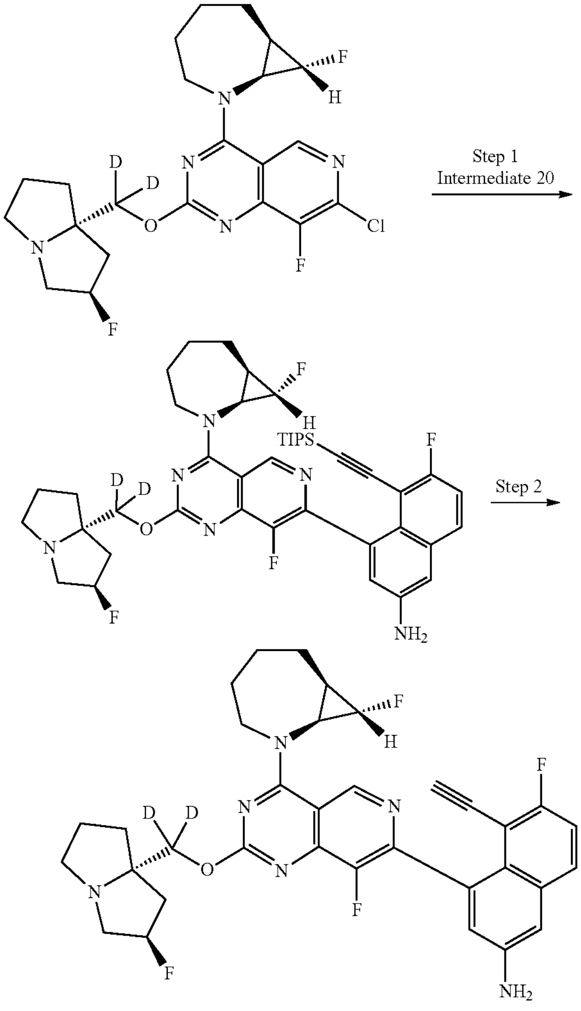

Example 82

Step 1: 6-Fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine A mixture of 7-chloro-8-fluoro-4-((15,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d] pyrimidine (440 mg, 936 μmol, refer to Example 16 for detail procedures), Intermediate 20 (788 mg, 1.69 mmol), $K_3PO_4$ (596 mg, 2.81 mmol) and AdanBuP-Pd-$G_3$ (cat-aCXiumAPdG$_3$) (137 mg, 187 μmol) in 1,4-dioxane (8 mL) and $H_2O$ (0.8 mL) was degassed and purged with $N_2$ three times, and then the mixture was stirred at 100° C. for 2 h under $N_2$ atmosphere. The reaction mixture was concentrated under reduced pressure. The residue was purified by silica gel flash chromatography (eluent: 0~10% MeOH in $CH_2Cl$) to give the title compound (500 mg, 69% yield) as a brown solid. MS: m/z=775.6 $[M+H]^{+}$·

Step 2: 5-Ethynyl-6-fluoro-4-(8-fluoro-4-((1S,7R, 8S)-8-fluoro-2-azabicyclo[5.1.0]octan-2-yl)-2-(((2R, 7aS)-2-fluorotetrahydro-1H-pyrrolizin-7a (5H)-yl) methoxy-$d_2$)pyrido[4,3-d]pyrimidin-7-yl) naphthalen-2-amine To a solution of 6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido [4,3-d]pyrimidin-7-yl)-5-((triisopropylsilyl) ethynyl) naphthalen-2-amine (500 mg, 645 μmol) in DMSO (5 mL) was added CsF (980 mg, 6.45 mmol). The mixture was stirred at 30° C. for 1 h. The residue was purified by reversed-phase column chromatography (column: C18; mobile phase: [Water ($NH_4HCO_3$)-MeOH); B %: 0%~70%, 30 min) to give the title compound (Example 82, 252 mg, 405 μmol, 63% yield) as a yellow solid. MS: m/z=619.2 $[M+H]^+$. $^1$H NMR (400 MHZ, Dimethylsulfoxide-$d_6$) δ 9.47-9.27 (m, 1H), 7.88-7.60 (m, 1H), 7.44-7.20 (m, 1H), 7.15-6.93 (m, 2H), 5.69-5.54 (m, 2H), 5.41-5.08 (m, 1H), 4.77-4.32 (m, 2H), 4.15-3.74 (m, 2H), 3.39-3.33 (m, 1H), 3.15-2.96 (m, 3H), 2.91-2.75 (m, 1H), 2.35-2.18 (m, 1H), 2.12 (s, 1H), 2.07-1.94 (m, 3H), 1.91-1.69 (m, 6H), 1.61-1.44 (m, 1H), 1.31-1.09 (m, 1H). $^{19}$F NMR (376 MHz, Dimethylsulfoxide-$d_6$) δ −113.41, −140.09, −140.63, −172.06, −172.17, −204.89.

-continued

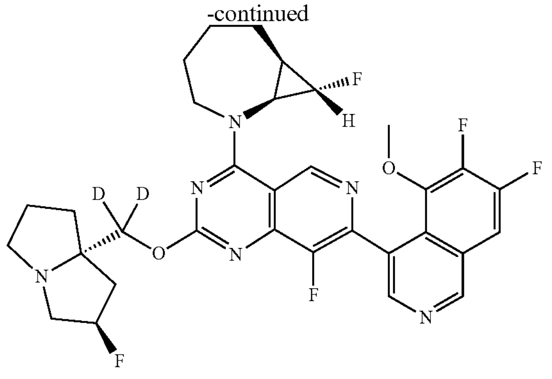

Example 83

A mixture of Intermediate 68 (50 mg, 97.2 μmol), Intermediate 70 (60 mg, 117 μmol), Pd (dppf) $Cl_2$ (14 mg, 19.4 μmol), CuI (28 mg, 146 μmol) and BINAP (24 mg, 39 μmol) in toluene (1 mL) was degassed, purged with $N_2$ three times, and stirred at 90° C. for 16 hr under $N_2$ atmosphere. The mixture was diluted with $H_2O$ (50 mL) and extracted with EtOAc (50 mL×2). The combined organic layers were washed with brine (20 mL), dried over $Na_2SO_4$, filtered and concentrated under reduced pressure. After purification by silica gel flash chromatography (Eluent of 0~8% MeOH in $CH_2Cl_2$), the title compound (Example 83, 11.6 mg, yield: 18%) was obtained as a yellow solid. MS: m/z=629.4 $[M+H]^+$. $^1$H NMR (400 MHZ, Methanol-$d_4$) δ 9.56-9.52 (m, 1H), 9.45-9.28 (m, 1H), 8.56-8.36 (m, 1H), 8.03-7.87 (m, 1H), 5.56-5.52 (m, 0.5H), 5.43-5.38 (m, 0.5H), 4.66-4.35 (m, 2H), 4.03-3.89 (m, 1H), 3.82-3.43 (m, 8H), 2.62-2.40 (m, 3H), 2.33-2.18 (m, 3H), 2.14-2.01 (m, 3H), 1.88-1.76 (m, 1H), 1.73-1.60 (m, 1H), 1.33-1.26 (m, 1H), 1.22-1.11 (m, 1H). $^{19}$F NMR (400 MHZ, Methanol-$d_4$) δ −133.530, −133.590, −140.494, −140.960, −148.195, −148.247, −148.270, −148.322, −173.975, −174.050.

Example 83: 7-(6, 7-Difluoro-5-methoxyisoquinolin-4-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido [4,3-d]pyrimidine

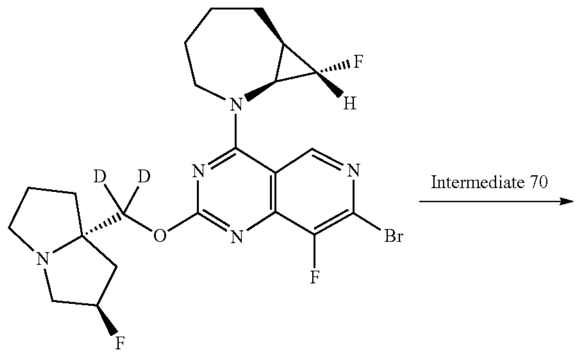

Intermediate 68

Example 84: (1S,7S,8S)-8-Fluoro-2-(8-fluoro-7-(6-fluoro-5-(methoxy-$d_3$) isoquinolin-4-yl)-2-(((2R, 7aS)-2-fluorotetrahydro-1H-pyrrolizin-7a (5H)-yl) methoxy-$d_2$)pyrido[4,3-d]pyrimidin-4-yl)-5-oxa-2-azabicyclo[5.1.0]octane

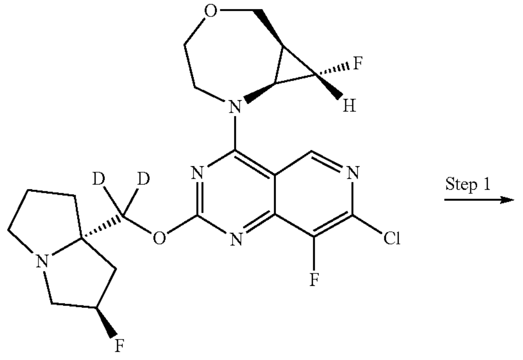

Intermediate 34

-continued

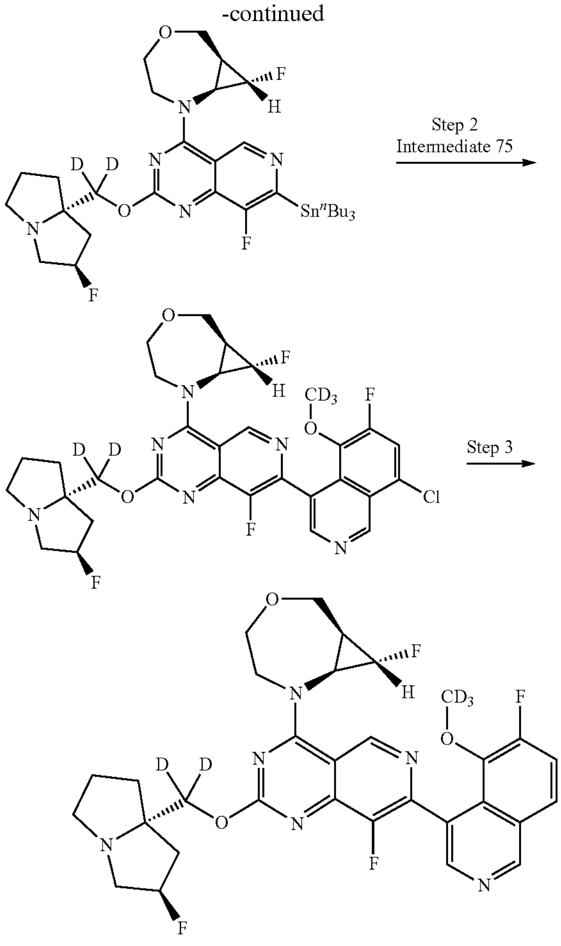

Example 84

Step 1: (1S,7S,8S)-8-fluoro-2-(8-fluoro-2-(((2R,7aS)-2-fluorotetrahydro-1H-pyrrolizin-7a (5H)-yl) methoxy-(2)-7-(tributylstannyl)pyrido[4,3-d]pyrimidin-4-yl)-5-oxa-2-azabicyclo[5.1.0]octane To a stirred solution of Intermediate 34 (250 mg, 0.53 mmol) in 1,4-dioxane (5 mL) under nitrogen atmosphere were added LiCl (113 mg, 2.67 mmol), 1,1,1,2,2,2-hexabutyldistannane (620 mg, 1.07 mmol), tricyclohexylphosphane (12 mg, 0.04 mmol) and $Pd_2(dba)_3.HCl_3$ (55 mg, 0.05 mmol) at room temperature. The reaction mixture was heated at 110° C. for 12 hours. The resulting mixture was cooled to room temperature, filtered, and concentrated under reduced pressure. The residue was purified by RP-Flash with the following conditions: Column: C18, 40 g, 40-60 um; Mobile Phase A: water; Mobile Phase B: MeCN, Gradient: 2% B hold 5 min, up to 90% B within 15 min, 90% B hold 10 min, up to 98% B within 5 min, 98% B hold 10 min; Flow rate: 40 mL/min; Detector: UV 254 & 210 nm. The product-containing fractions were collected and concentrated to afford the title compound (110 mg, 28% yield) as a brown-yellow semi-solid. MS: m/z=728.40 $[M+H]^+$. $^1H$ NMR (400 MHZ, Acetonitrile-$d_3$) δ 9.45 (s, 1H), 5.31-5.18 (m, 1H), 4.52-4.46 (m, 2H), 4.37-4.33 (m, 2H), 4.05-3.92 (m, 2H), 3.81-3.75 (m, 1H), 3.63-3.57 (m, 1H), 3.16-3.09 (m, 2H), 3.06-3.03 (m, 1H), 2.92-2.83 (m, 1H), 2.38-2.16 (m, 1H), 2.14-1.97 (m, 2H), 1.93-1.75 (m, 2H), 1.67-1.50 (m, 6H), 1.38-1.12 (m, 14H), 0.97-0.78 (m, 9H). $^{19}F$ NMR (376 MHz, Acetonitrile-$d_3$) 8-130.43 (s, 1F), −173.70 (s, 1F), −208.84 (s, 1F).

Step 2: (15,75,8S)-2-(7-(8-chloro-6-fluoro-5-(methoxy-$d_3$) isoquinolin-4-yl)-8-fluoro-2-(((2R,7aS)-2-fluorotetrahydro-1H-pyrrolizin-7a (5H)-yl) methoxy-$d_2$)pyrido[4,3-d]pyrimidin-4-yl)-8-fluoro-5-oxa-2-azabicyclo[5.1.0]octane To a solution of (1S,7S,8S)-8-fluoro-2-(8-fluoro-2-(((2R,7aS)-2-fluorotetrahydro-1H-pyrrolizin-7a (5H)-yl)methoxy-(2)-7-(tributylstannyl)pyrido[4,3-d]pyrimidin-4-yl)-5-oxa-2-azabicyclo[5.1.0]octane (50 mg, 0.07 mmol) and Intermediate 75 (43.4 mg, 0.15 mmol) in 1,4-dioxane (1.4 mL) were added CuI (14.9 mg, 0.08 mmol), BINAP (9.9 mg, 0.02 mmol) and Pd (dppf) $Cl_2$ (5.12 mg, 0.007 mmol) at room temperature under argon atmosphere in glove box. The reaction mixture was heated at 105° C. for 10 hours. The resulting mixture was cooled to room temperature, filtered and concentrated under reduced pressure. The residue was purified by Prep-TLC ($CH_2Cl_2$/MeOH=10: 1) to afford the title compound (5 mg, 11% yield) as a yellow solid. MS: m/z=650.20 $[M+H]^{+\cdot}$ Step 3: (1S,7S,8S)-8-fluoro-2-(8-fluoro-7-(6-fluoro-5-(methoxy-$d_3$) isoquinolin-4-yl)-2-(((2R,7aS)-2-fluorotetrahydro-1H-pyrrolizin-7a (5H)-yl)methoxy-$d_2$)pyrido[4,3-d]pyrimidin-4-yl)-5-oxa-2-azabicyclo [5.1.0]octane To a solution of (1S,7S,8S)-2-(7-(8-chloro-6-fluoro-5-(methoxy-$d_3$) isoquinolin-4-yl)-8-fluoro-2-(((2R,7aS)-2-fluorotetrahydro-1H-pyrrolizin-7a (5H)-yl)methoxy-$d_2$) pyrido[4,3-d]pyrimidin-4-yl)-8-fluoro-5-oxa-2-azabicyclo [5.1.0]octane (15 mg, 0.023 mmol) in 1,4-dioxane (0.8 mL) under nitrogen atmosphere were added $Et_3N$ (5.3 mg, 0.05 mmol), $Et_3SiH$ (13.5 mg, 0.12 mmol), Pd (dba) 2 (13.3 mg, 0.02 mmol) and SPhos (10.5 mg, 0.03 mmol) at room temperature. The reaction mixture was heated at 100° C. for 2 hours. The resulting mixture was cooled to room temperature, filtered, and concentrated under reduced pressure. The residue was purified by Prep-TLC ($CH_2Cl_2$/MeOH/$NH_3H_2O$=200: 8: 5) to afford a crude product. The crude product was purified by RP-Flash with the following conditions: Column: C18, 20 g, 20-35 um; Mobile Phase A: 5 mM aq. $NH_4HCO_3$; Mobile Phase B: MeCN; Gradient: 2% B hold 5 min, up to 40% B within 10 min, 40% B hold 10 min, up to 98% B within 5 min; Flow rate: 30 mL/min; Detector: UV 254 & 210 nm. The collected fractions were combined, concentrated and lyophilized overnight to give the title compound (Example 84, 8.0 mg, 56% yield) as a lyophilized powder. MS: m/z=616.30 $[M+H]^+$. $^1H$ NMR (300 MHz, Acetonitrile-d'3) δ 9.53-9.43 (m, 1H), 9.34 (s, 1H), 8.49-8.45 (m, 1H), 8.00-7.95 (m, 1H), 7.62-7.55 (m, 1H), 5.35-5.16 (m, 1H), 4.69-4.36 (m, 3H), 4.11-3.97 (m, 2H), 3.89-3.76 (m, 1H), 3.72-3.59 (m, 1H), 3.30-3.07 (m, 3H), 3.07-3.01 (m, 1H), 2.94-2.82 (m, 1H), 2.44-2.21 (m, 1H), 2.11-1.99 (m, 3H), 1.92-1.76 (m, 3H). $^{19}F$ NMR (282 MHz, Acetonitrile-$d_6$) δ −125.67-−125.82 (d, 1F), −141.20-−141.36 (d, 1F), −173.75 (s, 1F), −209.37 (bs, 1F).

Example 85: 7-(5-Chloro-6-fluoroisoquinolin-4-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine

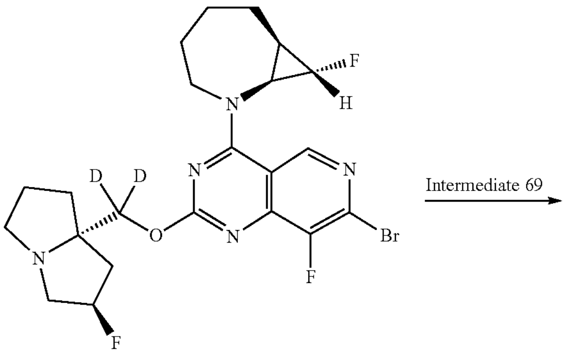

Intermediate 68

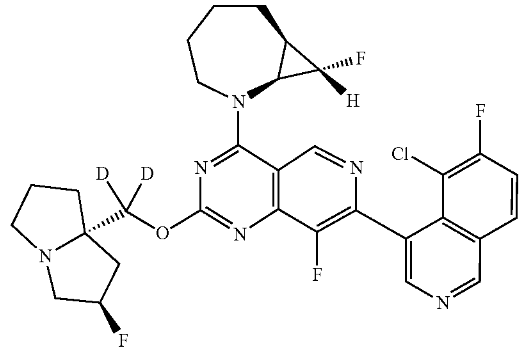

Example 85

To a solution of Intermediate 68 (150 mg, 292 μmol) in toluene (2 mL) were added Intermediate 69 (301 mg, 875 μmol), Pd (dppf) $Cl_2$ (21 mg, 29.2 μmol), BINAP (36 mg, 58.3 μmol) and CuI (17 mg, 87.5 μmol). The mixture was stirred at 90° C. for 16 hr under $N_2$ atmosphere. The mixture was concentrated under reduced pressure. After purification by silica gel flash chromatography (Bluent of 0~5% MeOH in $CH_2Cl_2$), the title compound (Example 85, 104.6 mg, yield: 55%) was obtained as a light yellow solid. MS: m/z=615.2 $[M+H]^+$. $^1H$ NMR (400 MHz, Dimethylsulfoxide-$d_6$) 89.61-9.56 (m, 1H), 9.51-9.38 (m, 1H), 8.68-8.56 (m, 1H), 8.50-8.40 (m, 1H), 7.98-7.87 (m, 1H), 5.57-5.29 (m, 1H), 4.76-4.55 (m, 1H), 4.51-4.37 (m, 1H), 4.15-4.02 (m, 1H), 3.61-3.37 (m, 4H), 3.20-2.97 (m, 1H), 2.38-2.20 (m, 3H), 2.12-1.80 (m, 7H), 1.74-1.65 (m, 1H), 1.58-1.44 (m, 1H), 1.24-1.08 (m, 1H). $^{19}F$ NMR (400 MHz, Dimethylsulfoxide-$d_6$) δ −103.18, −103.26, ~103.24, −139.42, −140.33, −140.39, −140.45, −172.55, −172.64, −172.67, −172.85, −204.73, −204.81.

Example 86: (1R,7S,8R)-8-Fluoro-6-(8-fluoro-7-(7-fluoro-8-(methoxy-$d_3$)naphthalen-1-yl)-2-(((2R,7aS)-2-fluorotetrahydro-1H-pyrrolizin-7a (5H)-yl)methoxy-$d_2$)pyrido[4,3-d]pyrimidin-4-yl)-2-oxa-6-azabicyclo[5.1.0]octane

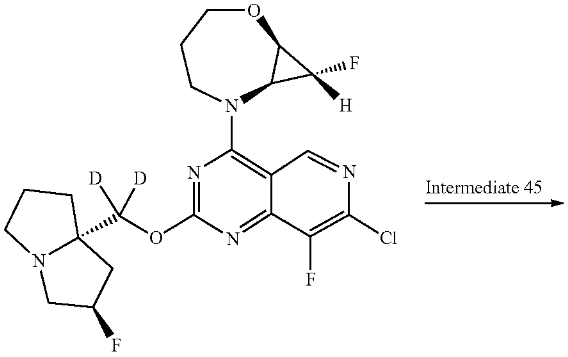

Intermediate 28

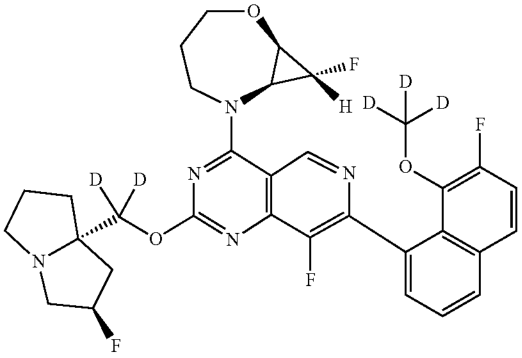

Example 86

Example 86 was prepared in a manner similar to Example 43. MS: m/z=615.40 $[M+H]^+$. $^1H$ NMR (400 MHZ, DMSO-$d_6$) δ 9.35-9.33 (m, 1H), 8.13-8.11 (m, 1H), 7.90-7.86 (m, 1H), 7.65-7.48 (m, 3H), 5.35-5.21 (m, 1H), 4.84-4.70 (m, 1H), 4.53-4.45 (m, 1H), 4.21-4.03 (m, 2H), 3.93-3.85 (m, 1H), 3.84-3.81 (m, 1H), 3.57-3.54 (m, 1H), 3.10-3.01 (m, 3H), 2.86-2.81 (m, 1H), 2.20-1.70 (m, 8H). $^{19}F$ NMR (376 MHz, DMSO-$d_6$) δ −131.26−−131.29 (d, 1F), −140.55−−140.61 (d, 1F), −172.08−−172.14 (d, 1F), −211.74−−212.35 (d, 1F).

Example 87: 5-Ethynyl-6-fluoro-4-(8-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine

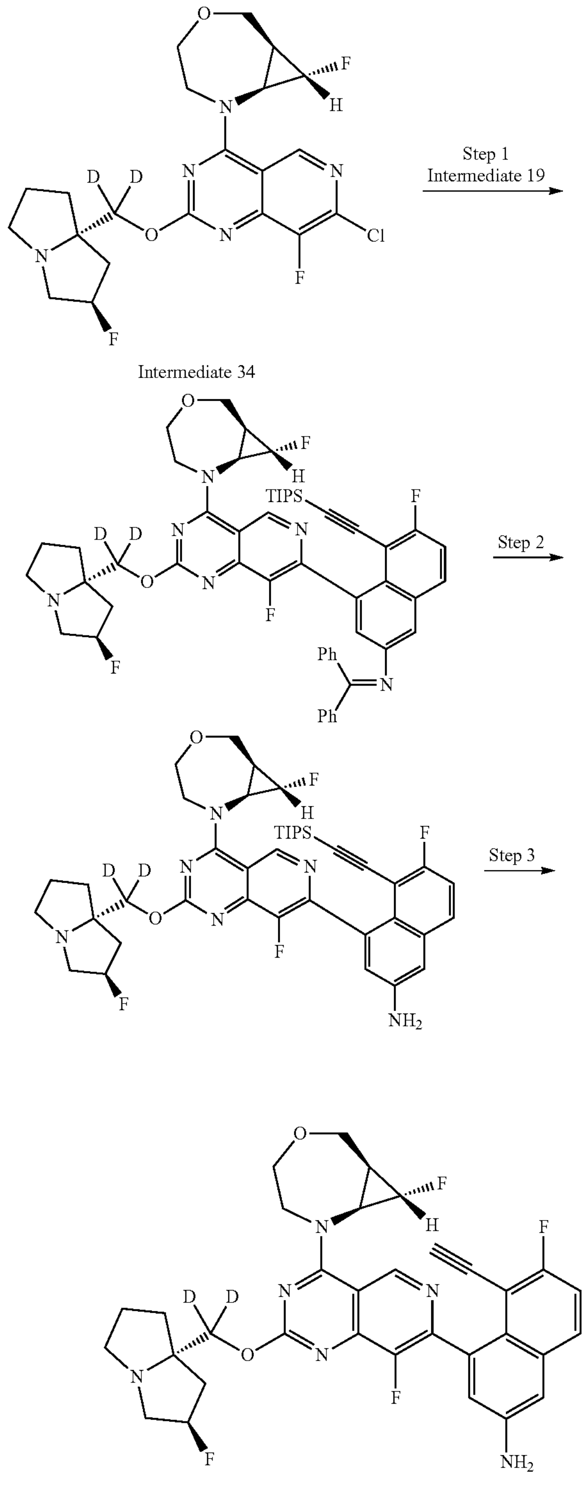

Intermediate 34

Example 87

Step 1: N-(6-Fluoro-4-(8-fluoro-4-((15,75,8S)-8-fluoro-S-oxa-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-yl)-1,1-diphenylmethanimine To a solution of Intermediate 34 (500 mg, 1.06 mmol) and Intermediate 19 (1204.76 mg, 1.90 mmol) in THF (21.2 mL) and $H_2O$ (4.24 mL) were added $K_3PO_4$ (1349.40 mg, 6.36 mmol) and CataCXium A Pd G3 (154.33 mg, 0.21 mmol) at room temperature under nitrogen atmosphere. The reaction mixture was heated at 80° C. for 3 hours. The resulting mixture was cooled to room temperature, diluted with $H_2O$ (10 mL), and extracted with ethyl acetate (3×40 mL). The combined organic layers were washed with brine (30 mL), dried over anhydrous $Na_2SO_4$, filtered and concentrated under reduced pressure. The residue was purified by silica gel flash chromatography, eluted with ($CH_2Cl_2$/MeOH 10: 1) to afford two peaks. The first eluting peak was concentrated to afford the title compound (750 mg, 75% yield) as a brown yellow solid. MS: m/z=941.55 $[M+H]^+$. The second eluting peak was concentrated to afford 6-fluoro-4-(8-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5)-yl)methoxy-$d_2$)pyrido[4,3-d]pyrimidin-7-yl)-5-((triisopropylsilyl) ethynyl)naphthalen-2-amine (100 mg, 12% yield) as a yellow solid. MS: m/z=777.50 $[M+H]^{+\cdot}$ Step 2: 6-Fluoro-4-(8-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine To a solution of N-(6-fluoro-4-(8-fluoro-4-((1S,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-yl)-1,1-diphenylmethanimine (750 mg, 0.79 mmol) in EtOH (10 mL) were added NaOAc (130.74 mg, 1.59 mmol) and $NH_2OH\cdot HCl$ (110.75 mg, 1.59 mmol) at room temperature. The reaction mixture was stirred at room temperature for 1 hour. The resulting mixture was concentrated under reduced pressure. The residue was purified by silica gel flash chromatography, eluted with ($CH_2Cl_2$/MeOH 10: 1) to afford the title compound (550 mg, 88% yield) as a yellow solid. MS: m/z=777.50 $[M+H]^{+\cdot}$ Step 3: 5-Ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine A solution of 6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-amine (650 mg, 0.83 mmol) and CsF (1270.76 mg, 8.37 mmol) in DMF (6 mL) was stirred at room temperature for 3 hours. The resulting mixture was purified by RP-Flash with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 54% B in 15 min, 54% B to 54% B in 3 min, 54% B to 95% B in 4 min;

Detector: UV 254 & 210 nm. The collected fractions were combined, concentrated and lyophilized overnight to give the title compound (Example 87, 342.9 mg, 65% yield) as a yellow lyophilized powder. MS: m/z=621.10 $[M+H]^+$. $^1H$ NMR (400 MHZ, DMSO-$d_6$) δ 9.42-9.37 (m, 1H), 7.80-7.76 (m, 1H), 7.36-7.32 (m, 1H), 7.06 (s, 2H), 5.66 (s, 2H), 5.35-5.21 (m, 1H), 4.88-4.73 (m, 1H), 4.51-4.30 (m, 3H), 4.07-3.80 (m, 2H), 3.74–3.57 (m, 2H), 3.31-3.18 (m, 1H) 3.16-3.00 (m, 3H), 2.88-2.80 (m, 1H), 2.42-2.26 (m, 1H), 2.19-1.92 (m, 3H), 1.89-1.70 (m, 3H). $^{19}F$ NMR (376 MHZ, DMSO-$d_6$) δ −113.35--113.42 (d, 1F), −139.87--140.46 (d, 1F), −172.06--172.17 (d, 1F), −207.73 (s, 1F).

Example 88: 6, 7-Difluoro-4-(8-fluoro-4-((18,7S, 8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-(fluoromethoxy-$d_2$)naphthalen-2-amine

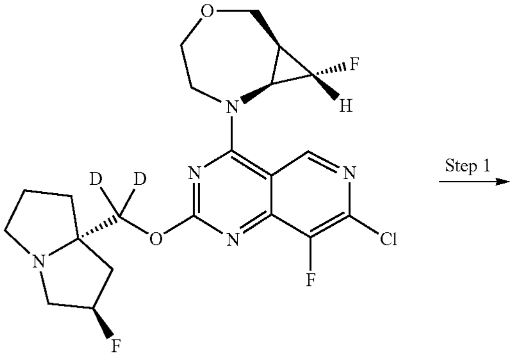

Intermediate 34

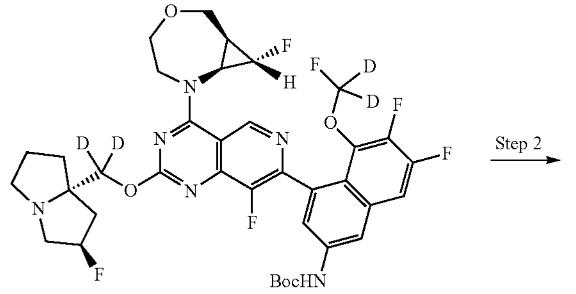

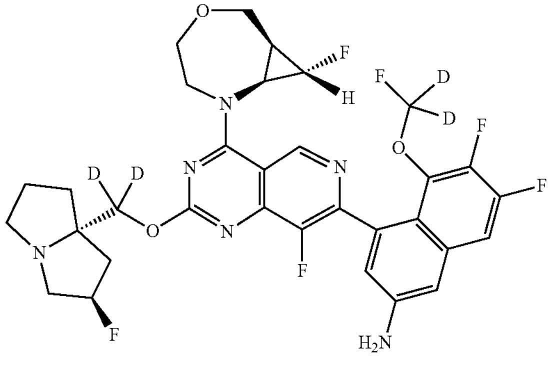

Example 88

Step 1: tert-Butyl (6,7-difluoro-4-(8-fluoro-4-((15, 75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-(fluoromethoxy-$d_2$)naphthalen-2-yl) carbamate To a mixture of Intermediate 34 (100 mg, 0.21 mmol) and ter-butyl (6,7-difluoro-5-(fluoromethoxy-$d_2$)-4-(4,4,5,5-tetramethyl-1,3,2-dioxaborolan-2-yl)naphthalen-2-yl) carbamate (192.95 mg, 0.42 mmol, refer to Intermediate 65 for detail procedures) in THF (4 mL) and $H_2O$ (0.8 mL) under nitrogen atmosphere were added CataCXium A Pd G3 (30.87 mg, 0.04 mmol) and $K_3PO_4$ (269.88 mg, 1.27 mmol) at room temperature. The reaction mixture was heated at 80° C. for 2 hours. The resulting mixture was cooled to room temperature, filtered, and concentrated under reduced pressure. The residue was purified by silica gel flash chromatography, eluted with $CH_2Cl_2$/MeOH (15: 1) to afford the title compound (140 mg, 86% yield) as a yellow solid. MS: m/z=765.40 $[M+H]^+$.

Step 2: 6,7-Difluoro-4-(8-fluoro-4-((15,7S,8S)-8-fluoro-5-oxa-2-azabicyclo[5.1.0]octan-2-yl)-2-(((2R, 7aS)-2-fluorotetrahydro-1H-pyrrolizin-7a (5H)-yl) methoxy-$d_2$)pyrido[4,3-d]pyrimidin-7-yl)-5-(fluoromethoxy-$d_2$)naphthalen-2-amine To an ice-cooled solution of tert-butyl (6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-(fluoromethoxy-$d_2$)naphthalen-2-yl) carbamate (140 mg, 0.18 mmol) in DCM (5 mL) was added TFA (1 mL) dropwise under nitrogen atmosphere. The reaction mixture was stirred in an ice bath for 3 hours. The resulting mixture was concentrated with toluene (3×5 mL) under reduced pressure. The residue was purified by RP-Flash with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 51% B in 15 min, 51% B to 51% B in 10 min, 51% B to 95% B in 4 min; Detector: UV 254 & 210 nm; RT: 20 min. The collected fractions were combined, concentrated and then lyophilized overnight to give the title compound (Example 88, 65.9 mg, 52% yield) as a white lyophilized powder. MS: m/z=665.20 $[M+H]^+$. $^1H$ NMR (400 MHZ, DMSO-$d_6$) δ 9.44-9.39 (m, 1H), 7.62-7.57 (m, 1H), 7.03-6.89 (m, 2H), 5.82-5.80 (m, 2H), 5.35-5.21 (m, 1H), 4.97-4.82 (m, 1H), 4.52-4.48 (m, 1H), 4.40-4.28 (m, 2H), 4.03-4.00 (m, 1H), 3.70-3.59 (m, 2H), 3.32-3.00 (m, 4H), 2.85-2.81 (m, 1H), 2.40-2.28 (m, 1H), 2.11-1.75 (m, 6H). $^{19}F$ NMR (376 MHz, DMSO-$d_6$) δ −137.15--137.27 (m, 1F), −140.24--140.34 (m, 1F), −150.81--150.84 (m, 1F), −159.26--159.71 (m, 1F), ~172.09--172.16 (d, 1F), −208.33 (bs, 1F).

Example 89: 5-Ethynyl-6-fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine

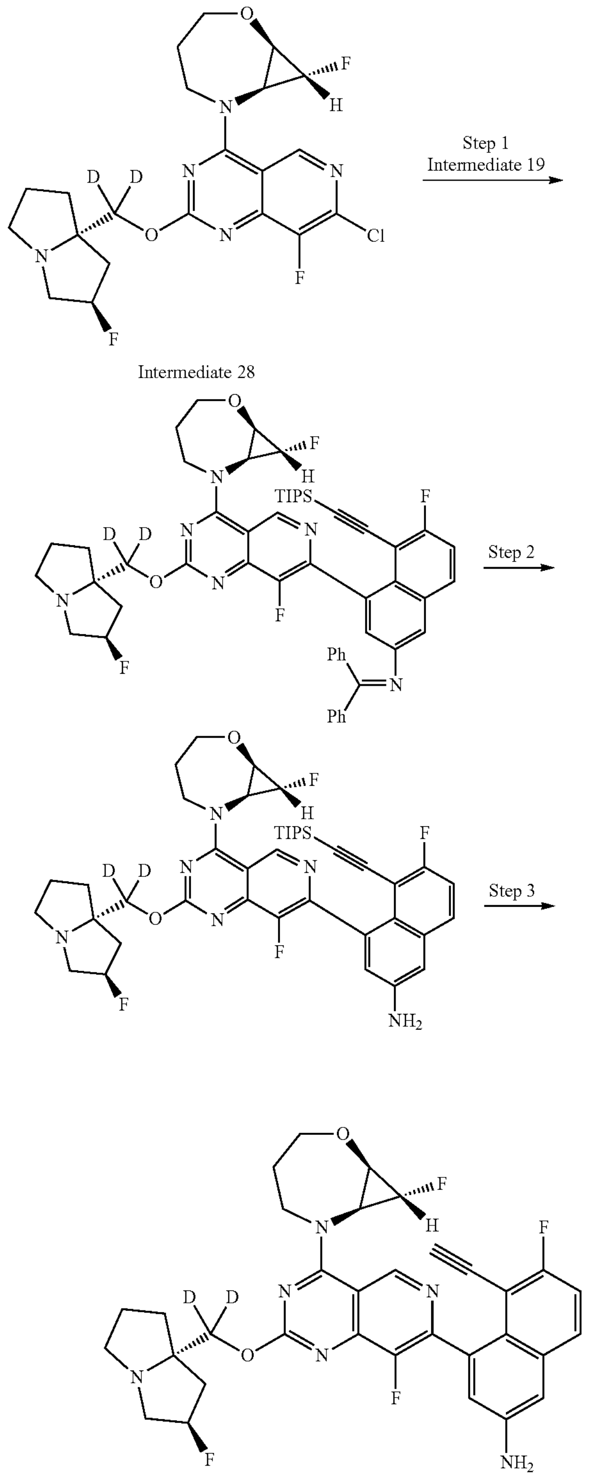

Intermediate 28

Example 89

Step 1: N-(6-Fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-yl)-1,1-diphenylmethanimine To a solution of Intermediate 28 (100 mg, 0.21 mmol) and Intermediate 19 (267.72 mg, 0.42 mmol) in THE (4.25 mL) and $H_2O$ (0.85 mL) were added $K_3PO_4$ (269.88 mg, 1.27 mmol) and CataCXium A Pd G3 (30.87 mg, 0.04 mmol) at room temperature under nitrogen atmosphere. The reaction mixture was heated at 80° C. for 3 hours. The resulting mixture was cooled to room temperature, diluted with $H_2O$ (10 mL), and extracted with ethyl acetate (3×20 mL). The combined organic layers were washed with brine (10 mL), dried over anhydrous $Na_2SO_4$, filtered, and concentrated under reduced pressure. The residue was purified by Prep-TLC ($CH_2Cl_2$/MeOH 10: 1) to afford two compounds. The first eluting peak was concentrated to afford the title compound (150 mg, 75% yield) as a brown yellow solid. MS: m/z=941.60 $[M+H]^+$. The second eluting peak was concentrated to afford 6-fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-amine (20 mg, 12% yield) as a brown yellow solid. MS: m/z=777.50 $[M+H]^{+\cdot}$ Step 2: 6-Fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine To a solution of N-(6-fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$)pyrido[4,3-d]pyrimidin-7-yl)-S-((triisopropylsilyl) ethynyl)naphthalen-2-yl)-1,1-diphenylmethanimine (150 mg, 0.16 mmol) in EtOH (2 mL) were added NaOAc (26.15 mg, 0.32 mmol) and $NH_2OH \cdot HCl$ (22.15 mg, 0.32 mmol) at room temperature. The reaction mixture was stirred at room temperature for 1 hour. The resulting mixture was concentrated under reduced pressure. The residue was purified by Prep-TLC ($CH_2Cl_2$/MeOH 10: 1) to afford the title compound (120 mg, 96% yield) as a yellow solid. MS: m/z=777.50 $[M+H]^{+\cdot}$ Step 3: 5-Ethynyl-6-fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine A solution of 6-fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-amine (140 mg, 0.18 mmol) and CsF (254.15 mg, 1.67 mmol) in DMF (1.5 mL) was stirred at room temperature for 16 hours. The resulting mixture was filtered and purified by RP-Flash with the following conditions: C18 spherical, 20-30 μm, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 54% B in 15 min, 54% B to 54% B in 3 min, 54% B to 95% B in 4 min;

Detector: UV 254 & 210 nm. The collected fractions were combined, concentrated and lyophilized overnight to give the title compound (Example 89, 74.3 mg, 65% yield) as a yellow lyophilized powder. MS: m/z=621.15 $[M+H]^+$. $^1H$ NMR (400 MHz, DMSO-$d_6$) δ 9.31-9.28 (m, 1H), 7.79-7.75 (m, 1H), 7.36-7.31 (m, 1H), 7.05-7.04 (m, 2H), 5.66-5.63 (m, 2H), 5.35-5.22 (m, 1H), 4.97-4.70 (m, 1H), 4.54-4.41 (m, 1H), 4.22-4.10 (m, 3H), 3.94-3.79 (m, 2H), 3.60-3.54 (m, 1H), 3.10-3.02 (m, 3H), 2.86-2.82 (m, 1H), 2.20-1.70 (m, 8H). $^{19}F$ NMR (376 MHz, DMSO-$d_6$) δ −113.52 (s, 1F), −140.21 (s, 1F), −172.03 (s, 1F), −211.81--212.58 (d, 1F).

Example 90: 6-Fluoro-4-(8-fluoro-4-((15,75,8S)-8-fluoro-5-oxa-2-azabicyclo[5.1.0]octan-2-yl)-2-(((2R, 7aS)-2-fluorotetrahydro-1H-pyrrolizin-7a (5H)-yl) methoxy-$d_2$)pyrido[4,3-d]pyrimidin-7-yl)-5-(methoxy-d'3)naphthalen-2-amine

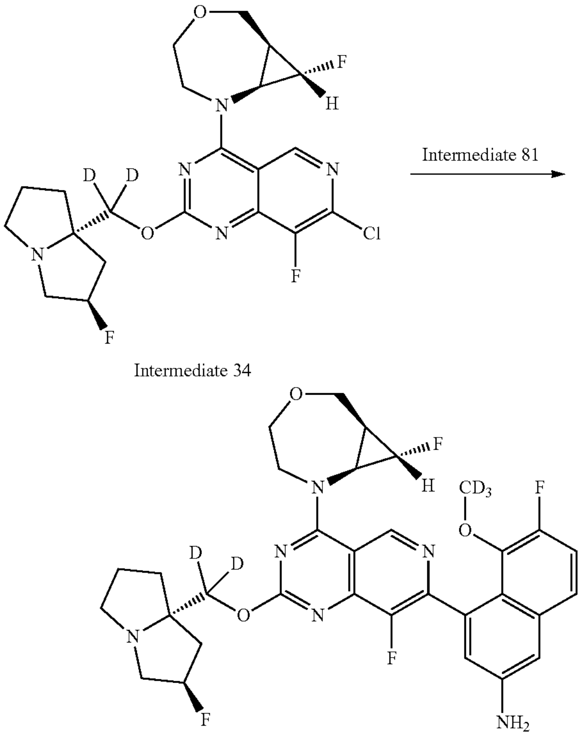

Intermediate 34

Example 90

To a solution of Intermediate 34 (200 mg, 0.42 mmol) and Intermediate 81 (271.40 mg, 0.84 mmol) in THF (8.5 mL) and $H_2O$ (1.7 mL) were added CataCXium A Pd G3 (61.73 mg, 0.08 mmol) and $K_3PO_4$ (539.76 mg, 2.54 mmol) at room temperature under nitrogen atmosphere. The reaction mixture was heated at 80° C. for 2 hours. The resulting mixture was cooled to room temperature, diluted with water (10 mL), and extracted with EtOAc (3×30 mL). The combined organic layers were washed with brine (20 mL), dried over anhydrous $Na_2SO_4$, filtered, and concentrated under reduced pressure. The residue was purified by Prep-TLC ($CH_2Cl_2$/MeOH 10: 1) to afford a crude product. The crude product was purified by RP-Flash with the following conditions: Column, C18; Mobile phase A: 5 mM aq. $NH_4HCO_3$; Mobile phase B: MeCN; Gradient: 2% B to 64% B in 20 min; Detector: UV 254 nm. The collected fractions were combined, concentrated and lyophilized overnight to afford the title compound (Example 90, 169.9 mg, 63% yield) as a light yellow lyophilized powder. MS: m/z=630.20 $[M+H]^+$. $^1H$ NMR (400 MHZ, DMSO-$d_6$) δ 9.41-9.38 (m, 1H), 7.43-7.40 (m, 1H), 7.32-7.27 (m, 1H), 6.98-6.93 (m, 2H), 5.57-5.55 (m, 2H), 5.34-5.21 (m, 1H), 4.96-4.76 (m, 1H), 4.52-4.48 (m, 1H), 4.37-4.29 (m, 2H), 4.02-3.99 (m, 1H), 3.74-3.68 (m, 1H), 3.62-3.56 (m, 1H), 3.32-3.20 (m, 1H), 3.09-3.00 (m, 3H), 2.85-2.81 (m, 1H), 2.35-2.33 (m, 1H), 2.14-1.75 (m, 6H). $^{19}F$ NMR (376 MHZ, DMSO-$d_6$) δ −138.75--138.76 (d, 1F), −140.54--140.89 (d, 1F), −172.10--172.15 (d, 1F), −207.88 (s, 1F).

Example 91: 6-Fluoro-4-(8-fluoro-4-((1R,7S,8R)-8-fluoro-2-oxa-6-azabicyclo[5.1.0]octan-6-yl)-2-(((2R, 7aS)-2-fluorotetrahydro-1H-pyrrolizin-7a (5H)-yl) methoxy-$d_2$)pyrido[4,3-d]pyrimidin-7-yl)-5-(methoxy-d'3)naphthalen-2-amine

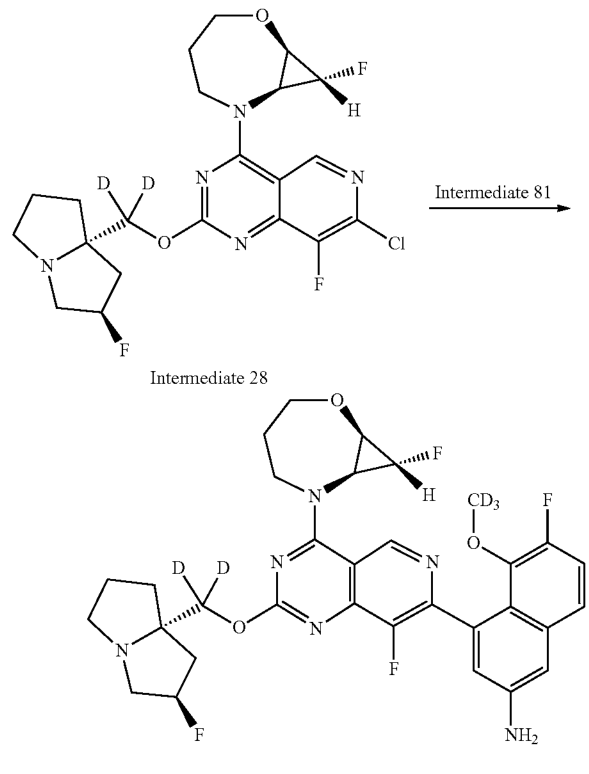

Intermediate 28

Example 91

To a solution of Intermediate 28 (80 mg, 0.17 mmol) and Intermediate 81 (108.56 mg, 0.34 mmol) in THF (3.65 mL) and $H_2O$ (0.72 mL) were added $K_3PO_4$ (215.90 mg, 1.02 mmol) and CataCXium A Pd G3 (24.69 mg, 0.03 mmol) at room temperature under nitrogen atmosphere. The reaction mixture was heated at 80° C. for 3 hours. The resulting mixture was cooled to room temperature, diluted with $H_2O$ (10 mL), and extracted with ethyl acetate (3×20 mL). The combined organic layers were washed with brine (20 mL), dried over anhydrous $Na_2SO_4$, filtered, and concentrated under reduced pressure. The residue was purified by Prep-TLC ($CH_2Cl$/MeOH 10: 1) to afford a crude product. The crude product was purified by RP-Flash with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 61% B in 15 min, 61% B to 61% B in 3 min, 61% B to 95% B in 4 min; Detector: UV 254 & 210 nm. The collected fractions were combined, concentrated and lyophilized overnight to give the title compound (Example 91, 52.0 mg, 48% yield) as a yellow lyophilized powder. MS: m/z=630.10 $[M+H]^+$. JH NMR (400 MHZ, DMSO-$d_6$) δ 9.33-9.30 (m, 1H), 7.43-7.39 (m, 1H), 7.33-7.27 (m, 1H), 6,98-6.93 (m, 2H), 5.57-5.55 (m, 2H), 5.35-5.22 (m, 1H), 4.88-4.66 (m, 1H), 4.51-4.48 (m, 1H), 4.22-4.14 (m, 2H), 3.93-3.90 (m, 1H), 3.84-3.81 (m, 1H), 3.59-3.53 (m, 1H), 3.09-3.01 (m, 3H), 2.88-2.82 (m, 1H), 2.16-1.77 (m, 8H). $^{19}F$ NMR (376 MHz, DMSO-$d_6$) δ −138.73-−138.76 (d, 1F), −140.50-−140.62 (d, 1F), −172.07-−172.14 (d, 1F), −211.78-−212.030 (d, 1F).

Example 92: (1R,7S,8R)-8-Fluoro-6-(8-fluoro-7-(7-fluoro-8-(fluoromethoxy)naphthalen-1-yl)-2-(((2R,7aS)-2-fluorotetrahydro-1H-pyrrolizin-7a (5H)-yl)methoxy-$d_2$)pyrido[4,3-d]pyrimidin-4-yl)-2-oxa-6-azabicyclo[5.1.0]octane

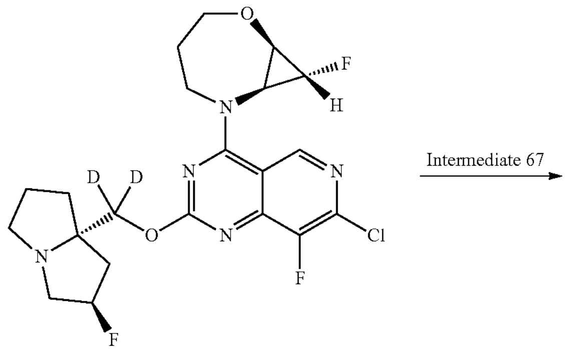

Intermediate 28

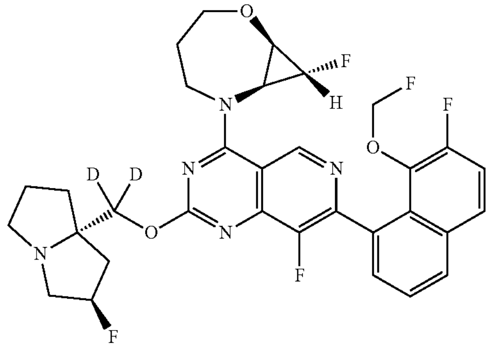

Example 92

Example 92 was prepared in a manner similar to Example 71. MS: m/z=630.25 $[M+H]^+$. $^1H$ NMR (400 MHZ, DMSO-$d_6$) δ 9.36-9.30 (m, 1H), 8.19-8.17 (m, 1H), 8.06-8.02 (m, 1H), 7.71-7.58 (m, 3H), 5.35-5.22 (m, 1H), 5.17-4.70 (m, 3H), 4.52-4.49 (m, 1H), 4.22-4.08 (m, 2H), 3.93-3.81 (m, 2H), 3.60-3.50 (m, 1H), 3.10-3.01 (m, 3H), 2.87-2.81 (m, 1H), 2.14-1.70 (m, 8H). $^{19}F$ NMR (376 MHz, DMSO-$d_6$) δ −129.08-−129.50 (m, 1F), −140.04-−140.22 (d, 1F), −149.75-−150.81 (m, 1F), −172.054-−172.145 (d, 1F), −211.80-−212.69 (m, 1F).

Example 93: 5-Ethynyl-6,7,8-trifluoro-4-(8-fluoro-4-((15,7S,8S)-8-fluoro-5-oxa-2-azabicyclo[5.1.0]octan-2-yl)-2-(((2R,7aS)-2-fluorotetrahydro-LH-pyrrolizin-7a (5H)-yl)methoxy-$d_2$)pyrido[4,3-d]pyrimidin-7-yl)naphthalen-2-amine

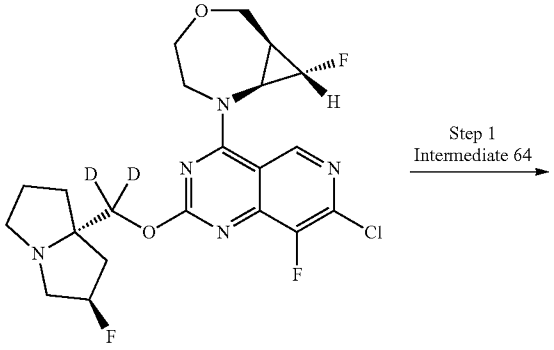

Intermediate 34

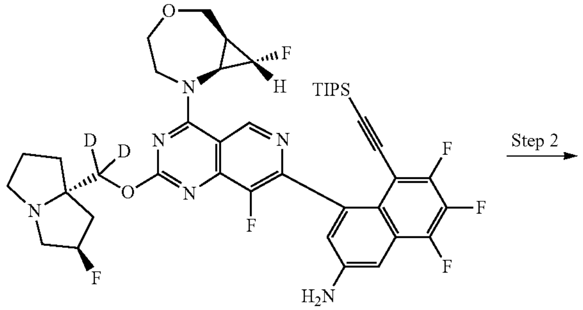

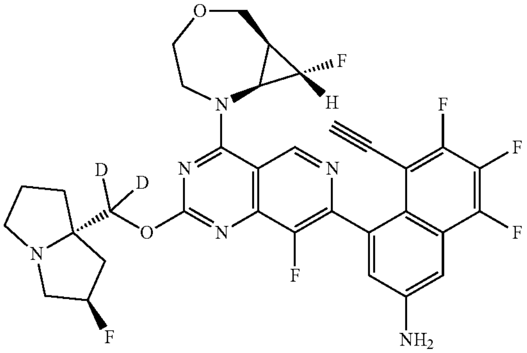

Example 93

Step 1: 6,7,8-Trifluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-((triisopropylsilyl) ethynyl)naphthalen-2-amine To a mixture of Intermediate 34 (120 mg, 0.25 mmol) and Intermediate 64 (256.06 mg, 0.50 mmol) in $H_2O$ (1 mL) and THF (5 mL) under nitrogen atmosphere were added CataCXium A Pd $G_3$ (37.04 mg, 0.05 mmol) and $K_3PO_4$ (323.86 mg, 1.52 mmol) at room temperature. The reaction mixture was heated at 80° C. for 2 hours. The resulting mixture was cooled to room temperature, filtered, and concentrated under reduced pressure. The residue was purified by silica gel flash chromatography, eluted with $CH_2Cl_2$/MeOH (15: 1) to afford the title compound (175 mg, 84% yield) as a yellow solid. MS: m/z=813.50 [M+H]+·

Step 2: S-Ethynyl-6,7,8-trifluoro-4-(8-fluoro-4-((1S, 75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine To a solution of 6,7,8-trifluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-((triisopropylsilyl)ethynyl)naphthalen-2-amine (175 mg, 0.21 mmol) in DMF (2 mL) was added CsF (326.99 mg, 2.15 mmol) at room temperature. The reaction mixture was stirred at room temperature for 2 hours. The resulting mixture was filtered and purified by RP-Flash with the following conditions: C18 spherical, 20-30 um, 100 A, 20 g; Mobile Phase A: 5 mM aq. $NH_4HCO_3$; Mobile Phase B: MeCN; Flow rate: 40 mL/min; Gradient: 5% B to 5% B in 3 min, 5% B to 57% B in 15 min, 57% B to 57% B in 5 min, 57% B to 95% B in 45 min; Detector: UV 254 & 210 nm. The collected fractions were combined, concentrated, and then lyophilized overnight to give the title compound (Example 93, 61 mg, 42% yield) as a yellow lyophilized powder. MS: m/z=657.15 [M+H]$^+$. $^1$H NMR (400 MHZ, DMSO-$d_6$) δ 9.45-9.37 (m, 1H), 7.11 (s, 2H), 6.09-6.08 (m, 2H), 5.35-5.21 (m, 1H), 4.94-4.72 (m, 1H), 4.51-4.30 (m, 3H), 4.24-3.97 (m, 2H), 3.74-3.57 (m, 2H), 3.32-3.20 (m, 1H), 3.13-3.01 (m, 3H), 2.85-2.80 (m, 1H), 2.37-2.20 (m, 1H), 2.12-1.73 (m, 6H). $^{19}$F NMR (376 MHz, DMSO-$d_6$) δ −136.37−−136.54 (m, 1F), −139.59−−140.43 (d, 1F), −144.10−−144.15 (d, 1F), −161.79−−161.90 (m, 1F), −172.08−−172.19 (d, 1F), −207.92−−208.13 (m, 1F).

Example 97: 7-(5-Ethynyl-6-fluoroisoquinolin-4-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine

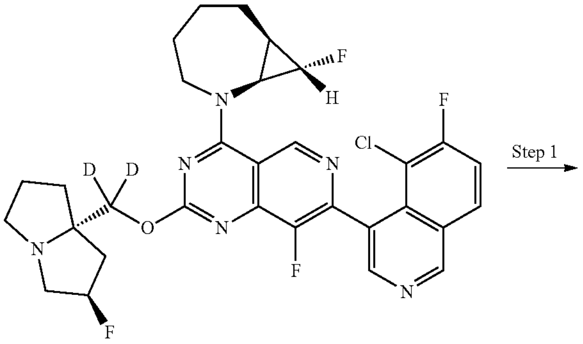

Example 85

-continued

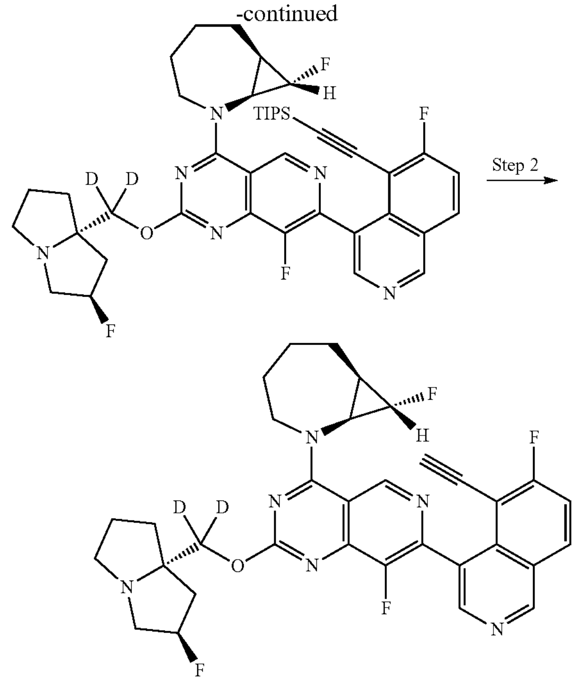

Example 97

Step 1: 8-Fluoro-7-(6-fluoro-5-((triisopropylsilyl)ethynyl) isoquinolin-4-yl)-4-((1S,7R,8S)-8-fluoro-2-azabicyclo[5.1.0]octan-2-yl)-2-(((2R,7aS)-2-fluoro-tetrahydro-1H-pyrrolizin-7a (5H)-yl)methoxy-$d_2$)pyrido[4,3-d]pyrimidine To a solution of Example 85 (70 mg, 114 μmol) in ACN (3 mL) were added ethynyltriisopropylsilane (128 μL, 569 μmol), $Cs_2CO_3$ (74 mg, 228 μmol), XPhos (32 mg, 68.3 μmol) and Pd ($CH_3CN$) $2Cl_2$ (6 mg, 22.7 μmol). The mixture was stirred at 85° C. for 20 hr under $N_2$ atmosphere. The reaction mixture was concentrated under reduced pressure. After purification by silica gel flash chromatography (Eluent of 0~4% MeOH in $CH_2Cl_2$), the title compound (55 mg, yield: 50%) was obtained as a yellow solid. MS: m/z=761.3 [M+H]$^+$. $^1$H NMR (400 MHz, Dimethylsulfoxide-$d_6$) δ 9.52 (s, 1H), 9.39 (s, 1H), 8.54 (s, 1H), 8.46 (dd, J=8.8, 6.0 Hz, 1H), 7.85-7.77 (m, 1H), 5.39-5.21 (m, 1H), 4.75-4.57 (m, 1H), 4.40-4.33 (m, 1H), 3.91-3.84 (m, 1H), 3.12-3.01 (m, 4H), 2.86-2.81 (m, 1H), 2.34-2.25 (m, 2H), 2.09-1.99 (m, 3H), 1.89-1.85 (m, 2H), 1.77-1.70 (m, 2H), 1.53-1.48 (m, 1H), 1.09-0.99 (m, 3H), 0.83 (dd, J=10.4, 7.6 Hz, 18H), 0.54-0.44 (m, 3H).

Step 2: 7-(5-Ethynyl-6-fluoroisoquinolin-4-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine To a solution of 8-fluoro-7-(6-fluoro-5-((triisopropylsilyl)ethynyl) isoquinolin-4-yl)-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine (55 mg, 72.3 μmol) in DMSO (1 mL) was added CsF (11 mg, 72.3 μmol). The mixture was stirred at 25° C. for 1 hr. The reaction mixture was diluted with $H_2O$ (20 mL) and extracted with EtOAc (20 mL×2). The combined organic layers were washed with $H_2O$ (50 mL×2), dried over $Na_2SO_4$, filtered and concentrated under reduced pressure. After purification by silica gel flash chromatography (Eluent of 0~5% MeOH in $CH_2Cl_2$), the title compound (Example 97, 24.5 mg, yield: 53%) was obtained as a light yellow solid. MS: m/z=605.2 $[M+H]^+$. $^1H$ NMR (400 MHZ, Dimethylsulfoxide-$d_6$) δ 9.54 (s, 1H), 9.44-9.36 (m, 1H), 8.62-8.54 (m, 1H), 8.47 (dd, J=8.8, 6.0 Hz, 1H), 7.85-7.77 (m, 1H), 5.40-5.17 (m, 1H), 4.76-4.49 (m, 1H), 4.44-4.36 (m, 1H), 4.10-4.03 (m, 1H), 3.16-2.95 (m, 4H), 2.86-2.79 (m, 1H), 2.40-2.18 (m, 2H), 2.14-1.94 (m, 5H), 1.89-1.75 (m, 5H), 1.57-1.48 (m, 1H), 1.25-1.22 (m, 1H). $^{19}F$ NMR (400 MHZ, Dimethylsulfoxide-$d_6$) δ −99.26, −139.61, −140.06, −172.07, −172.17.

Example 98: 8-Fluoro-7-(6-fluoro-5-methoxyisoquinolin-4-yl)-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine

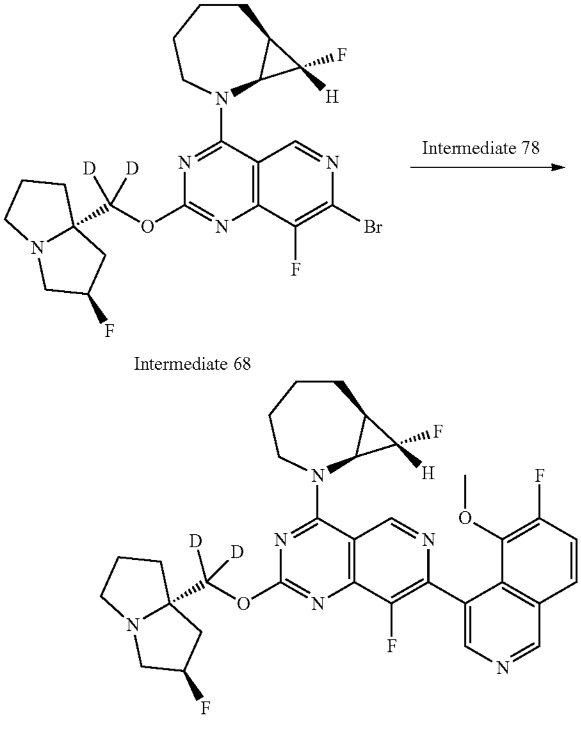

Intermediate 68

Example 98

A mixture of Intermediate 68 (150 mg, 292 μmol), Intermediate 78 (119 mg, 350 μmol), Pd (dppf) $Cl_2$ (42.7 mg, 58.3 μmol), CuI (11.1 mg, 58.3 μmol) and BINAP (72.6 mg, 117 μmol) in toluene (2 mL) was degassed and purged with $N_2$ three times, and then the mixture was stirred at 90° C. for 16 hr under $N_2$ atmosphere. The mixture was diluted with $H_2O$ (50 mL) and extracted with EtOAc (50 mL×2). The combined organic layers were washed with brine (20 mL), dried over $Na_2SO_4$, filtered, and concentrated under reduced pressure. After purification by silica gel flash chromatography (Eluent of 0~8% MeOH in $CH_2Cl_2$), the title compound (Example 98, 14.4 mg, yield: 7%) was obtained as a yellow solid. MS: m/z=611.2 $[M+H]^+$. $^1H$ NMR (400 MHZ, Methanol-$d_4$) δ 9.54-9.47 (m, 1H), 9.37 (s, 1H), 8.43 (s, 1H), 8.11-8.04 (m, 1H), 7.69-7.63 (m, 1H), 5.43-5.25 (m, 1H), 4.65-4.58 (m, 1H), 4.57-4.32 (m, 1H), 4.04-3.85 (m, 1H), 3.65-3.55 (m, 2H), 3.54-3.45 (m, 3H), 3.38-3.33 (m, 2H), 3.12-3.03 (m, 1H), 2.46-2.40 (m, 1H), 2.31-2.26 (m, 1H), 2.14-1.85 (m, 9H), 1.69-1.62 (m, 1H), 1.19-1.11 (m, 1H). $^{19}F$ NMR. (400 MHZ, Methanol-$d_4$) δ −124.636, −124.696, −140.149, −140.600, −173.743.

Example 100: 6-Fluoro-4-(8-fluoro-4-((1S,7R,85)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-(fluoromethoxy-$d_2$)naphthalen-2-amine

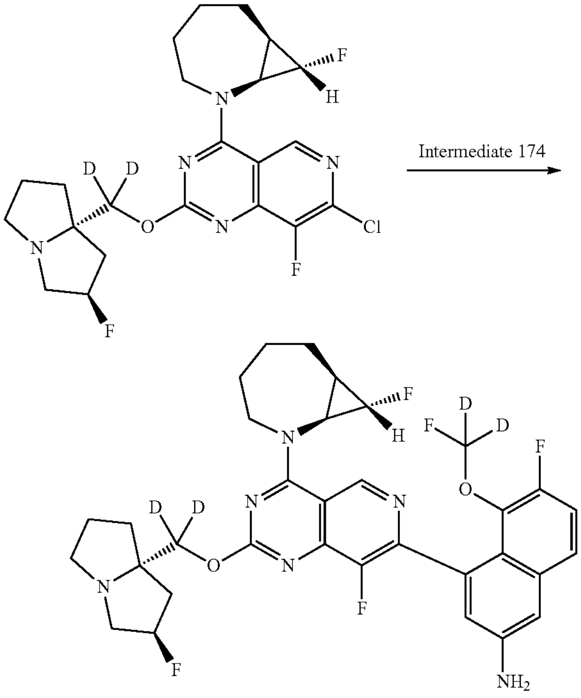

Example 100

A mixture of 7-chloro-8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidine (70 mg, 149 μmol, refer to Example 16 for detail procedures), Intermediate 174 (100 mg, 298 μmol), AdanBuP-Pd-Gs (cataCXiumAPdG$_3$) (22 mg, 29.8 μmol) and $K_3PO_4$ (95 mg, 449 μmol) in 1,4-dioxane (3 mL) and $H_2O$ (0.3 mL) was degassed and purged with $N_2$ for 3 times, and then the mixture was stirred at 100° C. for 2 h under $N_2$ atmosphere. The reaction mixture was concentrated under reduce pressure. The residue was purified by silica gel flash chromatography (eluent: 0~7% of MeOH in dichloromethane) to give 6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-(fluoromethoxy-$d_2$)naphthalen-2-amine (Example 100, 62.7 mg, 63% yield) as a yellow solid. MS: m/z=645.2 $[M+H]^+$. $^1H$ NMR (400 MHZ, Dimethylsulfoxide-$d_6$) δ 9.55-9.32 (m, 1H), 7.63-7.49 (m, 1H), 7.41-7.31 (m, 1H), 7.10-6.97 (m, 2H), 5.71-5.58 (m, 2H), 5.43-5.16 (m, 1H), 4.82-4.56 (m, 1H), 4.47-4.36 (m, 1H), 4.11-3.96

(m, 1H), 3.24-2.95 (m, 4H), 2.93-2.78 (m, 1H), 2.30-2.20 (m, 1H), 2.16-1.93 (m, 5H), 1.90-1.71 (m, 6H), 1.57-1.47 (m, 1H). $^{19}F$ NMR (376 MHZ, Dimethylsulfoxide-$d_6$) δ −136.84, −137.32, −140.38, −150.58, −151.12, −172.08, −205.80.

Example 102: (1S,7S,8S)-2-(2-(((S)-2-(Difluoromethylene) tetrahydro-1H-pyrrolizin-7a (5H)-yl) methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane

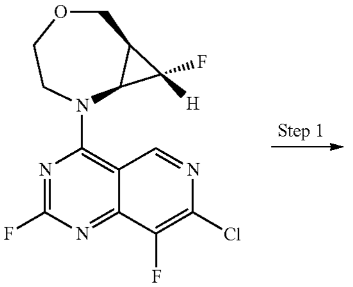

Intermediate 112

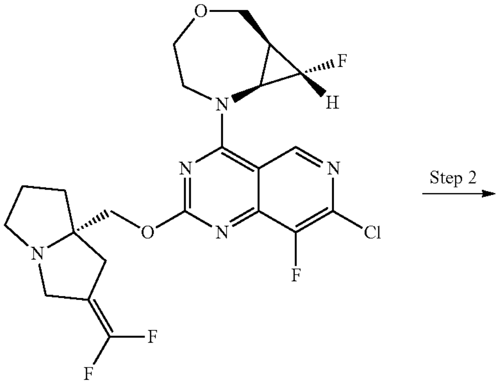

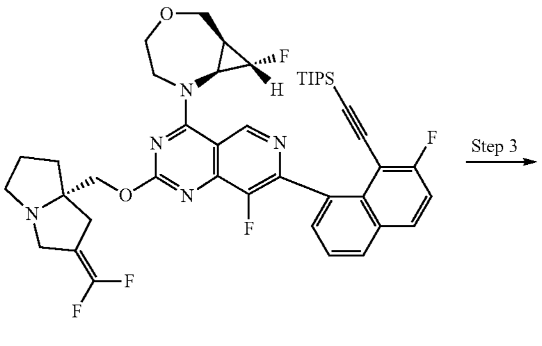

-continued

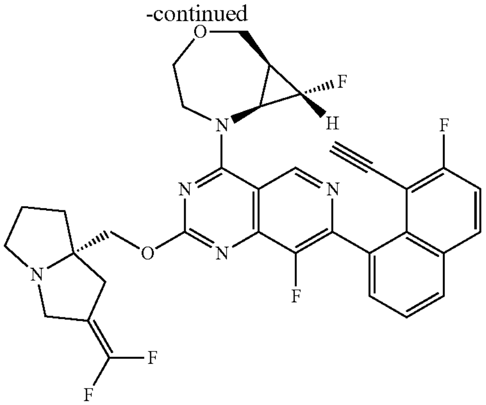

Example 102

Step 1: (1S,7S,8S)-2-(7-Chloro-2-(((S)-2-(difluoromethylene) tetrahydro-1H-pyrrolizin-7a (5H)-yl) methoxy)-8-fluoropyrido[4,3-d]pyrimidin-4-yl)-8-fluoro-5-oxa-2-azabicyclo[5.1.0]octane To an ice-cooled stirred mixture of(S)-(2-(difluoromethylene) tetrahydro-1H-pyrrolizin-7a (5H)-yl) methanol (137.31 mg, 0.76 mmol) in THF (4 mL) was added t-BuOK (81.44 mg, 0.72 mmol) under $N_2$. The mixture was stirred an an ice bath for 30 min. Intermediate 112 (200 mg, 0.60 mmol) was added to the above mixture. The ice bath was removed, and the reaction mixture was stirred at room temperature for 1 hour. The resulting mixture was quenched with sat. $NH_4Cl$ aq. (50 mL) and extracted with $CH_2Cl_2$ (3×50 mL). The combined organic layers were washed with brine (50 mL), dried over anhydrous $Na_2SO_4$, filtered and concentrated under reduced pressure. The residue was purified by Prep-TLC ($CH_2Cl_2$/MeOH 10: 1) to afford the title compound (220 mg, 72% yield) as an off-white solid. MS: m/z=500.05 $[M+H]^{+\cdot}$ Step 2: (1S,7S,8S)-2-(2-(((S)-2-(Difluoromethylene) tetrahydro-1H-pyrrolizin-7a (5H)-yl)methoxy)-8-fluoro-7-(7-fluoro-8-((triisopropylsilyl) ethynyl) naphthalen-1-yl)pyrido[4,3-d]pyrimidin-4-yl)-8-fluoro-5-oxa-2-azabicyclo[5.1.0]octane To a mixture of (1S,7S,8S)-2-(7-Chloro-2-(((S)-2-(difluoromethylene) tetrahydro-1H-pyrrolizin-7a (5H)-yl) methoxy)-8-fluoropyrido[4,3-d]pyrimidin-4-yl)-8-fluoro-5-oxa-2-azabicyclo[5.1.0]octane (110 mg, 0.22 mmol) and ((2-fluoro-8-(4,4,5,5-tetramethyl-1,3,2-dioxaborolan-2-yl) naphthalen-1-yl) ethynyl) triisopropylsilane (298.71 mg, 0.66 mmol) in THE (5 mL) and $H_2O$) (1 mL) under $N_2$ were added CataCXium A Pd Gs (32.05 mg, 0.04 mmol) and $K_3PO_4$ (280.25 mg, 1.32 mmol) at room temperature. The reaction mixture was heated at 80° C. for 3 hours. The resulting mixture was cooled to room temperature, filtered and concentrated under reduced pressure. The residue was purified by silica gel flash chromatography (eluted with 10% MeOH in DCM) to afford the title compuond (160 mg, 92% yield) as a yellow solid. MS: m/z=790.55 $[M+H]^{+\cdot}$ Step 3: (1S,7S,8S)-2-(2-(((S)-2-(Difluoromethylene) tetrahydro-1H-pyrrolizin-7a (5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo [5.1.0]octane To a stirred solution of (1S,7S,8S)-2-(2-(((S)-2-(difluoromethylene) tetrahydro-1H-pyrrolizin-7a (5H)-yl)

methoxy)-8-fluoro-7-(7-fluoro-8-((triisopropylsilyl) ethynyl)naphthalen-1-yl)pyrido[4,3-d]pyrimidin-4-yl)-8-fluoro-5-oxa-2-azabicyclo[5.1.0]octane (160 mg, 0.20 mmol) in DMF (1 mL) was added CsF (615.33 mg, 4.06 mmol) at room temperature. The reaction mixture was stirred at room temperature for 5 hours. The resulting mixture was filtered and purified by RP-Flash with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 74% B in 15 min, 74% B to 74% B in 5 min, 74% B to 95% B in 4 min; Detector: UV 254 & 210 nm. The collected fractions were combined, concentrated and lyophilized overnight to afford the title compound (Example 102, 75.7 mg, 58% yield) as white lyophilized powder. MS: m/z=634.10 $[M+H]^+$. $^1H$ NMR (400 MHZ, DMSO-$d_6$) δ 9.45-9.40 (m, 1H), 8.26-8.20 (m, 2H), 7.73-7.60 (m, 3H), 4.91-4.75 (m, 1H), 4.52-4.34 (m, 3H), 4.22-3.98 (m, 4H), 3.72-3.61 (m, 3H), 3.33-3.20 (m, 2H), 2.99-2.98 (m, 1H), 2.70-2.50 (m, 2H), 2.43-2.30 (m, 2H), 1.96-1.76 (m, 4H). $^{19}F$ NMR (376 MHZ, DMSO-$d_6$) δ −90.87--91.52 (m, 2F), −105.71--105.84 (m, 1F), −139.89--140.32 (m, 1F), −207.70 (s, 1F).

Example 114: (1S,7S,8S)-2-(7-(5-Ethynyl-6-fluoroisoquinolin-4-yl)-8-fluoro-2-(((2R,7aS)-2-fluorotetrahydro-1H-pyrrolizin-7a (5H)-yl)methoxy-$d_2$) pyrido[4,3-d]pyrimidin-4-yl)-8-fluoro-5-oxa-2-azabicyclo[5.1.0]octane

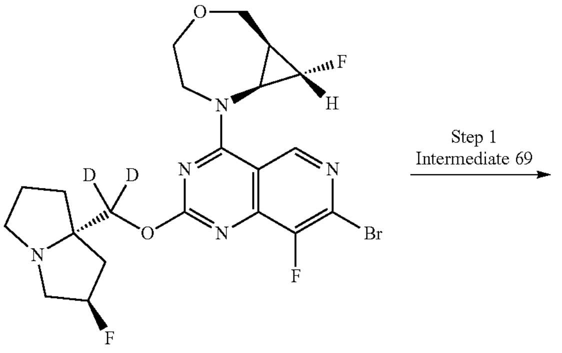

Intermediate 76

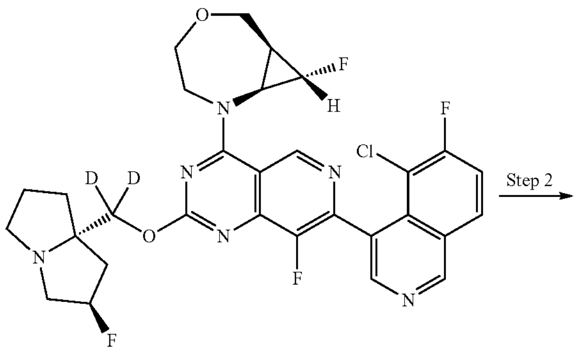

-continued

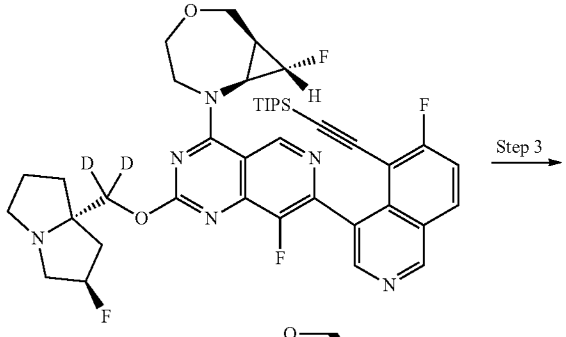

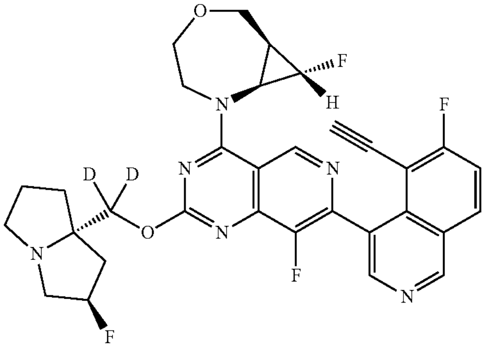

Example 114

Step 1: (1S,7S,8S)-2-(7-(5-Chloro-6-fluoroisoquinolin-4-yl)-8-fluoro-2-(((2R,7aS)-2-fluorotetrahydro-1H-pyrrolizin-7a (5H)-yl)methoxy-$d_2$)pyrido[4,3-d] pyrimidin-4-yl)-8-fluoro-5-oxa-2-azabicyclo[5.1.0] octane To a solution of Intermediate 76 (200 mg, 387 μmol) in toluene (2 mL) were added Intermediate 69 (400 mg, 1.16 mmol), Pd (dppf) $Cl_2$ (28 mg, 38.7 μmol), BINAP (48 mg, 77.5 μmol) and CuI (22 mg, 116 μmol). The mixture was stirred at 90° C. for 16 hr under $N_2$ atmosphere. The mixture was concentrated under reduced pressure. After purification by silica gel flash chromatography (Eluent of 0~4% MeOH in $CH_2Cl_2$), (1S,7S,8S)-2-(7-(5-chloro-6-fluoroisoquinolin-4-yl)-8-fluoro-2-(((2R,7aS)-2-fluorotetrahydro-1H-pyrrolizin-7a (5H)-yl)methoxy-$d_2$)pyrido[4,3-d]pyrimidin-4-yl)-8-fluoro-5-oxa-2-azabicyclo[5.1.0]octane (146.2 mg, yield: 59%) was obtained as a light yellow solid. MS: m/z=617.2 $[M+H]^+$. JH NMR (400 MHz, Dimethylsulfoxide-$d_6$) δ 9.60-9.57 (m, 1H), 9.53-9.44 (m, 1H), 8.69-8.58 (m, 1H), 8.68-8.57 (m, 1H), 7.97-7.88 (m, 1H), 5.54-5.26 (m, 1H), 4.98-4.76 (m, 1H), 4.58-4.48 (m, 1H), 4.39-4.31 (m, 2H), 4.03-3.93 (m, 1H), 3.77-3.50 (m, 3H), 3.23-2.90 (m, 4H), 2.38-2.11 (m, 4H), 2.01-1.82 (m, 3H). $^{19}F$ NMR (400 MHz, Dimethylsulfoxide-$d_6$) δ −103.24, −103.28, −139.20, −140.22, −172.31, −172.39, −172.50, −172.55, −172.63, −172.72, −172.82.

Step 2: (1S,7S,8S)-8-Fluoro-2-(8-fluoro-7-(6-fluoro-5-((triisopropylsilyl) ethynyl) isoquinolin-4-yl)-2-(((2R,7aS)-2-fluorotetrahydro-1H-pyrrolizin-7a (5H)-yl)methoxy-$d_2$)pyrido[4,3-d]pyrimidin-4-yl)-5-oxa-2-azabicyclo[5.1.0]octane To a solution of (1S,7S,85)-2-(7-(5-chloro-6-fluoroisoquinolin-4-yl)-8-fluoro-2-(((2R,7aS)-2-fluorotetrahydro-1H-pyrrolizin-7a (5H)-yl)methoxy-$d_2$)pyrido[4,3-d]pyrimidin-4-yl)-8-fluoro-5-oxa-2-azabicyclo[5.1.0]octane (120 mg, 194 μmol) in ACN (2 mL) were added ethynyltriisopropylsilane (218 μL, 972 μmol), $Cs_2CO_3$ (127 mg, 389 μmol), X Phos (56 mg, 117 μmol) and Pd ($CH_3CN$) $2Cl_2$ (10 mg, 38.9 μmol). The mixture was stirred at 85° C. for 20 hr under $N_2$ atmosphere. The reaction mixture was concentrated under reduced pressure. After purification by silica gel flash chromatography (Eluent of 0~4% MeOH in $CH_2Cl_2$), (15,75,8S)-8-fluoro-2-(8-fluoro-7-(6-fluoro-5-((triisopropylsilyl) ethynyl) isoquinolin-4-yl)-2-(((2R,7aS)-2-fluorotetrahydro-1H-pyrrolizin-7a (5H)-yl)methoxy-$d_2$)pyrido[4,3-d] pyrimidin-4-yl)-5-oxa-2-azabicyclo[5.1.0]octane (75 mg, yield: 46%) was obtained as a black brown solid. MS: m/z=763.4 $[M+H]^+$. $^1H$ NMR (400 MHZ, Dimethylsulfoxide-$d_6$) δ 9.53 (s, 1H), 9.45 (s, 1H), 8.56 (s, 1H), 8.47 (dd, J=8.8, 6.0 Hz, 1H), 7.88-7.72 (m, 1H), 5.36-5.21 (m, 1H), 4.97-4.81 (m, 1H), 4.48-4.42 (m, 1H), 4.41-4.34 (m, 1H), 4.19 (dd, J=15.6, 9.2 Hz, 1H), 4.05-3.98 (m, 1H), 3.74-3.68 (m, 1H), 3.66-3.59 (m, 1H), 3.24-3.14 (m, 1H), 3.12-3.08 (m, 2H), 3.33-2.99 (m, 1H), 2.87-2.80 (m, 1H), 2.41-2.33 (m, 1H), 2.15-2.13 (m 1H), 2.08-2.03 (m, 1H), 2.01-1.96 (m, 1H), 1.88-1.82 (m, 1H), 1.81-1.71 (m, 2H), 0.84 (dd, J=10.4, 7.6 Hz, 18H), 0.54-0.43 (m, 3H). $^{19}F$ NMR (400 MHz, Dimethylsulfoxide-$d_6$) δ −96.92, −97.48, −97.56, −136.17, −139.81, −139.93, −140.00, −172.12, −172.14, −172.32, −172.42

Step 3: (15,7S,8S)-2-(7-(5-Ethynyl-6-fluoroisoquinolin-4-yl)-8-fluoro-2-(((2R,7aS)-2-fluorotetrahydro-1H-pyrrolizin-7a (5H)-yl)methoxy-$d_2$)pyrido [4,3-d]pyrimidin-4-yl)-8-fluoro-5-oxa-2-azabicyclo [5.1.0]octane To a solution of (1S,7S,8S)-8-fluoro-2-(8-fluoro-7-(6-fluoro-5-((triisopropylsilyl) ethynyl) isoquinolin-4-yl)-2-(((2R,7aS)-2-fluorotetrahydro-1H-pyrrolizin-7a (5H)-yl) methoxy-$d_2$)pyrido[4,3-d]pyrimidin-4-yl)-5-oxa-2-azabicyclo[5.1.0]octane (75 mg, 98.3 μmol) in DMSO (1 mL) was added CsF (15 mg, 98.3 μmol). The mixture was stirred at 25° C. for 1 hr. The reaction mixture was diluted with $H_2O$ (20 mL) and extracted with EtOAc (20 mL×2). The combined organic layers were washed with HO (50 mL×2), dried over $Na_2SO_4$, filtered and concentrated under reduced pressure. After purification by silica gel flash chromatography (Eluent of 0~5% MeOH in $CH_2Cl_2$), the title compound (Example 114, 26.7 mg, yield: 43%) was obtained as a light yellow solid. MS: m/z=607.2 $[M+H]^+$. $^1H$ NMR (400 MHz, Dimethylsulfoxide-$d_6$) δ 9.54 (s, 1H), 9.49-9.40 (m, 1H), 8.64-8.56 (m, 1H), 8.47 (dd, J=9.2, 6.4 Hz, 1H), 7.85-7.75 (m, 1H), 5.38-5.18 (m, 1H), 4.97-4.70 (m, 1H), 4.54-4.46 (m, 1H), 4.45-4.33 (m, 2H), 4.31-4.10 (m, 1H), 4.06-3.95 (m, 1H), 3.77-3.68 (m, 1H), 3.66-3.57 (m, 1H), 3.27-3.19 (m, 1H), 3.12-3.05 (m, 2H), 3.03-2.98 (m, 1H), 2.87-2.78 (m, 1H), 2.39-2.30 (m, 1H), 2.12-1.98 (m, 3H), 1.86-1.73 (m, 3H). $^{19}F$ NMR (400 MHZ, Dimethylsulfoxide-$d_6$) δ −99.20, −139.35, −139.87, −172.08, −172.17.

Example 116: 6-Fluoro-4-(8-fluoro-4-((15,75,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-(fluoromethoxy-$d_2$)naphthalen-2-amine

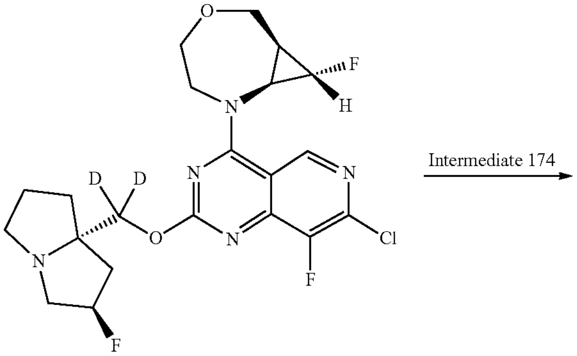

Intermediate 34

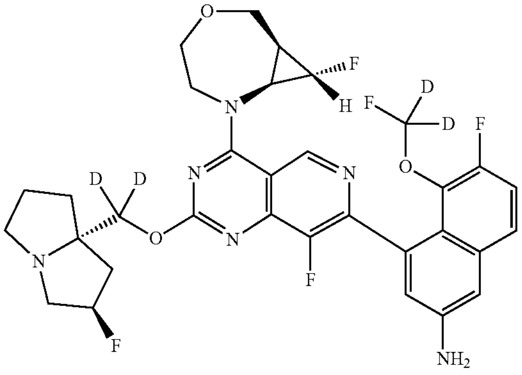

Example 116

To a mixture of Intermediate 34 (110 mg, 0.23 mmol) and Intermediate 174 (157.19 mg, 0.46 mmol) in THF (5 mL) and $H_2O$ (1 mL) under $N_2$ were added CataCXium A Pd G3 (50.93 mg, 0.07 mmol) and $K_3PO_4$ (296.87 mg, 1.39 mmol) at room temperature. The reaction mixture was heated at 80° C. for 2.5 hours. The resulting mixture was cooled to room temperature, filtered and concentrated under reduced pressure. The residue was purified by silica gel flash chromatography (eluted with $CH_2Cl$/MeOH (15: 1)) to afford a crude product. The crude product was purified by RP-Flash with the following conditions: C18 spherical, 20-30 um, 100 A, 20 g; Mobile Phase A: 5 mM aq. $NH_4HCO_3$; Mobile Phase B: MeCN; Flow rate: 20 mL/min; Gradient: 5% B to 5% B in 3 min, 5% B to 53% B in 15 min, 53% B to 53% B in 3 min, 53% B to 95% B in 4 min; Detector: UV 254 & 210 nm. The collected fractions were combined, concentrated and lyophilized overnight to afford the title compound (Example 116, 53.0 mg, 35% yield) as a yellow lyophilized powder. MS: m/z=647.20 $[M+H]^+$. $^1H$ NMR (400 MHZ, DMSO-$d_6$) δ 9.45-9.39 (m, 1H), 7.58-7.54 (m, 1H), 7.40-7.34 (m, 1H), 7.08-7.03 (m, 2H), 5.67-5.65 (m, 2H), 5.35-5.21 (m, 1H), 4.96-4.81 (m, 1H), 4.52-4.49 (m, 1H), 4.39-4.29 (m, 2H), 4.05-3.95 (m, 1H), 3.71-3.59 (m, 2H), 3.33-3.15 (m, 1H), 3.14-3.00 (m, 3H), 2.86-2.81 (m, 1H), 2.45-2.30 (m, 1H), 2.12-1.70 (m, 6H). $^{19}F$ NMR (376 MHZ, DMSO-$d_6$) δ −136.83−−137.31 (m, 1F), −140.06−−140.21 (d, 1F), −150.64−−151.00 (m, 1F), −172.08−~172.15 (d, 1F), −207.65−−208.25 (m, 1F).

Example 126: (1S,7S,8S)-8-Fluoro-2-(8-fluoro-7-(6-fluoro-5-(fluoromethoxy) isoquinolin-4-yl)-2-(((2R,7aS)-2-fluorotetrahydro-1H-pyrrolizin-7a (5H)-yl) methoxy-$d_2$)pyrido[4,3-d]pyrimidin-4-yl)-5-oxa-2-azabicyclo[5.1.0]octane

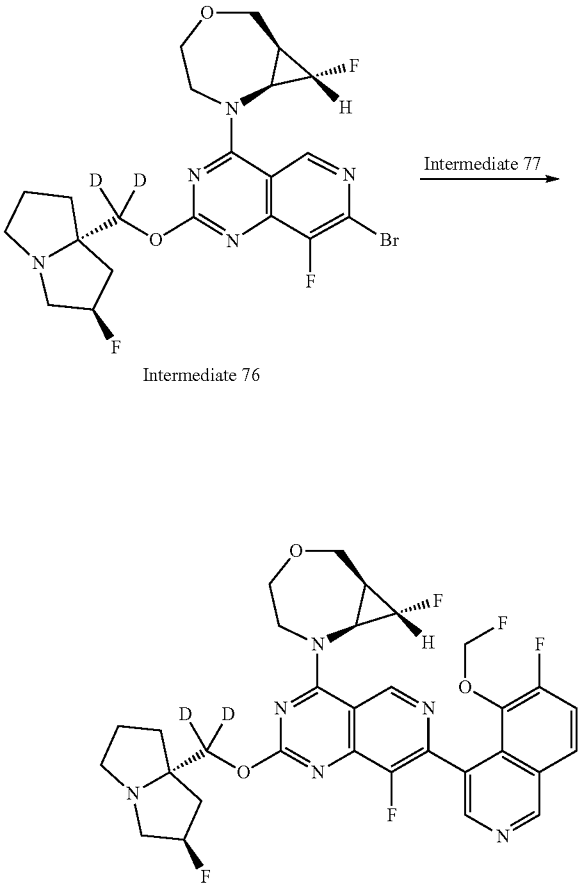

Intermediate 76

Example 126

A mixture of Intermediate 76 (80 mg, 154 μmol), Intermediate 77 (100 mg, 279 μmol), Pd (dppf) $Cl_2$ (22 mg, 30 μmol), CuI (6 mg, 31 μmol) and BINAP (38 mg, 62 μmol) in toluene (2 mL) was degassed and purged with $N_2$ three times, and then the mixture was stirred at 90° C. for 16 hr under $N_2$ atmosphere. The mixture was concentrated under reduced pressure. After purification by silica gel flash chromatography (Eluent of 0~6% MeOH in $CH_2Cl_2$), the title compound (Example 126, 23.1 mg, yield: 22%) was obtained as a yellow solid. MS: m/z=631.2 $[M+H]^+$. $^1$H NMR (400 MHZ, Dimethylsulfoxide-$d_6$) δ 9.58-9.50 (m, 1H), 9.46 (s, 1H), 8.70-8.41 (m, 1H), 8.29 (dd, J=8.4, 5.2 Hz, 1H), 7.91-7.81 (m, 1H), 5.46-5.25 (m, 1H), 5.23-5.15 (m, 1H), 5.10-5.01 (m, 1H), 4.96-4.78 (m, 1H), 4.55-4.48 (m, 1H), 4.41-4.32 (m, 2H), 4.03-3.95 (m, 1H), 3.73-3.61 (m, 2H), 3.26-2.75 (m, 5H), 2.39-2.32 (m, 1H), 2.20-1.80 (m, 6H). $^{19}$F NMR (400 MHZ, Dimethylsulfoxide-$d_6$) δ −122.022, −122.074, −122.360, −139.612, −139.702, −149.736, −150.066, −150.119, −172.167, −172.204, −172.272.

Example 127: (15,7S,8S)-8-Fluoro-2-(8-fluoro-7-(6-fluoro-5-(fluoromethoxy-$d_2$) isoquinolin-4-yl)-2-(((2R,7aS)-2-fluorotetrahydro-1H-pyrrolizin-7a (5H)-yl)methoxy-$d_2$)pyrido[4,3-d]pyrimidin-4-yl)-5-oxa-2-azabicyclo[5.1.0]octane

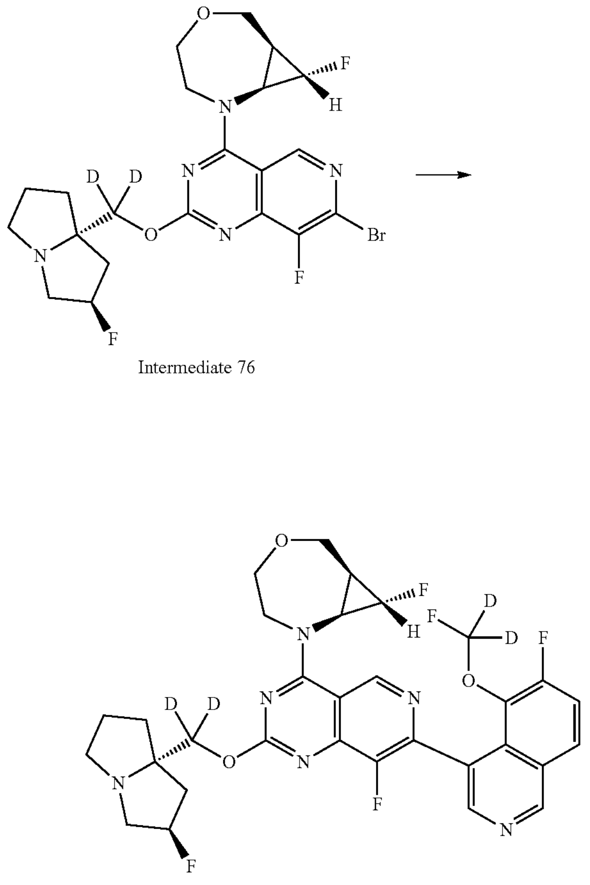
Intermediate 76

Example 127

A mixture of Intermediate 76 (180 mg, 348 μmol), Intermediate 79 (200 mg, 555 μmol), Pd (dppf) $Cl_2$ (51 mg, 69 μmol), CuI (13 mg, 69 μmol) and BINAP (86 mg, 139 μmol) in toluene (4 mL) was degassed and purged with $N_2$ three times, and then the mixture was stirred at 110° C. for 8 hr under $N_2$ atmosphere. The mixture was concentrated under reduced pressure. After purification by silica gel flash chromatography (Eluent of 0~5% MeOH in $CH_2Cl_2$), the title compound (Example 127, 38.1 mg, yield: 17%) was obtained as an off-white solid. MS: m/z=633.2 $[M+H]^+$. $^1$H NMR (400 MHZ, Dimethylsulfoxide-$d_6$) δ 9.55 (s, 1H), 9.17 (s, 1H), 8.67 (s, 1H), 8.14-8.04 (m, 1H), 8.04-7.93 (m, 1H), 5.37-5.19 (m, 1H), 4.98-4.77 (m, 1H), 4.57-4.47 (m, 1H), 4.42-4.30 (m, 2H), 4.06-3.95 (m, 1H), 3.73-3.59 (m, 2H), 3.23-3.16 (m, 1H), 3.11-2.98 (m, 3H), 2.87-2.78 (m, 1H), 2.40-2.30 (m, 1H), 2.16-1.96 (m, 4H), 1.84-1.75 (m, 2H). $^{19}$F NMR (400 MHZ, Dimethylsulfoxide-$d_6$) δ −125.902, −139.717, −149.015, −149.030,−172.144.

Example 129: (1S,7S,8S)-2-(7-(8-Ethynyl-7-fluoronaphthalen-1-yl)-8-fluoro-2-(((S,E)-2-(fluoromethylene) tetrahydro-1H-pyrrolizin-7a (5H)-yl) methoxy)pyrido[4,3-d]pyrimidin-4-yl)-8-fluoro-5-oxa-2-azabicyclo[5.1.0]octane

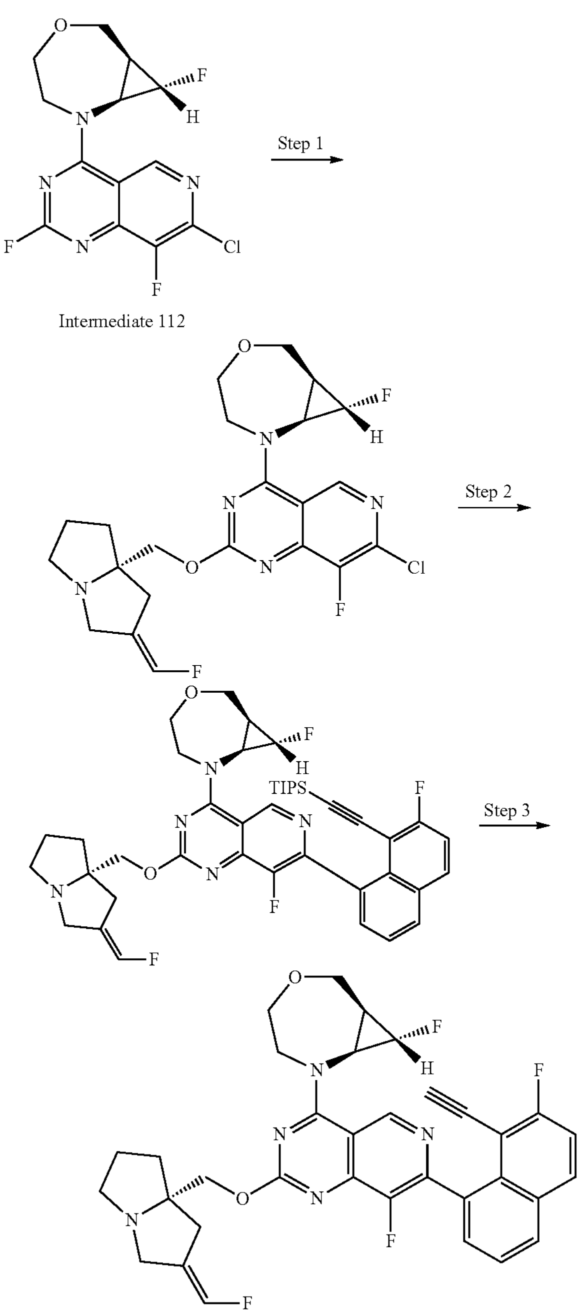

Intermediate 112

Example 129

Example 129 was prepared in a manner similar to Example 130. MS: m/z=616.2 $[M+H]^+$. $^1H$ NMR (400 MHz, DMSO-$d_6$) δ 9.45-9.40 (m, 1H), 8.26-8.20 (m, 2H), 7.73-7.60 (m, 3H), 6.93-6.72 (m, 1H), 4.95-4.75 (m, 1H), 4.52-4.49 (m, 1H), 4.43-4.33 (m, 2H), 4.21-3.97 (m, 4H), 3.72-3.52 (m, 3H), 3.29-3.14 (m, 2H), 3.02-2.92 (m, 1H), 2.76-2.63 (m, 1H), 2.57-2.52 (m, 1H), 2.45-2.25 (m, 2H), 1.98-1.70 (m, 4H). $^{19}F$ NMR (376 MHz, DMSO-$d_6$) δ-105.71--105.83 (d, 1F), −132.39--132.46 (d, 1F), −139.89--140.33 (d, 1F), −207.65 (s, 1F).

Example 130: (1S,7S,8S)-2-(7-(8-Ethynyl-7-fluoronaphthalen-1-yl)-8-fluoro-2-(((S,Z)-2-(fluoromethylene) tetrahydro-1H-pyrrolizin-7a (5H)-yl) methoxy)pyrido[4,3-d]pyrimidin-4-yl)-8-fluoro-5-oxa-2-azabicyclo[5.1.0]octane

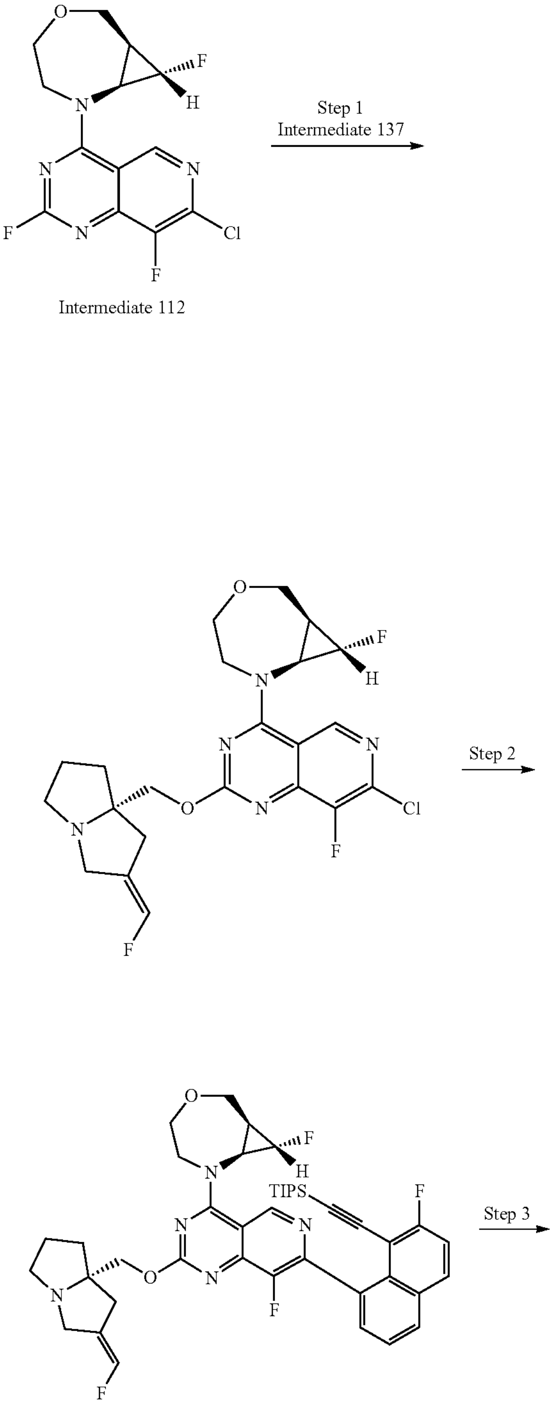

Intermediate 112

-continued

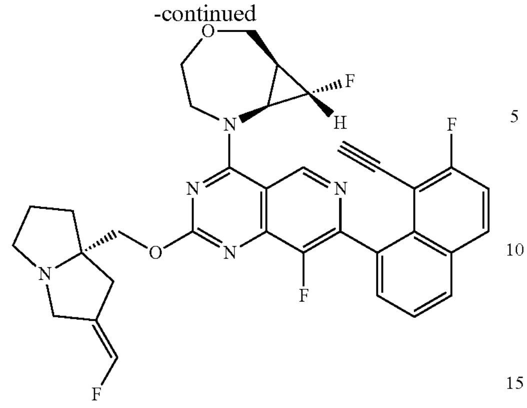

Example 130

Step 1: (1S,7S,8S)-2-(7-Chloro-8-fluoro-2-(((S,Z)-2-(fluoromethylene) tetrahydro-1H-pyrrolizin-7a (5H)-yl)methoxy)pyrido[4,3-d]pyrimidin-4-yl)-8-fluoro-5-oxa-2-azabicyclo[5.1.0]octane To an ice-cooled solution of Intermediate 137 (116.49 mg, 0.68 mmol) in THE (3 mL) under $N_2$ was added t-BuOK (61.08 mg, 0.54 mmol). The mixture was stirred in an ice bath for 30 min. Intermediate 112 (150 mg, 0.45 mmol) was added to the above mixture in portions. The ice bath was removed, and the resulting mixture was stirred at room temperature for 1 hour. The resulting mixture was quenched with sat. $NH_4Cl$ aq. (15 mL) and extracted with DCM (3×30 mL). The combined organic layers were washed with brine (50 mL), dried over anhydrous $Na_2SO_4$, filtered and concentrated under reduced pressure. The residue was purified by Prep-TLC ($CH_2Cl_2$/MeOH 10: 1) to afford the title compound (210 mg, 96% yield) as a light yellow solid. MS: m/z=482.05 $[M+H]^{+}$.

Step 2: (1S,7S,8S)-8-Fluoro-2-(8-fluoro-7-(7-fluoro-8-((triisopropylsilyl) ethynyl)naphthalen-1-yl)-2-(((S,Z)-2-(fluoromethylene) tetrahydro-1H-pyrrolizin-7a (5H)-yl)methoxy)pyrido[4,3-d]pyrimidin-4-yl)-5-oxa-2-azabicyclo[5.1.0]octane To a solution of (18,7S,8S)-2-(7-chloro-8-fluoro-2-(((S, Z)-2-(fluoromethylene) tetrahydro-1H-pyrrolizin-7a (5H)-yl)methoxy)pyrido[4,3-d]pyrimidin-4-yl)-8-fluoro-5-oxa-2-azabicyclo[5.1.0]octane (100 mg, 0.20 mmol) and ((2-fluoro-8-(4,4,5,5-tetramethyl-1,3,2-dioxaborolan-2-yl) naphthalen-1-yl) ethynyl) triisopropylsilane (281.69 mg, 0.62 mmol) in THF (4 mL) and $H_2O$ (0.8 mL) were added CataCXium A Pd G3 (30.23 mg, 0.04 mmol) and $K_3PO_4$ (264.29 mg, 1.24 mmol) at room temperature under $N_2$. The reaction mixture was irradiated with microwave radiation at 60° C. for 1.5 hours. The resulting mixture was cooled to room temperature, diluted with $H_2O$ (10 mL), and extracted with ethyl acetate (3×15 mL). The combined organic layers were washed with brine (20 mL), dried over anhydrous sodium sulfate, filtered and concentrated under reduced pressure. The residue was purified by Prep-TLC ($CH_2Cl_2$/MeOH 15: 1) to afford the title compound (130 mg, 81% yield) as a brown yellow solid. MS: m/z=772.35 $[M+H]^{+}$.

Step 3: (1S,7S,8S)-2-(7-(8-ethynyl-7-fluoronaphthalen-1-yl)-8-fluoro-2-(((S,Z)-2-(fluoromethylene) tetrahydro-1H-pyrrolizin-7a (5H)-yl)methoxy)pyrido [4,3-d]pyrimidin-4-yl)-8-fluoro-5-oxa-2-azabicyclo [5.1.0]octane To a stirred solution of (1S,7S,8S)-8-Fluoro-2-(8-fluoro-7-(7-fluoro-8-((triisopropylsilyl) ethynyl)naphthalen-1-yl)-2-(((S,Z)-2-(fluoromethylene) tetrahydro-1H-pyrrolizin-7a (5H)-yl)methoxy)pyrido[4,3-d]pyrimidin-4-yl)-5-oxa-2-azabicyclo[5.1.0]octane (130 mg, 0.16 mmol) in DMF (1.5 mL) was added CsF (255.80 mg, 1.68 mmol) at room temperature. The reaction mixture was stirred at room temperature for 3 hours. The resulting mixture was filtered and purified by RP-Flash with the following conditions: C18 spherical, 20-30 μm, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 57% B in 15 min, 57% B to 57% B in 3 min, 59% B to 95% B in 8 min; Detector: UV 254 & 210 nm. The collected fractions were combined, concentrated and then lyophilized overnight to give the title compound (Example 130, 70.6 mg, 67% yield) as a light-yellow lyophilized powder. MS: m/z=616.20 $[M+H]^{+}$. $^{1}H$ NMR (400 MHZ, DMSO-$d_6$) δ 9.45-9.40 (m, 1H), 8.26-8.20 (m, 2H), 7.73-7.60 (m, 3H), 6.93-6.72 (m, 1H), 4.95-4.75 (m, 1H), 4.52-4.49 (m, 1H), 4.43-4.33 (m, 2H), 4.21-3.97 (m, 4H), 3.72-3.52 (m, 3H), 3.29-3.14 (m, 2H), 3.02-2.92 (m, 1H), 2.76-2.63 (m, 1H), 2.57-2.52 (m, 1H), 2.45-2.25 (m, 2H), 1.98-1.70 (m, 4H). $^{19}F$ NMR (376 MHZ, DMSO-$d_6$) δ −105.71−−105.83 (d, 1F), −132.39−−132.46 (d, 1F), −139.89−−140.33 (d, 1F), −207.65 (s, 1F).

Example 137: 5-Ethynyl-6,7-difluoro-4-(8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine

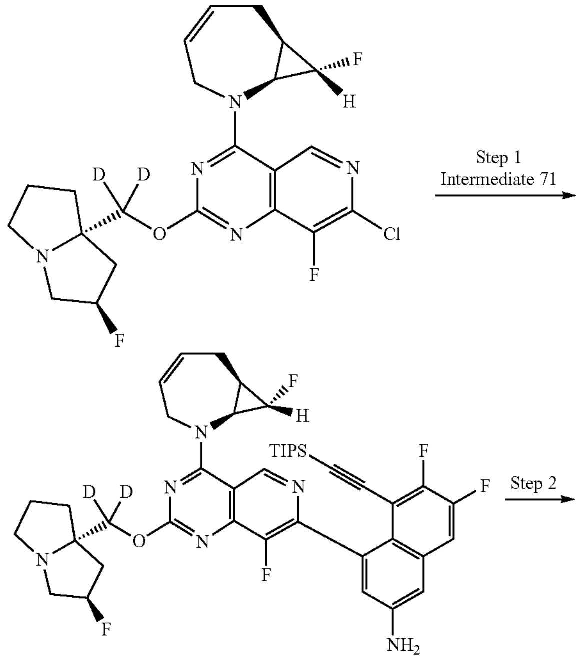

-continued

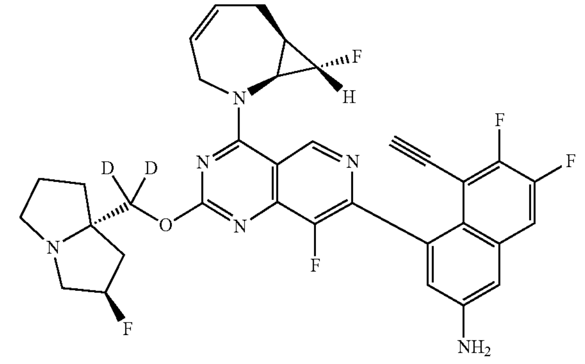

Example 137

Example 137 was prepared in a manner similar to Example 174. MS: m/z=635.3 $[M+H]^+$. $^1H$ NMR (400 MHz, Dimethylsulfoxide-$d_6$) δ 9.32-9.12 (m, 1H), 7.85-7.73 (m, 1H), 7.06-6.79 (m, 2H), 5.88-5.64 (m, 4H), 5.38-5.18 (m, 1H), 5.03-4.86 (m, 1H), 4.79-4.53 (m, 1H), 4.41-3.93 (m, 3H), 3.14-2.98 (m, 3H), 2.88-2.77 (m, 1H), 2.68-2.56 (m, 1H), 2.35-2.06 (m, 3H), 2.06-1.96 (m, 2H), 1.89-1.70 (m, 3H). $^{19}F$ NMR (376 MHz, Dimethylsulfoxide-$d_6$) δ −137.74, −137.79, −138.60, −138.66, −140.03, −140.54, −172.05, −172.17, −205.78, −205.98.

Example 147: 7-(8-Ethynyl-7-fluoronaphthalen-1-yl)-8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a (5H)-yl)methoxy-$d_2$)pyrido[4,3-d]pyrimidine

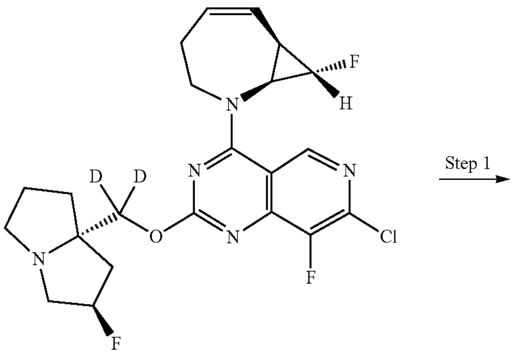

Intermediate 110

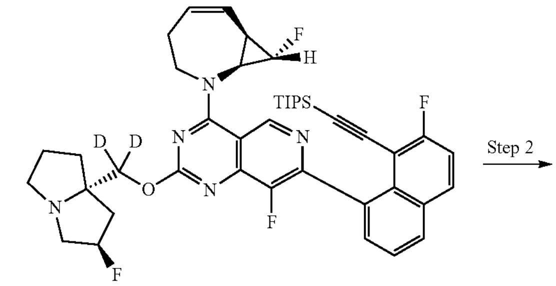

-continued

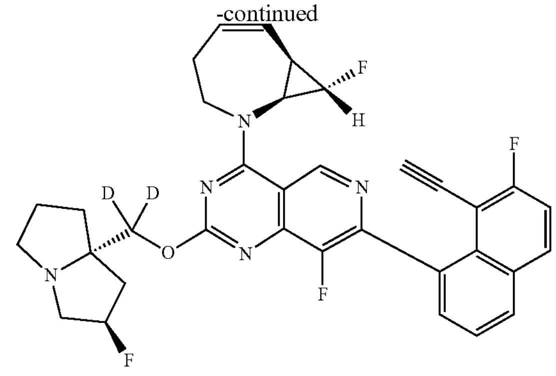

Example 147

Example 147 was prepared in a manner similar to Example 45. MS: m/z=602.3 $[M+H]^+$. $^1$HNMR (400 MHZ, Dimethylsulfoxide-$d_6$) δ 9.45-9.30 (m, 1H), 8.30-8.14 (m, 2H), 7.75-7.54 (m, 3H), 5.88-5.69 (m, 1H), 5.53-5.43 (m, 1H), 5.39-5.17 (m, 1H), 4.86-4.64 (m, 1H), 4.61-4.41 (m, 2H), 4.33-3.92 (m, 1H), 3.84-3.73 (m, 1H), 3.14-2.94 (m, 4H), 2.87-2.78 (m, 1H), 2.49-2.30 (m, 2H), 2.12-1.96 (m, 3H), 1.87-1.73 (m, 3H). $^{19}F$ NMR (376 MHZ, Dimethylsulfoxide-$d_6$) δ −105.88, −140.18, −172.02, −172.14, −205.07.

Example 148: 6,7,8-Trifluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a (5H)-yl)methoxy-$d_2$)pyrido[4,3-d]pyrimidin-7-yl)-5-(methoxy-$d_3$)naphthalen-2-amine

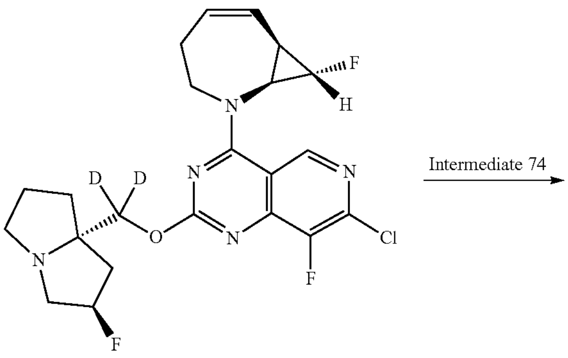

Intermediate 110

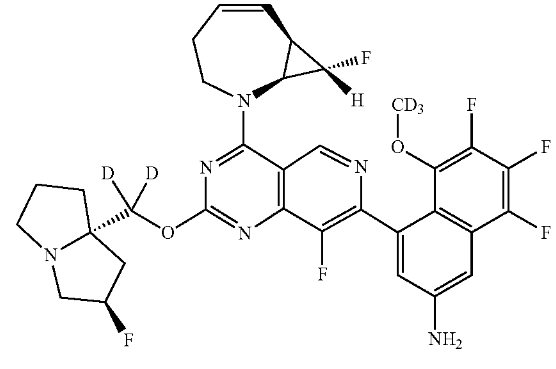

Example 148

Example 148 was prepared in a manner similar to Example 41. MS: m/z=662.3 $[M+H]^+$. $^1$HNMR (400 MHz, Dimethylsulfoxide-$d_6$) δ 9.45-9.30 (m, 1H), 7.11-6.92 (m, 2H), 6.10-5.90 (m, 2H), 5.84-5.41 (m, 2H), 5.38-5.18 (m, 1H), 4.76-4.39 (m, 3H), 3.77 (t, J=12.4 Hz, 1H), 3.16-2.91 (m, 4H), 2.87-2.75 (m, 1H), 2.49-2.29 (m, 2H), 2.16-1.94 (m, 3H), 1.87-1.70 (m, 3H). $^{19}$F NMR (376 MHz, Dimethylsulfoxide-$d_6$) δ −140.49, −140.74, −154.14, −154.20, −161.06, −172.07, −172.13, −204.19, −204.87.

Example 150: 5-Ethynyl-6-fluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine

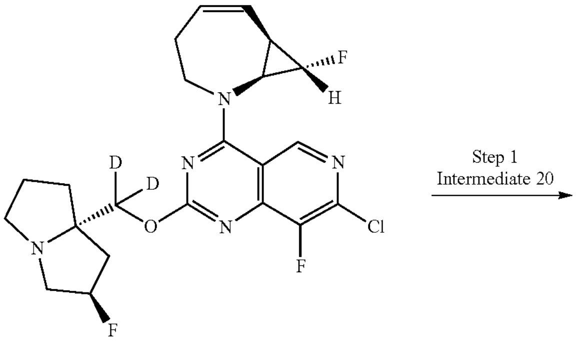

Intermediate 110

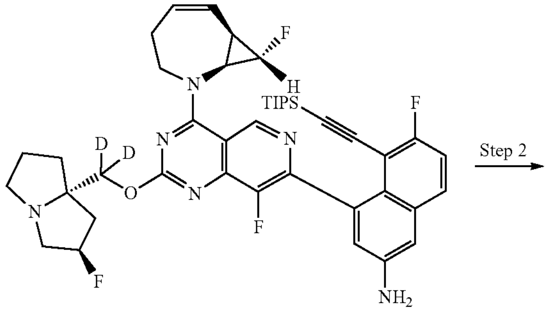

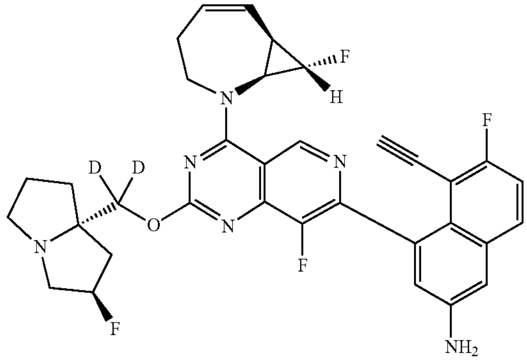

Example 150

Step 1: 6-Fluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a (5H)-yl)methoxy-$d_2$)pyrido[4,3-d]pyrimidin-7-yl)-5-((triisopropylsilyl) ethynyl)naphthalen-2-amine A mixture of Intermediate 110 (150 mg, 321 μmol), Intermediate 20 (270 mg, 577 μmol), $K_3PO_4$ (204 mg, 962 μmol) and $Ad_2nBuP$-Pd-$G_3$ (cataCXiumAPdG$_3$) (23 mg, 32 μmol) in 1,4-dioxane (5 mL) and $H_2O$ (1 mL) was degassed and purged with $N_2$ three times, and the mixture was stirred at 100° C. for 1 h under $N_2$ atmosphere. The reaction mixture was concentrated under reduced pressure. The residue was purified by silica gel flash chromatography (eluent: 0~5% MeOH in $CH_2Cl_2$) to give the title compound (90 mg, 35% yield) as a brown solid. MS: m/z=773.5 $[M+H]^{+}$.

Step 2: 5-Ethynyl-6-fluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a (5H)-yl)methoxy-$d_2$)pyrido[4,3-d]pyrimidin-7-yl)naphthalen-2-amine To a solution of 6-fluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-amine (90 mg, 116 μmol) in DMSO (1 mL) was added CsF (53 mg, 349 μmol). The mixture was stirred at 25° C. for 1 h. The residue was purified by silica gel flash chromatography (eluent: 0~8% of MeOH in $CH_2Cl_2$) to give the title compound (Example 150, 42 mg, 57% yield) as a brown solid. MS: m/z=617.2 $[M+H]^+$. $^1$H NMR (400 MHz, Dimethylsulfoxide-$d_6$) δ 9.42-9.30 (m, 1H), 7.84-7.70 (m, 1H), 7.33 (t, J=9.2 Hz, 1H), 7.05 (s, 2H), 5.84-5.72 (m, 1H), 5.70-5.55 (m, 2H), 5.52-5.41 (m, 1H), 5.39-5.17 (m, 1H), 4.82-4.40 (m, 3H), 4.16-3.74 (m, 2H), 3.18-3.06 (m, 2H), 3.05-2.92 (m, 2H), 2.89-2.80 (m, 1H), 2.48-2.29 (m, 2H), 2.15-1.97 (m, 3H), 1.88-1.73 (m, 3H). $^{19}$F NMR (376 MHz, Dimethylsulfoxide-$d_6$) δ −113.44, −113.50, −139.73, −140.28, −172.05, −204.18, −205.02.

Example 155: 5-Ethynyl-6-fluoro-4-(8-fluoro-4-((15,7S,8S)-8-fluoro-5-oxa-2-azabicyclo[5.1.0]octan-2-yl)-2-(((S,Z)-2-(fluoromethylene) tetrahydro-1H-pyrrolizin-7a (5H)-yl)methoxy)pyrido[4,3-d] pyrimidin-7-yl)naphthalen-2-amine

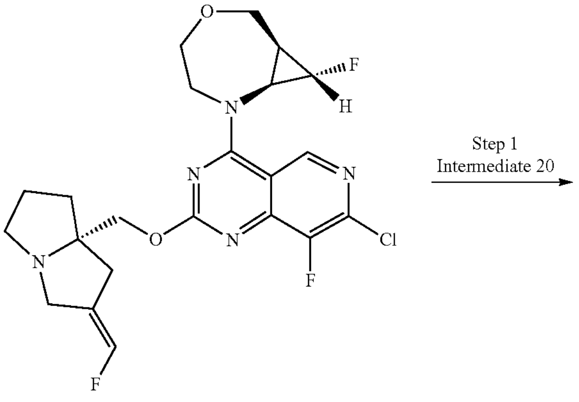

Intermediate 138

-continued

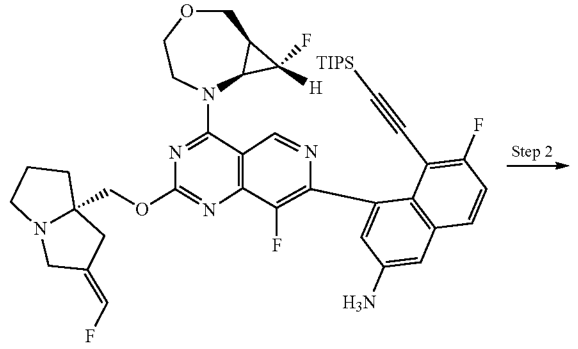

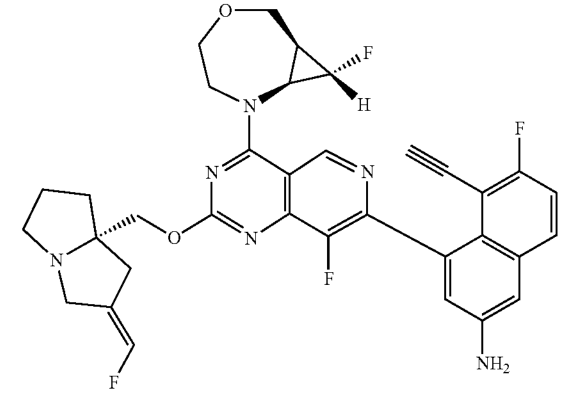

Example 155

Example 155 was prepared in a manner similar to Example 150. MS: m/z=631.60 [M+H]$^+$. $^1$H NMR (400 MHz, DMSO-$d_6$) δ 9.43-9.37 (m, 1H), 7.80-7.76 (m, 1H), 7.37-7.32 (m, 1H), 7.06-7.04 (m, 2H), 6.86-6.65 (m, 1H), 5.66-5.65 (m, 2H), 4.97-4.73 (m, 1H), 4.51-4.47 (m, 1H), 4.42-4.34 (m, 2H), 4.10-3.81 (m, 4H), 3.71-3.50 (m, 3H), 3.30-3.20 (m, 2H), 3.01-2.98 (m, 1H), 2.56-2.50 (m, 2H), 2.40-2.31 (m, 2H), 1.95-1.69 (m, 4H). $^{19}$F NMR (376 MHz, DMSO-$d_6$) δ −113.34--113.43 (d, 1F), −130.92--130.97 (d, 1F), −139.91--144.46 (d, 1F), −207.71 (s, 1F).

Example 158: 5-Ethynyl-6-fluoro-4-(8-fluoro-4-((15,75,8S)-8-fluoro-5-oxa-2-azabicyclo[5.1.0]octan-2-yl)-2-(((S)-2-methylenetetrahydro-1H-pyrrolizin-7a (5H)-yl)methoxy)pyrido[4,3-d]pyrimidin-7-yl)naphthalen-2-amine

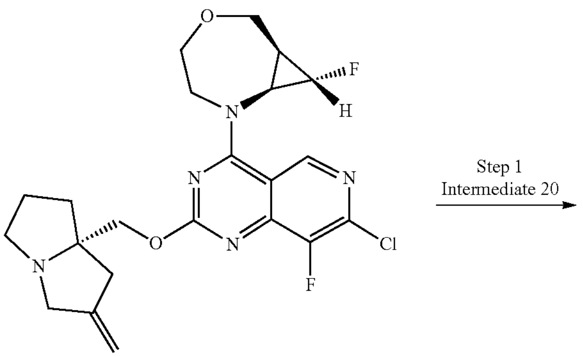

-continued

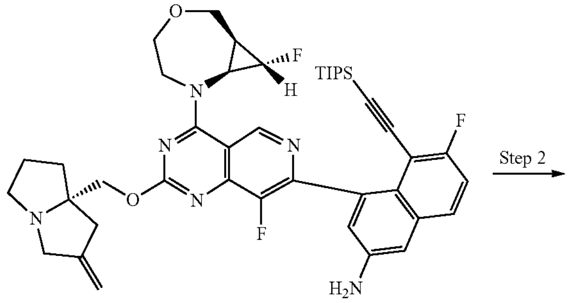

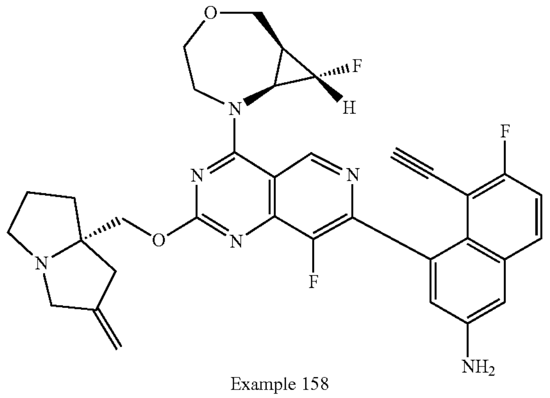

Example 158

Example 158 was prepared in a manner similar to Example 150. MS: m/z=613.60 [M+H]$^+$. $^1$H NMR (400 MHZ, DMSO-$d_6$) δ 9.43-9.37 (m, 1H), 7.80-7.76 (m, 1H), 7.36-7.32 (m, 1H), 7.06-7.05 (m, 2H), 5.66-5.64 (m, 2H), 5.00-4.73 (m, 3H), 4.51-4.47 (m, 1H), 4.42-4.34 (m, 2H), 4.06-3.82 (m, 4H), 3.78-3.71 (m, 1H), 3.62-3.53 (m, 2H), 3.30-3.20 (m, 2H), 3.01-2.98 (m, 1H), 2.60-2.50 (m, 2H), 2.49-2.30 (m, 2H), 1.96-1.67 (m, 4H). $^{19}$F NMR (376 MHz, DMSO-$d_6$) δ −113.35--113.44 (d, 1F), −139.96--140.51 (d, 1F), −207.75 (s, 1F).

Example 159: 6-(6-Chloro-8-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) quinazolin-7-yl)-4-methyl-5-(trifluoromethyl)pyridin-2-amine

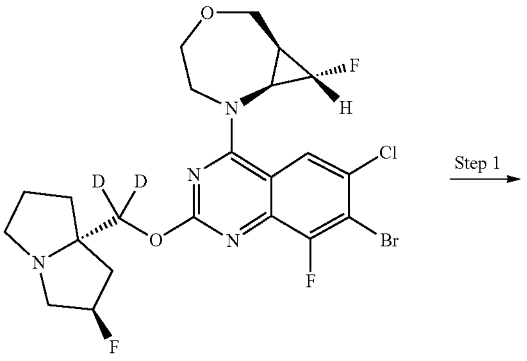

Intermediate 134

-continued

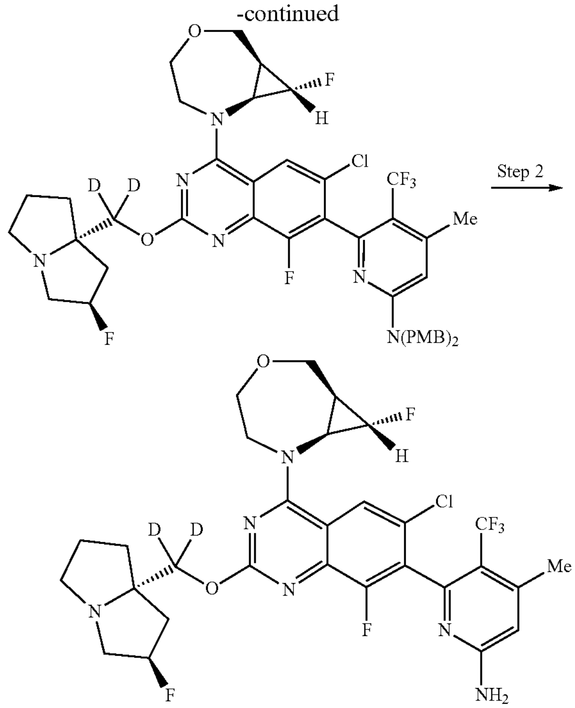

Example 159

Step 1: 6-(6-Chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$) quinazolin-7-yl)-N,N-bis(4-methoxybenzyl)-4-methyl-5-(trifluoromethyl) pyridin-2-amine To a mixture of Intermediate 134 (220 mg, 0.400 mmol) in THF (5 mL) was added isopropylmagnesium chloride-Lithium chloride complex (0.32 mL, 0.416 mmol, 1.3 M in THF) dropwise at −78° C. under argon atmosphere. The reaction mixture was stirred at −78° C. for 20 minutes. To the above mixture was added zinc chloride (0.22 mL, 0.440 mmol, 2.0 M in 2-MeTHF) dropwise at −78° C. The resulting mixture was stirred for an additional 20 minutes at −78° C. The mixture was slowly warmed to 10° C. and stirred for 10 minutes. To the above mixture was added sodium 2,2,2-trifluoroacetate (150.3 mg, 1.11 mmol) at 10° C. under argon atmosphere. To the above mixture was added 6-bromo-N,N-bis(4-methoxybenzyl)-4-methyl-5-(trifluoromethyl)pyridin-2-amine (180 mg, 0.36 mmol) in degassed THF (2.5 mL) at 10° C. Then di-chlorobis [(1,2,3-)-1-phenyl-2-propenyl]dipalladium (II) (9.4 mg, 0.018 mmol) and (R,R)-Chiraphite (31.9 mg, 0.036 mmol) in degassed THF (2.5 mL) were added to the above mixture at 10° C. under argon atmosphere. The resulting mixture was heated at 50° C. for 12 hours. The reaction was monitored by LCMS. After completion of the reaction, the mixture was quenched with sat. aq. $NH_4Cl$ (0.5 mL), filtered and concentrated under reduced pressure. The residue was purified by reverse phase flash chromatography with the following conditions (Column, C18 column, 40 g, 20-35 um, 100 A; Mobile phase A: 1 mM aq. HCOOH; Mobile phase B: 1 mM HCOOH in acetonitrile, 2% to 80% gradient in 25 min; detector, UV 254 & 210 nm) to afford the title compound (80 mg, 25%) as a light yellow solid. MS: m/z=885.25 $[M+H]^{+}$.

Step 2: 6-(6-Chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$) quinazolin-7-yl)-4-methyl-5-(trifluoromethyl)pyridin-2-amine A solution of 6-(6-chloro-8-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) quinazolin-7-yl)-N,N-bis(4-methoxybenzyl)-4-methyl-5-(trifluoromethyl)pyridin-2-amine (65 mg, 0.073 mmol) in 2,2,2-trifluoroacetic acid (3 mL) was heated at 80° C. for 3 hours. The mixture was concentrated under reduced pressure. The residue was purified by reverse phase flash chromatography with the following conditions: Column, C18 column, 20 g, 20-35 um, 100 A; Mobile phase A: 1 mM aq. HCOOH; Mobile phase B: 1 mM aq. HCOOH in acetonitrile, Gradient: 2% B hold 5 min, up to 50% B within 6 min, 50% B hold 10 min, up to 98% B within 5 min; Flow rate: 40 mL/min; Detector, UV 254 & 210 nm. The product-containing fractions were collected, concentrated, and then dissolved in MeOH (1 mL). To the above solution was added Amberlyst A-21 (200 mg) and the mixture was stirred at room temperature for 10 minutes. Then the mixture was filtered and concentrated under reduced pressure. The residue was purified by reverse phase flash chromatography with the following conditions: Column, C18 column, 20 g, 20-35 um, 100 A; Mobile phase A: 5 mM aq. $NH_4HCO_3$; Mobile phase B: Acetonitrile, Gradient: 2% B hold 5 min, up to 54% B within 9 min, 50% B hold 10 min, up to 98% B within 5 min; Flow rate: 40 mL/min; Detector, UV 254 & 210 nm. The product-containing fractions were collected, concentrated, and lyophilized overnight to give the title compound (Example 159, 24.2 mg, 55%) as a white lyophilized powder. MS: m/z=645.15 $[M+H]^{+}$. $^{1}H$ NMR (300 MHz, DMSO-$d_6$) δ 8.29 (s, 1H), 6.86 (s, 2H), 6.49 (s, 1H), 5.26 (d,J=53.6 Hz, 1H), 4.71 (d, J=60.5 Hz, 1H), 4.47-4.16 (m, 3H), 4.03-3.91 (m, 1H), 3.77-3.65 (m, 1H), 3.60-3.48 (m, 1H), 3.24-3.03 (m, 3H), 3.01-2.95 (m, 1H), 2.89-2.70 (m, 1H), 2.39-2.27 (m, 5H), 2.15-2.09 (m, 1H), 2.03-1.93 (m, 2H), 1.82-1.72 (m, 2H). $^{19}F$ NMR (282 MHZ, DMSO-$d_6$) δ −53.49 (3F), −126.42 (1F), −172.14 (1F), −207.71 (1F).

Example 161: 5-Ethynyl-6-fluoro-4-(8-fluoro-4-((1S,7S,8S)-8-fluoro-5-oxa-2-azabicyclo[5.1.0]octan-2-yl)-2-(((S,E)-2-(fluoromethylene) tetrahydro-1H-pyrrolizin-7a (5H)-yl)methoxy)pyrido[4,3-d] pyrimidin-7-yl)naphthalen-2-amine

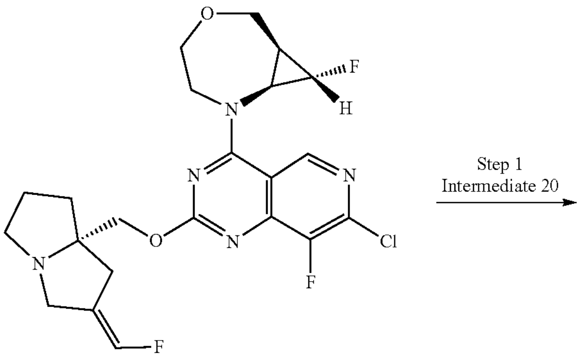

-continued

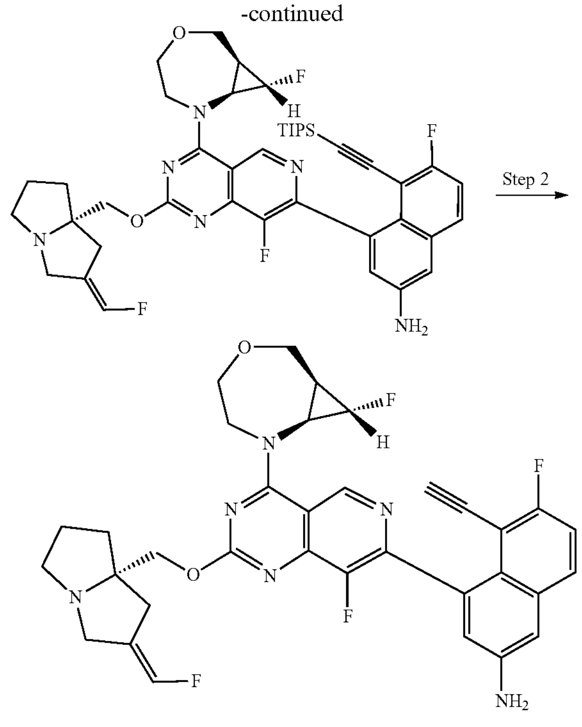

Example 161

Example 161 was prepared in a manner similar to Example 150. MS: m/z=631.2 $[M+H]^+$. $^1H$ NMR (400 MHz, DMSO-$d_6$) δ 9.42-9.36 (m, 1H), 7.80-7.76 (m, 1H), 7.37-7.32 (m, 1H), 7.06-7.05 (m, 2H), 6.93-6.72 (m, 1H), 5.66-5.65 (m, 2H), 4.93-4.73 (m, 1H), 4.51-4.34 (m, 3H), 4.11-3.81 (m, 4H), 3.71-3.53 (m, 3H), 3.31-3.16 (m, 2H), 3.03-2.92 (m, 1H), 2.77-2.64 (m, 1H), 2.51-2.50 (m, 1H), 2.43-2.23 (m, 2H), 2.06-1.70 (m, 4H). $^{19}F$ NMR (376 MHz, DMSO-$d_6$) δ −113.35--113.44 (d, 1F), −132.38--132.47 (d, 1F), −139.91--140.47 (d, 1F), −207.70 (s, 1F)

Example 162: 6,7-Difluoro-4-(8-fluoro-4-((15,75, 8S)-8-fluoro-5-oxa-2-azabicyclo[5.1.0]octan-2-yl)-2-(((S,Z)-2-(fluoromethylene) tetrahydro-LH-pyrrolizin-7a (5H)-yl)methoxy)pyrido[4,3-d]pyrimidin-7-yl)-5-(fluoromethoxy-$d_2$)naphthalen-2-amine

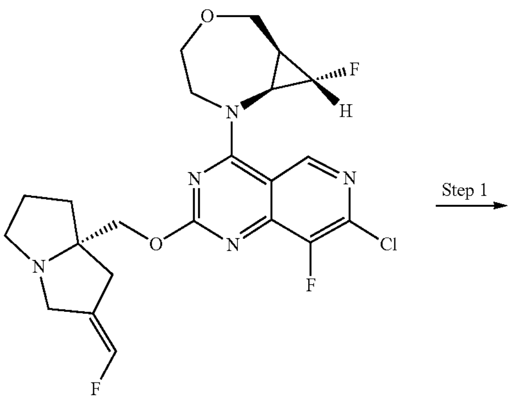

Intermediate 138

-continued

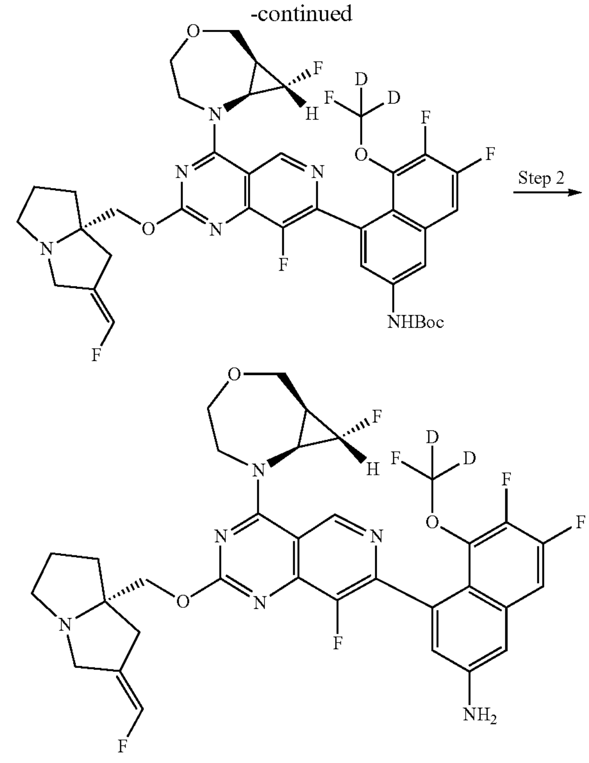

Example 162

Example 162 was prepared in a manner similar to Example 88. MS: m/z=675.15 $[M+H]^+$. $^1H$ NMR (400 MHZ, DMSO-$d_6$) δ 9.44-9.39 (m, 1H), 7.62-7.57 (m, 1H), 7.03-6.99 (m, 2H), 6.86-6.65 (m, 1H), 5.83-5.81 (m, 2H), 4.97-4.82 (m, 1H), 4.52-4.48 (m, 1H), 4.39-4.31 (m, 2H), 4.11-3.99 (m, 3H), 3.71-3.59 (m, 3H), 3.33-3.13 (m, 2H), 3.05-2.95 (m, 1H), 2.61-2.52 (m, 2H), 2.45-2.29 (m, 2H), 1.95-1.71 (m, 4H). $^{19}F$ NMR (376 MHZ, DMSO-$d_6$) δ −130.93--130.98 (d, 1F), −137.14--137.27 (m, 1F), −140.27--140.36 (d, 1F), −150.51--150.85 (m, 1F), −159.24--159.69 (m, 1F), −208.28--208.30 (m, 1F).

Example 166: (1S,7S,8S)-2-(7-(8-Ethynyl-7-fluoronaphthalen-1-yl)-8-fluoro-2-(((R)-6'-methylenetetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane

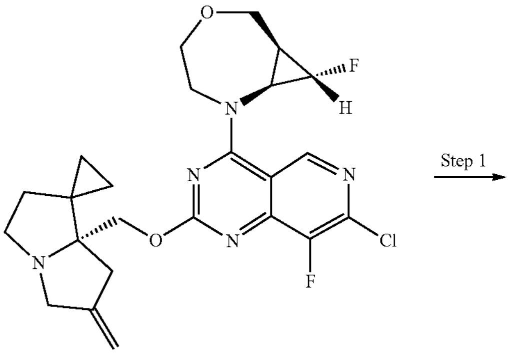

-continued

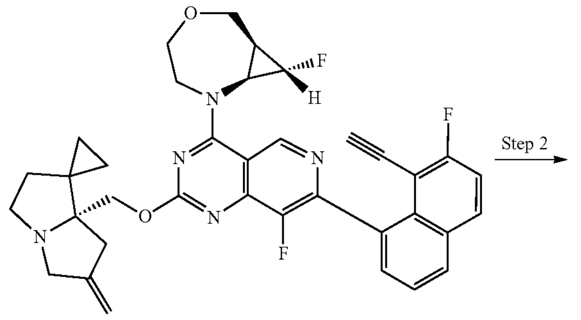

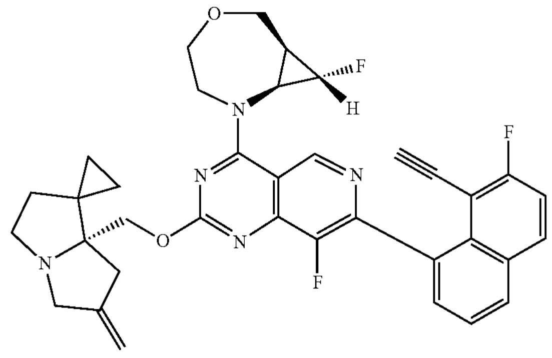

Example 166

Example 166 was prepared in a manner similar to Example 150. MS: m/z=624.45 $[M+H]^+$. $^1H$ NMR (400 MHz, DMSO-$d_6$) & 9.44-9.38 (m, 1H), 8.26-8.20 (m, 2H), 7.73-7.60 (m, 3H), 4.96-4.76 (m, 3H), 4.54-4.34 (m, 3H), 4.22-3.98 (m, 4H), 3.80-3.59 (m, 3H), 3.33-3.20 (m, 2H), 3.04-3.02 (m, 1H), 2.64-2.62 (m, 1H), 2.49-2.23 (m, 3H), 2.00-1.90 (m, 1H) 1.72-1.67 (m, 1H), 0.79-0.76 (m, 1H), 0.62-0.59 (m, 1H), 0.52-0.42 (m, 2H). $^{19}F$ NMR (376 MHZ, DMSO-$d_6$) δ −105.73-−105.84 (d, 1F), −138.93-−140.27 (d, 1F), −207.75 (s, 1F).

Example 167: 2-Fluoro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-3-methyl-4-(trifluoromethyl) aniline

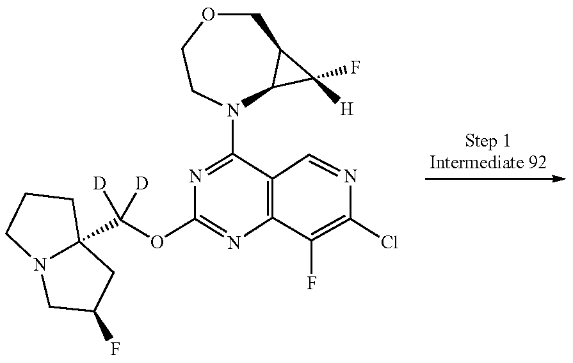

Intermediate 34

-continued

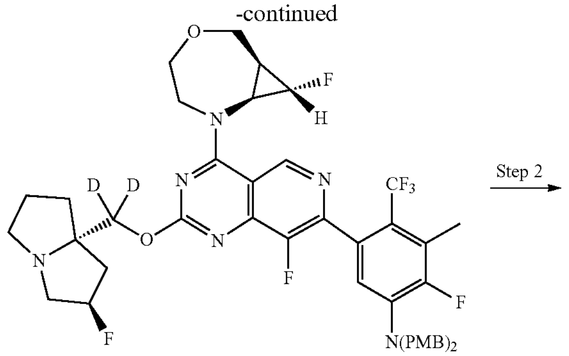

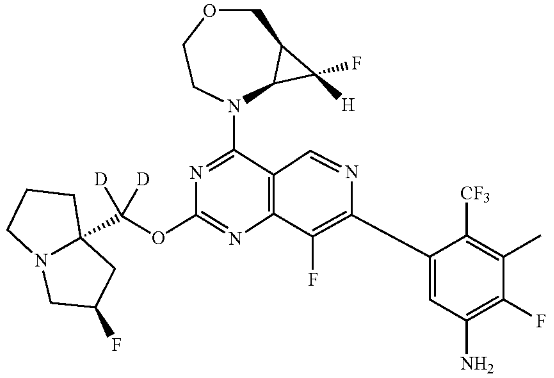

Example 167

Step 1: 2-Fluoro-5-(8-fluoro-4-((1S,75,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-N,N-bis(4-methoxybenzyl)-3-methyl-4-(trifluoromethyl) aniline To a stirred solution of Intermediate 34 (120 mg, 0.25 mmol) and Intermediate 92 (213.38 mg, 0.38 mmol) in 1,4-dioxane (5 mL) and $H_2O$ (1 mL) were added Cat-aCXium A Pd G3 (37.04 mg, 0.05 mmol) and $K_3PO_4$ (323.86 mg, 1.52 mmol) at room temperature under nitrogen atmosphere. The reaction mixture was heated at 100° C. for 2 hours. The resulting mixture was cooled to room temperature, diluted with water (15 mL), and extracted with EtOAc (3×20 mL) The combined organic layers were washed with brine (30 mL), dried over anhydrous $Na_2SO_4$, filtered, and concentrated under reduced pressure. The residue was purified by Prep-TLC ($CH_2Cl_2$/MeOH 17: 1) to afford the title compound (130 mg, 58% yield) as a light yellow solid. MS: m/z=869.40 $[M+H]^{+\cdot}$ Step 2: 2-Fluoro-5-(8-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-3-methyl-4-(trifluoromethyl) aniline A solution of 2-fluoro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) pyrido[4,3-d]pyrimidin-7-yl)-N,N-bis(4-methoxybenzyl)-3-methyl-4-(trifluoromethyl) aniline (130 mg, 0.15 mmol) in TFA (2 mL) was heated at 50° C. for 2 hours under air atmosphere. The resulting mixture was cooled to room temperature, and co-evaporated with toluene (three times, 10 mL each). The residue was purified by Prep-TLC (DCM/MeOH 15: 1) to afford a crude product. The crude product was purified by RP-flash with the following conditions: Column, C18; Mobile phase A: 5 mM aq. $NH_4HCO_3$; Mobile phase B: MeCN; Gradient: 2% B to 51% B in 20 min; Detector: UV 254 nm. The collected fractions were combined, concentrated and lyophilized overnight to afford the title compound (Example 167, 39.4 mg, 40% yield) as an off-white lyophilized powder. MS: m/z=629.25 $[M+H]^+$. $^1H$ NMR (400 MHZ, DMSO-$d_6$) δ 9.39 (s, 1H), 6.60 (s, 1H), 6.05 (s, 2H), 5.34-5.21 (m, 1H), 4.95-4.65 (m, 1H), 4.49-4.46 (m, 1H), 4.36-4.27 (m, 2H), 3.99-3.96 (m, 1H), 3.69-3.54 (m, 2H), 3.20-3.00 (m, 4H), 2.85-2.80 (m, 1H), 2.40-2.29 (m, 4H), 2.13-1.71 (m, 6H). $^{19}F$ NMR (376 MHz, DMSO-$d_6$) &-52.26--52.40 (m, 3F), −135.53--135.59 (d, 1F), −141.44 (s, 1F), −172.15 (s, 1F), −207.68--207.84 (m, 1F).

Example 171: 5-Ethynyl-6-fluoro-4-(8-fluoro-4-((15,75,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'W)-yl)methoxy)pyrido[4,3-d]pyrimidin-7-yl)naphthalen-2-amine

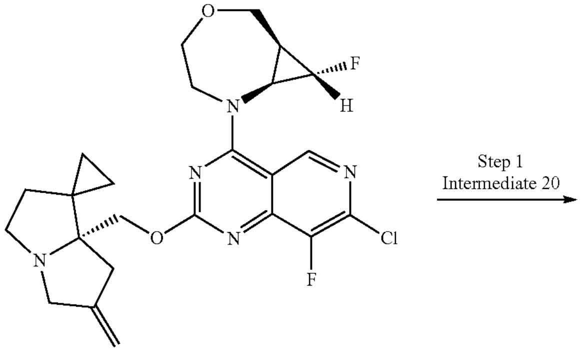

Intermediate 101

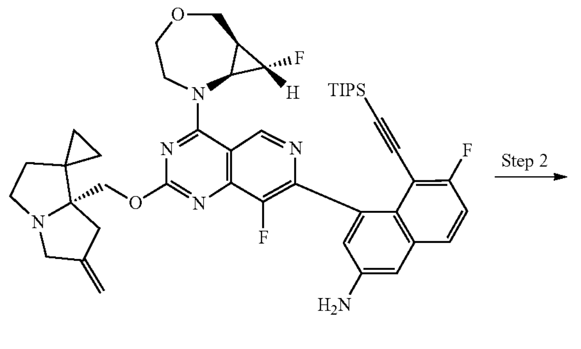

-continued

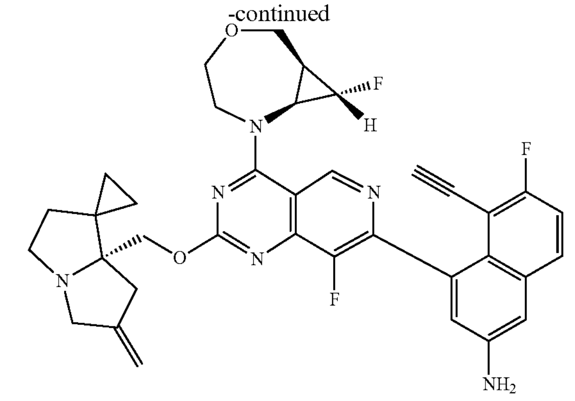
Example 171

Step 1: 6-Fluoro-4-(8-fluoro-4-((1S,7S,8S)-8-fluoro-S-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)-5-((triisopropylsilyl) ethynyl)naphthalen-2-amine To a mixture of Intermediate 101 (90 mg, 0.18 mmol) and Intermediate 20 (171.76 mg, 0.36 mmol) in THF (3.7 mL) and $H_2O$ (0.74 mL) under nitrogen atmosphere were added CataCXium A Pd G3 (26.76 mg, 0.03 mmol) and $K_2PO_4$ (233.95 mg, 1.10 mmol) at room temperature. The reaction mixture was heated at 80° C. for 3 hours. The resulting mixture was cooled to room temperature, diluted with $H_2O$ (8 mL) and extracted with ethyl acetate (3x15 mL). The combined organic layers were washed with brine (10 mL), dried over anhydrous sodium sulfate, filtered and concentrated under reduced pressure. The residue was purified by Prep-TLC ($CH_2Cl$/MeOH 15: 1) to afford the title compound (100 mg, 68% yield) as a yellow solid. MS: m/z=795.50 $[M+H]^{+\cdot}$ Step 2: 5-Ethynyl-6-fluoro-4-(8-fluoro-4-((15,75,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'W)-yl)methoxy)pyrido[4,3-d]pyrimidin-7-yl)naphthalen-2-amine To a stirred solution of 6-fluoro-4-(8-fluoro-4-((15,75,8S)-8-fluoro-5-oxa-2-azabicyclo[5.1.0]octan-2-yl)-2-(((R)-6'-methylenetetrahydrospiro[cyclopropane-1, 1'-pyrrolizin]-7a'(5'H)-yl)methoxy)pyrido[4,3-d]pyrimidin-7-yl)-5-((triisopropylsilyl) ethynyl)naphthalen-2-amine (100 mg, 0.12 mmol) in DMSO (1 mL) was added CsF (286.60 mg, 1.89 mmol) at room temperature. The reaction mixture was stirred at room temperature for 3 hours. The resulting mixture was filtered and purified by RP-Flash with the following conditions: C18 spherical, 20-30 μm, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 61% B in 15 min, 61% B to 61% B in 3 min, 61% B to 95% B in 4 min; Detector: UV 254 & 210 nm. The collected fractions were combined, concentrated and lyophilized overnight to give the title compound (Example 171, 36.9 mg, 45% yield) as a yellow lyophilized powder. MS: m/z=639.20 $[M+H]^+$. $^1H$ NMR (400 MHZ, DMSO-$d_6$) δ 9.42-9.36 (m, 1H), 7.80-7.76 (m, 1H), 7.36-7.32 (m, 1H), 7.06-7.05 (m, 2H), 5.66-5.65 (m, 2H), 4.99-4.70 (m, 3H), 4.53-4.33 (m, 3H), 4.17-3.81 (m, 4H), 3.78-3.59 (m, 3H), 3.30-3.20 (m, 2H), 3.09-3.00 (m, 1H), 2.68-2.60 (m, 1H), 2.46-2.23 (m, 3H), 2.00-1.95 (m, 1H), 1.74-1.67 (m, 1H), 0.79-0.73 (m, 1H), 0.67-0.55 (m, 1H), 0.52-0.40 (m, 2H). $^{19}F$ NMR (376 MHz, DMSO-$d_6$) δ -113.36--113.44 (d, 1F), -139.93--140.41 (d, 1F), -207.77 (s, 1F).

Example 174: 5-Ethynyl-6-fluoro-4-(8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine

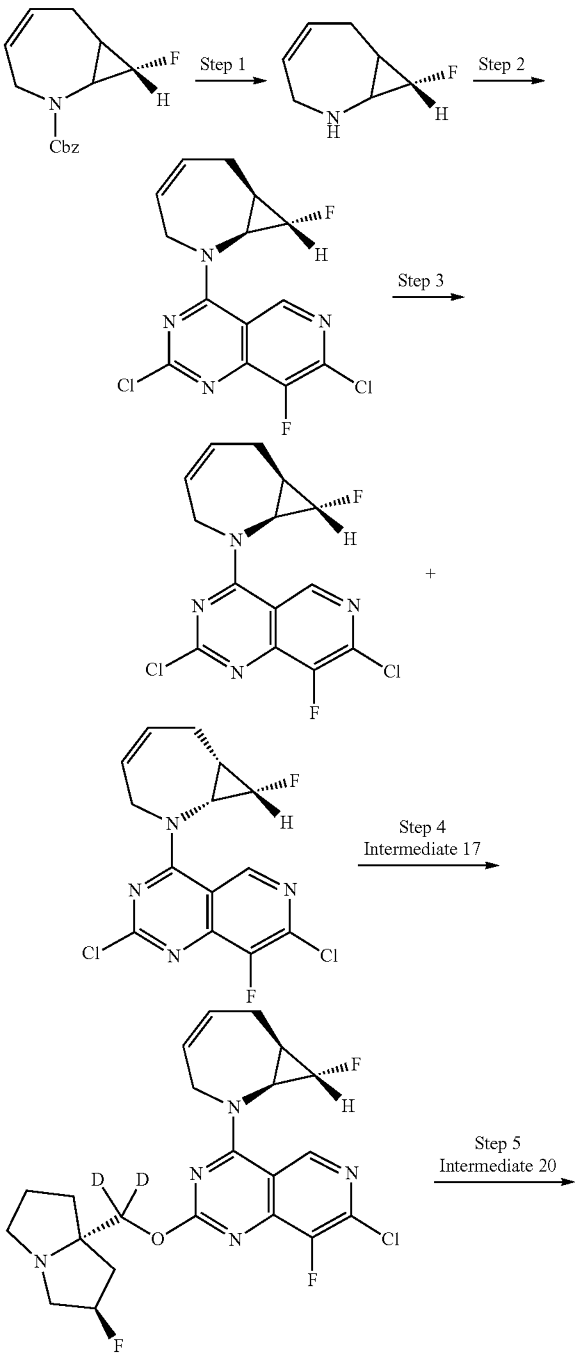

-continued

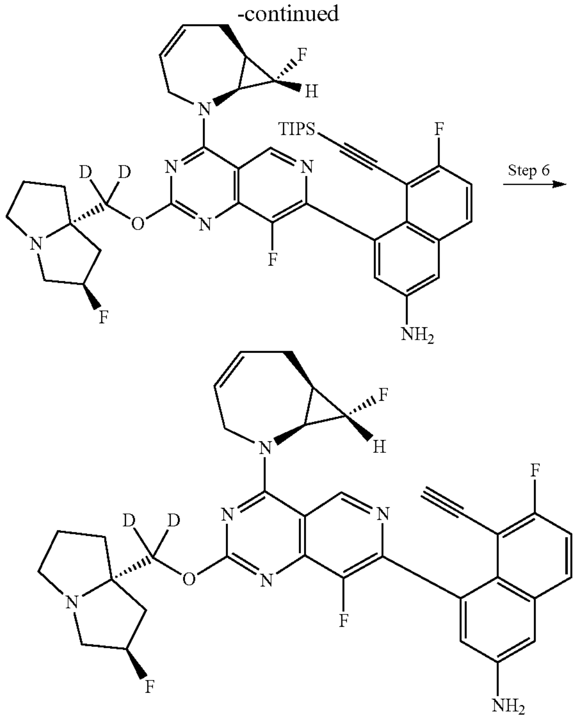

Example 174

Step 1: 8-Fluoro-2-azabicyclo[5.1.0]oct-4-ene (trans)

To a solution of benzyl-8-fluoro-2-azabicyclo[5.1.0]oct-4-ene-2-carboxylate (trans) (600 mg, 2.30 mmol) in $CH_2Cl_2$ (5 mL) was added HBr in AcOH (33%, 1.2 mL) at 0° C. The reaction mixture was stirred at 25° C. for 1 h. The reaction mixture was concentrated under reduced pressure to give the title compound (477 mg, crude, HBr salt) as a yellow oil. It was used into the next step without further purification. MS: m/z=127.9 $[M+H]^+$. $^1H$ NMR (400 MHZ, Chloroform-d) & 10.53-10.06 (m, 1H), 9.92-9.47 (m, 1H), 5.86-5.77 (m, 1H), 5.48-5.40 (m, 1H), 4.12-3.74 (m, 2H), 3.25-3.10 (m, 1H), 2.89-2.71 (m, 2H), 2.67-2.60 (m, 1H), 2.28-2.10 (m, 1H). $^{19}F$ NMR (376 MHz, Chloroform-d) 8-206.54.

Step 2 & 3: 2,7-Dichloro-8-fluoro-4-(1S,7R,89)-8-fluoro-2-azabicyclo[5.1.0]oct-4-en-2-yl)pyrido[4,3-d]pyrimidine & 2,7-Dichloro-8-fluoro-4-((1R,7S,8R)-8-fluoro-2-azabicyclo[5.1.0]oct-4-en-2-yl)pyrido[4,3-d]pyrimidine To a solution of 2,4,7-trichloro-8-fluoropyrido[4,3-d]pyrimidine (579 mg, 2.29 mmol), DIPEA (2 mL, 11.5 mmol) in $CH_2Cl_2$ (20 mL) was added a solution of 8-fluoro-2-azabicyclo[5.1.0]oct-4-ene (trans) (477 mg, HBr) in $CH_2Cl_2$ (2 mL) at -40° C. under $N_2$ atmosphere. The reaction mixture was stirred at -40° C. for 1 h under $N_2$ atmosphere. The reaction mixture was diluted with water (50 mL) and extracted with EtOAc (60 mL×2). The combined organic layers were washed with brine (50 mL), dried over anhydrous $Na_2SO_4$, filtered and concentrated under reduced pressure. The residue was purified by silica gel flash chromatography (eluent: 0~1% of MeOH in $CH_2Cl_2$), and then separated by SFC (column: DAICEL CHIRALPAK IC (250 mm×30 mm, 10 um); mobile phase: [$CO_2$-MeOH (0.1%

$NH_3$ $H_2O$)]; B %: 40%, isocratic elution mode) to give the title compound (74 mg, 9% yield over 3 steps, SFC peak 1: 2.019 min) as a yellow solid (MS: m/z=343.1 $[M+H]^+$) and the other title compound (110 mg, 14% yield over 3 steps, SFC peak 1: 1.805 min) as a yellow solid (MS: m/z=343.1 $[M+H]^+$).

Step 4: 7-Chloro-8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a (5H)-yl)methoxy-$d_2$) pyrido[4,3-d]pyrimidine To a solution of 2,7-dichloro-8-fluoro-4-((1S,7R,8S)-8-fluoro-2-azabicyclo[5.1.0]oct-4-en-2-yl)pyrido[4,3-d]pyrimidine (74 mg, 216 μmol), DIPEA (113 μL, 647 μmol) and Intermediate 17 (63 mg, 388 μmol) in 1,4-dioxane (2 mL) was stirred at 105° C. under $N_2$ for 8 h. The reaction mixture was concentrated under reduced pressure to give a residue. The residue was purified by silica gel chromatography (eluent: 0~4% of MeOH in $CH_2Cl_2$) to give 7-chloro-8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a (5H)-yl)methoxy-$d_2$)pyrido[4,3-d]pyrimidine (77 mg, 76% yield) as a yellow solid. MS: m/z=468.1 $[M+H]^+$.

Step 5: 6-Fluoro-4-(8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine A mixture of 7-chloro-8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a (5H)-yl)methoxy-$d_2$)pyrido[4,3-d] pyrimidine (77 mg, 165 μmol), Intermediate 20 (138 mg, 296 μmol), $K_3PO_4$ (105 mg, 494 μmol) and $Ad_2nBuP$-Pd-$G_3$ (cataC XiumAPdG$_3$) (12 mg, 16.5 μmol) in 1,4-dioxane (2 mL) and $H_2O$ (0.4 mL) was degassed, purged with $N_2$ three times, and stirred at 105° C. under $N_2$ for 0.5 h. The reaction mixture was concentrated under reduced pressure. The residue was purified by silica gel flash chromatography (eluent: 0~5% of MeOH in $CH_2Cl_2$) to give the title compound (85 mg, 65% yield) as a yellow solid. MS: m/z=773.4 $[M+H]^+$.

Step 6: 5-Ethynyl-6-fluoro-4-(8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine To a solution of 6-fluoro-4-(8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-amine (85 mg, 110 μmol) in DMSO (1 mL) was added CsF (50 mg, 330 μmol). The reaction mixture was purified by reversed-phase column: (column C18; mobile phase: [Water ($NH_4HCO_3$)-ACN)]; B %: 0%~58%, 40 min) to give 5-ethynyl-6-fluoro-4-(8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a (5H)-yl)methoxy-$d_2$) pyrido[4,3-d]pyrimidin-7-yl)naphthalen-2-amine (Example 174, 33.8 mg, 50% yield) as a yellow solid. MS: m/z=617.2 $[M+H]^+$. $^1H$ NMR (400 MHZ, Dimethylsulfoxide-$d_6$) δ 9.33-9.14 (m, 1H), 7.85-7.70 (m, 1H), 7.30-7.25 (m, 1H), 7.05 (s, 2H), 5.77-5.58 (m, 4H), 5.38-5.17 (m, 1H), 5.01-4.88 (m, 1H), 4.81-4.51 (m, 1H), 4.34-4.22 (m, 1H), 4.13-3.74 (m, 2H), 3.12-2.98 (m, 3H), 2.86-2.79 (m, 1H), 2.69-2.57 (m, 1H), 2.33-2.07 (m, 3H), 2.06-1.98 (m, 2H), 1.88-1.73 (m, 3H). $^{19}F$ NMR (376 MHz, Dimethylsulfoxide-$d_6$) δ −113.36, −139.93, −140.50, −172.05, −172.16, −205.74, −205.90.

Example 188: 6-Fluoro-4-(8-fluoro-4-((15,75,8S)-8-fluoro-5-oxa-2-azabicyclo[5.1.0]octan-2-yl)-2-(((S, Z)-2-(fluoromethylene) tetrahydro-1H-pyrrolizin-7a (5H)-yl)methoxy)pyrido[4,3-d]pyrimidin-7-yl)-5-(fluoromethoxy-$d_2$)naphthalen-2-amine

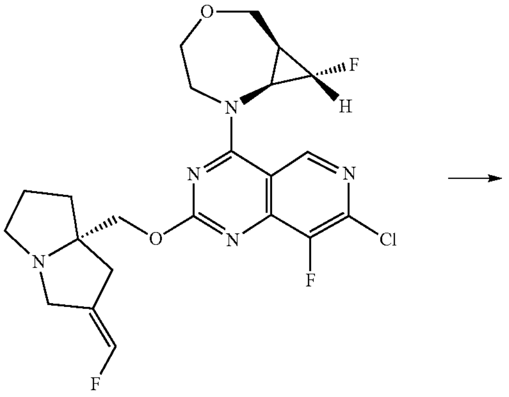

Intermediate 138

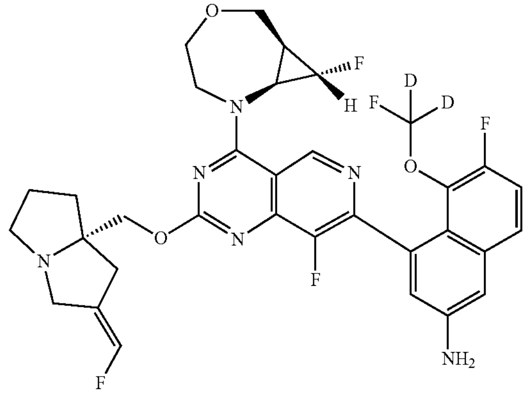

Example 188

Example 188 was prepared in a manner similar to Example 100. MS: m/z=657.35 $[M+H]^+$. $^1H$ NMR (400 MHz, DMSO-$d_6$) δ 9.45-9.36 (m, 1H), 7.58-7.55 (m, 1H), 7.40-7.34 (m, 1H), 7.07-7.02 (m, 2H), 7.90-7.51 (m, 1H), 5.67-5.65 (m, 2H), 4.96-4.81 (m, 1H), 4.52-4.48 (m, 1H), 4.39-4.32 (m, 2H), 4.10-3.95 (m, 3H), 3.73-3.59 (m, 3H), 3.30-3.10 (m, 2H), 3.01 (s, 1H), 2.65-2.52 (m, 2H), 2.40-2.30 (m, 2H), 1.96-1.72 (m, 4H). $^{19}F$ NMR (376 MHZ, DMSO-46) 8-130.92 (s, 1F), −136.83--137.30 (m, 1F), −140.08--140,22 (d, 1F), −150,62-151.02 (d, 1F), −208.11--208.19 (m, 1F).

Example 199 & 201: 6-Fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)-5-vinylnaphthalen-2-amine & 5-ethyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine

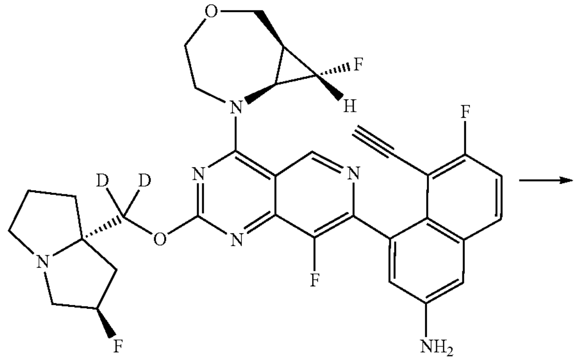

Example 87

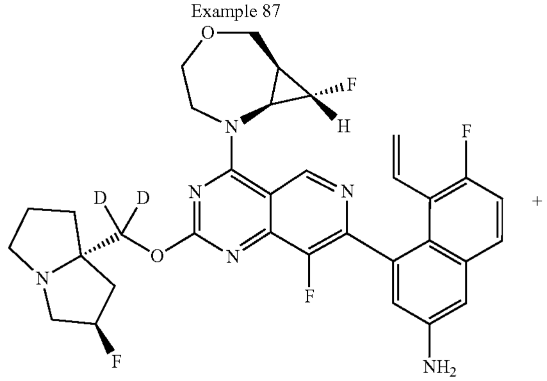

+

Example 199

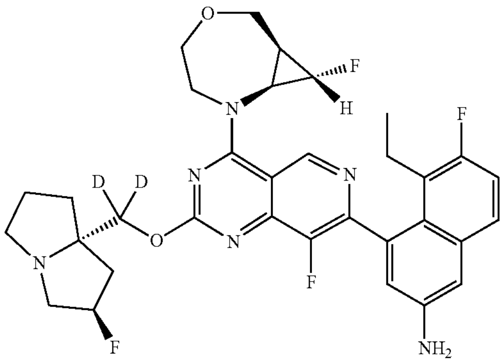

Example 201

To a mixture of Example 87 (200 mg, 0.32 mmol) in MeOH (2 mL) under $N_2$ was added Pd/C (171.47 mg, 10 wt %) at room temperature. The reaction mixture was hydrogenated at room temperature for 30 min under $H_2$ using a hydrogen balloon. The resulting mixture was filtered through a Celite pad and concentrated under reduced pressure. The residue was purified by Prep-HPLC with following conditions: Column: YMC-Actus Triart C18 ExRS30×150 mm, 5 um; Mobile Phase A: 5 mM aq. $NH_4HCO_{3+0.05}$%

$NH_3$ $H_2O$); Mobile Phase B: MeCN; Flow rate: 60 mL/min; Gradient: 40% B to 65% B in 10 min; Detector: 254 nm/220 nm; RT1 (min): 7.6 min; RT2 (min): 7.9 min. The first eluting peak (RT1: 7.6 min) was combined, concentrated and lyophilized to give the title compound (Example 199, 26.9 mg, 17% yield) as a light-yellow lyophilized powder. MS: m/z=623.40 $[M+H]^+$. $^1H$ NMR (400 MHZ, DMSO-$d_6$) δ 9.43-9.37 (m, 1H), 7.67-7.63 (m, 1H), 7.29-7.24 (m, 1H), 7.05-7.02 (m, 2H), 6.01-5.85 (m, 1H), 5.56-5.53 (m, 2H), 5.34-5.21 (m, 1H), 5.02-4.72 (m, 3H), 4.51-4.33 (m, 3H), 4.06-3.93 (m, 1H), 3.70-3.59 (m, 2H), 3.30-3.20 (m, 1H), 3.14-3.00 (m, 3H), 2.86-2.81 (m, 1H), 2.43-2.30 (m, 1H), 2.13-1.76 (m, 6H). $^{19}F$ NMR (376 MHz, DMSO-$d_6$) &-120.39--120.53 (d, 1F), -139.82--141.01 (m, 1F), -172.06--172.15 (m, 1F), -207.80--208.04 (m, 1F). The second eluting peak (RT2: 7.9 min) was combined, concentrated and lyophilized to give the other title compound (Example 201, 35.2 mg, 22% yield) as a light-yellow lyophilized powder. MS: m/z=625.40 $[M+H]^+$. JH NMR (400 MHZ, DMSO-$d_6$) δ 9.46-9.41 (m, 1H), 7.58-7.55 (m, 1H), 7.25-7.23 (m, 1H), 7.02-7.01 (m, 1H), 6,92-6.90 (m, 1H), 5.49-5.46 (m, 2H), 5.35-5.21 (m, 1H), 5.00-4.68 (m, 1H), 4.53-4.49 (m, 1H), 4.37-4.34 (m, 2H), 4.03-3.95 (m, 1H), 3.76-3.54 (m, 2H), 3.30-3.00 (m, 4H), 2.86-2.80 (m, 1H), 2.40-1.69 (m, 9H), 0.83-0.63 (m, 3H). $^{19}F$ NMR (376 MHz, DMSO-$d_6$) δ -122.11--122.16 (d, 1F), -139.20--139.84 (d, 1F), -172.11--172.16 (d, 1F), -207.69 (s, 1F).

Example 202: 5-Ethynyl-6-fluoro-4-(8-fluoro-4-((18,7S,8S)-8-fluoro-5-oxa-2-azabicyclo[5.1.0]octan-2-yl)-2-(((6'R,7a'R)-6'-fluorotetrahydrospiro[cyclopropane-1,1'-pyrrolizin]-7a'(5'H)-yl-3',3',6'-$d_3$)methoxy-$d_2$)pyrido[4,3-d]pyrimidin-7-yl)naphthalen-2-amine

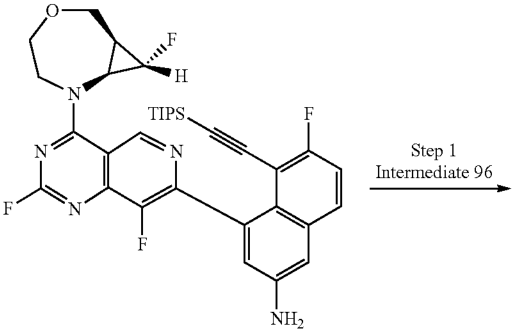

Intermediate 118

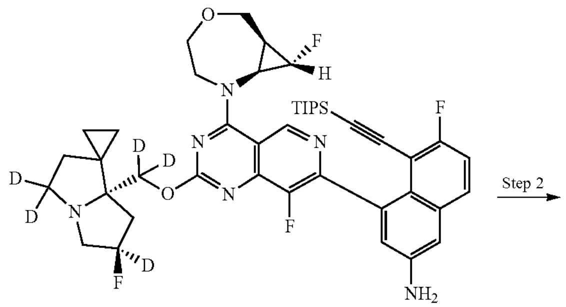

-continued

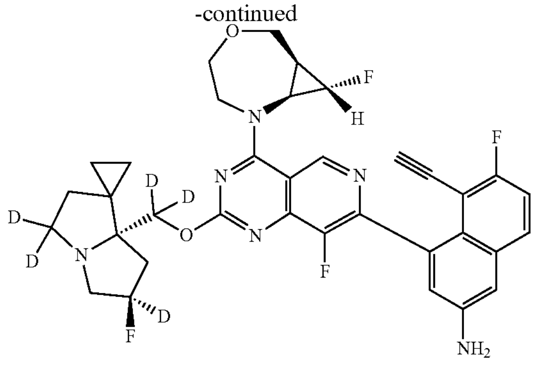

Example 202

Step 1: 6-Fluoro-4-(8-fluoro-4-((15,7S,8S)-8-fluoro-5-oxa-2-azabicyclo[5.1.0]octan-2-yl)-2-(((6'R,7a'R)-6'-fluorotetrahydrospiro[cyclopropane-1,1'-pyrrolizin]-7a'(5'H)-yl-3',3',6'-$d_3$)methoxy-$d_2$)pyrido[4,3-d]pyrimidin-7-yl)-5-((triisopropylsilyl) ethynyl) naphthalen-2-amine To a mixture of Intermediate 96 (100 mg, 525 μmol) in THF (1.5 mL) was added t-BuOK (716 AL, 1M in THF) 25° C. under $N_2$, and the mixture was stirred at 25° C. for 30 min under $N_2$. A solution of Intermediate 118 (304 mg, 478 μmol) in THF (1 mL) was added to the mixture at 0° C. under $N_2$. The mixture was stirred at 0° C. for 30 min under $N_2$. The reaction mixture was quenched with $NH_4Cl$ (20 mL) at 25° C., diluted with $H_2O$ (20 mL), and extracted with EtOAc (20 mL×3). The combined organic layers were washed with brine (20 mL×2), dried over anhydrous $Na_2SO_4$, filtered, and concentrated under reduced pressure. The residue was purified by silica gel flash chromatography (eluent: 4~8% MeOH in $CH_2Cl_2$) to give the title compound (350 mg, 54% yield) as a yellow solid. MS: m/z=806.5 $[M+H]^{+}$.

Step 2: 5-Ethynyl-6-fluoro-4-(8-fluoro-4-((1S,7S,8S)-8-fluoro-5-oxa-2-azabicyclo[5.1.0]octan-2-yl)-2-(((6'R,7a'R)-6'-fluorotetrahydrospiro[cyclopropane-1,1'-pyrrolizin]-7a'(5' #)-yl-3',3',6'-$d_3$)methoxy-$d_2$)pyrido[4,3-d]pyrimidin-7-yl)naphthalen-2-amine To a solution of 6-fluoro-4-(8-fluoro-4-((1S,7S,8S)-8-fluoro-5-oxa-2-azabicyclo[5.1.0]octan-2-yl)-2-(((6'R,7a'R)-6'-fluorotetrahydrospiro[cyclopropane-1, l'-pyrrolizin]-7a'(5'H)-yl-3',3',6'-$d_3$)methoxy-$d_2$)pyrido[4,3-d]pyrimidin-7-yl)-5-((triisopropylsilyl) ethynyl)naphthalen-2-amine (300 mg, 220 μmol) in DMSO (2 mL) was added CsF (117 mg, 769 μmol). The mixture was stirred at 20° C. for 30 min. The reaction mixture was diluted with water (50 mL) and extracted with EtOAc (20 mL×3). The combined organic layers were washed with brine (50 mL×2), dried over anhydrous $Na_2SO_4$, filtered and concentrated under reduced pressure. The crude product was purified by reversed-phase column (column: C18, mobile phase: [water ($NH_3$ $H_2O$) -ACN]; B %: 5%~38%, 35 min) to give the title compound (Example 202, 58.4 mg, 41% yield) as a yellow solid. MS: m/z=650.1 $[M+H]^{+}$. $^{1}H$ NMR (400 MHZ, Dimethylsulfoxide-$d_6$) δ 9.46-9.29 (m, 1H), 7.83-7.70 (m, 1H), 7.34 (t, J=9.2 Hz, 1H), 7.11-6.99 (m, 2H), 5.73-5.56 (m, 2H), 4.96-4.68 (m, 1H), 4.51-4.43 (m, 1H), 4.42-4.26 (m, 2H), 4.08-3.67 (m, 4H), 3.20-3.08 (m, 2H), 3.06-3.03 (m, 1H), 2.39-2.30 (m, 1H), 1.98-1.75 (m, 3H), 1.63-1.56 (m, 1H), 0.77-0.64 (m, 2H), 0.53-0.41 (m, 2H). $^{19}F$ NMR (376 MHz, Dimethylsulfoxide-$d_6$) δ −113.33,-113.40, 139.85, −140.38, −173.86, −173.99, −207.92.

Example 203: 5-Ethynyl-6-fluoro-4-(8-fluoro-4-((1S,7S,8S)-8-fluoro-5-oxa-2-azabicyclo[5.1.0]octan-2-yl)-2-(((6'S,7a'R)-6'-fluorotetrahydrospiro[cyclopropane-1,1'-pyrrolizin]-7a'(5'H)-yl-3',3',6'-$d_3$)methoxy-$d_2$)pyrido[4,3-d]pyrimidin-7-yl) naphthalen-2-amine

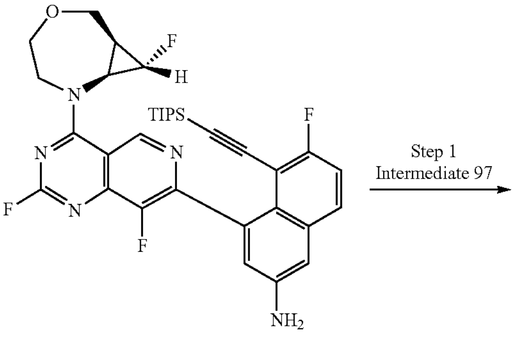

Intermediate 118

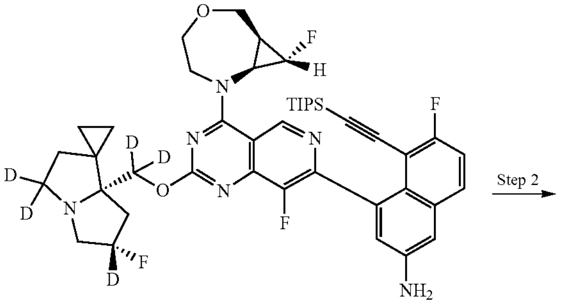

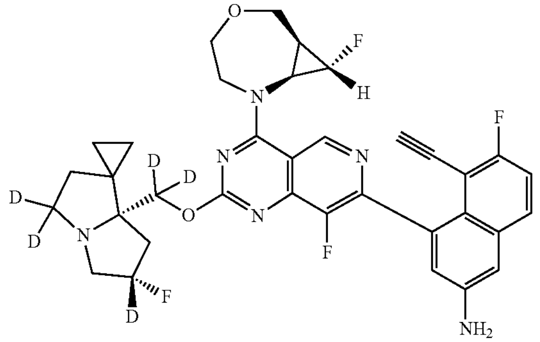

Example 203

Example 203 was prepared in a manner similar to Example 202. MS: m/z=650.1 $[M+H]^{+}$. $^{1}H$ NMR (400 MHZ, Dimethylsulfoxide-$d_6$) δ 9.45-9.29 (m, 1H), 7.77 (m, 1H), 7.42-7.26 (m, 1H), 7.16-6.95 (m, 2H), 5.75-5.53 (m, 2H), 4.98-4.70 (m, 1H), 4.53-4.29 (m, 3H), 4.08-3.79 (m, 2H), 3.79-3.52 (m, 2H), 3.23-3.19 (m, 2H), 3.00-2.87 (m, 1H), 2.37-2.27 (m, 1H), 2.16-1.86 (m, 2H), 1.78 (s, 2H), 0.83-0.59 (m, 2H), 0.47 (s, 2H). $^{19}F$ NMR (376 MHZ, Dimethylsulfoxide-$d_6$) δ −113.36, −113.45, −139.98, −140.46, −172.75, −172.93, −207.73.

Example 206: 4-(2-(((R)-Dihydro-5'W-dispiro[cyclopropane-1,1'-pyrrolizine-6',1"-cyclopropan]-7a'(7'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine

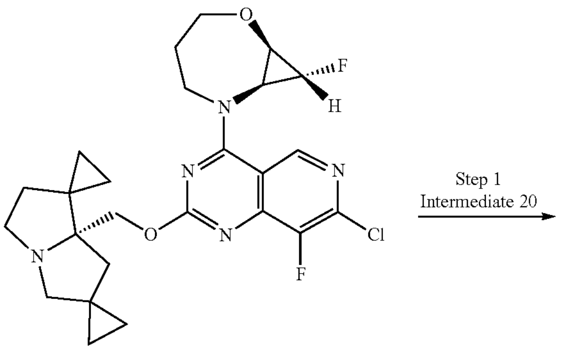

Intermediate 103

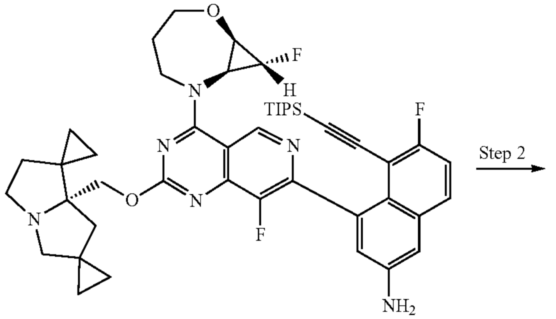

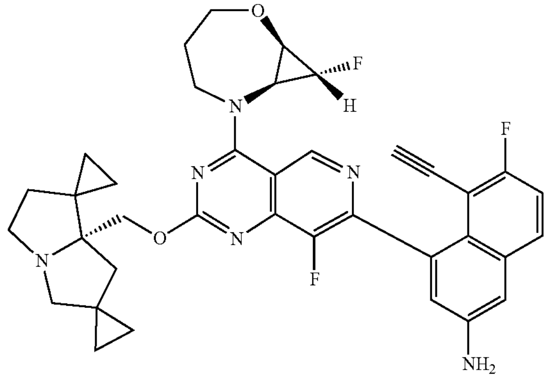

Example 206

Step 1: 4-(2-(((R)-dihydro-5'H-dispiro[cyclopropane-1, 1'-pyrrolizine-6',1"-cyclopropan]-7a (7'H)-yl)methoxy)-8-fluoro-4-((1S,75,8S)-8-fluoro-5-oxa-2-azabicyclo[5.1.0]octan-2-yl)pyrido[4,3-d]pyrimidin-7-yl)-6-fluoro-5-((triisopropylsilyl)ethynyl)naphthalen-2-amine To a solution of Intermediate 103 (50 mg, 0.10 mmol) and Intermediate 20 (150.00 mg, 0.29 mmol, HCl salt) in 1,4-dioxane (2.0 mL) and $H_2O$ (0.4 mL) under nitrogen atmosphere were added $K_3PO_4$ (127.41 mg, 0.60 mmol) and CataCXium A Pd G3 (15.17 mg, 0.02 mmol) at room temperature. The reaction mixture was heated at 100° C. for 2 hours. The resulting mixture was cooled to room temperature, diluted with $H_2O$ (5 mL), and extracted with ethyl acetate (3×10 mL). The combined organic layers were washed with brine (15 mL), dried over anhydrous sodium sulfate, filtered and concentrated under reduced pressure. The residue was purified by Prep-TLC ($CH_2Cl_2$: MeOH=6:1) to afford the title compound (63 mg, 78% yield) as a brown solid. MS: m/z=809.60 $[M+H]^{+.}$ Step 2: 4-(2-(((R)-dihydro-5'H-dispiro[cyclopropane-1,1'-pyrrolizine-6',1"-cyclopropan]-7a'(7'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine To a solution of 4-(2-(((R)-dihydro-5'H-dispiro[cyclopropane-1,1'-pyrrolizine-6',1"-cyclopropan]-7a'(7H)-yl)methoxy)-8-fluoro-4-((15,75,8S)-8-fluoro-5-oxa-2-azabicyclo[5.1.0]octan-2-yl)pyrido[4,3-d]pyrimidin-7-yl)-6-fluoro-5-((triisopropylsilyl) ethynyl)naphthalen-2-amine (63 mg, 0.08 mmol) in DMSO (0.6 mL) was added CsF (213 mg, 1.40 mmol) at room temperature. The reaction mixture was stirred at room temperature for 2 hours. The resulting mixture was filtered and purified by RP-Flash with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 56% B in 15 min, 56% B to 56% B in 7 min, 56% B to 95% B in 4 min; Detector: UV 254 & 210 nm. The product-containing fractions were collected, concentrated and lyophilized overnight to give the title compound (Example 206, 14.6 mg, 28% yield) as a yellow lyophilized powder. MS: m/z=653.30 $[M+H]^+$. $^1H$ NMR (400 MHZ, DMSO-$d_6$) δ 9.42-9.33 (m, 1H), 7.80-7.76 (m, 1H), 7.37-7.32 (m, 1H), 7.06-7.05 (m, 2H), 5.66-5.65 (m, 2H), 4.97-4.75 (m, 1H), 4.50-4.12 (m, 5H), 4.08-3.80 (m, 2H), 3.72-3.61 (m, 2H), 3.33-3.20 (m, 1H), 3.03-3.01 (m, 1H), 2.80-2.67 (m, 3H), 2.40-2.30 (m, 1H), 1.90-1.52 (m, 4H), 0.81-0.39 (m, 8H). $^{19}F$ NMR (376 MHz, DMSO-$d_6$) δ −113.37--113.45 (d, 1F), −139.97--140.43 (d, 1F), −207.72 (s, 1F).

Example 210 & 211: 4-(2-(((1R,7a'S)-2,2-Difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine & 4-(2-(((1S,7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine

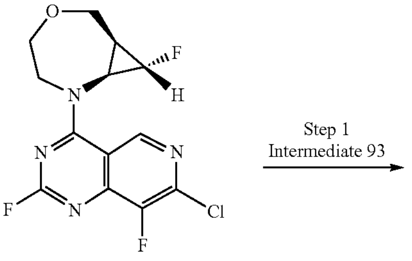

Intermediate 112

-continued

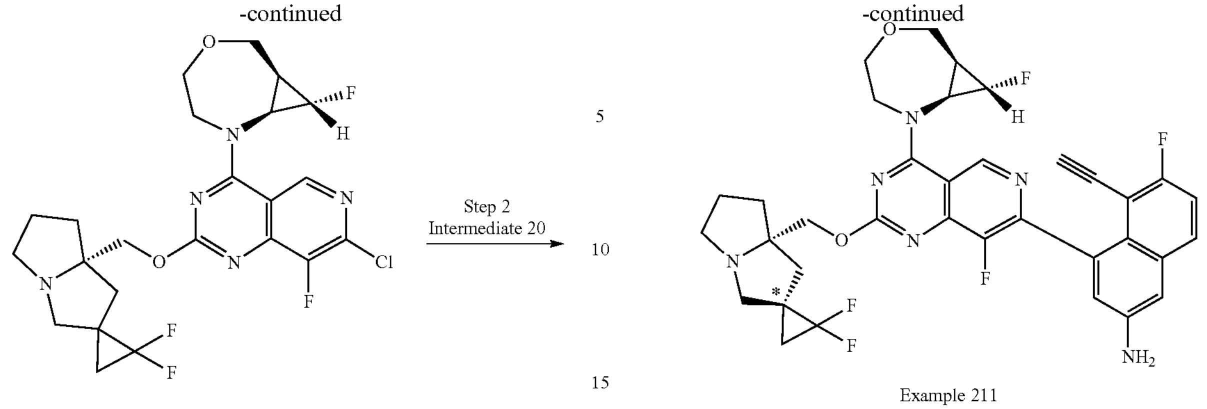

Example 211 structure arbitrarily assigned

-continued

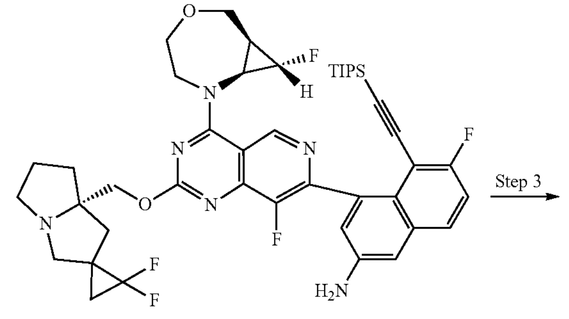

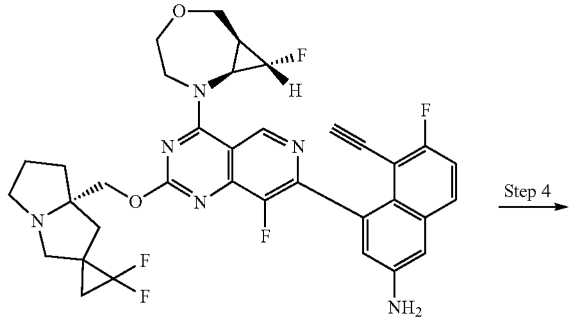

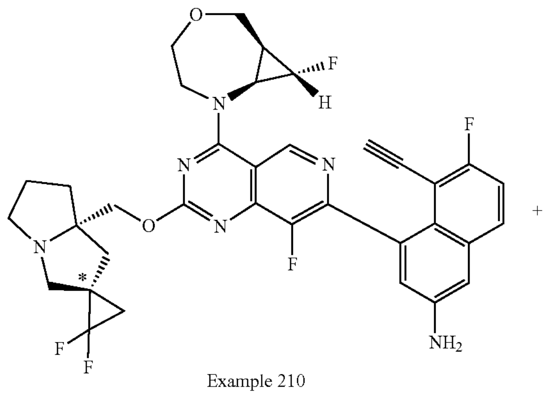

Example 210

Step 1: (1S,7S,8S)-2-(7-Chloro-2-(((7a'S)-2,2-difluorodihydro-1'H,3'H-spiro[cyclopropane-1,2'-pyrrolizin]-7a'(5'H)-yl)methoxy)-8-fluoropyrido[4,3-d]pyrimidin-4-yl)-8-fluoro-5-oxa-2-azabicyclo[5.1.0]octane To an ice-cooled solution of Intermediate 93 (414.82 mg, crude) in THF (5 mL) under nitrogen atmosphere was added NaH (65.31 mg, 2.72 mmol, 60% dispersion in mineral oil). After stirring in an ice bath for 30 min, a solution of Intermediate 112 (450 mg, 1.36 mmol) in THF (5 mL) was added to the above mixture. The ice bath was removed, and the reaction mixture was stirred at room temperature for 1 hour. The resulting mixture was quenched with saturated aq. $NH_4Cl$ (30 mL) in an ice bath and extracted with EtOAc (3×50 mL). The combined organic layers were dried over anhydrous $Na_2SO_4$, filtered and concentrated under reduced pressure. The residue was purified by Prep-TLC (MeOH/DCM=1: 15) to afford the title compound (310 mg, 44% yield) as a yellow solid. MS: m/z=514.10 $[M+H]^{+\cdot}$

Step 2: 4-(2-(((7a'S)-2,2-Difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-((triisopropylsilyl) ethynyl) naphthalen-2-amine To a solution of (1S,7S,8S)-2-(7-chloro-2-(((7a'S)-2,2-difluorodihydro-1'H,3'H-spiro[cyclopropane-1,2'-pyrrolizin]-7a'(5'H)-yl)methoxy)-8-fluoropyrido[4,3-d]pyrimidin-4-yl)-8-fluoro-5-oxa-2-azabicyclo[5.1.0]octane (130 mg, 0.25 mmol) and Intermediate 20 (254.97 mg, 0.50 mmol, HCl salt) in THF (2.5 mL) and $H_2O$ (0.5 mL) under nitrogen atmosphere were added $K_3PO_4$ (322.16 mg, 1.51 mmol) and CataCXium A Pd G3 (36.84 mg, 0.05 mmol) at room temperature. The reaction mixture was heated at 100° C. for 2 hours. The resulting mixture was cooled to room temperature, diluted with $H_2O$ (5 mL) and extracted with ethyl acetate (3×10 mL). The combined organic layers were washed with brine (15 mL), dried over anhydrous sodium sulfate, filtered and concentrated under reduced pressure. The residue was purified by Prep-TLC ($CH_2Cl$/MeOH=15: 1) to afford the title compound (160 mg, 77% yield) as a brown solid. MS: m/z=819.45 $[M+H]^{+\cdot}$ Step 3: 4-(2-(((7a'S)-2,2-difluorodihydro-1'H,3'H-spiro[cyclopropane-1,2'-pyrrolizin]-7a'(5'H)-yl) methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine To a stirred solution of 4-(2-(((7a'S)-2,2-difluorodihydro-1'H,3'H-spiro[cyclopropane-1,2'-pyrrolizin]-7a'(5'H)-yl) methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-((triisopropylsilyl) ethynyl)naphthalen-2-amine (160 mg, 0.19 mmol) in DMF (2.0 mL) was added CsF (593.51 mg, 3.90 mmol) at room temperature. The reaction mixture was stirred at room temperature for 3 hours. The resulting mixture was filtered and purified by RP-Flash with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 54% B in 15 min, 54% B to 54% B in 3 min, 54% B to 95% B in 4 min; Detector: UV 254 & 210 nm. The collected fractions were combined, concentrated, and lyophilized overnight to give the title compound (80 mg, 61% yield) as a yellow lyophilized powder. MS: m/z=663.25 $[M+H]^{+.}$ Step 4: 4-(2-(((1R, 7a'S)-2,2-Difluorodihydro-1'H, 3'H-spiro[cyclopropane-1,2'-pyrrolizin]-7a'(5'H)-yl) methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine & 4-(2-(((18,7a'S)-2,2-difluorodihydro-1'H,3'H-spiro [cyclopropane-1,2'-pyrrolizin]-7a'(5'H)-yl)methoxy)-8-fluoro-4-((1S,7S,8S)-8-fluoro-5-oxa-2-azabicyclo [5.1.0]octan-2-yl)pyrido[4,3-d]pyrimidin-7-yl)-5-ethynyl-6-fluoronaphthalen-2-amine 4-(2-(((7a'S)-2,2-Difluorodihydro-1'H,3'H-spiro[cyclopropane-1,2'-pyrrolizin]-7a (S'H)-yl)methoxy)-8-fluoro-4-((1S,7S,8S)-8-fluoro-5-oxa-2-azabicyclo[5.1.0]octan-2-yl) pyrido[4,3-d]pyrimidin-7-yl)-5-ethynyl-6-fluoronaphthalen-2-amine (80 mg, 0.12 mmol) was separated by Prep-HPLC with the following conditions: Column: X-select CSH Prep, 19×250 mm, 5 um; Mobile Phase A: 10 mM aq. $NH_4HCO_3$; Mobile Phase B: MeCN; Flow rate: 25 mL/min; Gradient: 35% B to 65% B in 10 min; Detector: UV 254 nm & 220 nm; RT1: 7.80 min; RT2: 8.14 min. The first eluting peak (RT1: 7.80 min) was combined, concentrated, and lyophilized overnight to give the title compound (Example 210, 7.6 mg, 9% yield) as a yellow lyophilized powder. MS: m/z=663.20 $[M+H]^+$. $^1H$ NMR (400 MHZ, DMSO-$d_6$) δ 9.43-9.37 (m, 1H), 7.80-7.76 (m, 1H), 7.37-7.32 (m, 1H), 7.06-7.05 (m, 2H), 5.66-5.65 (m, 2H), 4.94-4.74 (m, 1H), 4.51-4.48 (m, 1H), 4.37-4.34 (m, 2H), 4.10-3.81 (m, 4H), 3.75-3.58 (m, 2H), 3.30-3.20 (m, 1H), 3.05-2.96 (m, 2H), 2.79-2.67 (m, 2H), 2.40-2.30 (m, 1H), 2.11-2.08 (m, 1H), 1.93-1.76 (m, 5H), 1.56-1.52 (m, 2H). $^{19}F$ NMR (376 MHz, DMSO-$d_6$) δ −113.34-−113.46 (d, 1F), −135.21-−135.67 (m, 1F), −137.46-−137.90 (m, 1F), −139.94-−140.49 (d, 1F), −207.64 (s, 1F). The second eluting peak (RT2: 8.14 min) was combined, concentrated, and lyophilized overnight to give the title compound (Example 211, 34.4 mg, 43% yield) as a yellow lyophilized powder. MS: m/z=663.25 $[M+H]^+$. $^1H$ NMR (400 MHZ, DMSO-$d_6$) $9.43-9.37 (m, 1H), 7.80-7.76 (m, 1H), 7.37-7.32 (m, 1H), 7.06-7.05 (m, 2H), 5.66-5.65 (m, 2H), 4.96-4.74 (m, 1H), 4.52-4.48 (m, 1H), 4.38-4.34 (m, 2H), 4.18-3.81 (m, 4H), 3.72-3.60 (m, 2H), 3.30-3.20 (m, 1H), 3.12-3.01 (m, 2H), 2.75-2.69 (m, 1H), 2.53-2.49 (m, 1H), 2.40~2.30 (m, 1H), 2.11-1.46 (m, 8H). $^{19}F$ NMR (376 MHz, DMSO-$d_6$) δ −113.35-−113.44 (d, 1F), ~132.15-−132.57 (m, 1F), −134.64-−135.07 (m, 1F), −139.87-−140.43 (d, 1F), −207.70 (s, 1F).

Example 212: 5-Ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy)pyrido[4,3-d]pyrimidin-7-yl)naphthalen-2-amine

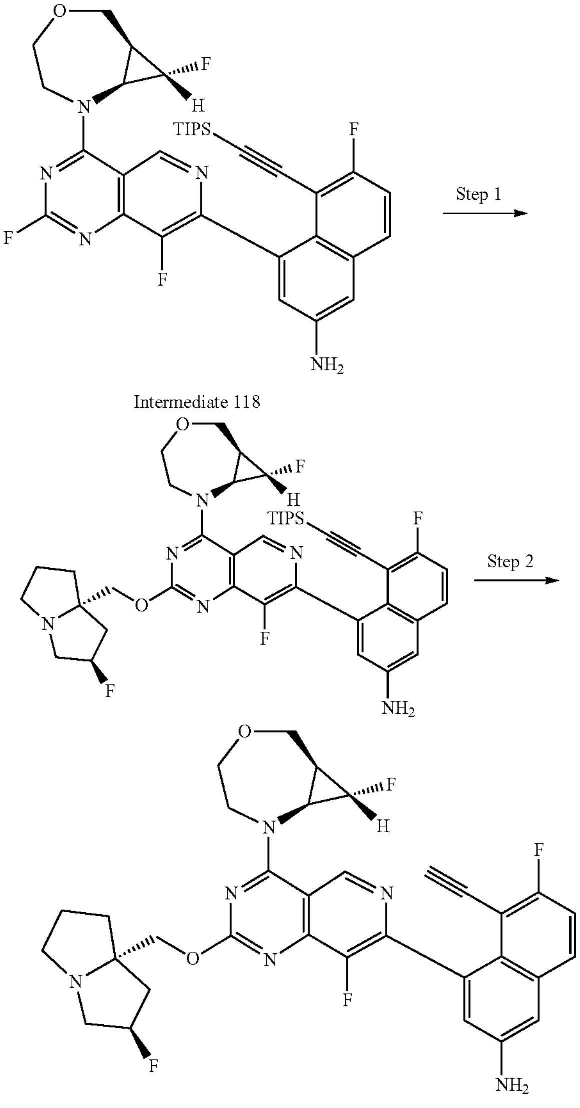

Examle 212

Step 1: 6-Fluoro-4-(8-fluoro-4-((15,7S,8S)-8-fluoro-5-oxa-2-azabicyclo[5.1.0]octan-2-yl)-2-(((2R,7aS)-2-fluorotetrahydro-1/H-pyrrolizin-7a (5H)-yl) methoxy)pyrido[4,3-d]pyrimidin-7-yl)-5-((triisopropylsilyl) ethynyl)naphthalen-2-amine To an ice-cooled solution of ((2R,7aS)-2-fluorotetrahydro-1H-pyrrolizin-7a (5H)-yl) methanol (15.02 mg, 0.095 mmol) in THF (1 mL) under nitrogen atmosphere was added t-BuOK (10.57 mg, 0.095 mmol). After stirring in an ice bath for 30 min, Intermediate 118 (50 mg, 0.079 mmol) was added to the above mixture. The ice bath was removed, and the reaction mixture was stirred at room temperature for 1 hour. The resulting mixture was quenched with sat. $NH_4Cl$ aq. (10 mL) in an ice bath and extracted with EtOAc (3×10 mL). The combined organic layers were washed with brine (10 mL), dried over anhydrous $Na_2SO_4$, filtered and concentrated under reduced pressure. The residue was purified by Prep-TLC ($CH_2Cl_2$/MeOH 10: 1) to the title compound (46 mg, 75% yield) as a light yellow solid. MS: m/z=775.35 $[M+H]^{+\cdot}$ Step 2: 5-Ethynyl-6-fluoro-4-(8-fluoro-4-((1S,7S, 8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy)pyrido[4,3-d]pyrimidin-7-yl)naphthalen-2-amine To a stirred solution of 6-fluoro-4-(8-fluoro-4-((15,7S, 8S)-8-fluoro-5-oxa-2-azabicyclo[5.1.0]octan-2-yl)-2-(((2R, 7aS)-2-fluorotetrahydro-1H-pyrrolizin-7a (5H)-yl)methoxy) pyrido[4,3-d]pyrimidin-7-yl)-5-((triisopropylsilyl) ethynyl) naphthalen-2-amine (160 mg, 0.20 mmol) in DMF (1.0 mL) was added CsF (470.42 mg, 3.09 mmol) at room temperature. The reaction mixture was stirred at room temperature for 3 hours. The resulting mixture was filtered and purified by RP-Flash directly with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 47% B in 15 min, 47% B to 47% B in 3 min, 47% B to 95% B in 4 min; Detector: UV 254 & 210 nm. The collected fractions were combined, concentrated and lyophilized overnight to give the title compound (Example 212, 77.5 mg, 60% yield) as a light-yellow lyophilized powder. MS: m/z=619.20 $[M+H]^+$. $^1H$ NMR (400 MHZ, DMSO-$d_6$) δ 9.40-9.37 (m, 1H), 7.80-7.76 (m, 1H), 7.36-7.32 (m, 1H), 7.06-7.05 (m, 2H), 5.66-5.65 (m, 2H), 5.35-5.21 (m, 1H), 4.96-4.73 (m, 1H), 4.51-4.30 (m, 3H), 4.13-3.81 (m, 4H), 3.75-3.55 (m, 2H), 3.30-3.20 (m, 1H), 3.13-3.00 (m, 3H), 2.86-2.82 (m, 1H), 2.45-2.25 (m, 1H), 2.12-1.92 (m, 3H), 1.89-1.73 (m, 3H). $^{19}F$ NMR (376 MHz, DMSO-$d_6$) δ −113.35−−113.43 (d, 1F), −139.87−−140.46 (d, 1F), −172.06−−172.17 (d, 1F), −207.76 (s, 1F).

Example 217: 5-Ethynyl-6-fluoro-4-(8-fluoro-4-((15,75,8S)-8-fluoro-5-oxa-2-azabicyclo[5.1.0]octan-2-yl)-2-(((2R,7aS)-2-fluorotetrahydro-LH-pyrrolizin-7a (5H)-yl)methoxy-$d_2$)pyrido[4,3-d] pyrimidin-7-yl)naphthalen-2-ol

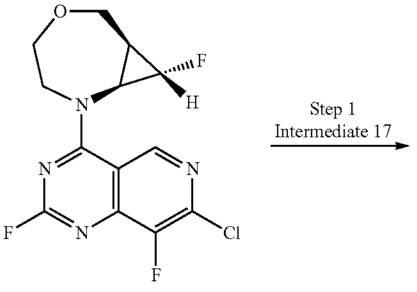

Intermediate 112

-continued

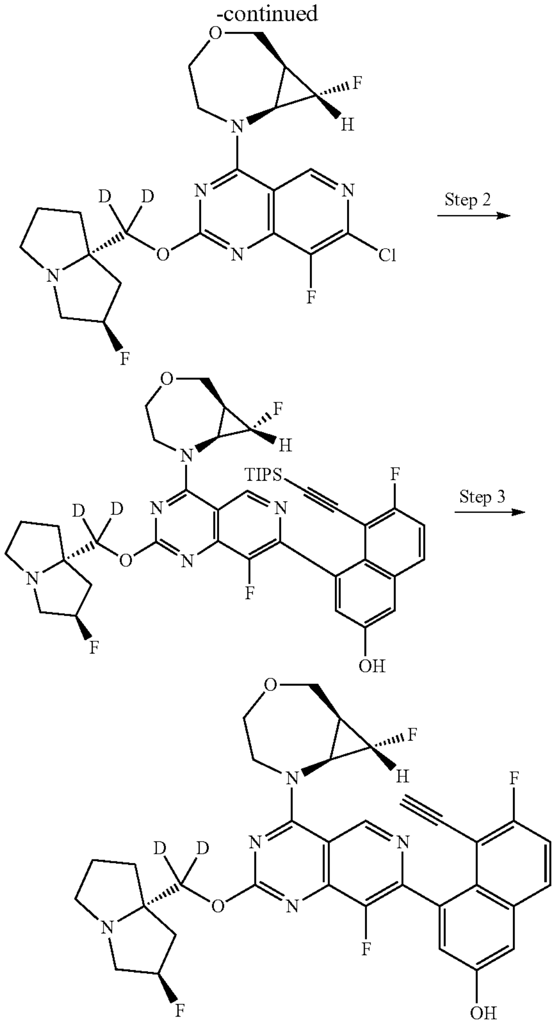

Example 217

Step 1: (1S,7S,8S)-2-(7-Chloro-8-fluoro-2-(((2R, 7aS)-2-fluorotetrahydro-1H-pyrrolizin-7a (5H)-yl) methoxy-$d_2$)pyrido[4,3-d]pyrimidin-4-yl)-8-fluoro-5-oxa-2-azabicyclo[5.1.0]octane To a solution of Intermediate 17 (7.68 g, 47.7 mmol) in THE (195 mL) was added dropwise t-BuOK (1 M in THF, 48 mL, 48 mmol) at 20° C. under $N_2$. The mixture was stirred at this temperature for 0.5 h and then cooled to −40° C. A solution of Intermediate 112 (15 g, 45.3 mmol) in THF (195 mL) was added dropwise into the mixture at −40° C. under $N_2$. The resulting mixture was stirred at −40° C. for 0.5 h. The reaction mixture was quenched with sat $NH_4Cl$ aq (600 mL) at 0° C., and then diluted with $H_2O$ (300 mL) and extracted with EtOAc 300 mL (150 mL×2). The combined organic layers were washed with brine (600 mL), dried over $Na_2SO_4$, filtered and concentrated under reduced pressure. The residue was purified by silica gel flash chromatography (eluent: 0~4% MeOH in $CH_2Cl_2$) to give the title compound (24.6 g, 96% yield) as a yellow solid. MS: m/z=472.0 $[M+H]^+$. $^1H$ NMR (400 MHZ, Dimethylsulfoxide-$d_6$) δ 9.20 (s, 1H), 5.35-5.15 (m, 1H), 4.67-4.57 (m, 1H), 4.46-4.21 (m, 2H), 4.01-3.79 (m, 3H), 3.72-3.56 (m, 1H), 3.37-3.09 (m, 4H), 3.03-2.89 (m, 1H), 2.35-2.05 (m, 4H), 1,99-1.76 (m, 3H). $^{19}F$ NMR (376 MHz, Dimethylsulfoxide-$d_6$) δ −134.29, −173.13.

Step 2: 6-Fluoro-4-(8-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidn-7-yl)-5-(( ) thynyl)naphthalen-2-ol A mixture of (1S,7S,8S)-2-(7-chloro-8-fluoro-2-(((2R, 7aS)-2-fluorotetrahydro-1H-pyrrolizin-7a (5H)-yl)methoxy-$d_2$)pyrido[4,3-d]pyrimidin-4-yl)-8-fluoro-5-oxa-2-azabicyclo[5.1.0]octane (13.0 g, 27.6 mmol), 6-fluoro-4-(4,4,5,5-tetramethyl-1,3,2-dioxaborolan-2-yl)-5-((triisopropylsilyl) ethynyl)naphthalen-2-ol (14.2 g, 30.4 mmol), $K_3PO_4$ (17.5 g, 82.6 mmol) and $Ad_2nBuP-Pd-G_3$ (cataCXiumAPdG$_3$) (2 g, 2.76 mmol) in 1,4-dioxane (100 mL) and $H_2O$ (20 mL) was degassed and purged with $N_2$ three times, and the mixture was stirred at 105° C. under $N_2$ for 1 h. The reaction mixture was diluted with water (100 mL) and extracted with EtOAc (200 mL×3). The combined organic layers were washed with brine (200 mL), dried over anhydrous $Na_2SO_4$, filtered and the filtrate was concentrated under reduced pressure. The residue was purified by silica gel flash chromatography (eluent: 0~4% of MeOH in $CH_2Cl_2$) to give the title compound (20 g, 87% yield) as a yellow solid. MS: m/z=778.3 [M+H]$^+$. $^1H$ NMR (400 MHZ, Dimethylsulfoxide-$d_6$) δ 10.15 (s, 1H), 9.40 (s, 1H), 8.03-7.94 (m, 1H), 7.53-7.43 (m, 1H), 7.42-7.38 (m, 1H), 7.19-7.15 (m, 1H), 5.38-5.19 (m, 1H), 4.99-4.79 (m, 1H), 4.48-4.34 (m, 2H), 4.23-4.14 (m, 1H), 3.74-3.58 (m, 2H), 3.12-3.00 (m, 3H), 2.88-2.79 (m, 1H), 2.40-2.28 (m, 1H), 2.17-1.95 (m, 4H), 1.94-1.64 (m, 4H), 0.82 (dd, J=7.9, 9.1 Hz, 18H), 0.53-0.37 (m, 3H). $^{19}F$ NMR (376 MHz, Dimethylsulfoxide-$d_6$) δ −106.62, −106.83, −138.90, −140.39, −172.14, −172.33, −207.49.

Step 3: 5-Ethynyl-6-fluoro-4-(8-fluoro-4-((15,75, 8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-ol To a solution of 6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-ol (20 g, 25.7 mmol) in DMSO (80 mL) was added CsF (19.5 g, 128.5 mmol). The mixture was stirred at 30° C. for 0.5 h. The reaction mixture was diluted with water (500 mL) and extracted with EtOAc (300 mL×3). The combined organic layers were washed with brine (500 mL×2), dried over anhydrous $Na_2SO_4$, filtered, and the concentrated under reduced pressure. The residue was dissolved with $CH_2Cl$ (20 mL), n-hexane (200 mL) was added to the solution to give a precipitate. The precipitate was filtered, and the filter cake was washed with n-hexane (20 mL), dried under reduced pressure to give the crude product. The crude product was purified by reversed-phase column (column: C18; mobile phase: [water ($NH_3$ $H_2O$)-MeOH]; B %: 0%~64%, 40 min) to give the title compound (Example 217, 9.2 g, 45% yield) as a yellow solid. MS: m/z=622.1 [M+H]$^+$. $^1H$ NMR (400 MHz, Dimethylsulfoxide-$d_6$) δ 10.15 (br s, 1H), 9.46-9.34 (m, 1H), 8.05-7.93 (m, 1H), 7.51-7.37 (m, 2H), 7.23-7.13 (m, 1H), 5.39-5.17 (m, 1H), 4.96-4.72 (m, 1H), 4.49 (d, J=13.5 Hz, 1H), 4.43-4.29 (m, 2H), 4.14-3.87 (m, 2H), 3.77-3.56 (m, 2H), 3.28-3.20 (m, 1H), 3.13-3.04 (m, 2H), 3.03-2.97 (m, 1H), 2.86-2.78 (m, 1H), 2.39-2.30 (m, 1H), 2.13-1.95 (m, 3H), 1.88-1.73 (m, 3H). $^{19}F$ NMR (376 MHz, Dimethylsulfoxide-$d_6$) δ −110.71, −139.92, −140.40, −172.07, −172.17, −207.67, −207.76.

Example 218 & 219: 4-(2-(((6'S,7a'R)-2",2"-Difluorodihydro-5'H-dispiro[cyclopropane-1,l'-pyrrolizine-6',1"-cyclopropan]-7a'(7'H)-yl)methoxy)-8-fluoro-4-((15,75,8S)-8-fluoro-5-oxa-2-azabicyclo [5.1.0]octan-2-yl)pyrido[4,3-d]pyrimidin-7-yl)-5-ethynyl-6-fluoronaphthalen-2-amine & 4-(2-(((6'R, 7a'R)-2",2"-difluorodihydro-5'H-dispiro [cyclopropane-1, l'-pyrrolizine-6',1"-cyclopropan]-7a (7H)-yl)methoxy)-8-fluoro-4-((1S,7S,8S)-8-fluoro-5-oxa-2-azabicyclo[5.1.0]octan-2-yl)pyrido[4, 3-d]pyrimidin-7-yl)-5-ethynyl-6-fluoronaphthalen-2-amine

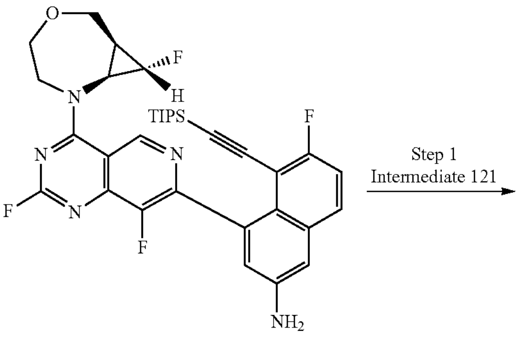

Intermediate 118

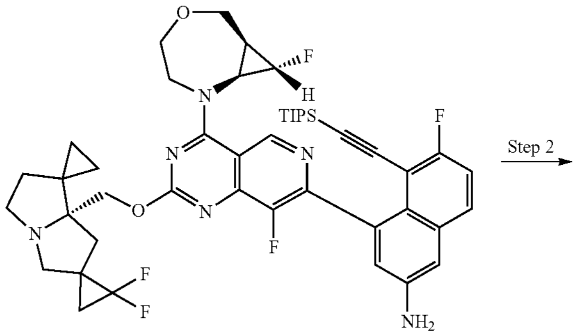

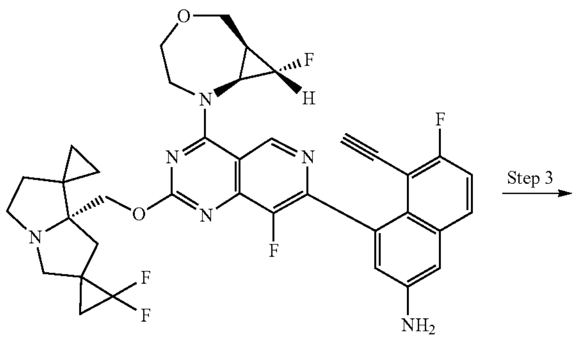

-continued

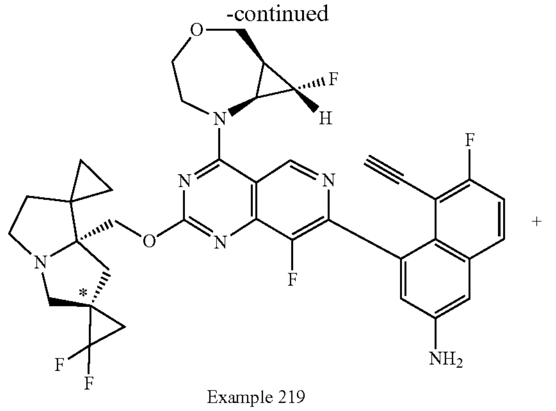

Example 219

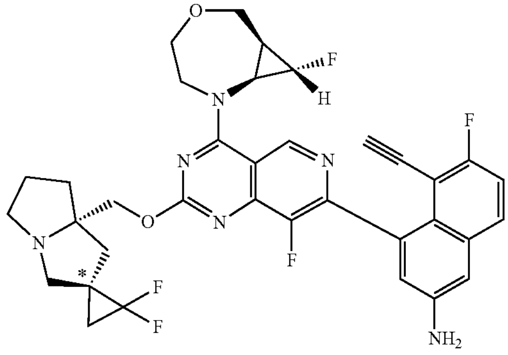

Example 218 structure arbitrarily assigned

Step 1: 4-(2-(((7a'R)-2",2"-Difluorodihydro-5'H-dispiro[cyclopropane-1,1'-pyrrolizine-6',1"-cyclopropan]-7a'(7'H)-yl)methoxy)-8-fluoro-4-((15,75,8S)-8-fluoro-5-oxa-2-azabicyclo[5.1.0]octan-2-yl)pyrido[4,3-d]pyrimidin-7-yl)-6-fluoro-5-((triisopropylsilyl) ethynyl)naphthalen-2-amine To a stirred solution of Intermediate 121 (88 mg, 0.39 mmol) in THF (1 mL) was added sodium hydride (23 mg, 0.58 mmol, 60% dispersion in mineral oil) under argon atmosphere in an ice bath. The resulting mixture was stirred in an ice bath for 30 minutes under argon atmosphere. To the above mixture was added Intermediate 118 (245 mg, 0.39 mmol) in an ice bath. The resulting mixture was stirred in an ice bath for 30 minutes. Then the reaction was warmed to room temperature and stirred for 2 hours. The reaction progress was monitored by TLC and LCMS. After completion of the reaction, the mixture was quenched with sat. aq. $NH_4Cl$ (5 drops) and concentrated under reduced pressure. The residue was purified by silica gel flash chromatography with the following conditions: column, C18 column, 40 g, 20-35 um, 100 A; mobile phase A: 5% aq. $NH_4HCO_3$; mobile phase B: MeCN, 2% to 98% gradient in 25 min; detector, UV 254 & 210 nm. The fractions containing desired product were combined and concentrated under reduced pressure to afford the title compound (250 mg, 77%) as a yellow solid. MS: m/z=845.55 $[M+H]^+$. $^1H$ NMR (400 MHZ, Methanol-$d_4$) δ 9.61-9.43 (m, 1H), 7.81-7.67 (m, 1H), 7.34-7.06 (m, 3H), 4.82-4.54 (m, 2H), 4.51-4.40 (m, 1H), 4.38-4.13 (m, 2H), 4.12-3.70 (m, 4H), 3.30-3.10 (m, 3H), 3.04-2.95 (m, 1H), 2.91-2.74 (m, 1H), 2.48-2.29 (m, 1H), 2.17-1.96 (m, 3H), 1.95-1.72 (m, 1H), 1.52-1.21 (m, 3H), 0.96-0.62 (m, 20H), 0.59-0.49 (m, 4H). $^{19}F$ NMR (376 MHz, $CD_3OD$) δ −111.18-−111.27 (m, 1F), −135.79-140.72 (m, 3F), −209.47 (1F).

Step 2: 4-(2-(((7a'R)-2",2"-Difluorodihydro-5'H-dispiro[cyclopropane-1,1'-pyrrolizine-6',1"-cyclopropan]-7a'(7'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine To a stirred solution of 4-(2-(((7a'R)-2",2"-difluorodihydro-5'H-dispiro[cyclopropane-1,1'-pyrrolizine-6',1"-cyclopropan]-7a'(7'H)-yl)methoxy)-8-fluoro-4-((15,75,8S)-8-fluoro-5-oxa-2-azabicyclo[5.1.0]octan-2-yl)pyrido[4,3-d] pyrimidin-7-yl)-6-fluoro-5-((triisopropylsilyl) ethynyl) naphthalen-2-amine (320 mg, 0.38 mmol) was added CsF (1.15 g, 7.58 mmol) under argon atmosphere at room temperature. The resulting mixture was stirred at room temperature for 3 hours under argon atmosphere. The reaction progress was monitored by TLC and LCMS. After completion of the reaction, the mixture was filtered and the filtrate was purified by silica gel flash chromatography with the following conditions: column, C18 column, 80 g, 20-35 um, 100 A; mobile phase A: 5% aq. $NH_4HCO_3$; mobile phase B: MeCN, 2% to 98% gradient in 25 min; detector, UV 254 & 210 nm. The fractions containing desired product were combined and concentrated under reduced pressure to afford the title compound (220 mg, 84%) as a yellow solid. MS: m/z=689.35 $[M+H]^{+\cdot}$ Step 3: 4-(2-(((6'S,7a'R)-2",2"-Difluorodihydro-S'W-dispiro[cyclopropane-1, l'-pyrrolizine-6',1"-cyclopropan]-7a'(7'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine & 4-(2-(((6'R, 7a'R)-2",2"-difluorodihydro-5'W-dispiro[cyclopropane-1, 1'-pyrrolizine-6',1"-cyclopropan]-7a'(7'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine 4-(2-(((7a'R)-2",2"-Difluorodihydro-5'W-dispiro[cyclopropane-1,1'-pyrrolizine-6',1"-cyclopropan]-7a'(7'H)-yl)methoxy)-8-fluoro-4-((15,7S,8S)-8-fluoro-5-oxa-2-azabicyclo[5.1.0]octan-2-yl)pyrido[4,3-d] pyrimidin-7-yl)-5-ethynyl-6-fluoronaphthalen-2-amine (220 mg, 0.32 mmol) was separated by Prep-SFC with the following conditions: Column: CHIRALPAK IA, 2*25 cm, 5 um; Mobile Phase A: MTBE (0.5% 2M $NH_3$-MeOH)--HPLC, Mobile Phase B: EtOH--HPLC; Flow rate: 20 mL/min; Gradient: isocratic 15; RT1 (min): 7.60; RT2 (min): 10.07. The first eluting peak (RT1: 7.60 min) was concentrated and lyophilized to give the title compound (Example 219, 20 mg, 9%) as a light yellow solid. MS: m/z=689.25 $[M+H]^+$. $^1H$ NMR (400 MHZ, DMSO-$d_6$) δ 9.52-9.31 (m, 1H), 7.93-7.69 (m, 1H), 7.47-7.29 (m, 1H), 7.18-6.98 (m, 2H), 5.81-5.56 (m, 2H), 5.05-4.70 (m, 1H), 4.57-4.44 (m, 1H), 4.44-4.25 (m, 2H), 4.20-4.12 (m, 1H), 4.12-4.04 (m, 1H), 4.06-3.90 (m, 2H), 3,78-3.65 (m, 1H), 3.65-3.52 (m, 1H), 3.31-3.19 (m, 1H), 3.15-3.09 (m, 1H), 3.08-2.98 (m, 1H), 2.91-2.79 (m, 1H), 2.78-2.64 (m, 1H), 2.42-2.25 (m, 1H), 2.03-1.75 (m, 4H), 1.68-1.44 (m, 2H), 0.82-0.71 (m, 1H), 0.71-0.59 (m, 1H), 0.60-0.37 (m, 2H). $^{19}F$ NMR (376 MHZ, DMSO-$d_6$) δ −113.37-−113.45 (d, 1F), −135.35-−135.88 (m, 1F), −137.06-−137.60 (m, 1F), −139.92-−140.37 (d, 1F), −207.75 (1F). The second eluting peak (RT2: 10.07 min) was concentrated and lyophilized to give the title compound (Example 218, 126 mg, 57%) as a light-yellow solid. MS: m/z=689.25 $[M+H]^+$. $^1H$ NMR (400 MHZ, DMSO-$d_6$) δ 9.58-9.17 (m, 1H), 7.90-7.64 (m, 1H), 7.51-7.27 (m, 1H), 7.19-6.95 (m, 2H), 5.87-5.59 (m, 2H), 5.04-4.68 (m, 1H), 4.54-4.45 (m, 1H), 4.43-4.28 (m, 2H), 4.27-4.14 (m, 2H), 4.11-4.07 (m, 1H), 4.06-3.93 (m, 1H), 3.78-3.68 (m, 1H), 3.66-3.55 (m, 1H), 3.29-3.22 (m, 1H), 3.20-3.09 (m, 1H), 3.08-2.96 (m, 1H), 2.88-2.75 (m, 1H), 2.68-2.58 (m, 1H), 2.43-2.26 (m, 1H), 2.02-1.84 (m, 2H), 1.83-1.73 (m, 1H), 1.68-1.56 (m, 1H), 1.55-1.39 (m, 2H), 0.82-0.60 (m, 2H), 0.57-0.40 (m, 2H). $^{19}F$ NMR (376 MHz, DMSO-$d_6$) δ −113.36-−113.45 (d, 1F), −132.50-−132.89 (d, 1F), −134.16-−134.55 (d, 1F), −139.86-−140.34 (d, 1F), −207.81 (1F).

Example 222: 5-Ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-5-methoxypyrido[4,3-d]pyrimidin-7-yl)naphthalen-2-amine

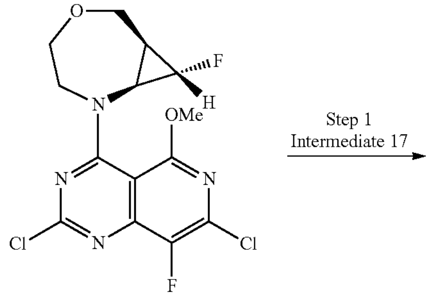

Intermediate 132

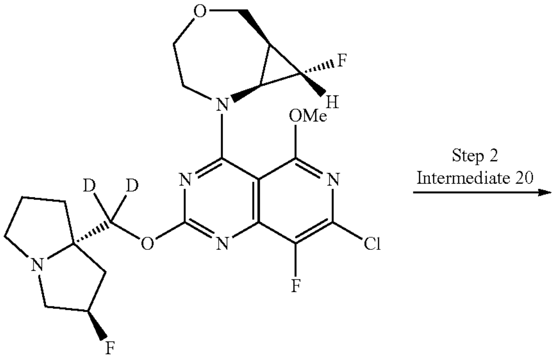

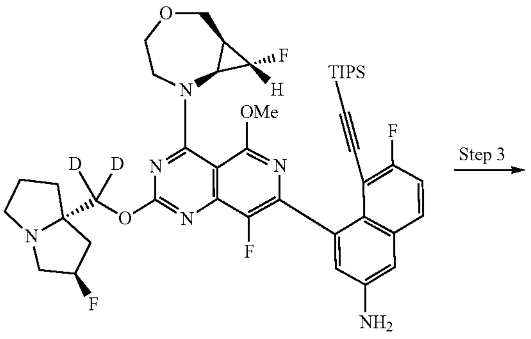

-continued

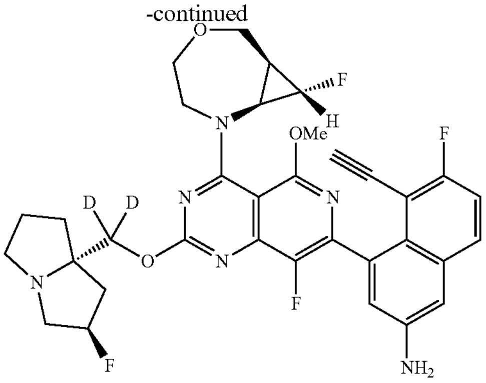

Example 222

Step 1: (1S,7S,8S)-2-(7-chloro-8-fluoro-2-(((2R,7aS)-2-fluorotetrahydro-1H-pyrrolizin-7a (5H)-yl) methoxy-$d_2$)-5-methoxypyrido[4,3-d]pyrimidin-4-yl)-8-fluoro-5-oxa-2-azabicyclo[5.1.0]octane To a solution of Intermediate 132 (2.8 g. 7.42 mmol) in 1,4-dioxane (30 mL) was added DIPEA (2.88 g, 22.3 mmol) and Intermediate 17 (2.39 g, 14.8 mmol). And then, the mixture was stirred at 100° C. for 16 h under $N_2$. The reaction mixture was concentrated under reduced pressure to give a residue. The residue was purified by silica gel chromatography (cluent: 0~3% of MeOH in $CH_2Cl_2$) to give (1S,7S,8S)-2-(7-chloro-8-fluoro-2-(((2R,7aS)-2-fluorotetrahydro-1H-pyrrolizin-7a (5H)-yl)methoxy-(2)-5-methoxy-pyrido[4,3-d]pyrimidin-4-yl)-8-fluoro-5-oxa-2-azabicyclo [5.1.0]octane (1.9 g, 18% yield over 4 steps) as a yellow solid. MS: m/z=502.1 $[M+H]^{+\cdot}$ Step 2: 6-Fluoro-4-(8-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)-5-methoxypyrido[4,3-d]pyrimidin-7-yl)-5-((triisopropylsilyl) ethynyl)naphthalen-2-amine A mixture of (1S,7S,8S)-2-(7-chloro-8-fluoro-2-(((2R,7aS)-2-fluorotetrahydro-1H-pyrrolizin-7a (5H)-yl)methoxy-$d_2$)-5-methoxypyrido[4,3-d]pyrimidin-4-yl)-8-fluoro-5-oxa-2-azabicyclo[5.1.0]octane (860 mg, 1.71 mmol), Intermediate 20 (641 mg, 1.37 mmol), $K_3PO_4$ (1.45 g, 6.85 mmol), and AdanBuP-Pd-Gs (cataCXiumAPdG$_3$) (125 mg, 171 μmol) in 1,4-dioxane (5 mL) and $H_2O$ (1 mL) was degassed and purged with $N_2$ three times, and the mixture was stirred at 110° C. for 1 h under $N_2$ atmosphere. The reaction mixture was concentrated under reduced pressure. The residue was purified by silica gel flash chromatography (eluent: 0~5% of MeOH in $CH_2Cl_2$) to give the title compound (180 mg, 12% yield) as a yellow solid. MS: m/z=807.3 $[M+H]^+$. $^1$HNMR (400 MHZ, Dimethylsulfoxide-$d_6$) δ 7.82-7.73 (m, 1H), 7.42-7.40 (m, 1H), 7.06-6.95 (m, 2H), 5.72-5.51 (m, 2H), 5.38-5.17 (m, 1H), 4.54-4.27 (m, 3H), 3.99-3.83 (m, 5H), 3.79-3.69 (m, 1H), 3.62-3.51 (m, 1H), 3.15-3.00 (m, 3H), 2.88-2.78 (m, 2H), 2.16-2.02 (m, 3H), 1.90-1.70 (m, 4H), 0.87-0.75 (m, 18H), 0.62-0.45 (m, 3H). $^{19}F$ NMR (376 MHz, Dimethylsulfoxide-$d_6$) δ −113.34, −150.49, −172.34, −206.57.

Step 2: 5-Ethynyl-6-fluoro-4-(8-fluoro-4-((15,75, 8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-5-methoxypyrido[4,3~ d]pyrimidin-7-yl)naphthalen-2-amine To a solution of 6-fluoro-4-(8-fluoro-4-((1S,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-5-methoxypyrido[4,3-d]pyrimidin-7-yl)-5-((triisopropylsilyl) ethynyl)naphthalen-2-amine (170 mg, 211 μmol) in DMSO (2 mL) was added CsF (256 mg, 1.69 mmol). The mixture was stirred at 30° C. for 10 min. The reaction mixture was diluted with water (10 mL) and extracted with EtOAc (20 mL×3). The combined organic layers were washed with brine (50 mL×2), dried over anhydrous $Na_2SO_4$, filtered and the filtrate was concentrated under reduced pressure to give a residue. The residue was purified by prep-HPLC (column: CD07-Daisogel SP-100-8-ODS-PK 150×25×10 um; mobile phase [water ($NH_4HCO_3$)-ACN], gradient: 34%-64% B over 11 min) to give the title compound (Example 222, 31.8 mg, 22% yield) as a yellow solid. MS: m/z=651.3 $[M+H]^+$. $^1$HNMR (400 MHZ, Dimethylsulfoxide-$d_6$) δ 7.91-7.66 (m, 1H), 7.34 (t, J=9.2 Hz, 1H), 7.17-6.92 (m, 2H), 5.78-5.51 (m, 2H), 5.39-5.13 (m, 1H), 4.60-4.28 (m, 3H), 4.19-3.91 (m, 3H), 3.91-3.80 (m, 3H), 3.80-3.68 (m, 1H), 3.62-3.50 (m, 1H), 3.11-2.78 (m, 5H), 2.23-1.95 (m, 4H), 1.87-1.66 (m, 3H). $^{19}$F NMR (376 MHz, Dimethylsulfoxide-$d_6$) δ −113.03, −113.18, −149.49, −150.31, −172.05, 172.15, −206.58.

Example 229 & 230: 4-(2-(((1S,7a'S)-2,2-Difluorodihydro-1'H,3'H-spiro[cyclopropane-1,2'-pyrrolizin]-7a'(5'H)-yl)methoxy)-8-fluoro-4-((15,75,8S)-8-fluoro-5-oxa-2-azabicyclo[5.1.0]octan-2-yl)pyrido[4,3-d]pyrimidin-7-yl)-6-fluoro-5-(fluoromethoxy-$d_2$) naphthalen-2-amine & 4-(2-(((1R,7a'S)-2,2-difluorodihydro-1'H,3'H-spiro[cyclopropane-1,2'-pyrrolizin]-7a'(5'H)-yl)methoxy)-8-fluoro-4-((1S,7S, 8S)-8-fluoro-5-oxa-2-azabicyclo[5.1.0]octan-2-yl) pyrido[4,3-d]pyrimidin-7-yl)-6-fluoro-5-(fluoromethoxy-$d_2$)naphthalen-2-amine

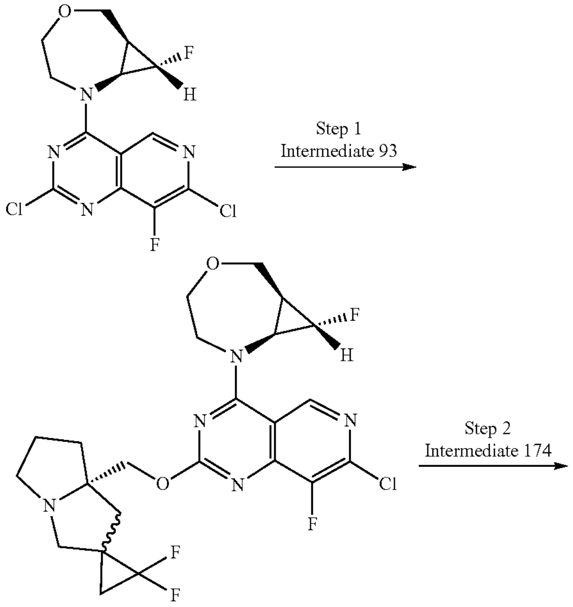

-continued

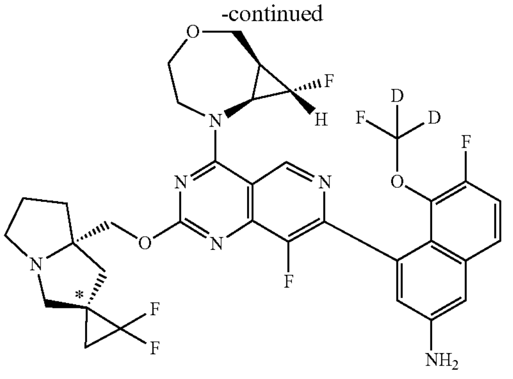

+

Example 229

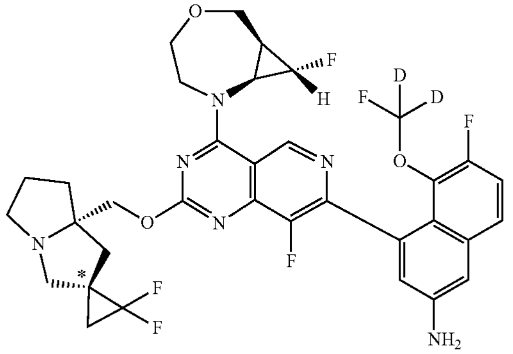

Example 230 structure arbitrarily assigned

Step 1: (1S,7S,8S)-2-(7-chloro-2-(((7a'S)-2,2-difluorodihydro-1'H,3'H-spiro[cyclopropane-1,2'-pyrrolizin]-7a'(5'H)-yl)methoxy)-8-fluoropyrido[4,3-d] pyrimidin-4-yl)-8-fluoro-5-oxa-2-azabicyclo[5.1.0] octane To a solution of Intermediate 93 (234 mg, 1.15 mmol) in 1,4-dioxane (10 mL) were added DIPEA (301 μL, 1.73 mmol) and (1S,7S,8S)-2-(2,7-dichloro-8-fluoropyrido[4,3-d]pyrimidin-4-yl)-8-fluoro-S-oxa-2-azabicyclo[5.1.0]octane (200 mg, 576 μmol). The mixture was stirred at 110° C. for 16 h. The mixture was concentrated under reduced pressure. The residue was purified by silica gel flash chromatography (Eluent: 0~5% of MeOH in $CH_2Cl$) to give the title compound (130 mg, 36% yield) as a yellow solid. MS: m/z=514.0 $[M+H]^+$.

Step 2: 4-(2-(((15,7a'S)-2,2-difluorodihydro-1'H, 3'H-spiro[cyclopropane-1,2'-pyrrolizin]-7a'(5'H)-yl) methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-$d_2$)naphthalen-2-amine & 4-(2-(((1R,7a'S)-2,2-difluorodihydro-1'H, 3'H-spiro[cyclopropane-1,2'-pyrrolizin]-7a'(5'H)-yl) methoxy)-8-fluoro-4-((15,7S,8S)-8-fluoro-5-oxa-2-azabicyclo[5.1.0]octan-2-yl)pyrido[4,3-d]pyrimidin-7-yl)-6-fluoro-5-(fluoromethoxy-$d_2$)naphthalen-2-amine A mixture of (1S,7S,8S)-2-(7-chloro-2-(((7a'S)-2,2-difluorodihydro-1'H,3'H-spiro[cyclopropane-1,2'-pyrrolizin]-7a'(5'H)-yl)methoxy)-8-fluoropyrido[4,3-d]pyrimidin-4-yl)-

8-fluoro-5-oxa-2-azabicyclo[5.1.0]octane (90 mg, 175 μmol), Intermediate 174 (118 mg, 350 μmol), $K_3PO_4$ (112 mg, 525 μmol), and AdanBuP-Pd-$G_3$ (cataCXiumAPdG$_3$) (26 mg, 35.0 μmol) in 1,4-dioxane (5 mL) and $H_2O$ (0.5 mL) was degassed and purged with $N_2$ three times, and then the mixture was stirred at 100° C. for 2 h under $N_2$ atmosphere. The reaction mixture was concentrated under reduced pressure. The residue was purified by silica gel flash chromatography (Eluent: 0~10% of MeOH in $CH_2Cl_2$) to give crude product. Then it was separated by SFC (column: CD02-Waters Xbidge BEH C18 150*25*10 um; mobile phase: [water ($NH_4HCO_3$)-ACN]; gradient: 35%~65% B over 10 min) to give the title compound (Example 229, 31.4 mg, 26% yield) and the title compound (Example 230, 4.7 mg, 3.9% yield) as a yellow solid. Spectra for Example 229: MS: m/z=689.1 $[M+H]^+$. $^1H$ NMR (400 MHz, Dimethylsulfoxide-$d_6$) δ 9.50-9.25 (m, 1H), 7.63-7.50 (m, 1H), 7.42-7.32 (m, 1H), 7.10-6.98 (m, 2H), 5.75-5.56 (m, 2H), 5.00-4.77 (m, 1H), 4.51 (d, J=14.0 Hz, 1H), 4.43-4.25 (m, 2H), 4.22-4.14 (m, 2H), 4.07-3.90 (s, 1H), 3.79-3.49 (m, 2H), 3.28-3.14 (m, 1H), 3.13-3.04 (m, 1H), 3.04-2.96 (m, 1H), 2.74-2.68 (m, 1H), 2.57-2.52 (m, 1H), 2.43-2.26 (m, 1H), 2.12-2.03 (m, 1H), 2.01-1,93 (m, 1H), 1.93-1.87 (m, 1H), 1.84-1.68 (m, 2H), 1.65-1.51 (m, 2H), 1.50-1.42 (m, 1H). $^{19}F$ NMR (376 MHz, Dimethylsulfoxide-$d_6$) δ −132.17, ~132.19, −132.56, −132.58, −134.67, −135.07, −136.84, −136.89, −137.28, −137.32, −140.06, −140.20, −150.64, −151.03, −208.48. Spectra for Example 230; MS: m/z=689.1 $[M+H]^+$. $^1H$ NMR (400 MHZ, Dimethylsulfoxide-$d_6$) 9.51-9.31 (m, 1H), 7.61-7.52 (m, 1H), 7.42-7.32 (m, 1H), 7.15-6.92 (m, 2H), 5.71-5.59 (m, 2H), 5.01-4.79 (m, 1H), 4.50 (d, J=14.0 Hz, 1H), 4.40-4.28 (m, 2H), 4.20-3.93 (m, 3H), 3.72-3.55 (m, 2H), 3.27-3.13 (m, 1H), 3.06-3.01 (m, 1H), 3.00-3.92 (m, 1H), 2.82-2.73 (m, 1H), 2.71-2.65 (m, 1H), 2.39-2.29 (m, 1H), 2.14-2.07 (m, 1H), 1.96-1.86 (m, 3H), 1.84-1.72 (m, 2H), 1.60-1.48 (m, 2H). $^{19}F$ NMR (376 MHz, Dimethylsulfoxide-$d_6$) δ −135.30, −135.68, −135.70, −136.78, −136.82, −137.26, −137.30, −137.52, −137.54, −137.92, −137.93, −140.12, −140.27, −150.62, −151.00, −208.29

Example 233: 5-Ethynyl-6-fluoro-4-(8-fluoro-4-((1S,7S,8S)-8-fluoro-5-oxa-2-azabicyclo[5.1.0]octan-2-yl)-2-(((2"R,6'R,7a'R)-2"-fluorodihydro-5'H-dispiro[cyclopropane-1,1'-pyrrolizine-6',1"-cyclopropan]-7a'(7H)-yl)methoxy)pyrido[4,3-d] pyrimidin-7-yl)naphthalen-2-amine

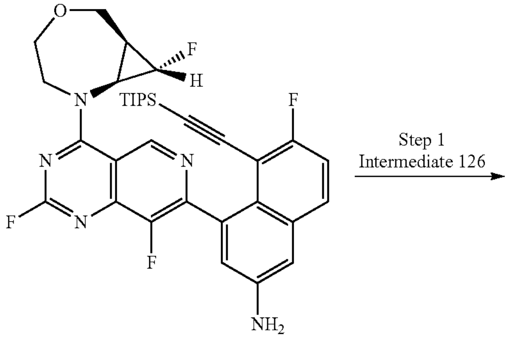

Intermediate 118

-continued

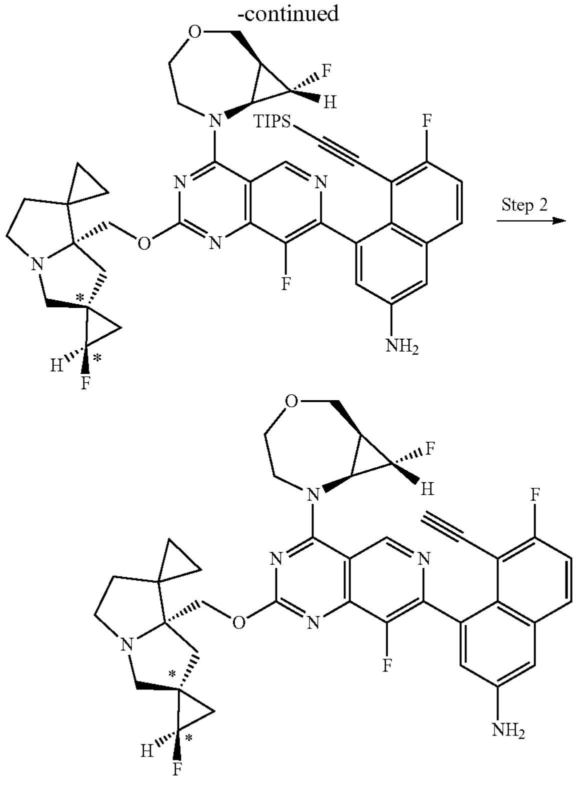

Example 233
structure arbitrarily assigned

Step 1: 6-Fluoro-4-(8-fluoro-4-((1S,75,8S)-8-fluoro-5-oxa-2-azabicyclo[5.1.0]octan-2-yl)-2-(((2"R,6'R,7a'R)-2"-fluorodihydro-5'H-dispiro[cyclopropane-1,1'-pyrrolizine-6',1"-cyclopropan]-7a'(7'W)-yl) methoxy)pyrido[4,3-d]pyrimidin-7-yl)-5-((triisopropylsilyl) ethynyl)naphthalen-2-amine To a solution of Intermediate 126 (184 mg, crude) in THE (2 mL) was added t-BuOK (686 μL, 1 M in THF) dropwise at 25° C. under $N_2$. The mixture was stirred at 25° C. for 0.5 h. A solution of Intermediate 118 (397 mg, 623 μmol) in THF (2 mL) was added dropwise to the mixture at −40° C. under $N_2$ and stirred at −40° C. for 0.5 h under $N_2$. The reaction mixture was quenched with sat. $NH_4Cl$ aq. (10 mL) and extracted with EtOAc (10 mL×3). The combined organic layers were washed with brine (30 mL×2), dried over anhydrous $Na_2SO_4$, filtered and concentrated under reduced pressure. The residue was purified by silica gel flash chromatography (eluent: 0~3% of MeOH in $CH_2Cl_2$) to give the title compound (488 mg, 44% yield over 2 steps) as a yellow solid. MS: m/z=827.2 $[M+H]^+$. JH NMR (400 MHZ, Dimethylsulfoxide-$d_6$) δ 9.39 (s, 1H), 7.78 (dd, J=6.0, 10.0 Hz, 1H), 7.34 (t,J=8.8 Hz, 2H), 7.04 (d, J=4.0 Hz, 1H), 5.65 (s, 2H), 5.01-4.62 (m, 2H), 4.44-4.34 (m, 2H), 4.23-4.10 (m, 3H), 4.06-3.95 (m, 1H), 3.76-3.58 (m, 2H), 3.18-2.99 (m, 3H), 2.79-2.73 (m, 1H), 2.67 (s, 1H), 2.35-2.31 (m, 1H), 2.03-1.90 (m, 1H), 1.69-1.45 (m, 3H), 0.88-0.77 (m, 23H), 0.48-0.42 (m, 4H), $^{19}F$ NMR (376 MHz, Dimethylsulfoxide-$d_6$) δ −111.37, −140.26, −206.84, −209.48.

Step 2: 5-Ethynyl-6-fluoro-4-(8-fluoro-4-((1S,7S,8S)-8-fluoro-5-oxa-2-azabicyclo[5.1.0]octan-2-yl)-2-(((2"R,6'R,7a'R)-2"-fluorodihydro-S'H-dispiro[cyclopropane-1, 1'-pyrrolizine-6',1"-cyclopropan]-7a(H)-yl)methoxy)pyrido[4,3-d]pyrimidin-7-yl)naphthalen-2-amine To a solution of 6-fluoro-4-(8-fluoro-4-((15,7S,8S)-8-fluoro-5-oxa-2-azabicyclo[5.1.0]octan-2-yl)-2-(((2"R,6'R,7a'R)-2"-fluorodihydro-5'H-dispiro[cyclopropane-1,1'-pyrrolizine-6',1"-cyclopropan]-7a'(7H)-yl)methoxy)pyrido[4,3-d]pyrimidin-7-yl)-5-((triisopropylsilyl) ethynyl)naphthalen-2-amine (488 mg, 590 μmol) in DMSO (5 mL) was added CsF (269 mg, 1.77 mmol). The mixture was stirred at 25° C. for 2 h. The mixture was diluted with $H_2O$ (50 mL) and extracted with EtOAc (30 mL×3). The combined organic layers were washed with brine (50 mL), dried over anhydrous $Na_2SO_4$, filtered and concentrated under reduced pressure. The residue was purified by reversed-phase column (column: C18; mobile phase: [Water (0.5% $NH_4HCO_3$)-ACN)]; B %: 5%~65%, 30 min) to give the title compound (Example 233, 184.8 mg, 51% yield) as a yellow solid. MS: m/z=671.3 $[M+H]^+$. $^1H$ NMR (400 MHz, Dimethylsulfoxide-$d_6$) δ 9.47-9.32 (m, 1H), 7.78 (dd, J=6.0, 8.8 Hz, 1H), 7.38-7.30 (m, 1H), 7.13-7.02 (m, 2H), 5.70-5.59 (m, 2H), 4.96-4.62 (m, 2H), 4.52-4.45 (m, 1H), 4.43-4.28 (m, 2H), 4.23-4.15 (m, 2H), 4.08-3.78 (m, 2H), 3.77-3.57 (m, 2H), 3.28-3.19 (m, 1H), 3.17-3.10 (m, 1H), 3.08-2.97 (m, 1H), 2.74 (d, J=10.8 Hz, 1H), 2.68-2.62 (m, 1H), 2.38-2.27 (m, 1H), 2.04-1.95 (m, 1H), 1.71-1.62 (m, 1H), 1.60-1.52 (m, 1H), 1.48-1.41 (m, 1H), 0.88-0.76 (m, 2H), 0.75-0.60 (m, 2H), 0.52-0.42 (m, 2H). $^{19}F$ NMR (376 MHZ, Dimethylsulfoxide-$d_6$) δ −113.36, −139.89, −206.65, −207.68.

Example 248: 4-(4-((15,7S,8S)-8-Chloro-5-oxa-2-azabicyclo[5.1.0]octan-2-yl)-8-fluoro-2-(((2R,7aS)-2-fluorotetrahydro-1H-pyrrolizin-7a (5H)-yl) methoxy-$d_2$)pyrido[4,3-d]pyrimidin-7-yl)-5-ethynyl-6-fluoronaphthalen-2-amine

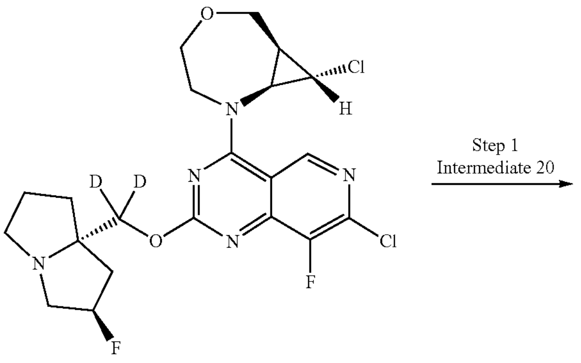

Intermediate 116

-continued

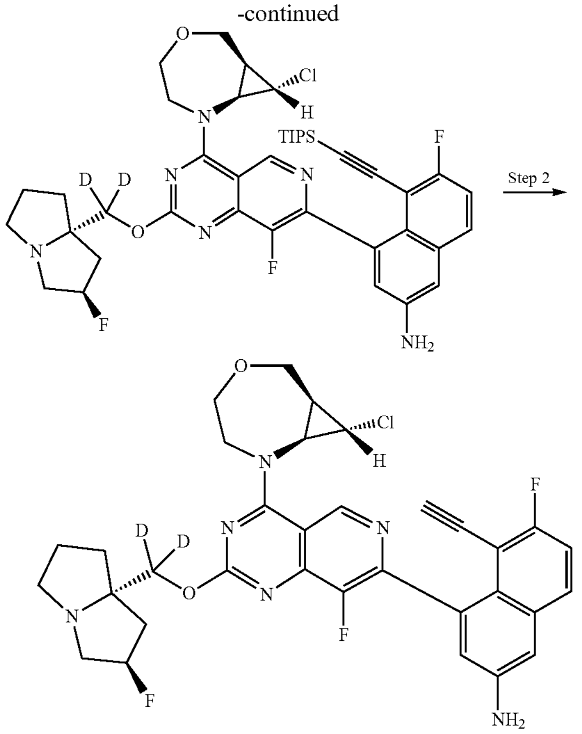

Example 248

Step 1: 4-(4-((15,7S,8S)-8-chloro-5-oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-6-fluoro-5-((triisopropylsilyl) ethynyl)naphthalen-2-amine To a mixture of Intermediate 116 (90 mg, 0.18 mmol) and Intermediate 20 (185.75 mg, 0.37 mmol, HCl salt) in THF (3.5 mL) and $H_2O$ (0.7 mL) under nitrogen atmosphere were added CataCXium A Pd G3 (26.84 mg, 0.04 mmol) and $K_3PO_4$ (234.71 mg, 1.10 mmol) at room temperature. The reaction mixture was heated at 80° C. for 3 hours. The resulting mixture was cooled to room temperature, filtered and concentrated under reduced pressure. The residue was purified by Prep-TCL (MeOH: DCM=1: 10) to afford the title compound (110 mg, 75% yield) as a yellow solid. MS: m/z=793.50 $[M+H]^{+.}$ Step 2: 4-(4-((15,7S,8S)-8-Chloro-5-oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-5-ethynyl-6-fluoronaphthalen-2-amine To a stirred solution of 4-(4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-6-fluoro-5-((triisopropylsilyl) ethynyl)naphthalen-2-amine (110 mg, 0.14 mmol) in DMF (1.5 mL) was added CsF (210.59 mg, 1.39 mmol) at room temperature. The reaction mixture was stirred at room temperature for 2 hours. The resulting mixture was filtered and purified by RP-Flash with the following conditions: C18 spherical, 20-30 um, 100 A, 40 g; Mobile Phase A: 5 mM aq. $NH_4HCO_3$; Mobile Phase B: MeCN; Flow rate: 40 mL/min;

Gradient: 5% B to 5% B in 3 min, 5% B to 56% B in 15 min, 56% B to 56% B in 3 min, 56% B to 95% B in 4 min; Detector: UV 254 & 210 nm; RT: 20 min. The collected fractions were combined, concentrated and then lyophilized overnight to give the title compound (56.0 mg, 63% yield) as a yellow lyophilized powder. MS: m/z=637.10 $[M+H]^+$. $^1$H NMR (400 MHZ, DMSO-$d_6$) δ 9.40-9.32 (m, 1H), 7.80-7.76 (m, 1H), 7.36-7.32 (m, 1H), 7.06-7.03 (m, 2H), 5.67-5.64 (m, 2H), 5.35-5.21 (m, 1H), 4.47-4.40 (m, 2H), 4.22-4.19 (m, 1H), 4.05-3.77 (m, 3H), 3.66-3.56 (m, 2H), 3.31-3.21 (m, 1H), 3.09-3.01 (m, 3H), 2.85-2.81 (m, 1H), 2.18-1.73 (m, 7H). $^{19}$F NMR (376 MHz, DMSO-$d_6$) δ −113.40--113.43 (d, 1F), −140.24--140.62 (d, 1F), −172.04--172.16 (d, 1F).

Example 252: 5-Ethynyl-6-fluoro-4-(8-fluoro-4-((1S,75,8S)-8-fluoro-5-oxa-2-azabicyclo[5.1.0]octan-2-yl)-2-(((15,2S,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine

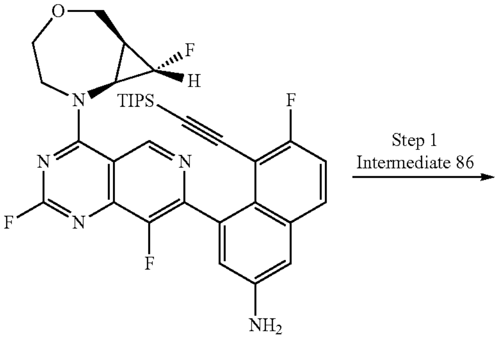

Intermediate 118

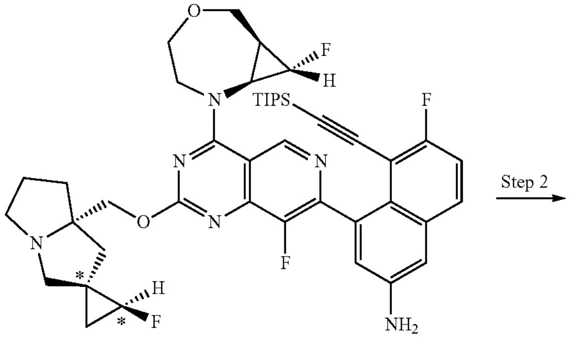

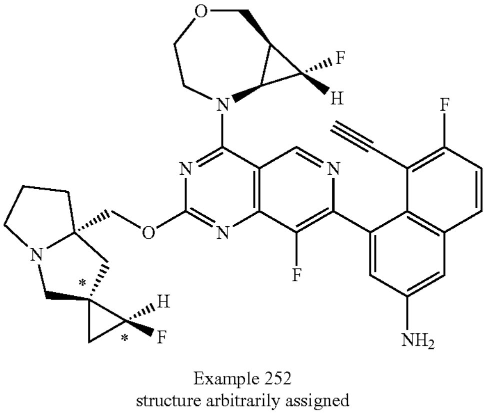

Example 252
structure arbitrarily assigned

Step 1: 6-Fluoro-4-(8-fluoro-4-((1S,75,8S)-8-fluoro-5-oxa-2-azabicyclo[5.1.0]octan-2-yl)-2-(((1S,2S,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)-5-((triisopropylsilyl) ethynyl)naphthalen-2-amine To a solution of Intermediate 86 (90 mg, 486 μmol) in THE was added dropwiseH-BuOK (486 AL, 1 M in THF) at 20° C. under $N_2$. The mixture was stirred at 20° C. for 30 min. A solution of Intermediate 118 (281 mg, 442 μmol) in THE was added dropwise at −40° C. under $N_2$. The resulting mixture was stirred at 20° C. for 2 h. The reaction mixture was quenched with sat. $NH_4Cl$ aq. (100 mL) and extracted with EtOAc (100 mL×3). The combined organic layers were washed with brine (30 mL), dried over anhydrous $Na_2SO_4$, filtered and concentrated under reduced pressure. The residue was purified by silica gel flash chromatography (eluent: 0~5% MeOH in $CH_2Cl_2$) to give the title compound (300 mg, 85% yield) as a yellow solid. MS: m/z=801.4 $[M+H]^{+}$.

Step 2: 5-Ethynyl-6-fluoro-4-(8-fluoro-4-((1S,7S,8S)-8-fluoro-5-oxa-2-azabicyclo[5.1.0]octan-2-yl)-2-(((15,2S,7a'S)-2-fluorodihydro-1'H,3'W-spiro[cyclopropane-1,2'-pyrrolizin]-7a'(5'H)-yl)methoxy)pyrido[4,3-d]pyrimidin-7-yl)naphthalen-2-amine To a solution of 6-fluoro-4-(8-fluoro-4-((15,7S,8S)-8-fluoro-5-oxa-2-azabicyclo[5.1.0]octan-2-yl)-2-(((1S,25,7a'S)-2-fluorodihydro-1'H,3'H-spiro[cyclopropane-1,2'-pyrrolizin]-7a'(S'H)-yl)methoxy)pyrido[4,3-d]pyrimidin-7-yl)-5-((triisopropylsilyl) ethynyl)naphthalen-2-amine (290 mg, 362 μmol) in DMSO (5 mL) was added CsF (275 mg, 1.81 mmol). The mixture was stirred at 25° C. for 2 h. The reaction mixture was diluted with water (100 mL) and extracted with EtOAc (100 mL×2). The combined organic layers were washed with brine (30 mL), dried over anhydrous $Na_2SO_4$, filtered and concentrated under reduced pressure. The residue was purified by reversed-phase column (column: C18; mobile phase: [Water ($NH_3$ $H_2O$)-ACN)]; B %: 5%~40%, 20 min) to give the title compound (Example 252, 110.2 mg, 47% yield) as a yellow solid. MS: m/z=645.2 $[M+H]^+$. $^1$H NMR (400 MHZ, DimethylSulfoxide-$d_6$) δ 9.50-9.31 (m, 1H), 7.78 (dd, J=6.0, 9.2 Hz, 1H), 7.39-7.29 (m, 1H), 7.06 (s, 2H), 5.72-5.56 (m, 2H), 4.96-4.46 (m, 3H), 4.45-4.28 (m, 2H), 4.27-4.14 (m, 1H), 4.11-3.78 (m, 3H), 3.77-3.54 (m, 2H), 3.29-3.12 (m, 1H), 3.06-2.90 (m, 2H), 2.76 (d, J=9.6 Hz, 1H), 2.72-2.64 (m, 1H), 2.41-2.27 (m, 1H), 1.95-1.64 (m, 6H), 0.97-0.78 (m, 2H). $^{19}$F NMR (376 MHz, Dimethyl Sulfoxide-$d_6$) δ −113.34, −113.44, −139.95, −140.49, −207.78, −212.82, −212.85.

Example 253: 5-Ethynyl-6-fluoro-4-(8-fluoro-4-((1S,7S,8S)-8-fluoro-5-oxa-2-azabicyclo[5.1.0]octan-2-yl)-2-(((1S,2R,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine

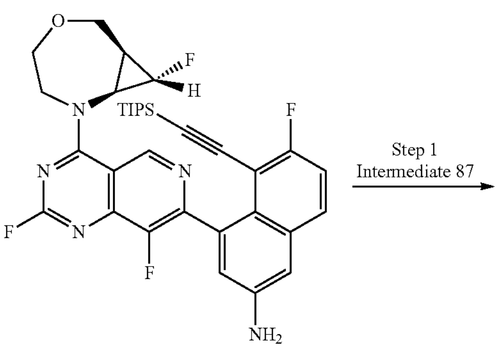

Intermediate 118

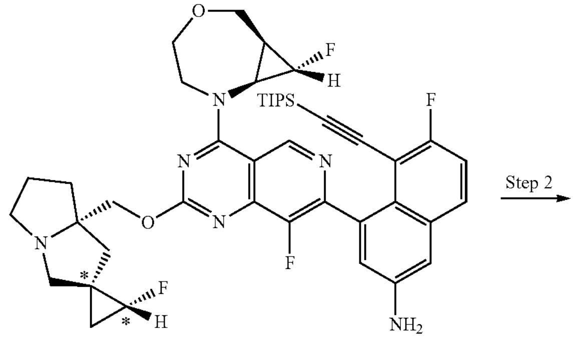

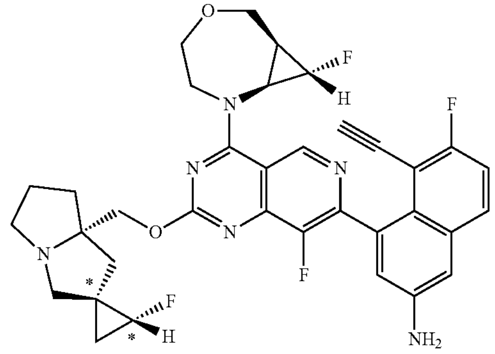

Example 253
structure arbitrarily assigned

Example 253 was prepared in a manner similar to Example 252. MS: m/z=645.2 $[M+H]^+$. $^1H$ NMR (400 MHZ, Dimethylsulfoxide-$d_6$) δ 9.44-9.33 (m, 1H), 7.78 (dd, J=6.0, 9.2 Hz, 1H), 7.39-7.28 (m, 1H), 7.05 (s, 2H), 5.71-5.59 (m, 2H), 4.98-4.73 (m, 1H), 4.72-4.47 (m, 2H), 4.43-4.27 (m, 2H), 4.11-3.80 (m, 4H), 3.73-3.56 (m, 2H), 3.25-3.18 (m, 1H), 2.96-2.89 (m, 1H), 2.67-2.56 (m, 3H), 2.40-2.28 (m, 1H), 2.10-2.01 (m, 1H), 1.94-1.85 (m, 3H), 1.83-1.72 (m, 2H), 0.95-0.82 (m, 2H). $^{19}F$ NMR (376 MHz, Dimethylsulfoxide-$d_6$) δ −113.36,-113.46, −140.01, −140.57, −207.85, −210.28.

Example 254: 5-Ethynyl-6-fluoro-4-(8-fluoro-4-((15,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine

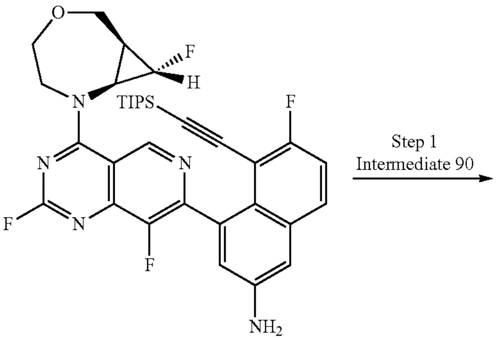

Intermediate 118

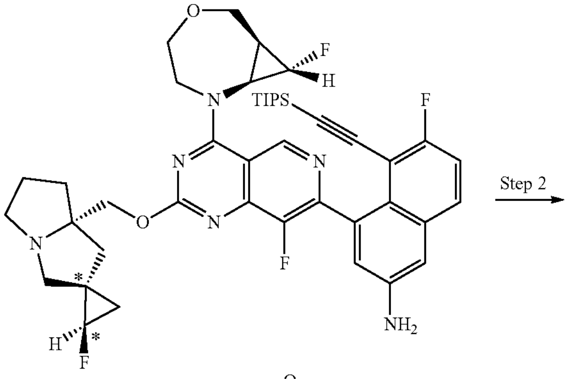

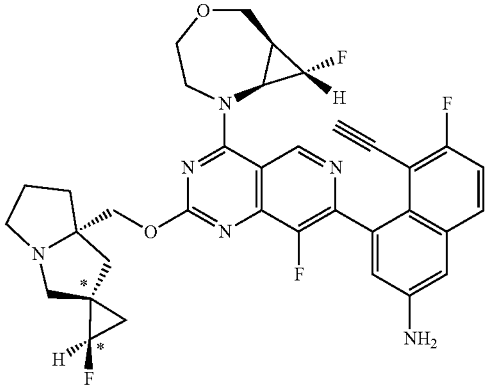

Example 254
structure arbitrarily assigned

Step 1: 6-Fluoro-4-(8-fluoro-4-((15,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)-5-((triisopropylsilyl) ethynyl)naphthalen-2-amine To a solution of Intermediate 90 (178 mg, 961 μmol) in THF (3 mL) was added dropwise t-BuOK (0.96 mL, 1 M in THF) at 0° C. under $N_2$. The mixture was stirred at 20° C.

for 0.5 h. A solution of Intermediate 118 (582 mg, 915 μmol) in THF (3 mL) was added dropwise to the above mixture at −40° C., and the mixture was stirred at −40° C. for 0.5 h under $N_2$ and then at 25° C. for 16 h. The reaction mixture was quenched with sat. $NH_4Cl$ aq. (50 mL) and extracted with EtOAc (100 mL×2). The combined organic layers were washed with brine (200 mL), dried over anhydrous $Na_2SO_4$, filtered and concentrated under reduced pressure. The residue was purified by silica gel flash chromatography (eluent: 0~12% of MeOH in $CH_2Cl_2$) to give the title compound (565 mg, 72% yield) as a yellow solid. MS: m/z=801.3 $[M+H]^{+\cdot}$ Step 2: 5-Ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'/H-spiro[cyclopropane-1,2'-pyrrolizin]-7a'(5'H)-yl)methoxy)pyrido[4,3-d]pyrimidin-7-yl)naphthalen-2-amine To a solution of 6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)-5-((triisopropylsilyl) ethynyl)naphthalen-2-amine (565 mg, 705 μmol) in DMSO (5 mL) was added CsF (321 mg, 2.12 mmol). The mixture was stirred at 20° C. for 0.5 h. The reaction mixture was diluted with $H_2O$ (50 mL) and extracted with EtOAc (30 mL×3). The combined organic layers were washed with brine (50 mL), dried over anhydrous $Na_2SO_4$, filtered and the filtrate was concentrated under reduced pressure to give a residue. The residue was purified by reversed-phase column (column: C18; mobile phase: [Water ($NH_4HCO_3$)-ACN)]; B %: 0%~54% over 35 min) to give the title compound (Example 254, 357.2 mg, 76% yield) as a yellow solid. MS: m/z=645.1 $[M+H]^+$. $^1H$ NMR (400 MHZ, Dimethylsulfoxide-$d_6$) δ 9.50-9.30 (m, 1H), 7.85-7.73 (m, 1H), 7.38-7.30 (m, 1H), 7.05 (s, 2H), 5.77-5.56 (m, 2H), 4.98-4.59 (m, 2H), 4.54-4.45 (m, 1H), 4.44-4.26 (m, 2H), 4.20-3.79 (m, 4H), 3.77-3.56 (m, 2H), 3.30-3.16 (m, 1H), 3.12-3.05 (m, 1H), 3.04-2.94 (m, 1H), 2.72-2.64 (m, 1H), 2.62-2.56 (m, 1H), 2.43-2.27 (m, 1H), 2.03-1.92 (m, 1H), 1.89-1.78 (m, 2H), 1.77-1.60 (m, 3H), 0.97-0.72 (m, 2H). $^{19}F$ NMR (376 MHz, Dimethylsulfoxide-$d_6$) δ −113.36, −113.45, −139.92, −140.48, −206.81, −206.90, −207.59.

Example 255: 5-Ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine

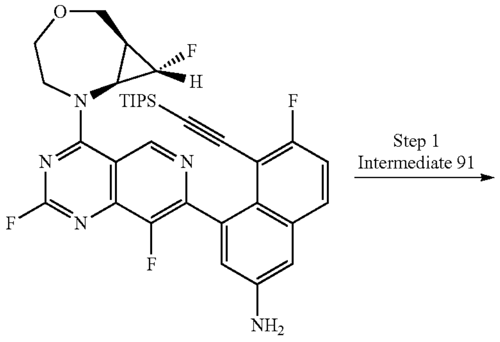

Intermediate 118

-continued

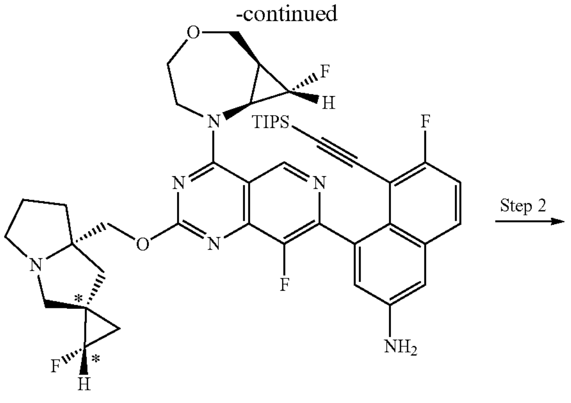

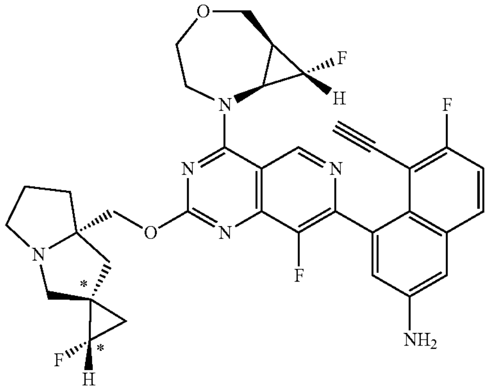

Example 255
structure arbitrarily assigned

Step 1: 6-Fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)-5-((triisopropylsilyl) ethynyl)naphthalen-2-amine To a solution of Intermediate 91 (190 mg, 1.03 mmol) in THE (3 mL) was added dropwiseH-BuOK (1.03 mL, 1 M in THF) at 20° C. under $N_2$. The mixture was stirred at this temperature for 30 min. A solution of Intermediate 118 (593 mg, 932 μmol) in THF (4 mL) was added dropwise to the reaction mixture at −40° C. under $N_2$, the mixture was stirred at −40° C. for 0.5 h under $N_2$. The reaction mixture was stirred at 20° C. for 16 h. The reaction mixture was quenched with sat. $NH_4Cl$ aq. (60 mL) at 20° C. and extracted with EtOAc (30 mL×2). The combined organic phases were washed with brine (30 mL), dried over anhydrous $Na_2SO_4$, filtered and the filtrate was concentrated under reduced pressure to give a residue. The residue was purified by flash silica gel chromatography (eluent: 0~20% of MeOH in CHzCl2) to give 6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)-5-((triisopropylsilyl) ethynyl)naphthalen-2-amine (550 mg, 74% yield) as a yellow solid. MS: m/z=801.3 $[M+H]^{+\cdot}$ Step 2: 5-Ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'/H-spiro[cyclopropane-1,2'-pyrrolizin]-7a'(5'H)-yl)methoxy)pyrido[4,3-d]pyrimidin-7-yl)naphthalen-2-amine To a solution of 6-fluoro-4-(8-fluoro-4-((15,75,8S)-8-fluoro-S-oxa-2-azabicyclo[5.1.0]octan-2-yl)-2-(((1R,2S,7a'S)-2-fluorodihydro-1'W,3'H-spiro[cyclopropane-1,2'-pyrrolizin]-7a'(5'H)-yl)methoxy)pyrido[4,3-d]pyrimidin-7-yl)-5-((triisopropylsilyl) ethynyl)naphthalen-2-amine (550 mg, 687 μmol) in DMSO (5 mL) was added CsF (522 mg, 3.43 mmol). The mixture was stirred at 30° C. for 1 h. The reaction mixture was diluted with $H_2O$ (50 mL) and extracted with EtOAc (30 mL×3). The combined organic phases were separated, washed with brine (40 mL), dried over anhydrous $Na_2SO_4$, filtered and concentrated under reduced pressure. The residue was dissolved with $CH_2Cl_2$ (5 mL), and then n-hexane (50 mL) was added to the above solution to give a precipitate. The precipitate was filtered, and the filter cake was washed with n-hexane (30 mL), dried under reduced pressure to give the title compound (Example 255, 363.8 mg, 81% yield). MS: m/z=645.2 $[M+H]^+$. $^1H$ NMR (400 MHZ, Dimethylsulfoxide-$d_6$) δ 9.48-9.31 (m, 1H), 7.85-7.70 (m, 1H), 7.42-7.29 (m, 1H), 7.06 (s, 2H), 5.75-5.55 (m, 2H), 4.99-4.63 (m, 2H), 4.75-5.55 (m, 1H), 4.44-4.25 (m, 2H), 4.23-4.13 (m, 2H), 4.09-3.78 (m, 2H), 3.76-3.55 (m, 2H), 3.30-3.14 (m, 1H), 3.06-2.96 (m, 1H), 2.88-2.80 (m, 1H), 2.74-2.64 (m, 1H), 2.56-2.53 (m, 1H), 2.42-2.24 (m, 1H), 2.08-2.00 (m, 1H), 1.99-1.92 (m, 1H), 1.91-1.80 (m, 2H), 1.80-1.70 (m, 1H), 1.69-1.59 (m, 1H), 0.93-0.73 (m, 2H). $^{19}F$ NMR (376 MHZ, Dimethylsulfoxide-$d_6$) δ −113.35, −113.44, −139.90, −140.47, −207.61, −207.65, −207.73, −207.88, −209.90, −209.96

Example 259: 5-Ethynyl-6-fluoro-4-(8-fluoro-2-(((2R,5S,7aS)-2-fluoro-5-methyltetrahydro-1H-pyrrolizin-7a (5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine

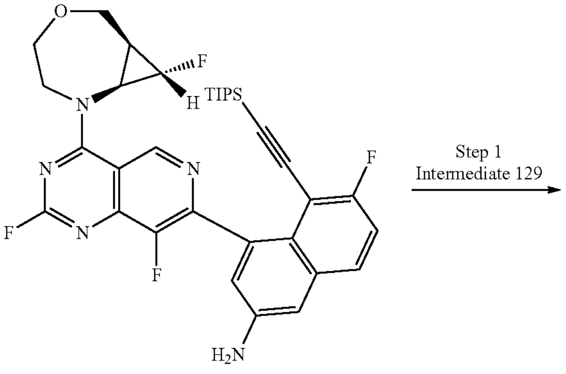

Intermediate 118

-continued

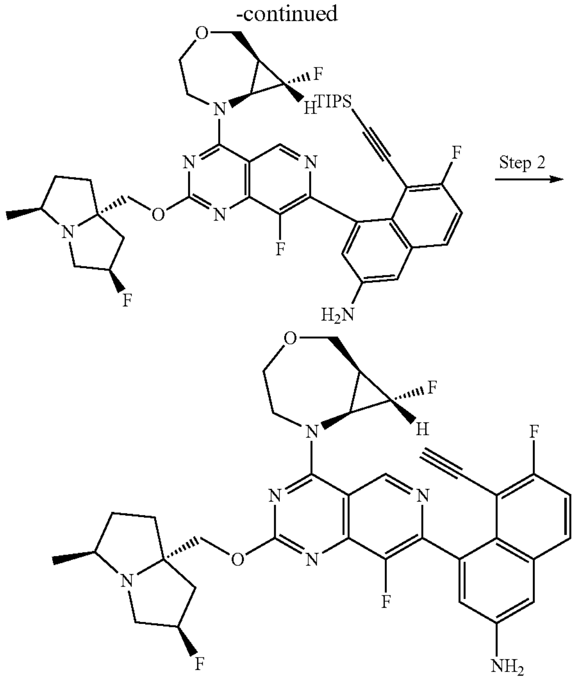

Example 259

Step 1: 6-Fluoro-4-(8-fluoro-2-(((2R,5S,7aS)-2-fluoro-5-methyltetrahydro-1H-pyrrolizin-7a (5H)-yl)methoxy)-4-((1S,7S,8S)-8-fluoro-5-oxa-2-azabicyclo[5.1.0]octan-2-yl)pyrido[4,3-d]pyrimidin-7-yl)-S-((triisopropylsilyl) ethynyl)naphthalen-2-amine To an ice-cooled solution of Intermediate 129 (70.69 mg, 0.37 mmol) in THF (1.0 mL) under nitrogen atmosphere was addedH-BuOK (42.36 mg, 0.37 mmol). The mixture was at in an ice bath for 30 min. Intermediate 118 (200 mg, 0.31 mmol) was added to the above mixture. The ice bath was removed, and the reaction mixture was stirred at room temperature for 1 hour. The resulting mixture was quenched with sat. aq. $NH_4Cl$ (20 mL) in an ice bath and extracted with EtOAc (3×30 mL). The combined organic layers were washed with brine (30 mL), dried over anhydrous $Na_2SO_4$, filtered and concentrated under reduced pressure. The residue was purified by Prep-TLC ($CH_2Cl_2$/MeOH 10: 1) to afford the title compound (180 mg, 71% yield) as a light yellow solid. MS: m/z=803.35 $[M+H]^{+}$.

Step 2: 5-Ethynyl-6-fluoro-4-(8-fluoro-2-(((2R,5S,7aS)-2-fluoro-5-methyltetrahydro-1H-pyrrolizin-7a (5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine To a stirred solution of 6-fluoro-4-(8-fluoro-2-(((2R,5S,7aS)-2-fluoro-5-methyltetrahydro-1H-pyrrolizin-7a (5H)-yl)methoxy)-4-((1S,7S,8S)-8-fluoro-5-oxa-2-azabicyclo[5.1.0]octan-2-yl)pyrido[4,3-d]pyrimidin-7-yl)-5-((triisopropylsilyl) ethynyl)naphthalen-2-amine (180 mg, 0.22 mmol) in DMF (1.0 mL) was added CsF (510.74 mg, 3.36 mmol) at room temperature. The reaction mixture was stirred at room temperature for 3 hours. The resulting mixture was filtered and purified by RP-Flash with the following conditions: C18 spherical, 20-30 um, 100 A, 40 g;

Mobile Phase A: 5 mM aq. $NH_4HCO_3$; Mobile Phase B: MeCN; Flow rate: 40 mL/min; Gradient: 5% B to 5% B in 3 min, 5% B to 61% B in 15 min, 61% B to 61% B in 3 min, 61% B to 95% B in 4 min; Detector: UV 254 & 210 nm. The collected fractions were combined, concentrated and then lyophilized overnight to give the title compound (Example 259, 84.1 mg, 58% yield) as a light yellow lyophilized powder. MS: m/z=647.25 $[M+H]^+$. $^1H$ NMR (300 MHz, DMSO-$d_6$) δ 9.43-9.37 (m, 1H), 7.80-7.75 (m, 1H), 7.37-7.31 (m, 1H), 7.06-7.05 (m, 2H), 5.64 (s, 2H), 5.35-5.17 (m, 1H), 4.91-4.71 (m, 1H), 4.52-4.32 (m, 3H), 4.17-4.13 (m, 1H), 4.06-3.64 (m, 5H), 3.30-3.15 (m, 2H), 3.08-2.83 (m, 1H), 2.45-2.14 (m, 2H), 1.96-1.75 (m, 5H), 1.09-1.06 (m, 6H). $^{19}F$ NMR (282 MHZ, DMSO-$d_6$) δ −113.35--113.41 (d, 1F), −139.84--140.40 (d, 1F), −172.84--172.93 (d, 1F), −207.71 (s, 1F).

Example 267: 6-Chloro-5-ethynyl-4-(8-fluoro-4-((1S,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)naphthalen-2-amine

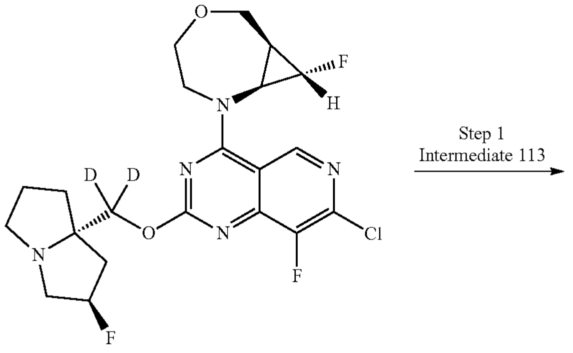

Intermediate 34

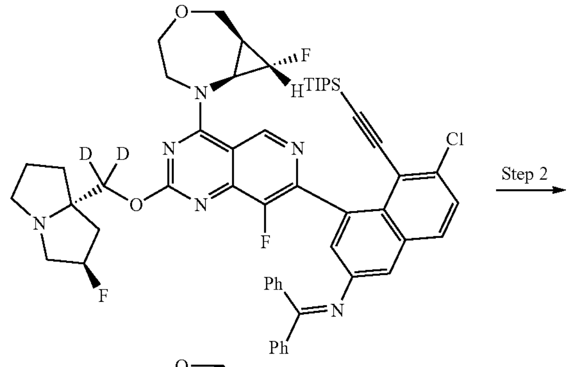

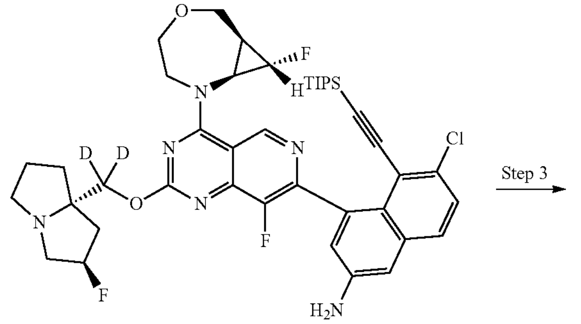

-continued

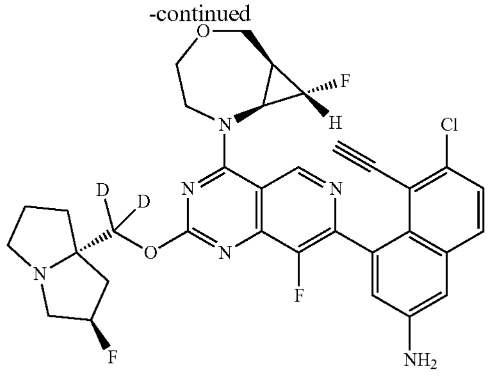

Example 267

Step 1: N-(4-(8-Fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-((triisopropylsilyl) ethynyl)naphthalen-2-yl)-1,1-diphenylmethanimine & N-(6-chloro-4-(8-fluoro-4-((1S,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-((triisopropylsilyl) ethynyl)naphthalen-2-yl)-1,1-diphenylmethanimine To a solution of Intermediate 34 (200 mg, 0.42 mmol) and Intermediate 113 (549.40 mg, 0.84 mmol) in THE (8.5 mL) and $H_2O$ (1.7 mL) under nitrogen atmosphere were added CataCXium A Pd G3 (62 mg, 0.08 mmol) and $K_3PO_4$ (540 mg, 2.54 mmol) at room temperature. The reaction mixture was heated at 80° C. for 1 hour. The resulting mixture was cooled to room temperature, diluted with $H_2O$ (5 mL) and extracted with ethyl acetate (3×10 mL). The combined organic layers were washed with brine (10 mL), dried over anhydrous sodium sulfate, filtered and concentrated under reduced pressure. The residue was purified by Prep-TLC (DCM: MeOH=28: 1) to afford a mixture. The mixture was separated by Prep-Achiral-SFC with following condition: Column: GreenSep Naphthyl 3×25 cm, 5 um; Mobile Phase A: $CO_2$; Mobile Phase B: MeCN: MeOH=4: 1 (20 mM. NHs MeOH); Flow rate: 75 mL/min; Gradient: isocratic 40% B; Column Temperature (° C.): 35; Back Pressure (bar): 100; Detector: UV 254 nm; RT1: 7.76 min; RT2: 8.04 min. The first eluting peak (RT1: 7.76 min) was concentrated under reduced pressure to afford the title compound (70 mg, 18% yield) as a yellow solid. MS: m/z=923.65 $[M+H]^+$. The second eluting peak (RT2: 8.04 min) was concentrated under reduced pressure to afford the title compound (105 mg, 26% yield) as a yellow solid. MS: m/z=957.65 $[M+H]^+$.

Step 2: 6-Chloro-4-(8-fluoro-4-((15,75,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-((triisopropylsilyl) ethynyl)naphthalen-2-amine To a solution of N-(6-chloro-4-(8-fluoro-4-(15,75,85)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-yl)-1,1-diphenylmethanimine (100 mg, 0.10 mmol) in EtOH (1.0 mL) under nitrogen atmosphere was added NaOAc (17.13 mg, 0.20 mmol) and $NH_2OH{\cdot}HCl$ (14.51 mg, 0.20 mmol) at room temperature. The reaction mixture was stirred at room temperature for 2 hours. The resulting mixture was quenched with sat. aq. $NaHCO_3$ (5 mL) and extracted with ethyl acetate (3x10 mL). The combined organic layers were washed with brine (10 mL), dried over anhydrous sodium sulfate, filtered and concentrated under reduced pressure. The residue was purified by Prep-TLC (DCM: MeOH=25: 1) to afford the title compound (77 mg, 92% yield) as a yellow solid. MS: m/z=793.35 $[M+H]^{+}$.

Step 3: 6-Chloro-5-ethynyl-4-(8-fluoro-4-((15,75, 8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl) naphthalen-2-amine To a solution of 6-chloro-4-(8-fluoro-4-((15,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) pyrido[4,3-d]pyrimidin-7-yl)-5-((triisopropylsilyl) ethynyl) naphthalen-2-amine (77 mg, 0.09 mmol) in DMF (0.4 mL) was added CsF (221.6 mg, 1.45 mmol) at room temperature. The reaction mixture was stirred at room temperature for 3 hours. The resulting mixture was filtered and purified by RP-Flash with the following conditions: Column: C18, 40 g, 20-35 um; Mobile Phase A: 5 mM aq. $NH_4HCO_3$; Mobile Phase B: MeCN; Gradient: 5% B to 5% B in 3 min, 5% B to 68% B in 15 min, 68% B to 68% B in 3 min, 68% B to 95% B in 4 min; Flow rate: 40 mL/min; Detector: UV 254 & 210 nm. The product-containing fractions were collected, concentrated, and lyophilized overnight to give the title compound (Example 267, 26.5 mg, 42% yield) as a yellow lyophilized powder. MS: m/z=637.20 $[M+H]^{+}$. $^{1}H$ NMR (400 MHZ, DMSO-$d_6$) & 9.43-9.36 (m, 1H), 7.73-7.71 (m, 1H), 7.46-7.44 (m, 1H), 7.05-7.02 (m, 2H), 5.80-5.78 (m, 2H), 5.35-5.22 (m, 1H), 4.97-4.72 (m, 1H), 4.51-4.32 (m, 3H), 4.15-3.91 (m, 2H), 3.71-3.56 (m, 2H), 3.33-3.02 (m, 4H), 2.92-2.81 (m, 1H), 2.44-2.27 (m, 1H), 2.23-1.97 (m, 3H), 1.95-1.71 (m, 3H). $^{19}F$ NMR (376 MHz, DMSO-$d_6$) δ −139.97--140.51 (d, 1F), −172.08--172.19 (d, 1F), −207.59 (s, 1F).

Example 269: 4-(8-Chloro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)pyrido[4,3-d]pyrimidin-7-yl)-5-ethynyl-6-fluoronaphthalen-2-amine

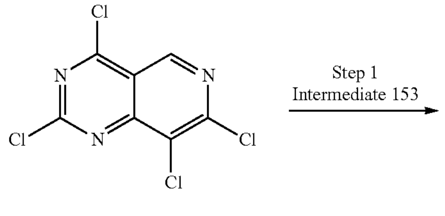

-continued

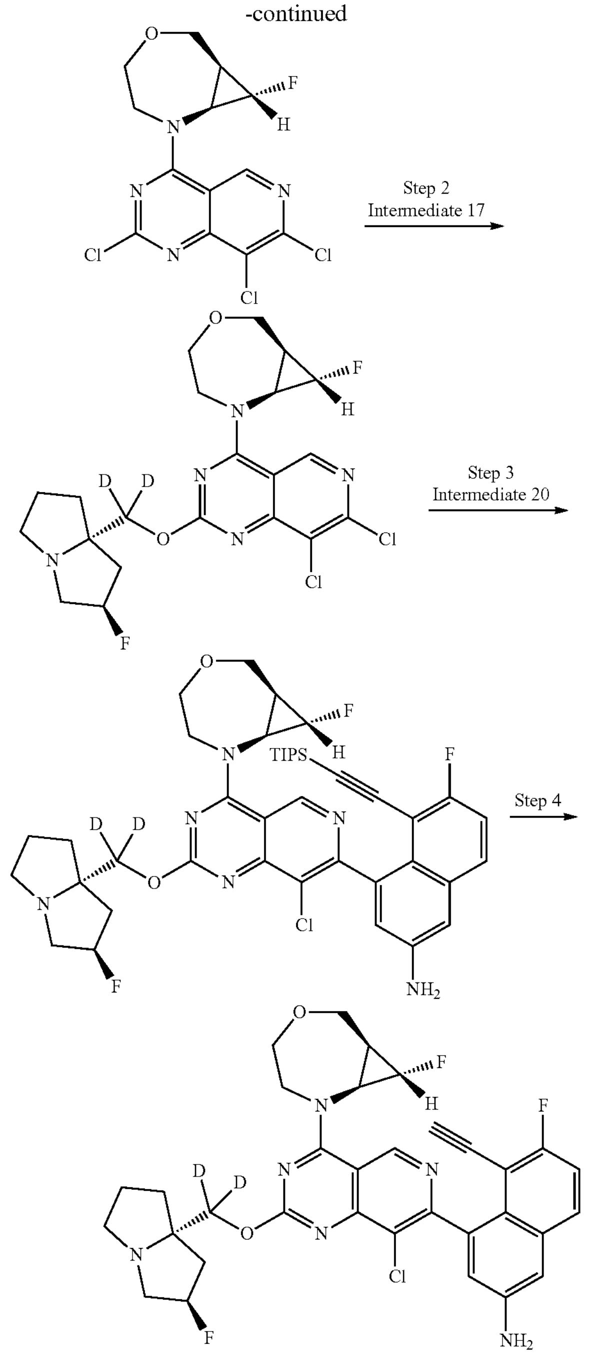

Example 269

Step 1: (1S,7S,8S)-8-Fluoro-2-(2,7,8-trichloropyrido [4,3-d]pyrimidin-4-yl)-5-oxa-2-azabicyclo[5.1.0] octane To a stirred solution of 2,4,7,8-tetrachloropyrido[4,3-d] pyrimidine (500 mg, 1.86 mmol) in DCM (5 mL) were added DIEA (720.95 mg, 5.58 mmol) and Intermediate 153 (394.30 mg, 1.86 mmol) at −40° C. under $N_2$. The reaction mixture was stirred at −40° C. for 1 hour. The resulting mixture was diluted with water (20 mL) and extracted with DCM (3x30 mL). The combined organic layers were washed with brine (50 mL), dried over anhydrous $Na_2SO_4$, filtered and concentrated under reduced pressure. The residue was purified by silica gel flash chromatography (eluted with 40% EA in PE) to afford the title compound (600 mg, 88% yield) as a yellow solid. MS: m/z=363.00, 365.00 $[M+H]^{+\cdot}$ Step 2: (1S,7S,8S)-2-(7,8-Dichloro-2-(((2R,7aS)-2-fluorotetrahydro-1H-pyrrolizin-7a (5H)-yl)methoxy-$d_2$)pyrido[4,3-d]pyrimidin-4-yl)-8-fluoro-5-oxa-2-azabicyclo[5.1.0]octane To a stirred solution of (1S,7S,8S)-8-fluoro-2-(2,7,8-trichloropyrido[4,3-d]pyrimidin-4-yl)-5-oxa-2-azabicyclo [5.1.0]octane (580 mg, 1.59 mmol) in DMSO (6 mL) were added KF (324.36 mg, 5.58 mmol) and Intermediate 17 (411.47 mg, 2.55 mmol) at room temperature under $N_2$. The reaction mixture was heated at 100° C. for 16 hours. The resulting mixture was cooled down to room temperature, diluted with water (50 mL), and extracted with DCM (3×100 mL). The combined organic layers were washed with brine (3×80 mL), dried over anhydrous $Na_2SO_4$, filtered and concentrated under reduced pressure. The residue was purified by silica gel flash chromatography (eluted with 5% MeOH in DCM) to afford the title compound (340 mg, 43% yield) as a light yellow solid. MS: m/z=488.10, 490.10 $[M+H]^{+\cdot}$ Step 3: 4-(8-Chloro-4-((1S,75,8S)-8-fluoro-5-oxa-2-azabicyclo[5.1.0]octan-2-yl)-2-(((2R,7aS)-2-fluoro-tetrahydro-1H-pyrrolizin-7a (5H)-yl)methoxy-$d_2$) pyrido[4,3-d]pyrimidin-7-yl)-6-fluoro-5-((triisopropylsilyl) ethynyl)naphthalen-2-amine To a mixture of (1S,7S,8S)-2-(7,8-dichloro-2-(((2R,7aS)-2-fluorotetrahydro-1H-pyrrolizin-7a (5H)-yl)methoxy-$d_2$) pyrido[4,3-d]pyrimidin-4-yl)-8-fluoro-5-oxa-2-azabicyclo [5.1.0]octane (180 mg, 0.37 mmol) and Intermediate 20 (371.51 mg, 0.74 mmol) in THF (7.5 mL) and HLO (1.5 mL) under nitrogen atmosphere were added CataCXium A Pd G3 (53.69 mg, 0.07 mmol) and $K_3PO_4$ (469.42 mg, 2.21 mmol) at room temperature. The reaction mixture was heated at 80° C. for 3 hours. The resulting mixture was cooled to room temperature, filtered and concentrated under reduced pressure. The residue was purified by Prep-TCL (MeOH: DCM=1: 10) to afford the title compound (110 mg, 37% yield) as a yellow solid. MS: m/z=793.60 $[M+H]^{+\cdot}$ Step 4: 4-(8-chloro-4-((15,7S,8S)-8-fluoro-5-oxa-2-azabicyclo[5.1.0]octan-2-yl)-2-(((2R,7aS)-2-fluoro-tetrahydro-1H-pyrrolizin-7a (5H)-yl)methoxy-$d_2$) pyrido[4,3-d]pyrimidin-7-yl)-5-ethynyl-6-fluoronaphthalen-2-amine To a stirred solution of 4-(8-chloro-4-((1S,75,8S)-8-fluoro-S-oxa-2-azabicyclo[5.1.0]octan-2-yl)-2-(((2R,7aS)-2-fluorotetrahydro-1H-pyrrolizin-7a (5H)-yl)methoxy-$d_2$) pyrido[4,3-d]pyrimidin-7-yl)-6-fluoro-5-((triisopropylsilyl) ethynyl)naphthalen-2-amine (100 mg, 0.12 mmol) in DMF (1.5 mL) was added CsF (191.45 mg, 1.26 mmol) at room temperature. The reaction mixture was stirred at room temperature for 2 hours. The resulting mixture was filtered and purified by RP-Flash directly with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 56% B in 15 min, 56% B to 56% B in 3 min, 56% B to 95% B in 4 min; Detector: UV 254 & 210 nm; RT: 20 min. The collected fractions were combined, concentrated and lyophilized overnight to give the title compound (Example 269, 67.1 mg, 83% yield) as a yellow lyophilized powder. MS: m/z=637.15 $[M+H]^+$. $^1H$ NMR (400 MHZ, DMSO-$d_6$) δ 9.50-9.44 (m, 1H), 7.78-7.74 (m, 1H), 7.34-7.30 (m, 1H), 7.03-7.02 (m, 1H), 6.97-6.94 (m, 1H), 5.62 (s, 2H), 5.35-5.21 (m, 1H), 4.95-4.65 (m, 1H), 4.51-4.48 (m, 1H), 4.38-4.37 (m, 2H), 4.10-3.55 (m, 4H), 3.30-3.00 (m, 4H), 2.85-2.78 (m, 1H), 2.41-2.30 (m, 1H), 2.13-1.90 (m, 3H), 1.89-1.70 (m, 3H). $^{19}F$ NMR (376 MHz, DMSO-$d_6$) δ −113.56--113.64 (d, 1F), −172.15 (s, 1F), −207.79 (s, 1F).

Example 274: 5-Ethynyl-6-fluoro-4-(8-fluoro-4-((15,75,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl-5',5'-$d_2$)methoxy-$d_2$)pyrido[4,3-d]pyrimidin-7-yl) naphthalen-2-amine

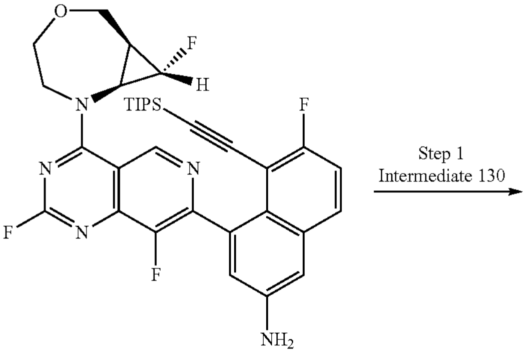

Intermediate 118

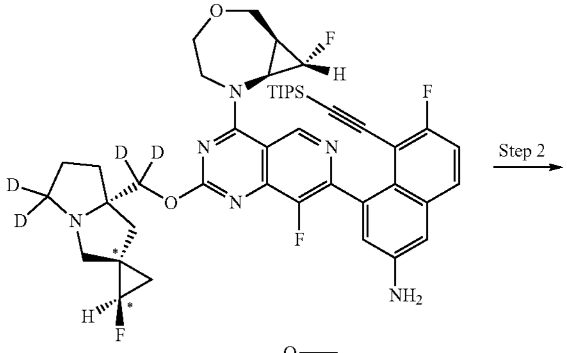

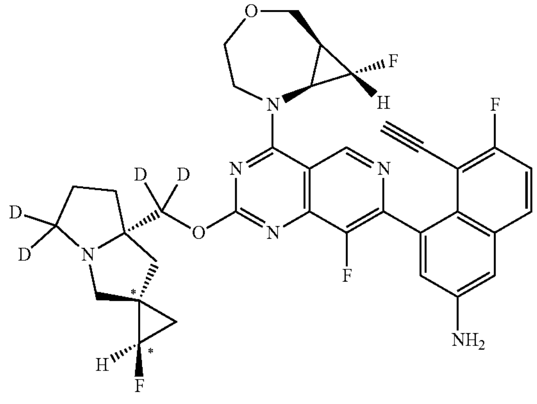

Example 274
structure arbitrarily assigned

Step 1: 6-Fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl-5',5'-$d_2$)methoxy-$d_2$)pyrido[4,3-d]pyrimidin-7-yl)-5-((triisopropylsilyl)ethynyl)naphthalen-2-amine To a solution of Intermediate 130 ($^{19}F$ NMR: −207.35 ppm, 92 mg, 486 μmol) in THF (3 mL) was added t-BuOK (0.48 mL, 1 M in THF) dropwise at 0° C. under $N_2$. The mixture was stirred at 20° C. for 0.5 h. A solution of Intermediate 118 (294 mg, 463 μmol) in THE (3 mL) was added dropwise to the above mixture at −40° C., and the resulting mixture was stirred at −40° C. for 0.5 h under $N_2$. The mixture was stirred at 20° C. for 16 h. The reaction mixture was quenched with sat. $NH_4Cl$ aq. (50 mL) and extracted with EtOAc (100 mL×2). The combined organic layers were washed with brine (200 mL), dried over anhydrous $Na_2SO_4$, filtered and the filtrate was concentrated under reduced pressure. The residue was purified by silica gel flash chromatography (eluent: 0~12% of MeOH in $CH_2Cl_2$)) to give the title compound (198 mg, 53% yield) as a yellow solid. MS: m/z=805.3 $[M+H]^{+}$.

Step 2: 5-Ethynyl-6-fluoro-4-(8-fluoro-4-((15,75,8S)-8-fluoro-5-oxa-2-azabicyclo[5.1.0]octan-2-yl)-2-(((1R,2R,7a'S)-2-fluorodihydro-1'W,3'H-spiro[cyclopropane-1,2'-pyrrolizin]-7a'(5'H)-yl-5',5'-$d_2$)methoxy-$d_2$)pyrido[4,3-d]pyrimidin-7-yl)naphthalen-2-amine To a solution of 6-fluoro-4-(8-fluoro-4-((15,7S,8S)-8-fluoro-5-oxa-2-azabicyclo[5.1.0]octan-2-yl)-2-(((1R,2R,7a'S)-2-fluorodihydro-1'H,3'/H-spiro[cyclopropane-1,2'-pyrrolizin]-7a'(5'H)-yl-5',5'-$d_2$)methoxy-$d_2$)pyrido[4,3-d]pyrimidin-7-yl)-5-((triisopropylsilyl) ethynyl)naphthalen-2-amine (198 mg, 246 μmol) in DMSO (5 mL) was added CsF (112 mg, 738 μmol). The mixture was stirred at 20° C. for 0.5 h. The reaction mixture was diluted with $H_2O$ (50 mL) and extracted with EtOAc (30 mL×3). The combined organic phases were washed with brine (40 mL), dried over anhydrous $Na_2SO_4$, filtered and concentrated under reduced pressure. The residue was purified by silica gel flash chromatography (eluent: 0~5% of MeOH in $CH_2Cl_2$) to give the title compound (Example 274, 104.2 mg, 64% yield) as a yellow solid. MS: m/z=649.1 $[M+H]^{+}$. $^{1}H$ NMR (400 MHZ, Dimethylsulfoxide-$d_6$) δ 9.51-9.29 (m, 1H), 7.78 (dd,J=6.0, 9.2 Hz, 1H), 7.41-7.29 (m, 1H), 7.17-6.95 (m, 2H), 5.74-5.52 (m, 2H), 5.02-4.58 (m, 2H), 4.49 (d, J=13.6 Hz, 1H), 4.44-4.28 (m, 2H), 4.12-3.79 (m, 2H), 3.77-3.55 (m, 2H), 3.30-3.16 (m, 1H), 3.14-3.04 (m, 1H), 2.73-2.63 (m, 1H), 2.42-2.26 (m, 1H), 2.03-1.91 (m, 1H), 1.90-1.77 (m, 2H), 1.76-1.61 (m, 3H), 0.95-0.73 (m, 2H). $^{19}F$ NMR (376 MHz, Dimethylsulfoxide-$d_6$) δ −113.35, −113.43, −139.90, −140.46, −206.91, −207.00, −207.71, −207.74, −207.82.

Example 275: 5-Ethynyl-6-fluoro-4-(8-fluoro-4-((15,75,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl-S',S'-$d_2$)methoxy-$d_2$)pyrido[4,3-d]pyrimidin-7-yl)naphthalen-2-amine

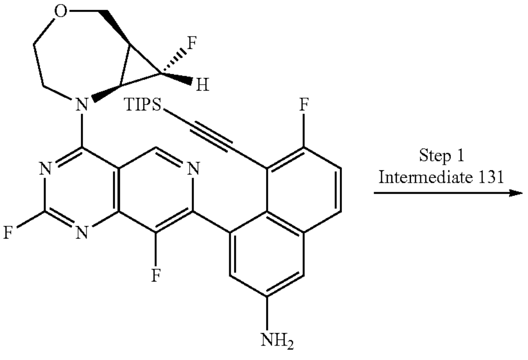

Intermediate 118

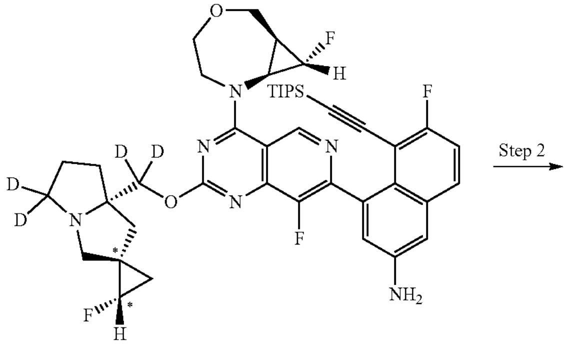

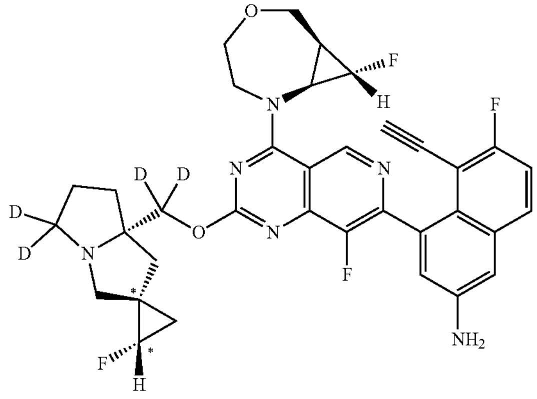

Example 275
structure arbitrarily assigned

Example 275 was prepared in a manner similar to Example 274. MS: m/z=649.3 $[M+H]^{+}$. $^{1}H$ NMR (400 MHz, Dimethylsulfoxide-$d_6$) δ 9.48-9.29 (m, 1H), 7.86-7.68 (m, 1H), 7.40-7.29 (m, 1H), 7.11-7.00 (m, 2H), 5.72-5.56 (m, 2H), 4.98-4.63 (m, 2H), 4.55-4.46 (m, 1H), 4.44-4.26 (m, 2H), 4.11-3.78 (m, 2H), 3.76-3.55 (m, 2H), 3.26-3.19 (m, 1H), 2.87-2.80 (m, 1H), 2.54 (s, 1H), 2.40-2.28 (m, 1H), 2.06-1.99 (m, 1H), 1.98-1.90 (m, 1H), 1.89-1.77 (m, 2H), 1.77-1.58 (m, 2H), 0.93-0.71 (m, 2H). $^{19}F$ NMR (376 MHz, Dimethylsulfoxide-$d_6$) δ −113.36, −113.40, −133.44, −139.91, −140.48, −207.70, −207.78, −209.89, −209.95.

Example 287: 5-Ethynyl-6-fluoro-4-(8-fluoro-2-(((2R,5R,7aS)-2-fluoro-5-methyltetrahydro-1H-pyrrolizin-7a (5H)-yl)methoxy)-4-((15,7S,8S)-8-fluoro-5-oxa-2-azabicyclo[5.1.0]octan-2-yl)pyrido[4,3-d]pyrimidin-7-yl)naphthalen-2-amine

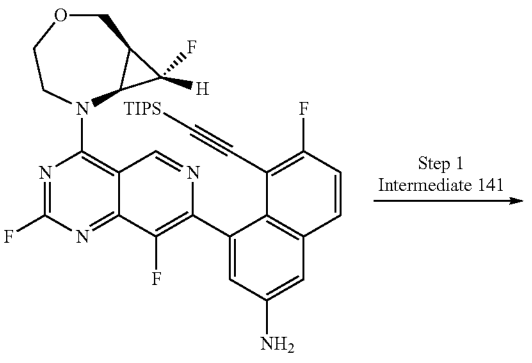

Intermediate 118

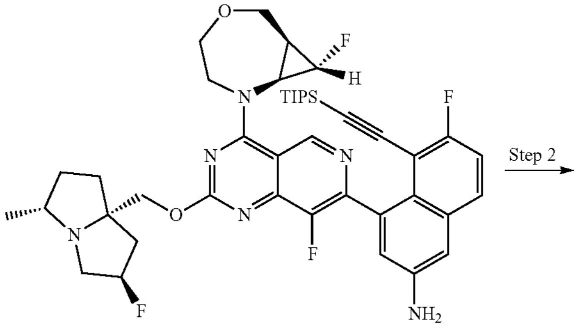

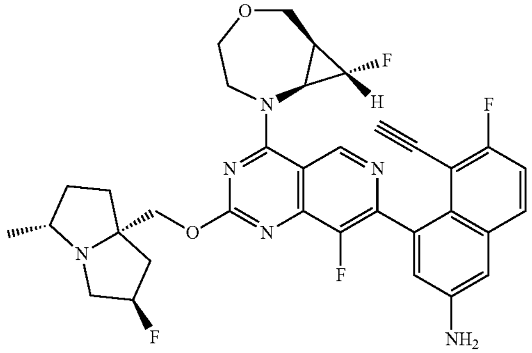

Example 287

Step 1: 6-Fluoro-4-(8-fluoro-2-(((2R,5R,7aS)-2-fluoro-5-methyltetrahydro-1H-pyrrolizin-7a (5H)-yl)methoxy)-4-((15,7S,8S)-8-fluoro-S-oxa-2-azabicyclo[5.1.0]octan-2-yl)pyrido[4,3-d]pyrimidin-7-yl)-5-((triisopropylsilyl) ethynyl)naphthalen-2-amine To an ice-cooled solution of Intermediate 141 (35.97 mg, 0.20 mmol) in THE (2 mL) under $N_2$ was added t-BuOK (23.30 mg, 0.20 mmol). The mixture was stirred in an ice bath for 30 min. Intermediate 118 (110 mg, 0.17 mmol) was added to the above mixture. The ice bath was removed, and the reaction mixture was stirred at room temperature for 1 hour. The resulting mixture was quenched with aq. $NH_4Cl$ (10 mL) in an ice bath and extracted with EtOAc (3×20 mL). The combined organic layers were washed with brine (20 mL), dried over anhydrous $Na_2SO_4$, filtered and concentrated under reduced pressure. The residue was purified by Prep-TLC ($CH_2Cl_2$/MeOH 15: 1) to afford the title compound (120 mg, 87% yield) as a yellow solid. MS: m/z=789.30 $[M+H]^{+\cdot}$ Step 2: S-Ethynyl-6-fluoro-4-(8-fluoro-2-(((2R,5R,7aS)-2-fluoro-5-methyltetrahydro-1H-pyrrolizin-7a (5H)-yl)methoxy)-4-((15,75,8S)-8-fluoro-5-oxa-2-azabicyclo[5.1.0]octan-2-yl)pyrido[4,3-d]pyrimidin-7-yl)naphthalen-2-amine To a solution of 6-fluoro-4-(8-fluoro-2-(((2R,5R,7aS)-2-fluoro-5-methyltetrahydro-1H-pyrrolizin-7a (5H)-yl) methoxy)-4-((1S,75,8S)-8-fluoro-5-oxa-2-azabicyclo[5.1.0]octan-2-yl)pyrido[4,3-d]pyrimidin-7-yl)-5-((triisopropylsilyl) ethynyl)naphthalen-2-amine (120 mg, 0.15 mmol) in DMF (2 mL) was added CsF (462.06 mg, 3.04 mmol) at room temperature. The reaction mixture was stirred at room temperature for 1 hour. The resulting mixture was filtered and purified by RP-Flash directly with the following conditions: Column, C18; Mobile phase A: 5 mM aq. $NH_4HCO_3$; Mobile phase B: MeCN; Gradient: 2% B~95% B in 40 min, 53% B hold 3 mins; Flow rate: 25 mL/min; Detector UV: 254 & 210 nm. The collected fractions were combined, concentrated and lyophilized overnight to give the title compound (Example 287, 66 mg, 68% yield) as a yellow lyophilized powder. MS: m/z=633.45 $[M+H]^+$. $^1H$ NMR (400 MHz, DMSO-$d_6$) δ 9.42-9.37 (m, 1H), 7.80-7.76 (m, 1H), 7.36-7.32 (m, 1H), 7.06-7.05 (m, 2H), 5.66-5.64 (m, 2H), 5.27-5.13 (m, 1H), 4.97-4.73 (m, 1H), 4.51-4.32 (m, 3H), 4.11-3.80 (m, 4H), 3.72-3.56 (m, 2H), 3.30-2.95 (m, 4H), 2.40-2.31 (m, 2H), 1.90-1.67 (m, 4H), 1.64-1.51 (m, 1H), 1.13-1.11 (m, 3H). $^{19}F$ NMR (376 MHz, DMSO-$d_6$) δ −113.43--113.43 (d, 1F), −139.86--140.27 (d, 1F), −172.07--179.04 (m, 1F), −207.73 (s, 1F).

Example 291: 4-(5-Chloro-8-fluoro-4-((15,7S,8S)-8-fluoro-5-oxa-2-azabicyclo[5.1.0]octan-2-yl)-2-(((2R,7aS)-2-fluorotetrahydro-LH-pyrrolizin-7a (5H)-yl) methoxy-$d_2$)pyrido[4,3-d]pyrimidin-7-yl)-5-ethynyl-6-fluoronaphthalen-2-amine

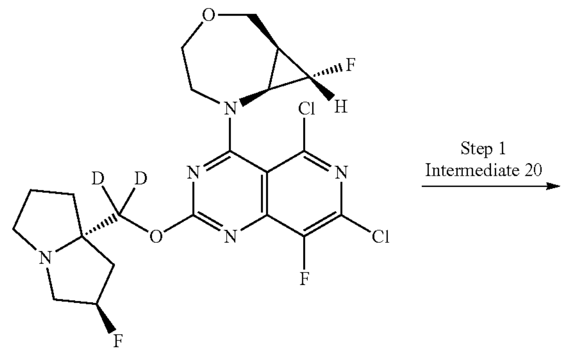

Intermediate 149

-continued

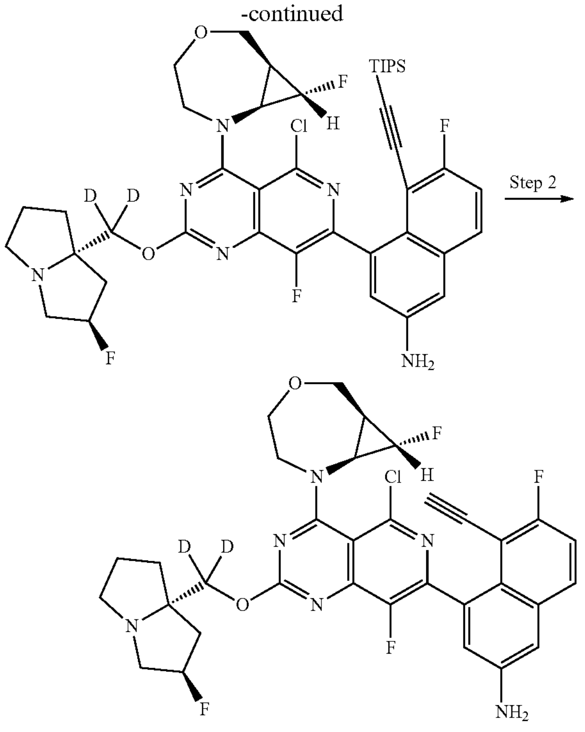

Example 291

Step 1: 4-(5-Chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-6-fluoro-5-((triisopropylsilyl) ethynyl)naphthalen-2-amine A mixture of Intermediate 149 (250 mg, 494 μmol), Intermediate 20 (311 mg, 617 μmol), $Cs_2CO_3$ (603 mg, 1.85 mmol) and $Ad_2nBuP\text{-}Pd\text{-}G_3$ (cataCXiumAPdG$_3$) (45 mg, 62 μmol) in 1,4-dioxane (3 mL) and $H_2O$ (0.5 mL) was degassed and purged with $N_2$ three times, and the mixture was stirred at 100° C. for 2 h under $N_2$. The reaction mixture was concentrated under reduced pressure. The residue was purified by silica gel flash chromatography (eluent: 0~5% of MeOH in $CH_2Cl$) to give the title compound (120 mg, 25% yield) as a yellow solid and crude desired product (80 mg, 70% purity) as a yellow solid. MS: m/z=811.3 $[M+H]^+$

Step 2: 4-(5-Chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6-fluoronaphthalen-2-amine To a solution of 4-(5-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-6-fluoro-5-((triisopropylsilyl) ethynyl)naphthalen-2-amine (40 mg, 49.3 μmol) in DMSO (1 mL) was added CsF (15 mg, 99 μmol). The mixture was stirred at 25° C. for 10 min. The residue was diluted with water (10 mL) and extracted with EtOAc (20 mL×3). The combined organic layers were washed with brine (50 mL), dried over anhydrous $Na_2SO_4$, filtered and concentrated under reduced pressure. The residue was dissolved with $CH_2Cl_2$ (1 mL). MTBE (10 mL) was added to the solution. The mixture was filtered, and the filter cake was washed with MTBE (5 mL) and dried under reduced pressure to give the title compound (Example 291, 27.3 mg, 84% yield) as a yellow solid. MS: m/z=655.0 $[M+H]^+$. $^1H$ NMR (400 MHZ, Dimethylsulfoxide-$d_6$) δ 7.85-7.74 (m, 1H), 7.40-7.31 (m, 1H), 7.23-6.90 (m, 2H), 5.79-5.61 (m, 2H), 5.39-5.12 (m, 1H), 4.56-4.23 (m, 4H), 4.20-3.95 (m, 2H), 3.84-3.60 (m, 2H), 3.11-2.79 (m, 5H), 2.25-1.96 (m, 4H), 1.87-1.69 (m, 3H). $^{19}F$ NMR (376 MHZ, Dimethylsulfoxide-$d_6$) δ −112.85, −130.05, −140.96, −142.00, −172.11, −172.20, −206.13.

Example 303: 4-(5,8-Difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6-fluoronaphthalen-2-amine

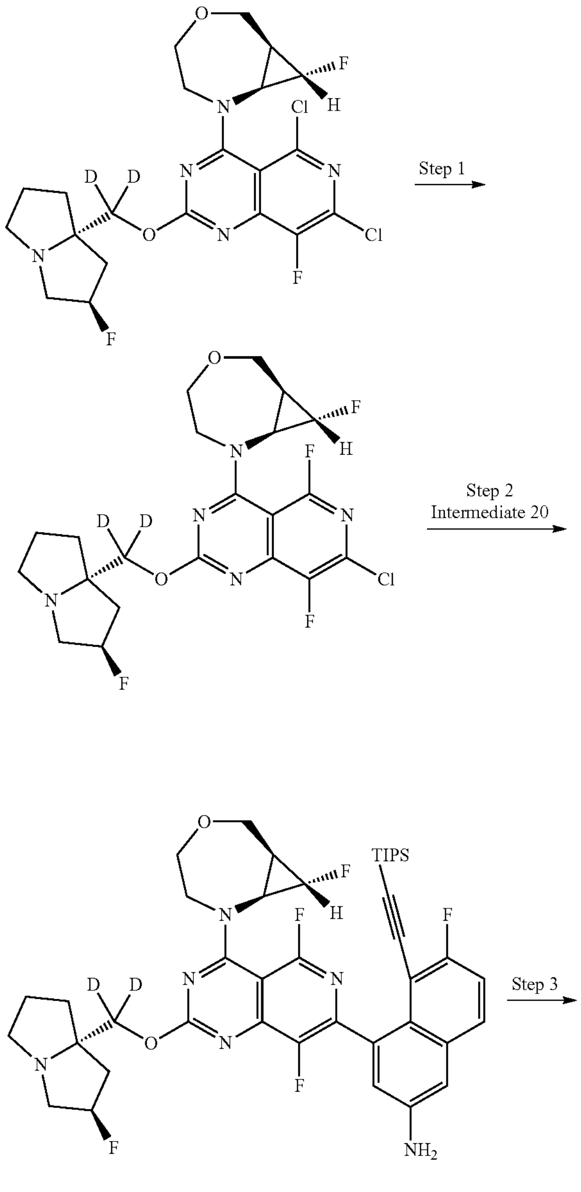

-continued

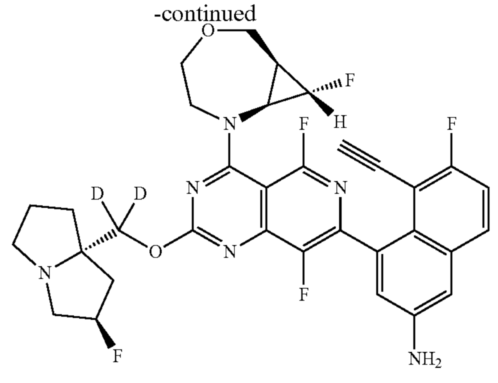

Example 303

Step 1: (15,75,8S)-2-(7-Chloro-5,8-difluoro-2-(((2R, 7aS)-2-fluorotetrahydro-1H-pyrrolizin-7a (5H)-yl) methoxy-$d_2$)pyrido[4,3-d]pyrimidin-4-yl)-8-fluoro-5-oxa-2-azabicyclo[5.1.0]octane To a solution of (1S,75,8S)-2-(5,7-dichloro-8-fluoro-2-(((2R,7aS)-2-fluorotetrahydro-1H-pyrrolizin-7a (5H)-yl) methoxy-$d_2$)pyrido[4,3-d]pyrimidin-4-yl)-8-fluoro-5-oxa-2-azabicyclo[5.1.0]octane (50 mg, 98.8 μmol, refer to Example 291 for detail procedures) in DMSO (1 mL) was added CsF (30 mg, 197 μmol). The mixture was stirred at 50° C. for 5 h. The reaction mixture was diluted with water (10 mL) and extracted with EtOAc (20 mL×3). The combined organic layers were washed with brine (50 mL), dried over $Na_2SO_4$, filtered and concentrated under reduced pressure to give the title compound (48 mg, crude) as a yellow solid. MS: m/z=489.9 $[M+H]^{+\cdot}$ Step 2: 4-(5,8-Difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-6-fluoro-5-((triisopropylsilyl) ethynyl)naphthalen-2-amine A mixture of (1S,7S,8S)-2-(7-chloro-5,8-difluoro-2-(((2R,7aS)-2-fluorotetrahydro-1H-pyrrolizin-7a (5H)-yl) methoxy-$d_2$)pyrido[4,3-d]pyrimidin-4-yl)-8-fluoro-5-oxa-2-azabicyclo[5.1.0]octane (43 mg, 74 μmol), Intermediate 20 (74 mg, 147 μmol), $Cs_2CO_3$ (96 mg, 295 μmol) and AdenBuP-Pd-$G_3$ (cataCXiumAPdGs) (5 mg, 7.37 μmol) in 1,4-dioxane (5 mL) and $H_2O$ (1 mL) was degassed and purged with $N_2$ three times. The mixture was stirred at 110° C. for 1 h under $N_2$. The reaction mixture was concentrated under reduced pressure. The residue was purified by silica gel flash chromatography (eluent: 0~5% of MeOH in $CH_2Cl_2$) to give the title compound (30 mg, 50% yield over 2 steps) as a yellow solid MS: m/z=795.3 $[M+H]^{+\cdot}$ Step 3: 4-(5,8-Difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6-fluoronaphthalen-2-amine To a solution of 4-(5,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido [4,3-d]pyrimidin-7-yl)-6-fluoro-5-((triisopropylsilyl) ethynyl)naphthalen-2-amine (30 mg, 37.7 μmol) in DMSO (1 mL) was added CsF (17 mg, 113 μmol). The mixture was stirred at 25° C. for 0.5 h. The reaction mixture was diluted with water (10 mL) and extracted with EtOAc (20 mL×3). The combined organic layers were washed with brine (50 mL), dried over $Na_2SO_4$, filtered and concentrated under reduced pressure. The residue was dissolved in $CH_2Cl$ (1 mL). MTBE (10 mL) was added to the solution. The mixture was filtered, and the filter cake was washed with MTBE (5 mL), dried under reduced pressure to give the title compound (Example 303, 13.8 mg, 57% yield) as a yellow solid. MS: m/z=639.0 $[M+H]^+$. $^1H$ NMR (400 MHZ, Dimethylsulfoxide-$d_6$) δ 7.84-7.70 (m, 1H), 7.46-7.30 (m, 1H), 7.16-6.96 (m, 2H), 5.74-5.59 (m, 2H), 5.37-5.18 (m, 1H), 4.84-4.49 (m, 1H), 4.48-4.26 (m, 2H), 4.22-3.90 (m, 3H), 3.78-3.58 (m, 2H), 3.13-2.93 (m, 4H), 2.87-2.78 (m, 1H), 2.31-2.12 (m, 2H), 2.06-1.95 (m, 2H), 1.89-1.69 (m, 3H). $^{19}F$ NMR (376 MHz, Dimethylsulfoxide-$d_6$) δ −51.04, −51.49, −113.00, −113.13, −142.30, −142.47, −142.60, −171.96, −172.08, −172.17, −172.28, −206.51.

Example 312: 5-Ethynyl-6-fluoro-4-(8-fluoro-4-((15,75,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl) methoxy-$d_2$)pyrido[4,3-d]pyrimidin-7-yl) naphthalen-2-amine

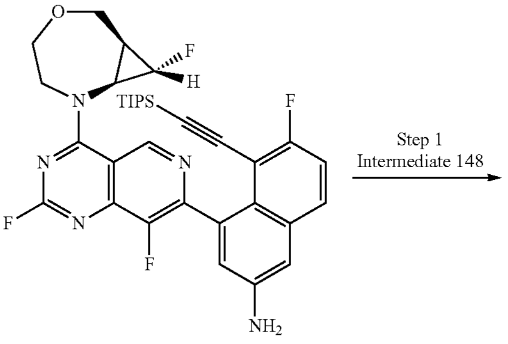

Intermediate 118

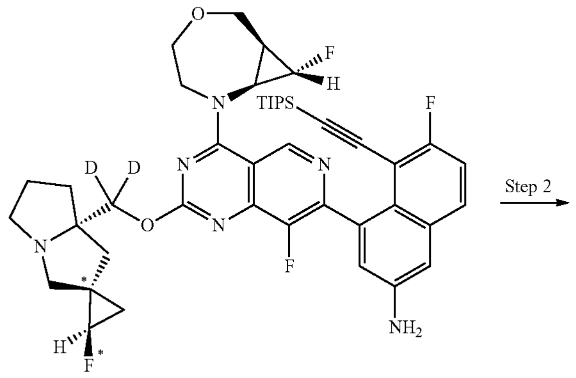

-continued

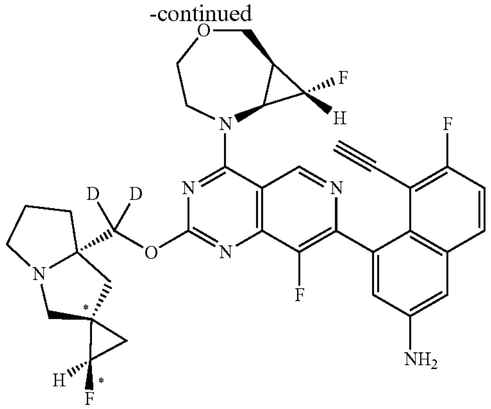

Example 312
structure arbitrarily assigned

Step 1: 6-Fluoro-4-(8-fluoro-4-((15,75,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy-$d_2$)pyrido[4,3-d]pyrimidin-7-yl)-5-((triisopropylsilyl) ethynyl) naphthalen-2-amine To a solution of Intermediate 148 (80 mg, 427 μmol) in THF (2 mL) was added dropwise t-BuOK (650 AL, 1 M in THF) at 25° C. under $N_2$. The mixture was stirred at this temperature for 30 min, and then Intermediate 118 (247 mg, 388 μmol) in THF (2 mL) was added dropwise at 0° C. The resulting mixture was stirred at 25° C. for 16 h. The mixture was quenched with sat. $NH_4Cl$ aq. (50 mL) and extracted with EtOAc (100 mL×3). The combined organic layers were washed with brine (100 mL), dried over $Na_2SO_4$, filtered and concentrated under reduced pressure. The residue was purified by silica gel flash chromatography (eluent: 0~10% MeOH in $CH_2Cl_2$) to give the title compound (200 mg, 64% yield) as a yellow solid. MS: m/z=803.2 $[M+H]^{+\cdot}$ Step 2: 5-Ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy-$d_2$) pyrido[4,3-d]pyrimidin-7-yl)naphthalen-2-amine To a solution of 6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy-$d_2$)pyrido[4,3-d]pyrimidin-7-yl)-5-((triisopropylsilyl) ethynyl)naphthalen-2-amine (200 mg, 249 μmol) in DMSO (2 mL) was added CsF (133 mg, 871 μmol). The mixture was stirred at 25° C. for 0.5 h and filtered. The filtrate was purified by reversed-phase column (column: C18; mobile phase: [Water (0.1% $NH_3$ $H_2O$)-ACN)]; B %: 5%~52% 30 min) to give the title compound (Example 312, 77.8 mg, 48% yield) as a yellow solid. MS: m/z=647.2 $[M+H]^+$. $^1H$ NMR (400 MHz, DimethylSulfoxide-$d_6$) 9.46-9.31 (m, 1H), 7.84-7.70 (m, 1H), 7.34 (t, J=8.8 Hz, 1H), 7.05 (s, 2H), 5.63 (s, 2H), 4.98-4.58 (m, 2H), 4.49 (d, J=14.0 Hz, 1H), 4.43-4.26 (m, 2H), 4.08-3.77 (m, 2H), 3.73-3.58 (m, 2H), 3.27-3.25 (m, 1H), 3.08 (d, J=11.2 Hz, 1H), 3.03-2.96 (m, 1H), 2.69-2.64 (m, 1H), 2.55-2.53 (m, 1H), 2.40-2.29 (m, 1H), 2.00-1.90 (m, 1H), 1.87-1.61 (m, 5H), 0.91-0.75 (m, 2H). $^{19}F$ NMR (376 MHz, Dimethyl Sulfoxide-$d_6$) δ −113.32, −113.40, −139.89, −140.47, −206.82, −206.91, −207.70.

Example 316: 4-(4-((1R,75,8R)-8-Chloro-2-oxa-6-azabicyclo[5.1.0]octan-6-yl)-8-fluoro-2-(((2R,7aS)-2-fluorotetrahydro-1H-pyrrolizin-7a (5H)-yl) methoxy-$d_2$)pyrido[4,3-d]pyrimidin-7-yl)-5-ethynyl-6-fluoronaphthalen-2-amine

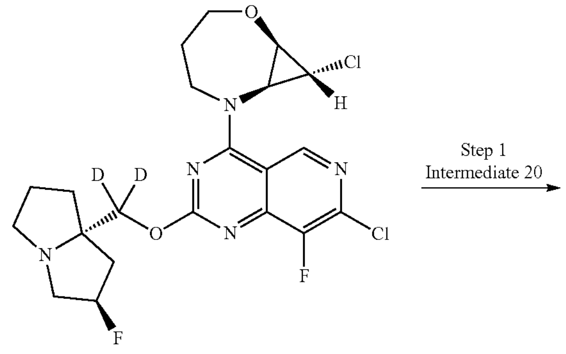

Intermediate 173

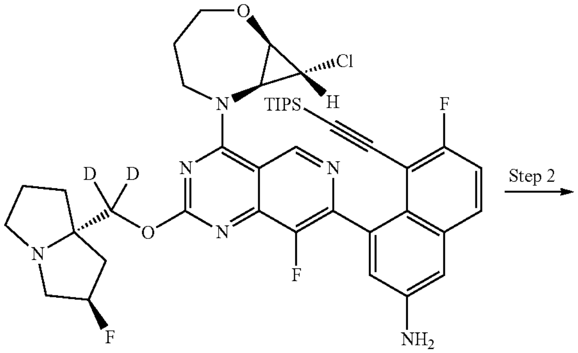

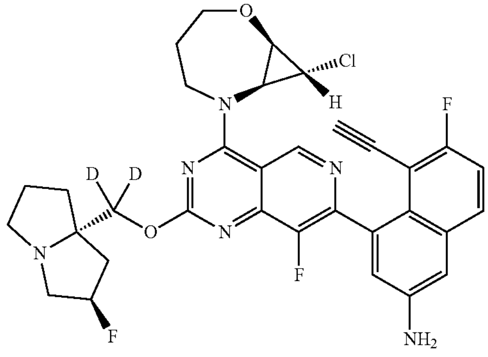

Example 316

Step 1: 4-(4-((1R,7S,8R)-8-chloro-2-oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-6-fluoro-5-((triisopropylsilyl) ethynyl)naphthalen-2-amine To a mixture of Intermediate 173 (100 mg, 0.21 mmol) and Intermediate 20 (206.39 mg, 0.41 mmol) in THF (4.0 mL) and $H_2O$ (0.8 mL) under $N_2$ were added CataCXium A Pd G3 (29.83 mg, 0.04 mmol) and $K_3PO_4$ (260.79 mg, 1.23 mmol) at room temperature. The reaction mixture was heated at 80° C. for 3 hours. The resulting mixture was cooled to room temperature, filtered and concentrated under reduced pressure. The residue was purified by Prep-TCL (MeOH: DCM=1: 10) to afford the title compound (90 mg, 55% yield) as a yellow solid. MS: m/z=793.50 $[M+H]^{+.}$ Step 2: 4-(4-((1R,7S,8R)-8-chloro-2-oxa-6-azabicyclo[5.1.0]octan-6-yl)-8-fluoro-2-(((2R,7aS)-2-fluoro-tetrahydro-1H-pyrrolizin-7a (5H)-yl)methoxy-$d_2$) pyrido[4,3-d]pyrimidin-7-yl)-5-ethynyl-6-fluoronaphthalen-2-amine To a stirred solution of 4-(4-((1R,7S,8R)-8-chloro-2-oxa-6-azabicyclo[5.1.0]octan-6-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-6-fluoro-5-((triisopropylsilyl) ethynyl)naphthalen-2-amine (80 mg, 0.10 mmol) in DMF (2.0 mL) was added CsF (153.16 mg, 1.0 mmol) at room temperature. The reaction mixture was stirred at room temperature for 2 hours. The resulting mixture was filtered and purified by RP-Flash directly with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 56% B in 15 min, 56% B to 56% B in 3 min, 56% B to 95% B in 4 min; Detector: UV 254 & 210 nm; RT: 20 min. The collected fractions were combined, concentrated and lyophilized overnight to give the title compound (Example 316, 35.7 mg, 55% yield) as a yellow lyophilized powder. MS: m/z=637.20 $[M+H]^+$. $^1H$ NMR (400 MHz, DMSO-$d_6$) δ 9.25-9.22 (m, 1H), 7.79-7.75 (m, 1H), 7.36-7.31 (m, 1H), 7.05-7.03 (m, 2H), 5.66-5.63 (m, 2H), 5.36-5.22 (m, 1H), 4.46-4.43 (m, 1H), 4.15-3.81 (m, 5H), 3.77-3.53 (m, 2H), 3.10-3.02 (m, 3H), 2.84-2.82 (m, 1H), 2.19-1.70 (m, 8H). $^{19}F$ NMR (376 MHZ, DMSO-$d_6$) δ −113.45-−113.57 (d, 1F), −140.39 (s, 1F), −172.01-−172.13 (d, 1F).

Example 329: 5-Ethynyl-6-fluoro-4-(4-((15,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylpyrido[4,3-d]pyrimidin-7-yl)naphthalen-2-amine

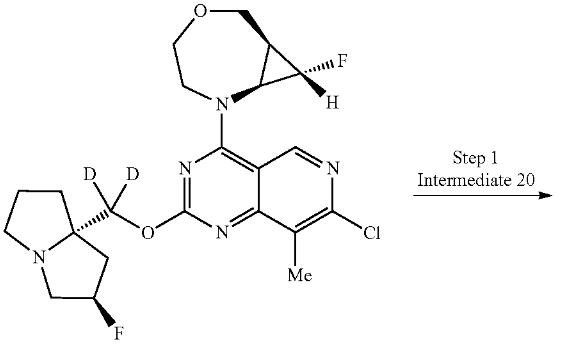

Intermediate 142

-continued

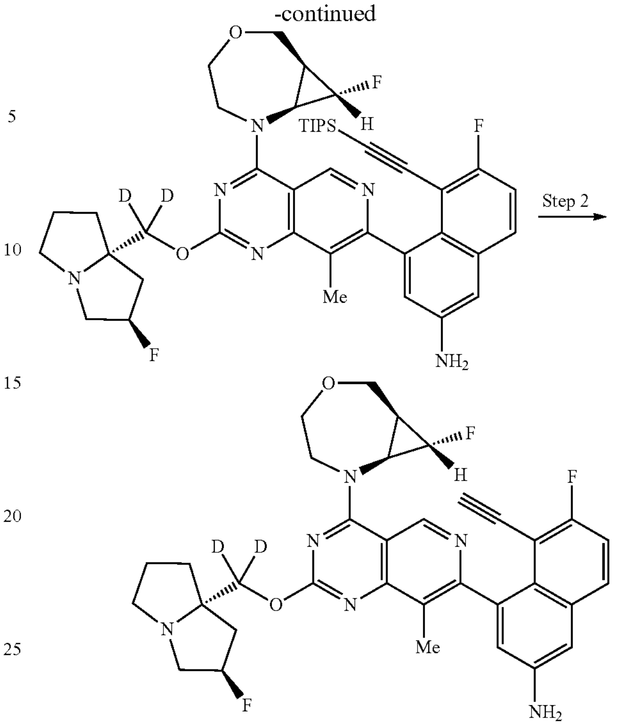

Example 329

Step 1: 6-Fluoro-4-(4-((15,7S,8S)-8-fluoro-5-oxa-2-azabicyclo[5.1.0]octan-2-yl)-2-(((2R,7aS)-2-fluoro-tetrahydro-1H-pyrrolizin-7a (5H)-yl)methoxy-$d_2$)-8-methylpyrido[4,3-d]pyrimidin-7-yl)-5-((triisopropylsilyl) ethynyl)naphthalen-2-amine To a solution of Intermediate 142 (110 mg, 0.24 mmol) and Intermediate 20 (296.17 mg, 0.59 mmol) in THF (4 mL) and $H_2O$ (0.8 mL) were added CataCXium A Pd G3 (34.24 mg, 0.05 mmol) and $K_3PO_4$ (299.39 mg, 1.41 mmol) at room temperature under $N_2$. The reaction mixture was heated at 80° C. for 16 hours. The resulting mixture was cooled to room temperature, diluted with $H_2O$ (8 mL), and extracted with ethyl acetate (3×15 mL). The combined organic layers were washed with brine (20 mL), dried over anhydrous sodium sulfate, filtered and concentrated under reduced pressure. The residue was purified by Prep-TLC ($CH_2Cl_2$/MeOH 15: 1) to afford the title compound (120 mg, 66% yield) as a brown yellow solid. MS: m/z=773.40 $[M+H]^{+.}$ Step 2: 5-Ethynyl-6-fluoro-4-(4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)-8-methylpyrido[4,3-d]pyrimidin-7-yl) naphthalen-2-amine To a stirred solution of 6-fluoro-4-(4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylpyrido[4,3-d]pyrimidin-7-yl)-5-((triisopropylsilyl) ethynyl)naphthalen-2-amine (120 mg, 0.16 mmol) in DMF (2.0 mL) was added CsF (235.81 mg, 1.55 mmol) at room temperature. The reaction mixture was stirred at room temperature for 3 hours. The resulting mixture was filtered and purified by RP-Flash directly with the following conditions: C18 spherical, 20-30 um, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 50% B in 15 min, 50% B to 50% B in 3 min, 50% B to 95% B in 8 min; Detector: UV 254 & 210 nm. The collected fractions were combined, concentrated and lyophilized overnight to give the title compound (Example 329, 37.1 mg, 38% yield) as a yellow lyophilized powder. MS: m/z=617.40 $[M+H]^+$. JH NMR (400 MHZ, DMSO-$d_6$) δ 9.43-9.38 (m, 1H), 7.77-7.73 (m, 1H), 7.33-7.28 (m, 1H), 7.01-6.98 (m, 1H), 6.91-6.88 (m, 1H), 5.58 (s, 2H), 5.36-5.22 (m, 1H), 4.88-4.62 (m, 1H), 4.49-4.25 (m, 3H), 4.05-3.96 (m, 1H), 3.92 (s, 1H), 3.75-3.69 (m, 1H), 3.61-3.55 (m, 1H), 3.30-3.00 (m, 4H), 2.90-2.78 (m, 1H), 2.42-2.24 (m, 1H), 2.15-1.95 (m, 6H), 1.86-1.70 (m, 3H). $^{19}F$ NMR (376 MHZ, DMSO-$d_6$) δ −113.59--113.64 (d, 1F), −172.12--172.22 (d, 1F), −207.40 (s, 1F).

Example 331: 5-Ethynyl-4-(8-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-d)pyrido[4,3-d]pyrimidin-7-yl)-6-methylnaphthalen-2-amine

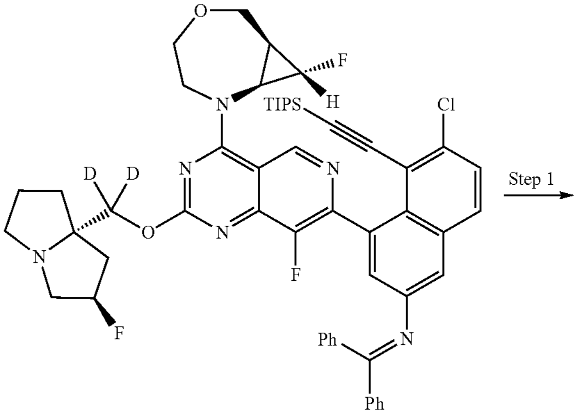

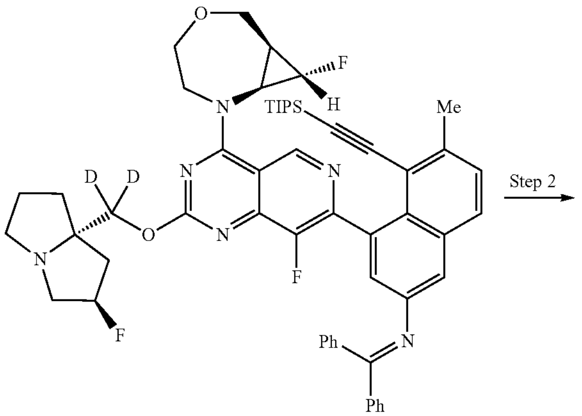

-continued

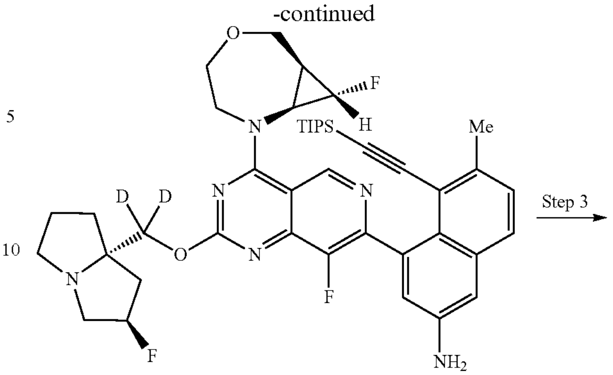

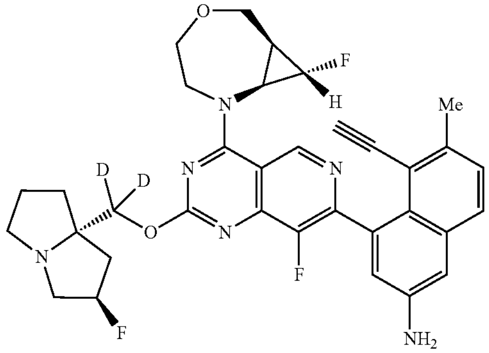

Example 331

Step 1: N-(4-(8-Fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-6-methyl-5-((triisopropylsilyl) ethynyl)naphthalen-2-yl)-1,1-diphenylmethanimine To a solution of N-(6-chloro-4-(8-fluoro-4-((15,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) pyrido[4,3~ d]pyrimidin-7-yl)-5-((triisopropylsilyl) ethynyl)naphthalen-2-yl)-1,1-diphenylmethanimine (130 mg, 0.14 mmol, refer to Example 267 for detail procedures) and trimethyl-1,3,5,2,4,6-trioxatriborinane (136.32 mg, 0.54 mmol, 50 wt % in THF) in 1,4-dioxane (1.3 mL) under $N_2$ were added CataCXium A Pd G3 (24 mg, 0.03 mmol) and $Cs_2CO_3$ (132.69 mg, 0.41 mmol) at room temperature. The reaction mixture was heated at 100° C. for 16 hours. The resulting mixture was cooled to room temperature, filtered and concentrated under reduced pressure. The residue was purified by Prep-TLC (DCM: MeOH=10: 1) to afford the title compound (100 mg, 78% yield, 55% purity, contained 22% De-C1 BP) as a brown solid. MS: m/z=937.45 $[M+H]^+$.

Step 2: 4-(8-fluoro-4-((15,7S,8S)-8-fluoro-5-oxa-2-azabicyclo[5.1.0]octan-2-yl)-2-(((2R,7aS)-2-fluoro-tetrahydro-1H-pyrrolizin-7a (5H)-yl)methoxy-$d_2$) pyrido[4,3-d]pyrimidin-7-yl)-6-methyl-5-((triisopropylsilyl) ethynyl)naphthalen-2-amine To a solution of N-(4-(8-fluoro-4-((15,7S,8S)-8-fluoro-5-oxa-2-azabicyclo[5.1.0]octan-2-yl)-2-(((2R,7aS)-2-fluoro-tetrahydro-1H-pyrrolizin-7a (5H)-yl)methoxy-$d_2$)pyrido[4,3-d]pyrimidin-7-yl)-6-methyl-5-((triisopropylsilyl) ethynyl) naphthalen-2-yl)-1,1-diphenylmethanimine (130 mg, 0.14 mmol) in EtOH (1.1 mL) were added NaOAc (22.76 mg, 0.28 mmol) and hydroxylamine hydrochloride (19.28 mg, 0.28 mmol) at room temperature. The reaction mixture was stirred at room temperature for 1 hour. The resulting was diluted with $H_2O$ (5 mL) and extracted with ethyl acetate (3×10 mL). The combined organic layers were washed with brine (10 mL), dried over anhydrous sodium sulfate, filtered and concentrated under reduced pressure. The residue was purified by Prep-TLC (DCM: MeOH=10: 1) to afford the title compound (99.8 mg, 93% yield, 50% purity) as a brown solid. MS: m/z=773.50 $[M+H]^{+\cdot}$ Step 3: 5-Ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-6-methylnaphthalen-2-amine To a solution of 4-(8-fluoro-4-((1S,7S,8S)-8-fluoro-5-oxa-2-azabicyclo[5.1.0]octan-2-yl)-2-(((2R,7aS)-2-fluoro-tetrahydro-1H-pyrrolizin-7a (5H)-yl)methoxy-$d_2$)pyrido[4,3-d]pyrimidin-7-yl)-6-methyl-5-((triisopropylsilyl) ethynyl) naphthalen-2-amine (100 mg, 0.13 mmol) in DMF (1 mL) was added CsF (393.01 mg, 2.58 mmol) at room temperature. The reaction mixture was stirred at room temperature for 1 hour. The resulting mixture was filtered and purified by Prep-HPLC with following conditions: Column: X-select CSH Prep Column, 19×250 mm, 5 um; Mobile Phase A: 10 mM aq. $NH_4HCO_3$; Mobile Phase B: MeCN; Flow rate: 25 mL/min; Gradient: 40% B to 70% B in 10 min; Detector: UV 254 nm & 220 nm. The product-containing fractions were combined, concentrated and lyophilized overnight to give the title compound (Example 331, 26.2 mg, 33% yield) as a yellow lyophilized powder. MS: m/z=617.30 $[M+H]^+$. $^1H$ NMR (400 MHz, DMSO-$d_6$) δ 9.41-9.34 (m, 1H), 7.62-7.60 (m, 1H), 7.30-7.28 (m, 1H), 6.98-6.94 (m, 2H), 5.54-5.53 (m, 2H), 5.35-5.21 (m, 1H), 4.98-4.77 (m, 1H), 4.51-4.31 (m, 3H), 4.11-3.53 (m, 4H), 3.33-2.98 (m, 4H), 2.89-2.79 (m, 1H), 2.40-2.22 (m, 4H), 2.15-1.93 (m, 3H), 1.91-1.69 (m, 3H). $^{19}F$ NMR (376 MHz, DMSO-$d_6$) δ −139.89--140.48 (d, 1F), −172.06--172.17 (d, 1F), −207.75 (s, 1F).

Example 333: 5-Ethynyl-6-fluoro-4-(8-fluoro-2-(((2R,3R,7aS)-2-fluoro-3-methyltetrahydro-1H-pyrrolizin-7a (5H)-yl)methoxy-$d_2$)-4-((1S,7S,8S)-8-fluoro-5-oxa-2-azabicyclo[5.1.0]octan-2-yl)pyrido[4,3-d]pyrimidin-7-yl)naphthalen-2-amine

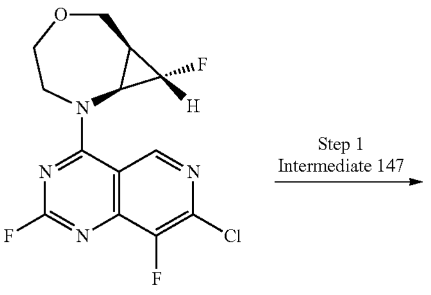

Intermediate 112

-continued

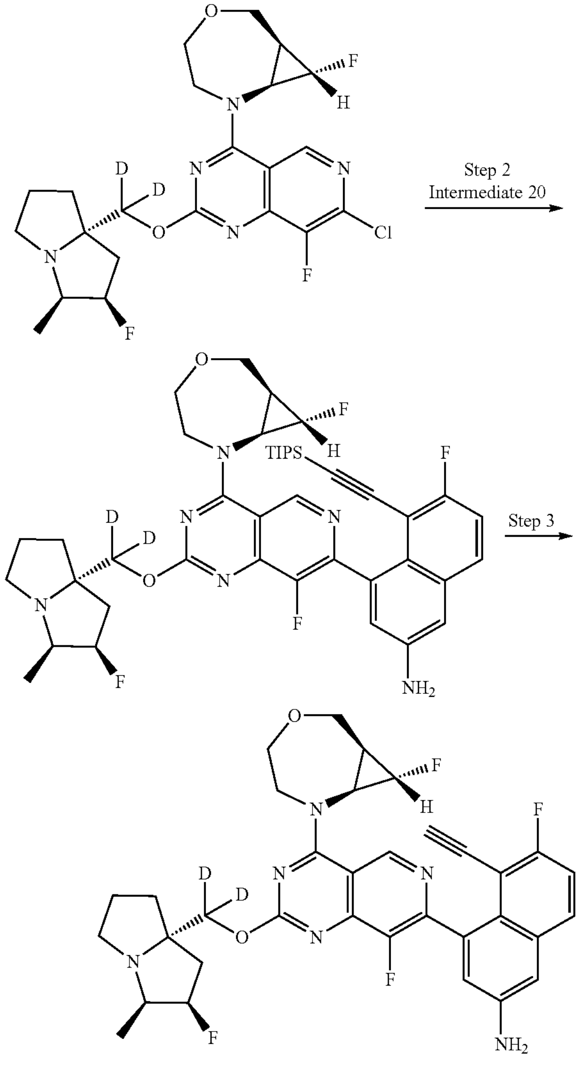

Example 333

Step 1: (1S,7S,8S)-2-(7-Chloro-8-fluoro-2-(((2R,3R,7aS)-2-fluoro-3-methyltetrahydro-1H-pyrrolizin-7a (5H)-yl)methoxy-$d_2$)pyrido[4,3-d]pyrimidin-4-yl)-8-fluoro-S-oxa-2-azabicyclo[5.1.0]octane To an ice-cooled solution of Intermediate 147 (100 mg, 0.57 mmol) in THF (1.6 mL) under $N_2$ was added t-BuOK (65.69 mg, 0.58 mmol). The mixture was stirred in an ice bath for 1 hour. A solution of Intermediate 112 (160 mg, 0.48 mmol) in THF (1.6 mL) was added to the above mixture. The ice bath was removed, and the reaction mixture was stirred at room temperature for 1 hour. The resulting mixture was quenched with sat. $NH_4Cl$ aq. (8 mL) and extracted with ethyl acetate (3×15 mL). The combined organic layers were washed with brine (15 mL), dried over anhydrous sodium sulfate, filtered and concentrated under reduced pressure. The residue was purified by Prep-TLC (DCM: MeOH=17: 1) to afford the title compound (170 mg, 72% yield) as a yellow solid. MS: m/z=486.05 $[M+H]^{+\cdot}$ Step 2: 6-Fluoro-4-(8-fluoro-2-(((2R,3R,7aS)-2-fluoro-3-methyltetrahydro-1H-pyrrolizin-7a (5H)-yl) methoxy-$d_2$)-4-((1S,7S,8S)-8-fluoro-5-oxa-2-azabicyclo[5.1.0]octan-2-yl)pyrido[4,3-d]pyrimidin-7-yl)-5-((triisopropylsilyl) ethynyl)naphthalen-2-amine To a solution of (1S,7S,8S)-2-(7-chloro-8-fluoro-2-(((2R,3R,7aS)-2-fluoro-3-methyltetrahydro-1H-pyrrolizin-7a (5H)-yl)methoxy-$d_2$)pyrido[4,3-d]pyrimidin-4-yl)-8-fluoro-5-oxa-2-azabicyclo[5.1.0]octane (100 mg, 0.21 mmol) and Intermediate 20 (278.6 mg, 0.54 mmol) in THF (4.4 mL) and $H_2O$ (0.89 mL) under $N_2$ were added CataCXium A Pd G3 (32.26 mg, 0.04 mmol) and $K_3PO_4$ (282 mg, 1.33 mmol) at room temperature. The reaction mixture was heated at 80° C. for 1 hour. The resulting mixture was cooled to room temperature, diluted with $H_2O$ (10 mL) and extracted with ethyl acetate (3x20 mL). The combined organic layers were washed with brine (20 mL), dried over anhydrous sodium sulfate, filtered and concentrated under reduced pressure. The residue was purified by Prep-TLC (DCM: MeOH=15:1) to afford the title compound (130 mg, 79% yield) as a brown solid. MS: m/z=791.25 $[M+H]^{+}$.

Step 3: 5-Ethynyl-6-fluoro-4-(8-fluoro-2-(((2R,3R,7aS)-2-fluoro-3-methyltetrahydro-LH-pyrrolizin-7a (5H)-yl)methoxy-$d_2$)-4-((15,75,8S)-8-fluoro-5-oxa-2-azabicyclo[5.1.0]octan-2-yl)pyrido[4,3-d]pyrimidin-7-yl)naphthalen-2-amine To a solution of 6-fluoro-4-(8-fluoro-2-(((2R,3R,7aS)-2-fluoro-3-methyltetrahydro-1H-pyrrolizin-7a (5/1)-yl) methoxy-$d_2$)-4-((1S,7S,8S)-8-fluoro-5-oxa-2-azabicyclo [5.1.0]octan-2-yl)pyrido[4,3-d]pyrimidin-7-yl)-5-((triisopropylsilyl) ethynyl)naphthalen-2-amine (124 mg, 0.16 mmol) in DMF (1.2 mL) was added CsF (476.25 mg, 3.14 mmol) at room temperature. The reaction mixture was stirred at room temperature for 2 hours. The resulting mixture was filtered and purified by RP-Flash with the following conditions: Column: C18, 40 g, 20-35 μm; Mobile Phase A: 5 mM aq. $NH_4HCO_3$; Mobile Phase B: MeCN; Gradient: 5% B to 5% B in 3 min, 5% B to 45% B in 15 min, 45% B to 45% B in 3 min, 45% B to 95% B in 4 min; Flow rate: 40 mL/min; Detector: UV 254 & 210 nm. The product-containing fractions were collected, concentrated and lyophilized overnight to give the title compound (Example 333, 59.2 mg, 59% yield) as a yellow lyophilized powder. MS: m/z=635.15 $[M+H]^+$. $^1$H NMR (400 MHZ, DMSO-$d_6$) δ 9.43-9.37 (m, 1H), 7.80-7.76 (m, 1H), 7.37-7.32 (m, 1H), 7.06-7.05 (m, 2H), 5.67-5.66 (m, 2H), 5.11-4.73 (m, 2H), 4.51-4.34 (m, 3H), 4.07-3.82 (m, 2H), 3.71-3.58 (m, 2H), 3.33-3.11 (m, 2H), 3.09-2.98 (m, 1H), 2.81-2.75 (m, 1H), 2.42-2.29 (m, 1H), 2.18-1.97 (m, 3H), 1.86-1.68 (m, 3H), 1.21-1.11 (m, 3H). $^{19}$F NMR (376 MHz, DMSO-$d_6$) δ −113.36--113.45 (d, 1F), −139.94--140.51 (d, 1F), −186.35--186.39 (d, 1F), −207.71 (s, 1F).

Example 340: 4-(4-((1S,75,8S)-8-Chloro-5-oxa-2-azabicyclo[5.1.0]octan-2-yl)-8-fluoro-2-(((2R,3R,7aS)-2-fluoro-3-methyltetrahydro-1H-pyrrolizin-7a (5H)-yl)methoxy-$d_2$)pyrido[4,3-d]pyrimidin-7-yl)-5-ethynyl-6-fluoronaphthalen-2-amine

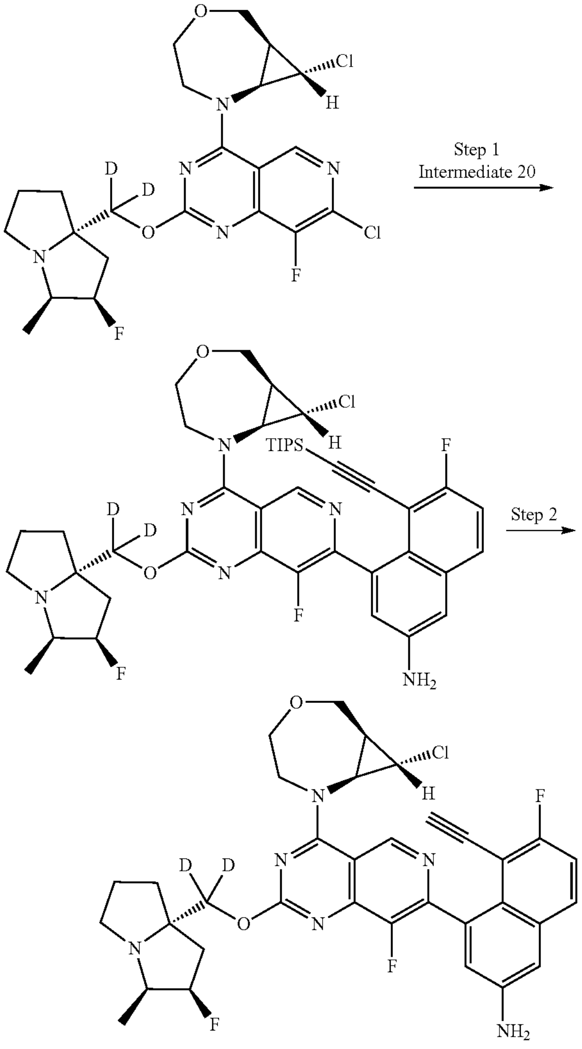

Example 340

Step 1: 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a (5H)-yl) methoxy-$d_2$)pyrido[4,3-d]pyrimidin-7-yl)-6-fluoro-5-((triisopropylsilyl) ethynyl)naphthalen-2-amine To a mixture of (15,75,8S)-8-chloro-2-(7-chloro-8-fluoro-2-(((2R,3R,7aS)-2-fluoro-3-methyltetrahydro-1H-pyrrolizin-7a (5H)-yl)methoxy-$d_2$)pyrido[4,3-d]pyrimidin-4-yl)-5-oxa-2-azabicyclo[5.1.0]octane (40 mg, 0.08 mmol) and Intermediate 20 (100.32 mg, 0.20 mmol) in THF (1.5 mL) and $H_2O$ (0.3 mL) were added CataCXium A Pd G3 (11.60 mg, 0.016 mmol) and $K_3PO_4$ (101.40 mg, 0.48 mmol) at room temperature under nitrogen atmosphere. The reaction mixture was heated at 80° C. for 3 hours. The resulting mixture was cooled to room temperature, diluted with water (10 mL) and extracted with DCM (3×10 mL). The combined organic layers were dried over anhydrous $Na_2SO_4$, filtered and concentrated under reduced pressure. The residue was purified by Prep-TLC ($CH_2Cl_2$/MeOH 15: 1) to afford the title compound (30 mg, 46% yield) as a yellow solid. MS: m/z=807.25 $[M+H]^{+\cdot}$ Step 2: 4-(4-((15,75,85)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a (5H)-yl) methoxy-$d_2$)pyrido[4,3-d]pyrimidin-7-yl)-5-ethynyl-6-fluoronaphthalen-2-amine To a solution of 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a (5H)-yl)methoxy-$d_2$) pyrido[4,3-d]pyrimidin-7-yl)-6-fluoro-5-((triisopropylsilyl) ethynyl)naphthalen-2-amine (30 mg, 0.04 mmol) in DMF (1.0 mL) was added CsF (112.87 mg, 0.74 mmol) at room temperature. The reaction mixture was stirred at room temperature for 1 hour. The resulting mixture was filtered and purified by RP-Flash directly with the following conditions: Column, C18; Mobile phase A: 5 mM aq. $NH_4HCO_3$; Mobile phase B: MeCN; Gradient: 2% B to 95% B in 40 min, 49% B hold 3 min; Flow rate: 25 mL/min; Detector: UV 254 & 210 nm. The collected fractions were combined, concentrated and then lyophilized overnight to give the title compound (Example 340, 7.1 mg, 29% yield) as a light-yellow lyophilized powder. MS: m/z=651.20 $[M+H]^+$. $^1H$ NMR (400 MHZ, DMSO-$d_6$) δ 9.38-9.32 (m, 1H), 7.80-7.76 (m, 1H), 7.36-7.31 (m, 1H), 7.06-7.02 (m, 2H), 5.66-5.64 (m, 2H), 5.10-4.97 (m, 1H), 4.48-4.34 (m, 2H), 4.22-4.18 (m, 1H), 4.05-3.76 (m, 3H), 3.79-3.55 (m, 2H), 3.30-3.10 (m, 2H), 3.05-2.95 (m, 1H), 2.86-2.80 (m, 1H), 2.19-1.95 (m, 4H), 1.78-1.65 (m, 3H), 1.25-1.22 (m, 3H). $^{19}F$ NMR (376 MHz, DMSO-$d_6$) δ-113.40--113.43 (d, 1F), −140.28--140.63 (d, 1F), −186.31--186.35 (d, 1F).

Example 341 & 342: 4-(4-((1R,7S,8R)-8-chloro-2-azabicyclo[5.1.0]octan-2-yl)-8-fluoro-2-(((2R,7aS)-2-fluorotetrahydro-1H-pyrrolizin-7a (5H)-yl) methoxy-$d_2$)pyrido[4,3-d]pyrimidin-7-yl)-5-ethynyl-6-fluoronaphthalen-2-amine & 4-(4-((1S,7R,8S)-8-chloro-2-azabicyclo[5.1.0]octan-2-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-S-ethynyl-6-fluoronaphthalen-2-amine

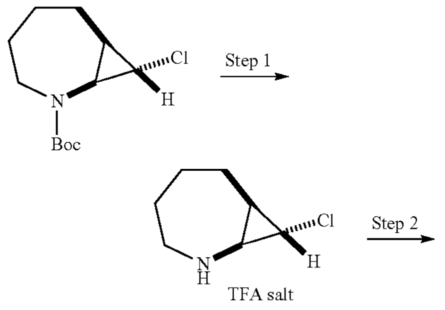

-continued

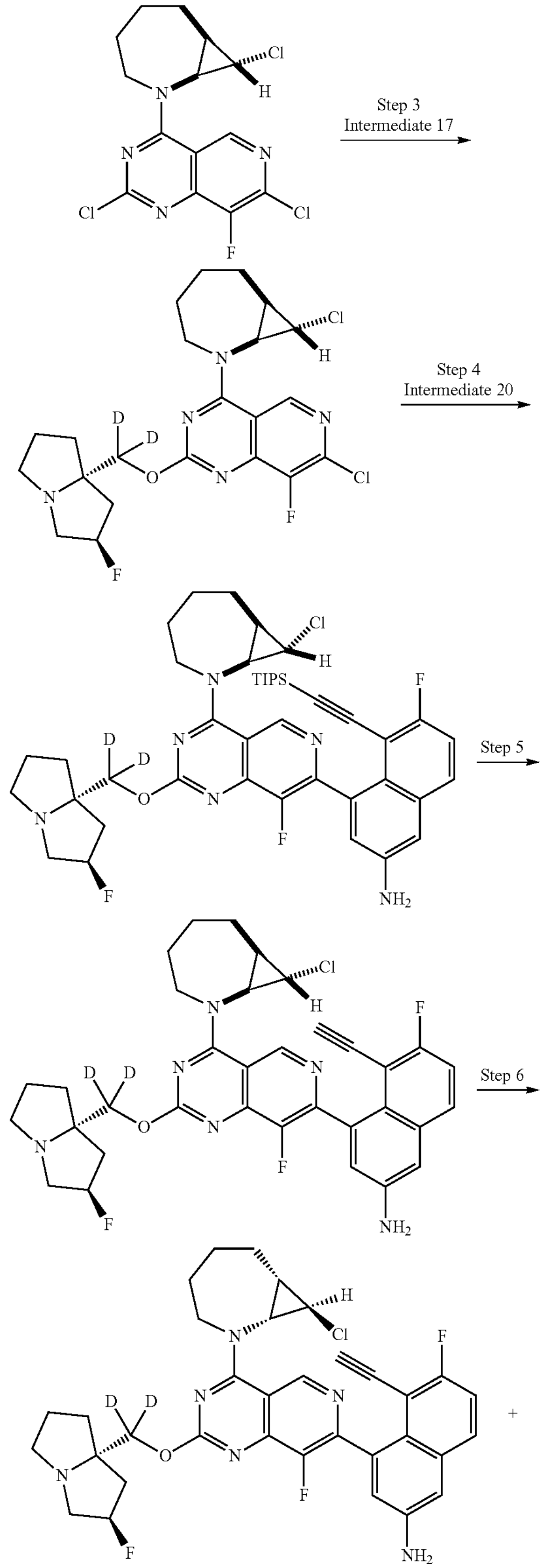

Example 341

-continued

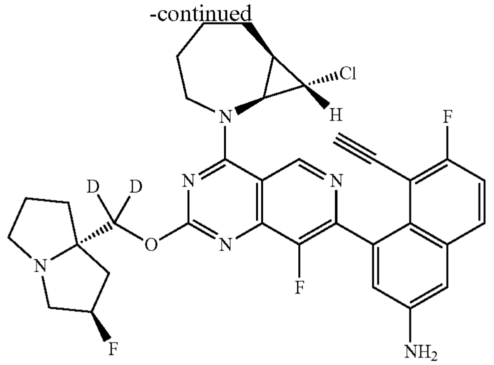

Example 342

Step 1: 8-Chloro-2-azabicyclo[5.1.0]octane (trans) (TFA salt)

To a solution of tert-butyl-8-chloro-2-azabicyclo[5.1.0] octane-2-carboxylate (trans) (380 mg, 1.55 mmol) in $CH_2Cl$ (6 mL) was added TFA (2 mL, 26.9 mmol) at 25° C. The reaction mixture was stirred at 25° C. for 0.5 h. The reaction mixture was concentrated under reduced pressure to the title compound (400 mg, crude, TFA salt) as a yellow oil, which was used in the next step without further purification. MS: m/z=146.2 $[M+H]^{+\cdot}$ Step 2: 2,7-Dichloro-4-(8-chloro-2-azabicyclo [5.1.0]octan-2-yl)-8-fluoropyrido[4,3-d]pyrimidine (trans)

To a solution of 2,4,7-trichloro-8-fluoropyrido[4,3-d]pyrimidine (428 mg, 1.69 mmol), DIPEA (1.34 mL, 7.70 mmol) in $CH_2Cl_2$ (16 mL) was added a solution of 8-chloro-2-azabicyclo[5.1.0]octane (trans) (400 mg, 1.54 mmol, TFA salt) in $CH_2Cl_2$ (2 mL) at −40° C. under $N_2$. The reaction mixture was stirred at −40° C. for 1 h under $N_2$. The reaction mixture was diluted with water (50 mL) and extracted with EtOAc (60 mL×2). The combined organic layers were washed with brine (50 mL×2), dried over anhydrous $Na_2SO_4$, filtered and concentrated under reduced pressure. The residue was purified by silica gel flash chromatography (eluent: 0~3% of MeOH in $CH_2Cl_2$) to give the title compound (437 mg, 74% yield over 2 steps) as a yellow solid. MS: m/z=360.9 $[M+H]^+$. $^1H$ NMR (400 MHZ, Dimethylsulfoxide-$d_6$) δ 9.25 (s, 1H), 4.44-4.29 (m, 1H), 4.12-3.94 (m, 1H), 3.42-3.35 (m, 2H), 2.36-2.21 (m, 1H), 1.96-1.76 (m, 3H), 1.71-1.60 (m, 1H), 1.53-1.40 (m, 1H), 1.17-1.03 (m, 1H). $^{19}F$ NMR (376 MHz, Dimethylsulfoxide-$d_6$) δ −136.04.

Step 3: 7-Chloro-4-(8-chloro-2-azabicyclo[5.1.0] octan-2-yl)-8-fluoro-2-(((2R,7aS)-2-fluorotetrahydro-1H-pyrrolizin-7a (5H)-yl)methoxy-$d_2$)pyrido [4,3-d]pyrimidine (trans)

To a solution of 2,7-dichloro-4-(8-chloro-2-azabicyclo [5.1.0]octan-2-yl)-8-fluoropyrido[4,3-d]pyrimidine (430 mg, 1.19 mmol), DIPEA (621 μL, 3.57 mmol) and Intermediate 17 (345 mg, 2.14 mmol) in 1,4-dioxane (4 mL) was stirred at 105° C. under $N_2$ for 16 h. The reaction mixture was concentrated under reduced pressure. The residue was purified by silica gel flash chromatography (eluent: 0~4% of MeOH in $CH_2Cl_2$) to give the title compound (460 mg, 78% yield) as a yellow solid. MS: m/z=486.1 $[M+H]^{+\cdot}$ Step 4: 4-(4-(8-chloro-2-azabicyclo[5.1.0]octan-2-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-6-fluoro-5-((triisopropylsilyl) ethynyl) naphthalen-2-amine (trans)

A mixture of 7-chloro-4-(8-chloro-2-azabicyclo[5.1.0]octan-2-yl)-8-fluoro-2-(((2R,7aS)-2-fluorotetrahydro-1H-pyrrolizin-7a (5H)-yl)methoxy-$d_2$)pyrido[4,3-d]pyrimidine (trans) (200 mg, 411 μmol), Intermediate 20 (249 mg, 493 μmol, HCl salt), $K_3PO_4$ (524 mg, 2.47 mmol) and AdenBuP-Pd-$G_3$ (cataCXiumAPd$G_3$) (60 mg, 82 μmol) in THE (5 mL) and $H_2O$ (1 mL) was degassed and purged with $N_2$ for 3 times and then the mixture was stirred at 80° C. under $N_2$ for 6 h. The reaction mixture was concentrated under reduced pressure to give a residue. The residue was purified by silica gel chromatography (eluent: 0~5% of MeOH in $CH_2Cl_2$) to give 4-(4-(8-chloro-2-azabicyclo[5.1.0]octan-2-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-6-fluoro-5-((triisopropylsilyl) ethynyl)naphthalen-2-amine (trans) (260 mg, 78% yield) as a yellow solid. MS: m/z=791.6 $[M+H]^{+\cdot}$ Step 5 & 6: 4-(4-((1R,7S,8R)-8-chloro-2-azabicyclo [5.1.0]octan-2-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-5-ethynyl-6-fluoronaphthalen-2-amine & 4-(4-((1S,7R,8S)-8-chloro-2-azabicyclo[5.1.0]octan-2-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6-fluoronaphthalen-2-amine To a solution of 4-(4-(8-chloro-2-azabicyclo[5.1.0]octan-2-yl)-8-fluoro-2-(((2R,7aS)-2-fluorotetrahydro-1H-pyrrolizin-7a (5H)-yl)methoxy-$d_2$)pyrido[4,3-d]pyrimidin-7-yl)-6-fluoro-5-((triisopropylsilyl) ethynyl)naphthalen-2-amine (trans) (255 mg, 322 μmol) in DMSO (3 mL) was added CsF (245 mg, 1.16 mmol). The reaction mixture was stirred at 25° C. for 1 h. The mixture was diluted with $H_2O$ (20 mL) and extracted with EtOAc (40 mL×2). The combined organic layers were dried over $Na_2SO_4$, filtered and concentrated under reduced pressure. The residue was dissolved with $CH_2Cl_2$ (2 mL). n-Hexane (20 mL) was added to the solution to give precipitate. The precipitate was filtered, and the filter cake was washed with n-hexane (10 mL), dried under reduced pressure to give 4-(4-(8-chloro-2-azabicyclo[5.1.0]octan-2-yl)-8-fluoro-2-(((2R,7aS)-2-fluorotetrahydro-1H-pyrrolizin-7a (5H)-yl)methoxy-$d_2$) pyrido[4,3-d]pyrimidin-7-yl)-5-ethynyl-6-fluoronaphthalen-2-amine (trans) (140 mg) as a yellow solid. It was separated by SFC (column: DAICEL CHIRALCEL OJ (250 mm×30 mm, 10 μm); mobile phase: [$CO_2$-MeOH (0.1% $NH_3$ $H_2O$)]; B %: 50%, isocratic elution mode) to give the title compound (Example 341, SFC peak RT: 1.841 min, 42.6 mg, 19% yield over 2 steps) as a yellow solid and the other compound (Example 342, SFC peak RT: 2.331 min, 43 mg, 20% yield over 2 steps) as a yellow solid. Spectra for Example 341: MS: m/z=635.1 $[M+H]^+$. $^1H$ NMR (400 MHZ, Dimethylsulfoxide-$d_6$) δ 9.37-9.23 (m, 1H), 7.83-7.72 (m, 1H), 7.40-7.24 (m, 1H), 7.09-6.97 (m, 2H), 5.70-5.57 (m, 2H), 5.39-5.15 (m, 1H), 4.43-4.30 (m, 1H), 4.08-3.73 (m, 2H), 3.43-3.33 (m, 2H), 3.12-2.99 (m, 3H), 2.87-2.77 (m, 1H), 2.36-2.30 (m, 1H), 2.15-2.10 (m, 1H), 2.06-1.97 (m, 2H), 1.95-1.90 (m, 1H), 1.87-1.72 (m, 5H), 1.58-1.15 (m, 3H). $^{19}$F NMR (376 MHz, Dimethylsulfoxide-$d_6$) δ −113.45, −113.47, −140.79, −172.06, −172.16. Spectra for Example 342: MS: m/z=635.1 $[M+H]^+$. $^1$H NMR (400 MHZ, Dimethylsulfoxide-$d_6$) δ 9.37-9.22 (m, 1H), 7.82-7.72 (m, 1H), 7.41-7.28 (m, 1H), 7.10-6.95 (m, 2H), 5.70-5.56 (m, 2H), 5.41-5.15 (m, 1H), 4.45-4.29 (m, 1H), 4.11-3.74 (m, 2H), 3.42-3.36 (m, 1H), 3.13-2.98 (m, 3H), 2.87-2.77 (m, 1H), 2.36-2.27 (m, 1H), 2.16-2.09 (m, 1H), 2.07-2.01 (m, 1H), 2.01-1.88 (m, 3H), 1.88-1.71 (m, 5H), 1.60-1.09 (m, 3H). $^{19}$F NMR (376 MHZ, Dimethylsulfoxide-$d_6$) δ −113.45, −140.79, −172.02, −172.13.

Example 353: 7-(3-Amino-8-ethynyl-7-fluoronaphthalen-1-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) quinazoline-6-carbonitrile

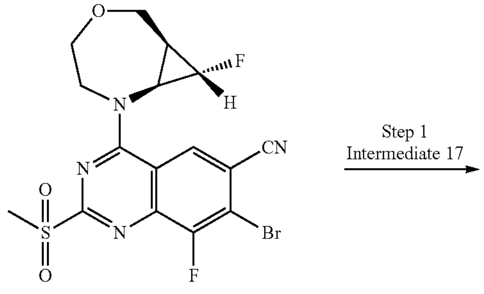

Intermediate 152

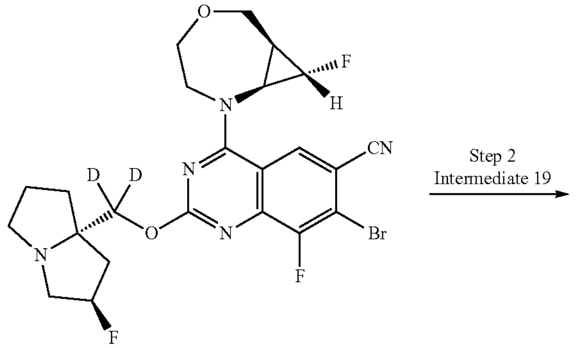

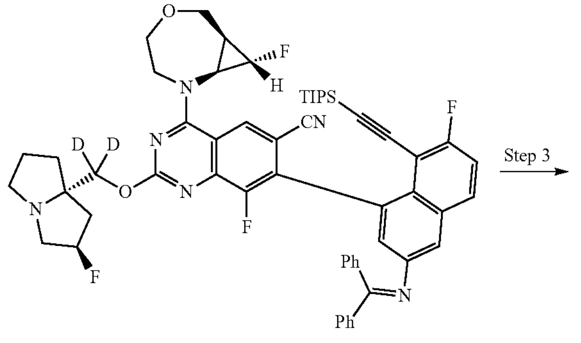

-continued

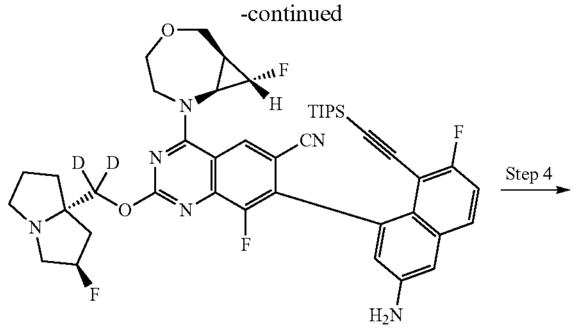

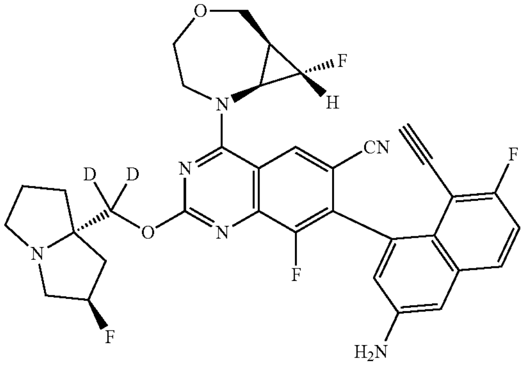

Example 353

Step 1: 7-Bromo-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) quinazoline-6-carbonitrile To an ice-cooled solution of Intermediate 17 (2.11 g, 13.06 mmol) in THF (40 mL) under $N_2$ was addedH-BuOK (1.47 g, 13.06 mmol). The mixture was stirred in an ice bath for 30 min. Intermediate 152 (4 g, 8.71 mmol) was added to the above mixture. The ice bath was removed, and the reaction mixture was heated at 40° C. for 2 hours. The resulting mixture was cooled, quenched with sat. $NH_4Cl$ (50 mL) aq. in an ice bath and extracted with EA (3×50 mL). The combined organic layers were washed with brine (50 mL), dried over anhydrous $Na_2SO_4$, filtered and concentrated under reduced pressure. The residue was purified by RP-Flash directly with the following conditions: C18 spherical, 20-30 μm, 100 A, 80 g; Mobile Phase A: 5 mM aq. $NH_4HCO_3$; Mobile Phase B: MeCN; Flow rate: 40 mL/min; Gradient: 5% B to 5% B in 3 min, 5% B to 65% B in 15 min, 65% B to 65% B in 3 min, 65% B to 95% B in 4 min; Detector: UV 254 & 210 nm. The collected fractions were combined, concentrated and lyophilized overnight to afford the title compound (3 g, 63% yield) as a yellow lyophilized powder. MS: m/z=540.15, 542.15 $[M+H]^{+\cdot}$ Step 2: 7-(3-((Diphenylmethylene) amino)-7-fluoro-8-((triisopropylsilyl) ethynyl)naphthalen-1-yl)-8-fluoro-4-((1S,7S,8S)-8-fluoro-5-oxa-2-azabicyclo [5.1.0]octan-2-yl)-2-(((2R,7aS)-2-fluorotetrahydro-1H-pyrrolizin-7a (5H)-yl)methoxy-$d_2$) quinazoline-6-carbonitrile To a mixture of 7-bromo-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) quinazoline-6-carbonitrile (300 mg, 0.56 mmol) and Intermediate 19 (701.41 mg, 1.11 mmol) in THF (1.0 mL) and $H_2O$ (0.2 mL) under $N_2$ were added CataCXium A Pd G3 (80.86 mg, 0.11 mmol) and $K_3PO_4$ (707.05 mg, 3.33 mmol) at room temperature. The reaction mixture was heated at 80° C. for 3 hours. The resulting mixture was cooled to room temperature, filtered and concentrated under reduced pressure. The residue was purified by silica gel flash chromatography (eluted with 8% MeOH in DCM) to afford the title compound (460 mg, 85% yield) as a yellow solid. MS: m/z=965,50 $[M+H]^{+\cdot}$ Step 3: 7-(3-Amino-7-fluoro-8-((triisopropylsilyl) ethynyl)naphthalen-1-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$) quinazoline-6-carbonitrile To a stirred solution of 7-(3-((diphenylmethylene) amino)-7-fluoro-8-((triisopropylsilyl) ethynyl)naphthalen-1-yl)-8-fluoro-4-((15,7S,8S)-8-fluoro-5-oxa-2-azabicyclo [5.1.0]octan-2-yl)-2-(((2R,7aS)-2-fluorotetrahydro-1H-pyrrolizin-7a (5H)-yl)methoxy-$d_2$) quinazoline-6-carbonitrile (460 mg, 0.48 mmol) in EtOH (5 mL) under $N_2$ were added NaOAc (78.19 mg, 0.95 mmol) and hydroxylamine hydrochloride (66.23 mg, 0.95 mmol) at room temperature. The reaction mixture was stirred at room temperature for 2 hours. The mixture was diluted with $H_2O$ (50 mL) and extracted with EA (3×50 mL). The combined organic layers were washed with brine (150 mL), dried over anhydrous $Na_2SO_4$, filtered and concentrated under reduced pressure. The residue was purified by silica gel flash chromatography (eluted with 8% MeOH in DCM) to afford the title compound (310 mg, 81% yield) as a light yellow solid. MS: m/z=801.40 $[M+H]^{+\cdot}$ Step 4: 7-(3-Amino-8-ethynyl-7-fluoronaphthalen-1-yl)-8-fluoro-4-((15,75,85)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) quinazoline-6-carbonitrile To a stirred solution of 7-(3-amino-7-fluoro-8-((triisopropylsilyl) ethynyl)naphthalen-1-yl)-8-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$) quinazoline-6-carbonitrile (310 mg, 0.387 mmol) in DMF (4.0 mL) was added CsF (881.82 mg, 5.81 mmol) at room temperature. The reaction mixture was stirred at room temperature for 2 hours. The resulting mixture was filtered and purified by RP-Flash directly with the following conditions: C18 spherical, 20-30 μm, 100 A, 40 g; Mobile Phase A: 5 mM aq. $NH_4HCO_3$; Mobile Phase B: MeCN; Flow rate: 40 mL/min; Gradient: 5% B to 5% B in 3 min, 5% B to 56% B in 15 min, 56% B to 56% B in 3 min, 56% B to 95% B in 4 min; Detector: UV 254 & 210 nm. The collected fractions were combined, concentrated and lyophilized overnight to give the title compound (Example 353, 170 mg, 75% yield) as a yellow lyophilized powder. MS: m/z=645.35 $[M+H]^+$. $^1H$ NMR (400 MHZ, DMSO-$d_6$) δ 8.70-8.67 (m, 1H), 7.84-7.80 (m, 1H), 7.40-7.35 (m, 1H), 7.10-7.09 (m, 1H), 7.04-7.01 (m, 1H), 5.73-5.71 (m, 2H), 5.34-5.21 (m, 1H), 4.84-4.70 (m, 1H), 4.49-4.37 (m, 3H), 4.08-3.90 (m, 2H), 3.75-3.55 (m, 2H), 3.40-3.00 (m, 4H), 2.88-2.80 (m, 1H), 2.40-2.25 (m, 1H), 2.12-1.75 (m, 6H). $^{19}F$ NMR (376 MHz, DMSO-$d_6$) δ −112.64--112.69 (d, 1F), ~124.93--125.42 (d, 1F), −172.09--172.21 (d, 1F), −208.18--208.59 (m, 1F).

Example 362: 5-Ethynyl-6-fluoro-4-(8-fluoro-4-((15,75,8S)-8-fluoro-5-oxa-2-azabicyclo[5.1.0]octan-2-yl)-2-(((R,E)-6'-(fluoromethylene) tetrahydrospiro[cyclopropane-1,1'-pyrrolizin]-7a'(5'H)-yl) methoxy)pyrido[4,3-d]pyrimidin-7-yl)naphthalen-2-amine

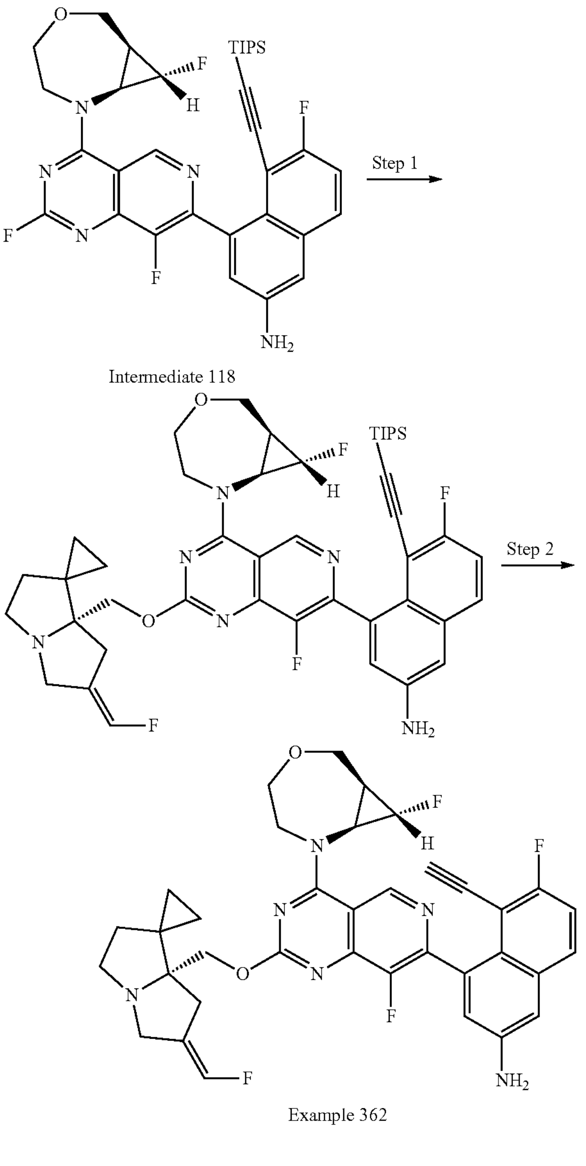

Step 1: 6-Fluoro-4-(8-fluoro-4-((15,7S,8S)-8-fluoro-5-oxa-2-azabicyclo[5.1.0]octan-2-yl)-2-(((R,E)-6'-(fluoromethylene) tetrahydrospiro[cyclopropane-1, 1'-pyrrolizin]-7a'(5'H)-yl)methoxy)pyrido[4,3-d] pyrimidin-7-yl)-5-((triisopropylsilyl) ethynyl) naphthalen-2-amine To a solution of (R,E)-(6'-(fluoromethylene) tetrahydrospiro[cyclopropane-1, 1'-pyrrolizin]-Ta'(5'H)-yl) methanol (50 mg, 253 μmol) in THE (1 mL) was added dropwise t-BuOK (304 AL, 1 M in THF) at 25° C. The mixture was stirred at this temperature for 30 min. A solution of Intermediate 118 (269 mg, 253 μmol) in THE (1 mL) was added dropwise to the above mixture at −40° C. The resulting mixture was stirred at 25° C. for 3 h. The reaction mixture was quenched with sat. $NH_4Cl$ aq. (2 mL) and extracted with EtOAc (5 mL×2). The combined organic layers were washed with brine (5 mL), dried over $Na_2SO_4$, filtered and concentrated under reduced pressure. The residue was purified by silica gel flash chromatography (cluent of 0~10% MeOH in $CH_2Cl_2$) to give the title compound (96 mg, 47% yield) as a yellow solid. MS: m/z=813.5 $[M+H]^{+}$.

Step 2: 5-Ethynyl-6-fluoro-4-(8-fluoro-4-((1S,7S,8S)-8-fluoro-5-oxa-2-azabicyclo[5.1.0]octan-2-yl)-2-(((R,E)-6'-(fluoromethylene) tetrahydrospiro[cyclopropane-1,1'-pyrrolizin]-7a'(5'H)-yl)methoxy)pyrido[4,3-d]pyrimidin-7-yl)naphthalen-2-amine To a solution of 6-fluoro-4-(8-fluoro-4-((1S,7S,8S)-8-fluoro-5-oxa-2-azabicyclo[5.1.0]octan-2-yl)-2-(((R,E)-6'-(fluoromethylene) tetrahydrospiro[cyclopropane-1, l'-pyrrolizin]-7a'(S'H)-yl)methoxy)pyrido[4,3-d]pyrimidin-7-yl)-5-((triisopropylsilyl) ethynyl)naphthalen-2-amine (96 mg, 118 μmol) in DMSO (2 mL) was added CsF (108 mg, 708 μmol) at 25° C. The mixture was stirred at 25° C. for 0.5 h. The reaction mixture was quenched with $H_2O$ (5 mL) and extracted with EtOAc (5 mL×2). The combined organic layers were washed with brine (5 mL), dried over $Na_2SO_4$, filtered and concentrated under reduced pressure. The residue was purified by silica gel flash chromatography (eluent of 0~10% MeOH in $CH_2Cl_2$) to give the title compound (Example 362, 34.7 mg, 45% yield) as a yellow solid. MS: m/z=657.0 $[M+H]^{+}$. $^{1}$H NMR (400 MHZ, Dimethylsulfoxide-$d_6$) δ 9.49-9.28 (m, 1H), 7.78 (dd, J=6.8, 9.2 Hz, 1H), 7.41-7.26 (m, 1H), 7.12-7.02 (m, 2H), 6.81 (d, J=86.0 Hz, 1H), 5.73-5.53 (m, 2H), 5.00-4.69 (m, 1H), 4.53-4.26 (m, 3H), 4.21-4.13 (m, 1H), 4.10-3.56 (m, 6H), 3.31-3.17 (m, 3H), 3.10-2.95 (m, 1H), 2.64-2.55 (m, 1H), 2.38-2.23 (m, 2H), 2.02-1,92 (m, 1H), 1.72-1.61 (m, 1H), 0.81-0.75 (m, 1H), 0.67-0.55 (m, 1H), 0.53-0.42 (m, 2H). $^{19}$F NMR (376 MHZ, Dimethylsulfoxide-$d_6$) δ −113.36, −113.42, −132.13, −132.22, −139.86, −140.37, −207.85.

Example 363: 5-Ethynyl-6-fluoro-4-(8-fluoro-4-((1S,7S,8S)-8-fluoro-5-oxa-2-azabicyclo[5.1.0]octan-2-yl)-2-(((R,Z)-6'-(fluoromethylene) tetrahydrospiro[cyclopropane-1,1'-pyrrolizin]-7a'(5'H)-yl) methoxy)pyrido[4,3-d]pyrimidin-7-yl)naphthalen-2-amine

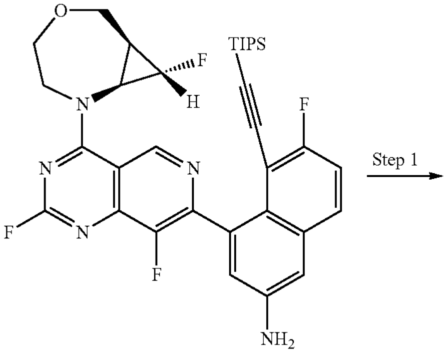

Intermediate 118

-continued

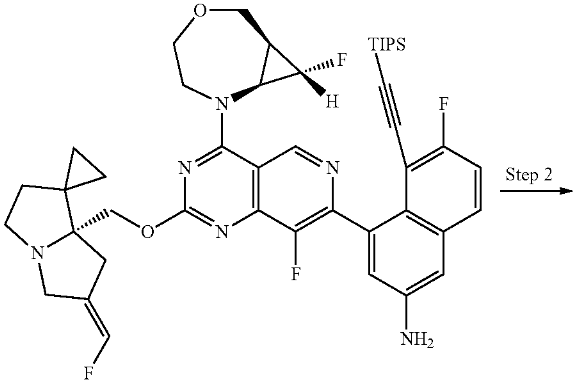

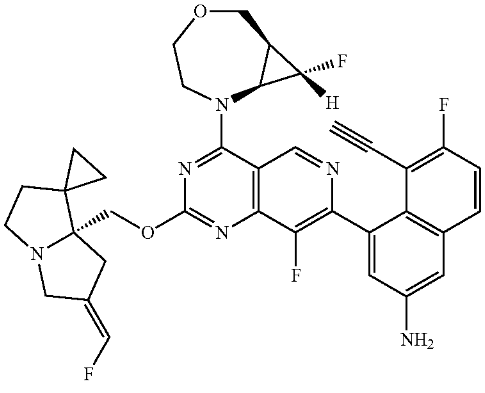

Example 363

Example 363 was prepared in a manner similar to Example 362. MS: m/z=657.3 $[M+H]^{+}$. $^{1}$H NMR (400 MHz, Dimethylsulfoxide-$d_6$) & 9.46-9.32 (m, 1H), 7.78 (dd, J=6.4, 9.2 Hz, 1H), 7.34 (t, J=9.2 Hz, 1H), 7.10-7.00 (m, 2H), 6.74 (d, J=85.2 Hz, 1H), 5.73-5.59 (m, 2H), 5.04-4.68 (m, 1H), 4.53-4.25 (m, 3H), 4.20-4.11 (m, 1H), 4.10-3.79 (m, 3H), 3.78-3.66 (m, 2H), 3.65-3.54 (m, 1H), 3.28-3.15 (m, 2H), 3.08-3.00 (m, 1H), 2.66-2.58 (m, 1H), 2.39-2.29 (m, 2H), 2.26-2.19 (m, 1H), 2.05-1.93 (m, 1H), 1.73-1.63 (m, 1H), 0.83-0.75 (m, 1H), 0.64-0.57 (m, 1H), 0.52-0.43 (m, 2H). $^{19}$F NMR (376 MHz, Dimethylsulfoxide-$d_6$) δ −113.37, −113.45, −131.20, −131.23, −139.91, −140.39, −207.67.

Example 375: (1S,7S,8S)-2-(7-(8-Ethynyl-7-fluoronaphthalen-1-yl)-8-fluoro-2-(((R,E)-6'-(fluoromethylene) tetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane

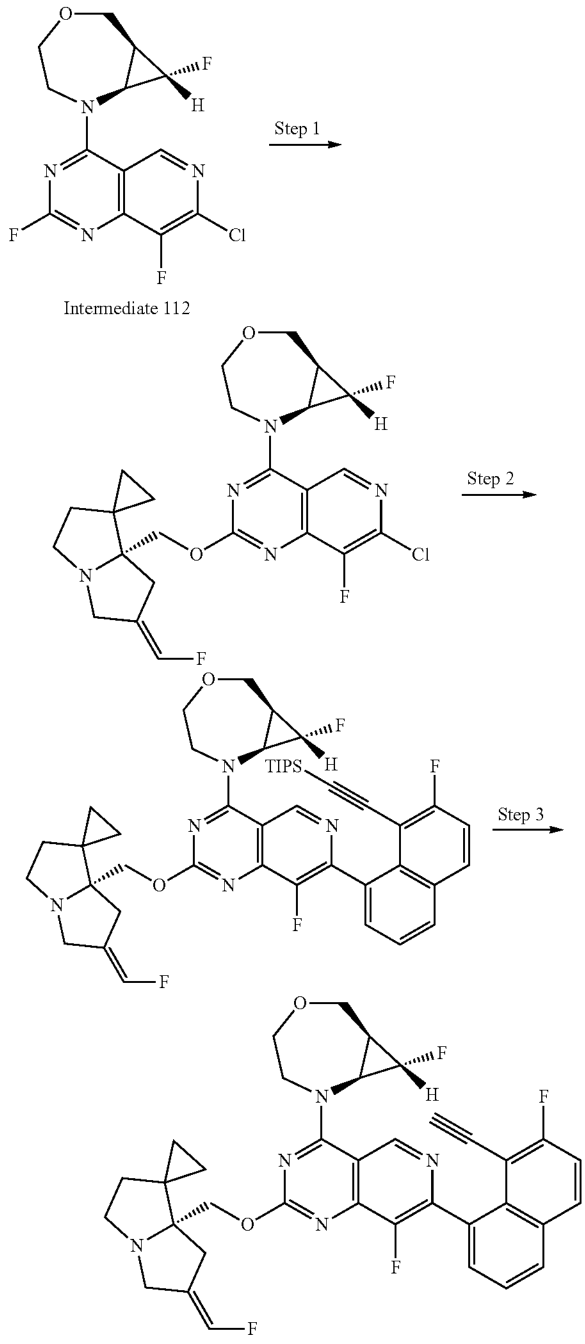

Intermediate 112

Example 375

Example 375 was prepared in a manner similar to Example 376. MS: m/z=642. 1 $[M+H]^+$. $^1H$ NMR (400 MHZ, Dimethylsulfoxide-$d_6$) δ 9.47-9.34 (m, 1H), 8.30-8.14 (m, 2H), 7.74-7.54 (m, 3H), 6.81 (d, J=86 Hz, 1H), 4.99-4.70 (m, 1H), 4.56-4.27 (m, 3H), 4.23-3.93 (m, 4H), 3.76-3.55 (m, 3H), 3.27-3.19 (m, 2H), 3.06-2.98 (m, 1H), 2.63-2.55 (m, 1H), 2.46-2.23 (m, 3H), 2.03-1.90 (m, 1H), 1.70-1.61 (m, 1H), 0.78 (d, J=10.0 Hz, 1H), 0.60 (d, J=9.6 Hz, 1H), 0.50-0.37 (m, 2H). $^{19}F$ NMR (376 MHz, Dimethylsulfoxide-$d_6$) δ −105.73, −105.84, −132.14, −139.85, −140.23, 207.98.

Example 376: (1S,7S,8S)-2-(7-(8-Ethynyl-7-fluoronaphthalen-1-yl)-8-fluoro-2-(((R,Z)-6'-(fluoromethylene) tetrahydrospiro[cyclopropane-1, l'-pyrrolizin]-7a'(5'H)-yl)methoxy)pyrido[4,3-d]pyrimidin-4-yl)-8-fluoro-5-oxa-2-azabicyclo[5.1.0]octane

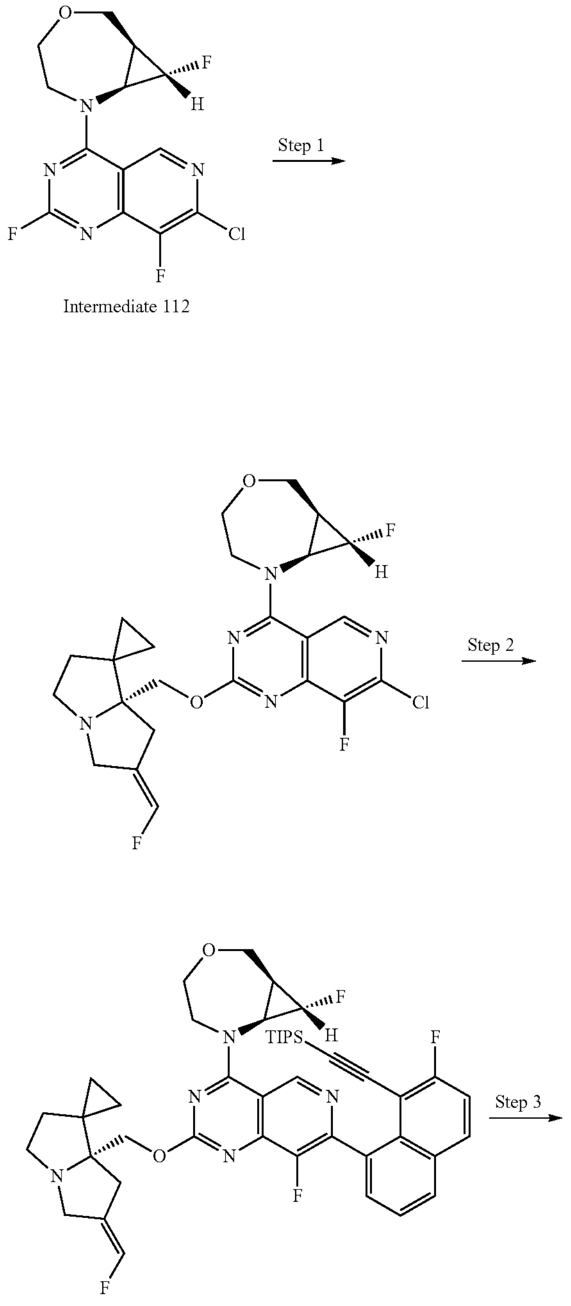

Intermediate 112

-continued

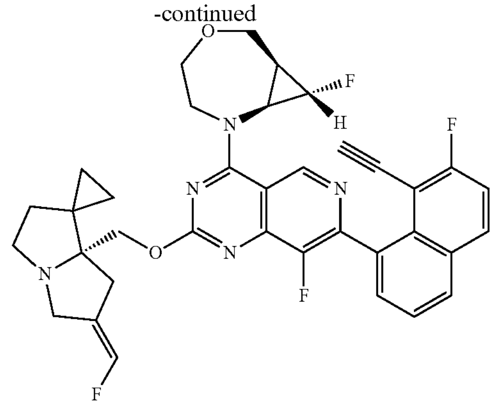

Example 376

Step 1: (1S,7S,8S)-2-(7-Chloro-8-fluoro-2-(((R,Z)-6'-(fluoromethylene) tetrahydrospiro[cyclopropane-1,1'-pyrrolizin]-7a'(5'H)-yl)methoxy)pyrido[4,3-d] pyrimidin-4-yl)-8-fluoro-5-oxa-2-azabicyclo [5.1.0] octane To a solution of (R,Z)-(6'-(fluoromethylene) tetrahydrospiro[cyclopropane-1,1'-pyrrolizin]-Ta'(5'H)-yl) methanol (100 mg, 506 μmol) in THF (1 mL) was addedH-BuOK (608 μL, 1 M in THF) under $N_2$. The reaction mixture was stirred at 25° C. for 30 min under $N_2$. A solution of Intermediate 112 (167 mg, 506 μmol) in THF (1 mL) was added to the above mixture at −40° C. under $N_2$. The reaction mixture was stirred at −40° C. for 1 h under $N_2$. The mixture was quenched with sat. $NH_4Cl$ aq. (2 mL), diluted with $H_2O$ (5 mL), and extracted with EtOAc (10 mL×3). The combined organic phases were washed with brine (10 mL), dried over anhydrous $Na_2SO_4$, filtered and concentrated under reduced pressure. The residue was purified by silica gel flash chromatography (eluent: 0~15% of methanol in dichloromethane) to give the title compound (180 mg, 53% purity, 37% yield) as a yellow solid. MS: m/z=508.0 $[M+H]^{+.}$ Step 2: (1S,7S,8S)-8-Fluoro-2-(8-fluoro-7-(7-fluoro-8-((triisopropylsilyl) ethynyl)naphthalen-1-yl)-2-(((R,Z)-6'-(fluoromethylene) tetrahydrospiro[cyclopropane-1,1'-pyrrolizin]-7d'(5'H)-yl)methoxy)pyrido [4,3-d]pyrimidin-4-yl)-5-oxa-2-azabicyclo[5.1.0] octane A mixture of (18,7S,8S)-2-(7-chloro-8-fluoro-2-(((R,Z)-6'-(fluoromethylene) tetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane (90 mg, 53% purity, 94 μmol), ((2-fluoro-8-(4,4,5,5-tetramethyl-1,3,2-dioxaborolan-2-yl)naphthalen-1-yl) ethynyl) triisopropylsilane (64 mg, 140 μmol), AdanBuP-Pd-$G_3$ (cataCXium-mAPd$G_3$) (14 mg, 18.7 μmol), and $K_3PO_4$ (60 mg, 281 μmol) in THF (4 mL) and $H_2O$ (0.8 mL) was degassed and purged with $N_2$ three times. The reaction mixture was stirred at 80° C. for 3 h under $N_2$. The mixture was treated with $H_2O$ (10 mL), and extracted with EtOAc (10 mL×3). The combined organic phases were washed with brine (10 mL), dried over anhydrous $Na_2SO_4$, filtered and concentrated under reduced pressure. The residue was purified by silica gel flash chromatography (eluent: 0~5% of methanol in dichloromethane) to give the title compound (120 mg, crude) as a yellow solid. MS: m/z=798.2 $[M+H]^{+.}$ Step 3: (1S,7S,8S)-2-(7-(8-ethynyl-7-fluoronaphthalen-1-yl)-8-fluoro-2-(((R,Z)-6'-(fluoromethylene) tetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane To a mixture of (1S,7S,8S)-8-fluoro-2-(8-fluoro-7-(7-fluoro-8-((triisopropylsilyl) ethynyl)naphthalen-1-yl)-2-(((R,Z)-6'-(fluoromethylene) tetrahydrospiro[cyclopropane-1,1'-pyrrolizin]-7a'(5'H)-yl)methoxy)pyrido[4,3-d] pyrimidin-4-yl)-5-oxa-2-azabicyclo[5.1.0]octane (120 mg, crude) in DMSO (2 mL) was added CsF (45 mg, 296 μmol) under $N_2$. The reaction mixture was stirred at 25° C. for 1 h under $N_2$. The reaction mixture was quenched with $H_2O$ (5 mL) and extracted with EtOAc (10 mL×3). The combined organic phases were washed with brine (10 mL), dried over anhydrous $Na_2SO_4$, filtered and concentrated under reduced pressure. The residue was purified by reversed-phases column (column: C18; mobile phase: [water ($NH_4HCO_3$)-ACN]; gradient: 0%~53% B over 10 min) to give the title compound (Example 376, 43.0 mg, 71% yield over 2 steps) as an off-white solid. MS: m/z=642.3 $[M+H]^+$. $^1$H NMR (400 MHZ, Dimethylsulfoxide-$d_6$) δ 9.47-9.35 (m, 1H), 8.31-8.13 (m, 2H), 7.82-7.53 (m, 3H), 6.98-6.48 (m, 1H), 5.00-4.69 (m, 1H), 4.48 (d, J=13.6 Hz, 1H), 4.44-4.28 (m, 2H), 4.23-3.95 (m, 4H), 3.79-3.67 (m, 2H), 3.66-3.56 (m, 1H), 3.41-3.39 (m, 1H), 3.27-3.20 (m, 1H), 3.08-2.99 (m, 1H), 2.69-2.59 (m, 1H), 2.44-2.31 (m, 2H), 2.28-2.18 (m, 1H), 2.03-1.93 (m, 1H), 1.75-1.61 (m, 1H), 0.83-0.73 (m, 1H), 0.64-0.55 (m, 1H), 0.50-0.40 (m, 2H). $^{19}$F NMR (376 MHZ, Dimethylsulfoxide-$d_6$) δ −105.73, 105.84, −131.21, −131.24, −139.89, −140.24, −207.69.

Example 377: (R,E)-7a'-(((7-(8-ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yl)oxy) methyl)-6'-(fluoromethylene) hexahydrospiro[cyclopropane-1,1'-pyrrolizine]

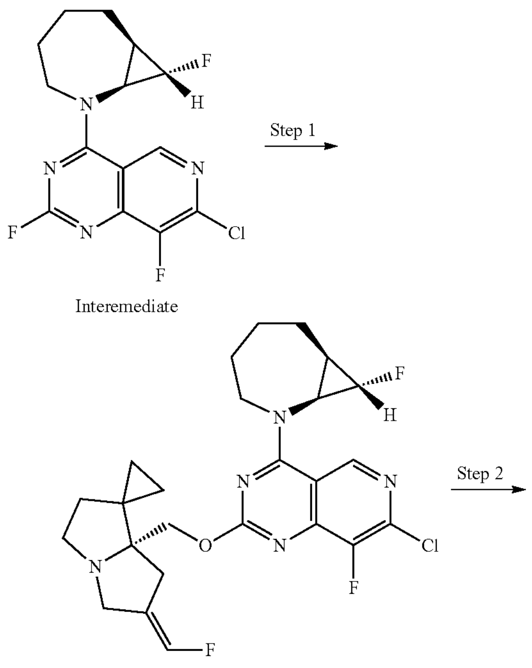

Intermediate

-continued

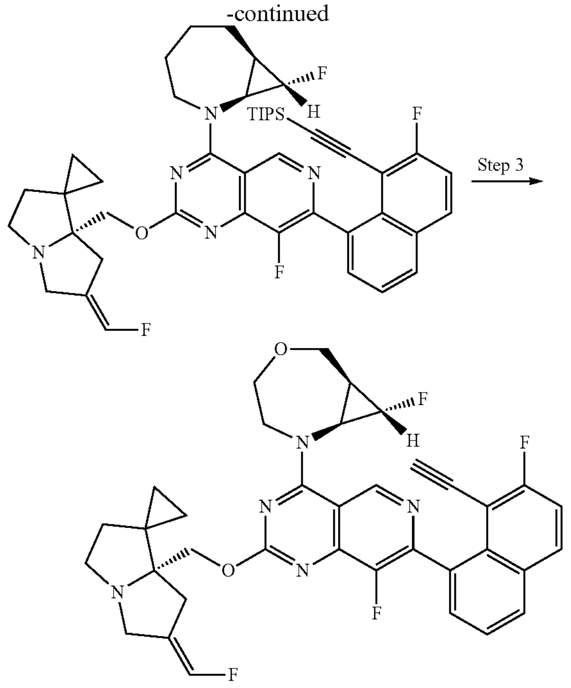

Example 377

Step 1; (R,E)-7a'-(((7-chloro-8-fluoro-4-((1S,7R, 8S)-8-fluoro-2-azabicyclo[5.1.0]octan-2-yl)pyrido[4, 3-d]pyrimidin-2-yl)oxy) methyl)-6'-(fluoromethylene) hexahydrospiro[cyclopropane-1,1'-pyrrolizine]

To a solution of (R,E)-(6'-(fluoromethylene) tetrahydrospiro[cyclopropane-1, 1'-pyrrolizin]-7a'(5'H)-yl) methanol (432 mg, 2.19 mmol) in THF (5 mL) was added t-BuOK (2.74 mL, 1 M in THF) at 25° C. under $N_2$. The mixture was stirred at 25° C. for 0.5 h under $N_2$. A solution of Intermediate 166 (600 mg, 1.83 mmol) in THF (1 mL) was added to the reaction mixture at −40° C. under $N_2$. The mixture was stirred at −40° C. for 1 h under $N_2$. The reaction mixture was quenched with sat. $NH_4Cl$ aq. (50 mL) and extracted with EtOAc (60 mL×3). The combined organic layers were washed with brine (50 mL), dried over anhydrous $Na_2SO_4$, filtered and concentrated under reduced pressure. The residue was purified by silica gel flash chromatography (eluent: 0~10% of MeOH in $CH_2Cl_2$) to give (R,E)-7a'-(((7-chloro-8-fluoro-4-((1S,7R,8S)-8-fluoro-2-azabicyclo[5.1.0]octan-2-yl)pyrido[4,3-d]pyrimidin-2-yl)oxy) methyl)-6'-(fluoromethylene) hexahydrospiro[cyclopropane-1,1'-pyrrolizine] (880 mg, 90% yield) as an off-white solid. MS: m/z=506.2 $[M+H]^{+\cdot}$ Step 2: (R,E)-7a'-(((8-fluoro-7-(7-fluoro-8-((triisopropylsilyl) ethynyl)naphthalen-1-yl)-4-((1S,7R,8S)-8-fluoro-2-azabicyclo[5.1.0]octan-2-yl)pyrido[4,3-d] pyrimidin-2-yl)oxy) methyl)-6'-(fluoromethylene) hexahydrospiro[cyclopropane-1,1'-pyrrolizine]

A mixture of (R,E)-7a'-(((7-chloro-8-fluoro-4-((1S,7R, 8S)-8-fluoro-2-azabicyclo[5.1.0]octan-2-yl)pyrido[4,3-d] pyrimidin-2-yl)oxy) methyl)-6'-(fluoromethylene) hexahydrospiro[cyclopropane-1,1'-pyrrolizine](100 mg, 198 μmol), ((2-fluoro-8-(4,4,5,5-tetramethyl-1,3,2-dioxaborolan-2-yl) naphthalen-1-yl) ethynyl) triisopropylsilane (125 mg, 277 μmol), $K_3PO_4$ (126 mg, 593 μmol) and AdenBuP-Pd-$G_3$ (cataCXiumAPdG$_3$) (29 mg, 40 μmol) in THF (5 mL) and $H_2O$ (1 mL) was degassed, purged with $N_2$ three times, and stirred at 80° C. for 1 h under $N_2$. The reaction mixture was concentrated under reduced pressure. The residue was purified by silica gel flash chromatography (eluent: 0~6% of MeOH in $CH_2Cl_2$) to give the title compound (140 mg, 87% yield) as a yellow solid. MS: m/z=796.4 $[M+H]^{+\cdot}$ Step 3: (R,E)-7a'-(((7-(8-ethynyl-7-fluoronaphthalen-1-yl)-8-fluoro-4-((15,7R,8S)-8-fluoro-2-azabicyclo[5.1.0]octan-2-yl)pyrido[4,3-d]pyrimidin-2-yl) oxy) methyl)-6'-(fluoromethylene) hexahydrospiro [cyclopropane-1,1'-pyrrolizine]

To a solution of (R,E)-7a'-(((8-fluoro-7-(7-fluoro-8-((triisopropylsilyl) ethynyl)naphthalen-1-yl)-4-((1S,7R,8S)-8-fluoro-2-azabicyclo[5.1.0]octan-2-yl)pyrido[4,3-d]pyrimidin-2-yl)oxy) methyl)-6'-(fluoromethylene) hexahydrospiro [cyclopropane-1,1'-pyrrolizine](140 mg, 176 μmol) in DMSO (2 mL) was added CsF (107 mg, 704 μmol). The reaction mixture was purified by reversed-phase column (column C18; mobile phase: [Water ($NH_4HCO_3$)-ACN)]; B %: 0%~55%, 18 min) to give the title compound (Example 377, 83.8 mg, 74% yield) as a yellow solid. MS: m/z=640.1 $[M+H]^+$. $^1H$ NMR (400 MHZ, Dimethylsulfoxide-$d_6$) δ 9.44-9.31 (m, 1H), 8.28-8.15 (m, 2H), 7.75-7.56 (m, 3H), 6.97-6.66 (m, 1H), 4.78-4.52 (m, 1H), 4.47-4.37 (m, 1H), 4.28-3.91 (m, 4H), 3.66-3.57 (m, 1H), 3.42-3.38 (m, 1H), 3.28-3.26 (m, 1H), 3.07~2.99 (m, 1H), 2.65-2.58 (m, 1H), 2.49-2.43 (m, 1H), 2.35-2.22 (m, 2H), 2.07-1.83 (m, 4H), 1.80-1.63 (m, 2H), 1.59-1.46 (m, 1H), 1.25-1.05 (m, 1H), 0.84-0.78 (m, 1H), 0.64-0.58 (m, 1H), 0.54-0.46 (m, 2H), $^{19}F$ NMR (376 MHz, Dimethylsulfoxide-$d_6$) δ −105.79, −105.87, −132.11, −140.07, −140.40, −204.60, −204.67, −204.98.

Example 402: (R,Z)-7a'-(((7-(8-Ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yl)oxy) methyl)-6'-(fluoromethylene) hexahydrospiro[cyclopropane-1,1'-pyrrolizine]

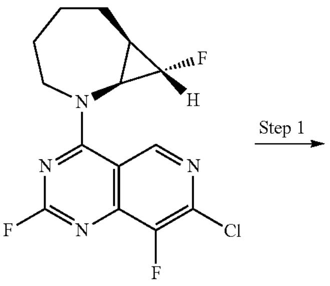

Intermediate 166

-continued

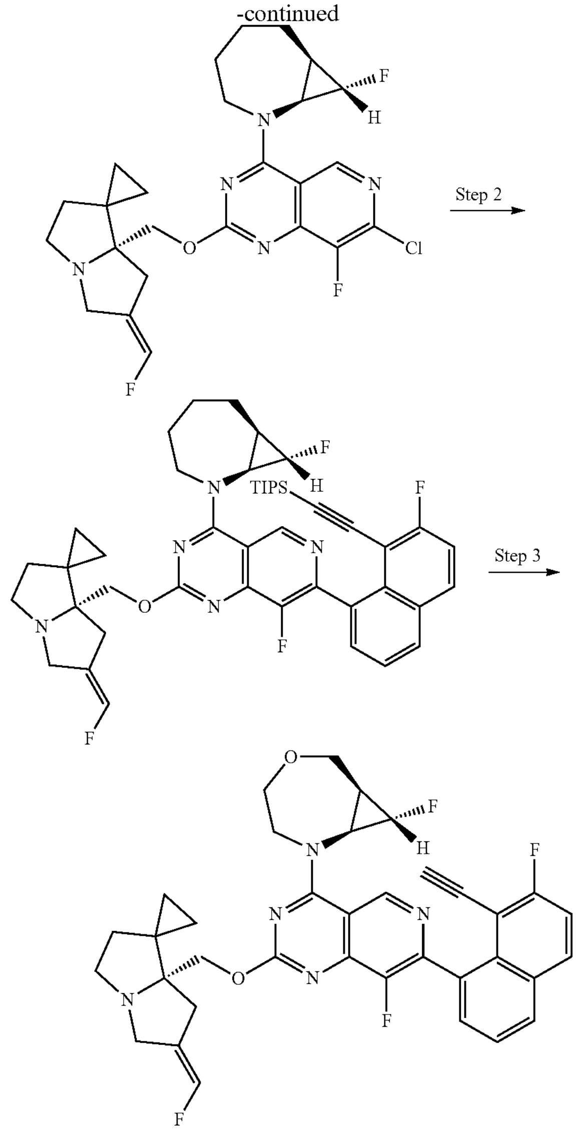

Example 402

Step 1: (R,Z)-7a'-(((7-chloro-8-fluoro-4-((1S,7R,8S)-8-fluoro-2-azabicyclo[5.1.0]octan-2-yl)pyrido[4,3-d]pyrimidin-2-yl)oxy) methyl)-6'-(fluoromethylene) hexahydrospiro[cyclopropane-1,1'-pyrrolizine]

To a solution of (R,Z)-(6'-(fluoromethylene) tetrahydrospiro[cyclopropane-1,1'-pyrrolizin]-7a'(5'H)-yl) methanol (395 mg, 2.00 mmol) in THE (3 mL) was addedH-BuOK (2 mL, 1 M in THF) under $N_2$ at 25° C. The mixture was stirred at 25° C. for 30 min. A solution of Intermediate 166 (598 mg, 1.82 mmol) in THF (2 mL) was added dropwise to the above mixture at −40° C. under $N_2$. The mixture was stirred at 25° C. for another 1 h. The reaction mixture was quenched with sat. $NH_4Cl$ aq. (5 mL) and extracted with EtOAc (5 mL×3). The combined organic layers were washed with brine (5 mL×2), dried over anhydrous $Na_2SO_4$, filtered and concentrated under reduced pressure. The residue was purified by silica gel flash chromatography (eluent: 0~5% MeOH in $CH_2Cl_2$) to give the compound (860 mg, 93% yield) as a yellow solid. MS: m/z=506.2 $[M+H]^+$. $^1H$ NMR (400 MHZ, Chloroform-d) δ 9.15 (s, 1H), 6.63-6.34 (m, 1H), 4.52 (d, J=14.0 Hz, 1H), 4.32-4.26 (m, 1H), 4.21-4.02 (m, 2H), 3.91 (d, J=15.2 Hz, 1H), 3.74 (t, J=6.0 Hz, 2H), 3.64-3.47 (m, 2H), 3.37-3.16 (m, 2H), 2.79-2.69 (m, 1H), 2.53 (d, J=15.6 Hz, 1H), 2.45-2.35 (m, 1H), 2.29 (d, J=15.6 Hz, 1H), 2.19-2.08 (m, 1H), 1.95-1.90 (m, 2H), 1.89-1.83 (m, 2H), 1.10-0.98 (m, 1H), 0.93-0.86 (m, 1H), 0.72-0.65 (m, 1H), 0.56-0.47 (m, 2H). $^{19}F$ NMR (376 MHz, Chloroform-d) 8-131.14, −134.57, −204.09.

Step 2; (R,Z)-Ta'-(((8-fluoro-7-(7-fluoro-8-((triisopropylsilyl) ethynyl)naphthalen-1-yl)-4-((1S,7R,8S)-8-fluoro-2-azabicyclo[5.1.0]octan-2-yl)pyrido[4,3-d]pyrimidin-2-yl)oxy) methyl)-6'-(fluoromethylene) hexahydrospiro[cyclopropane-1,1'-pyrrolizine]

A mixture of (R,Z)-7a'-(((7-chloro-8-fluoro-4-((1S,7R,8S)-8-fluoro-2-azabicyclo[5.1.0]octan-2-yl)pyrido[4,3-d]pyrimidin-2-yl)oxy) methyl)-6'-(fluoromethylene) hexahydrospiro[cyclopropane-1,1'-pyrrolizine](100 mg, 198 μmol), ((2-fluoro-8-(4,4,5,5-tetramethyl-1,3,2-dioxaborolan-2-yl) naphthalen-1-yl) ethynyl) triisopropylsilane (98 mg, 217 μmol), $K_3PO_4$ (126 mg, 593 μmol) and AdanBuP-Pd-$G_3$ (cataCXiumAPd$G_3$) (14 mg, 19.8 μmol) in 1,4-dioxane (4 mL) and $H_2O$ (0.8 mL) was degassed, purged with $N_2$ three times, and stirred at 100° C. for 1 h under $N_2$. The reaction mixture was concentrated under reduced pressure. The residue was purified by silica gel flash chromatography (eluent: 0~4% of MeOH in $CH_2Cl_2$) to give the compound (135 mg, 86% yield) as a yellow solid. MS: m/z=796.3 $[M+H]^{+\cdot}$ Step 3: (R,Z)-7a'-(((7-(8-ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yl) oxy) methyl)-6'-(fluoromethylene) hexahydrospiro[cyclopropane-1,1'-pyrrolizine]

To mixture of (R,Z)-7a-(( (8-fluoro-7-(7-fluoro-8-((triisopropylsilyl) ethynyl)naphthalen-1-yl)-4-((1S,7R,8S)-8-fluoro-2-azabicyclo[5.1.0]octan-2-yl)pyrido[4,3-d]pyrimidin-2-yl)oxy) methyl)-6'-(fluoromethylene) hexahydrospiro[cyclopropane-1,1'-pyrrolizine](130 mg, 163 μmol) in DMSO (3 mL) was added CsF (74 mg, 490 μmol) at 25° C. The mixture was stirred at 25° C. for 0.5 h under $N_2$. The reaction mixture was diluted with $H_2O$ (10 mL) and extracted with EtOAc (10 mL×3). The combined organic layers were washed with brine (10 mL), dried over anhydrous $Na_2SO_4$, filtered, and concentrated under reduced pressure. The residue was purified by reversed-phase column (column: C18; mobile phase: [Water ($NH_4HCO_3$)-MeCN)]; B %: 5%~ 60% over 30 min) to give the title compound (Example 402, 46.7 mg, 45% yield) as an off-white solid. MS: m/z=640.1 $[M+H]^+$. $^1H$ NMR (400 MHZ, Dimethylsulfoxide-$d_6$) δ 9.44-9.29 (m, 1H), 8.28-8.16 (m, 2H), 7.75-7.57 (m, 3H), 6.90-6.59 (m, 1H), 4.77-4.50 (m, 1H), 4.41 (d, J=12.8 Hz, 1H), 4.27-3.93 (m, 4H), 3.74 (d, J=14.8 Hz, 1H), 3.43-3.37 (m, 2H), 3.09-2.99 (m, 1H), 2.67-2.60 (m, 1H), 2.40-2.21 (m, 3H), 2.05-1.81 (m, 4H), 1.77-1.63 (m, 2H), 1.58-1.43 (m, 1H), 1.29-1.12 (m, 1H), 0.83-0.75 (m, 1H), 0.64-0.56 (m, 1H), 0.53-0.42 (m, 2H). $^{19}F$ NMR (376 MHz, Dimethylsulfoxide-$d_6$) δ −105.78, −131.20, −140.09, −140.41, −204.61, −204.97.

Example 403: 5-Ethynyl-6-fluoro-4-(8-fluoro-4-((1S,7R,8S)-8-fluoro-2-azabicyclo[5.1.0]octan-2-yl)-2-(((R,E)-6'-(fluoromethylene) tetrahydrospiro[cyclopropane-1,1'-pyrrolizin]-7a'(5'H)-yl)methoxy) pyrido[4,3-d]pyrimidin-7-yl)naphthalen-2-amine

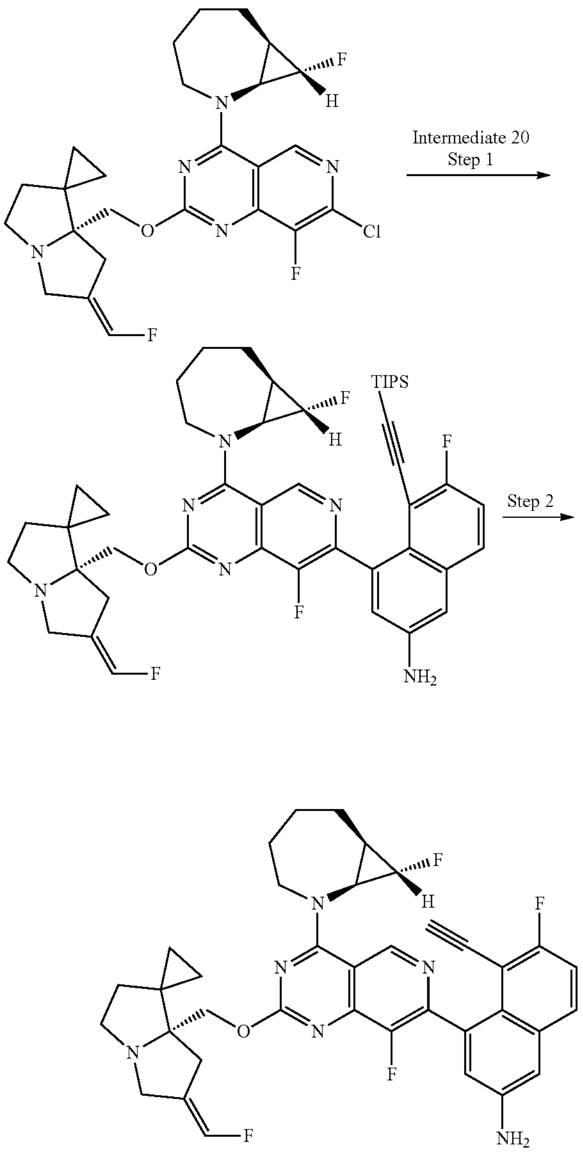

Example 403

Example 403 was prepared in a manner similar to Example 402. MS: m/z=655.1 $[M+H]^+$. $^1$HNMR (400 MHz, Dimethylsulfoxide-$d_6$) δ 9.40-9.30 (m, 1H), 7.77 (dd, J=6.0, 9.2 Hz, 1H), 7.39-7.26 (m, 1H), 7.09-7.00 (m, 2H), 6.95-6.68 (m, 1H), 5.70-5.58 (m, 2H), 4.80-4.48 (m, 1H), 4.39-4.47 (m, 1H), 4.20-3.74 (m, 4H), 3.64-3.57 (m, 1H), 3.45-3.35 (m, 1H), 3.30-3.26 (m, 1H), 3.05-2.95 (m, 1H), 2.65-2.55 (m, 1H), 2.47-2.42 (m, 1H), 2.35-2.20 (m, 2H), 2.02-1.83 (m, 4H), 1.77-1.64 (m, 2H), 1.57-1.46 (m, 1H), 1.26-1.12 (m, 1H), 0.84-0.75 (m, 1H), 0.66-0.55 (m, 1H), 0.53-0.44 (m, 2H). $^{19}$F NMR (376 MHz, Dimethylsulfoxide-$d_6$) δ −113.41, −113.44, −132.09, −132.17, −140.06, −140.53, −204.95.

Example 404: 5-Ethynyl-6-fluoro-4-(8-fluoro-4-((1S,7R,8S)-8-fluoro-2-azabicyclo[5.1.0]octan-2-yl)-2-(((R,Z)-6'-(fluoromethylene) tetrahydrospiro[cyclopropane-1,1'-pyrrolizin]-7a'(5'H)-yl)methoxy) pyrido[4,3-d]pyrimidin-7-yl)naphthalen-2-amine

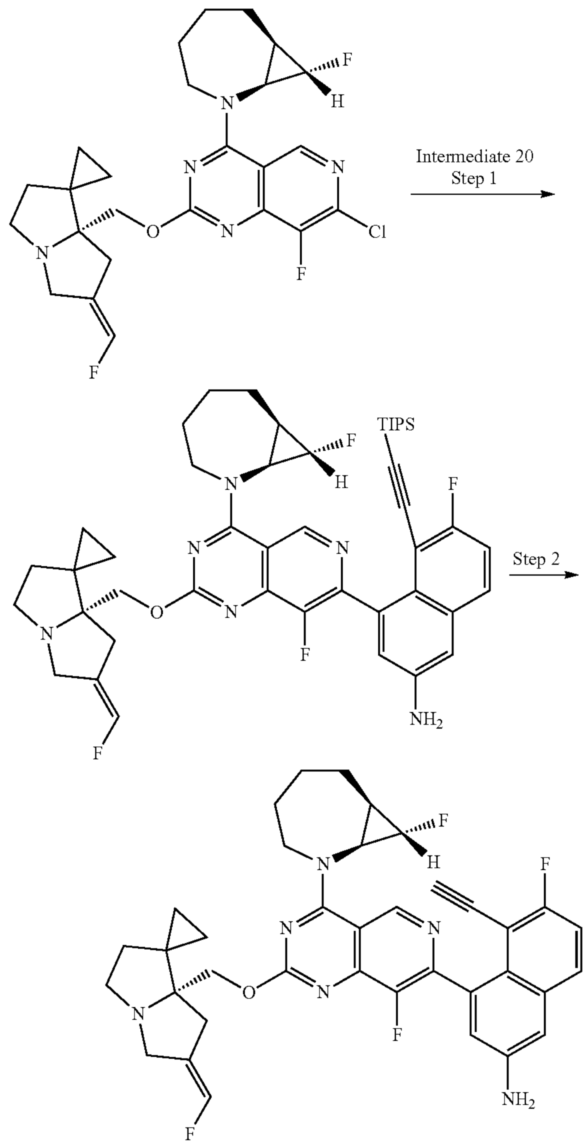

Example 404

Example 404 was prepared in a manner similar to Example 402. MS: m/z=655.1 $[M+H]^+$. $^1$H NMR (400 MHz, Dimethylsulfoxide-$d_6$) δ 9.42-9.26 (m, 1H), 7.81-7.74 (m, 1H), 7.34 (t,J=9.2 Hz, 1H), 7.10-6.99 (m, 2H), 6.88-6.61 (m, 1H), 5.70-5.58 (m, 2H), 4.84-4.48 (m, 1H), 4.47-4.32 (m, 1H), 4.24-3.97 (m, 4H), 3.80-3.70 (m, 1H), 3.38 (d, J=15.2 Hz, 1H), 3.08-3.00 (m, 1H), 2.67-2.62 (m, 1H), 2.43-2.31 (m, 2H), 2.29-2.20 (m, 2H), 2.02-1.94 (m, 2H), 1.91-1.83 (m, 2H), 1.75-1.65 (m, 2H), 1.58-1.47 (m, 1H), 1.27-1.12 (m, 1H), 0.83-0.77 (m, 1H), 0.64-0.58 (m, 1H), 0.52-0.41 (m, 2H). $^{19}$F NMR (376 MHz, Dimethylsulfoxide-$d_6$) δ -113.41, -113.46, -131.21, -140.09, -140.54, -204.96.

Example 405: (R)-6'-(Difluoromethylene)-7a'-(((7-(8-ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yl)oxy) methyl)hexahydrospiro[cyclopropane-1, 1'-pyrrolizine]

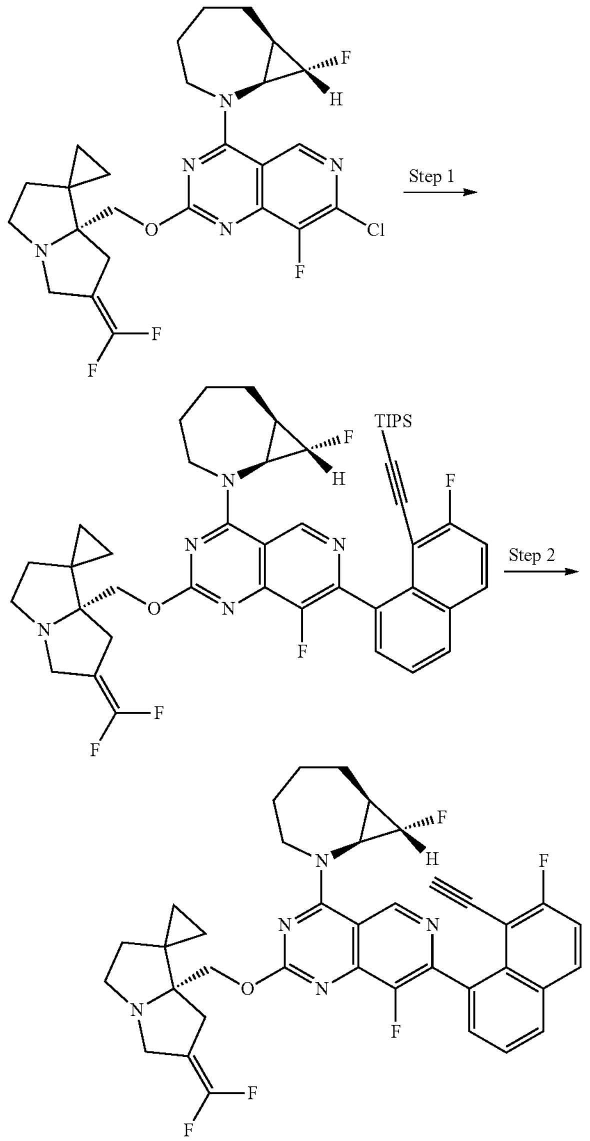

Example 405

Example 405 was prepared in a manner similar to Example 402. MS: m/z=658.3 $[M+H]^+$. $^1H$ NMR (400 MHZ, Dimethylsulfoxide-$d_6$) δ 9.43-9.30 (m, 1H), 8.27-8.16 (m, 2H), 7.76-7.55 (m, 3H), 4.77-4.51 (m, 1H), 4.45-4.36 (m, 1H), 4.27-4.18 (m, 1H), 4.17-3.90 (m, 3H), 3.74-3.66 (m, 1H), 3.49-3.44 (m, 2H), 3.06-2.98 (m, 1H), 2.64-2.61 (m, 1H), 2.46-2.42 (m, 1H), 2.33-2.22 (m, 2H), 2.04-1.84 (m, 4H), 1.77-1.66 (m, 2H), 1.57-1.46 (m, 1H), 1.26-1.13 (m, 1H), 0.86-0.78 (m, 1H), 0.65-0.46 (m, 3H). $^{19}F$ NMR (376 MHz, Dimethylsulfoxide-$d_6$) δ −91.11, −91.13, −105.79, −105.87, −140.06, −140.40, −204.99.

Example 416: 6-Chloro-5-ethynyl-4-(8-fluoro-2-(((2R,3R,7aS)-2-fluoro-3-methyltetrahydro-1H-pyrrolizin-7a (5H)-yl)methoxy-$d_2$)-4-((1S,7R,8S)-8-fluoro-2-azabicyclo[5.1.0]octan-2-yl)pyrido[4,3-d]pyrimidin-7-yl)naphthalen-2-amine

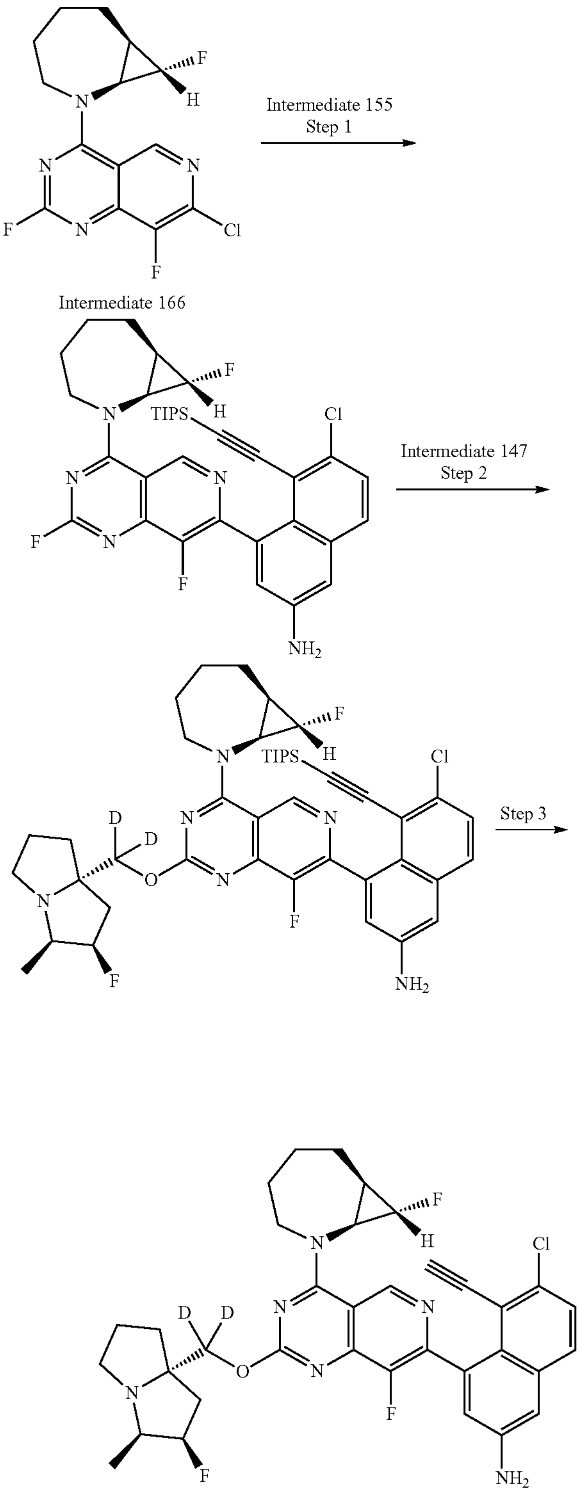

Example 416

Step 1: 6-Chloro-4-(2,8-difluoro-4-((1S,7R,8S)-8-fluoro-2-azabicyclo[5.1.0]octan-2-yl)pyrido[4,3-d]pyrimidin-7-yl)-5-((triisopropylsilyl) ethynyl)naphthalen-2-amine To a mixture of Intermediate 166 (200 mg, 0.60 mmol) and Intermediate 155 (633.27 mg, 1.21 mmol) in THF (12.0 mL) and $H_2O$ (2.4 mL) under $N_2$ were added CataCXium A Pd G3 (88.62 mg, 0.12 mmol) and $K_3PO_4$ (774.88 mg, 3.64 mmol) at room temperature. The reaction mixture was heated at 80° C. for 1 hour. The resulting mixture was cooled to room temperature, filtered and concentrated under reduced pressure. The residue was purified by Prep-TLC (PE/EA 1: 1) to afford a crude product. The crude product was purified by Prep-HPLC with the following conditions: Column: X-bridge Shield RP18 OBD Column 30×150 mm, 5 μm; Mobile Phase A: 10 mM aq. $NH_4HCO_3$; Mobile Phase B: MeCN; Flow rate: 25 mL/min; Gradient: 65% B to 90% B in 10 min; Detector: UV 254 & 220 nm. The collected fractions were combined, concentrated and lyophilized overnight to afford the title compound (80 mg, 20% yield) as a yellow lyophilized powder. MS: m/z=650.25 $[M+H]^{+.}$ Step 2: 6-Chloro-4-(8-fluoro-2-(((2R,3R,7aS)-2-fluoro-3-methyltetrahydro-1H-pyrrolizin-7a (5H)-yl) methoxy-$d_2$)-4-((1S,7R,8S)-8-fluoro-2-azabicyclo [5.1.0]octan-2-yl)pyrido[4,3-d]pyrimidin-7-yl)-5-((triisopropylsilyl) ethynyl)naphthalen-2-amine To an ice-cooled stirred solution of Intermediate 147 (32.34 mg, 0.18 mmol) in THF (1.0 mL) were added t-BuOK (12.01 mg, 0.10 mmol) under $N_2$. The mixture was stirred in an ice bath for 40 min before 6-chloro-4-(2,8-difluoro-4-((1S,7R,8S)-8-fluoro-2-azabicyclo[5.1.0]octan-2-yl)pyrido[4,3-d]pyrimidin-7-yl)-5-((triisopropylsilyl) ethynyl)naphthalen-2-amine (80 mg, 0.12 mmol) was added to the above mixture. The ice bath was removed, and the reaction mixture was stirred at room temperature for 1 hour. The resulting mixture was quenched with sat. $NH_4Cl$ aq. (5 mL) in an ice bath and extracted with EtOAc (3×10 mL). The combined organic layers were washed with brine (10 mL), dried over anhydrous $Na_2SO_4$, filtered and concentrated under reduced pressure. The residue was purified by Prep-TLC ($CH_2Cl_2$/MeOH 20: 1) to afford the title compound (80 mg, 80% yield) as a yellow solid. MS: m/z=805.30 $[M+H]^{+.}$ Step 3: 6-Chloro-S-ethynyl-4-(8-fluoro-2-(((2R,3R,7aS)-2-fluoro-3-methyltetrahydro-1H-pyrrolizin-7a (5H)-yl)methoxy-$d_2$)-4-((1S,7R,8S)-8-fluoro-2-azabicyclo[5.1.0]octan-2-yl)pyrido[4,3-d]pyrimidin-7-yl)naphthalen-2-amine To a stirred solution of 6-chloro-4-(8-fluoro-2-(((2R,3R,7aS)-2-fluoro-3-methyltetrahydro-1H-pyrrolizin-7a (5H)-yl)methoxy-$d_2$)-4-((1S,7R,8S)-8-fluoro-2-azabicyclo[5.1.0]octan-2-yl)pyrido[4,3-d]pyrimidin-7-yl)-5-((triisopropylsilyl) ethynyl)naphthalen-2-amine (30 mg, 0.03 mmol) in DMF (0.5 mL) was added CsF (84.86 mg, 0.55 mmol) at room temperature. The reaction mixture was stirred at room temperature for 3 hours. The resulting mixture was filtered and purified by RP-Flash directly with the following conditions: C18 spherical, 20-30 μm, 100 A, 12 g; Mobile Phase A: 5 mM aq. $NH_4HCO_3$; Mobile Phase B: MeCN; Flow rate: 10 mL/min; Gradient: 5% B to 5% B in 3 min, 5% B to 70% B in 15 min, 70% B to 70% B in 3 min, 70% B to 95% B in 4 min; Detector: UV 254 & 210 nm. The collected fractions were combined, concentrated and lyophilized overnight to afford the title compound (Example 416, 16.6 mg, 68% yield) as a yellow lyophilized powder. MS: m/z=649.20 $[M+H]^+$. $^1H$ NMR (400 MHZ, CD: OD) δ 9.38-9.30 (m, 1H), 7.67-7.65 (m, 1H), 7.41-7.39 (m, 1H), 7.14-7.11 (m, 2H), 5.11-4.97 (m, 1H), 4.64-4.34 (m, 2H), 3.89-3.71 (m, 2H), 3.46-3.33 (m, 2H), 3.20-3.16 (m, 1H), 3.00-2.94 (m, 1H), 2.45-1.80 (m, 11H), 1.75-1.60 (m, 1H), 1.37-1.35 (m, 3H), 1.30-1.10 (m, 1H). $^{19}F$ NMR (376 MHz, $CD_3OD$) δ −139.33--140.07 (d, 1F), −188.28 (s, 1F), −206.26 (s, 1F).

Example 417: 5-Ethynyl-4-(8-fluoro-2-(((2R,3R,7aS)-2-fluoro-3-methyltetrahydro-1H-pyrrolizin-7a (5H)-yl)methoxy-$d_2$)-4-((1S,7R,8S)-8-fluoro-2-azabicyclo[5.1.0]octan-2-yl)pyrido[4,3-d]pyrimidin-7-yl)-6-methylnaphthalen-2-amine

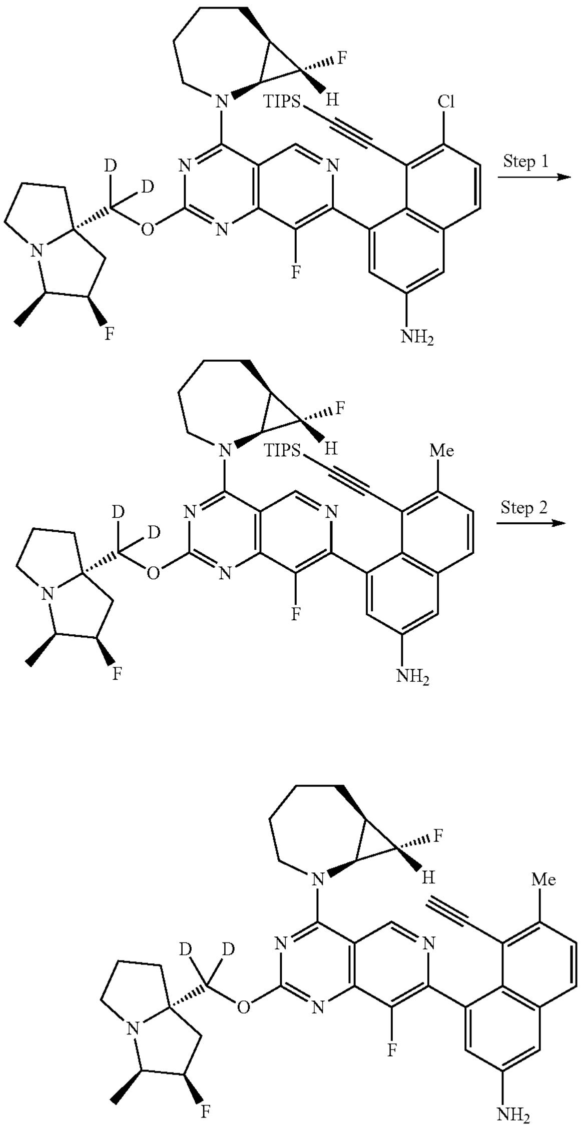

Example 417

Step 1: 4-(8-Fluoro-2-(((2R,3R,7aS)-2-fluoro-3-methyltetrahydro-1H-pyrrolizin-7a (5H)-yl) methoxy-$d_2$)-4-((1S,7R,8S)-8-fluoro-2-azabicyclo [5.1.0]octan-2-yl)pyrido[4,3-d]pyrimidin-7-yl)-6-methyl-5-((triisopropylsilyl) ethynyl)naphthalen-2-amine To a stirred solution of 6-chloro-4-(8-fluoro-2-(((2R,3R, 7aS)-2-fluoro-3-methyltetrahydro-1H-pyrrolizin-7a (5H)-yl)methoxy-$d_2$)-4-((1S,7R,8S)-8-fluoro-2-azabicyclo[5.1.0] octan-2-yl)pyrido[4,3-d]pyrimidin-7-yl)-5-((triisopropylsilyl) etbynyl)naphthalen-2-amine (50 mg, 0.06 mmol, refer to Example 416 for detail procedures) and trimethyl-1,3,5,2,4,6-trioxatriborinane (62.34 mg, 0.24 mmol) in 1,4-dioxane (0.5 mL) were added CataCXium A Pd G3 (9.04 mg, 0.01 mmol) and $Cs_2CO_3$ (60.67 mg, 0.18 mmol) at room temperature under $N_2$. The reaction mixture was heated at 100° C. for 3 hours. The resulting mixture was cooled to room temperature, filtered and concentrated under reduced pressure. The residue was purified by Prep-TLC ($CH_2Cl_2$/MeOH 20: 1) to afford the title compound (38 mg, 77% yield) as a yellow solid. MS: m/z=785.35 $[M+H]^{+\cdot}$ Step 2: 5-Ethynyl-4-(8-fluoro-2-(((2R,3R,7aS)-2-fluoro-3-methyltetrahydro-1H-pyrrolizin-7a (5H)-yl) methoxy-$d_2$)-4-((1S,7R,8S)-8-fluoro-2-azabicyclo [5.1.0]octan-2-yl)pyrido[4,3-d]pyrimidin-7-yl)-6-methylnaphthalen-2-amine To a stirred solution of 4-(8-fluoro-2-(((2R,3R,7aS)-2-fluoro-3-methyltetrahydro-1H-pyrrolizin-7a (5H)-yl) methoxy-$d_2$)-4-((1S,7R,8S)-8-fluoro-2-azabicyclo[5.1.0]octan-2-yl)pyrido[4,3-d]pyrimidin-7-yl)-6-methyl-5-((triisopropylsilyl) ethynyl)naphthalen-2-amine (38 mg, 0.04 mmol) in DMF (0.4 mL) was added CsF (110.29 mg, 0.72 mmol) at room temperature. The reaction mixture was stirred at room temperature for 3 hours. The residue was purified by RP-Flash directly with the following conditions: C18 spherical, 20-30 μm, 100 A, 12 g; Mobile Phase A: 5 mM aq. $NH_4HCO_3$; Mobile Phase B: MeCN; Flow rate: 10 mL/min; Gradient: 5% B to 5% B in 3 min, 5% B to 51% B in 15 min, 66% B to 66% B in 3 min, 66% B to 95% B in 4 min; Detector: UV 254 & 210 nm. The collected fractions were combined, concentrated and lyophilized overnight to afford the title compound (Example 417, 17.3 mg, 56% yield) as a yellow lyophilized powder. MS: m/z=629.25 $[M+H]^+$. $^1H$ NMR (400 MHZ, $CD_3OD$) δ 9.41-9.37 (m, 1H), 7.63-7.60 (m, 1H), 7.31-7.27 (m, 1H), 7.15-7.05 (m, 2H), 5.13-4.99 (m, 1H), 4.62-4.32 (m, 2H), 3.92-3.84 (m, 1H), 3.57-3.40 (m, 3H), 3.20-3.10 (m, 1H), 3.00-2.97 (m, 1H), 2.50-1.80 (m, 14H), 1.75-1.60 (m, 1H), 1.38-1.36 (m, 3H), 1.30-1.10 (m, 1H). $^{19}F$ NMR (376 MHz, $CD_3OD$) δ −139.28-−140.07 (d, 1F), −188.38 (s, 1F), −206.14 (s, 1F).

Example 423: (R)-7a'-(((7-(8-Ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yl)oxy) methyl)-6'-methylenehexahydrospiro [cyclopropane-1, 1'-pyrrolizine]

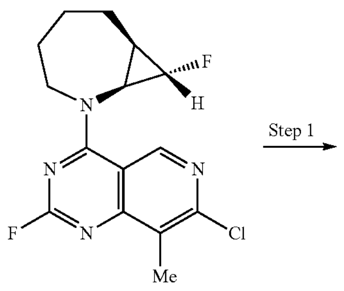

Intermediate 170

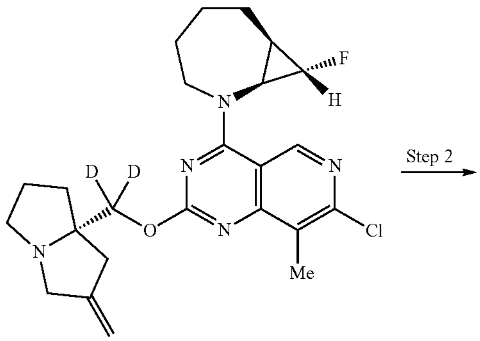

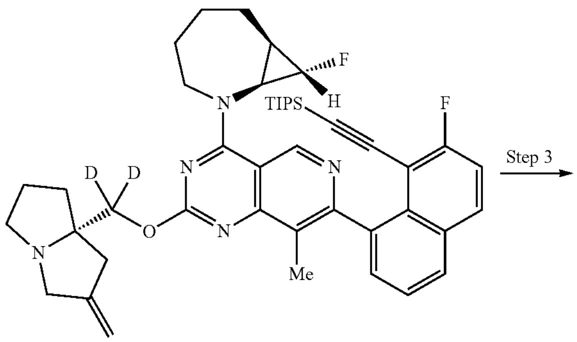

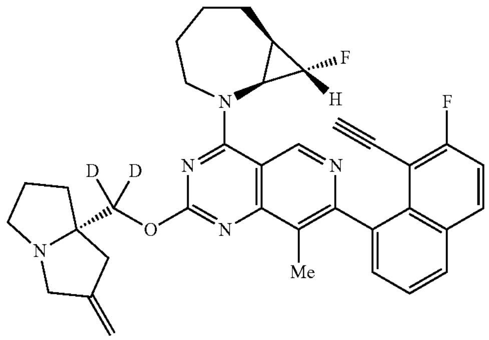

Example 423

Step 1: (R)-7a'-(((7-chloro-8-fluoro-4-((1S,7R,8S)-8-fluoro-2-azabicyclo[5.1.0]octan-2-yl)pyrido[4,3-d]pyrimidin-2-yl)oxy) methyl)-6'-methylenehexahydrospiro[cyclopropane-1,1'-pyrrolizine]

To a solution of (R)-(6'-methylenetetrahydrospiro[cyclopropane-1,1'-pyrrolizin]-7a'(5'H)-yl) methanol (90 mg, 502 μmol) in THF (5 mL) was added dropwise t-BuOK (502 μL, 1 M in THF) at 25° C. under $N_2$. The mixture was stirred at this temperature for 30 min. A solution of Intermediate 170 (150 mg, 456 μmol) in THF (5 mL) was added dropwise to the above mixture at −40° C. The resulting mixture was stirred at −40° C. for 1.5 h. The reaction mixture was quenched with sat. $NH_4Cl$ aq. (30 mL) at 25° C., diluted with $H_2O$ (40 mL) and extracted with EtOAc (20 mL×3). The combined organic layers were dried over $Na_2SO_4$, filtered and concentrated under reduced pressure. The residue was purified by silica gel flash chromatography (eluent: 0~10% of MeOH in $CH_2Cl_2$) to give the title compound (194 mg, 87% yield) as a yellow solid. MS: m/z=488.1 $[M+H]^{+\cdot}$ Step 2: (R)-7a'-(((8-fluoro-7-(7-fluoro-8-((triisopropylsilyl) ethynyl)naphthalen-1-yl)-4-((1S,7R,85)-8-fluoro-2-azabicyclo[5.1.0]octan-2-yl)pyrido[4,3-d]pyrimidin-2-yl)oxy) methyl)-6'-methylenehexahydrospiro[cyclopropane-1,1'-pyrrolizine]

A mixture of (R)-7a'-(((7-chloro-8-fluoro-4-((1S,7R,8S)-8-fluoro-2-azabicyclo[5.1.0]octan-2-yl)pyrido[4,3-d]pyrimidin-2-yl)oxy) methyl)-6'-methylenehexahydrospiro[cyclopropane-1,1'-pyrrolizine](80 mg, 164 μmol), ((2-fluoro-8-(4,4,5,5-tetramethyl-1,3,2-dioxaborolan-2-yl)naphthalen-1-yl) ethynyl) triisopropylsilane (104 mg, 230 μmol), $K_3PO_4$ (104 mg, 492 μmol), AdanBuP-Pd-$G_3$ (cataCXiumAPd$G_3$) (24 mg, 32.8 μmol) in THF (4 mL) and $H_2O$ (0.8 mL) was degassed, purged with $N_2$ three times, and stirred at 80° C. for 2 h under $N_2$ The reaction mixture was concentrated under reduced pressure. The residue was purified by silica gel flash chromatography (eluent: 0~5% of MeOH in $CH_2Cl_2$) to give the title compound (120 mg, 94% yield) as a yellow solid. MS: m/z=778.5 $[M+H]^{+\cdot}$ Step 3: (R)-7a'-(((7-(8-Ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yl)oxy) methyl)-6'-methylenehexahydrospiro[cyclopropane-1, l'-pyrrolizine]

To a solution of (R)-7a'-(((8-fluoro-7-(7-fluoro-8-((triisopropylsilyl) ethynyl)naphthalen-1-yl)-4-((1S,7R,8S)-8-fluoro-2-azabicyclo[5.1.0]octan-2-yl)pyrido[4,3-d]pyrimidin-2-yl)oxy) methyl)-6'-methylenehexahydrospiro[cyclopropane-1,1'-pyrrolizine] (124 mg, 154 μmol) in DMSO (2 mL) was added CsF (234 mg, 1.54 mmol). The mixture was stirred at 35° C. for 2 h. The residue was purified by reversed-phase column (column: C18; mobile phase: [Water ($NH_4HCO_3$)-ACN); B %: 0%~60%, 20 min) to give the title compound (Example 423, 40 mg, 41% yield) as a yellow solid. MS: m/z=622.1 $[M+H]^+$. $^1H$ NMR (400 MHZ, Dimethylsulfoxide-$d_6$) δ 9.46-9.30 (m, 1H), 8.30-8.14 (m, 2H), 7.75-7.54 (m, 3H), 4.97-4.80 (m, 2H), 4.75-4.49 (m, 1H), 4.42 (d, J=13.2 Hz, 1H), 4.30-3.91 (m, 4H), 3.67-3.57 (m, 1H), 3.47-3.40 (m, 2H), 3.10-2.98 (m, 1H), 2.65-2.60 (m, 1H), 2.43-2.37 (m, 1H), 2.32-2.22 (m, 2H), 2.05-1.82 (m, 4H), 1.79-1.62 (m, 2H), 1.60-1.44 (m, 1H), 1.26-1.22 (m, 1H), 0.84-0.75 (m, 1H), 0.67-0.59 (m, 1H), 0.51-0.44 (m, 2H), $^{19}F$ NMR (376 MHz, Dimethylsulfoxide-$d_6$) δ −105.80, −140.46, 205.03.

Example 431: 5-Ethynyl-6-fluoro-4-(4-((1S,75,8S)-8-fluoro-5-oxa-2-azabicyclo[5.1.0]octan-2-yl)-2-(((R,Z)-6'-(fluoromethylene) tetrahydrospiro[cyclopropane-1,1'-pyrrolizin]-7a'(5'H)-yl)methoxy)-8-methylpyrido[4,3-d]pyrimidin-7-yl)naphthalen-2-amine

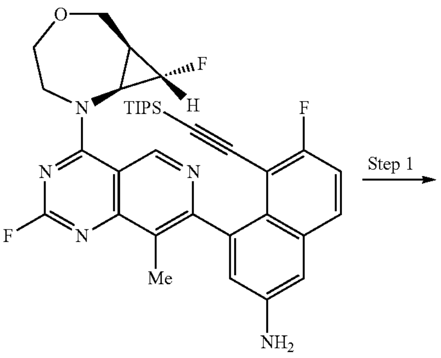

Intermediate 157

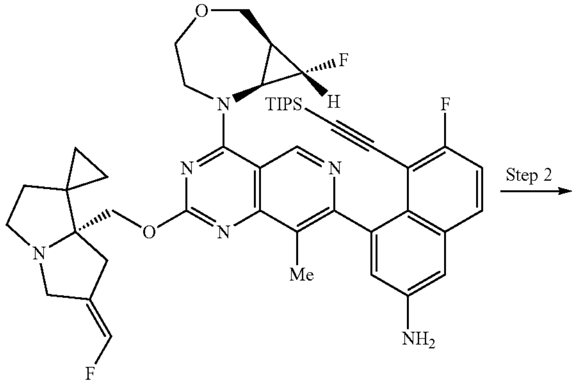

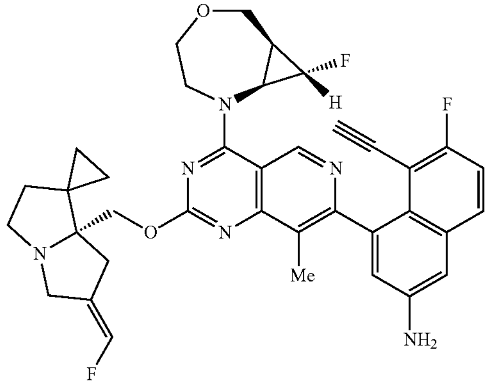

Example 431

Step 1: 6-Fluoro-4-(4-((15,7S,8S)-8-fluoro-5-oxa-2-azabicyclo[5.1.0]octan-2-yl)-2-(((R,Z)-6'-(fluoromethylene) tetrahydrospiro[cyclopropane-1,1'-pyrrolizin]-7a'(5'H)-yl)methoxy)-8-methylpyrido[4,3-d] pyrimidin-7-yl)-5-((triisopropylsilyl) ethynyl) naphthalen-2-amine To a solution of (R,Z)-(6'-(fluoromethylene) tetrahydrospiro[cyclopropane-1,1'-pyrrolizin]-Ta'(5'H)-yl) methanol (60 mg, 304 μmol) in THF (2 mL) was addedH-BuOK (0.4 mL, 1 M in THF) under $N_2$ at 25° C. The mixture was stirred at 25° C. for 30 min. A solution of Intermediate 157 (200 mg, 269 μmol) in THF (2 mL) was added to the above mixture at −40° C. under $N_2$. The mixture was warmed to 25° C. slowly and stirred at 25° C. for another 1 h. The reaction mixture was quenched with sat. $NH_4Cl$ aq. (5 mL) and extracted with EtOAc (5 mL×3). The combined organic layers were washed with brine (5 mL×2), dried over anhydrous $Na_2SO_4$, filtered and concentrated under reduced pressure. The residue was purified by silica gel flash chromatography (eluent: 0~5% of MeOH in $CH_2Cl_2$) to give the title compound (145 mg, 67% yield) as a yellow oil. MS: m/z=809.7 $[M+H]^{+.}$ Step 2: 5-Ethynyl-6-fluoro-4-(4-((1S,7S,8S)-8-fluoro-5-oxa-2-azabicyclo[5.1.0]octan-2-yl)-2-(((R,Z)-6'-(fluoromethylene) tetrahydrospiro[cyclopropane-1,1'-pyrrolizin]-7a'(5'H)-yl)methoxy)-8-methylpyrido[4,3-d]pyrimidin-7-yl)naphthalen-2-amine To a mixture of 6-fluoro-4-(4-((1S,7S,8S)-8-fluoro-5-oxa-2-azabicyclo[5.1.0]octan-2-yl)-2-(((R,Z)-6'-(fluoromethylene) tetrahydrospiro[cyclopropane-1, 1'-pyrrolizin]-7a'(5'H)-yl)methoxy)-8-methylpyrido[4,3-d]pyrimidin-7-yl)-5-((triisopropylsilyl) ethynyl)naphthalen-2-amine (140 mg, 173 μmol) in DMSO (4 mL) was added CsF (79 mg, 519 μmol) at 25° C. The mixture was stirred at 25° C. for 0.5 h. The reaction mixture was quenched with sat. $NH_4Cl$ aq. (5 mL) and extracted with EtOAc (5 mL×3). The combined organic layers were washed with brine (5 mL), dried over anhydrous $Na_2SO_4$, filtered and concentrated under reduced pressure. The residue was purified by reversed-phase column (column: C18; mobile phase: [Water ($NH_4HCO_3$)-MeCN)]; B %: 5%~55% over 40 min) to give the title compound (51.5 mg, 45% yield) as an off-white solid. MS: m/z=653.1 $[M+H]^+$. $^1H$ NMR (400 MHZ, Dimethylsulfoxide-$d_6$) δ 9.47-9.34 (m, 1H), 7.80-7.69 (m, 1H), 7.30 (t, J=8.8 Hz, 1H), 7.00 (s, 1H), 6.94-6.58 (m, 2H), 5.56 (s, 2H), 4.90-4.63 (m, 1H), 4.50-4.18 (m, 4H), 4.13-3.96 (m, 2H), 3.94-3.63 (m, 3H), 3.62-3.51 (m, 1H), 3.42-3.36 (m, 1H), 3.27-3.17 (m, 1H), 3.11-2.98 (m, 1H), 2.71-2.58 (m, 1H), 2.46-2.30 (m, 2H), 2.25-2.17 (m, 1H), 2.16-2.07 (m, 3H), 2.06-1.94 (m, 1H), 1.75-1.64 (m, 1H), 0.84-0.74 (m, 1H), 0.65-0.54 (m, 1H), 0.52-0.42 (m, 2H). $^{19}F$ NMR (376 MHz, Dimethylsulfoxide-$d_6$) δ −113.60, −113.63, −131.28, −207.52.

Example 434 & 435: 5-Ethynyl-6-fluoro-4-((R)-6-fluoro-4-((15,7S,8S)-8-fluoro-5-oxa-2-azabicyclo [5.1.0]octan-2-yl)-2-(((2R,7aS)-2-fluorotetrahydro-1H-pyrrolizin-7a (5H)-yl)methoxy-$d_2$)-8-methylquinazolin-7-yl)naphthalen-2-amine & 5-ethynyl-6-fluoro-4-((S)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)-8-methylquinazolin-7-yl)naphthalen-2-amine

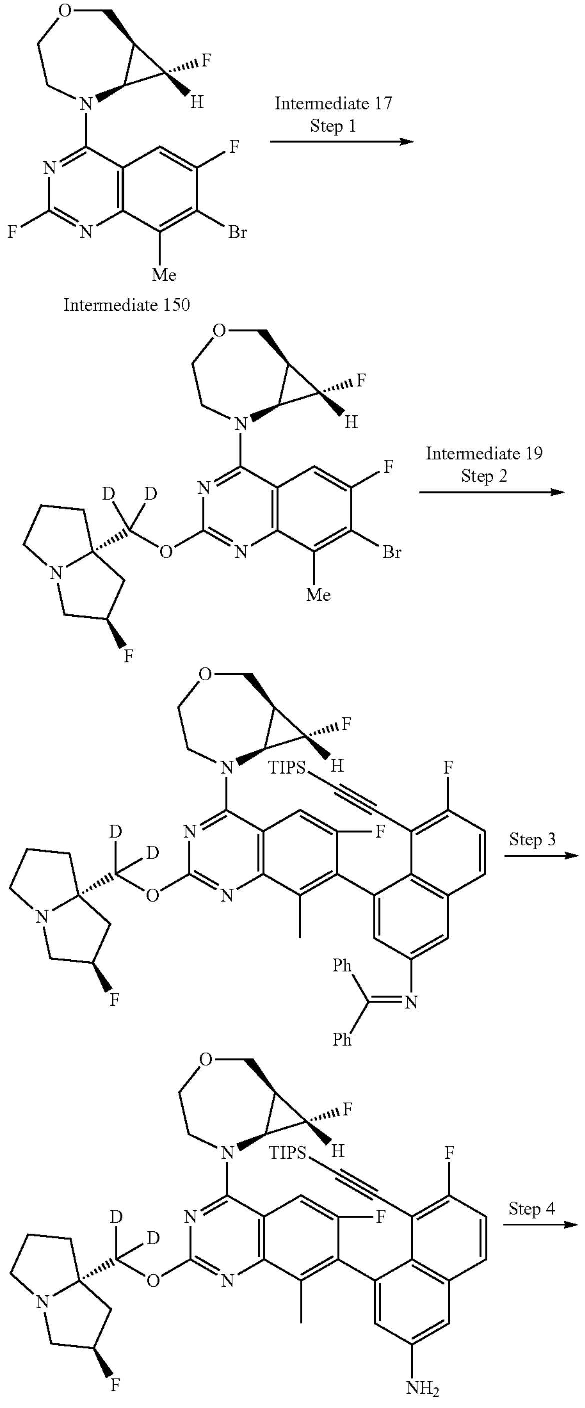

-continued

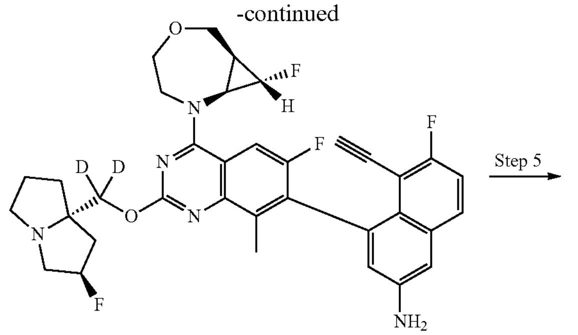

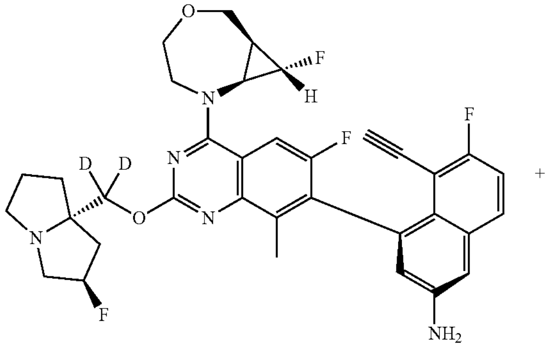

Example 434

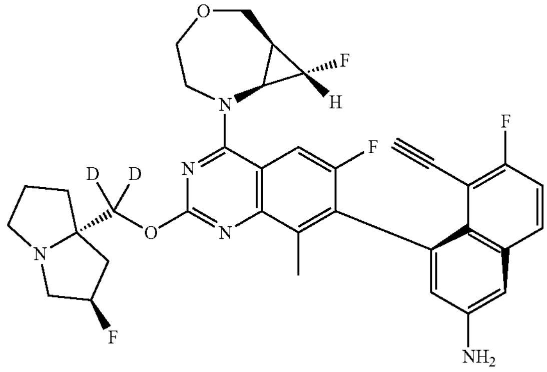

Example 435

Step 1: (1S,7S,8S)-2-(7-Bromo-6-fluoro-2-(((2R,7aS)-2-fluorotetrahydro-1H-pyrrolizin-7a (5H)-yl) methoxy-$d_2$)-8-methylquinazolin-4-yl)-8-fluoro-5-oxa-2-azabicyclo[5.1.0]octane To an ice-cooled stirred solution of Intermediate 17 (105.90 mg, 0.65 mmol) in THF (3.0 mL) under $N_2$ was addedH-BuOK (73.71 mg, 0.65 mmol). The mixture was stirred in an ice bath for 30 min, Intermediate 150 (170 mg, 0.43 mmol) was added to the above mixture. The ice bath was removed, and the reaction mixture was stirred at room temperature for 1 hour. The resulting mixture was quenched with sat. $NH_4Cl$ aq. (10 mL) in an ice bath and extracted with EtOAc (3x30 mL). The combined organic layers were washed with brine (30 mL), dried over anhydrous $Na_2SO_4$, filtered and concentrated under reduced pressure. The residue was purified by Prep-TLC (EA) to afford the title compound (200 mg, 86% yield) as an off-white solid. MS: m/z=529.15 $[M+H]^+$. $^1$H NMR (400 MHZ, Chloroform-d) δ 7.85-7.82 (m, 1H), 5.37-5.22 (m, 1H), 4.49-4.40 (m, 2H), 4.25-3.92 (m, 3H), 3.83-3.76 (m, 1H), 3.65-3.54 (m, 1H), 3.35-2.97 (m, 6H), 2.76 (s, 3H), 2.31-2.12 (m, 3H), 2.01-

1.88 (m, 3H), $^{19}$F NMR (376 MHZ, Chloroform-d) 8-109.43 (s, 1F), −172.91 (s, 1F), −207.07 (s, 1F).

Step 2: N-(6-fluoro-4-(6-fluoro-4-((1S,75,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)-8-methylquinazolin-7-yl)-5-((triisopropylsilyl) ethynyl)naphthalen-2-yl)-1,1-diphenylmethanimine To a stirred solution of (1S,7S,8S)-2-(7-bromo-6-fluoro-2-(((2R,7aS)-2-fluorotetrahydro-1H-pyrrolizin-7a (5H)-yl) methoxy-$d_2$)-8-methylquinazolin-4-yl)-8-fluoro-5-oxa-2-azabicyclo[5.1.0]octane (200 mg, 0.37 mmol) and Intermediate 19 (477.30 mg, 0.75 mmol) in THE (7.5 mL) and $H_2O$ (1.5 mL) were added CataCXium A Pd G3 (55.03 mg, 0.07 mmol) and $K_3PO_4$ (481.15 mg, 2.26 mmol) at room temperature under $N_2$. The reaction mixture was heated at 80° C. for 1 hour. The resulting mixture was cooled to room temperature, diluted with EtOAc (20 mL), washed with brine (20 mL), dried over anhydrous $Na_2SO_4$, filtered and concentrated under reduced pressure. The residue was purified by Prep-TLC (PE/EA 1: 10) to afford the title compound (200 mg, 55% yield) as a brown solid. MS: m/z=954.35 $[M+H]^{+.}$ Step 3: 6-Fluoro-4-(6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)-8-methylquinazolin-7-yl)-5-((triisopropylsilyl) ethynyl)naphthalen-2-amine To a solution of N-(6-fluoro-4-(6-fluoro-4-((1S,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)-5-((triisopropylsilyl) ethynyl) naphthalen-2-yl)-1,1-diphenylmethanimine (200 mg, 0.21 mmol) in EtOH (2.5 mL) under $N_2$ were added NaOAc (34.39 mg, 0.42 mmol) and hydroxylamine hydrochloride (29.13 mg, 0.42 mmol) at room temperature. The reaction mixture was stirred at room temperature for 1 hour. The resulting mixture was concentrated under reduced pressure, diluted with water (10 mL) and extracted with EtOAc (3x10 mL). The combined organic layers were washed with brine (20 mL), dried over anhydrous $Na_2SO_4$, filtered and concentrated under reduced pressure. The residue was purified by Prep-TLC (EA 1: 1) to afford the title compound (140 mg, 84% yield) as a light yellow solid. MS: m/z=790.60 $[M+H]^{+.}$ Step 4: 5-Ethynyl-6-fluoro-4-(6-fluoro-4-((15,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)naphthalen-2-amine To a solution of 6-fluoro-4-(6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)-5-((triisopropylsilyl) ethynyl) naphthalen-2-amine (140 mg, 0.17 mmol) in DMF (2.0 mL) under $N_2$ was added CsF (807.56 mg, 5.31 mmol) at room temperature. The reaction mixture was stirred at room temperature for 2 hours. The resulting mixture was filtered and purified by RP-flash chromatography with the following conditions: Column, C18; Mobile phase A: 5 mM aq. $NH_4HCO_3$; Mobile phase B: MeCN; Gradient 2% B to 65% B in 30 min; Detector: UV 254 nm. The collected fractions were combined, concentrated and lyophilized overnight to afford the title compound (65 mg, 57% yield) as an off-white lyophilized powder. MS: m/z=634.30 $[M+H]^{+\cdot}$ Step 5: 5-Ethynyl-6-fluoro-4-((R)-6-fluoro-4-((15,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)naphthalen-2-amine & 5-ethynyl-6-fluoro-4-((S)-6-fluoro-4-((1S,7S,8S)-8-fluoro-5-oxa-2-azabicyclo [5.1.0]octan-2-yl)-2-(((2R,7aS)-2-fluorotetrahydro-1H-pyrrolizin-7a (5H)-yl)methoxy-$d_2$)-8-methylquinazolin-7-yl)naphthalen-2-amine 5-Ethynyl-6-fluoro-4-(6-fluoro-4-((15,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)naphthalen-2-amine (65 mg, 0.10 mmol) was separated by Prep-Chiral-SFC with the following conditions: Column: CHIRALPAK IK 2×25 cm, 5 μm; Mobile Phase A: Hex (0.5% 2 M $NH_3$-MeOH); Mobile Phase B: EtOH; Flow rate: 20 mL/min; Gradient: isocratic 30%; Detector: UV 220 & 254 nm; RT1: 8.96 min; RT2: 12.454 min. The first eluting peak (RT1: 8.96 min) was concentrated and lyophilized to give the title compound (Example 434, 14.9 mg, 22% yield) as an off-white lyophilized powder. MS: m/z=634.25 $[M+H]^+$. $^1H$ NMR (400 MHz, $CD_3OD$) δ 7.91-7.89 (m, 1H), 7.74-7.70 (m, 1H), 7.23-7.15 (m, 2H), 6.96-6.95 (m, 1H), 5.36-5.18 (m, 1H), 4.50-4.35 (m, 3H), 4.05-3.95 (m, 3H), 3.67-3.65 (m, 1H), 3.31-3.15 (m, 4H), 3.05-2.95 (m, 2H), 2.33-2.10 (m, 7H), 2.00-1.80 (m, 3H). $^{19}F$ NMR (376 MHz, $CD_3OD$) δ −113.51 (s, 1F), −118.86 (s, 1F), −173.74 (s, 1F), −208.96 (s, 1F). The second eluting peak (RT2: 12.454 min) was concentrated and lyophilized to give the other title compound (Example 435, 30.8 mg, 47% yield) as an off-white lyophilized powder. MS: m/z=634.35 $[M+H]^+$. $^1H$ NMR (400 MHZ, $CD_3OD$) δ 7.89-7.86 (s, 1H), 7.73-7.70 (m, 1H), 7.24-7.14 (m, 2H), 6.91-6.90 (m, 1H), 5.35-5.21 (m, 1H), 4.58-4.41 (m, 3H), 4.04-3.98 (m, 3H), 3.70-3.67 (m, 1H), 3.33-3.18 (m, 5H), 3.02-3.00 (m, 1H), 2.35-2.12 (m, 7H), 2.00~ 1.85 (m, 3H). $^{19}F$ NMR (376 MHz, $CD_3OD$) δ −113.52 (s, 1F), −119.00 (s, 1F), −173.75 (s, 1F), −208.93 (s, 1F).

Example 436: 5-Ethynyl-6-fluoro-4-(4-((15,7S,8S)-8-fluoro-5-oxa-2-azabicyclo[5.1.0]octan-2-yl)-8-methyl-2-(((S)-2-methylenetetrahydro-1H-pyrrolizin-7a (5H)-yl)methoxy-$d_2$)pyrido[4,3-d] pyrimidin-7-yl)naphthalen-2-amine

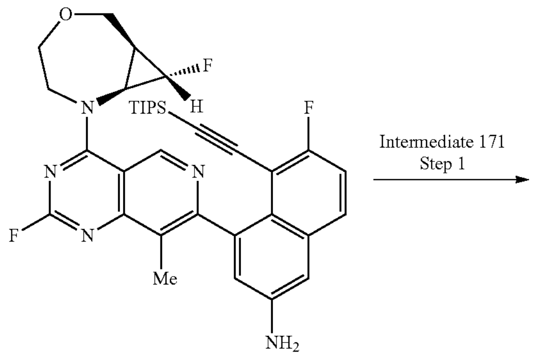

Intermediate 157

-continued

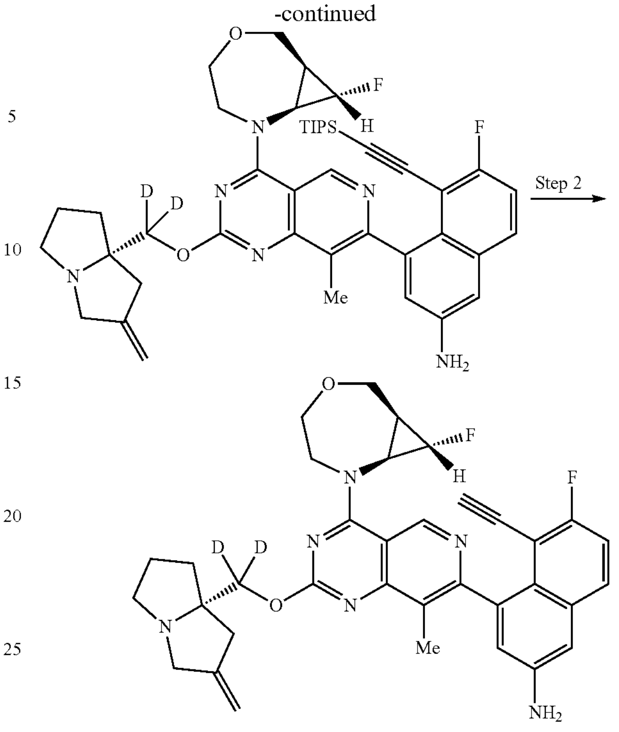

Example 436

Step 1: 6-Fluoro-4-(4-((15,7S,8S)-8-fluoro-5-oxa-2-azabicyclo[5.1.0]octan-2-yl)-8-methyl-2-(((S)-2-methylenetetrabydro-1H-pyrrolizin-7a (5H)-yl) methoxy-$d_2$)pyrido[4,3-d]pyrimidin-7-yl)-5-((triisopropylsilyl) ethynyl)naphthalen-2-amine To a solution of Intermediate 171 (25 mg, 161 μmol) in THE (2 mL) was added dropwise f-BuOK (161 μL, 1 M in THF) at 25° C. under $N_2$. The mixture was stirred at this temperature for 30 min. A solution of Intermediate 157 (102 mg, 161 μmol) in THF (2 mL) was added dropwise to the above mixture at −40° C. The resulting mixture was stirred at 25° C. for 15.5 h. The reaction was quenched with sat. $NH_4Cl$ aq. (30 mL) at 25° C., diluted with $H_2O$ (50 mL), and extracted with EtOAc (30 mL×3). The combined organic layers were dried over $Na_2SO_4$, filtered and concentrated under reduced pressure. The residue was purified by silica gel flash chromatography (eluent: 0~10% of MeOH in $CH_2Cl_2$) to give the title compound (67 mg, 54% yield) as a yellow solid. MS: m/z=767.3 $[M+H]^{+\cdot}$ Step 2: 5-Ethynyl-6-fluoro-4-(4-((1S,75,8S)-8-fluoro-5-oxa-2-azabicyclo[5.1.0]octan-2-yl)-8-methyl-2-(((S)-2-methylenetetrahydro-1H-pyrrolizin-7a (5H)-yl)methoxy-$d_2$)pyrido[4,3-d] pyrimidin-7-yl)naphthalen-2-amine To a solution of 6-fluoro-4-(4-((1S,7S,8S)-8-fluoro-5-oxa-2-azabicyclo[5.1.0]octan-2-yl)-8-methyl-2-(((S)-2-methylenetetrahydro-1H-pyrrolizin-7a (5H)-yl)methoxy-$d_2$) pyrido[4,3-d]pyrimidin-7-yl)-5-((triisopropylsilyl) ethynyl) naphthalen-2-amine (120 mg, 157 μmol) in DMSO (2 mL) was added CsF (238 mg, 1.56 mmol). The mixture was stirred at 35° C. for 1 h. The residue was purified by reversed-phase column (column: C18; mobile phase: [Water ($NH_4HCO_3$)-ACN); B %: 0%~59%, 20 min) to give the title compound (Example 436, 69.2 mg, 70% yield) as a yellow solid. MS: m/z=611.1 $[M+H]^+$. $^1H$ NMR (400 MHZ, Dimethylsulfoxide-$d_6$) δ 9.48-9.34 (m, 1H), 7.79-7.70 (m, 1H), 7.30 (t, J=9.2 Hz, 1H), 7.04-6.97 (m, 1H), 6.94-6.85 (m, 1H), 5.65-5.48 (m, 2H), 5.03-4.89 (m, 2H), 4.87-4.62 (m, 1H), 4.54-4.43 (m, 1H), 4.42-4.23 (m, 2H), 4.06-3.94 (m, 1H), 3.92-3.55 (m, 4H), 3.30-2.98 (m, 3H), 2.69-2.56 (m, 2H), 2.46-2.25 (m, 2H), 2.17-2.10 (m, 3H), 2.06-1.69 (m, 4H). $^{19}F$ NMR (376 MHz, Dimethylsulfoxide-$d_6$) δ −113.58, −113.62, 207.46.

Example 442: 5-Ethynyl-6-fluoro-4-(4-((15,75,8S)-8-fluoro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy-$d_2$)pyrido[4,3-d]pyrimidin-7-yl)naphthalen-2-amine

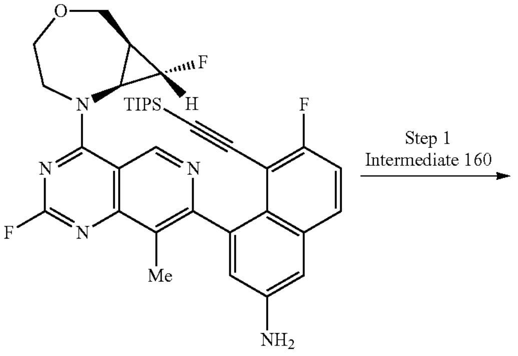

Intermediate 157

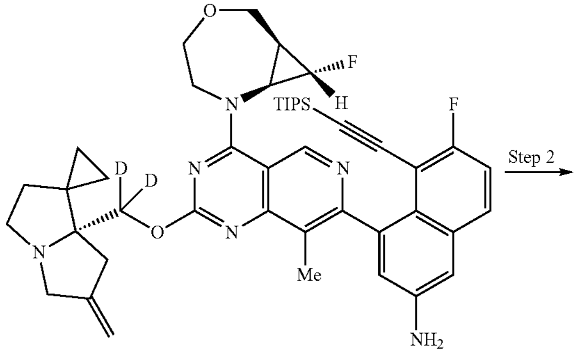

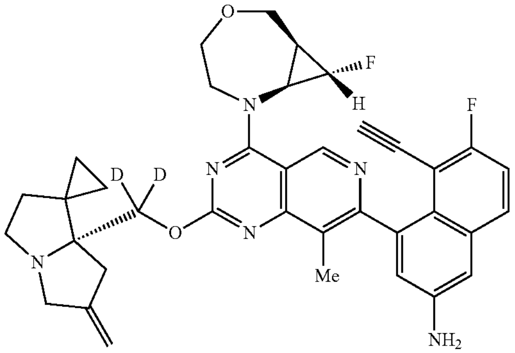

Example 442

Step 1: 6-Fluoro-4-(4-((1S,7S,8S)-8-fluoro-5-oxa-2-azabicyclo[5.1.0]octan-2-yl)-8-methyl-2-(((R)-6'-methylenetetrahydrospiro[cyclopropane-1, 1'-pyrrolizin]-7a'(5'H)-yl)methoxy-$d_2$)pyrido[4,3-d]pyrimidin-7-yl)-5-((triisopropylsilyl) ethynyl) naphthalen-2-amine To a solution of Intermediate 160 (20 mg, 110 μmol) in THF (1 mL) at 25° C. under $N_2$ was addedH-BuOK (132 μL, 1 M in THF). The mixture was stirred at 25° C. under $N_2$ for 30 min. A solution of Intermediate 157 (70 mg, 110 μmol) in THF (1 mL) was added to the mixture at −40° C. under $N_2$. The mixture was stirred at 25° C. for 30 min under $N_2$. The reaction mixture was quenched with sat. $NH_4Cl$ aq. (5 mL) and extracted with EtOAc (10 mL×2). The combined organic layers were washed with brine (10 mL), dried over anhydrous $Na_2SO_4$, filtered and concentrated under reduced pressure. The residue was purified by silica gel flash chromatography (eluent: 0~8% MeOH in $CH_2Cl_2$) to give the title compound (60 mg, 61% yield) as a yellow solid. MS: m/z=793.5 $[M+H]^{+.}$ Step 2: 5-Ethynyl-6-fluoro-4-(4-((15,75,8S)-8-fluoro-5-oxa-2-azabicyclo[5.1.0]octan-2-yl)-8-methyl-2-(((R)-6'-methylenetetrahydrospiro[cyclopropane-1, 1'-pyrrolizin]-7a'(5'H)-yl)methoxy-$d_2$)pyrido[4,3-d]pyrimidin-7-yl)naphthalen-2-amine To a solution of 6-fluoro-4-(4-((1S,7S,8S)-8-fluoro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy-$d_2$)pyrido[4,3-d]pyrimidin-7-yl)-5-((triisopropylsilyl) ethynyl)naphthalen-2-amine (60 mg, 75.6 μmol) in DMSO (2 mL) was added CsF (35 mg, 226 μmol). The mixture was stirred at 25° C. for 1 h. The reaction mixture was quenched with $H_2O$ (10 mL) and extracted with EtOAc (10 mL×2). The combined organic layers were washed with brine (5 mL×2), dried over anhydrous $Na_2SO_4$, filtered and concentrated under reduced pressure. The residue was purified by reversed-phases column (column: C18; mobile phase: [$H_2O$ ($NH_4HCO_3$)-ACN]; gradient: B %, 0~50%, over 30 min) to give the title compound (Example 442, 16.7 mg, 34% yield) as an off-white solid. MS: m/z=637.3 $[M+H]^+$. $^1H$ NMR (400 MHz, Dimethylsulfoxide-$d_6$) δ 9.45-9.34 (m, 1H), 7.75 (dd, J=6.0, 9.2 Hz, 1H), 7.30 (t, J=8.8 Hz, 1H), 7.00 (d, J=2.0 Hz, 1H), 6.92-6.85 (m, 1H), 5.57 (s, 2H), 4.87 (s, 2H), 4.84-4.64 (m, 1H), 4.48-4.22 (m, 3H), 4.12-3.55 (m, 5H), 3.46-3.40 (m, 1H), 3.23-3.16 (m, 1H), 3.07-3.00 (m, 1H), 2.64-2.61 (m, 1H), 2.39-2.22 (m, 3H), 2.15-2.09 (m, 3H), 2.01-1.93 (m, 1H), 1.72-1.64 (m, 1H), 0.81-0.74 (m, 1H), 0.64-0.57 (m, 1H), 0.48-0.41 (m, 2H). $^{19}F$ NMR (376 MHz, Dimethylsulfoxide-$d_6$) δ -113.62, −207.50.

Example 445: 5-Ethynyl-6-fluoro-4-(4-((1S,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylpyrido[4,3-d]pyrimidin-7-yl)naphthalen-2-ol

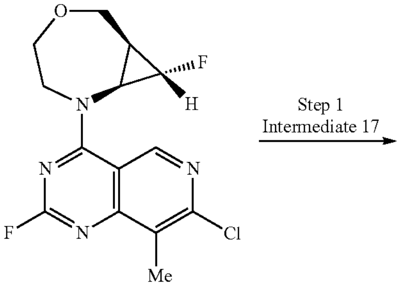

Intermediate 156

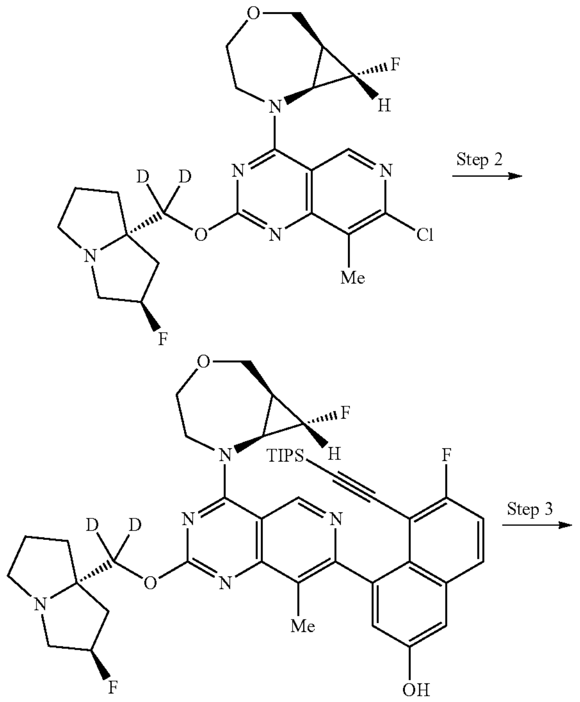

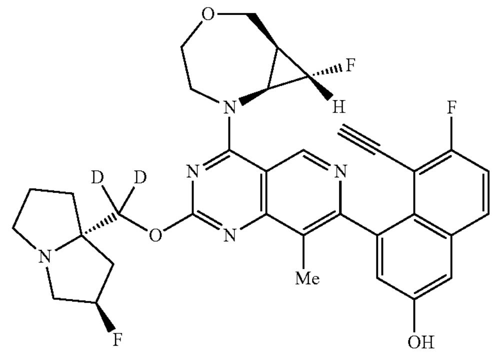

Example 445

Step 1: (1S,7S,8S)-2-(7-chloro-2-(((2R,7aS)-2-fluorotetrahydro-LH-pyrrolizin-7a (5H)-yl)methoxy-$d_2$)-8-methylpyrido[4,3-d]pyrimidin-4-yl)-8-fluoro-5-oxa-2-azabicyclo[5.1.0]octane To a solution of Intermediate 17 (50 mg, 306 μmol) in THE (2 mL) was added dropwiseH-BuOK. (370 AL, 1 M in THF) at 25° C. The mixture was stirred at this temperature for 30 min. A solution of Intermediate 156 (100 mg, 306 μmol) in THF (1 mL) at −40° C. was added to the above mixture. The resulting mixture was stirred at 25° C. for 2 h. The reaction mixture was quenched with sat. $NH_4Cl$ aq. (5 mL) at 25° C. and extracted with EtOAc (5 mL×2). The combined organic layers were washed with brine (10 mL), dried over $Na_2SO_4$, filtered and concentrated under reduced pressure. The residue was purified by silica gel flash chromatography (eluent: 0~7% MeOH in $CH_2Cl_2$) to give the title compound (120 mg, 81% yield) as a yellow solid. MS: m/z=468.2 $[M+H]^{+\cdot}$ Step 2: 6-Fluoro-4-(4-((15,75,8S)-8-fluoro-5-oxa-2-azabicyclo[5.1.0]octan-2-yl)-2-(((2R,7aS)-2-fluoro-tetrahydro-1H-pyrrolizin-7a (5H)-yl)methoxy-$d_2$)-8-methylpyrido[4,3-d]pyrimidin-7-yl)-5-((triisopropylsilyl) ethynyl)naphthalen-2-ol A mixture of (1S,7S,8S)-2-(7-chloro-2-(((2R,7aS)-2-fluorotetrahydro-1H-pyrrolizin-7a (5H)-yl)methoxy-$d_2$)-8-methylpyrido[4,3-d]pyrimidin-4-yl)-8-fluoro-5-oxa-2-azabicyclo[5.1.0]octane (110 mg, 235 μmol), 6-fluoro-4-(4,4,5,5-tetramethyl-1,3,2-dioxaborolan-2-yl)-5-((triisopropylsilyl) ethynyl)naphthalen-2-ol (165 mg, 352 μmol), AdanBuP-Pd-$G_3$ (cataCXiumAPd$G_3$) (17 mg, 23 μmol) and $K_3PO_4$ (150 mg, 705 μmol) in 1,4-dioxane (5 mL) and $H_2O$ (1 mL) was degassed, purged with $N_2$ three times, and stirred at 100° C. for 2 h under $N_2$. The reaction mixture was quenched with sat $NH_4Cl$ aq. (10 mL) and extracted with EtOAc (10 mL×2). The combined organic layers were washed with brine (20 mL), dried over $Na_2SO_4$, filtered and concentrated under reduced pressure. The residue was purified by silica gel flash chromatography (eluent: 0~7% MeOH in $CH_2Cl_2$) to give the title compound (183 mg, 83% yield) as yellow oil. MS: m/z=774.5 $[M+H]^{+\cdot}$ Step 3: 5-Ethynyl-6-fluoro-4-(4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylpyrido[4,3-d]pyrimidin-7-yl)naphthalen-2-ol To a solution of 6-fluoro-4-(4-((1S,7S,8S)-8-fluoro-5-oxa-2-azabicyclo[5.1.0]octan-2-yl)-2-(((2R,7aS)-2-fluoro-tetrahydro-1H-pyrrolizin-7a (5H)-yl)methoxy-$d_2$)-8-methylpyrido[4,3-d]pyrimidin-7-yl)-5-((triisopropylsilyl) ethynyl)naphthalen-2-ol (183 mg, 196 μmol) in DMSO (1 mL) was added CsF (90 mg, 590 μmol). The mixture was stirred at 25° C. for 1 h. The mixture was quenched with $H_2O$ (5 mL) and extracted with EtOAc (5 mL×2). The combined organic layers were washed with brine (10 mL), dried over $Na_2SO_4$, filtered and concentrated under reduced pressure. The residue was purified by prep-HPLC (column: C18; mobile phase: [water ($NH_4HCO_3$)-ACN]; gradient: 0%~50% B over 10 min) to give the title compound (Example 445, 60.7 mg, 49% yield) as a yellow solid. MS: m/z=618.2 $[M+H]^+$. $^1H$ NMR (400 MHZ, Dimethylsulfoxide-$d_6$) δ 10.06 (s, 1H), 9.48-9.33 (m, 1H), 7.95 (dd, J=5.6, 9.2 Hz, 1H), 7.43 (t, J=9.2 Hz, 1H), 7.34 (d,J=2.4 Hz, 1H), 7.08-6.93 (m, 1H), 5.28 (d, J=53.6 Hz, 1H), 4.91-4.61 (m, 1H), 4.47 (d, J=14.4 Hz, 1H), 4.43-4.23 (m, 2H), 4.05-3.52 (m, 4H), 3.27-3.16 (m, 1H), 3.13-2.98 (m, 3H), 2.89-2.76 (m, 1H), 2.37-2.23 (m, 1H), 2.19-2.10 (m, 4H), 2.07-1.95 (m, 2H), 1.87-1.69 (m, 3H). $^{19}$F NMR (376 MHz, Dimethylsulfoxide-$d_6$) δ −110.99, −111.05, −172.11, −172.21, −207.51.

Example 446: 5-Ethynyl-6-fluoro-4-(4-((1S,7S,8S)-8-fluoro-5-oxa-2-azabicyclo[5.1.0]octan-2-yl)-8-methyl-2-(((S)-2-methylenetetrahydro-1H-pyrrolizin-7a (5H)-yl)methoxy-$d_2$)pyrido[4,3-d]pyrimidin-7-yl)naphthalen-2-ol

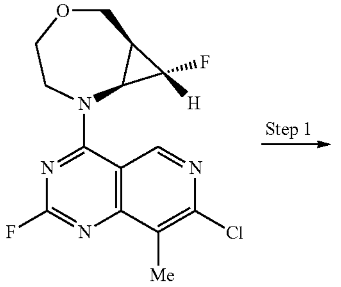

Intermediate 156

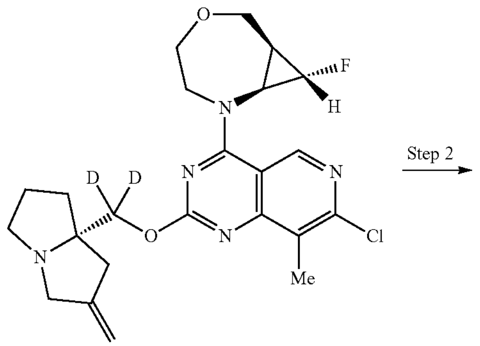

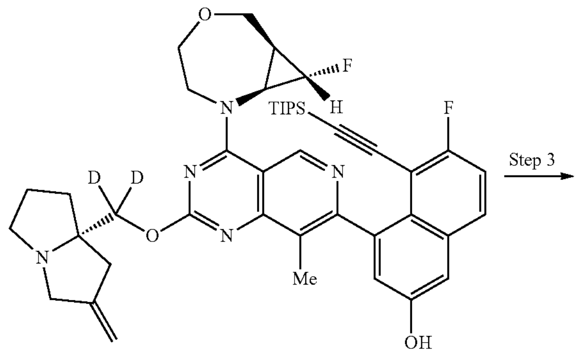

-continued

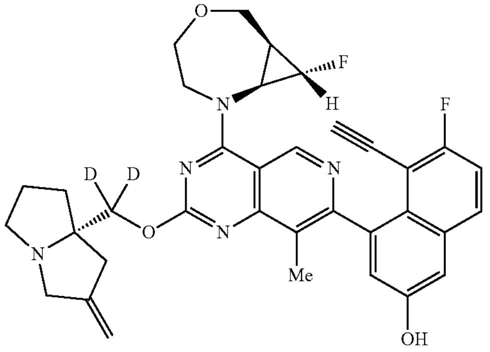

Example 446

Example 446 was prepared in a manner similar to Example 445. MS: m/z=612.1 [M+H]$^+$. $^1$H NMR (400 MHZ, Dimethylsulfoxide-$d_6$) δ 10.16-9.92 (m, 1H), 9.51-9.30 (m, 1H), 8.10-7.83 (m, 1H), 7.43 (t, J=8.8 Hz, 1H), 7.37-7.30 (m, 1H), 7.11-6.85 (m, 1H), 4.99-4.88 (m, 2H), 4.88-4.64 (m, 1H), 4.47 (d, J=13.6 Hz, 1H), 4.41-4.22 (m, 2H), 4.06-3.64 (m, 3H), 3.63-3.50 (m, 2H), 3.28-3.13 (m, 2H), 3.08-2.94 (m, 1H), 2.69-2.55 (m, 2H), 2.43-2.23 (m, 2H), 2.18-2.07 (m, 3H), 2.02-1.93 (m, 1H), 1.92-1.84 (m, 1H), 1.83-1.75 (m, 1H), 1.74-1.64 (m, 1H). $^{19}$F NMR (376 MHz, Dimethylsulfoxide-$d_6$) δ −111.00, −207.48.

Example 448: 5-Ethynyl-6-fluoro-4-(4-((15,75,8S)-8-fluoro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy-$d_2$)pyrido[4,3-d]pyrimidin-7-yl)naphthalen-2-ol

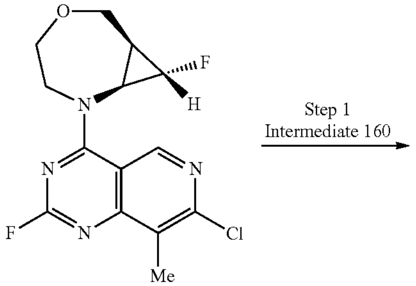

Intermediate 156

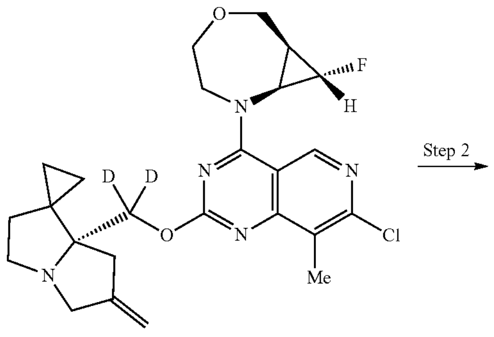

-continued

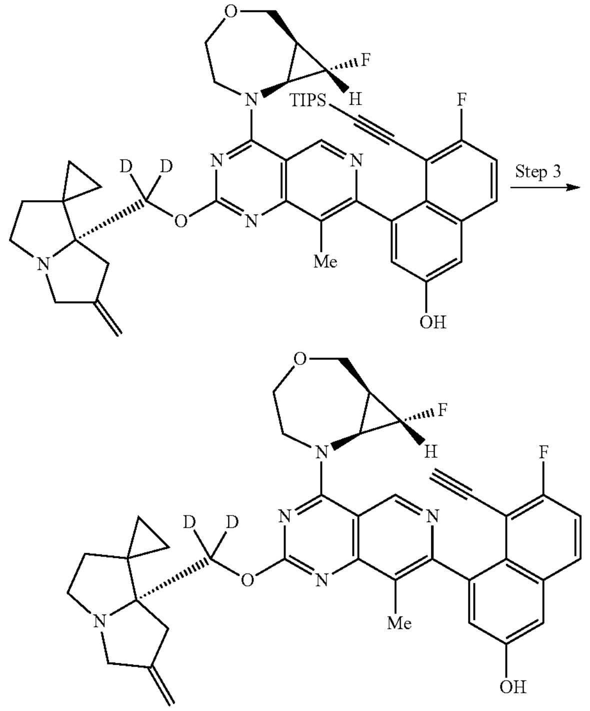

Example 448

Example 448 was prepared in a manner similar to Example 446. MS: m/z=638.1 $[M+H]^+$. $^1H$ NMR (400 MHz, Dimethylsulfoxide-$d_6$) δ 9.46-9.34 (m, 1H), 7.94 (dd, J=6.0, 9.6 Hz, 1H), 7.43 (t, J=8.8 Hz, 1H), 7.33 (d, J=2.4 Hz, 1H), 7.05-6.96 (m, 1H), 6.01 (s, 1H), 4.88 (d, J=1.4 Hz, 2H), 4.84-4.65 (m, 1H), 4.48-4.23 (m, 3H), 4.03-3.60 (m, 5H), 3.21-3.14 (m, 2H), 3.06-3.01 (m, 1H), 2.66-2.59 (m, 1H), 2.41-2.22 (m, 3H), 2.16-2.09 (m, 3H), 2.02-1.92 (m, 1H), 1.72-1.64 (m, 1H), 0.82-0.74 (m, 1H), 0.64-0.57 (m, 1H), 0.49-0.41 (m, 2H). $^{19}F$ NMR (376 MHz, Dimethylsulfoxide-$d_6$) δ −111.08, −207.41.

Example 456: 4-(8-Ethyl-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-5-ethynyl-6-fluoronaphthalen-2-amine

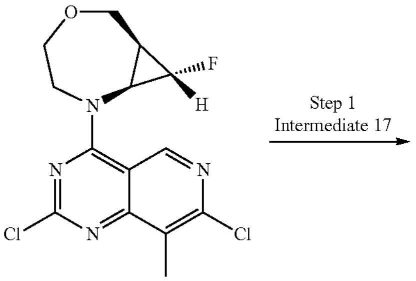

Intermediate 151

-continued

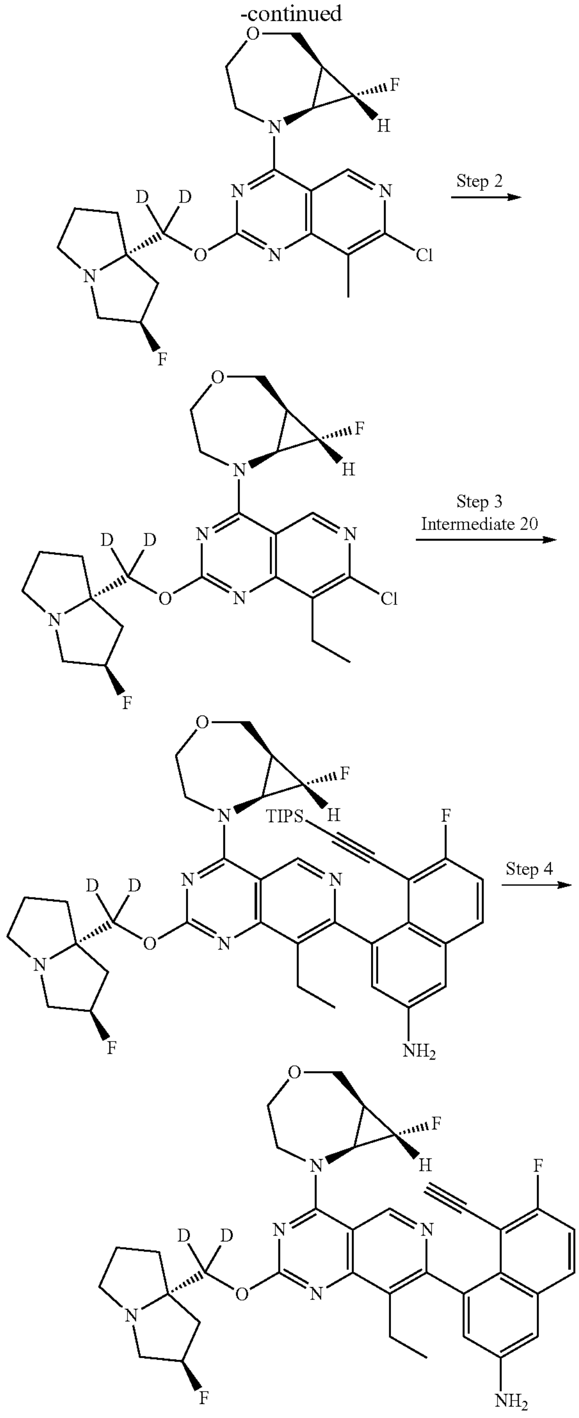

Example 456

Step 1: (1S,7S,8S)-2-(7-Chloro-2-(((2R,7aS)-2-fluorotetrahydro-1H-pyrrolizin-7a (5H)-yl)methoxy-$d_2$)-8-iodopyrido[4,3-d]pyrimidin-4-yl)-8-fluoro-5-oxa-2-azabicyclo[5.1.0]octane To a stirred solution of Intermediate 151 (1.0 g, 2.19 mmol) and Intermediate 17 (566.85 mg, 3.51 mmol) in DMSO (10 mL) was added KF (383.01 mg, 6.59 mmol) at room temperature under $N_2$. The reaction mixture was heated at 100° C. for 2 hours. The resulting mixture was cooled to room temperature, diluted with water (30 mL), and extracted with EtOAc (3x30 mL). The combined organic layers were washed with brine (20 mL), dried over anhydrous $Na_2SO_4$, filtered and concentrated under reduced pressure. The residue was purified by silica gel flash chromatography (eluted with $CH_2Cl_2$/MeOH (30: 1)) to afford the title compound (830 mg, 65% yield) as a light yellow solid. MS: m/z=580.10, 582.10 $[M+H]^+$. $^1H$ NMR (400 MHZ, Chloroform-d) δ 9.25 (s, 1H), 5.35-5.22 (m, 1H), 4.65-4.60 (m, 1H), 4.43-4.21 (m, 2H), 3.97-3.84 (m, 3H), 3.66-3.59 (m, 1H), 3.39-3.11 (m, 4H), 2.99-2.97 (m, 1H), 2.41-1.82 (m, 7H). $^{19}F$ NMR (376 MHz, Chloroform-d) 8-173.09 (s, 1F), −207.54 (s, 1F).

Step 2: (15,7S,8S)-2-(7-Chloro-8-ethyl-2-(((2R,7aS)-2-fluorotetrahydro-1H-pyrrolizin-7a (5H)-yl)methoxy-$d_2$)pyrido[4,3-d]pyrimidin-4-yl)-8-fluoro-S-oxa-2-azabicyclo[5.1.0]octane To a stirred solution of (15,75,8S)-2-(7-chloro-2-(((2R,7aS)-2-fluorotetrahydro-1H-pyrrolizin-7a (5)-yl)methoxy-$d_2$)-8-iodopyrido[4,3-d]pyrimidin-4-yl)-8-fluoro-5-oxa-2-azabicyclo[5.1.0]octane (300 mg, 0.51 mmol) and ethylboronic acid (76.46 mg, 1.03 mmol) in 1,4-dioxane (4.0 mL) and $H_2O$ (1.0 mL) were added Pd (dtbpf) $Cl_2$ (33.72 mg, 0.05 mmol) and $Cs_2CO_3$ (505.75 mg, 1.55 mmol) at room temperature under $N_2$. The reaction mixture was heated at 80° C. for 16 hours. The resulting mixture was cooled to room temperature, diluted with water (30 mL), extracted with EtOAc (3x30 mL). The combined organic layers were washed with brine (30 mL), dried over anhydrous $Na_2SO_4$, filtered and concentrated under reduced pressure. The residue was purified by Prep-TLC ($CH_2Cl_2$/MeOH 20: 1) to afford the title compound (190 mg, 76% yield) as a light yellow solid. MS: m/z=482.30 $[M+H]^{+}$.

Step 3: 4-(8-Ethyl-4-((15,7S,8S)-8-fluoro-5-oxa-2-azabicyclo[5.1.0]octan-2-yl)-2-(((2R,7aS)-2-fluoro-tetrahydro-1H-pyrrolizin-7a (5H)-yl)methoxy-$d_2$) pyrido[4,3-d]pyrimidin-7-yl)-6-fluoro-5-((triisopropylsilyl) ethynyl)naphthalen-2-amine To a stirred solution of (1S,75,8S)-2-(7-chloro-8-ethyl-2-(((2R,7aS)-2-fluorotetrahydro-1H-pyrrolizin-7a (5H)-yl) methoxy-$d_2$)pyrido[4,3-d]pyrimidin-4-yl)-8-fluoro-5-oxa-2-azabicyclo[5.1.0]octane (190 mg, 0.39 mmol) and Intermediate 20 (596.02 mg, 1.18 mmol) in THF (8.0 mL) and $H_2O$ (1.6 mL) were added CataCXium A Pd G3 (57.42 mg, 0.07 mmol) and $K_3PO_4$ (502.07 mg, 2.36 mmol) at room temperature under $N_2$. The reaction mixture was heated at 80° C. for 16 hours. The resulting mixture was cooled to room temperature, diluted with water (20 mL), and extracted with EtOAc (3x20 mL). The combined organic layers were washed with brine (30 mL), dried over anhydrous $Na_2SO_4$, filtered and concentrated under reduced pressure. The residue was purified by Prep-TLC ($CH_2Cl_2$/MeOH 20: 1) to afford the title compound (110 mg, 35% yield) as a brown solid. MS: m/z=787.30 $[M+H]^{+}$.

Step 4: 4-(8-Ethyl-4-((15,7S,8S)-8-fluoro-5-oxa-2-azabicyclo[5.1.0]octan-2-yl)-2-(((2R,7aS)-2-fluoro-tetrahydro-1H-pyrrolizin-7a (5H)-yl)methoxy-$d_2$) pyrido[4,3-d]pyrimidin-7-yl)-5-ethynyl-6-fluoronaphthalen-2-amine To a solution of 4-(8-ethyl-4-((1S,75,8S)-8-fluoro-S-oxa-2-azabicyclo[5.1.0]octan-2-yl)-2-(((2R,7aS)-2-fluorotetrahydro-1H-pyrrolizin-7a (5H)-yl)methoxy-$d_2$)pyrido[4,3-d]pyrimidin-7-yl)-6-fluoro-5-((triisopropylsilyl) ethynyl) naphthalen-2-amine (110 mg, 0.14 mmol) in DMSO (1.1 mL) under $N_2$ was added CsF (636.91 mg, 4.20 mmol) at room temperature. The reaction mixture was stirred at room temperature for 3 hours. The resulting mixture was filtered and purified by RP-Flash with the following conditions: Column, C18; Mobile phase A: 5 mM aq. $NH_4HCO_3$; Mobile phase B: MeCN; Gradient 2% B to 50% B in 20 min; Detector: UV 254 nm. The collected fractions were combined, concentrated and lyophilized overnight to afford the title compound (Example 456, 42.7 mg, 48% yield) as a light-yellow lyophilized powder. MS: m/z=631.25 $[M+H]^+$. $^1H$ NMR (400 MHZ, DMSO-$d_6$) δ 9.43-9.37 (m, 1H), 7.76-7.72 (m, 1H), 7.32-7.27 (m, 1H), 7.00-6.99 (m, 1H), 6.93-6.90 (m, 1H), 5.58 (s, 2H), 5.35-5.21 (m, 1H), 4.90-4.70 (m, 1H), 4.49-4.20 (m, 3H), 4.10-3.57 (m, 4H), 3.32-3.00 (m, 4H), 2.93-2.45 (m, 3H), 2.40-1.96 (m, 4H), 1.90-1.70 (m, 3H), 1.07-1.01 (m, 3H). $^{19}F$ NMR (376 MHZ, DMSO-$d_6$) δ −113.62 (s, 1F), −172.19-172.24 (d, 1F), −207.44 (s, 1F).

Example 457: 5-Ethynyl-6-fluoro-4-(4-((1S,7R,8S)-8-fluoro-2-azabicyclo[5.1.0]octan-2-yl)-8-methyl-2-(((S)-2-methylenetetrahydro-1H-pyrrolizin-7a (5H)-yl)methoxy-$d_2$)pyrido[4,3-d]pyrimidin-7-yl) naphthalen-2-amine

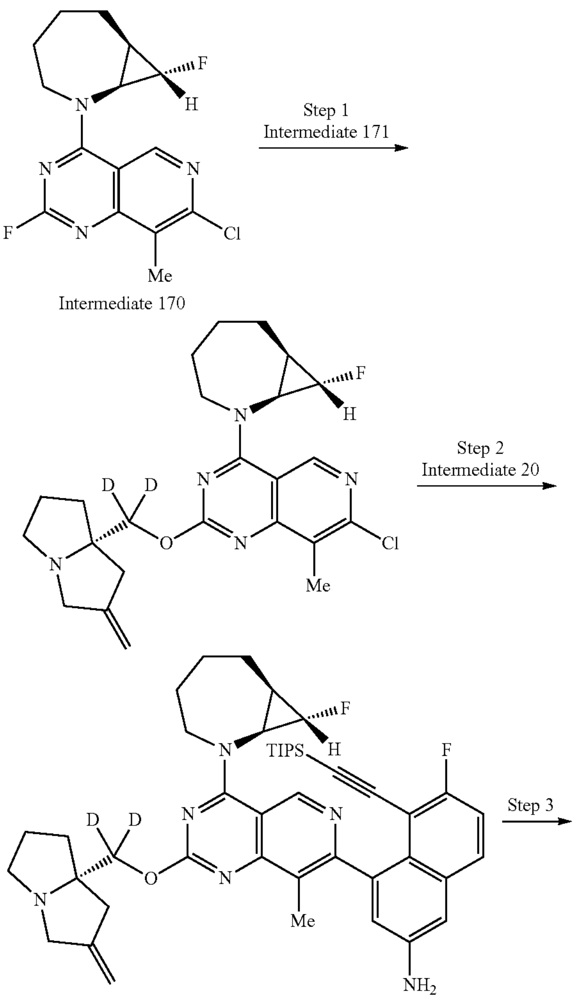

-continued

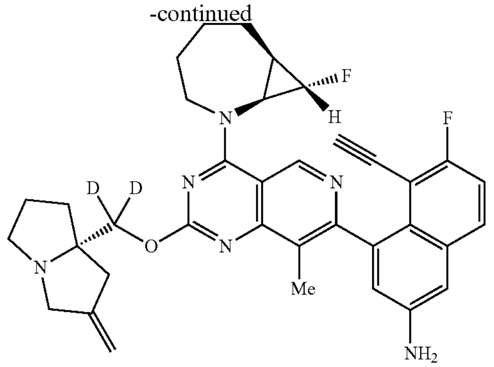

Example 457

Step 1: 7-Chloro-4-((1S,7R,8S)-8-fluoro-2-azabicyclo[5.1.0]octan-2-yl)-8-methyl-2-(((S)-2-methylenetetrahydro-1H-pyrrolizin-7a (5H)-yl)methoxy-$d_2$) pyrido[4,3-d]pyrimidine To a solution of Intermediate 171 (84 mg, 541 μmol) in THF (1 mL) was addedH-BuOK (591 μL, 1 M in THF) at 25° C. under $N_2$. The reaction mixture was stirred at 25° C. for 30 min under $N_2$. A solution of Intermediate 170 (160 mg, 492 μmol) in THF (2 mL) was added dropwise to the mixture at −40° C. under $N_2$. The reaction mixture was stirred at 25° C. for 1 h under $N_2$, quenched with sat. $NH_4Cl$ aq. (5 mL) and extracted with EtOAc (10 mL×2). The combined organic phases were washed with brine (10 mL), dried over anhydrous $Na_2SO_4$, filtered and concentrated under reduced pressure. The residue was purified by silica gel flash chromatography (eluent: 0~4% of methanol in dichloromethane) to give the title compound (140 mg, 61% yield) as a yellow oil. MS: m/z=460.1 $[M+H]^{+}$.

Step 2: 6-Fluoro-4-(4-((1S,7R,8S)-8-fluoro-2-azabicyclo[5.1.0]octan-2-yl)-8-methyl-2-(((S)-2-methylenetetrahydro-1H-pyrrolizin-7a (5H)-yl)methoxy-$d_2$) pyrido[4,3-d]pyrimidin-7-yl)-5-((triisopropylsilyl) ethynyl)naphthalen-2-amine A mixture of 7-chloro-4-((1S,7R,8S)-8-fluoro-2-azabicyclo[5.1.0]octan-2-yl)-8-methyl-2-(((S)-2-methylenetetrahydro-1H-pyrrolizin-7a (5H)-yl)methoxy-$d_2$)pyrido[4,3-d] pyrimidine (70 mg, 152 μmol), Intermediate 20 (85 mg, 169 μmol), $K_3PO_4$ (96 mg, 456 μmol), and AdanBuP-Pd-$G_3$ (cataCXiumAPd$G_3$) (11 mg, 15 μmol) in 1,4-dioxane (4 mL) and $H_2O$ (1 mL) was degassed, purged with $N_2$ three times, and was stirred at 100° C. for 1 h under $N_2$. The mixture was concentrated under reduced pressure. The residue was purified by silica gel flash chromatography (eluent: 0~4% of methanol in dichloromethane) to give the title compound (70 mg, 53% yield) as a yellow solid. MS: m/z=765.3 $[M+H]^{+}$.

Step 3: 5-Ethynyl-6-fluoro-4-(4-((1S,7R,8S)-8-fluoro-2-azabicyclo[5.1.0]octan-2-yl)-8-methyl-2-(((S)-2-methylenetetrahydro-1H-pyrrolizin-7a (5H)-yl)methoxy-$d_2$)pyrido[4,3-d]pyrimidin-7-yl) naphthalen-2-amine To a solution of 6-fluoro-4-(4-((1S,7R,8S)-8-fluoro-2-azabicyclo[5.1.0]octan-2-yl)-8-methyl-2-(((S)-2-methylenetetrahydro-LH-pyrrolizin-7a (5H)-yl)methoxy-$d_2$)pyrido [4,3-d]pyrimidin-7-yl)-5-((triisopropylsilyl) ethynyl) naphthalen-2-amine (86 mg, 75 μmol) in DMSO (1 mL) was added CsF (23 mg, 150 μmol) under $N_2$. The reaction mixture was stirred at 25° C. for 1 h under $N_2$. The reaction mixture was diluted with water (5 mL) and extracted with EtOAc (10 mL×3). The combined organic phases were washed with brine (10 mL), dried over anhydrous $Na_2SO_4$, filtered and concentrated under reduced pressure. The residue was purified by silica gel flash chromatography (eluent: 0~4% of methanol in dichloromethane) and further purified by recersed-phase column (column: C18; mobile phase: [$H_2O$ ($NH_4HCO_3$)-ACN]; gradient: 0%~ 55% B over 30 min) to give the title compound (Example 457, 17 mg, 34% yield) as an off-white solid. MS: m/z=609.3 $[M+H]^{+}$. $^{1}$H NMR (400 MHZ, Dimethylsulfoxide-$d_6$) 8. 9.42-9.33 (m, 1H), 7.74 (dd, J=6.0, 9.2 Hz, 1H), 7.30 (d, J=8.8 Hz, 1H), 7.01-6.99 (m, 1H), 6.92-6.84 (m, 1H), 5.61-5.52 (m, 2H), 4.90 (s, 2H), 4.64-4.36 (m, 2H), 4.00-3.52 (m, 3H), 3.19 (d,J=13.4 Hz, 1H), 3.02-2.97 (m, 1H), 2.64-2.58 (m, 2H), 2.38-2.33 (m, 1H), 2.28-2.22 (m, 1H), 2.14-2.10 (m, 3H), 2.00-1.84 (m, 6H), 1.80-1.68 (m, 3H), 1.53-1.46 (m, 1H), 1.21-1.12 (m, 1H). $^{19}$F NMR (376 MHz, Dimethylsulfoxide-$d_6$) δ −113.65, −113.66, −204.79.

Example 458: 5-Ethynyl-6-fluoro-4-(4-((1S,7R,8S)-8-fluoro-2-azabicyclo[5.1.0]octan-2-yl)-8-methyl-2-(((R)-6'-methylenetetrahydrospiro[cyclopropane-1, 1'-pyrrolizin]-7d'(5'H)-yl)methoxy-$d_2$)pyrido[4,3-d] pyrimidin-7-yl)naphthalen-2-amine

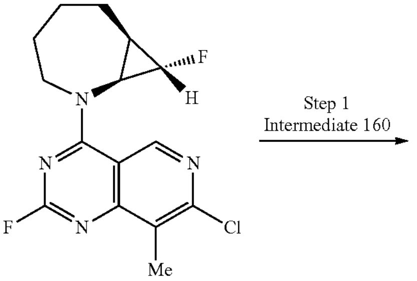

Intermediate 170

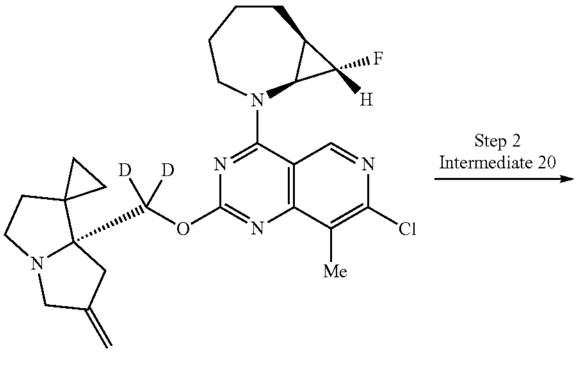

-continued

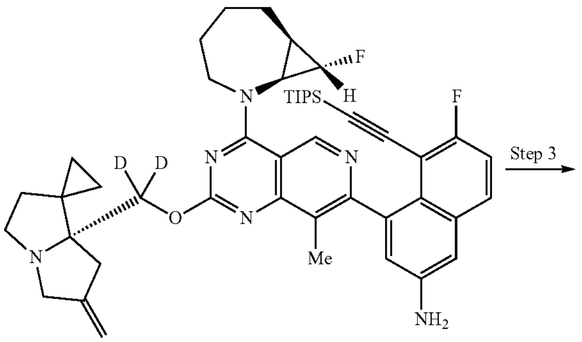

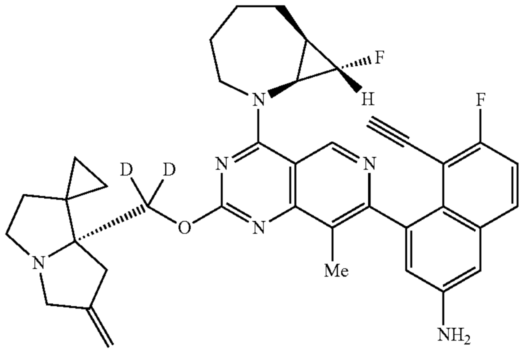

Example 458

Example 458 was prepared in a manner similar to Example 457. MS: m/z=635.4 $[M+H]^+$. $^1H$ NMR (400 MHz, Dimethylsulfoxide-$d_6$) δ 9.46-9.30 (m, 1H), 7.30 (dd, J=3.2 Hz, 9.2 Hz, 1H), 7.30 (t, J=9.2 Hz, 1H), 6.99 (s, 1H), 6.93-6.81 (m, 1H), 5.56 (s, 2H), 4.88 (s, 2H), 4.66-4.35 (m, 2H), 4.10-3.47 (m, 3H), 3.29-3.25 (m, 1H), 3.08-3.00 (m, 1H), 2.67-2.58 (m, 1H), 2.44-2.38 (m, 1H), 2.29-2.21 (m, 2H), 2.15-2.08 (m, 3H), 2.01-1.90 (m, 5H), 1.74-1.70 (m, 2H), 1.55-1.47 (m, 1H), 1.20-1.03 (m, 1H), 0.83-0.76 (m, 1H), 0.64-0.57 (m, 1H), 0.49-0.41 (m, 2H), $^{19}F$ NMR (376 MHz, Dimethylsulfoxide-$d_6$) δ −113.66, −204.35.

Example 459: 4-(4-((1S,7S,8S)-8-Chloro-5-oxa-2-azabicyclo[5.1.0]octan-2-yl)-8-methyl-2-(((R)-6'-methylenetetrahydrospiro[cyclopropane-1, l'-pyrrolizin]-7a (5'H)-yl)methoxy)pyrido[4,3-d]pyrimidin-7-yl)-5-ethynyl-6-fluoronaphthalen-2-amine

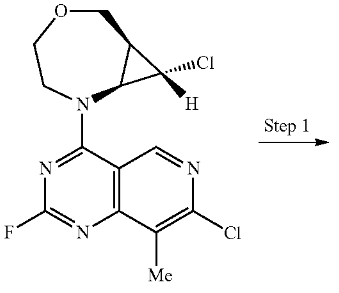

Intermediate 163

-continued

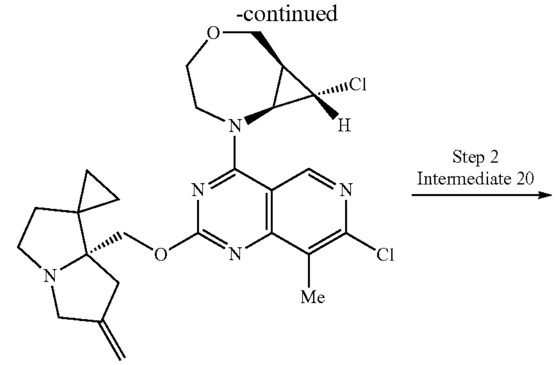

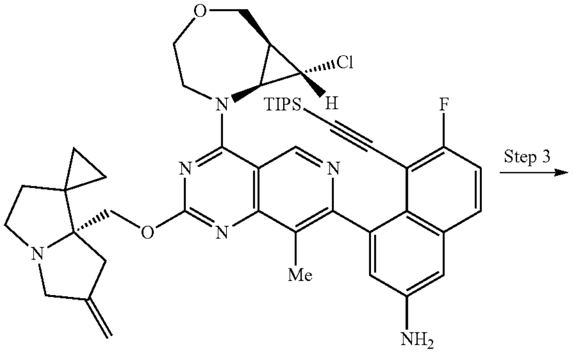

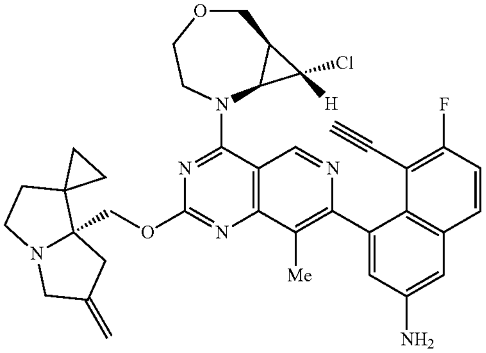

Example 459

Step 1: (1S,7S,8S)-8-Chloro-2-(7-chloro-8-methyl-2-(((R)-6'-methylenetetrahydrospiro[cyclopropane-1, 1'-pyrrolizin]-7a'(5'H)-yl)methoxy)pyrido[4,3-d]pyrimidin-4-yl)-5-oxa-2-azabicyclo[5.1.0]octane To a solution of (R)-(6'-methylenetetrahydrospiro[cyclopropane-1, l'-pyrrolizin]-7a'(5'H)-yl) methanol (60 mg, 335 μmol) in THF (2 mL) was added NaH (67 mg, 1.67 mmol, 60% purity) slowly at 0° C. under $N_2$. The mixture was stirred at 25° C. for 0.5 h. A solution of Intermediate 163 (112 mg, 301 μmol) in THF (2 mL) was added dropwise to the above mixture at 0° C. under $N_2$. The reaction mixture was stirred at 25° C. for 2 h under $N_2$. The reaction mixture was quenched with sat. $NH_4Cl$ aq. (3 mL) at 0° C. and extracted with EtOAc (4 mL×3). The combined organic layers were washed with brine (3 mL), dried over anhydrous $Na_2SO_4$, filtered and concentrated under reduced pressure. The residue was purified by silica gel flash chromatography (eluent: 0~7% of MeOH in $CH_2Cl_2$) to give the title compound (110 mg, 65% yield) as a brown solid. MS: m/z=502.3 $[M+H]^{+\cdot}$ Step 2: 4-(4-((1S,7S,8S)-8-Chloro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy)pyrido[4,3-d]pyrimidin-7-yl)-6-fluoro-5-((triisopropylsilyl) ethynyl)naphthalen-2-amine A mixture of (15,7S,8S)-8-chloro-2-(7-chloro-8-methyl-2-(((R)-6'-methylenetetrahydrospiro[cyclopropane-1,1'-pyrrolizin]-7a'(5'H)-yl)methoxy)pyrido[4,3-d]pyrimidin-4-yl)-5-oxa-2-azabicyclo[5.1.0]octane (101 mg, 201 μmol), Intermediate 20 (131 mg, 261 μmol, HCl salt), $K_3PO_4$ (128 mg, 602 μmol) and AdanBuP-Pd-$G_3$ (cataCXiumAPd$G_3$) (29 mg, 40 μmol) in 1,4-dioxane (4 mL) and $H_2O$ (1 mL) was degassed, purged with $N_2$ three times, and stirred at 110° C. for 1 h under $N_2$. The reaction mixture was concentrated under reduced pressure. The residue was purified by silica gel flash chromatography (eluent: 0~10% of MeOH in $CH_2Cl_2$) to give the title compound (75 mg, 44% yield) as a brown solid. MS: m/z=807.5 $[M+H]^{+\cdot}$ Step 3: 4-(4-((1S,7S,8S)-8-Chloro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy)pyrido[4,3-d]pyrimidin-7-yl)-5-ethynyl-6-fluoronaphthalen-2-amine To a solution of 4-(4-((1S,7S,8S)-8-chloro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl) methoxy)pyrido[4,3-d]pyrimidin-7-yl)-6-fluoro-5-((triisopropylsilyl) ethynyl)naphthalen-2-amine (70 mg, 87 μmol) in DMSO (1 mL) was added CsF (66 mg, 433 μmol). The mixture was stirred at 25° C. for 1 h. The reaction mixture was diluted with $H_2O$ (2 mL) and extracted with EtOAc (3 mL×3). The combined organic layers were washed with brine (3 mL), dried over anhydrous $Na_2SO_4$, filtered and concentrated under reduced pressure. The residue was purified by reversed-phase column (column: C18; mobile phase: [Water ($NH_4HCO_3$)-ACN)]; B %: 0%~55%, 30 min) to give the title compound (Example 459, 33.4 mg, 59% yield) as a yellow solid. MS: m/z=651.3 $[M+H]^+$. $^1H$ NMR (400 MHZ, Dimethylsulfoxide-$d_6$) δ 9.40-9.29 (m, 1H), 7.75 (dd, J=6.0, 9.2 Hz, 1H), 7.30 (t, J=9.2 Hz, 1H), 7.04-6.97 (m, 1H), 6.93-6.82 (m, 1H), 5.63-5.52 (m, 2H), 4.93-4.83 (m, 2H), 4.46-4.34 (m, 2H), 4.22-4.11 (m, 2H), 4.08-3.96 (m, 2H), 3.86-3.48 (m, 5H), 3.30-3.22 (m, 2H), 3.08-3.00 (m, 1H), 2.67-2.59 (m, 1H), 2.45-2.38 (m, 1H), 2.29-2.21 (m, 1H), 2.18-2.08 (m, 4H), 2.02-1.93 (m, 1H), 1.73-1.63 (m, 1H), 0.83-0.74 (m, 1H), 0.66-0.56 (m, 1H), 0.49-0,40 (m, 2H), $^{19}F$ NMR (376 MHZ, Dimethylsulfoxide-$d_6$) δ −113.67.

Example 460: 5-Ethynyl-6-fluoro-4-(4-((1S,7R,8S)-8-fluoro-2-azabicyclo[5.1.0]octan-2-yl)-2-(((2R,7aS)-2-fluorotetrahydro-1H-pyrrolizin-7a (5H)-yl) methoxy-$d_2$)-8-methylpyrido[4,3-d]pyrimidin-7-yl) naphthalen-2-amine

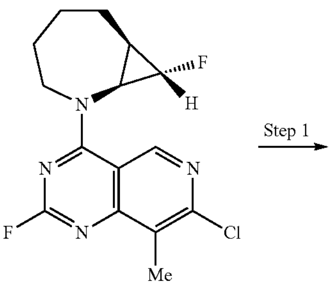

Intermediate 170

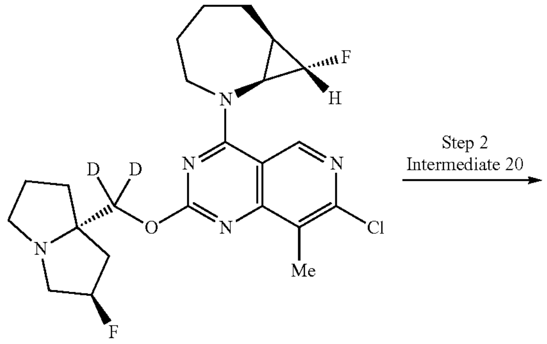

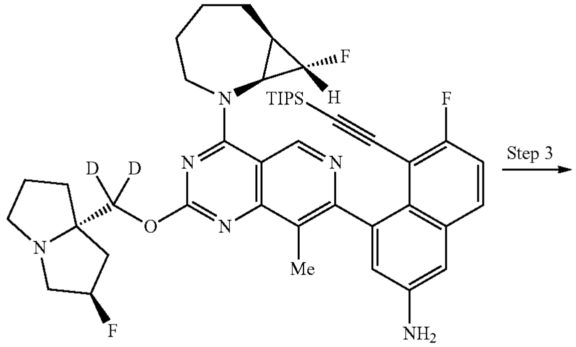

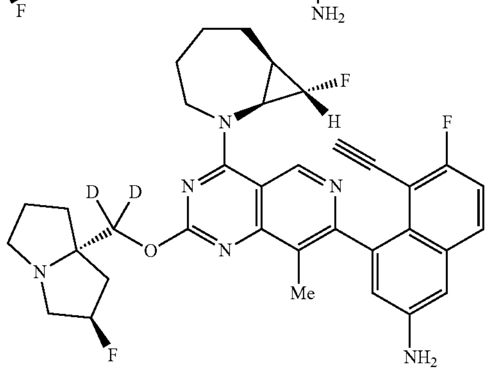

Example 460

Example 460 was prepared in a manner similar to Example 457. MS: m/z=615.2 $[M+H]^+$. $^1H$ NMR (400 MHZ, Dimethylsulfoxide-$d_6$) & 9.42-9.30 (m, 1H), 7.74 (dd, J=6.0, 8.8 Hz, 1H), 7.30 (t, J=9.2 Hz, 1H), 7.00 (d, J=2.0 Hz, 1H), 6.92-6.83 (m, 1H), 5.63-5.50 (m, 2H), 5.28 (d, J=54 Hz, 1H), 4.64-4.34 (m, 2H), 4.09-3.54 (m, 2H), 3.45-3.37

(m, 1H), 3.31-3.26 (m, 1H), 3.10-2.97 (m, 3H), 2.86-2.78 (m, 1H), 2.29-2.21 (m, 1H), 2.14-2.11 (m, 3H), 2.06-1.73 (m, 9H), 1.57-1.45 (m, 1H), 1.24-1.08 (m, 1H). $^{19}$F NMR (376 MHz, Dimethylsulfoxide-$d_6$) δ −113.63, −172.08, −172.19, −204.60.

Example 461: 5-Ethynyl-6-fluoro-4-(4-((1S,7R,8S)-8-fluoro-2-azabicyclo[5.1.0]octan-2-yl)-8-methyl-2-(((S)-2-methylenetetrahydro-LH-pyrrolizin-7a (5H)-yl)methoxy-$d_2$)pyrido[4,3-d]pyrimidin-7-yl) naphthalen-2-ol

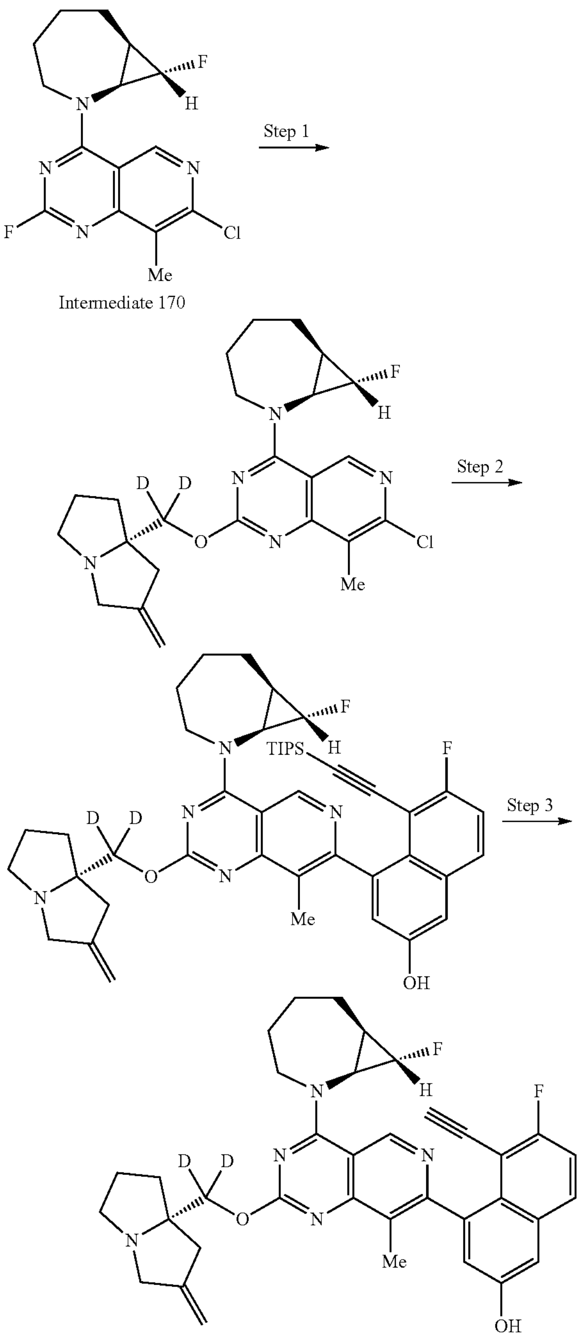

Example 461

Example 461 was prepared in a manner similar to Example 457. MS: m/z=610.3 [M+H]$^+$. $^1$H NMR. (400 MHZ, Dimethylsulfoxide-$d_6$) 8. 10.03 (s, 1H), 9.44-9.33 (m, 1H), 7.94 (dd, J=6.0, 8.8 Hz, 1H), 7.43 (t, J=8.8 Hz, 1H), 7.33 (d, J=2.4 Hz, 1H), 7.04-6.95 (m, 1H), 4.90 (s, 2H), 4.67-4.36 (m, 2H), 4.04-3.64 (m, 2H), 3.55 (d, J=14.0 Hz, 1H), 3.22-3.17 (m, 1H), 3.03-2.97 (m, 1H), 2.64-2.58 (m, 2H), 2.39-2.34 (m, 1H), 2.29-2.22 (m, 1H), 2.16-2.09 (m, 3H), 2.02-1.80 (m, 6H), 1.80-1.66 (m, 3H), 1,53-1.43 (m, 1H), 1.22-1.12 (m, 1H). $^{19}$F NMR (376 MHz, Dimethylsulfoxide-$d_6$) δ −111.06, −204.74.

Example 462: 5-Ethynyl-6-fluoro-4-(4-((1S,7R,8S)-8-fluoro-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy-$d_2$)pyrido[4,3-d]pyrimidin-7-yl)naphthalen-2-ol

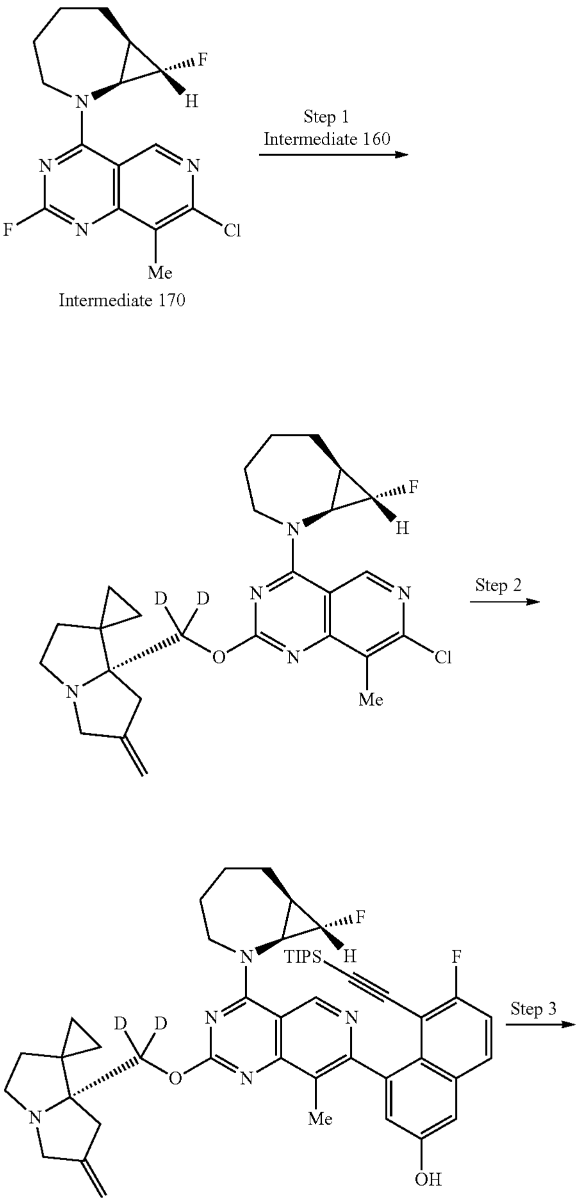

-continued

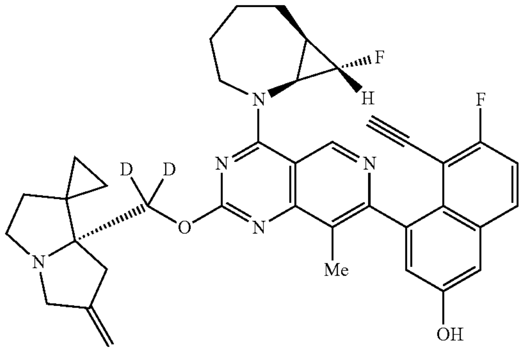

Example 462

Example 462 was prepared in a manner similar to Example 457. MS: m/z=636.2 $[M+H]^+$. $^1H$ NMR (400 MHz, Dimethylsulfoxide-$d_6$) δ 9.40-9.32 (m, 1H), 7.92-7.82 (m, 1H), 7.38 (t, J=8.8 Hz, 1H), 7.25 (s, 1H), 7.04-6.91 (m, 1H), 4.87 (s, 2H), 4.70-4.43 (m, 1H), 4.41-4.33 (m, 1H), 3.99-3.58 (m, 3H), 3.25-3.23 (m, 1H), 3.06-3.01 (m, 1H), 2.65-2.59 (m, 1H), 2.45-2.31 (m, 2H), 2.28-2.22 (m, 2H), 2.14-2.09 (m, 3H), 2.01-1.87 (m, 4H), 1.74-1.65 (m, 2H), 1.54-1.45 (m, 1H), 1.21-1.10 (m, 1H), 0.83-0.76 (m, 1H), 0.63-0.58 (m, 1H), 0.48-0.42 (m, 2H) $^{19}F$ NMR (376 MHz, Dimethylsulfoxide-$d_6$) δ −111.60, −112.01, −204.36, −204.66.

Example 463: 5-Ethynyl-6-fluoro-4-(4-((1S,7R,8S)-8-fluoro-2-azabicyclo[5.1.0]octan-2-yl)-2-(((2R,7aS)-2-fluorotetrahydro-1H-pyrrolizin-7a (5H)-yl)methoxy-$d_2$)-8-methylpyrido[4,3-d]pyrimidin-7-yl)naphthalen-2-ol

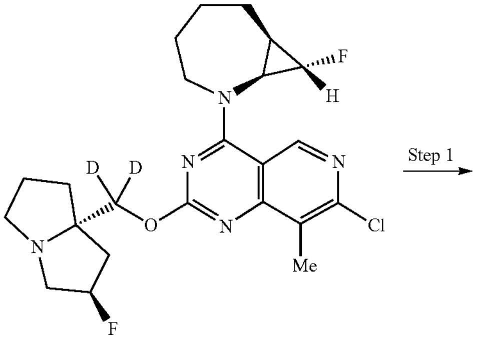

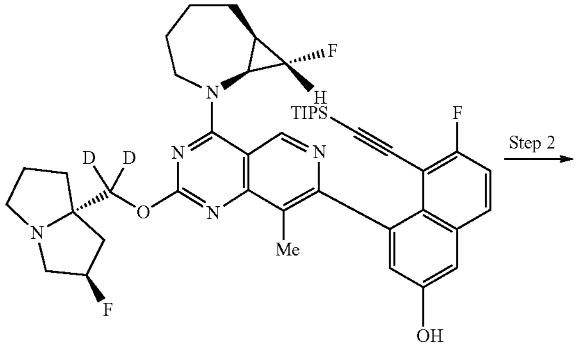

-continued

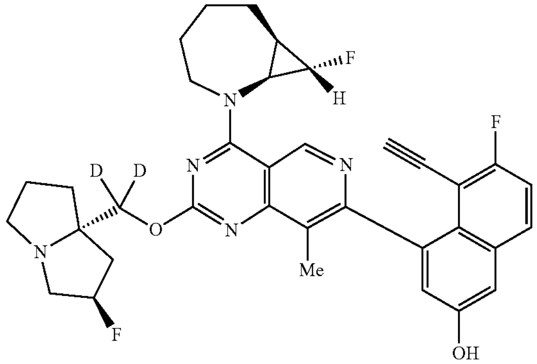

Example 463

Example 463 was prepared in a manner similar to Example 457. MS: m/z=616.2 $[M+H]^+$. $^1H$ NMR (400 MHz, Dimethylsulfoxide-$d_6$) δ 10.12-9.98 (m, 1H), 9.43-9.30 (m, 1H), 7.94 (dd, J=6.0, 9.2 Hz, 1H), 7.43 (t, J=9.2 Hz, 1H), 7.33 (d, J=2.8 Hz, 1H), 7.05-6.91 (m, 1H), 5.28 (d, J=54 Hz, 1H), 4.65-4.34 (m, 2H), 4.07-3.62 (m, 2H), 3.42-3.37 (m, 1H), 3.31-3.26 (m, 1H), 3.11-3.00 (m, 3H), 2.86-2.79 (m, 1H), 2.29-2.21 (m, 1H), 2.14-2.10 (m, 3H), 2.07-1.73 (m, 9H), 1.58-1.45 (m, 1H), 1.26-1.08 (m, 1H), $^{19}F$ NMR (376 MHz, Dimethylsulfoxide-$d_6$) δ −111.04, −172.08, −204.65.

Intermediate 464: 4-(4-((1S,7R,8S)-8-chloro-2-azabicyclo[5.1.0]octan-2-yl)-2-(((2R,7aS)-2-fluoro-tetrahydro-1H-pyrrolizin-7a (5H)-yl)methoxy-$d_2$)-8-methylpyrido[4,3-d]pyrimidin-7-yl)-5-ethynyl-6-fluoronaphthalen-2-amine

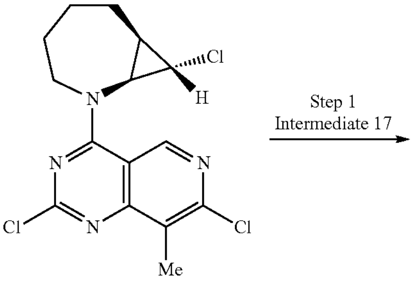

Intermediate 169

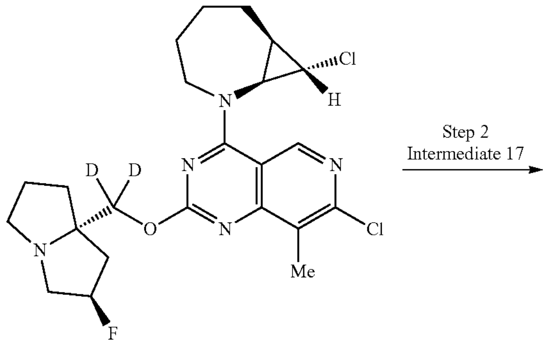

-continued

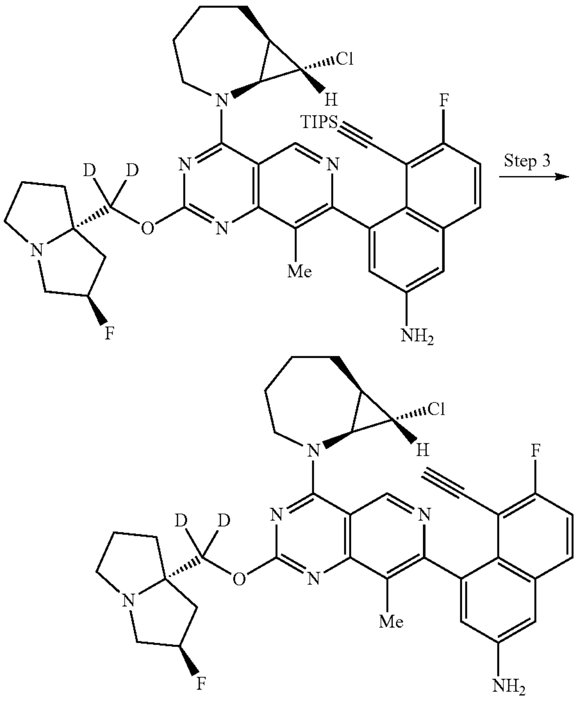

Example 484

Step 1: 7-Chloro-4-((1S,7R,8S)-8-chloro-2-azabicyclo[5.1.0]octan-2-yl)-2-(((2R,7aS)-2-fluorotetrahydro-1H-pyrrolizin-7a (5H)-yl)methoxy-$d_2$)-8-methylpyrido[4,3-d]pyrimidine To a solution of Intermediate 169 (180 mg, 503 μmol), DIPEA (438 μL, 2.52 mmol) and Intermediate 17 (146 mg, 906 μmol) in 1,4-dioxane (5 mL) was stirred at 110° C. under $N_2$ for 12 h. The reaction mixture was concentrated under reduced pressure. The residue was purified by silica gel flash chromatography (eluent: 0~4% of MeOH in $CH_2Cl_2$) to give the title compound (100 mg, 55% yield over 3 steps) as a yellow solid. MS: m/z=482.1 $[M+H]^{+\cdot}$ Step 2: 4-(4-((1S,7R,8S)-8-chloro-2-azabicyclo[5.1.0]octan-2-yl)-2-(((2R,7aS)-2-fluorotetrahydro-1H-pyrrolizin-7a (5H)-yl)methoxy-$d_2$)-8-methylpyrido[4,3-d]pyrimidin-7-yl)-6-fluoro-5-((triisopropylsilyl) ethynyl)naphthalen-2-amine A mixture of 7-chloro-4-((1S,7R,8S)-8-chloro-2-azabicyclo[5.1.0]octan-2-yl)-2-(((2R,7aS)-2-fluorotetrahydro-1H-pyrrolizin-7a (5H)-yl)methoxy-$d_2$)-8-methylpyrido[4,3-d]pyrimidine (100 mg, 207 μmol), Intermediate 20 (194 mg, 415 μmol), $K_2PO_4$ (176 mg, 829 μmol) and AdanBuP-Pd-$G_3$ (cataCXiumAPdGs) (30 mg, 41 μmol) in 1,4-dioxane (5 mL) and $H_2O$ (1 mL) was degassed, purged with $N_2$ three times, and stirred at 100° C. under $N_2$ for 2 h. The reaction mixture was concentrated under reduced pressure. The residue was purified by silica gel flash chromatography (eluent: 0~7% of MeOH in $CH_2Cl_2$) to give the title compound (85 mg, 52% yield) as a yellow solid. MS: m/z=787.2 $[M+H]^{+\cdot}$ Step 3: 4-(4-((1S,7R,8S)-8-chloro-2-azabicyclo[5.1.0]octan-2-yl)-2-(((2R,7aS)-2-fluorotetrahydro-1H-pyrrolizin-7a (5H)-yl)methoxy-$d_2$)-8-methylpyrido[4,3-d]pyrimidin-7-yl)-5-ethynyl-6-fluoronaphthalen-2-amine To a solution of 4-(4-((1S,7R,8S)-8-chloro-2-azabicyclo[5.1.0]octan-2-yl)-2-(((2R,7aS)-2-fluorotetrahydro-1H-pyrrolizin-7a (5H)-yl)methoxy-$d_2$)-8-methylpyrido[4,3-d]pyrimidin-7-yl)-6-fluoro-5-((triisopropylsilyl) ethynyl) naphthalen-2-amine (85 mg, 108 μmol) in DMSO (2 mL) was added CsF (164 mg, 1.08 mmol). The reaction mixture was stirred at 25° C. for 0.5 h. The mixture was diluted with $H_2O$ (20 ml) and extracted with EtOAc (40 ml×2). The combined organic layers were dried over $Na_2SO_4$, filtered and concentrated under reduced pressure. The residue was purified by reversed-phase column (column: C18; mobile phase: [water ($NH_3$°$H_2O$) -ACN]; B %: 0%~50%, 40 min) to give the title compound (Example 464, 22.7 mg, 33% yield) as a yellow solid. MS: m/z=631.2 $[M+H]^+$. $^1H$ NMR (400 MHz, Dimethylsulfoxide-$d_6$) δ 9.43-9.20 (m, 1H), 7.74 (dd, J=6.0, 9.2 Hz, 1H), 7.29 (t, J=9.2 Hz, 1H), 7.05-6.80 (m, 2H), 5.67-5.48 (m, 2H), 5.41-5.15 (m, 1H), 4.43-4.24 (m, 1H), 3.94-3.50 (m, 2H), 3.40-3.35 (m, 1H), 3.27-3.20 (m, 1H), 3.14-3.05 (m, 2H), 3.05-2.95 (m, 1H), 2.88-2.78 (m, 1H), 2.35-2.28 (m, 1H), 2.19-2.04 (m, 5H), 2.03-1.94 (m, 2H), 1.91-1.70 (m, 6H), 1.57-1.45 (m, 1H), 1.30-691.22 (m, 1H). $^{19}F$ NMR (376 MHz, Dimethylsulfoxide-$d_6$) δ −113.69, −172.05.

Example 467 & 469: 5-Ethynyl-6-fluoro-4-((R)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)naphthalen-2-ol & 5-ethynyl-6-fluoro-4-((S)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)naphthalen-2-ol

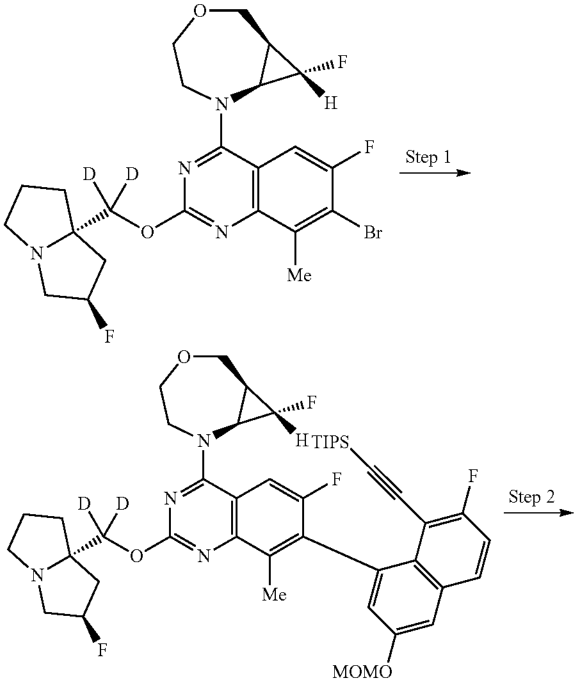

-continued

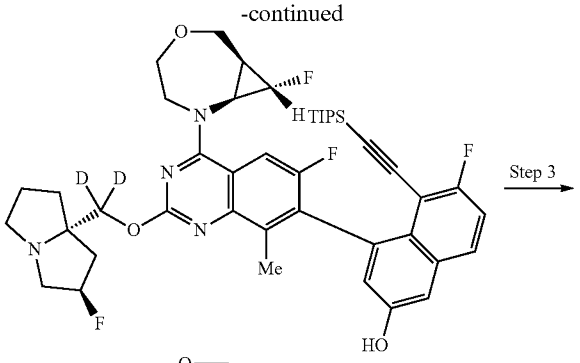

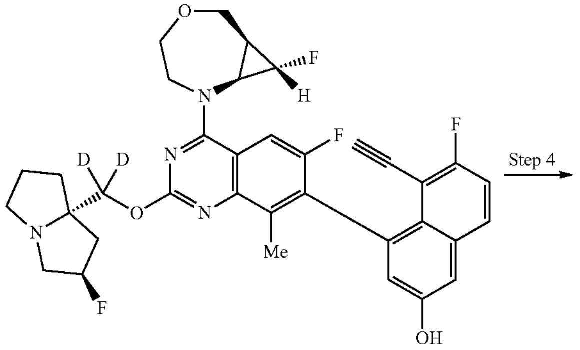

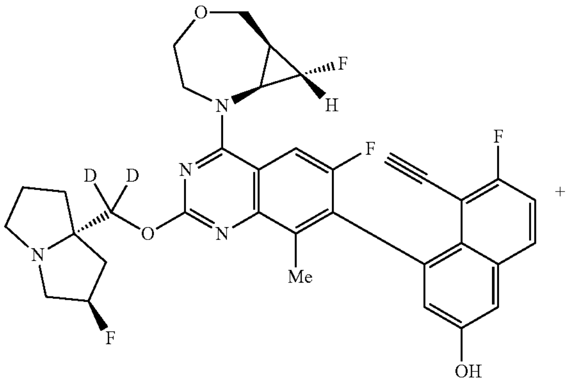

Example 467

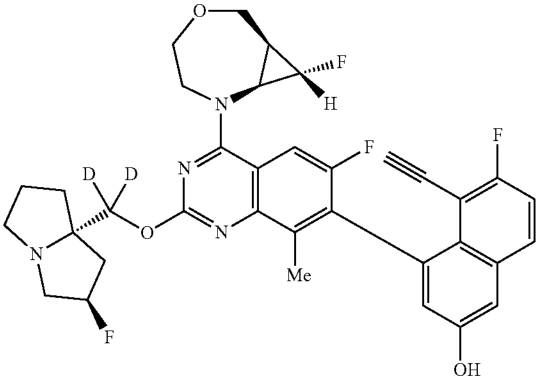

Example 469

Step 1: (1S,7S,8S)-8-Fluoro-2-(6-fluoro-7-(7-fluoro-3-(methoxymethoxy)-8-((triisopropylsilyl) ethynyl) naphthalen-1-yl)-2-(((2R,7aS)-2-fluorotetrahydro-1H-pyrrolizin-7a (5H)-yl)methoxy-$d_2$)-8-methylquinazolin-4-yl)-5-oxa-2-azabicyclo[5.1.0] octane To a mixture of (15,7S,8S)-2-(7-bromo-6-fluoro-2-(((2R,7aS)-2-fluorotetrahydro-1H-pyrrolizin-7a (5H)-yl)methoxy-$d_2$)-8-methylquinazolin-4-yl)-8-fluoro-5-oxa-2-azabicyclo [5.1.0]octane (300 mg, 0.57 mmol, refer to Example 434 & 435 for detail procedures) and (15,7S,8S)-2-(7-bromo-6-fluoro-2-(((2R,7aS)-2-fluorotetrahydro-1H-pyrrolizin-7a (5H)-yl)methoxy-$d_2$)-8-methylquinazolin-4-yl)-8-fluoro-5-oxa-2-azabicyclo[5.1.0]octane (871.34 mg, 1.70 mmol) in THF (10 mL) and $H_2O$ (2 mL) under $N_2$ were added CataCXium A Pd G3 (82.54 mg, 0.11 mmol) and $K_3PO_4$ (721.72 mg, 3.40 mmol) at room temperature. The reaction mixture was heated at 80° C. for 3 hours. The resulting mixture was cooled to room temperature and concentrated under reduced pressure. The residue was purified by Prep-TCL (MeOH: DCM=1: 10) to afford the title compound (200 mg, 42% yield) as a yellow solid. MS: m/z=835.50 $[M+H]^{+\cdot}$ Step 2: 6-fluoro-4-(6-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl) methoxy-$d_2$)-8-methylquinazolin-7-yl)-5-((triisopropylsilyl) ethynyl)naphthalen-2-ol To an ice-cooled solution of (1S,7S,8S)-8-fluoro-2-(6-fluoro-7-(7-fluoro-3-(methoxymethoxy)-8-((triisopropylsilyl) ethynyl)naphthalen-1-yl)-2-(((2R,7aS)-2-fluorotetrahydro-1H-pyrrolizin-7a (5H)-yl)methoxy-$d_2$)-8-methylquinazolin-4-yl)-5-oxa-2-azabicyclo[5.1.0]octane (200 mg, 0.24 mmol) in MeCN (10 mL) was added HCl in 1,4-dioxane (4.0 M, 2.10 mL, 8.40 mmol) dropwise. The reaction mixture was stirred in an ice bath for 1 hour. The resulting mixture was quenched with sat. NaHICOs aq. (30 mL) in an ice bath and extracted with DCM (3×50 mL). The combined organic layers were washed with brine (50 mL), dried over anhydrous $Na_2SO_4$, filtered and concentrated under reduced pressure to afford the title compound (150 mg, 79% yield) as a light yellow solid. MS: m/z=791.40 $[M+H]^{+\cdot}$ Step 3: 5-Ethynyl-6-fluoro-4-(6-fluoro-4-((15,7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)naphthalen-2-ol To a stirred solution of 6-fluoro-4-(6-fluoro-4-((15,75,8S)-8-fluoro-S-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)-5-((triisopropylsilyl) ethynyl) naphthalen-2-ol (100 mg, 0.13 mmol) in DMF (2 mL) was added CsF (288.05 mg, 1.89 mmol) at room temperature. The reaction mixture was stirred at room temperature for 2 hours. The resulting mixture was filtered and purified by Prep-HPLC directly with the following conditions: Column: X-bridge Shield RP18 OBD Column 30×150 mm, 5 μm; Mobile Phase A: 10 mM aq. $NH_4HCO_3$; Mobile Phase B: MeCN; Flow rate: 25 mL/min; Gradient: 35% B to 75% B in 10 min; Detector: UV 254 & 220 nm; RT: 8.12 min. The collected fractions were combined, concentrated and lyophilized overnight to give the title compound (57 mg, 71% yield) as a yellow lyophilized powder. MS: m/z=635.40 $[M+H]^+$, Step 4: 5-Ethynyl-6-fluoro-4-((R)-6-fluoro-4-((15, 7S,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)naphthalen-2-ol & 5-ethynyl-6-fluoro-4-((S)-6-fluoro-4-((1S,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)naphthalen-2-ol 5-Ethynyl-6-fluoro-4-(6-fluoro-4-((1S,75,8S)-8-fluoro-5-oxa-2-azabicyclo[5.1.0]octan-2-yl)-2-(((2R,7aS)-2-fluorotetrahydro-1H-pyrrolizin-7a (5H)-yl)methoxy-$d_2$)-8-methylquinazolin-7-yl)naphthalen-2-ol (60 mg, 0.09 mmol) was separated by Prep-Chiral-HPLC with the following conditions: Column: CHIRALPAK IB 2×25 cm, 5 μm; Mobile Phase A: Hex (0.5% 2 M $NH_3$.MeOH), Mobile Phase B: EtOH; Flow rate: 20 mL/min; Gradient: isocratic 10%; Detector: UV 220 & 254 nm; RT1: 10.476 min; RT2: 12.733 min. The first eluting peak (RT1: 10.476 min) was concentrated and lyophilized to give the title compound (Example 467, 5.3 mg, 8% yield) as an off-white lyophilized powder. MS: m/z=635.20 $[M+H]^+$. $^1$H NMR (400 MHZ, Methanol-$d_4$) δ 7.93-7.91 (m, 1H), 7.85-7.81 (m, 1H), 7.31-7.27 (m, 2H), 7.01 (s, 1H), 5.35-5.21 (m, 1H), 4.54-4.38 (m, 3H), 4.06-3.96 (m, 3H), 3.70-3.60 (m, 1H), 3.29-3.10 (m, 4H), 3.05-2.96 (m, 2H), 2.40-2.10 (m, 7H), 2.02-1.80 (m, 3H). $^{19}$F NMR (376 MHz, DMSO) δ −111.88 (s, 1F), −119.04 (s, 1F), −173.76--173.82 (d, 1F), −207.10--208.86 (m, 1F). The second eluting peak (RT2: 12.733 min) was concentrated and lyophilized to give the other title compound (Example 469, 27.3 mg, 45% yield) as an off-white lyophilized powder. MS: m/z=635.30 $[M+H]^+$. $^1$H NMR (400 MHZ, Methanol-$d_4$) δ 7.91-7.81 (m, 2H), 7.32-7.27 (m, 2H), 6.97-6.96 (m, 1H), 5.35-5.21 (m, 1H), 4.59-4.41 (m, 3H), 4.05-3.99 (m, 3H), 3.70-3.67 (m, 1H), 3.39 (s, 1H), 3.29-3.10 (m, 4H), 3.06-2.94 (m, 1H), 2.40-1.77 (m, 10H). $^{19}$F NMR (376 MHz, Methanol-$d_4$) δ −111.90 (s, 1F), −119.24 (s, 1F), −173.75 (s, 1F), −207.13--209.00 (m, 1F).

Each compound in Table 2 was prepared in a similar manner (using appropriately substituted reagents) as described in the examples.

TABLE 2

| Example | $^1$H NMR and $^{19}$F NMR data | Mass: $[M + H]^+$ |
|---|---|---|
| 94 | $^1$H NMR (400 MHz, Dimethylsulfoxide-$d_6$) δ 9.42-9.29 (m, 1H), 7.78 (dd, J = 8.8, 11.6 Hz, 1H), 7.04-6.94 (m, 2H), 5.87-5.71 (m, 3H), 5.53-5.43 (m, 1H), 5.37-5.19 (m, 1H), 4.83-4.38 (m, 3H), 4.35-3.95 (m, 1H), 3.84-3.72 (m, 1H), 3.11-3.05 (m, 2H), 3.02-2.91 (m, 2H), 2.86-2.78 (m, 1H), 2.46-2.31 (m, 2H), 2.15-2.09 (m, 1H), 2.05-1.96 (m, 2H), 1.88-1.74 (m, 3H). $^{19}$F NMR (376 MHz, Dimethylsulfoxide-$d_6$) δ −137.83, −137.90, −138.70, −139.85, −140.37, −172.02, −172.13, −204.23, −205.14 | 635.2 |
| 95 | $^1$H NMR (400 MHz, Dimethylsulfoxide-$d_6$) δ 9.45-9.33 (m, 1H), 8.21-8.00 (m, 2H), 7.78-7.69 (m, 1H), 7.66-7.53 (m, 1H), 5.40-5.17 (m, 1H), 4.80-4.56 (m, 1H), 4.42 (d, J = 12.8 Hz, 1H), 4.10-3.98 (m, 1H), 3.39-3.37 (m, 1H), 3.12-2.99 (m, 3H), 2.87-2.79 (m, 1H), 2.30-2.22 (m, 1H), 2.14-1.96 (m, 4H), 1.89-1.68 (m, 6H), 1.55-1.46 (m, 1H), 1.19-1.07 (m, 1H). $^{19}$F NMR (376 MHz, Dimethylsulfoxide-$d_6$) δ −135.75, −135.81, −135.91, −140.51, −140.61, −150.76, −151.17, −151.21, −151.46, −151.52, −172.08, −172.15, −204.68, −205.58 | 648.3 |
| 96 | $^1$H NMR (400 MHz, Dimethylsulfoxide-$d_6$) δ: 9.42-9.33 (m, 1H), 8.34-8.26 (m, 1H), 7.84-7.69 (m, 3H), 5.39-5.17 (m, 1H), 4.74-4.49 (m, 1H), 4.46-4.36 (m, 1H), 4.29-3.94 (m, 2H), 3.41-3.34 (m, 1H), 3.11-2.99 (m, 3H), 2.87-2.78 (m, 1H), 2.31-2.20 (m, 1H), 2.16-2.09 (m, 1H), 2.06-1.95 (m, 3H), 1.90-1,69 (m, 6H), 1.58-1.47 (m, 1H), 1.26-1.12 (m, 1H). $^{19}$F NMR (376 MHz, Dimethylsulfoxide-$d_6$) δ −102.77, −102.86, −113.44, −113.47, −140.05, −140.43, −172.07, −172.17, −204.61, −205.01 | 622.3 |
| 99 | $^1$H NMR (400 MHz, Dimethylsulfoxide-$d_6$) δ 9.42-9.27 (m, 1H), 7.84-7.73 (m, 1H), 7.06-6.91 (m, 2H), 5.86-5.73 (m, 3H), 5.52-5.41 (m, 1H), 5.36-5.17 (m, 1H), 4.83-4.39 (m, 3H), 4.33-3.99 (m, 1H), 3.82-3.72 (m, 1H), 3.11-3.05 (m, 2H), 3.03-2.96 (m, 2H), 2.86-2.78 (m, 1H), 2.46-2.31 (m, 2H), 2.14-2.09 (m, 1H), 2.07-1.95 (m, 2H), 1.88-1.73 (m, 3H). $^{19}$F NMR (376 MHz, Dimethylsulfoxide-$d_6$) δ −137.82, −137.89, −138.69, −139.89, −140.35, −172.08, −172.20, −204.21, −205.12 | 635.2 |
| 101 | $^1$H NMR (400 MHz, DMSO-$d_6$) δ 9.41-9.39 (m, 1H), 8.26-8.20 (m, 2H), 7.72-7.60 (m, 3H), 5.35-5.21 (m, 1H), 4.93-4.75 (m, 1H), 4.52-4.48 (m, 1H), 4.37-4.31 (m, 1H), 4.21-3.98 (m, 2H), 3.74-3.57 (m, 2H), 3.09-3.01 (m, 3H), 2.85-2.80 (m, 1H), 2.40-2.30 (m, 1H), 2.12-1.90 (m, 3H), 1.85-1.73 (m, 3H). $^{19}$F NMR (376 MHz, DMSO-$d_6$) δ −105.71--105.83 (d, 1F), −140.34 (s, 1F), −172.07--172.18 (d, 1F), −207.74 (s, 1F). | 608.3 |
| 104 | $^1$H NMR (400 MHz, DMSO-$d_6$) δ 9.45-9.39 (m, 1H), 8.26-8.19 (m, 2H), 7.73-7.60 (m, 3H), 4.90-4.75 (m, 1H), 4.52-4.48 (m, 1H), 4.43-4.34 (m, 2H), 4.21-3.98 (m, 4H), 3.77-3.61 (m, 3H), 3.33-3.18 (m, 2H), 3.06-2.95 (m, 1H), 2.67-2.53 (m, 2H), 2.43-2.28 (m, 2H), 1.96-1.70 (m, 4H). $^{19}$F NMR (376 MHz, DMSO-$d_6$) δ −90.94--91.63 (m, 2F), −105,71--105.85 (d, 1F), −139.91--140.32 (d, 1F), −207.69 (s, 1F) | 634.3 |

TABLE 2-continued

| Example | $^1H$ NMR and $^{19}F$ NMR data | Mass: $[M + H]^+$ |
|---|---|---|
| 105 | $^1H$ NMR (400 MHz, DMSO-$d_6$) δ 9.46-9.40 (m, 1H), 8.31-8.26 (m, 1H), 8.18-8.16 (m, 1H), 7.77-7.74 (m, 1H), 7.68-7.64 (m, 1H), 4.90-4.75 (m, 1H), 4.52-4.32 (m, 4H), 4.19-4.00 (m, 3H), 3.75-3.61 (m, 3H), 3.33-3.15 (m, 2H), 2.99-2.96 (m, 1H), 2.70-2.51 (m, 2H), 2.48-2.30 (m, 2H), 1.95-1.76 (m, 4H). $^{19}F$ NMR (376 MHz, DMSO-$d_6$) δ −90.88-−91.46 (m, 2F), −129.44-−129.66 (m, 1F), −137.12-−137.21 (m, 1F), −139.92-−140.32 (m, 1F), −207.65-−207.80 (m, 1F) | 652.3 |
| 107 | $^1H$ NMR (400 MHz, DMSO-$d_6$) δ 9.45-9.39 (m, 1H), 8.31-8.26 (m, 1H), 8.18-8.16 (m, 1H), 7.77-7.73 (m, 1H), 7.67-7.64 (m, 1H), 4.90-4.75 (m, 1H), 4.52-4.48 (m, 1H), 4.40-4.19 (m, 3H), 4.12-3.94 (m, 3H), 3.71-3.61 (m, 3H), 3.33-3.18 (m, 2H), 3.00-2.96 (m, 1H), 2.68-2.51 (m, 2H), 2.46-2.28 (m, 2H), 1.96-1.76 (m, 4H). $^{19}F$ NMR (376 MHz, DMSO-$d_6$) δ −90.90-−91.64 (m, 2F), −129.44-−129.68 (m, 1F), −137.14-−137.22 (m, 1F), −139.94-−142.80 (m, 1F), −207.66 (s, 1F) | 652.3 |
| 108 | $^1H$ NMR (400 MHz, DMSO-$d_6$) δ 9.46-9.37 (m, 1H), 7.48-7.43 (m, 1H), 7.15 (s, 2H), 5.92 (s, 2H), 5.35-5.21 (m, 1H), 4.94-4.73 (m, 1H), 4.51-4.30 (m, 3H), 4.07-3.81 (m, 2H), 3.74-3.57 (m, 2H), 3.32-3.20 (m, 1H), 3.09-3.01 (m, 3H), 2.85-2.82 (m, 1H), 2.42-2.27 (m, 1H), 2.16-1.68 (m, 6H). $^{19}F$ NMR (376 MHz, DMSO-$d_6$): δ −111.553-−111.650 (m, 1F), −116.393-−116.469 (m, 1F), −139.863-−140.434 (d, 1F), −172.079-−172.190 (m, 1F), −207.749 (s, 1F) | 639.1 |
| 109 | $^1H$ NMR (400 MHz, Dimethylsulfoxide-$d_6$) δ: 9.44-9.36 (m, 1H), 8.09 (d, J = 8.4 Hz, 1H), 7.90 (dd, J = 8.0, 10.8 Hz, 1H), 7.68 (t, J = 7.6 Hz, 1H), 7.55-7.44 (m, 1H), 5.39-5.17 (m, 1H), 4.77-4.52 (m, 1H), 4.48-4.37 (m, 1H), 4.11-3.97 (m, 1H), 3.40-3.36 (m, 1H), 3.10-2.98 (m, 3H), 2.87-2.77 (m, 1H), 2.30-2.21 (m, 1H), 2.18-2.09 (m, 1H), 2.05-1.94 (m, 3H), 1.89-1.68 (m, 6H), 1.57-1.43 (m, 1H), 1.21-1.07 (m, 1H). $^{19}F$ NMR (376 MHz, Dimethylsulfoxide-$d_6$) δ −136.07, −136.13, −136.19, −141.01, −141.13, −154.12, −154.18, −154.24, −172.10, −172.14, −204.59, −205.10 | 631.3 |
| 112 | $^1H$ NMR (400 MHz, Dimethylsulfoxide-$d_6$) δ: 9.42-9.33 (m, 1H), 8.34-8.26 (m, 1H), 7.84-7.69 (m, 3H), 5.39-5.17 (m, 1H), 4.74-4.49 (m, 1H), 4.46-4.36 (m, 1H), 4.29-3.94 (m, 2H), 3.41-3.34 (m, 1H), 3.11-2.99 (m, 3H), 2.87-2.78 (m, 1H), 2.31-2.20 (m, 1H), 2.16-2.09 (m, 1H), 2.06-1.95 (m, 3H), 1.90-1.69 (m, 6H), 1.58-1.47 (m, 1H), 1.26-1.12 (m, 1H). $^{19}F$ NMR (376 MHz, Dimethylsulfoxide-$d_6$) δ −102.77, −102.86, −113.44, −113.47, −140.05, −140.43, −172.07, −172.17, −204.61, −205.01. | 622.3 |
| 115 | $^1H$ NMR (400 MHz, DMSO-$d_6$) δ 9.32-9.28 (m, 1H), 7.11-7.08 (m, 2H), 6.10-6.08 (m, 2H), 5.35-5.22 (m, 1H), 4.98-4.70 (m, 1H), 4.48-4.41 (m, 1H), 4.38-3.94 (m, 4H), 3.86-3.75 (m, 1H), 3.60-3.54 (m, 1H), 3.08-3.01 (m, 3H), 2.86-2.82 (m, 1H), 2.15-1.77 (m, 8H). $^{19}F$ NMR (376 MHz, DMSO-$d_6$) δ −136.53-−136.64 (m, 1F), −139.89-−140.22 (m, 1F), −144.13-−144.29 (m, 1F), −161.79-−161.90 (m, 1F), −172.05-−172.17 (d, 1F), −211.88-−212.77 (d, 1F). | 657.5 |
| 116 | $^1H$ NMR (400 MHz, DMSO-$d_6$) δ 9.45-9.39 (m, 1H), 7.58-7.54 (m, 1H), 7.40-7.34 (m, 1H), 7.08-7.03 (m, 2H), 5.67-5.65 (m, 2H), 5.35-5.21 (m, 1H), 4.96-4.81 (m, 1H), 4.52-4.49 (m, 1H), 4.39-4.29 (m, 2H), 4.05-3.95 (m, 1H), 3.71-3.59 (m, 2H), 3.33-3.15 (m, 1H), 3.14-3.00 (m, 3H), 2.86-2.81 (m, 1H), 2.45-2.30 (m, 1H), 2.12-1.70 (m, 6H). $^{19}F$ NMR (376 MHz, DMSO-$d_6$) δ −136.83-−137.31 (m, 1F), −140.06-−140.21 (d, 1F), −150.64-−151.00 (m, 1F), −172.08-−172.15 (d, 1F), −207.65-−208.25 (m, 1F) | 647.2 |
| 117 | $^1H$ NMR (400 MHz, DMSO-$d_6$) δ 9.36-9.28 (m, 1H), 7.47-7.42 (m, 1H), 7.14-7.12 (m, 2H), 5.94-5.92 (m, 2H), 5.35-5.22 (m, 1H), 4.97-4.71 (m, 1H), 4.54-4.45 (m, 1H), 4.23-4.11 (m, 3H), 3.97-3.78 (m, 2H), 3.60-3.54 (m, 1H), 3.13-3.01 (m, 3H), 2.86-2.82 (m, 1H), 2.23-1.70 (m, 8H). $^{19}F$ NMR (376 MHz, DMSO-$d_6$) δ −111.66-−111.75 (m, 1F), −116.47-−116.58 (m, 1F), −139.85-−140.20 (d, 1F), −172.04-−172.16 (d, 1F), −211.84-−212.65 (d, 1F) | 639.1 |
| 118 | $^1H$ NMR (400 MHz, DMSO-$d_6$) δ 9.45-9.39 (m, 1H), 8.26-8.20 (m, 2H), 7.72-7.60 (m, 3H), 5.35-5.21 (m, 1H), 4.51-4.31 (m, 3H), 4.22-3.98 (m, 2H), 3.72-3.60 (m, 2H), 3.30-3.17 (m, 1H), 3.14-2.96 (m, 3H), 2.90-2.80 (m, 1H), 2.44-2.27 (m, 1H), 2.16-1.93 (m, 3H), 1.89-1.70 (m, 3H). $^{19}F$ NMR (376 MHz, DMSO-$d_6$) δ −105.71-−105.83 (d, 1F), −139.90-−140.34 (d, 1F), −172.07-−172.17 (d, 1F), −208.35-−208.39 (m, 1F) | 607.2 |
| 119 | $^1H$ NMR (400 MHz, DMSO-$d_6$) δ 9.50-9.40 (m, 1H), 7.05-6.98 (m, 2H), 6.03-6.01 (m, 2H), 5.35-5.21 (m, 1H), 4.52-4.48 (m, 1H), 4.43-4.29 (m, 2H), 4.10-3.99 (m, 1H), 3.73-3.56 (m, 2H), 3.33-3.20 (m, 1H), 3.11-3.00 (m, 3H), 2.85-2.81 (m, 1H), 2.40-2.30 (m, 1H), 2.20-1.76 (m, 6H). $^{19}F$ NMR (376 MHz, DMSO-$d_6$) δ −140.62-−140.94 (d, 2F), −154.09-−154.17 (m, 1F), −160.93-−161.06 (m, 1F), −172.12-−172.17 (d, 1F), −208.61 (s, 1F). | 667.2 |
| 120 | $^1H$ NMR (400 MHz, DMSO-$d_6$) δ 9.40-9.35 (m, 1H), 7.05-6.98 (m, 2H), 6.00 (s, 2H), 4.94-4.78 (m, 3H), 4.47-4.28 (m, 3H), 4.16-3.97 (m, 3H), 3.72-3.58 (m, 3H), 3.29-3.20 (m, 2H), 3.06-2.95 (m, 1H), 2.63-2.61 (m, 1H), 2.41-2.24 (m, 3H), 1.99-1.96 (m, 1H), 1.69-1.68 (m, 1H), 0.82-0.80 (m, 1H), 0.62-0.59 (m, 1H), 0.47-0.44 (m, 2H). $^{19}F$ NMR (376 MHz, DMSO-$d_6$) δ −140.59-−140.9 (d, 1F), −154.12 (s, 1F)-161.04-−161.07 (m, 2F), −207.69-−208.02 (m, 1F) | 684.1 |

TABLE 2-continued

| Example | $^{1}H$ NMR and $^{19}F$ NMR data | Mass: $[M + H]^+$ |
|---|---|---|
| 121 | $^{1}H$ NMR (400 MHz, DMSO-$d_6$) δ 9.44-9.39 (m, 1H), 7.05-7.03 (m, 1H), 7.00-6.97 (m, 1H), 6.03-6.01 (m, 2H), 4.93-4.78 (m, 3H), 4.50-4.47 (m, 1H), 4.35-4.28 (m, 2H), 4.19-4.15 (m, 1H), 4.04-3.98 (m, 2H), 3.70-3.59 (m, 3H), 3.29-3.15 (m, 2H), 3.04-2.97 (m, 1H), 2.64-2.62 (m, 1H), 2.42-2.23 (m, 3H), 2.05-1.96 (m, 1H), 1.69-1.66 (m, 1H), 0.79-0.76 (m, 1H), 0.61-0.59 (m, 1H), 0.47-0.44 (m, 2H). $^{19}F$ NMR (376 MHz, DMSO-$d_6$) δ −140.60-−140.90 (d, 1F), −154.08-−154.16 (m, 1F), −160.98-−161.06 (m, 2F), −207.97 (s, 1F) | 684.1 |
| 122 | $^{1}H$ NMR (400 MHz, DMSO-$d_6$) δ 9.45-9.39 (m, 1H), 8.31-8.26 (m, 1H), 8.18-8.16 (m, 1H), 7.77-7.73 (m, 1H), 7.67-7.62 (m, 1H), 5.35-5.21 (m, 1H), 4.51-4.48 (m, 1H), 4.43-4.19 (m, 3H), 4.05-3.97 (m, 1H), 3.78-3.61 (m, 2H), 3.30-3.20 (m, 1H), 3.09-3.01 (m, 3H), 2.88-2.80 (m, 1H), 2.40-2.32 (m, 1H), 2.12-1.70 (m, 6H). $^{19}F$ NMR (376 MHz, DMSO-$d_6$) δ −129.43-−129.65 (m, 1F), −137.12-−137.21 (m, 1F), −139.94-−140.34 (d, 1F), −172.08 (s, 1F), −208.45-−208.64 (m, 1F) | 625.2 |
| 124 | $^{1}H$ NMR (400 MHz, DMSO-$d_6$) δ 9.41-9.39 (m, 1H), 7.05-6.98 (m, 2H), 6.02-6.00 (m, 2H), 5.35-5.21 (m, 1H), 4.96-4.76 (m, 1H), 4.52-4.48 (m, 1H), 4.35-4.29 (m, 1H), 4.01-3.99 (m, 1H), 3.73-3.56 (m, 2H), 3.08-3.00 (m, 3H), 2.85-2.79 (m, 1H), 2.39-2.27 (m, 1H), 2.17-1.69 (m, 6H). $^{19}F$ NMR (376 MHz, DMSO-$d_6$) δ −140.62-−140.93 (d, 1F), −154.12-−154.15 (d, 1F), −160.99-−161.06 (m, 2F), −172.12-−172.16 (d, 1F), −207.67-−207.98 (m, 1F) | 668.1 |
| 125 | $^{1}H$ NMR (400 MHz, DMSO-$d_6$) δ 9.41-9.38 (m, 1H), 7.05-6.98 (m, 2H), 6.02-6.00 (m, 2H), 4.92-4.77 (m, 3H), 4.51-4.29 (m, 3H), 4.07-3.97 (m, 3H), 3.70-3.53 (m, 3H), 3.33-3.17 (m, 2H), 3.05-2.97 (m, 1H), 2.61-2.50 (m, 2H), 2.38-2.34 (m, 2H), 1.96-1.66 (m, 4H). $^{19}F$ NMR (376 MHz, DMSO-$d_6$) δ −140.68-−140.99 (d, 1F), −154.13-−154.16 (d, 1F), −161.00-−161.07 (m, 2F), −208.00 (s, 1F) | 658.1 |
| 128 | $^{1}H$ NMR (400 MHz, Dimethylsulfoxide-$d_6$) δ 9.51-9.28 (m, 1H), 7.21-6.95 (m, 2H), 6.21-5.90 (m, 2H), 5.40-5.14 (m, 1H), 5.01-4.77 (m, 1H), 4.54-4.45 (m, 1H), 4.41-4.24 (m, 2H), 4.05-3.94 (m, 1H), 3.74-3.55 (m, 2H), 3.25-3.13 (m, 1H), 3.12-3.03 (m, 2H), 3.02-2.95 (m, 1H), 2.87-2.77 (m, 1H), 2.40-2.26 (m, 1H), 2.15-2.09 (m, 1H), 2.06-2.02 (m, 1H), 2.01-1.93 (m, 1H), 1.89-1.68 (m, 3H). $^{19}F$ NMR (376 MHz, Dimethylsulfoxide-$d_6$) δ −140.16, −140.25, −150.73, −150.76, −151.00, −151.04, −151.10, −151.15, −151.29, −151.34, −157.92, −157.98, −158.03, −158.26, −158.31, −158.36, −160.65, −160.70, −160.77, 160.83, −172.08, −172.16 | 683.2 |
| 131 | $^{1}H$ NMR (400 MHz, DMSO-$d_6$) δ 9.42-9.39 (m, 1H), 7.41-7.35 (m, 1H), 7.07-7.01 (m, 2H), 5.86-5.83 (m, 2H), 5.34-5.21 (m, 1H), 4.97-4.76 (m, 1H), 4.52-4.48 (m, 1H), 4.38-4.29 (m, 2H), 4.02-3.99 (m, 1H), 3.73-3.59 (m, 2H), 3.31-3.15 (m, 1H), 3.09-3.00 (m, 3H), 2.85-2.78 (m, 1H), 2.42-2.25 (m, 1H), 2.14-1.70 (m, 6H). $^{19}F$ NMR (376 MHz, DMSO-$d_6$) δ −126.09-−126.13 (d, 1F), −137.45 (s, 1F), −140.45-−140.78 (d, 1F), −172.11-−172.16 (d, 1F), −207.68-−207.90 (m, 1F) | 648.2 |
| 132 | $^{1}H$ NMR (400 MHz, DMSO-$d_6$) δ 9.44-9.40 (m, 1H), 7.05-6.72 (m, 3H), 6.02-6.00 (m, 2H), 4.92-4.74 (m, 1H), 4.52-4.45 (m, 1H), 4.38-4.29 (m, 2H), 4.14-3.99 (m, 3H), 3.70-3.53 (m, 3H), 3.28-3.18 (m, 2H), 2.98-2.96 (m, 1H), 2.70-2.66 (m, 1H), 2.62-2.52 (m, 1H), 2.44-2.26 (m, 2H), 1.99-1.70 (m, 4H). $^{19}F$ NMR (376 MHz, DMSO-$d_6$) δ −132.42-−132.47 (d, 1F), −140.63-−140.93 (d, 1F), −154.10-−154.18 (m, 1F), −161.00-−161.07 (m, 2F), −207.66-−208.04 (m, 1F) | 676.2 |
| 133 | $^{1}H$ NMR (400 MHz, DMSO-$d_6$) δ 9.44-9.40 (m, 1H), 7.05-6.65 (m, 3H), 6.02-6.00 (m, 2H), 4.92-4.77 (m, 1H), 4.52-4.48 (m, 1H), 4.38-4.29 (m, 2H), 4.12-3.98 (m, 3H), 3.72-3.59 (m, 3H), 3.32-3.18 (m, 2H), 3.01-2.99 (m, 1H), 2.64-2.52 (m, 2H), 2.43-2.26 (m, 2H), 1.96-1.69 (m, 4H). $^{19}F$ NMR (376 MHz, DMSO-$d_6$) δ −130.93-−130,98 (d, 1F), −140.64-−140.94 (d, 1F), −154.10-−154.17 (m, 1F), −160.99-−161.06 (m, 2F), −207.98 (s, 1F) | 676.2 |
| 134 | $^{1}H$ NMR (400 MHz, DMSO-$d_6$) δ 9.43-9.37 (m, 1H), 7.80-7.76 (m, 1H), 7.36-7.32 (m, 1H), 7.06-7.05 (m, 2H), 5.66-5.65 (m, 2H), 4.99-4.73 (m, 1H), 4.51-4.34 (m, 3H), 4.16-3.79 (m, 4H), 3.71-3.60 (m, 3H), 3.30-3.20 (m, 2H), 3.04-2.97 (m, 1H), 2.70-2.51 (m, 2H), 2.47-2.28 (m, 2H), 1.96-1.76 (m, 4H). $^{19}F$ NMR (376 MHz, DMSO-$d_6$) δ −90.88-−91.47 (m, 2F), −113.35-−113.43 (m, 1F), −139.87-−140.44 (m, 1F), −207.62-−207.73 (m, 1F) | 649.2 |
| 135 | $^{1}H$ NMR (400 MHz, Dimethylsulfoxide-$d_6$) δ 9.58-9.42 (m, 2H), 8.62-8.51 (m, 1H), 8.33 (dd, J = 9.2, 7.2 Hz, 1H), 5.62-5.22 (m, 1H), 5.02-4.73 (m, 1H), 4.54-4.51 (m, 1H), 4.42-4.32 (m, 2H), 4.04-3.95 (m, 1H), 3.81-3.42 (m, 4H), 3.29-2.93 (m, 3H), 2.46-2.21 (m, 3H), 2.16-1.81 (m, 4H). $^{19}F$ NMR (400 MHz, Dimethylsulfoxide-$d_6$) δ −132.021, −132.149, −132.209, −139.609, −139.684, −139.729, −144.292, −144.360, −144.420, −144.577, −144.622, −150.589, −150.649, −150.904, −150.942, −172.219, −172.249, −172.362, −172.459, −172.617, −172.662 | 651.2 |
| 136 | $^{1}H$ NMR (400 MHz, Dimethylsulfoxide-$d_6$) δ 9.56-9.47 (m, 1H), 9.44 (s, 1H), 8.55-8.39 (m, 1H), 8.17-8.13 (m, 1H), 5.66-5.25 (m, 1H), 4.98-4.73 (m, 1H), 4.59-4.50 (m, 1H), 4.42-4.33 (m, 2H), 4.02-3.97 (m, 1H), 3.83-3.45 (m, 5H), 3.28-2.98 (m, 2H), 2.47-2.27 (m, 3H), 2.25-1.86 (m, 4H). $^{19}F$ NMR (400 MHz, Dimethylsulfoxide-$d_6$) δ −132.284, −132.381, −132.441, −132.509, −140.157, −147.077, −147.294, −147.212, −147.354, −147.437 | 634.1 |

TABLE 2-continued

| Example | $^1$H NMR and $^{19}$F NMR data | Mass: $[M + H]^+$ |
|---|---|---|
| 137 | $^1$H NMR (400 MHz, Dimethylsulfoxide-$d_6$) δ 9.32-9.12 (m, 1H), 7.85-7.73 (m, 1H), 7.06-6.79 (m, 2H), 5.88-5.64 (m, 4H), 5.38-5.18 (m, 1H), 5.03-4.86 (m, 1H), 4.79-4.53 (m, 1H), 4.41-3.93 (m, 3H), 3.14-2.98 (m, 3H), 2.88-2.77 (m, 1H), 2.68-2.56 (m, 1H), 2.35-2.06 (m, 3H), 2.06-1.96 (m, 2H), 1.89-1.70 (m, 3H). $^{19}$F NMR (376 MHz, Dimethylsulfoxide-$d_6$) δ −137.74, −137.79, −138.60, −138.66, −140.03, −140.54, −172.05, −172.17, −205.78, −205.98 | 635.3 |
| 139 | $^1$H NMR (400 MHz, Dimethylsulfoxide-$d_6$) δ: 9.49-9.35 (m, 1H), 7.51-7.40 (m, 1H), 7.17-7.08 (m, 2H), 6.00-5.84 (m, 2H), 5.39-5.15 (m, 1H), 5.00-4.76 (m, 1H), 4.50 (d, J = 14.0 Hz, 1H), 4.43-4.24 (m, 2H), 4.07-3.94 (m, 1H), 3.71-3.57 (m, 2H), 3.23-3.19 (m, 1H), 3.10-3.00 (m, 3H), 2.87-2.79 (m, 1H), 2.40-2.27 (m, 1H), 2.14-1.96 (m, 3H), 1.88-1.71 (m, 3H). $^{19}$F NMR (376 MHz, Dimethylsulfoxide-$d_6$) δ −123.40, −123.57, −135.02, −135.07, −135.45, −135.49, −140.01, −140.15, −150.97, −151.34, −172.06, −206.30, −206.39 | 665.2 |
| 141 | $^1$H NMR (400 MHz, Dimethylsulfoxide-$d_6$) δ 9.38 (d, J = 15.8 Hz, 1H), 7.37 (t, J = 11.0 Hz, 1H), 7.06 (s, 1H), 7.00 (d, J = 5.2 Hz, 1H), 5.83 (d, J = 10.8 Hz, 2H), 5.40-5.16 (m, 1H), 4.81-4.48 (m, 1H), 4.42 (d, J = 14.2 Hz, 1H), 4.05 (dd, J = 9.6, 17.2 Hz, 1H), 3.42-3.34 (m, 1H), 3.13-2.97 (m, 3H), 2.88-2.76 (m, 1H), 2.29-1.95 (m, 5H), 1.91-1.67 (m, 6H), 1.58-1,43 (m, 1H), 1.26-1.10 (m, 1H). $^{19}$F NMR (376 MHz, Dimethylsulfoxide-$d_6$) δ −126.14, −126.17, −137.48, −140.66, −140.97, −172.10, −172.15, −204.56, −204.64, −205.06 | 646.3 |
| 142 | $^1$H NMR (400 MHz, DMSO-$d_6$) δ 9.45-9.40 (m, 1H), 7.05-6.98 (m, 2H), 6.03-6.00 (m, 2H), 4.92-4.77 (m, 1H), 4.52-4.48 (m, 1H), 4.36-4.30 (m, 2H), 4.18-3.98 (m, 3H), 3.70-3.59 (m, 3H), 3.30-3.20 (m, 2H), 3.00-2.97 (m, 1H), 2.68-2.53 (m, 2H), 2.47-2.26 (m, 2H), 1.96-1.75 (m, 4H). $^{19}$F NMR (376 MHz, DMSO-$d_6$) δ −90.90-−91.56 (m, 2F), −140.61-−140.92 (m, 1F), −154.09-−154.18 (m, 1F), −160.98-−161.06 (m, 2F), −207.76-−208.08 (m, 1F) | 694.2 |
| 143 | $^1$H NMR (400 MHz, DMSO-$d_6$) δ 9.45-9.39 (m, 1H), 8.26-8.20 (m, 2H), 7.72-7.60 (m, 3H), 5.47-4.75 (m, 3H), 4.60-4.51 (m, 1H), 4.50-4.34 (m, 2H), 4.25-4.19 (m, 2H), 4.04-3.96 (m, 2H), 3.80-3.55 (m, 2H), 3.30-2.70 (m, 3H), 2.60-2.33 (m, 3H), 1.95-1.59 (m, 6H). $^{19}$F NMR (376 MHz, DMSO-$d_6$) δ −105.71-−105.85 (m, 1F), −139.89-−140.41 (m, 1F), −207.74 (s, 1F) | 598.2 |
| 144 | $^1$H NMR (400 MHz, DMSO-$d_6$) δ 9.42-9.36 (m, 1H), 7.62-7.57 (m, 1H), 7.03-6.98 (m, 2H), 5.82-5.80 (m, 2H), 4.97-4.82 (m, 3H), 4.51-4.48 (m, 1H), 4.39-4.30 (m, 2H), 4.06-3.97 (m, 3H), 3.80-3.53 (m, 3H), 3.29-3.17 (m, 2H), 3.00-2.98 (m, 1H), 2.67-2.50 (m, 2H), 2.40-2.27 (m, 2H), 1.96-1.69 (m, 4H). $^{19}$F NMR (376 MHz, DMSO-$d_6$) δ −137.15-−137.28 (m, 1F), −140.31-−140.40 (d, 1F), −150.55-−150.84 (m, 1F), −159.25-−159.70 (m, 1F), −207.63-−208.28 (m, 1F) | 657.2 |
| 145 | $^1$H NMR (400 MHz, DMSO-$d_6$) δ 9.46-9.41 (m, 1H), 8.20-8.18 (m, 1H), 8.06-8.03 (m, 1H), 7.70-7.60 (m, 3H), 4.98-4.83 (m, 3H), 4.52-4.49 (m, 1H), 4.42-4.30 (m, 2H), 4.06-3.97 (m, 3H), 3.75-3.52 (m, 3H), 2.25-3.16 (m, 2H), 3.00-2.95 (m, 1H), 2.60-2.53 (m, 2H), 2.43-2.30 (m, 2H), 1.97-1.69 (m, 4H). $^{19}$F NMR (376 MHz, DMSO-$d_6$): δ −129.05-−129.51 (m, 1F), −140.31 (s, 1F), −151.01-−151.44 (d, 1F), −207.65-208.26 (m, 1F) | 624.3 |
| 146 | $^1$H NMR (400 MHz, DMSO-$d_6$) δ 9.44-9.42 (m, 1H), 8.20-8.18 (m, 1H), 8.07-8.03 (m, 1H), 7.72-7.60 (m, 3H), 4.98-4.83 (m, 1H), 4.53-4.49 (m, 1H), 4.39-4.28 (m, 2H), 4.17-3.99 (m, 3H), 3.77-3.53 (m, 3H), 3.30-3.13 (m, 2H), 2.99-2.97 (m, 1H), 2.70-2.55 (m, 2H), 2.46-2.30 (m, 2H), 1.96-1.70 (m, 4H). $^{19}$F NMR (376 MHz, DMSO-$d_6$) δ −90.90-−91.54 (m, 2F), −129.07-−129.52 (m, 1F), −140.23 (s, 1F), −151.02-−151.42 (d, 1F), −207.60-−208.20 (m, 1F) | 660.5 |
| 149 | $^1$HNMR (400 MHz, Dimethylsulfoxide-$d_6$) δ 9.43-9.32 (m, 1H), 7.37 (t, J = 11.2 Hz, 1H), 7.10-6.95 (m, 2H), 5.88-5.44 (m, 4H), 5.39-5.16 (m, 1H), 4.76-4.41 (m, 3H), 3.77 (t, J = 12.4 Hz, 1H), 3.15-2.89 (m, 4H), 2.87-2.75 (m, 1H), 2.48-2.31 (m, 2H), 2.17-1.94 (m, 3H), 1.88-1.70 (m, 3H). $^{19}$F NMR (376 MHz, Dimethylsulfoxide-$d_6$) δ −126.18, −137.44, −137.48, −140.32, −140.58, −172.07, −204.17, −204.82. | 644.2 |
| 151 | $^1$H NMR (400 MHz, Dimethylsulfoxide-$d_6$) δ: 9.49-9.38 (m, 1H), 8.32-8.22 (m, 1H), 7.87-7.65 (m, 3H), 5.39-5.17 (m, 1H), 5.00-4.77 (m, 1H), 4.51 (d, J = 13.6 Hz, 1H), 4.41-4.26 (m, 2H), 4.05-3.95 (m, 1H), 3.76-3.55 (m, 2H), 3.23-3.17 (m, 1H), 3.11-3.05 (m, 2H), 3.01-2.98 (m, 1H), 2.85-2.77 (m, 1H), 2.41-2.30 (m, 1H), 2.14-2.10 (m, 1H), 2.06-1.95 (m, 2H), 1.87-1.73 (m, 3H). $^{19}$F NMR (376 MHz, Dimethylsulfoxide-$d_6$) δ −120.21, −120.22, −120.40, −120.42, −126.03, −126.43, −140.15, −151.35, −151.75, −172.09, −206.17, −206.26. | 650.2 |
| 152 | $^1$H NMR (400 MHz, Methanol-$d_4$) δ. 9.51-9.47 (m, 1H), 7.76 (dd, J = 9.6, 6.0 Hz, 1H), 7.47-7.38 (m, 1H), 7.03-7.01 (m, 1H), 5.39-5.22 (m, 1H), 4.76-4.58 (m, 2H), 4.49-4.39 (m, 1H), 4.27-4.14 (m, 1H), 4.06-3.97 (m, 1H), 3.80-3.74 (m, 1H), 3.76 (s, 1H), 3.39 (s, 1H), 3.30-3.18 (m, 4H), 3.07-2.98 (m, 1H), 2.38-2.31 (m, 1H), 2.27-2.21 (m, 1H), 2.18-2.09 (m, 1H), 2.02-1.95 (m, 2H), 1.93-1.83 (m, 1H), 1.37-1.25 (m, 1H). $^{19}$F NMR (400 MHz, Methanol-$d_4$) δ −110.97, −111.04, −141.21, −141.66, −173.75 | 632.2 |

TABLE 2-continued

| Example | $^1$H NMR and $^{19}$F NMR data | Mass: $[M + H]^+$ |
|---|---|---|
| 153 | $^1$H NMR (400 MHz, Methanol-$d_4$) δ 9.53-9.39 (m, 1H), 7.75-7.66 (m, 1H), 7.51-7.44 (m, 1H), 7.03 (s, 1H), 5.56-5.34 (m, 1H), 4.65-4.57 (m, 1H), 4.52-4.30 (m, 1H), 3.98-3.86 (m, 1H), 3.73-3.47 (m, 4H), 3.28-3.22 (m, 1H), 2.56-2.37 (m, 3H), 2.28-2.23 (m, 1H), 2.20-2.17 (m, 1H), 2.04-1.96 (m, 3H), 1.87-1.76 (m, 1H), 1.70-1.59 (m, 1H), 1.37-1.25 (m, 2H), 1.19-1.07 (m, 1H). $^{19}$F NMR (400 MHz, Methanol-$d_4$) δ −116.57, −142.08, −142.61, −173.82, −173.85, −173.95, −174.04 | 630.2, 631.2 |
| 154 | $^1$H NMR (400 MHz, Methanol-$d_4$) δ 9.52-9.45 (m, 1H), 7.76 (dd, J = 9.6, 6.0 Hz, 1H), 7.46-7.38 (m, 1H), 7.04-7.01 (m, 1H), 5.39-5.22 (m, 1H), 4.76-4.58 (m, 2H), 4.49-4.39 (m, 1H), 4.27-4.14 (m, 1H), 4.06-3.97 (m, 1H), 3.95-3.86 (m, 1H), 3.80-3.74 (m, 1H), 3.41-3.35 (m, 1H), 3.30-3.18 (m, 4H), 3.07-2.98 (m, 1H), 2.38-2.31 (m, 1H), 2.27-2.21 (m, 1H), 2.18-2.09 (m, 1H), 2.02-1.95 (m, 2H), 1.93-1.83 (m, 1H), 1.37-1.25 (m, 1H). $^{19}$F NMR (400 MHz, Methanol-$d_4$) −110.97, −111.04, −141.21, −141.66, −173.73, −173.75 | 622.2 |
| 156 | $^1$H NMR (400 MHz, DMSO-$d_6$) δ 9.46-9.41 (m, 1H), 8.20-8.18 (m, 1H), 8.06-8.03 (m, 1H), 7.70-7.60 (m, 3H), 6.93-6.72 (m, 1H), 4.98-4.83 (m, 1H), 4.53-4.49 (m, 1H), 4.39-4.33 (m, 2H), 4.12-4.00 (m, 3H), 3.70-3.53 (m, 3H), 3.30-3.18 (m, 2H), 3.05-2.96 (m, 1H), 2.70-2.66 (m, 1H), 2.50-2.49 (m, 1H), 2.40-2.30 (m, 2H), 1.98-1.73 (m, 4H). $^{19}$F NMR (376 MHz, DMSO-$d_6$) δ −129.06-−129.52 (m, 1F), −132.41-−132.46 (d, 1F), −140.25 (s, 1F), −151.03-−151.45 (d, 1F), −207.60-−208.25 (m, 1F) | 642.5 |
| 157 | $^1$H NMR (400 MHz, DMSO-$d_6$) δ 9.50-9.36 (m, 1H), 8.20-8.18 (m, 1H), 8.06-8.03 (m, 1H), 7.75-7.55 (m, 3H), 6.86-6.65 (m, 1H), 4.98-4.83 (m, 1H), 4.53-4.31 (m, 3H), 4.11-3.92 (m, 3H), 3.71-3.51 (m, 3H), 3.33-3.12 (m, 2H), 3.05-2.93 (m, 1H), 2.63-2.54 (m, 2H), 2.42-2.25 (m, 2H), 2.03-1.62 (m, 4H). $^{19}$F NMR (376 MHz, DMSO-$d_6$) δ −129.06-−129.52 (m, 1F), −130.94-−130.98 (d, 1F), −140.26 (s, 1F), −151.00-−151.44 (d, 1F), −207.69-−208.29 (m, 1F) | 642.2 |
| 172 | $^1$H NMR (400 MHz, DMSO-$d_6$) δ 9.42-9.40 (m, 1H), 7.41-7.35 (m, 1H), 7.07-7.01 (m, 2H), 6.86-6.65 (m, 1H), 5.86-5.83 (m, 2H), 4.91-4.76 (m, 1H), 4.52-4.48 (m, 1H), 4.36-4.30 (m, 2H), 4.11-3.98 (m, 3H), 3.71-3.58 (m, 3H), 3.32-3.16 (m, 2H), 3.01-2.98 (m, 1H), 2.61-2.52 (m, 2H), 2.41-2.30 (m, 2H), 1.94-1.68 (m, 4H). $^{19}$F NMR (376 MHz, DMSO-$d_6$) δ −126.10-−126.13 (d, 1F), −130.94-−130.99 (d, 1F), −137.45 (s, 1F), −140.49-−140.81 (d, 1F), −207.97 (s, 1F) | 658.2 |
| 173 | $^1$H NMR (400 MHz, Dimethylsulfoxide-$d_6$) δ 9.45-9.31 (m, 1H), 7.50-7.39 (m, 1H), 7.17-7.05 (m, 2H), 5.98-5.84 (m, 2H), 5.42-5.18 (m, 1H), 4.80-4.56 (m, 1H), 4.46-4.35 (m, 1H), 4.12-3.97 (m, 1H), 3.18-3.01 (m, 3H), 2.89-2.80 (m, 1H), 2.32-1.66 (m, 12H), 1.57-1.44 (m, 1H), 1.23-1.06 (m, 1H). $^{19}$F NMR (376 MHz, Dimethylsulfoxide-$d_6$) δ −123.41, −123.57, −135.05, −135.45, −135.49, −140.20, −140.30, −150.92, −151.45, −151.48, −172.11, −172.20, −204.65, −205.50 | 663.2 |
| 175 | $^1$H NMR (400 MHz, Dimethylsulfoxide-$d_6$) δ 9.33-9.14 (m, 1H), 7.85-7.70 (m, 1H), 7.30-7.25 (m, 1H), 7.05 (s, 2H), 5.77-5.58 (m, 4H), 5.38-5.17 (m, 1H), 5.01-4.88 (m, 1H), 4.81-4.51 (m, 1H), 4.34-4.22 (m, 1H), 4.13-3.74 (m, 2H), 3.12-2.98 (m, 3H), 2.86-2.79 (m, 1H), 2.69-2.57 (m, 1H), 2.33-2.07 (m, 3H), 2.06-1.98 (m, 2H), 1.88-1.73 (m, 3H). $^{19}$F NMR (376 MHz, Dimethylsulfoxide-$d_6$) δ −113.36, −139.93, −140.50, −172.05, −172.16, −205.74, −205.90 | 617.2 |
| 177 | $^1$H NMR (400 MHz, DMSO-$d_6$) δ 8.00-7.97 (m, 1H), 6.59-6.52 (m, 1H), 6.09-6.07 (m, 2H), 5.34-5.20 (m, 1H), 4.77-4.62 (m, 1H), 4.38-4.20 (m, 3H), 3.98-3.95 (m, 1H), 3.73-3.70 (m, 1H), 3.56-3.50 (m, 1H), 3.23-3.00 (m, 4H), 2.85-2.80 (m, 1H), 2.40-2.20 (m, 4H), 2.12-1.75 (m, 6H). $^{19}$F NMR (376 MHz, DMSO-$d_6$) δ −52.82-−53.07 (m, 1F), −120.61 (s, 1F), −125.80 (s, 1F), −135.11 (s, 1F), −172.11-−172.13 (d, 1F), −207.58 (s, 1F) | 646.3 |
| 185 | $^1$H NMR (400 MHz, DMSO-$d_6$) δ 9.43-9.37 (m, 1H), 7.80-7.76 (m, 1H), 7.36-7.32 (m, 1H), 7.06-7.05 (m, 2H), 5.66-5.65 (m, 2H), 5.35-5.22 (m, 1H), 4.51-4.47 (m, 1H), 4.41-4.30 (m, 2H), 4.07-3.81 (m, 2H), 3.80-3.57 (m, 2H), 3.29-3.20 (m, 1H), 3.19-3.02 (m, 3H), 2.88-2.82 (m, 1H), 2.45-2.25 (m, 1H), 2.12-1.70 (m, 6H). $^{19}$F NMR (376 MHz, DMSO-$d_6$) δ −113.35-−113.43 (d, 1F), −139.88-−140.47 (d, 1F), −172.07-−172.19 (d, 1F), −208.35 (s, 1F) | 622.5 |
| 187 | $^1$H NMR (400 MHz, DMSO-$d_6$) δ 9.47-9.35 (m, 1H), 7.85-7.70 (m, 1H), 7.42-7.27 (m, 1H), 7.13-7.03 (m, 2H), 5.73-5.58 (m, 2H), 4.97-4.73 (m, 1H), 4.50 (d, J = 13.7 Hz, 1H), 4.44-4.27 (m, 2H), 4.26-4.16 (m, 1H), 4.13-3.79 (m, 3H), 3.77-3.54 (m, 2H), 3.27-3.19 (m, 1H), 3.03-2.93 (m, 1H), 2.77-2.69 (m, 1H), 2.68-2.59 (m, 2H), 2.43-2.24 (m, 1H), 1.97-1.62 (m, 6H), 0.56-0.41 (m, 4H) | 627.3 |
| 189 | $^1$H NMR (400 MHz, DMSO-$d_6$) δ 9.43-9.38 (m, 1H), 7.58-7.55 (m, 1H), 7.39-7.34 (m, 1H), 7.07-7.02 (m, 2H), 5.67-5.65 (m, 2H), 5.01-4.81 (m, 3H), 4.51-4.30 (m, 3H), 4.06-3.96 (m, 3H), 3.75-3.53 (m, 3H), 3.20-3.16 (m, 2H), 3.00-2.98 (m, 1H), 2.60-2.50 (m, 2H), 2.38-2.34 (m, 2H), 1.96-1.69 (m, 4H). $^{19}$F NMR (376 MHz, DMSO-$d_6$) δ −136.82-−137.29 (m, 1F), −140.14-−140.28 (d, 1F), −150.63-−151.02 (m, 1F), −208.29-−208.31 (m, 1F) | 639.3 |

TABLE 2-continued

| Example | $^{1}$H NMR and $^{19}$F NMR data | Mass: [M + H]$^{+}$ |
|---|---|---|
| 192 | $^{1}$H NMR (400 MHz, DMSO-$d_6$) δ 9.45-9.41 (m, 1H), 7.41-7.35 (m, 1H), 7.07-7.01 (m, 2H), 5.86-5.84 (m, 2H), 4.90-4.76 (m, 3H), 4.52-4.48 (m, 1H), 4.36-4.29 (m, 2H), 4.08-3.97 (m, 3H), 3.80-3.61 (m, 1H), 3.58-3.53 (m, 2H), 3.30-3.17 (m, 2H), 3.00-2.98 (m, 1H), 2.65-2.50 (m, 2H), 2.40-2.25 (m, 2H), 1.96-1.66 (m, 4H). $^{19}$F NMR (376 MHz, DMSO-$d_6$) δ −126.10-−126.13 (m, 1F), −137.45 (s, 1F), −140.52-−140.84 (m, 1F), −207.60-−207.91 (m, 1F) | 640.4 |
| 193 | $^{1}$H NMR (400 MHz, DMSO-$d_6$) δ 9.43-9.37 (m, 1H), 7.80-7.76 (m, 1H), 7.36-7.32 (m, 1H), 7.06-7.05 (m, 2H), 5.66-5.65 (m, 2H), 4.95-4.73 (m, 1H), 4.51-4.32 (m, 3H), 4.07-3.81 (m, 2H), 3.71-3.55 (m, 2H), 3.30-3.00 (m, 3H), 2.41-2.28 (m, 1H), 2.13-1.72 (m, 6H). $^{19}$F NMR (376 MHz, DMSO-$d_6$) δ −113.35-−113.43 (d, 1F), −139.88-−140.47 (d, 1F), −172.86-−172.97 (d, 1F), −207.71-−207.75 (m, 1F) | 624.3 |
| 195 | $^{1}$H NMR (400 MHz, Dimethylsulfoxide-$d_6$) δ 9.77-9.56 (m, 1H), 7.88-7.70 (m, 1H), 7.10-6.94 (m, 2H), 5.79 (d, J = 9.8 Hz, 2H), 5.39-5.18 (m, 1H), 5.18-4.94 (m, 1H), 4.60-4.36 (m, 1H), 4.03-3.48 (m, 3H), 3.12-2.95 (m, 4H), 2.89-2.77 (m, 3H), 2.70-2.60 (m, 1H), 2.17-1.98 (m, 3H), 1.88-1.70 (m, 4H). $^{19}$F NMR (376 MHz, Dimethylsulfoxide-$d_6$) δ −137.51, −137.57, −137.81, −138.55, −138.62, −139.74, −140.02, −172.06, −172.16, −229.84 | 651.2 |
| 196 | $^{1}$H NMR (400 MHz, Dimethylsulfoxide-$d_6$) δ 9.44-9.34 (m, 1H), 7.80 (dd, J = 8.6, 12 Hz, 1H), 7.10-6.95 (m, 2H), 5.84-5.77 (m, 2H), 5.38-5.18 (m, 1H), 4.84-4.59 (m, 1H), 4.46-4.23 (m, 2H), 4.22-3.97 (m, 1H), 3.68-3.52 (m, 1H), 3.21-2.63 (m, 8H), 2.17-1.99 (m, 4H), 1.89-1.75 (m, 3H). $^{19}$F NMR (376 MHz, Dimethylsulfoxide-$d_6$) δ −137.70, −137.82, −138.60, −139.93, −140.44, −172.12, −172.23, −203.85, −204.12 | 651.2 |
| 200 | $^{1}$H NMR (400 MHz, Dimethylsulfoxide-$d_6$) δ 9.49-9.33 (m, 1H), 7.60-7.52 (m, 1H), 7.42-7.31 (m, 1H), 7.10-6.98 (m, 2H), 5.65 (d, J = 8.4 Hz, 2H), 5.00-4.77 (m, 1H), 4.50 (d, J = 14.0 Hz, 1H), 4.42-4.10 (m, 4H), 4.05-3.94 (m, 1H), 3.76-3.55 (m, 2H), 3.26-3.14 (m, 2H), 3.04-2.95 (m, 1H), 2.80-2.62 (m, 3H), 2.39-2.29 (m, 1H), 1.96-1.85 (m, 2H), 1.80-1.75 (m, 2H), 1.73-1.66 (m, 1H), 0.58-0.42 (m, 4H). $^{19}$F NMR (376 MHz, Dimethylsulfoxide-$d_6$) δ −136.82, −137.26, −140.14, −140.30, −150.59, −150.96, −208.26 | 653.2 |
| 204 | $^{1}$HNMR (400 MHz, Dimethylsulfoxide-$d_6$) δ 9.52-9.30 (m, 1H), 7.82-7.72 (m, 1H), 7.47-7.24 (m, 1H), 7.05 (s, 2H), 5.74-5.55 (m, 2H), 4.99-4.69 (m, 1H), 4.55-4.24 (m, 3H), 4.12-3.52 (m, 4H), 3.29-3.23 (m, 1H), 3.20-3.02 (m, 2H), 2.41-2.24 (m, 1H), 2.01-1.79 (m, 3H), 1.66-1.53 (m, 1H), 0.80-0.65 (m, 2H), 0.54-0.37 (m, 2H). $^{19}$F NMR (376 MHz, Dimethylsulfoxide-$d_6$) δ −113.36, −139.86, −140.38, −173.98, −174.14, −207.82 | 650.1 |
| 205 | $^{1}$HNMR (400 MHz, Dimethylsulfoxide-$d_6$) δ 9.47-9.31 (m, 1H), 7.78 (dd, J = 6.0, 9.2 Hz, 1H), 7.34 (m, 1H), 7.09-6.96 (m, 2H), 5.72-5.55 (m, 2H), 5.03-4.71 (m, 1H), 4.58-4.25 (m, 3H), 4.15-3.48 (m, 4H), 3.29-3.15 (m, 2H), 3.02-2.85 (m, 1H), 2.37-2.29 (m, 1H), 2.12-1.83 (m, 2H), 1.77 (s, 2H), 0.81 (m, 1H), 0.69-0.57 (m, 1H), 0.51-0.40 (m, 2H). $^{19}$F NMR (376 MHz, Dimethylsulfoxide-$d_6$) δ −113.39, −139.96, −140.46, −172.79, −172.83, −207.88. | 650.2 |
| 207 | $^{1}$H NMR (400 MHz, DMSO-$d_6$) δ 9.45-9.36 (m, 1H), 7.84-7.76 (m, 1H), 7.37-7.32 (m, 1H), 7.06-7.05 (m, 2H), 5.66-5.64 (m, 2H), 4.95-4.76 (m, 1H), 4.50-4.18 (m, 5H), 4.08-3.80 (m, 2H), 3.73-3.54 (m, 2H), 3.30-3.10 (m, 1H), 3.06-3.01 (m, 1H), 2.89-2.64 (m, 3H), 2.40-2.30 (m, 1H), 1.91-1.70 (m, 3H), 1.58-1.55 (m, 1H), 0.81-0.42 (m, 8H). $^{19}$F NMR (376 MHz, DMSO-$d_6$) δ −113.38-−113.41 (d, 1F), −139.86-−140.45 (d, 1F), −207.65 (s, 1F) | 653.3 |
| 208 | $^{1}$H NMR (400 MHz, DMSO-$d_6$) δ 9.43-9.36 (m, 1H), 7.80-7.76 (m, 1H), 7.37-7.32 (m, 1H), 7.06-7.05 (m, 2H), 5.66-5.65 (m, 2H), 4.94-4.74 (m, 1H), 4.51-4.33 (m, 3H), 4.13-3.81 (m, 4H), 3.71-3.60 (m, 2H), 3.33-3.20 (m, 1H), 3.00-2.95 (m, 1H), 2.71-2.68 (m, 1H), 2.50-2.37 (m, 3H), 1.97-1.91 (m, 2H), 1.89-1.69 (m, 2H), 1.66-1.40 (m, 1H), 1.34-1.23 (m, 2H), 0.96-0.94 (m, 3H). $^{19}$F NMR (376 MHz, DMSO-$d_6$) δ −113.36-−113.45(d, 1F), −139.96-−140.54 (d, 1F), −207.67 (s, 1F) | 615.1 |
| 209 | $^{1}$H NMR (400 MHz, DMSO-$d_6$) δ 9.43-9.36 (m, 1H), 7.80-7.76 (m, 1H), 7.37-7.32 (m, 1H), 7.06-7.05 (m, 2H), 5.66-5.65 (m, 2H), 4.95-4.73 (m, 1H), 4.51-4.34 (m, 3H), 4.08-3.82 (m, 4H), 3.71-3.60 (m, 2H), 3.33-3.10 (m, 2H), 2.90-2.85 (m, 1H), 2.60-2.49 (m, 1H), 2.34-2.22 (m, 2H), 2.20-2.10 (m, 2H), 1.99-1.63 (m, 4H), 1.20-1.15 (m, 1H), 0.99-0.97 (m, 3H). $^{19}$F NMR (376 MHz, DMSO-$d_6$) δ −113.36-−113.45(d, 1F), −140.02-−140.55 (d, 1F), −207.36-−207.65 (m, 1F) | 615.2 |
| 213 | $^{1}$H NMR (400 MHz, DMSO-$d_6$) δ 9.45-9.34 (m, 1H), 7.82-7.74 (m, 1H), 7.39-7.29 (m, 1H), 7.08-7.03 (m, 2H), 5.69-5.63 (m, 2H), 4.99-4.70 (m, 1H), 4.54-4.46 (m, 1H), 4.45-4.27 (m, 2H), 4.14-3.78 (m, 2H), 3.77-3.66 (m, 1H), 3.65-3.55 (m, 1H), 3.31-3.17 (m, 1H), 2.97-2.87 (m, 2H), 2.57-2.50 (m, 1H), 2.44-2.25 (m, 1H), 1.95-1.83 (m, 2H), 1.81-1.66 (m, 4H), 1.62-1.51 (m, 2H). $^{19}$F NMR (376 MHz, DMSO-$d_6$) δ −113.36-−113.44 (d, 1F), −139.99-−140.55 (d, 1F), −207.22-−207.75 (m, 1F) | 603.2 |
| 214 | $^{1}$H NMR (400 MHz, Dimethylsulfoxide-$d_6$) δ 9.23 (s, 1H), 4.91-4.65 (m, 1H), 4.41-4.51 (m, 1H), 4.38-4.24 (m, 2H), 4.18-4.02 (m, 1H), 3.99-3.87 (m, 1H), 3.70-3.60 (m, 2H), 3.29-3.08 (m, 3H), 2.99-2.81 (m, 1H), 2.40- | 641.1 |

TABLE 2-continued

| Example | $^1H$ NMR and $^{19}F$ NMR data | Mass: $[M + H]^+$ |
|---|---|---|
| | 2.24 (m, 3H), 2.22-2.03 (m, 2H), 2.00-1.61 (m, 4H), 1.32-1.15 (m, 1H), 1.05-0.96 (m, 3H). $^{19}F$ NMR (376 MHz, Dimethylsulfoxide-$d_6$) δ −137.15, −208.23. | |
| 215 | $^1H$ NMR (400 MHz, Dimethylsulfoxide-$d_6$) δ 9.47-9.34 (m, 1H), 7.59-7.53 (m, 1H), 7.40-7.33 (m, 1H), 7.08-7.01 (m, 1H), 7.02 (s, 1H), 5.69-5.60 (m, 2H), 5.00-4.77 (m, 1H), 4.55-4.46 (m, 1H), 4.40-4.26 (m, 2H), 4.17-4.10 (m, 1H), 4.05-3.95 (m, 2H), 3.75-3.55 (m, 2H), 3.30-2.96 (m, 3H), 2.76-2.65 (m, 1H), 2.45-2.35 (m, 2H), 2.29-2.17 (m, 1H), 2.01-1.89 (m, 2H), 1.76-1.60 (m, 2H), 1.56-1.45 (m, 1H), 1.39-1.28 (m, 1H), 0.98-0.93 (m, 3H). $^{19}F$ NMR (376 MHz, Dimethylsulfoxide-$d_6$) δ −136.84, −136.88, −137.27, −137.31, −140.14, −140.29, −150.63, −151.00, −208.39, −208.43 | 641.2 |
| 216 | $^1H$ NMR (400 MHz, Dimethylsulfoxide-$d_6$) δ 10.14 (s, 1H), 9.42-9.28 (m, 1H), 7.98 (dd, J = 6.0, 9.2, 1H), 7.47 (t, J = 8.8 Hz, 1H), 7.39 (d, J = 2.4 Hz, 1H), 7.21-7.12 (m, 1H), 5.37-5.18 (m, 1H), 4.75-4.49 (m, 1H), 4.45-4.36 (m, 1H), 4.19-3.86 (m, 2H), 3.40-3.34 (m, 1H), 3.12-2.99 (m, 3H), 2.86-2.77 (m, 1H), 2.30-2.21 (m, 1H), 2.16-2.09 (m, 1H), 2.06-1.70 (m, 10H), 1.56-1.46 (m, 1H). $^{19}F$ NMR (376 MHz, Dimethylsulfoxide-$d_6$) δ −110.77, −140.14, −140.57, −172.06, −172.17, −240.95, −205.02 | 620.2 |
| 220 | $^1H$ NMR (400 MHz, DMSO-$d_6$) δ 9.43-9.37 (m, 1H), 7.80-7.76 (m, 1H), 7.37-7.32 (m, 1H), 7.06-7.05 (m, 2H), 5.67-5.65 (m, 2H), 4.95-4.75 (m, 1H), 4.51-4.33 (m, 3H), 4.12-3.82 (m, 2H), 3.71-3.60 (m, 2H), 3.30-3.02 (m, 4H), 2.78-2.66 (m, 1H), 2.46-2.28 (m, 3H), 2.04-1.72 (m, 4H). $^{19}F$ NMR (376 MHz, DMSO-$d_6$) δ −94.82--97.10 (m, 2F), −113.34--113.45 (d, 1F), −139.90--140.46 (d, 1F), −207.67--207.77 (m, 1F) | 639.2 |
| 221 | $^1H$ NMR (400 MHz, DMSO-$d_6$) δ 9.43-9.37 (m, 1H), 7.80-7.76 (m, 1H), 7.37-7.32 (m, 1H), 7.06-7.05 (m, 2H), 5.67-5.65 (m, 2H), 5.34-5.21 (m, 1H), 4.88-4.73 (m, 1H), 4.51-4.32 (m, 3H), 4.07-3.82 (m, 2H), 3.78-3.59 (m, 2H), 3.30-3.20 (m, 1H), 3.09-3.01 (m, 3H), 2.86-2.81 (m, 1H), 2.40-2.30 (m, 1H), 2.12-1.95 (m, 3H), 1.85-1.74 (m, 3H). $^{19}F$ NMR (376 MHz, DMSO-$d_6$) δ −113.35--113.46 (d, 1F), −139.96--140.47 (d, 1F), −172.08--172.20 (d, 1F), −207.67--207.74 (m, 1F) | 621.2 |
| 224 | $^1H$ NMR (400 MHz, DMSO-$d_6$) δ 9.70-9.57 (m, 1H), 7.81-7.76 (m, 1H), 7.37-7.31 (m, 1H), 7.06-7.05 (m, 2H), 5.66-5.64 (m, 2H), 5.34-5.21 (m, 1H), 5.14-4.96 (m, 1H), 4.59-4.51 (m, 1H), 4.30-4.29 (m, 1H), 4.17-4.14 (m, 1H), 3.89-3.70 (m, 3H), 3.48-3.34 (m, 2H), 3.08-3.01 (m, 3H), 2.90-2.81 (m, 1H), 2.12-1.70 (m, 7H). $^{19}F$ NMR (376 MHz, DMSO-$d_6$) δ −113.24--113.44 (d, 1F), −139.97--140.07 (d, 1F), −172.09--172.18 (d, 1F), −229.40--230.52 (d, 1F) | 621.3 |
| 225 | $^1H$ NMR (400 MHz, DMSO-$d_6$) δ 9.75-9.56 (m, 1H), 7.81-7.76 (m, 1H), 7.37-7.32 (m, 1H), 7.06-7.05 (m, 2H), 5.66-5.64 (m, 2H), 5.35-5.21 (m, 1H), 5.14-4,95 (m, 1H), 4.55-4.51 (m, 1H), 4.32-4.29 (m, 1H), 4.18-4.14 (m, 1H), 3.88-3.70 (m, 3H), 3.53-3.31 (m, 2H), 3.09-3.01 (m, 3H), 2.88-2.82 (m, 1H), 2.14-1.77 (m, 7H). $^{19}F$ NMR (376 MHz, DMSO-$d_6$) δ −113.25--113.42 (d, 1F), −139.91--140.09 (d, 1F), −172.07--172.17 (d, 1F), −229.40--230.52 (d, 1F) | 621.2 |
| 226 | $^1H$ NMR (400 MHz, DMSO-$d_6$) δ 9.37 (s, 1H), 6.62-6.58 (m, 1H), 6.06-6.04 (m, 2H), 4.99-4.65 (m, 1H), 4.50-3.80 (m, 7H), 3.70-3.57 (m, 2H), 3.33-3.00 (m, 4H), 2.85-2.62 (m, 1H), 2.50-2.30 (m, 5H), 2.28-1.58 (m, 3H), 1.40-1.23 (m, 1H), 0.89-0.45 (m, 4H). $^{19}F$ NMR (376 MHz, DMSO-$d_6$) δ −52.26--52.39 (d, 3F), −135.59 (s, 1F), −141.43 (s, 1F), −207.83 (s, 1F) | 647.4 |
| 227 | $^1HNMR$ (400 MHz, Dimethylsulfoxide-$d_6$) δ 9.48-9.34 (m, 1H), 7.60-7.53 (m, 1H), 7.43-7.33 (m, 1H), 7.11-6.98 (m, 2H), 5.73-5.59 (m, 2H), 5.06-4.74 (m, 1H), 4.55-4.44 (m, 1H), 4.41-4.14 (m, 4H), 4.05-3.93 (m, 1H), 3.75-3.56 (m, 2H), 3.24-3.16 (m, 1H), 3.07-2.96 (m, 1H), 2.82-2.65 (m, 3H), 2.39-2.28 (m, 1H), 1.92-1.84 (m, 1H), 1.81-1,66 (m, 2H), 1.53 (d, J = 12.0 Hz, 1H), 0.84-0.76 (m, 1H), 0.66-0.59 (m, 1H), 0.57-0.39 (m, 6H). $^{19}F$ NMR (376 MHz, Dimethylsulfoxide-$d_6$) δ −136.81, −136.85, −137.23, −137.27, −140.08-140.22, −150.63, −151.01, −208.87 | 679.3 |
| 228 | $^1HNMR$ (400 MHz, Methanol-$d_4$) δ 9.51-9.43 (m, 1H), 7.58-7.48 (m, 1H), 7.34-7.23 (m, 1H), 7.22-7.06 (m, 2H), 4.76-4.55 (m, 2H), 4.50-4.30 (m, 3H), 4.26-4.12 (m, 1H), 4.04-3.89 (m, 2H), 3.82-3.71 (m, 1H), 3.41-3.34 (m, 1H), 3.27-3.19 (m, 1H), 3.06-2.83 (m, 3H), 2.44-2.27 (m, 1H), 2.05-1.86 (m, 3H), 1.83-1.73 (m, 1H), 0.94-0.85 (m, 1H), 0.83-0.75 (m, 1H), 0.72-0.46 (m, 6H). $^{19}F$ NMR (376 MHz, Methanol-$d_4$) δ −138.42, −138.45, −138.54, −139.43, −139.89, −152.90, −153.01, −209.41, −209.50, −209.60, −209.63, −209.87, −209.96 | 679.1 |
| 231 | $^1H$ NMR (400 MHz, Dimethylsulfoxide-$d_6$) δ 9.48-9.28 (m, 1H), 7.78 (dd, J = 6.0, 9.2 Hz, 1H), 7.34 (t, J = 9.2 Hz, 1H), 7.12-6.95 (m, 2H), 5.73-5.52 (m, 2H), 5.00-4.72 (m, 1H), 4.71-4.45 (m, 2H), 4.43-4.26 (m, 2H), 4.25-4.17 (m, 1H), 4.09-3.75 (m, 3H), 3.75-3.56 (m, 2H), 3.29-3.17 (m, 1H), 3.07-2.96 (m, 1H), 2.77-2.60 (m, 3H), 2.40-2.28 (m, 1H), 1.90-1.77 (m, 4H), 0.99-0.82 (m, 2H), 0.78-0.64 (m, 2H), 0.55-0.42 (m, 2H) . $^{19}F$ NMR (376 MHz, Dimethylsulfoxide-$d_6$) δ −113.37, −113.44, −139.97, −140.46, −207.63, −210.49 | 671.0 |
| 232 | $^1H$ NMR (400 MHz, Dimethylsulfoxide-$d_6$) δ 9.47-9.33 (m, 1H), 7.83-7.74 (m, 1H), 7.38-7.31 (m, 1H), 7.11-7.00 (m, 2H), 5.72-5.59 (m, 2H), 4.99-4.73 (m, 1H), 4.72-4.46 (m, 2H), 4.44-4.28 (m, 2H), 4.24-4.10 (m, 2H), | 671.3 |

TABLE 2-continued

| Example | $^1$H NMR and $^{19}$F NMR data | Mass: [M + H]$^+$ |
|---|---|---|
| | 4.10-3.79 (m, 2H), 3.79-3.56 (m, 2H), 3.31-3.16 (m, 1H), 3.13-2.99 (m, 2H), 2.89-2.80 (m, 1H), 2.79-2.64 (m, 1H), 2.44-2.26 (m, 1H), 1.93-1.76 (m, 2H), 1.68-1.50 (m, 2H), 0.94-0.84 (m, 2H), 0.82-0.70 (m, 1H), 0.61-0.55 (m, 1H), 0.54-0.43 (m, 2H). $^{19}$F NMR (376 MHz, Dimethylsulfoxide-d$_6$) δ −113.35, −113.45, 139.94, −140.36, −207.74, −207.83, −212.49 | |
| 234 | $^1$H NMR (400 MHz, DimethylSulfoxide-d$_6$) δ 9.44-9.34 (m, 1H), 7.81-7.74 (dd, J = 6.0, 9.2 Hz, 1H), 7.39-7.30 (m, 1H), 7.09-7.01 (m, 2H), 5.70-5.60 (m, 2H), 5.00-4.64 (m, 2H), 4.54-4.45 (m, 1H), 4.43-4.28 (m, 2H), 4.22 (s, 2H), 4.12-3.77 (m, 2H), 3.77-3.54 (m, 2H), 3.29-3.20 (m, 1H), 3.09-2.99 (m, 1H), 2.91-2.83 (m, 1H), 2.79-2.72 (m, 1H), 2.68-2.59 (m, 1H), 2.36-2.29 (m, 1H), 1.95-1.66 (m, 4H), 0.87-0.73 (m, 3H), 0.70-0.63 (m, 1H), 0.52-0.41 (m, 2H). $^{19}$F NMR (376 MHz, Dimethyl Sulfoxide-d$_6$) δ −113.37, −113.44, −139.89, −140.38, −207.80, −209.11 | 671.2 |
| 237 | $^1$H NMR (400 MHz, DMSO-d$_6$) δ 9.43-9.37 (m, 1H), 7.80-7.76 (m, 1H), 7.37-7.32 (m, 1H), 7.06-7.05 (m, 2H), 5.67-5.65 (m, 2H), 4.89-4.74 (m, 1H), 4.61-4.48 (m, 2H), 4.38-4.34 (m, 2H), 4.07-3.83 (m, 2H), 3.72-3.60 (m, 2H), 3.30-3.20 (m, 1H), 3.13-3.09 (m, 1H), 3.01-2.97 (m, 2H), 2.59-2.50 (m, 1H), 2.40-2.29 (m, 2H), 2.08-2.05 (m, 1H), 1.94-1.92 (m, 1H), 1.76-1.63 (m, 3H). $^{19}$F NMR (376 MHz, DMSO-d$_6$) δ −113.35-−113.45(m, 1F), −139.94-−140.49 (m, 1F), −207.67-−207.68 (m, 1F) | 637.1 |
| 238 | $^1$H NMR (300 MHz, DMSO-d$_6$) δ 9.43-9.37 (m, 1H), 7.80-7.75 (m, 1H), 7.37-7.31 (m, 1H), 7.06 (s, 2H), 5.64 (s, 2H), 5.00-4.27 (m, 5H), 4.06-3.56 (m, 4H), 3.40-3.22 (m, 2H), 3.00-2.74 (m, 3H), 2.60-2.50 (m, 1H), 2.40-2.20 (m, 1H), 2.00-1.70 (m, 5H). $^{19}$F NMR (282 MHz, DMSO-d$_6$) δ −113.35-−113.42 (d, 1F), −139.87-−140.43 (d, 1F), −207.74-−207.87 (m, 1F). | 637.1 |
| 239 | $^1$H NMR (300 MHz, DMSO-d$_6$) δ 9.43-9.37 (m, 1H), 7.80-7.75 (m, 1H), 7.37-7.31 (m, 1H), 7.06-7.05 (m, 2H), 5.64 (s, 2H), 5.35-5.17 (m, 1H), 4.91-4.71 (m, 1H), 4.52-4.32 (m, 3H), 4.17-4.13 (m, 1H), 4.06-3.64 (m, 5H), 3.30-3.15 (m, 2H), 3.08-2.83 (m, 1H), 2.45-2.14 (m, 2H), 1.96-1.75 (m, 5H), 1.09-1.06 (m, 6H). $^{19}$F NMR (282 MHz, DMSO-d$_6$) δ −113.35-−113.41 (d, 1F), −139.84-−140.40 (d, 1F), −172.84-−172.93 (d, 1F), −207.71 (s, 1F) | 647.3 |
| 240 | $^1$H NMR (400 MHz, DMSO-d$_6$) δ 9.35-9.15 (m, 1H), 7.79-7.77 (m, 1H), 7.36-7.32 (m, 1H), 7.08-7.03 (m, 2H), 5.67 (s, 2H), 5.36-5.23 (m, 1H), 4.63-3.64 (m, 8H), 3.11-3.02 (m, 3H), 2.86-2.82 (m, 1H), 2.66-2.59 (m, 1H), 2.16-1.75 (m, 6H). $^{19}$F NMR (376 MHz, DMSO-d$_6$) δ −113.28-−113.33 (m, 1F), −139.38 (s, 1F), −171.82-−172.03 (m, 1F) | 671.4 |
| 241 | $^1$HNMR (400 MHz, Dimethylsulfoxide-d$_6$) δ 10.16 (s, 1H), 8.04-7.93 (m, 1H), 7.47 (t, J = 9.2 Hz, 1H), 7.39 (d, J = 2.4 Hz, 1H), 7.29-7.11 (m, 1H), 5.37-5.17 (m, 1H), 4.61-4.29 (m, 3H), 4.26-3.93 (m, 3H), 3.91-3.84 (m, 3H), 3.80-3.70 (m, 1H), 3.61-3.50 (m, 1H), 3.10-2.78 (m, 5H), 2.19-1.95 (m, 4H), 1.86-1.69 (m, 3H). $^{19}$F NMR (376 MHz, Dimethylsulfoxide-d$_6$) δ −110.39, −110.55, −149.47, −150.39, −171.92, −172.04, −172.16, −206.63 | 652.2 |
| 242 | $^1$H NMR (400 MHz, Dimethylsulfoxide-d$_6$) δ 9.53-9.34 (m, 1H), 7.91-7.75 (m, 1H), 7.45-7.33 (m, 1H), 7.17-7.04 (m, 2H), 5.79-5.59 (m, 2H), 5.07-4.73 (m, 1H), 4.57-4.29 (m, 3H), 4.16-3.82 (m, 4H), 3.82-3.60 (m, 2H), 3.22-3.16 (m, 1H), 3.05-2.96 (m, 1H), 2.65-2.59 (m, 1H), 2.44-2.34 (m, 2H), 2.28-2.20 (m, 1H), 2.01-1.87 (m, 2H), 1.79-1.68 (m, 1H), 1.34-1.18 (m, 2H), 1.08-1.02 (m, 3H), 0.85-0.78 (m, 1H), 0.69-0.62 (m, 1H), 0.58-0.52 (m, 1H), 0.51-0.42 (m, 1H). $^{19}$F NMR (376 MHz, Dimethylsulfoxide-d$_6$) δ −113.37, −113.44, −139.97, −140.47, −207.61, −207.75, −207.90, −207.96 | 641.3 |
| 243 | $^1$H NMR (400 MHz, Dimethylsulfoxide-d$_6$) δ 9.43-9.33 (m, 1H), 7.81-7.74 (m, 1H), 7.38-7.30 (m, 1H), 7.05 (s, 2H), 5.70-5.60 (m, 2H), 4.98-4.70 (m, 1H), 4.51-4.43 (m, 1H), 4.43-4.27 (m, 2H), 4.08-3.78 (m, 4H), 3.76-3.55 (m, 2H), 3.28-3.10 (m, 2H), 2.99-2.90 (m, 1H), 2.41-2.34 (m, 1H), 2.31-2.25 (m, 1H), 2.21-2.14 (m, 1H), 1.94-1.82 (m, 2H), 1.74-1.65 (m, 1H), 1.25-1.14 (m, 2H), 0.99 (d, J = 6 Hz, 3H), 0.82-0.73 (m, 1H), 0.65-0.56 (m, 1H), 0.53-0.39 (m, 2H). $^{19}$F NMR (376 MHz, Dimethylsulfoxide-d$_6$) δ −113.39, −113.16, −139.95, −140.49, −207.80 | 641.2 |
| 244 | $^1$H NMR (400 MHz, Dimethylsulfoxide-d$_6$) δ 9.45-9.32 (m, 1H), 7.81-7.74 (m, 1H), 7.38-7.29 (m, 1H), 7.08-7.00 (m, 2H), 5.73-5.56 (m, 2H), 5.25-5.16 (m, 1H), 4.96-4.70 (m, 1H), 4.51-4.42 (m, 1H), 4.41-4.27 (m, 2H), 4.20-4.12 (m, 1H), 4.08-3.77 (m, 3H), 3.76-3.64 (m, 2H), 3.64-3.55 (m, 1H), 3.30-3.16 (m, 3H), 3.16-3.03 (m, 1H), 2.14-2.01 (m, 1H), 1.69 (s, 3H), 1.46-1.34 (m, 1H), 1.23 (s, 1H), 0.86-0.81 (m, 1H), 0.60-0.45 (m, 2H), 0.38-0.27 (m, 1H). $^{19}$F NMR (376 MHz, Dimethylsulfoxide-d$_6$) δ −113.38, −113.45, −139.94, −140.49, −207.90 | 639.2 |
| 245 | $^1$H NMR (400 MHz, DMSO-d$_6$) δ 9.45-9.40 (m, 1H), 8.26-8.20 (m, 2H), 7.87-7.86 (m, 1H), 7.73-7.60 (m, 3H), 5.40-5.10 (m, 1H), 4.92-4.75 (m, 1H), 4.51-4.34 (m, 3H), 4.22-3.98 (m, 4H), 3.66-3.61 (m, 2H), 3.30-2.90 (m, 5H), 2.80-2.24 (m, 4H), 2.20-1.90 (m, 3H), 1.78-1.76 (m, 3H), 1.65-1.42 (m, 1H). $^{19}$F NMR (376 MHz, DMSO-d$_6$) δ −105.70-−105.82 (m, 1F), −139.82-−140.31(m, 1F), −170.84-−171.43 (m, 1F), −207.71 (s, 1F). | 675.2 |

TABLE 2-continued

| Example | $^1$H NMR and $^{19}$F NMR data | Mass: [M + H]$^+$ |
|---|---|---|
| 247 | $^1$H NMR (400 MHz, DMSO-$d_6$) δ 9.60-9.40 (m, 1H), 7.80-7.76 (m, 1H), 7.37-7.31 (m, 1H), 7.06-7.04 (m, 2H), 5.65 (s, 2H), 5.35-5.21 (m, 1H), 4.59-4.39 (m, 2H), 4.25-3.60 (m, 7H), 3.10-3.00 (m, 3H), 2.86-2.82 (m, 1H), 2.14-1.98 (m, 4H), 1.92-1.77 (m, 3H). $^{19}$F NMR (376 MHz, DMSO-$d_6$) δ −113.30-−113.45 (m, 1F), −139.33-−141.11 (m, 1F), −172.02-−172.16 (m, 1F) | 637.2/ 639.2 |
| 249 | $^1$H NMR (400 MHz, DMSO-$d_6$) δ 9.50-9.20 (m, 1H), 7.90-7.65 (m, 1H), 7.50-7.20 (m, 1H), 7.20-6.90 (m, 2H), 5.80-5.50 (m, 2H), 5.45-5.01 (m, 1H), 4.60-4.30 (m, 2H), 4.30-4.12 (m, 1H), 4.10-3.71 (m, 3H), 3.70-3.51 (m, 2H), 3.30-3.20 (m, 1H), 3.20-2.90 (m, 3H), 2.90-2.70 (m, 1H), 2.20-1.80 (m, 7H). $^{19}$F NMR (376 MHz, DMSO-$d_6$) δ −113.40-−113.45 (d, 1F), −140.31-−140.61 (d, 1F), −172.08-−172.19 (d, 1F) | 637.1 |
| 251 | $^1$H NMR (400 MHz, Dimethylsulfoxide-$d_6$) δ 9.49-9.27 (m, 1H), 7.85-7.71 (m, 1H), 7.38-7.29 (m, 1H), 7.12-7.98 (m, 2H), 5.80-5.38 (m, 2H), 5.02-4.64 (m, 1H), 4.52-4.18 (m, 4H), 4.14-3.77 (m, 3H), 3.76-3.53 (m, 2H), 3.14-3.07 (m, 1H), 2.84-2.72 (m, 1H), 2.63-2.54 (m, 1H), 2.42-2.27 (m, 2H), 2.21-2.08 (m, 2H), 1.52-1.42 (m, 1H), 1.38-1.09 (m, 3H), 1.02-0.89 (m, 3H), 0.74-0.63 (m, 1H), 0.60-0.48 (m, 2H), 0.38-0.24 (m, 1H). $^{19}$F NMR (376 MHz, Dimethylsulfoxide-$d_6$) δ −113.36, −113.42, −139.90, −140.41, −207.74, −207.88 | 641.3 |
| 256 | $^1$H NMR (400 MHz, Dimethylsulfoxide-$d_6$) δ 9.50-9.32 (m, 1H), 7.77 (d, J = 6.0 Hz, 1H), 7.11-6.92 (m, 2H), 5.73-5.51 (m, 2H), 5.39-5.14 (m, 1H), 4.97-4.69 (m, 1H), 4.55-4.24 (m, 3H), 4.11-3.77 (m, 2H), 3.75-3.56 (m, 2H), 3.20-3.15 (m, 1H)22, 3.10-2.99 (m, 3H), 2.85-2.79 (m, 1H), 2.41-2.34 (m, 1H), 2.13-2.06 (m, 1H), 2.04-1.94 (m, 2H), 1.85-1.68 (m, 3H) $^{19}$F NMR (376 MHz, Dimethylsulfoxide-$d_6$) δ −113.35, −113.61, −113.69, −139.86, −140.46, −172.06, −172.17, −207.67 | 622.1 |
| 257 | $^1$H NMR (400 MHz, DMSO-$d_6$) δ 9.43-9.37 (m, 1H), 7.87-7.76 (m, 2H), 7.37-7.32 (m, 1H), 7.06-7.05 (m, 2H), 5.67-5.65 (m, 2H), 5.40-5.15 (m, 1H), 4.94-4.73 (m, 1H), 4.50-4.33 (m, 3H), 4.14-3.81 (m, 4H), 3.71-3.60 (m, 2H), 3.29-2.90 (m, 6H), 2.60-2.45 (m, 2H), 2.42-2.22 (m, 2H), 2.20-1.90 (m, 3H), 1.77 (d, J = 4.8 Hz, 3H). $^{19}$F NMR (376MHz, DMSO-$d_6$) δ −113.35-−113.43 (d, 1F), −139.88-−140.44 (m, 1F), −170.84-−171.43 (m, 1F), −207.71 (s, 1F) | 690.3 |
| 260 | $^1$H NMR (400 MHz, DMSO-$d_6$) δ 10.27 (s, 1H), 9.44-9.37 (m, 1H), 7.94-7.92 (m, 1H), 7.61-7.59 (m, 1H), 7.39-7.38 (m, 1H), 7.20-7.17 (m, 1H), 5.35-5.21 (m, 1H), 4.91-4.76 (m, 1H), 4.51-4.30 (m, 3H), 4.23-3.97 (m, 2H), 3.81-3.56 (m, 2H), 3.33-2.96 (m, 4H), 2.86-2.80 (m, 1H), 2.44-2.25 (m, 1H), 2.14-1.76 (m, 6H). $^{19}$F NMR (376 MHz, DMSO-$d_6$) δ −140.03-−140.45 (d, 1F), −172.06-−172.18 (d, 1F), −207.73 (s, 1F) | 638.2 |
| 261 | $^1$H NMR (400 MHz, DMSO-$d_6$) δ 9.54-9.50 (m, 1H), 7.76-7.73 (m, 1H), 7.38-7.29 (m, 2H), 7.03-7.00 (m, 2H), 5.60 (s, 2H), 5.35-5.21 (m, 1H), 4.90-4.75 (m, 1H), 4.49-4.27 (m, 3H), 4.11-3.82 (m, 2H), 3.75-3.55 (m, 2H), 3.30-3.24 (m, 1H), 3.09-3.00 (m, 3H), 2.85-2.81 (m, 1H), 2.42-2.24 (m, 1H), 2.20-1,93 (m, 3H), 1.90-1.73 (m, 3H). $^{19}$F NMR (376 MHz, DMSO-$d_6$) δ −113.74 (s, 1F), −172.02-−172.11 (d, 1F), −207.29-−207.78 (m, 1F) | 603.3 |
| 262 | $^1$H NMR (400 MHz, DMSO-$d_6$) δ 9,43-9.37 (m, 1H), 7.80-7.76 (m, 1H), 7.36-7.32 (m, 1H), 7.06 (s, 2H), 5.65-5.64 (m, 2H), 4.93-4.73 (m, 2H), 4.50-4.47 (m, 1H), 4.39-4.32 (m, 2H), 4.11-3.79 (m, 4H), 3.71-3.60 (m, 2H), 3.28-3.20 (m, 1H), 3.09-3.00 (m, 1H), 2.79-2.70 (m, 1H), 2.42-2.17 (m, 2H), 2.11-1.89 (m, 2H), 1.83-1.53 (m, 3H), 1.14 (s, 3H), 1.03 (s, 3H). $^{19}$F NMR (376 MHz, DMSO-$d_6$) δ −113.34-−113.43 (d, 1F), −139.92-−140.48 (d, 1F), −183.22-−183.28 (d, 1F), −207.72 (s, 1F) | 647.5 |
| 263 | $^1$H NMR (400 MHz, Dimethylsulfoxide-$d_6$) δ 10.42-10.30 (m, 1H), 9.49-9.37 (m, 1H), 8.54-8.43 (m, 1H), 8.19-8.05 (m, 1H), 7.82-7.71 (m, 1H), 7.54 (t, J = 8.8 Hz, 1H), 5.40-5.15 (m, 1H), 5.03-4.70 (m, 1H), 4.54-4.45 (m, 1H), 4.43-4.30 (m, 2H), 4.22-3.92 (m, 2H), 3.75-3.56 (m, 2H), 3.30-3.15 (m, 1H), 3.13-2.98 (m, 3H), 2.87-2.77 (m, 1H), 2.43-2.26 (m, 1H), 2.16-2.07 (m, 4H), 2.06-1.94 (m, 2H), 1.87-1.71 (m, 3H). $^{19}$F NMR (376 MHz, Dimethylsulfoxide-$d_6$) δ −108.24, −108.37, −139.75, −140.37, −172.07, −172.18, −207.85 | 663.2 |
| 264 | $^1$H NMR (400 MHz, Dimethylsulfoxide-$d_6$) δ 9.45-9.34 (m, 1H), 7.34 (d, J = 9.2 Hz, 1H), 7.09-7.01 (m, 2H), 5.68-5.61 (m, 2H), 5.37-5.19 (m, 1H), 4.95-4.71 (m, 1H), 4.49 (d, J = 13.2 Hz, 1H), 4.44-4.28 (m, 2H), 4.07-3.79 (m, 2H), 3.75-3.67 (m, 1H), 3.64-3.56 (m, 1H), 3.29-3.18 (m, 1H), 3.12-3.30 (m, 2H), 3.03-2.96 (m, 1H), 2.86-2.79 (m, 1H), 2.40-2.27 (m, 1H), 2.14-2.02 (m, 2H), 2.01-1.93 (m, 1H), 1.87-1.73 (m, 3H). $^{19}$F NMR (376 MHz, Dimethylsulfoxide-$d_6$) δ −113.35, −113.42, −139.88, −140.47, −172.06, −172.17, −207.75 | 622.3 |
| 265 | $^1$H NMR (400 MHz, DMSO-$d_6$) δ 9.43-9.37 (m, 1H), 7.80-7.76 (m, 1H), 7.37-7.32 (m, 1H), 7.06-7.05 (m, 2H), 5.67-5.65 (m, 2H), 4.96-4.73 (m, 1H), 4.53-4.33 (m, 5H), 4.07-3.81 (m, 2H), 3.71-3.60 (m, 2H), 3.33-3.15 (m, 1H), 3.00-2.97 (m, 1H), 2.79-2.76 (m, 1H), 2.70-2.50 (m, 3H), 2.44-2.30 (m, 1H), 1.99-1.50 (m, 6H). $^{19}$F NMR (376 MHz, DMSO-$d_6$) δ −113.36-−113.45 (d, 1F), −139.94-−140.52 (d, 1F), −207.73 (s, 1F), −216.60-−216.64 (d, 1F) | 635.3 |

TABLE 2-continued

| Example | $^1$H NMR and $^{19}$F NMR data | Mass: [M + H]$^+$ |
|---|---|---|
| 266 | $^1$H NMR (400 MHz, DMSO-$d_6$) δ 9.43-9.37 (m, 1H), 7.80-7.76 (m, 1H), 7.37-7.32 (m, 1H), 7.06-7.05 (m, 2H), 5.67-5.65 (m, 2H), 4.94-4.73 (m, 1H), 4.51-4.34 (m, 5H), 4.07-3.82 (m, 2H), 3.80-3.60 (m, 2H), 3.34-3.20 (m, 1H), 3.14-3.10 (m, 1H), 2.88-2.85 (m, 1H), 2.80-2.50 (m, 2H), 2.40-2.31 (m, 2H), 2.13-2.10 (m, 1H), 1.88-1.65 (m, 4H), 1.38-1.32 (m, 1H). $^{19}$F NMR (376 MHz, DMSO-$d_6$) δ −113.36-−113.45 (d, 1F), −139.98-−140.52 (d, 1F), −207.64-−207.83 (m, 1F), −218.27-−218.34 (d, 1F) | 635.3 |
| 268 | $^1$H NMR (400 MHz, DMSO-$d_6$) δ 9.42-9.36 (m, 1H), 7.71-7.68 (m, 1H), 7.31-7.28 (m, 2H), 7.01-6.99 (m, 2H), 5.73-5.68 (m, 2H), 5.35-5.21 (m, 1H), 4.97-4.72 (m, 1H), 4.51-4.33 (m, 3H), 4.09-3.96 (m, 1H), 3.73-3.45 (m, 3H), 3.33-2.97 (m, 4H), 2.85-2.79 (m, 1H), 2.42-2.27 (m, 1H), 2.11-1.96 (m, 3H), 1.93-1.76 (m, 3H). $^{19}$F NMR (376MHz, DMSO-$d_6$) δ −139.839-−140.48 (d, 1F), −172.072-−172.17 (d, 1F), −207.68 (s, 1F) | 603.4 |
| 271 | $^1$H NMR (400 MHz, DMSO-$d_6$) δ 9.44-9.39 (m, 1H), 6.85-6.83 (m, 1H), 6.02 (s, 2H), 5.334-5.21 (m, 1H), 4.93-4.66 (m, 1H), 4.50-4.47 (m, 1H), 4.35-4.25 (m, 2H), 4.00-3.97 (m, 1H), 3.69-3.54 (m, 2H), 3.30-3.17 (m, 1H), 3.15-3.00 (m, 3H), 2.85-2.80 (m, 1H), 2.40-2.30 (m, 4H), 2.17-1.70 (m, 6H). $^{19}$F NMR (376 MHz, DMSO-$d_6$) δ −52.07-−52.13 (d, 3F), −139.14-−139.39 (d, 1F), −140.49-−140.90 (d, 1F), −172.13-−172.15 (d, 1F), −207.99 (s, 1F) | 629.4 |
| 272 | $^1$H NMR (400 MHz, DMSO-$d_6$) δ 9.40-9.37 (m, 1H), 6.88 (s, 1H), 6.52-6.49 (m, 1H), 6.35 (s, 2H), 5.35-5.21 (m, 1H), 4.92-4.64 (m, 1H), 4.49-4.46 (m, 1H), 4.40-4.24 (m, 2H), 3.99-3.96 (m, 1H), 3.69-3.54 (m, 2H), 3.29-3.00 (m, 4H), 2.85-2.80 (m, 1H), 2.42-2.23 (m, 1H), 2.20-1.70 (m, 6H). $^{19}$F NMR (376 MHz, DMSO-$d_6$) δ −53.08-−53.18 (m, 3F), −141.56 (s, 1F), −172.15 (s, 1F), −207.81 (s, 1F) | 631.2 |
| 273 | $^1$H NMR (400 MHz, Dimethylsulfoxide-$d_6$) δ 9.51-9.26 (m, 1H), 7.18-6.93 (m, 2H), 5.75-5.52 (m, 2H), 5.38-5.17 (m, 1H), 4.97-4.70 (m, 1H), 4.49 (d, J = 13.6 Hz, 1H), 4.43-4.27 (m, 2H), 4.09-3.77 (m, 2H), 3.76-3.54 (m, 2H), 3.29-3.16 (m, 1H), 3.13-2.97 (m, 3H), 2.88-2.77 (m, 1H), 2.40-2.29 (m, 1H), 2.14-1.96 (m, 3H), 1.88-1.71 (m, 3H). $^{19}$F NMR (376 MHz, Dimethylsulfoxide-$d_6$) δ −113.35, −113.61, −113.69, −139.86, −140.46, −172.07, −172.17, −207.70, −207.73, −207.84 | 623.3 |
| 276 | $^1$H NMR (400 MHz, DMSO-$d_6$) δ 9.43-9.37 (m, 1H), 7.80-7.76 (m, 1H), 7.36-7.32 (m, 1H), 7.06 (s, 2H), 5.66-5.64 (m, 2H), 4.95-4.73 (m, 1H), 4.51-4.48 (m, 1H), 4.41-4.32 (m, 2H), 4.06-3.80 (m, 2H), 3.71-3.60 (m, 2H), 3.41-3.20 (m, 3H), 2.95-2.73 (m, 3H), 2.44-2.30 (m, 2H), 1.95-1.78 (m, 5H). $^{19}$F NMR (376 MHz, DMSO-$d_6$) δ −113.34-−113.42 (d, 1F), −139.85-−140.40 (d, 1F), −207.73 (s, 1F) | 628.3 |
| 277 | $^1$H NMR (400 MHz, DMSO-$d_6$) δ 9.43-9.37 (m, 1H), 7.80-7.76 (m, 1H), 7.36-7.32 (m, 1H), 7.06-7.05 (m, 2H), 5.66-5.64 (m, 2H), 5.10-4.73 (m, 2H), 4.51-4.48 (m, 1H), 4.44-4.30 (m, 2H), 4.12-3.60 (m, 6H), 3.30-2.98 (m, 3H), 2.85-2.78 (m, 1H), 2.40-2.30 (m, 1H), 2.16-1.97 (m, 3H), 1.82-1.69 (m, 3H), 1.25-1.23 (m, 3H). $^{19}$F NMR (376 MHz, DMSO-$d_6$) δ −113.35-−113.43 (d, 1F), −139.91-−140.48 (d, 1F), −186.35-−186.40 (d, 1F), −207.67 (s, 1F) | 633.2 |
| 278 | $^1$H NMR (400 MHz, DMSO-$d_6$) δ 9.43-9.37 (m, 1H), 7.80-7.76 (m, 1H), 7.36-7.32 (m, 1H), 7.06-7.05 (m, 2H), 5.66-5.64 (m, 2H), 4.95-4.74 (m, 2H), 4.50-4.34 (m, 3H), 4.07-3.60 (m, 6H), 3.30-3.15 (m, 1H), 2.98-2.92 (m, 2H), 2.80-2.70 (m, 1H), 2.39-2.33 (m, 2H), 2.00-1.75 (m, 5H), 1.06-1.03 (m, 3H). $^{19}$F NMR (376 MHz, DMSO-$d_6$) δ −113.35-−113.42 (d, 1F), −139.87-−140.42 (d, 1F), −171.20-−181.21 (m, 1F), −207.69 (s, 1F) | 633.35 |
| 279 | $^1$H NMR (400 MHz, DMSO-$d_6$) δ 9.45-9.41 (m, 1H), 6.20 (s, 2H), 5.39-5.25 (m, 1H), 4.93-4.66 (m, 1H), 4.51-4.47 (m, 1H), 4.40-4.30 (m, 2H), 3.99-3.96 (m, 1H), 3.69-3.55 (m, 2H), 3.30-2.80 (m, 4H), 2.40-1.70 (m, 10H). $^{19}$F NMR (376 MHz, DMSO-$d_6$) δ −51.60-−51.67 (m, 3F), −129.67-−129.75 (m, 1F), −134.02-−134.32 (m, 1F), −140.31-−140.73 (d, 1F), −172.13-−172.15 (d, 1F), −207.90 (s, 1F) | 647.1 |
| 284 | $^1$H NMR (400 MHz, DMSO-$d_6$) δ 10.19-10.13 (m, 1H), 9.45-9.37 (m, 1H), 8.03-7.96 (m, 1H), 7.52-7.44 (m, 1H), 7.43-7.38 (m, 1H), 7.22-7.15 (m, 1H), 4.97-4.89 (m, 1H), 4.82-4.71 (m, 1H), 4.44-4.31 (m, 3H), 4.27-4.18 (m, 1H), 4.07-3.87 (m, 2H), 3.77-3.65 (m, 1H), 3.66-3.56 (m, 1H), 3.30-3.17 (m, 1H), 3.04-2.93 (m, 1H), 2.70-2.57 (m, 1H), 2.41-2.33 (m, 4H), 2.25-2.17 (m, 1H), 2.02-1.91 (m, 1H), 1.74-1.60 (m, 3H). $^{19}$F NMR (376 MHz, DMSO) δ −110.70-−110.77 (1F), −139.97-−140.41 (1F), −207.63-−207.73 (1F) | 576.4 |
| 285 | $^1$H NMR (400 MHz, DMSO-$d_6$) δ 10.25-10.09 (m, 1H), 9.47-9.37 (m, 1H), 8.08-7.94 (m, 1H), 7.54-7.43 (m, 1H), 7.43-7.37 (m, 1H), 7.24-7.15 (m, 1H), 4.98-4.72 (m, 1H), 4.56-4.27 (m, 4H), 4.27-4.17 (m, 1H), 4.16-4.12 (m, 1H), 4.07-3.95 (m, 1H), 3.76-3.55 (m, 2H), 3.27-3.14 (m, 1H), 3.09-2.92 (m, 1H), 2.78-2.59 (m, 1H), 2.44-2.34 (m, 3H), 2.30-2.17 (m, 1H), 2.02-1.91 (m, 1H), 1.78-1.57 (m, 4H). $^{19}$F NMR (376 MHz, DMSO-$d_6$) δ −110.69-−110.77 (1F), −139.91-−140.42 (1F), 207.72 (1F) | 576.3 |
| 286 | $^1$H NMR (400 MHz, DMSO-$d_6$) δ 9.44-9.37 (m, 1H), 7.80-7.76 (m, 1H), 7.37-7.32 (m, 1H), 7.06 (s, 2H), 5.65 (s, 2H), 4.95-4.74 (m, 1H), 4.52-4.49 (m, 1H), 4.42-4.31 (m, 2H), 4.06-3.81 (m, 2H), 3.75-3.58 (m, 2H), 3.31-3.18 (m, 2H), 3.12-2.91 (m, 3H), 2.59-2.53 (m, 1H), 2.44-2.26 (m, 1H), | 628.2 |

TABLE 2-continued

| Example | $^1$H NMR and $^{19}$F NMR data | Mass: $[M + H]^+$ |
|---|---|---|
| | 2.20-1.90 (m, 3H), 1.79-1.53 (m, 3H). $^{19}$F NMR (376 MHz, DMSO-$d_6$) δ −113.33-−113.43 (d, 1F), −139.86-−140.43 (d, 1F), −207.67 (s, 1F) | |
| 288 | $^1$H NMR (400 MHz, DMSO-$d_6$) δ 9.42-9.37 (m, 1H), 7.80-7.76 (m, 1H), 7.36-7.32 (m, 1H), 7.06-7.05 (m, 2H), 5.66-5.64 (m, 2H), 4.92-4.76 (m, 1H), 4.52-4.33 (m, 4H), 4.17-4.13 (m, 1H), 4.07-3.81 (m, 2H), 3.71-3.60 (m, 2H), 3.33-3.18 (m, 1H), 3.01-2.92 (m, 1H), 2.63-2.60 (m, 1H), 2.45-2.26 (m, 4H), 2.19-2.17 (m, 1H), 2.01-1.91 (m, 1H), 1.79-1.59 (m, 3H). $^{19}$F NMR (376 MHz, DMSO-$d_6$) δ −113.35-−113.42 (d, 1F), −139.88-−140.51 (d, 1F), −207.73 (s, 1F) | 575.3 |
| 289 | $^1$H NMR (400 MHz, DMSO-$d_6$) δ 9.41 (s, 1H), 6.75-6.73 (m, 1H), 6.51 (s, 2H), 5.36-5.23 (m, 1H), 4.92-4.65 (m, 1H), 4.50-4.47 (m, 1H), 4.35-4.32 (m, 2H), 3.99-3.96 (m, 1H), 3.76-3.55 (m, 2H), 3.33-3.05 (m, 4H), 2.90-2.84 (m, 1H), 2.41-2.30 (m, 1H), 2.20-1.92 (m, 3H), 1.90-1.69 (m, 3H). $^{19}$F NMR (376 MHz, DMSO-$d_6$): δ −53.73-−53.84 (m, 3F), −132.73-−132.80 (m, 1F), −141.28 (s, 1F), −172.19 (s, 1F) | 649.3 |
| 290 | $^1$H NMR (400 MHz, DMSO-$d_6$) δ 9.40-9.35 (m, 1H), 8.26-8.20 (m, 2H), 7.73-7.59 (m, 3H), 5.35-5.21 (m, 1H), 4.48-4.30 (m, 2H), 4.22-3.96 (m, 3H), 3.85-3.75 (m, 1H), 3.64-3.57 (m, 2H), 3.30-3.20 (m, 1H), 3.09-2.95 (m, 1H), 2.85-2.78 (m, 1H), 2.20-1.70 (m, 7H). $^{19}$F NMR (376 MHz, DMSO-$d_6$) δ −105.76-−105.86 (d, 1F), −140.16-−140.49 (d, 1F), −172.05-−172.16 (d, 1F) | 622.1 |
| 292 | $^1$H NMR (400 MHz, DMSO-$d_6$) δ 9.39-8.97 (m, 1H), 7.80-7.76 (m, 1H), 7.36-7.32 (m, 1H), 7.08-7.04 (m, 2H), 5.66 (s, 2H), 5.36-5.23 (m, 1H), 4.29-3.75 (m, 7H), 3.12-3.00 (m, 3H), 2.86-2.80 (m, 1H), 2.19-1.76 (m, 8H). $^{19}$F NMR (376 MHz, DMSO-$d_6$) δ −110.98-−113.33 (m, 1F), −139.50-−140.21 (m, 1F), −171.85-−172.06 (m, 1F) | 671.3, 673.3 |
| 293 | $^1$H NMR (400 MHz, DMSO-$d_6$) δ 9.36-9.31 (m, 1H), 7.73-7.71 (m, 1H), 7.46-7.44 (m, 1H), 7.05-7.02 (m, 2H), 5.81-5.79 (m, 2H), 5.10-4.96 (m, 1H), 4.48-4.40 (m, 2H), 4.21-4.19 (m, 1H), 4.09-3.91 (m, 2H), 3.85-3.72 (m, 1H), 3.66-3.57 (m, 2H), 3.28-3.10 (m, 2H), 3.03-2.95 (m, 1H), 2.85-2.80 (m, 1H), 2.20-1.97 (m, 4H), 1.84-1.63 (m, 3H), 1.25-1.22 (m, 3H). $^{19}$F NMR (376 MHz, DMSO-$d_6$) δ −140.40-−140.71 (d, 1F), −186.32-−186.38 (d, 1F) | 667.2, 669.2 |
| 294 | $^1$H NMR (400 MHz, DMSO-$d_6$) δ 10.32 (s, 1H), 9.44-9.38 (m, 1H), 7.94-7.92 (m, 1H), 7.61-7.58 (m, 1H), 7.40-7.38 (m, 1H), 7.20-7.17 (m, 1H), 4.98-4.76 (m, 1H), 4.52-4.34 (m, 4H), 4.24-3.96 (m, 3H), 3.71-3.60 (m, 2H), 3.33-3.18 (m, 1H), 3.02-2.92 (m, 1H), 2.63-2.54 (m, 1H), 2.47-2.28 (m, 4H), 2.24-2.16 (m, 1H), 2.01-1.89 (m, 1H), 1.77-1.59 (m, 3H). $^{19}$F NMR (376 MHz, DMSO-$d_6$) δ −140.04-−140.50 (d, 1F), −207.66 (s, 1F) | 592.2, 594.2 |
| 295 | $^1$H NMR (400 MHz, DMSO-$d_6$) δ 10.16 (s, 1H), 9.43-9.38 (m, 1H), 7.90-7.88 (m, 1H), 7.49-7.41 (m, 2H), 7.35-7.34 (m, 1H), 7.15-7.11 (m, 1H), 4.94-4.70 (m, 1H), 4.52-4.34 (m, 4H), 4.18-4.13 (m, 1H), 4.10-3.99 (m, 1H), 3.81-3.54 (m, 3H), 3.30-3.20 (m, 1H), 2.96-2.90 (m, 1H), 2.57-2.50 (m, 1H), 2.40-2.30 (m, 4H), 2.20-2.10 (m, 1H), 2.00-1.90 (m, 1H), 1.70-1.60 (m, 3H). $^{19}$F NMR (376 MHz, DMSO-$d_6$) δ −139.89-−140.46 (m, 1F), −207.64-−207.86 (m, 1F) | 558.2 |
| 296 | $^1$H NMR (400 MHz, DMSO-$d_6$) δ 9.43-9.36 (m, 1H), 7.73-7.71 (m, 1H), 7.47-7.44 (m, 1H), 7.06-7.02 (m, 2H), 5.80-5.78 (m, 2H), 4.96-4.76 (m, 1H), 4.52-4.33 (m, 4H), 4.17-3.92 (m, 3H), 3.71-3.60 (m, 2H), 3.33-3.15 (m, 1H), 3.01-2.92 (m, 1H), 2.63-2.54 (m, 1H), 2.43-2.25 (m, 4H), 2.19-2.08 (m, 1H), 2.02-1.90 (m, 1H), 1.77-1.57 (m, 3H). $^{19}$F NMR (376 MHz, DMSO-$d_6$): δ −139.99-−140.57 (d, 1F), −207.64 (s, 1F) | 591.2, 593.2 |
| 297 | $^1$H NMR (400 MHz, DMSO-$d_6$) δ 9.43-9.36 (m, 1H), 7.71-7.68 (m, 1H), 7.31-7.28 (m, 2H), 7.01-6.99 (m, 2H), 5.67-5.66 (m, 2H), 4.93-4.73 (m, 1H), 4.52-4.48 (m, 1H), 4.43-4.33 (m, 3H), 4.17-4.12 (m, 1H), 4.05-3.95 (m, 1H), 3.79-3.45 (m, 3H), 3.30-3.19 (m, 1H), 2.99-2.92 (m, 1H), 2.63-2.54 (m, 1H), 2.45-2.30 (m, 4H), 2.18-2.10 (m, 1H), 2.02-1.90 (m, 1H), 1.77-1.58 (m, 3H). $^{19}$F NMR (376 MHz, DMSO-$d_6$): δ −139.83-−140.51 (d, 1F), −207.60 (s, 1F) | 557.3 |
| 298 | $^1$H NMR (400 MHz, DMSO-$d_6$) δ 11.30-11.10 (bs, 1H), 9.41 (s, 1H), 7.21-7.20 (m, 1H), 6.84-6.80 (m, 1H), 5.35-5.21 (m, 1H), 4.94-4.65 (m, 1H), 4.50-4.47 (m, 1H), 4.36-4.27 (m, 2H), 4.05-3.96 (m, 1H), 3.69-3.55 (m, 2H), 3.30-3.00 (m, 4H), 2.86-2.82 (m, 1H), 2.40-2.30 (m, 1H), 2.14-1.74 (m, 6H). $^{19}$F NMR (376 MHz, DMSO-$d_6$) δ −54.16-−54.32 (m, 3F), −141.40 (s, 1F), −172.16 (s, 1F), −207.87 (s, 1F) | 632.2, 634.2 |
| 299 | $^1$H NMR (400 MHz, DMSO-$d_6$) δ 9.39 (s, 1H), 7.52-7.49 (m, 1H), 6.84-6.82 (m, 1H), 6.12 (s, 2H), 5.34-5.21 (m, 1H), 4.88-4.73 (m, 1H), 4.50-4.46 (m, 1H), 4.36-4.27(m, 2H), 3.99-3.96 (m, 1H), 3.66-3.57 (m, 2H), 3.32-3.20 (m, 1H), 3.13-3.00 (m, 3H), 2.85-2.81 (m, 1H), 2.43-2.24 (m, 1H), 2.19-1,96 (m, 3H), 1.89-1.66 (m, 3H). $^{19}$F NMR (376 MHz, DMSO-$d_6$) δ −55.77-−55.78 (m, 3F), −134.23 (s, 1F), −140.34 (s, 1F), −172.13 (s, 1F) | 615.3 |
| 300 | $^1$H NMR (400 MHz, DMSO-$d_6$) δ 10.12-10.01 (m, 1H), 9.43-9.38 (m, 1H), 7.90-7.88 (m, 1H), 7.48-7.41 (m, 2H), 7.35-7.34 (m, 1H), 7.14-7.11 (m, 1H), 5.35-5.21 (m, 1H), 4.95-4.73 (m, 1H), 4.51-4.47 (m, 1H), 4.39-4.30 | 604.4 |

TABLE 2-continued

| Example | $^{1}$H NMR and $^{19}$F NMR data | Mass: [M + H]$^{+}$ |
|---|---|---|
| | (m, 2H), 4.10-3.95 (m, 1H), 3.80-3.53 (m, 3H), 3.33-3.01 (m, 4H), 2.88-2.80 (m, 1H), 2.40-2.30 (m, 1H), 2.12-1.96 (m, 6H). $^{19}$F NMR (376 MHz, DMSO-$d_6$) δ −139.87-−140.42 (d, 1F), −170.07-−172.18 (d, 1F), −207.72 (s, 1F) | |
| 301 | $^{1}$H NMR (400 MHz, DMSO-$d_6$) δ 9.38-9.32 (m, 1H), 7.80-7.76 (m, 1H), 7.36-7.32 (m, 1H), 7.06-7.03 (m, 2H), 5.67-5.64 (m, 2H), 4.49-4.36 (m, 3H), 4.22-4.20 (m, 2H), 4.08-3.72 (m, 3H), 3.70-3.58 (m, 2H), 3.30-3.20 (m, 1H), 2.97-2.93 (m, 1H), 2.59-2.50 (m, 1H), 2.38-2.32 (m, 3H), 2.23-2.17 (m, 2H), 2.00-1.90 (m, 1H), 1.77-1.62 (m, 3H). $^{19}$F NMR (376 MHz, DMSO-$d_6$) δ −113.40-−113.42 (d, 1F), −140.30-−140.64 (d, 1F) | 591.2 |
| 302 | $^{1}$H NMR (400 MHz, DMSO-$d_6$) δ 9.38-9.33 (m, 1H), 7.80-7.76 (m, 1H), 7.36-7.32 (m, 1H), 7.06-7.03 (m, 2H), 5.67-5.64 (m, 2H), 4.50-4.38 (m, 3H), 4.21-4.14 (m, 2H), 4.08-3.76 (m, 3H), 3.66-3.57 (m, 2H), 3.29-3.21 (m, 1H), 3.00-2.92 (m, 1H), 2.58-2.50 (m, 1H), 2.39-2.32 (m, 3H), 2.23-2.15 (m, 2H), 2.01-1.89 (m, 1H), 1.76-1.57 (m, 3H). $^{19}$F NMR (376 MHz, DMSO-$d_6$) δ −113.40-−113.42 (d, 1F), −140.26-−140.78 (m, 1F) | 591.2, 593.2 |
| 304 | $^{1}$H NMR (400 MHz, Dimethylsulfoxide-$d_6$) δ 9.40-9.28 (m, 1H), 7.78 (dd, J = 6.0, 9.2 Hz, 1H), 7.37-7.29 (m, 1H), 7.09-7.00 (m, 2H), 5.69-5.59 (m, 2H), 5.39-5.17 (m, 1H), 4.91-4.56 (m, 1H), 4.49-4.37 (m, 1H), 4.33-4.18 (m, 1H), 4.08-3.75 (m, 1H), 3.58-3.47 (m, 1H), 3.13-2.99 (m, 3H), 2.88-2.78 (m, 1H), 2.18-1.96 (m, 7H) , 1,87-1.74 (m, 3H) , 1.63-1.39 (m, 2H). $^{19}$F NMR (376 MHz, Dimethylsulfoxide-$d_6$) δ −113.33, −113.42, −140.01, −140.56, −172.07, −172.18, −205.15 | 644.3 |
| 305 | $^{1}$H NMR (400 MHz, Dimethylsulfoxide-$d_6$) δ 9.37-9.27 (m, 1H), 7.83-7.72 (m, 1H), 7.38-7.28 (m, 1H), 7.09-7.00 (m, 2H), 5.74-5.56 (m, 2H), 5.42-5.15 (m, 1H), 4.85-4.47 (m, 1H), 4.44-4.32 (m, 1H), 4.18-4.07 (m, 1H), 4.07-3.73 (m, 1H), 3.53-3.38 (m, 1H), 3.24-3.15 (m, 1H), 3.12-3.00 (m, 3H), 2.88-2.77 (m, 1H), 2.63-2.54 (m, 1H), 2.32-2.25 (m, 1H), 2.14-2.00 (m, 5H), 1.87-1.75 (m, 3H), 1.65-1.52 (m, 1H). $^{19}$F NMR (376 MHz, Dimethylsulfoxide-$d_6$) δ −113.30, −113.45, −140.11, −140.55, −172.05, −172.19, −205.24 | 644.3 |
| 306 | $^{1}$H NMR (400 MHz, Dimethylsulfoxide-$d_6$) δ 9.37-9.26 (m, 1H), 7.78 (dd, J = 6.0, 9.2 Hz, 1H), 7.39-7.29 (m, 1H), 7.09-7.01 (m, 2H), 5.69-5.58 (m, 2H), 5.41-5.18 (m, 1H), 4.82-4.50 (m, 1H), 4.45-4.33 (m, 1H), 4.19-4.05 (m, 1H), 4.05-3.72 (m, 1H), 3.49-3.42 (m, 1H), 3.22-3.18 (m, 1H), 3.13-3.01 (m, 3H), 2.88-2.80 (m, 1H), 2.62-2.55 (m, 1H), 2.34-2.27 (m, 1H), 2.16-1.98 (m, 5H), 1.90-1.74 (m, 3H) , 1.65-1.52 (m, 1H). $^{19}$F NMR (376 MHz, Dimethylsulfoxide-$d_6$) δ −113.29, −113.41, −140.01, −140.54, −172.04, −172.16, −204.97, −205.21 | 644.2 |
| 307 | $^{1}$H NMR (400 MHz, Dimethylsulfoxide-$d_6$) δ 9.42-9.25 (m, 1H), 7.84-7.70 (m, 1H), 7.40-7.27 (m, 1H), 7.09-6.99 (m, 2H), 5.72-5.57 (m, 2H), 5.42-5.11 (m, 1H), 4.93-4.54 (m, 1H), 4.50-4.37 (m, 1H), 4.32-4.19 (m, 1H), 4.06-3.77 (m, 1H), 3.61-3.48 (m, 1H), 3.44-3.35 (m, 1H), 3.13-2.98 (m, 3H), 2.87-2.78 (m, 1H), 2.62-2.53 (m, 1H), 2.16-1.98 (m, 6H), 1.87-1.72 (m, 3H), 1.60-1.50 (m, 1H). $^{19}$F NMR (376 MHz, Dimethylsulfoxide-$d_6$) δ −113.33, −113.45, −140.08, −140.56, − 172.07, −172.20, −205.22 | 644.4 |
| 308 | $^{1}$H NMR (400 MHz, Dimethylsulfoxide-$d_6$) δ 9.71-9.48 (m, 1H), 7.82-7.72 (m, 1H), 7.34 (m, 1H), 7.05 (d, J = 4.8 Hz, 2H), 5.63 (d, J = 8.0 Hz, 2H), 5.40-5.17 (m, 1H), 5.09-4.86 (m, 1H), 4.48-4.27 (m, 1H), 3.80-3.36 (m, 3H), 3.12-2.98 (m, 3H), 2.83 (m, 1H), 2.43-2.17 (m, 4H), 2.15-2.00 (m, 3H), 1.87-1.67 (m, 5H). $^{19}$F NMR (376 MHz, Dimethylsulfoxide-$d_6$) δ −113.25, −113.45, −140.04, −140.12, −172.07, −172.16, −230.53 | 644.3 |
| 309 | $^{1}$H NMR (400 MHz, Dimethylsulfoxide-$d_6$) δ 9.71-9.43 (m, 1H), 7.88-7.68 (m, 1H), 7.34 (m, 1H), 7.05 (d, J = 5.2 Hz, 2H), 5.63 ( d, J = 8.0 Hz, 2H), 5.41-5.17 (m, 1H), 5.10-4.84 (m, 1H), 4.48-4.30 (m, 1H), 3.78-3.37 (m, 3H), 3.12-3.00 (m, 3H), 2.87-2.78 (m, 1H), 2.46-2.16 (m, 4H), 2.13-1.91 (m, 3H), 1.87-1.66 (m, 5H). $^{19}$F NMR (376 MHz, Dimethylsulfoxide-$d_6$) δ −113.15, −113.25, −113.42, −139.76, −139.84, −139.98, −140.13, −171.75, −171.89, −171.94, −172.01, −172.11, −172.22, −230.52 | 644.2 |
| 310 | $^{1}$H NMR (400 MHz, Dimethylsulfoxide-$d_6$) δ 9.67-9.50 (m, 1H), 7.82-7.74 (m, 1H), 7.34 (dt, J = 3.6, 9.2 Hz, 1H), 7.08-7.03 (m, 2H), 5.63 (d, J = 8.4 Hz, 2H), 5.39-5.17 (m, 1H), 5.14-4.90 (m, 1H), 4.45 (t, J = 14.8 Hz, 1H), 3.81-3.73 (m, 1H), 3.70-3.59 (m, 1H), 3.51-3.42 (m, 1H), 3.37-3.35 (m, 1H), 3.12-3.05 (m, 2H), 3.02-2.98 (m, 1H), 2.87-2.78 (m, 1H), 2.36-2.23 (m, 3H), 2.16-2.10 (m, 1H), 2.06-1.97 (m, 2H), 1.86-1.66 (m, 5H). $^{19}$F NMR (376 MHz, Dimethylsulfoxide-$d_6$) δ −113.24, −113.41, −139.93, −140.14, −172.04, −172.13, −229.68 | 644.3 |
| 311 | $^{1}$H NMR (400 MHz, Dimethylsulfoxide-$d_6$) δ 9.71-9.47 (m, 1H), 7.83-7.71 (m, 1H), 7.34 (dt, J = 4.4, 8.8 Hz, 1H), 7.05 (d, J = 4.4 Hz, 2H), 5.63 (d, J = 7.6 Hz, 2H), 5.38-4.88 (m, 2H), 4.54-4.36 (m, 1H), 3.88-3.41 (m, 4H), 3.12-2.98 (m, 3H), 2.88-2.77 (m, 1H), 2.36-2.22 (m, 3H), 2.14-1.99 (m, 3H), 1.87-1.64 (m, 5H). $^{19}$F NMR (376 MHz, Dimethylsulfoxide-$d_6$) δ −113.23, −113.43, −139.99, −140.11, −172.07, −172.17, −229.65 | 644.3 |
| 313 | $^{1}$H NMR (400 MHz, Dimethylsulfoxide-$d_6$) δ 9.50-9.28 (m, 1H), 7.78 (dd, J = 6.0, 9.2 Hz, 1H), 7.40-7.29 (m, 1H), 7.13-6.98 (m, 2H), 5.73-5.55 (m, 2H), 5.00-4.63 (m, 2H), 4.50 (d, J = 13.6 Hz, 1H), 4.43-4.25 (m, 2H), 4.12-3.78 (m, 2H), 3.77-3.55 (m, 2H), 3.29-3.16 (m, 1H), 3.07-2.96 (m, 1H), | 647.1 |

TABLE 2-continued

| Example | $^{1}H$ NMR and $^{19}F$ NMR data | Mass: $[M + H]^+$ |
|---|---|---|
| | 2.85-2.83(m, 1H) , 2.77-2.65 (m, 1H), 2.57-2.52 (m, 1H), 2.43-2.26 (m, 1H), 2.10-1.98 (m, 1H), 1.98-1.57 (m, 5H), 0.94-0.71 (m, 2H). $^{19}F$ NMR (376 MHz, Dimethylsulfoxide-$d_6$) δ −113.35, −113.44, −139.91, −140.48, −207.94, −209.90, −209.96 | |
| 314 | $^{1}H$ NMR (400 MHz, DMSO-$d_6$) δ 9.43-9.37 (m, 1H), 7.80-7.76 (m, 1H), 7.36-7.32 (m, 1H), 7.06-7.05 (m, 2H), 5.66-5.64 (m, 2H), 4.98-4.74 (m, 1H), 4.52-4.34 (m, 3H), 4.08-3.80 (m, 2H), 3.72-3.60 (m, 2H), 3.30-3.18 (m, 1H), 3.07-2.97 (m, 1H), 2.86-2.79 (m, 1H), 2.67-2.30 (m, 6H), 2.03-1.94 (m, 2H), 1.80-1.53 (m, 4H). $^{19}F$ NMR (376 MHz, DMSO-$d_6$) δ −113.35- −113.43 (d, 1F), −139.87-−140.47 (d, 1F), −207.42-−207.68 (m, 1F) | 642.3 |
| 315 | $^{1}H$ NMR (400 MHz, DMSO-$d_6$) δ 9.43-9.37 (m, 1H), 7.80-7.76 (m, 1H), 7.36-7.32 (m, 1H), 7.06-7.05 (m, 2H), 5.66-5.64 (m, 2H), 4.98-4.73 (m, 1H), 4.52-4.34 (m, 3H), 4.10-3.81 (m, 2H), 3.72-3.60 (m, 2H), 3.30-3.10 (m, 2H), 2.86-2.81 (m, 1H), 2.70-2.53 (m, 4H), 2.43-2.20 (m, 3H), 1.93-1.59 (m, 4H), 1.42-1.30 (m, 1H). $^{19}F$ NMR (376 MHz, DMSO-$d_6$) δ −113.35- −113.43 (d, 1F), −139.92-−140.48 (d, 1F), −207.68 (s, 1F) | 642.3 |
| 317 | $^{1}H$ NMR (400 MHz, DMSO-$d_6$) δ 9.25-9.22 (m, 1H), 7.79-7.75 (m, 1H), 7.36-7.31 (m, 1H), 7.05-7.03 (m, 2H), 5.66-5.63 (m, 2H), 5.35-5.21 (m, 1H), 4.45-4.40 (m, 1H), 4.15-3.54 (m, 7H), 3.10-3.01 (m, 3H), 2.85-2.80 (m, 1H), 2.22-1.70 (m, 8H). $^{19}F$ NMR (376 MHz, DMSO-$d_6$) δ −113.47- −113.56 (d, 1F), −140.37 (s, 1F), −172.09-−172.21 (d, 1F) | 637.2 |
| 318 | $^{1}H$ NMR (400 MHz, DMSO-$d_6$) δ 9.45-9.38 (m, 1H), 8.21-8.15 (m, 2H), 7.77-7.66 (m, 3H), 5.35-7.21 (m, 1H), 4.92-4.77 (m, 1H), 4.52-4.09 (m, 4H), 4.02-3.95 (m, 1H), 3.72-3.58 (m, 2H), 3.30-3.20 (m, 1H), 3.09-3.01 (m, 3H), 2.90-2.80 (m, 1H), 2.45-2.28 (m, 1H), 2.12-1.95 (m, 3H), 1.91-1.70 (m, 3H). $^{19}F$ NMR (376MHz, DMSO-$d_6$) δ −140.00-−140.39 (m, 1F), −172.07-−172.17 (d, 1F), −207.68 (s, 1F) | 622.3, 624.3 |
| 319 | $^{1}H$ NMR (400 MHz, DMSO-$d_6$) δ 9.44-9.39 (m, 1H), 8.17-8.13 (m, 2H), 7.75-7.69 (m, 2H), 7.62-7.56 (m, 2H), 5.35-5.21 (m, 1H), 4.96-4.69 (m, 1H), 4.51-4.48 (m, 1H), 4.38-4.30 (m, 2H), 4.10-4.01 (m, 1H), 3.88-3.60 (m, 3H), 3.30-3.20 (m, 1H), 3.10-3.01 (m, 3H), 2.84-2.78 (m, 1H), 2.44-2.26 (m, 1H), 2.15-1.95 (m, 3H), 1.90-1.69 (m, 3H). $^{19}F$ NMR (376 MHz, DMSO-$d_6$) δ −140.35 (s, 1F), −172.07-−172.17 (d, 1F), −207.86 (s, 1F) | 588.4 |
| 320 | $^{1}H$ NMR (400 MHz, DMSO-$d_6$) δ 9.40-9.34 (m, 1H), 8.21-8.16 (m, 2H), 7.76-7.64 (m, 3H), 5.35-5.21 (m, 1H), 4.48-4.41 (m, 2H), 4.26-3.95 (m, 3H), 3.80-3.70 (m, 1H), 3.67-3.60 (m, 2H), 3.40-3.20 (m, 1H), 3.09-3.01 (m, 3H), 2.85-2.80 (m, 1H), 2.20-1.70 (m, 7H). $^{19}F$ NMR (376 MHz, DMSO-$d_6$) δ −140.57 (s, 1F), −172.04-−172.15 (d, 1F) | 638.2, 640.2 |
| 321 | $^{1}H$ NMR (400 MHz, DMSO-$d_6$) δ 9.39-9.32 (m, 1H), 7.73-7.71 (m, 1H), 7.46-7.44 (m, 1H), 7.05-7.02 (m, 2H), 5.80-5.77 (m, 2H), 4.48-4.38 (m, 3H), 4.21-4.14 (m, 2H), 4.09-3.90 (m, 2H), 3.87-3.60 (m, 3H), 3.33-3.20 (m, 1H), 3.00-2.91 (m, 1H), 2.65-2.54 (m, 1H), 2.37 (s, 3H), 2.21-2.17 (m, 2H), 2.03-1.89 (m, 1H), 1.76-1.58 (m, 3H). $^{19}F$ NMR (376 MHz, DMSO-$d_6$) δ −140.36-−140.73 (d, 1F) | 607.0, 609.0 |
| 322 | $^{1}H$ NMR (400 MHz, DMSO-$d_6$) δ 9.38-9.32 (m, 1H), 7.71-7.68 (m, 1H), 7.31-7.28 (m, 2H), 7.01-6.91 (m, 2H), 5.68-5.65 (m, 2H), 4.48-4.40 (m, 3H), 4.20-4.15 (m, 2H), 4.05-3.95 (m, 1H), 3.85-3.75 (m, 1H), 3.70-3.44 (m, 3H), 3.33-3.17 (m, 1H), 3.00-2.94 (m, 1H), 2.64-2.54 (m, 1H), 2.36 (s, 3H), 2.19-2.17 (m, 2H), 2.03-1.89 (m, 1H), 1.78-1.56 (m, 3H). $^{19}F$ NMR (376 MHz, DMSO-$d_6$) δ −140.21-−140.68 (d, 1F) | 573.2 |
| 323 | $^{1}H$ NMR (400 MHz, Dimethylsulfoxide-$d_6$) δ 7.79-7.74 (m, 1H), 7.38-7.26 (m, 1H), 7.13-6.95 (m, 2H), 5.70-5.59 (m, 2H), 5.39-5.18 (m, 2H), 4.51-4.29 (m, 3H), 4.15-3.90 (m, 3H), 3.87-3.74 (m, 1H), 3.63-3.52 (m, 1H), 3.47-3.43 (m, 1H), 3.08-2.98 (m, 3H), 2.85-2.80 (m, 1H), 2.15-1.94 (m, 4H), 1.88-1.73 (m, 3H), 1.36-1.31 (m, 3H), 1.27-1.22 (m, 3H). $^{19}F$ NMR (376 MHz, Dimethylsulfoxide-$d_6$) δ −113.20, −150.17, −150.94, −172.08, −172.18, −206.50 | 679.2 |
| 324 | $^{1}H$ NMR (400 MHz, DMSO-$d_6$) δ 10.07-9.96 (m, 1H), 9.46-9.34 (m, 1H), 7.80-7.78 (m, 1H), 7.42-7.40 (m, 1H), 7.30-7.29 (m, 1H), 7.09-7.06 (m, 1H), 5.35-5.21 (m, 1H), 4.96-4.76 (m, 1H), 4.51-4.31 (m, 3H), 4.09-3.80 (m, 2H), 3.78-3.56 (m, 2H), 3.33-3.18 (m, 1H), 3.18-2.96 (m, 3H), 2.88-2.78 (m, 1H), 2.47-2.26 (m, 4H), 2.16-1.68 (m, 6H). $^{19}F$ NMR (376 MHz, DMSO-$d_6$) δ −139.96-−140.45 (d, 1F), −172.06-−172.17 (d, 1F), −207.66 (s, 1F) | 618.3 |
| 325 | $^{1}H$ NMR (300 MHz, Methanol-$d_4$) δ 9.48-9.45 (m, 1H), 8.05-8.02 (m, 1H), 7.96-7.93 (m, 1H), 7.60-7.47 (m, 3H), 5.35-5.20 (m, 1H), 4.84-4.63 (m, 2H), 4.50-4.40 (m, 1H), 4.24-4.12 (m, 1H), 4.09-3.68 (m, 4H), 3.40-3.12 (m, 4H), 3.07-2.94 (m, 1H), 2.56-2.53 (m, 3H), 2.40-1.80 (m, 7H). $^{19}F$ NMR (282 MHz, Methanol-$d_4$) δ −139.01-−139.78 (d,1F), −173.68 (s, 1F) | 602.3 |
| 326 | $^{1}H$ NMR (400 MHz, DMSO-$d_6$) δ 9.38-9.32 (m, 1H), 7.73-7.71 (m, 1H), 7.46-7.44 (m, 1H), 7.05-7.02 (m, 2H), 5.80-5.77 (m, 2H), 4.56-4.37 (m, 3H), 4.22-4.18 (m, 2H), 4.10-3.90 (m, 2H), 3.83-3.73 (m, 1H), 3.71-3.57 (m, 2H), 3.33-3.22 (m, 1H), 3.00-2.94 (m, 1H), 2.67-2.54 (m, 1H), 2.35 (s, 3H), 2.26-2.15 (m, 2H), 2.08-1.91 (m, 1H), 1.77-1,58 (m, 3H). $^{19}F$ NMR (376 MHz, DMSO-$d_6$) δ −140.40-−140.71 (d, 1F) | 607.0 |
| 327 | $^{1}H$ NMR (400 MHz, DMSO-$d_6$) δ 9.37-9.32 (m, 1H), 7.71-7.68 (m, 1H), 7.32-7.28 (m, 2H), 7.01-6.97 (m, 2H), 5.68-5.66 (m, 2H), 4.48-4.35 (m, | 573.1 |

TABLE 2-continued

| Example | $^1H$ NMR and $^{19}F$ NMR data | Mass: $[M + H]^+$ |
|---|---|---|
| | 3H), 4.21-4.17 (m, 2H), 4.07-3.95 (m, 1H), 3.85-3.75 (m, 1H), 3.72-3.43 (m, 3H), 3.33-3.21 (m, 1H), 3.00-2.93 (m, 1H), 2.64-2.56 (m, 1H), 2.35 (s, 3H), 2.21-2.13 (m, 2H), 2.00-1.88 (m, 1H), 1.77-1.58 (m, 3H). $^{19}F$ NMR (376 MHz, DMSO-$d_6$) δ −140.25-−140.66 (d, 1F) | |
| 328 | $^1H$ NMR (400 MHz, DMSO-$d_6$) δ 8.62 (s, 1H), 8.20 (s, 1H), 8.05-8.03 (m, 1H), 7.77-7.73 (m, 1H), 7.43- 7.34 (m, 2H), 7.01 (m, 1H), 5.33-5.19 (m, 1H), 4.87 (s, 1H), 4.83-4.68 (m, 1H), 4.46-4.25 (m, 3H), 4.00-3.96 (m, 1H), 3.70-3.57 (m, 2H), 3.20-2.97 (m, 4H), 2.85-2.75 (m, 1H), 2.40-2.25 (m, 1H), 2.11-1.70 (m, 6H). $^{19}F$ NMR (376 MHz, DMSO-$d_6$) δ −59.07 (s, 3F), −113.65 (s, 1F), −128.42 (s, 1F), −172.12 (s, 1F), −207.99 (s, 1F) | 688.4 |
| 330 | $^1H$ NMR (400 MHz, $CD_3OD$) δ 9.44 (s, 1H), 6.79-6.77 (m, 1H), 5.37-5.24 (m, 1H), 4.86-4.62 (m, 2H), 4.43-4.39 (m, 1H), 4.19-4.13 (m, 1H), 3.96-3.72 (m, 3H), 3.40-3.20 (m, 4H), 3.05-3.01 (m, 1H), 2.43-1.80 (m, 10H). $^{19}F$ NMR (376 MHz, $CD_3OD$) δ −55.52 (s, 3F), −138.03 (s, 1F), −140.91-141.12 (d, 1F), −173.69 (s, 1F) | 630.3 |
| 332 | $^1H$ NMR (400 MHz, DMSO-$d_6$) δ 9.45-9.39 (m, 1H),8.36-8.29 (m, 2H).7.94-7.85(m, 2H). 7.78-7.76 (m, 1H), 5.35-5.21 (m, 1H), 4.91-4.75 (m, 1H), 4.52-4.49 (m, 1H), 4.37-4.18 (m, 3H), 4.02-3.95 (m, 1H), 3.72-3.61 (m, 2H), 3.33-3.20 (m, 1H), 3.10-3.00 (m, 3H), 2.85-2.81 (m, 1H), 2.43-2.20 (m, 1H), 2.12-1.99 (m, 3H), 1.86-1.76 (m, 3H). $^{19}F$ NMR (376 MHz, DMSO-$d_6$) δ −59.69-−59.78 (m, 3F), −140.17-−140.67 (m, 1F), −172.07-−172.17 (m, 1F), −208.02 (s, 1F) | 656.3 |
| 334 | $^1H$ NMR (400 MHz, DMSO-$d_6$) δ 9.43-9.37 (m, 1H), 7.80-7.76 (m, 1H), 7.37-7.32 (m, 1H), 7.06-7.05 (m, 2H), 5.67-5.66 (m, 2H), 4.95-4.74 (m, 2H), 4.57-4.24 (m, 3H), 4.08-3.81 (m, 2H), 3.71-3.54 (m, 2H), 3.30-3.20 (m, 1H), 3.00-2.87 (m, 2H), 2.79-2.68 (m, 1H), 2.42-2.28 (m, 2H), 2.03-1.69 (m, 5H), 1.06-1.00 (m, 3H). $^{19}F$ NMR (376 MHz, DMSO-$d_6$) δ −133.37-−113.44 (d, 1F), −139.91-−140.45 (d, 1F), −181.22-−181.24 (d, 1F), −207.69 (s, 1F) | 635.3 |
| 335 | $^1H$ NMR (400 MHz, DMSO-$d_6$) δ 10.46 (s, 1H), 9.39 (s, 1H), 6.93 (s, 1H), 6.63 (s, 1H), 5.34-5.21 (m, 1H), 4.97-4.65 (m, 1H), 4.50-4.46 (m, 1H), 4.37-4.29 (m, 2H), 3.99-3.96 (m, 1H), 3.67-3.57 (m, 2H), 3.30-2.95 (m, 4H), 2.84-2.81 (m, 1H), 2.52-2.46 (m, 3H), 2.40-2.31 (m, 1H), 2.12-1.73 (m, 6H). $^{19}F$ NMR (376 MHz, DMSO-$d_6$) δ −52.99-−53.15(m, 3F), −141.54 (s, 1F), −172.13 (s, 1F), −207.85 (s, 1F) | 612.2 |
| 336 | $^1H$ NMR (400 MHz, DMSO-$d_6$) δ 9.46-9.40 (m, 1H), 8.36-8.29 (m, 2H), 7.95-7.86 (m, 2H), 7.78-7.76 (m, 1H), 5.42-5.15 (m, 1H), 4.91-4.76 (m, 1H), 4.52-4.33 (m, 4H), 4.20-3.94 (m, 3H), 3.75-3.61 (m, 2H), 3.20-2.90 (m, 5H), 2.80-2.69 (m, 1H), 2.62-2.56 (m, 2H), 2.43-1.90 (m, 6H), 1.68-1.40 (m, 1H). $^{19}F$ NMR (376 MHz, DMSO-$d_6$): δ −59.68-−59.78 (m, 3F), −140.15-−140.69 (m, 1F), −171.21-−171.43 (m, 1F), −208.03 (s, 1F) | 683.4 |
| 337 | $^1H$ NMR (400 MHz, DMSO-$d_6$) δ 9.43-9.36 (m, 1H), 7.73-7.71 (m, 1H), 7.46-7.44 (m, 1H), 7.04-7.02 (m, 2H), 5.80-5.79 (m, 2H), 5.10-4.75 (m, 2H), 4.51-4.32 (m, 3H), 4.15-3.92 (m, 2H), 3.71-3.60 (m, 2H), 3.30-2.97 (m, 3H), 2.87-2.78 (m, 1H), 2.42-2.25 (m, 1H), 2.10-1.98 (m, 3H), 1.78-1.68 (m, 3H), 1.25-1.22 (m, 3H). $^{19}F$ NMR (376 MHz, DMSO-$d_6$) δ −140.03-−140.56 (d, 1F), −186.34-−186.38 (d, 1F), −207.69 (s, 1F) | 651.2, 653.2 |
| 338 | $^1H$ NMR (400 MHz, DMSO-$d_6$) δ 9.43-9.36 (m, 1H), 7.71-7.68 (m, 1H), 7.33-7.28 (m, 2H), 7.00-6.99 (m, 2H), 5.67 (s, 2H), 5.10-4.72 (m, 2H), 4.51-4.32 (m, 3H), 4.10-3.93 (m, 1H), 3.73-3.45 (m, 3H), 3.30-2.97 (m, 3H), 2.88-2.78 (m, 1H), 2.42-2.24 (m, 1H), 2.18-1,97 (m, 3H), 1.87-1.68 (m, 3H), 1.24-1.20 (m, 3H). $^{19}F$ NMR (376 MHz, DMSO-$d_6$) δ −139.89-−140.51 (d, 1F), −186.35-−186.39 (d, 1F), −207.67 (s, 1F) | 617.2 |
| 339 | $^1H$ NMR (400 MHz, DMSO-$d_6$) δ 9.38-9.32 (m, 1H), 7.80-7.76 (m, 1H), 7.36-7.31 (m, 1H), 7.05-7.02 (m, 2H), 5.67-5.64 (m, 2H), 5.10-4.96 (m, 1H), 4.48-4.40 (m, 2H), 4.23-4.18 (m, 1H), 4.05-3.76 (m, 3H), 3.66-3.55 (m, 2H), 3.30-2.97 (m, 3H), 2.89-2.77 (m, 1H), 2.18-2.00 (m, 4H), 1.86-1.66 (m, 3H), 1.25-1.23 (m, 3H). $^{19}F$ NMR (376 MHz, DMSO-$d_6$) δ −113.39-−113.44 (d, 1F), −140.30-−140.61 (d, 1F), −186.38-−186.43 (d, 1F) | 651.2, 653.2 |
| 343 | $^1H$ NMR (400 MHz, Dimethylsulfoxide-$d_6$) δ 9.66-9.08 (m, 1H), 7.83-7.71 (m, 1H), 7.37-7.29 (m, 1H), 7.09-6.99 (m, 2H), 5.63 (s, 2H), 5.39-5.18 (m, 1H), 4.39-4.16 (m, 1H), 3.85-3.73 (m, 2H), 3.60-3.45 (m, 1H), 3.14-2.98 (m, 3H), 2.88-2.77 (m, 1H), 2.18-2.04 (m, 4H), 2.04-1.94 (m, 2H), 1.92-1.75 (m, 5H), 1.74-1.64 (m, 2H), 1.61-1.42 (m, 1H). $^{19}F$ NMR (376 MHz, Dimethylsulfoxide-$d_6$) δ −113.33, −113.43, −140.03, −172.02, −172.15 | 635.1, 637.1 |
| 344 | $^1H$ NMR (400 MHz, Dimethylsulfoxide-$d_6$) δ 9.66-9.06 (m, 1H), 7.83-7.70 (m, 1H), 7.36-7.30 (m, 1H), 7.07-7.01 (m, 2H), 5.63 (s, 2H), 5.38-5.18 (m, 1H), 4.37-4.18 (m, 1H), 3.84-3.73 (m, 2H), 3.60-3.49 (m, 1H), 3.14-2.99 (m, 3H), 2.87-2.78 (m, 1H), 2.19-2.04 (m, 4H), 2.04-1.94 (m, 2H), 1.92-1.75 (m, 5H), 1.75-1.66 (m, 2H), 1.61-1.46 (m, 1H). $^{19}F$ NMR (376 MHz, Dimethylsulfoxide-$d_6$) δ −113.32, −113.45, −140.07, −172.03, −172.19 | 635.1, 637.1 |
| 345 | $^1H$ NMR (400 MHz, DMSO-$d_6$) δ 9.38-9.31 (m, 1H), 7.73-7.71 (m, 1H), 7.46-7.44 (m, 1H), 7.05-7.02 (m, 2H), 5.81-5.78 (m, 2H), 5.09-4.95 (m, 1H), 4.52-4.35 (m, 2H), 4.21-4.18 (m, 1H), 4.09-3.91 (m, 2H), 3.88-3.57 (m, 3H), 3.33-2.97 (m, 3H), 2.88-2.79 (m, 1H), 2.21-2.00 (m, 4H), 1.80-1.68 (m, 3H), 1.25-1.23 (m, 3H). $^{19}F$ NMR (376MHz, DMSO-$d_6$) δ −140.41-−140.69 (d, 1F), −186.35-−186.41 (d, 1F) | 667.2, 669.2 |

TABLE 2-continued

| Example | $^1H$ NMR and $^{19}F$ NMR data | Mass: $[M + H]^+$ |
|---|---|---|
| 346 | $^1H$ NMR (400 MHz, DMSO-$d_6$) δ 9.40-9.33 (m, 1H), 7.70-7.68 (m, 1H), 7.32-7.27 (m, 2H), 7.01-6.96 (m, 2H), 5.69-5.66 (m, 2H), 5.09-4.95 (m, 1H), 4.47-4.44 (m, 2H), 4.20-4.18 (m, 1H), 4.10-3.95 (m, 1H), 3.85-3.75 (m, 1H), 3.70-3.44 (m, 3H), 3.30-3.10 (m, 2H), 3.03-2.95 (m, 1H), 2.84-2.78 (m, 1H), 2.19-1.99 (m, 4H), 1.80-1.66 (m, 3H), 1.25-1.23 (m, 3H). $^{19}F$ NMR (376 MHz, DMSO-$d_6$) δ −140.27-−140.65 (d, 1F), −186.35-−186.40 (d, 1F) | 633.2 |
| 347 | $^1H$ NMR (400 MHz, Dimethylsulfoxide-$d_6$) δ 9.40-9.28 (m, 1H), 7.74 (dd, J = 6.0, 9.2 Hz, 1H), 7.30 (t, J = 9.2 Hz, 1H), 7.00 (s, 1H), 6.88 (dd, J = 2.0, 16.4 Hz, 1H), 5.56 (d, J = 10.0 Hz, 2H), 4.88 (s, 2H), 4.45-4.33 (m, 2H), 4.18-4.05 (m, 3H), 4.04-3.94 (m, 1H), 3.86-3.55 (m, 4H), 3.54-3.48 (m, 1H), 3.26-3.21 (m, 1H), 3.07-3.01 (m, 1H), 2.69-2.56 (m, 2H), 2.43-2.38 (m, 1H), 2.28-2.22 (m, 1H), 2.18-2.09 (m, 4H), 2.02-1.93 (m, 1H), 1.73-1.65 (m, 1H), 0.86-0.80 (m, 1H), 0.64-0.59 (m, 1H), 0.49-0.41 (m, 2H). $^{19}F$ NMR (376 MHz, Dimethylsulfoxide-$d_6$) δ −113.65 | 651.3 |
| 348 | $^1H$ NMR (400 MHz, DMSO-$d_6$) δ 9.36-9.31 (m, 1H), 7.71-7.68 (m, 1H), 7.32-7.27 (m, 2H), 7.01-6.96 (m, 2H), 5.69-5.67 (m, 2H), 5.10-4.96 (m, 1H), 4.48-4.34 (m, 2H), 4.20-4.16 (m, 1H), 4.04-3.92 (m, 1H), 3.83-3.74 (m, 1H), 3.71-3.50 (m, 3H), 3.27-3.07 (m, 2H), 3.03-2.93 (m, 1H), 2.86-2.80 (m, 1H), 2.20-2.00 (m, 4H), 1.80-1.64 (m, 3H), 1.22-1.25 (m, 3H). $^{19}F$ NMR (376 MHz, DMSO-$d_6$) δ −140.25-−140.68 (d, 1F), −186.33-−186.38 (d, 1F) | 633.2 |
| 349 | $^1H$ NMR (400 MHz, DMSO-$d_6$) δ 8.75 (s, 1H), 8.21 (s, 2H), 7.39-7.35 (m, 1H), 7.22-7.17 (m, 1H), 5.34-5.20 (m, 1H), 4.83-4.68 (m, 1H), 4.49-4.33 (m, 3H), 4.02-3.97 (m, 1H), 3.73-3.55 (m, 2H), 3.30-3.00 (m, 4H), 2.86-2.79 (m, 1H), 2.40-2.30 (m, 1H), 2.15-1.70 (m, 6H). $^{19}F$ NMR (376 MHz, DMSO-$d_6$) δ −115.49 (s, 1F), −124.22 (s, 1F), −172.16 (s, 1F) | 652.23 |
| 350 | $^1H$ NMR (400 MHz, DMSO-$d_6$) δ 8.35 (s, 1H), 8.11 (s, 2H), 7.28-7.24 (m, 1H), 7.17-7.13 (m, 1H), 5.34-5.20 (m, 1H), 4.85-4.70 (m, 1H), 4.43-4.27 (m, 3H), 3.99-3.96 (m, 1H), 3.77-3.71 (m, 1H), 3.59-3.53 (m, 1H), 3.21-2.96 (m, 4H), 2.89-2.76 (m, 1H), 2.38-2.22 (m, 1H), 2.18-1.67 (m, 6H). $^{19}F$ NMR (376 MHz, DMSO-$d_6$) δ −116.38 (s, 1F), −122.47 (s, 1F), −172.15 (s, 1F), −207.30 (s, 1F) | 661.1 |
| 351 | $^1H$ NMR (400 MHz, DMSO-$d_6$) δ 8.73 (s, 1H), 8.20 (s, 2H), 7.45-7.41 (m, 1H), 7.23-7.18 (m, 1H), 5.34-5.20 (m, 1H), 4.57-4.28 (m, 4H), 3.95-3.90 (m, 1H), 3.74-3.56 (m, 2H), 3.25-3.00 (m, 4H), 2.85-2.80 (m, 1H), 2.40-2.30 (m, 1H), 2.14-1.70 (m, 6H). $^{19}F$ NMR (376 MHz, DMSO-$d_6$) δ −115.61 (s, 1F), −125.16 (s, 1F), −172.10 (s, 1F), −206.70-−207.07 (m, 1F) | 652.3 |
| 352 | $^1H$ NMR (400 MHz, DMSO-$d_6$) δ 8.33 (s, 1H), 8.10 (s, 2H), 7.32-7.14 (m, 2H), 5.34-5.20 (m, 1H), 4.48-4.22 (m, 4H), 3.96-3.93 (m, 1H), 3.77-3.72 (m, 1H), 3.60-3.54 (m, 1H), 3.18-2.92 (m, 4H), 2.87-2.74 (m, 1H), 2.36-2.21 (m, 1H), 2.18-1.95 (m, 3H), 1.88-1.63 (m, 3H). $^{19}F$ NMR (376 MHz, DMSO-$d_6$) δ −116.49 (s, 1F), −123.30 (s, 1F), −172.10 (s, 1F), −205.93 (s, 1F) | 661.1 |
| 354 | $^1H$ NMR (400 MHz, DMSO-$d_6$) δ 8.29-8.26 (m, 1H), 7.79-7.75 (m, 1H), 7.37-7.32 (m, 1H), 7.05-7.04 (m, 1H), 6.95-6.91 (m, 1H), 5.65 (s, 2H), 5.34-5.21 (m, 1H), 4.88-4.73 (m, 1H), 4.43-4.25 (m, 3H), 4.04-3.70 (m, 3H), 3.63-3.51 (m, 1H), 3.29-2.96 (m, 4H), 2.88-2.76 (m, 1H), 2.40-2.20 (m, 1H), 2.16-1.94 (m, 3H), 1.89-1.69 (m, 3H). $^{19}F$ NMR (376 MHz, DMSO-$d_6$) δ −113.07-−113.07 (d, 1F), −123.09-−123.48 (d, 1F), −172.06-−172.18 (d, 1F), −207.46-−207.80 (m, 1F) | 653.9 |
| 355 | $^1H$ NMR (400 MHz, DMSO-$d_6$) δ 7.95-7.93 (m, 1H), 7.81-7.77 (m, 1H), 7.38-7.34 (m, 1H), 7.07-6.95 (m, 2H), 5.68-5.66 (m, 2H), 5.34-5.21 (m, 1H), 4.87-4.71 (m, 1H), 4.41-4.26 (m, 3H), 4.09-3.87 (m, 2H), 3.81-3.75 (m, 1H), 3.60-3.51 (m, 1H), 3.25-3.00 (m, 4H), 2.88-2.81 (m, 1H), 2.30-2.20 (m, 1H), 2.10-1.70 (m, 6H). $^{19}F$ NMR (376 MHz, DMSO) δ −112.84-−112.85 (m, 1F), −119.64-−119.71(m, 1F), −124.97-−125.56 (m, 1F), −172.05-−172.17 (m, 1F), −207.65 (s, 1F) | 638.3 |
| 356 | $^1H$ NMR (400 MHz, DMSO-$d_6$) δ 8.14 (s, 2H), 8.03-8.01 (m, 1H), 7.39-7.35 (m, 1H), 7.19-7.15 (m, 1H), 5.35-5.22 (m, 1H), 4.48-4.21 (m, 4H), 3.96-3.93 (m, 1H), 3.77-3.74 (m, 1H), 3.60-3.57 (m, 1H), 3.23-2.99 (m, 4H), 2.90-2.80 (m, 1H), 2.33-1.70 (m, 7H). $^{19}F$ NMR (376 MHz, DMSO-$d_6$) δ −116.10 (s, 1F), −119.93 (s, 1F), −124.91 (s, 1F), −172.10 (s, 1F), −206.01 (s, 1F) | 645.0 |
| 357 | $^1H$ NMR (400 MHz, DMSO-$d_6$) δ 8.17 (s, 2H), 8.04-8.01 (m, 1H), 7.37-7.33 (m, 1H), 7.19-7.14 (m, 1H), 5.36-5.22 (m, 1H), 4.82-4.67 (m, 1H), 4.40-4.26 (m, 3H), 3.99-3.96 (m, 1H), 3.80-3.74 (m, 1H), 3.59-3.53 (m, 1H), 3.20-3.00 (m, 4H), 2.91-2.79 (m, 1H), 2.35-1.72 (m, 7H). $^{19}F$ NMR (376 MHz, DMSO-$d_6$) δ −115.96 (s, 1F), −119.62 (s, 1F), −124.24 (s, 1F), −172.18 (s, 1F), −207.14-−207.32 (d, 1F) | 645.2 |
| 358 | $^1H$ NMR (400 MHz, DMSO-$d_6$) δ 8.80 (s, 1H), 7.84-7.80 (m, 1H), 7.40-7.36 (m, 1H), 7.10-7.02 (m, 2H), 5.71 (s, 2H), 5.34-5.21 (m, 1H), 4.84-4.69 (m, 1H), 4.49-4.37 (m, 3H), 4.07-4.00 (m, 2H), 3.75-3.69 (m, 1H), 3.61-3.55 (m, 1H), 3.30-3.20 (m, 1H), 3.08-−3.00 (m, 3H), 2.85-2.81 (m, 1H), 2.41-2.30 (m, 1H), 2.11-1.72 (m, 6H). $^{19}F$ NMR (376 MHz, DMSO-$d_6$) δ −112.64 (s, 1F), −125.43 (s, 1F), −172.09 (s, 1F), −208.67 (s, 1F) | 645.3 |
| 359 | $^1H$ NMR (400 MHz, DMSO-$d_6$) δ 8.26 (s, 1H), 7.79-7.75 (m, 1H), 7.36-7.32 (m, 1H), 7.05-7.04 (m, 1H), 6.92-6.91 (m, 1H), 5.64 (s, 2H), 5.34- | 654.3 |

TABLE 2-continued

| Example | $^{1}H$ NMR and $^{19}F$ NMR data | Mass: $[M + H]^+$ |
|---|---|---|
| | 5.21 (m, 1H), 4.88-4.73 (m, 1H), 4.43-4.36 (m, 2H), 4.29-4.22 (m, 1H), 4.03-3.96 (m, 2H), 3.79-3.73 (m, 1H), 3.59-3.54 (m, 1H), 3.27-2.98 (m, 4H), 2.88-2.77 (m, 1H), 2.38-2.23 (m, 1H), 2.15-1.93 (m, 3H), 1.91-1.69 (m, 3H). $^{19}F$ NMR (376 MHz, DMSO-$d_6$) δ −113.07 (s, 1F), −123.47 (s, 1F), −172.07 (s, 1F), −207.86 (s, 1F) | |
| 360 | $^{1}H$ NMR (400 MHz, DMSO-$d_6$) δ 8.80 (s, 1H), 7.84-7.80 (m, 1H), 7.40-7.35 (m, 1H), 7.10-7.04 (m, 2H), 5.73 (s, 2H), 5.34-5.21 (m, 1H), 4.86-4.71 (m, 1H), 4.49-4.33 (m, 3H), 4.05-3.97 (m, 1H), 3.90 (s, 1H), 3.73-3.58 (m, 2H), 3.20-3.00 (m, 4H), 2.86-2.80 (m, 1H), 2.41-2.30 (m, 1H), 2.13-1.73 (m, 6H). $^{19}F$ NMR (376 MHz, DMSO-$d_6$) δ −112.69 (s, 1F), −124.94 (s, 1F), −172.21 (s, 1F), −208.21 (s, 1F) | 645.3 |
| 361 | $^{1}H$ NMR (400 MHz, DMSO-$d_6$) δ 8.29 (s, 1H), 7.79-7.75 (m, 1H), 7.36-7.31 (m, 1H), 7.05-7.04 (m, 1H), 6.95-6.94 (m, 1H), 5.65 (s, 2H), 5.34-5.20 (m, 1H), 4.87-4.72 (m, 1H), 4.43-4.24 (m, 3H), 3.99-3.96 (m, 1H), 3.82-3.71 (m, 2H), 3.63-3.49 (m, 1H), 3.22-2.96 (m, 4H), 2.89-2.76 (m, 1H), 2.36-2.22 (m, 1H), 2.17-1.94 (m, 3H), 1.92-1.72 (m, 3H). $^{19}F$ NMR (376 MHz, DMSO-$d_6$) δ −113.05-−113.65 (m, 1F), −123.08 (s, 1F), −172.18 (s, 1F), −207.46 (s, 1F) | 654.3 |
| 364 | $^{1}H$ NMR (400 MHz, Dimethylsulfoxide-$d_6$) δ 9.46-9.28 (m, 1H), 7.83-7.72 (m, 1H), 7.41-7.25 (m, 1H), 7.12-6.99 (m, 2H), 5.72-5.58 (m, 2H), 5.41-5.18 (m, 1H), 5.01 (d, J = 13.2 Hz, 2H), 4.95-4.72 (m, 1H), 4,50-4.29 (m, 3H), 4.20-4.11 (m, 2H), 4.06-3.77 (m, 2H), 3.75-3.57 (m, 2H), 3.43-3.38 (m, 1H), 3.28-3.18 (m, 1H), 3.16-3.01 (m, 3H), 2.87-2.77 (m, 1H), 2.59-2.55 (m, 1H), 2.38-2.22 (m, 2H), 2.20-2.07 (m, 1H). $^{19}F$ NMR (376 MHz, Dimethylsulfoxide-$d_6$) δ −113.36, −113.42, −139.83, −140.38, −168.58, −168.73, −207.74 | 631.1 |
| 365 | $^{1}H$ NMR (400 MHz, Methanol-$d_4$) δ 8.72 (s, 1H), 7.24-7.20 (m, 1H), 7.03-6.99 (m, 1H), 5.35-5.22 (m, 1H), 4.61-4.40 (m, 3H), 4.17-4.11 (m, 1H), 4.03-3.87 (m, 2H), 3.80-3.70 (m, 1H), 3.29-3.17 (m, 4H), 3.00-2.93 (m, 1H), 2.35-2.10 (m, 4H), 2.02-1.78 (m, 3H). $^{19}F$ NMR (376 MHz, Methanol-$d_4$) δ −59.90 (s, 3F), −118.97 (s, 1F), −124.29 (s, 1F), −173.72 (s, 1F), −209.48-−209.70 (m, 1F) | 695.0 |
| 366 | $^{1}H$ NMR (400 MHz, DMSO-$d_6$) δ 9.39-9.30 (m, 1H), 7.62-7.60 (m, 1H), 7.30-7.28 (m, 1H), 6.97-6.92 (m, 2H), 5.55-5.53 (m, 2H), 5.10-4.96 (m, 1H), 4.50-4.38 (m, 2H), 4.20-4.17 (m, 1H), 4.10-3.96 (m, 1H), 3.93-3.58 (m, 4H), 3.33-3.09 (m, 2H), 3.07-2.97 (m, 1H), 2.87-2.77 (m, 1H), 2.38-2.37 (m, 3H), 2.17-1.99 (m, 4H), 1.78-1.71 (m, 3H), 1.25-1.22 (m, 3H). $^{19}F$ NMR (376 MHz, DMSO-$d_6$) δ −140.30-−140.71 (d, 1F), −186.30-−186.34 (d, 1F) | 647.0 |
| 367 | $^{1}H$ NMR (400 MHz, DMSO-$d_6$) δ 9.40-9.36 (m, 1H), 6.89-6.88 (m, 1H), 6.48 (s, 1H), 6.34 (s, 2H), 4.89 (s, 2H), 4.75-4.45 (m, 1H), 4.40-4.37 (m, 1H), 4.07-3.95 (m, 3H), 3.56-3.53 (m, 1H), 3.33-3.27 (m, 1H), 3.20-3.17 (m, 1H), 3.00-2.96 (m, 1H), 2.64-2.52 (m, 2H), 2.37-2.33 (m, 1H), 2.26-2.17 (m, 1H), 2.02-1.76 (m, 8H), 1.56-1.41 (m, 1H), 1.15-1.05 (m, 1H). $^{19}F$ NMR (376MHz, DMSO-$d_6$): δ −53.06-−53.17 (m, 3F), −141.81 (s, 1F), −204.90 (s, 1F) | 621.2 |
| 368 | $^{1}H$ NMR (400 MHz, DMSO-$d_6$) δ 9.38-9.36 (m, 1H), 6.89- 6.88 (m, 1H), 6.49 (s, 1H), 6.35 (s, 2H), 4.89 (s, 2H), 4.78-4.45 (m, 1H), 4.40-4.37 (m, 1H), 4.10-3.93 (m, 3H), 3.56-3.52 (m, 1H), 3.32-3.26 (m, 1H), 3.20-3.17 (m, 1H), 3.01-2.96 (m, 1H), 2.64-2.53 (m, 2H), 2.37-2.30 (m, 1H), 2.29-2.15 (m, 1H), 2.00-1.64 (m, 8H), 1.54-1.40 (m, 1H), 1.19-1.05 (m, 1H). $^{19}F$ NMR (376 MHz, DMSO-$d_6$) δ −53.07-−53.16 (d, 1F), −141.76-−141.81 (d, 1F), −204.91 (s, 1F) | 621.2 |
| 369 | $^{1}H$ NMR (400 MHz, DMSO-$d_6$) δ 9.40-9.32 (m, 1H), 6.89-6.88 (m, 1H), 6.49 (s, 1H), 6.35 (s, 2H), 4.80-4.45 (m, 1H), 4.40-4.36 (m, 1H), 4.18-4.11 (m, 2H), 4.09-3.90 (m, 1H), 3.65-3.62 (m, 1H), 3.33-3.28 (m, 2H), 3.01-2.96 (m, 1H), 2.64-2.51 (m, 2H), 2.45-2.42 (m, 1H), 2.30-2.22 (m, 1H), 2.10-1.67 (m, 8H), 1.58-1.48 (m, 1H), 1.20-1.05 (m, 1H). $^{19}F$ NMR (376 MHz, DMSO-$d_6$) δ −53.09-−53.19 (m, 3F), −90.94-−91.50 (m, 2F), −141.69-−141.75 (d, 1F), −204.91 (s, 1F) | 657.2 |
| 370 | $^{1}H$ NMR (400 MHz, DMSO-$d_6$) δ 9.37-9.34 (m, 1H), 6.89 (s, 1H), 6.53-6.48 (m, 1H), 6.35 (s, 2H), 4.79-4.46 (m, 1H), 4.41-4.37 (m, 1H), 4.15 (s, 2H), 4.04-3.99 (m, 1H), 3.66-3.62 (m, 1H), 3.31-3.27 (m, 2H), 3.02-2.97 (m, 1H), 2.71-2.20 (m, 4H), 2.00-1.70 (m, 8H), 1.57-1.41 (m, 1H), 1.21-1.02 (m, 1H). $^{19}F$ NMR (376 MHz, DMSO-$d_6$) δ −53.09-−53.16 (d, 3F), −90.96-−91.60 (m, 2F), −141.71-−141.77 (d, 1F), −204.89 (s, 1F) | 657.2 |
| 371 | $^{1}H$ NMR (400 MHz, DMSO-$d_6$) δ 9.40-9.34 (m, 1H), 6.93-6.72 (m, 2H), 6.49 (s, 1H), 6.35 (s, 2H), 4.77-4.37 (m, 2H), 4.10-3.93 (m, 3H), 3.55-3.52 (m, 1H), 3.30-3.27 (m, 1H), 3.21-3.18 (m, 1H), 3.01-2.91 (m, 1H), 2.69-2.65 (m, 1H), 2.55-2.51 (m, 1H), 2.40-2.36 (m, 1H), 2.23-2.13 (m, 1H), 2.07-1.67 (m, 8H), 1.52-1.45 (m, 1H), 1.20-1.05 (m, 1H). $^{19}F$ NMR (376 MHz, DMSO-$d_6$) δ −53.06 (s, 3F), −132.42 (s, 1F), −141.74-−141.77 (d, 1F), −240.91 (s, 1F) | 639.2 |
| 372 | $^{1}H$ NMR (400 MHz, DMSO-$d_6$) δ 9.40-9.36 (m, 1H), 6.93-6.88 (m, 2H), 6.71 (s, 1H), 6.40-6.34 (m, 2H), 4.80-4.50 (m, 1H), 4.50-4.40 (m, 1H), 4.15-3.90 (m, 3H), 3.55-3.52 (m, 1H), 3.35-3.30 (m, 1H), 3.22-3.18 (m, 1H), 3.05-2.95 (m, 1H), 2.68-2.64 (m, 1H), 2.53-2.50 (m, 1H), 2.40-2.30 | 639.0 |

TABLE 2-continued

| Example | $^{1}H$ NMR and $^{19}F$ NMR data | Mass: $[M + H]^+$ |
|---|---|---|
| | (m, 1H), 2.30-2.20 (m, 1H), 2.05-1.65 (m, 8H), 1.55-1.40 (m, 1H), 1.20-1.10 (m, 1H). $^{19}F$ NMR (376 MHz, DMSO-$d_6$) δ −53.06-−53.16 (d, 3F), −132.54 (s, 1F), −141.71-−141.77 (d, 1F), −204.87 (s, 1F) | |
| 373 | $^{1}H$ NMR (400 MHz, DMSO-$d_6$) δ 9.37-9.34 (m, 1H), 6.89-6.65 (m, 2H), 6.49 (s, 1H), 6.35 (s, 2H), 4.75-4.37 (m, 2H), 4.09-3.96 (m, 3H), 3.71-3.67 (m, 1H), 3.31-3.27 (m, 2H), 3.01-2.97 (m, 1H), 2.58-2.52 (m, 2H), 2.34-2.22 (m, 2H), 2.06-1.67 (m, 8H), 1.59-1.40 (m, 1H), 1.20-1.03 (m, 1H). $^{19}F$ NMR (376 MHz, DMSO-$d_6$) δ −53.06-−53.17 (d, 3F), −130.98 (s, 1F), −141.76 (s, 1F), −204.90 (s, 1F) | 639.20 |
| 374 | $^{1}H$ NMR (400 MHz, DMSO-$d_6$) δ 9.40-9.35 (m, 1H), 6.88-6.84 (m, 1H), 6.63 (s, 1H), 6.48 (s, 1H), 6.35 (s, 2H), 4.72-4.46 (m, 1H), 4.40-4.37 (m, 1H), 4.13-3.90 (m, 3H), 3.71-3.68 (m, 1H), 3.32-3.23 (m, 2H), 3.02-2.97 (m, 1H), 2.65-2.52 (m, 2H), 2.42-2.13 (m, 2H), 2.06-1.65 (m, 8H), 1.55-1.42 (m, 1H), 1.20-1.04 (m, 1H). $^{19}F$ NMR (376 MHz, DMSO-$d_6$) δ −53.07-−53.15 (d, 1F), −131.02 (s, 1F), −141.72-−141.77 (d, 1F), −204.91 (s, 1F) | 639.2 |
| 375 | $^{1}H$ NMR (400 MHz, Dimethylsulfoxide-$d_6$) δ 9.47-9.34 (m, 1H), 8.30-8.14 (m, 2H), 7.74-7.54 (m, 3H), 6.81 (d, J = 86 Hz, 1H), 4.99-4.70 (m, 1H), 4.56-4.27 (m, 3H), 4.23-3.93 (m, 4H), 3.76-3.55 (m, 3H), 3.27-3.19 (m, 2H), 3.06-2.98 (m, 1H), 2.63-2.55 (m, 1H), 2.46-2.23 (m, 3H), 2.03-1.90 (m, 1H), 1.70-1.61 (m, 1H), 0.78 (d, J = 10.0 Hz, 1H), 0.60 (d, J = 9.6 Hz, 1H), 0.50-0.37 (m, 2H). $^{19}F$ NMR (376 MHz, Dimethylsulfoxide-$d_6$) δ −105.73, −105.84, −132.14, −139.85, −140.23, 207.98 | 642.1 |
| 378 | $^{1}H$ NMR (400 MHz, Dimethylsulfoxide-$d_6$) δ 9.34 (s, 1H), 6.94-6.68 (m, 2H), 6.55-6.45 (m, 1H), 6.40-6.20 (m, 2H), 4.76-4.45 (m, 1H), 4.43-4.33 (m, 1H), 4.23-3.93 (m, 3H), 3.67-3.56 (m, 1H), 3.42-3.34 (m, 1H), 3.30-3.22 (m, 1H), 3.09-2.97 (m, 1H), 2.65-2.57 (m, 1H), 2.49-2.44 (m, 1H), 2.34-2.20 (m, 2H), 2.03-1.91 (m, 2H), 1.88-1.79 (m, 2H), 1.72-1.63 (m, 2H), 1.55-1.42 (m, 1H), 1.19-1.05 (m, 1H), 0.83-0.76 (m, 1H), 0.64-0.57 (m, 1H), 0.54-0.44 (m, 2H). $^{19}F$ NMR (376 MHz, Dimethylsulfoxide-$d_6$) δ −53.07, −53.17, −55.38, −131.90, −132.09, −141.58, −141.64, −204.56, −204.64, −204.88 | 665.1, 657.1 |
| 379 | $^{1}H$ NMR (400 MHz, Dimethylsulfoxide-$d_6$) δ 9.33 (s, 1H), 6.69-6.52 (m, 1H), 6.02 (s, 2H), 4.93-4.82 (m, 2H), 4.76-4.45 (m, 1H), 4.43-4.31 (m, 1H), 4.21-4.12 (m, 1H), 4.10-3.92 (m, 2H), 3.66-3.55 (m, 1H), 3.30-3.24 (m, 2H), 3.08-2.99 (m, 1H), 2.65-2.58 (m, 1H), 2.42-2.37 (m, 1H), 2.36-2.32 (m, 3H), 2.29-2.19 (m, 2H), 2.02-1.93 (m, 2H), 1.89-1.79 (m, 2H), 1.72-1.65 (m, 2H), 1.54-1.43 (m, 1H), 1.17-1.09 (m, 1H), 0.80-0.75 (m, 1H), 0.63-0.57 (m, 1H), 0.49-0.41 (m, 2H). $^{19}F$ NMR (376 MHz, Dimethylsulfoxide-$d_6$) δ −52.26, −52.38, −135.66, −141.57, −204.85 | 645.2 |
| 380 | $^{1}H$ NMR (400 MHz, Dimethylsulfoxide-$d_6$) δ 9.33 (s, 1H), 6.93-6.68 (m, 1H), 6.65-6.52 (m, 1H), 6.02 (s, 2H), 4.82-4.45 (m, 1H), 4.43-4.32 (m, 1H), 4.22-4.07 (m, 2H), 4.05-3.94 (m, 1H), 3.64-3.55 (m, 1H), 3.38-3.33 (m, 1H), 3.30-3.26 (m, 1H), 3.05-2.97 (m, 1H), 2.63-2.55 (m, 1H), 2.47-2.44 (m, 1H), 2.36-2.31 (m, 3H), 2.31-2.19 (m, 2H), 2.02-1.92 (m, 2H), 1.88-1.79 (m, 2H), 1.71-1.62 (m, 2H), 1.55-1.41 (m, 1H), 1.18-1.04 (m, 1H), 0.82-0.75 (m, 1H), 0.63-0.55 (m, 1H), 0.53-0.43 (m, 2H). $^{19}F$ NMR (376 MHz, Dimethylsulfoxide-$d_6$) δ −52.26, −52.38, −132.16, −135.60, −135.66, −141.53, −204.87 | 663.2 |
| 381 | $^{1}H$ NMR (400 MHz, Dimethylsulfoxide-$d_6$) δ 9.33 (s, 1H), 6.87-6.53 (m, 2H), 6.02 (s, 2H), 4.78-4.45 (m, 1H), 4.45-4.32 (m, 1H), 4.19 (d, J = 11.2 Hz, 1H), 4.09 (d, J = 10.8 Hz, 1H), 4.04-3.93 (m, 1H), 3.74 (d, J = 15.6 Hz, 1H), 3.41-3.36 (m, 2H), 3.09-2.99 (m, 1H), 2.66-2.56 (m, 2H), 2.34 (s, 3H), 2.26-2.18 (m, 2H), 2.02-1.94 (m, 2H), 1.88-1.78 (m, 2H), 1.75-1.62 (m, 2H), 1.54-1.41 (m, 1H), 1.20-1.08 (m, 1H), 0.82-0.75 (m, 1H), 0.64-0.57 (m, 1H), 0.53-0.40 (m, 2H). $^{19}F$ NMR (376 MHz, Dimethylsulfoxide-$d_6$) δ −52.26, −52.39, −131.23, −135.59, −135.66, −136.28, −141.53, −204.90, −204.93 | 663.1 |
| 382 | $^{1}H$ NMR (400 MHz, Dimethylsulfoxide-$d_6$) δ 9.47-9.32 (m, 1H), 8.22-8.13 (m, 1H), 8.08-7.99 (m, 1H), 7.72-7.55 (m, 3H), 6.94-6.68 (m, 1H), 4.84-4.58 (m, 1H), 4.47-4.35 (m, 1H), 4.22-4.00 (m, 3H), 3.65-3.55 (m, 1H), 3.40-3.34 (m, 1H), 3.05-2.97 (m, 1H), 2.63-2.53 (m, 2H), 2.31-2.23 (m, 2H), 2.06-1.79 (m, 5H), 1.73-1.64 (m, 2H), 1.55-1.46 (m, 1H), 1.25-1.13 (m, 1H), 0.84-0.77 (m, 1H), 0.64-0.57 (m, 1H), 0.51-0.46 (m, 2H). $^{19}F$ NMR (376 MHz, Dimethylsulfoxide-$d_6$) δ −129.20, −129.50, −129.54, −132.10, −132.20, −140.33, −140.42, −150.99, −151.55, −205.57 | 666.2 |
| 383 | $^{1}HNMR$ (400 MHz, Dimethylsulfoxide-$d_6$) δ 9.44-9.29 (m, 1H), 7.62-7.49 (m, 1H), 7.43-7.30 (m, 1H), 7.10-6.97 (m, 2H), 6.95-6.66 (m, 1H), 5.70-5.57 (m, 2H), 4.81-4.57 (m, 1H), 4.47-4.36 (m, 1H), 4.25-3.95 (m, 3H), 3.68-3.56 (m, 1H), 3.31-3.23 (m, 2H), 3.09-2.96 (m, 1H), 2.65-2.57 (m, 1H), 2.34-2.22 (m, 2H), 2.04-1.64 (m, 7H), 1.57-1.44 (m, 1H), 1.21-1.11 (m, 1H), 0.87-0.73 (m, 1H), 0.67-0.57 (m, 1H), 0.53-0.46 (m, 2H). $^{19}F$ NMR (376 MHz, Dimethylsulfoxide-$d_6$) δ −132.08, −132.18, −136.85, 137.26, −140.21, −140.29, −150.57, −151.11, −151-14, −204.87, −205.49 | 681.1 |
| 384 | $^{1}H$ NMR (400 MHz, Dimethylsulfoxide-$d_6$) δ 9.53-9.33 (m, 1H), 8.18 (d, J = 8.0 Hz, 1H), 8.10-7.98 (m, 1H), 7.76-7.55 (m, 3H), 5.00-4.79 (m, 3H), 4.49 (d, J = 14.0 Hz, 1H), 4.41-4.25 (m, 2H), 4.21-4.10 (m, 1H), 4.06-3.94 (m, 2H), 3.76-3.65 (m, 1H), 3.60 (d, J = 14.0 Hz, 2H), 3.30-3.17 (m, 2H), | 650.2 |

TABLE 2-continued

| Example | $^1H$ NMR and $^{19}F$ NMR data | Mass: $[M + H]^+$ |
|---|---|---|
| | 3.08-2.98 (m, 1H), 2.66-2.58 (m, 1H), 2.41-2.22 (m, 3H), 2.03-1.91 (m, 1H), 1.73-1.62 (m, 1H), 0.81-0.74 (m, 1H), 0.65-0.56 (m, 1H), 0.51-0.42 (m, 2H). $^{19}F$ NMR (376 MHz, Dimethylsulfoxide-$d_6$) δ −129.07, −129.54, −137.09, −140.19, −150.99, −151.43, −207.52, −207.65, −207.77, −208.13, −208.25 | |
| 385 | $^1H$ NMR (400 MHz, Dimethylsulfoxide-$d_6$) δ 9.53-9.30 (m, 1H), 8.18 (d, J = 8.0 Hz, 1H), 8.09-7.99 (m, 1H), 7.76-7.55 (m, 3H), 6.80 (d, J = 85.6 Hz , 1H), 5.02-4.78 (m, 1H), 4.50 (d, J = 13.6 Hz, 1H), 4.42-4.25 (m, 2H), 4.21-3.95 (m, 3H), 3.79-3.53 (m, 3H), 3.31-3.15 (m, 3H), 3.06-2.96 (m, 1H), 2.63-2.55 (m, 1H), 2.41-2.23 (m, 2H), 2.04-1.90 (m, 1H), 1.72-1.61 (m, 1H), 0.79 (d, J = 10.4 Hz, 1H), 0.59 (d, J = 10.0 Hz, 1H), 0.52-0.40 (m, 2H). $^{19}F$ NMR (376 MHz, Dimethylsulfoxide-$d_6$) δ −129.08, −129.54, −132.13, −132.23, −140.16, −151.01, −151.48, −208.32 | 668.1 |
| 386 | $^1H$ NMR (400 MHz, Dimethylsulfoxide-$d_6$) δ 9.47-9.38 (m, 1H), 8.23-8.16 (m, 1H), 8.09-8.00 (m, 1H), 7.73-7.56 (m, 3H), 6.74 (d, J = 85.6 Hz, 1H), 5.01-4.81 (m, 1H), 4.54-4.46 (m, 1H), 4.40-4.27 (m, 2H), 4.20-4.15 (m, 1H), 4.09-4.04 (m, 1H), 4.02-3.95 (m, 1H), 3.76-3.68 (m, 2H), 3.63-3.59 (m, 1H), 3.22-3.17 (m, 1H), 3.06-3.01 (m, 1H), 2.67-2.62 (m, 2H), 2.41-2.31 (m, 2H), 2.26-2.20 (m, 1H), 2.06-1.89 (m, 1H), 1.77-1.61 (m, 1H), 0.82-0.76 (m, 1H), 0.64-0.57 (m, 1H), 0.52-0.44 (m, 2H). $^{19}F$ NMR (376 MHz, Dimethylsulfoxide-$d_6$) δ −129.07, −129.11, −129.49, −129.53, −131.22, −131.25, −140.17, −140.21, −150.98, −151.45, −208.26 | 668.3 |
| 387 | $^1H$ NMR (400 MHz, Dimethylsulfoxide-$d_6$) δ 9.49-9.30 (m, 1H), 7.64-7.48 (m, 1H), 7.42-7.30 (m, 1H), 7.10-6.94 (m, 2H), 5.64 (d, J = 8.0 Hz, 2H), 5.00-4.80 (m, 3H), 4.49 (d, J = 14.0 Hz, 1H), 4.42-4.26 (m, 2H), 4.22-4.11 (m, 1H), 4.08-3.93 (m, 2H), 3.74-3.54 (m, 3H), 3.23-3.16 (m, 1H), 3.09-2.99 (m, 1H), 2.69-2.62 (m, 1H), 2.42-2.18 (m, 4H), 2.03-1.95 (m, 1H), 1.74-1.64 (m, 1H), 0.81-0.74 (m, 1H), 0.64-0.56 (m, 1H), 0.47-0.35 (m, 2H). $^{19}F$ NMR (376 MHz, Dimethylsulfoxide-$d_6$) δ −136.83, −137.31, −140.16, −150.62, −151.01, −207.65, −208.19, −208.50 | 665.2 |
| 388 | $^1H$ NMR (400 MHz, Dimethylsulfoxide-$d_6$) δ 9.49-9.29 (m, 1H), 7.61-7.52 (m, 1H), 7.36 (t, J = 9.6 Hz, 1H), 7.10-6,99 (m, 2H), 6.94-6.65 (m, 1H), 5.75-5.55 (m, 2H), 4.89 (d, J = 60.8 Hz, 1H), 4.56-4.44 (m, 1H), 4.40-4.25 (m, 2H), 4.21-4.14 (m, 1H), 4.12-3.95 (m, 2H), 3.73-3.56 (m, 3H), 3.24-3.16 (m, 2H), 3.03-2.98 (m, 1H), 2.61-2.56 (m, 1H), 2.40-2.20 (m, 3H), 2.01-1.92 (m, 1H), 1.71-1.64 (m, 1H), 0.79 (d, J = 9.6 Hz, 1H), 0.59 (d, J = 9.2 Hz, 1H), 0.53-0.44 (m, 2H). $^{19}F$ NMR (376 MHz, Dimethylsulfoxide-$d_6$) δ −132.13, −132.24, −136.82, −136.87, −137.26, −137.30, −140.01, −140.13, −150.63, −151.05, −208.30 | 683.2 |
| 389 | $^1H$ NMR (400 MHz, Dimethylsulfoxide-$d_6$) δ 9.48-9.30 (m, 1H), 7.64-7.49 (m, 1H), 7.41-7.32 (m, 1H), 7.12-6.96 (m, 2H), 6.74 (d, J = 85.6 Hz, 1H), 5.72-5.58 (m, 2H), 4.90 (d, J = 59.6 Hz, 1H), 4.49 (d, J = 13.2 Hz, 1H), 4.40-4.27 (m, 2H), 4.18 (d, J = 11.0 Hz, 1H), 4.08-3.96 (m, 2H), 3.77-3.67 (m, 2H), 3.62-3.57 (m, 1H), 3.24-3.18 (m, 1H), 3.07-3.01 (m, 1H), 2.66-2.60 (m, 2H), 2.39-2.31 (m, 2H), 2.26-2.20 (m, 1H), 2.03-1.95 (m, 1H), 1.72-1.64 (m, 1H), 0.82-0.76 (m, 1H), 0.64-0.57 (m, 1H), 0.52-0.43 (m, 2H). $^{19}F$ NMR (376 MHz, Dimethylsulfoxide-$d_6$) δ −131.22, −131.25, −136.87, −137.26, −137.26, −137.31, −140.13, −140.02, −150.58, −150.64, −151.03, −208.29 | 683.2 |
| 390 | $^1H$ NMR (400 MHz, Methanol-$d_4$) δ 8.68 (s, 1H), 7.26-7.23 (m, 1H), 7.04-6.99 (m, 1H), 5.35-5.22 (m, 1H), 4.65-4.39 (m, 3H), 4.10-3.85 (m, 3H), 3.80-3.71 (m, 1H), 3.30-2.93 (m, 5H), 2.36-2.08 (m, 4H), 2.00-1.80 (m, 3H). $^{19}F$ NMR (376 MHz, Methanol-$d_4$) δ −59.79-−59.91 (d, 3F), −118.85-−119.00 (m, 1F), −125.00 (s, 1F), −173.65 (s, 1F), −208.21-−208.37 (m, 1F) | 695.4 |
| 391 | $^1H$ NMR (400 MHz, DMSO-$d_6$) δ 8.00-7.95 (m, 1H), 7.81-7.77 (m, 1H), 7.37-7.33 (m, 1H), 7.04-7.03 (m, 2H), 5.67 (s, 2H), 5.34-5.21 (m, 1H), 4.83-4.68 (m, 1H), 4.41-4.23 (m, 3H), 3.99-3.96 (m, 1H), 3.86 (m, 1H), 3.82-3.74 (m, 1H), 3.62-3.50 (m, 1H), 3.23-3.01 (m, 4H), 2.88-2.78 (m, 1H), 2.34-2.19 (m, 1H), 2.16-1.93 (m, 3H), 1.89-1.70 (m, 3H). $^{19}F$ NMR (376 MHz, DMSO-$d_6$) δ −112.85 (s, 1F), −119.61-−119.62 (d, 1F), −124.95-−124.96 (d, 1F), −172.17 (d, 1F), −207.17-−207.26 (d, 1F) | 638.3 |
| 392 | $^1H$ NMR (400 MHz, DMSO-$d_6$) δ 9.35 (s, 1H), 6.60 (s, 1H), 6.04 (s, 2H), 4.90 (s, 2H), 4.72-4.37 (m, 2H), 4.07-3.93 (m, 3H), 3.56-3.53 (m, 1H), 3.31-3.26 (m, 1H), 3.20-3.17 (m, 1H), 3.01-2.96 (m, 1H), 2.67-2.53 (m, 2H), 2.37-2.21 (m, 5H), 2.05-1.66 (m, 8H), 1.57-1.40 (m, 1H), 1.19-1.00 (m, 1H). $^{19}F$ NMR (376 MHz, DMSO-$d_6$) δ −52.25-−52.38 (d, 3F), −135.60 (s, 1F), −141.69 (s, 1F), −204.87 (s, 1F) | 619.3 |
| 393 | $^1H$ NMR (400 MHz, DMSO-$d_6$) δ 9.32 (s, 1H), 6.60-6.58 (m, 1H), 6.04 (s, 2H), 4.89 (s, 2H), 4.79-4.45 (m, 1H), 4.44-4.38 (m, 1H), 4.07-3.99 (m, 3H), 3.56-3.52 (m, 1H), 3.33-3.26 (m, 1H), 3.20-3.16 (m, 1H), 3.06-2.96 (m, 1H), 2.59-2.51 (m, 2H), 2.41-2.30 (m, 4H), 2.28-2.18 (m, 1H), 2.07-1.62 (m, 8H), 1.58-1.41 (m, 1H), 1.20-1.03 (m, 1H). $^{19}F$ NMR (376 MHz, DMSO-$d_6$) δ −52.26-−52.37 (d, 3F), −135.60-−135.66 (m, 1F), −141.68-−142.45 (m, 1F), −204.87 (s, 1F) | 619.1 |
| 394 | $^1H$ NMR (400 MHz, DMSO-$d_6$) δ 9.35 (s, 1H), 6.60-6.58 (m, 1H), 6.04 (s, 2H), 4.78-4.37 (m, 2H), 4.18-3.90 (m, 3H), 3.65-3.62 (m, 1H), 3.33-3.28 (m, 2H), 3.01-2.97 (m, 1H), 2.64-2.54 (m, 2H), 2.40-2.20 (m, 5H), 2.05- | 655.3 |

TABLE 2-continued

| Example | $^{1}$H NMR and $^{19}$F NMR data | Mass: [M + H]$^{+}$ |
|---|---|---|
| | 1.70 (m, 8H), 1.60-1.45 (m, 1H), 1.20-1.05 (m, 1H). $^{19}$F NMR (376 MHz, DMSO-$d_6$) δ −52.28-−52.78 (m, 3F), −90.94-−91.50 (m, 2F), −135.58-−135.65 (m, 1F), −141.62-−142.39 (m, 1F), −204.87 (s, 1F) | |
| 395 | $^{1}$H NMR (400 MHz, DMSO-$d_6$) δ 9.36-9.31 (m, 1H), 6.60-6.58 (m, 1H), 6.04 (s, 2H), 4.79-4.42 (m, 1H), 4.42-4.34 (m, 1H), 4.14 (s, 2H), 4.08-3.93 (m, 1H), 3.66-3.62 (m, 1H), 3.31-3.26 (m, 2H), 3.01-2.97 (m, 1H), 2.67-2.54 (m, 2H), 2.42-2.19 (m, 5H), 2.01-1.60 (m, 8H), 1.58-1.40 (m, 1H), 1.21-1.03 (m, 1H). $^{19}$F NMR (376 MHz, DMSO-$d_6$) δ −52.283 (s, 3F), −90.96-−91.61 (m, 2F), −135.58-−136.25 (m, 1F), −140.41-−142.40 (m, 1F), −204.82 (s, 1F) | 655.4 |
| 396 | $^{1}$H NMR (400 MHz, DMSO-$d_6$) δ 9.35 (s, 1H), 6.92-6.72 (m, 1H), 6.60-6.58 (m, 1H), 6.04 (s, 2H), 4.81-4.37 (m, 2H), 4.11-3.96 (m, 3H), 3.57-3.54 (m, 1H), 3.31-3.27 (m, 1H), 3.24-3.20 (m, 1H) 3.02-2.95 (m, 1H), 2.70-2.66 (m, 1H), 2.58-2.53 (m, 1H), 2.44-2.31 (m, 4H), 2.30-2.17 (m, 1H), 2.01-1.67 (m, 8H), 1.55-1.45 (m, 1H), 1.20-1.05 (m, 1H). $^{19}$F NMR (376 MHz, $CDCl_3$) δ −52.25-−52.39 (d, 3F), −132.36 (s, 1F), −135.65 (s, 1F), −141.63 (s, 1F), −240.85 (s, 1F) | 637.3 |
| 397 | $^{1}$H NMR (400 MHz, DMSO-$d_6$) δ 9.34 (s, 1H), 6.93-6.71 (m, 1H), 6.60 (s, 1H), 6.04 (s, 2H), 4.78-4.37 (m, 2H), 4.13-3.93 (m, 3H), 3.55-3.51(m, 1H), 3.31-3.26 (m, 1H), 3.21-3.18 (m, 1H), 3.01-2.92 (m, 1H), 2.68-2.64 (m, 1H), 2.40-2.21 (m, 6H), 2.01-1.66 (m, 8H), 1.55-1.40 (m, 1H), 1.20-1.05 (m, 1H). $^{19}$F NMR (376 MHz, DMSO-$d_6$) δ −52.25 (s, 3F), −132.56 (s, 1F), −136.27 (s, 1F), −141.64 (s, 1F), −240.87 (s, 1F) | 637.2 |
| 398 | $^{1}$H NMR (400 MHz, DMSO-$d_6$) δ 9.35 (s, 1H), 6.86-6.59 (m, 2H), 6.04 (s, 2H), 4.73-4.37 (m, 2H), 4.11-3.92 (m, 3H), 3.71-3.64 (m, 1H), 3.32-3.20 (m, 2H), 3.04-2.97 (m, 1H), 2.63-2.52 (m, 2H), 2.40-2.20 (m, 5H), 2.08-1.60 (m, 8H), 1.57-1.42 (m, 1H), 1.15-1.05 (m, 1H). $^{19}$F NMR (376 MHz, DMSO-$d_6$) δ −52.25-−52.38 (d, 3F), −130.98 (s, 1F), −135.58-−135.64 (d, 1F), −141.64 (s, 1F), −204.85 (s, 1F) | 637.4 |
| 399 | $^{1}$H NMR (400 MHz, DMSO-$d_6$) δ 9.40-9.30 (m, 1H), 6.84-6.59 (m, 2H), 6.04 (s, 2H), 4.76-4.36 (m, 2H), 4.09-4.00 (m, 3H), 3.71-3.68 (m, 1H), 3.33-3.26 (m, 2H), 3.02-2.97 (m, 1H), 2.60-2.50 (m, 2H), 2.40-2.18 (m, 5H), 2.00-1.60 (m, 8H), 1.66-1.48 (m, 1H), 1.20-1.05 (m, 1H). $^{19}$F NMR (376 MHz, DMSO-$d_6$) δ −52.26-−52.36 (m, 3F), −131.03 (s, 1F), −135.59-−135.65 (m, 1F), −141.64-−142.41 (m, 1F), −204.87 (s, 1F) | 637.3 |
| 400 | $^{1}$H NMR (400 MHz, DMSO-$d_6$) δ 7.80-7.93 (m, 1H), 7.81-7.77 (m, 1H), 7.38-7.34 (m, 1H), 7.07-7.00 (m, 2H), 5.66 (s, 2H), 5.34-5.21 (m, 1H), 4.87-4.71 (m, 1H), 4.41-4.37 (m, 2H), 4.28-4.22 (m, 1H), 4.04-3.99 (m, 2H), 3.82-3.76 (m, 1H), 3.59-3.56 (m, 1H), 3.30-3.00 (m, 4H), 2.88-2.78 (m, 1H), 2.35-2.22 (m, 1H), 2.13-1.95 (m, 3H), 1.92-1.70 (m, 3H). $^{19}$F NMR (376 MHz, DMSO-$d_6$) δ −112.83 (s, 1F), −119.68-−119.70 (d, 1F), −125.53-−125.54 (d, 1F), −172.05 (s, 1F), −207.65 (s, 1F) | 638.2 |
| 401 | $^{1}$H NMR (400 MHz, Dimethylsulfoxide-$d_6$) δ 11.44-11.28 (m, 1H), 7.82-7.73 (m, 1H), 7.36 (t, J = 8.8 Hz, 1H), 7.16-6.99 (m, 2H), 5.76-5.60 (m, 2H), 5.35-5.20 (m, 1H), 4.63-4.54 (m, 1H), 4.43-4.36 (m, 2H), 4.24-4.21 (m, 1H), 3.95-3.90 (m, 2H), 3.83-3.77 (m, 2H), 3.50-3.49 (m, 1H), 3.09-3.06 (m, 2H), 3.00-2.98 (m, 1H), 2.84-2.81 (m, 1H), 2.15-2.10 (m, 2H), 2.04-1.94 (m, 2H), 1.87-1.70 (m, 3H). $^{19}$F NMR (376 MHz, Dimethylsulfoxide-$d_6$) δ −112.87, −162.70, −162.82, −172.08, −172.17, −205.50, −205.52 | 637.2 |
| 402 | $^{1}$H NMR (400 MHz, Dimethylsulfoxide-$d_6$) δ 9.44-9.29 (m, 1H), 8.28-8.16 (m, 2H), 7.75-7.57 (m, 3H), 6.90-6.59 (m, 1H), 4.77-4.50 (m, 1H), 4.41 (d, J = 12.8 Hz, 1H), 4.27-3.93 (m, 4H), 3.74 (d, J = 14.8 Hz, 1H), 3.43-3.37 (m, 2H), 3.09-2.99 (m, 1H), 2.67-2.60 (m, 1H), 2.40-2.21 (m, 3H), 2.05-1.81 (m, 4H), 1.77-1.63 (m, 2H), 1.58-1.43 (m, 1H), 1.29-1.12 (m, 1H), 0.83-0.75 (m, 1H), 0.64-0.56 (m, 1H), 0.53-0.42 (m, 2H). $^{19}$F NMR (376 MHz, Dimethylsulfoxide-$d_6$) δ −105.78, −131.20, −140.09, −140.41, −204.61, −204.97 | 640.1 |
| 403 | $^{1}$HNMR (400 MHz, Dimethylsulfoxide-$d_6$) δ 9.40-9.30 (m, 1H), 7.77 (dd, J = 6.0, 9.2 Hz, 1H), 7.39-7.26 (m, 1H), 7.09-7.00 (m, 2H), 6.95-6.68 (m, 1H), 5.70-5.58 (m, 2H), 4.80-4.48 (m, 1H), 4.39-4.47 (m, 1H), 4.20-3.74 (m, 4H), 3.64-3.57 (m, 1H), 3.45-3.35 (m, 1H), 3.30-3.26 (m, 1H), 3.05-2.95 (m, 1H), 2.65-2.55 (m, 1H), 2.47-2.42 (m, 1H), 2.35-2.20 (m, 2H), 2.02-1.83 (m, 4H), 1.77-1.64 (m, 2H), 1.57-1.46 (m, 1H), 1.26-1.12 (m, 1H), 0.84-0.75 (m, 1H), 0.66-0.55 (m, 1H), 0.53-0.44 (m, 2H). $^{19}$F NMR (376 MHz, Dimethylsulfoxide-$d_6$) δ −113.41, −113.44, −132.09, −132.17, −140.06, −140.53, −204.95 | 655.1 |
| 404 | $^{1}$H NMR (400 MHz, Dimethylsulfoxide-$d_6$) δ 9.42-9.26 (m, 1H), 7.81-7.74 (m, 1H), 7.34 (t, J = 9.2 Hz, 1H), 7.10-6.99 (m, 2H), 6.88-6.61 (m, 1H), 5.70-5.58 (m, 2H), 4.84-4.48 (m, 1H), 4.47-4.32 (m, 1H), 4.24-3.97 (m, 4H), 3.80-3.70 (m, 1H), 3.38 (d, J = 15.2 Hz, 1H), 3.08-3.00 (m, 1H), 2.67-2.62 (m, 1H), 2.43-2.31 (m, 2H), 2.29-2.20 (m, 2H), 2.02-1.94 (m, 2H), 1.91-1.83 (m, 2H), 1.75-1.65 (m, 2H), 1.58-1.47 (m, 1H), 1.27-1.12 (m, 1H), 0.83-0.77 (m, 1H), 0.64-0.58 (m, 1H), 0.52-0.41 (m, 2H). $^{19}$F NMR (376 MHz, Dimethylsulfoxide-$d_6$) δ −113.41, −113.46, −131.21, −140.09, −140.54, −204.96 | 655.1 |

TABLE 2-continued

| Example | $^1$H NMR and $^{19}$F NMR data | Mass: $[M + H]^+$ |
|---|---|---|
| 405 | $^1$H NMR (400 MHz, Dimethylsulfoxide-$d_6$) δ 9.43-9.30 (m, 1H), 8.27-8.16 (m, 2H), 7.76-7.55 (m, 3H), 4.77-4.51 (m, 1H), 4.45-4.36 (m, 1H), 4.27-4.18 (m, 1H), 4.17-3.90 (m, 3H), 3.74-3.66 (m, 1H), 3.49-3.44 (m, 2H), 3.06-2.98 (m, 1H), 2.64-2.61 (m, 1H), 2.46-2.42 (m, 1H), 2.33-2.22 (m, 2H), 2.04-1.84 (m, 4H), 1.77-1.66 (m, 2H), 1.57-1.46 (m, 1H), 1.26-1.13 (m, 1H), 0.86-0.78 (m, 1H), 0.65-0.46 (m, 3H). $^{19}$F NMR (376 MHz, Dimethylsulfoxide-$d_6$) δ −91.11, −91.13, −105.79, −105.87, −140.06, −140.40, −204.99 | 658.3 |
| 406 | $^1$H NMR (400 MHz, Dimethylsulfoxide-$d_6$) δ 9.35 (s, 1H), 6.88 (d, J = 2.0 Hz, 1H), 6.85-6.62 (m, 1H), 6.54-6.46 (m, 1H), 6.34 (s, 2H), 4.75-4.46 (m, 1H), 4.38 (d, J = 13.6 Hz, 1H), 4.23-4.16 (m, 1H), 4.13-4.06 (m, 1H), 4.05-3.93 (m, 1H), 3.73 (d, J = 15.2 Hz, 1H), 3.35-3.40 (m, 1H), 3.33-3.28 (m, 1H), 3.06-3.00 (m, 1H), 2.66-2.59 (m, 1H), 2.41-2.34 (m, 1H), 2.23 (d, ,J = 15.2 Hz, 2H), 2.03-1.93 (m, 2H), 1.78-187 (m, 2H), 1.72-1.64 (m, 2H), 1.54-1.43 (m, 1H), 1.10-1.12 (m, 1H), 0.83-0.75 (m, 1H), 0.63-0.56 (m, 1H), 0.51-0.43 (m, 2H). $^{19}$F NMR (376 MHz, Dimethylsulfoxide-$d_6$) δ −53.08, −131.22, −141.65, −204.89 | 665.0 |
| 407 | $^1$H NMR (400 MHz, Dimethylsulfoxide-$d_6$) δ 9.44-9.32 (m, 1H), 8.22-8.13 (m, 1H), 8.07-7.98 (m, 1H), 7.72-7.54 (m, 3H), 4.97-4.84 (m, 2H), 4.80-4.57 (m, 1H), 4.47-4.36 (m, 1H), 4.26-3.95 (m, 3H), 3.70-3.34 (m, 2H), 3.14-2.99 (m, 1H), 2.70-2.59 (m, 1H), 2.42-2.37 (m, 1H), 2.30-2.21 (m, 2H), 2.04-1.81 (m, 5H), 1.74-1.64 (m, 2H), 1.54-1.46 (m, 1H), 1.19-1.10 (m, 1H), 0.76-0.82 (m, 1H), 0.65-0.57 (m, 1H), 0.53-0.42 (m, 2H). $^{19}$F NMR (376 MHz, Dimethylsulfoxide-$d_6$) δ −129.10, −129.50, −140.34, −150.93, −151.51, −205.51 | 648.2 |
| 408 | $^1$H NMR (400 MHz, Dimethylsulfoxide-$d_6$) δ 9.48-9.29 (m, 1H), 8.29-7.96 (m, 2H), 7.81-7.52 (m, 3H), 6.88-6.50 (m, 1H), 4.82-4.58 (m, 1H), 4.42 (d, J = 13.6 Hz, 1H), 4.23-3.93 (m, 3H), 3.74 (d, J = 14.8 Hz, 1H), 3.42-3.33 (m, 2H), 3.10-2.96 (m, 1H), 2.72-2.58 (m, 1H), 2.43- 2.33 (m, 1H), 2.30-2.20 (m, 2H), 2.05-1.93 (m, 2H), 1.91-1.81 (m, 2H), 1.74-1.63 (m, 2H), 1.57-1.43 (m, 1H), 1.24-1.10 (m, 1H), 0.83-0.76 (m, 1H), 0.64-0.57 (m, 1H), 0.53-0.41 (m, 2H). $^{19}$F NMR (376 MHz, Dimethylsulfoxide-$d_6$) δ −129.09.-129.50, −129.53, −131.19, −131.24, −140.33, −140.43, −150.95, −151.55, −205.52 | 666.2 |
| 409 | $^1$H NMR (400 MHz, Dimethylsulfoxide-$d_6$) δ 9.48-9.30 (m, 1H), 7.62-7.48 (m, 1H), 7.44-7.28 (m, 1H), 7.12-6.99 (m, 2H), 6.89-6.51 (m, 1H), 5.64 (d, J = 10 Hz, 2H), 4.83-4.58 (m, 1H), 4.48-4.34 (m, 1H), 4.24-4.16 (m, 1H), 4.12-3,97 (m, 2H), 3.80-3.68 (m, 1H), 3.42-3.36 (m, 2H), 3.09-2.99 (m, 1H), 2.69-2.59 (m, 1H), 2.46-2.35 (m, 1H), 2.30-2.17 (m, 2H), 2.05-1.93 (m, 2H), 1.90-1.81 (m, 2H), 1.76-1.64 (m, 2H), 1.60-1.42 (m, 1H), 1.21-1.03 (m, 1H), 0.87-0.77 (m, 1H), 0.64-0.57 (m, 1H), 0.54-0.39 (m, 2H). $^{19}$F NMR (376 MHz, Dimethylsulfoxide-$d_6$) δ −131.19, −136.81, −136.85, −137.30, −140.31, −150.56, −151.11, −204.64, −205.44 | 681.2 |
| 410 | $^1$H NMR (400 MHz, DMSO-$d_6$) δ 9.45-9.35 (m, 1H), 7.62-7.60 (m, 1H), 7.30-7.28 (m, 1H), 6.97-6.95 (m, 2H), 5.54-5.53 (m, 2H), 5.10-4.75 (m, 2H), 4.61-4.51 (m, 1H), 4.48-4.31 (m, 2H), 4.05-3.59 (m, 4H), 3.32-3.10 (m, 2H), 3.05-2.98 (m, 1H), 2.86-2.81 (m, 1H), 2.49-2.30 (m, 4H), 2.15-2.03 (m, 3H), 1.82-1.70 (m, 3H), 1.25-1.23 (m, 3H). $^{19}$F NMR (376 MHz, DMSO-$d_6$) δ −139.92--140.50 (d, 1F), −186.34--186.38 (d, 1F), −207.65 (s, 1F) | 631.1 |
| 411 | $^1$H NMR (400 MHz, Dimethylsulfoxide-$d_6$) δ 9.39-9.29 (m, 1H), 6.88 (d, J = 1.6 Hz, 1H), 6.52-6.44 (m, 1H), 6.41-6.29 (m, 2H), 4.74-4.47 (m, 1H), 4.42-4.33 (m, 1H), 4.22-4.10 (m, 2H), 4.05-3.95 (m, 1H), 3.72-3.65 (m, 1H), 3.40-3.37 (m, 2H), 3.07-2.97 (m, 1H), 2.68-2.59 (m, 2H), 2.44-2.32 (m, 1H), 2.30-2.21 (m, 1H), 2.02-1.92 (m, 2H), 1.88-1.78 (m, 2H), 1.75-1.63 (m, 2H), 1.54-1.42 (m, 1H), 1.20-1.05 (m, 1H), 0.84-0.77 (m, 1H), 0.64-0.45 (m, 3H). $^{19}$F NMR (376 MHz, Dimethylsulfoxide-$d_6$) δ −53.09, −53.18, −91.13, −141.59, −141.67, −205.01 | 683.0 |
| 412 | $^1$H NMR (400 MHz, Dimethylsulfoxide-$d_6$) δ 9.33 (s, 1H), 6.58 (d, J = 9.2 Hz, 1H), 6.02 (s, 2H), 4.78-4.45 (m, 1H), 4.38 (d, J = 13.6 Hz, 1H), 4.25-4.10 (m, 2H), 4.06-3.92 (m, 1H), 3.75-3.64 (m, 1H), 3.43-3.34 (m, 2H), 3.09-2.97 (m, 1H), 2.66-2.60 (m, 1H), 2.59-2.55 (m, 1H), 2.45-2.41 (m, 1H), 2.34 (s, 3H), 2.26-2.17 (m , 1H), 2.03-1.92 (m, 2H), 1.88-1.78 (m, 2H), 1.76-1.64 (m, 2H), 1.54-1.39 (m, 1H), 1.19-1.06 (m, 1H), 0.86-0.78 (m, 1H), 0.63-0.45 (m, 3H). $^{19}$F NMR (376 MHz, Dimethylsulfoxide-$d_6$) δ −52.28, −52.39, −91.13, −135.64, −141.52, −204.79, −204.86 | 681.1 |
| 413 | $^1$H NMR (400 MHz, Dimethylsulfoxide-$d_6$) δ 9.47-9.31 (m, 1H), 8.24-8.14 (m, 1H), 8.11-7.99 (m, 1H), 7.74-7.51 (m, 3H), 4.84-4.57 (m, 1H), 4.41 (d, J = 12.4 Hz, 1H), 4.29-3.93 (m, 3H), 3.78-3.66 (m, 1H), 3.41-3.39 (m, 2H), 3.06-3.01 (m, 1H), 2.68-2.60 (m, 1H), 2.46-2.42 (m, 1H), 2.37-2.19 (m, 2H), 2.01-1.92 (m, 2H), 1.90-1.82 (m, 2H), 1.74-1.66 (m, 2H), 1.55-1.45 (m, 1H), 1.20-1.07 (m, 1H), 0.85-0.77 (m, 1H), 0.62-0.43 (m, 3H). $^{19}$F NMR (376 MHz, Dimethylsulfoxide-$d_6$) δ −91.12, −91.29, −129.10, −129.50, −129.54, −140.33, −140.41, −150.94, −151.54, −205.49 | 684.1 |
| 414 | $^1$H NMR (400 MHz, Dimethylsulfoxide-$d_6$) δ 9.45-9.35 (m, 1H), 7.80-7.75 (m, 1H), 7.37-7.30 (m, 1H), 7.07-7.03 (m, 2H), 5.68-5.60 (m, 2H), 5.34-5.15 (m, 1H), 4.95-4.69 (m, 1H), 4.51-4.44 (m, 1H), 4.38-4.23 (m, 4H), | 633.0 |

TABLE 2-continued

| Example | $^{1}H$ NMR and $^{19}F$ NMR data | Mass: $[M + H]^+$ |
|---|---|---|
| | 4.06-3.76 (m, 2H), 3.74-3.56 (m, 2H), 3.52-3.39 (m, 2H), 3.24-3.07 (m, 3H), 2.60-2.54 (m, 2H), 2.44-2.35 (m, 1H), 2.18-2.14 (m, 1H), 2.12-2.05 (m, 1H). $^{19}F$ NMR (376 MHz, Dimethylsulfoxide-$d_6$) δ −113.33, −113.42, −139.64, −140.25, −169.10.-169.25, −207.80 | |
| 415 | $^{1}H$ NMR (400 MHz, DMSO-$d_6$) δ 8.75 (s, 1H), 8.10-8.04 (m, 2H), 7.67-7.45 (m, 4H), 7.37-7.28 (m, 1H), 5.34-5.20 (m, 1H), 5.01-4.76 (m, 1H), 4.51-4.48 (m, 1H), 4.39-4.29 (m, 2H), 4.05-3.95 (m, 1H), 3.80-3.60 (m, 2H), 3.24-2.99 (m, 4H), 2.86-2.80 (m, 1H), 2.44-2.25 (m, 1H), 2.20-1.70 (m, 6H). $^{19}F$ NMR (376 MHz, DMSO-$d_6$) δ −56.80-−56.96 (m, 3F), −123.43-−123.76 (d, 1F), −172.16-−172.18 (d, 1F), −208.05 (s, 1F) | 631.2 |
| 418 | $^{1}H$ NMR (400 MHz, DMSO-$d_6$) δ 8.49 (s, 1H), 8.05 (s, 2H), 7.34-7.30 (m, 1H), 7.17-7.12 (m, 1H), 5.34-5.20 (m, 1H), 4.44-4.33 (m, 2H), 4.19-4.17 (m, 1H), 3.99-3.96 (m, 1H), 3.86-3.81 (m, 1H), 3.67-3.64 (m, 1H), 3.14-2.96 (m, 5H), 2.86-2.77 (m, 1H), 2.18-1.98 (m, 4H), 1.90-1.73 (m, 3H). $^{19}F$ NMR (376 MHz, DMSO-$d_6$) δ −56.94 (s, 3F), −116.67 (s, 1F), −124.55 (s, 1F), −172.10 (s, 1F) | 711.1, 713.1 |
| 419 | $^{1}H$ NMR (400 MHz, DMSO-$d_6$) δ 8.49 (s, 1H), 8.05 (s, 2H), 7.33-7.30 (m, 1H), 7.17-7.12 (m, 1H), 5.37-5.23 (m, 1H), 4.45-4.34 (m, 2H), 4.19-4.17 (m, 1H), 3.99-3.96 (m, 1H), 3.87-3.81 (m, 1H), 3.68-3.62 (m, 1H), 3.24-2.80 (m, 6H), 2.20-2.00 (m, 4H), 1.95-1.74 (m, 3H). $^{19}F$ NMR (376 MHz, DMSO-$d_6$) δ −56.95 (s, 3F), −116.67 (s, 1F), −124.50 (s, 1F), −172.24 (s, 1F) | 711.1, 713.1 |
| 420 | $^{1}H$ NMR (400 MHz, DMSO-$d_6$) δ 8.55 (s, 1H), 8.08 (s, 2H), 7.23-7.10 (m, 2H), 5.34-5.20 (m, 1H), 4.42-4.35 (m, 2H), 4.23-4.21 (m, 1H), 4.03-4.00 (m, 1H), 3.84-3.78 (m, 1H), 3.65-3.51 (m, 2H), 3.20-2.95 (m, 4H), 2.84-2.79 (m, 1H), 2.20-1.94 (m, 4H), 1.91-1.72 (m, 3H). $^{19}F$ NMR (376 MHz, DMSO-$d_6$) δ −56.80 (s, 3F), −116.59 (s, 1F), −123.92 (s, 1F), −172.17 (s, 1F) | 711.1, 713.1 |
| 421 | $^{1}H$ NMR (400 MHz, DMSO-$d_6$) δ 8.55 (s, 1H), 8.07 (s, 2H), 7.23-7.20 (m, 1H), 7.15-7.10 (m, 1H), 5.37-5.24 (m, 1H), 4.43-4.36 (m, 2H), 4.24-4.22 (m, 1H), 4.02-3.99 (m, 1H), 3.88-3.79 (m, 1H), 3.66-3.53 (m, 2H), 3.25-3.02 (m, 4H), 2.90-2.82 (m, 1H), 2.20-1.95 (m, 4H), 1.94-1.72 (m, 3H). $^{19}F$ NMR (376 MHz, DMSO-$d_6$) δ −52.82-−56.86 (d, 3F), −116.59 (s, 1F), −123.89 (s, 1F), −172.13 (s, 1F) | 711.1, 713.1 |
| 422 | $^{1}H$ NMR (400 MHz, Methanol-$d_4$) δ 8.81-8.58 (m 1H), 7.77-7.73 (m, 1H), 7.26-6.95 (m, 3H), 5.40-5.10 (m, 1H), 4.60-4.35 (m, 3H), 4.20-4.10 (m, 1H), 4.00-3.90 (m, 2H), 3.75-2.80 (m, 7H), 2.40-1.81 (m, 9H). $^{19}F$ NMR (376 MHz, $CD_3OD$) δ −113.14-−113.22 (m, 1F), −173.78-−173.85 (m, 1F), −209.75 (s, 1F) | 641.1 |
| 423 | $^{1}H$ NMR (400 MHz, Dimethylsulfoxide-$d_6$) δ 9.46-9.30 (m, 1H), 8.30-8.14 (m, 2H), 7.75-7.54 (m, 3H), 4.97-4.80 (m, 2H), 4.75-4.49 (m, 1H), 4.42 (d, J = 13.2 Hz, 1H), 4.30-3.91 (m, 4H), 3.67-3.57 (m, 1H), 3.47-3.40 (m, 2H), 3.10-2.98 (m, 1H), 2.65-2.60 (m, 1H), 2.43-2.37 (m, 1H), 2.32-2.22 (m, 2H), 2.05-1.82 (m, 4H), 1.79-1.62 (m, 2H), 1.60-1.44 (m, 1H), 1.26-1.22 (m, 1H), 0.84-0.75 (m, 1H), 0.67-0.59 (m, 1H), 0.51-0.44 (m, 2H). $^{19}F$ NMR (376 MHz, Dimethylsulfoxide-$d_6$) δ −105.80, −140.46, 205.03 | 622.1 |
| 424 | $^{1}H$ NMR (400 MHz, Dimethylsulfoxide-$d_6$) δ 9.40-9.26 (m, 1H), 6.88 (d, J = 1.6 Hz, 1H), 6.52-6.45 (m, 1H), 6.35 (s, 2H), 4.89 (d, J = 4.4 Hz, 2H), 4.75-4.47 (m, 1H), 4.38 (d, J = 13.2 Hz, 1H), 4.20-4.14 (m, 1H), 4.10-3.97 (m, 2H), 3.61 (d, J = 14.8 Hz, 1H), 3.32-3.24 (m, 2H), 3.08-3.01 (m, 1H), 2.67-2.59 (m, 1H), 2.44-2.36 (m, 1H), 2.30-2.19 (m, 2H), 2.03-1.93 (m, 2H), 1.87-1.78 (m, 2H), 1.73-1.64 (m, 2H), 1.54-1.43 (m, 1H), 1.19-1.05 (m, 1H), 0.77 (d, J = 9.6 Hz, 1H), 0.60 (d, J = 9.6 Hz, 1H), 0.50-0.43 (m, 2H). $^{19}F$ NMR(376 MHz, Dimethylsulfoxide-$d_6$) δ −53.07, −53.17, −141.71, −204.89 | 647.2 |
| 425 | $^{1}H$ NMR (400 MHz, Dimethylsulfoxide-$d_6$) δ 9.51-9.33 (m, 1H), 7.84-7.69 (m, 1H), 7.30 (t, J = 9.2 Hz, 1H), 7.04-6.84 (m, 2H), 5.57 (s, 2H), 4.90 (s, 2H), 4.87-4.65 (m, 1H), 4.47 (d, J = 14.0 Hz, 1H), 4.41-4.24 (m, 2H), 4.09-3.94 (m, 3H), 3.92-3.53 (m, 4H), 3.25-3.13 (m, 2H), 3.02-2.95 (m, 1H), 2.64-2.53 (m, 2H), 2.39-2.28 (m, 2H), 2.16-2.11 (m, 3H), 2.00-1.84 (m, 2H), 1.82-1.64 (m, 2H). $^{19}F$ NMR (376 MHz, Dimethylsulfoxide-$d_6$) δ −113.61, −113.65, −207.39 | 609.1 |
| 426 | $^{1}H$ NMR (400 MHz, Dimethylsulfoxide-$d_6$) δ 9.53-9.31 (m, 1H), 7.75 (dd, J = 6.4, 9.2 Hz, 1H), 7.36-7.23 (m, 1H), 7.04-6.98 (m, 1H), 6.93-6.61 (m, 2H), 5.64-5.50 (m, 2H), 4.89-4.61 (m, 1H), 4.47 (d, J = 13.2 Hz, 1H), 4.42-4.23 (m, 2H), 4.12 (dd, J = 4.4, 10.8 Hz, 1H), 4.05-3.94 (m, 2H), 3.92-3.53 (m, 4H), 3.31-3.24 (m, 2H), 3.23-3.15 (m, 1H), 3.03-2.94 (m, 1H), 2.60-2.50 (m, 1H), 2.38-2.27 (m, 2H), 2.16-2.08 (m, 3H), 1.97-1.65 (m, 4H). $^{19}F$ NMR (376 MHz, Dimethylsulfoxide-$d_6$) δ −113.64, −130.99, −207.48 | 627.2 |
| 427 | $^{1}H$ NMR (400 MHz, Dimethylsulfoxide-$d_6$) δ 9.46-9.34 (m, 1H), 7.74 (dd, J = 6.4, 9.2 Hz, 1H), 7.30 (t, J = 9.2 Hz, 1H), 7.02-6.98 (m, 1H), 6.94-6.70 (m, 2H), 5.56 (s, 2H), 4.86-4.63 (m, 1H), 4.47 (d, J = 14.0 Hz, 1H), 4.41-4.31 (m, 1H), 4.31-4.23 (m, 1H), 4.11 (d, J = 10.4 Hz, 1H), 4.06-3.87 (m, 3H), 3.72 (t, J = 11.6 Hz, 1H), 3.62-3.56 (m, 2H), 3.28-3.16 (m, 3H), 2.99-2.94 (m, 1H), 2.72-2.65 (m, 1H), 2.39-2.27 (m, 2H), 2.17-2.10 (m, 3H), 2.00-1.93 (m, 1H), 1.87-1.80 (m, 1H), 1.80-1.68 (m, 2H). $^{19}F$ NMR (376 MHz, Dimethylsulfoxide-$d_6$) δ −113.57, −132.48, −207.44 | 627.1 |
| 428 | $^{1}H$ NMR (400 MHz, Dimethylsulfoxide-$d_6$) δ 9.46-9.35 (m, 1H), 7.75 (dd, J = 6.0, 9.2 Hz, 1H), 7.34-7.26 (m, 1H), 7.02-6.98 (m, 1H), 6.93-6.86 (m, 1H), 5.62-5,52 (m, 2H), 4.89-4.63 (m, 1H), 4.51-4.44 (m, 1H), 4.41-4.23 | 645.1 |

TABLE 2-continued

| Example | $^1H$ NMR and $^{19}F$ NMR data | Mass: $[M + H]^+$ |
|---|---|---|
| | (m, 2H), 4.19-4.14 (m, 1H), 4.12-3.95 (m, 2H), 3.91-3.56 (m, 4H), 3.39-3.38 (m, 1H), 3.28-3.17 (m, 2H), 3.03-2.95 (m, 1H), 2.64-2.55 (m, 2H), 2.44-2.38 (m, 1H), 2.18-2.10 (m, 3H), 2.01-1.92 (m, 1H), 1.91-1.73 (m, 3H). $^{19}F$ NMR (376 MHz, Dimethylsulfoxide-$d_6$) δ −90.93, −91.10, −91.34, −91.40, −91.52, −113.60, −207.32 | |
| 429 | $^1H$ NMR (400 MHz, Dimethylsulfoxide-$d_6$) δ 9.51-9.29 (m, 1H), 7.81-7.65 (m, 1H), 7.30 (t, J = 9.2 Hz, 1H), 7.00 (d, J = 2.0 Hz, 1H), 6.94-6.82 (m, 1H), 5.57 (s, 2H), 4.88 (s, 2H), 4.84-4.62 (m, 1H), 4.48-4.17 (m, 4H), 4.07-3.94 (m, 2H), 3.91-3.52 (m, 4H), 3.27-3.20 (m, 2H), 3.07-3.00 (m, 1H), 2.66-2.59 (m, 1H), 2.45-2.38 (m, 1H), 2.34-2.21 (m, 2H), 2.17-2.08 (m, 3H), 2.02-1.92 (m, 1H), 1.73-1.64 (m, 1H), 0.83-0.73 (m, 1H), 0.65-0.57 (m, 1H), 0.51-0.38 (m, 2H). $^{19}F$ NMR (376 MHz, Dimethylsulfoxide-$d_6$) δ −113.61, −207.45 | 635.3 |
| 430 | $^1H$ NMR (400 MHz, Dimethylsulfoxide-$d_6$) δ 9.47-9.33 (m, 1H), 7.8-7.70 (m, 1H), 7.30 (t, J = 9.2 Hz, 1H), 7.00 (t, J = 2.0 Hz, 1H), 6.95-6.66 (m, 2H), 5.57 (d, J = 3.6 Hz, 2H), 4.98-4.65 (m, 1H), 4.49-4.17 (m, 4H), 4.12-3.95 (m, 2H), 3.93-3.53 (m, 4H), 3.29-3.26 (m, 1H), 3.24-3.16 (m, 1H), 3.05-2.99 (m, 1H), 2.63-2.56 (m, 1H), 2.55-2.52 (m, 1H), 2.32-2.23 (m, 2H), 2.17-2.10 (m, 3H), 2.00-1.93 (m, 1H), 1.72-1.62 (m, 1H), 0.83-0.75 (m, 1H), 0.64-0.58 (m, 1H), 0.51-0.40 (m, 2H). $^{19}F$ NMR (376 MHz, Dimethylsulfoxide-$d_6$) δ −113.61, −132.16, −132.27, −207.40 | 653.1 |
| 432 | $^1H$ NMR (400 MHz, Methanol-$d_4$) δ 8.72 (s, 1H), 7.24-7.20 (m, 1H), 7.03-6.99 (m, 1H), 4.96 (s, 2H), 4.62-4.37 (m, 3H), 4.25-4.11 (m, 3H), 4.03-3.88 (m, 2H), 3.78-3.65 (m, 2H), 3.30-3.10 (m, 3H), 2.78-2.69 (m, 2H), 2.47-2.43 (m, 1H), 2.40-2.24 (m, 1H), 2.13-2.10 (m, 1H), 2.01-1.78 (m, 3H). $^{19}F$ NMR (376 MHz, Methanol-$d_4$) δ −59.89-−59.90 (d, 3F), −118.97 (s, 1F), −124.16 (s, 1F), −209.02 (s, 1F) | 687.0 |
| 433 | $^1H$ NMR (400 MHz, Methanol-$d_4$) δ 8.68 (s, 1H), 7.26-7.23 (m, 1H), 7.04-6.97 (m, 1H), 4.97 (s, 2H), 4.65-4.41 (m, 3H), 4.26-4.19 (m, 2H), 4.12-3.84 (m, 3H), 3.72-3.66 (m, 2H), 3.36-3.34 (m, 1H), 3.19-3.10 (m, 2H), 2.78-2.70 (m, 2H), 2.47-2.43 (m, 1H), 2.38-2.25 (m, 1H), 2.12-2.09 (m, 1H), 2.02-1.79 (m, 3H). $^{19}F$ NMR (376 MHz, Methanol-$d_4$) δ −59.90-−59.91 (d, 3F), −119.02 (s, 1F), −124.86 (s, 1F), −209.02 (s, 1F) | 687.3 |
| 437 | $^1H$ NMR (400 MHz, Dimethylsulfoxide-$d_6$) δ 9.47-9.33 (m, 1H), 7.75 (dd, J = 6.0, 9.2 Hz, 1H), 7.30 (t, J = 9.2 Hz, 1H), 7.00 (d, J = 2.0 Hz, 1H), 6.93-6.85 (m, 1H), 5.56 (d, J = 4.0 Hz, 2H), 4.90-4.63 (m, 1H), 4.48-4.19 (m, 4H), 4.16-4.08 (m, 1H), 4.05-3.93 (m, 1H), 3.90-3.53 (m, 4H), 3.42-3.36 (m, 1H), 3.26-3.16 (m, 1H), 3.07-2.99 (m, 1H), 2.68-2.61 (m, 1H), 2.47-2.42 (m, 1H), 2.37-2.26 (m, 2H), 2.17-2.10 (m, 3H), 2.01-1.92 (m, 1H), 1.76-1.67 (m, 1H), 0.86-0.77 (m, 1H), 0.63-0.44 (m, 3H). $^{19}F$ NMR (376 MHz, Dimethylsulfoxide-$d_6$) δ −90.99, −91.16, −91.19, −91.36, −113.60, −207.27, −207.32, −207.44, −207.54 | 671.1 |
| 438 | $^1H$ NMR (400 MHz, Methanol-$d_4$) δ 8.68 (s, 1H), 7.26-7.23 (m, 1H), 7.04-6.99 (m, 1H), 4.65-4.40 (m, 3H), 4.31-4.28 (m, 1H), 4.23-4.20 (m, 1H), 4.13-3.98 (m, 2H), 3.92-3.85 (m, 1H), 3.80-3.70 (m, 2H), 3.43-3.40 (m, 1H), 3.15-3.03 (m, 2H), 2.81-2.69 (m, 2H), 2.51-2.47 (m, 1H), 2.42-2.25 (m, 1H), 2.10-1.83 (m, 4H). $^{19}F$ NMR (376 MHz, Methanol-$d_4$) δ −59.91-−59.92 (d, 3F), −92.59-−93.30 (m, 2F), −119.03 (s, 1F), −124.87 (s, 1F), −208.01 (s, 1F) | 723.0 |
| 439 | $^1H$ NMR (400 MHz, Methanol-$d_4$) δ 8.72 (s, 1H), 7.24-7.20 (m, 1H), 7.03-6.99 (m, 1H), 4.62-4.40 (m, 3H), 4.29-4.11 (m, 3H), 4.05-3.93 (m, 2H), 3.79-3.73 (m, 2H), 3.44-3.40 (m, 1H), 3.27-3.10 (m, 2H), 2.81-2.68 (m, 2H), 2.55-2.48 (m, 1H), 2.43-2.25 (m, 1H), 2.18-1.83 (m, 4H). $^{19}F$ NMR (376 MHz, Methanol-$d_4$) δ −59.91 (s, 3F), −92.76-−93.13 (m, 2F), −118.97 (s, 1F), −124.17 (s, 1F), −209.46 (s, 1F) | 723.1 |
| 440 | $^1H$ NMR (400 MHz, DMSO-$d_6$) δ 8.75 (s, 1H), 8.10 (s, 2H), 7.22-7.14 (m, 2H), 5.35-5.21 (m, 1H), 4.75-4.60 (m, 1H), 4.47-4.32 (m, 3H), 4.00-3.97 (m, 1H), 3.75-3.69 (m, 1H), 3.59-3.53 (m, 1H), 3.18-2.96 (m, 4H), 2.90-2.80 (m, 1H), 2.40-1.96 (m, 7H), 1.92-1.70 (m, 3H). $^{19}F$ NMR (376 MHz, DMSO-$d_6$) δ −116.80 (s, 1F), −172.21 (s, 1F), −207.92 (s, 1F) | 648.4 |
| 441 | $^1H$ NMR (400 MHz, DMSO-$d_6$) δ 8.72 (s, 1H), 8.09 (s, 2H), 7.31-7.27 (m, 1H), 7.20-7.16 (m, 1H), 5.34-5.21 (m, 1H), 4.50-4.47 (m, 1H), 4.37-4.23 (m, 3H), 3.96-3.94 (m, 1H), 3.74-3.68 (m, 1H), 3.60-3.54 (m, 1H), 3.08-2.94 (m, 4H), 2.95-2.78 (m, 1H), 2.33-1.94 (m, 7H), 1.90-1.66 (m, 3H). $^{19}F$ NMR (376 MHz, DMSO-$d_6$) δ −116.93 (s, 1F), −172.15 (s, 1F), −206.59 (s, 1F) | 648.2 |
| 442 | $^1H$ NMR (400 MHz, Dimethylsulfoxide-$d_6$) δ 9.45-9.34 (m, 1H), 7.75 (dd, J = 6.0, 9.2 Hz, 1H), 7.30 (t, J = 8.8 Hz, 1H), 7.00 (d, J = 2.0 Hz, 1H), 6.92-6.85 (m, 1H), 5.57 (s, 2H), 4.87 (s, 2H), 4.84-4.64 (m, 1H), 4.48-4.22 (m, 3H), 4.12-3.55 (m, 5H), 3.46-3.40 (m, 1H), 3.23-3.16 (m, 1H), 3.07-3.00 (m, 1H), 2.64-2.61 (m, 1H), 2.39-2.22 (m, 3H), 2.15-2.09 (m, 3H), 2.01-1.93 (m, 1H), 1.72-1.64 (m, 1H), 0.81-0.74 (m, 1H), 0.64-0.57 (m, 1H), 0.48-0.41 (m, 2H). $^{19}F$ NMR (376 MHz, Dimethylsulfoxide-$d_6$) δ −113.62, −207.50 | 637.3 |
| 443 | $^1H$ NMR (400 MHz, Dimethylsulfoxide-$d_6$) δ 9.42-9.29 (m, 1H), 7.75 (dd, J = 6.0, 9.2 Hz, 1H), 7.30 (t, J = 9.2 Hz, 1H), 7.00 (s, 1H), 6.92-6.80 (m, 1H). 5.62-5.51 (m, 2H), 4.89 (s, 2H), 4.47-4.34 (m, 2H), 4.18-4.13(m, 1H), | 625.1, 626.8 |

TABLE 2-continued

| Example | $^{1}H$ NMR and $^{19}F$ NMR data | Mass: $[M + H]^+$ |
|---|---|---|
| | 4.09-3.93 (m, 3H), 3.86-3.48 (m, 5H), 3.29-3.23 (m, 1H), 3.21-3.15 (m, 1H), 3.04-2.93 (m, 1H), 2.68-2.54 (m, 2H), 2.39-2.31 (m, 1H), 2.18-2.07 (m, 4H), 2.02-1.92 (m, 1H), 1.89-1.62 (m, 3H). $^{19}F$ NMR (376 MHz, Dimethylsulfoxide-$d_6$) δ −113.66 | |
| 444 | $^{1}H$ NMR (400 MHz, Dimethylsulfoxide-$d_6$) δ 9.43-9.27 (m, 1H), 7.75 (dd, J = 6.0, 9.2 Hz, 1H), 7.30 (t, J = 9.2 Hz, 1H), 7.02-6.83 (m, 2H), 5.65-5.48 (m, 2H), 4.88 (s, 2H), 4.47-4.34 (m, 2H), 4.22-3.95 (m, 4H), 3.87-3.49 (m, 5H), 3.30-3.24 (m, 2H), 3.08-3.01 (m, 1H), 2.68-2.57 (m, 1H), 2.44-2.37 (m, 1H), 2.30-2.21 (m, 1H), 2.18-2.08 (m, 4H), 2.02-1.93 (m, 1H), 1.73-1.62 (m, 1H), 0.85-0.77 (m, 1H), 0.65-0.57(m, 1H), 0.50-0.41 (m, 2H). $^{19}F$ NMR (376 MHz, Dimethylsulfoxide-$d_6$) δ −113.67 | 650.9, 652.7 |
| 447 | $^{1}H$ NMR (400 MHz, Dimethylsulfoxide-$d_6$) δ 10.22-9.92 (m, 1H), 9.51-9.33 (m, 1H), 7.98-7.90 (m, 1H), 7.43 (t, J = 9.2 Hz, 1H), 7.33 (d, J = 2.4 Hz, 1H), 7.06-6.96 (m, 1H), 6.95-6.69 (m, 1H), 4.92-4.63 (m, 1H), 4.51-4.44 (m, 1H), 4.42-4.21 (m, 2H), 4.16-3.94 (m, 4H), 3.76-3.67 (m, 1H), 3.63-3.46 (m, 2H), 3.23-3.15 (m, 2H), 3.03-2.91 (m, 1H), 2.76-2.66 (m, 1H), 2.56-2.52 (m, 1H), 2.41-2.29 (m, 2H), 2.19-2.09 (m, 3H), 2.03-1.93 (m, 1H), 1.87-1.67 (m, 3H). $^{19}F$ NMR (376 MHz, Dimethylsulfoxide-$d_6$) δ −111.02, −132.50, −132.55, −207.53 | 628.0 |
| 449 | $^{1}H$ NMR (400 MHz, Dimethylsulfoxide-$d_6$) δ 10.13-9.99 (m, 1H), 9.50-9.28 (m, 1H), 7.95 (dd, J = 6.0, 9.2 Hz, 1H), 7.43 (t, J = 8.8 Hz, 1H), 7.34 (d, J = 2.4 Hz, 1H), 7.06-6.94 (m, 1H), 6.88-6.57 (m, 1H), 4.89-4.66 (m, 1H), 4.45 (d, J = 14.4 Hz, 1H), 4.42-4.25 (m, 2H), 4.20 (d, J = 10.4 Hz, 1H), 4.07 (d, J = 11.2 Hz, 1H), 4.02-3.64 (m, 4H), 3.61-3.54 (m, 1H), 3.40-3.38 (m, 1H), 3.28-3.17 (m, 1H), 3.08-3.00 (m, 1H), 2.65-2.61 (m, 1H), 2.38-2.20 (m, 3H), 2.18-2.10 (m, 3H), 2.02-1.93 (m, 1H), 1.74-1.62 (m, 1H), 0.84-0.75 (m, 1H), 0.64-0.57 (m, 1H), 0.52-0.42 (m, 2H). $^{19}F$ NMR (376 MHz, Dimethylsulfoxide-$d_6$) δ −111.00, −131.27, −207.49 | 654.2 |
| 450 | $^{1}H$ NMR (400 MHz, DMSO-$d_6$) δ 8.10-7.90 (m, 3H), 7.25-7.12 (m, 2H), 5.34-5.21 (m, 1H), 4.41-4.15 (m, 4H), 4.00-3.90 (m, 1H), 3.85-3.75 (m, 1H), 3.60-3.50 (m, 1H), 3.09-2.95 (m, 4H), 2.90-2.80 (m, 1H), 2.30-1.70 (m, 10H). $^{19}F$ NMR (376 MHz, DMSO-$d_6$) δ −117,46 (s, 1F)-119.47 (s, 1F), −172.11 (s, 1F), −205.58 (s, 1F) | 641.2 |
| 451 | $^{1}H$ NMR (400 MHz, DMSO-$d_6$) δ 8.10-7.95 (m, 3H), 7.20-7.11 (m, 2H), 5.34-5.21 (m, 1H), 4.74-4.59 (m, 1H), 4.37-4.21 (m, 3H), 3.99-3.96 (m, 1H), 3.83-3.77 (m, 1H), 3.58-3.52 (m, 1H), 3.13-3.00 (m, 4H), 2.85-2.80 (m, 1H), 2.30-1.95 (m, 7H), 1.90-1.70 (m, 3H). $^{19}F$ NMR (376 MHz, DMSO-$d_6$) δ −117.33 (s, 1F)-118.96 (s, 1F), −172.14 (s, 1F), −206.94 (s, 1F) | 641.2 |
| 452 | $^{1}H$ NMR (400 MHz, DMSO-$d_6$) δ 9.40-9.29 (m, 1H), 7.75-7.71 (m, 1H), 7.31-7.27 (m, 1H), 6.98-6.91 (m, 2H), 5.55-5.54 (m, 2H), 5.35-5.22 (m, 1H), 4.80-4.65 (m, 1H), 4.46-4.26 (m, 3H), 4.08-3.55 (m, 4H), 3.25-2.99 (m, 4H), 2.85-2.80 (m, 1H), 2.40-2.20 (m, 1H), 2.13-1.98 (m, 4H), 1.90-1.73 (m, 3H), 1.09-1.00 (m, 2H), 0.70-0.49 (m, 2H). $^{19}F$ NMR (376 MHz, DMSO-$d_6$) δ −113.91 (s, 1F), −172.08 (s, 1F), −207.20 (s, 1F) | 643.3 |
| 453 | $^{1}H$ NMR (400 MHz, DMSO-$d_6$) δ 10.21 (s, 1H), 8.02-7.84 (m, 2H), 7.52-7.42 (m, 2H), 7.16-7.15 (m, 1H), 5.36-5.22 (m, 1H), 4.87-4.72 (m, 1H), 4.41-4.38 (m, 2H), 4.29-4.22 (m, 1H), 4.11 (s, 1H), 4.02-3.99 (m, 1H), 3.82-3.76 (m, 1H), 3.60-3.54 (m, 1H), 3.28-3.00 (m, 4H), 2.84-2.80 (m, 1H), 2.32-2.21 (m, 1H), 2.14-1.70 (m, 6H). $^{19}F$ NMR (376 MHz, DMSO-$d_6$) δ −110.15 (s, 1F), −119.82 (s, 1F), −125.46-−125.47 (d, 1F), −172.08 (s, 1F), −207.62-−207.82 (m, 1F) | 639.2 |
| 454 | $^{1}H$ NMR (400 MHz, Methanol-$d_4$) δ 7.99-7.96 (m, 1H), 7.86-7.83 (m, 1H), 7.34-7.29 (m, 2H), 7.15-7.14 (m, 1H), 5.36-5.23 (m, 1H), 4.64-4.40 (m, 3H), 4.11-3.93 (m, 3H), 3.77-3.70 (m, 1H), 3.26-3.20 (m, 4H), 3.05-2.95 (m, 1H), 2.38-1.80 (m, 7H). $^{19}F$ NMR (376 MHz, Methanol-$d_4$) δ −111.61 (s, 1F), −119.66-−119.67 (d, 1F), −125.47 (s, 1F), −173.63 (s, 1F), −209.47 (s, 1F) | 639.4 |
| 455 | $^{1}H$ NMR (400 MHz, DMSO-$d_6$) δ 9.43-9.38 (m, 1H), 7.76-7.72 (m, 1H), 7.32-2.28 (m, 1H), 6.99-6.71 (m, 3H), 5.90-5.84 (m, 1H), 5.57 (s, 2H), 5.29-5.25 (m, 2H), 4.93-4.63 (m, 1H), 4.49-4.46 (m, 1H), 4.44-4.21 (m, 2H), 4.11-3.66 (m, 3H), 3.61-3.58 (m, 1H), 3.25-3.00 (m, 4H), 2.85-2.78 (m, 1H), 2.40-2.25 (m, 1H), 2.20-1.98 (m, 3H), 1.90-1.70 (m, 3H). $^{19}F$ NMR (376 MHz, DMSO-$d_6$) δ −113.66-−113.70 (d, 1F), −172.10-−172.18(d, 1F), −207.41 (s, 1F) | 629.3 |
| 466 | $^{1}H$ NMR (400 MHz, $CD_3OD$) δ 8.73 (s, 1H), 7.68-7.65 (m, 1H), 7.25-7.18 (m, 2H), 5.35-5.21 (m, 1H), 4.61-4.41 (m, 3H), 4.17-4.11 (m, 1H), 4.00-3.88 (m, 2H), 3.70-3.60 (m, 1H), 3.29-2.94 (m, 5H), 2.43-1.80 (m, 7H). $^{19}F$ NMR (376 MHz, $CD_3OD$) δ −59.90 (s, 3F), −124.46 (s, 1F), −173.71 (s, 1F), −209.48 (s, 1F) | 677.2 |
| 468 | $^{1}H$ NMR (400 MHz, $CD_3OD$) δ 8.69 (s, 1H), 7.68-7.65 (m, 1H), 7.25-7.22 (m, 2H), 5.35-5.22 (m, 1H), 4.65-4.39 (m, 3H), 4.12-4.01 (m, 2H), 3.95-3.85 (m, 1H), 3.78-3.71 (m, 1H), 3.29-2.95 (m, 5H), 2.40-1.80 (m, 7H). $^{19}F$ NMR (376 MHz, $CD_3OD$) δ −59.89 (s, 3F), −125.17 (s, 1F), −173.63 (s, 1F), −208.15 (s, 1F) | 677.2 |
| 470 | $^{1}H$ NMR (400 MHz, DMSO-$d_6$) δ 8.38 (m, 1H), 8.02 (s, 2H), 7.15-7.10 (m, 2H), 5.34-5.20 (m, 1H), 4.77-4.62 (m, 1H), 4.40-4.22 (m, 3H), 4.00-3.97 (m, 1H), 3.79-3.74 (m, 1H), 3.58-3.52 (m, 1H), 3.10-3.00 (m, 4H), 2.85- | 657.2 |

TABLE 2-continued

| Example | $^1$H NMR and $^{19}$F NMR data | Mass: [M + H]$^+$ |
|---|---|---|
| | 2.81 (m, 1H), 2.40-1.95 (m, 7H), 1.90-1.70 (m, 3H). $^{19}$F NMR (376 MHz, DMSO-d$_6$) δ 117.66 (s, 1F)-172.16 (s, 1F), −207.19 (s, 1F) | |
| 471 | $^1$H NMR (400 MHz, Dimethylsulfoxide-d$_6$) δ. 10.14-9.99 (m, 1H), 9.48-9.32 (m, 1H), 7.95 (dd, J = 6.0, 8.8 Hz, 1H), 7.43 (t, J = 9.2 Hz, 1H), 7.34 (d, J = 1.6 Hz, 1H), 7.07-6.90 (m, 1H), 5.11-4.96 (m, 1H), 4.86-4.67 (m, 1H), 4.47 (d, J = 13.6 Hz, 1H), 4.41-4.27 (m, 2H), 4.05-3.96 (m, 2H), 3.75-3.70 (m, 1H), 3.61-3.56 (m, 1H), 3.20-3.09 (m, 2H), 3.00-2.97 (m, 1H), 2.83-2.79 (m, 1H), 2.34-2.30 (m, 1H), 2.15-2.01 (m, 6H), 1.79-1.68 (m, 3H), 1.28-1.22 (m, 3H) $^{19}$F NMR (376 MHz, Dimethylsulfoxide-d$_6$) δ −111.00, −110.06, −186.34, −208.09 | 632.3 |
| 472 | $^1$H NMR (400 MHz, Dimethylsulfoxide-d$_6$) δ. 10.16 (s, 1H), 9.49-9.31 (m, 1H), 7.98 (dd, J = 6.0, 9.2 Hz, 1H), 7.47 (t, J = 9.2 Hz, 1H), 7.40 (d, J = 2.8 Hz, 1H), 7.23-7.12 (m, 1H), 5.11-4.73 (m, 2H), 4.49 (d, J = 13.6 Hz, 1H), 4.43-4.29 (m, 2H), 4.14-3.86 (m, 2H), 3.77-3.65 (m, 1H), 3.64-3.56 (m, 1H), 3.28-3.07 (m, 2H), 3.04-2.94 (m, 1H), 2.85-2.77 (m, 1H), 2.39-2.27 (m, 1H), 2.15-1.98 (m, 3H), 1.82-1.68 (m, 3H), 1.27-1.18 (m, 3H). $^{19}$F NMR (376 MHz, Dimethylsulfoxide-d$_6$) δ −110.71, −110.79, −139.97, −140.43, −186.32, −207.83 | 636.3 |
| 473 | $^1$H NMR (400 MHz, Dimethylsulfoxide-d$_6$) δ 10.09-9.99 (m, 1H), 9.41-9.30 (m, 1H), 7.95 (dd, J = 6.0, 9.2 Hz, 1H), 7.43 (t, J = 9.2 Hz, 1H), 7.34 (d, J = 2.4 Hz, 1H), 7.06-6.93 (m, 1H), 5.03 (d, J = 55.6 Hz, 1H), 4.47-4.34 (m, 2H), 4.19-4.11 (m, 1H), 4.07-3.96 (m, 1H), 3.94-3.66 (m, 2H), 3.65-3.57 (m, 1H), 3.55-3.47 (m, 1H), 3.24-3.06 (m, 2H), 3.02-2.94 (m, 1H), 2.84-2.77 (m, 1H), 2.17-2.00 (m, 7H), 1.80-1.66 (m, 3H), 1.26-1.21 (m, 3H). $^{19}$F NMR (376 MHz, Dimethylsulfoxide-d$_6$) δ −111.04, −186.32 | 648.2 |
| 474 | $^1$H NMR (400 MHz, Dimethylsulfoxide-d$_6$) δ 10.19-10.08 (m, 1H), 9.43-9.29 (m, 1H), 7.98 (dd, J = 5.6, 8.8 Hz, 1H), 7.47 (t, J = 8.8 Hz, 1H), 7.39 (d, J = 2.4 Hz, 1H), 7.21-7.11 (m, 1H), 5.16-4.87 (m, 1H), 4.79-4.48 (m, 1H), 4.47-4.34 (m, 1H), 4.25-3.84 (m, 2H), 3.41-3.34 (m, 1H), 3.25-3.07 (m, 1H), 3.05-2.92 (m, 1H), 2.86-2.75 (m, 1H), 2.31-2.21 (m, 1H), 2.10-1.68 (m, 10H), 1.58-1.44 (m, 1H), 1.29-1.17 (m, 4H). $^{19}$F NMR (376 MHz, Dimethylsulfoxide-d$_6$) δ −110.76, −110.82, −140.21, −140.60, 186.34, −204.95 | 634.2 |
| 475 | $^1$H NMR (400 MHz, Dimethylsulfoxide-d$_6$) δ 10.15 (s, 1H), 9.39-9.31 (m, 1H), 7.98 (dd, J = 6.0, 9.2 Hz, 1H), 7.47 (t, J = 8.8 Hz, 1H), 7.42-7.38 (m, 1H), 7.20-7.12 (m, 1H), 5.11-4.94 (m, 1H), 4.49-4.38 (m, 2H), 4.24-4.17 (m, 1H), 4.08-3.87 (m, 2H), 3.83-3.74 (m, 1H), 3.67-3.55 (m, 2H), 3.22-3.07 (m, 2H), 3.02-2.95 (m, 1H), 2.83-2.78 (m, 1H), 2.20-2.14 (m, 1H), 2.10-1.98 (m, 3H), 1.79-1.68 (m, 3H), 1.25-1.21 (m, 3H). $^{19}$F NMR (376 MHz, Dimethylsulfoxide-d$_6$) δ −111.75, −140.25, −140.59, −186.30, −186.35 | 652.4 |
| 476 | $^1$H NMR (400 MHz, Dimethylsulfoxide-d$_6$) δ 9.49-9.33 (m, 1H), 7.78 (dd, J = 6.0, 8.8 Hz, 1H), 7.42-7.25 (m, 1H), 7.14-6.95 (m, 2H), 5.73-5.53 (m, 2H), 4.98-4.71 (m, 1H), 4.51 (d, J = 13.6 Hz, 1H), 4.45-4.26 (m, 4H), 4.11-3.78 (m, 2H), 3.78-3,49 (m, 3H), 3.29-3.02 (m, 4H), 2.72-2.57 (m, 1H), 2.48-2.27 (m, 4H). $^{19}$F NMR (376 MHz, Dimethylsulfoxide-d$_6$) δ −88.85, −89.02, −89.47, −89.63, −97.08, −97.20, −97.30, −97.41, −97.70, −97.82, −98.02, −113.33, −113.42, −139.74, −140.33, −207.80 | 623.2 |
| 477 | $^1$H NMR (400 MHz, Dimethylsulfoxide-d$_6$) δ 9.51-9.29 (m, 1H), 7.78 (dd, J = 6.0, 9.2 Hz, 1H), 7.41-7.28 (m, 1H), 7.14-6.97 (m, 2H), 5.78-5.51 (m, 2H), 5.00-4.68 (m, 1H), 4.58-4.27 (m, 4H), 4.19-3.78 (m, 3H), 3.75-3.42 (m, 6H), 3.28-3.20 (m, 1H), 3.14 (t, J = 10.4 Hz, 1H), 3.02-2.81 (m, 3H), 2.40-2.28 (m, 1H), 2.13-1.99 (m, 1H), 1.82-1.68 (m, 1H), 1.65-1.53 (m, 1H), 1.36-1.24 (m, 1H). $^{19}$F NMR (376 MHz, Dimethylsulfoxide-d$_6$) δ −113.36, −139.81, −140.49, −207.70 | 617.2 |

II. Biological Evaluation

"Ras" refers to a protein in the Ras superfamily of small GTPases, such as in the Ras subfamily. Ras proteins are small guanine nucleotide-binding proteins that act as molecular switches by cycling between active GTP-bound and inactive GDP-bound conformations. The Ras proteins play a critical role in the regulation of cell behaviors, including proliferation, differentiation, and survival. Mutation of any one of the three Ras isoforms (K-Ras, N-Ras, or H-Ras) has been shown to lead to oncogenic transformation, and in fact, K-Ras mutations are by far the most common in human cancers. KRAS G12V, G12D, and G12S variants are common in human cancers and Ras inhibitors binding in or near the Switch II pocket may provide mutant binding selectivity. RAS mutations are known to be often associated with pancreatic, colorectal and non-small-cell lung carcinomas (Lone, A. M. et al. J. Am. Chem. Soc. 2011, 133, 11665-74, which is entirely incorporated herein by reference; Dillon, M. B.; Bachovchin, D. A.; Brown, S. J.; Finn, M. G.; Rosen, H.; Cravatt, B. F.; Mowen, K. A. ACS Chem. Biol. 2012, 7, 1198-204, which is entirely incorporated herein by reference; Bachovchin, D. A.; Brown, S. J.; Rosen, H.; Cravatt, B. F. Nat. Biotechnol. 2009, 27, 387-94, Ostrem, J. M.; Peters, U.; Sos, M. L.; Wells, J. A.; Shokat, K. M. Nature 2013, 503, 548-551. Ryan M.B. and Corcoran R.B, Nat. Rev Clin Onco. 2018, 11, 709-720.). Ras proteins are key members in the Ras/Raf/Mitogen-activated protein kinase (MAPK) signaling pathway. This pathway regulates a wide variety of cellular processes, including proliferation, differentiation, apoptosis, and stress responses. One way to measure the impact of an inhibitor of Ras proteins is to measure downstream phosphorylation of proteins in the MAPK pathway. The MAPK pathway includes extracellular signal-regulated kinases named ERK1 and ERK2, which are serine-threonine kinases that regulate cellular signaling under both normal and oncogenic conditions. ERK expression and hyperactivation via phosphorylation plays a major role in cancer progression and are downstream of Ras proteins. The assay used for measuring the downstream impact of Ras inhibition is the use of a highly sensitive cell-based readout of ERK phosphorylation (pERK) specifically on Threonine (Thr) 202 and Tyrosine (Tyr) 204 in a KRAS $G_{12}V$ dependent lung adenocarcinoma cell line, NCl-$H_{441}$ (ATCC Cat #HTB-174). The assay described herein is suitable for assessing inhibition of Ras and can be tailored for any of the predominant oncogenic mutations in any isoform of Ras (e.g., KRAS, HRAS, and NRAS) by changing the cell line.

Example 1: Cellular Assay-Fluorescence Resonance Energy Transfer (FRET)

pERK was measured using an advanced pERK assay designed for the robust and highly sensitive quantification of ERK phosphorylation on Thr202/Tyr204. This assay is intended for the simple, rapid, and direct detection of endogenous levels of ERK1/2 in cells, but only when ERK is phosphorylated at Thr202 and Tyr204 (Perkin Elmer Catalog #64AERPEH). pERK was detected in a FRET based sandwich assay format using 2 different specific antibodies, one labelled with Eu3+-Cryptate (donor) and the second with $d_2$ (acceptor). When the dyes are in close proximity, the excitation of the donor with a light source (laser or flash lamp) triggers a Fluorescence Resonance Energy Transfer (FRET) towards the acceptor, which in turn fluoresces at a specific wavelength (665 nm). The specific signal modulates positively in proportion to p-ERK1/2 (Thr202/Tyr204). The simple mix-and-read protocol eliminates all wash steps for faster analysis and high-quality output. Briefly, cells were diluted to the desired concentration per well based on a growth curve showing ~75% confluence within a 24-hour time period at no less than 95% viability. Cell suspension (24 μL) were added into each well of 384-well culture plate and maintained in 37° C. 5% CO2 incubator overnight prior to assay. All compounds were transferred to stock plates using TECAN (EVO200) liquid handler using DMSO as the solubilizing and dilution agent. Test compounds were transferred onto adherent cells using an Echo655 liquid handler. DMSO was employed as negative control. Cells were incubated with test compounds for 1 hr in a 37° C., 5% CO2 incubator following compound addition. Following compound incubation, plates were removed from incubator and lysed with 4X lysis buffer (1X phosphatase inhibitor cocktail included) from the FRET kit. Antibodies and detection reagent were dispensed onto cell lysate and the plate was incubated at room temperature prior to reading. Twenty-five microliters of lysate plus detection reagent were transferred to an optiplate reading plate and measured using a Perkin Elmer Envision Reader using standard HTRF settings. The IC50 was calculated by fitting the curve using Xlfit (v5.3.1.3). Table 3 provides the assay results for select examples. Activity is defined as "+" for affinity less than 10 micromolar, but greater (>) than 500 nanomolar; "++" for affinity less than (<) 500 nanomolar, but greater than 50 nanomolar; or "+++" for affinity less than 50 nanomolar.

TABLE 3

| Example No. | Name | HTRF KRas G12V IC50 (nM) | Mass $[M + H]^+$ |
|---|---|---|---|
| 1 | 4-(4-((1S,7R)-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-ol | + | 600.3 |
| 2 | 4-(4-((1R,7S)-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-ol | +++ | 600.2 |
| 3 | 4-(4-(4-azabicyclo[5.1.0]octan-4-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-ol | +++ | 600.3 |
| 4 | 4-(4-(1S,7R)-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-amine | + | 599.2 |
| 5 | 4-(4-((1R,7S)-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-amine | +++ | 599.3 |
| 6 | 4-(4-(8,8-difluoro-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-ol | +++ | 636.2 |
| 7 | 4-(4-((1S,7R)-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | + | 619.3 |
| 8 | 4-(4-((1R,7S)-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | +++ | 619.3 |
| 9 | 4-(4-(4-azabicyclo[5.1.0]octan-4-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | ++ | 619.3 |

TABLE 3-continued

| Example No. | Name | HTRF KRas G12V IC50 (nM) | Mass [M + H]+ |
|---|---|---|---|
| 10 | 4-(4-((1S,7R)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-ol | +++ | 604.2 |
| 11 | 4-(4-((1R,7S)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-etbynyl-6-fluoronaphthalen-2-ol | ++ | 604.4 |
| 12 | 4-(4-(3-azabicyclo[5.1.0]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-ol | +++ | 600.3 |
| 13 | 5-ethynyl-6,7-difluoro-4-(8-fluoro-4-((1S,7R,8R)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | ++ | 637.2 |
| 14 | 5-ethynyl-6,7-difluoro-4-(8-fluoro-4-((1R,7S,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | + | 637.2 |
| 15 | 5-ethynyl-6,7-difluoro-4-(8-fluoro-4-((1R,7S,8R)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | + | 637.3 |
| 16 | 5-ethynyl-6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 637.2 |
| 17 | 4-(4-((1S,7R)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | +++ | 621.4 |
| 18 | 4-(4-((1R,7S)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | + | 621.3 |
| 19 | 4-(4-(1S,7S)-8,8-difluoro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | +++ | 657.35 |
| 20 | 4-(4-((1R,7R)-8,8-difluoro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | + | 657.25 |
| 21 | 5-ethynyl-6,7-difluoro-4-(8-fluoro-4-((1R,7S,8S)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | + | 639.35 |
| 22 | 5-ethynyl-6,7-difluoro-4-(8-fluoro-4-((1S,7R,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | ++ | 639.30 |
| 23 | 5-ethynyl-6,7-difluoro-4-(8-fluoro-4-((1S,7R,8S)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | + | 639.15 |
| 24 | 5-ethynyl-6,7-difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 639.15 |
| 25 | 4-(4-((1S,7R)-2-oxa-6-azabicyclo[5.1.0]octan-6-yl-5,5-d2)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | +++ | 623.25 |
| 26 | 4-(4-((1R,7S)-2-oxa-6-azabicyclo[5.1.0]octan-6-yl-5,5-d2)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | ++ | 623.20 |
| 27 | 5-ethynyl-6,7-difluoro-4-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | ++ | 639.40 |

TABLE 3-continued

| Example No. | Name | HTRF KRas G12V IC50 (nM) | Mass [M + H]+ |
|---|---|---|---|
| 28 | 5-ethynyl-6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 639.15 |
| 29 | 5-Ethynyl-6,7-difluoro-4-(8-fluoro-4-((1R,7R,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphtbalen-2-amine | ++ | 639.15 |
| 30 | 5-Ethynyl-6,7-difluoro-4-(8-fluoro-4-((1S,75,8R)-8-fluoro-5-oxa-2-azabicyclo[5.1.0]octan-2-yl)-2-(2R,7aS)-2-fluorotetrahydro-1H-pyrrolizin-7a(5H)-yl)methoxy-d2)pyrido[4,3-d]pyrimidin-7-yl)naphthalen-2-amine | +++ | 639.10 |
| 31 | 4-(4-((1R,6S)-2-oxa-5-azabicyclo[4.1.0]heptan-5-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | ++ | 607.20 |
| 32 | 4-(4-((1S,6R)-2-oxa-5-azabicyclo[4.1.0]heptan-5-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | ++ | 607.20 |
| 33 | 4-(4-((1R,7S)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)-5-methoxypyrido[4,3-d]pyrimidin-7-yl)-5-ethynyl-6,7-difluoronaphthalen-2-amine | ++ | 651.30 |
| 34 | 4-(4-((1S,7R)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)-5-methoxypyrido[4,3-d]pyrimidin-7-yl)-5-ethynyl-6,7-difluoronaphthalen-2-amine | +++ | 651.10 |
| 35 | 4-(4-((1R,7S)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)-5-methoxypyrido[4,3-d]pyrimidin-7-yl)-5-ethynyl-6-fluoronaphthalen-2-ol | ++ | 634.30 |
| 36 | 4-(4-((1S,7R)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)-5-methoxypyrido[4,3-d]pyrimidin-7-yl)-5-ethynyl-6-fluoronaphthalen-2-ol | +++ | 634.15 |
| 37 | 5-ethynyl-6,7-difluoro-4-(8-fluoro-4-((1S,6R,7S)-7-fluoro-2-oxa-5-azabicyclo[4.1.0]heptan-5-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine | ++ | 625.20 |
| 38 | 5-ethynyl-6,7-difluoro-4-(8-fluoro-4-((1R,6S,7R)-7-fluoro-2-oxa-5-azabicyclo[4.1.0]heptan-5-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 625.20 |
| 39 | 4-(4-((1S,7R)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-2-amino-7-fluorobenzo[b]thiophene-3-carbonitrile | ++ | 610.20 |
| 40 | 4-(4-((1R,7S)-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-2-amino-7-fluorobenzo[b]thiophene-3-carbonitrile | + | 610.20 |
| 41 | 6,7,8-trifluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 665.65 |
| 42 | (1S,7S,8S)-2-(7-(8-ethynyl-6,7-difluoronaphthalen-1-yl)-8-fluoro-2-(((2R,7aS)-2-fluorotetrahydro-1H-pyrrolizin-7a(5H)-yl)methoxy-$d_2$)pyrido[4,3-d]pyrimidin-4-yl)-8-fluoro-5-oxa-2-azabicyclo[5.1.0]octane | +++ | 624.45 |
| 43 | (1S,7S,8S)-8-fluoro-2-(8-fluoro-7-(7-fluoro-8-(methoxy-d3)naphthalen-1-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane | +++ | 615.15 |
| 44 | 6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 648.35 |

TABLE 3-continued

| Example No. | Name | HTRF KRas G12V IC50 (nM) | Mass $[M + H]^+$ |
|---|---|---|---|
| 45 | (1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane | +++ | 606.20 |
| 46 | (1R,7R,8R)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane | + | 606.20 |
| 47 | 4-(4-((1S,7R)-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-2-amino-7-fluorobenzo[b]thiophene-3-carbonitrile | + | 610.15 |
| 48 | 4-(4-((1R,7S)-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-2-amino-7-fluorobenzo[b]thiophene-3-carbonitrile | ++ | 610.15 |
| 49 | 6-amino-8-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-1-(methoxy-d3)-2-naphthonitrile | +++ | 635.2 |
| 50 | 6-amino-3-fluoro-8-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-1-(methoxy-d3)-2-naphthonitrile | +++ | 653.7 |
| 51 | 4-(4-((1S,6R)-2-azabicyclo[4.1.0]heptan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | + | 605.2 |
| 52 | 4-(4-((1R,6S)-2-azabicyclo[4.1.0]heptan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | ++ | 605.2 |
| 53 | 5-ethynyl-6,7-difluoro-4-(8-fluoro-4-((1R,6S,7R)-7-fluoro-2-azabicyclo[4.1.0]heptan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | ++ | 623.2 |
| 54 | 5-ethynyl-6,7-difluoro-4-(8-fluoro-4-((1S,6R,7S)-7-fluoro-2-azabicyclo[4.1.0]heptan-2-yl)-2-(((2R,7aS)-2-fluorotetrabydro-1H-pyrrolizin-7a(5H)-yl)methoxy-d2)pyrido[4,3-d]pyrimidin-7-yl)naphthalen-2-amine | +++ | 623.2 |
| 55 | 4-(4-((1S,8R)-2-azabicyclo[6.1.0]nonan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | + | 633.2 |
| 56 | 4-(4-((1R,8S)-2-azabicyclo[6.1.0]nonan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | +++ | 633.2 |
| 57 | 4-(4-(8,8-difluoro-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-amine | ++ | 635.2 |
| 58 | 6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 628.3 |
| 59 | 5-ethynyl-6,7-difluoro-4-(8-fluoro-4-((1R,8S,9R)-9-fluoro-2-azabicyclo[6.1.0]nonan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | + | 651.2 |
| 60 | 5-ethynyl-6,7-difluoro-4-(8-fluoro-4-((1S,8R,9S)-9-fluoro-2-azabicyclo[6.1.0]nonan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 651.2 |
| 61 | 4-(4-((1S,7R)-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | + | 621.25 |
| 62 | 4-(4-((1R,7S)-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | +++ | 620.25 |

TABLE 3-continued

| Example No. | Name | HTRF KRas G12V IC50 (nM) | Mass [M + H]+ |
|---|---|---|---|
| 63 | 5-ethynyl-6,7-difluoro-4-(8-fluoro-4-((1R,6S,7S)-7-fluoro-2-azabicyclo[4.1.0]heptan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | + | 623.2 |
| 64 | 5-ethynyl-6,7-difluoro-4-(8-fluoro-4-((1S,6R,7R)-7-fluoro-2-azabicyclo[4.1.0]heptan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | + | 623.2 |
| 65 | 6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 646.3 |
| 66 | 6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy)naphthalen-2-amine | +++ | 661.2 |
| 67 | 5-(difluoromethoxy)-6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 679.2 |
| 68 | 8-fluoro-7-(7-fluoro-8-(methoxy-d3)naphthalen-1-yl)-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | +++ | 613.3 |
| 69 | 6,7,8-trifluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 664.2 |
| 70 | 5-ethynyl-6,7,8-trifluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 655.1 |
| 71 | 6,7-difluoro-4-(8-fluoro-4-((1S,7R,8S)-8-fluoro-2-azabicyclo[5.1.0]octan-2-yl)-2-(((2R,7aS)-2-fluorotetrabydro-1H-pyrrolizin-7a(5H)-yl)methoxy-d2)pyrido[4,3-d]pyrimidin-7-yl)-5-(fluoromethoxy-d2)naphthalen-2-amine | +++ | 663.2 |
| 72 | 8-fluoro-7-(7-fluoro-8-(fluoromethoxy-d2)naphthalen-1-yl)-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | +++ | 630.2 |
| 73 | 8-fluoro-7-(7-fluoro-8-(fluoromethoxy)naphthalen-1-yl)-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | +++ | 628.1 |
| 74 | 6,7-difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 648.3 |
| 75 | (1R,7S,8R)-6-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-oxa-6-azabicyclo[5.1.0]octane | +++ | 606.3 |
| 76 | (1R,7S,8R)-6-(7-(8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-oxa-6-azabicyclo[5.1.0]octane | +++ | 624.2 |
| 77 | 6,7,8-trifluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 666.2 |
| 78 | 7-(8-ethynyl-7-fluoronaphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | +++ | 604.4 |
| 79 | 7-(8-ethynyl-6,7-difluoronaphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | +++ | 622.4 |

TABLE 3-continued

| Example No. | Name | HTRF KRas G12V IC50 (nM) | Mass [M + H]+ |
|---|---|---|---|
| 80 | (1S,7S,8S)-8-fluoro-2-(8-fluoro-7-(7-fluoro-8-(fluoromethoxy-d2)naphthalen-1-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane | +++ | 632.3 |
| 81 | 6-amino-8-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-1-(methoxy-d3)-2-naphthonitrile | +++ | 637.4 |
| 82 | 5-ethynyl-6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 619.2 |
| 83 | 7-(6,7-difluoro-5-methoxyisoquinolin-4-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | ++ | 629.4 |
| 84 | (1S,7S,8S)-8-fluoro-2-(8-fluoro-7-(6-fluoro-5-(methoxy-d3)isoquinolin-4-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane | +++ | 616.3 |
| 85 | 7-(5-chloro-6-fluoroisoquinolin-4-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | ++ | 615.2 |
| 86 | (1R,7S,8R)-8-fluoro-6-(8-fluoro-7-(7-fluoro-8-(methoxy-d3)naphthalen-1-yl)-2-(((2R,7aS)-2-fluorotetrabydro-1H-pyrrolizin-7a(5H)-yl)methoxy-d2)pyrido[4,3-d]pyrimidin-4-yl)-2-oxa-6-azabicyclo[5.1.0]octane | +++ | 615.4 |
| 87 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrabydro-1H-pyrrolizin-7a(5H)-yl)methoxy-d2)pyrido[4,3-d]pyrimidin-7-yl)naphthalen-2-amine | +++ | 621.1 |
| 88 | 6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine | +++ | 665.2 |
| 89 | 5-ethynyl-6-fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 621.2 |
| 90 | 6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 630.2 |
| 91 | 6-fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 630.1 |
| 92 | (1R,7S,8R)-8-fluoro-6-(8-fluoro-7-(7-fluoro-8-(fluoromethoxy)naphthalen-1-yl)-2-(((2R,7aS)-2-fluorotetrahydro-1H-pyrrolizin-7a(5H)-yl)methoxy-d2)pyrido[4,3-d]pyrimidin-4-yl)-2-oxa-6-azabicyclo[5.1.0]octane | +++ | 630.3 |
| 93 | 5-ethynyl-6,7,8-trifluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 657.2 |
| 94 | 5-ethynyl-6,7-difluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 635.2 |
| 95 | 7-(6,7-difluoro-8-(fluoromethoxy-d2)naphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | +++ | 648.3 |
| 96 | 5-ethynyl-6,8-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 637.2 |

TABLE 3-continued

| Example No. | Name | HTRF KRas G12V IC50 (nM) | Mass [M + H]+ |
|---|---|---|---|
| 97 | 7-(5-ethynyl-6-fluoroisoquinolin-4-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | +++ | 605.2 |
| 98 | 8-fluoro-7-(6-fluoro-5-methoxyisoquinolin-4-yl)-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | +++ | 611.2 |
| 99 | 5-ethynyl-6,7-difluoro-4-(8-fluoro-4-((1R,7S,8R)-8-fluoro-2-azabicyclo[5.1.0]oct-5-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 635.2 |
| 100 | 6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine | +++ | 645.2 |
| 101 | (1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane-6,6-d2 | +++ | 608.3 |
| 102 | (1S,7S,8S)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane | +++ | 634.1 |
| 103 | (1R,7R,8R)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane | + | 634.2 |
| 104 | (1S,7S,8S)-2-(2-(((R)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane | +++ | 634.3 |
| 105 | (1S,7S,8S)-2-(2-(((S)-2-(difluoromethylene)tetrahydro-1H-pyrrolizin-7a(5H)-yl)methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane | +++ | 652.3 |
| 106 | (1R,7R,8R)-2-(2-(((S)-2-(difluoromethylene)tetrahydro-1H-pyrrolizin-7a(5H)-yl)methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane | + | 652.4 |
| 107 | (1S,7S,8S)-2-(2-(((R)-2-(difluoromethylene)tetrahydro-1H-pyrrolizin-7a(5H)-yl)methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane | ++ | 652.3 |
| 108 | 5-ethynyl-6,8-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 639.1 |
| 109 | 7-(6,7-difluoro-8-(methoxy-d3)naphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | ++ | 631.3 |
| 110 | 8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)-7-(5,6,7-trifluoro-8-(methoxy-d3)naphthalen-1-yl)pyrido[4,3-d]pyrimidine | + | 649.4 |
| 111 | 7-(8-ethynyl-5,6,7-trifluoronaphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | + | 649.4 |
| 112 | 7-(8-ethynyl-5,7-difluoronaphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | ++ | 622.3 |
| 113 | (1S,7S,8S)-2-(7-(5-chloro-6-fluoroisoquinolin-4-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane | + | 617.2 |
| 114 | (1S,7S,8S)-2-(7-(5-ethynyl-6-fluoroisoquinolin-4-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane | +++ | 607.2 |

TABLE 3-continued

| Example No. | Name | HTRF KRas G12V IC50 (nM) | Mass [M + H]+ |
|---|---|---|---|
| 115 | 5-ethynyl-6,7,8-trifluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 657.5 |
| 116 | 6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine | +++ | 647.2 |
| 117 | 5-ethynyl-6,8-difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 639.1 |
| 118 | (1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane-8-d | +++ | 607.2 |
| 119 | 6,7,8-trifluoro-4-(8-fluoro-4-((1S,7S,8S)-8-fluoro-5-oxa-2-azabicyclo[5.1.0]octan-2-yl-8-d)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 667.2 |
| 120 | 6,7,8-trifluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)-5-(methoxy-d3)naphthalen-2-amine | +++ | 684.1 |
| 121 | 6,7,8-trifluoro-4-(8-fluoro-4-((1S,7S,8S)-8-fluoro-5-oxa-2-azabicyclo[5.1.0]octan-2-yl)-2-(((S)-6'-methylenetetrahydrospiro[cyclopropane-1,1'-pyrrolizin]-7a'(5'H)-yl)methoxy)pyrido[4,3-d]pyrimidin-7-yl)-5-(methoxy-d3)naphthalen-2-amine | +++ | 684.1 |
| 122 | (1S,7S,8S)-2-(7-(8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane-8-d | +++ | 625.2 |
| 123 | (1S,7S,8S)-8-fluoro-2-(8-fluoro-2-(((2R,7aS)-2-fluorotetrahydro-1H-pyrrolizin-7a(5H)-yl)methoxy-d2)-7-(5,6,7-trifluoro-8-(methoxy-d3)naphthalen-1-yl)pyrido[4,3-d]pyrimidin-4-yl)-5-oxa-2-azabicyclo[5.1.0]octane | ++ | 651.3 |
| 124 | 6,7,8-trifluoro-4-(8-fluoro-4-((1S,7S,8S)-8-fluoro-5-oxa-2-azabicyclo[5.1.0]octan-2-yl-6,6-d2)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 668.1 |
| 125 | 6,7,8-trifluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(methoxy-d3)naphthalen-2-amine | +++ | 658.1 |
| 126 | (1S,7S,8S)-8-fluoro-2-(8-fluoro-7-(6-fluoro-5-(fluoromethoxy)isoquinolin-4-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane | +++ | 631.2 |
| 127 | (1S,7S,8S)-8-fluoro-2-(8-fluoro-7-(6-fluoro-5-(fluoromethoxy-d2)isoquinolin-4-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane | + | 633.2 |
| 128 | 6,7,8-trifluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine | +++ | 683.2 |
| 129 | (1S,7S,8S)-2-(7-(8-ethynyl-7-fluoronaphthalen-1-yl)-8-fluoro-2-(((S,E)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane | +++ | 616.2 |
| 130 | (1S,7S,8S)-2-(7-(8-ethynyl-7-fluoronaphthalen-1-yl)-8-fluoro-2-(((S,Z)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane | +++ | 616.4 |
| 131 | 6,8-difluoro-4-(8-fluoro-4-((1S,7S,8S)-8-fluoro-5-oxa-2-azabicyclo[5.1.0]octan-2-yl)-2-(((2R,7aS)-2- | +++ | 684.2 |

TABLE 3-continued

| Example No. | Name | HTRF KRas G12V IC50 (nM) | Mass [M + H]$^+$ |
|---|---|---|---|
| | fluorotetrabydro-1H-pyrrolizin-7a(5H)-yl)methoxy-d2)pyrido[4,3-d]pyrimidin-7-yl)-5-(methoxy-d3)naphthalen-2-amine | | |
| 132 | 6,7,8-trifluoro-4-(8-fluoro-4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)-5-(methoxy-d3)naphthalen-2-amine | +++ | 676.2 |
| 133 | 6,7,8-trifluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(methoxy-d3)naphthalen-2-amine | +++ | 676.2 |
| 134 | 4-(2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 649.2 |
| 135 | (1S,7S,8S)-2-(7-(6,7-difluoro-5-(fluoromethoxy-d2)isoquinolin-4-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane | +++ | 651.2 |
| 136 | (1S,7S,8S)-2-(7-(6,7-difluoro-5-(methoxy-d3)isoquinolin-4-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane | ++ | 634.1 |
| 137 | 5-ethynyl-6,7-difluoro-4-(8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 635.3 |
| 138 | 5-ethynyl-6,7-difluoro-4-(8-fluoro-4-((1R,75,8R)-8-fluoro-2-azabicyclo[5.1.0]oct-4-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | + | 635.2 |
| 139 | 6,8-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine | +++ | 665.2 |
| 140 | 7-(5,7-difluoro-8-(methoxy-d3)naphthalen-1-yl)-8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidine | ++ | 631.3 |
| 141 | 6,8-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 646.3 |
| 142 | 4-(2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6,7,8-trifluoro-5-(methoxy-d3)naphthalen-2-amine | +++ | 694.2 |
| 143 | (1S,7S,8S)-2-(7-(8-ethynyl-7-fluoronaphthalen-1-yl)-8-fluoro-2-(((S)-2-methylenetetrahydro-1H-pyrrolizin-7a(5H)-yl)methoxy)pyrido[4,3-d]pyrimidin-4-yl)-8-fluoro-5-oxa-2-azabicyclo[5.1.0]octane | +++ | 598.2 |
| 144 | 6,7-difluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(fluoromethoxy-d2)naphthalen-2-amine | +++ | 657.2 |
| 145 | (1S,7S,8S)-8-fluoro-2-(8-fluoro-7-(7-fluoro-8-(fluoromethoxy-d2)naphthalen-1-yl)-2-(((S)-2-methylenetetrahydro-1H-pyrrolizin-7a(5H)-yl)methoxy)pyrido[4,3-d]pyrimidin-4-yl)-5-oxa-2-azabicyclo[5.1.0]octane | +++ | 624.3 |
| 146 | (1S,7S,8S)-2-(2-(((S)-2-(difluoromethylene)tetrahydro-1H-pyrrolizin-7a(5H)-yl)methoxy)-8-fluoro-7-(7-fluoro-8-(fluoromethoxy-d2)naphthalen-1-yl)pyrido[4,3-d]pyrimidin-4-yl)-8-fluoro-5-oxa-2-azabicyclo[5.1.0]octane | +++ | 660.5 |
| 147 | 7-(8-ethynyl-7-fluoronaphthalen-1-yl)-8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a(5H)-yl)methoxy-d2)pyrido[4,3-d]pyrimidine | +++ | 602.3 |

TABLE 3-continued

| Example No. | Name | HTRF KRas G12V IC50 (nM) | Mass [M + H]+ |
|---|---|---|---|
| 148 | 6,7,8-trifluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | ++ | 662.3 |
| 149 | 6,8-difluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | +++ | 644.2 |
| 150 | 5-ethynyl-6-fluoro-4-(8-fluoro-4-((1S,7R,8S)-8-fluoro-2-azabicyclo[5.1.0]oct-5-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 617.2 |
| 151 | (1S,7S,8S)-2-(7-(5,7-difluoro-8-(fluoromethoxy-d2)naphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane | +++ | 650.2 |
| 152 | 8-chloro-7-fluoro-1-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)isoquinolin-3-amine | ++ | 632.2 |
| 153 | 8-chloro-7-fluoro-1-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)isoquinolin-3-amine | ++ | 630.2/ 632.2 |
| 154 | 8-ethynyl-7-fluoro-1-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)isoquinolin-3-amine | +++ | 622.2 |
| 155 | 5-ethynyl-6-fluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)naphthalen-2-amine | +++ | 631.6 |
| 156 | (1S,7S,8S)-8-fluoro-2-(8-fluoro-7-(7-fluoro-8-(fluoromethoxy-d2)naphthalen-1-yl)-2-(((S,E)-2-(fluoromethylene)tetrahydro-1H-pyrrolizin-7a(5H)-yl)methoxy)pyrido[4,3-d]pyrimidin-4-yl)-5-oxa-2-azabicyclo[5.1.0]octane | +++ | 642.5 |
| 157 | (1S,7S,8S)-8-fluoro-2-(8-fluoro-7-(7-fluoro-8-(fluoromethoxy-d2)naphthalen-1-yl)-2-(((S,Z)-2-(fluoromethylene)tetrahydro-1H-pyrrolizin-7a(5H)-yl)methoxy)pyrido[4,3-d]pyrimidin-4-yl)-5-oxa-2-azabicyclo[5.1.0]octane | +++ | 642.2 |
| 158 | 5-ethynyl-6-fluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)naphthalen-2-amine | +++ | 613.6 |
| 159 | 6-(6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-4-methyl-5-(trifluoromethyl)pyridin-2-amine | +++ | 645.1 |
| 160 | 6-(6-chloro-8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-4-methyl-5-(trifluoromethyl)pyridin-2-amine | ++ | 645.2 |
| 161 | 5-ethynyl-6-fluoro-4-(8-fluoro-4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)naphthalen-2-amine | +++ | 631.2 |
| 162 | 6,7-difluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(fluoromethoxy-d2)naphthalen-2-amine | +++ | 675.2 |
| 163 | 3-cyclopropyl-5-(6,8-difluoro-4-((1S,7S,8S)-8-fluoro-5-oxa-2-azabicyclo[5.1.0]octan-2-yl)-2-(((2R,7aS)-2-fluorotetrabydro-1H-pyrrolizin-7a(5H)-yl)methoxy-d2)quinazolin-7-yl)-4-(trifluoromethyl)aniline | + | 654.6 |

TABLE 3-continued

| Example No. | Name | HTRF KRas G12V IC50 (nM) | Mass [M + H]+ |
|---|---|---|---|
| 164 | 3-cyclopropyl-5-(6,8-difluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-4-(trifluoromethyl)aniline | + | 654.5 |
| 165 | 3-cyclopropyl-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-(trifluoromethyl)aniline | ++ | 637.2 |
| 166 | (1S,7S,8S)-2-(7-(8-ethynyl-7-fluoronaphthalen-1-yl)-8-fluoro-2-(((R)-6'-methylenctetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane | +++ | 624.5 |
| 167 | 2-fluoro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-3-methyl-4-(trifluoromethyl)aniline | +++ | 629.3 |
| 168 | 3-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-methyl-4-(trifluoromethyl)aniline | + | 611.4 |
| 169 | 3-(6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-methyl-4-(trifluoromethyl)aniline | + | 628.2 |
| 170 | 3-(6,8-difluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-methyl-4-(trifluoromethyl)aniline | + | 628.2 |
| 171 | 5-ethynyl-6-fluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)naphthalen-2-amine | +++ | 639.2 |
| 172 | 6,8-difluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(methoxy-d3)naphthalen-2-amine | +++ | 658.2 |
| 173 | 6,8-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine | +++ | 663.2 |
| 174 | 5-ethynyl-6-fluoro-4-(8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 617.2 |
| 175 | 6-(6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-4-methyl-5-(trifluoromethyl)pyridin-2-amine | ++ | 629.2 |
| 176 | 6-(6,8-difluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-4-methyl-5-(trifluoromethyl)pyridin-2-amine | + | 629.3 |
| 177 | 5-(6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-2-fluoro-3-methyl-4-(trifluoromethyl)aniline | +++ | 646.2 |
| 178 | 5-(6,8-difluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-2-fluoro-3-methyl-4-(trifluoromethyl)aniline | + | 646.2 |
| 179 | 3-(6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-methyl-4-(trifluoromethyl)aniline | + | 644.4/646.4 |
| 180 | 3-(8-fluoro-4-((1S,7S,8S)-8-fluoro-5-oxa-2-azabicyclo[5.1.0]octan-2-yl)-2-(((2R,7aS)-2- | + | 610.4 |

TABLE 3-continued

| Example No. | Name | HTRF KRas G12V IC50 (nM) | Mass [M + H]+ |
|---|---|---|---|
| | fluorotetrahydro-1H-pyrrolizin-7a(5H)-yl)methoxy-d2)quinazolin-7-yl)-5-methyl-4-(trifluoromethyl)aniline | | |
| 181 | 3-(6-chloro-8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-methyl-4-(trifluoromethyl)aniline | + | 644.4/646.4 |
| 182 | 3-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-methyl-4-(trifluoromethyl)aniline | + | 610.4 |
| 183 | 3-(6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-cyclopropyl-4-(trifluoromethyl)aniline | + | 670.2/672.2 |
| 184 | 3-(6-chloro-8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-cyclopropyl-4-(trifluoromethyl)aniline | + | 670.2/672.2 |
| 185 | 5-ethynyl-6-fluoro-4-(8-fluoro-4-((1S,7S,8S)-8-fluoro-5-oxa-2-azabicyclo[5.1.0]octan-2-yl-8-d)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 622.5 |
| 186 | 6-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-methyl-5-(trifluoromethyl)pyridin-2-amine | ++ | 612.4 |
| 187 | 4-(2-(((S)-dihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 627.3 |
| 188 | 6-fluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(fluoromethoxy-d2)naphthalen-2-amine | +++ | 657.4 |
| 189 | 6-fluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(fluoromethoxy-d2)naphthalen-2-amine | +++ | 639.3 |
| 190 | 5-(6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-2-fluoro-3-methyl-4-(trifluoromethyl)aniline | ++ | 662.2 |
| 191 | 5-(6-chloro-8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-2-fluoro-3-methyl-4-(trifluoromethyl)aniline | + | 662.2 |
| 192 | 6,8-difluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(methoxy-d3)naphthalen-2-amine | +++ | 640.4 |
| 193 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl-2,5,5-d3)methoxy-d2)pyrido[4,3-d]pyrimidin-7-yl)naphthalen-2-amine | +++ | 624.3 |
| 194 | (1R,7S,8S)-2-(7-(3-amino-8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octan-5-one | ++ | 651.3 |
| 195 | (1S,7R,8S)-2-(7-(3-amino-8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octan-5-one | +++ | 651.1 |
| 196 | (1R,7S,8R)-2-(7-(3-amino-8-ethynyl-6,7-difluoronaphthalen-1-yl)-8-fluoro-2-(((2R,7aS)-2-fluorotetrahydro-1H-pyrrolizin-7a(5H)-yl)methoxy- | +++ | 651.2 |

TABLE 3-continued

| Example No. | Name | HTRF KRas G12V IC50 (nM) | Mass [M + H]+ |
|---|---|---|---|
| | d2)pyrido[4,3-d]pyrimidin-4-yl)-8-fluoro-2-azabicyclo[5.1.0]octan-5-one | | |
| 197 | (1S,7R,8R)-2-(7-(3-amino-8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octan-5-one | ++ | 651.2 |
| 198 | 4-(2-(((2R,6R,7aS)-2-(aminomethyl)-6-fluorotetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-ol | ++ | 649.5 |
| 199 | 6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-vinylnaphthalen-2-amine | +++ | 623.4 |
| 200 | 4-(2-(((S)-dihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine | +++ | 653.2 |
| 201 | 5-ethyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 625.4 |
| 202 | 5-ethynyl-6-fluoro-4-(8-fluoro-4-((1S,7S,8S)-8-fluoro-5-oxa-2-azabicyclo[5.1.0]octan-2-yl)-2-(((6'R,7a'R)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine | +++ | 650.1 |
| 203 | 5-ethynyl-6-fluoro-4-(8-fluoro-4-((1S,7S,8S)-8-fluoro-5-oxa-2-azabicyclo[5.1.0]octan-2-yl)-2-(((6'S,7a'R)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine | +++ | 650.1 |
| 204 | 5-ethynyl-6-fluoro-4-(8-fluoro-4-((1S,7S,8S)-8-fluoro-5-oxa-2-azabicyclo[5.1.0]octan-2-yl)-2-(((6'S,7a'S)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine | +++ | 650.1 |
| 205 | 5-ethynyl-6-fluoro-4-(8-fluoro-4-((1S,7S,8S)-8-fluoro-5-oxa-2-azabicyclo[5.1.0]octan-2-yl)-2-(((6'R,7a'S)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine | +++ | 650.2 |
| 206 | 4-(2-(((R)-dihydro-5'H-dispiro[cyclopropane-1,1'-pyrrolizine-6',1''-cyclopropan]-7a'(7'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 653.3 |
| 207 | 4-(2-(((S)-dihydro-5'H-dispiro[cyclopropane-1,1'-pyrrolizine-6',1''-cyclopropan]-7a'(7'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 653.3 |
| 208 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-methyltetrahydro-1H-pyrrolizin-7a(5H)-yl)methoxy)pyrido[4,3-d]pyrimidin-7-yl)naphthalen-2-amine | +++ | 615.1 |
| 209 | 5-ethynyl-6-fluoro-4-(8-fluoro-4-((1S,7S,8S)-8-fluoro-5-oxa-2-azabicyclo[5.1.0]octan-2-yl)-2-(((2S,7aS)-2-methyltetrahydro-1H-pyrrolizin-7a(5H)-yl)methoxy)pyrido[4,3-d]pyrimidin-7-yl)naphthalen-2-amine | +++ | 615.2 |
| 210 | 4-(2-(((1R,7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 663.2 |
| 211 | 4-(2-(((1S,7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 663.3 |

TABLE 3-continued

| Example No. | Name | HTRF KRas G12V IC50 (nM) | Mass [M + H]+ |
|---|---|---|---|
| 212 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy)pyrido[4,3-d]pyrimidin-7-yl)naphthalen-2-amine | +++ | 619.2 |
| 213 | 5-ethynyl-6-fluoro-4-(8-fluoro-4-((1S,7S,8S)-8-fluoro-5-oxa-2-azabicyclo[5.1.0]octan-2-yl)-2-((tetrahydro-1H-pyrrolizin-7a(5H)-yl)methoxy-d2)pyrido[4,3-d]pyrimidin-7-yl)naphthalen-2-amine | +++ | 603.2 |
| 214 | 6-fluoro-4-(8-fluoro-4-((1S,7S,8S)-8-fluoro-5-oxa-2-azabicyclo[5.1.0]octan-2-yl)-2-(((2S,7aS)-2-methyltetrahydro-1H-pyrrolizin-7a(5H)-yl)methoxy)pyrido[4,3-d]pyrimidin-7-yl)-5-(fluoromethoxy-d2)naphthalen-2-amine | +++ | 641.1 |
| 215 | 6-fluoro-4-(8-fluoro-4-((1S,7S,8S)-8-fluoro-5-oxa-2-azabicyclo[5.1.0]octan-2-yl)-2-(((2R,7aS)-2-methyltetrahydro-1H-pyrrolizin-7a(5H)-yl)methoxy)pyrido[4,3-d]pyrimidin-7-yl)-5-(fluoromethoxy-d2)naphthalen-2-amine | +++ | 641.2 |
| 216 | 5-ethynyl-6-fluoro-4-(8-fluoro-4-((1S,7R,8S)-8-fluoro-2-azabicyclo[5.1.0]octan-2-yl)-2-(((2R,7aS)-2-fluorotetrabydro-1H-pyrrolizin-7a(5H)-yl)methoxy-d2)pyrido[4,3-d]pyrimidin-7-yl)naphtbalen-2-ol | +++ | 620.2 |
| 217 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol | +++ | 622.1 |
| 218 | 4-(2-(((6'S,7a'R)-2'',2''-difluorodihydro-5'H-dispiro[cyclopropane-1,1'-pyrrolizine-6',1''-cyclopropan]-7a'(7'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 689.3 |
| 219 | 4-(2-(((6'R,7a'R)-2'',2''-difluorodihydro-5'H-dispiro[cyclopropane-1,1'-pyrrolizine-6',1''-cyclopropan]-7a'(7'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 689.3 |
| 220 | 4-(2-(((S)-2,2-difluorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 639.2 |
| 221 | 5-ethynyl-6-fluoro-4-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | + | 621.2 |
| 222 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-5-methoxypyrido[4,3-d]pyrimidin-7-yl)naphthalen-2-amine | +++ | 651.3 |
| 223 | 5-ethynyl-6-fluoro-4-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-5-methoxypyrido[4,3-d]pyrimidin-7-yl)naphthalen-2-amine | + | 651.2 |
| 224 | 5-ethynyl-6-fluoro-4-(8-fluoro-4-((1R,7R,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | + | 621.3 |
| 225 | 5-ethynyl-6-fluoro-4-(8-fluoro-4-((1S,7S,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 621.2 |
| 226 | 2-fluoro-5-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)-3-methyl-4-(trifluoromethyl)aniline | +++ | 647.4 |
| 227 | 4-(2-(((S)-dihydro-5'H-dispiro[cyclopropane-1,1'-pyrrolizine-6',1''-cyclopropan]-7a'(7'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine | +++ | 679.3 |
| 228 | 4-(2-(((R)-dihydro-5'H-dispiro[cyclopropane-1,1'-pyrrolizine-6',1''-cyclopropan]-7a'(7'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine | +++ | 679.1 |

TABLE 3-continued

| Example No. | Name | HTRF KRas G12V IC50 (nM) | Mass [M + H]$^+$ |
|---|---|---|---|
| 229 | 4-(2-(((1S,7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine | +++ | 689.1 |
| 230 | 4-(2-(((1R,7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine | +++ | 689.1 |
| 231 | 5-ethynyl-6-fluoro-4-(8-fluoro-4-((1S,7S,8S)-8-fluoro-5-oxa-2-azabicyclo[5.1.0]octan-2-yl)-2-(((2"R,6'S,7a'R)-2"-fluorodihydro-5'H-dispiro[cyclopropane-1,1'-pyrrolizine-6',1"-cyclopropan]-7a'(7'H)-yl)methoxy)pyrido[4,3-d]pyrimidin-7-yl)naphthalen-2-amine | +++ | 671.0 |
| 232 | 5-ethynyl-6-fluoro-4-(8-fluoro-4-((1S,7S,8S)-8-fluoro-5-oxa-2-azabicyclo[5.1.0]octan-2-yl)-2-(((2"S,6'S,7a'R)-2"-fluorodihydro-5'H-dispiro[cyclopropane-1,1'-pyrrolizine-6',1"-cyclopropan]-7a'(7'H)-yl)methoxy)pyrido[4,3-d]pyrimidin-7-yl)naphthalen-2-amine | +++ | 671.3 |
| 233 | 5-ethynyl-6-fluoro-4-(8-fluoro-4-((1S,7S,8S)-8-fluoro-5-oxa-2-azabicyclo[5.1.0]octan-2-yl)-2-(((2"R,6'R,7a'R)-2"-fluorodihydro-5'H-dispiro[cyclopropane-1,1'-pyrrolizine-6',1"-cyclopropan]-7a'(7'H)-yl)methoxy)pyrido[4,3-d]pyrimidin-7-yl)naphthalen-2-amine | +++ | 671.3 |
| 234 | 5-ethynyl-6-fluoro-4-(8-fluoro-4-((1S,7S,8S)-8-fluoro-5-oxa-2-azabicyclo[5.1.0]octan-2-yl)-2-(((2"S,6'R,7a'R)-2"-fluorodihydro-5'H-dispiro[cyclopropane-1,1'-pyrrolizine-6',1"-cyclopropan]-7a'(7'H)-yl)methoxy)pyrido[4,3-d]pyrimidin-7-yl)naphthalen-2-amine | +++ | 671.2 |
| 235 | (1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)-5-methoxypyrido[4,3-d]pyrimidin-4-yl)-8-fluoro-5-oxa-2-azabicyclo[5.1.0]octane | + | 636.3 |
| 236 | (1R,7R,8R)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)-5-methoxypyrido[4,3-d]pyrimidin-4-yl)-8-fluoro-5-oxa-2-azabicyclo[5.1.0]octane | + | 636.3 |
| 237 | 4-(2-(((2S,7aS)-2-chlorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 637.1 |
| 238 | 4-(2-(((2R,7aS)-2-chlorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 637.1 |
| 239 | 5-ethynyl-6-fluoro-4-(8-fluoro-2-(((2R,7aS)-2-fluoro-5,5-dimethyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine | +++ | 647.3 |
| 240 | 4-(4-(8,8-dichloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | + | 671.4 |
| 241 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-5-methoxypyrido[4,3-d]pyrimidin-7-yl)naphthalen-2-ol | +++ | 652,2 |
| 242 | 5-ethynyl-6-fluoro-4-(8-fluoro-4-((1S,7S,8S)-8-fluoro-5-oxa-2-azabicyclo[5.1.0]octan-2-yl)-2-(((6'R,7a'R)-6'-methyltetrahydrospiro[cyclopropane-1,1'-pyrrolizin]-7a'(5'H)-yl)methoxy)pyrido[4,3-d]pyrimidin-7-yl)naphthalen-2-amine | +++ | 641.3 |
| 243 | 5-ethynyl-6-fluoro-4-(8-fluoro-4-((1S,7S,8S)-8-fluoro-5-oxa-2-azabicyclo[5.1.0]octan-2-yl)-2-(((6'S,7a'S)-6'-methyltetrahydrospiro[cyclopropane-1,1'-pyrrolizin]-7a'(5'H)-yl)methoxy)pyrido[4,3-d]pyrimidin-7-yl)naphthalen-2-amine | +++ | 641.2 |
| 244 | 5-ethynyl-6-fluoro-4-(8-fluoro-4-((1S,7S,8S)-8-fluoro-5-oxa-2-azabicyclo[5.1.0]octan-2-yl)-2-(((S)-6'-methyl-2',3'-dihydrospiro[cyclopropane-1,1'-pyrrolizin]-7a'(5'H)-yl)methoxy)pyrido[4,3-d]pyrimidin-7-yl)naphthalen-2-amine | +++ | 639.2 |

TABLE 3-continued

| Example No. | Name | HTRF KRas G12V IC50 (nM) | Mass [M + H]$^+$ |
|---|---|---|---|
| 245 | N-(((2R,6R,7aS)-7a-(((7-(8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-2-yl)methyl)acetamide | ++ | 675.2 |
| 246 | ((2R,6R,7aS)-7a-(((7-(8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-2-yl)methanamine | + | 633.3 |
| 247 | 4-(4-((1S,7S,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | ++ | 637.2/ 639.2 |
| 248 | 4-(4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | +++ | 637.1 |
| 249 | 4-(4-((1R,7R,8R)-8-chloro-5-oxa-2-azabicyclo[5.1.0]octan-2-yl)-8-fluoro-2-(((2R,7aS)-2-fluorotetrabydro-1H-pyrrolizin-7a(5H)-yl)methoxy-d2)pyrido[4,3-d]pyrimidin-7-yl)-5-ethynyl-6-fluoronaphthalen-2-amine | +++ | 637.1 |
| 250 | 4-(4-((1R,7R,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | ++ | 637.4/ 639.4 |
| 251 | 5-ethynyl-6-fluoro-4-(8-fluoro-4-((1S,7S,8S)-8-fluoro-5-oxa-2-azabicyclo[5.1.0]octan-2-yl)-2-(((6'S,7a'R)-6'-metbyltetrahydrospiro[cyclopropane-1,1'-pyrrolizin]-7a'(5'H)-yl)methoxy)pyrido[4,3-d]pyrimidin-7-yl)naphthalen-2-amine | +++ | 641.3 |
| 252 | 5-ethynyl-6-fluoro-4-(8-fluoro-4-((1S,7S,8S)-8-fluoro-5-oxa-2-azabicyclo[5.1.0]octan-2-yl)-2-(((1S,2S,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine | +++ | 645.2 |
| 253 | 5-ethynyl-6-fluoro-4-(8-fluoro-4-((1S,7S,8S)-8-fluoro-5-oxa-2-azabicyclo[5.1.0]octan-2-yl)-2-(((1S,2R,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine | +++ | 645.2 |
| 254 | 5-ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine | +++ | 645.1 |
| 255 | 5-ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine | +++ | 645.2 |
| 256 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-7-d-2-amine | +++ | 622.1 |
| 257 | N-(((2R,6R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-2-yl)methyl)acetamide | ++ | 690.3 |
| 258 | 4-(2-(((2R,6R,7aS)-2-(aminomethyl)-6-fluorotetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | ++ | 648.2 |
| 259 | 5-ethynyl-6-fluoro-4-(8-fluoro-2-(((2R,5S,7aS)-2-fluoro-5-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine | +++ | 633.2 |

TABLE 3-continued

| Example No. | Name | HTRF KRas G12V IC50 (nM) | Mass [M + H]+ |
|---|---|---|---|
| 260 | 6-chloro-5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol | +++ | 638.2, 640.2 |
| 261 | 5-ethynyl-6-fluoro-4-(4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 603.3 |
| 262 | 5-ethynyl-6-fluoro-4-(8-fluoro-2-(((2R,7aS)-2-fluoro-3,3-dimethyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine | +++ | 647.5 |
| 263 | N-(5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-yl)acetamide | ++ | 663.2 |
| 264 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-8-d-2-amine | +++ | 622.3 |
| 265 | 5-ethynyl-6-fluoro-4-(8-fluoro-4-((1S,7S,8S)-8-fluoro-5-oxa-2-azabicyclo[5.1.0]octan-2-yl)-2-(((2S,7aS)-2-(fluorometbyl)tetrahydro-1H-pyrrolizin-7a(5H)-yl)methoxy-d2)pyrido[4,3-d]pyrimidin-7-yl)naphthalen-2-amine | +++ | 635.3 |
| 266 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-(fluoromethyl)tetrahydro-1H-pyrrolizin-7a(5H)-yl)methoxy-d2)pyrido[4,3-d]pyrimidin-7-yl)naphthalen-2-amine | +++ | 635.3 |
| 267 | 6-chloro-5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 637.2, 637.2 |
| 268 | 5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | +++ | 603.4 |
| 269 | 4-(8-chloro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | +++ | 637.2, 639.2 |
| 270 | 3-cyclopropyl-2-fluoro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-(trifluoromethyl)aniline | ++ | 655.2 |
| 271 | 2-fluoro-3-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-methyl-4-(trifluoromethyl)aniline | ++ | 629.4 |
| 272 | 3-chloro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-(trifluoromethyl)aniline | +++ | 631.2 |
| 273 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-7,8-d2-2-amine | +++ | 623.3 |
| 274 | 5-ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl-5',5'-d2)methoxy-d2)pyrido[4,3-d]pyrimidin-7-yl)naphthalen-2-amine | +++ | 649.1 |
| 275 | 5-ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl-5',5'-d2)methoxy-d2)pyrido[4,3-d]pyrimidin-7-yl)naphthalen-2-amine | +++ | 649.3 |
| 276 | (2R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizine-2-carbonitrile | +++ | 628.3 |

TABLE 3-continued

| Example No. | Name | HTRF KRas G12V IC50 (nM) | Mass [M + H]+ |
|---|---|---|---|
| 277 | 5-ethynyl-6-fluoro-4-(8-fluoro-2-(((2R,3R,7aS)-2-fluoro-3-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine | +++ | 633.2 |
| 278 | 5-ethynyl-6-fluoro-4-(8-fluoro-2-(((2R,3S,7aS)-2-fluoro-3-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine | +++ | 633.4 |
| 279 | 2,6-difluoro-3-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-methyl-4-(trifluoromethyl)aniline | ++ | 647.1 |
| 280 | 4-(4-((1R,7S)-2-oxa-6-azabicyclo[5.1.0]octan-6-yl)-8-fluoro-2-(((R)-1-methylpyrrolidin-2-yl)methoxy)pyrido[4,3-d]pyrimidin-7-yl)-5-ethynyl-6-fluoronaphthalen-2-ol | ++ | 558.1 |
| 281 | 4-(4-((1S,7R)-2-oxa-6-azabicyclo[5.1.0]octan-6-yl)-8-fluoro-2-(((R)-2-methylpyrrolidin-2-yl)methoxy)pyrido[4,3-d]pyrimidin-7-yl)-5-ethynyl-6-fluoronaphthalen-2-ol | + | 558.3 |
| 282 | 4-(4-((1R,7S)-2-oxa-6-azabicyclo[5.1.0]octan-6-yl)-8-fluoro-2-(((R)-2-methylpyrrolidin-2-yl)methoxy)pyrido[4,3-d]pyrimidin-7-yl)-5-ethynyl-6-fluoronaphthalen-2-ol | + | 558.3 |
| 283 | 4-(4-((1S,7R)-2-oxa-6-azabicyclo[5.1.0]octan-6-yl)-2-(((R)-1,2-dimethylpyrrolidin-2-yl)methoxy)-8-fluoropyrido[4,3-d]pyrimidin-7-yl)-5-ethynyl-6-fluoronaphthalen-2-ol | +++ | 572.3 |
| 284 | 5-ethynyl-6-fluoro-4-(8-fluoro-4-((1S,7S,8S)-8-fluoro-5-oxa-2-azabicyclo[5.1.0]octan-2-yl)-2-(((R)-1-methylpyrrolidin-2-yl)methoxy)pyrido[4,3-d]pyrimidin-7-yl)naphthalen-2-ol | +++ | 576.4 |
| 285 | 5-ethynyl-6-fluoro-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol | +++ | 576.3 |
| 286 | (2S,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizine-2-carbonitrile | +++ | 628.2 |
| 287 | 5-ethynyl-6-fluoro-4-(8-fluoro-2-(((2R,5R,7aS)-2-fluoro-5-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine | +++ | 633.5 |
| 288 | 5-ethynyl-6-fluoro-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-amine | +++ | 575.3 |
| 289 | 3-chloro-2-fluoro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-(trifluoromethyl)aniline | +++ | 649.3, 651.3 |
| 290 | (1S,7S,8S)-8-chloro-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane | +++ | 622.1 |
| 291 | 4-(5-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | +++ | 655.0, 657.0 |
| 292 | 4-(4-(8,8-dichloro-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | ++ | 671.3 |
| 293 | 6-chloro-4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-cthynylnaphthalen-2-amine | n/a | 667.2, 669.2 |

TABLE 3-continued

| Example No. | Name | HTRF KRas G12V IC50 (nM) | Mass [M + H]$^+$ |
|---|---|---|---|
| 294 | 6-chloro-5-ethynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol | +++ | 592.2, 594.2 |
| 295 | 5-ethynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol | +++ | 558.2 |
| 296 | 6-chloro-5-cthynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-amine | +++ | 591.2. 593.2 |
| 297 | 5-ethynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-amine | +++ | 557.3 |
| 298 | 3-chloro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-(trifluoromethyl)phenol | +++ | 632.2, 634.2 |
| 299 | 2-fluoro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-4-(trifluoromethyl)aniline | ++ | 615.3 |
| 300 | 5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol | +++ | 604.4 |
| 301 | 4-(4-((1R,7R,8R)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynyl-6-fluoronaphthalen-2-amine | ++ | 591.2 |
| 302 | 4-(4-((1S,7S,8S)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynyl-6-fluoronaphthalen-2-amine | +++ | 591.2, 593.2 |
| 303 | 4-(5,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-cthynyl-6-fluoronaphthalen-2-amine | +++ | 639.0 |
| 304 | (1S,5S,7R,8S)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile | +++ | 644.3 |
| 305 | (1R,5S,7S,8R)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile | ++ | 644.3 |
| 306 | (1S,5R,7R,8S)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile | ++ | 644.2 |
| 307 | (1R,5R,7S,8R)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile | ++ | 644.4 |
| 308 | (1S,5S,7R,8R)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile | ++ | 644.2 |
| 309 | (1R,5R,7S,8S)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile | ++ | 644.2 |

TABLE 3-continued

| Example No. | Name | HTRF KRas G12V IC50 (nM) | Mass [M + H]+ |
|---|---|---|---|
| 310 | (1S,5R,7R,8R)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-2-azabicyclo[5.1.0]octane-5-carbonitrile | ++ | 644.3 |
| 311 | (1R,5S,7S,8S)-2-(7-(3-amino-8-ethynyl-7-fluoronaphthalen-1-yl)-8-fluoro-2-(((2R,7aS)-2-fluorotetrahydro-1H-pyrrolizin-7a(5H)-yl)metboxy-d2)pyrido[4,3-d]pyrimidin-4-yl)-8-fluoro-2-azabicyclo[5.1.0]octane-5-carbonitrile | ++ | 644.3 |
| 312 | 5-ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy-d2)pyrido[4,3-d]pyrimidin-7-yl)naphthalen-2-amine | +++ | 647.2 |
| 313 | 5-ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl)methoxy-d2)pyrido[4,3-d]pyrimidin-7-yl)naphthalen-2-amine | +++ | 647.1 |
| 314 | 2-((2R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizin-2-yl)acetonitrile | +++ | 642.3 |
| 315 | 2-((2S,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizin-2-yl)acetonitrile | +++ | 642.3 |
| 316 | 4-(4-((1R,7S,8R)-8-chloro-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | +++ | 637.2, 639.2 |
| 317 | 4-(4-((1S,7R,8S)-8-chloro-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | ++ | 637.2. 639.2 |
| 318 | (1S,7S,8S)-2-(7-(7-chloro-8-ethynylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane | +++ | 622.3, 624.3 |
| 319 | (1S,7S,8S)-2-(7-(8-ethynylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-S-oxa-2-azabicyclo[5.1.0]octane | +++ | 588.4 |
| 320 | (1S,7S,8S)-8-chloro-2-(7-(7-chloro-8-ethynylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane | +++ | 638.2, 640.2 |
| 321 | 6-chloro-4-(4-((1S,7S,8S)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine | +++ | 607.0, 609.0 |
| 322 | 4-(4-((1S,7S,8S)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine | +++ | 573.2 |
| 323 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-5-isopropoxypyrido[4,3-d]pyrimidin-7-yl)naphthalen-2-amine | +++ | 679.2 |
| 324 | 5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-6-methylnaphthalen-2-ol | +++ | 618.3 |
| 325 | (1S,7S,8S)-2-(7-(8-ethynyl-7-methylnaphthalen-1-yl)-8-fluoro-2-(((2R,7aS)-2-fluorotetrahydro-1H- | +++ | 602.3 |

TABLE 3-continued

| Example No. | Name | HTRF KRas G12V IC50 (nM) | Mass [M + H]+ |
|---|---|---|---|
| | pyrrolizin-7a(5H)-yl)methoxy-d2)pyrido[4,3-d]pyrimidin-4-yl)-8-fluoro-5-oxa-2-azabicyclo[5.1.0]octane | | |
| 326 | 6-chloro-4-(4-((1R,7R,8R)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine | ++ | 607.0 |
| 327 | 4-(4-((1R,7R,8R)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-cthynylnaphthalen-2-amine | ++ | 573.1 |
| 328 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-6-(trifluoromethyl)quinazolin-7-yl)naphthalen-2-amine | + | 688.4 |
| 329 | 5-ethynyl-6-fluoro-4-(4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-yl)naphthalen-2-amine | +++ | 617.4 |
| 330 | 2-fluoro-5-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-3-methyl-4-(trifluoromethyl)phenol | ++ | 630.3 |
| 331 | 5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-6-methylnaphthalen-2-amine | +++ | 617.3 |
| 332 | (1S,7S,8S)-2-(7-(8-ethynyl-7-(trifluoromethyl)naphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane | ++ | 656.3 |
| 333 | 5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine | +++ | 635.2 |
| 334 | 5-ethynyl-6-fluoro-4-(8-fluoro-2-(((2R,3S,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine | +++ | 635.3 |
| 335 | 3-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-methyl-4-(trifluoromethyl)phenol | +++ | 612.2 |
| 336 | ((2R,6R,7aS)-7a-(((7-(8-cthynyl-7-(trifluoromethyl)naphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorobexahydro-1H-pyrrolizin-2-yl)mcthanamine | + | 683.4 |
| 337 | 6-chloro-5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine | +++ | 651.2. 653.2 |
| 338 | 5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine | +++ | 617.2 |
| 339 | 4-(4-((1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-cthynyl-6-fluoronaphthalen-2-amine | + | 651.2, 653.2 |
| 340 | 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3- | +++ | 651.2, 653.2 |

TABLE 3-continued

| Example No. | Name | HTRF KRas G12V IC50 (nM) | Mass [M + H]+ |
|---|---|---|---|
| | d]pyrimidin-7-yl)-5-ethynyl-6-fluoronaphthalen-2-amine | | |
| 341 | 4-(4-((1R,7S,8R)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | + | 635.1, 637.1 |
| 342 | 4-(4-((1S,7R,8S)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-cthynyl-6-fluoronaphthalen-2-amine | +++ | 635.1, 637.1 |
| 343 | 4-(4-((1R,7S,8S)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | + | 635.1, 637.1 |
| 344 | 4-(4-((1S,7R,8R)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | + | 635.1, 637.1 |
| 345 | 6-chloro-4-(4-((1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynylnaphthalen-2-amine | + | 667.2, 669.2 |
| 346 | 4-(4-((1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynylnaphthalen-2-amine | + | 633.2 |
| 347 | 4-(4-((1R,7R,8R)-8-chloro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy)pyrido[4,3-d]pyrimidin-7-yl)-5-ethynyl-6-fluoronaphthalen-2-amine | + | 651.3 |
| 348 | 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-cthynylnaphthalen-2-amine | +++ | 633.2 |
| 349 | (S)-7-(2-amino-3-cyano-7-fluorobenzo[b]thiophen-4-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazoline-6-carbonitrile | +++ | 652.3 |
| 350 | 2-amino-4-((R)-6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-7-fluorobenzo[b]thiophene-3-carbonitrile | +++ | 661.1 |
| 351 | (R)-7-(2-amino-3-cyano-7-fluorobenzo[b]thiophen-4-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazoline-6-carbonitrile | + | 652.3 |
| 352 | 2-amino-4-((S)-6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-7-fluorobenzo[b]thiophene-3-carbonitrile | + | 661.1 |
| 353 | 7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazoline-6-carbonitrile | +++ | 645.4 |
| 354 | 4-(6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-amine | +++ | 653.9 |
| 355 | 4-(6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy- | +++ | 638.3 |

TABLE 3-continued

| Example No. | Name | HTRF KRas G12V IC50 (nM) | Mass [M + H]+ |
|---|---|---|---|
| | d2)quinazolin-7-yl)-5-ethynyl-6-fluoronaphthalen-2-amine | | |
| 356 | 2-amino-4-((R)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-7-fluorobenzo[b]thiophene-3-carbonitrile | + | 645.0 |
| 357 | 2-amino-4-((S)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-7-fluorobenzo[b]thiophene-3-carbonitrile | +++ | 645.0 |
| 358 | (S)-7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazoline-6-carbonitrile | +++ | 645.3 |
| 359 | 4-((R)-6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-amine | +++ | 654.3 |
| 360 | (R)-7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazoline-6-carbonitrile | + | 645.3 |
| 361 | 4-((S)-6-chloro-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-amine | + | 654.3 |
| 362 | 5-ethynyl-6-fluoro-4-(8-fluoro-4-((1S,7S,8S)-8-fluoro-5-oxa-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine | +++ | 657.0 |
| 363 | 5-ethynyl-6-fluoro-4-(8-fluoro-4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine | +++ | 657.3 |
| 364 | 5-ethynyl-6-fluoro-4-(8-fluoro-2-(((6R,7aR)-6-fluoro-1-methylenetetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine | +++ | 633.1 |
| 365 | 2-amino-7-fluoro-4-((S)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-6-(trifluoromethyl)quinazolin-7-yl)benzo[b]thiophene-3-carbonitrile | +++ | 695.0 |
| 366 | 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-methylnaphthalen-2-amine | +++ | 647.0 |
| 367 | 3-chloro-5-(8-fluoro-4-((1S,7R,8S)-8-fluoro-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-4-(trifluoromethyl)aniline | +++ | 621.2, 623.2 |
| 368 | 3-chloro-5-(8-fluoro-4-((1R,7S,8R)-8-fluoro-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-4-(trifluoromethyl)aniline | + | 621.2 |
| 369 | 3-chloro-5-(2-(((S)-2-(difluoromethylene)tetrahydro-1H-pyrrolizin-7a(5H)-yl)methoxy)-8-fluoro-4-((1S,7R,8S)-8-fluoro-2-azabicyclo[5.1.0]octan-2-yl)pyrido[4,3-d]pyrimidin-7-yl)-4-(trifluoromethyl)aniline | ++ | 657.2 |

TABLE 3-continued

| Example No. | Name | HTRF KRas G12V IC50 (nM) | Mass [M + H]$^+$ |
|---|---|---|---|
| 370 | 3-chloro-5-(2-(((S)-2-(difluoromethylene)tetrahydro-1H-pyrrolizin-7a(5H)-yl)methoxy)-8-fluoro-4-((1R,7S,8R)-8-fluoro-2-azabicyclo[5.1.0]octan-2-yl)pyrido[4,3-d]pyrimidin-7-yl)-4-(trifluoromethyl)aniline | + | 657.2 |
| 371 | 3-chloro-5-(8-fluoro-4-((1S,7R,8S)-8-fluoro-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)-4-(trifluoromethyl)aniline | +++ | 639.2 |
| 372 | 3-chloro-5-(8-fluoro-4-((1R,7S,8R)-8-fluoro-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)-4-(trifluoromethyl)aniline | + | 639.0 |
| 373 | 3-chloro-5-(8-fluoro-4-((1S,7R,8S)-8-fluoro-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-4-(trifluoromethyl)aniline | +++ | 639.2 |
| 374 | 3-chloro-5-(8-fluoro-4-((1R,7S,8R)-8-fluoro-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-4-(trifluoromethyl)aniline | + | 639.2, 641.2 |
| 375 | (1S,7S,8S)-2-(7-(8-ethynyl-7-fluoronaphthalen-1-yl)-8-fluoro-2-(((R,E)-6'-(fluoromethylene)tetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane | +++ | 642.1 |
| 376 | (1S,7S,8S)-2-(7-(8-ethynyl-7-fluoronaphthalen-1-yl)-8-fluoro-2-(((R,Z)-6'-(fluoromethylene)tetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane | +++ | 642.3 |
| 377 | (R,E)-7a'-(((7-(8-ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yl)oxy)methyl)-6'-(fluoromethylene)hexahydrospiro[cyclopropane-1,1'-pyrrolizine] | +++ | 640.1 |
| 378 | 3-chloro-5-(8-fluoro-4-((1S,7R,8S)-8-fluoro-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)-4-(trifluoromethyl)aniline | ++ | 665.1, 657.1 |
| 379 | 2-fluoro-5-(8-fluoro-4-((1S,7R,8S)-8-fluoro-2-azabicyclo[5.1.0]octan-2-yl)-2-(((R)-6'-methylenetetrahydrospiro[cyclopropane-1,1'-pyrrolizin]-7a(5'H)-yl)methoxy)pyrido[4,3-d]pyrimidin-7-yl)-3-methyl-4-(trifluoromethyl)aniline | ++ | 645.2 |
| 380 | 2-fluoro-5-(8-fluoro-4-((1S,7R,8S)-8-fluoro-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)-3-methyl-4-(trifluoromethyl)aniline | ++ | 663.2 |
| 381 | 2-fluoro-5-(8-fluoro-4-((1S,7R,8S)-8-fluoro-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)-3-methyl-4-(trifluoromethyl)aniline | ++ | 663.1 |
| 382 | (R,E)-7a'-(((8-fluoro-7-(7-fluoro-8-(fluoromethoxy-d2)naphthalen-1-yl)-4-((1S,7R,8S)-8-fluoro-2-azabicyclo[5.1.0]octan-2-yl)pyrido[4,3-d]pyrimidin-2-yl)oxy)methyl)-6'-(fluoromethylene)hexahydrospiro[cyclopropane-1,1'-pyrrolizine] | +++ | 666.2 |
| 383 | 6-fluoro-4-(8-fluoro-4-((1S,7R,8S)-8-fluoro-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine | +++ | 681.1 |
| 384 | (1S,7S,8S)-8-fluoro-2-(8-fluoro-7-(7-fluoro-8-(fluoromethoxy-d2)naphthalen-1-yl)-2-(((R)-6'-methylenetetrahydrospiro[cyclopropane-1,1'-pyrrolizin]-7a'(5'H)-yl)methoxy)pyrido[4,3-d]pyrimidin-4-yl)-5-oxa-2-azabicyclo[5.1.0]octane | +++ | 650.2 |

TABLE 3-continued

| Example No. | Name | HTRF KRas G12V IC50 (nM) | Mass [M + H]+ |
|---|---|---|---|
| 385 | (1S,7S,8S)-8-fluoro-2-(8-fluoro-7-(7-fluoro-8-(fluoromethoxy-d2)naphthalen-1-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-4-yl)-5-oxa-2-azabicyclo[5.1.0]octane | +++ | 668.1 |
| 386 | (1S,7S,8S)-8-fluoro-2-(8-fluoro-7-(7-fluoro-8-(fluoromethoxy-d2)naphthalen-1-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-4-yl)-5-oxa-2-azabicyclo[5.1.0]octane | +++ | 668.3 |
| 387 | 6-fluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine | +++ | 665.2 |
| 388 | 6-fluoro-4-(8-fluoro-4-((1S,7S,8S)-8-fluoro-5-oxa-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine | +++ | 683.2 |
| 389 | 6-fluoro-4-(8-fluoro-4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine | +++ | 683.2 |
| 390 | 2-amino-7-fluoro-4-((R)-8-fluoro-4-((1S,7S,8S)-8-fluoro-5-oxa-2-azabicyclo[5.1.0]octan-2-yl)-2-(((2R,7aS)-2-fluorotetrabydro-1H-pyrrolizin-7a(5H)-yl)methoxy-d2)-6-(trifluoromethyl)quinazolin-7-yl)benzo[b]thiophene-3-carbonitrile | +++ | 695.4 |
| 391 | 4-((R)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-amine | +++ | 638.3 |
| 392 | 2-fluoro-5-(8-fluoro-4-((1S,7R,8S)-8-fluoro-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-3-methyl-4-(trifluoromethyl)aniline | ++ | 619.3 |
| 393 | 2-fluoro-5-(8-fluoro-4-((1R,7S,8R)-8-fluoro-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-3-methyl-4-(trifluoromethyl)aniline | + | 619.1 |
| 394 | 5-(2-(((S)-2-(difluoromethylene)tetrahydro-1H-pyrrolizin-7a(5H)-yl)methoxy)-8-fluoro-4-((1S,7R,8S)-8-fluoro-2-azabicyclo[5.1.0]octan-2-yl)pyrido[4,3-d]pyrimidin-7-yl)-2-fluoro-3-methyl-4-(trifluoromethyl)aniline | + | 655.3 |
| 395 | 5-(2-(((S)-2-(difluoromethylene)tetrahydro-1H-pyrrolizin-7a(5H)-yl)methoxy)-8-fluoro-4-((1R,7S,8R)-8-fluoro-2-azabicyclo[5.1.0]octan-2-yl)pyrido[4,3-d]pyrimidin-7-yl)-2-fluoro-3-methyl-4-(trifluoromethyl)aniline | + | 655.4 |
| 396 | 2-fluoro-5-(8-fluoro-4-((1S,7R,8S)-8-fluoro-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)-3-methyl-4-(trifluoromethyl)aniline | + | 637.3 |
| 397 | 2-fluoro-5-(8-fluoro-4-((1R,7S,8R)-8-fluoro-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)-3-methyl-4-(trifluorometbyl)aniline | + | 637.2 |
| 398 | 2-fluoro-5-(8-fluoro-4-((1S,7R,8S)-8-fluoro-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-3-methyl-4-(trifluoromethyl)aniline | ++ | 637.4 |
| 399 | 2-fluoro-5-(8-fluoro-4-((1R,7S,8R)-8-fluoro-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-3-methyl-4-(trifluoromethyl)aniline | + | 637.3 |
| 400 | 4-((S)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-amine | + | 638.3 |

TABLE 3-continued

| Example No. | Name | HTRF KRas G12V IC50 (nM) | Mass [M + H]+ |
|---|---|---|---|
| 401 | 7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-5-ol | + | 637.2 |
| 402 | (R,Z)-7a'-(((7-(8-ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yl)oxy)methyl)-6'-(fluoromethylene)hexahydrospiro[cyclopropane-1,1'-pyrrolizine] | +++ | 640.1 |
| 403 | 5-ethynyl-6-fluoro-4-(8-fluoro-4-((1S,7R,8S)-8-fluoro-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine | +++ | 655.1 |
| 404 | 5-ethynyl-6-fluoro-4-(8-fluoro-4-((1S,7R,8S)-8-fluoro-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine | +++ | 655.1 |
| 405 | (R)-6'-(difluoromethylene)-7a'-(((7-(8-ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yl)oxy)methyl)hexahydrospiro[cyclopropane-1,1'-pyrrolizine] | +++ | 658.3 |
| 406 | 3-chloro-5-(8-fluoro-4-((1S,7R,8S)-8-fluoro-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)-4-(trifluoromethyl)aniline | +++ | 665.0 |
| 407 | (R)-7a'-(((8-fluoro-7-(7-fluoro-8-(fluoromethoxy-d2)naphthalen-1-yl)-4-((1S,7R,8S)-8-fluoro-2-azabicyclo[5.1.0]octan-2-yl)pyrido[4,3-d]pyrimidin-2-yl)oxy)methyl)-6'-methylenehexahydrospiro[cyclopropane-1,1'-pyrrolizine] | +++ | 648.2 |
| 408 | (R,Z)-7a'-(((8-fluoro-7-(7-fluoro-8-(fluoromethoxy-d2)naphthalen-1-yl)-4-((1S,7R,8S)-8-fluoro-2-azabicyclo[5.1.0]octan-2-yl)pyrido[4,3-d]pyrimidin-2-yl)oxy)methyl)-6'-(fluoromethylene)hexahydrospiro[cyclopropane-1,1'-pyrrolizine] | +++ | 666.2 |
| 409 | 6-fluoro-4-(8-fluoro-4-((1S,7R,8S)-8-fluoro-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine | +++ | 681.2 |
| 410 | 5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)-6-methylnaphthalen-2-amine | +++ | 631.1 |
| 411 | 3-chloro-5-(2-(((R)-6'-(difluoromethylene)tetrahydrospiro[cyclopropane-1,1'-pyrrolizin]-7a'(5'H)-yl)methoxy)-8-fluoro-4-((1S,7R,8S)-8-fluoro-2-azabicyclo[5.1.0]octan-2-yl)pyrido[4,3-d]pyrimidin-7-yl)-4-(trifluoromethyL)aniline | + | 683.0, 685.0 |
| 412 | 5-(2-(((R)-6'-(difluoromethylene)tetrahydrospiro[cyclopropane-1,1'-pyrrolizin]-7a'(5'H)-yl)methoxy)-8-fluoro-4-((1S,7R,8S)-8-fluoro-2-azabicyclo[5.1.0]octan-2-yl)pyrido[4,3-d]pyrimidin-7-yl)-2-fluoro-3-methyl-4-(trifluoromethyl)aniline | + | 681.1 |
| 413 | (R)-6'-(difluoromethylene)-7a'-(((8-fluoro-7-(7-fluoro-8-(fluoromethoxy-d2)naphthalen-1-yl)-4-((1S,7R,8S)-8-fluoro-2-azabicyclo[5.1.0]octan-2-yl)pyrido[4,3-d]pyrimidin-2-yl)oxy)methyl)hexahydrospiro[cyclopropane-1,1'-pyrrolizine] | ++ | 684.1 |
| 414 | (6R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-1-one | +++ | 633.0 |
| 415 | (1S,7S,8S)-8-fluoro-2-(8-fluoro-2-(((2R,7aS)-2-fluorotetrahydro-1H-pyrrolizin-7a(5H)-yl)methoxy-d2)-7-(naphthalen-1-yl)-6-(trifluoromethyl)quinazolin-4-yl)-5-oxa-2-azabicyclo[5.1.0]octane | + | 631.2 |

TABLE 3-continued

| Example No. | Name | HTRF KRas G12V IC50 (nM) | Mass [M + H]+ |
|---|---|---|---|
| 416 | 6-chloro-5-ethynyl-4-(8-fluoro-2-(((2R,3R,7aS)-2-fluoro-3-methyltetrahydro-1H-pyrrolizin-7a(5H)-yl)methoxy-d2)-4-((1S,7R,8S)-8-fluoro-2-azabicyclo[5.1.0]octan-2-yl)pyrido[4,3-d]pyrimidin-7-yl)naphthalen-2-amine | +++ | 649.2, 651.2 |
| 417 | 5-ethynyl-4-(8-fluoro-2-(((2R,3R,7aS)-2-fluoro-3-methyltetrahydro-1H-pyrrolizin-7a(5H)-yl)methoxy-d2)-4-((1S,7R,8S)-8-fluoro-2-azabicyclo[5.1.0]octan-2-yl)pyrido[4,3-d]pyrimidin-7-yl)-6-methylnaphthalen-2-amine | +++ | 629.3 |
| 418 | 2-amino-4-((R)-4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)-6-(trifluoromethyl)quinazolin-7-yl)-7-fluorobenzo[b]thiophene-3-carbonitrile | + | 711.1, 713.1 |
| 419 | 2-amino-4-((S)-4-((1R,7R,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)-6-(trifluorometbyl)quinazolin-7-yl)-7-fluorobenzo[b]thiophene-3-carbonitrile | ++ | 711.1, 713.1 |
| 420 | 2-amino-4-((S)-4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)-6-(trifluoromethyl)quinazolin-7-yl)-7-fluorobenzo[b]thiophene-3-carbonitrile | +++ | 711.1 |
| 421 | 2-amino-4-((R)-4-((1R,7R,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)-6-(trifluoromethyl)quinazolin-7-yl)-7-fluorobenzo[b]thiophene-3-carbonitrile | + | 711.1, 713.1 |
| 422 | 7-(3-amino-8-ethynyl-7-fluoronaphthalen-1-yl)-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazoline-6-carbonitrile | +++ | 641.1 |
| 423 | (R)-7a'-(((7-(8-ethynyl-7-fluoronaphthalen-1-yl)-8-fluoro-4-((1S,7R,8S)-8-fluoro-2-azabicyclo[5.1.0]octan-2-yl)pyrido[4,3-d]pyrimidin-2-yl)oxy)methyl)-6'-methylenehexahydrospiro[cyclopropane-1,1'-pyrrolizine] | +++ | 622.1 |
| 424 | 3-chloro-5-(8-fluoro-4-((1S,7R,8S)-8-fluoro-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)-4-(trifluoromethyl)aniline | +++ | 647.2 |
| 425 | 5-ethynyl-6-fluoro-4-(4-((1S,7S,8S)-8-fluoro-5-oxa-2-azabicyclo[5.1.0]octan-2-yl)-8-methyl-2-(((S)-2-methylenetetrahydro-1H-pyrrolizin-7a(5H)-yl)methoxy)pyrido[4,3-d]pyrimidin-7-yl)naphthalen-2-amine | +++ | 609.1 |
| 426 | 5-ethynyl-6-fluoro-4-(4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)-8-methylpyrido[4,3-d]pyrimidin-7-yl)naphthalen-2-amine | +++ | 627.1 |
| 427 | 5-ethynyl-6-fluoro-4-(4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)-8-methylpyrido[4,3-d]pyrimidin-7-yl)naphthalen-2-amine | +++ | 627.1 |
| 428 | 4-(2-(((S)-2-(difluoromethylene)tetrahydro-1H-pyrrolizin-7a(5H)-yl)methoxy)-4-((1S,7S,8S)-8-fluoro-5-oxa-2-azabicyclo[5.1.0]octan-2-yl)-8-methylpyrido[4,3-d]pyrimidin-7-yl)-5-ethynyl-6-fluoronaphthalen-2-amine | +++ | 645.1 |
| 429 | 5-ethynyl-6-fluoro-4-(4-((1S,7S,8S)-8-fluoro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy)pyrido[4,3-d]pyrimidin-7-yl)naphthalen-2-amine | +++ | 635.3 |
| 430 | 5-ethynyl-6-fluoro-4-(4-((1S,7S,8S)-8-fluoro-5-oxa-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)-8-methylpyrido[4,3-d]pyrimidin-7-yl)naphthalen-2-amine | +++ | 653.1 |
| 431 | 5-ethynyl-6-fluoro-4-(4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)-8-methylpyrido[4,3-d]pyrimidin-7-yl)naphthalen-2-amine | +++ | 653.1 |

TABLE 3-continued

| Example No. | Name | HTRF KRas G12V IC50 (nM) | Mass [M + H]+ |
|---|---|---|---|
| 432 | 2-amino-7-fluoro-4-((S)-8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)-6-(trifluoromethyl)quinazolin-7-yl)benzo[b]thiophene-3-carbonitrile | +++ | 687.0 |
| 433 | 2-amino-7-fluoro-4-((R)-8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)-6-(trifluoromethyl)quinazolin-7-yl)benzo[b]thiophene-3-carbonitrile | + | 687.3 |
| 434 | 5-ethynyl-6-fluoro-4-((R)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)naphthalen-2-amine | + | 634.3 |
| 435 | 5-ethynyl-6-fluoro-4-((S)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)naphthalen-2-amine | +++ | 634.4 |
| 436 | 5-ethynyl-6-fluoro-4-(4-((1S,7S,8S)-8-fluoro-5-oxa-2-azabicyclo[5.1.0]octan-2-yl)-8-methyl-2-(((S)-2-methylenetetrahydro-1H-pyrrolizin-7a(5H)-yl)methoxy-d2)pyrido[4,3-d]pyrimidin-7-yl)naphthalen-2-amine | +++ | 611.1 |
| 437 | 4-(2-(((R)-6'-(difluoromethylene)tetrahydrospiro[cyclopropane-1,1'-pyrrolizin]-7a'(5'H)-yl)methoxy)-4-((1S,7S,8S)-8-fluoro-5-oxa-2-azabicyclo[5.1.0]octan-2-yl)-8-methylpyrido[4,3-d]pyrimidin-7-yl)-5-ethynyl-6-fluoronaphthalen-2-amine | +++ | 671.3 |
| 438 | 2-amino-4-((R)-2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)-6-(trifluoromethyl)quinazolin-7-yl)-7-fluorobenzo[b]thiophene-3-carbonitrile | + | 723.0 |
| 439 | 2-amino-4-((S)-2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)-6-(trifluoromethyl)quinazolin-7-yl)-7-fluorobenzo[b]thiophene-3-carbonitrile | +++ | 723.1 |
| 440 | (R)-7-(2-amino-3-cyano-7-fluorobenzo[b]thiophen-4-yl)-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazoline-6-carbonitrile | +++ | 648.4 |
| 441 | (S)-7-(2-amino-3-cyano-7-fluorobenzo[b]thiophen-4-yl)-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazoline-6-carbonitrile | + | 648.2 |
| 442 | 5-ethynyl-6-fluoro-4-(4-((1S,7S,8S)-8-fluoro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy-d2)pyrido[4,3-d]pyrimidin-7-yl)naphthalen-2-amine | +++ | 637.1 |
| 443 | 4-(4-(8-chloro-5-oxa-2-azabicyclo[5.1.0]octan-2-yl)-8-methyl-2-(((S)-2-methylenetetrahydro-1H-pyrrolizin-7a(5H)-yl)methoxy)pyrido[4,3-d]pyrimidin-7-yl)-5-ethynyl-6-fluoronaphthalen-2-amine | +++ | 625.1, 626.8 |
| 444 | 4-(4-(8-chloro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy)pyrido[4,3-d]pyrimidin-7-yl)-5-ethynyl-6-fluoronaphthalen-2-amine | +++ | 650.9, 652.7 |
| 445 | 5-ethynyl-6-fluoro-4-(4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-yl)naphthalen-2-ol | +++ | 618.2 |
| 446 | 5-ethynyl-6-fluoro-4-(4-((1S,7S,8S)-8-fluoro-5-oxa-2-azabicyclo[5.1.0]octan-2-yl)-8-methyl-2-(((S)-2-methylenetetrahydro-1H-pyrrolizin-7a(5H)-yl)methoxy-d2)pyrido[4,3-d]pyrimidin-7-yl)naphthalen-2-o1 | +++ | 612.1 |
| 447 | 5-ethynyl-6-fluoro-4-(4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)-8-methylpyrido[4,3-d]pyrimidin-7-yl)naphthalen-2-ol | +++ | 628.0 |
| 448 | 5-ethynyl-6-fluoro-4-(4-((1S,7S,8S)-8-fluoro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy-d2)pyrido[4,3-d]pyrimidin-7-yl)naphthalen-2-ol | +++ | 638.1 |

TABLE 3-continued

| Example No. | Name | HTRF KRas G12V IC50 (nM) | Mass [M + H]+ |
|---|---|---|---|
| 449 | 5-ethynyl-6-fluoro-4-(4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)-8-methylpyrido[4,3-d]pyrimidin-7-yl)naphthalen-2-ol | +++ | 654.2 |
| 450 | 2-amino-7-fluoro-4-((S)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)benzo[b]thiophene-3-carbonitrile | + | 641.2 |
| 451 | 2-amino-7-fluoro-4-((R)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)benzo[b]thiophene-3-carbonitrile | +++ | 641.2 |
| 452 | 4-(8-cyclopropyl-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | + | 643.3 |
| 453 | 4-((R)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-ol | +++ | 639.2 |
| 454 | 4-((S)-6,8-difluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)quinazolin-7-yl)-5-ethynyl-6-fluoronaphthalen-2-ol | + | 639.4 |
| 455 | 5-ethynyl-6-fluoro-4-(4-(1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-vinylpyrido[4,3-d]pyrimidin-7-yl)naphthalen-2-amine | +++ | 629.3 |
| 456 | 4-(8-ethyl-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | +++ | 631.3 |
| 457 | 5-ethynyl-6-fluoro-4-(4-((1S,7R,8S)-8-fluoro-2-azabicyclo[5.1.0]octan-2-yl)-8-methyl-2-(((S)-2-methylenetetrahydro-1H-pyrrolizin-7a(5H)-yl)methoxy-d2)pyrido[4,3-d]pyrimidin-7-yl)naphthalen-2-amine | +++ | 609.3 |
| 458 | 5-ethynyl-6-fluoro-4-(4-((1S,7R,8S)-8-fluoro-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy-d2)pyrido[4,3-d]pyrimidin-7-yl)naphthalen-2-amine | +++ | 635.4 |
| 459 | 4-(4-((1S,7S,8S)-8-chloro-5-oxa-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy)pyrido[4,3-d]pyrimidin-7-yl)-5-ethynyl-6-fluoronaphthalen-2-amine | +++ | 615.2 |
| 460 | 5-ethynyl-6-fluoro-4-(4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-yl)naphthalen-2-amine | +++ | 615.2 |
| 461 | 5-ethynyl-6-fluoro-4-(4-((1S,7R,8S)-8-fluoro-2-azabicyclo[5.1.0]octan-2-yl)-8-methyl-2-(((S)-2-methylenetetrahydro-1H-pyrrolizin-7a(5H)-yl)methoxy-d2)pyrido[4,3-d]pyrimidin-7-yl)naphthalen-2-o1 | +++ | 610.3 |
| 462 | 5-ethynyl-6-fluoro-4-(4-((1S,7R,8S)-8-fluoro-2-azabicyclo[5.1.0]octan-2-yl)-8-methyl-2-(((R)-6'-methylenetetrahydrospiro[cyclopropane-1,1'-pyrrolizin]-7a'(5'H)-yl)methoxy-d2)pyrido[4,3-d]pyrimidin-7-yl)naphthalen-2-ol | +++ | 636.2 |
| 463 | 5-ethynyl-6-fluoro-4-(4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-yl)naphthalen-2-ol | +++ | 616.2 |
| 464 | 4-(4-((1S,7R,8S)-8-chloro-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-yl)-5-ethynyl-6-fluoronaphthalen-2-amine | +++ | 631.2 |
| 465 | 4-(4-((1R,7S,8R)-8-chloro-2-azabicyclo[5.1.0]octan-2-yl)-2-(((2R,7aS)-2-fluorotetrahydro-1H-pyrrolizin-7a(5H)-yl)methoxy-d2)-8-methylpyrido[4,3-d]pyrimidin-7-yl)-5-ethynyl-6-fluoronaphthalen-2-amine | + | 631.2 |
| 466 | 2-amino-4-((S)-8-fluoro-4-((1S,7S,8S)-8-fluoro-5-oxa-2-azabicyclo[5.1.0]octan-2-yl)-2-(((2R,7aS)-2- | +++ | 677.2 |

TABLE 3-continued

| Example No. | Name | HTRF KRas G12V IC50 (nM) | Mass [M + H]+ |
|---|---|---|---|
| | fluorotetrahydro-1H-pyrrolizin-7a(5H)-yl)methoxy-d2)-6-(trifluoromethyl)quinazolin-7-yl)benzo[b]thiophene-3-carbonitrile | | |
| 467 | 5-ethynyl-6-fluoro-4-((R)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)naphthalen-2-ol | + | 635.2 |
| 468 | 2-amino-4-((R)-8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-6-(trifluoromethyl)quinazolin-7-yl)benzo[b]thiophene-3-carbonitrile | +++ | 677.2 |
| 469 | 5-ethynyl-6-fluoro-4-((S)-6-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)naphthalen-2-ol | +++ | 635.3 |
| 470 | 2-amino-4-(6-chloro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-8-methylquinazolin-7-yl)-7-fluorobenzo[b]thiophene-3-carbonitrile | +++ | 657.2 |
| 471 | 5-ethynyl-6-fluoro-4-(2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)-8-methylpyrido[4,3-d]pyrimidin-7-yl)naphthalen-2-ol | +++ | 632.2 |
| 472 | 5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-ol | +++ | 636.3 |
| 473 | 5-ethynyl-6-fluoro-4-(2-(((2R,3R,7aS)-2-fluoro-3-methyltetrahydro-1H-pyrrolizin-7a(5H)-yl)methoxy-d2)-4-((1S,7R,8S)-8-fluoro-2-azabicyclo[5.1.0]octan-2-yl)-8-methylpyrido[4,3-d]pyrimidin-7-yl)naphthalen-2-o1 | +++ | 630.3 |
| 474 | 5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7R,8S)-8-fluoro-2-azabicyclo[5.1.0]octan-2-yl)pyrido[4,3-d]pyrimidin-7-yl)naphthalen-2-ol | +++ | 634.2 |
| 475 | 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-ol | +++ | 652.4 |
| 476 | 4-(2-((3,3-difluoro-1-azabicyclo[3.2.0]heptan-5-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine | +++ | 623.2 |
| 477 | 5-ethynyl-6-fluoro-4-(8-fluoro-4-((1S,7S,8S)-8-fluoro-5-oxa-2-azabicyclo[5.1.0]octan-2-yl)-2-((hexahydro-1H-pyrrolo[2,1-c][1,4]oxazin-6-yl)methoxy)pyrido[4,3-d]pyrimidin-7-yl)naphthalen-2-amine | +++ | 617.2 |

Example 2: TR-FRET Biochemical Assay to Evaluate KRAS: CRAF Protein: Protein Interaction The effect of test compounds on KRAS and CRAF protein: protein interaction (PPI) was measured by time resolved fluorescence resonance energy transfer (TR-FRET) Ras binding domain (RBD) assay, which uses a signal generated through fluorescent resonance energy transfer between a donor and an acceptor molecule when in close proximity to each other. Interference from buffer, media, etc. is reduced by dual-wavelength detection; the energy pulse from the excitation source is followed by a time delay, which allows interfering short-lived fluorescence to decay (Degorce et al. 2009).

The KRAS: CRAF PPI assay can be utilized to identify KRAS 'ON' state inhibitors, as the KRAS protein is loaded with GMPPNP (a non-hydrolyzable GTP analog), which represents the active KRAS 'ON' state. FLAG-tagged CRAF RBD binding to the GMPPNP loaded biotin-tagged KR.AS will result in a fluorescence energy transfer from the donor (Tb-anti-FLAG, emission 620 nm) to the acceptor (SA-XL665, emission 665 nm). Disruption of KRAS and CRAF binding will reduce the TR-FRET signal.

Test compound was dissolved in DMSO to create a 1 mM stock solution. A 45 μL volume of stock solution was transferred to a 384well polypropylene plate. A 3fold, 10point dilution was performed by transferring 15 μL of test compound solution into 30 μL of DMSO.

Assay buffer A was prepared with 25 nM Hepes, pH7.3, 0.002% Tween 20, 0.1% BSA, 100 nM NaCl, 5 mM MgCl2, and 10 uM GMP-PNP. 4X KRAS Solution was prepared with 80 nM of Biotin-KRAS ($G_{12}$D/V), GMPPNP loaded or Biotin-KRAS (WT), GMPPNP loaded protein in assay buffer A. 4X Raf RBD Solution was prepared with 400 nM FLAG CRAF RBD in assay buffer A. 2X Detection Mixture was prepared with 2 nM Tb-anti-FLAG antibody and 10 nM and 10 nM SA-XL665 in assay buffer A.

A volume of 100 nL of 100x test compound working solution or DMSO vehicle control solution was dispensed to each well (duplicate for each concentration) of a 384-well ProxiPlate Plus assay plate. A volume of 2.5 AL of 4X KRAS Solution was added to each well of the assay plate for a final concentration of 20 nM Biotin-KRAS ($G_{12}$D/V), GMPPNP loaded or 20 nM Biotin-KRAS (WT), GMPPNP. For low control, add 2.5 μL of assay buffer (no KRAS protein). Pre-incubate assay plate for 30 minutes at room temperature. Following pre-incubation of test compound or DMSO with Biotin-KRAS ($G_{12}$D/V),GMPPNP loaded or Biotin-KRAS (WT),GMPPNP, a volume of 2.5 AL of 4X FLAG cRAF RBD Solution was added to each well of the assay plate for a final concentration of 100 nM FLAG CRAF RBD. The assay plate was subjected to centrifuge at 1000 rpm for 1 minute and pre-incubate assay plate for 150 minutes at room temperature. Following the pre-incubation with FLAG cRAF RBD, a volume of 5 μl of 2X Detection Mixture was added to each well of the assay plate for a final concentration of 1 nM Tb-anti-FLAG and 5 nM SA-XL665. The assay plate was centrifuged at 1000 rpm for 1 minute and incubated for 90 minutes at room temperature. TR-FRET signal was measured on a BioTek Synergy Neo2 microplate reader (excitation at 340 nm, emission at 665 nn and 620 nm).

TR-FRET ratios were calculated by dividing the acceptor emission value (665 nm) by the donor emission value (620 nm) for each sample.

TR-FRET ratio=(Acceptor Signal 665 nm)/(Donor Signal 620 nm)

Percent inhibition was calculated by multiplying the normalized TR-FRET ratio by 100, where TR-FRET ratio$^{HIGH}$ was the TR-FRET ratio obtained from wells with 1% DMSO and complete reaction mixture, TR-FRET ratio$^{LOW}$ was the ratio obtained from wells with 1% DMSO and reaction mixture without KRAS protein and TR-FRET ratio$^{SAMPLE}$ was the TR-FRET ratio from wells with test compound and complete reaction mixture. The $IC_{50}$ values were calculated from normalized TR-FRET ratios with the Levenberg-Marquardt 4 parameter fitting procedure.

$$\% \text{ Inhibition} = 100\times\left(TR\text{-}FRET \text{ ratio}^{SAMPLE} - \text{mean } TR\text{-}FRET \text{ ratio}^{LOW}\right) \Big/ \left(\text{mean } TR\text{-}FRET \text{ ratio}^{HIGH} - \text{mean } HTRF \text{ ratio}^{LOW}\right)$$

This assay quantifies the interaction of a KRAS mutant protein (e.g., G12V) with the CRAF Ras-binding domain (RBD). This interaction occurs when KRAS is in the GTP bound "ON state." Compound binding in the allosteric pocket while GMP-PNP is loaded in the KRAS protein is a direct measure of the compound's ON state affinity. The interaction of KRAS with the CRAF RBD is disrupted when a compound has affinity for the KRAS ON state. Compounds with potent inhibition in this protein-protein interaction assay correlate with potent inhibition of cellular MAPK pathway signaling as quantified by pERK levels. Importantly, this TR-FRET is done biochemically and turnover of GTP cannot occur due to GEF and GAP activity that regulates the cycling of GTP (ON) and GDP (OFF) KRAS states in the cellular environment.

Compounds that are very potent in the assay (KRAS G12D/CRAF $IC_{50}$ under 20 nM; KRAS G12V/CRAF $IC_{50}$ under 80 nM) are effective in the cellular pERK assays at both 1 h and 24 h readouts. Compounds that do not meet the above thresholds can typically inhibit the cellular pERK at 1 h quite well ($EC_{50}$ <5 nM), but typically have poor 24 h pERK potencies ($EC_{50}$ >50 nM). Table 4 provides the $IC_{50}$ values for select compounds disclosed herein in the TR-FRET biochemical assay.

TABLE 4

| Example No. | Name | TR-Fret_PPI KRAS (G12D)/CRAF $IC_{50}$(nM) | TR-Fret_PPI KRAS (G12V)/CRAF $IC_{50}$(nM) |
|---|---|---|---|
| 5 | 4-(4-((1R,7S)-2-azabicyclo[5.1.0]octan-2-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethynyl-6-fluoronaphthalen-2-amine | 24.19 | 233.55 |
| 8 | 4-(4-((1R,7S)-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | 27.50 | 213.28 |
| 13 | 5-ethynyl-6,7-difluoro-4-(8-fluoro-4-((1S,7R,8R)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 430.37 | 2833.58 |
| 14 | 5-ethynyl-6,7-difluoro-4-(8-fluoro-4-((1R,7S,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 10000.00 | 10000.00 |
| 15 | 5-ethynyl-6,7-difluoro-4-(8-fluoro-4-((1R,7S,8R)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 10000.00 | 10000.00 |
| 16 | 5-ethynyl-6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 9.98 | 56.65 |

TABLE 4-continued

| Example No. | Name | TR-Fret_PPI KRAS (G12D)/CRAF $IC_{50}$(nM) | TR-Fret_PPI KRAS (G12V)/CRAF $IC_{50}$(nM) |
|---|---|---|---|
| 28 | 5-ethynyl-6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 11.57 | 89.70 |
| 62 | 4-(4-((1R,7S)-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6,7-difluoronaphthalen-2-amine | 62.59 | 443.14 |
| 82 | 5-ethynyl-6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 8.11 | 39.19 |
| 87 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 9.92 | 60.01 |
| 137 | 5-ethynyl-6,7-difluoro-4-(8-fluoro-4-((1S,7R,8S)-8-fluoro-2-azabicyclo[5.1.0]oct-4-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 27.40 | 154.68 |
| 138 | 5-ethynyl-6,7-difluoro-4-(8-fluoro-4-((1R,7S,8R)-8-fluoro-2-azabicyclo[5.1.0]oct-4-en-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 10000.00 | 10000.00 |
| 221 | 5-ethynyl-6-fluoro-4-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | >3000 | >3000 |
| 222 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-5-methoxypyrido[4,3-d]pyrimidin-7-yl)naphthalen-2-amine | 11.65 | 53.67 |
| 223 | 5-ethynyl-6-fluoro-4-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)-5-methoxypyrido[4,3-d]pyrimidin-7-yl)naphthalen-2-amine | 3000.00 | 3000.00 |
| 224 | 5-ethynyl-6-fluoro-4-(8-fluoro-4-((1R,7R,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | >3000 | >3000 |
| 225 | 5-ethynyl-6-fluoro-4-(8-fluoro-4-((1S,7S,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 264.01 | 2913.5 |
| 247 | 4-(4-((1S,7S,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | 1393.09 | 3000.00 |
| 248 | 4-(4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | 8.25 | 52.60 |
| 249 | 4-(4-((1R,7R,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | 648.13 | 3000.00 |
| 250 | 4-(4-((1R,7R,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | 1669.12 | 3000.00 |

TABLE 4-continued

| Example No. | Name | TR-Fret_PPI KRAS (G12D)/CRAF $IC_{50}$(nM) | TR-Fret_PPI KRAS (G12V)/CRAF $IC_{50}$(nM) |
|---|---|---|---|
| 316 | 4-(4-((1R,7S,8R)-8-chloro-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | 14.13 | 51.19 |
| 317 | 4-(4-((1S,7R,8S)-8-chloro-2-oxa-6-azabicyclo[5.1.0]octan-6-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | 3000.00 | 3000.00 |
| 339 | 4-(4-((1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-amine | 3000.00 | 10000.00 |
| 340 | 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-amine | 7.14 | 50.09 |
| 341 | 4-(4-((1R,7S,8R)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | 1791.30 | 10000.00 |
| 342 | 4-(4-((1S,7R,8S)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | 9.04 | 54.69 |
| 343 | 4-(4-((1R,7S,8S)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | 3000.00 | 10000.00 |
| 344 | 4-(4-((1S,7R,8R)-8-chloro-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine | 1927.49 | 10000.00 |

Example 3: Pharmacokinetic Evaluation

Pharmacokinetic profile for test compound was measured by single dosing in male Sprague-Dawley rats. Animal weights were typically over 200 grams, and animals were allowed to acclimate to their new environment for at least 3 days prior to the initiation of any studies. One set of animals was dosed intravenous with test compound, 2 mg/kg in 20% PEG400, 10% HS-15 Solutol, 70% 50 mM citrate buffer (pH 4.0). Intravenous dosing solution concentration was 1.0 mg/mL. Time of blood sampling was 5 minutes, 15 minutes, 30 minutes, 1 hour, 2 hours, 4 hours, 8 hours, and 24 hours following intravenous dosing. Another set of animals was dosed orally with test compound, 30 mg/kg in 20% PEG400, 10% HS-15 Solutol, 70% 50 mM citrate buffer (pH 4.0). Oral dosing solution concentration was 3.0 mg/mL. Time of blood sampling was 15 minutes, 30 minutes, 1 hour, 2 hours, 4 hours, 8 hours, and 24 hours following oral dosing. Blood samples (~0.2 mL/sample) were collected via jugular vein and placed in tubes containing Heparin-Na. The blood samples in tubes were mixed and then placed on wet ice prior to centrifugation for plasma. The blood samples were centrifuged at 4000 g for 5 minutes at 4° C. to obtain plasma. The obtained plasma was separated and stored frozen at approximately-80° C.

All the plasma samples were analyzed using a Shimadzu (DGU-405) HPLC with an API 6500+MS/MS system following the manufacturer's instructions. All the analytes were detected with positive-mode electrospray ionization (ES+). A standard curve for each test compound was generated and used to measure test compound concentrations in the rat plasma samples. Based on the time course sampling, an area under the curve (AUC) was calculated for the oral group and intravenous group. The percentage of rat bioavailability is calculated based on the equation shown below.

$$F(rat) = \frac{AUC_{PO} * \text{Dose}_{IV}}{AUC_{IV} * \text{Dose}_{PO}}$$

where F is bioavailability, $AUC_{PO}$ is area under curve of oral dosing, $AUC_{IV}$ is area under curve of intravenous dosing, $\text{Dose}_{IV}$ is the intravenous dose and $\text{Dose}_{PO}$ is the oral dose. Table 5 provides pharmacokinetic parameters for select compounds disclosed herein. The oral dosing for the experiments presented in Table 5 was performed at 10 mg/kg unless noted otherwise.

TABLE 5

| Example No. | Name | PO (dose 10 mg/kg) (AUC/D) (h * mg/mL) | IV (dose 2 mg/kg) (AUC/D) (h * mg/mL) |
|---|---|---|---|
| 16 | 5-ethynyl-6,7-difluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 75 | 718 |
| 24 | 5-ethynyl-6,7-difluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 35 | 405 |
| 28 | 5-ethynyl-6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 141 | 993 |
| 58 | 6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | 432 | 1401 |
| 82 | 5-ethynyl-6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 115 | 490 |
| 87 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 122 (dose 30 mg/kg) | 494 |
| 89 | 5-ethynyl-6-fluoro-4-(8-fluoro-4-((1R,7S,8R)-8-fluoro-2-oxa-6-azabicyclo[5.1.0]octan-6-y])-2-(((2R,7aS)-2-fluorotetrahydro-1H-pyrrolizin-7a(5H)-yl)methoxy-d2)pyrido[4,3-d]pyrimidin-7-yl)naphthalen-2-amine | 22 | 323 |
| 90 | 6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | 352 (dose 30 mg/kg) | 1086 |
| 91 | 6-fluoro-4-(8-fluoro-4-((1R,7S,8R)-8-fluoro-2-oxa-6-azabicyclo[5.1.0]octan-6-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine | 142 | 609 |
| 216 | 5-ethynyl-6-fluoro-4-(8-fluoro-4-((1S,7R,8S)-8-fluoro-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol | 0.0 (BLOQ at each time point) | 96 |
| 217 | 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol | 0.5 (dose 30 mg/kg) | 143 |
| 260 | 6-chloro-5-ethynyl-4-(8-fluoro-4-((1S,7S,8S)-8-fluoro-5-oxa-2- | 0.4 | 129 |

TABLE 5-continued

| Example No. | Name | PO (dose 10 mg/kg) (AUC/D) (h * mg/mL) | IV (dose 2 mg/kg) (AUC/D) (h * mg/mL) |
|---|---|---|---|
| | azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol | | |
| 267 | 6-chloro-5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine | 97 | 1066 |

III. Preparation of Pharmaceutical Dosage Forms

Example 1: Oral Capsule

The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt or solvate thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:

1. A compound, or a pharmaceutically acceptable salt, deuteroisotope, stereoisomer, or tautomer thereof, selected from the group consisting of:

5-ethynyl-6,7-difluoro-4-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-ethynyl-6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-Ethynyl-6,7-difluoro-4-(8-fluoro-4-((1R,7R,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-Ethynyl-6,7-difluoro-4-(8-fluoro-4-((1S,7S,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

6,7,8-trifluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine;

(1S,7S,8S)-2-(7-(8-ethynyl-6,7-difluoronaphthalen-1-yl)-8-fluoro-2-(((2R,7aS)-2-fluorotetrahydro-1H-pyrrolizin-7a(5H)-yl)methoxy-$d_2$)pyrido[4,3-d]pyrimidin-4-yl)-8-fluoro-5-oxa-2-azabicyclo[5.1.0]octane;

(1S,7S,8S)-8-fluoro-2-(8-fluoro-7-(7-fluoro-8-(methoxy-d3)naphthalen-1-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane;

6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine;

(1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

(1R, 7R, 8R)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

(1S,7S,8S)-8-fluoro-2-(8-fluoro-7-(7-fluoro-8-(fluoromethoxy-d2)naphthalen-1-yl)-2-(((2R, 7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane;

6-amino-8-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-1-(methoxy-d3)-2-naphthonitrile;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

6,7-difluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine;

6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine;

5-ethynyl-6,7,8-trifluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl) methoxy-d2)pyrido[4,3-d]pyrimidin-7-yl)naphthalen-2-amine;

(1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane-6,6-d2;

(1S,7S,8S)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane;

(1R,7R,8R)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane;

(1S,7S,8S)-2-(2-(((R)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane;

(1S,7S,8S)-2-(2-(((S)-2-(difluoromethylene)tetrahydro-1H-pyrrolizin-7a(5H)-yl)methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane;

(1R, 7R, 8R)-2-(2-(((S)-2-(difluoromethylene)tetrahydro-1H-pyrrolizin-7a(5H)-yl)methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane;

(1S,7S,8S)-2-(2-(((R)-2-(difluoromethylene)tetrahydro-1H-pyrrolizin-7a(5H)-yl)methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane;

5-ethynyl-6,8-difluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl) methoxy-d2)pyrido[4,3-d]pyrimidin-7-yl)naphthalen-2-amine;

6-fluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido [4,3-d]pyrimidin-7-yl)-5-(fluoromethoxy-d2) naphthalen-2-amine;

(1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane-8-d;

6,7,8-trifluoro-4-(8-fluoro-4-((1S,7S,8S)-8-fluoro-5-oxa-2-azabicyclo[5.1.0]octan-2-yl-8-d)-2-(((2R,7aS)-2-fluorotetrahydro-1H-pyrrolizin-7a(5H)-yl)methoxy-d2)pyrido[4,3-d]pyrimidin-7-yl)-5-(methoxy-d3) naphthalen-2-amine;

6,7,8-trifluoro-4-(8-fluoro-4-((1S,7S,8S)-8-fluoro-5-oxa-2-azabicyclo[5.1.0]octan-2-yl)-2-(((R)-6'-methyl-enetetrahydrospiro[cyclopropane-1,1'-pyrrolizin]-7a' (5'H)-yl)methoxy)pyrido[4,3-d]pyrimidin-7-yl)-S-(methoxy-d3)naphthalen-2-amine;

6,7,8-trifluoro-4-(8-fluoro-4-((1S,7S,8S)-8-fluoro-5-oxa-2-azabicyclo[5.1.0]octan-2-yl)-2-(((S)-6'-methyl-enetetrahydrospiro[cyclopropane-1,1'-pyrrolizin]-7a' (5'H)-yl)methoxy)pyrido[4,3-d]pyrimidin-7-yl)-5-(methoxy-d3)naphthalen-2-amine;

(1S,7S,8S)-2-(7-(8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-S-oxa-2-azabicyclo[5.1.0]octane-8-d;

(1S,7S,8S)-8-fluoro-2-(8-fluoro-2-(((2R,7aS)-2-fluoro-tetrahydro-1H-pyrrolizin-7a(5H)-yl)methoxy-d2)-7-(5,6,7-trifluoro-8-(methoxy-d3)naphthalen-1-yl)pyrido[4,3-d]pyrimidin-4-yl)-5-oxa-2-azabicyclo[5.1.0]octane;

6,7,8-trifluoro-4-(8-fluoro-4-((1S,7S,8S)-8-fluoro-5-oxa-2-azabicyclo[5.1.0]octan-2-yl-6,6-d2)-2-(((2R,7aS)-2-fluorotetrahydro-1H-pyrrolizin-7a(5H)-yl)methoxy-d2)pyrido[4,3-d]pyrimidin-7-yl)-5-(methoxy-d3) naphthalen-2-amine;

6,7,8-trifluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(methoxy-d3)naphthalen-2-amine;

6,7,8-trifluoro-4-(8-fluoro-4-((1S,7S,8S)-8-fluoro-5-oxa-2-azabicyclo[5.1.0]octan-2-yl)-2-(((2R,7aS)-2-fluoro-tetrahydro-1H-pyrrolizin-7a(5H)-yl)methoxy-d2) pyrido[4,3-d]pyrimidin-7-yl)-5-(fluoromethoxy-d2) naphthalen-2-amine;

(1S,7S,8S)-2-(7-(8-ethynyl-7-fluoronaphthalen-1-yl)-8-fluoro-2-(((S,E)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane;

(1S,7S,8S)-2-(7-(8-ethynyl-7-fluoronaphthalen-1-yl)-8-fluoro-2-(((S,Z)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane;

6,8-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido [4,3-d]pyrimidin-7-yl)-5-(methoxy-d3)naphthalen-2-amine;

6,7,8-trifluoro-4-(8-fluoro-4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl) methoxy)pyrido[4,3-d]pyrimidin-7-yl)-5-(methoxy-d3)naphthalen-2-amine;

6,7,8-trifluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl) methoxy)pyrido[4,3-d]pyrimidin-7-yl)-5-(methoxy-d3)naphthalen-2-amine;

4-(2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

6,8-difluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido [4,3-d]pyrimidin-7-yl)-5-(fluoromethoxy-d2) naphthalen-2-amine;

4-(2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6,7,8-trifluoro-S-(methoxy-d3) naphthalen-2-amine;

(1S,7S,8S)-2-(7-(8-ethynyl-7-fluoronaphthalen-1-yl)-8-fluoro-2-(((S)-2-methylenetetrahydro-1H-pyrrolizin-7a(5H)-yl)methoxy)pyrido[4,3-d]pyrimidin-4-yl)-8-fluoro-5-oxa-2-azabicyclo[5.1.0]octane;

6,7-difluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(fluoromethoxy-d2)naphthalen-2-amine;

(1S,7S,8S)-8-fluoro-2-(8-fluoro-7-(7-fluoro-8-(fluoromethoxy-d2)naphthalen-1-yl)-2-(((S)-2-methyl-enetetrahydro-1H-pyrrolizin-7a(5H)-yl)methoxy)pyrido[4,3-d]pyrimidin-4-yl)-5-oxa-2-azabicyclo[5.1.0]octane;

(1S,7S,8S)-2-(2-(((S)-2-(difluoromethylene)tetrahydro-1H-pyrrolizin-7a(5H)-yl)methoxy)-8-fluoro-7-(7-fluoro-8-(fluoromethoxy-d2)naphthalen-1-yl)pyrido[4,3-d]pyrimidin-4-yl)-8-fluoro-5-oxa-2-azabicyclo[5.1.0]octane;

(1S,7S,8S)-2-(7-(5,7-difluoro-8-(fluoromethoxy-d2)naphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

5-ethynyl-6-fluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)naphthalen-2-amine;

(1S,7S,8S)-8-fluoro-2-(8-fluoro-7-(7-fluoro-8-(fluoromethoxy-d2)naphthalen-1-yl)-2-(((S,E)-2-(fluoromethylene)tetrahydro-1H-pyrrolizin-7a(5H)-yl)methoxy)pyrido[4,3-d]pyrimidin-4-yl)-5-oxa-2-azabicyclo[5.1.0]octane;

(1S,7S,8S)-8-fluoro-2-(8-fluoro-7-(7-fluoro-8-(fluoromethoxy-d2)naphthalen-1-yl)-2-(((S,Z)-2-(fluoromethylene)tetrahydro-1H-pyrrolizin-7a(5H)-yl)methoxy)pyrido[4,3-d]pyrimidin-4-yl)-5-oxa-2-azabicyclo[5.1.0]octane;

5-ethynyl-6-fluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)naphthalen-2-amine 6,7-difluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(fluoromethoxy-d2)naphthalen-2-amine;

(1S,7S,8S)-2-(7-(8-ethynyl-7-fluoronaphthalen-1-yl)-8-fluoro-2-(((R)-6'-methylenetetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane;

5-ethynyl-6-fluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)naphthalen-2-amine;

6,8-difluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(methoxy-d3)naphthalen-2-amine;

5-ethynyl-6-fluoro-4-(8-fluoro-4-((1S,7S,8S)-8-fluoro-5-oxa-2-azabicyclo[5.1.0]octan-2-yl-8-d)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

4-(2-(((S)-dihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

6-fluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(fluoromethoxy-$d_2$)naphthalen-2-amine;

6-fluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(fluoromethoxy-d2)naphthalen-2-amine;

6,8-difluoro-4-(8-fluoro-4-((1S, 7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(methoxy-d3)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl-2,5,5-d3)methoxy-d2)pyrido[4,3-d]pyrimidin-7-yl)naphthalen-2-amine;

4-(2-(((2R,6R,7aS)-2-(aminomethyl)-6-fluorotetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-ol;

6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-vinylnaphthalen-2-amine;

4-(2-(((S)-dihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine;

5-ethyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'R,7a'R)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'S,7a'R)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'S,7a'S)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'R,7a'S)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-methyltetrahydro-1H-pyrrolizin-7a(5H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2S,7aS)-2-methyltetrahydro-1H-pyrrolizin-7a(5H)-yl)methoxy)pyrido[4,3-d]pyrimidin-7-yl)naphthalen-2-amine;

4-(2-(((1R,7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

4-(2-((((1S, 7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-((tetrahydro-1H-pyrrolizin-7a(5H)-yl)methoxy-d2)pyrido[4,3-d]pyrimidin-7-yl)naphthalen-2-amine;

6-fluoro-4-(8-fluoro-4-((1S,7S,8S)-8-fluoro-5-oxa-2-azabicyclo[5.1.0]octan-2-yl)-2-(((2S,7aS)-2-methyltetrahydro-1H-pyrrolizin-7a(5H)-yl)methoxy)pyrido[4,3-d]pyrimidin-7-yl)-5-(fluoromethoxy-d2)naphthalen-2-amine;

6-fluoro-4-(8-fluoro-4-((1S,7S,8S)-8-fluoro-5-oxa-2-azabicyclo[5.1.0]octan-2-yl)-2-(((2R,7aS)-2-methyltetrahydro-1H-pyrrolizin-7a(5H)-yl)methoxy)pyrido[4,3-d]pyrimidin-7-yl)-5-(fluoromethoxy-d2)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol;

4-(2-(((S)-2,2-difluorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

5-ethynyl-6-fluoro-4-(8-fluoro-4-((1R, 7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-ethynyl-6-fluoro-4-(8-fluoro-4-((1R,7R,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-ethynyl-6-fluoro-4-(8-fluoro-4-((1S,7S,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

4-(2-(((1S,7a'S)-2,2-difluorodibydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine;

4-(2-(((1R,7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine;

4-(2-(((2S,7aS)-2-chlorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

4-(2-(((2R,7aS)-2-chlorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

5-ethynyl-6-fluoro-4-(8-fluoro-2-(((2R,7aS)-2-fluoro-5,5-dimethyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'R,7a'R)-6'-methyltetrahydrospiro[cyclopropane-1,1'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'S,7a'S)-6'-methyltetrahydrospiro[cyclopropane-1,1'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((S)-6'-methyl-2',3'-dihydrospiro[cyclopropane-1,1'-pyrrolizin]-7a'(5'H)-yl)methoxy)pyrido[4,3-d]pyrimidin-7-yl)naphthalen-2-amine;

N-(((2R,6R,7aS)-7a-(((7-(8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-2-yl)methyl)acetamide;

((2R,6R,7aS)-7a-(((7-(8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-2-yl)methanamine;

4-(4-((1S,7S,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

4-(4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

4-(4-((1R, 7R,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

4-(4-((1R,7R,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'S, 7a'R)-6'-methyltetrahydrospiro[cyclopropane-1,1'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1S,2S,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1S,2R,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1R,2S, 7a'S)-

2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-7-d-2-amine;

N-(((2R,6R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-2-yl)methyl)acetamide;

4-(2-(((2R,6R,7aS)-2-(aminomethyl)-6-fluorotetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

5-ethynyl-6-fluoro-4-(8-fluoro-2-(((2R,5S,7aS)-2-fluoro-5-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

6-chloro-5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol;

5-ethynyl-6-fluoro-4-(4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)naphthalen-2-amine;

5-ethynyl-6-fluoro-4-(8-fluoro-2-(((2R,7aS)-2-fluoro-3,3-dimethyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

N-(5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-yl)acetamide;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-8-d-2-amine;

5-ethynyl-6-fluoro-4-(8-fluoro-4-((1S,7S,8S)-8-fluoro-5-oxa-2-azabicyclo[5.1.0]octan-2-yl)-2-(((2S,7aS)-2-(fluoromethyl)tetrahydro-1H-pyrrolizin-7a(5H)-yl)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-(fluoromethyl)tetrahydro-1H-pyrrolizin-7a(5H)-yl)methoxy-d2)pyrido[4,3-d]pyrimidin-7-yl)naphthalen-2-amine;

6-chloro-5-ethynyl-4-(8-fluoro-4-((1S,7S,8S)-8-fluoro-S-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

4-(8-chloro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-7,8-d2-2-amine;

5-ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl-5',5'-d2)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl-5',5'-d2)methoxy-d2)pyrido[4,3-d]pyrimidin-7-yl)naphthalen-2-amine;

(2R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizine-2-carbonitrile;

5-ethynyl-6-fluoro-4-(8-fluoro-2-(((2R,3R,7aS)-2-fluoro-3-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

5-ethynyl-6-fluoro-4-(8-fluoro-2-(((2R,3S,7aS)-2-fluoro-3-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((R)-1-methylpyrrolidin-2-yl)methoxy)pyrido[4,3-d]pyrimidin-7-yl)naphthalen-2-ol;

5-ethynyl-6-fluoro-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol;

(2S,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizine-2-carbonitrile;

5-ethynyl-6-fluoro-4-(8-fluoro-2-(((2R,5R,7aS)-2-fluoro-5-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-amine;

(1S,7S,8S)-8-chloro-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane;

6-chloro-4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynylnaphthalen-2-amine;

6-chloro-5-ethynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol;

5-ethynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol;

6-chloro-5-ethynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-amine;

5-ethynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-amine;

5-ethynyl-4-(8-fluoro-4-((1S,7S,8S)-8-fluoro-S-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)naphthalen-2-ol;

4-(4-((1R,7R,8R)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynyl-6-fluoronaphthalen-2-amine;

4-(4-((1S,7S,8S)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl)methoxy-d2)pyrido[4,3-d]pyrimidin-7-yl)naphthalen-2-amine;

2-((2R,7aS)-7a-(((7-(3-amino-8-ethynyl-7-fluoronaphthalen-1-yl)-8-fluoro-4-((1,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizin-2-yl)acetonitrile;

2-((2S,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizin-2-yl)acetonitrile;

(1S,7S,8S)-2-(7-(7-chloro-8-ethynylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

(1S,7S,8S)-2-(7-(8-ethynylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

(1S,7S,8S)-8-chloro-2-(7-(7-chloro-8-ethynylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane;

6-chloro-4-(4-((1S,7S,8S)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine;

4-(4-((1S,7S,8S)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine;

5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-6-methylnaphthalen-2-ol;

(1S,7S,8S)-2-(7-(8-ethynyl-7-methylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

6-chloro-4-(4-((1R,7R,8R)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine;

4-(4-((1R,7R,8R)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine;

5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-6-methylnaphthalen-2-amine;

(1S,7S,8S)-2-(7-(8-ethynyl-7-(trifluoromethyl)naphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine;

5-ethynyl-6-fluoro-4-(8-fluoro-2-(((2R,3S,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine;

((2R,6R,7aS)-7a-(((7-(8-ethynyl-7-(trifluoromethyl)naphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-2-yl)methanamine;

6-chloro-5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine;

5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine;

4-(4-((1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-amine;

4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-amine;

6-chloro-4-(4-((1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynylnaphthalen-2-amine;

4-(4-((1R, 7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynylnaphthalen-2-amine;

4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynylnaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine;

5-ethynyl-6-fluoro-4-(8-fluoro-2-(((6R,7aR)-6-fluoro-1-methylenetetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-methylnaphthalen-2-amine;

(1S,7S,8S)-2-(7-(8-ethynyl-7-fluoronaphthalen-1-yl)-8-fluoro-2-(((R,E)-6'-(fluoromethylene)tetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane;

(1S,7S,8S)-2-(7-(8-ethynyl-7-fluoronaphthalen-1-yl)-8-fluoro-2-(((R,Z)-6'-(fluoromethylene)tetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane;

(1S,7S,8S)-8-fluoro-2-(8-fluoro-7-(7-fluoro-8-(fluoromethoxy-d2)naphthalen-1-yl)-2-(((R)-6'-methylenetetrahydrospiro[cyclopropane-1,1'-pyrrolizin]-7a'(5'H)-yl)methoxy)pyrido[4,3-d]pyrimidin-4-yl)-5-oxa-2-azabicyclo[5.1.0]octane;

(1S,7S,8S)-8-fluoro-2-(8-fluoro-7-(7-fluoro-8-(fluoromethoxy-d2)naphthalen-1-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-4-yl)-5-oxa-2-azabicyclo[5.1.0]octane;

(1S,7S,8S)-8-fluoro-2-(8-fluoro-7-(7-fluoro-8-(fluoromethoxy-d2)naphthalen-1-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-4-yl)-5-oxa-2-azabicyclo[5.1.0]octane;

6-fluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine;

6-fluoro-4-(8-fluoro-4-((1S,7S,8S)-8-fluoro-5-oxa-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine;

6-fluoro-4-(8-fluoro-4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine;

5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)-6-methylnaphthalen-2-amine;

(6R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-1-one;

5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-ol;

4-(4-((1S,7S,8S)-8-chloro-S-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-ol;

4-(2-((3,3-difluoro-1-azabicyclo[3.2.0]heptan-5-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine; and 5-ethynyl-6-fluoro-4-(8-fluoro-4-((1S,7S,8S)-8-fluoro-5-oxa-2-azabicyclo[5.1.0]octan-2-yl)-2-((hexahydro-1H-pyrrolo[2,1-c][1,4]oxazin-6-yl)methoxy)pyrido[4,3-d]pyrimidin-7-yl)naphthalen-2-amine.

2. The compound of claim 1, or a pharmaceutically acceptable salt, deuteroisotope, stereoisomer, or tautomer thereof, wherein the compound is selected from the group consisting of:

6,7-difluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-$d_2$)pyrido[4,3-d]pyrimidin-7-yl)-5-(methoxy-$d_3$)naphthalen-2-amine;

(1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-$d_2$)pyrido[4,3-d]pyrimidin-4-yl)-8-fluoro-5-oxa-2-azabicyclo[5.1.0]octane;

5-ethynyl-6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine;

5-ethynyl-6-fluoro-4-(8-fluoro-4-((18,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine;

6,7-difluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-$d_2$)pyrido[4,3-d]pyrimidin-7-yl)-5-(fluoromethoxy-$d_2$)naphthalen-2-amine;

6-fluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-$d_2$)pyrido[4,3-d]pyrimidin-7-yl)-5-(methoxy-$d_3$)naphthalen-2-amine;

(1S,7S,8S)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane;

6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)-5-(fluoromethoxy-$d_2$)naphthalen-2-amine;

(1S,7S,8S)-2-(7-(8-ethynyl-7-fluoronaphthalen-1-yl)-8-fluoro-2-(((S,E)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane;

(1S,7S,8S)-2-(7-(8-ethynyl-7-fluoronaphthalen-1-yl)-8-fluoro-2-(((S,Z)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane;

4-(2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)naphthalen-2-amine;

5-ethynyl-6-fluoro-4-(8-fluoro-4-((18,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)naphthalen-2-amine;

5-ethynyl-6-fluoro-4-(8-fluoro-4-((18,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)naphthalen-2-amine;

(1S,7S,8S)-2-(7-(8-ethynyl-7-fluoronaphthalen-1-yl)-8-fluoro-2-(((R)-6'-methylenetetrahydrospiro[cyclopropane-1, 1'-pyrrolizin]-7a'(5'H)-yl)methoxy)pyrido[4,3-d]pyrimidin-4-yl)-8-fluoro-5-oxa-2-azabicyclo[5.1.0]octane;

5-ethynyl-6-fluoro-4-(8-fluoro-4-((18,7S,8S)-8-fluoro-5-oxa-2-azabicyclo [5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)naphthalen-2-amine;

5-ethyl-6-fluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-$d_2$)pyrido[4,3-d]pyrimidin-7-yl)naphthalen-2-amine;

4-(4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-$d_2$)pyrido[4,3-d]pyrimidin-7-yl)-5-ethynyl-6-fluoronaphthalen-2-amine;

5-ethynyl-6-fluoro-4-(8-fluoro-2-(((2R,5S,7aS)-2-fluoro-5-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

6-chloro-5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine;

4-(8-chloro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)-5-ethynyl-6-fluoronaphthalen-2-amine;

5-ethynyl-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-$d_2$)pyrido[4,3-d]pyrimidin-7-yl)-6-methylnaphthalen-2-amine;

5-ethynyl-6-fluoro-4-(8-fluoro-2-(((2R,3R,7aS)-2-fluoro-3-methyltetrahydro-1H-pyrrolizin-7a(5H)-yl)methoxy-$d_2$)-4-((1S,7S,8S)-8-fluoro-5-oxa-2-azabicyclo[5.1.0]octan-2-yl)pyrido[4,3-d]pyrimidin-7-yl)naphthalen-2-amine;

4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-$d_2$)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine; and 5-ethynyl-6-fluoro-4-(8-fluoro-4-((18,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine.

3. The compound of claim 2, or a pharmaceutically acceptable salt, deuteroisotope, stereoisomer, or tautomer thereof, wherein the compound is:

6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)-5-(methoxy-$d_3$)naphthalen-2-amine; or (1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-$d_2$)pyrido[4,3-d]pyrimidin-4-yl)-8-fluoro-5-oxa-2-azabicyclo[5.1.0]octane.

4. The compound of claim 2, or a pharmaceutically acceptable salt, deuteroisotope, stereoisomer, or tautomer thereof, wherein the compound is:

5-ethynyl-6,7-difluoro-4-(8-fluoro-4-((18,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-$d_2$)pyrido[4,3-d]pyrimidin-7-yl)naphthalen-2-amine; or 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine.

5. The compound of claim 2, or a pharmaceutically acceptable salt, deuteroisotope, stereoisomer, or tautomer thereof, wherein the compound is:

6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)-5-(fluoromethoxy-$d_2$)naphthalen-2-amine; or 6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)-5-(methoxy-$d_3$)naphthalen-2-amine.

6. The compound of claim 2, or a pharmaceutically acceptable salt, deuteroisotope, stereoisomer, or tautomer thereof, wherein the compound is:

(1S,7S,8S)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane; or 6-fluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-$d_2$)pyrido[4,3-d]pyrimidin-7-yl)-5-(fluoromethoxy-$d_2$)naphthalen-2-amine.

7. The compound of claim 2, or a pharmaceutically acceptable salt, deuteroisotope, stereoisomer, or tautomer thereof, wherein the compound is:

(1S,7S,8S)-2-(7-(8-ethynyl-7-fluoronaphthalen-1-yl)-8-fluoro-2-(((S,E)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane; or (1S,7S,8S)-2-(7-(8-ethynyl-7-fluoronaphthalen-1-yl)-8-fluoro-2-(((S,Z)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane.

8. The compound of claim 2, or a pharmaceutically acceptable salt, deuteroisotope, stereoisomer, or tautomer thereof, wherein the compound is:

4-(2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine; or 5-ethynyl-6-fluoro-4-(8-fluoro-4-((18,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)naphthalen-2-amine.

9. The compound of claim 2, or a pharmaceutically acceptable salt, deuteroisotope, stereoisomer, or tautomer thereof, wherein the compound is:

5-ethynyl-6-fluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)naphthalen-2-amine; or 5-ethynyl-6-fluoro-4-(8-fluoro-4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)naphthalen-2-amine.

10. The compound of claim 2, or a pharmaceutically acceptable salt, deuteroisotope, stereoisomer, or tautomer thereof, wherein the compound is:

(1S,7S,8S)-2-(7-(8-ethynyl-7-fluoronaphthalen-1-yl)-8-fluoro-2-(((R)-6'-methylenetetrahydrospiro[cyclopropane-1, 1'-pyrrolizin]-7a'(5'H)-yl)methoxy)pyrido[4,3-d]pyrimidin-4-yl)-8-fluoro-5-oxa-2-azabicyclo[5.1.0]octane; or 5-ethynyl-6-fluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1, l'-pyrrolizin]-7a'(5'H)-yl)methoxy)pyrido[4,3-d]pyrimidin-7-yl)naphthalen-2-amine.

11. The compound of claim 2, or a pharmaceutically acceptable salt, deuteroisotope, stereoisomer, or tautomer thereof, wherein the compound is:

5-ethyl-6-fluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-$d_2$)pyrido[4,3-d]pyrimidin-7-yl)naphthalen-2-amine; or 4-(4-((1S,7S,8S)-8-chloro-5-oxa-2-azabicyclo[5.1.0]octan-2-yl)-8-fluoro-2-(((2R, 7aS)-2-fluorotetrahydro-1H-pyrrolizin-7a(5H)-yl)methoxy-$d_2$)pyrido[4,3-d]pyrimidin-7-yl)-5-ethynyl-6-fluoronaphthalen-2-amine.

12. The compound of claim 2, or a pharmaceutically acceptable salt, deuteroisotope, stereoisomer, or tautomer thereof, wherein the compound is:

5-ethynyl-6-fluoro-4-(8-fluoro-2-(((2R,5S,7aS)-2-fluoro-5-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine; or 6-chloro-5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)naphthalen-2-amine.

13. The compound of claim 2, or a pharmaceutically acceptable salt, deuteroisotope, stereoisomer, or tautomer thereof, wherein the compound is:

4-(8-chloro-4-((1S,75,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-$d_2$)pyrido[4,3-d]pyrimidin-7-yl)-5-ethynyl-6-fluoronaphthalen-2-amine; or 5-ethynyl-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-$d_2$)pyrido[4,3-d]pyrimidin-7-yl)-6-methylnaphthalen-2-amine.

14. The compound of claim 2, or a pharmaceutically acceptable salt, deuteroisotope, stereoisomer, or tautomer thereof, wherein the compound is:

5-ethynyl-6-fluoro-4-(8-fluoro-2-(((2R,3R,7aS)-2-fluoro-3-methyltetrahydro-1H-pyrrolizin-7a(5H)-yl)methoxy-$d_2$)-4-((1S,7S,8S)-8-fluoro-5-oxa-2-azabicyclo[5.1.0]octan-2-yl)pyrido[4,3-d]pyrimidin-7-yl)naphthalen-2-amine; or fluoro-3-methyltetrahydro-1H-pyrrolizin-7a(5H)-yl)methoxy-$d_2$)pyrido[4,3-d]pyrimidin-7-yl)-5-ethynyl-6-fluoronaphthalen-2-amine.

15. The compound of claim 2, or a pharmaceutically acceptable salt, deuteroisotope, stereoisomer, or tautomer thereof, wherein the compound is:

5-ethynyl-6-fluoro-4-(8-fluoro-4-((1S,7S,8S)-8-fluoro-5-oxa-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine; or 5-ethynyl-6-fluoro-4-(8-fluoro-4-((18,7S,8S)-8-fluoro-5-oxa-2-azabicyclo [5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine.

16. A pharmaceutical composition comprising at least one pharmaceutically acceptable excipient and a compound, or a pharmaceutically acceptable salt, deuteroisotope, stereoisomer, or tautomer thereof, wherein the compound is selected from the group consisting of:

5-ethynyl-6,7-difluoro-4-(8-fluoro-4-((1R, 7R,8R)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)naphthalen-2-amine;

5-ethynyl-6,7-difluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)naphthalen-2-amine;

5-Ethynyl-6,7-difluoro-4-(8-fluoro-4-((1R,7R,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)naphthalen-2-amine;

5-Ethynyl-6,7-difluoro-4-(8-fluoro-4-((1S,7S,8R)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)naphthalen-2-amine;

6,7,8-trifluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine;

(1S,7S,8S)-2-(7-(8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

(1S,7S,8S)-8-fluoro-2-(8-fluoro-7-(7-fluoro-8-(methoxy-d3)naphthalen-1-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane;

6,7-difluoro-4-(8-fluoro-4-((1S, 7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine;

(1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

(1R,7R,8R)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

(1S,7S,8S)-8-fluoro-2-(8-fluoro-7-(7-fluoro-8-(fluoromethoxy-d2)naphthalen-1-yl)-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane;

6-amino-8-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-1-(methoxy-d3)-2-naphthonitrile;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine;

6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine;

5-ethynyl-6,7,8-trifluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

(1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-S-oxa-2-azabicyclo[5.1.0]octane-6,6-d2;

(1S,7S,8S)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane;

(1R,7R,8R)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane;

(1S,7S,8S)-2-(2-(((R)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane;

(1S,7S,8S)-2-(2-(((S)-2-(difluoromethylene)tetrahydro-1H-pyrrolizin-7a(5H)-yl)methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane;

(1R,7R,8R)-2-(2-(((S)-2-(difluoromethylene)tetrahydro-1H-pyrrolizin-7a(5H)-yl)methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane;

(1S,7S,8S)-2-(2-(((R)-2-(difluoromethylene)tetrahydro-1H-pyrrolizin-7a(5H)-yl)methoxy)-7-(8-ethynyl-6,7-difluoronaphthalen-1-yl)-8-fluoropyrido[4,3-d]pyrimidin-4-yl)-8-fluoro-5-oxa-2-azabicyclo[5.1.0]octane;

5-ethynyl-6,8-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine;

(1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane-8-d;

6,7,8-trifluoro-4-(8-fluoro-4-((1S,7S,8S)-8-fluoro-5-oxa-2-azabicyclo[5.1.0]octan-2-yl-8-d)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine;

6,7,8-trifluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)-5-(methoxy-d3)naphthalen-2-amine;

6,7,8-trifluoro-4-(8-fluoro-4-((1S,7S,8S)-8-fluoro-5-oxa-2-azabicyclo[5.1.0]octan-2-yl)-2-(((S)-6'-methylenetetrahydrospiro[cyclopropane-1,1'-pyrrolizin]-7a'(5'H)-yl)methoxy)pyrido[4,3-d]pyrimidin-7-yl)-5-(methoxy-d3)naphthalen-2-amine;

(1S,7S,8S)-2-(7-(8-ethynyl-6,7-difluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane-8-d;

(1S,7S,8S)-8-fluoro-2-(8-fluoro-2-(((2R,7aS)-2-fluorotetrahydro-1H-pyrrolizin-7a(5H)-yl)methoxy-d2)-7-(5,6,7-trifluoro-8-(methoxy-d3)naphthalen-1-yl)pyrido[4,3-d]pyrimidin-4-yl)-5-oxa-2-azabicyclo[5.1.0]octane;

6,7,8-trifluoro-4-(8-fluoro-4-((1S,7S,8S)-8-fluoro-5-oxa-2-azabicyclo[5.1.0]octan-2-yl-6,6-d2)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine;

6,7,8-trifluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(methoxy-d3)naphthalen-2-amine;

6,7,8-trifluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine;

(1S,7S,8S)-2-(7-(8-ethynyl-7-fluoronaphthalen-1-yl)-8-fluoro-2-(((S,E)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane;

(1S,7S,8S)-2-(7-(8-ethynyl-7-fluoronaphthalen-1-yl)-8-fluoro-2-(((S,Z)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane;

6,8-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine;

6,7,8-trifluoro-4-(8-fluoro-4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)-5-(methoxy-d3)naphthalen-2-amine;

6,7,8-trifluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(methoxy-d3)naphthalen-2-amine;

4-(2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

6,8-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine;

4-(2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6,7,8-trifluoro-5-(methoxy-d3)naphthalen-2-amine;

(1S,7S,8S)-2-(7-(8-ethynyl-7-fluoronaphthalen-1-yl)-8-fluoro-2-(((S)-2-methylenetetrahydro-1H-pyrrolizin-7a(5H)-yl)methoxy)pyrido[4,3-d]pyrimidin-4-yl)-8-fluoro-5-oxa-2-azabicyclo[5.1.0]octane;

6,7-difluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(fluoromethoxy-d2)naphthalen-2-amine;

(1S,7S,8S)-8-fluoro-2-(8-fluoro-7-(7-fluoro-8-(fluoromethoxy-d2)naphthalen-1-yl)-2-(((S)-2-methylenetetrahydro-1H-pyrrolizin-7a(5H)-yl)methoxy)pyrido[4,3-d]pyrimidin-4-yl)-5-oxa-2-azabicyclo[5.1.0]octane;

(1S,7S,8S)-2-(2-(((S)-2-(difluoromethylene)tetrahydro-1H-pyrrolizin-7a(5H)-yl)methoxy)-8-fluoro-7-(7-fluoro-8-(fluoromethoxy-d2)naphthalen-1-yl)pyrido[4,3-d]pyrimidin-4-yl)-8-fluoro-5-oxa-2-azabicyclo[5.1.0]octane;

(1S,7S,8S)-2-(7-(5,7-difluoro-8-(fluoromethoxy-d2)naphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-S-oxa-2-azabicyclo[5.1.0]octane;

5-ethynyl-6-fluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)naphthalen-2-amine;

(1S,7S,8S)-8-fluoro-2-(8-fluoro-7-(7-fluoro-8-(fluoromethoxy-d2)naphthalen-1-yl)-2-(((S,E)-2-(fluoromethylene)tetrahydro-1H-pyrrolizin-7a(5H)-yl)methoxy)pyrido[4,3-d]pyrimidin-4-yl)-5-oxa-2-azabicyclo[5.1.0]octane;

(1S,7S,8S)-8-fluoro-2-(8-fluoro-7-(7-fluoro-8-(fluoromethoxy-d2)naphthalen-1-yl)-2-(((S,Z)-2-(fluoromethylene)tetrahydro-1H-pyrrolizin-7a(5H)-yl)methoxy)pyrido[4,3-d]pyrimidin-4-yl)-5-oxa-2-azabicyclo[5.1.0]octane;

5-ethynyl-6-fluoro-4-(8-fluoro-4-(1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)naphthalen-2-amine 6,7-difluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(fluoromethoxy-d2)naphthalen-2-amine;

(1S,7S,8S)-2-(7-(8-ethynyl-7-fluoronaphthalen-1-yl)-8-fluoro-2-(((R)-6'-methylenetetrahydrospiro[cyclopropane-1, 1'-pyrrolizin]-7a'(S'H)-yl)methoxy)pyrido[4,3-d]pyrimidin-4-yl)-8-fluoro-5-oxa-2-azabicyclo[5.1.0]octane;

5-ethynyl-6-fluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)naphthalen-2-amine;

6,8-difluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(methoxy-d3)naphthalen-2-amine;

5-ethynyl-6-fluoro-4-(8-fluoro-4-((1S,7S,8S)-8-fluoro-5-oxa-2-azabicyclo[5.1.0]octan-2-yl-8-d)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

4-(2-(((S)-dihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

6-fluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)-5-(fluoromethoxy-d2)naphthalen-2-amine;

6-fluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(fluoromethoxy-d2)naphthalen-2-amine;

6,8-difluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)-5-(methoxy-d3)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl-2,5,5-d3)methoxy-d2)pyrido[4,3-d]pyrimidin-7-yl)naphthalen-2-amine;

4-(2-(((2R,6R,7aS)-2-(aminomethyl)-6-fluorotetrahydro-1H-pyrrolizin-7a(5H)-yl)methoxy)-8-fluoro-4-((18,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-ol;

6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-vinylnaphthalen-2-amine;

4-(2-(((S)-dihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine;

5-ethyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'R,7a'R)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'S,7a'R)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'S,7a'S)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'R,7a'S)-6'-fluorotetrahydrospiro[cyclopropane-1,1'-pyrrolizin]-7a'(5'H)-yl-3',3',6'-d3)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-methyltetrahydro-1H-pyrrolizin-7a(5H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2S,7aS)-2-methyltetrahydro-1H-pyrrolizin-7a(5H)-yl)methoxy)pyrido[4,3-d]pyrimidin-7-yl)naphthalen-2-amine;

4-(2-(((1R,7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

4-(2-(((1S,7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-((tetrahydro-1H-pyrrolizin-7a(5H)-yl)methoxy-d2)pyrido[4,3-d]pyrimidin-7-yl)naphthalen-2-amine;

6-fluoro-4-(8-fluoro-4-((1S,7S,8S)-8-fluoro-5-oxa-2-azabicyclo[5.1.0]octan-2-yl)-2-(((2S,7aS)-2-methyltetrahydro-1H-pyrrolizin-7a(5H)-yl)methoxy)pyrido[4,3-d]pyrimidin-7-yl)-5-(fluoromethoxy-d2)naphthalen-2-amine;

6-fluoro-4-(8-fluoro-4-((1S,7S,8S)-8-fluoro-5-oxa-2-azabicyclo[5.1.0]octan-2-yl)-2-(((2R,7aS)-2-methyltetrahydro-1H-pyrrolizin-7a(5H)-yl)methoxy)pyrido[4,3-d]pyrimidin-7-yl)-5-(fluoromethoxy-d2)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol;

4-(2-(((S)-2,2-difluorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

5-ethynyl-6-fluoro-4-(8-fluoro-4-((1R,7R,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d ]pyrimidin-7-yl)naphthalen-2-amine;

5-ethynyl-6-fluoro-4-(8-fluoro-4-((1R,7R,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-ethynyl-6-fluoro-4-(8-fluoro-4-((1S,7S,8R)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

4-(2-(((1S,7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine;

4-(2-(((1R,7a'S)-2,2-difluorodihydro-1'H,3'H-spiro[cyclopropane-1,2'-pyrrolizin]-7a'(5'H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-6-fluoro-5-(fluoromethoxy-d2)naphthalen-2-amine;

4-(2-(((2S,7aS)-2-chlorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

4-(2-(((2R,7aS)-2-chlorotetrahydro-1H-pyrrolizin-7a(5H)-yl)methoxy-d2)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

5-ethynyl-6-fluoro-4-(8-fluoro-2-(((2R,7aS)-2-fluoro-5,5-dimethyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'R,7a'R)-6'-methyltetrahydrospiro[cyclopropane-1,1'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'S,7a'S)-6'-methyltetrahydrospiro[cyclopropane-1,1'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((S)-6'-methyl- 2',3'-dihydrospiro[cyclopropane-1,1'-pyrrolizin]-7a'(5'H)-yl)methoxy)pyrido[4,3-d]pyrimidin-7-yl)naphthalen-2-amine;

N-(((2R,6R,7aS)-7a-(((7-(8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-2-yl)methyl)acetamide;

((2R,6R,7aS)-7a-(((7-(8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-2-yl)methanamine;

4-(4-((1S,7S,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

4-(4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

4-(4-((1R,7R,8R)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

4-(4-((1R,7R,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((6'S,7a'R)-6'-methyltetrahydrospiro[cyclopropane-1,1'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1S,2S,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1S,2R,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo [5.1.0]octan-2-yl)-2-(((1R,2S,7a'S)-2-fluorodihydro-1'H,3'H-spiro[cyclopropane-1,2'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-7-d-2-amine;

N-(((2R,6R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl)-6-fluorohexahydro-1H-pyrrolizin-2-yl)methyl)acetamide;

4-(2-(((2R,6R,7aS)-2-(aminomethyl)-6-fluorotetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

5-ethynyl-6-fluoro-4-(8-fluoro-2-(((2R,5S,7aS)-2-fluoro-5-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

6-chloro-5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol;

5-ethynyl-6-fluoro-4-(4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-ethynyl-6-fluoro-4-(8-fluoro-2-(((2R,7aS)-2-fluoro-3,3-dimethyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

N-(5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-yl)acetamide;

5-ethynyl-6-fluoro-4-(8-fluoro-4-((1S,7S,8S)-8-fluoro-S-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-8-d-2-amine;

5-ethynyl-6-fluoro-4-(8-fluoro-4-((1S,7S,8S)-8-fluoro-5-oxa-2-azabicyclo[5.1.0]octan-2-yl)-2-(((2S,7aS)-2-(fluoromethyl)tetrahydro-1H-pyrrolizin-7a(5H)-yl)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-(fluoromethyl)tetrahydro-1H-pyrrolizin-7a(5H)-yl)methoxy-d2)pyrido[4,3-d]pyrimidin-7-yl)naphthalen-2-amine;

6-chloro-5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

4-(8-chloro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-7,8-d2-2-amine;

5-ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl-5',5'-d2)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl-5',5'-d2)methoxy-d2)pyrido[4,3-d]pyrimidin-7-yl)naphthalen-2-amine;

(2R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizine-2-carbonitrile;

5-ethynyl-6-fluoro-4-(8-fluoro-2-(((2R,3R,7aS)-2-fluoro-3-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

5-ethynyl-6-fluoro-4-(8-fluoro-2-(((2R,3S,7aS)-2-fluoro-3-methyltetrahydro-1H-pyrrolizin-7a(5H)-yl)methoxy)-4-((18,7S,8S)-8-fluoro-5-oxa-2-azabicyclo[5.1.0]octan-2-yl)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((R)-1-methylpyrrolidin-2-yl)methoxy)pyrido[4,3-d]pyrimidin-7-yl)naphthalen-2-ol;

5-ethynyl-6-fluoro-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol;

(2S,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizine-2-carbonitrile;

5-ethynyl-6-fluoro-4-(8-fluoro-2-(((2R,5R,7aS)-2-fluoro-5-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-amine;

(1S,7S,8S)-8-chloro-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane;

6-chloro-4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynylnaphthalen-2-amine;

6-chloro-5-ethynyl-4-(8-fluoro-4-((1S,7S,8S)-8-fluoro-S-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol;

5-ethynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-ol;

6-chloro-5-ethynyl-4-(8-fluoro-4-((1S,7S,8S)-8-fluoro-S-oxa-2-azabicyclo [5.1.0]octan-2-yl)-2-(((S)-1-methylpyrrolidin-2-yl)methoxy)pyrido[4,3-d]pyrimidin-7-yl)naphthalen-2-amine;

5-ethynyl-4-(8-fluoro-4-((1S,7S,8S)-8-fluoro-5-oxa-2-azabicyclo[5.1.0]octan-2-yl)-2-(((S)-1-methylpyrrolidin-2-yl)methoxy)pyrido[4,3-d]pyrimidin-7-yl)naphthalen-2-amine;

5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-ol;

4-(4-((1R, 7R,8R)-8-chloro-S-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynyl-6-fluoronaphthalen-2-amine;

4-(4-(1S,7S,8S)-8-chloro-5-oxa-2-azabicyclo[5.1.0]octan-2-yl)-8-fluoro-2-(S)-1-methylpyrrolidin-2-yl)methoxy)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1R,2R,7a'S)-2-fluorodihydro-1'H,3'H-spiro[cyclopropane-1,2'-pyrrolizin]-7a'(5'H)-yl)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((1R,2S,7a'S)-2-fluorodihydro-1'H,3'H-spiro[cyclopropane-1,2'-pyrrolizin]-7a'(5'H)-yl)methoxy-d2)pyrido[4,3-d]pyrimidin-7-yl)naphthalen-2-amine;

2-((2R,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizin-2-yl)acetonitrile;

2-((2S,7aS)-7a-(((7-(3-amino-8-ethynyl-7-fluoronaphthalen-1-yl)-8-fluoro-4-((1S,7S,8S)-8-fluoro-5-oxa-2-azabicyclo[5.1.0]octan-2-yl)pyrido[4,3-d]pyrimidin-2-yl)oxy)methyl-d2)hexahydro-1H-pyrrolizin-2-yl)acetonitrile;

(1S,7S,8S)-2-(7-(7-chloro-8-ethynylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

(1S,7S,8S)-2-(7-(8-ethynylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

(1S,7S,8S)-8-chloro-2-(7-(7-chloro-8-ethynylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-5-oxa-2-azabicyclo[5.1.0]octane;

6-chloro-4-(4-((1S,7S,8S)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine;

4-(4-((1S,7S,8S)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine;

5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-6-methylnaphthalen-2-ol;

(1S,7S,8S)-2-(7-(8-ethynyl-7-methylnaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

6-chloro-4-(4-((1R,7R,8R)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine;

4-(4-((1R, 7R,8R)-8-chloro-5-oxa-2-azabicyclo[5.1.0]octan-2-yl)-8-fluoro-2-(((S)-1-methylpyrrolidin-2-yl)methoxy)pyrido[4,3-d]pyrimidin-7-yl)-5-ethynylnaphthalen-2-amine;

5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-6-methylnaphthalen-2-amine;

(1S,7S,8S)-2-(7-(8-ethynyl-7-(trifluoromethyl)naphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine;

5-ethynyl-6-fluoro-4-(8-fluoro-2-(((2R,3S,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine;

((2R,6R,7aS)-7a-(((7-(8-ethynyl-7-(trifluoromethyl)naphthalen-1-yl)-8-fluoro-4-((1S,7S,8S)-8-fluoro-S-oxa-2-azabicyclo[5.1.0]octan-2-yl)pyrido[4,3-d]pyrimidin-2-yl)oxy)methyl)-6-fluorohexahydro-1H-pyrrolizin-2-yl)methanamine;

6-chloro-5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine;

5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine;

4-(4-((1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-amine;

4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-S-ethynyl-6-fluoronaphthalen-2-amine;

6-chloro-4-(4-((1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynylnaphthalen-2-amine;

4-(4-((1R,7R,8R)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-S-ethynylnaphthalen-2-amine;

4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-S-ethynylnaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine;

5-ethynyl-6-fluoro-4-(8-fluoro-2-(((6R,7aR)-6-fluoro-1-methylenetetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-methylnaphthalen-2-amine;

(1S,7S,8S)-2-(7-(8-ethynyl-7-fluoronaphthalen-1-yl)-8-fluoro-2-(((R,E)-6'-(fluoromethylene)tetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane;

(1S,7S,8S)-2-(7-(8-ethynyl-7-fluoronaphthalen-1-yl)-8-fluoro-2-(((R,Z)-6'-(fluoromethylene)tetrahydrospiro[cyclopropane-1,1'-pyrrolizin]-7a'(5'H)-yl)methoxy)pyrido[4,3-d]pyrimidin-4-yl)-8-fluoro-5-oxa-2-azabicyclo[5.1.0]octane;

(1S,7S,8S)-8-fluoro-2-(8-fluoro-7-(7-fluoro-8-(fluoromethoxy-d2)naphthalen-1-yl)-2-(((R)-6'-methylenetetrahydrospiro[cyclopropane-1,1'-pyrrolizin]-7a'(5'H)-yl)methoxy)pyrido[4,3-d]pyrimidin-4-yl)-5-oxa-2-azabicyclo[5.1.0]octane;

(1S,7S,8S)-8-fluoro-2-(8-fluoro-7-(7-fluoro-8-(fluoromethoxy-d2)naphthalen-1-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-4-yl)-5-oxa-2-azabicyclo [5.1.0]octane;

(1S,7S,8S)-8-fluoro-2-(8-fluoro-7-(7-fluoro-8-(fluoromethoxy-d2)naphthalen-1-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-4-yl)-5-oxa-2-azabicyclo[5.1.0]octane;

6-fluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine;

6-fluoro-4-(8-fluoro-4-((1S,7S,8S)-8-fluoro-5-oxa-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine;

6-fluoro-4-(8-fluoro-4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)-5-(fluoromethoxy-d2)naphthalen-2-amine;

5-ethynyl-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)-6-methylnaphthalen-2-amine;

(6R,7aS)-7a-(((7-(3-amino-8-ethynyl-7-fluoronaphthalen-1-yl)-8-fluoro-4-((1S,7S,8S)-8-fluoro-S-oxa-2-azabicyclo[5.1.0]octan-2-yl)pyrido[4,3-d]pyrimidin-2-yl)oxy)methyl)-6-fluorohexahydro-1H-pyrrolizin-1-one;

5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-ol;

4-(4-((1S,7S,8S)-8-chloro-5-oxa-2-azabicyclo[5.1.0]octan-2-yl)-8-fluoro-2-(((2R,3R,7aS-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-ol;

4-(2-((3,3-difluoro-1-azabicyclo[3.2.0]heptan-5-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine; and 5-ethynyl-6-fluoro-4-(8-fluoro-4-((1S,7S,8S)-8-fluoro-5-oxa-2-azabicyclo[5.1.0]octan-2-yl)-2-((hexahydro-1H-pyrrolo[2,1-c][1,4]oxazin-6-yl)methoxy)pyrido[4,3-d]pyrimidin-7-yl)naphthalen-2-amine.

17. The pharmaceutical composition of claim 16, wherein the compound, or a pharmaceutically acceptable salt, deuteroisotope, stereoisomer, or tautomer thereof, is selected from the group consisting of:

6,7-difluoro-4-(8-fluoro-4-((18,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine;

(1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane;

5-ethynyl-6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

6,7-difluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine;

6-fluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine;

(1S,7S,8S)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane;

6-fluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine;

(1S,7S,8S)-2-(7-(8-ethynyl-7-fluoronaphthalen-1-yl)-8-fluoro-2-(((S,E)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane;

(1S,7S,8S)-2-(7-(8-ethynyl-7-fluoronaphthalen-1-yl)-8-fluoro-2-(((S,Z)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane;

4-(2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)naphthalen-2-amine;

5-ethynyl-6-fluoro-4-(8-fluoro-4-((18,7S,8S)-8-fluoro-5-oxa-2-azabicyclo [5.1.0]octan-2-yl)-2-(((S)-2-methylenetetrahydro-1H-pyrrolizin-7a(5H)-yl)methoxy)pyrido[4,3-d]pyrimidin-7-yl)naphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)naphthalen-2-amine;

(1S,7S,8S)-2-(7-(8-ethynyl-7-fluoronaphthalen-1-yl)-8-fluoro-2-(((R)-6'-methylenetetrahydrospiro[cyclopropane-1, 1'-pyrrolizin]-7a'(S'H)-yl)methoxy)pyrido[4,3-d]pyrimidin-4-yl)-8-fluoro-5-oxa-2-azabicyclo[5.1.0]octane;

5-ethynyl-6-fluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1, l'-pyrrolizin]-7a'(5'H)-yl)methoxy)pyrido[4,3-d]pyrimidin-7-yl)naphthalen-2-amine;

5-ethyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

4-(4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

5-ethynyl-6-fluoro-4-(8-fluoro-2-(((2R,5S,7aS)-2-fluoro-5-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine;

6-chloro-5-ethynyl-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine;

4-(8-chloro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine;

5-ethynyl-4-(8-fluoro-4-((1S,7S,8S)-8-fluoro-5-oxa-2-azabicyclo [5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-6-methylnaphthalen-2-amine;

5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine;

4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-5-ethynyl-6-fluoronaphthalen-2-amine;

5-ethynyl-6-fluoro-4-(8-fluoro-4-((1S,7S,8S)-8-fluoro-5-oxa-2-azabicyclo[5.1.0]octan-2-yl)-2-(((R,E)-6'-(fluoromethylene)tetrahydrospiro[cyclopropane-1, l'-pyrrolizin]-7a'(5'H)-yl)methoxy)pyrido[4,3-d]pyrimidin-7-yl)naphthalen-2-amine; and 5-ethynyl-6-fluoro-4-(8-fluoro-4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine.

18. The pharmaceutical composition of claim 17, wherein the compound is:

6,7-difluoro-4-(8-fluoro-4-((1S, 7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine; or (1S,7S,8S)-2-(7-(8-ethynyl-7-fluoronaphthalen-1-yl)-8-fluoro-2-(((2R,7aS)-2-fluorotetrahydro-1H-pyrrolizin-7a(5H)-yl)methoxy-d2)pyrido[4,3-d]pyrimidin-4-yl)-8-fluoro-5-oxa-2-azabicyclo[5.1.0]octane or a pharmaceutically acceptable salt, deuteroisotope, stereoisomer, or tautomer thereof.

19. The pharmaceutical composition of claim 17, wherein the compound is:

5-ethynyl-6,7-difluoro-4-(8-fluoro-4-((18,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)naphthalen-2-amine; or 5-ethynyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine or a pharmaceutically acceptable salt, deuteroisotope, stereoisomer, or tautomer thereof.

20. The pharmaceutical composition of claim 17, wherein the compound is:

6,7-difluoro-4-(8-fluoro-4-((1S, 7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine; or 6-fluoro-4-(8-fluoro-4-((1S,78,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-(methoxy-d3)naphthalen-2-amine or a pharmaceutically acceptable salt, deuteroisotope, stereoisomer, or tautomer thereof.

21. The pharmaceutical composition of claim 17, wherein the compound is:

(1S,7S,8S)-2-(2-(((S)-2-(difluoromethylene)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-8-fluoro-5-oxa-2-azabicyclo[5.1.0]octane; or 6-fluoro-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-5-(fluoromethoxy-d2)naphthalen-2-amine or a pharmaceutically acceptable salt, deuteroisotope, stereoisomer, or tautomer thereof.

22. The pharmaceutical composition of claim 17, wherein the compound is:

(1S,7S,8S)-2-(7-(8-ethynyl-7-fluoronaphthalen-1-yl)-8-fluoro-2-(((S,E)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane; or (1S,7S,8S)-2-(7-(8-ethynyl-7-fluoronaphthalen-1-yl)-8-fluoro-2-(((S,Z)-2-(fluoromethylene)tetrahydro-1H-pyrrolizin-7a(5H)-yl)methoxy)pyrido[4,3-d]pyrimidin-4-yl)-8-fluoro-5-oxa-2-azabicyclo[5.1.0]octane or a pharmaceutically acceptable salt, deuteroisotope, stereoisomer, or tautomer thereof.

23. The pharmaceutical composition of claim 17, wherein the compound is:

4-(2-(((S)-2-(difluoromethylene)tetrahydro-1H-pyrrolizin-7a(5H)-yl)methoxy)-8-fluoro-4-((1S,7S,8S)-8-fluoro-5-oxa-2-azabicyclo[5.1.0]octan-2-yl)pyrido[4,3-d]pyrimidin-7-yl)-5-ethynyl-6-fluoronaphthalen-2-amine; or 5-ethynyl-6-fluoro-4-(8-fluoro-4-((1S,7S,8S)-8-fluoro-5-oxa-2-azabicyclo[5.1.0]octan-2-yl)-2-(((S,Z)-2-(fluoromethylene)tetrahydro-1H-pyrrolizin-7a(5H)-yl)methoxy)pyrido[4,3-d]pyrimidin-7-yl)naphthalen-2-amine or a pharmaceutically acceptable salt, deuteroisotope, stereoisomer, or tautomer thereof.

24. The pharmaceutical composition of claim 17, wherein the compound is:

5-ethynyl-6-fluoro-4-(8-fluoro-4-((1S,7S,8S)-8-fluoro-5-oxa-2-azabicyclo[5.1.0]octan-2-yl)-2-(((S)-2-methylenetetrahydro-1H-pyrrolizin-7a(5H)-yl)methoxy)pyrido[4,3-d]pyrimidin-7-yl)naphthalen-2-amine; or 5-ethynyl-6-fluoro-4-(8-fluoro-4-((1S,7S,8S)-8-fluoro-5-oxa-2-azabicyclo[5.1.0]octan-2-yl)-2-(((S,E)-2-(fluoromethylene)tetrahydro-1H-pyrrolizin-7a(5H)-yl)methoxy)pyrido[4,3-d]pyrimidin-7-yl)naphthalen-2-amine or a pharmaceutically acceptable salt, deuteroisotope, stereoisomer, or tautomer thereof.

25. The pharmaceutical composition of claim 17, wherein the compound is:

(1S,7S,8S)-2-(7-(8-ethynyl-7-fluoronaphthalen-1-yl)-8-fluoro-2-(((R)-6'-methylenetetrahydrospiro[cyclopropane-1, l'-pyrrolizin]-7a'(5'H)-yl)methoxy)pyrido[4,3-d]pyrimidin-4-yl)-8-fluoro-5-oxa-2-azabicyclo[5.1.0]octane; or 5-ethynyl-6-fluoro-4-(8-fluoro-4-((1S,7S,8S)-8-fluoro-5-oxa-2-azabicyclo[5.1.0]octan-2-yl)-2-(((R)-6'-methylenetetrahydrospiro[cyclopropane-1, l'-pyrrolizin]-7a'(5'H)-yl)methoxy)pyrido[4,3-d]pyrimidin-7-yl)naphthalen-2-amine or a pharmaceutically acceptable salt, deuteroisotope, stereoisomer, or tautomer thereof.

26. The pharmaceutical composition of claim 17, wherein the compound is:

5-ethyl-6-fluoro-4-(8-fluoro-4-((1S,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine; or 4-(4-((1S,7S,8S)-8-chloro-5-oxa-2-azabicyclo[5.1.0]octan-2-yl)-8-fluoro-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine or a pharmaceutically acceptable salt, deuteroisotope, stereoisomer, or tautomer thereof.

27. The pharmaceutical composition of claim 17, wherein the compound is:

5-ethynyl-6-fluoro-4-(8-fluoro-2-(((2R,5S,7aS)-2-fluoro-5-methyltetrahydro-1H-pyrrolizin-7a(5H)-yl)methoxy)-4-((1S,7S,8S)-8-fluoro-5-oxa-2-azabicyclo[5.1.0]octan-2-yl)pyrido[4,3-d]pyrimidin-7-yl)naphthalen-2-amine; or 6-chloro-5-ethynyl-4-(8-fluoro-4-((1S,7S,8S)-8-fluoro-S-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)naphthalen-2-amine or a pharmaceutically acceptable salt, deuteroisotope, stereoisomer, or tautomer thereof.

28. The pharmaceutical composition of claim 17, wherein the compound is:

4-(8-chloro-4-((18,7S,8S)-8-fluoro-5-oxa-2-azabicyclo[5.1.0]octan-2-yl)-2-(((2R,7aS)-2-fluorotetrahydro-1H-pyrrolizin-7a(5H)-yl)methoxy-d2)pyrido[4,3-d]pyrimidin-7-yl)-5-ethynyl-6-fluoronaphthalen-2-amine; or 5-ethynyl-4-(8-fluoro-4-((1S,7S,8S)-8-fluoro-5-oxa-2-azabicyclo[5.1.0]octan-2-yl)-2-(((2R, 7aS)-2-fluorotetrahydro-1H-pyrrolizin-7a(5H)-yl)methoxy-d2)pyrido[4,3-d]pyrimidin-7-yl)-6-methylnaphthalen-2-amine or a pharmaceutically acceptable salt, deuteroisotope, stereoisomer, or tautomer thereof.

29. The pharmaceutical composition of claim 17, wherein the compound is:

5-ethynyl-6-fluoro-4-(8-fluoro-2-(((2R,3R,7aS)-2-fluoro-3-methyltetrahydro-1H-pyrrolizin-7a(5H)-yl)methoxy-d2)-4-((1S,7S,8S)-8-fluoro-5-oxa-2-azabicyclo[5.1.0]octan-2-yl)pyrido[4,3-d]pyrimidin-7-yl)naphthalen-2-amine; or 4-(4-((1S,7S,8S)-8-chloro-5-oxa-2-azabicyclo[5.1.0]octan-2-yl)-8-fluoro-2-(((2R,3R,7aS)-2-fluoro-3-methyltetrahydro-1H-pyrrolizin-7a(5H)-yl)methoxy-d2)pyrido[4,3-d]pyrimidin-7-yl)-S-ethynyl-6-fluoronaphthalen-2-amine or a pharmaceutically acceptable salt, deuteroisotope, stereoisomer, or tautomer thereof.

30. The pharmaceutical composition of claim 17, wherein the compound is:

5-ethynyl-6-fluoro-4-(8-fluoro-4-((1S,7S,8S)-8-fluoro-5-oxa-2-azabicyclo[5.1.0]octan-2-yl)-2-(((R,E)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine; or 5-ethynyl-6-fluoro-4-(8-fluoro-4-((1S,7S,8S)-8-fluoro-5-oxa-2-azabicyclo[5.1.0]octan-2-yl)-2-(((R,Z)-6'-(fluoromethylene)tetrahydrospiro[cyclopropane-1,1'-pyrrolizin]-7a'(5'H)-yl)methoxy)pyrido[4,3-d]pyrimidin-7-yl)naphthalen-2-amine or a pharmaceutically acceptable salt, deuteroisotope, stereoisomer, or tautomer thereof.

* * * * *